(12) United States Patent
Schnell et al.

(10) Patent No.: US 11,975,067 B2
(45) Date of Patent: May 7, 2024

(54) CORONAVIRUS DISEASE (COVID-19) VACCINE

(71) Applicant: Thomas Jefferson University, Philadelphia, PA (US)

(72) Inventors: Matthias Johannes Schnell, Harleysville, PA (US); Christoph Wirblich, Wernau (DE); Drishya Kurup, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 18/186,874

(22) Filed: Mar. 20, 2023

(65) Prior Publication Data

US 2023/0338513 A1 Oct. 26, 2023

Related U.S. Application Data

(62) Division of application No. 17/817,708, filed on Aug. 5, 2022, now Pat. No. 11,660,336, which is a division of application No. 17/193,890, filed on Mar. 5, 2021, now Pat. No. 11,478,543.

(60) Provisional application No. 63/017,241, filed on Apr. 29, 2020, provisional application No. 62/986,396, filed on Mar. 6, 2020.

(51) Int. Cl.
| | |
|---|---|
| *A61P 31/14* | (2006.01) |
| *A61K 39/215* | (2006.01) |
| *A61P 31/12* | (2006.01) |
| *A61P 37/04* | (2006.01) |
| *C07K 14/005* | (2006.01) |
| *C07K 14/165* | (2006.01) |
| *C12N 7/00* | (2006.01) |
| *A61K 39/00* | (2006.01) |

(52) U.S. Cl.
CPC .............. *A61K 39/215* (2013.01); *C12N 7/00* (2013.01); *A61K 2039/5252* (2013.01); *A61K 2039/55572* (2013.01); *C12N 2760/20042* (2013.01); *C12N 2770/20034* (2013.01)

(58) Field of Classification Search
CPC ....... A61K 39/12; A61K 39/215; A61P 37/04; A61P 31/12; C07K 14/165
See application file for complete search history.

(56) References Cited

U.S. PATENT DOCUMENTS

2019/0062785 A1 2/2019 Johnson et al.

OTHER PUBLICATIONS

"International Search Report and Written Opinion dated Aug. 5, 2021 for International Appln. No. PCT/US21/21200".

Bhandari, et al., "A dose-escalation safety and immunogenicity study of live attenuated oral rotavirus vaccine 116E in infants: a randomized, double-blind, placebo-controlled trial", J Infect Dis., 200(3), Epub Jun. 24, 2009. doi: 10.1086/600104. PubMed PMID: 19545211, 2009, 421-9.

Bhandari, et al., "Efficacy of a monovalent human-bovine (116E) rotavirus vaccine in Indian children in the second year of life", Vaccine, 32 Suppl 1, doi: 10.1016/j.vaccine.2014.04.079. PubMed PMID: 25091663; PMCID: 25091663, 2014, A110-6.

Bhandari, et al., "Efficacy of a monovalent human-bovine (116E) rotavirus vaccine in Indian infants: a randomised, double-blind, placebo-controlled trial", Lancet, 383(9935), Epub Mar. 19, 2014. doi: 10.1016/s0140-6736(13)62630-6. PubMed PMID: 24629994; PMCID: PMC4532697, 2014, 2136-43.

Bhandari, et al., "Safety and immunogenicity of two live attenuated human rotavirus vaccine candidates, 116E and 321, in infants: results of a randomised controlled trial", Vaccine., 24(31-32), Epub Jun. 1, 2006. doi: 10.1016/j.vaccine.2006.05.001. PubMed PMID: 16735085, 2006, 5817-23.

Blaney, et al., "Antibody quality and protection from lethal Ebola virus challenge in nonhuman primates immunized with rabies virus based bivalent vaccine", PLoS pathogens, 9(5):e1003389. doi: 10.1371/journal.ppat.1003389. PubMed PMID: 23737747; PMCID: 3667758., 2013.

Blaney, et al., "Inactivated or live-attenuated bivalent vaccines that confer protection against rabies and Ebola viruses", J Virol., 85(20), Epub Aug. 19, 2011. doi: 10.1128/JVI.00558-11. PubMed PMID: 21849459; PMCID: 3187516., 2011, 10605-16.

Burkard, et al., "Coronavirus cell entry occurs through the endo-/lysosomal pathway in a proteolysis-dependent manner", PLoS pathogens, 10(11):e1004502. doi: 10.1371/journal.ppat.1004502. PubMed PMID: 25375324; PMCID: PMC422306, 2014.

Conzelmann, et al., "Molecular cloning and complete nucleotide sequence of the attenuated rabies virus SAD B19", Virology, 175(2), PubMed PMID: 2139267, 1990, 485-99.

Hudacek, et al., "Recombinant rabies virus particles presenting botulinum neurotoxin antigens elicit a protective humoral response in vivo", Molecular therapy Methods & clinical development. 2014;1:14046

(56) References Cited

OTHER PUBLICATIONS

Kurup, et al., "Rhabdoviral-Based Vaccine Platforms against Henipaviruses", J Virol., doi: 10.1128/JVI. PubMed PMID: 25320306, 2014, 02308-14.

Ma, et al., "Searching for an ideal vaccine candidate among different MERS coronavirus receptor-binding fragments—the importance of immunofocusing in subunit vaccine design", Vaccine. 2014;32(46), doi: 10.1016/j.vaccine.2014.08.086, doi: 10.1016/j.vaccine.2014.08.086. PubMed PMID: 25240756; PMCID: PMC4194190, 2014, 6170-6.

McGettigan, et al., "Functional human immunodeficiency virus type 1 (HIV-1) Gag-Pol or HIV-1 Gag-Pol and env expressed from a single rhabdovirus-based vaccine vector genome", J Virol., 77(20), Epub Sep. 27, 2003. PubMed PMID: 14512539; PMCID: 224996, 2003, 10889-99.

McGettigan, et al., "Second-generation rabies virus-based vaccine vectors expressing human immunodeficiency virus type 1 gag have greatly reduced pathogenicity but are highly immunogenic", J Virol., 77(1), Epub Dec. 13, 2002. PubMed PMID: 12477829; PMCID: 140592, 2003, 237-44.

Mohan, et al., "Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study", Clinical infectious diseases: an official publication of the Infectious Diseases Society of America, 61(3), Epub Apr. 15, 2015. doi: 10.1093/cid/civ295. PubMed PMID: 25870324, 2015, 393-402.

Muthumani, et al., "A synthetic consensus anti-spike protein DNA vaccine induces protective immunity against Middle East respiratory syndrome coronavirus in nonhuman primates", Sci Transl Med., 7(301):301ra132. doi: 10.1126/scitranslmed.aac7462. PubMed PMID: 26290414; PMCID: PMC4573558, 2015.

Papaneri, et al., "Alanine scanning of the rabies virus glycoprotein antigenic site III using recombinant rabies virus: Implication for post-exposure treatment", Vaccine, 31(49), Epub Oct. 15, 2013. doi: 10.1016/j.vaccine.2013.09.038. PubMed PMID: 24120673, 2013, 5897-902.

Pfaller, et al., "Reverse genetics of Mononegavirales: How they work, new vaccines, and new cancer therapeutics", Virology, 479-480, doi: 10.1016/j.virol.2015.01.029. PubMed PMID: 25702088; PMCID: 4557643, 331-44.

Raj, et al., "Dipeptidyl peptidase 4 is a functional receptor for the emerging human coronavirus-EMC", Nature, 495 (7440), doi: 10.1038/nature12005. PubMed PMID: 23486063, 2013, 251-4.

Servat, et al., "A quantitative indirect ELISA to monitor the effectiveness of rabies vaccination in domestic and wild carnivores", J Immunol Methods., 318(1-2), doi: 10.1016/j.jim.2006.07.026. PubMed PMID: 17166510, 2007, 1-10.

Shakya, et al., "Phase 3 Efficacy Analysis of a Typhoid Conjugate Vaccine Trial in Nepal", New England Journal of Medicine, 381(23), doi: 10.1056/NEJMoa1905047, 2019, 2209-18.

Shi, et al., "Susceptibility of ferrets, cats, dogs, and other domesticated animals to SARS-coronavirus 2", Science, vol. 368, Issue 6494, May 29, 2020, 1016-1020.

Singh, et al., "A Japanese Encephalitis Vaccine From India Induces Durable and Cross-protective Immunity Against Temporally and Spatially Wide-ranging Global Field Strains", The Journal of Infectious Diseases, 212(5),. doi: 10.1093/infdis/jiv023, 2015, 715-25.

Sun, et al., "SARS-CoV-2 and SARS-CoV Spike-RBD Structure and Receptor Binding Comparison and Potential Implications on Neutralizing Antibody and Vaccine Development", bioRxiv. Feb. 20, 2020 [online]. [Retrieved on Jun. 28, 2021]. Retrieved from the internet: <URL: https://www.biorxiv.org/contenUbiorxiv/early/2020/02/20/2020.02.16.951723. full.pdf>.

Vadrevu, et al., "Persistence of Immune Responses With an Inactivated Japanese Encephalitis Single-Dose Vaccine, JENVAC and Interchangeability With a Live-Attenuated Vaccine", The Journal of Infectious Diseases, doi: 10.1093/infdis/jiz672, 2019.

Volz, et al., "Protective Efficacy of Recombinant Modified Vaccinia Virus Ankara Delivering Middle East Respiratory Syndrome Coronavirus Spike Glycoprotein", J Virol., 89(16). doi: 10.1128/JVI.00614-15. PubMed PMID: 26018172; PMCID: PMC4524222, 2015, 8651-6.

Voysey, et al., "Seroefficacy of Vi Polysaccharide-Tetanus Toxoid Typhoid Conjugate Vaccine (Typbar TCV)", Clinical Infectious Diseases, 67(1), doi: 10.1093/cid/cix1145, 2018, 18-24.

Wasniewski, et al., "Evaluation of an ELISA to detect rabies antibodies in orally vaccinated foxes and raccoon dogs sampled in the field", J Virol Methods, 187(2):264-70. doi: 10.1016/j.jviromet.2012.11.022. PubMed PMID: 23201293, 2013, 264-70.

Wasniewski, et al., "Evaluation of ELISA for detection of rabies antibodies in domestic carnivores", J Virol Methods., 179(1), doi: 10.1016/j.jviromet.2011.10.019. PubMed PMID: 22080853, 2012, 166-75.

Willet, et al., "Preclinical Development of Inactivated Rabies Virus-Based Polyvalent Vaccine Against Rabies and Filoviruses", J Infect Dis., 212 Suppl 2:. doi: 10.1093/infdis/jiv251. PubMed PMID: 26063224; PMCID: 4564550, 2015, S414-24.

Wirblich, et al., "One-Health: a Safe, Efficient, Dual-Use Vaccine for Humans and Animals against Middle East Respiratory Syndrome Coronavirus and Rabies Virus", Journal of virology, 91(2). Epub Nov. 4, 2016. doi: 10.1128/JVI.02040-16. PubMed PMID: 27807241; PMCID: PMC5215356, 2017.

Zhao, et al., "Rapid generation of a mouse model for Middle East respiratory syndrome", Proc Natl Acad Sci U S A., 111(13), Epub Mar. 7, 2014. doi: 10.1073/pnas.1323279111. PubMed PMID: 24599590; PMCID: 3977243, 2014, 4970-5.

FIG. 1

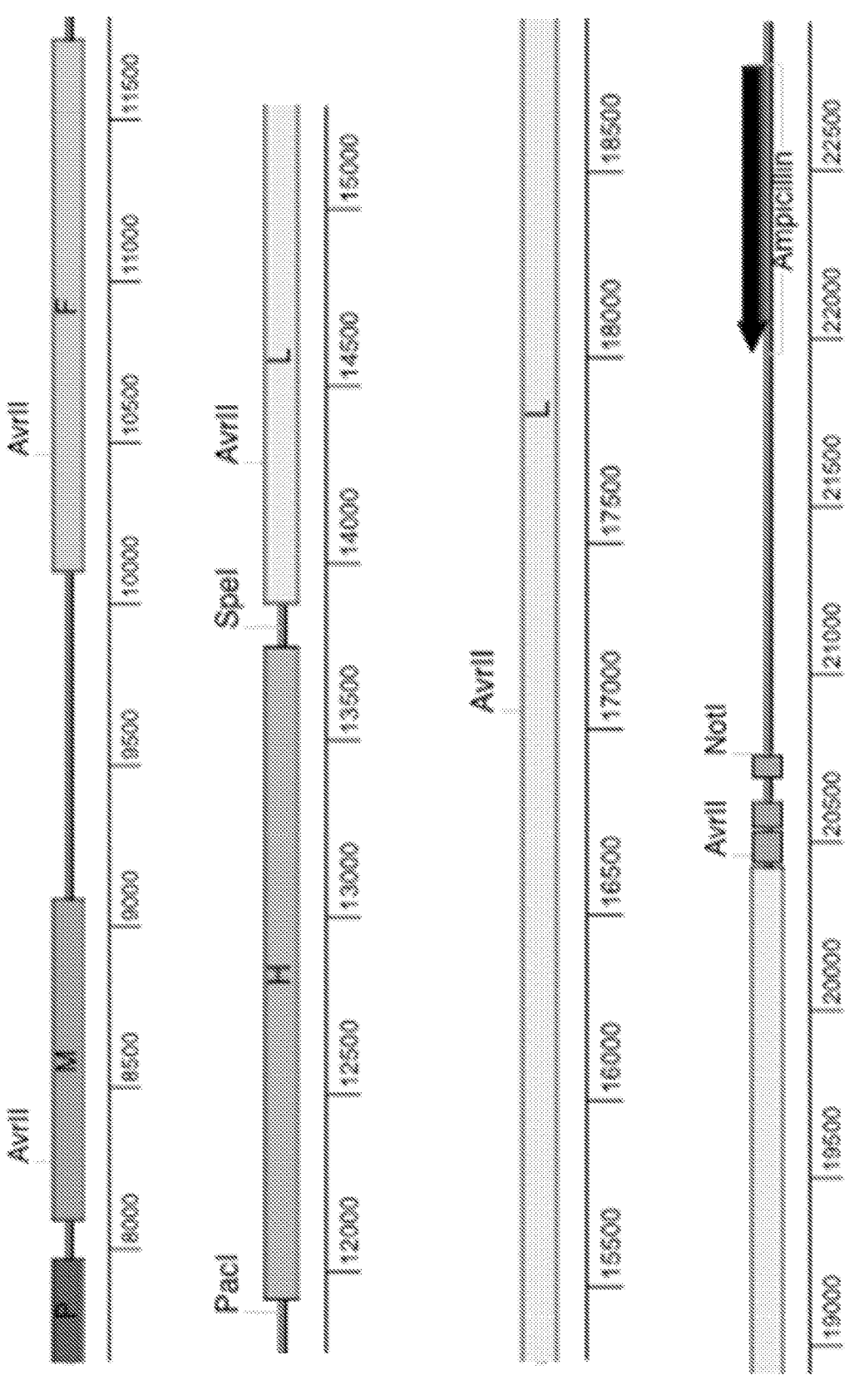
FIG. 3 - continued

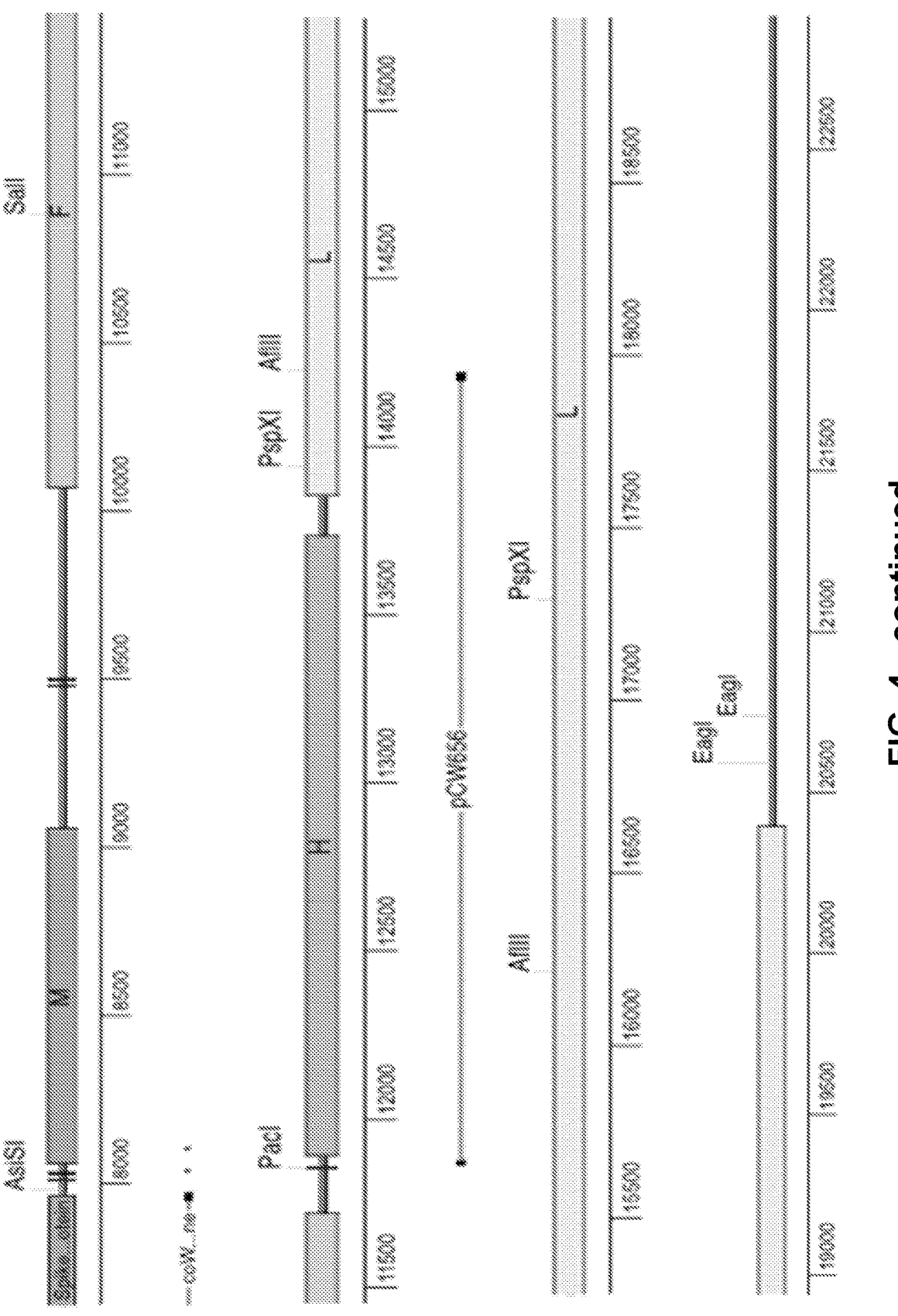
FIG. 4 - continued

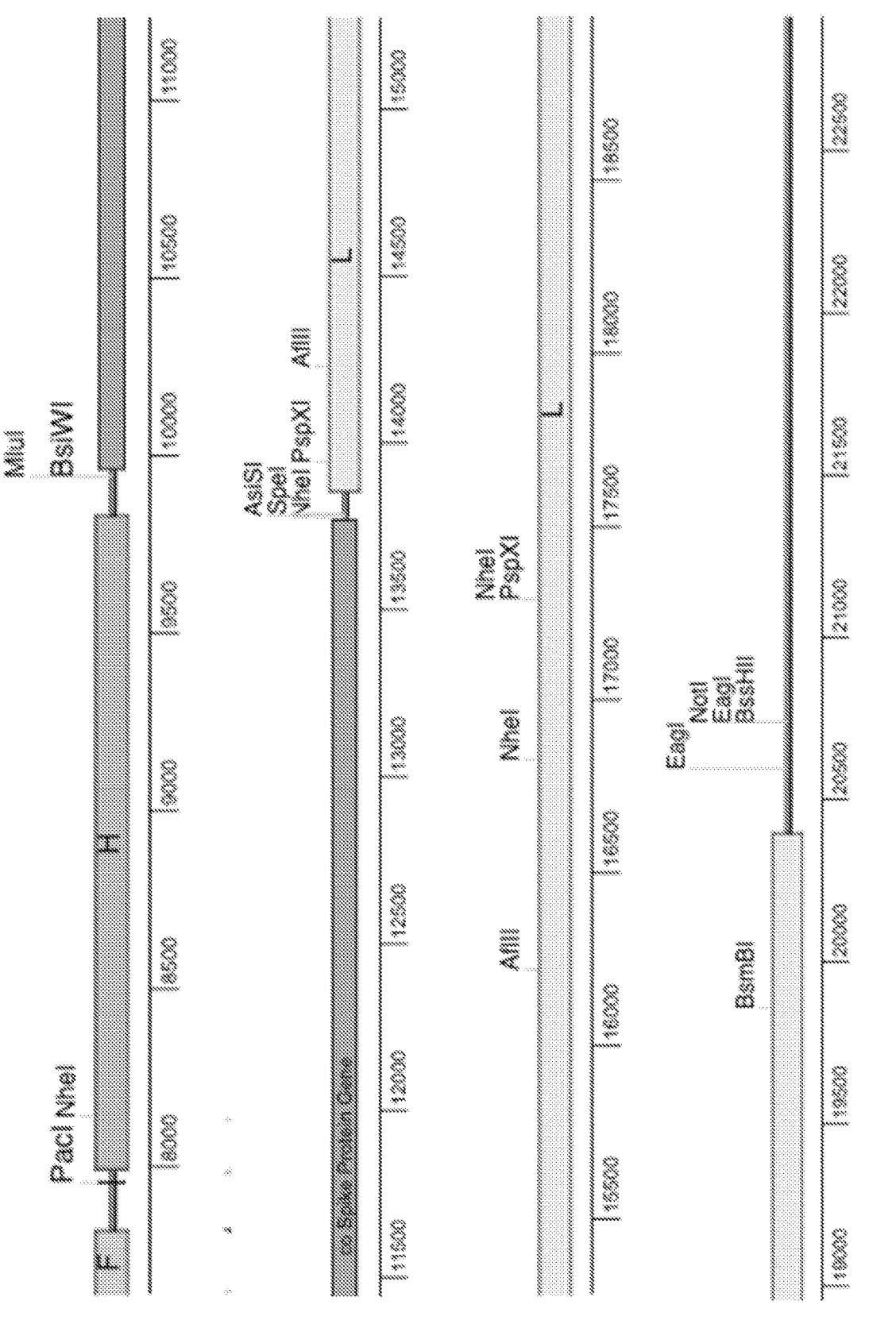
FIG. 5 - continued

| Show | Type | Name | Range | Strand | Length | Description |
|---|---|---|---|---|---|---|
| ✓ | misc_feature | Ampicillin | complement(16204..17061) | ▼ | 858 | Ampicillin |
| ✓ | misc_feature | CMV promoter | 626..1206 | ▲ | 581 | CMV promoter |
| ✓ | misc_feature | CP1685M | 8023..8041 | ▲ | 19 | CP1685M |
| ✓ | misc_feature | HH ribozyme | 1276..1323 | ▲ | 48 | HH ribozyme |
| ✓ | misc_feature | HdR | 14799..14894 | ▲ | 96 | HdR |
| ✓ | misc_feature | Leader | 1324..1386 | ▲ | 63 | Leader |
| ✓ | insert | PCR 676B+677 | 1324..3397 | ▲ | 2074 | |
| ✓ | insert | PCW469-1 | 8048..8257 | ▼ | 210 | |
| ✓ | misc_feature | RP659M | complement(2085..2104) | ▲ | 20 | RP659M |
| ✓ | misc_feature | RP660 | 5051..5070 | ▼ | 20 | RP660 |
| ✓ | misc_feature | RP77 | complement(3496..3516) | ▲ | 21 | RP77 |
| ✓ | misc_feature | Signal Peptide | 5996..6040 | ▲ | 45 | Signal Peptide |
| ✓ | misc_feature | Stop | 2700..2706 | ▲ | 7 | Stop |
| ✓ | misc_feature | Stop | 8351..8357 | ▲ | 7 | Stop |
| ✓ | misc_feature | T7 | 1238..1258 | ▲ | 21 | T7 |
| ✓ | misc_feature | T7Term | 14965..15012 | ▲ | 48 | T7Term |
| ✓ | misc_feature | TM | 8125..8193 | ▲ | 69 | TM |
| ✓ | misc_feature | Trailer | 14700..14798 | ▲ | 99 | Trailer |
| ✓ | misc_feature | VP1F | 1710..1729 | ▲ | 20 | VP1F |
| ✓ | misc_feature | VP2F | 2196..2215 | ▲ | 20 | VP2F |
| ✓ | misc_feature | VP3F | 3229..3248 | ▲ | 20 | VP3F |
| ✓ | misc_feature | VP4F | 3710..3729 | ▲ | 20 | VP4F |
| ✓ | misc_feature | VP5F | 4227..4246 | ▲ | 20 | VP5F |
| ✓ | misc_feature | VP6F | 4693..4713 | ▲ | 21 | VP6F |

FIG. 7

| | | | | | | |
|---|---|---|---|---|---|---|
| V | misc_feature | VP7F | 5228..5247 | ▲ | 20 | VP7F |
| V | misc_feature | VP8F | 5692..5712 | ▲ | 21 | VP8F |
| V | misc_feature | VSV-G | 4401..5936 | ▲ | 1536 | VSV-G |
| V | misc_feature | VSV-G | 8048..8257 | ▲ | 210 | VSV-G |
| V | misc_feature | VSV-L | 8370..14699 | ▲ | 6330 | VSV-L |
| V | misc_feature | VSV-M | 3573..4262 | ▲ | 690 | VSV-M |
| V | misc_feature | VSV-N | 1387..2655 | ▲ | 1269 | VSV-N |
| V | misc_feature | VSV-P | 2719..3516 | ▲ | 798 | VSV-P |
| V | misc_feature | WuV-S-Fwd1184 | 7159..7178 | ▲ | 20 | WuV-S-Fwd1184 |
| V | misc_feature | WuV-S-Fwd1814 | 7789..7808 | ▲ | 20 | WuV-S-Fwd1814 |
| V | misc_feature | WuV-S-Fwd581 | 6556..6575 | ▲ | 20 | WuV-S-Fwd581 |
| V | misc_feature | WuV-S1 | 5996..8041 | ▲ | 2046 | WuV-S1 |

FIG. 7 - continued

| Show | Type | Name | Range | Strand | Length | Description |
|---|---|---|---|---|---|---|
| ✓ | misc_feature | Ampicillin | complement(16626..17483) | ▼ | 858 | Ampicillin |
| | coverage_below | Below threshold | 2772..4270 | ▲ | 1499 | |
| ✓ | misc_feature | CMV promoter | 626..1206 | ▲ | 581 | CMV promoter |
| | contig | Contig 1(1)> | 2772..4270 | ▲ | 1499 | |
| ✓ | misc_feature | O | 0979..8553 | ▲ | 1575 | O |
| ✓ | misc_feature | G-tail | 4834..5124 | ▲ | 291 | G-tail |
| ✓ | misc_feature | HH ribozyme | 1277..1323 | ▲ | 47 | HH ribozyme |
| | misc_signal | Hammerhead ribozyme | 1277..1323 | ▲ | 47 | self-splicing site |
| ✓ | misc_feature | HdR | 15231..15322 | ▲ | 92 | HdR |
| ✓ | misc_feature | Helix I | 1277..1284 | ▲ | 8 | Helix I |
| ✓ | misc_feature | Helix I | 1324..1331 | ▲ | 8 | Helix I |
| ✓ | misc_feature | Helix II | 1292..1295 | ▲ | 4 | Helix II |
| ✓ | misc_feature | Helix III | 1300..1303 | ▲ | 4 | Helix II |
| ✓ | misc_feature | Helix III | 1307..1312 | ▲ | 6 | Helix III |
| ✓ | misc_feature | Helix III | 1317..1322 | ▲ | 6 | Helix III |
| ✓ | misc_feature | L | 8716..15099 | ▲ | 6384 | L |
| ✓ | misc_feature | M | 6158..6766 | ▲ | 609 | M |
| | coverage_one | One_strand | 3382..3538 | ▲ | 157 | |
| | coverage_once | Only_once | 3539..4270 | ▲ | 732 | |
| | coverage_once | Only_once | 2772..3381 | ▲ | 610 | |

FIG. 8

| | | | | | | | |
|---|---|---|---|---|---|---|---|
| ✓ | | misc_feature | P | 5176..6069 | ▶ | 894 | P |
| | | misc_feature | RP381 | 1383..1401 | ▶ | 19 | RP381 |
| ✓ | | misc_feature | RP951 | 2630..2657 | ▶ | 28 | RP951 |
| ✓ | | misc_feature | RP952M | complement (5216..5244) | ◀ | 29 | RP952M |
| | | misc_feature | RTP-1 qPCR primer | 1421..1450 | ▶ | 30 | RTP-1 qPCR primer |
| ✓ | | misc_feature | RV leader | 1324..1381 | ▶ | 58 | RV leader |
| ✓ | | misc_feature | SAD-N | 1394..2746 | ▶ | 1353 | SAD-N |
| | | 5'UTR | SPBN leader | 1324..1393 | ▶ | 70 | SPBN leader |
| | | misc_feature | T7 | 1239..1255 | ▶ | 17 | T7 |
| ✓ | | misc_feature | T7 promotor | 1238..1258 | ▶ | 21 | T7 promotor |
| ✓ | | misc_feature | T7Term | 15387..15434 | ▶ | 48 | T7Term |
| ✓ | | misc_feature | TM | 4927..4992 | ▶ | 66 | TM |
| ✓ | | misc_feature | Trailer | 15100..15230 | ▶ | 131 | Trailer |
| ✓ | | misc_feature | WuS1-RABVG | 2782..5127 | ▶ | 2346 | WuS1-RABVG |
| | | insert | cSPBN | 987..1519 | ▶ | 533 | |
| | | insert | pBS-CMV-N2C-HdR | 620..986, 15261..15442 | ▶ | 549 | |
| | | insert | pCW367 | 1520..2771, 5129..15260 | ▶ | 11384 | |
| ✓ | | insert | pCW751-2 plasmid sequence | 2772..5128 | ▶ | 2357 | |
| | | misc_feature | qPCR T7 standard forward primer | 1371..1392 | ▶ | 22 | qPCR T7 standard forward primer |

FIG. 8 - continued

| Show | | Type | Name | Range | Strand | Length | Description |
|---|---|---|---|---|---|---|---|
| ✓ | | misc_feature | | 4555..4560 | ▶ | 6 | |
| ✓ | | misc_feature | | 4546..4551 | ▶ | 6 | |
| ✓ | | misc_feature | Ampicillin | complement (21955..22815) | ◀ | 861 | Ampicillin |
| ✓ | | misc_feature | CP1685M | complement (4530..4561) | ◀ | 32 | CP1685M |
| ✓ | | misc_feature | F | 10095..11756 | ▶ | 1662 | F |
| ✓ | | misc_feature | H | 11917..13770 | ▶ | 1854 | H |
| ✓ | | misc_feature | HH Ribozyme | 667..716 | ▶ | 50 | HH Ribozyme |
| ✓ | | misc_feature | L | 13880..20431 | ▶ | 6552 | L |
| ✓ | | misc_feature | M | 8084..9091 | ▶ | 1008 | M |
| | | insert | MV-GFP corrected | 824..2471 | ▶ | 1648 | |
| | | insert | MV-GFP corrected | 6336..6689 | ▶ | 354 | |
| ✓ | | misc_feature | MV33F | 19986..20005 | ▶ | 20 | MV33F |
| ✓ | | misc_feature | MV4F | 2158..2177 | ▶ | 20 | MV4F |
| ✓ | | misc_feature | MV5F | 6573..6591 | ▶ | 19 | MV5F |
| ✓ | | misc_feature | N | 824..2398 | ▶ | 1575 | N |
| ✓ | | misc_feature | P | 6453..7976 | ▶ | 1524 | P |
| ✓ | | misc_feature | RP1686P | 4542..4569 | ▶ | 28 | RP1686P |
| ✓ | | misc_feature | RP602 | complement (20729..20746) | ◀ | 18 | RP602 |
| ✓ | | misc_feature | Signal peptide | 2503..2547 | ▶ | 45 | Signal peptide |
| ✓ | | misc_feature | Spike Protein | 2503..6321 | ▶ | 3819 | Spike Protein |
| ✓ | | misc_feature | T7 TERM | 20688..20763 | ▶ | 76 | T7 TERM |
| ✓ | | misc_feature | T7 promoter | 629..645 | ▶ | 17 | T7 promoter |
| ✓ | | misc_feature | UTR | 20432..20540 | ▶ | 109 | UTR |
| ✓ | | misc_feature | UTR | 717..820 | ▶ | 104 | UTR |
| ✓ | | insert | coWuhan-Virus Spike protein Gene | 2490..6335 | ▶ | 3846 | |
| ✓ | | misc_feature | hHdVRzym | 20541..20626 | ▶ | 86 | hHdVRzym |

FIG. 9

| Show | Type | Name | Range | Strand | Length | Description |
|---|---|---|---|---|---|---|
| ✓ | misc_feature | | 3870..3889 | ▲ | 20 | |
| ✓ | misc_feature | Ampicillin | complement (21925..22785) | ▼ | 861 | Ampicillin |
| ✓ | misc_feature | F | 10065..11726 | ▲ | 1662 | F |
| ✓ | misc_feature | GE | 2450..2460 | ▲ | 11 | GE |
| ✓ | misc_feature | GE | 758..768 | ▲ | 11 | GE |
| ✓ | misc_feature | GE | 9477..9487 | ▲ | 11 | GE |
| ✓ | misc_feature | GE | 4097..4107 | ▲ | 11 | GE |
| ✓ | misc_feature | GE | 11853..11858 | ▲ | 6 | GE |
| ✓ | misc_feature | GE | 8008..8018 | ▲ | 11 | GE |
| ✓ | misc_feature | GE | 20460..20470 | ▲ | 11 | GE |
| ✓ | misc_feature | GS | 2464..2480 | ▲ | 17 | GS |
| ✓ | misc_feature | GS | 772..788 | ▲ | 17 | GS |
| ✓ | misc_feature | GS | 9491..9507 | ▲ | 17 | GS |
| ✓ | misc_feature | GS | 20474..20490 | ▲ | 17 | GS |
| ✓ | misc_feature | GS | 8022..8038 | ▲ | 17 | GS |
| ✓ | misc_feature | GS | 4111..4127 | ▲ | 17 | GS |
| ✓ | misc_feature | H | 11887..13740 | ▲ | 1854 | H |
| ✓ | misc_feature | HH Ribozyme | 667..716 | ▲ | 50 | HH Ribozyme |
| ✓ | misc_feature | L | 13850..20401 | ▲ | 6552 | L |
| ✓ | misc_feature | M | 8054..9061 | ▲ | 1008 | M |
| ✓ | insert | MV-GFP corrected | 2523..2759 | | 237 | |
| ✓ | insert | MV-GFP corrected | 824..2401 | ▲ | 1578 | |

FIG. 10

| | | | | | | | |
|---|---|---|---|---|---|---|---|
| ✓ | | misc_feature | MV33F | 19956..19975 | ► | 20 | MV33F |
| ✓ | | misc_feature | MV4F | 2158..2177 | ► | 20 | MV4F |
| ✓ | | misc_feature | MV5F | 2643..2661 | ► | 19 | MV5F |
| ✓ | | misc_feature | MV6F | 3147..3166 | ► | 20 | MV6F |
| ✓ | | misc_feature | MV7F | 3639..3658 | ► | 20 | MV7F |
| ✓ | | misc_feature | MV8F | 8030..8049 | ► | 20 | MV8F |
| ✓ | | misc_feature | MVPos3 Rev | complement (8093..8111) | ◄ | 19 | MVPos3 Rev |
| ✓ | | misc_feature | N | 824..2398 | ► | 1575 | N |
| ✓ | | misc_feature | P | 2523..4046 | ► | 1524 | P |
| ✓ | | insert | PCR 240-1 | 713..820 | ► | 108 | |
| ✓ | | insert | PCR 240-2 | 713..823 | ► | 111 | |
| ✓ | | insert | PCR 245-3 | 713..2401 | ► | 1689 | |
| ✓ | | insert | PCR 254 | 2523..2759 | ► | 237 | |
| ✓ | | insert | PCR238-1 | 20740..20743 | ► | 4 | |
| ✓ | | misc_feature | RP602 | complement (20699..20716) | ◄ | 18 | RP602 |
| ✓ | | misc_feature | Spike Protein | 4150..7968 | ► | 3819 | Spike Protein |
| ✓ | | misc_feature | T7 TERM | 20658..20733 | ► | 76 | T7 TERM |
| ✓ | | misc_feature | T7 promoter | 629..645 | ► | 17 | T7 promoter |
| ✓ | | misc_feature | UTR | 717..820 | ► | 104 | UTR |
| ✓ | | misc_feature | UTR | 20402..20510 | ► | 109 | UTR |
| ✓ | | insert | coWuhan-Virus Spike protein Gene | 4137..7982 | ► | 3846 | |
| ✓ | | misc_feature | hHdVRzym | 20511..20596 | ► | 86 | hHdVRzym |
| ✓ | | insert | pCW640D1 | 2402..2522 | ► | 121 | |
| ✓ | | insert | pCW656 | 11859..14230 | ► | 2372 | |

FIG. 10 - continued

| | | | | | |
|---|---|---|---|---|---|
| misc_feature | Ampicillin | | complement(21925..22785) | | 861 | Ampicillin |
| misc_feature | F | | 8165..7826 | | 1662 | F |
| PCR_primer | GCAGAGACGCGTCTCACTTGGTTCCTAAGTTTTTATAACAATG | | complement(9900..9943) | ▼ | 44 | RP1418M:MV IGR PCR |
| PCR_primer | GCTATAACGCGTATCACTTGGTTCCTAAGTTTTTATAACAATG | | complement(9900..9943) | ▲ | 44 | RP1474:MV full length |
| misc_feature | GE | | 758..768 | ▼ | 11 | GE |
| misc_feature | GE | | 2450..2460 | ▲ | 11 | GE |
| misc_feature | GE | | 4108..4118 | ▲ | 11 | GE |
| misc_feature | GE | | 5577..5587 | ▲ | 11 | GE |
| misc_feature | GE | | 7963..7968 | ▲ | 6 | GE |
| misc_feature | GE | | 20460..20470 | ▲ | 11 | GE |
| misc_feature | GS | | 5591..5607 | ▲ | 17 | GS |
| misc_feature | GS | | 4122..4138 | ▲ | 17 | GS |
| misc_feature | GS | | 20474..20490 | ▲ | 17 | GS |
| misc_feature | GS | | 2464..2480 | ▲ | 17 | GS |
| misc_feature | GS | | 772..788 | ▲ | 17 | GS |
| misc_feature | H | | 7937..9837 | ▲ | 1851 | H |
| insert | H-MCS-L | | 8813..9943,12788..13791 | | 135 | |
| misc_feature | HH Ribozyme | | 667..716 | | 50 | HH Ribozyme |
| misc_feature | L | | 13860..20401 | | 6552 | L |
| misc_feature | M | | 4154..5161 | | 1008 | M |
| insert | MV Wu S in position 3 | | 8944..13787 | | 3844 | |
| insert | MV-GFP corrected | | 2523..2759 | | 237 | |
| insert | MV-GFP corrected | | 824..2401 | | 1578 | |

FIG. 11

| | | | | | |
|---|---|---|---|---|---|
| > | misc_feature | MV93F | 19956..19975 | ▲ | 20 | MV93F |
| > | misc_feature | MV4F | 2158..2177 | ▲ | 20 | MV4F |
| > | misc_feature | MV5F | 2643..2661 | ▲ | 19 | MV5F |
| > | misc_feature | N | 824..2398 | ▲ | 1575 | N |
| > | misc_feature | P | 2523..4046 | ▲ | 1524 | P |
| > | insert | PCR 240-1 | 713..820 | ▲ | 108 | |
| > | insert | PCR 240-2 | 713..823 | ▲ | 111 | |
| > | insert | PCR 245-3 | 713..2401 | ▲ | 1689 | |
| > | insert | PCR 254 | 2523..2759 | ▲ | 237 | |
| > | insert | PCR238-1 | 20740..20743 | ▲ | 4 | |
| > | misc_feature | RP602 | complement(20699..20716) | ▼ | 18 | RP602 |
| > | misc_feature | T7 TERM | 20658..20733 | ▲ | 76 | T7 TERM |
| > | misc_feature | T7 promoter | 629..645 | ▲ | 17 | T7 promoter |
| > | PCR_primer | TATCACTCTGTGTGGACCTGGTTCCTAAGTTTTTATAACAATG | complement(9900..9943) | ▼ | 44 | RP1433:MV PCR |
| > | misc_feature | UTR | 717..820 | ▲ | 104 | UTR |
| > | misc_feature | UTR | 20402..20510 | ▲ | 109 | UTR |
| > | misc_feature | co Spike Protein Gene | 9957..13775 | ▲ | 3819 | co Spike Protein Gene |
| > | insert | coWuhan-Virus Spike protein Gene | 9944..13787 | ▲ | 3844 | |
| > | misc_feature | hHdVRzym | 20511..20596 | ▲ | 86 | hHdVRzym |
| > | insert | pCW840D1 | 2402..2522 | ▲ | 121 | |
| > | insert | pCW661 | 7959..9943, 13738..13791 | ▲ | 1989 | |

FIG. 11 - continued

BBV151 Vaccine Presentations

BBV151 Vaccine Presentations

Antigen+SEPIVAC SWE (pre-mixed)

FIG. 16B

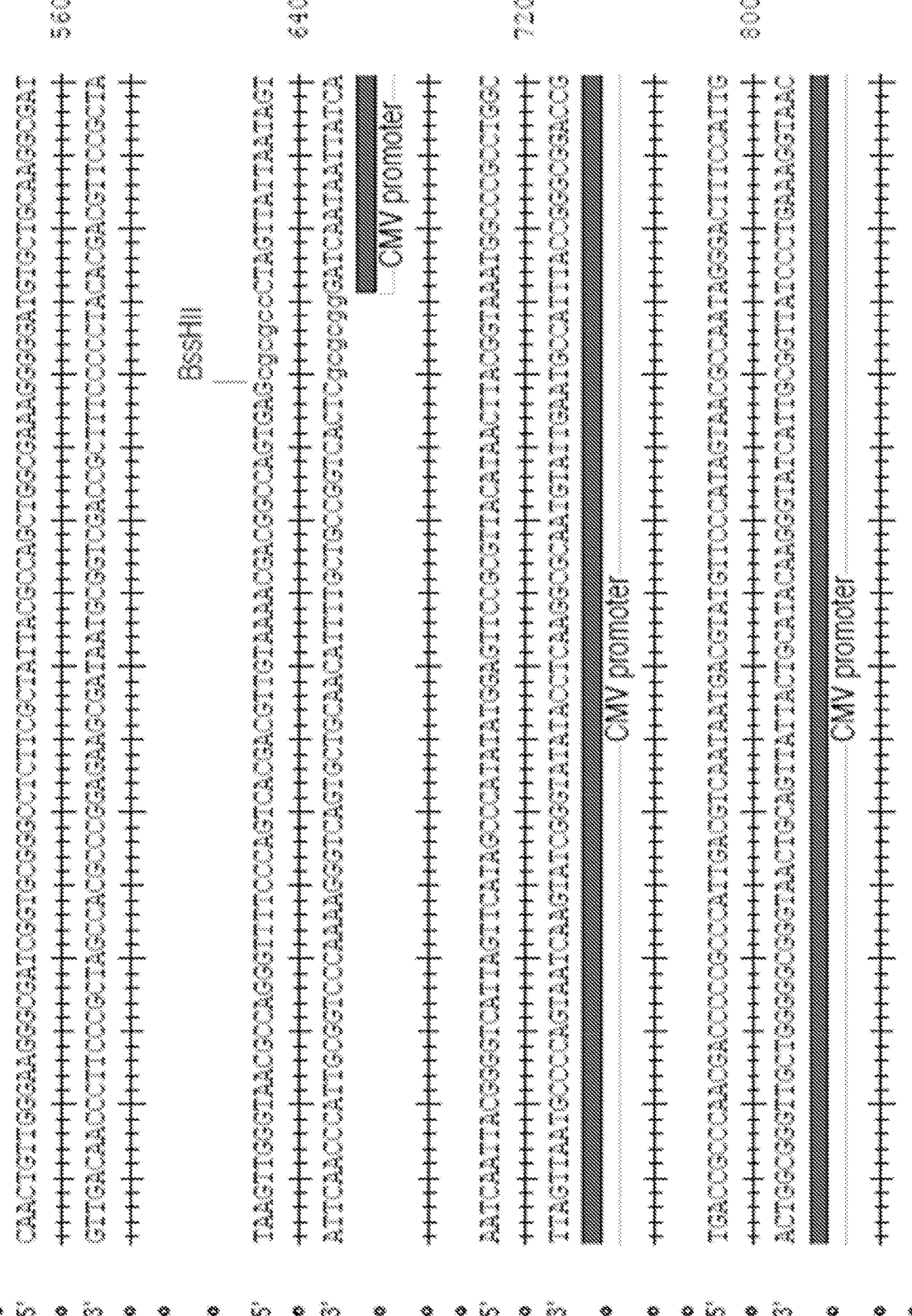
FIG. 17 – continued

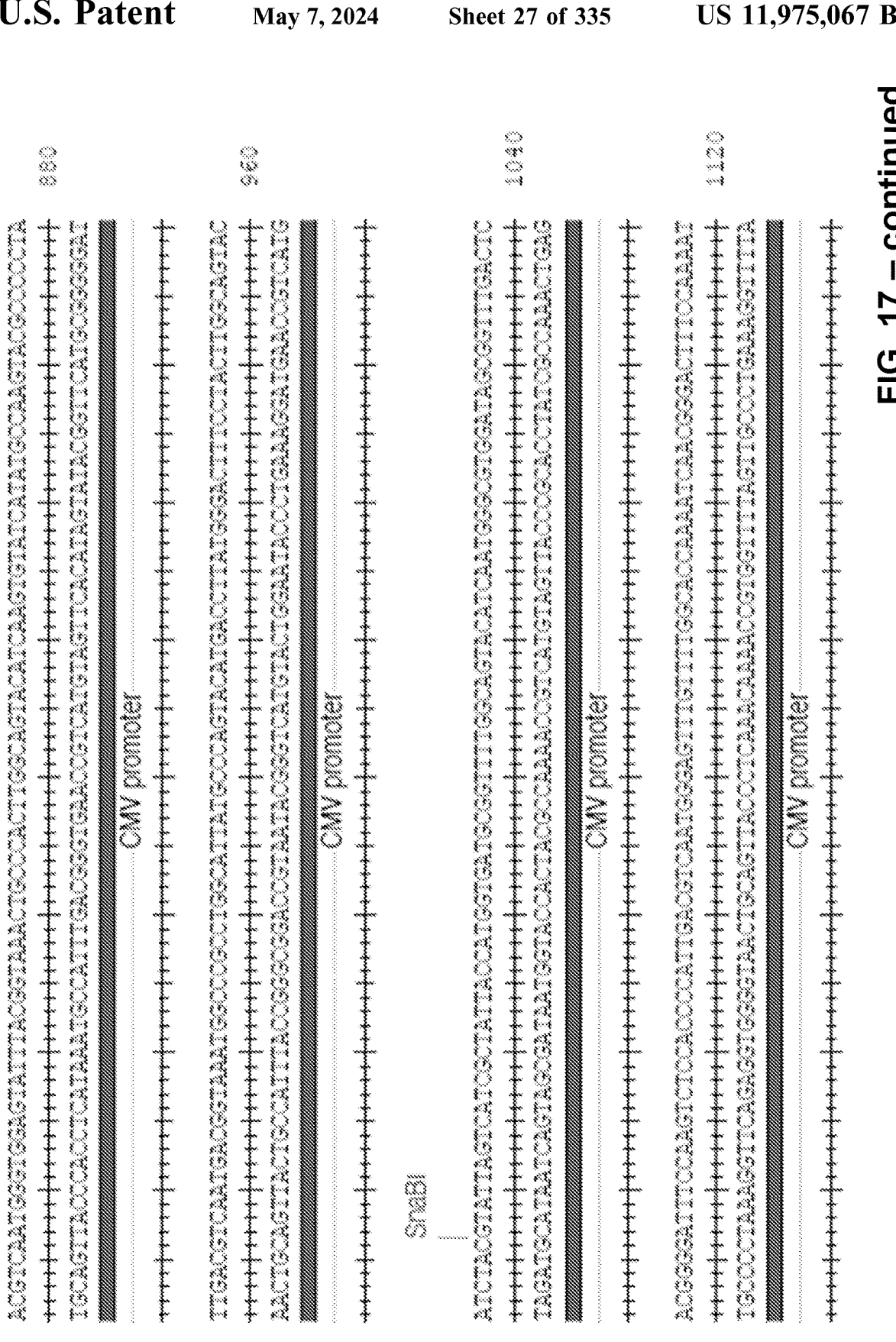
FIG. 17 – continued

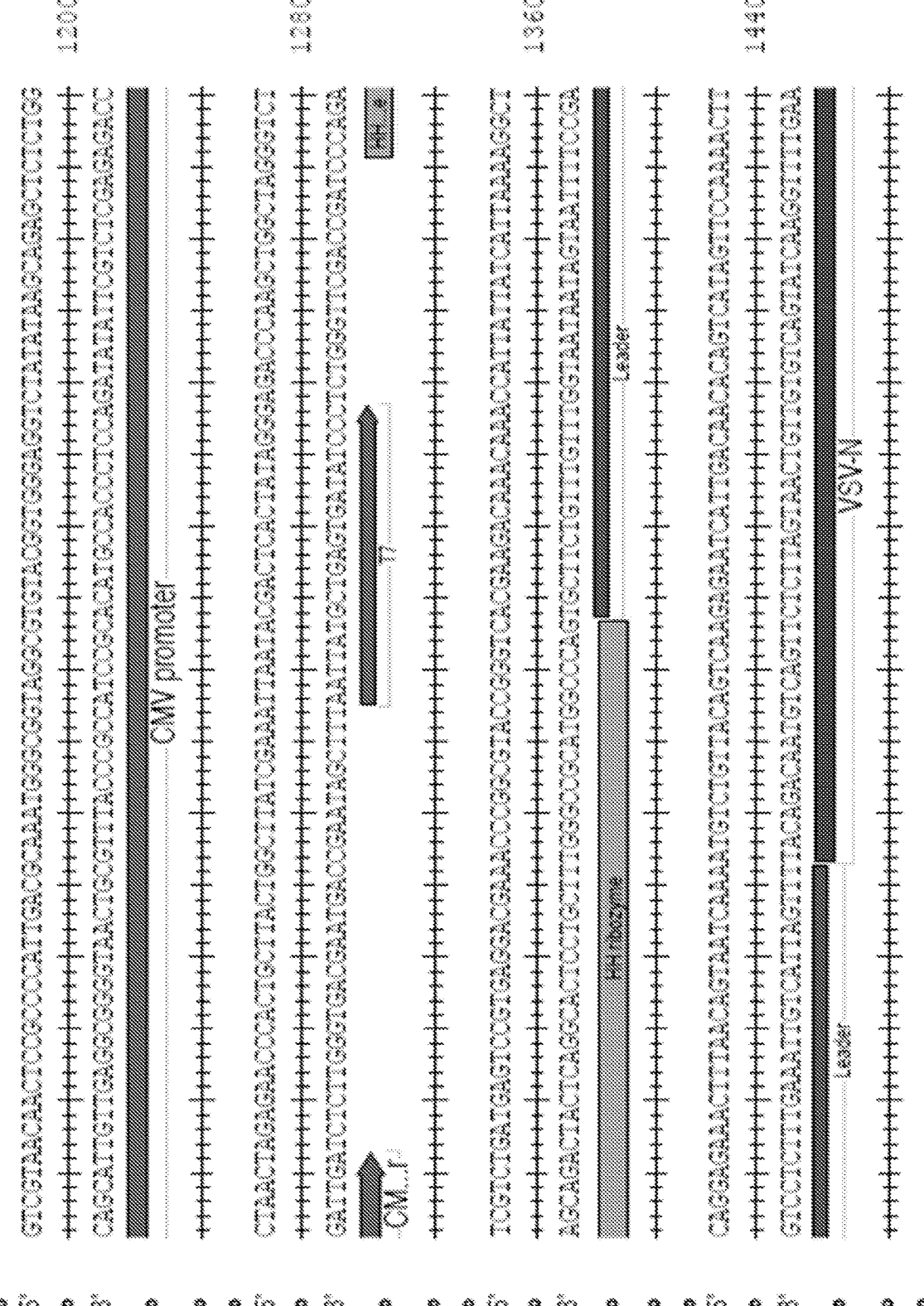
FIG. 17 – continued

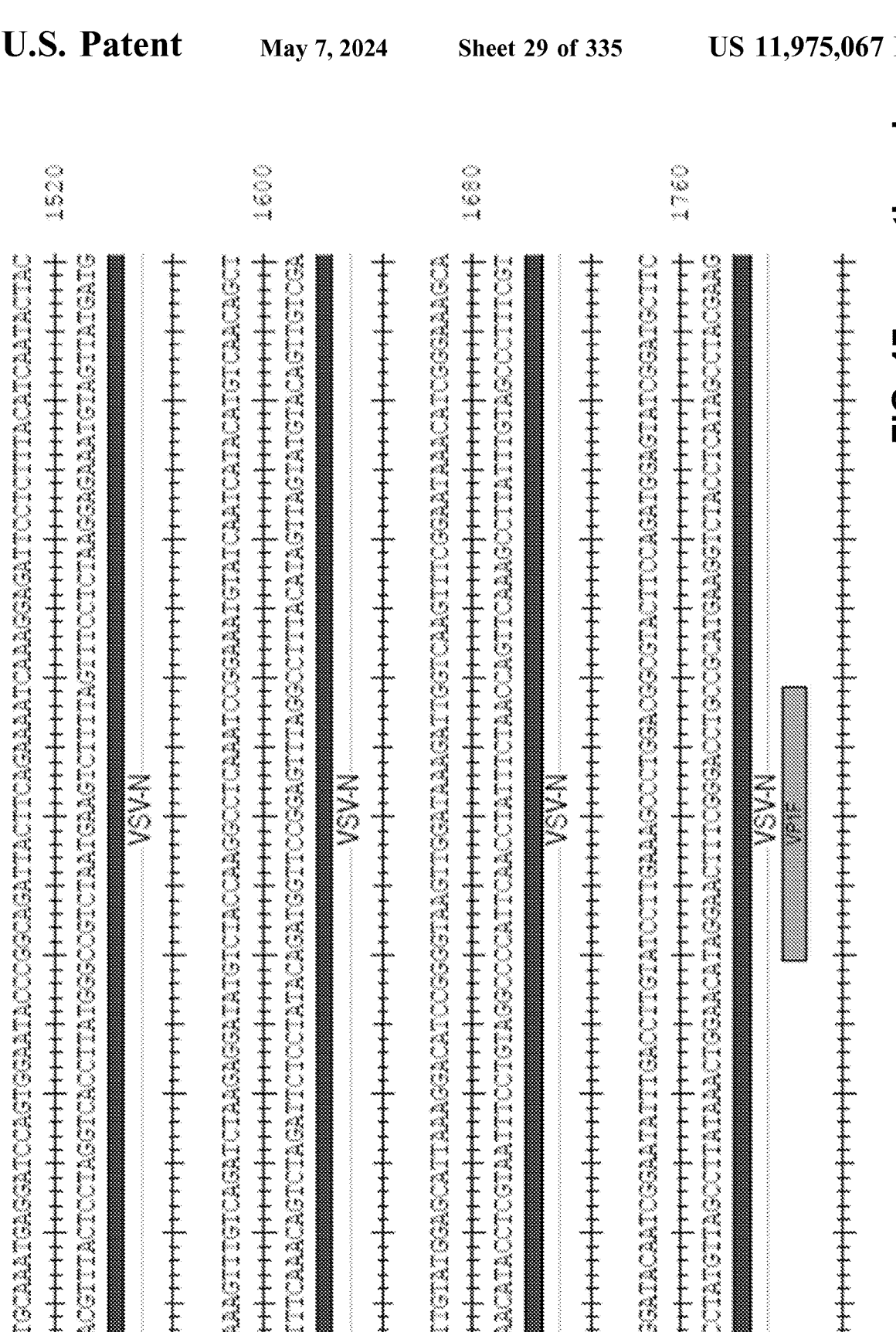
FIG. 17 – continued

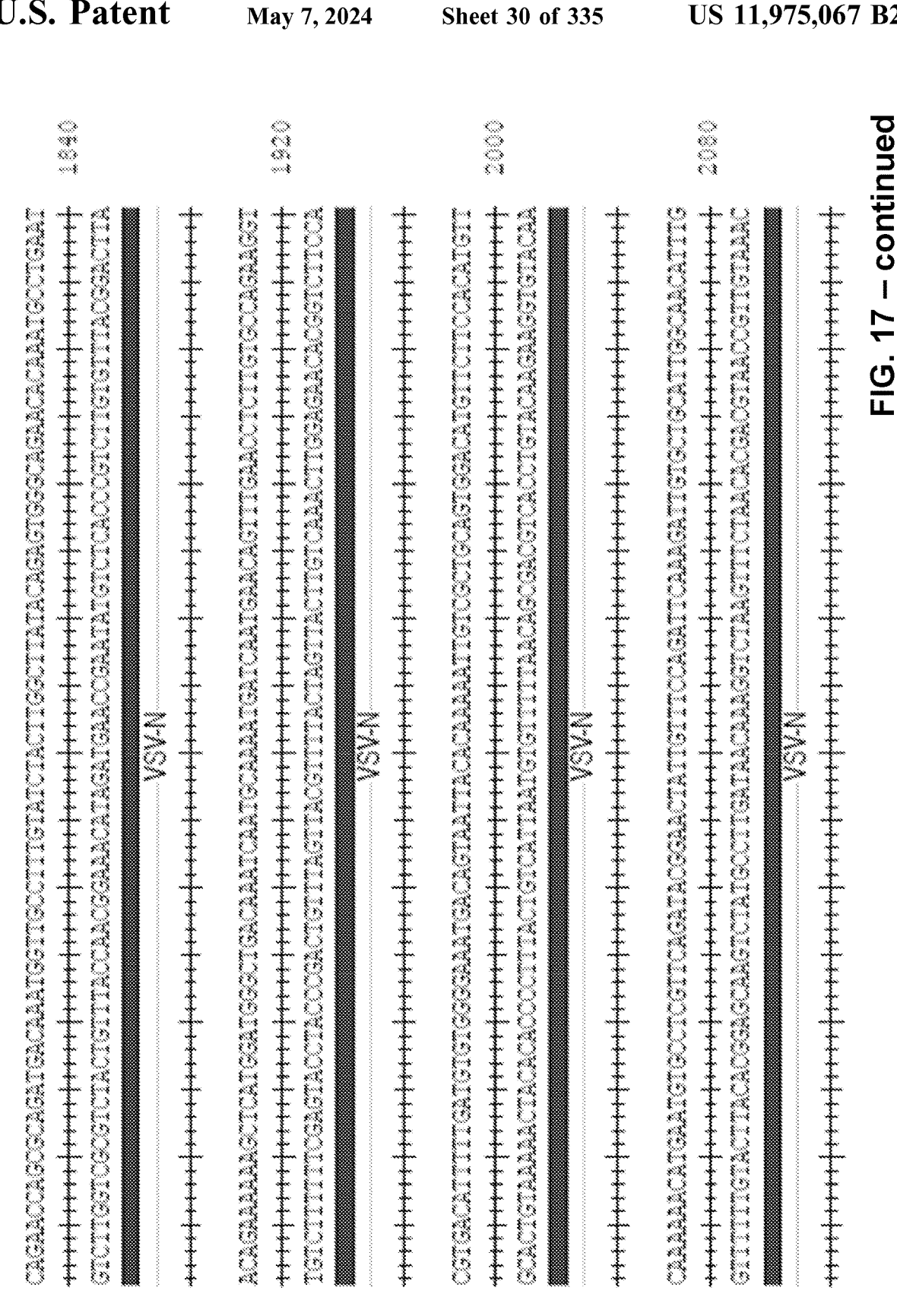
FIG. 17 – continued

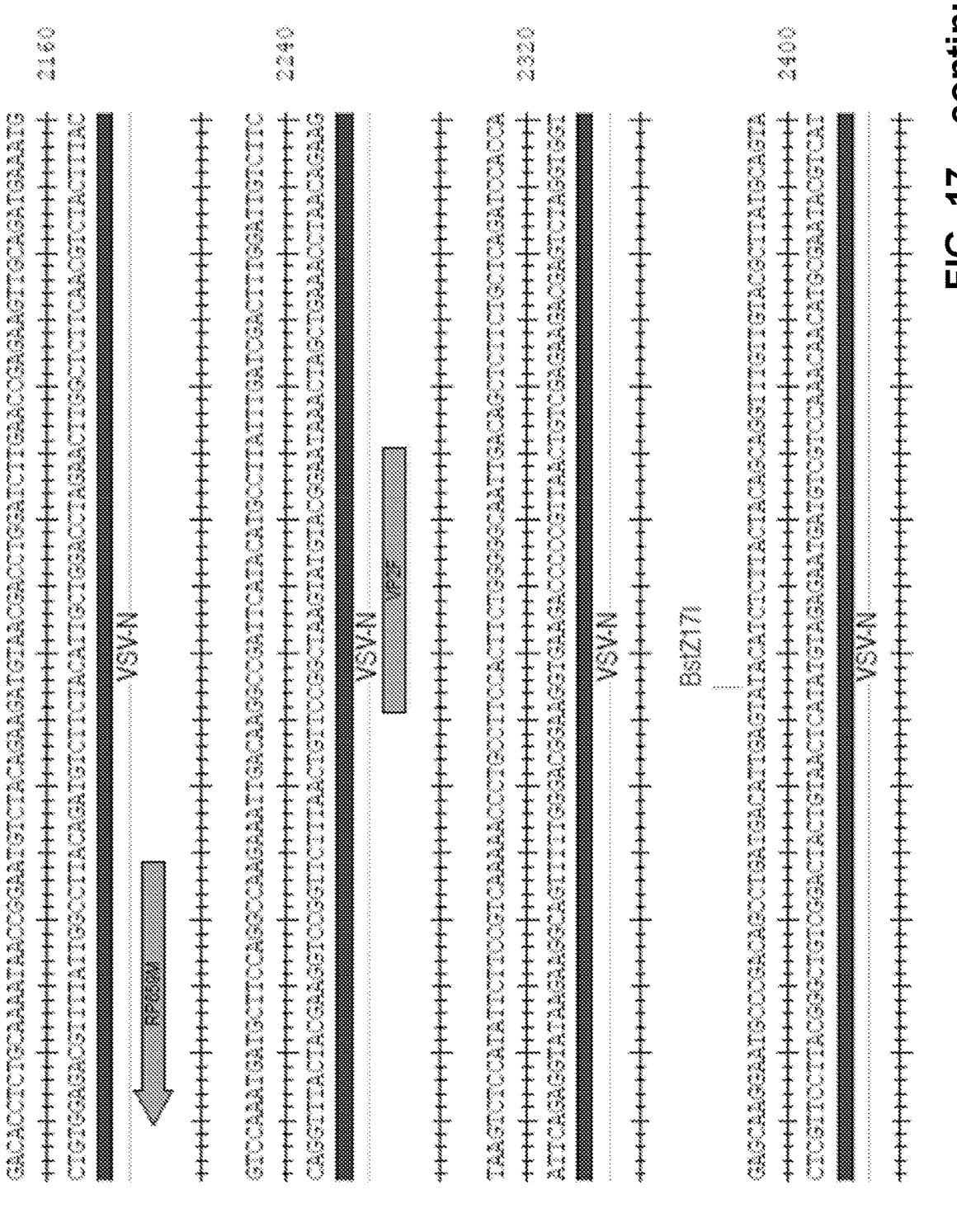
FIG. 17 – continued

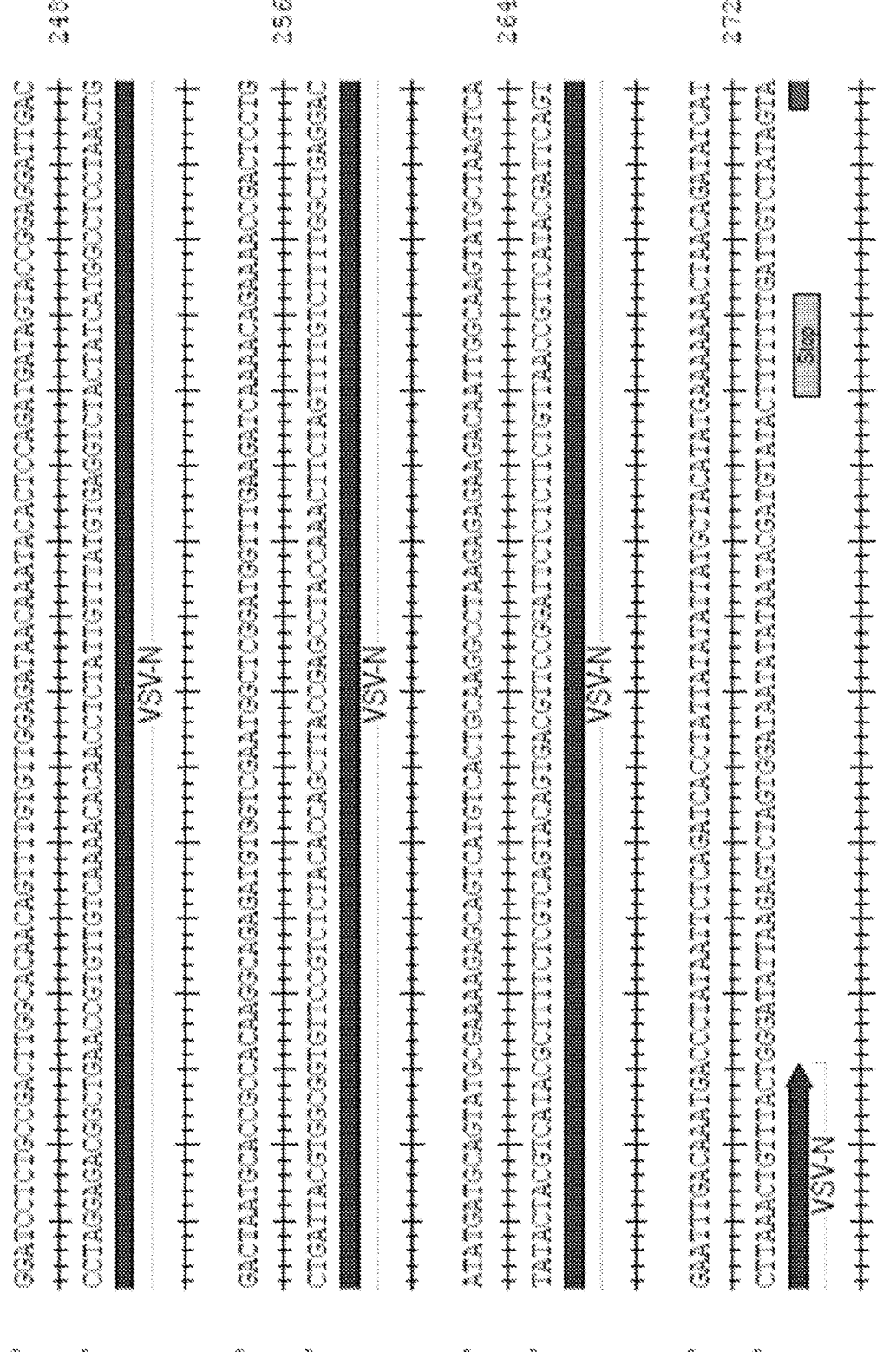
FIG. 17 – continued

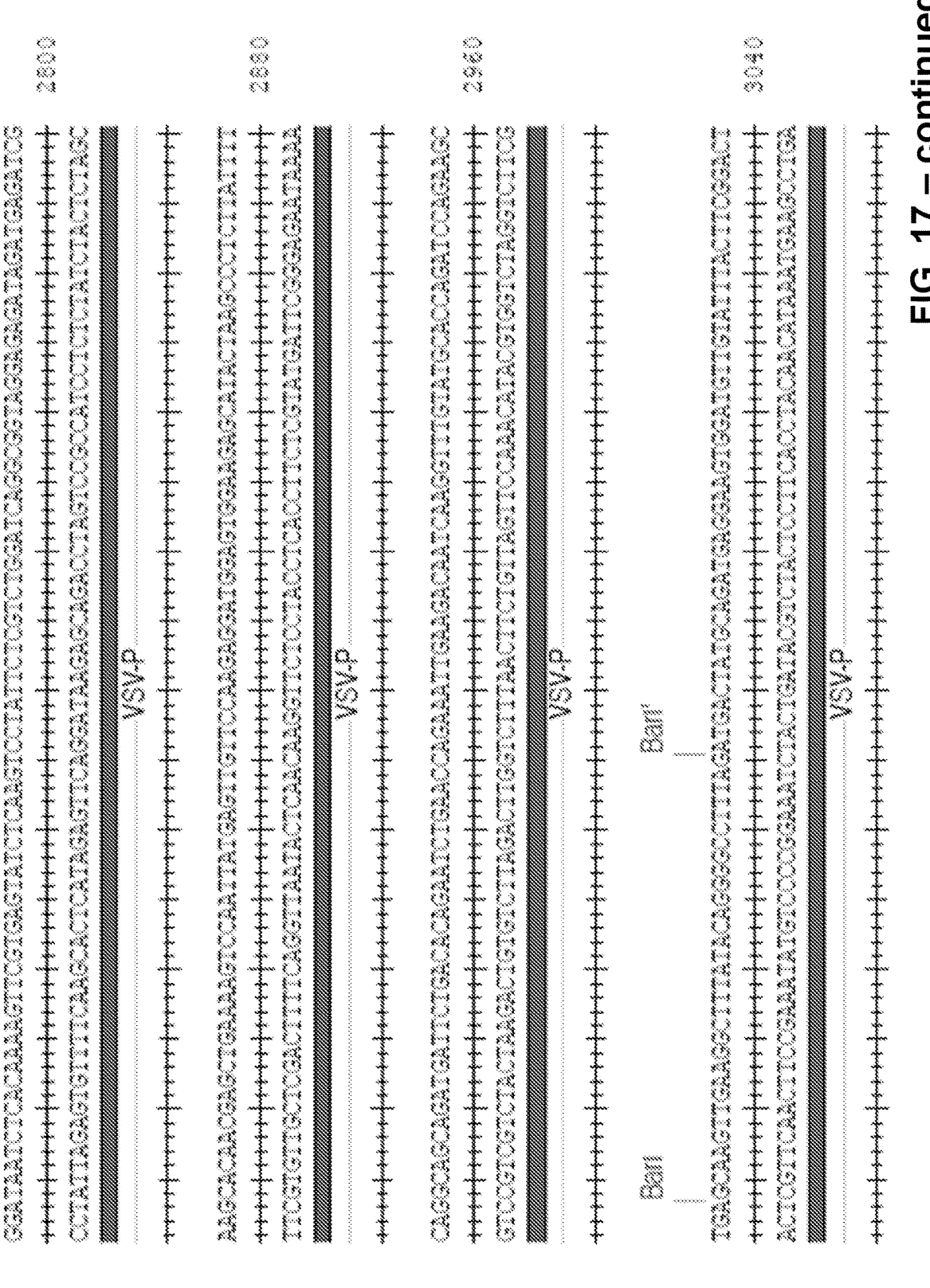
FIG. 17 – continued

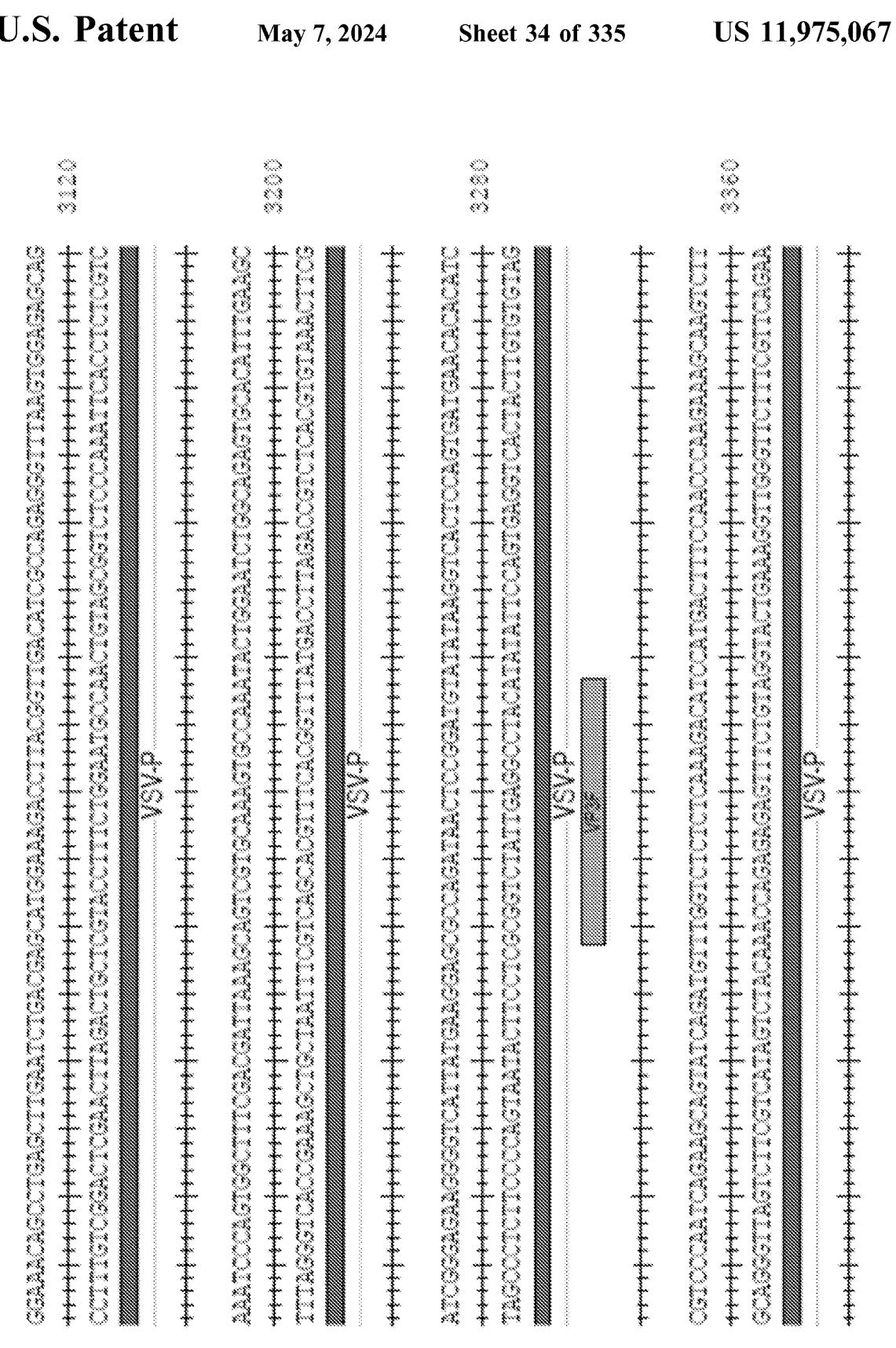
FIG. 17 – continued

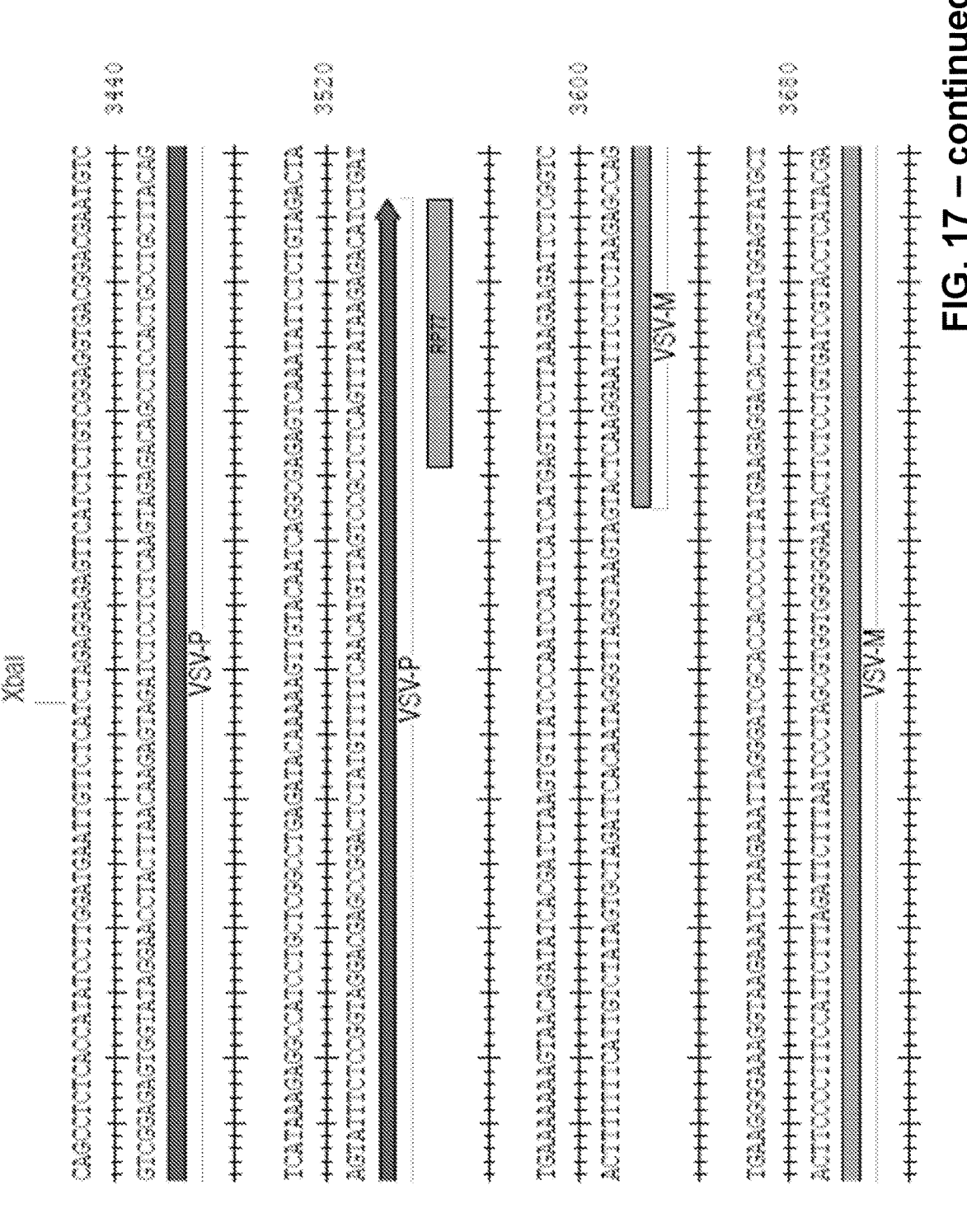
FIG. 17 – continued

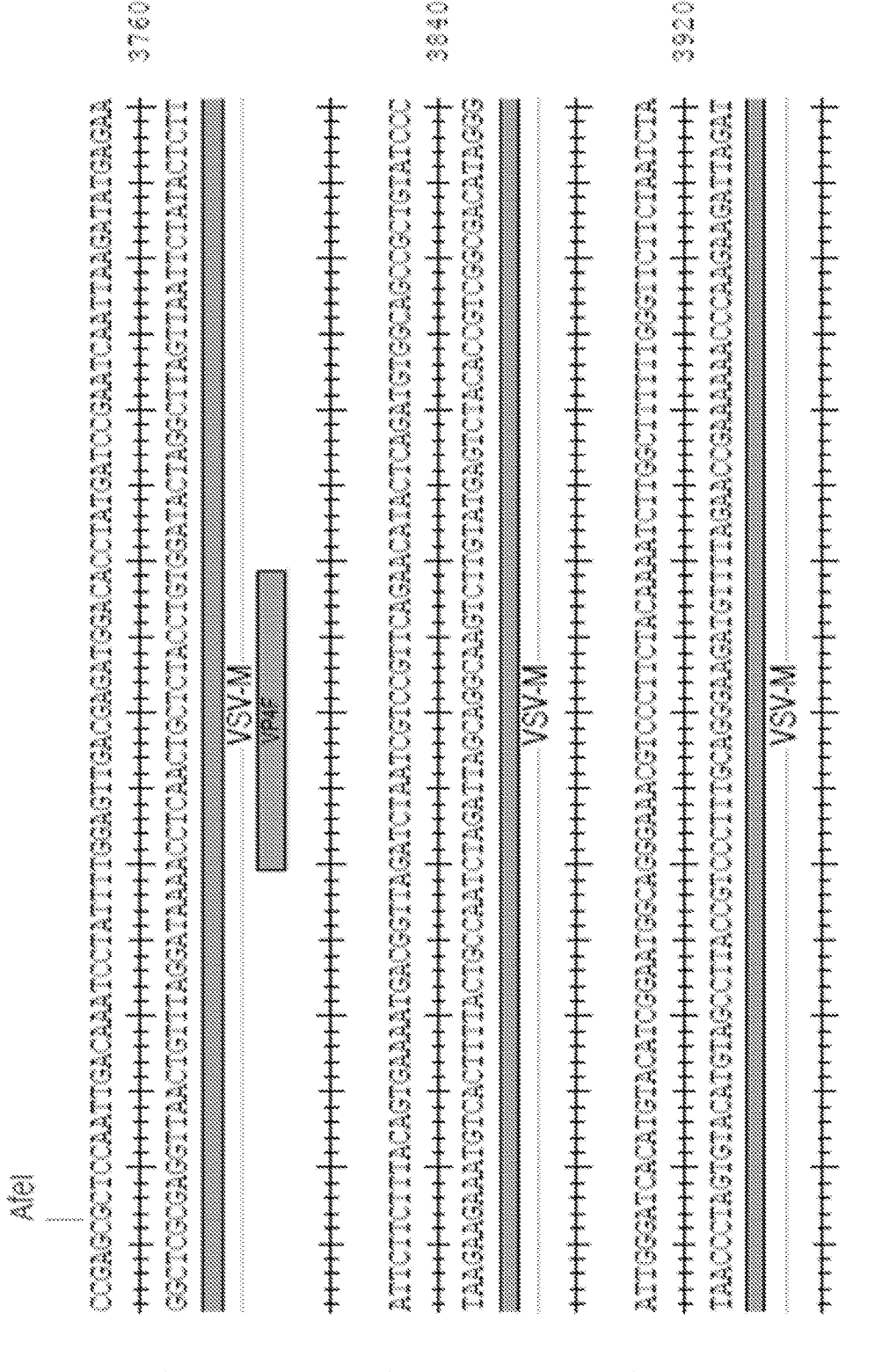
FIG. 17 – continued

FIG. 17 – continued

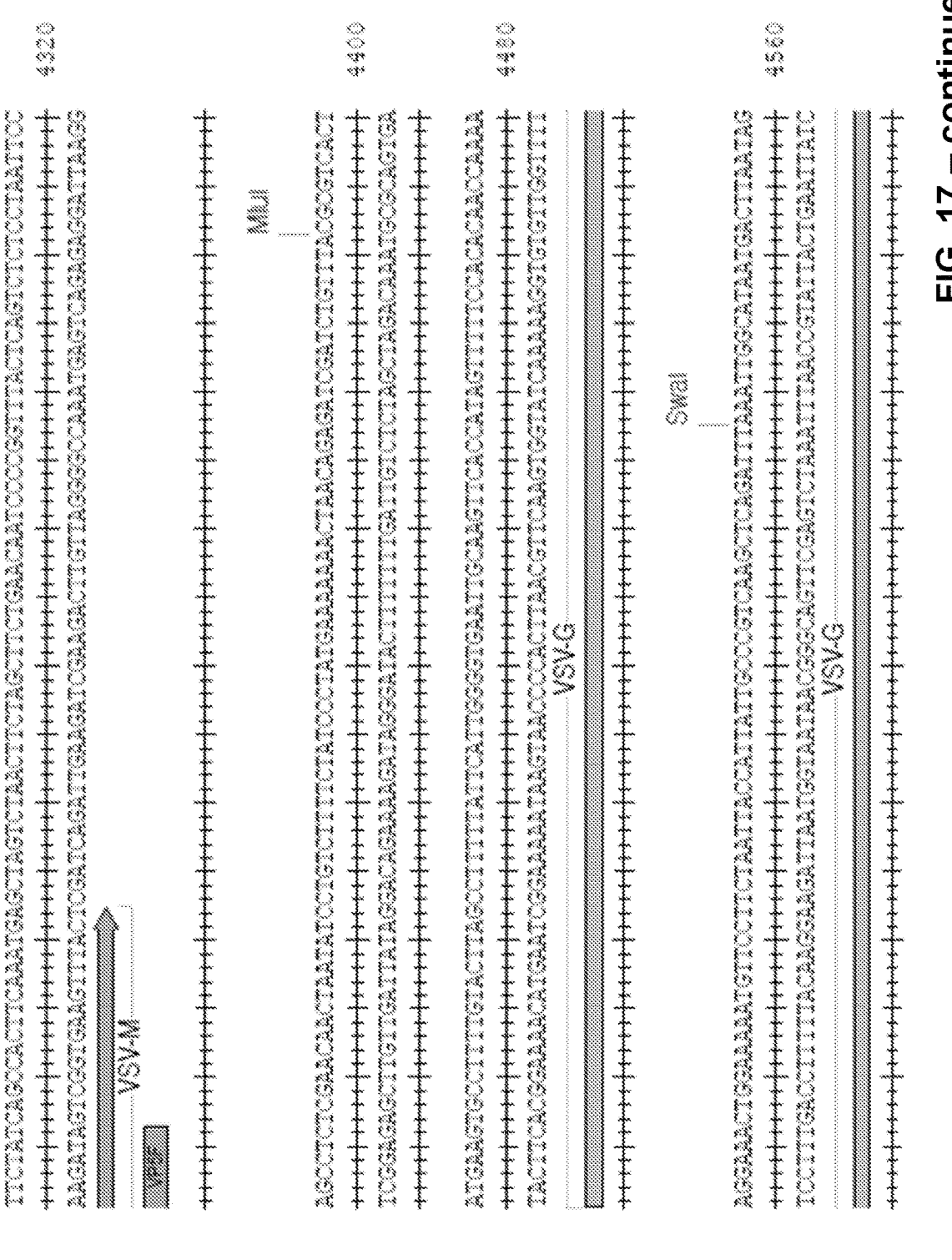
FIG. 17 – continued

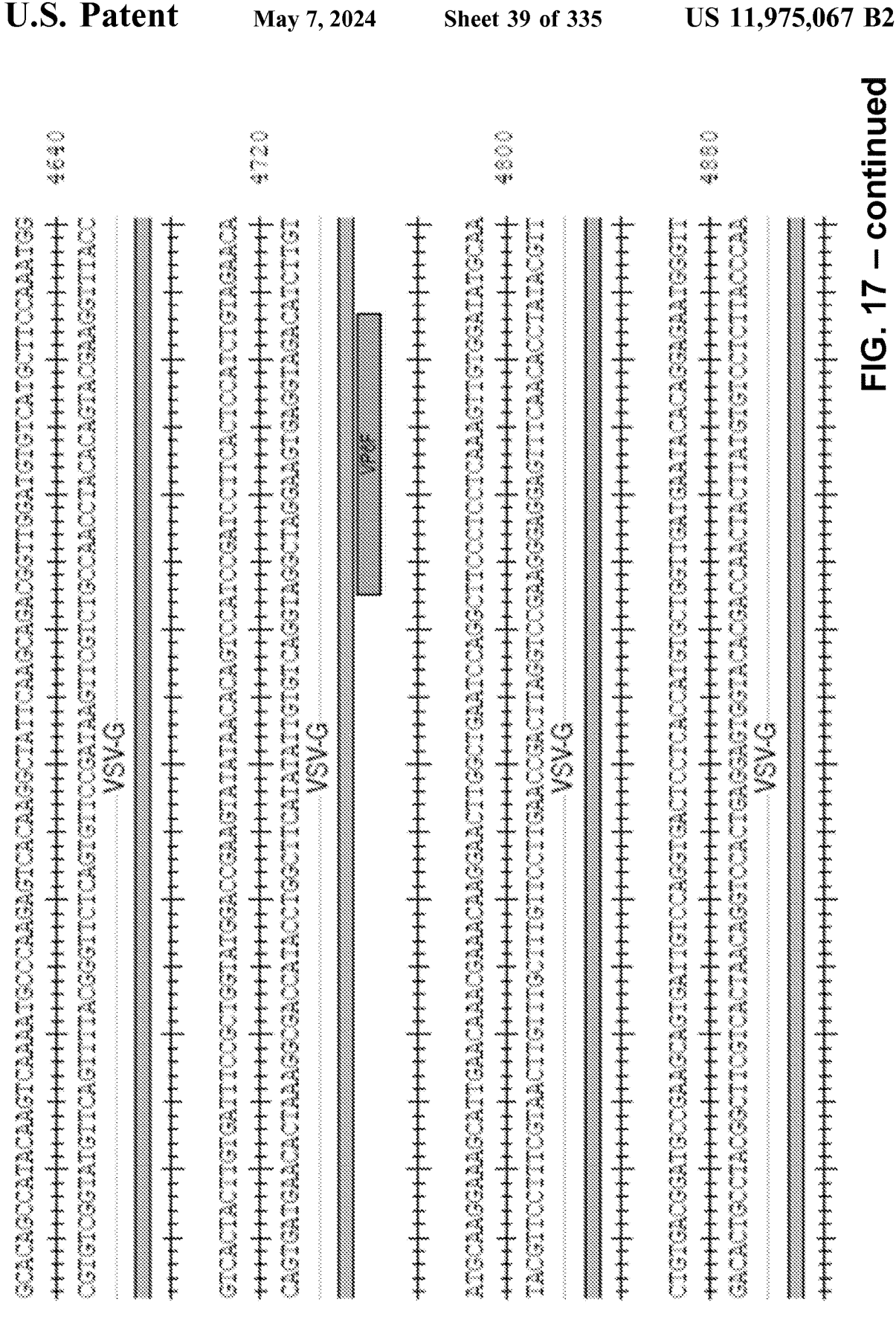
FIG. 17 – continued

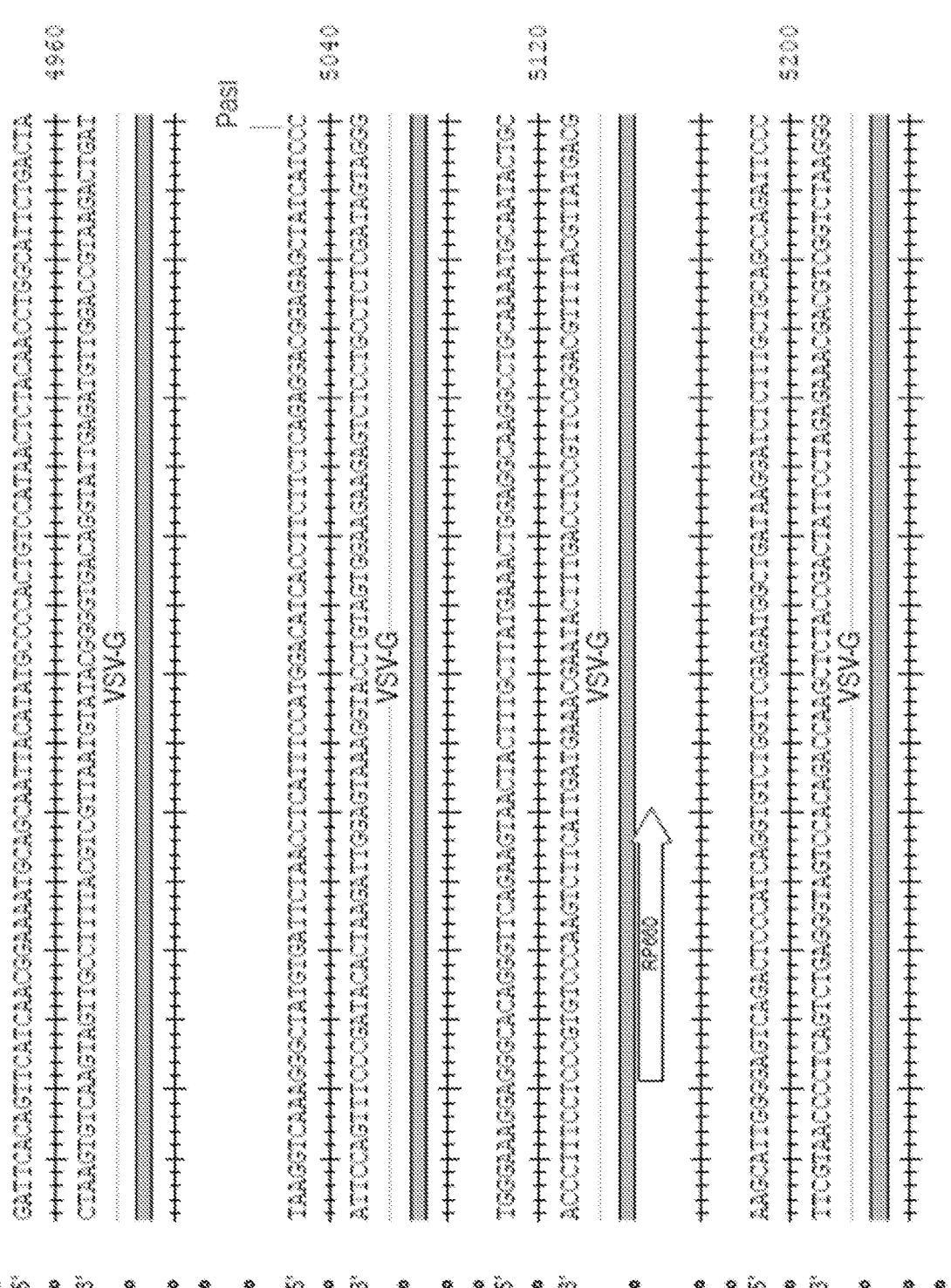
FIG. 17 – continued

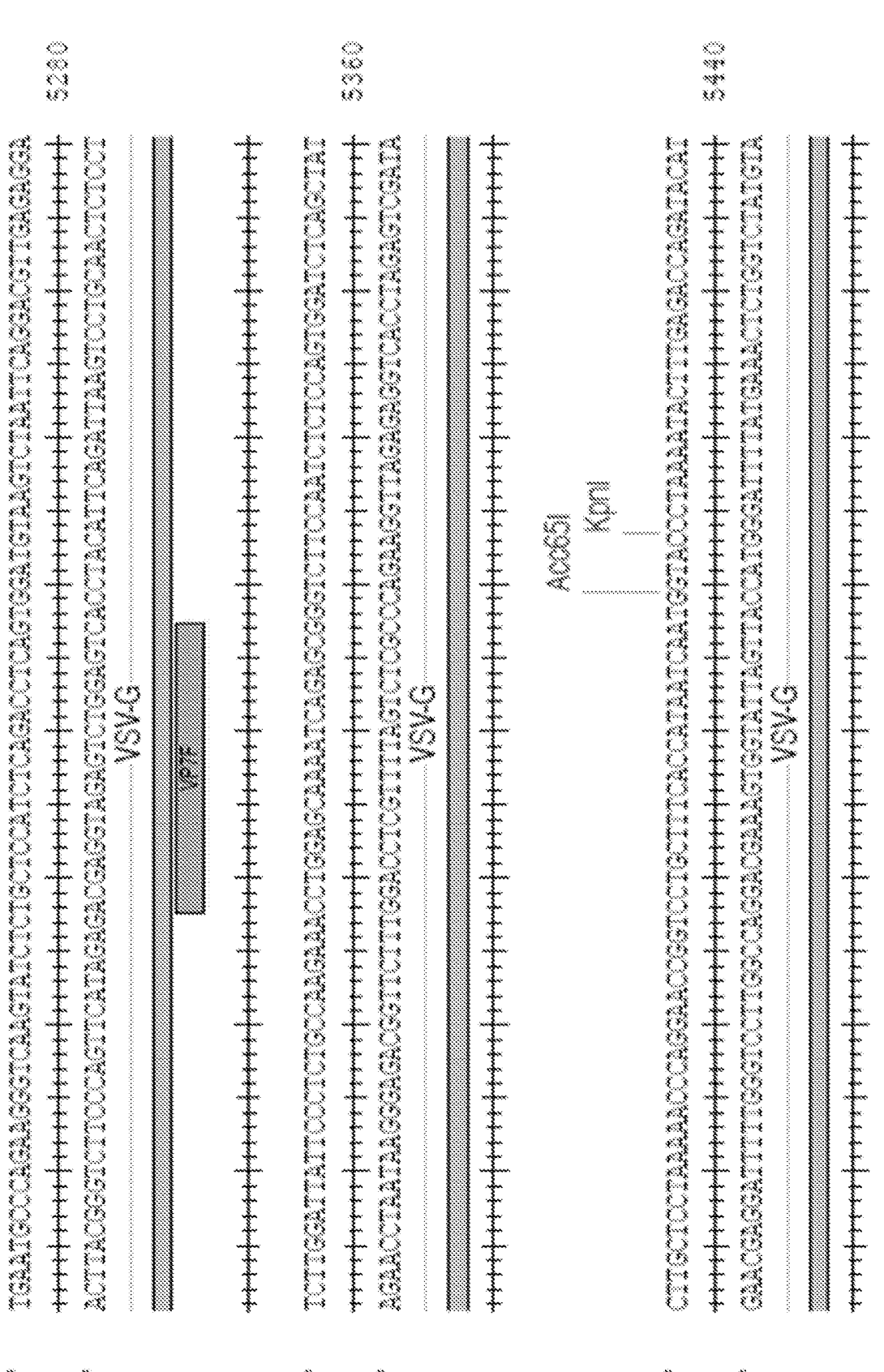
FIG. 17 – continued

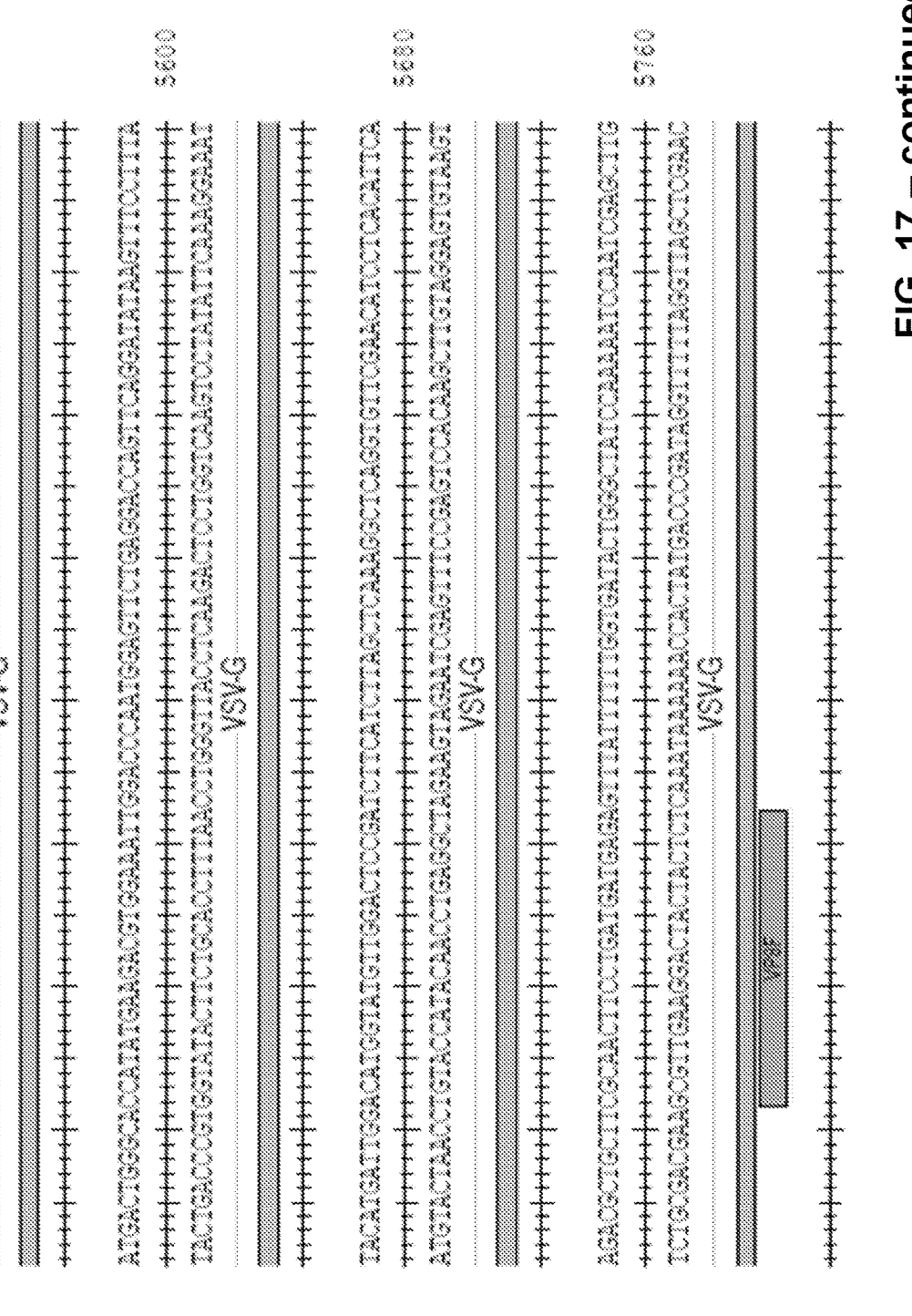
FIG. 17 – continued

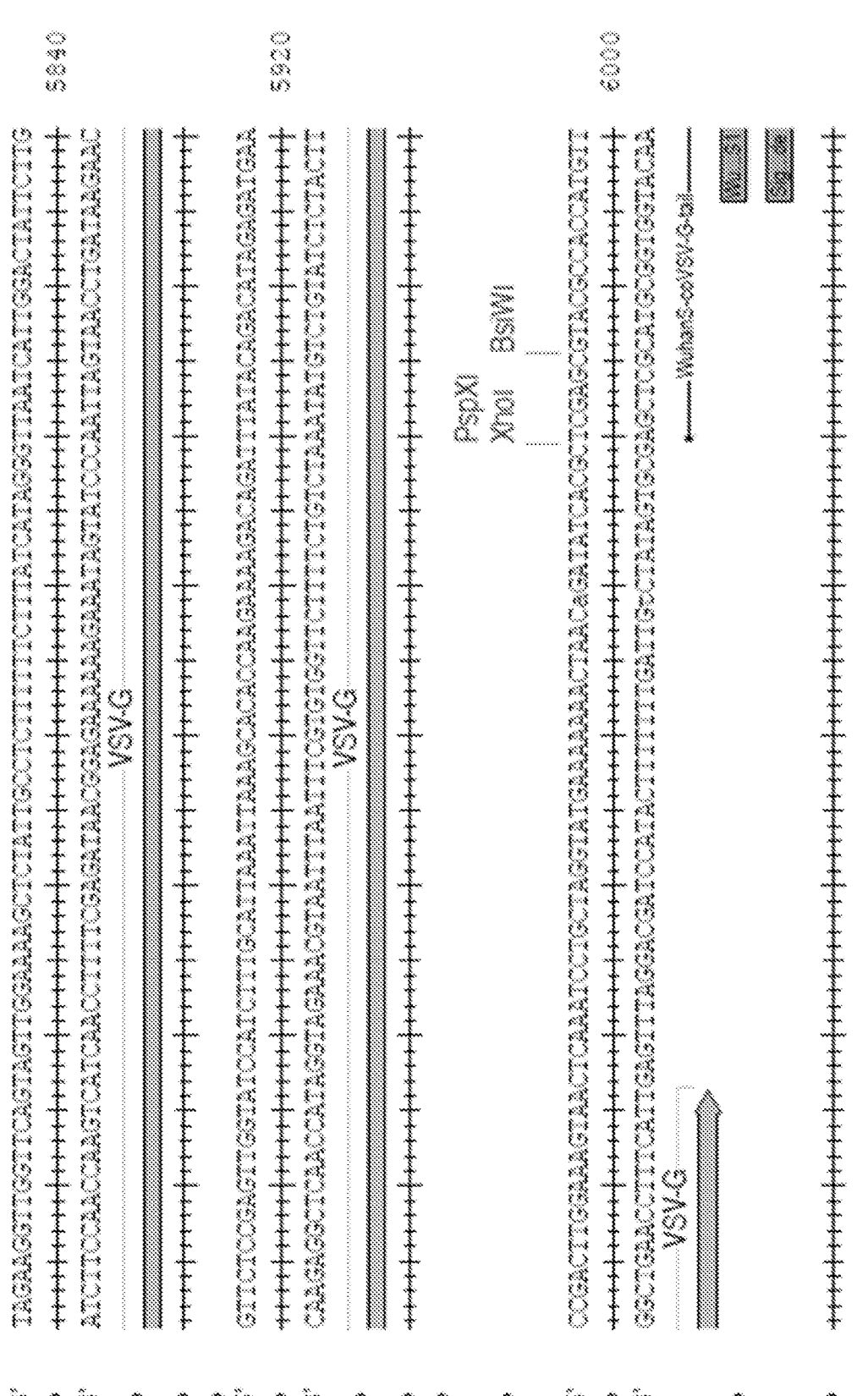
FIG. 17 – continued

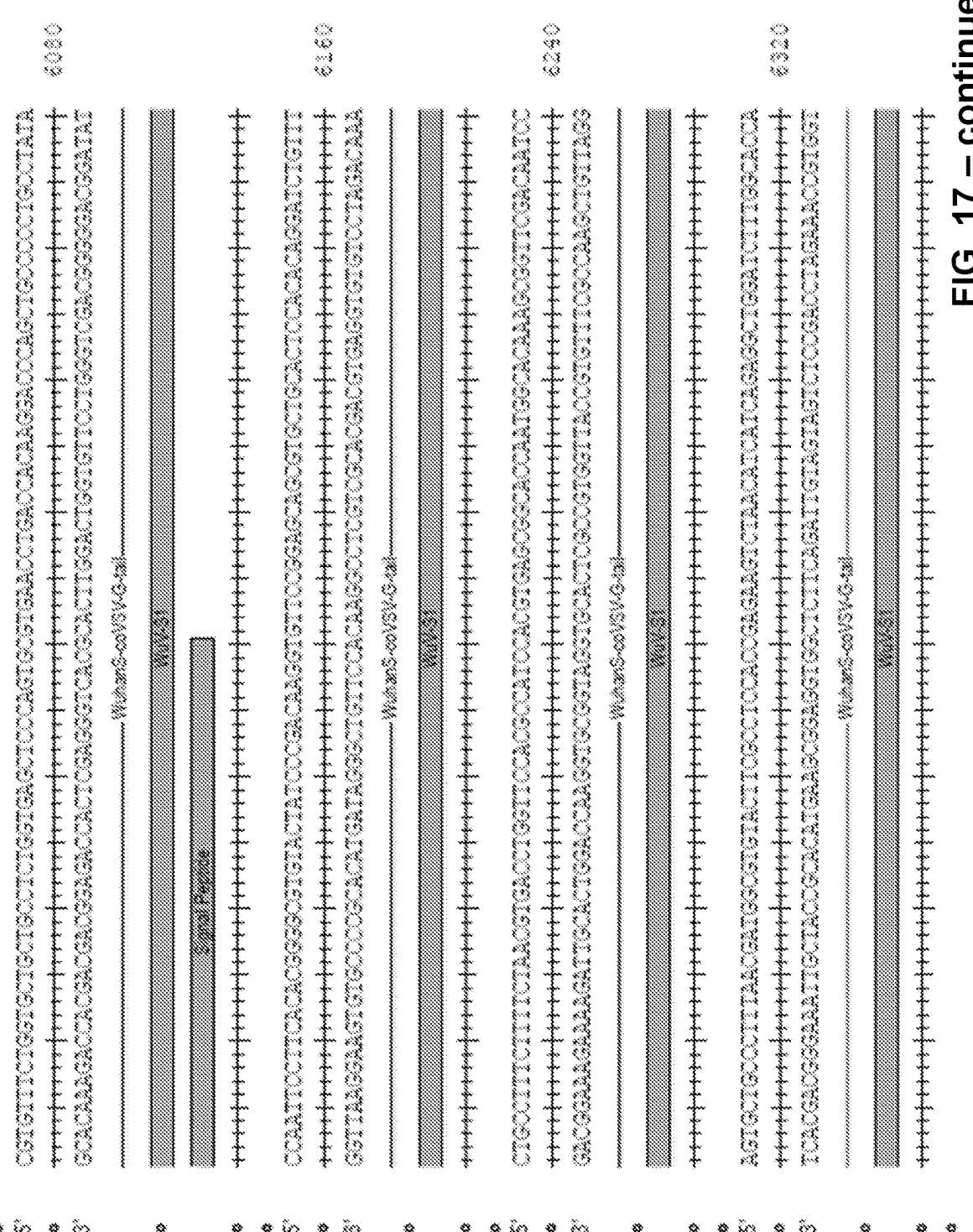
FIG. 17 – continued

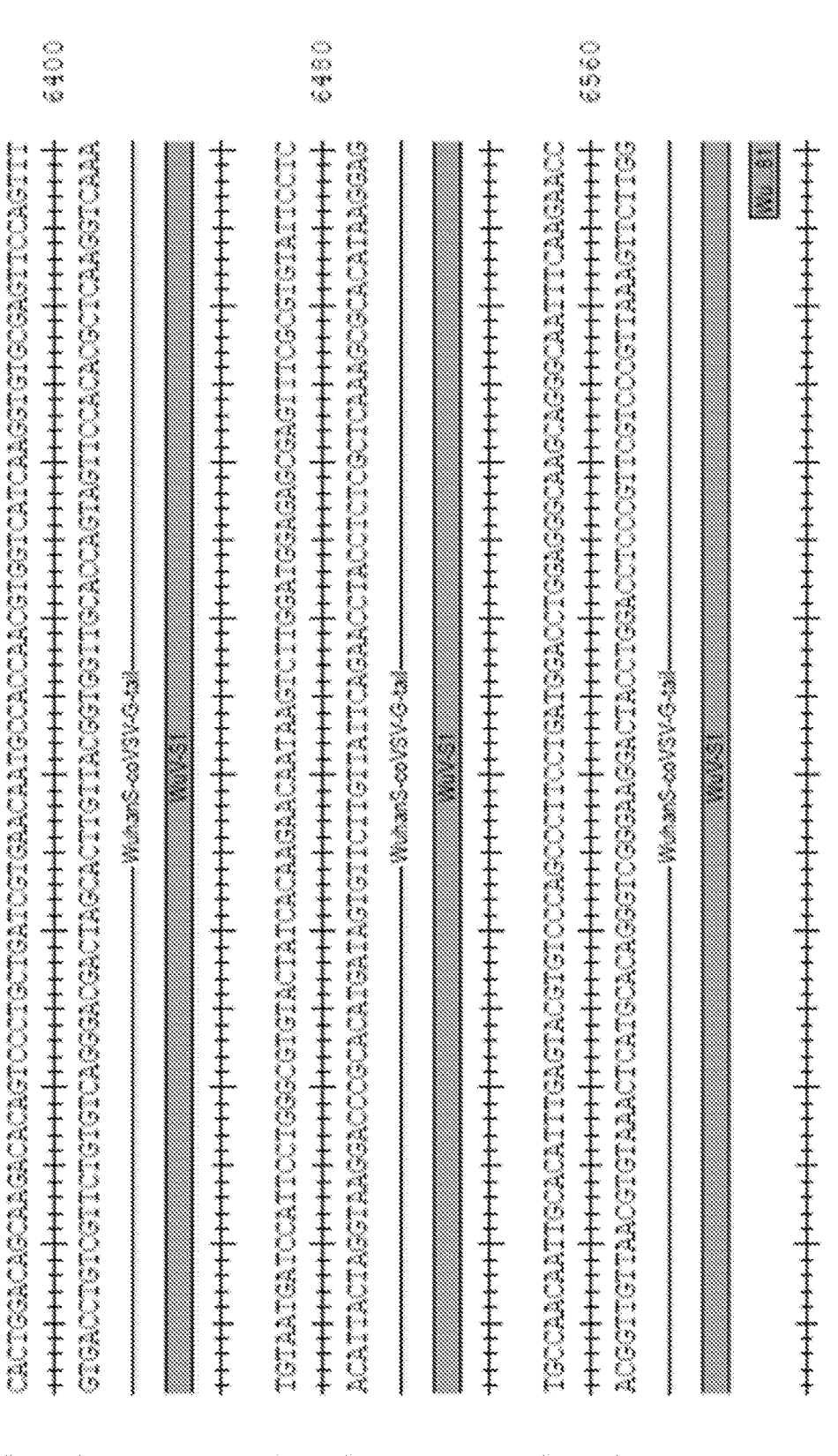
FIG. 17 – continued

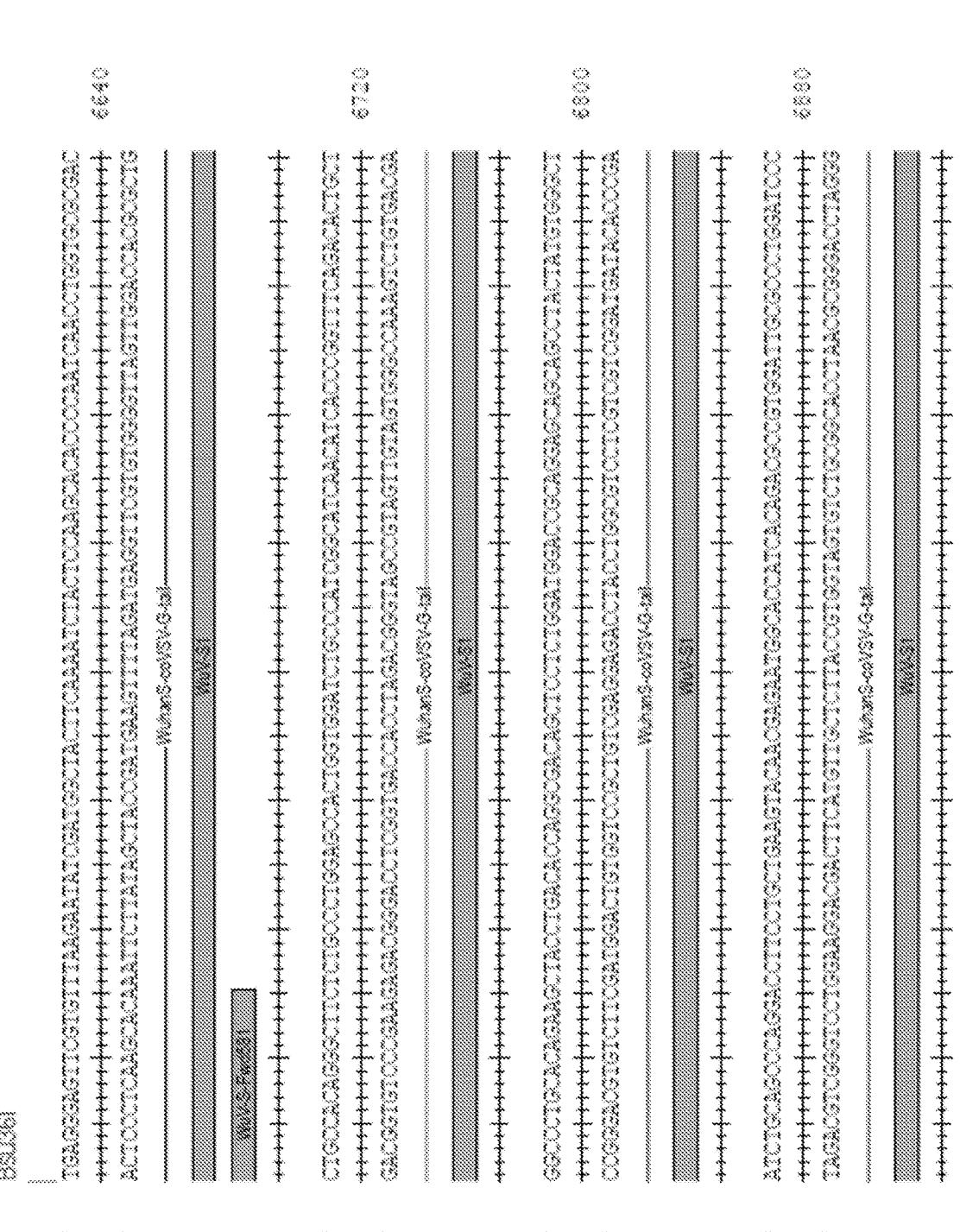
FIG. 17 – continued

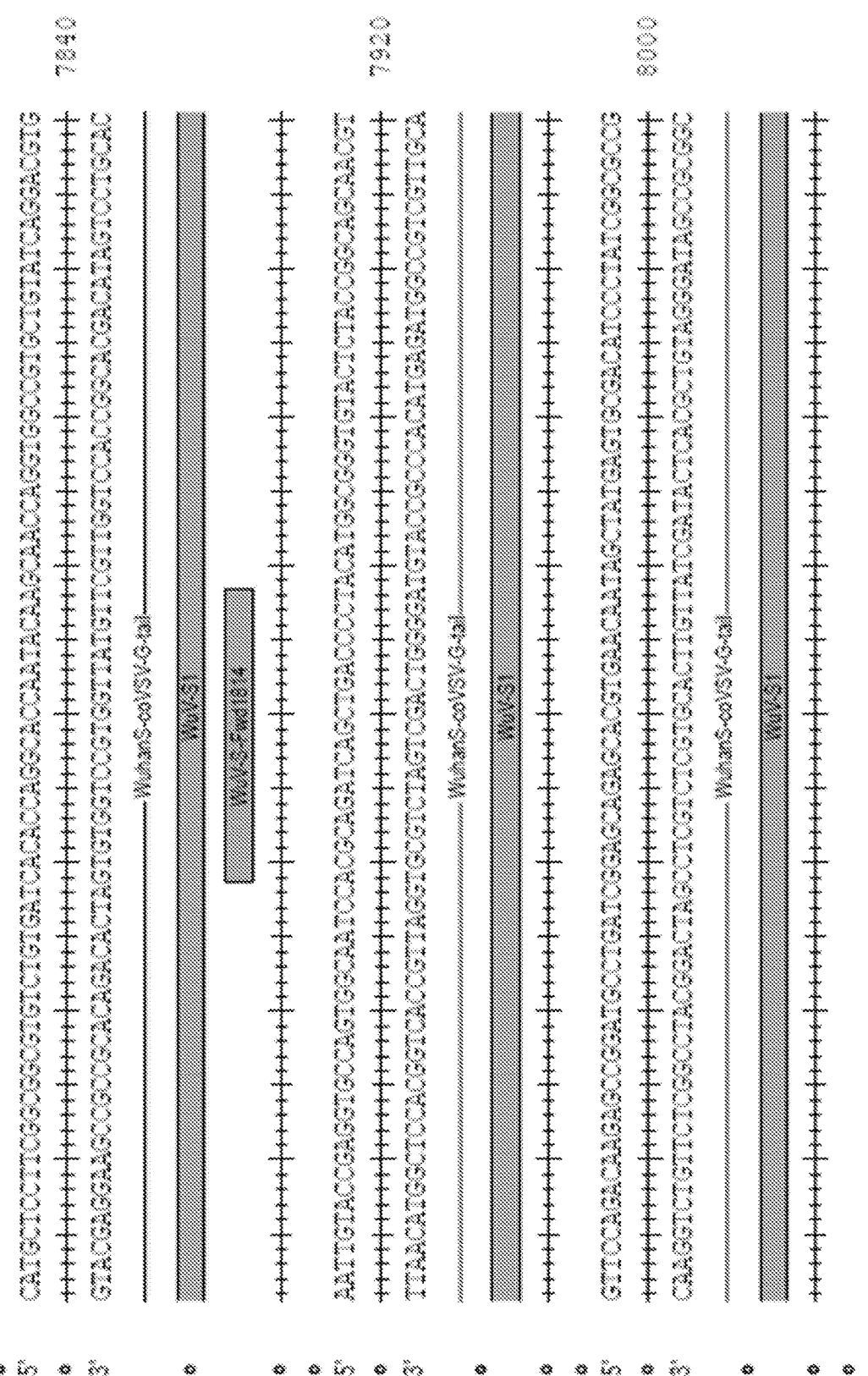
FIG. 17 – continued

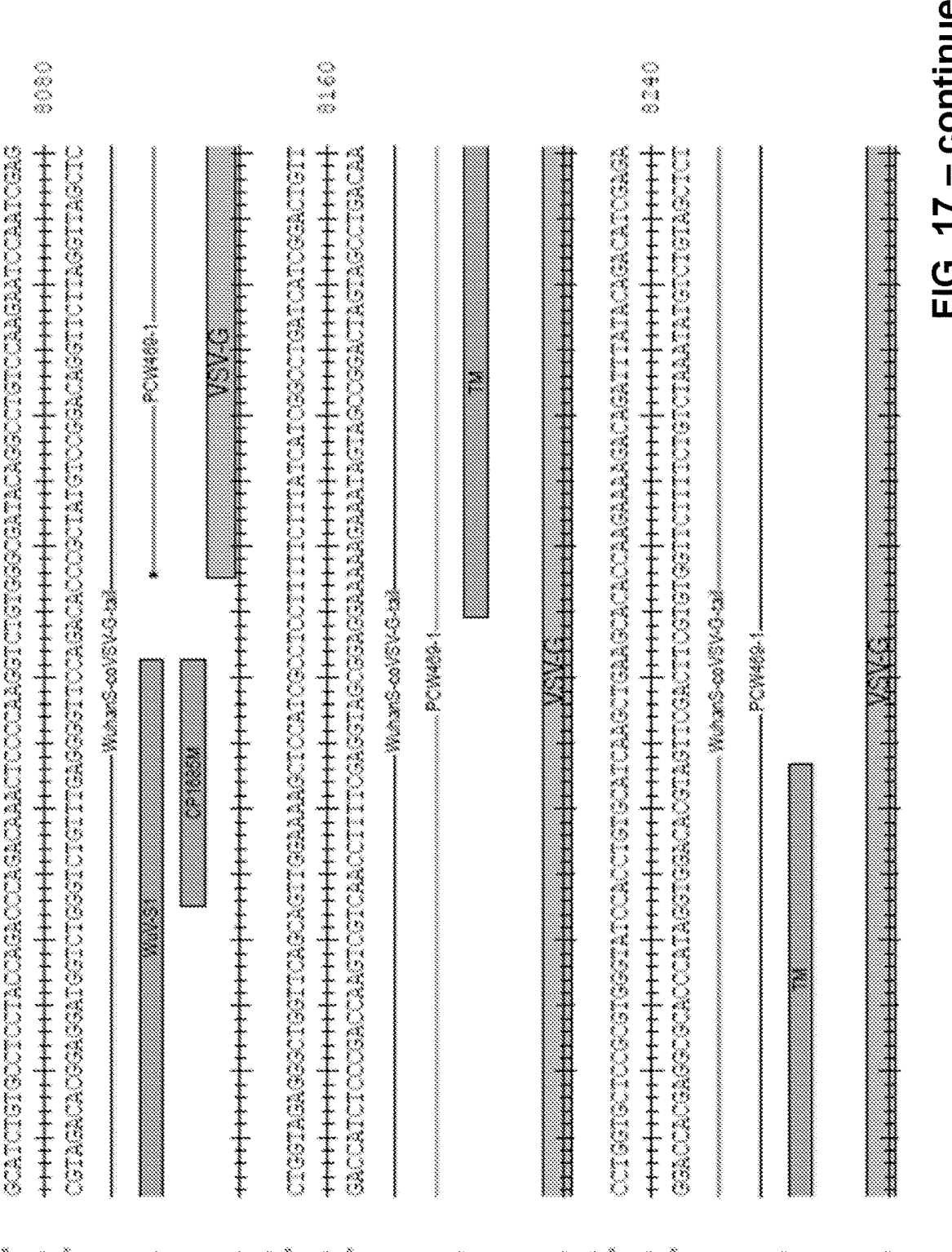
FIG. 17 – continued

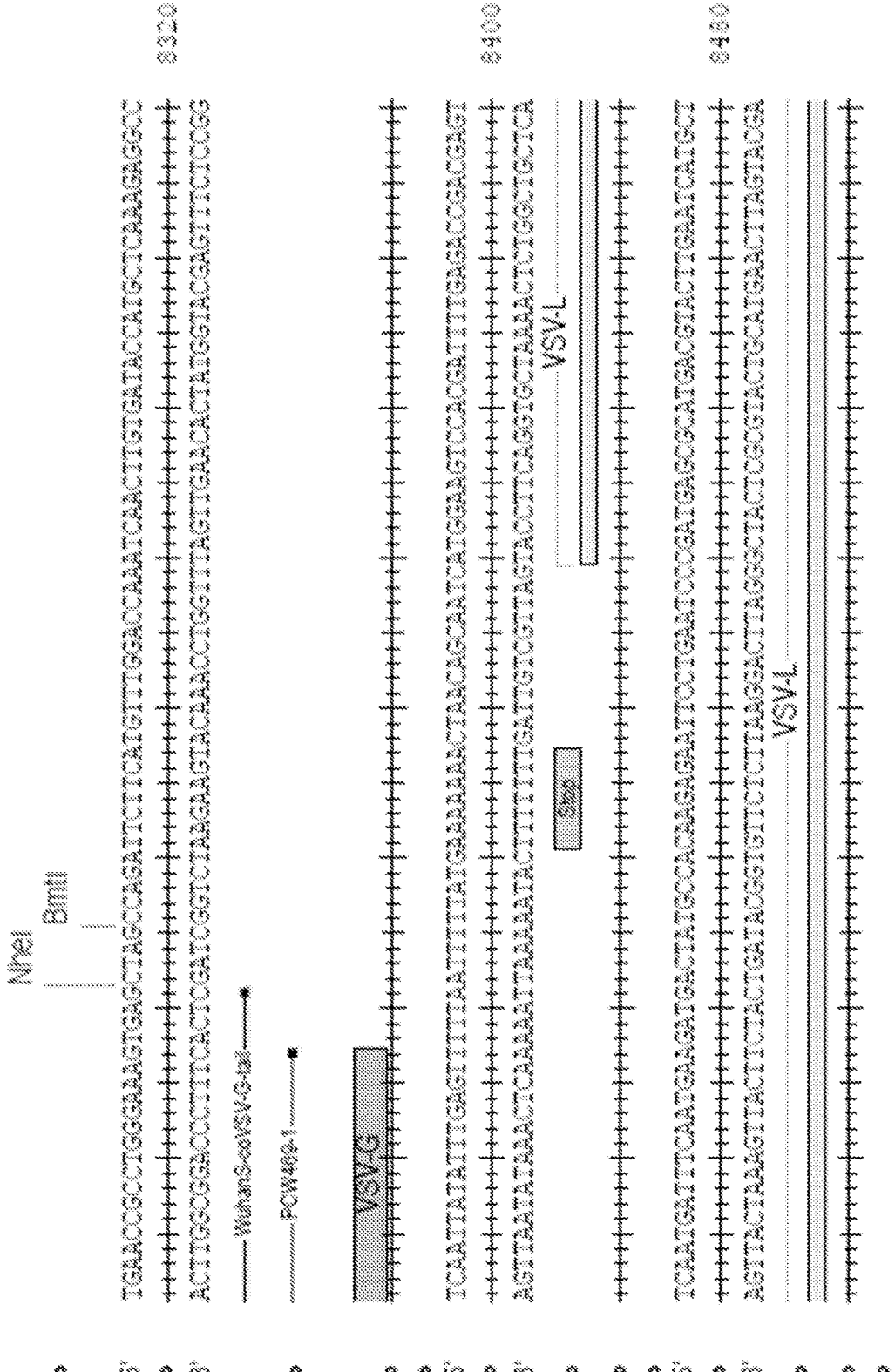
FIG. 17 – continued

FIG. 17 – continued

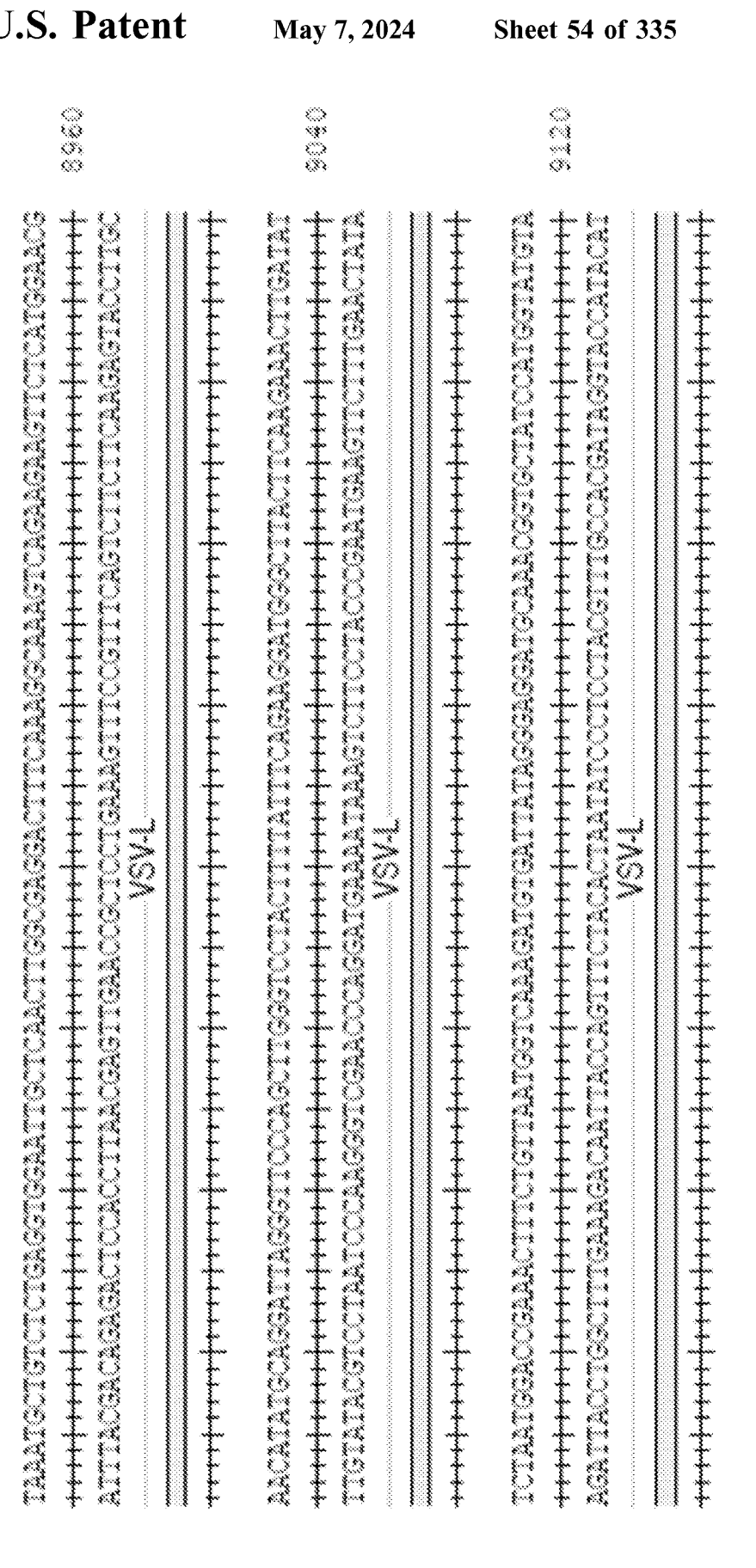
FIG. 17 – continued

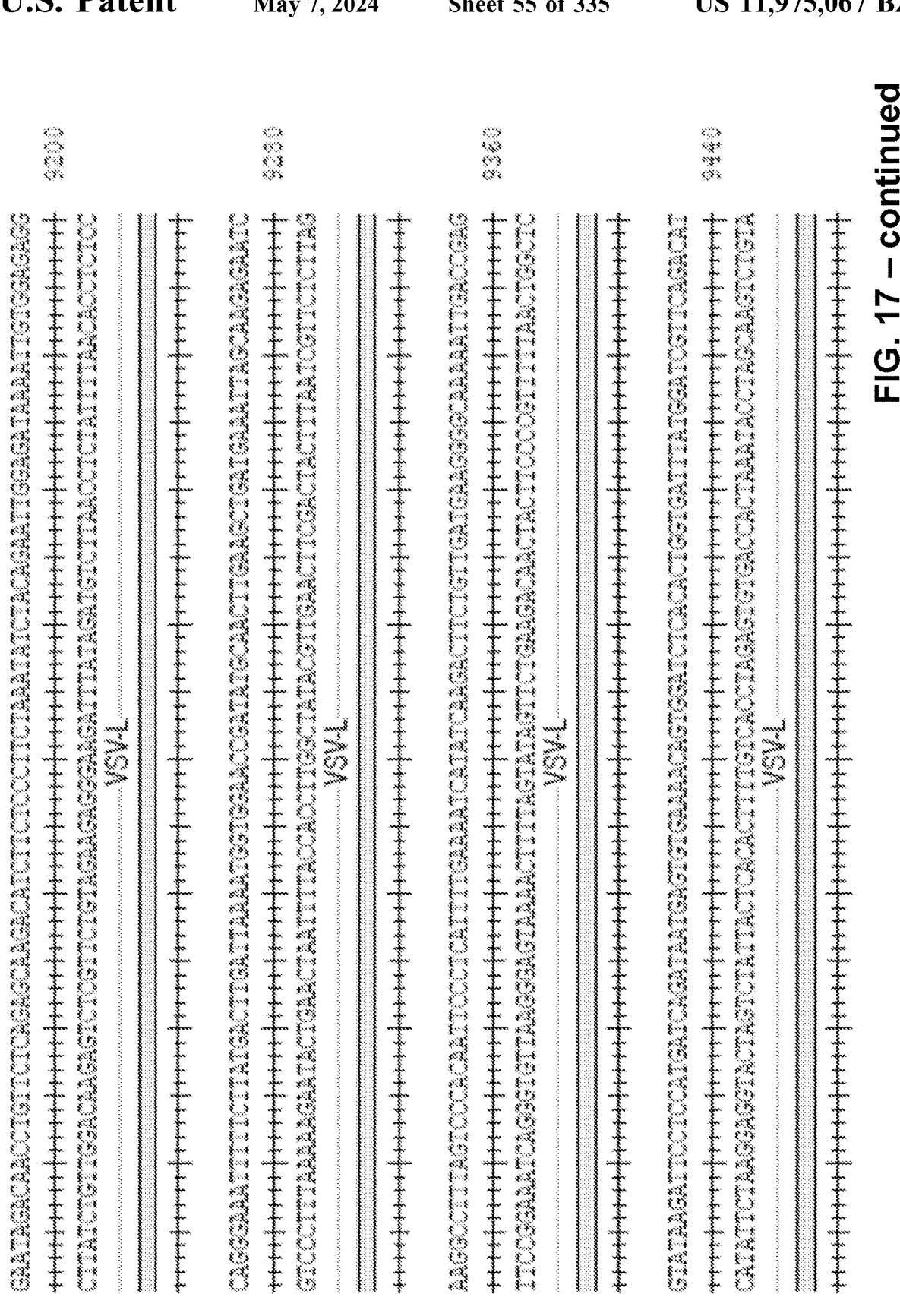
FIG. 17 – continued

FIG. 17 – continued

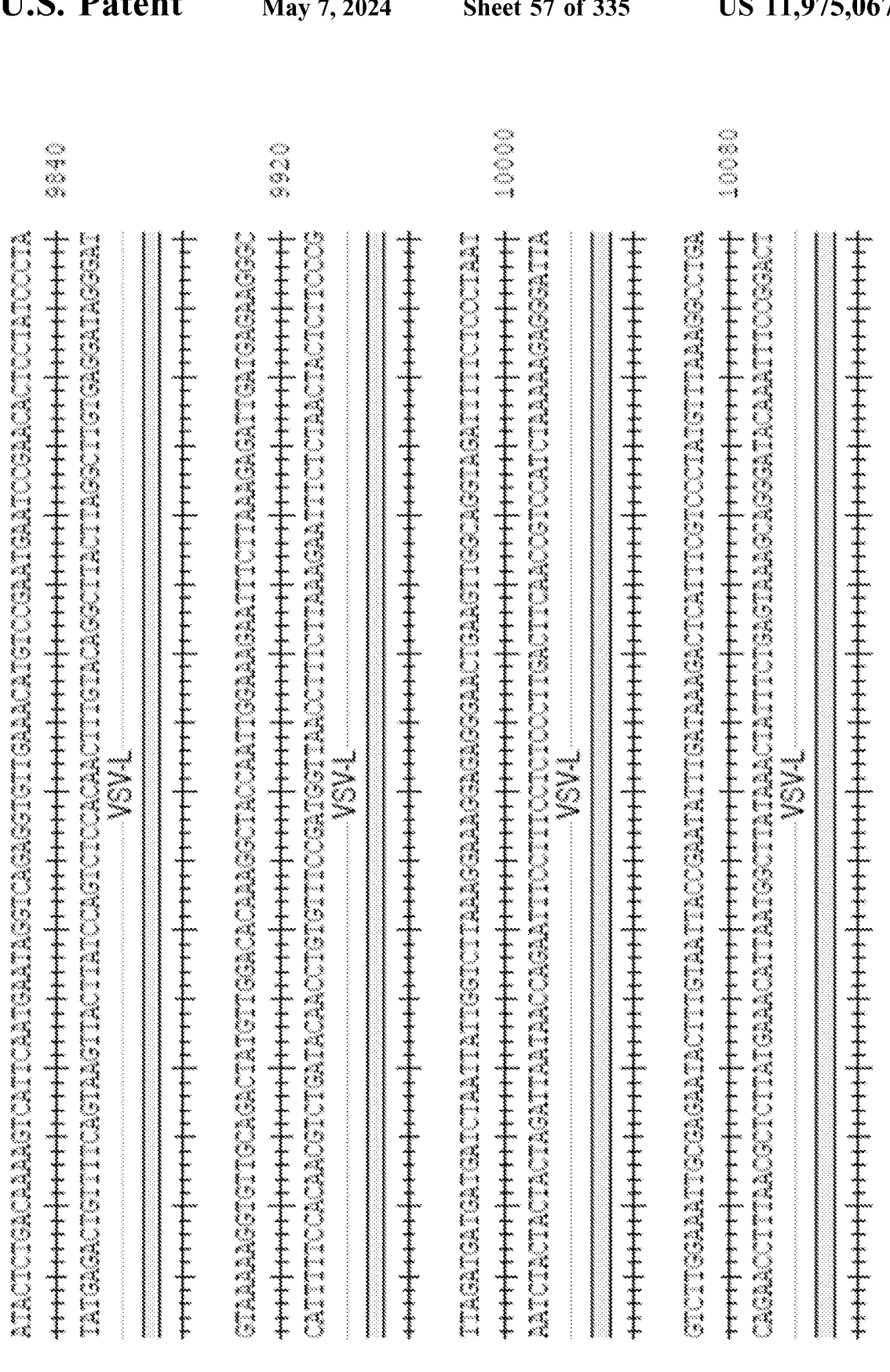

FIG. 17 – continued

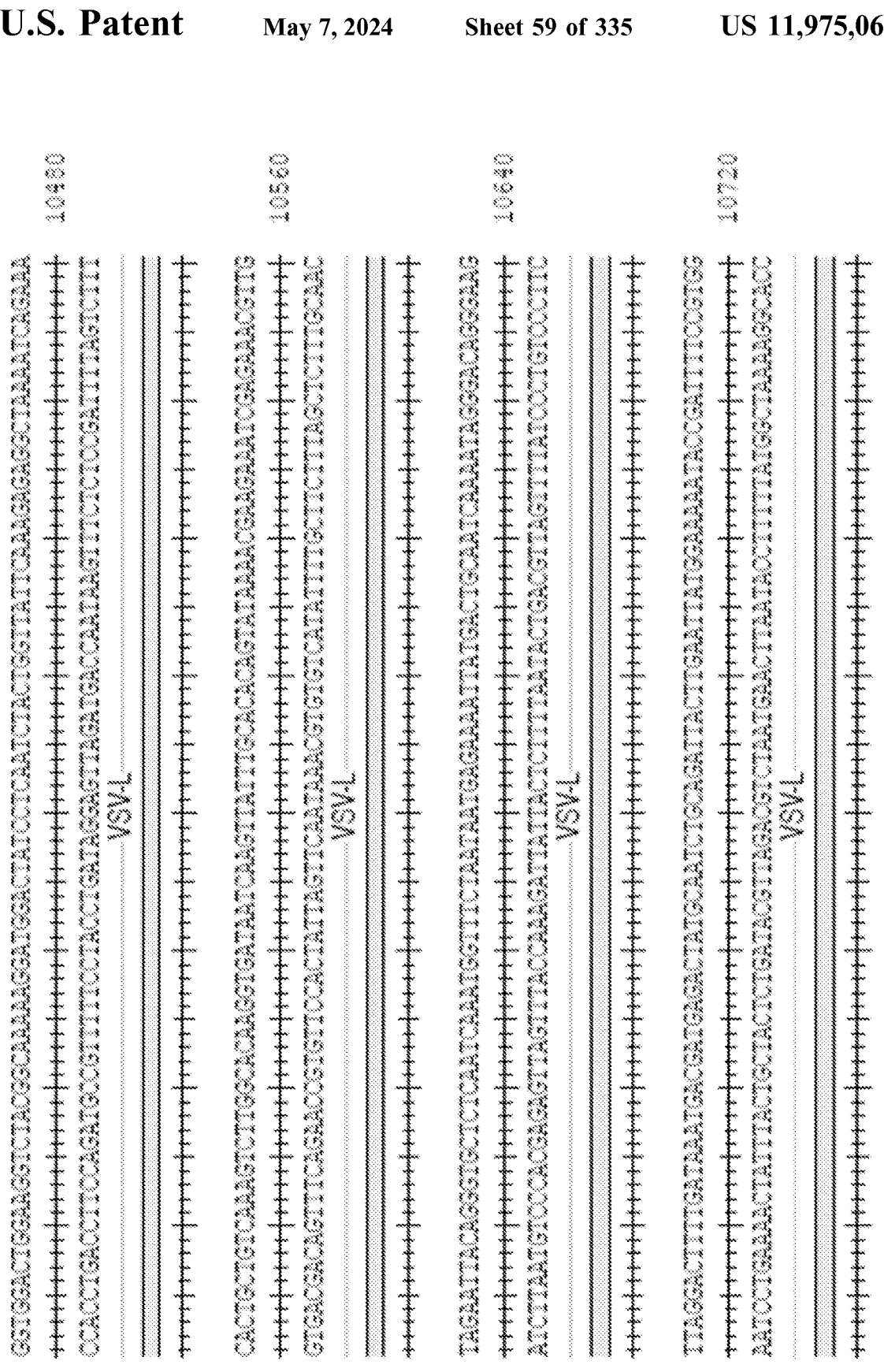
FIG. 17 – continued

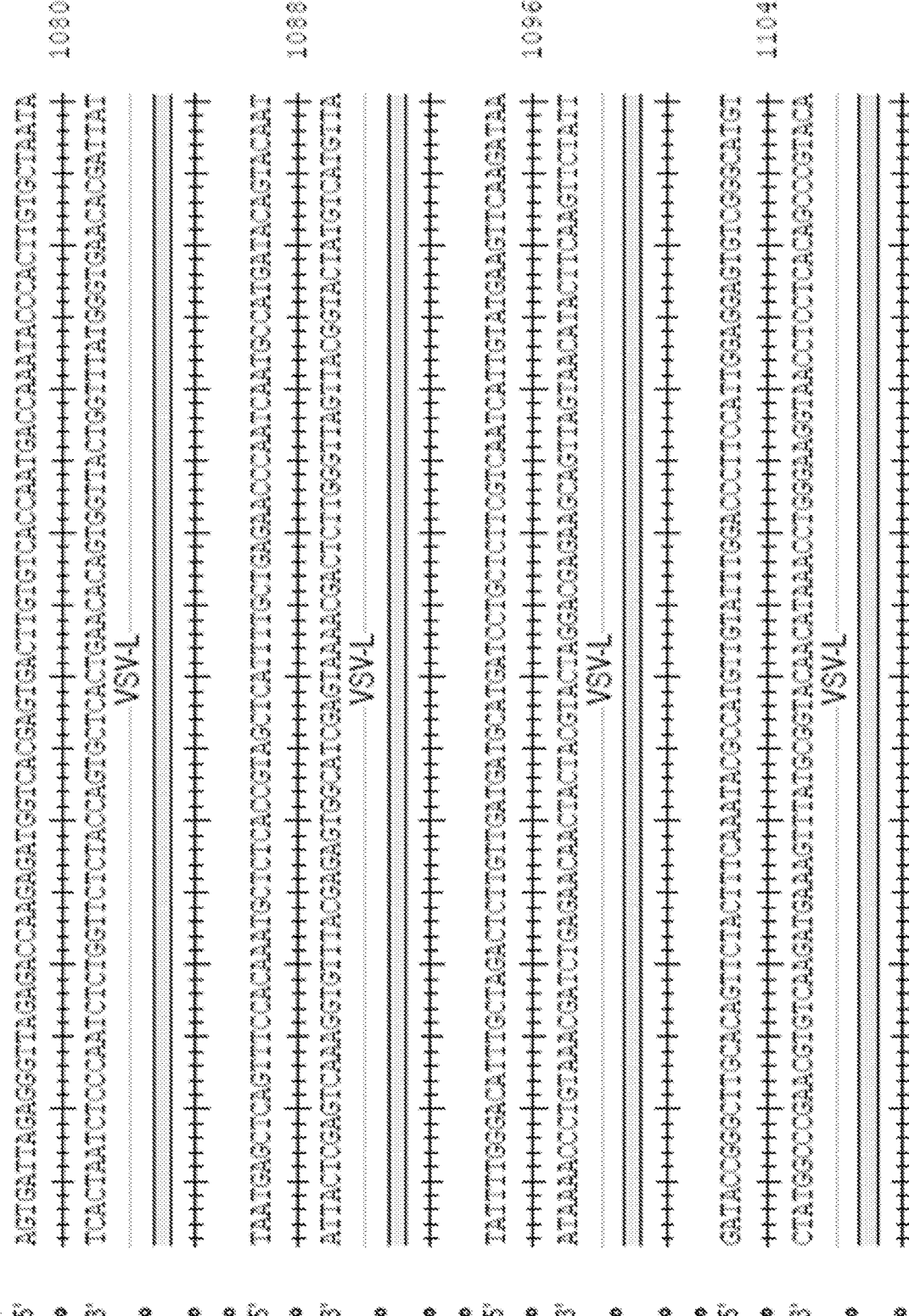
FIG. 17 – continued

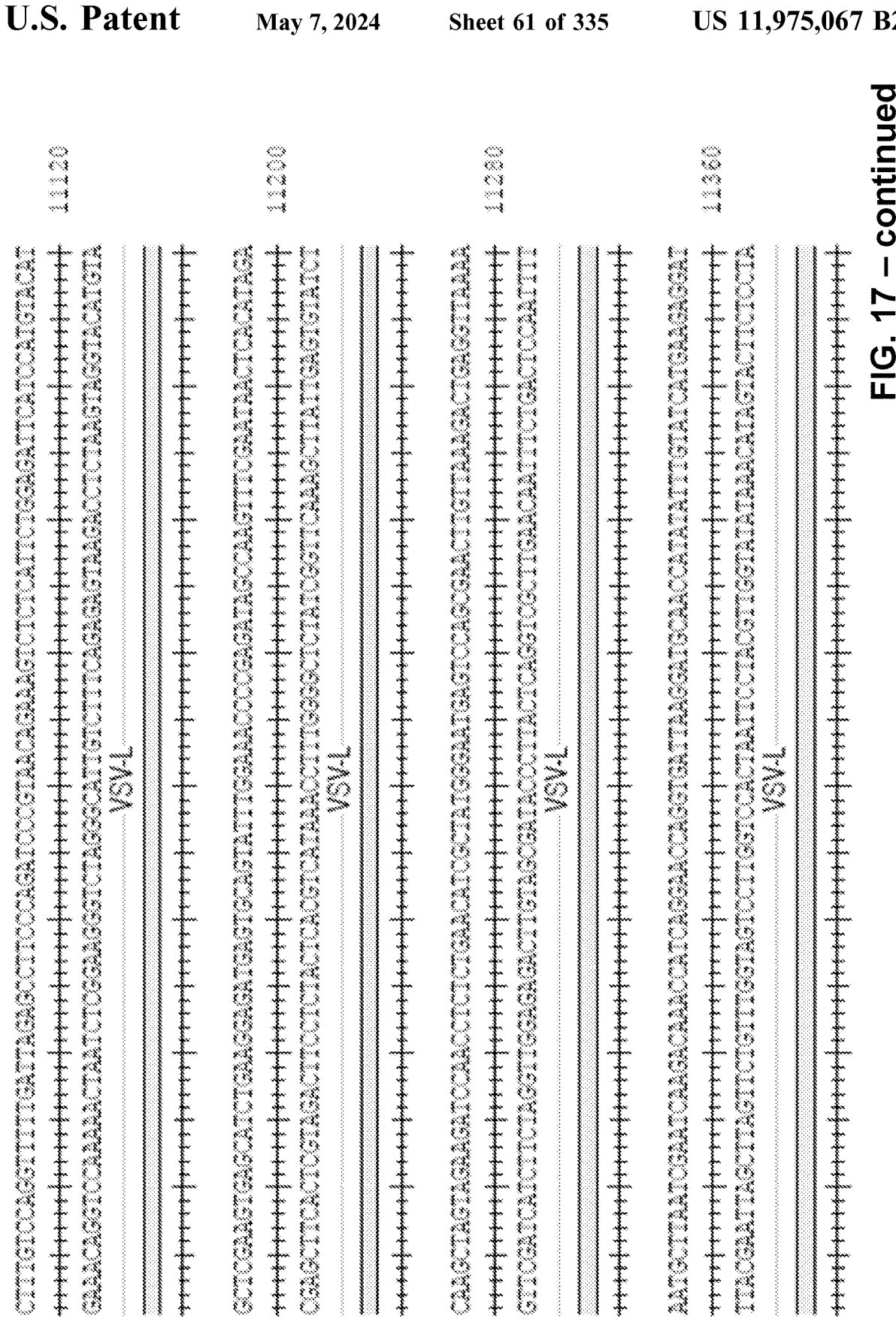
FIG. 17 – continued

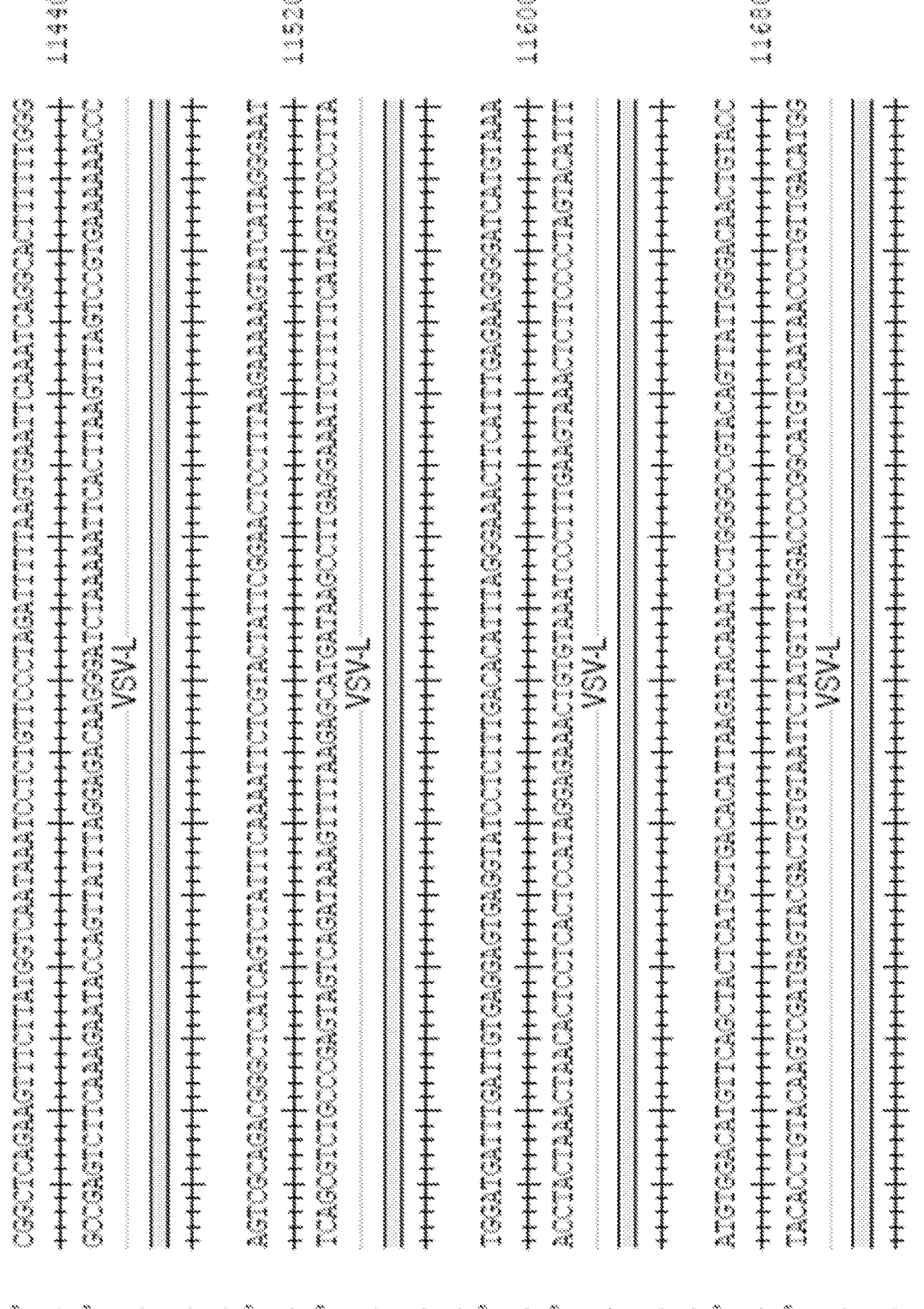
FIG. 17 – continued

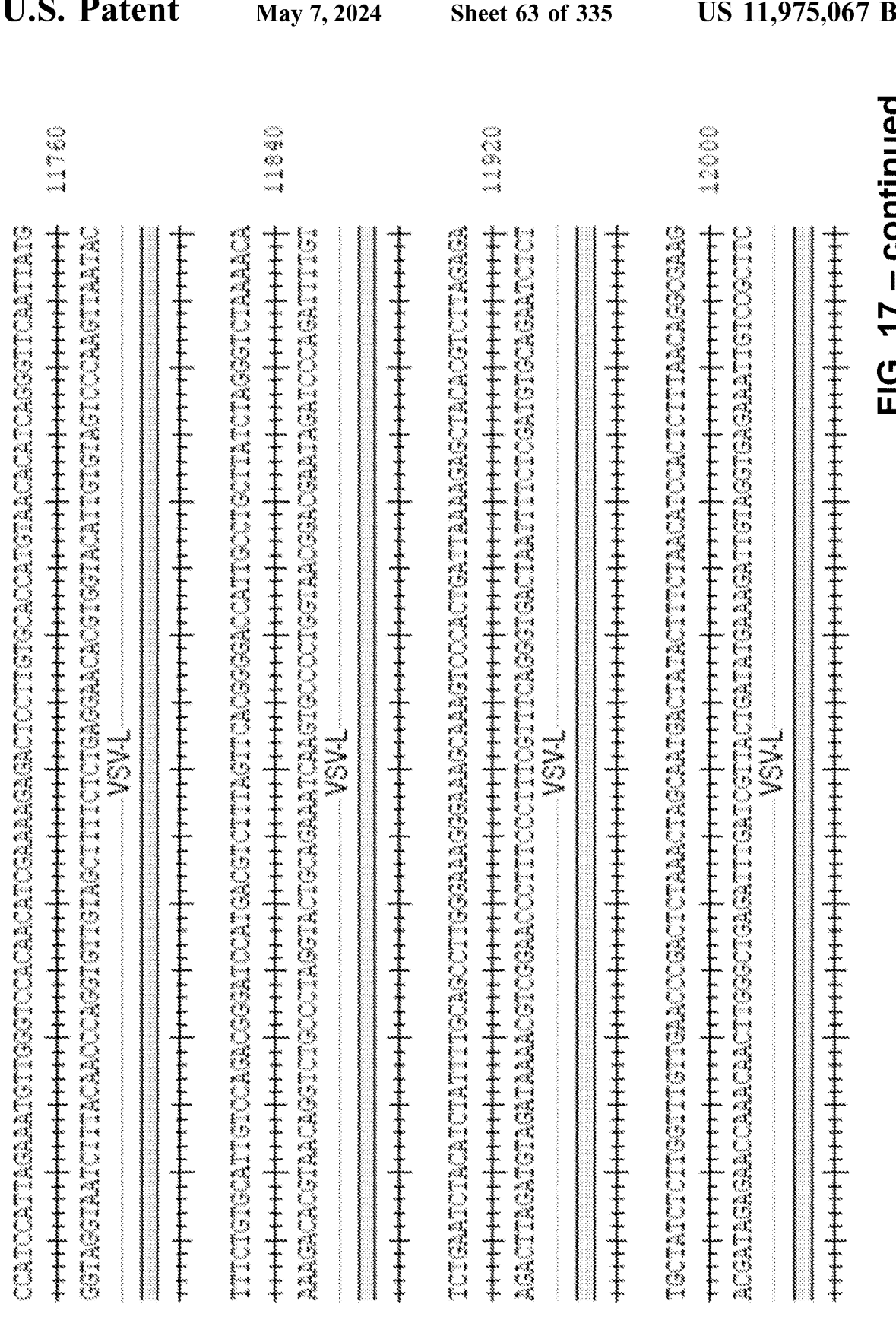
FIG. 17 – continued

FIG. 17 – continued

FIG. 17 – continued

FIG. 17 – continued

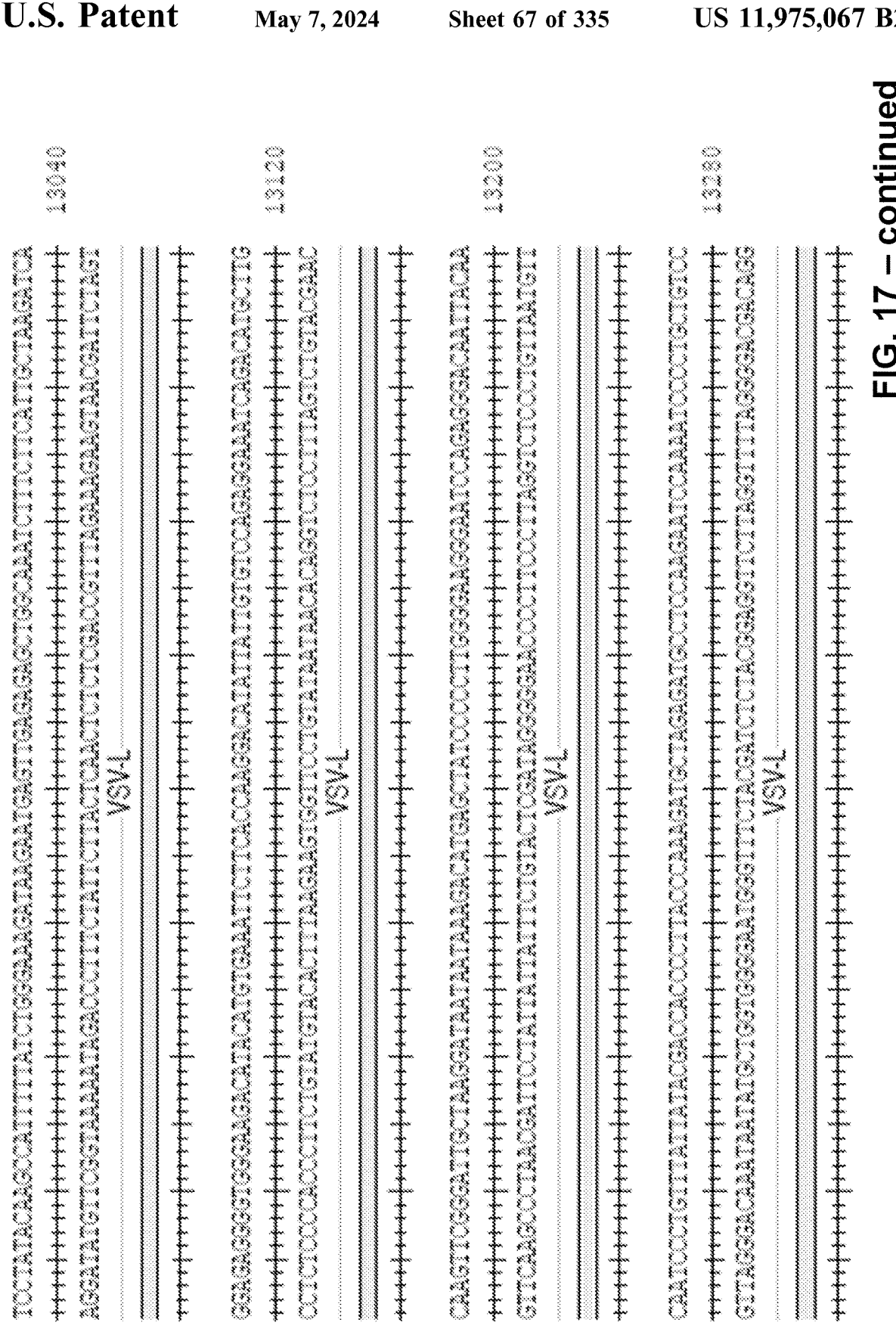
FIG. 17 – continued

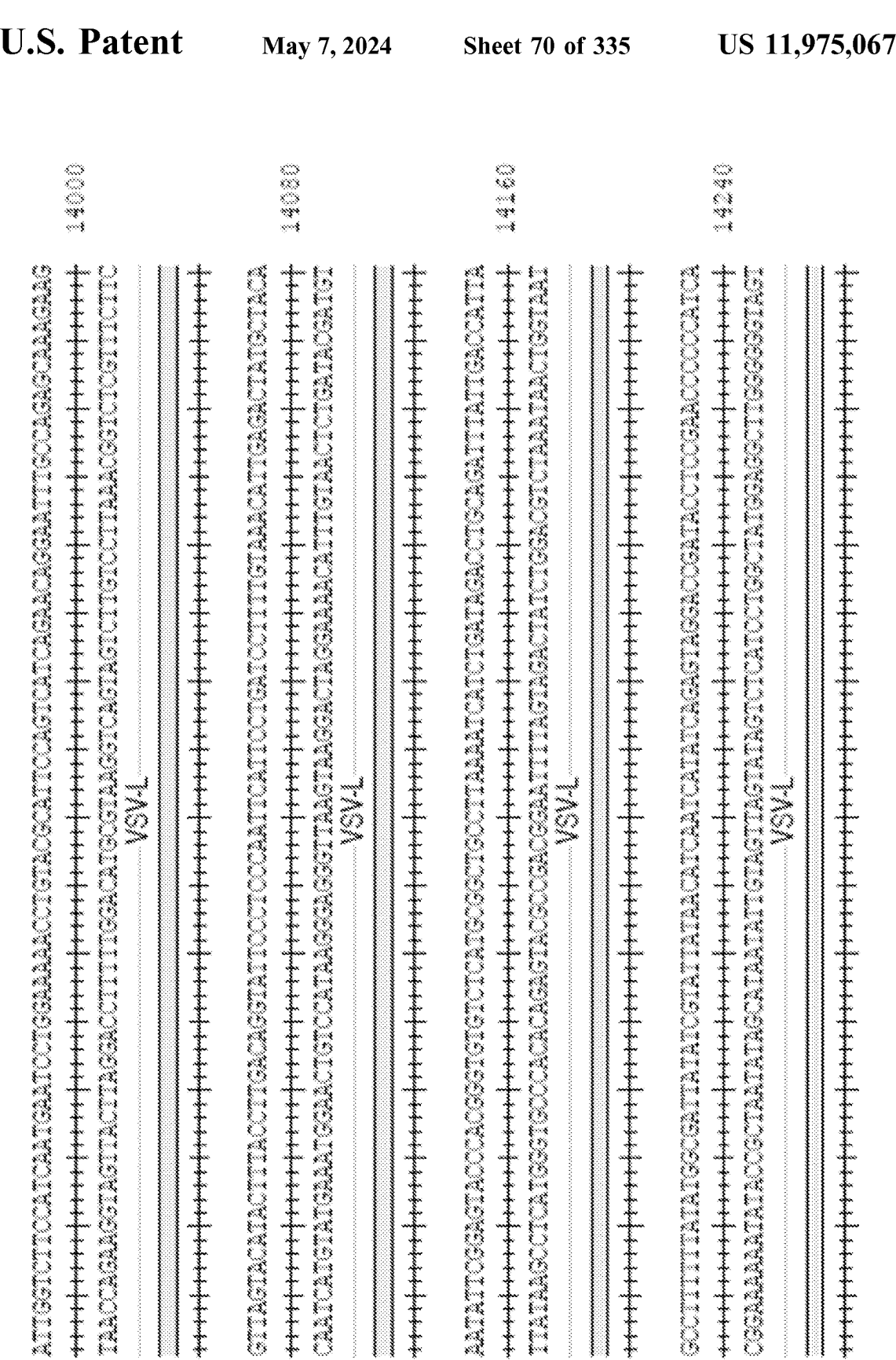
FIG. 17 – continued

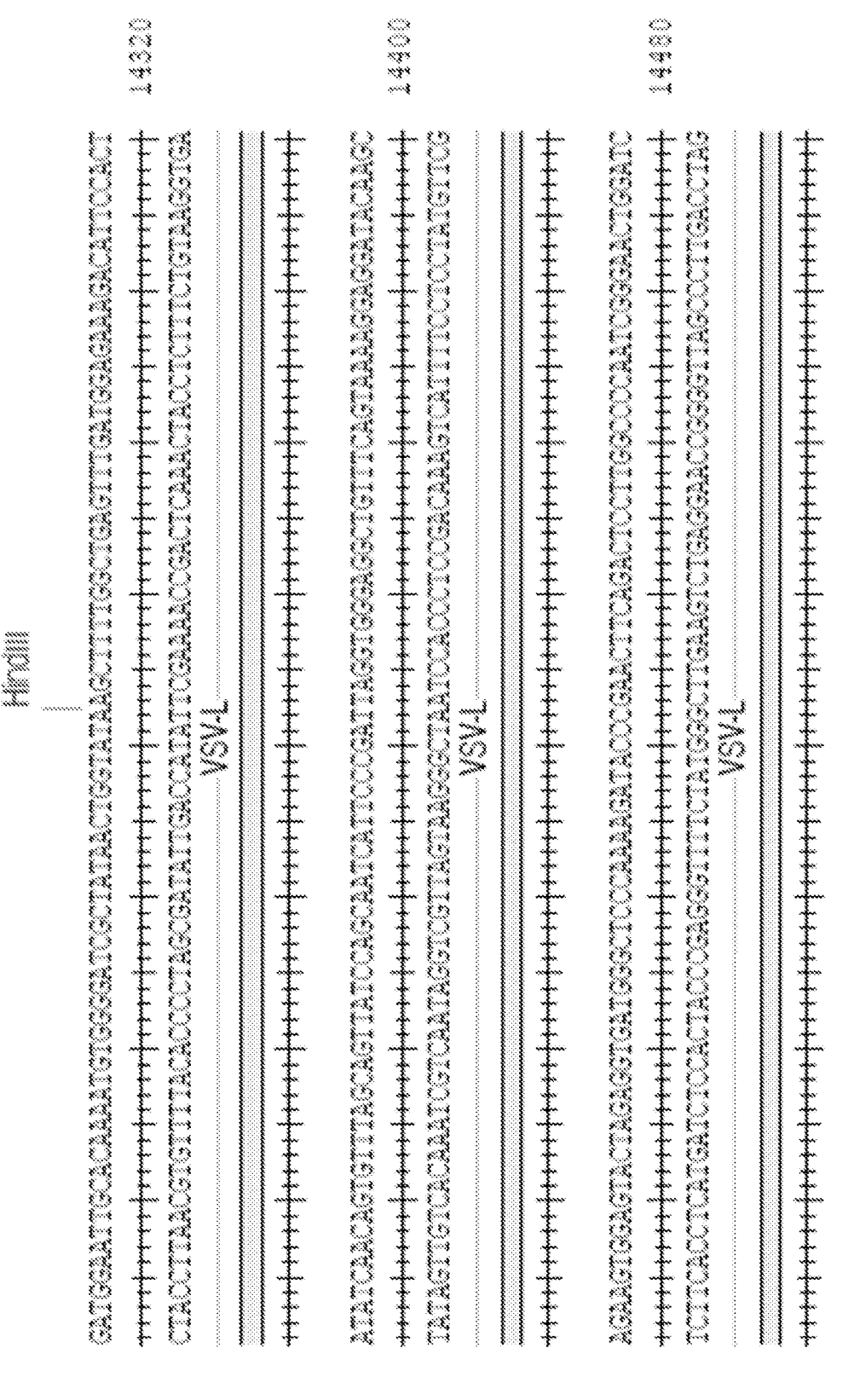
FIG. 17 – continued

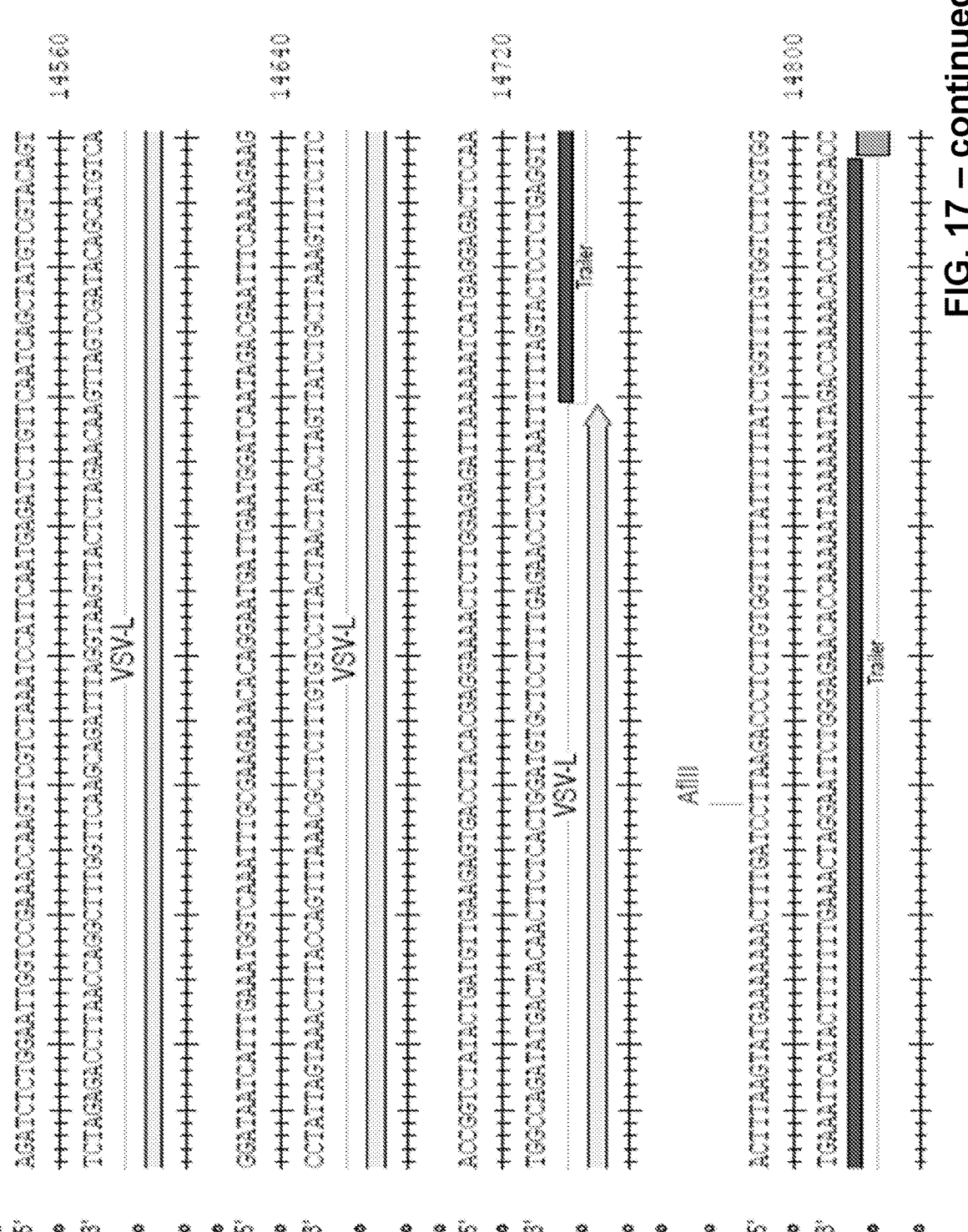
FIG. 17 – continued

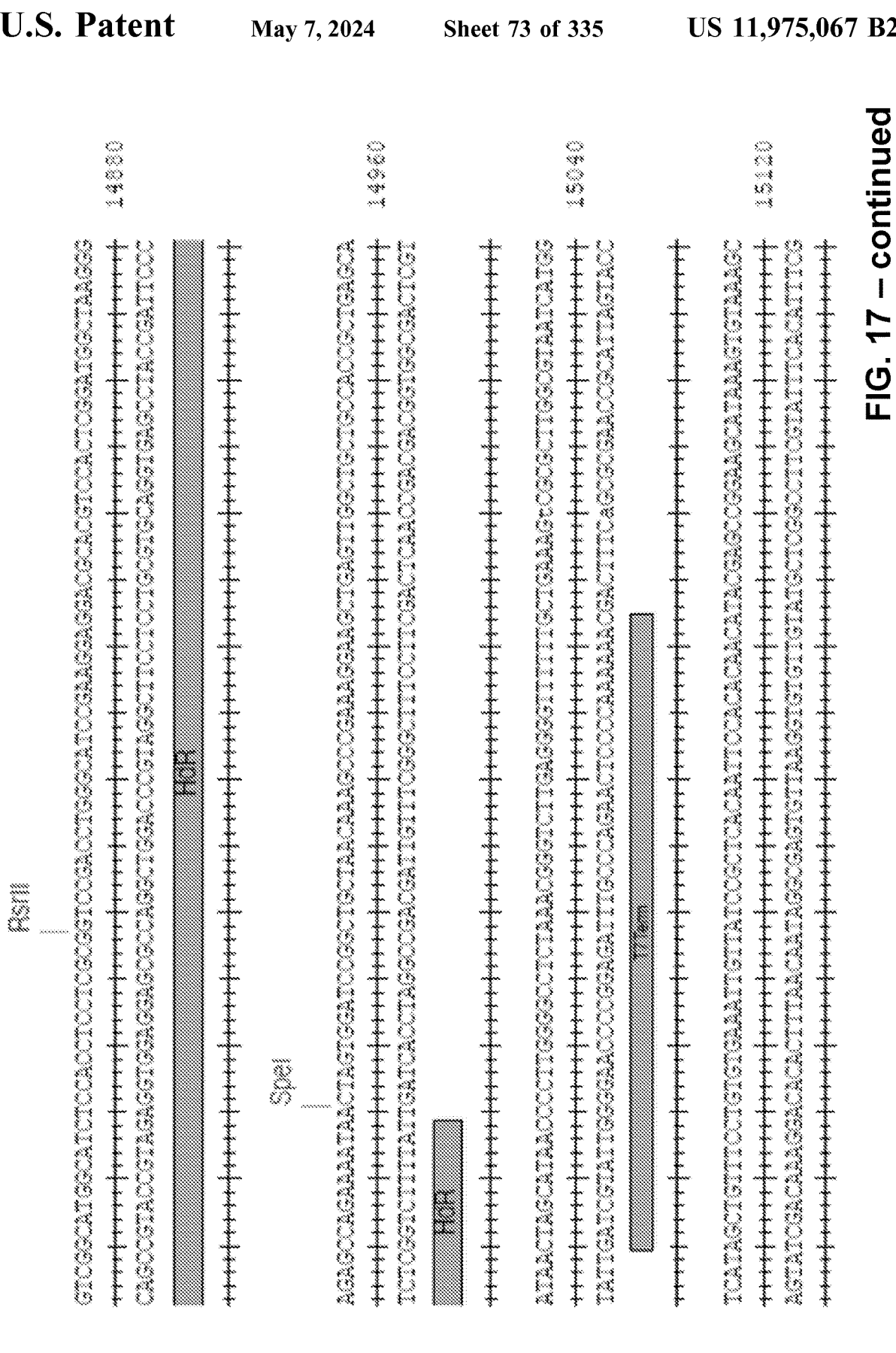
FIG. 17 – continued

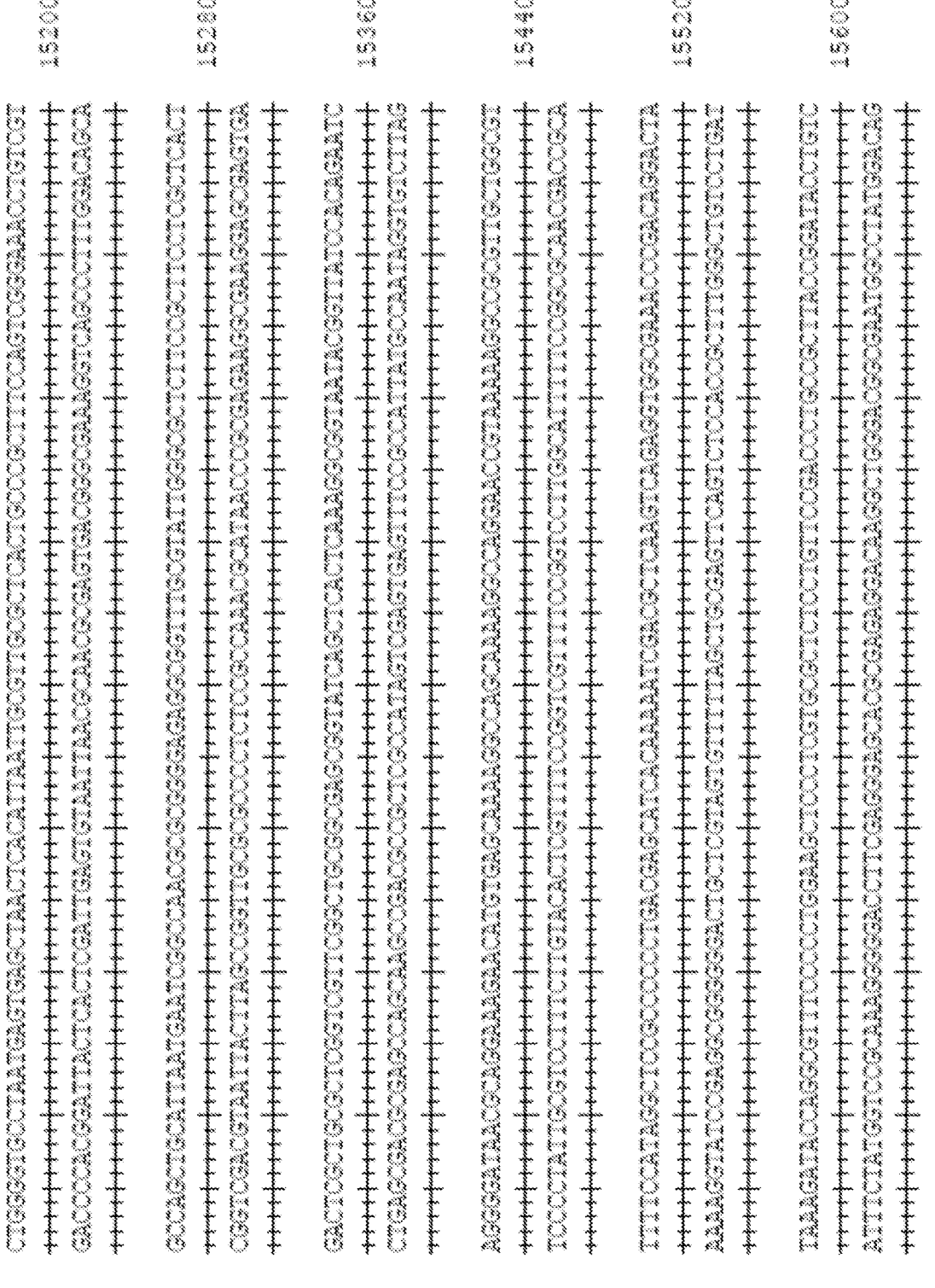
FIG. 17 – continued

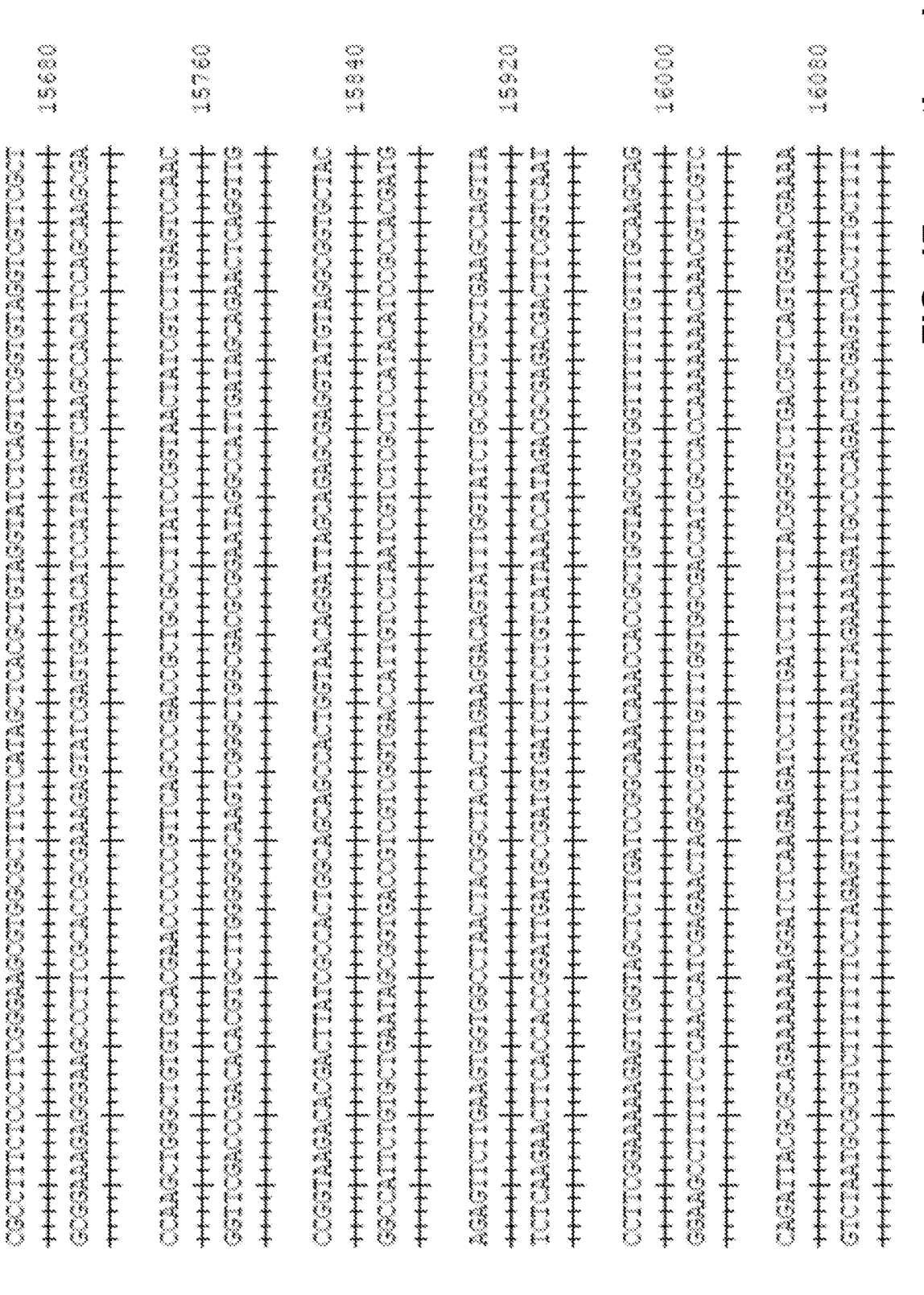
FIG. 17 – continued

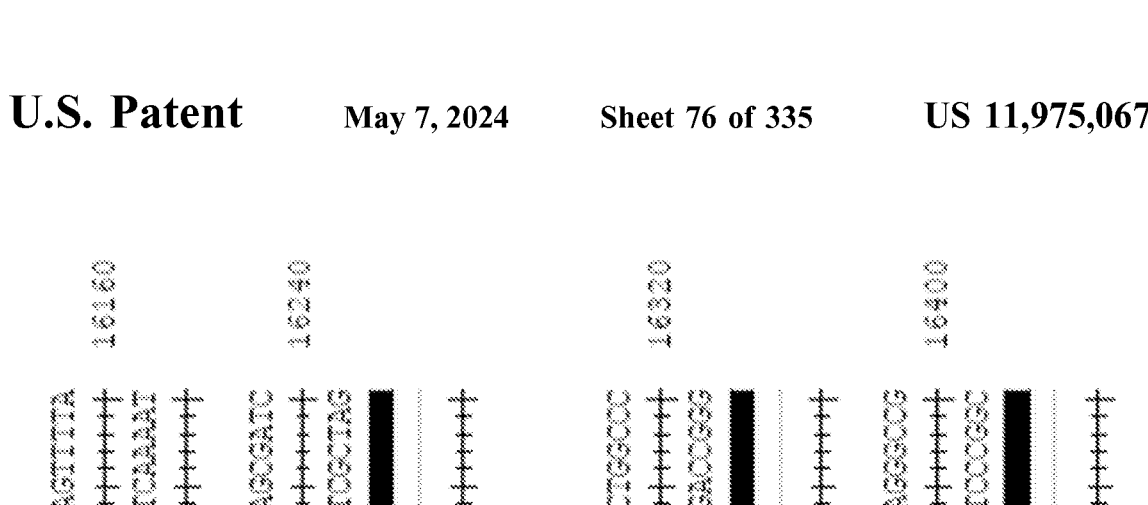
FIG. 17 – continued

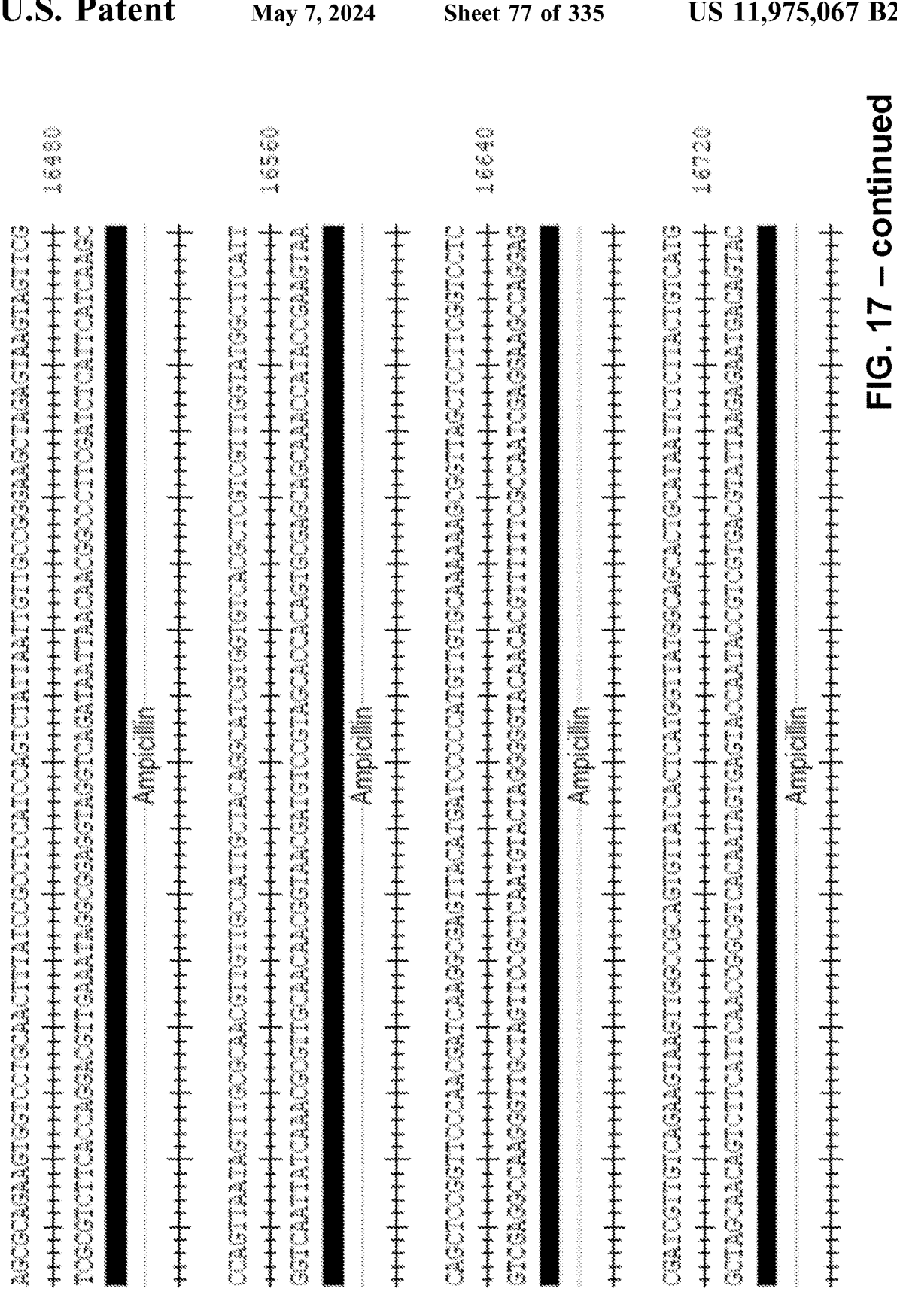
FIG. 17 – continued

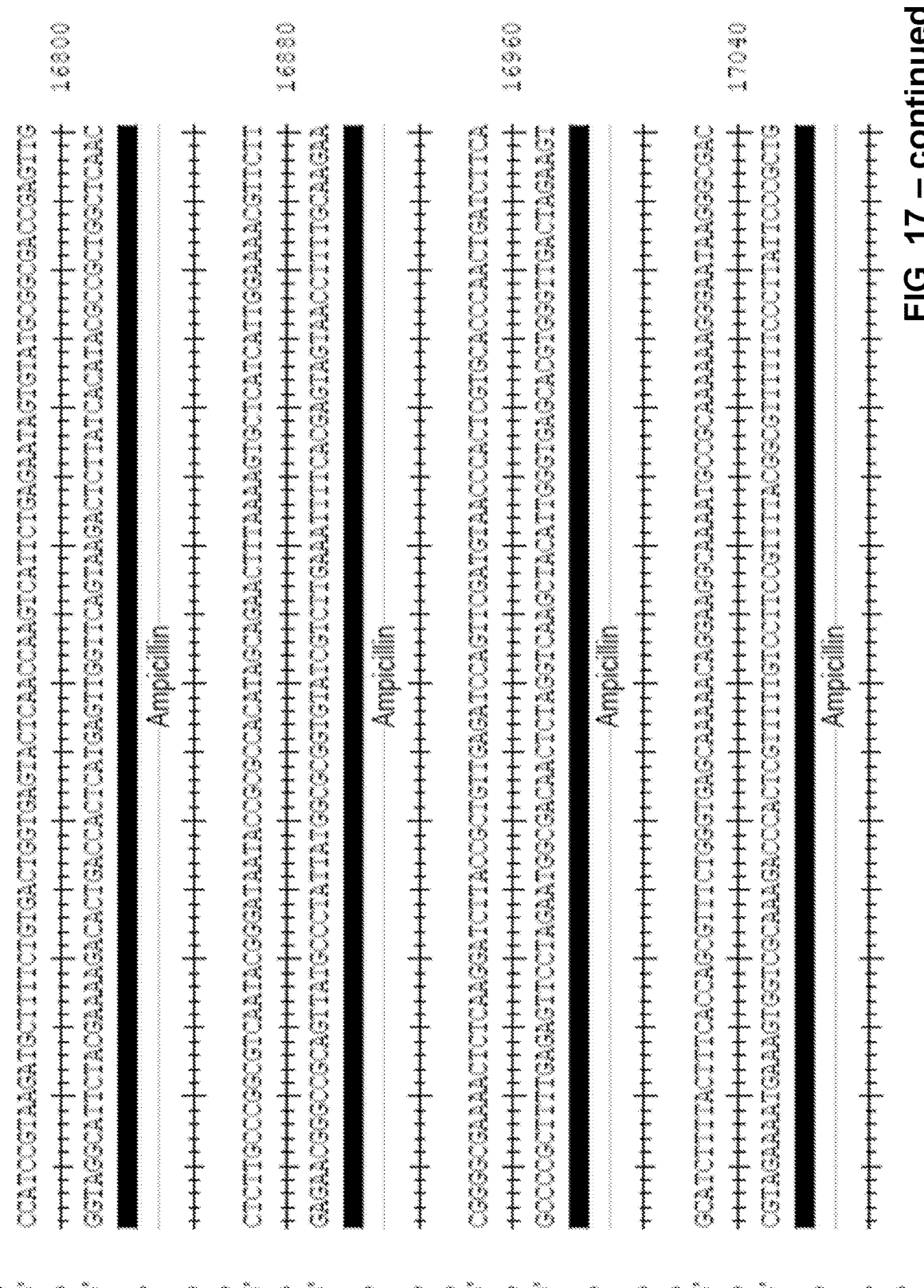
FIG. 17 – continued

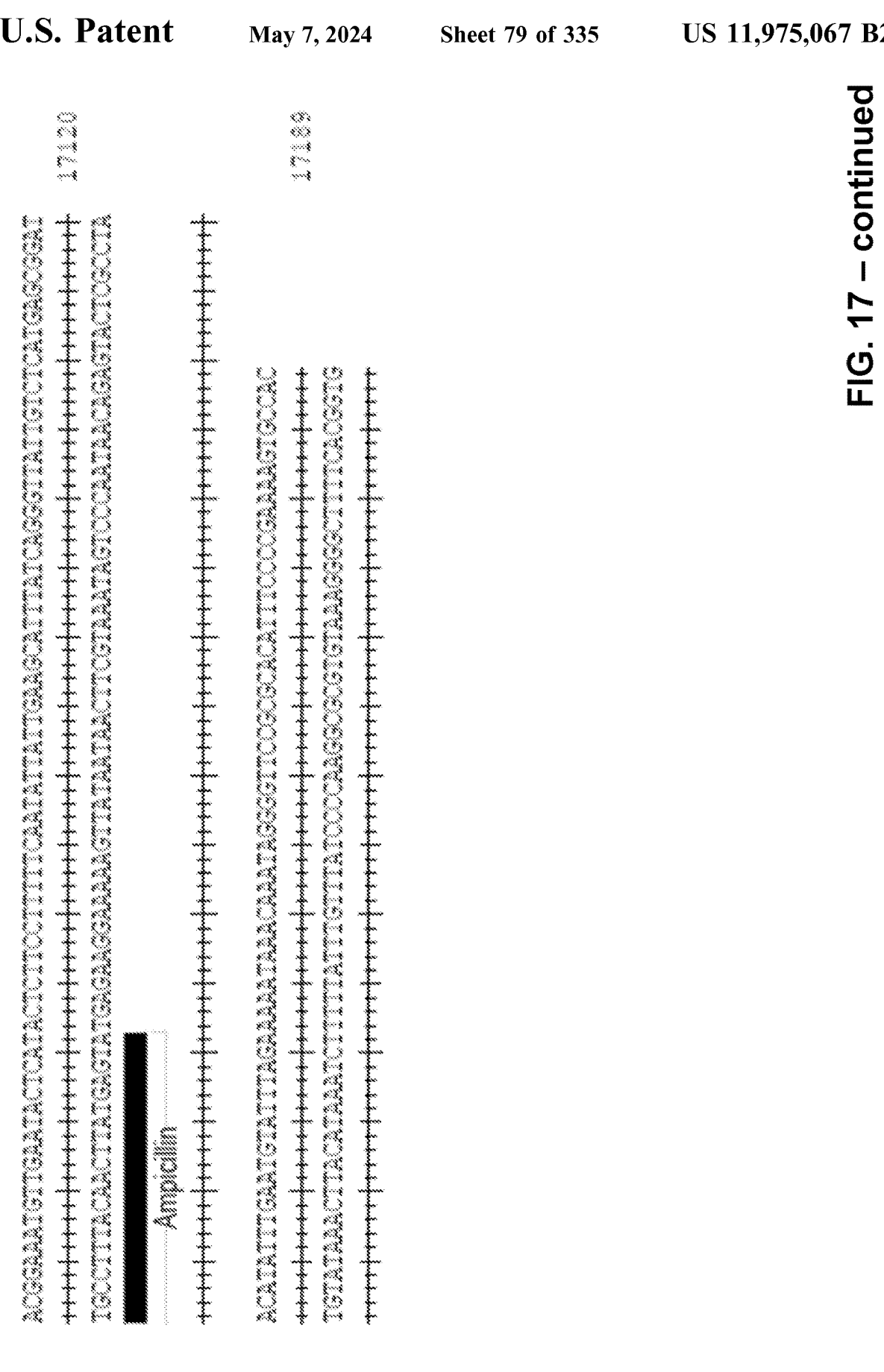
FIG. 17 – continued

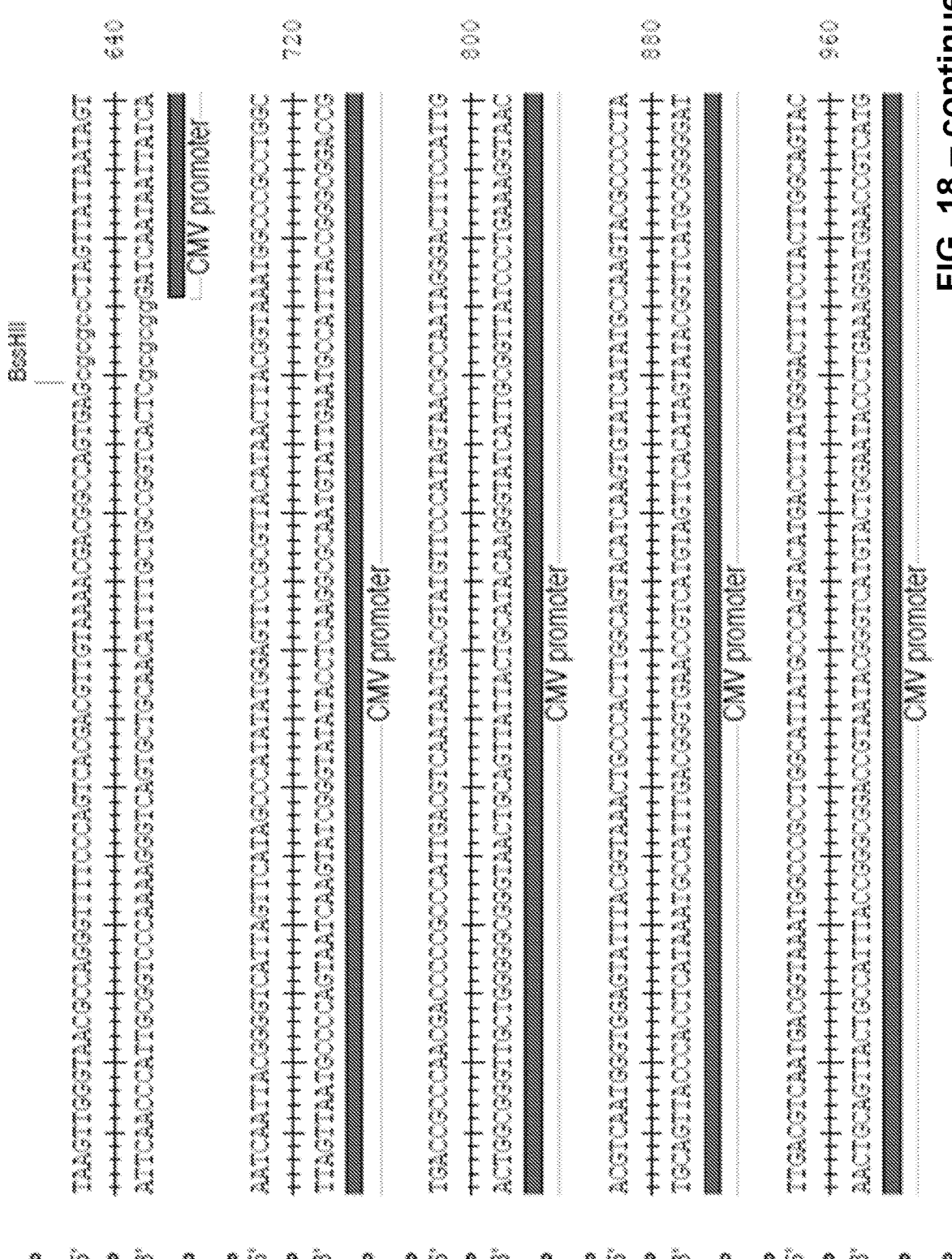
FIG. 18 – continued

FIG. 18 – continued

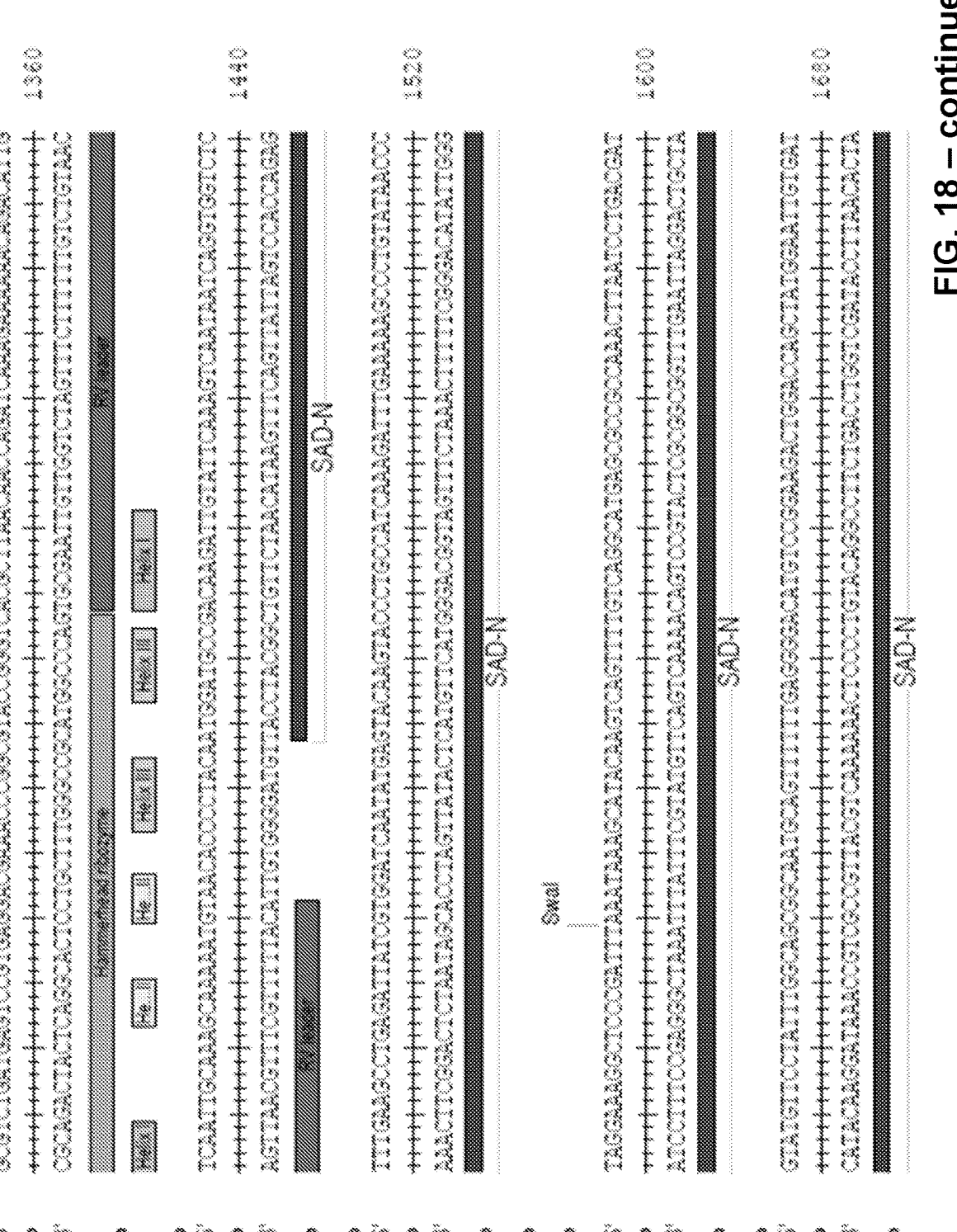
FIG. 18 – continued

FIG. 18 – continued

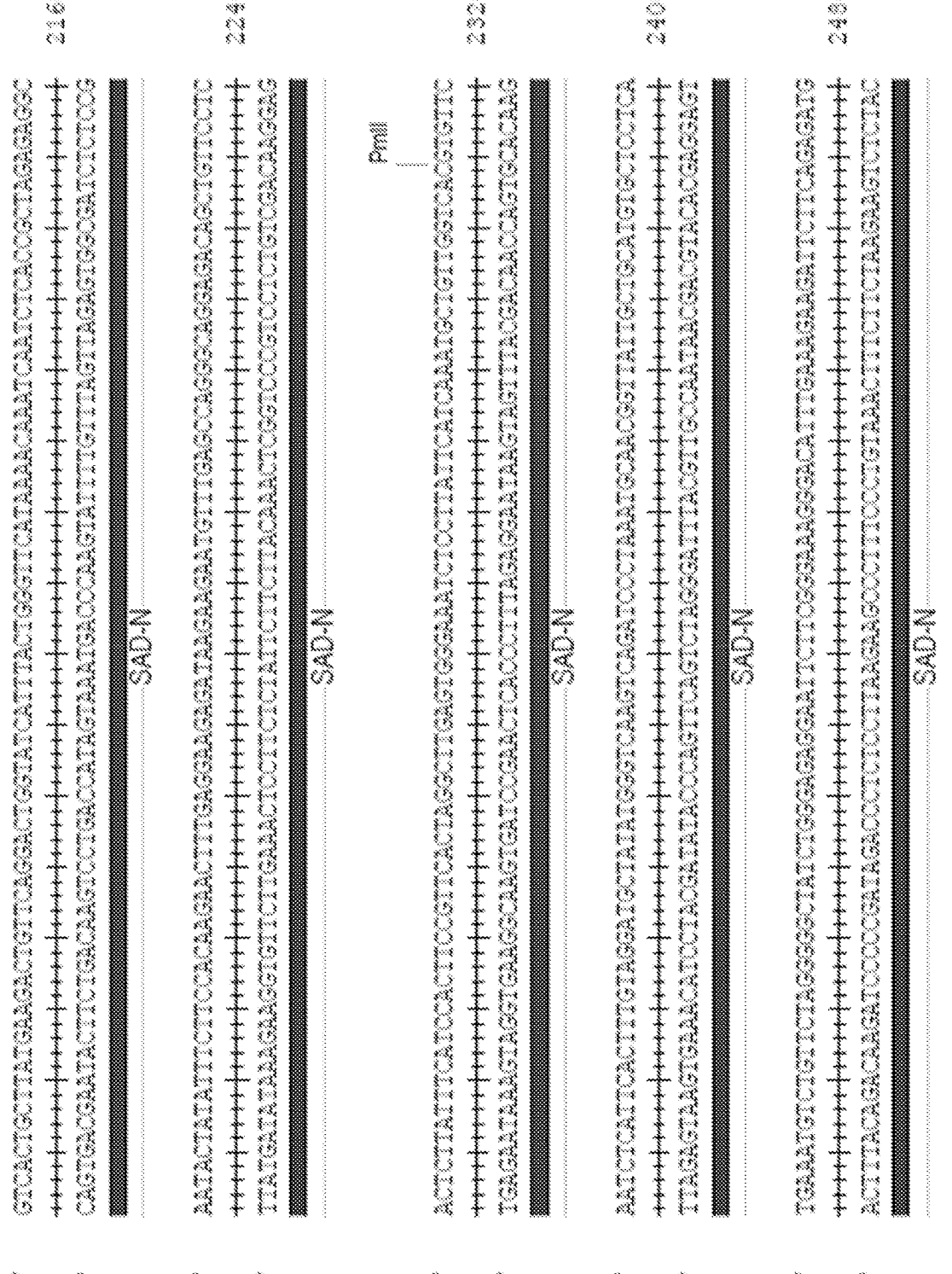
FIG. 18 – continued

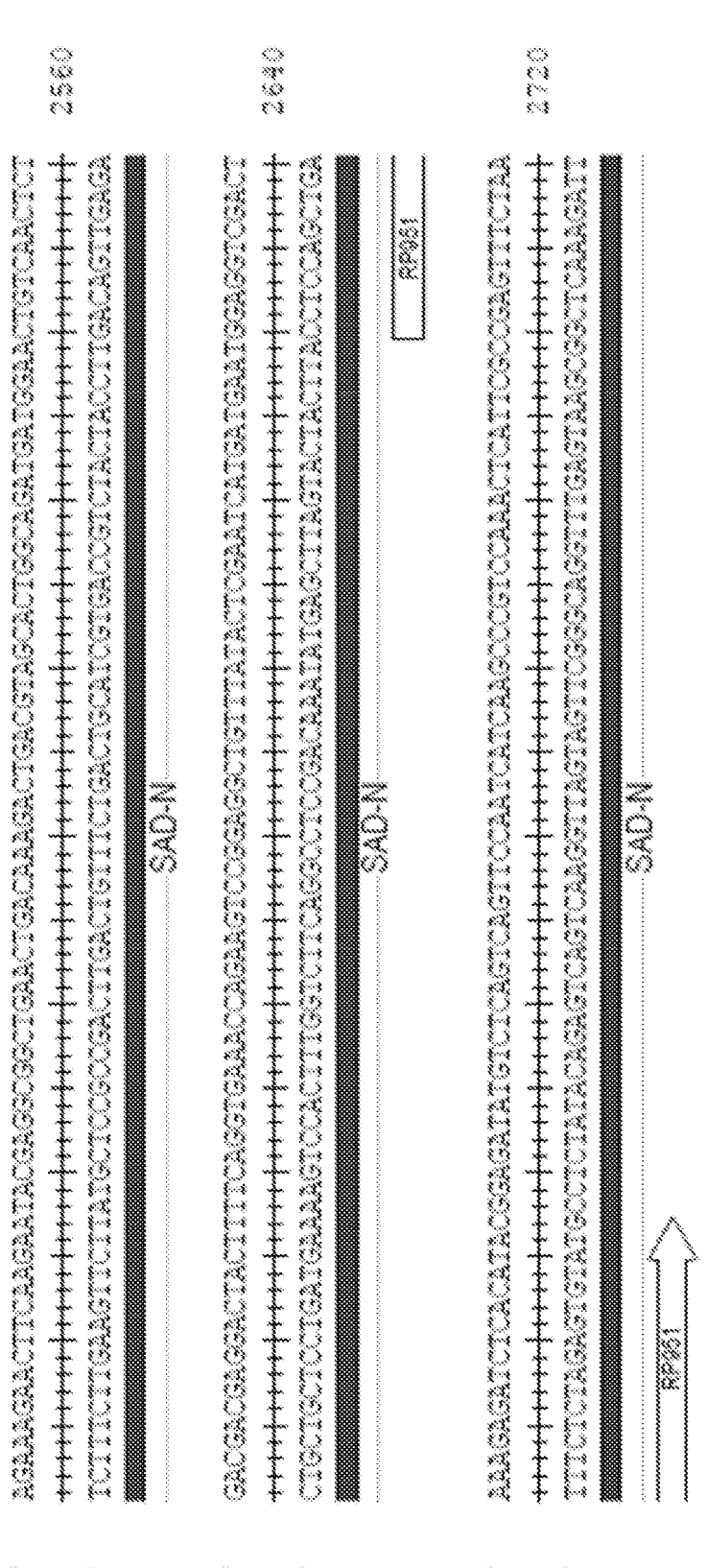
FIG. 18 – continued

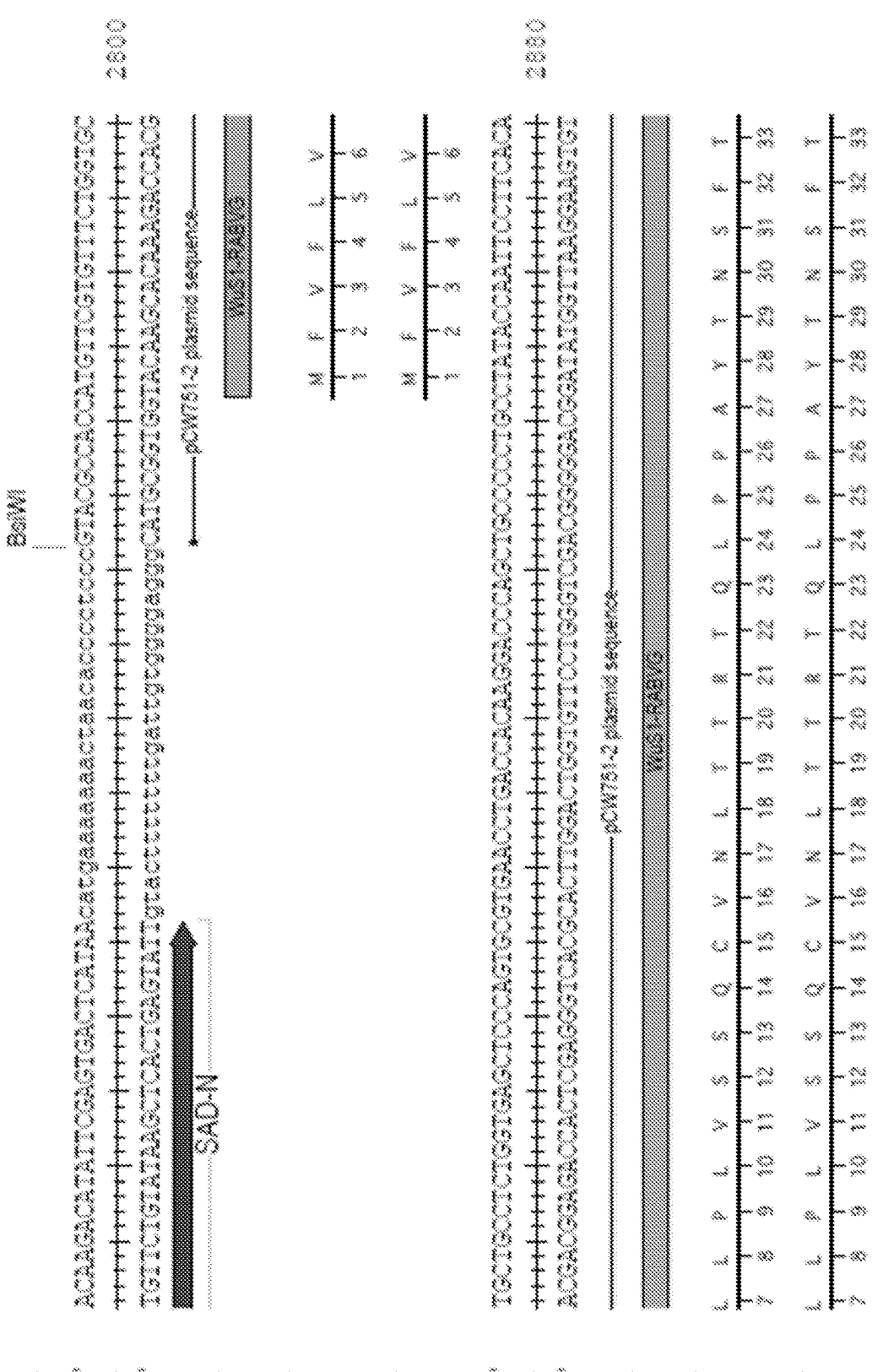
FIG. 18 – continued

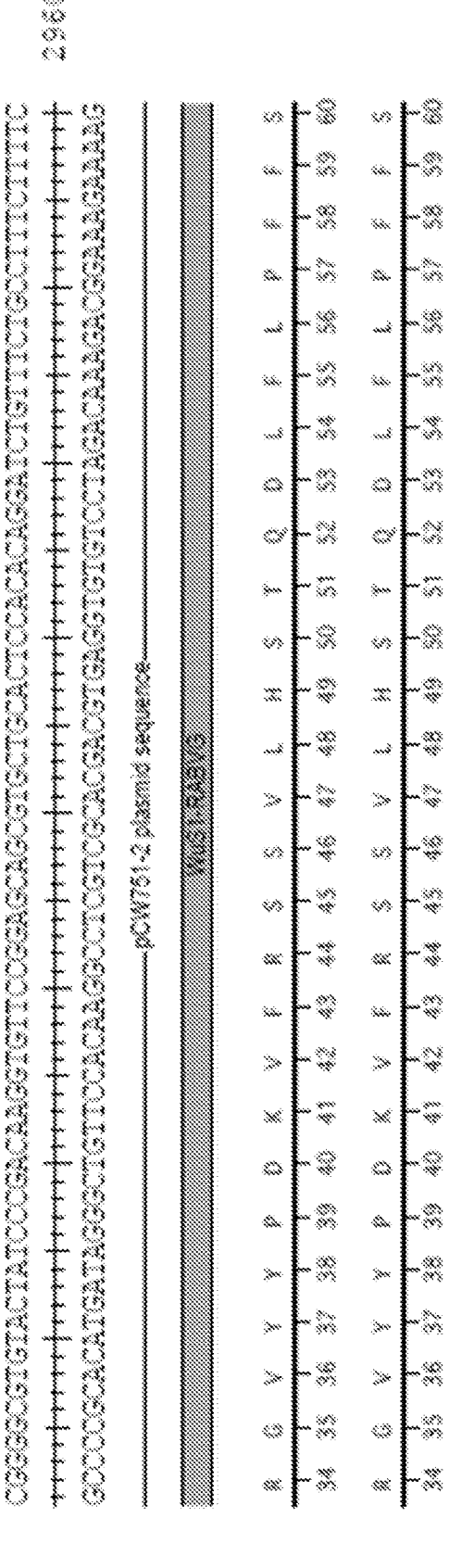
FIG. 18 – continued

FIG. 18 – continued

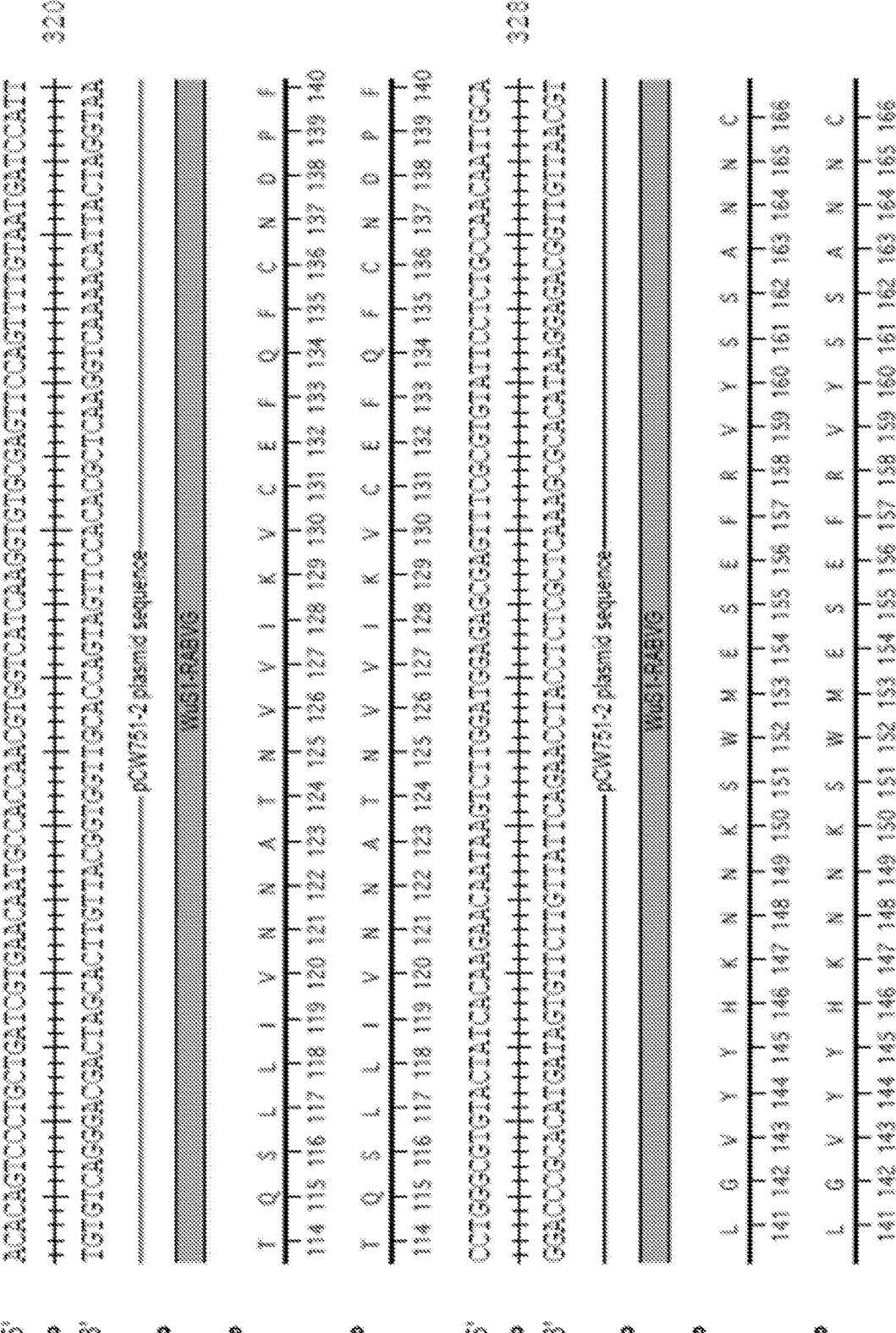
FIG. 18 – continued

FIG. 18 – continued

FIG. 18 – continued

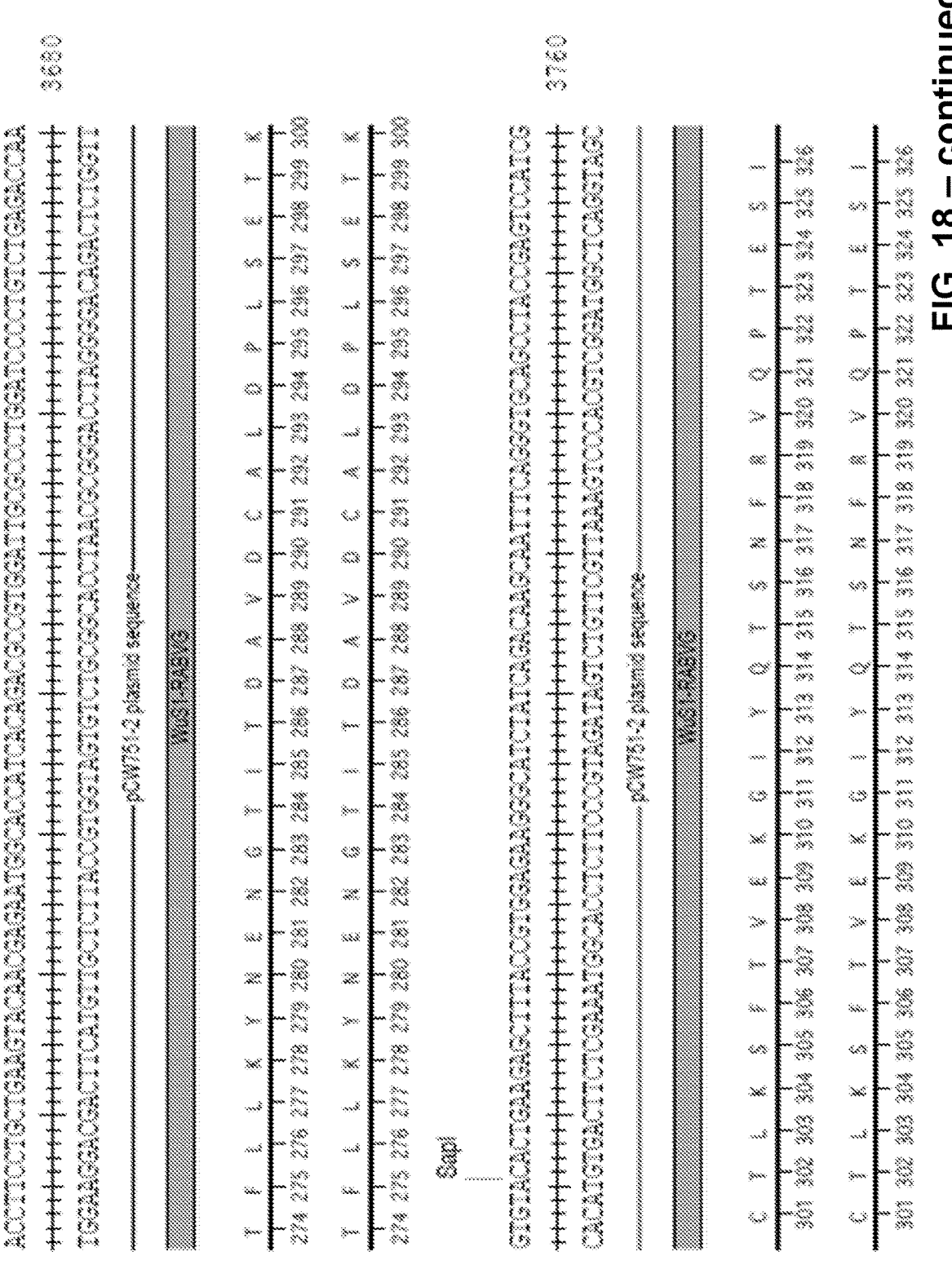
FIG. 18 – continued

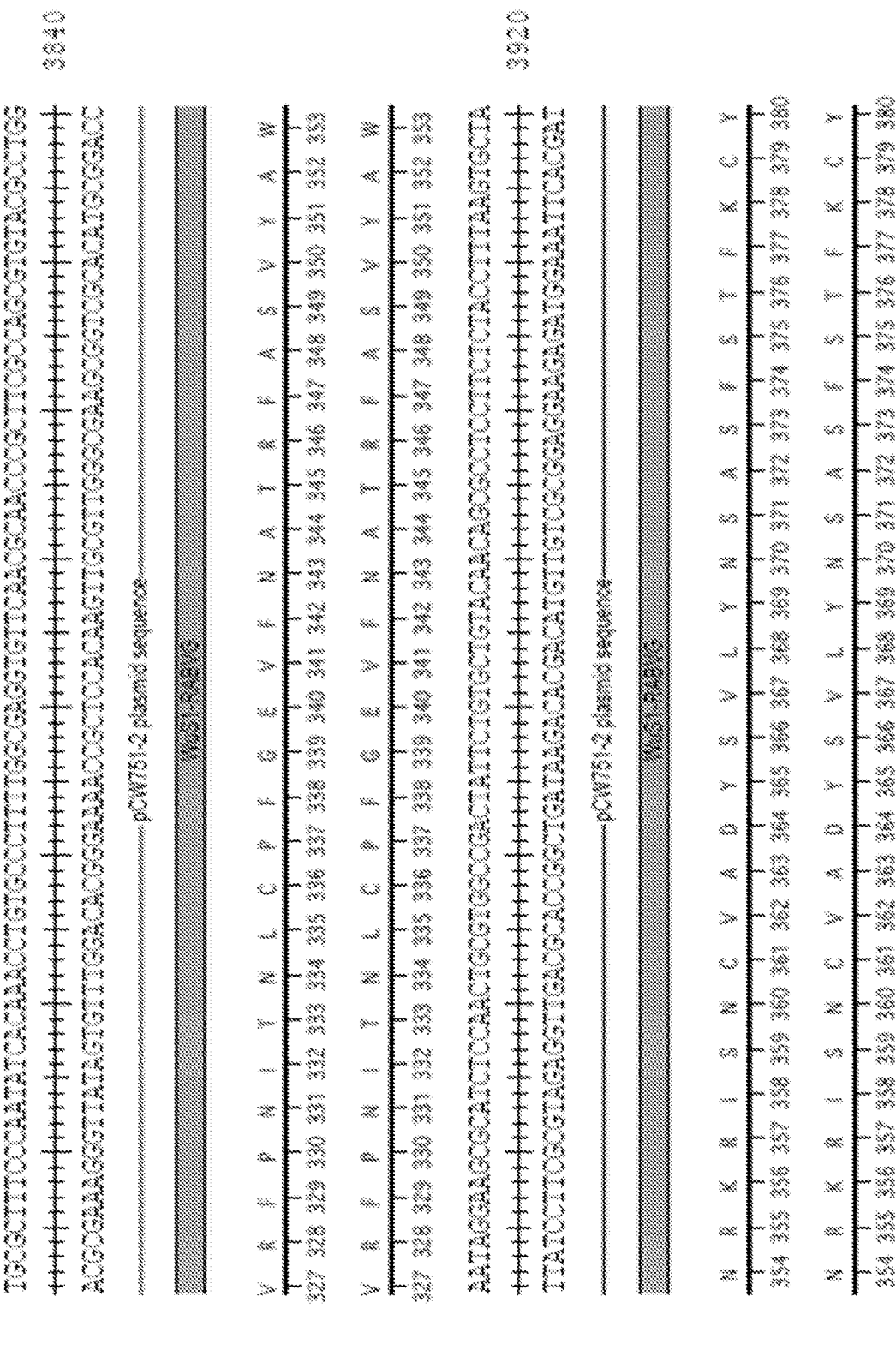
FIG. 18 – continued

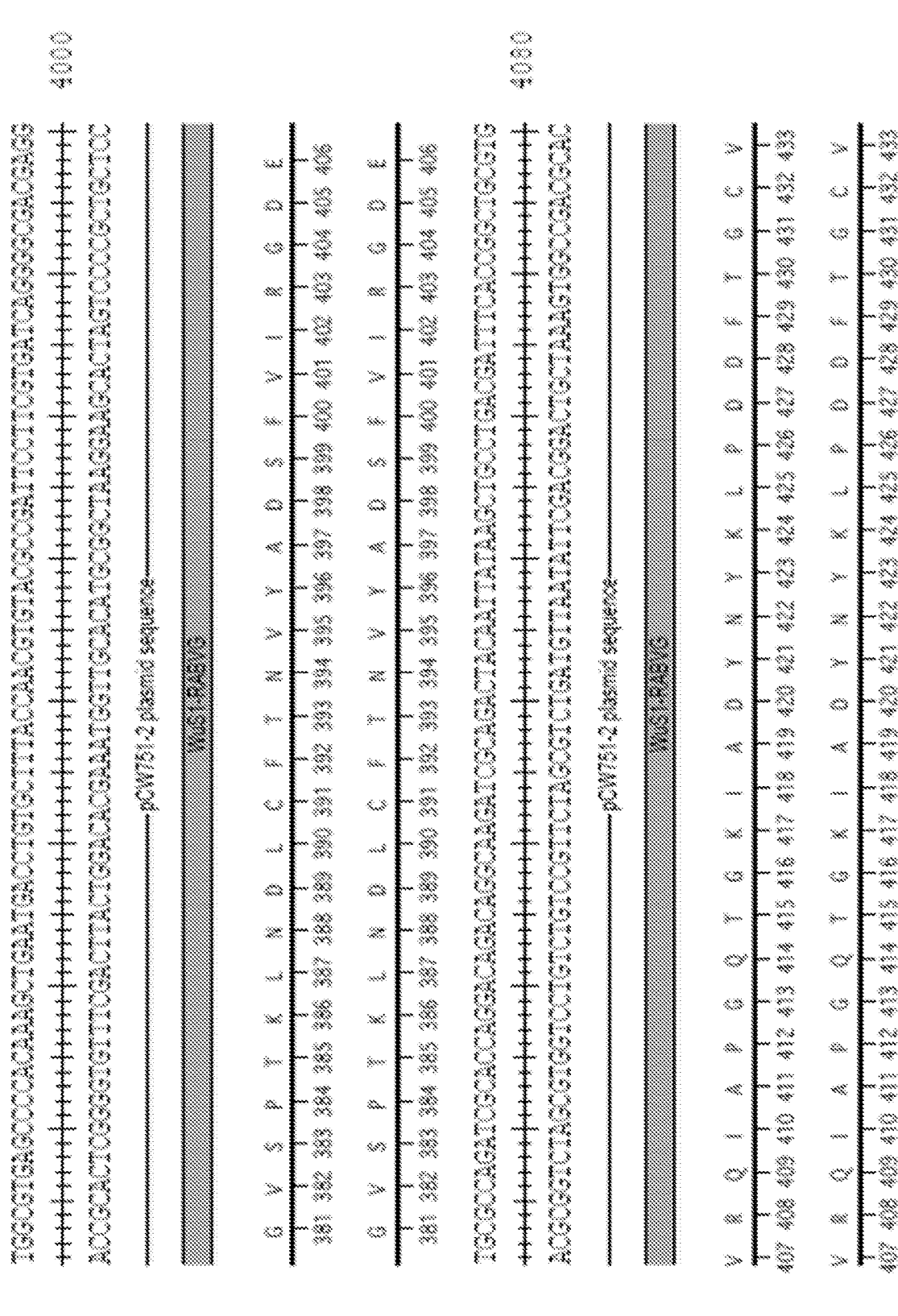
FIG. 18 – continued

FIG. 18 – continued

FIG. 18 – continued

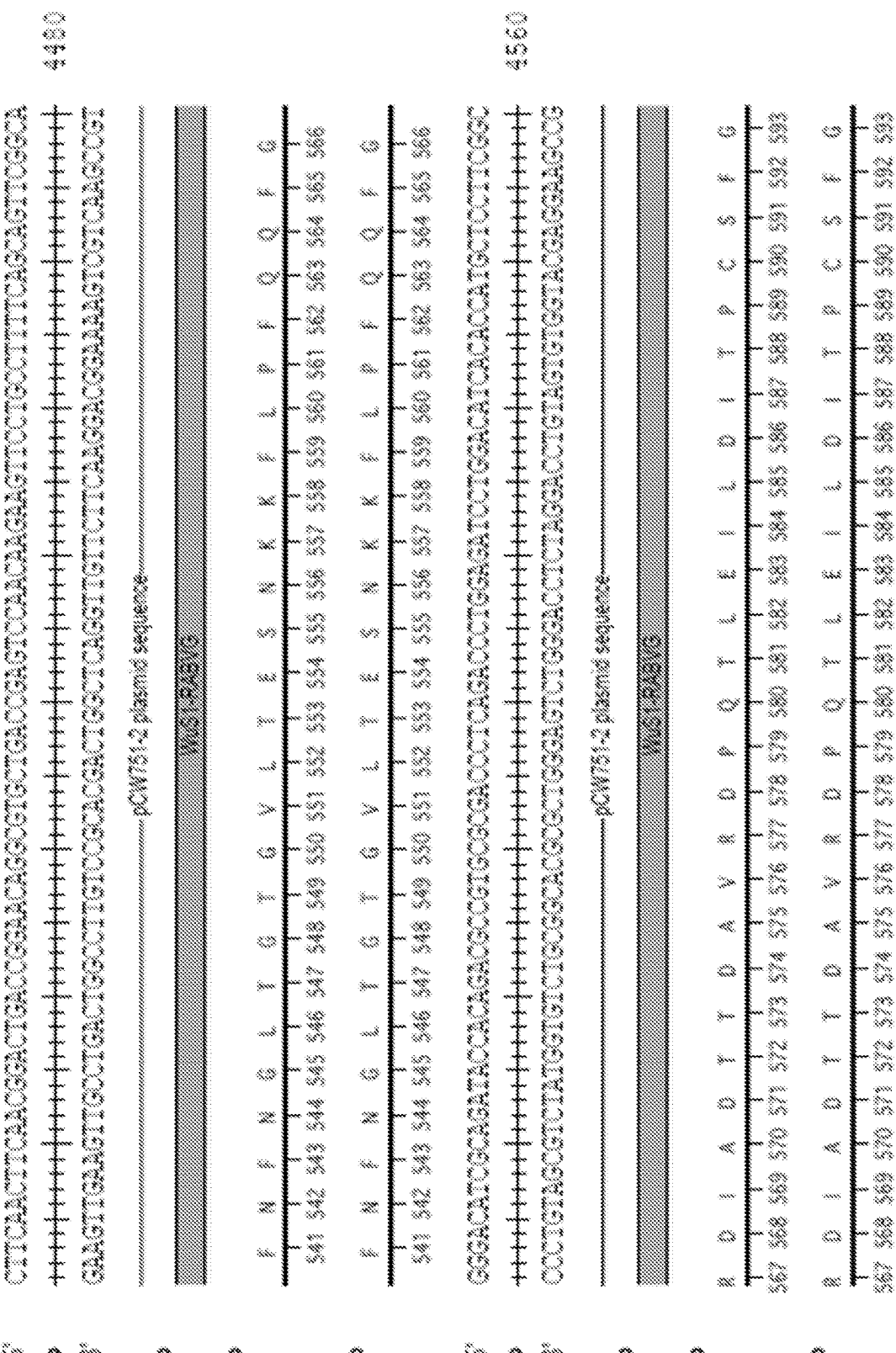
FIG. 18 – continued

FIG. 18 – continued

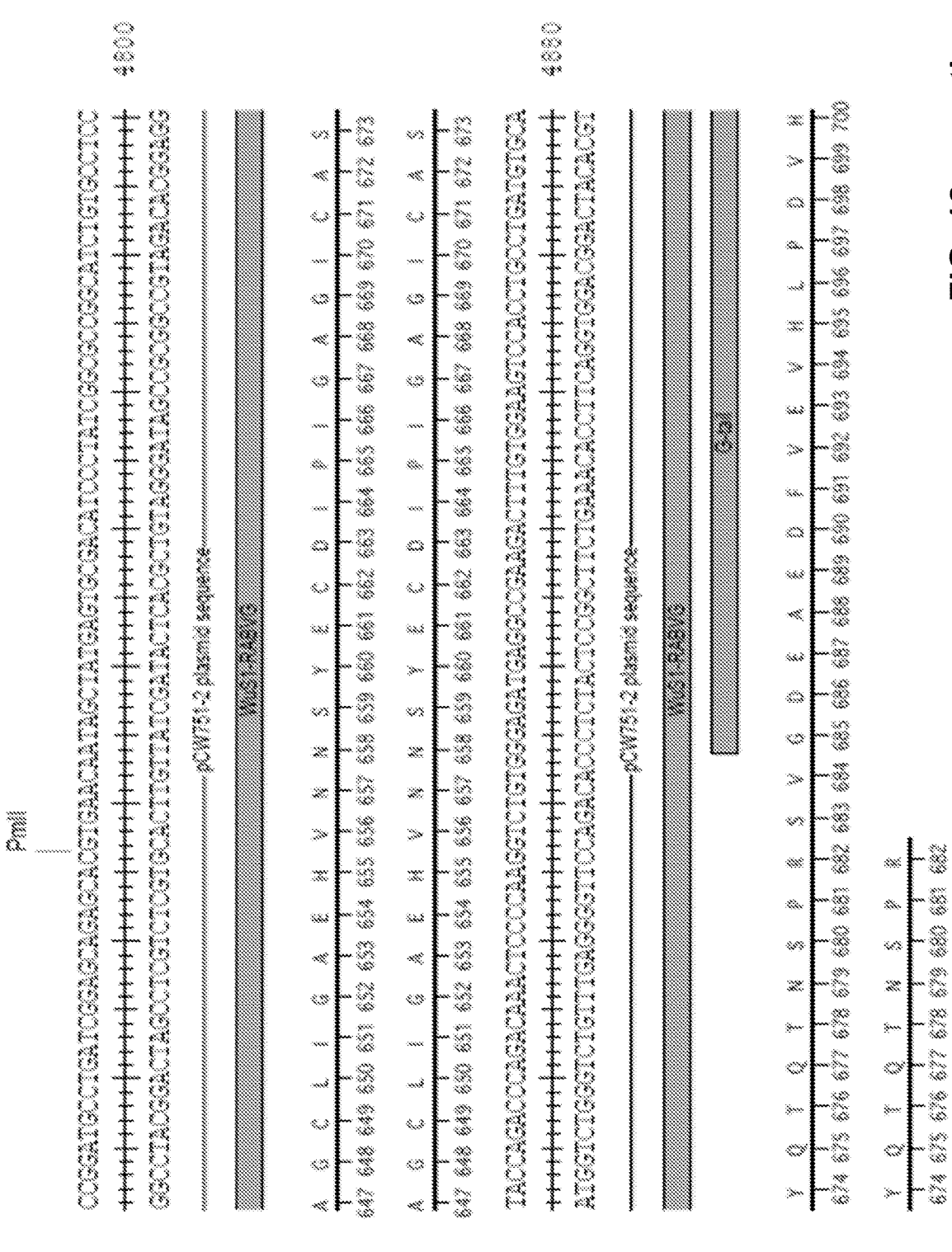
FIG. 18 – continued

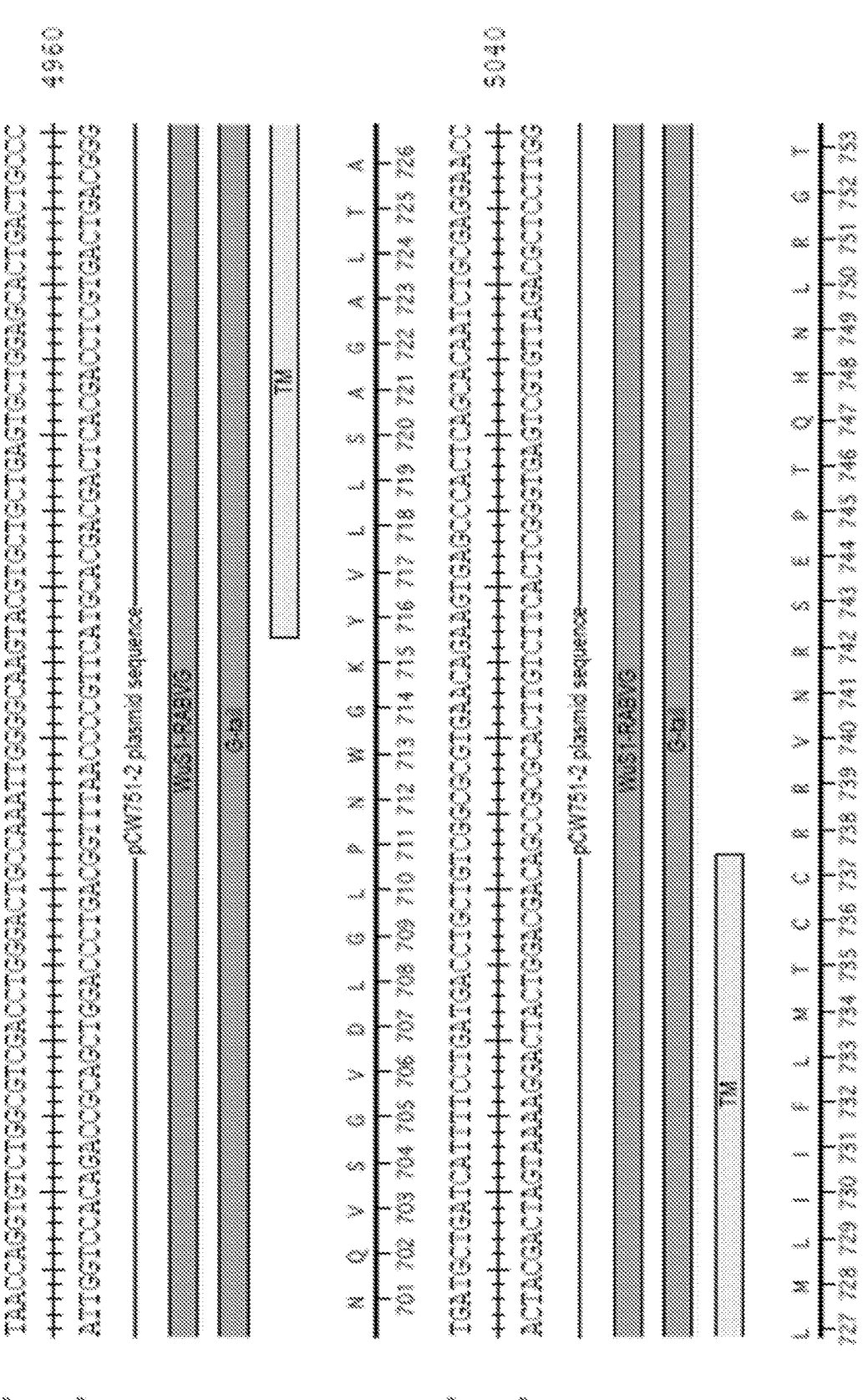
FIG. 18 – continued

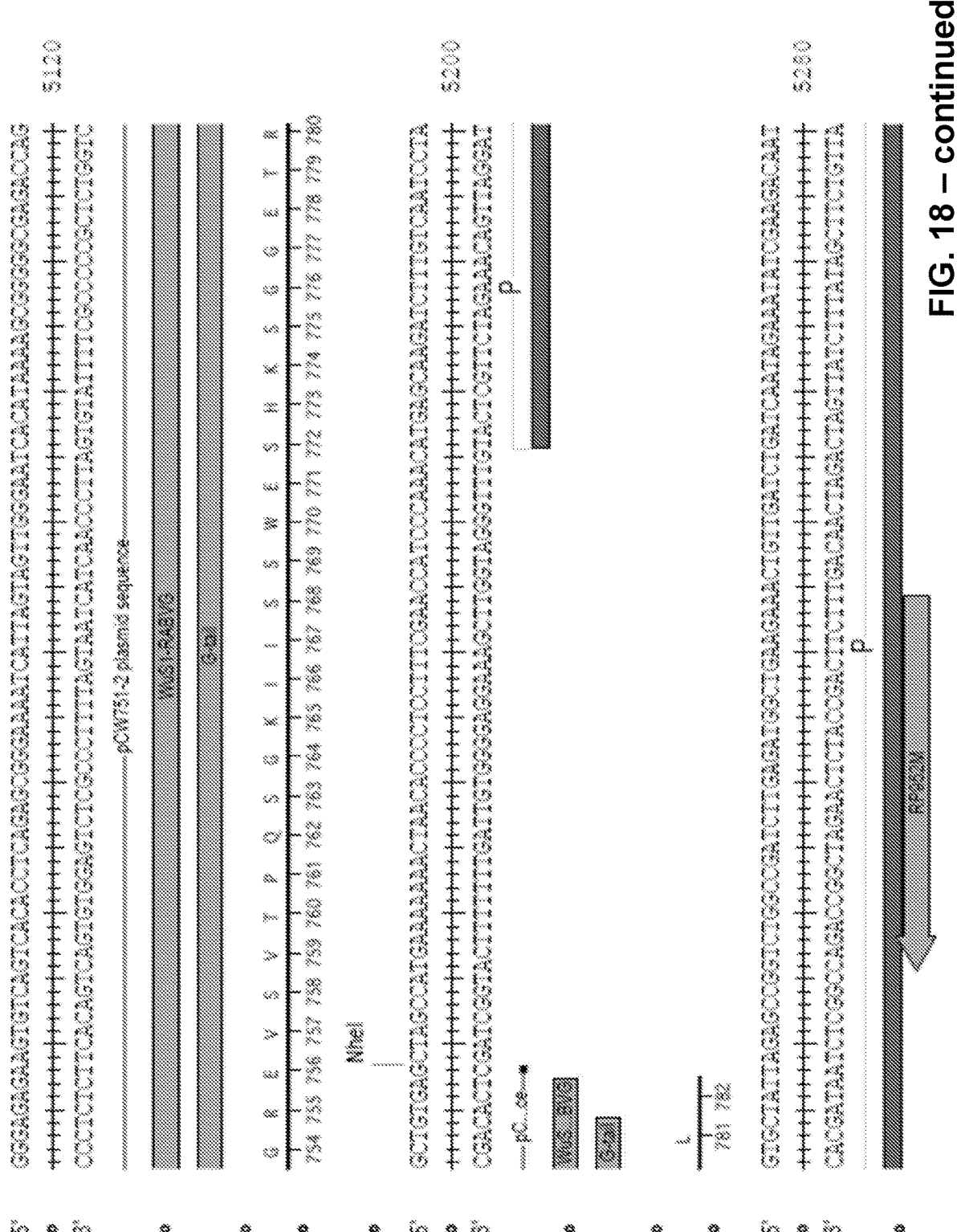
FIG. 18 – continued

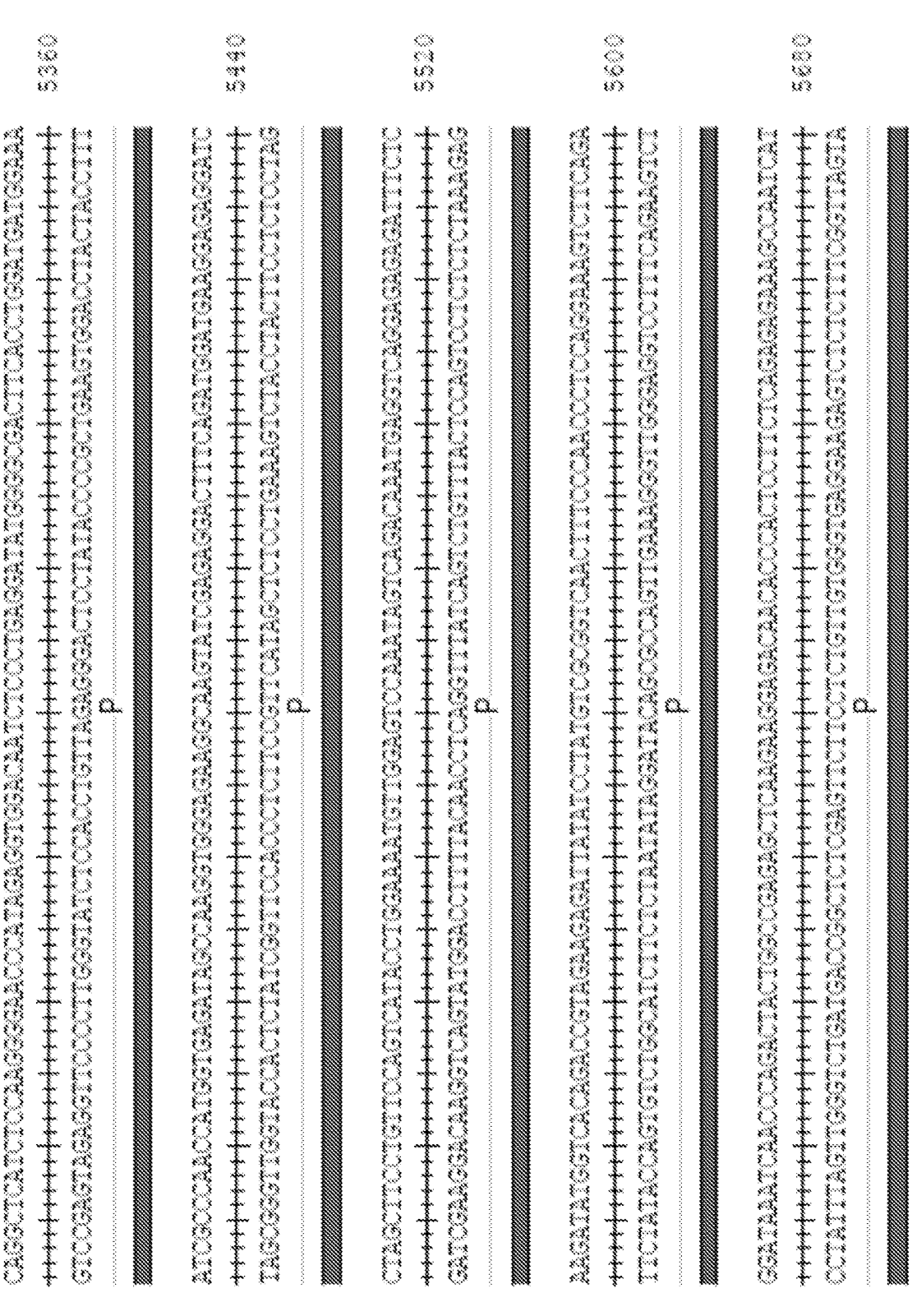
FIG. 18 – continued

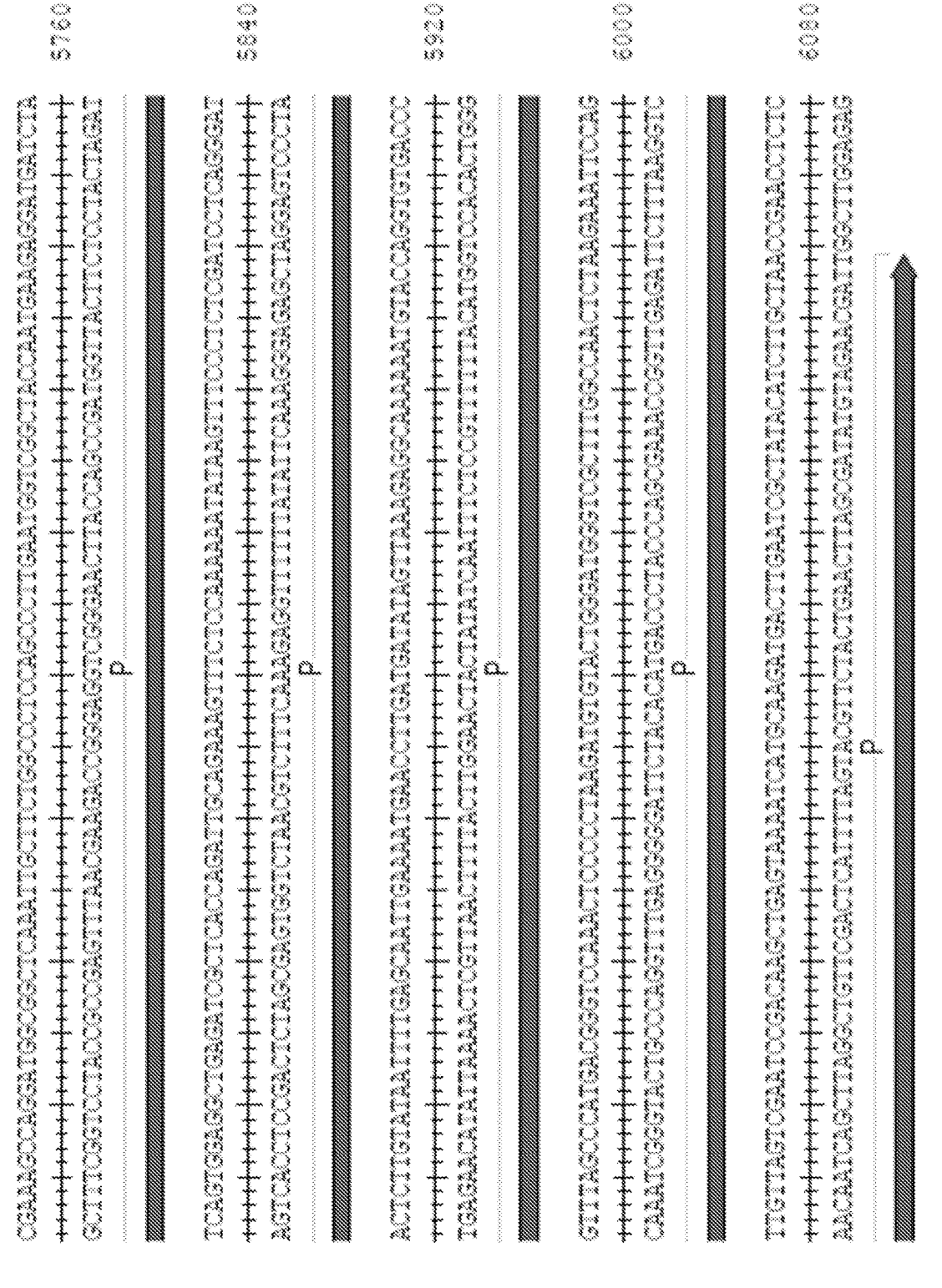
FIG. 18 – continued

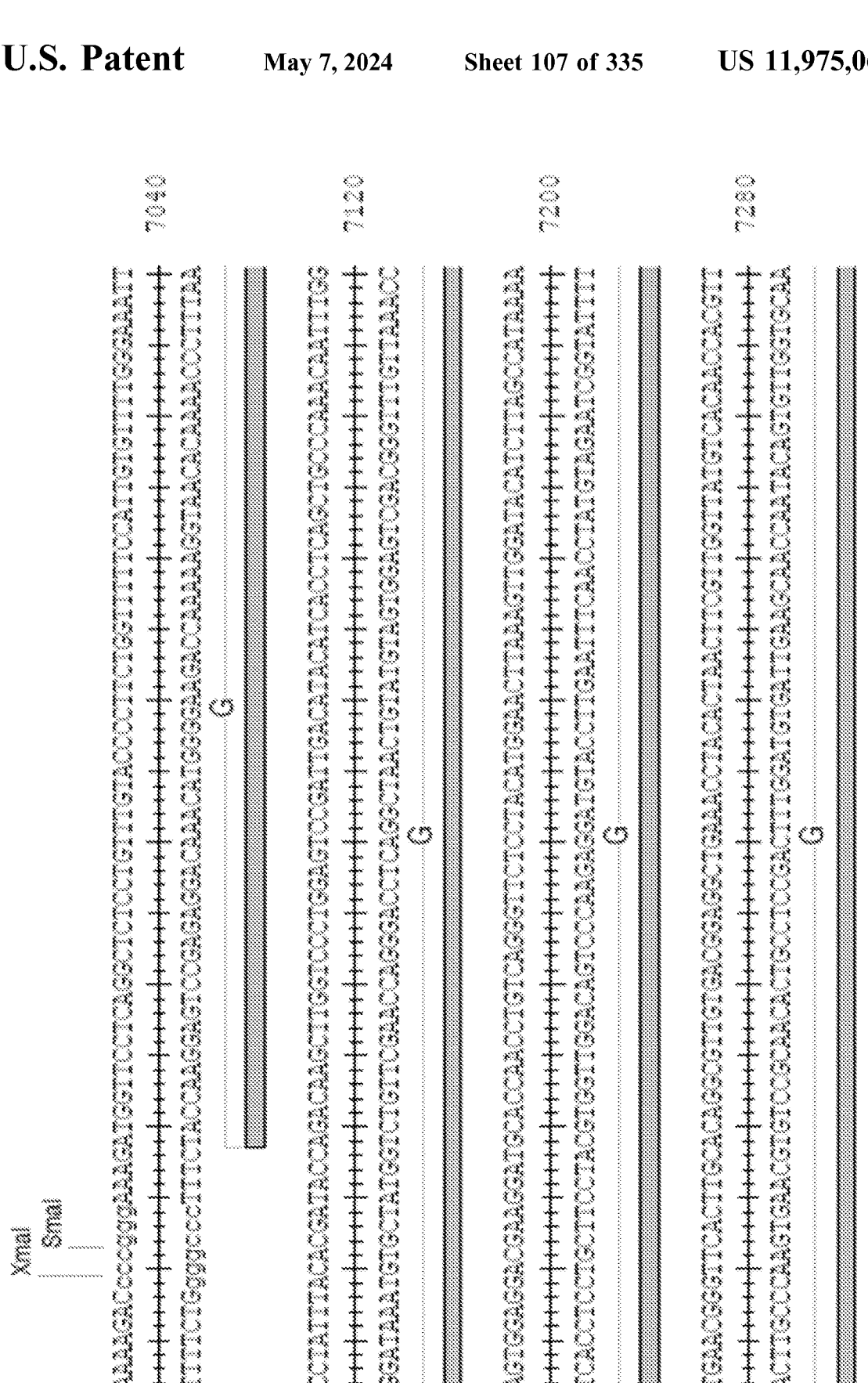
FIG. 18 – continued

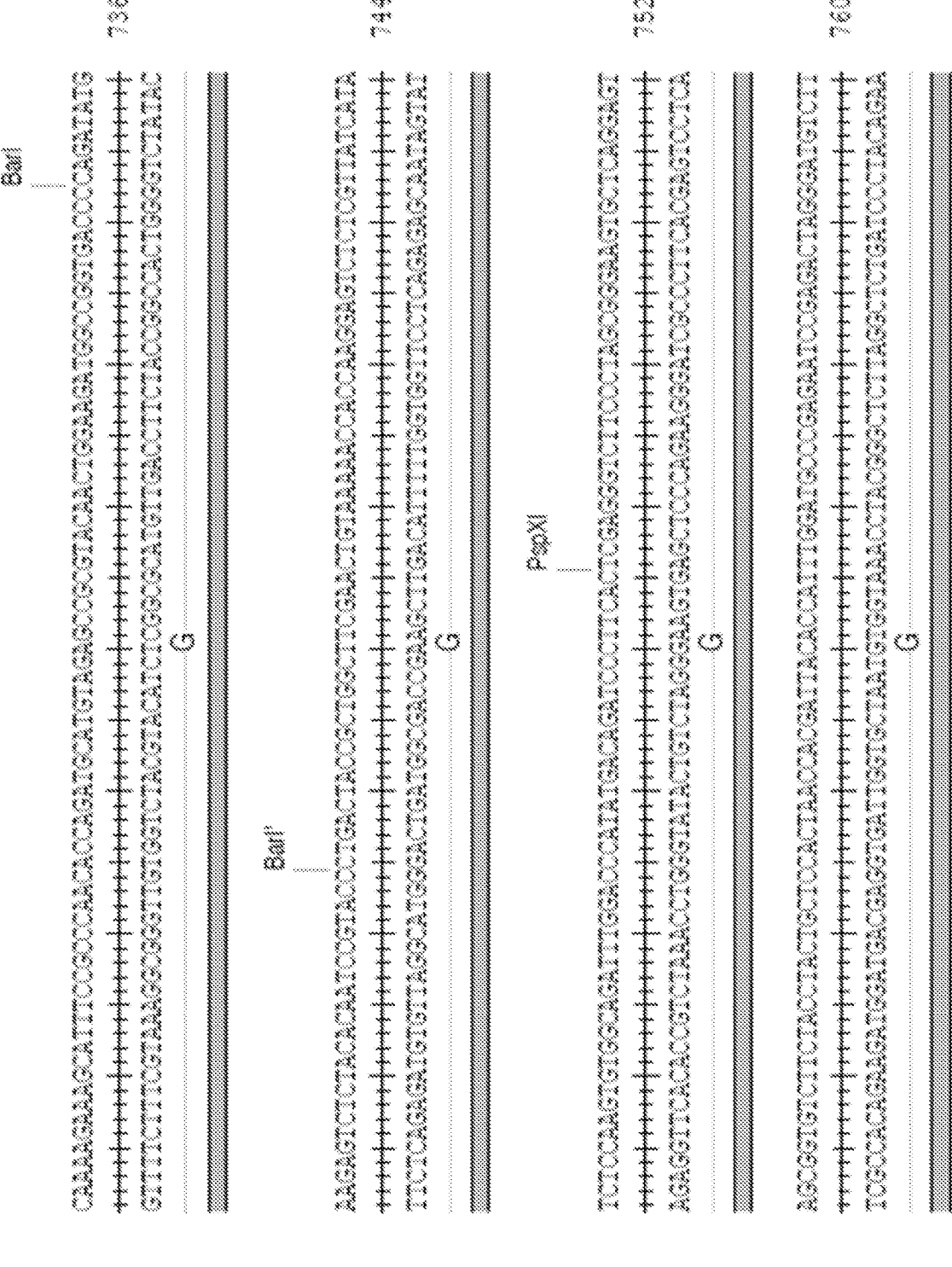
FIG. 18 – continued

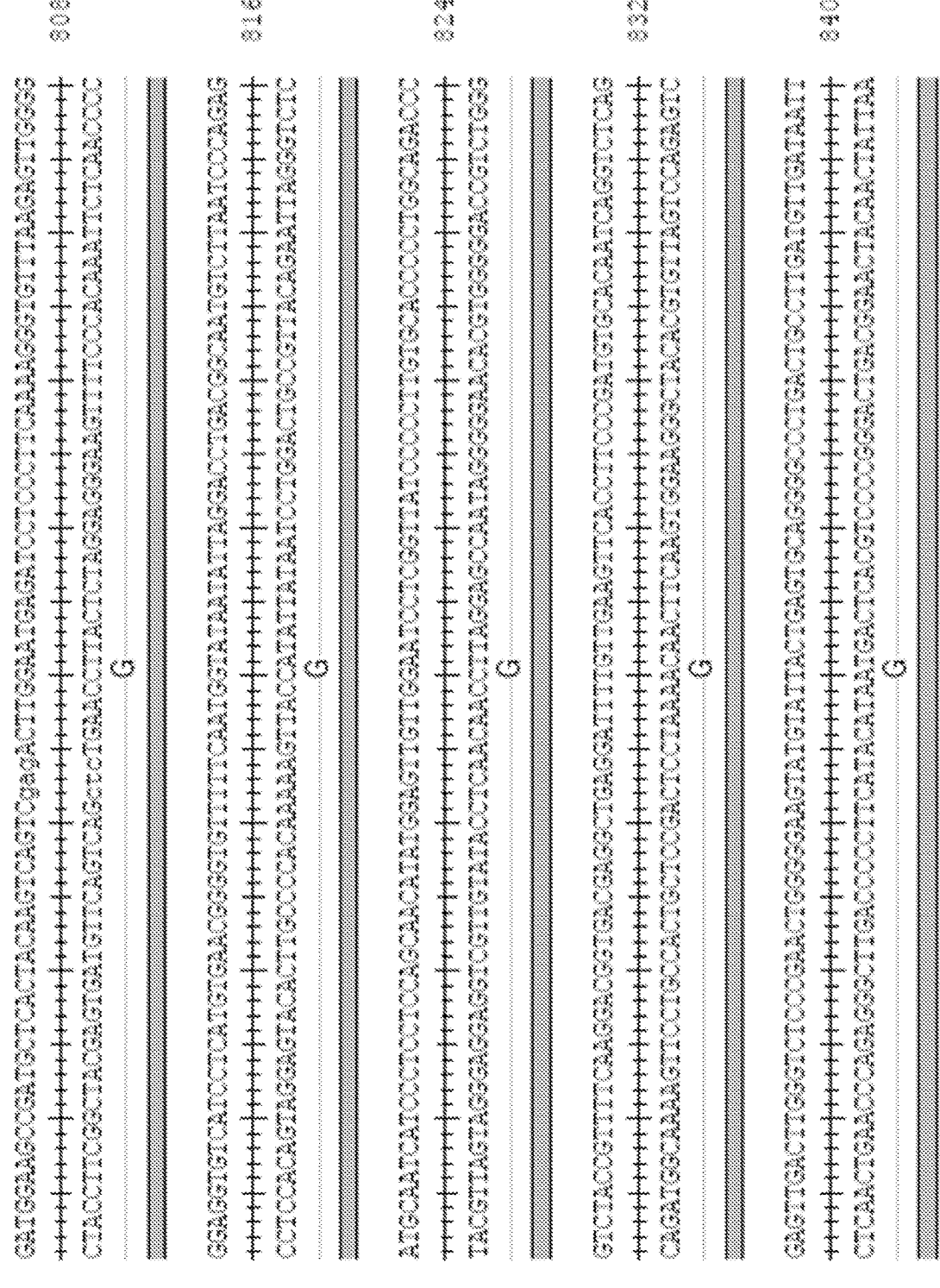
FIG. 18 – continued

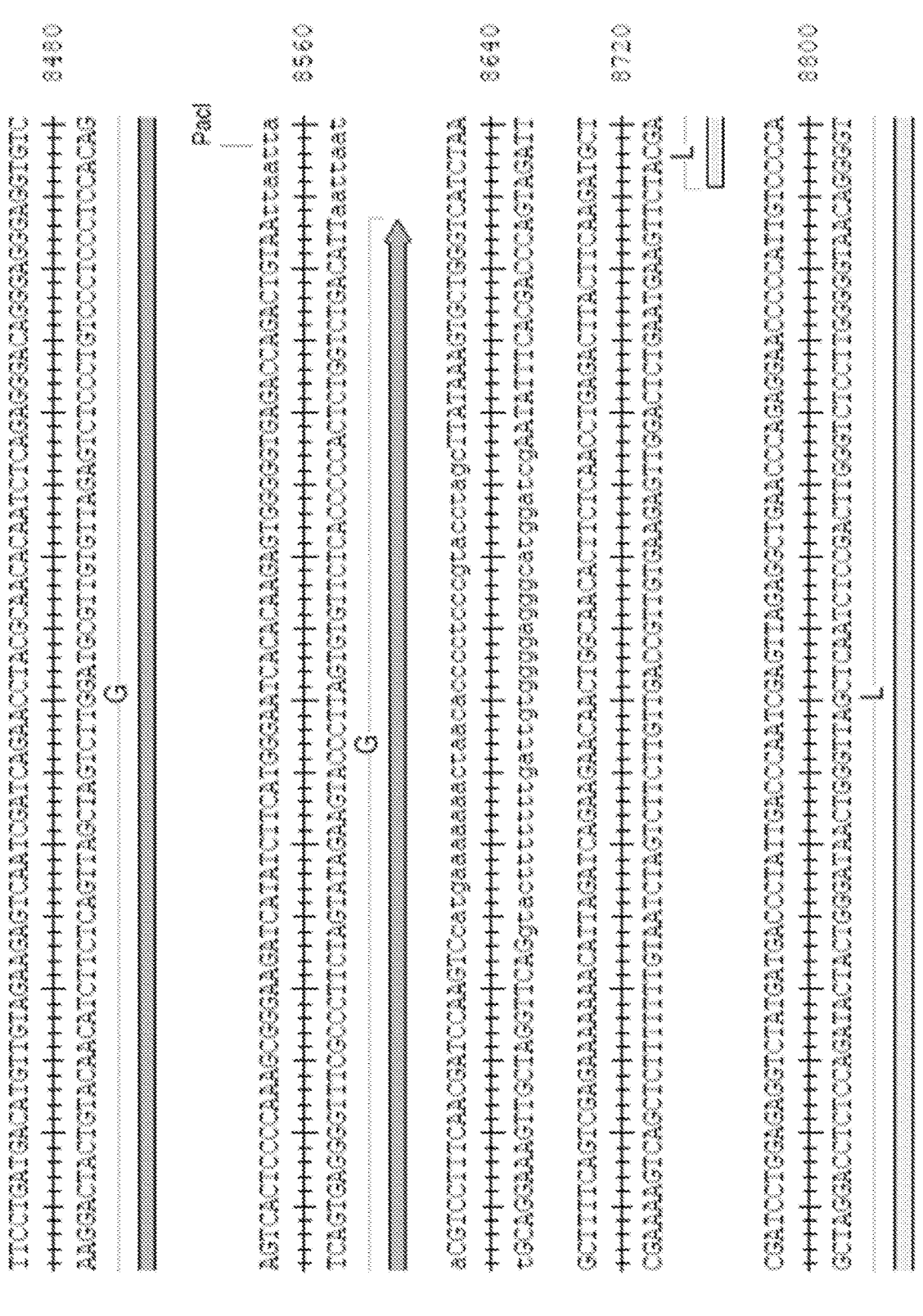
FIG. 18 – continued

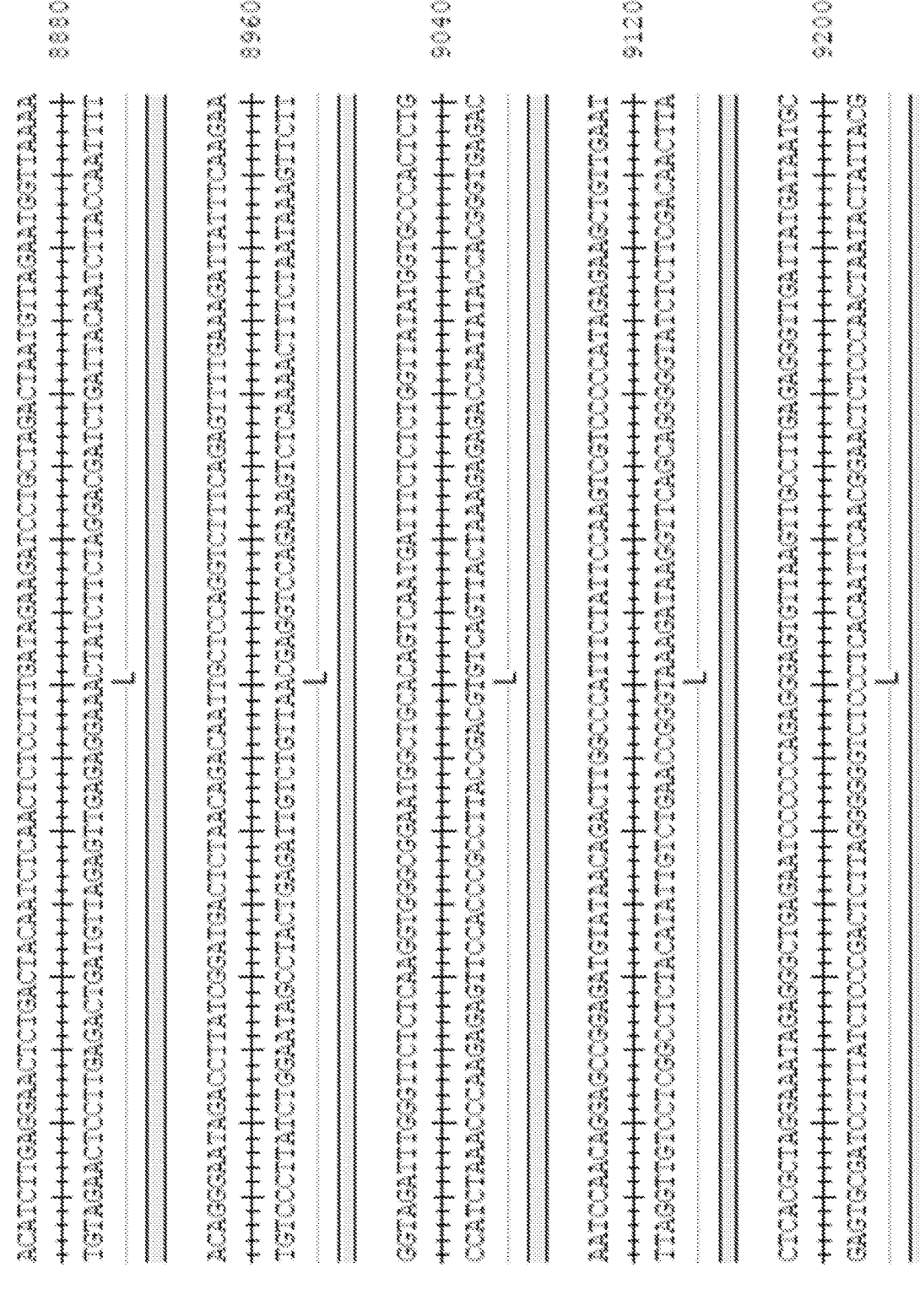
FIG. 18 – continued

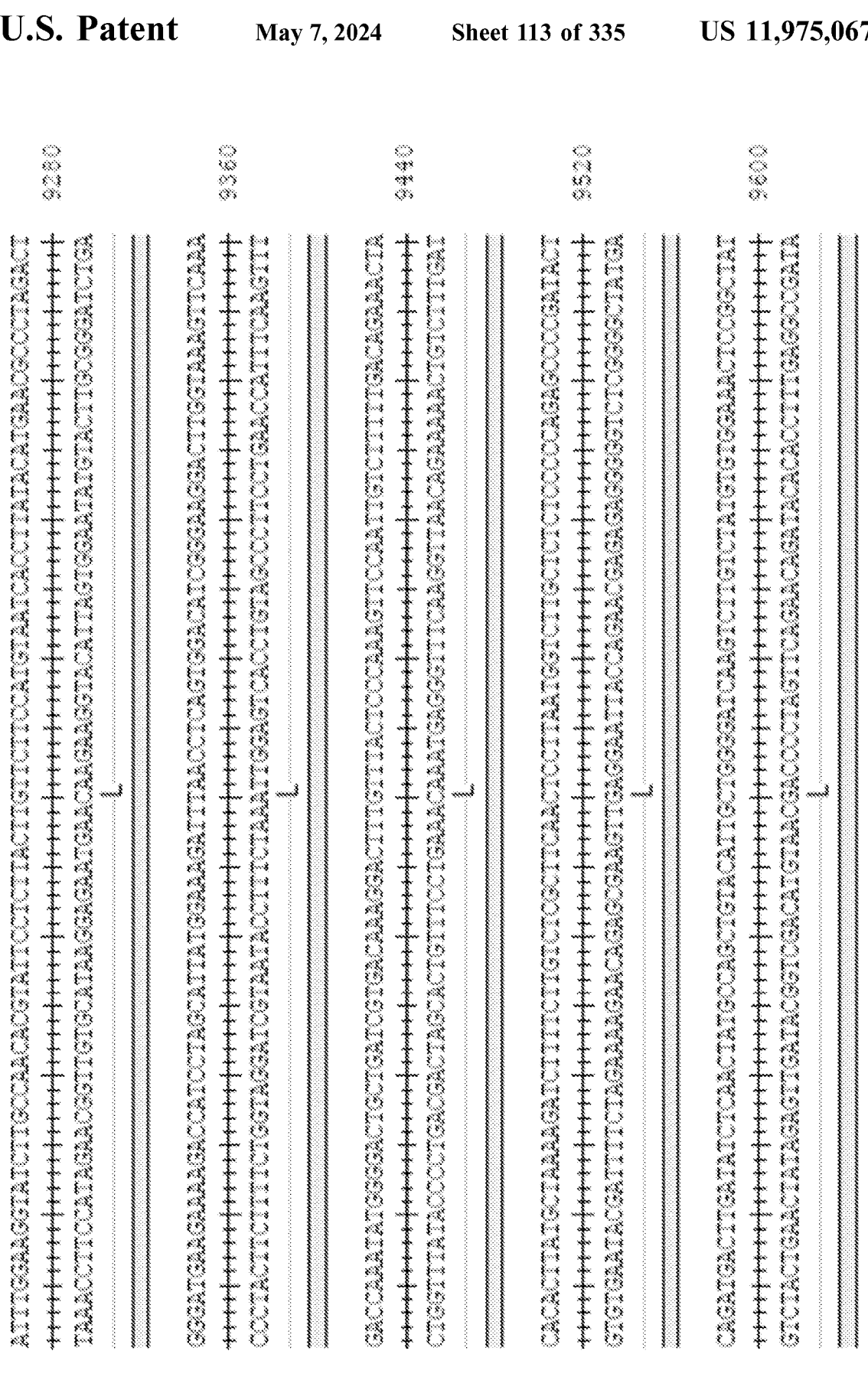
FIG. 18 – continued

FIG. 18 – continued

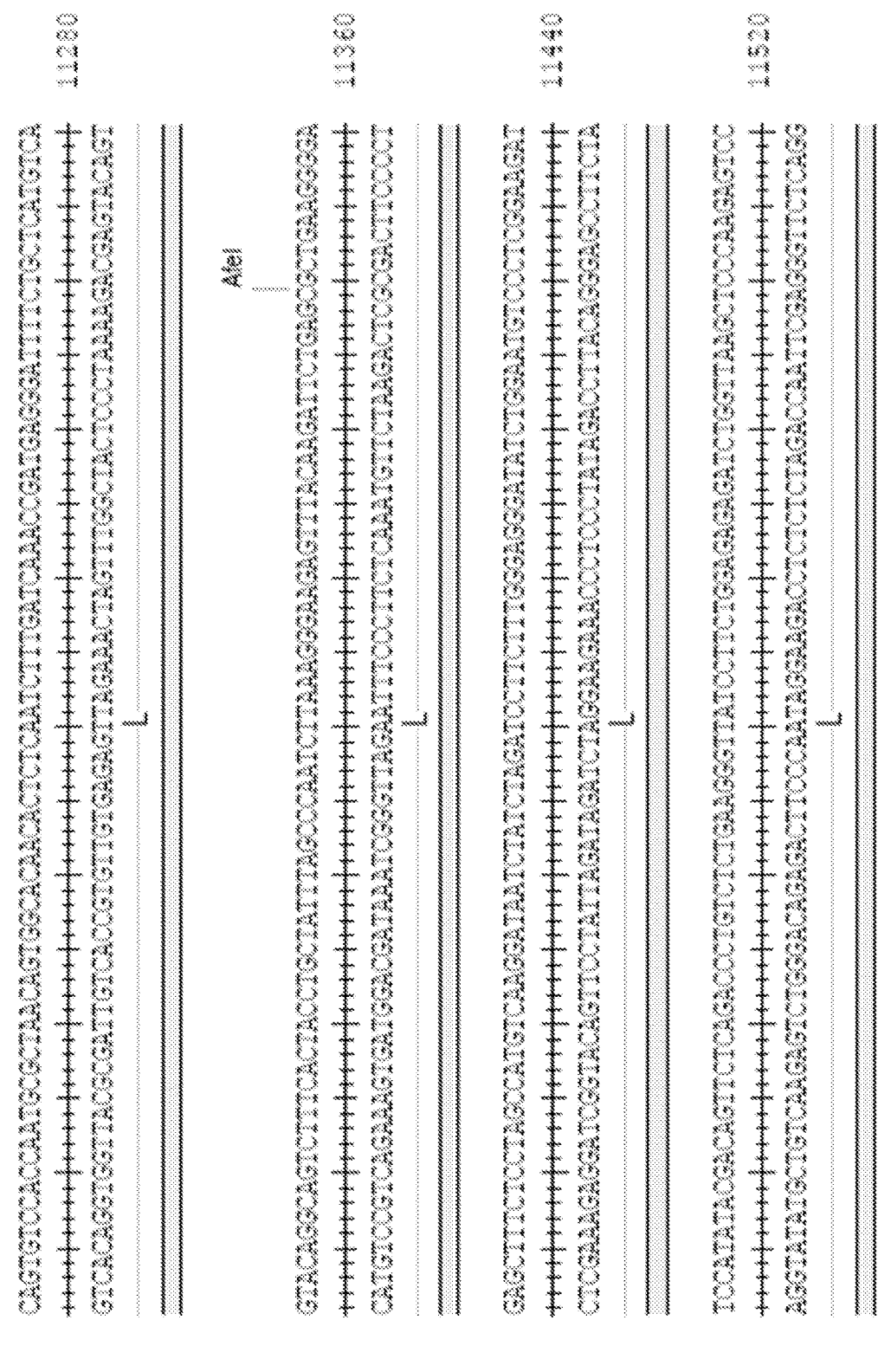
FIG. 18 – continued

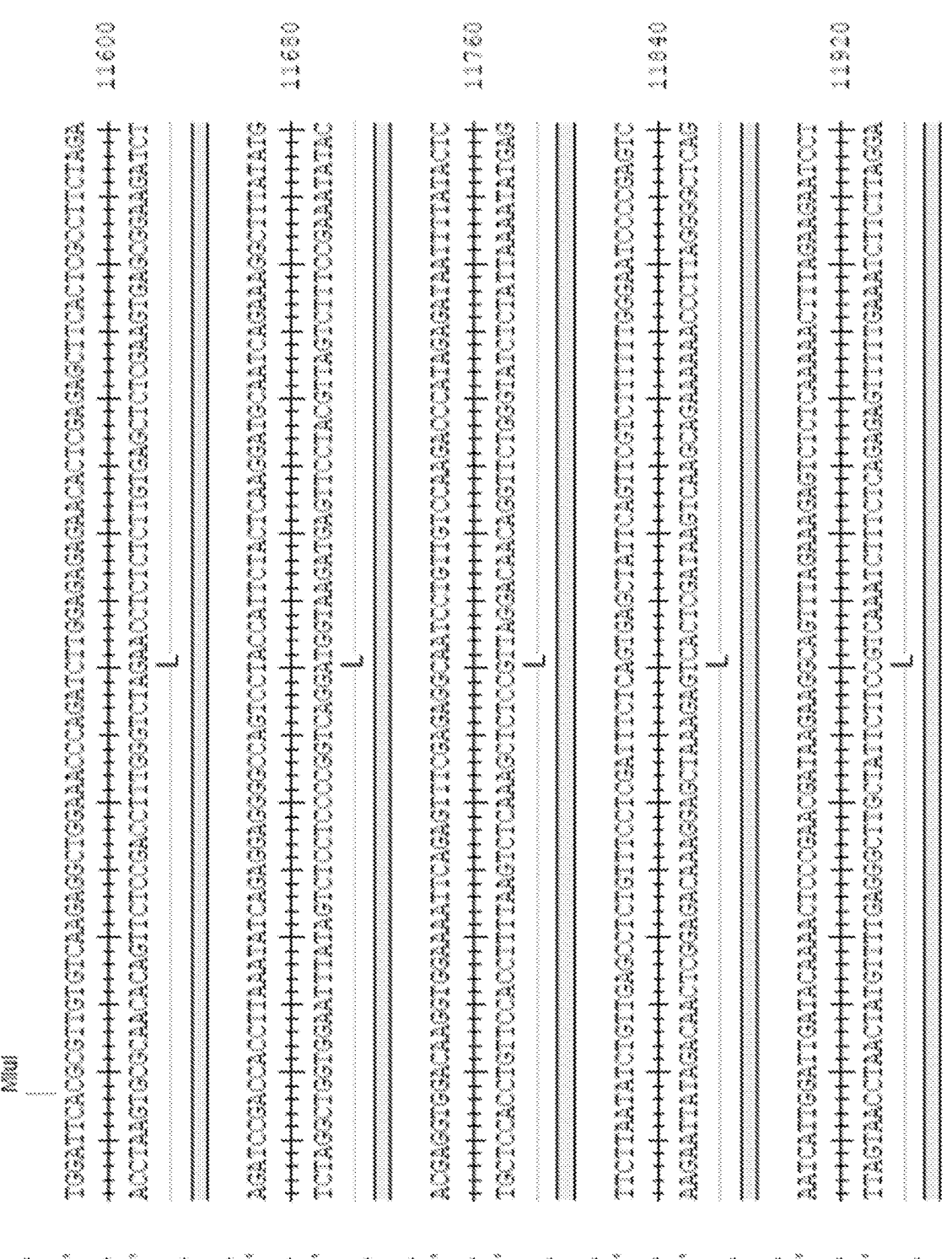
FIG. 18 – continued

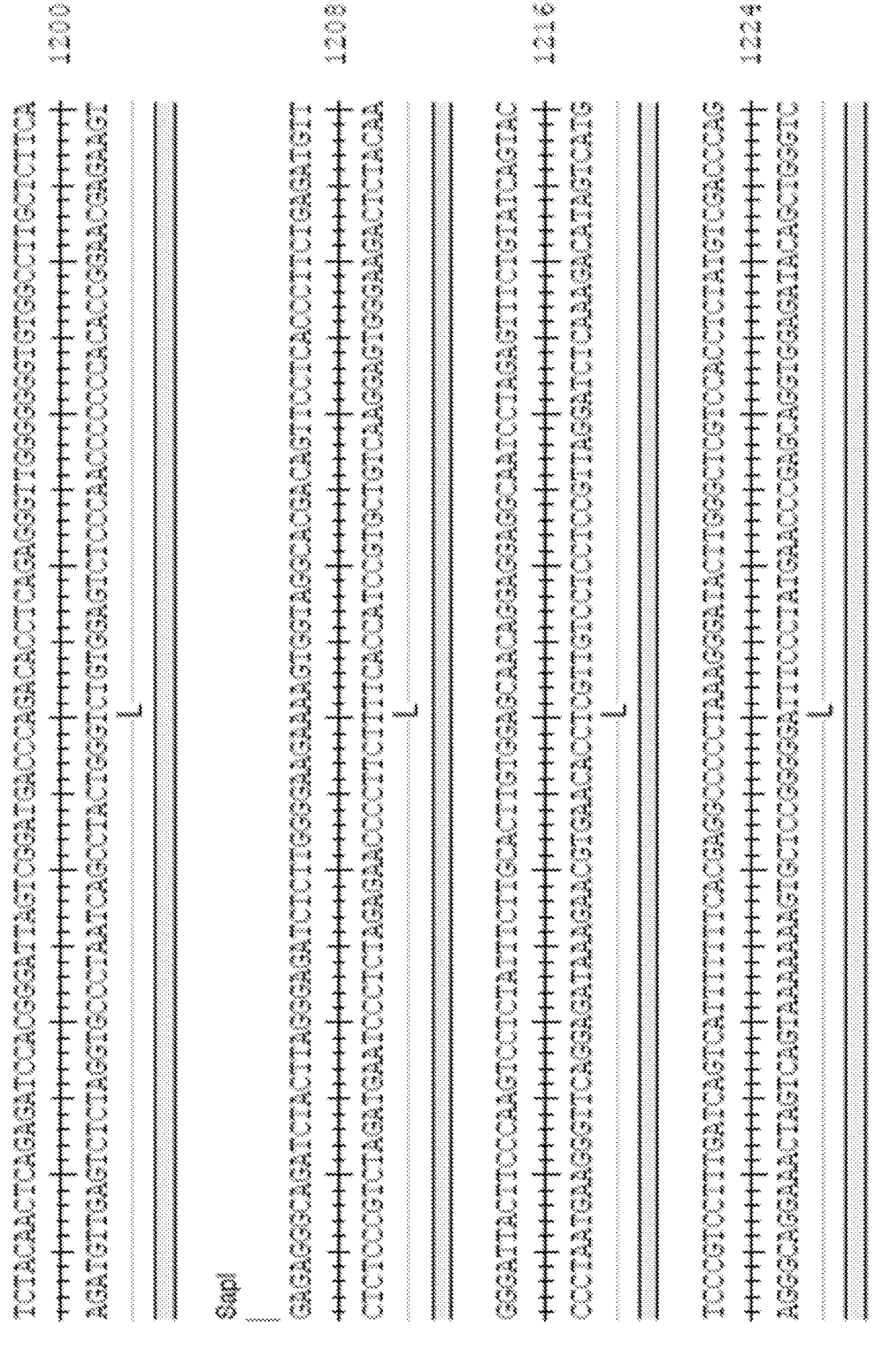
FIG. 18 – continued

FIG. 18 – continued

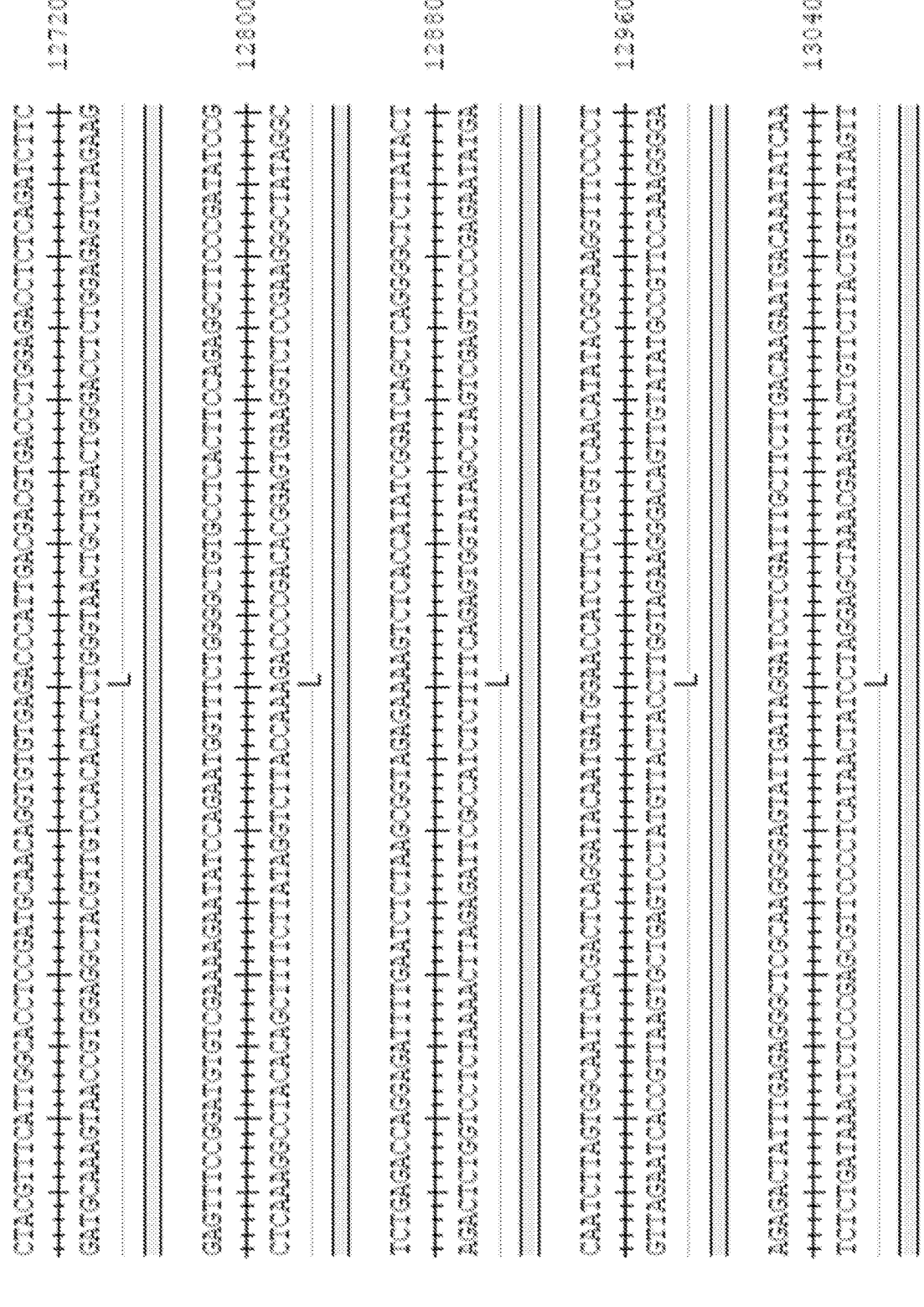
FIG. 18 – continued

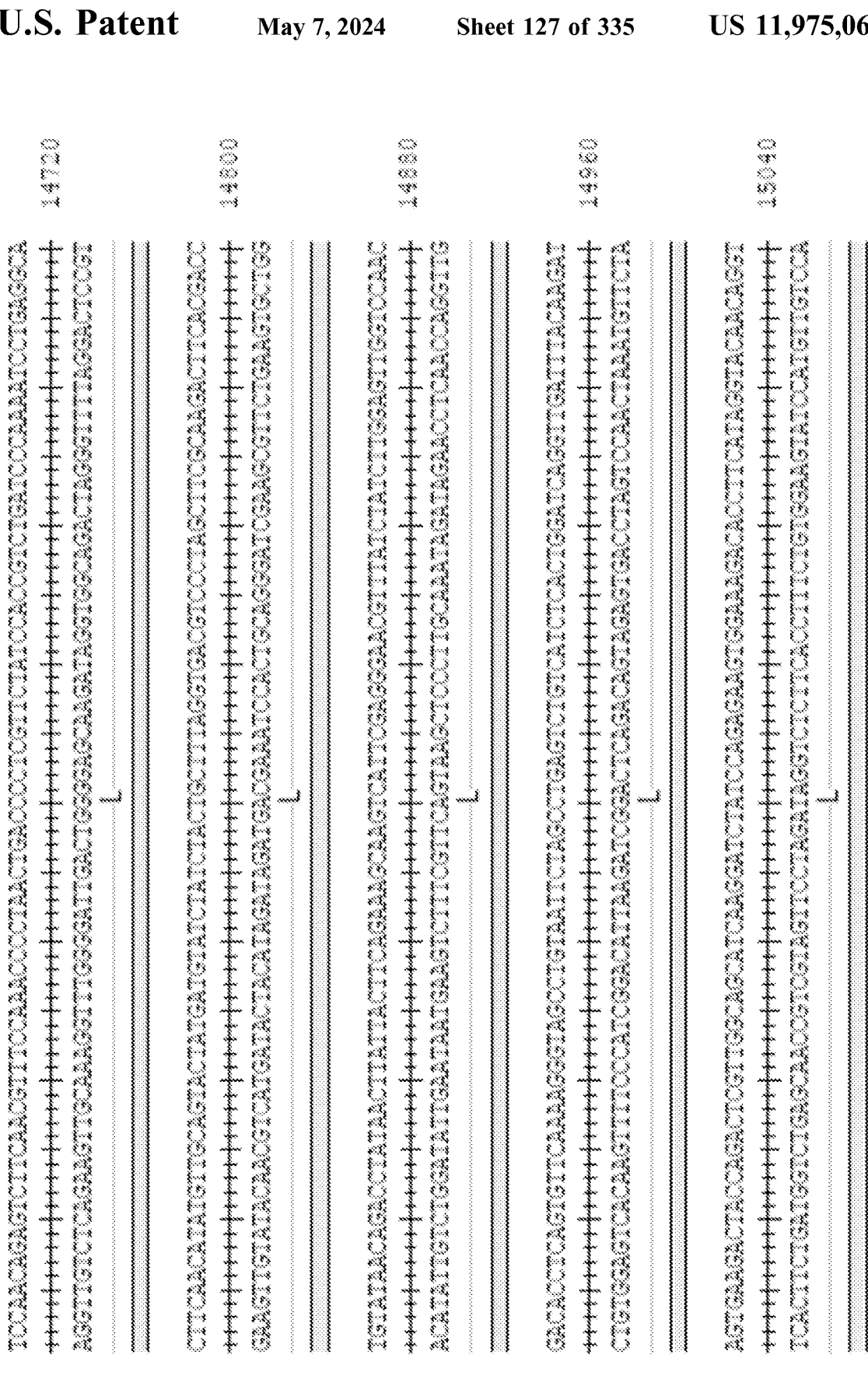
FIG. 18 – continued

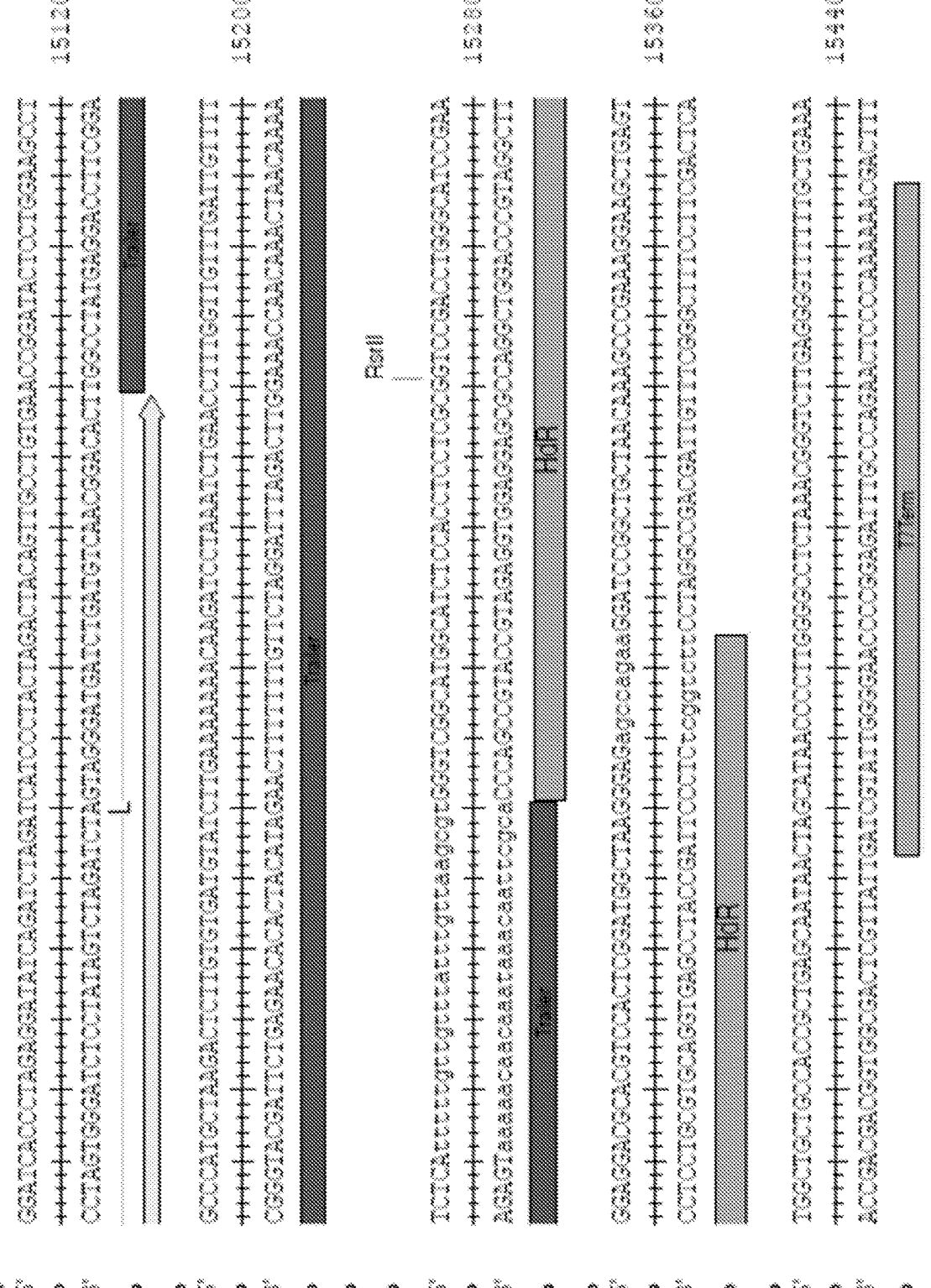
FIG. 18 – continued

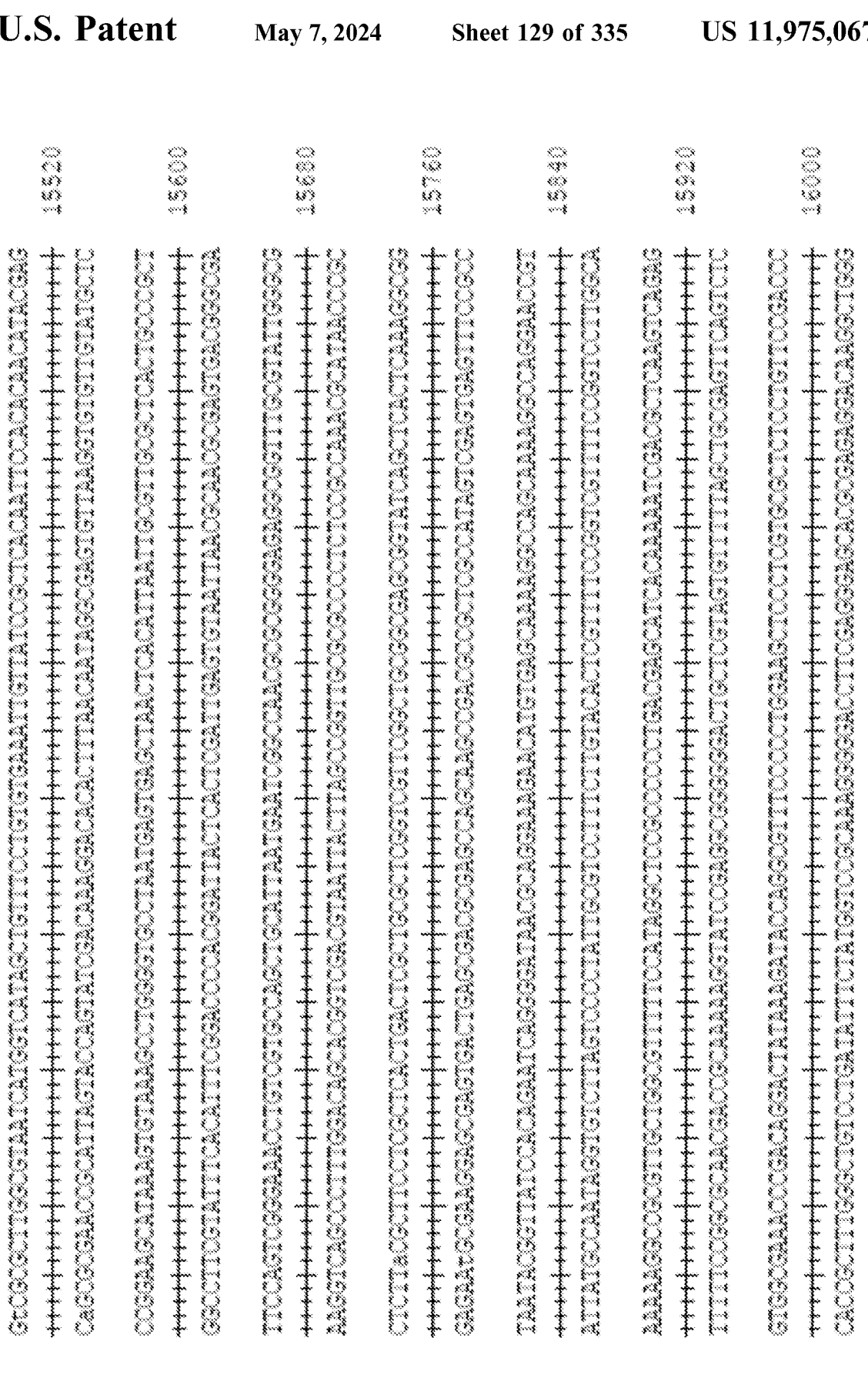
FIG. 18 – continued

FIG. 18 – continued

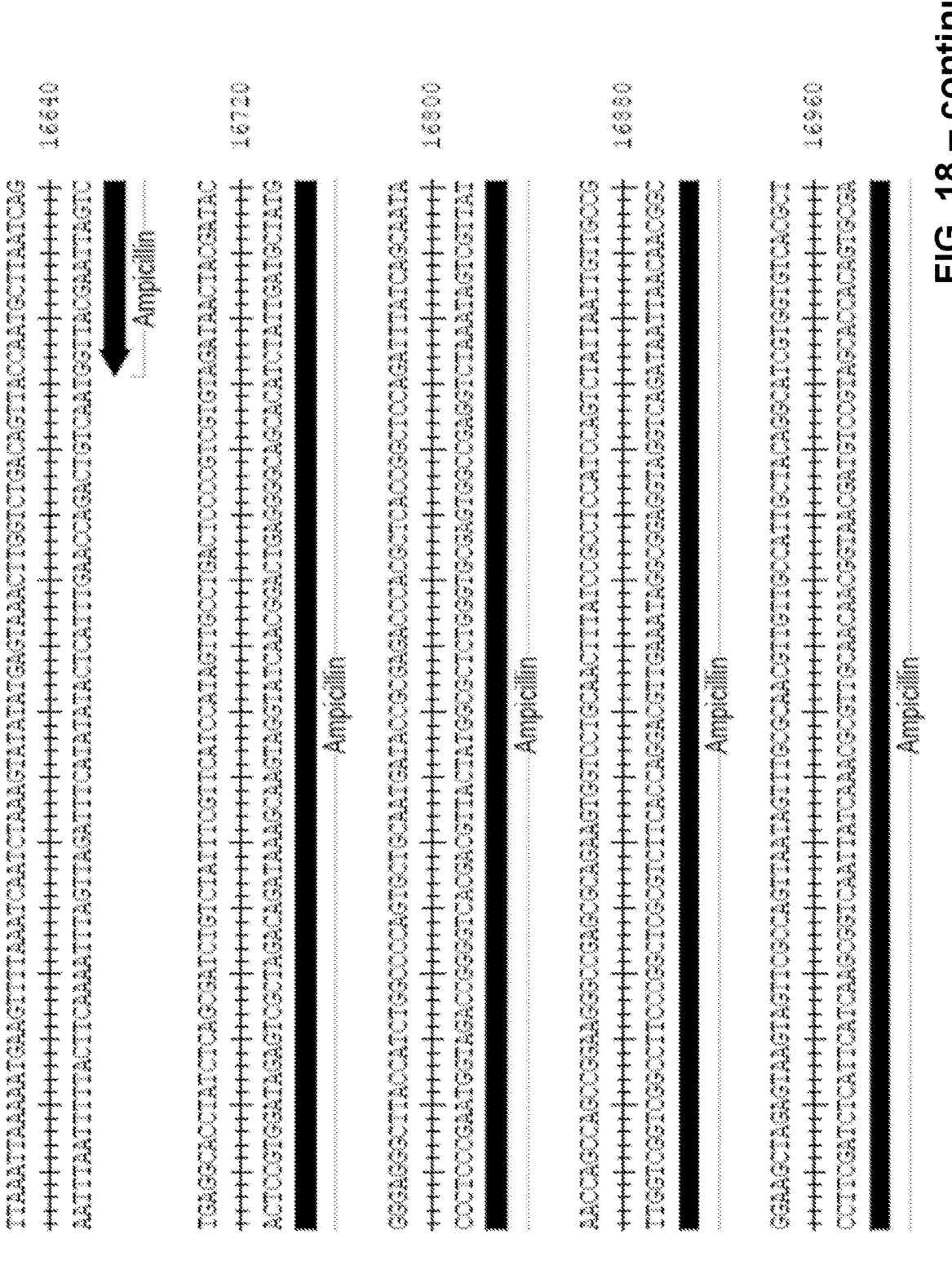
FIG. 18 – continued

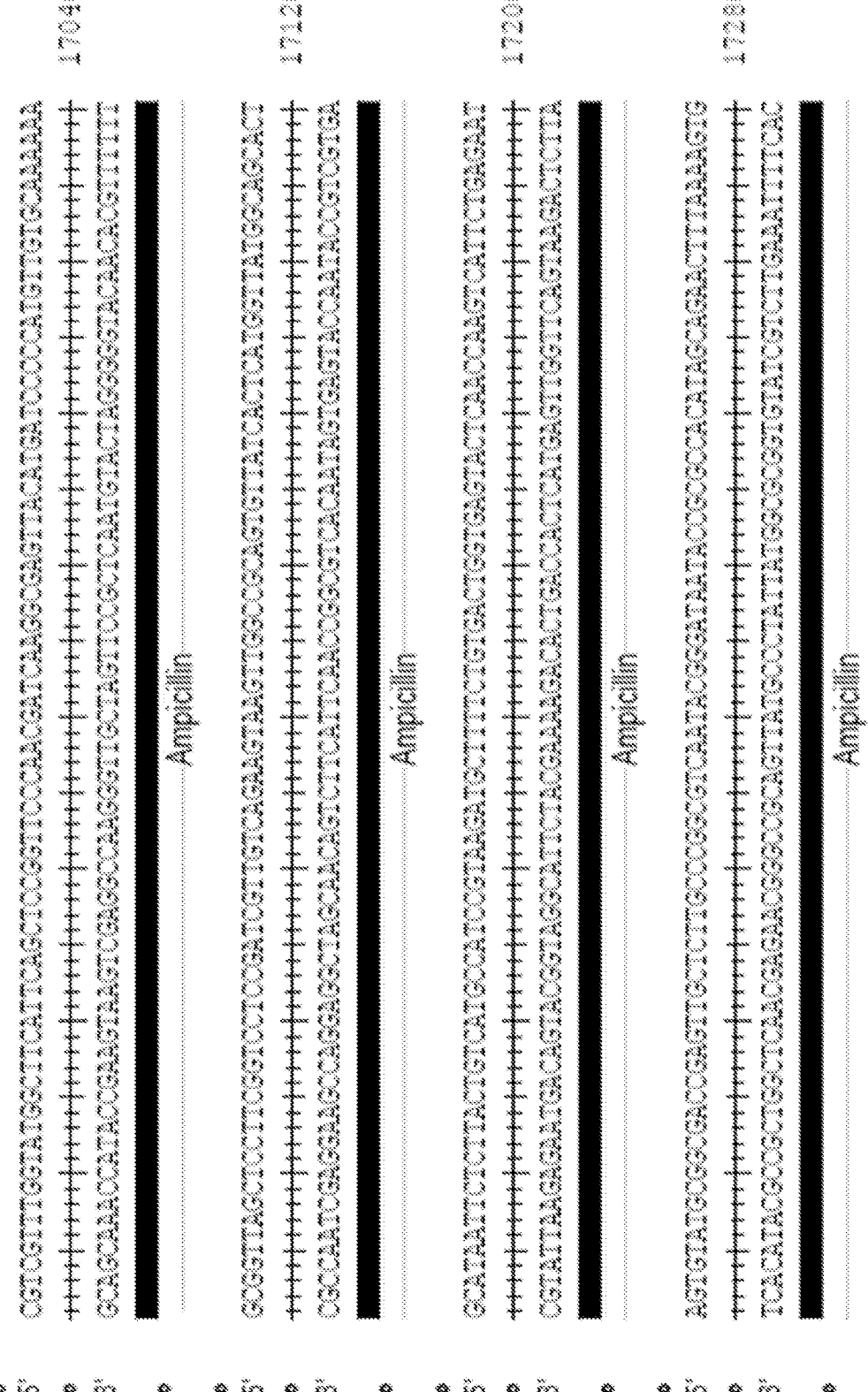
FIG. 18 – continued

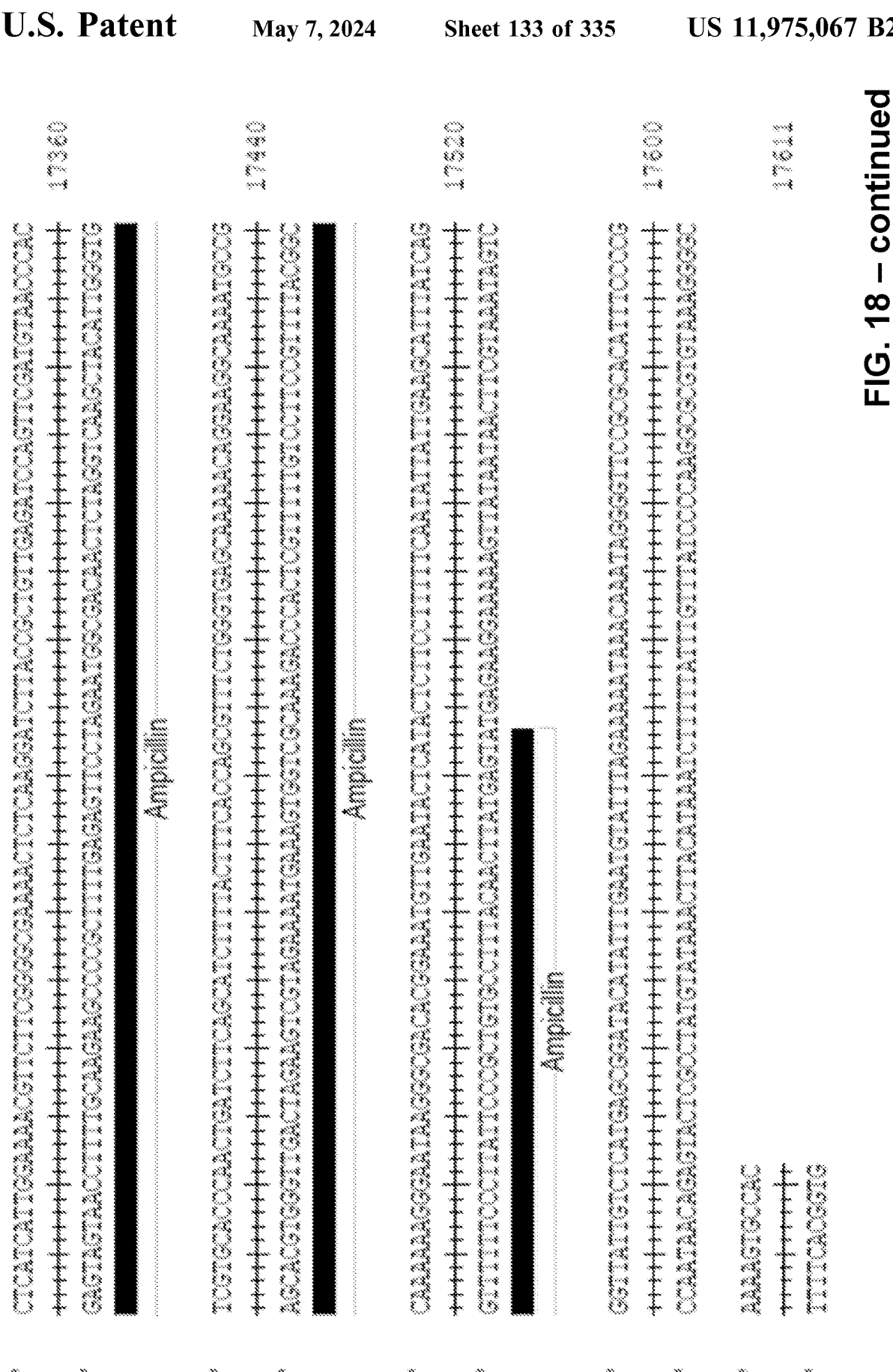
FIG. 18 – continued

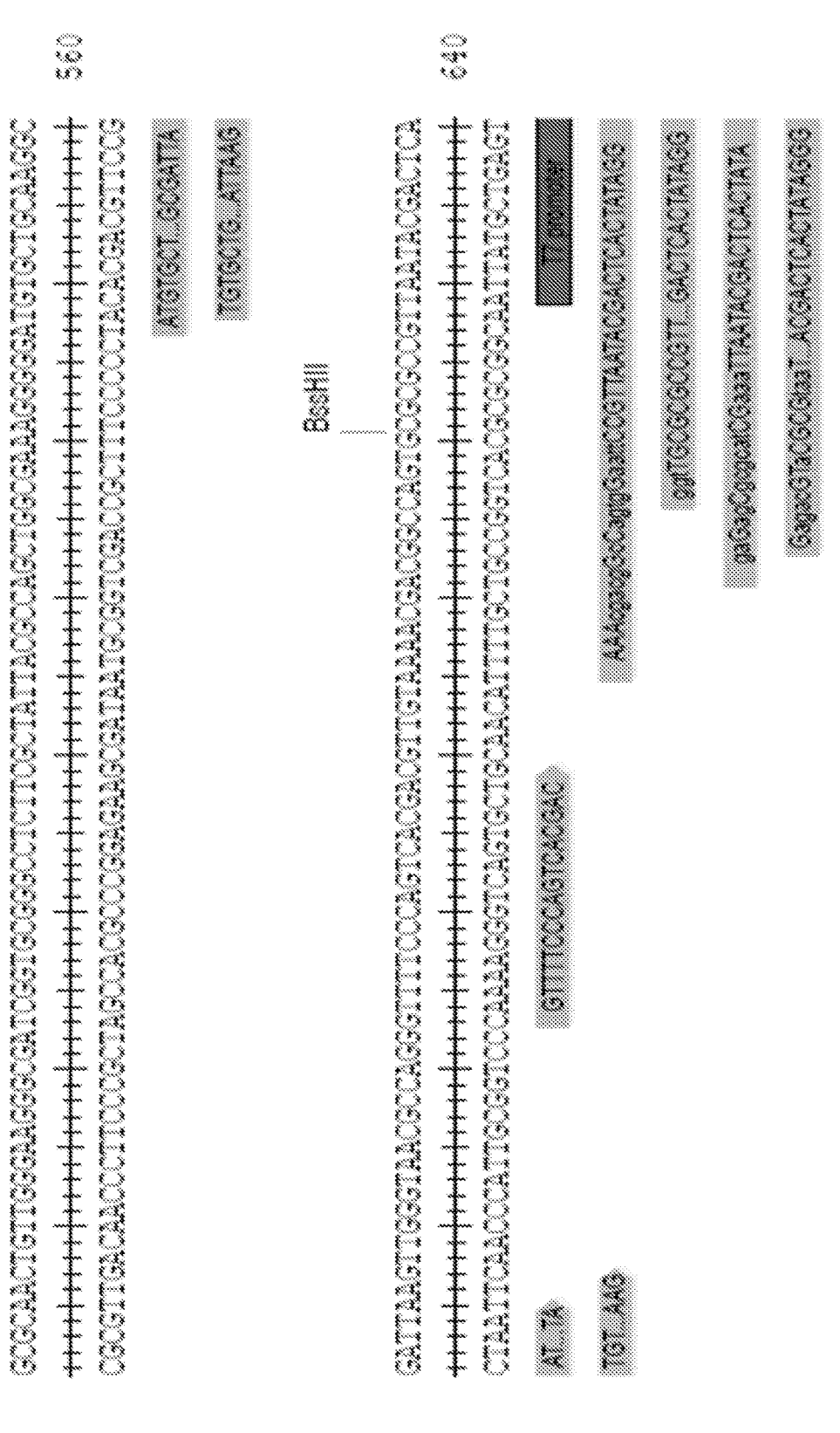
FIG. 19 – continued

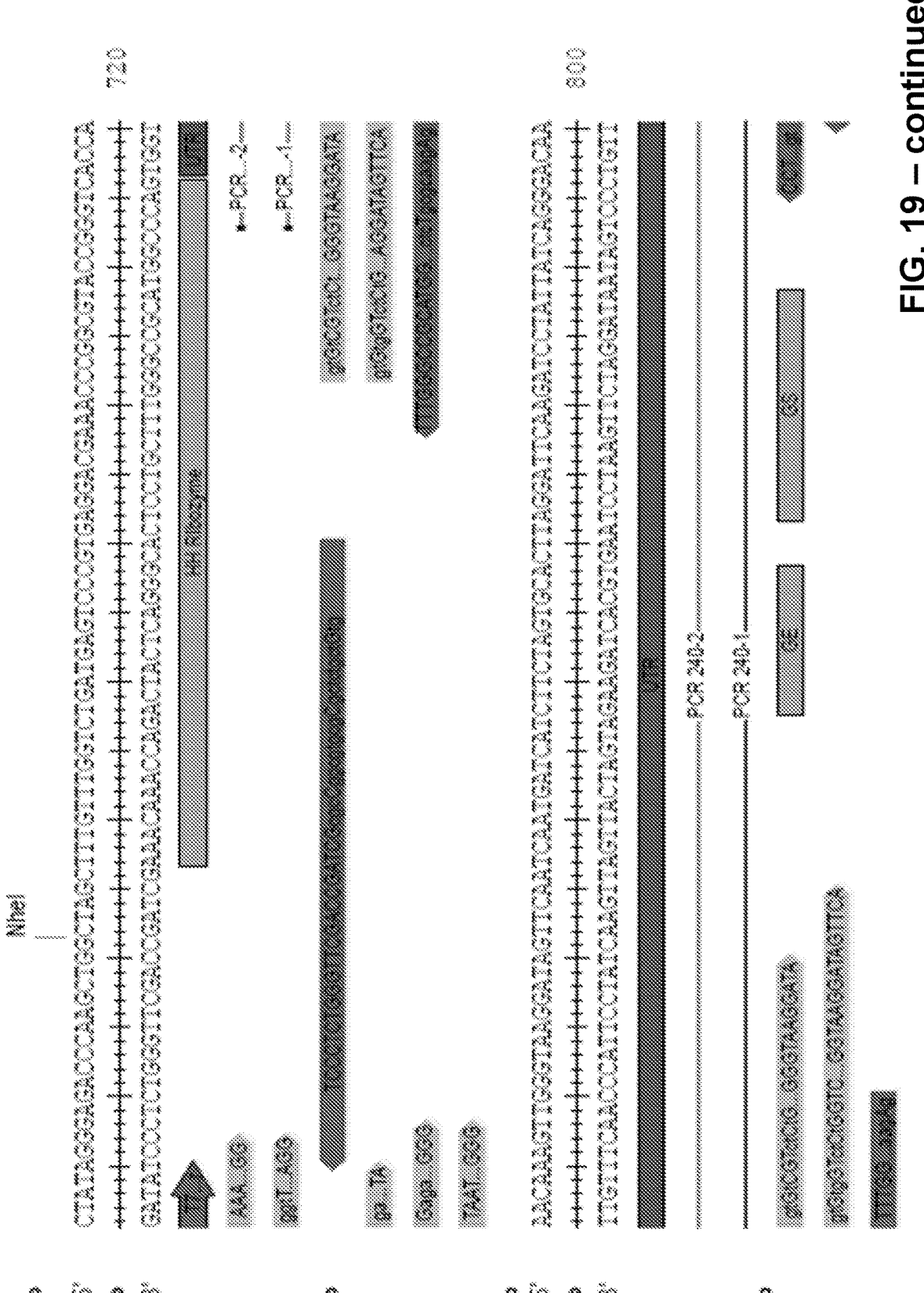
FIG. 19 – continued

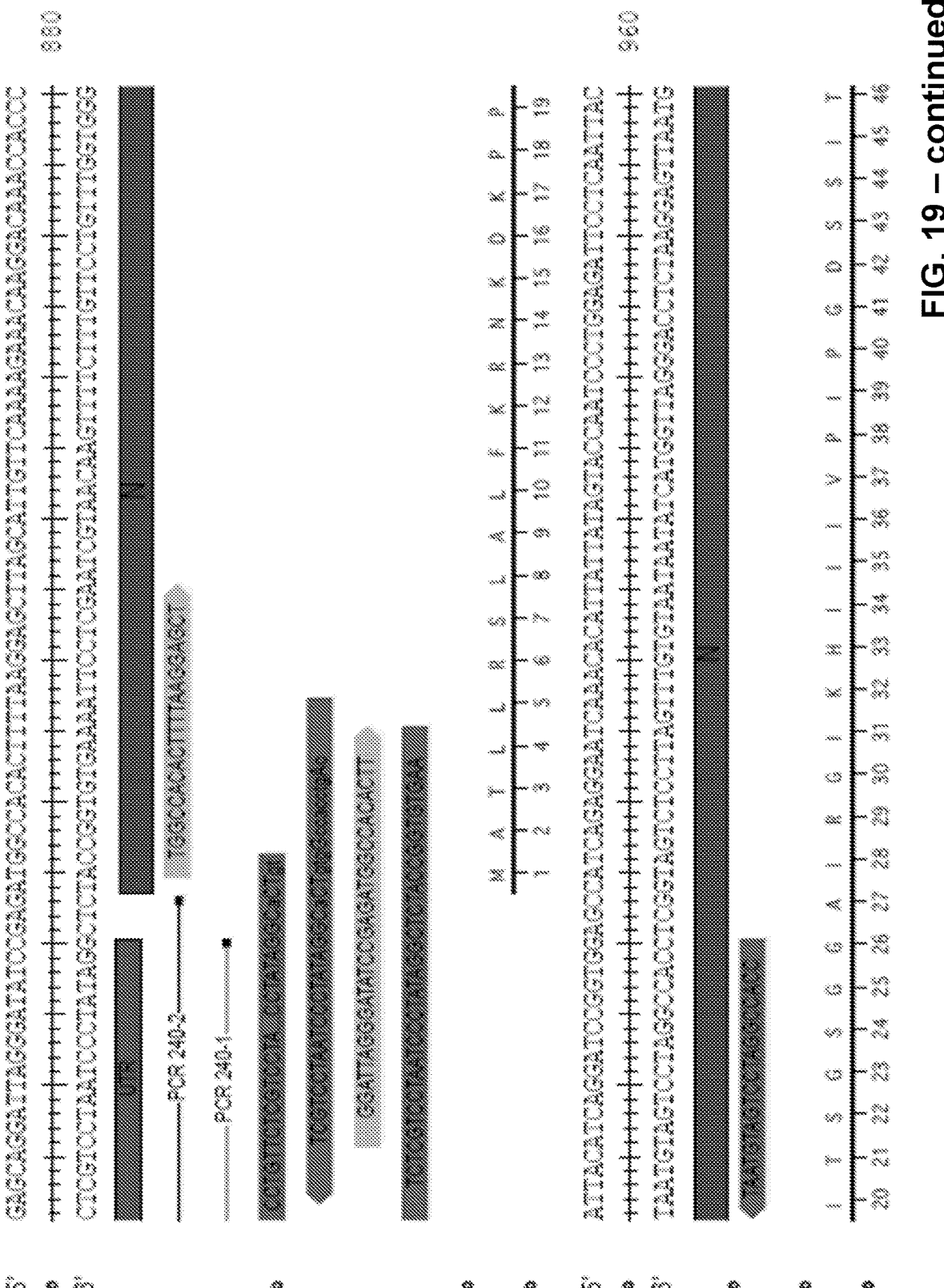
FIG. 19 – continued

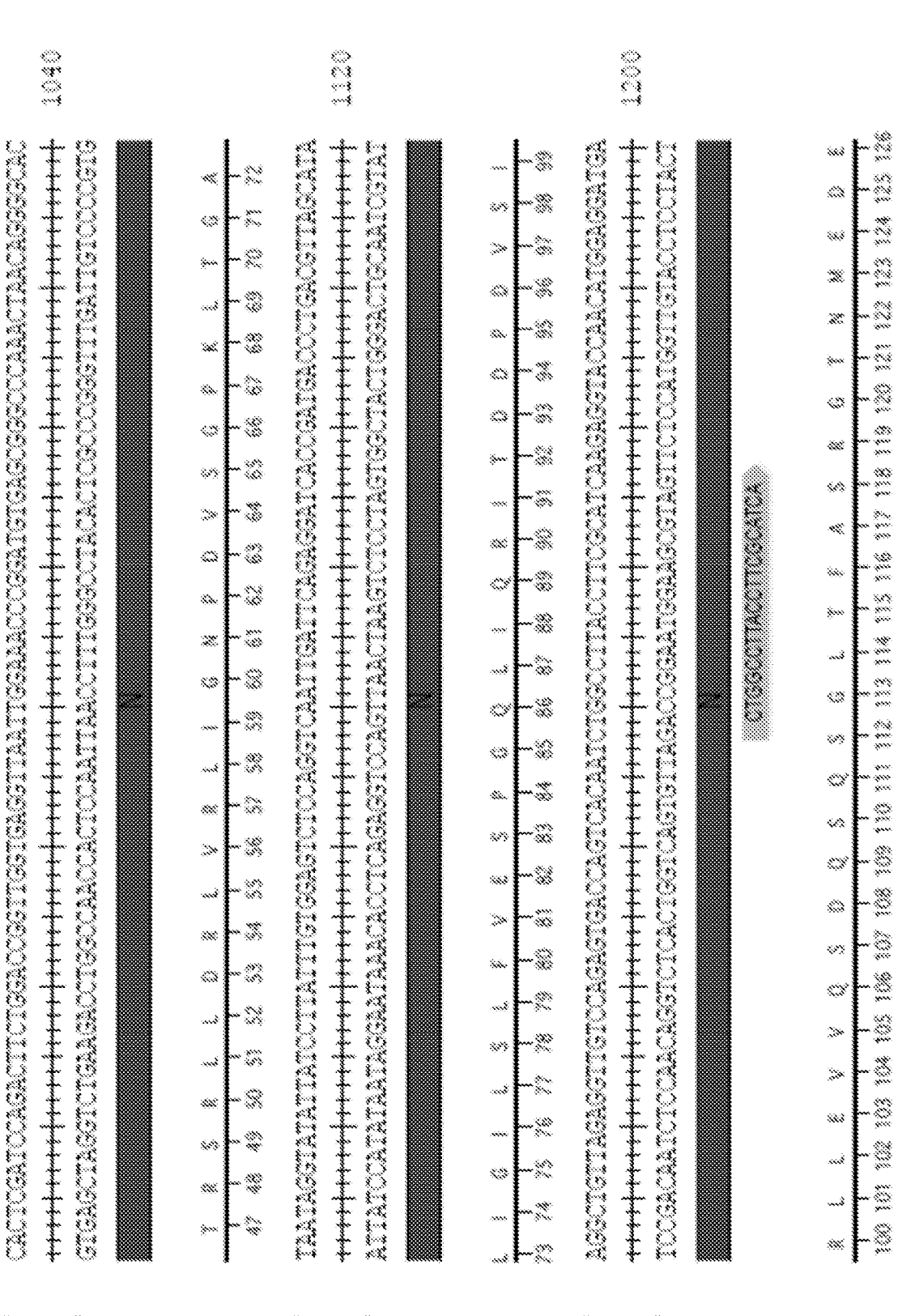
FIG. 19 – continued

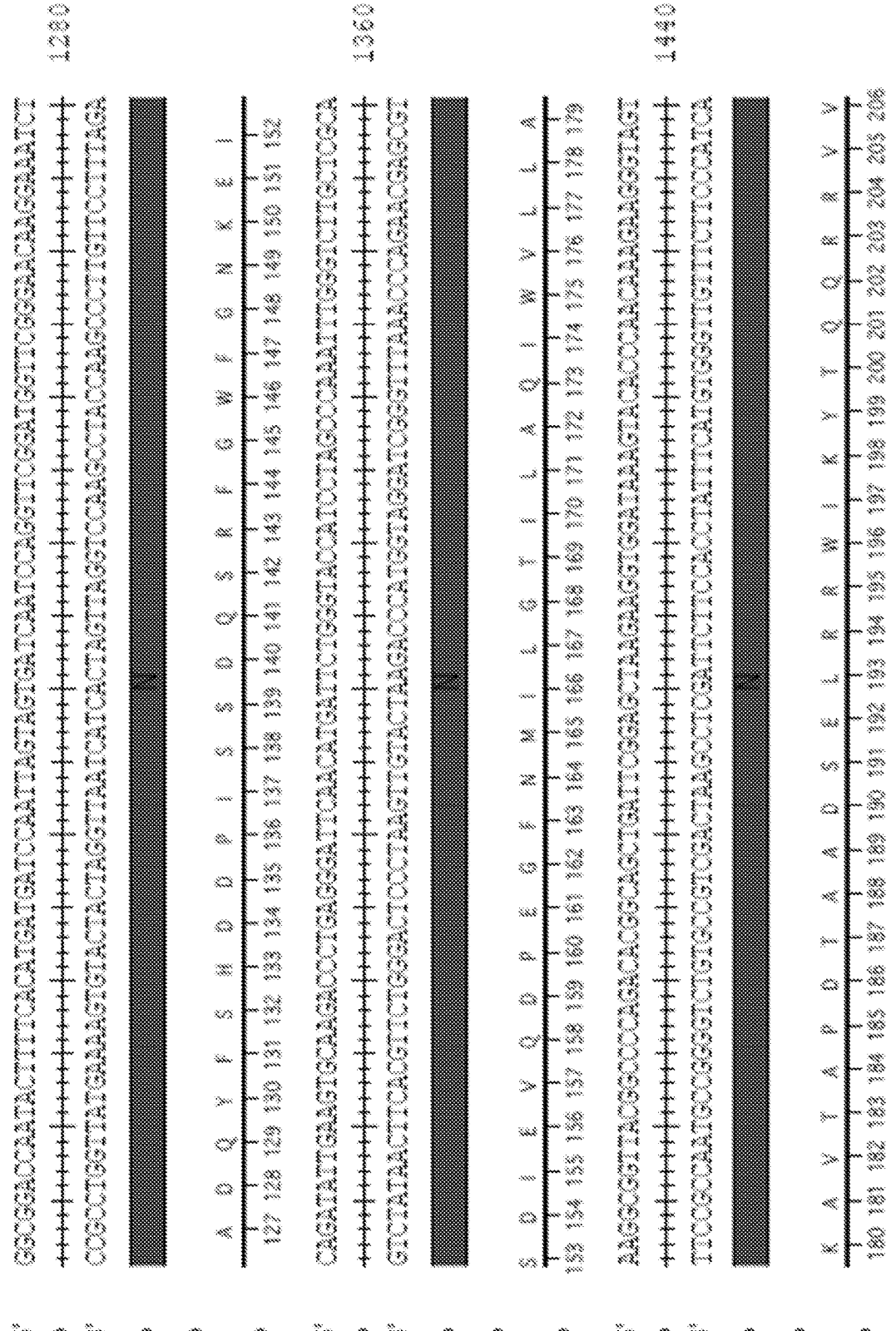
FIG. 19 – continued

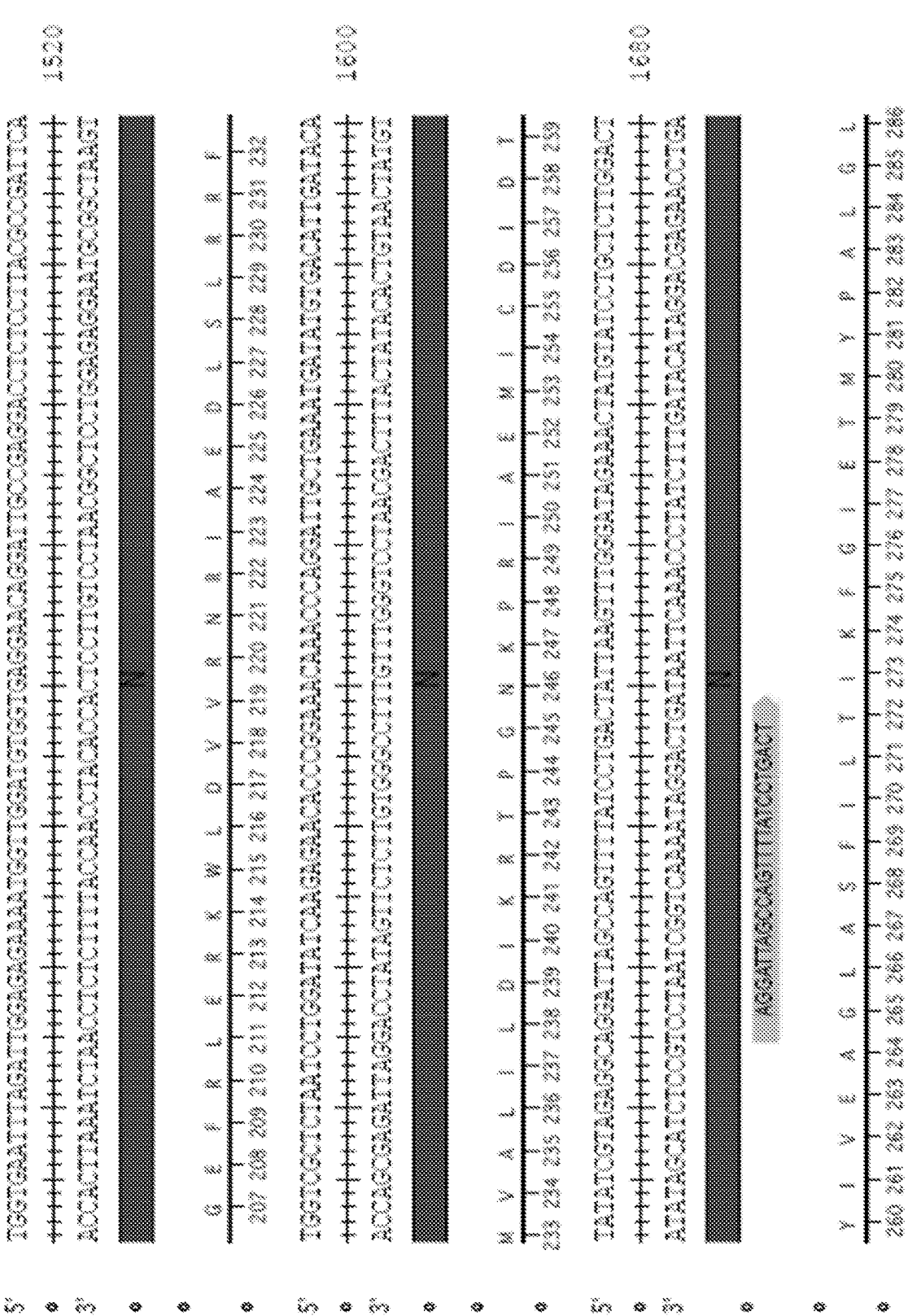
FIG. 19 – continued

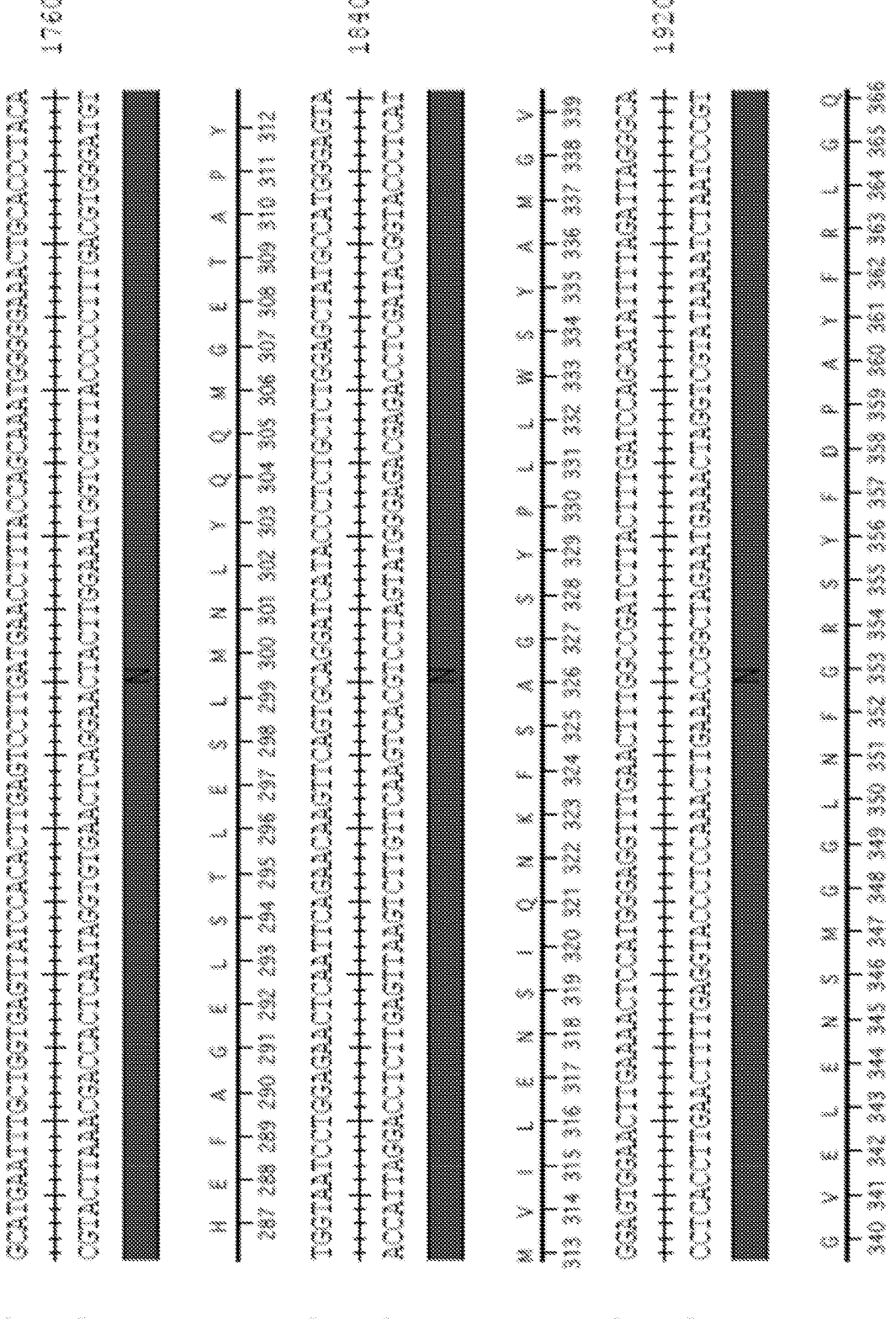
FIG. 19 – continued

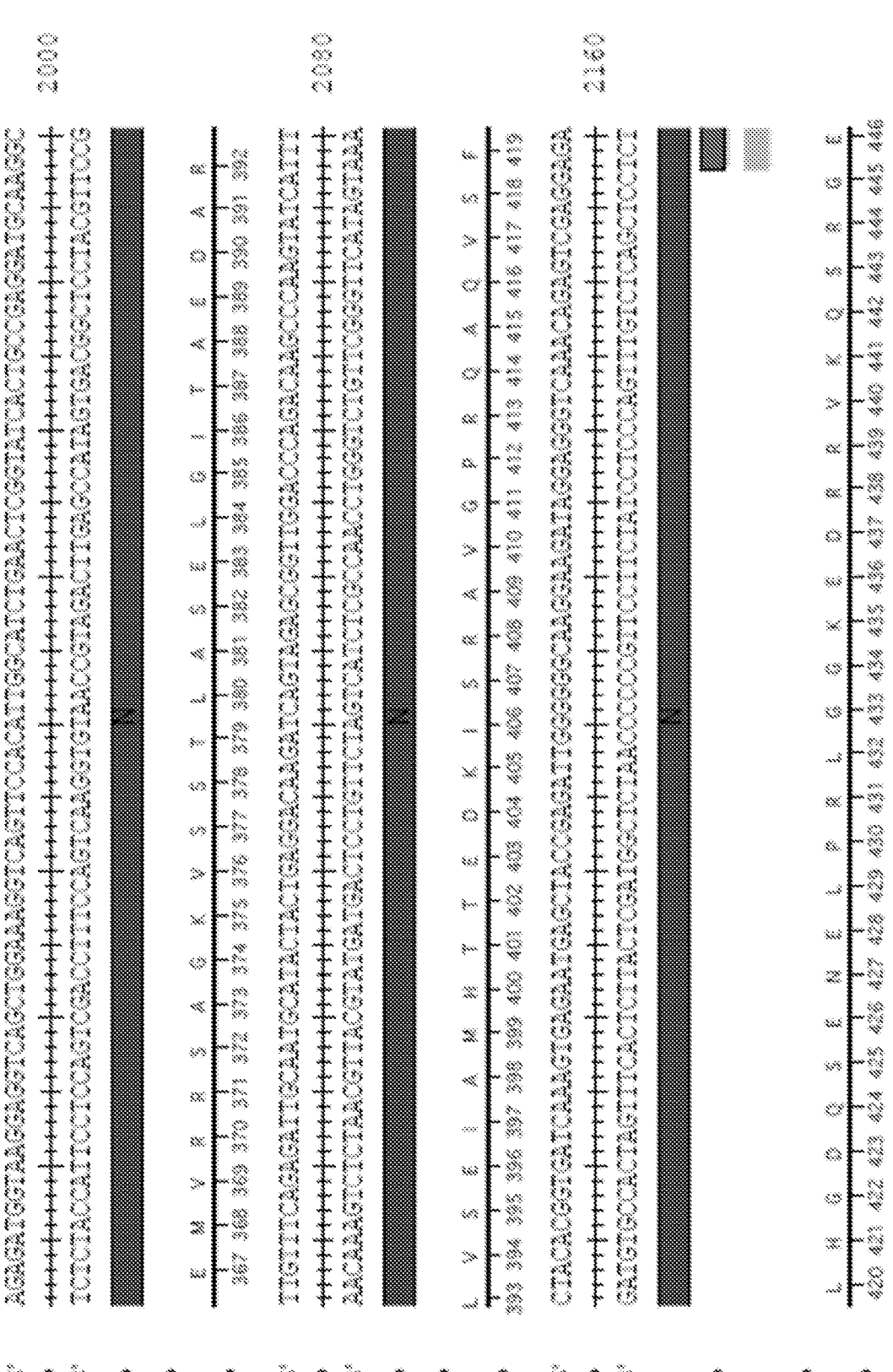
FIG. 19 – continued

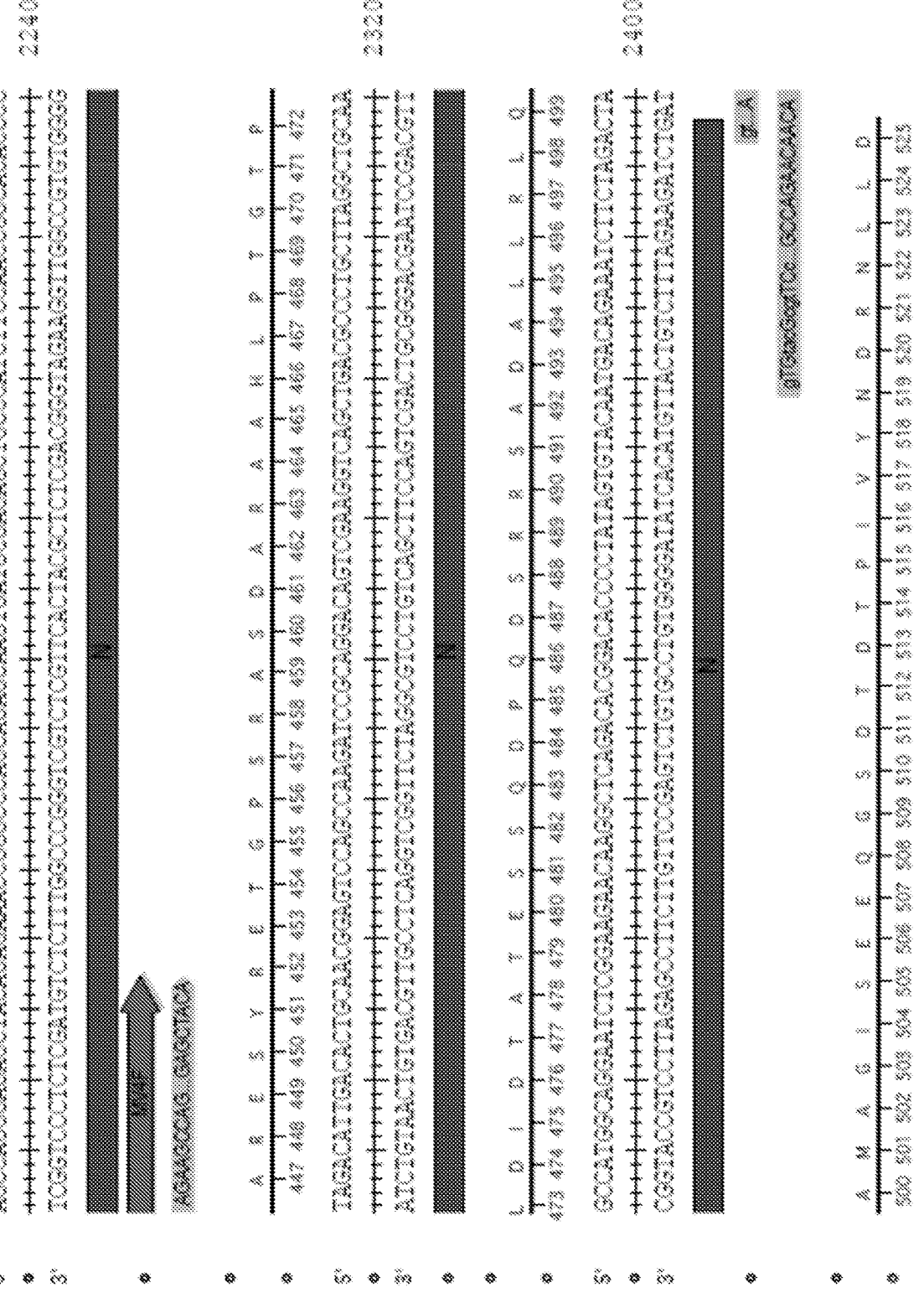
FIG. 19 – continued

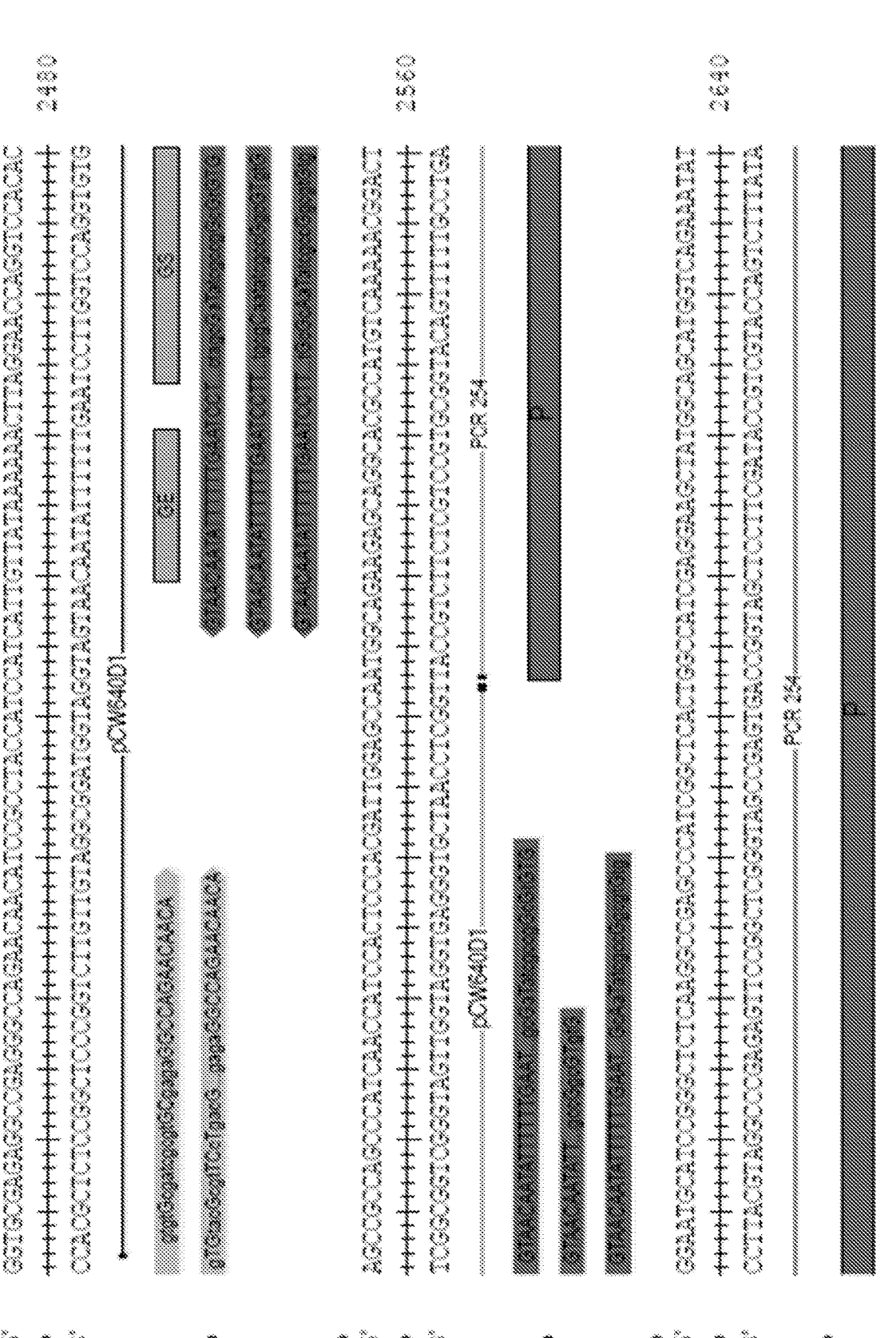
FIG. 19 – continued

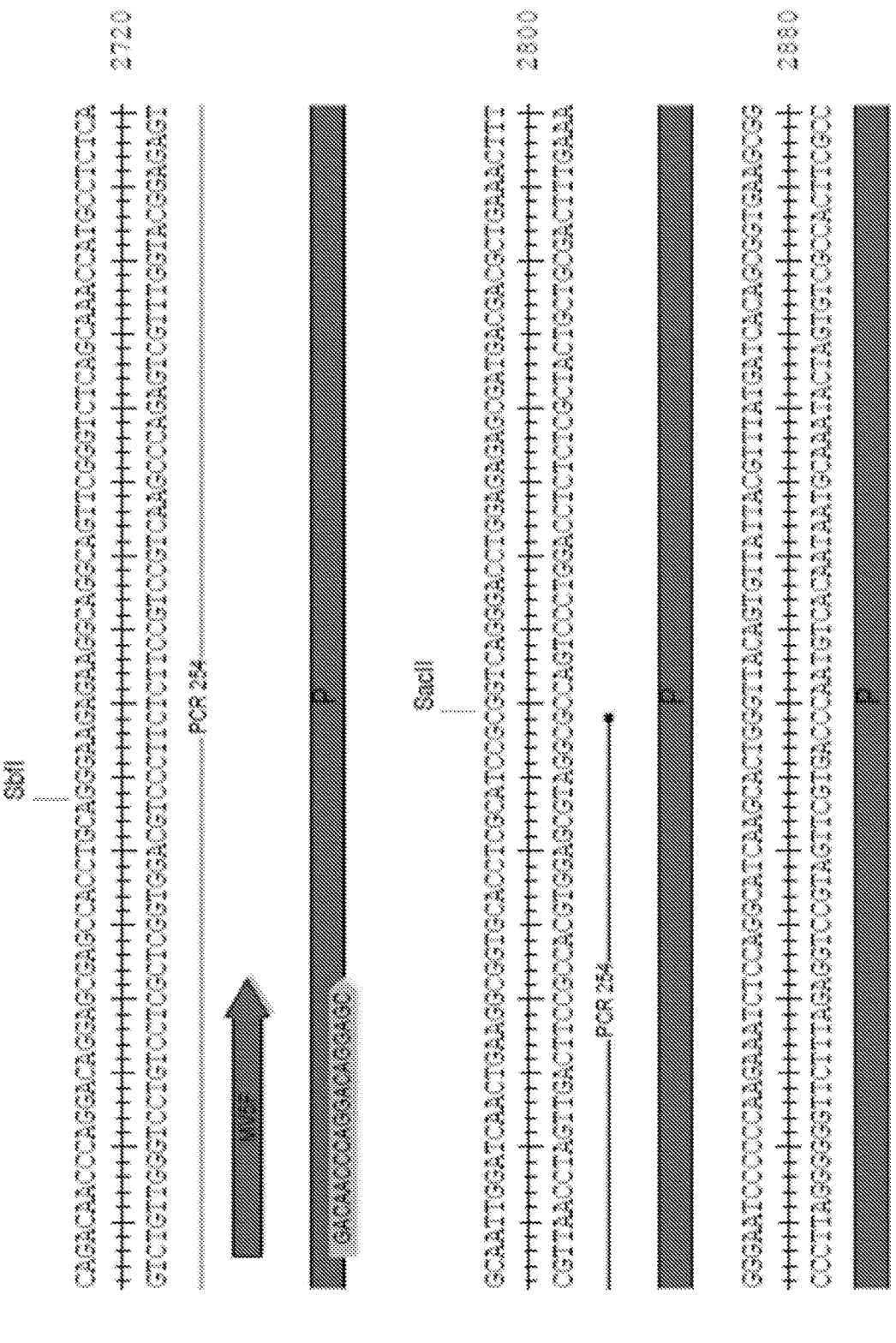
FIG. 19 – continued

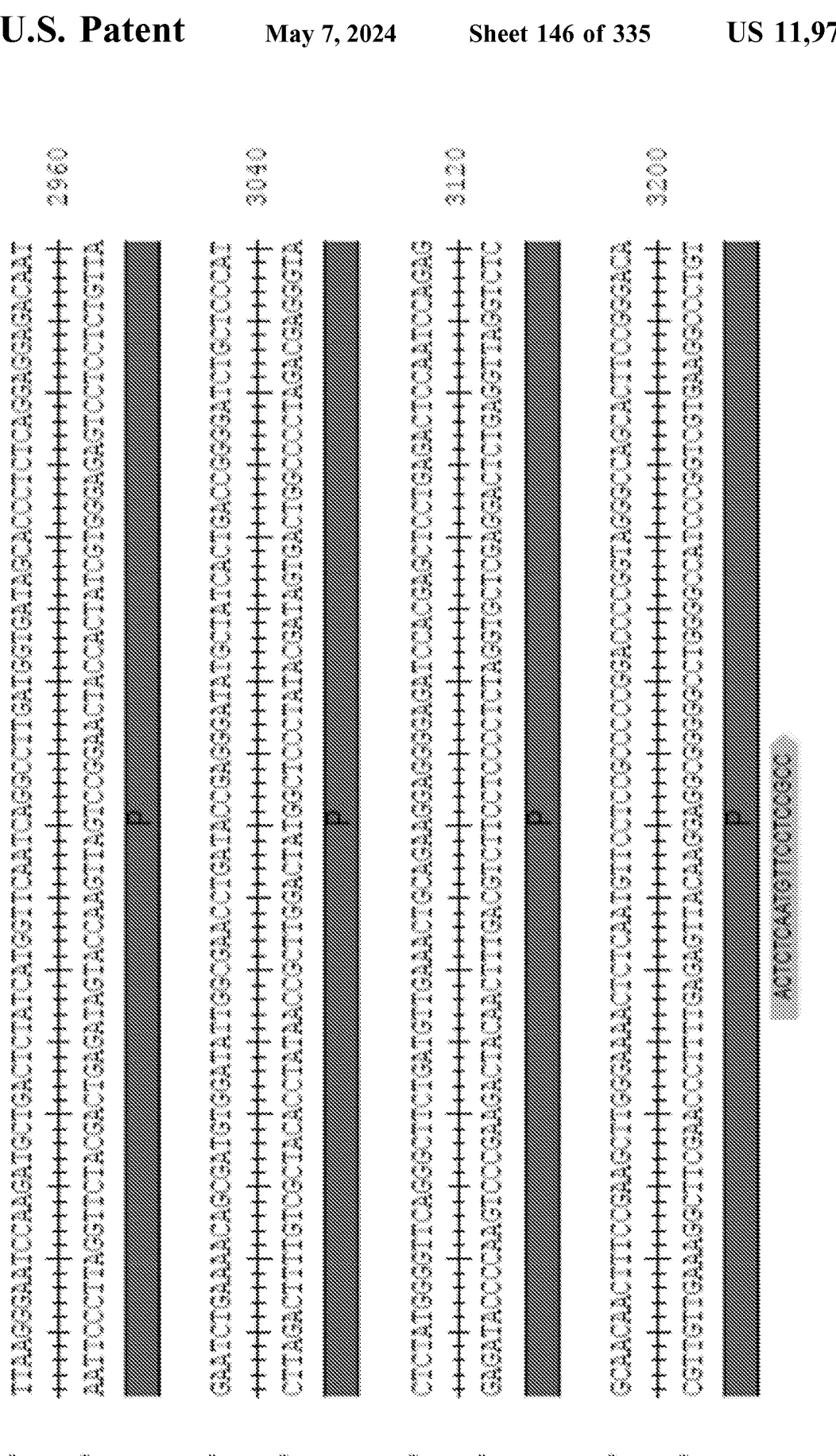
FIG. 19 – continued

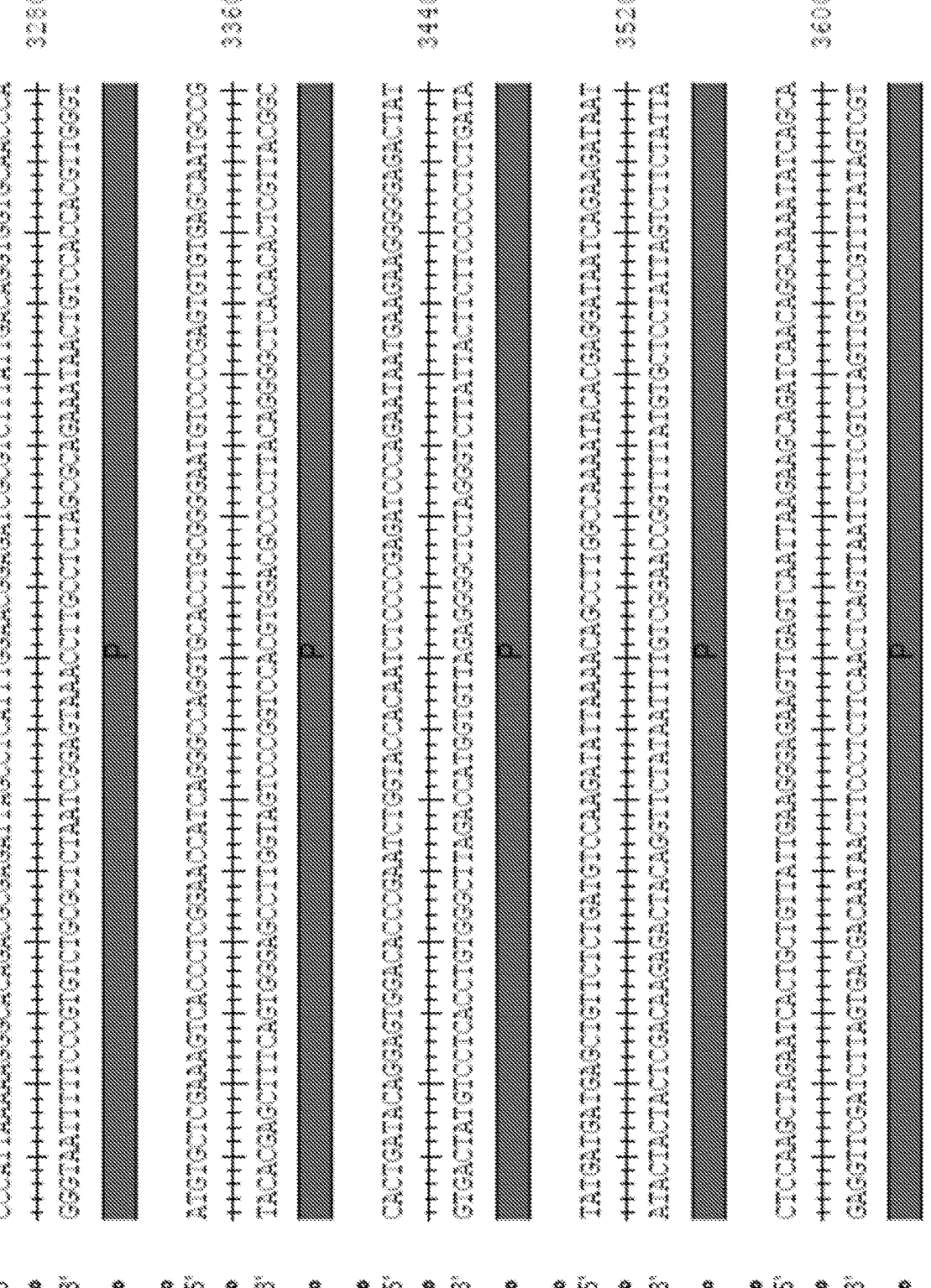
FIG. 19 – continued

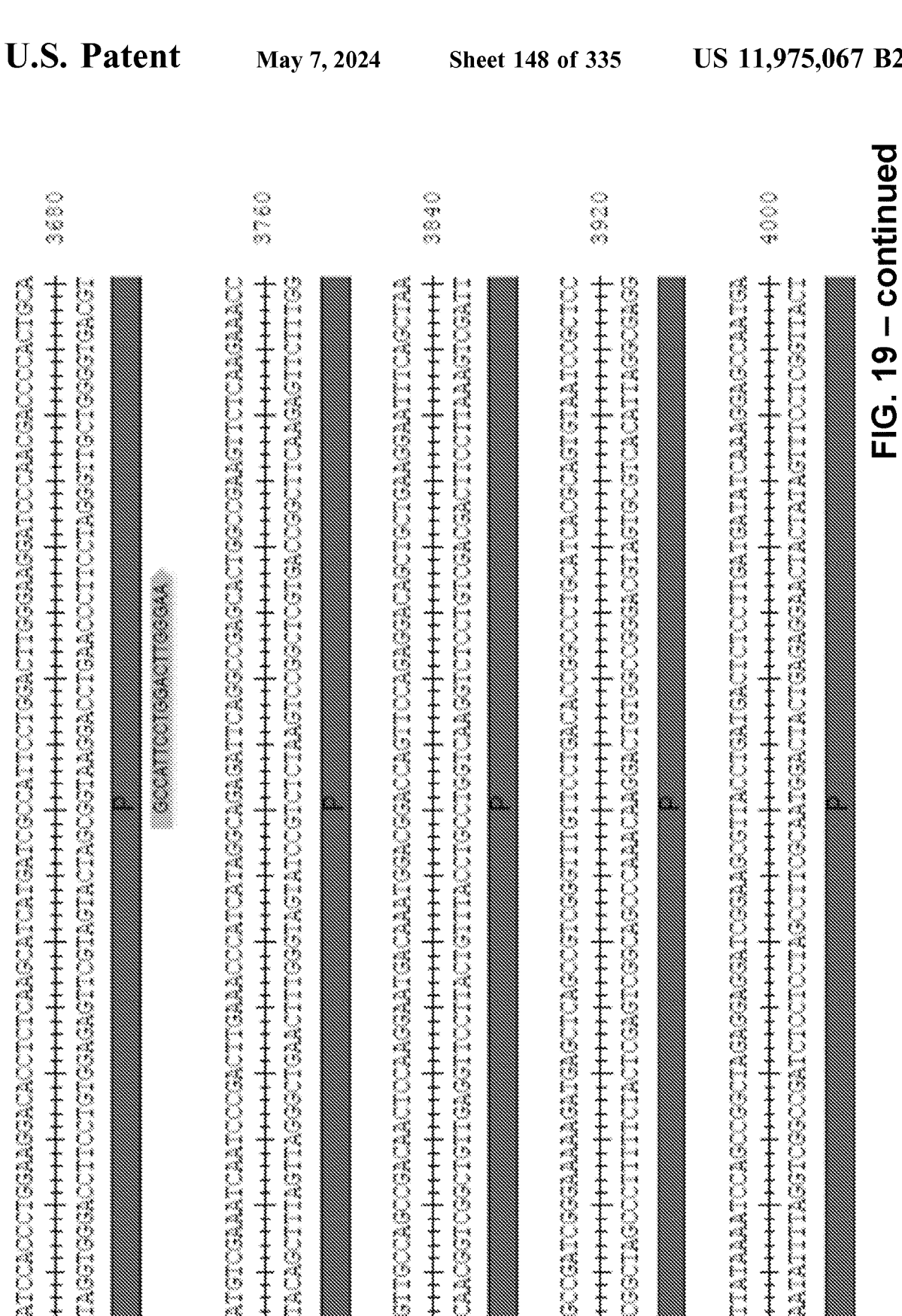
FIG. 19 – continued

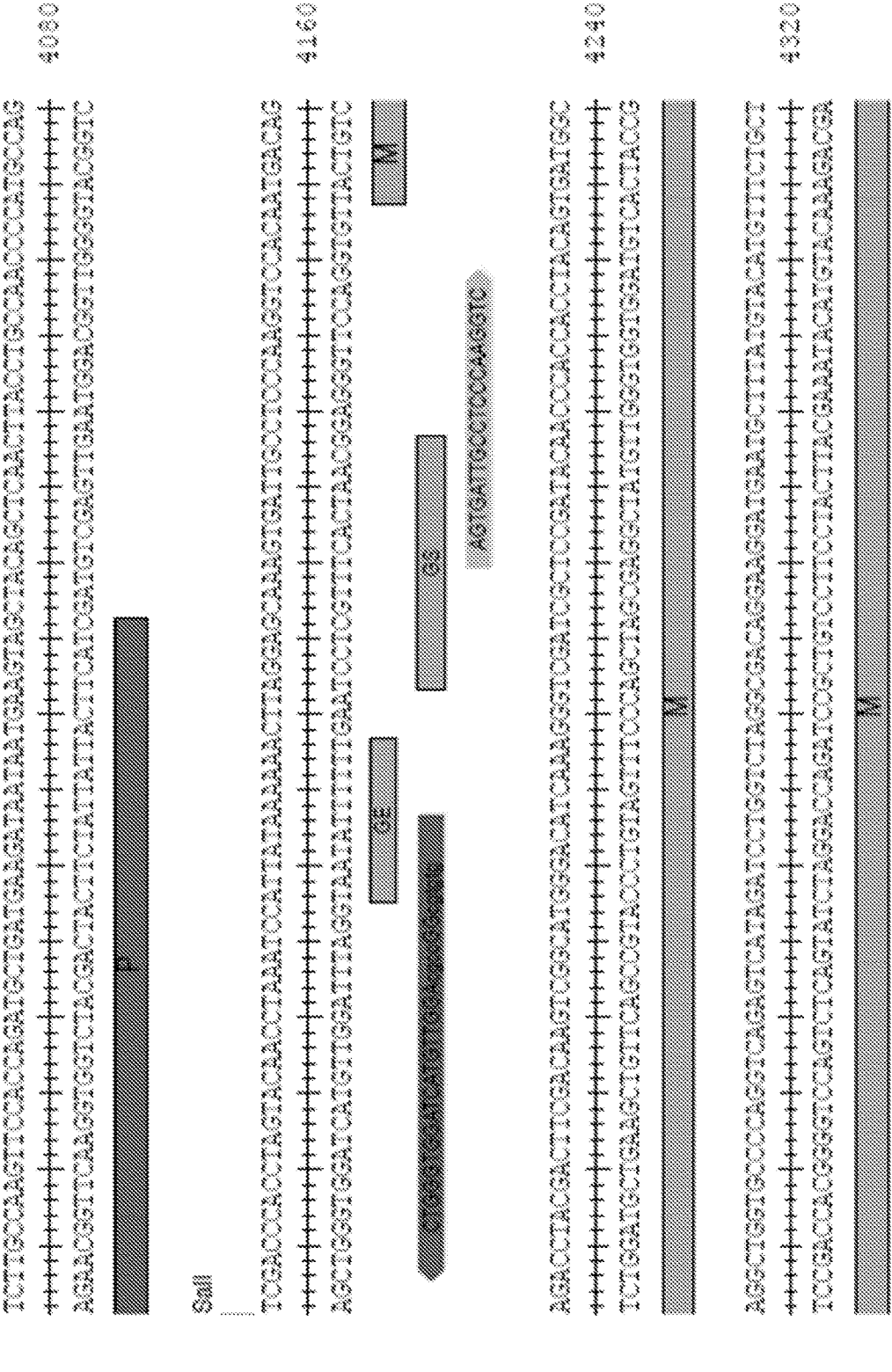
FIG. 19 – continued

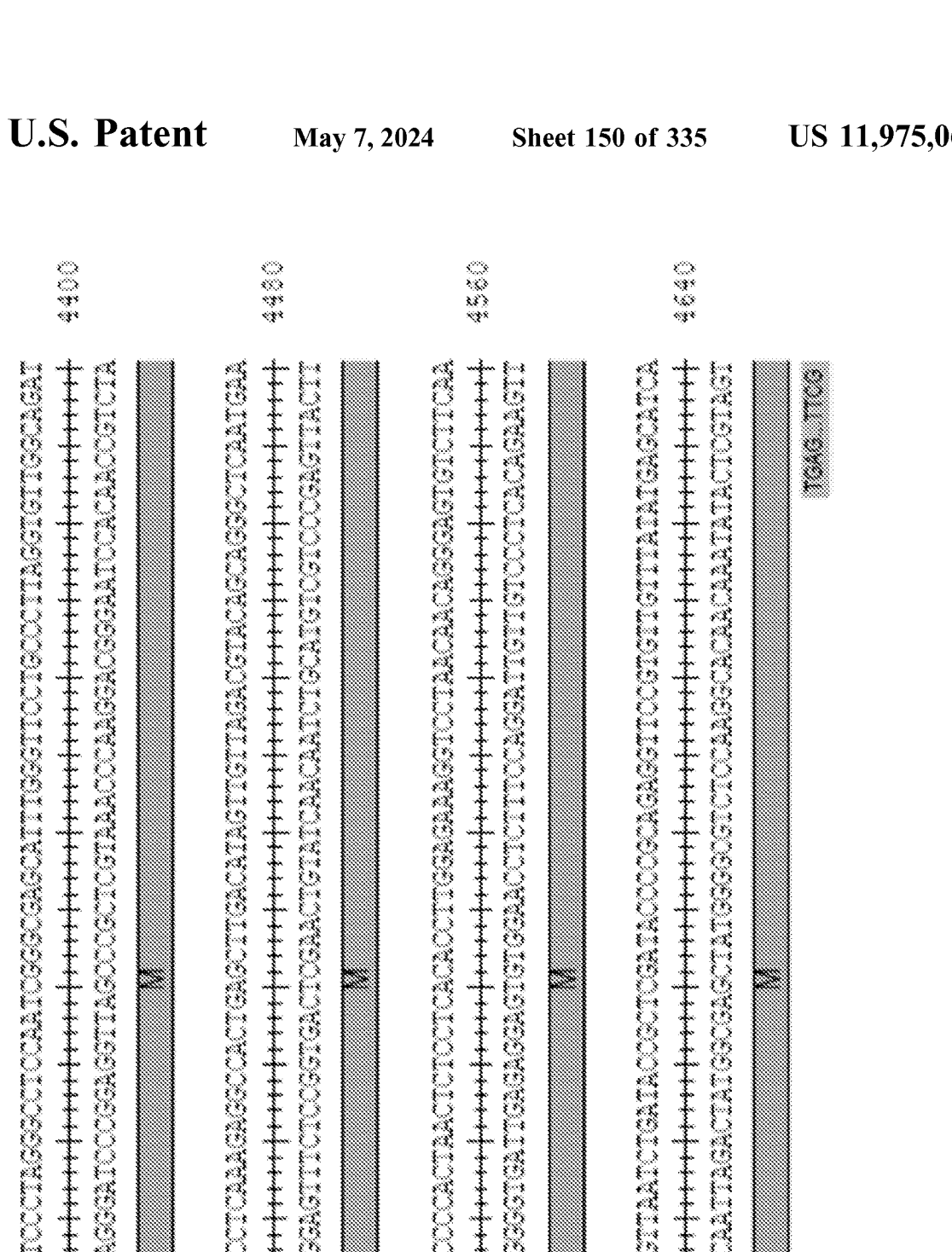
FIG. 19 – continued

FIG. 19 – continued

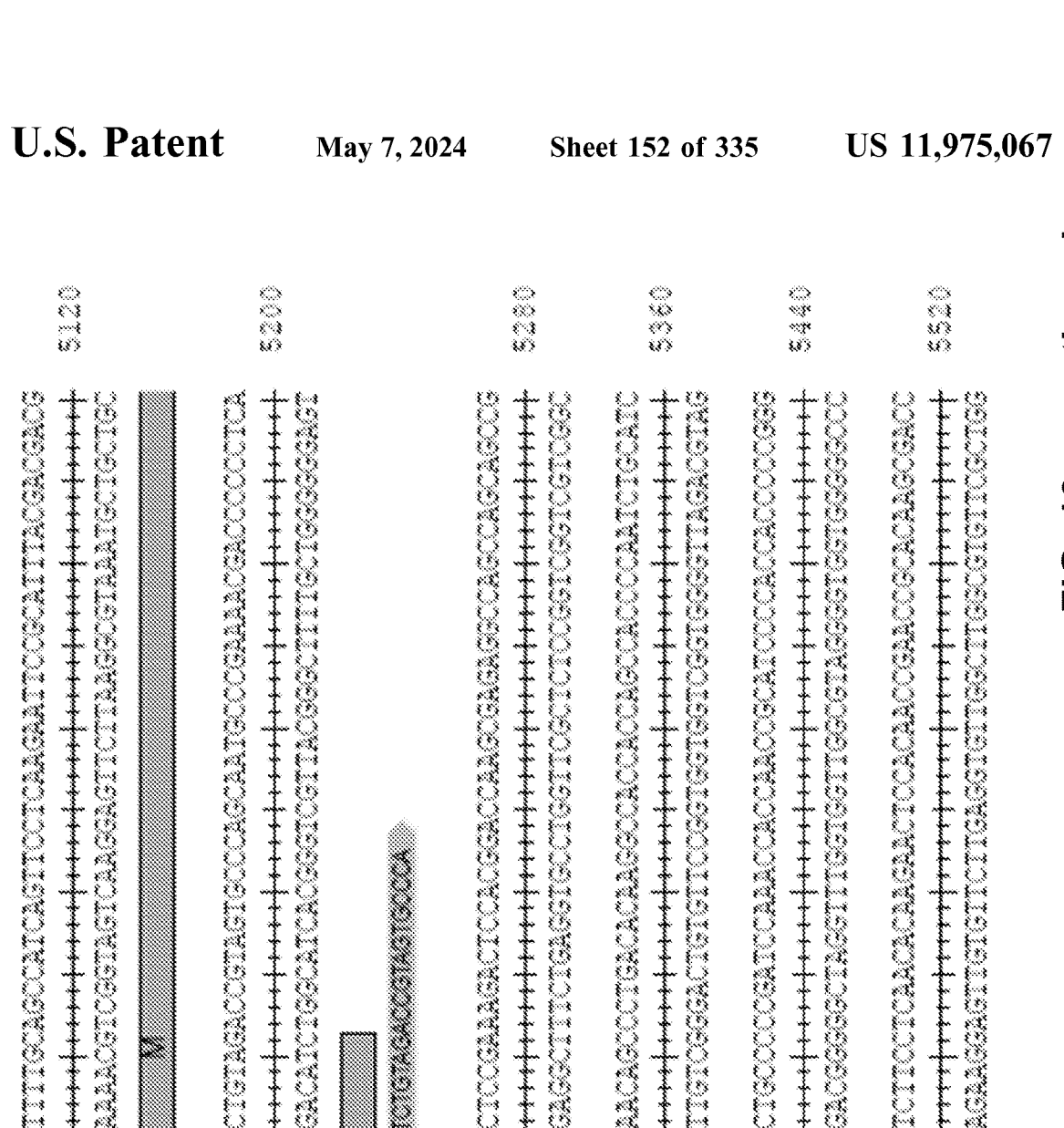
FIG. 19 – continued

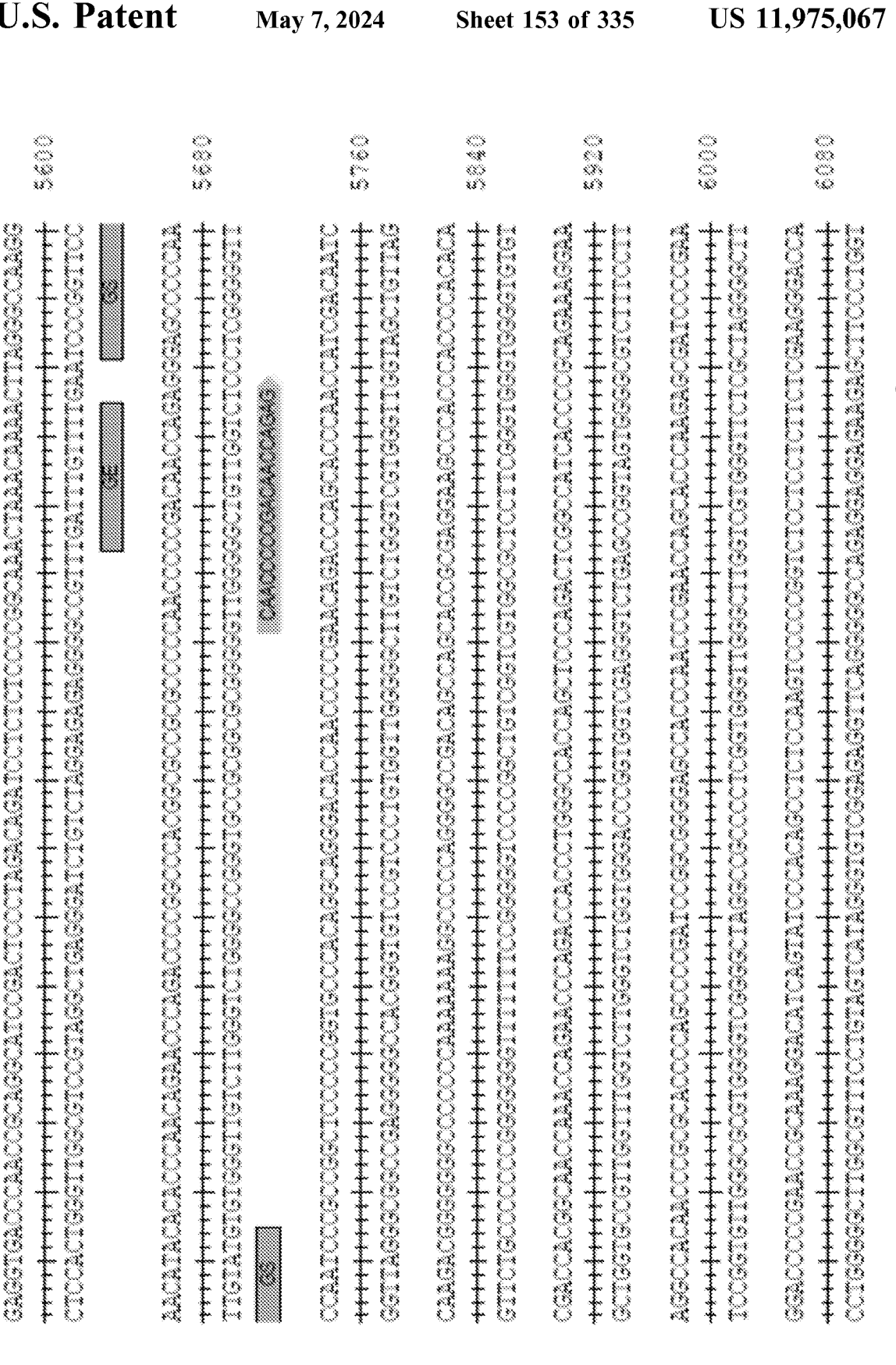
FIG. 19 – continued

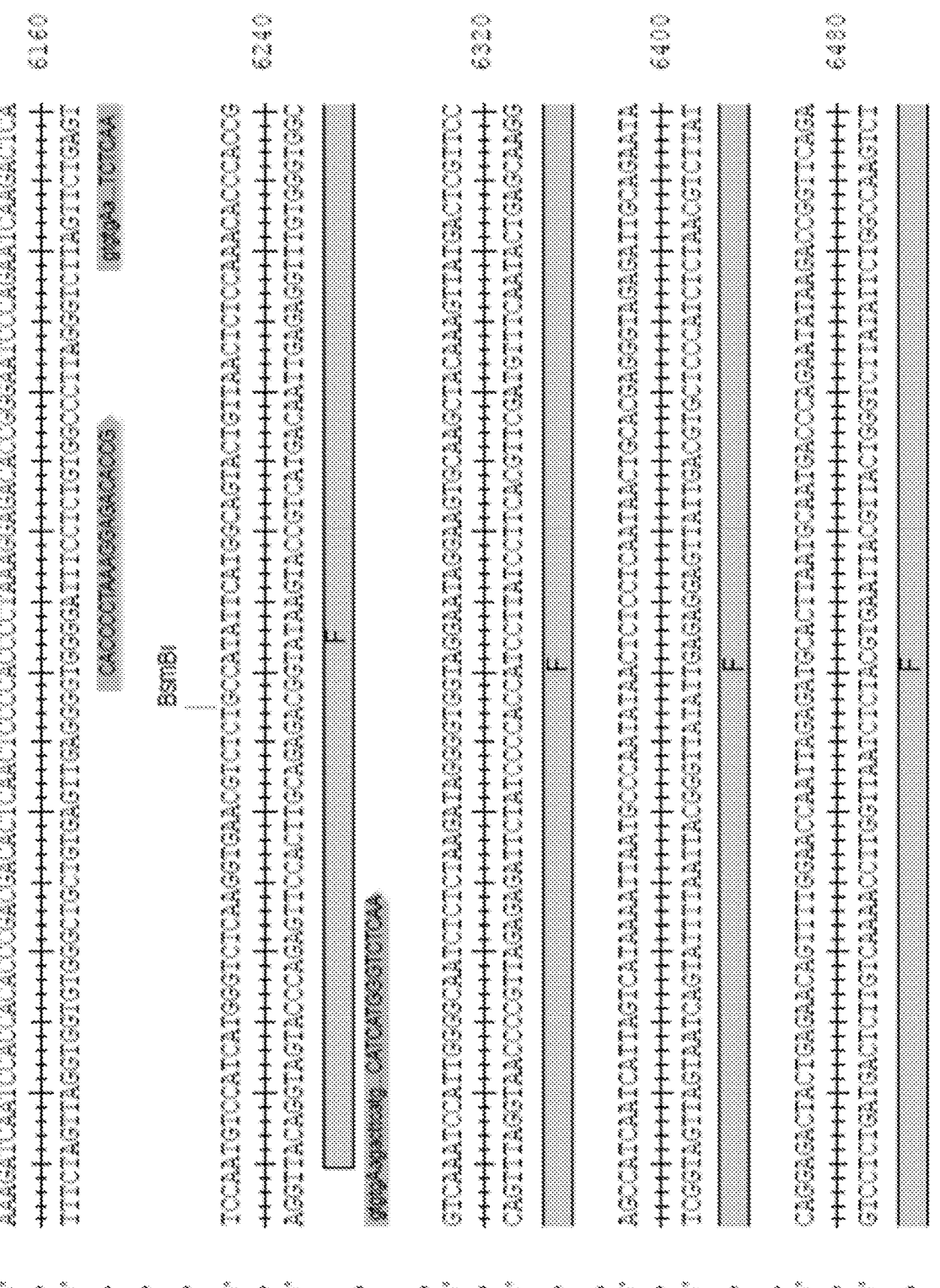
FIG. 19 – continued

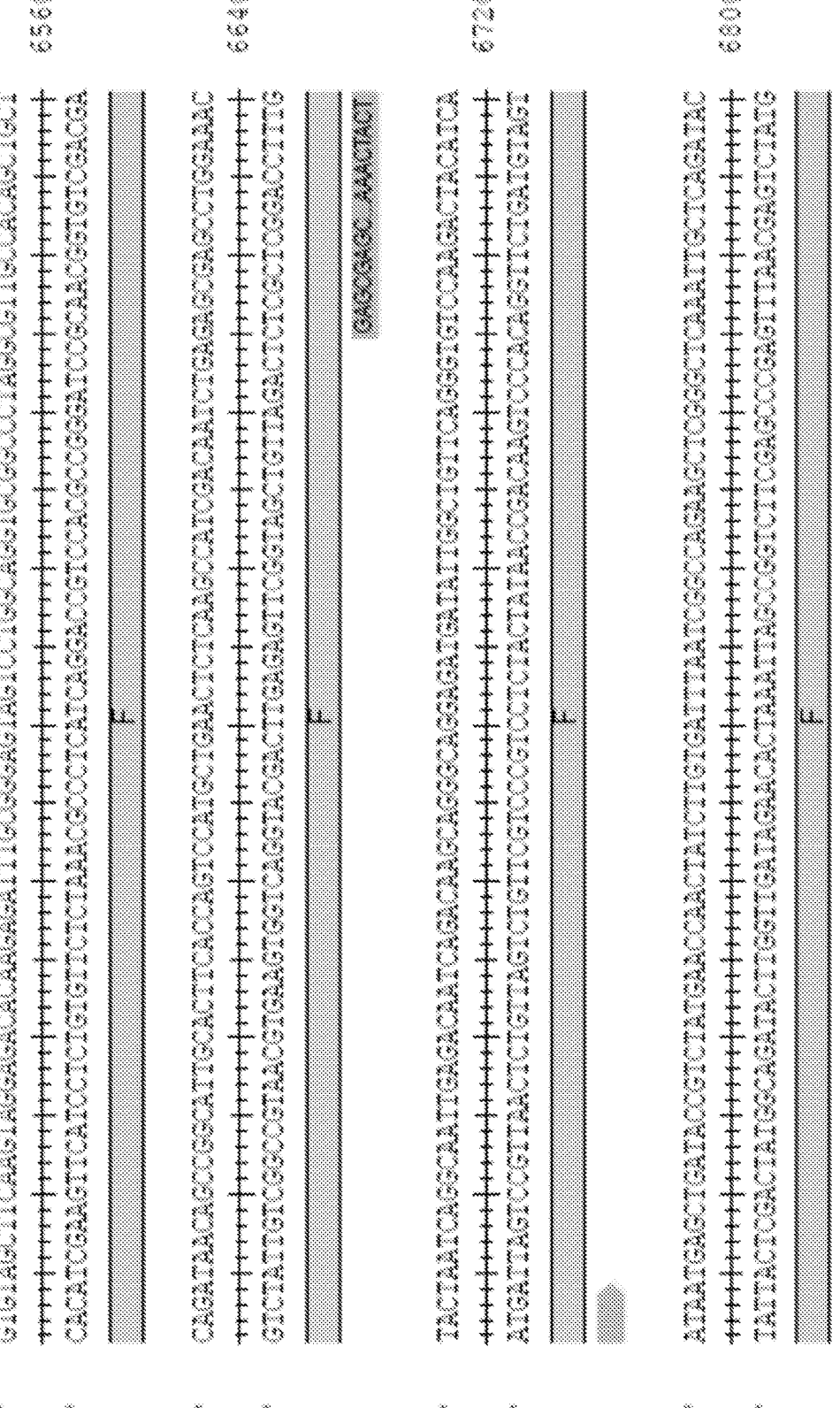
FIG. 19 – continued

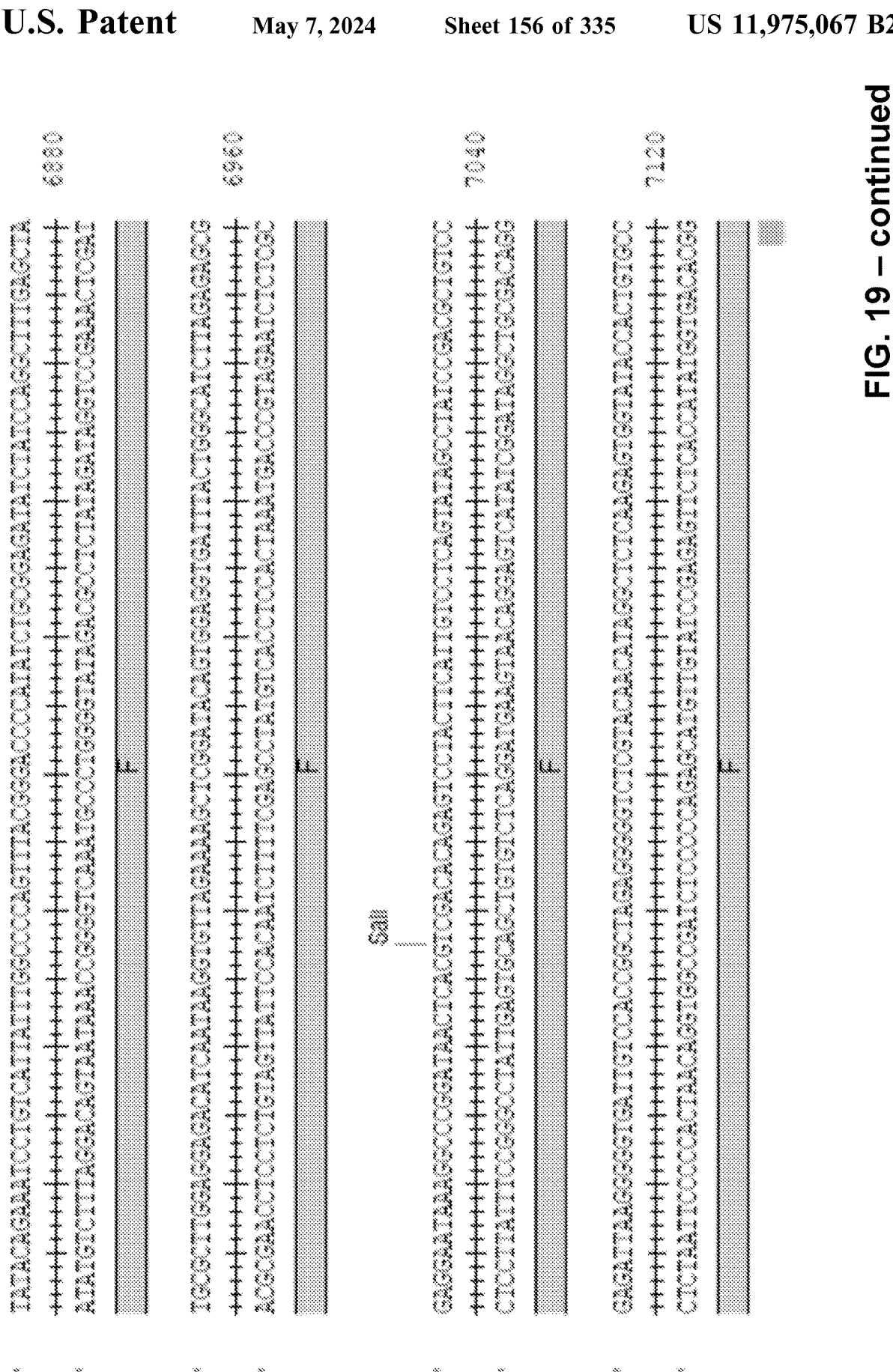
FIG. 19 – continued

FIG. 19 – continued

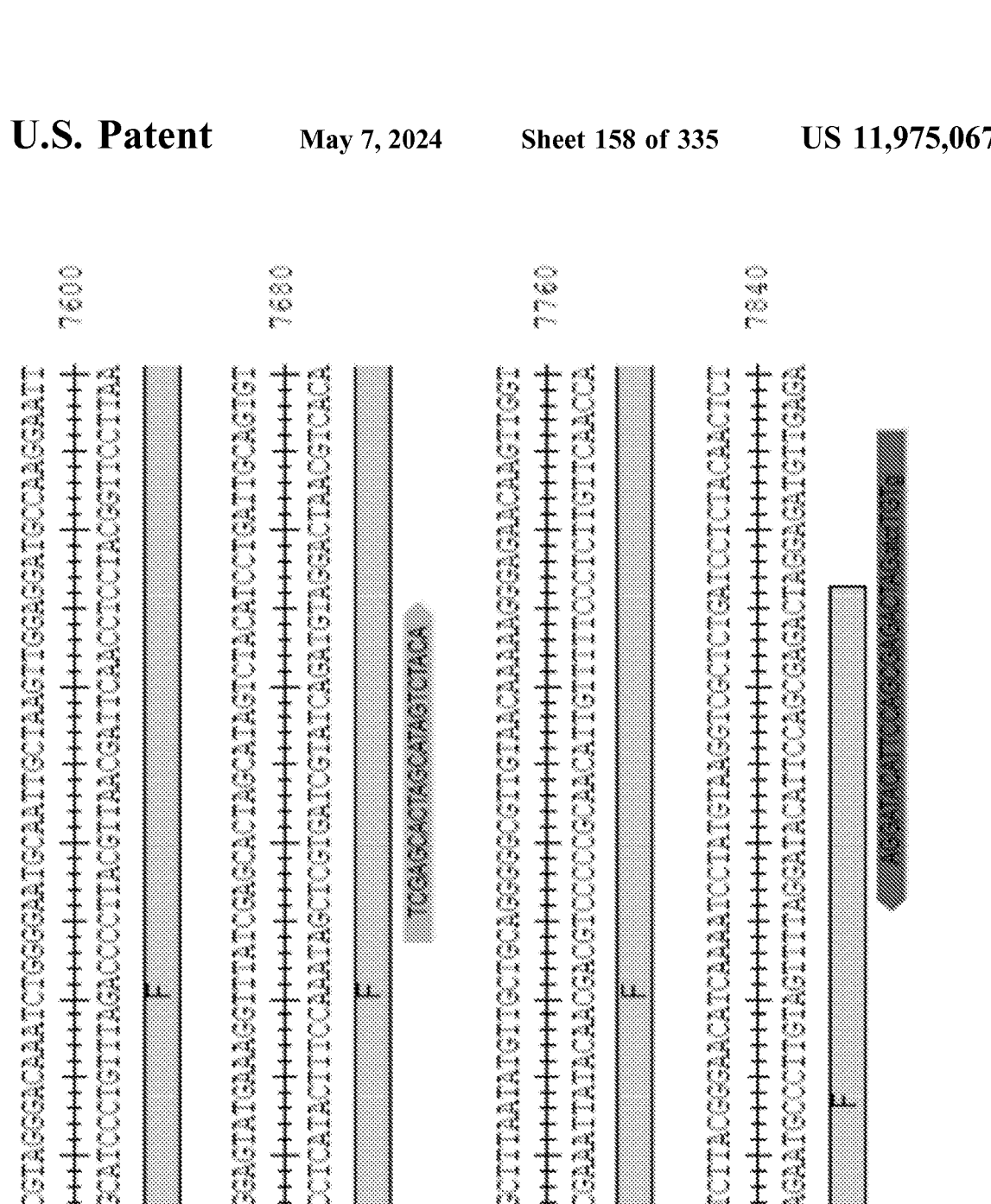
FIG. 19 – continued

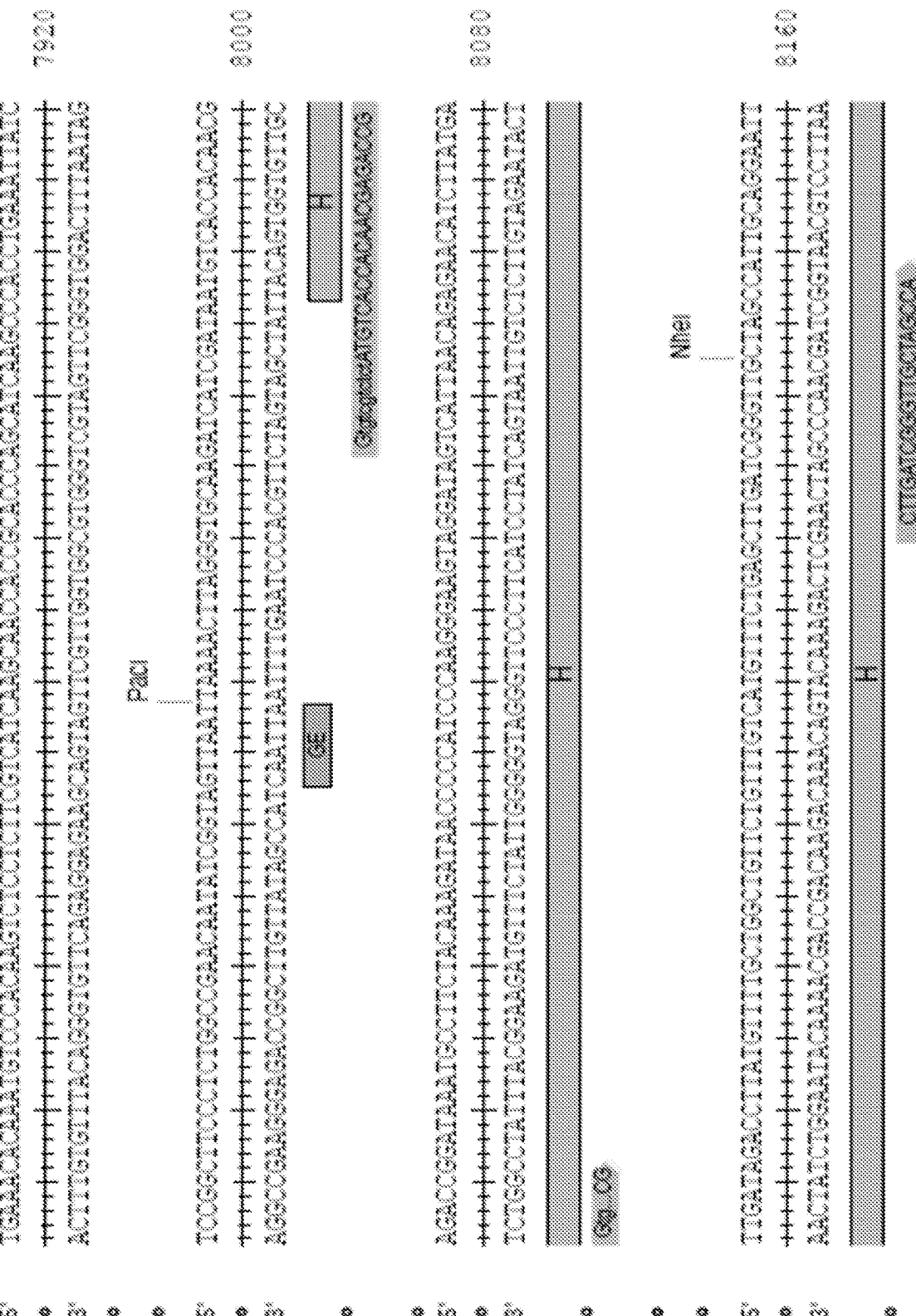
FIG. 19 – continued

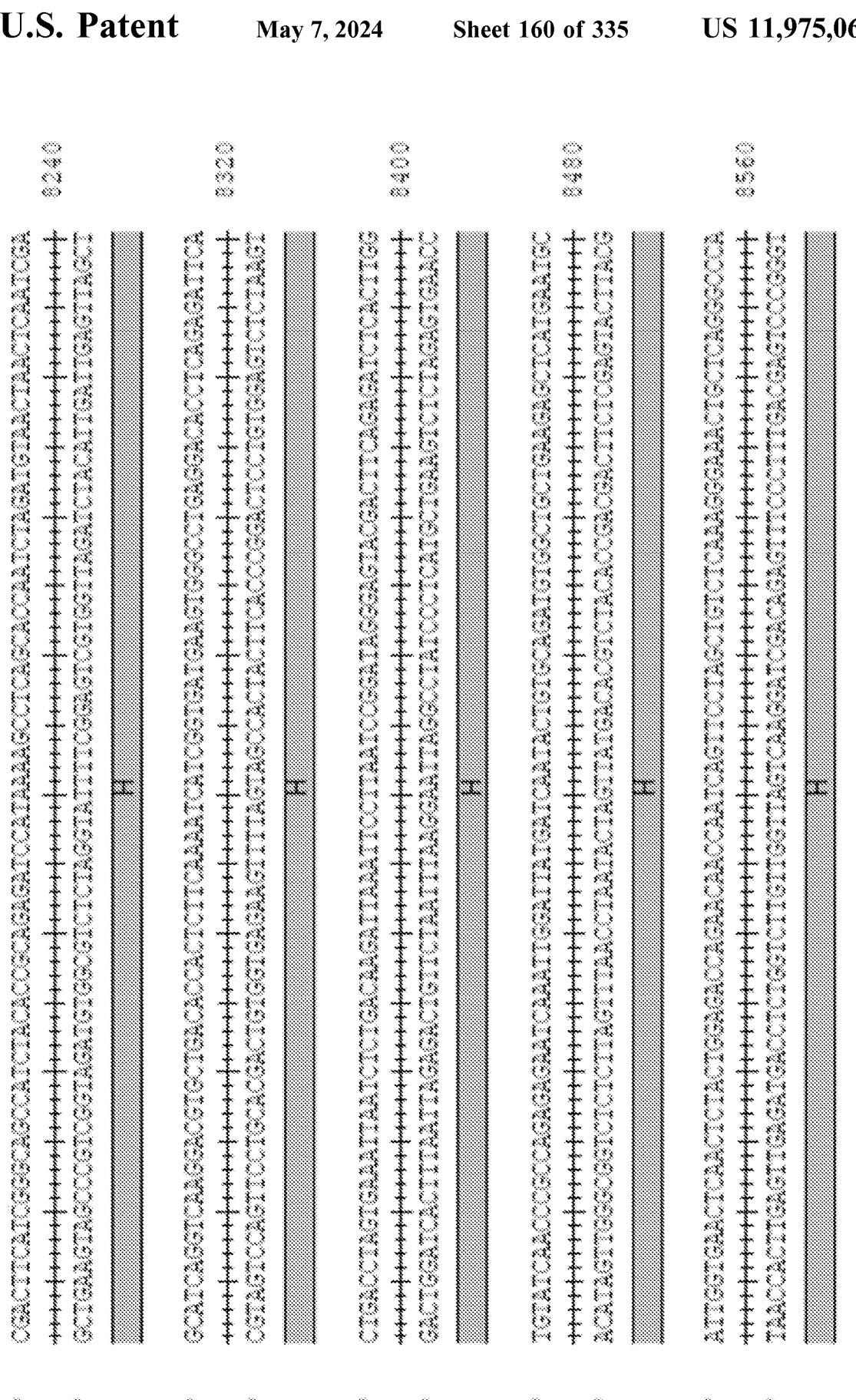
FIG. 19 – continued

FIG. 19 – continued

FIG. 19 – continued

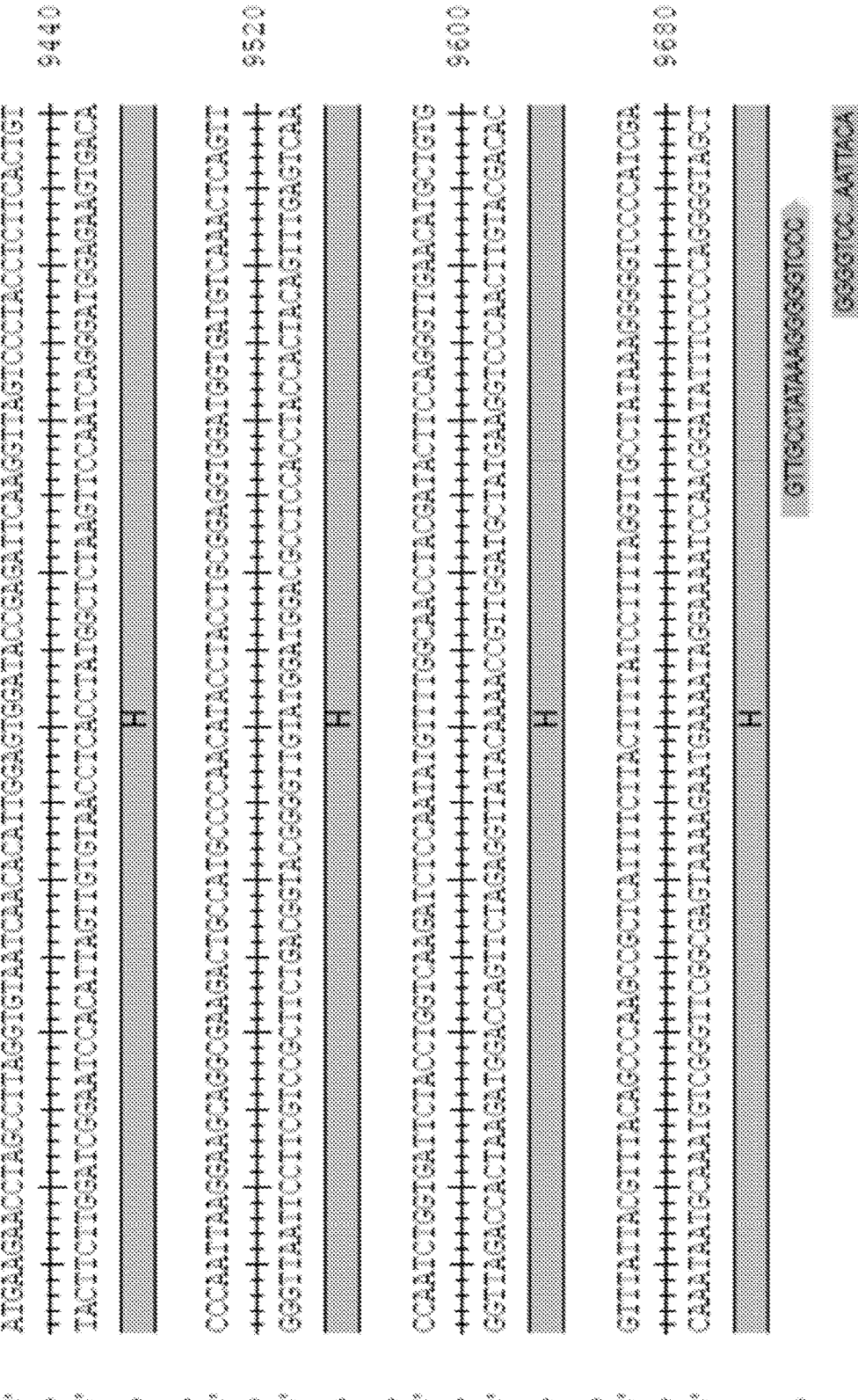
FIG. 19 – continued

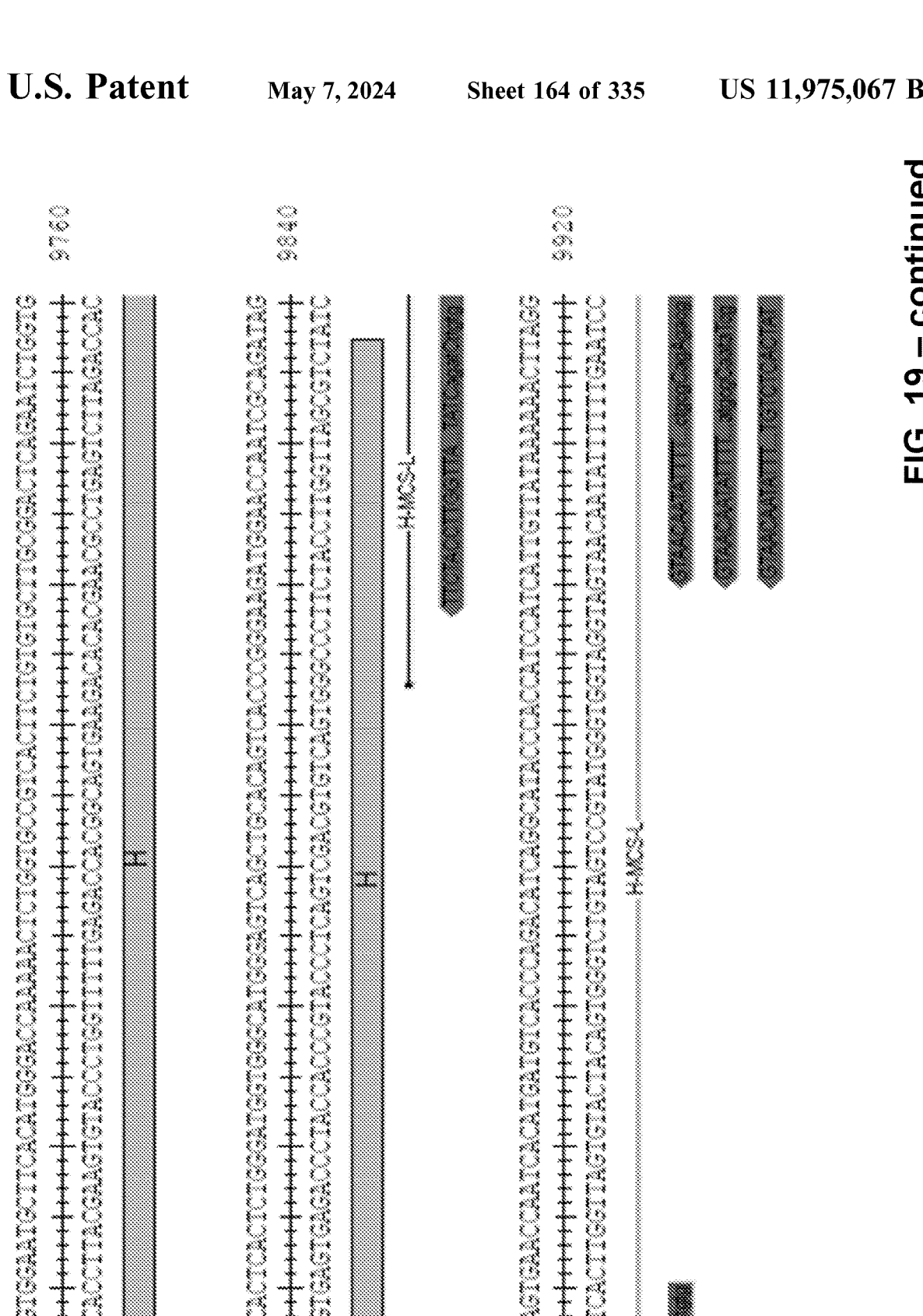
FIG. 19 – continued

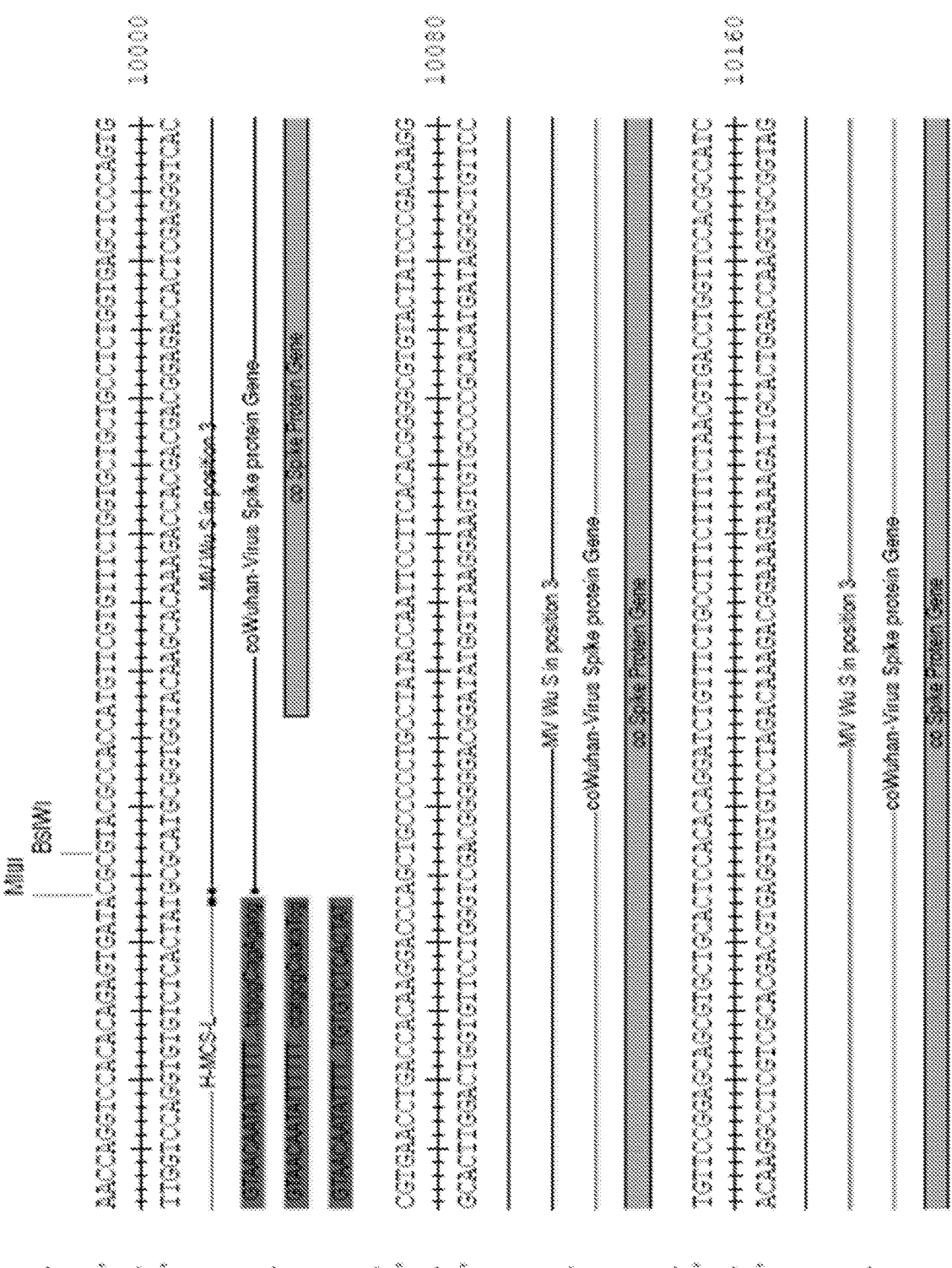
FIG. 19 – continued

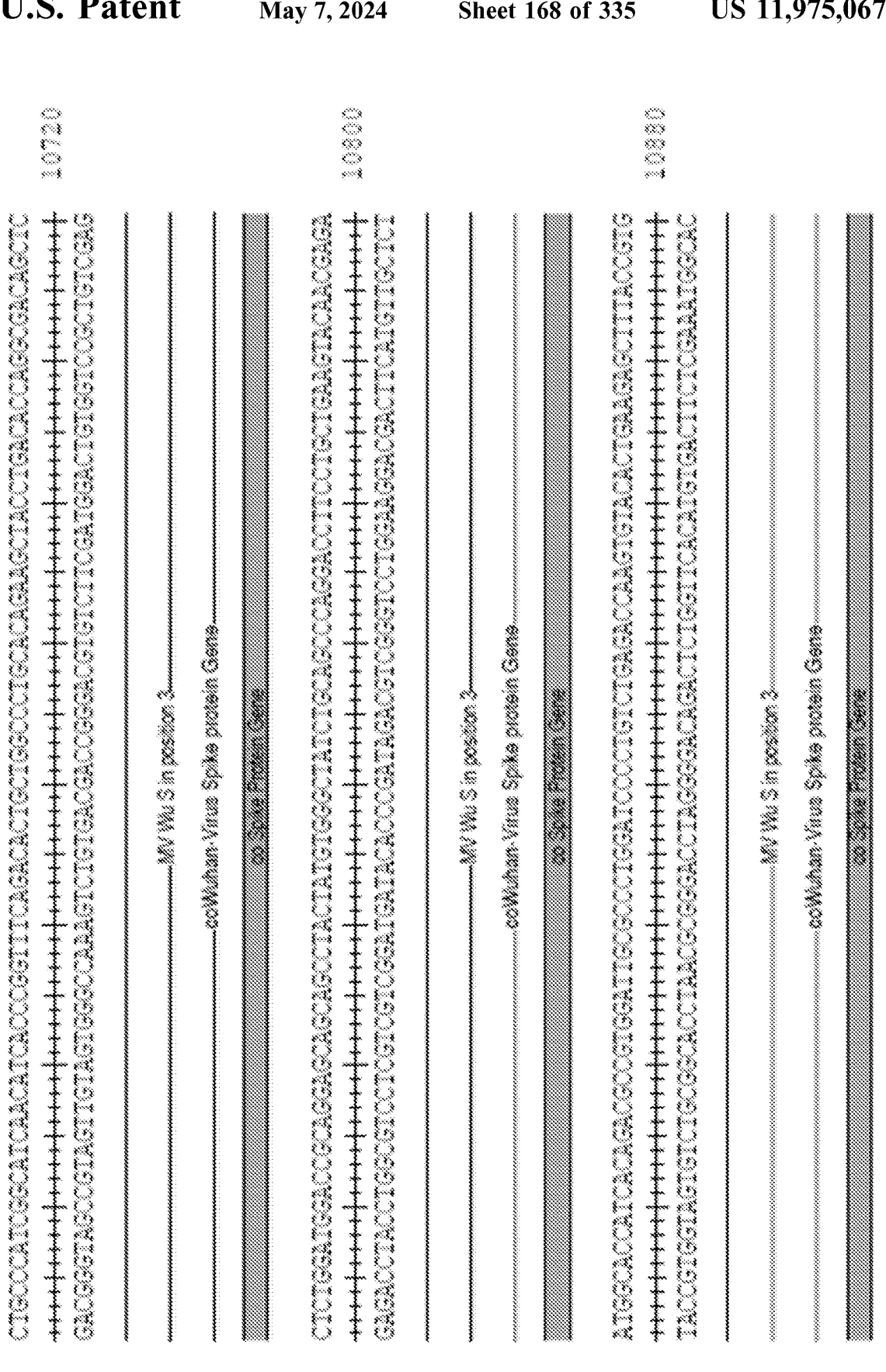
FIG. 19 – continued

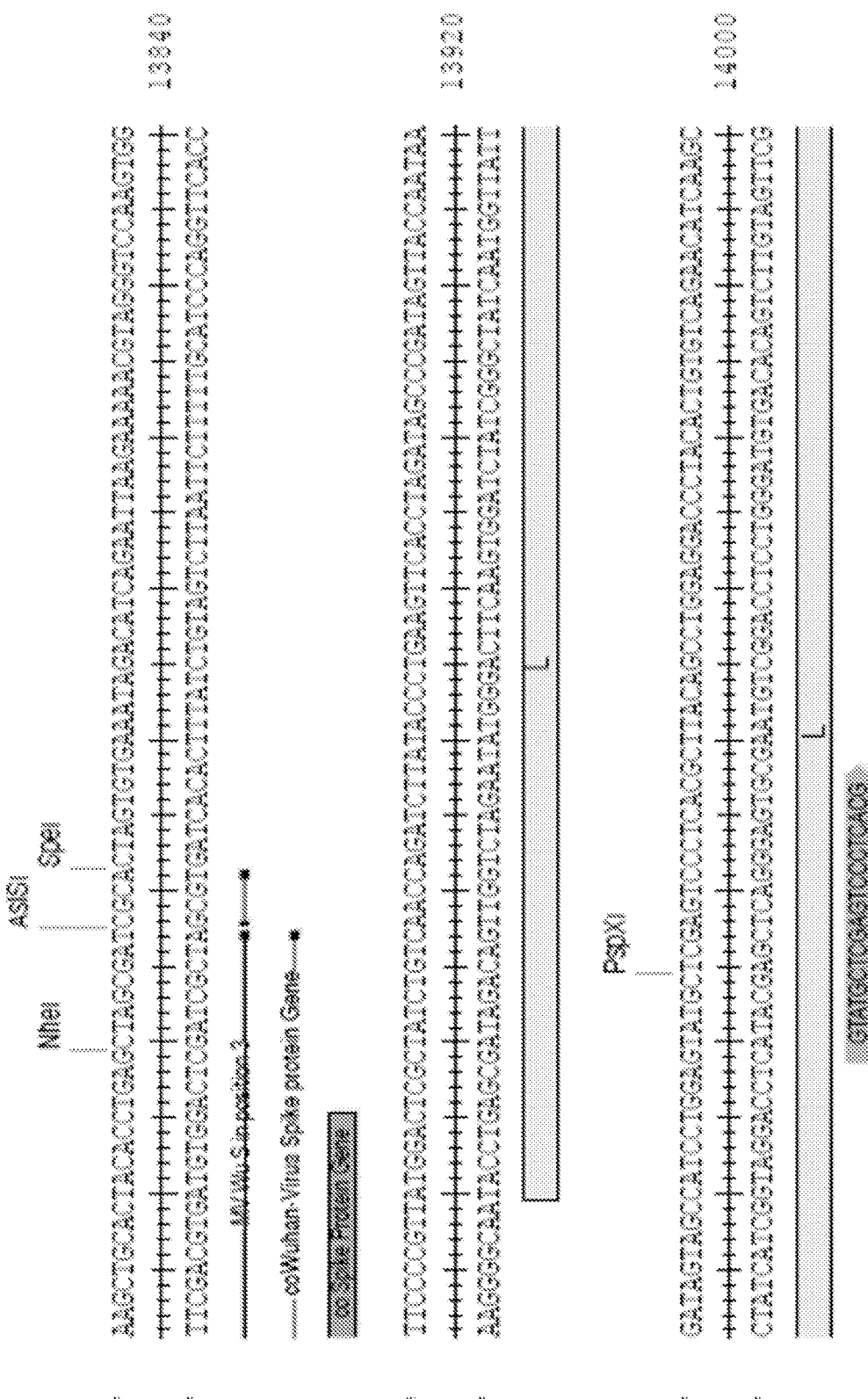
FIG. 19 – continued

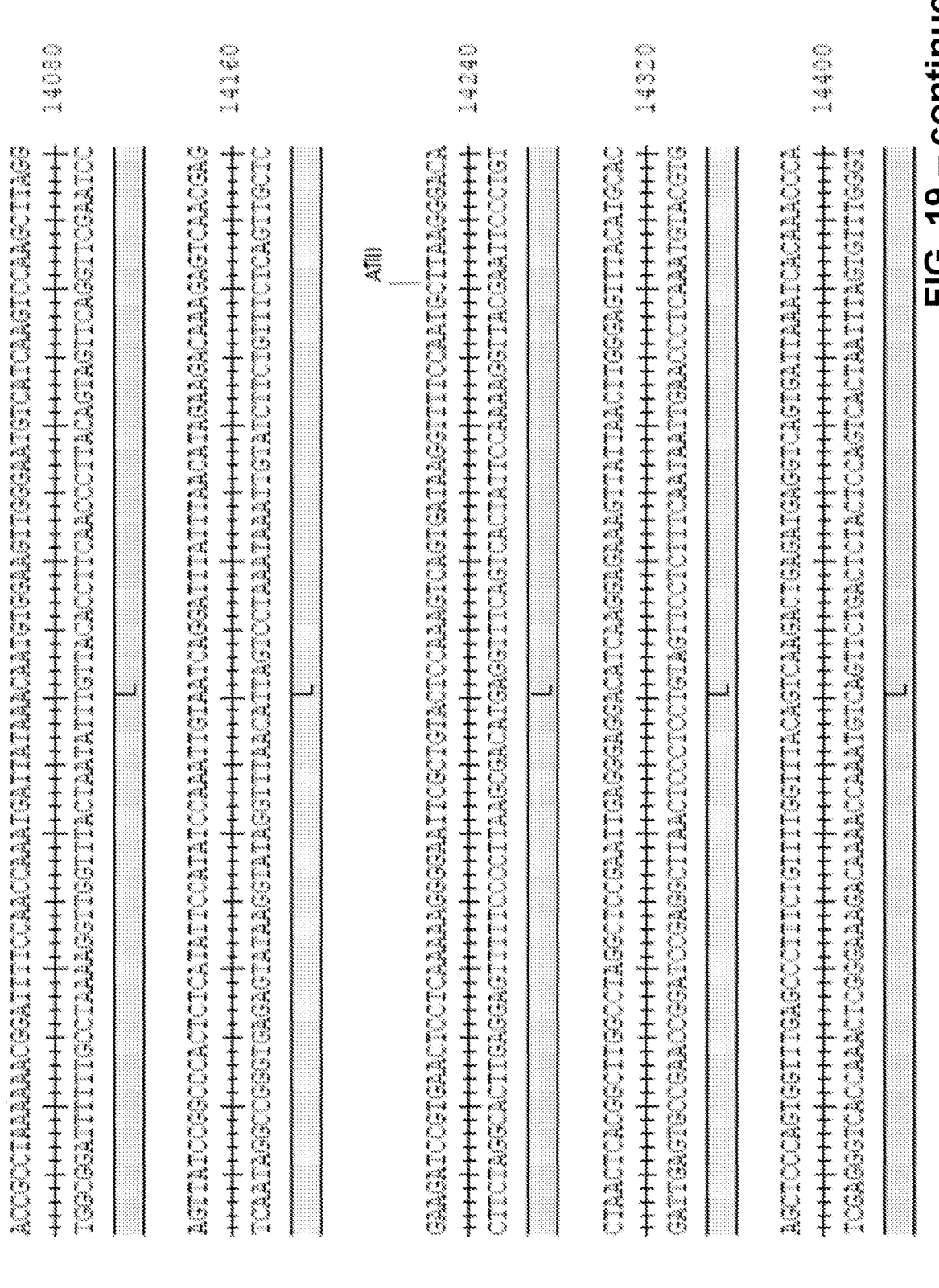
FIG. 19 – continued

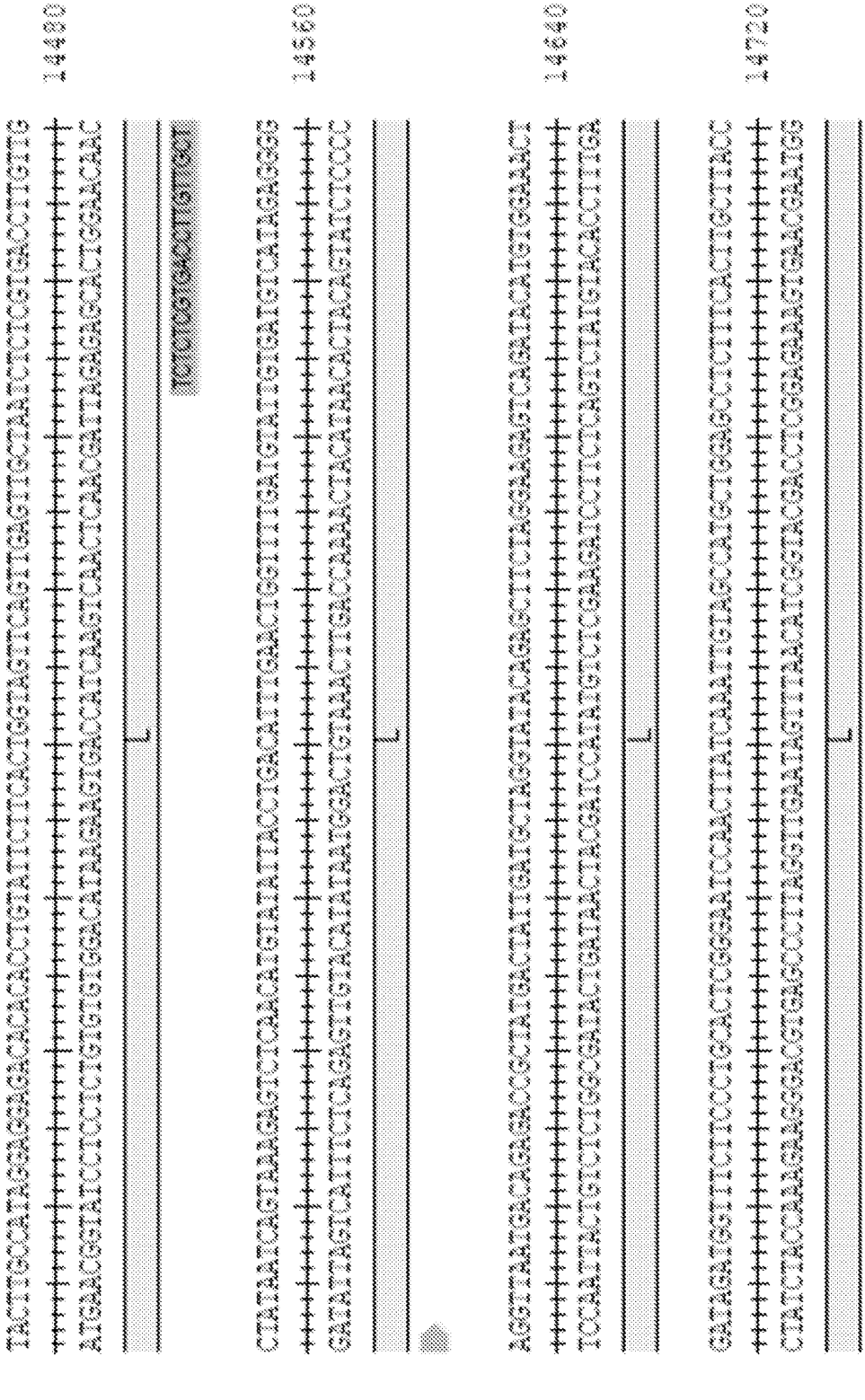
FIG. 19 – continued

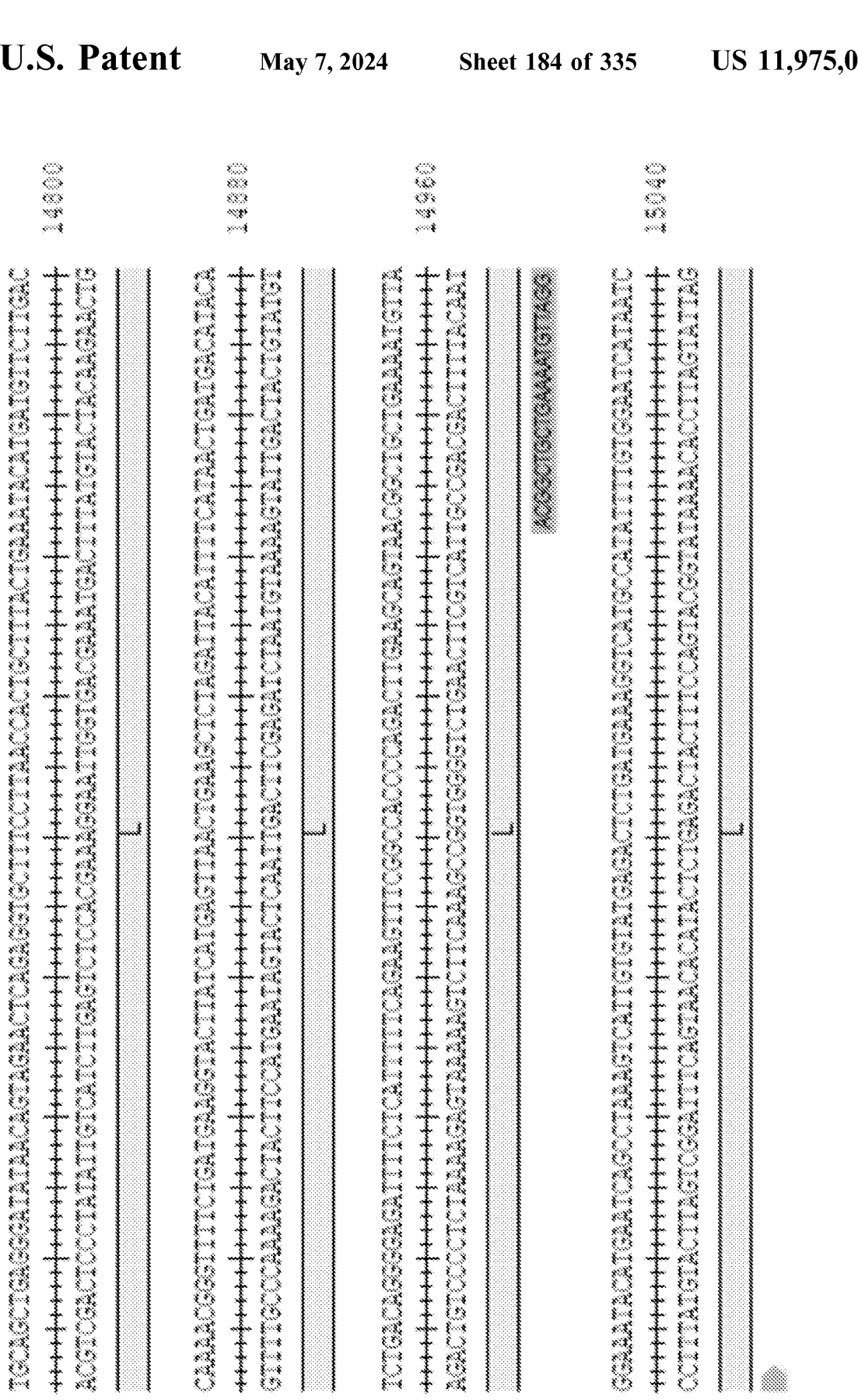
FIG. 19 – continued

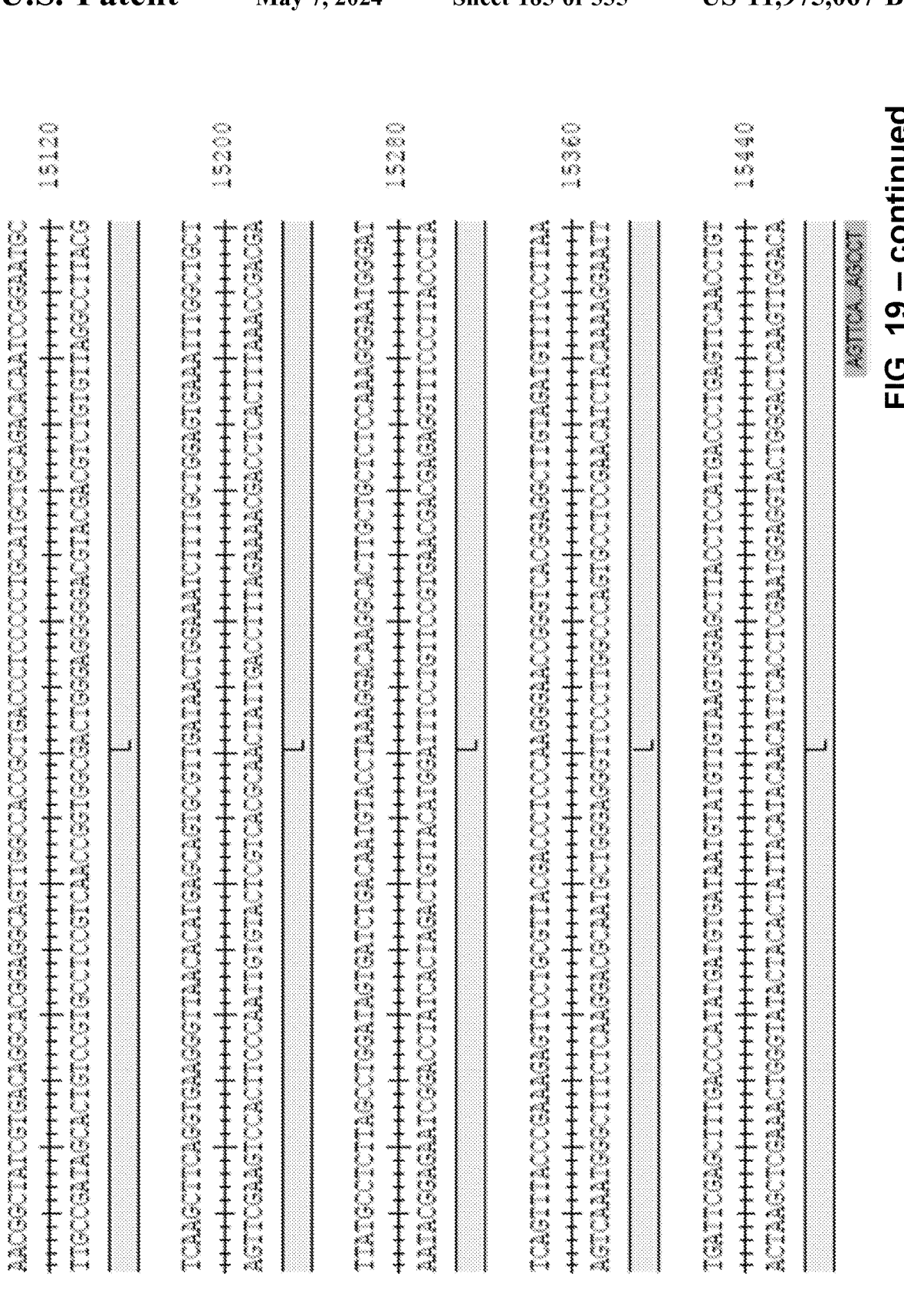
FIG. 19 – continued

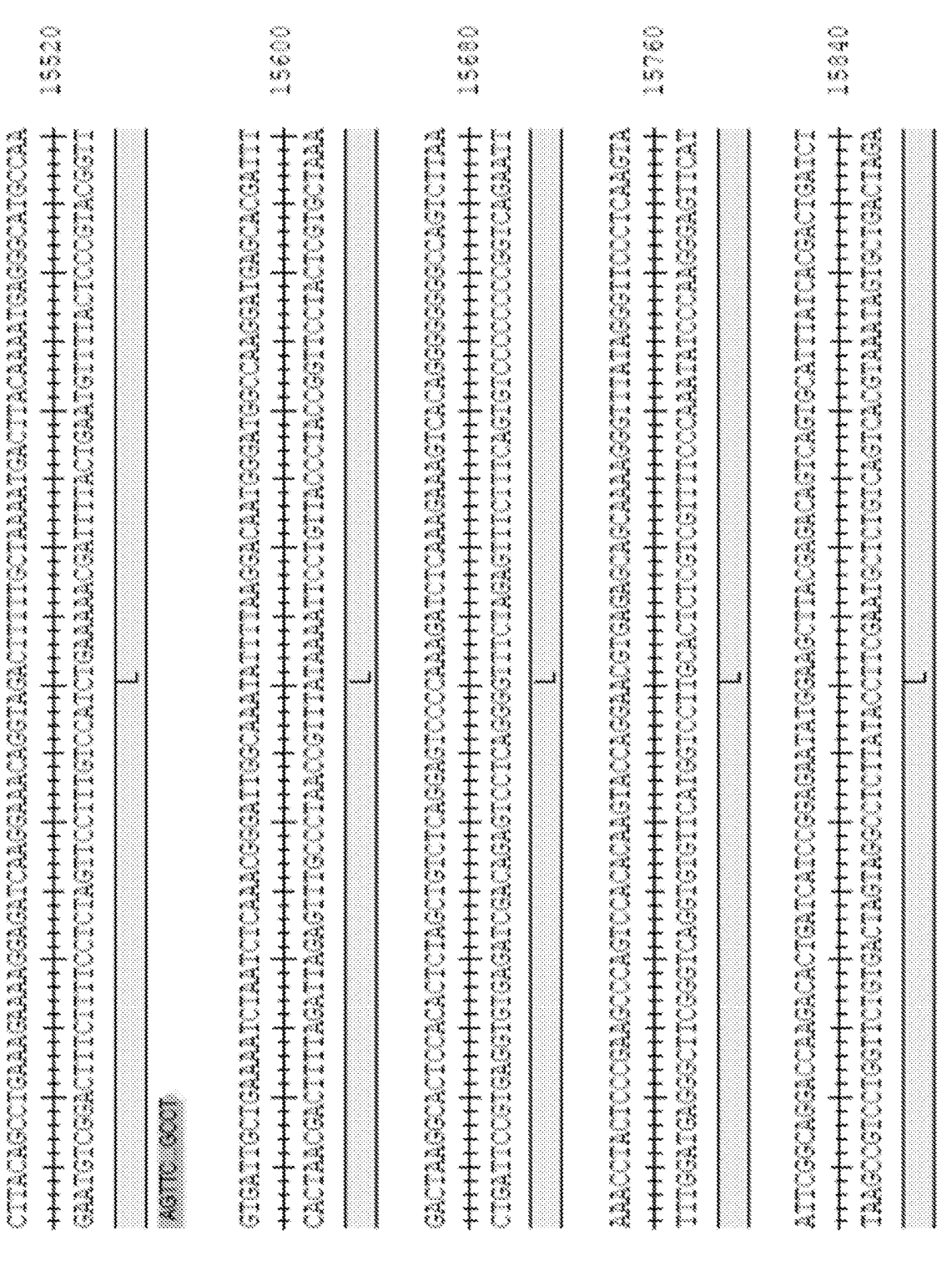
FIG. 19 – continued

FIG. 19 – continued

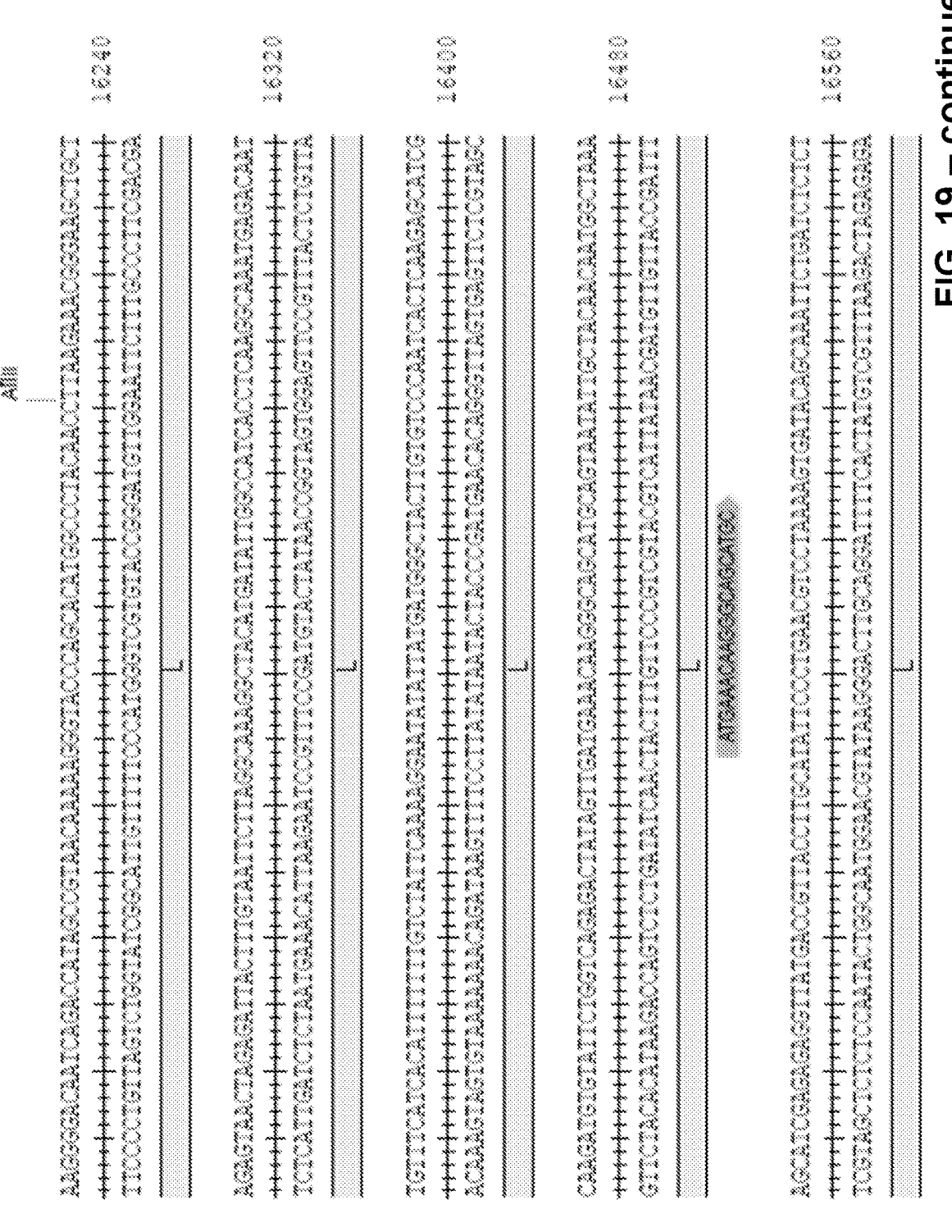
FIG. 19 – continued

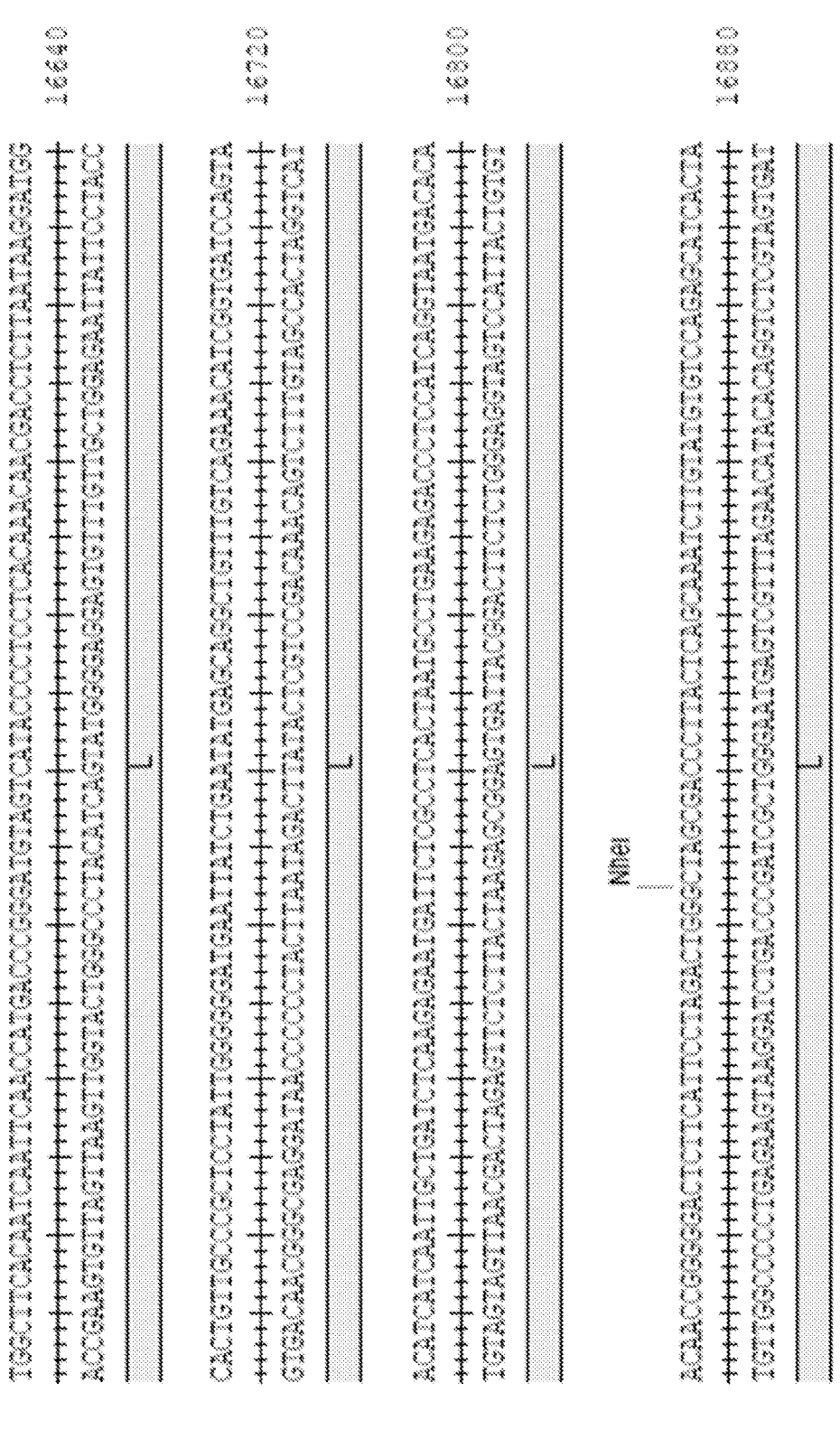
FIG. 19 – continued

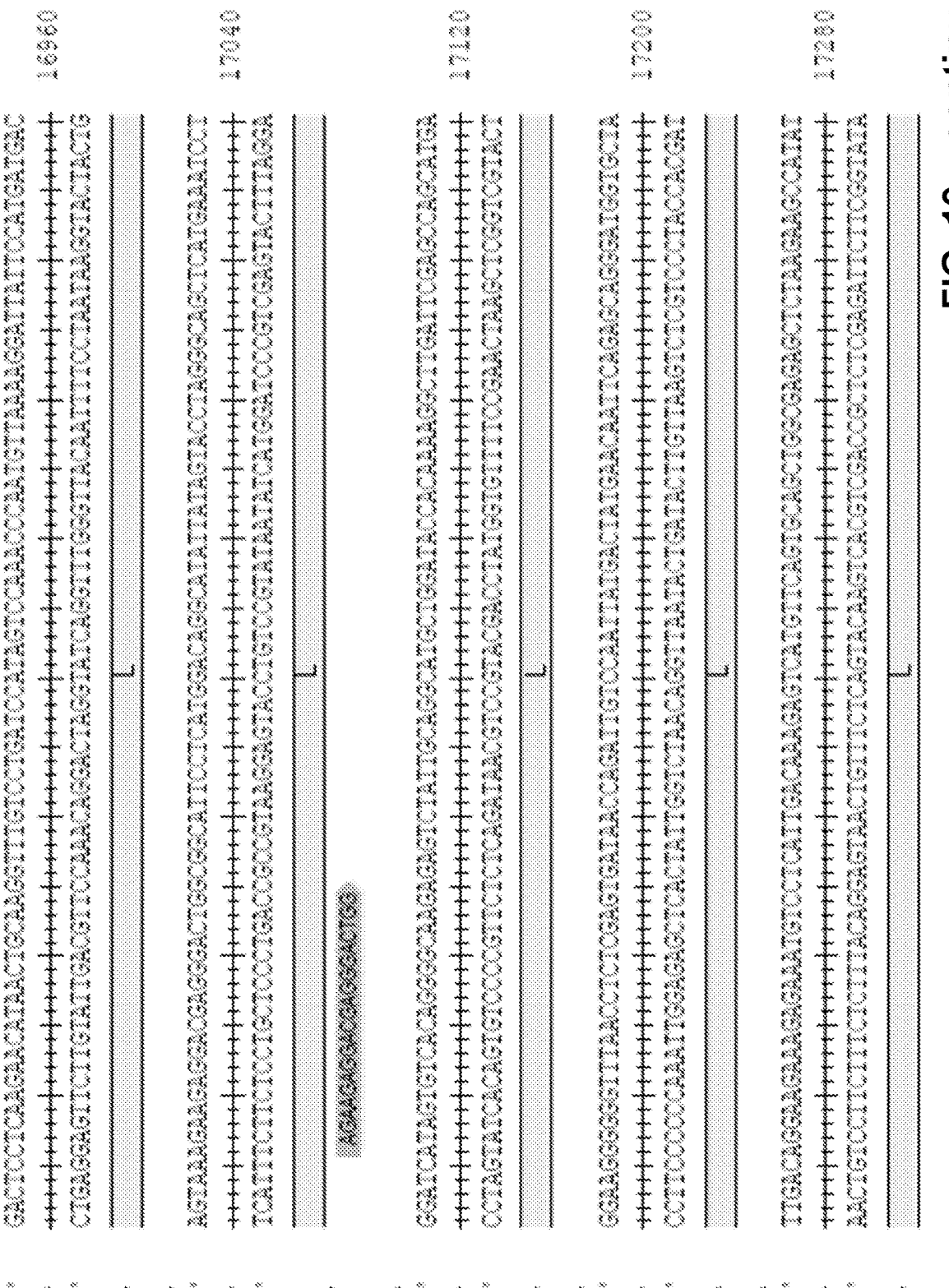
FIG. 19 – continued

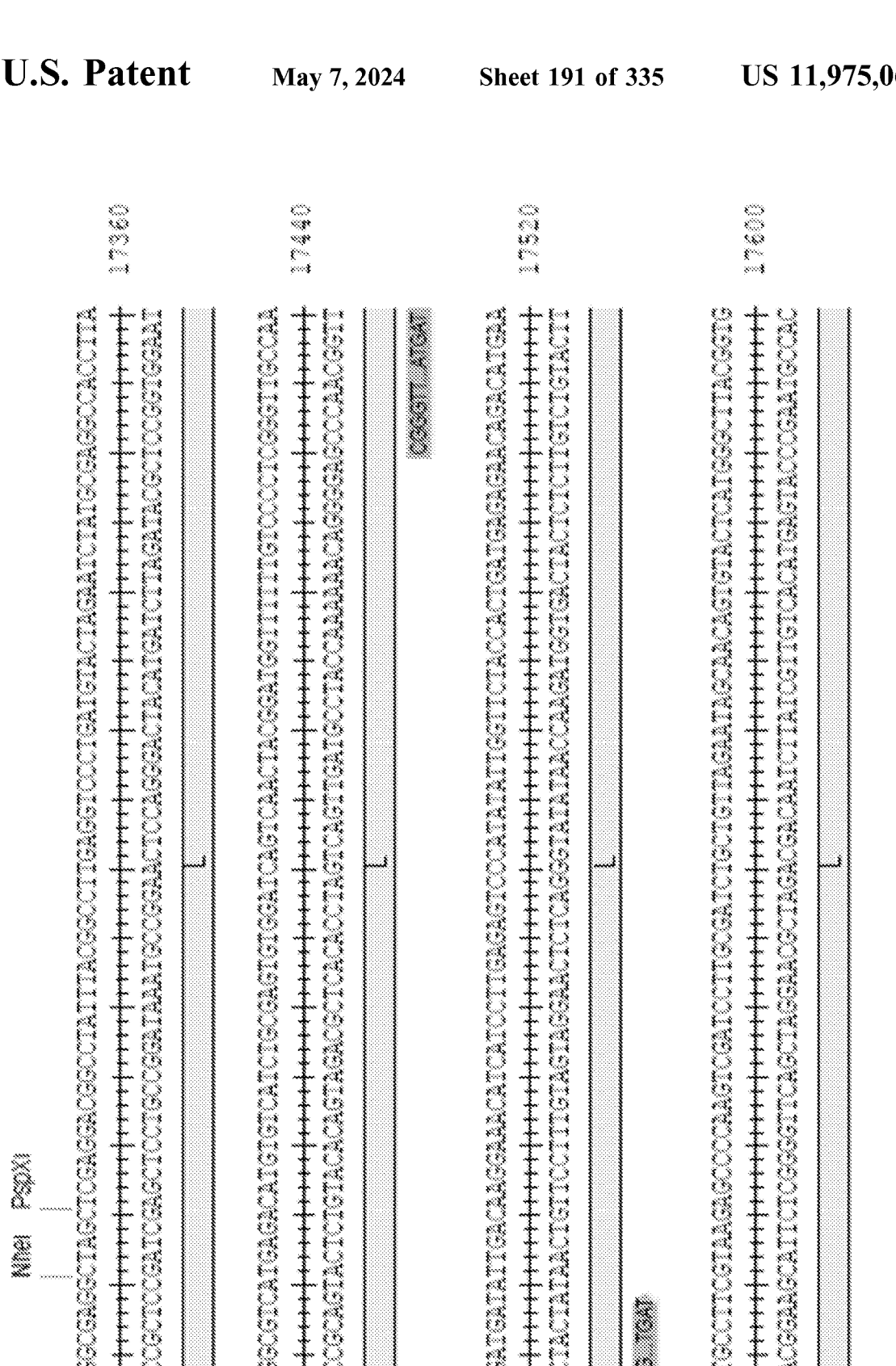
FIG. 19 – continued

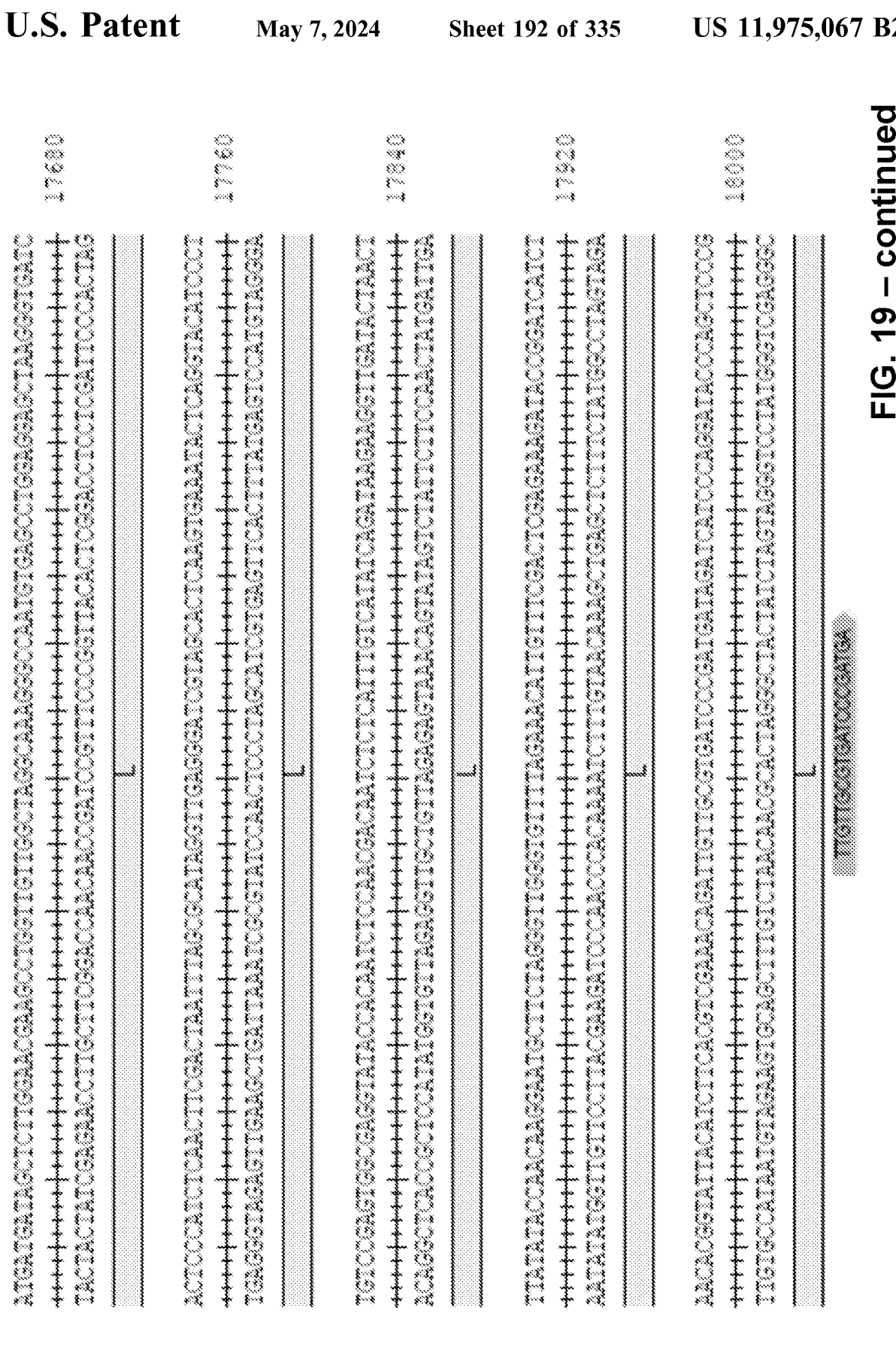
FIG. 19 – continued

FIG. 19 – continued

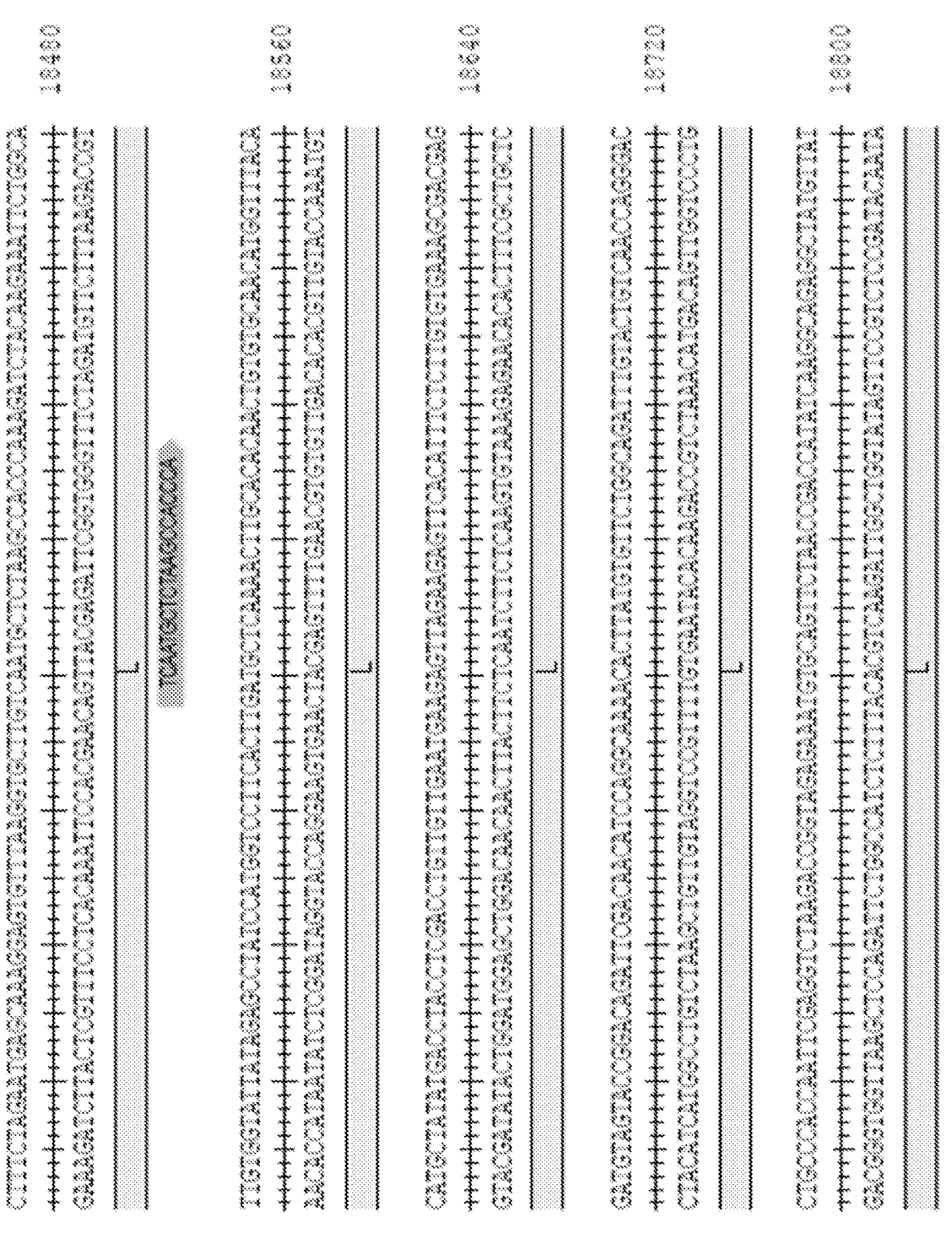
FIG. 19 – continued

FIG. 19 – continued

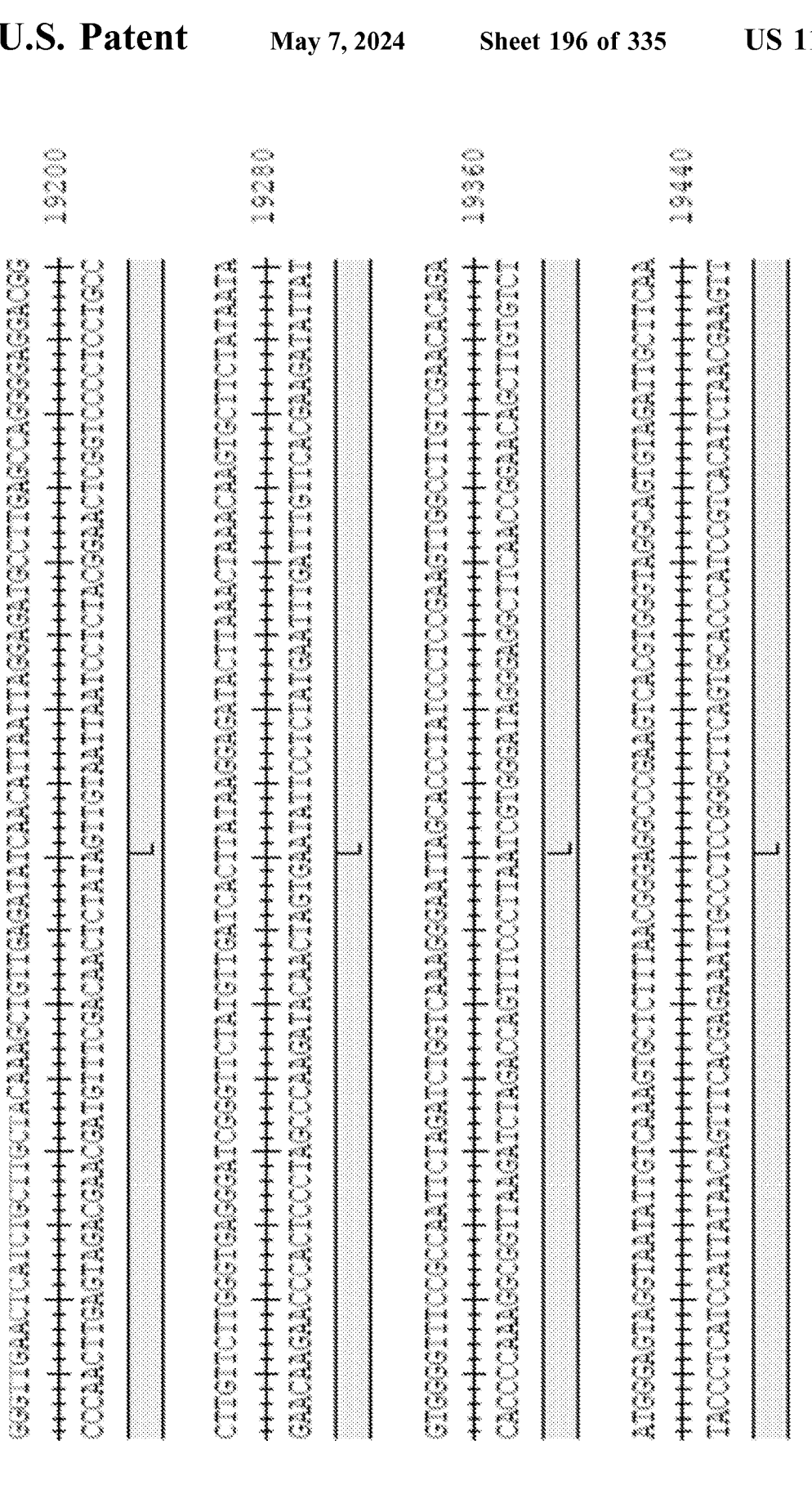
FIG. 19 – continued

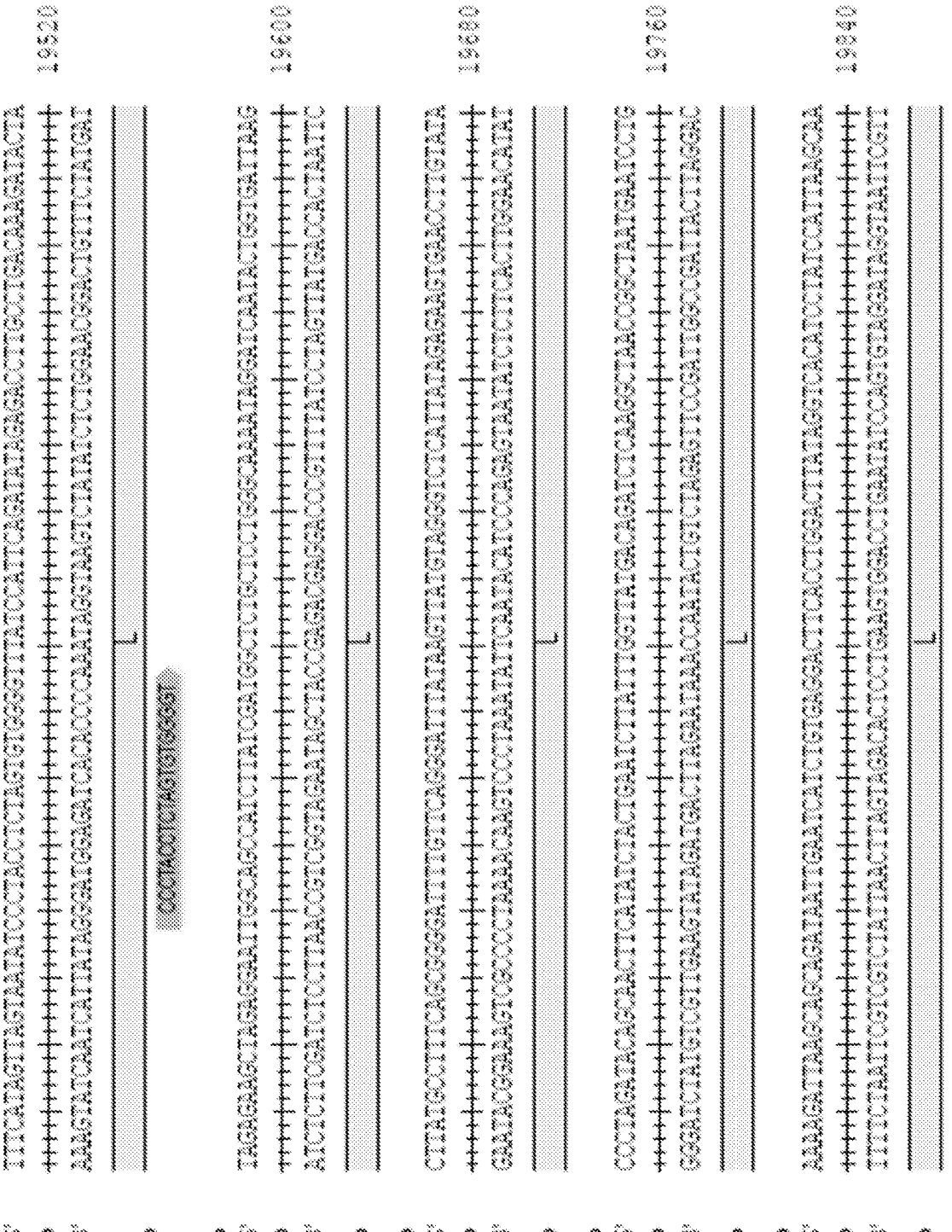
FIG. 19 – continued

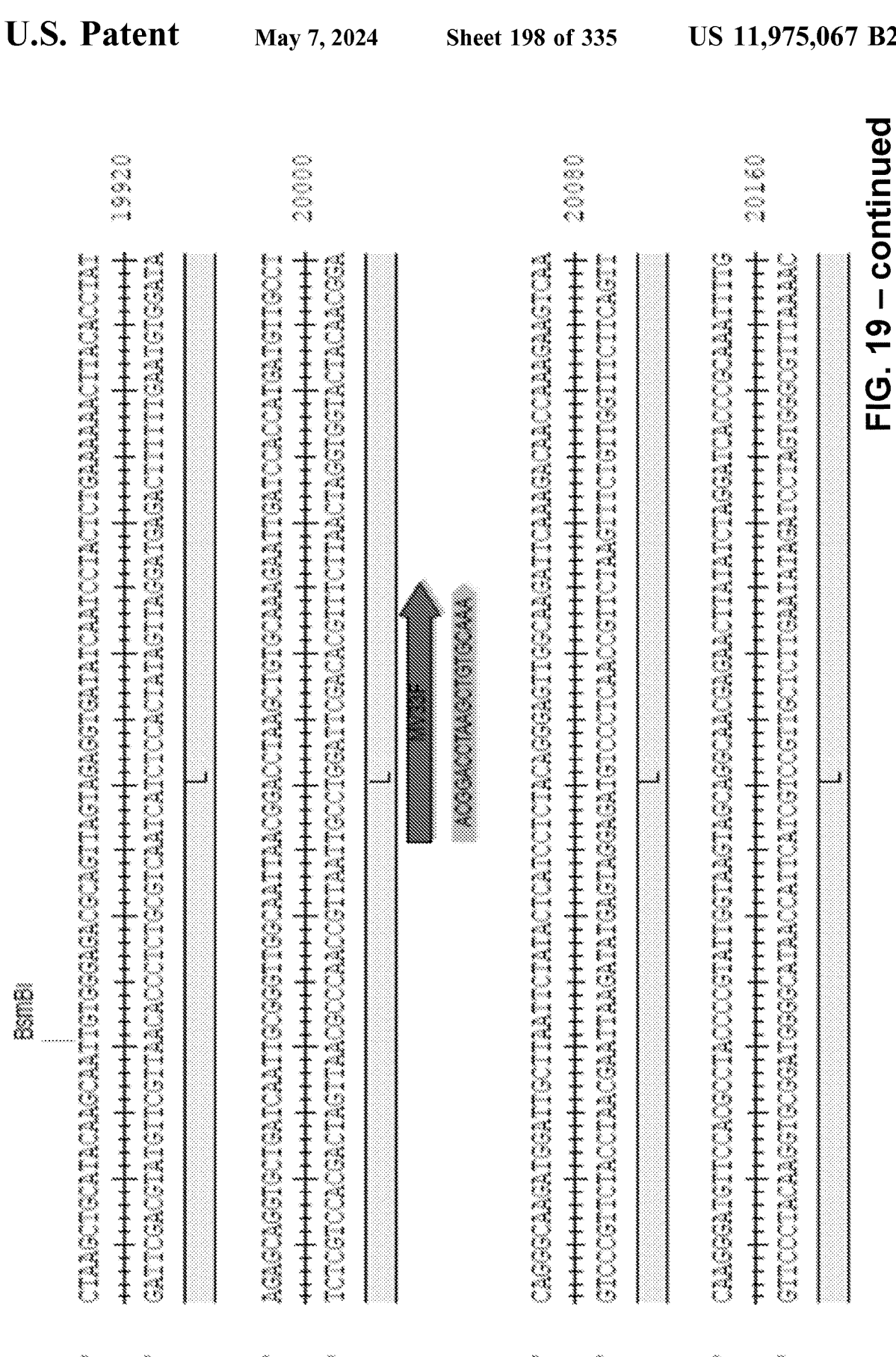
FIG. 19 – continued

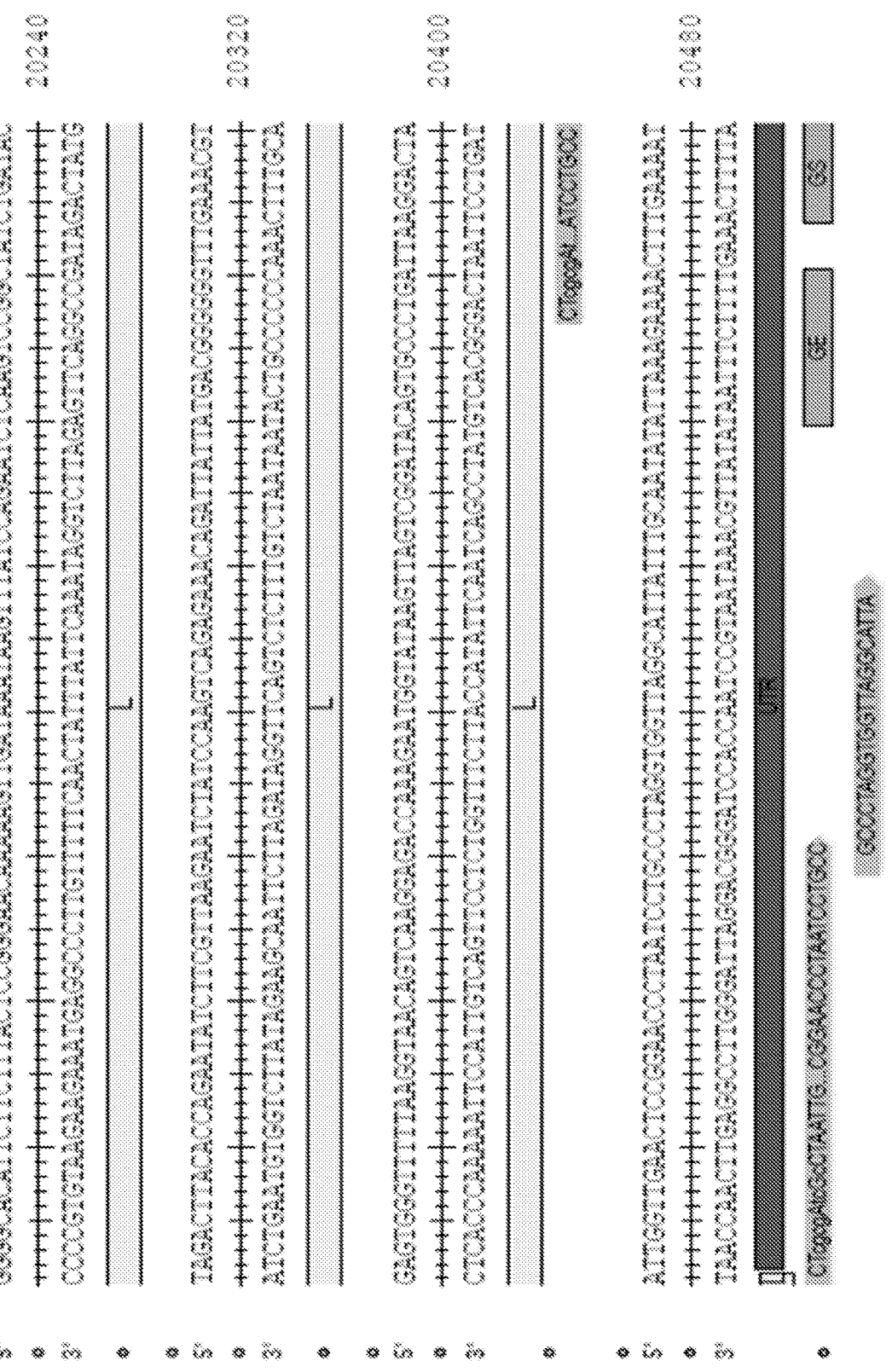
FIG. 19 – continued

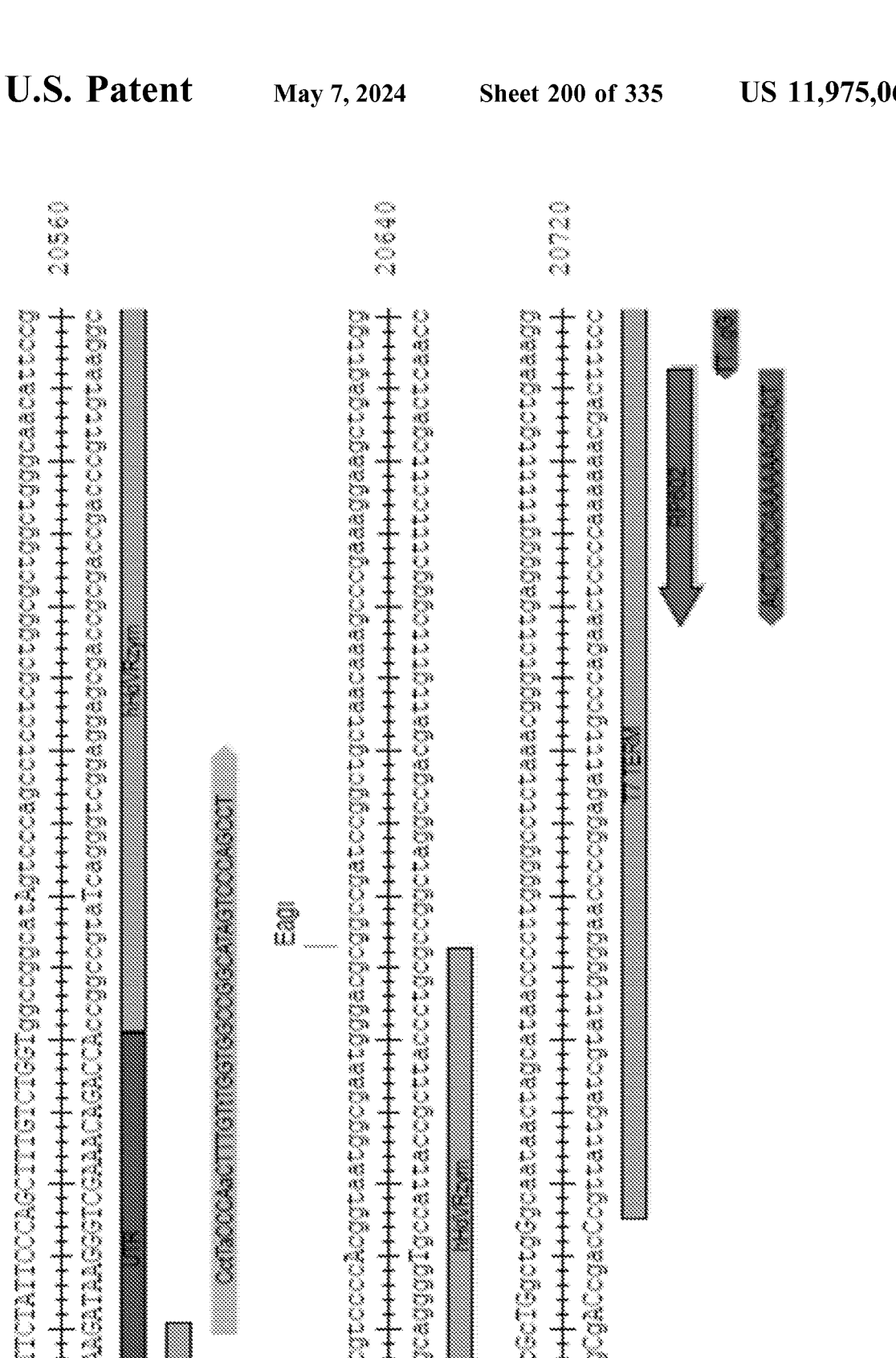
FIG. 19 – continued

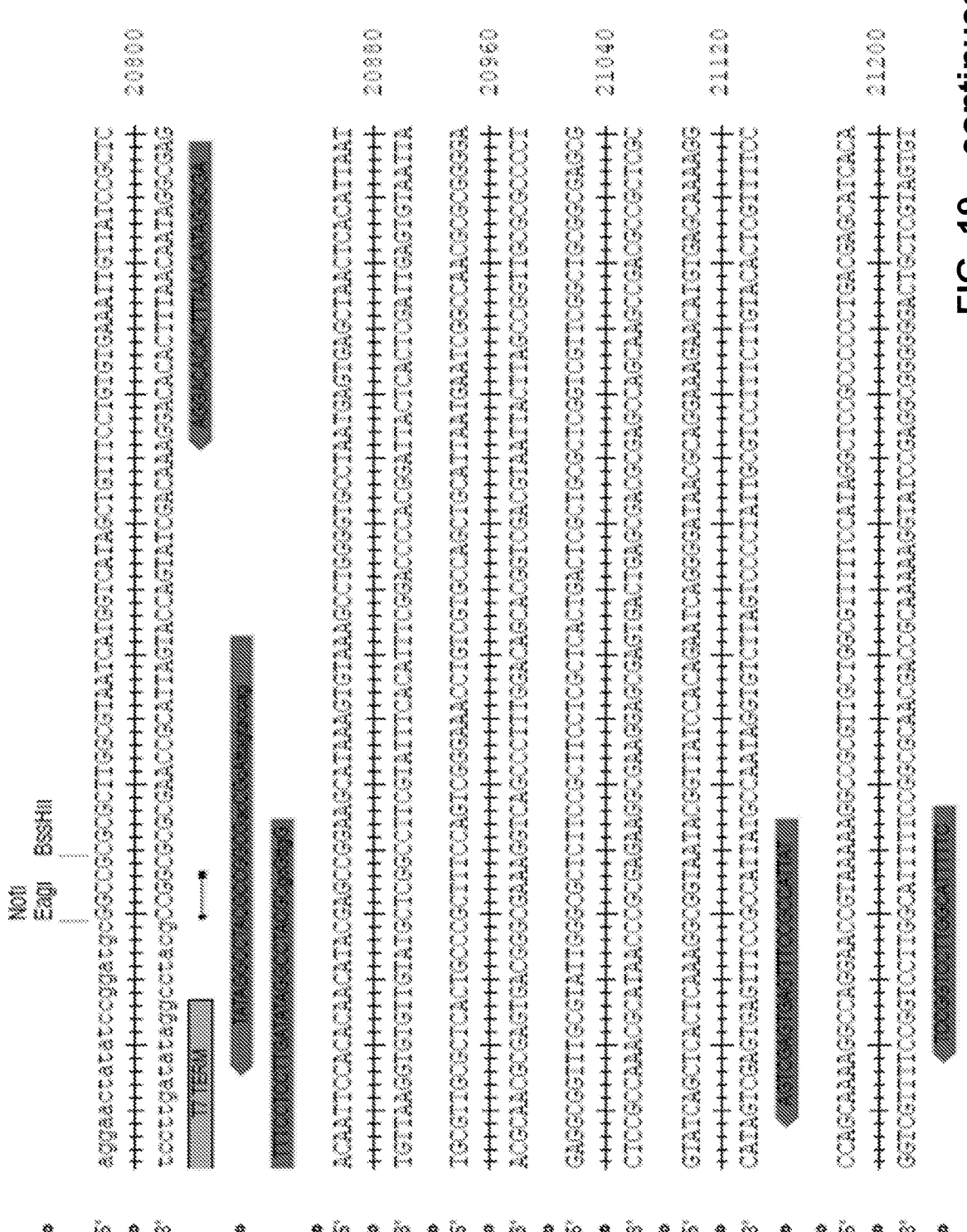
FIG. 19 – continued

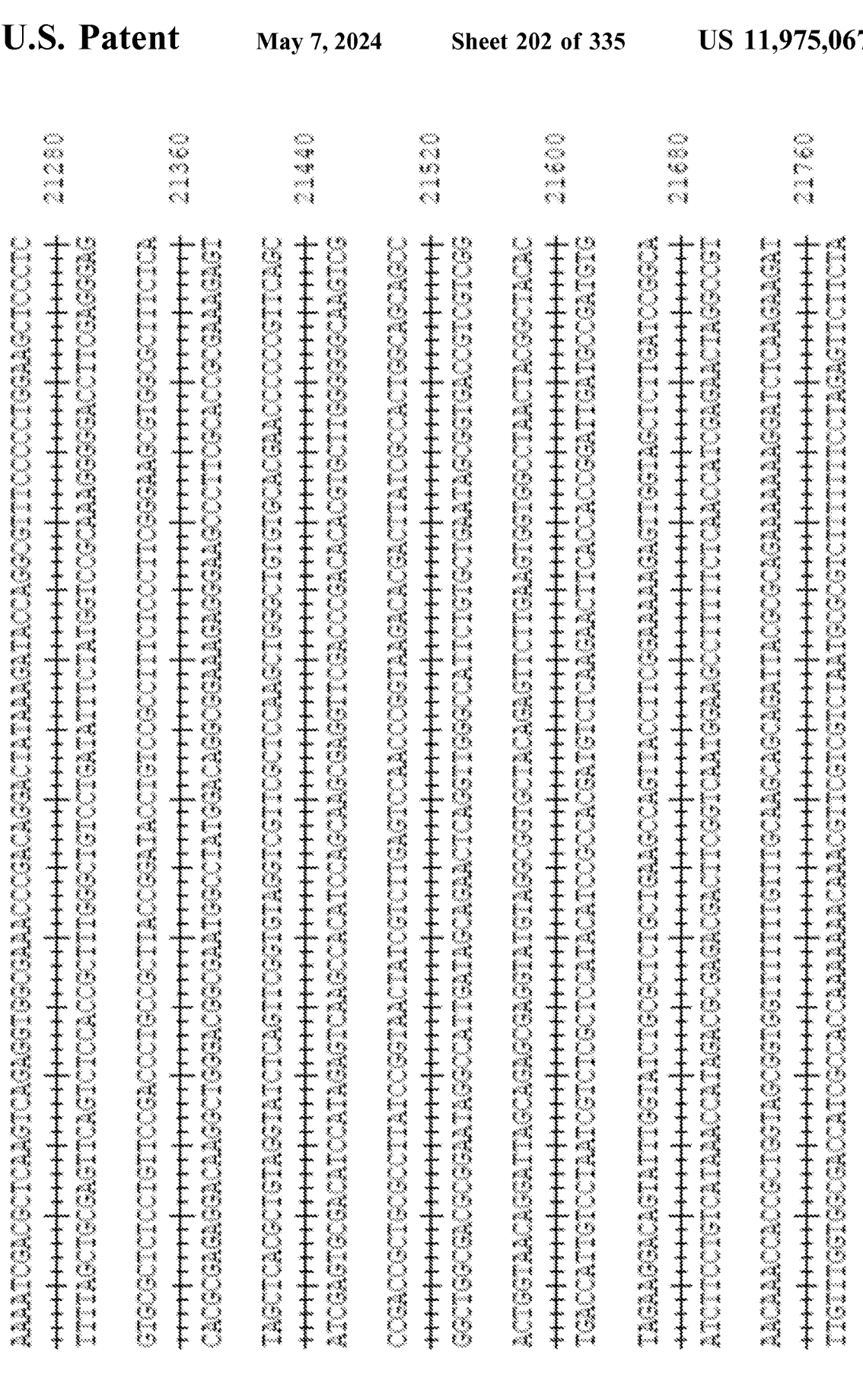
FIG. 19 – continued

FIG. 19 – continued

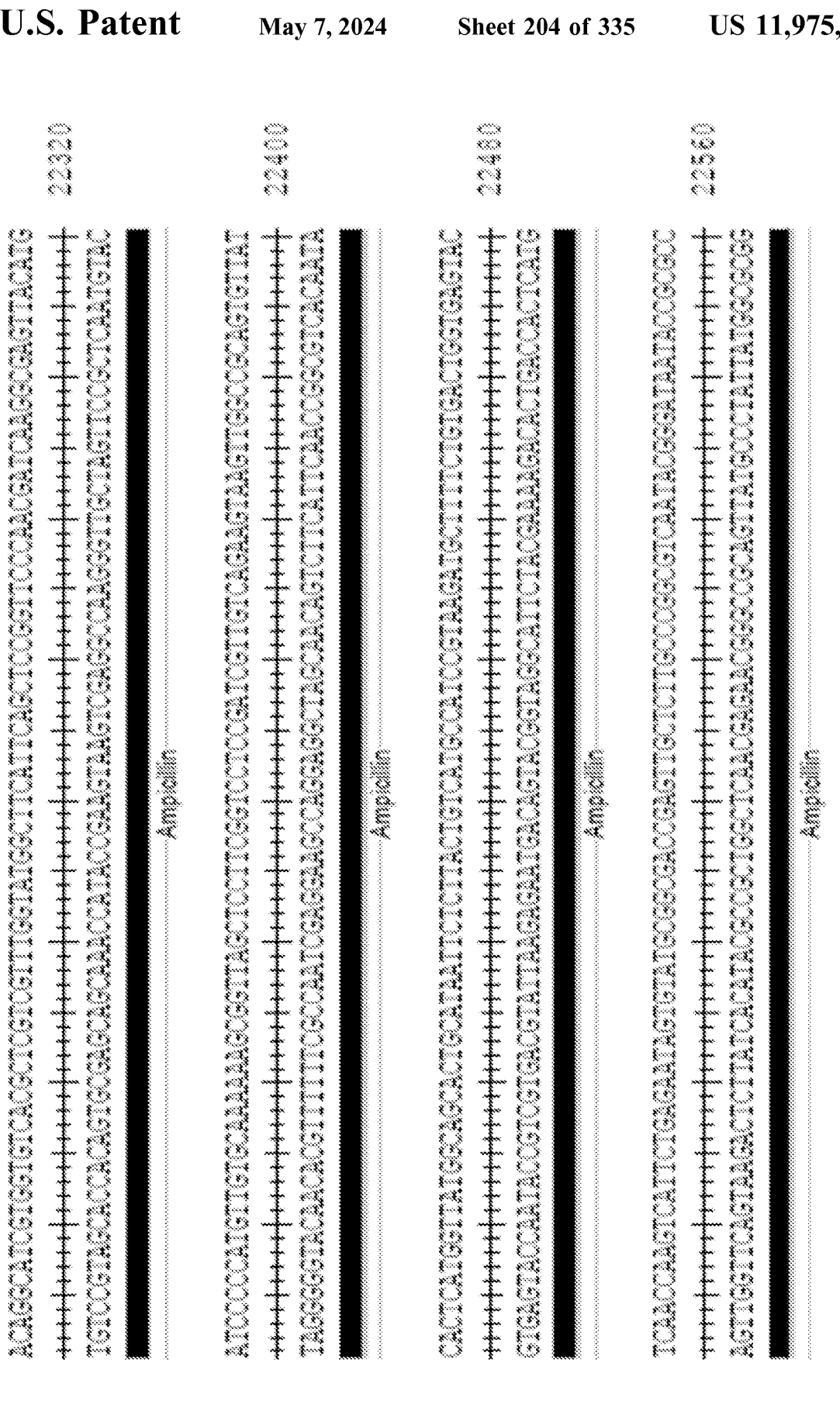
FIG. 19 – continued

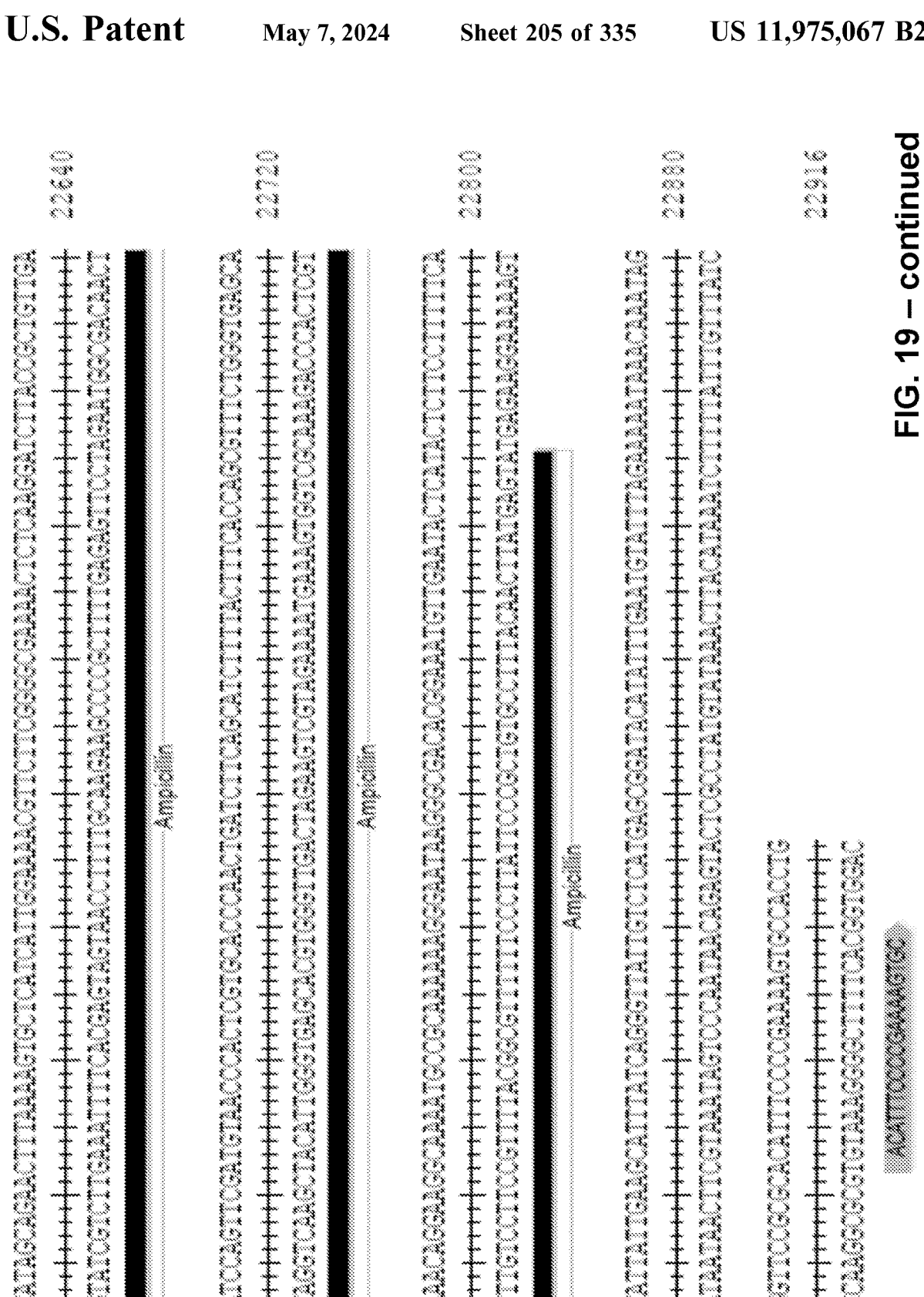
FIG. 19 – continued

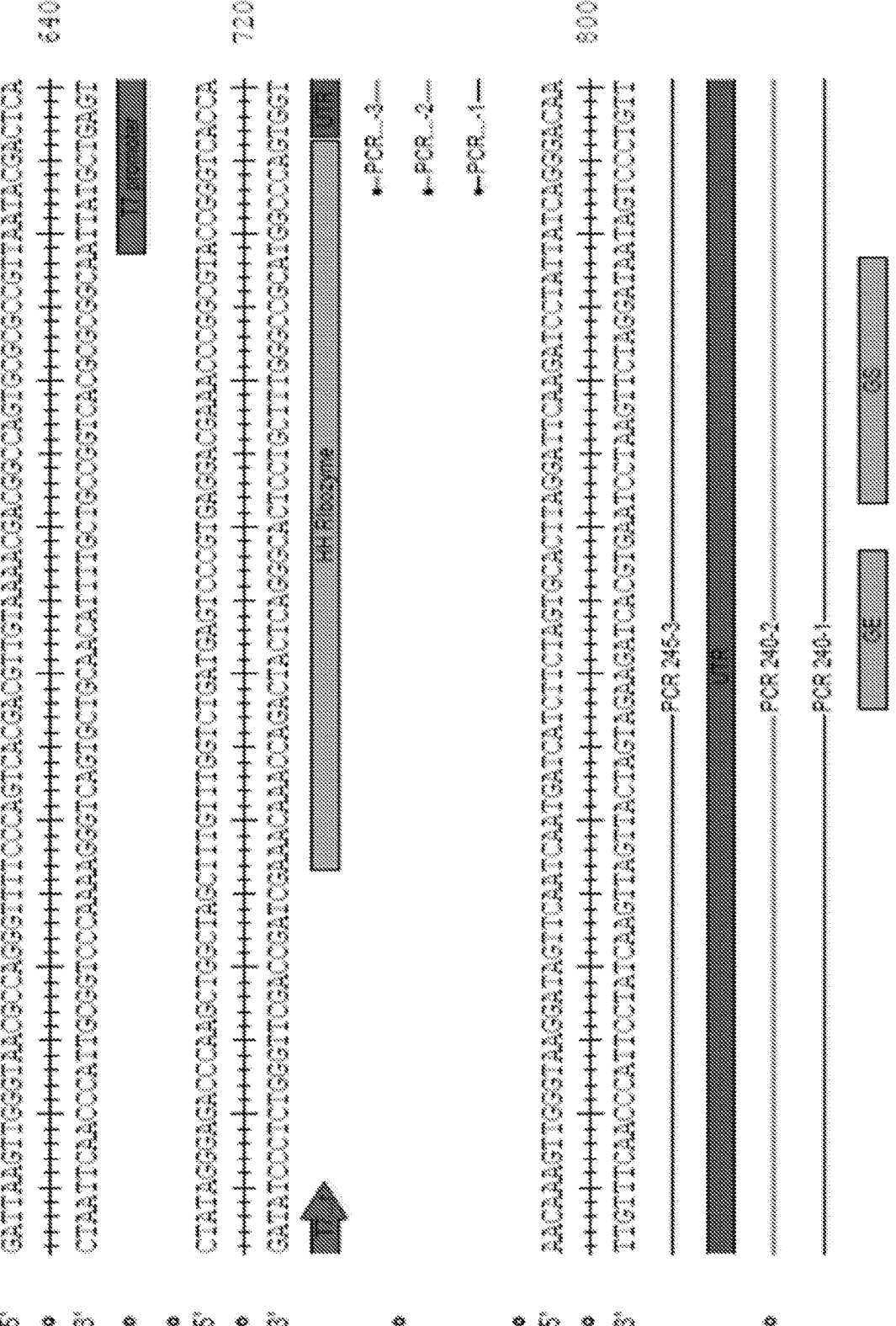
FIG. 20 – continued

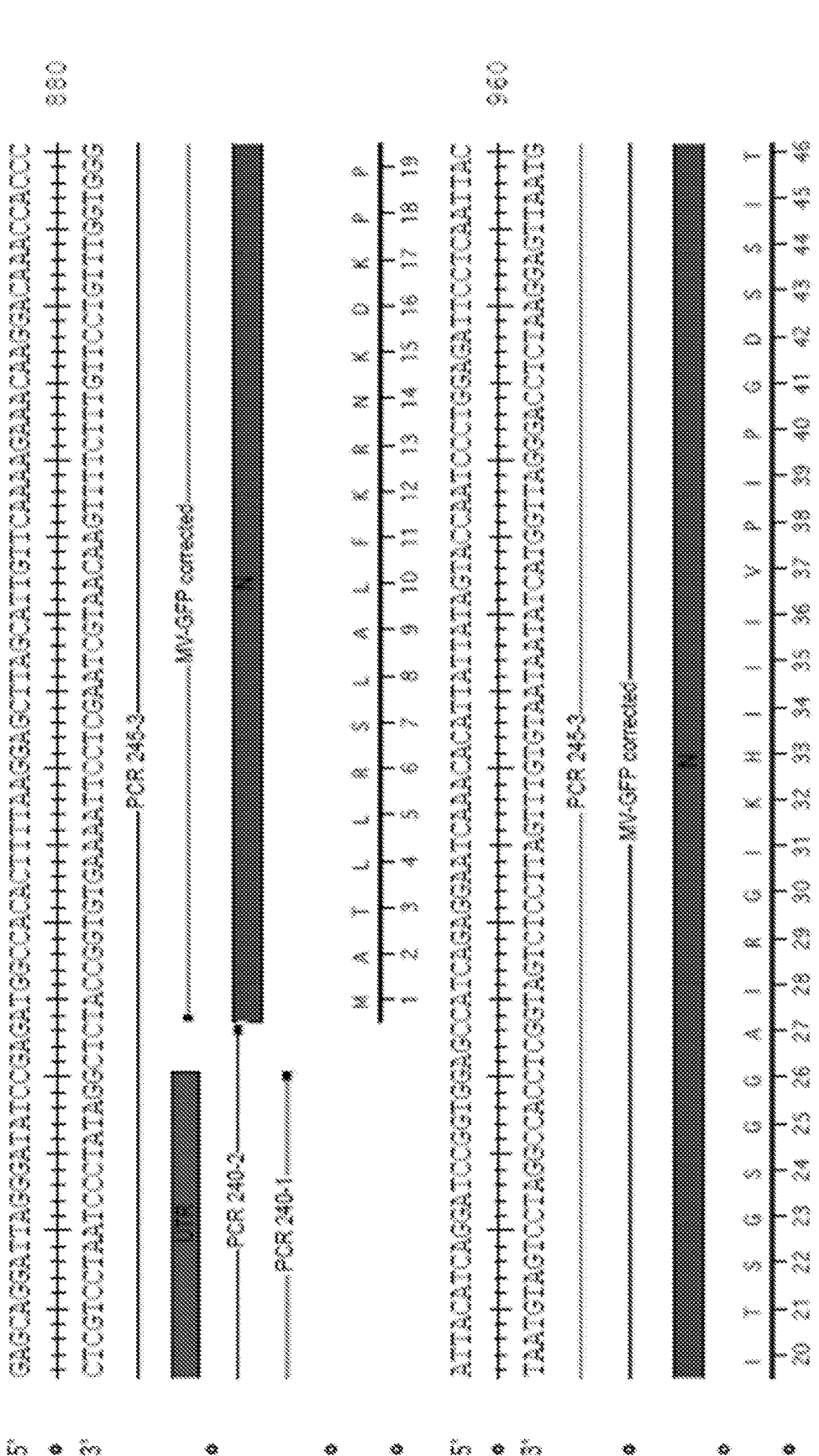
FIG. 20 – continued

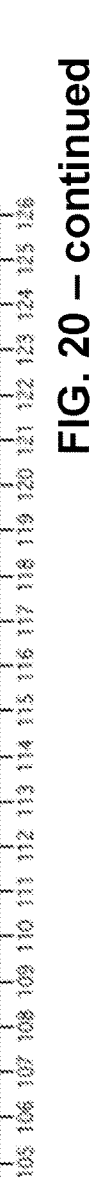
FIG. 20 – continued

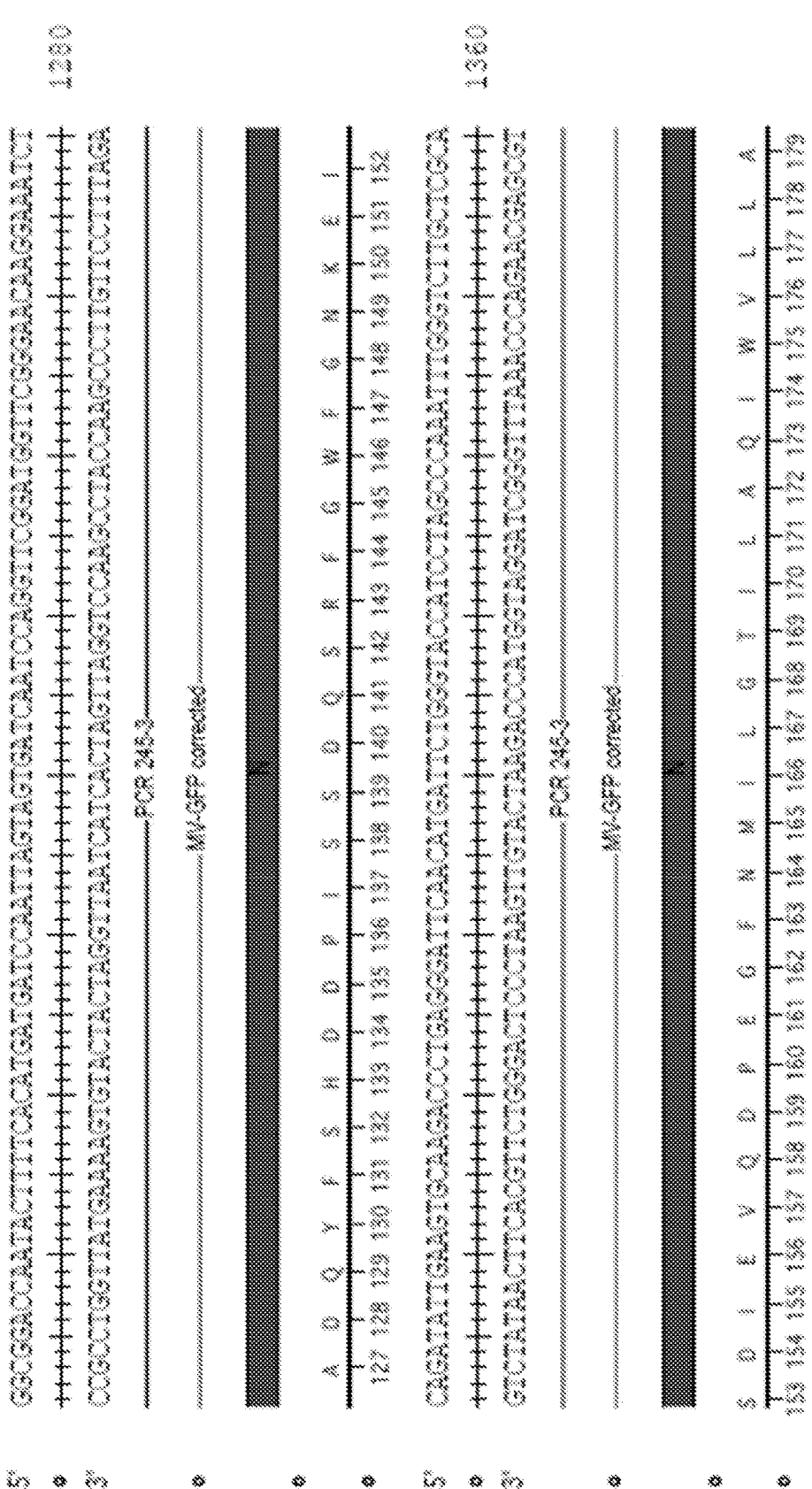
FIG. 20 – continued

FIG. 20 – continued

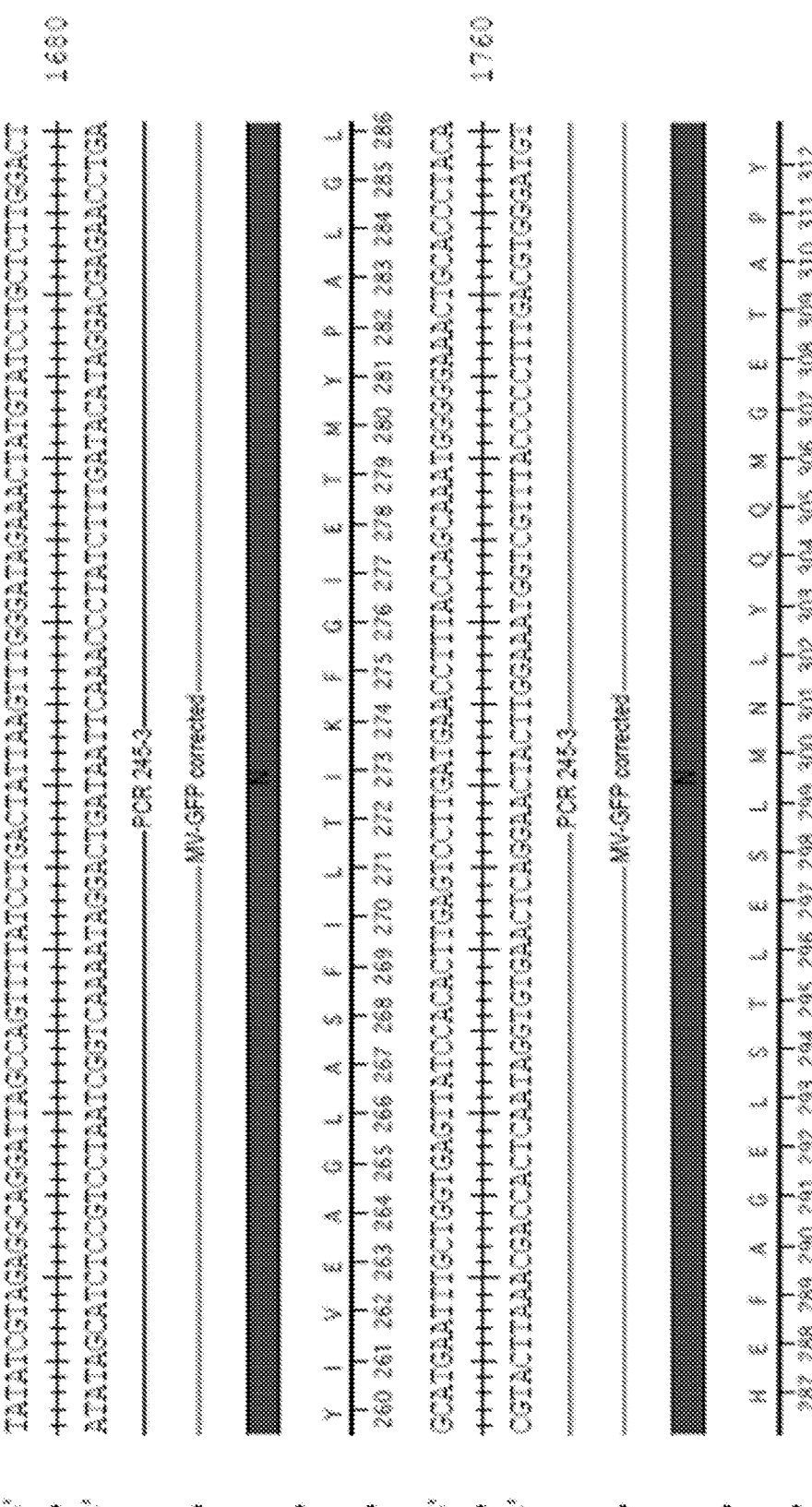
FIG. 20 – continued

FIG. 20 – continued

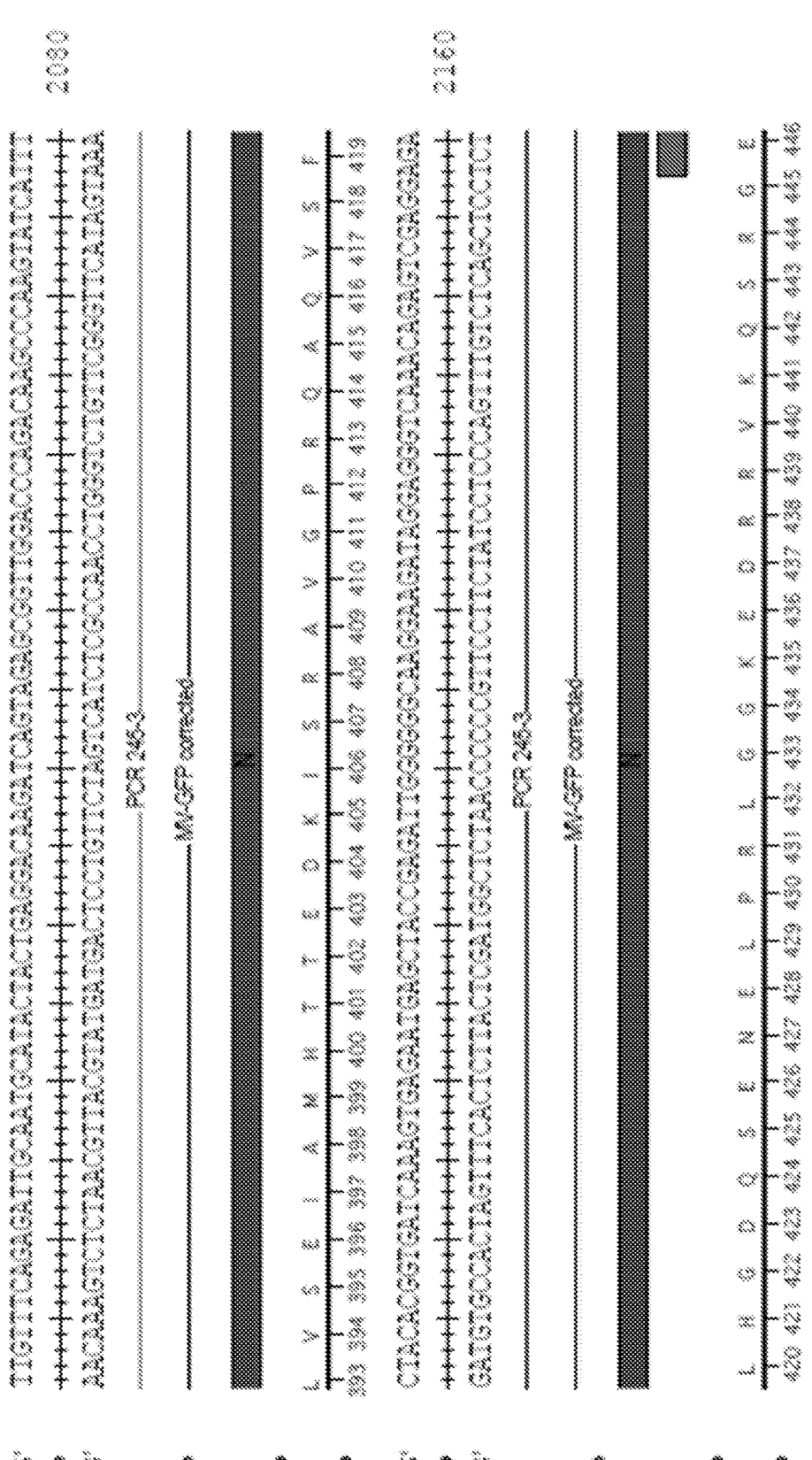
FIG. 20 – continued

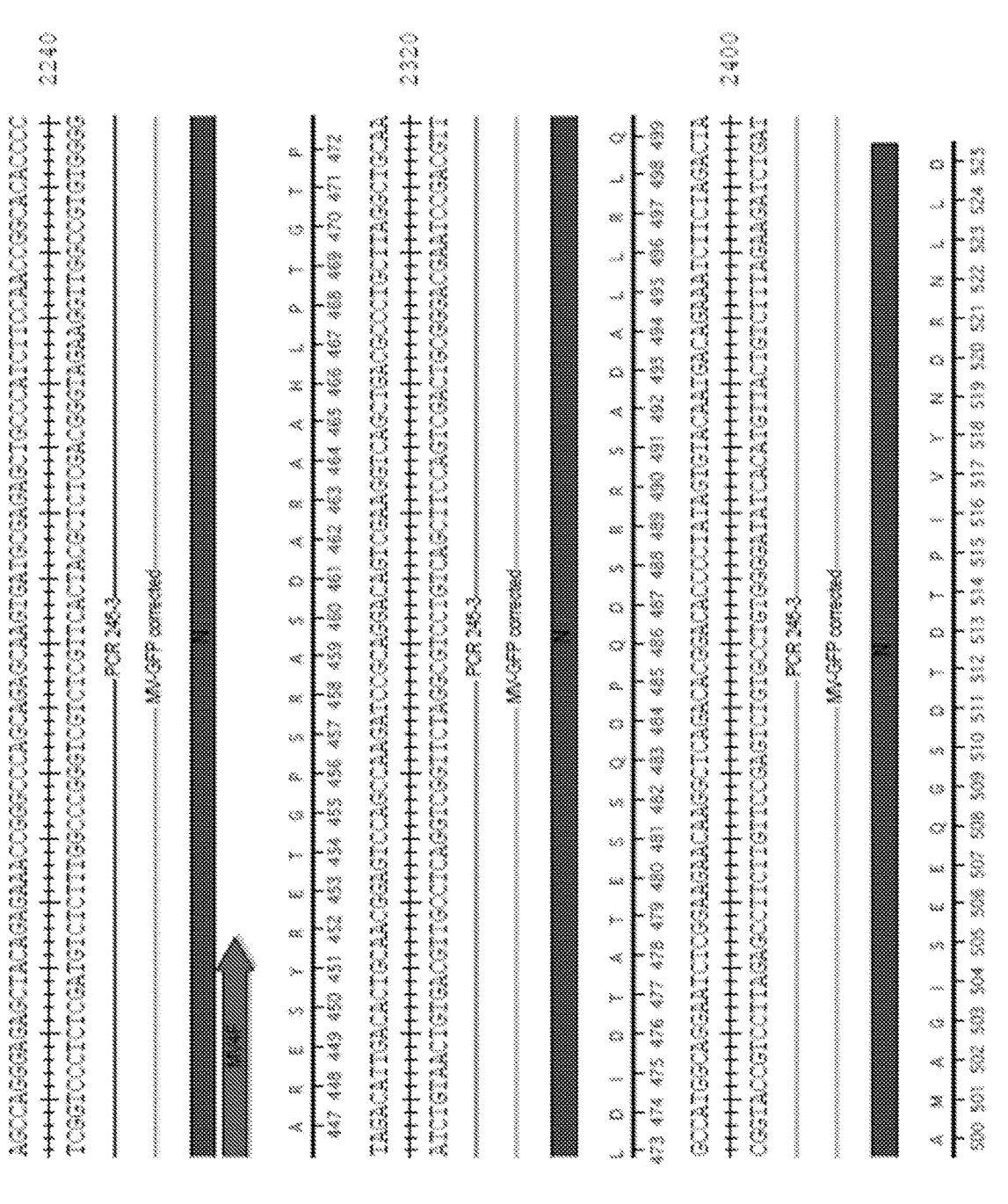
FIG. 20 – continued

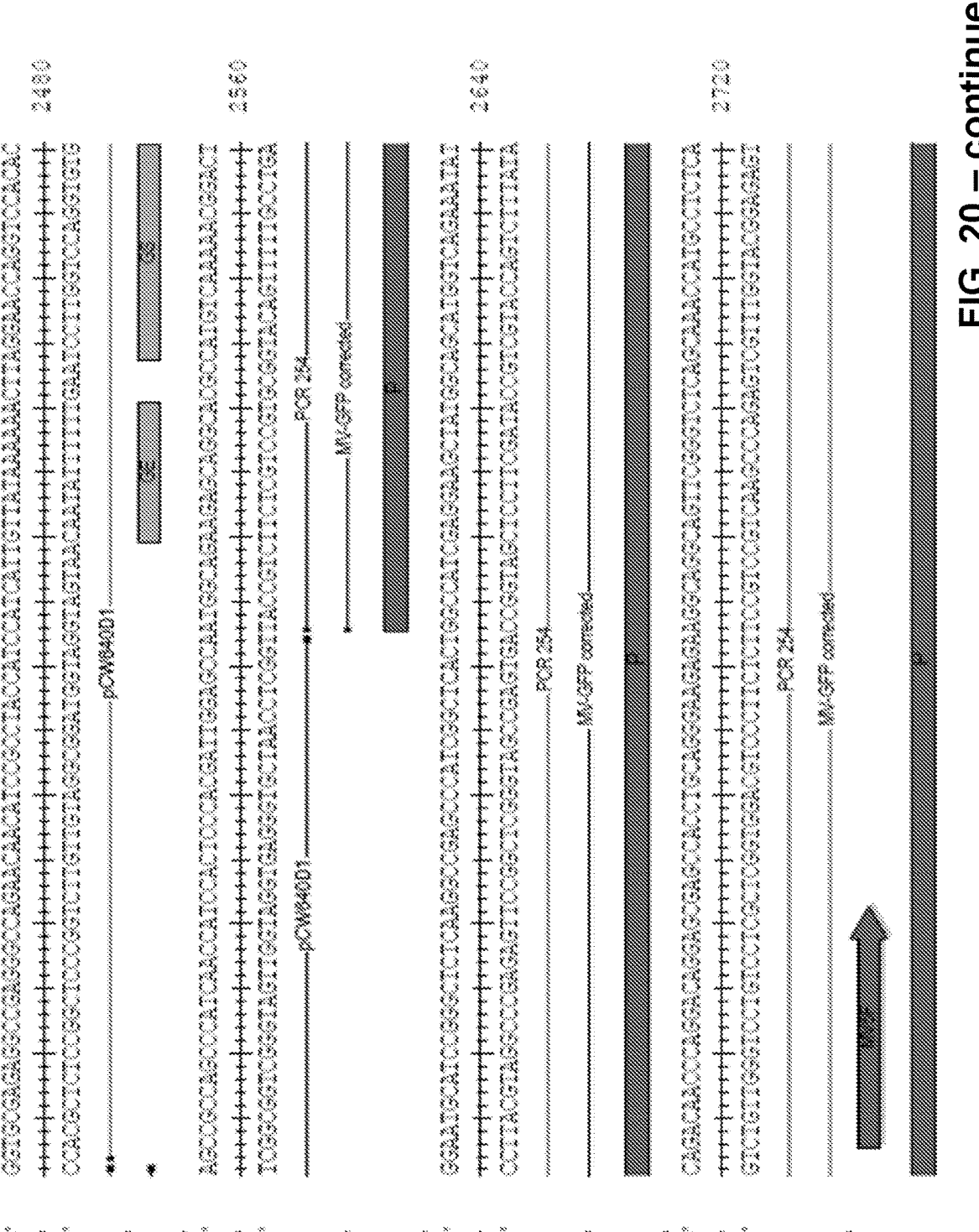
FIG. 20 – continued

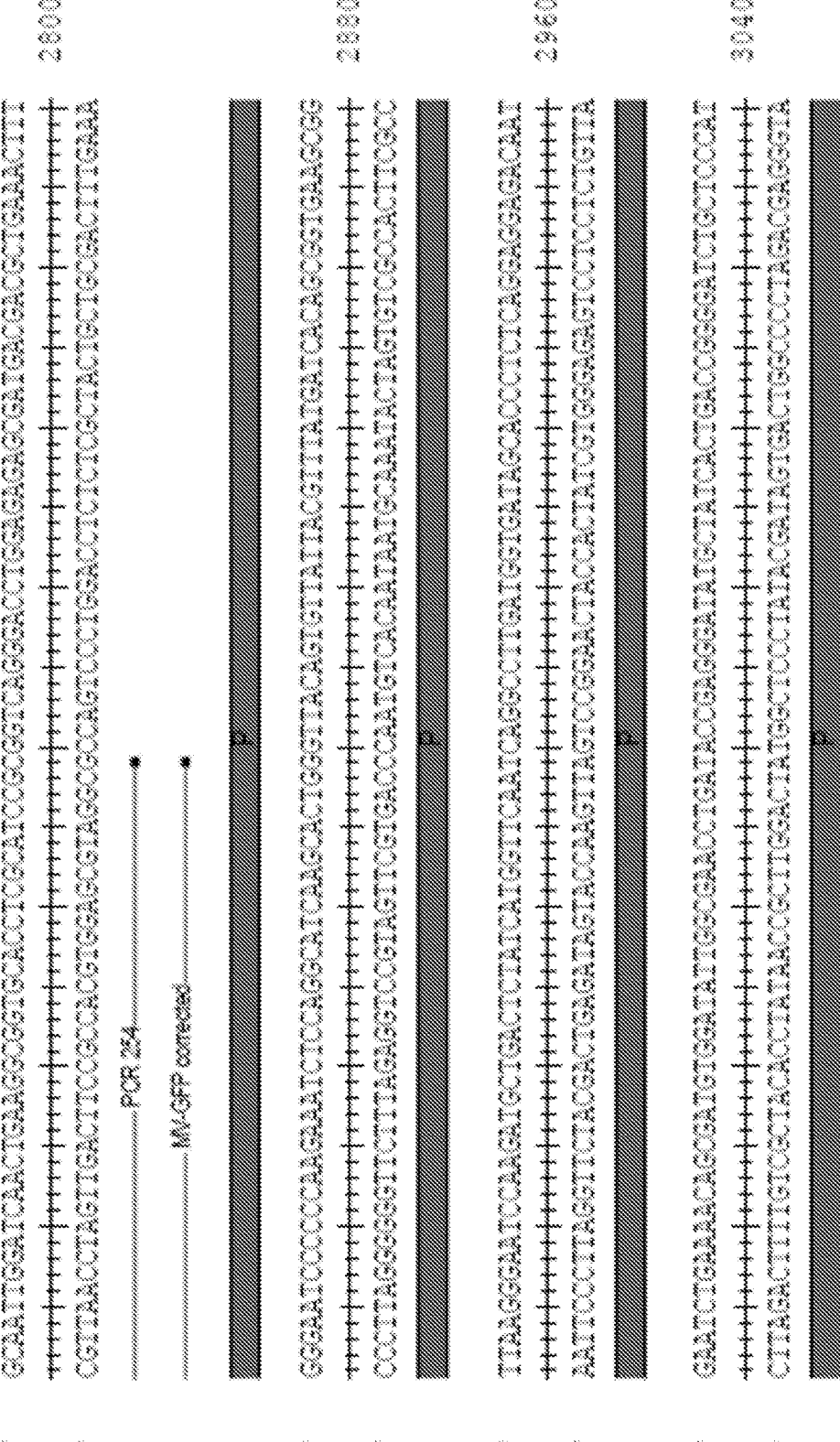
FIG. 20 – continued

FIG. 20 – continued

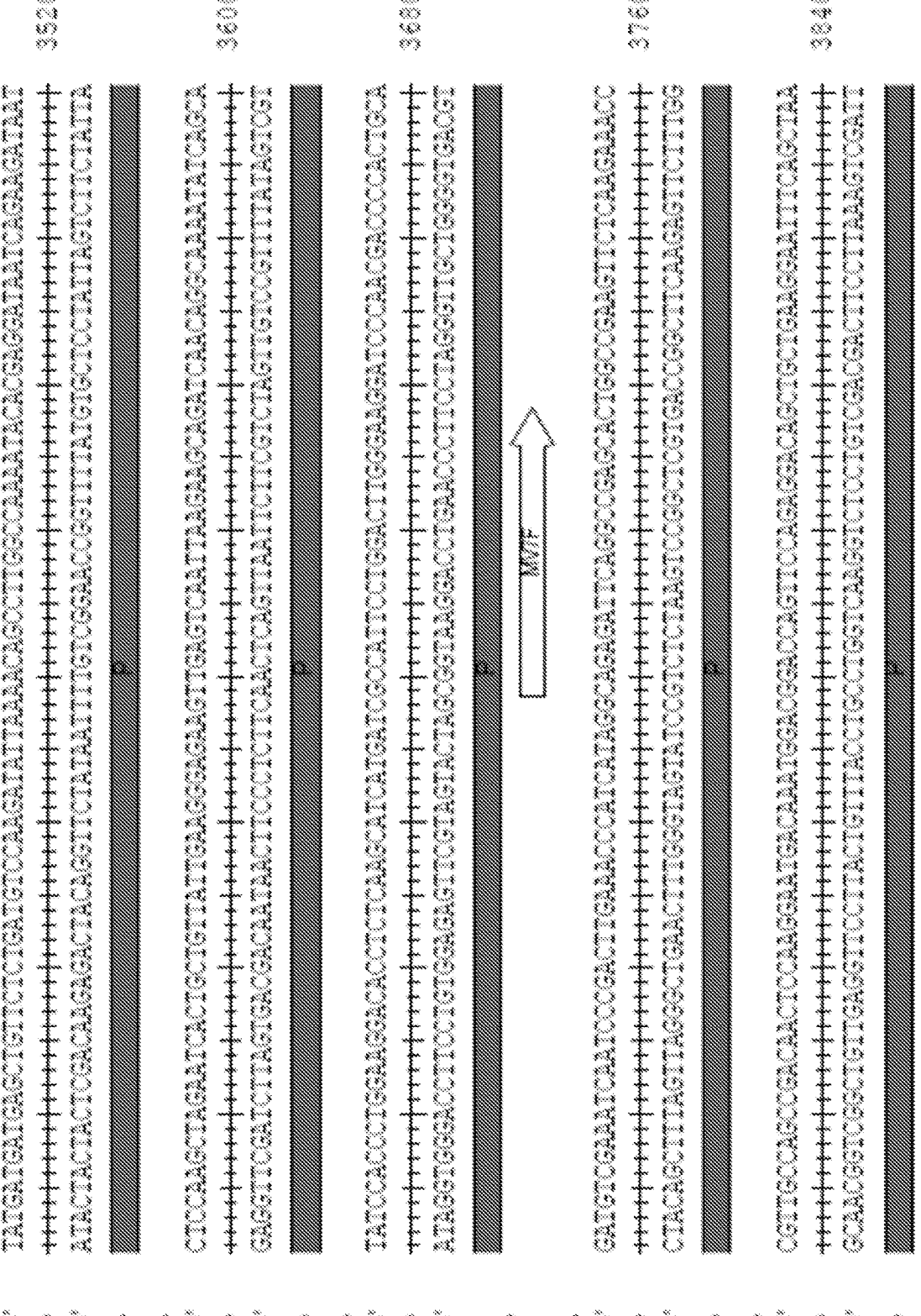
FIG. 20 – continued

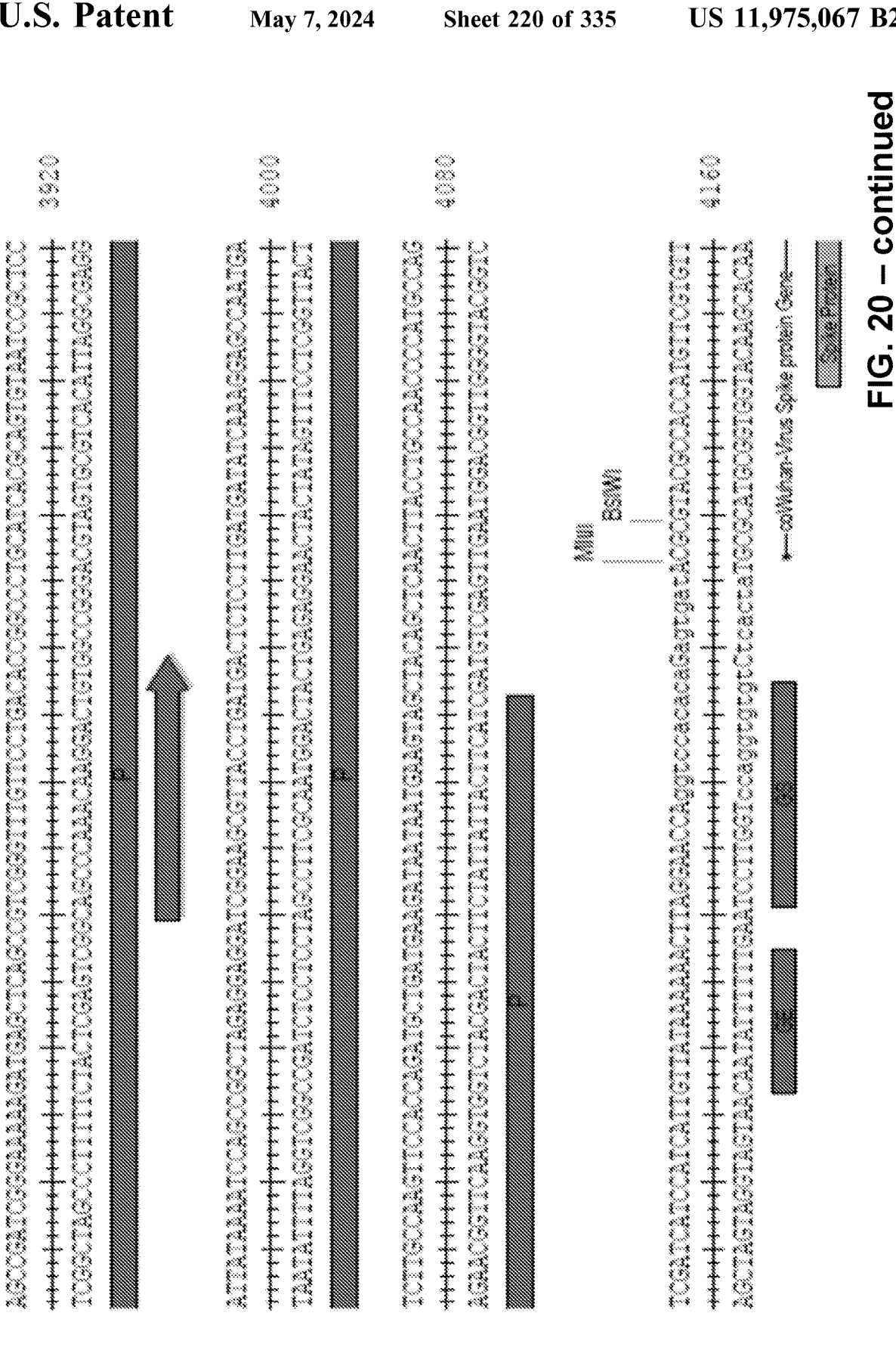
FIG. 20 – continued

FIG. 20 – continued

FIG. 20 – continued

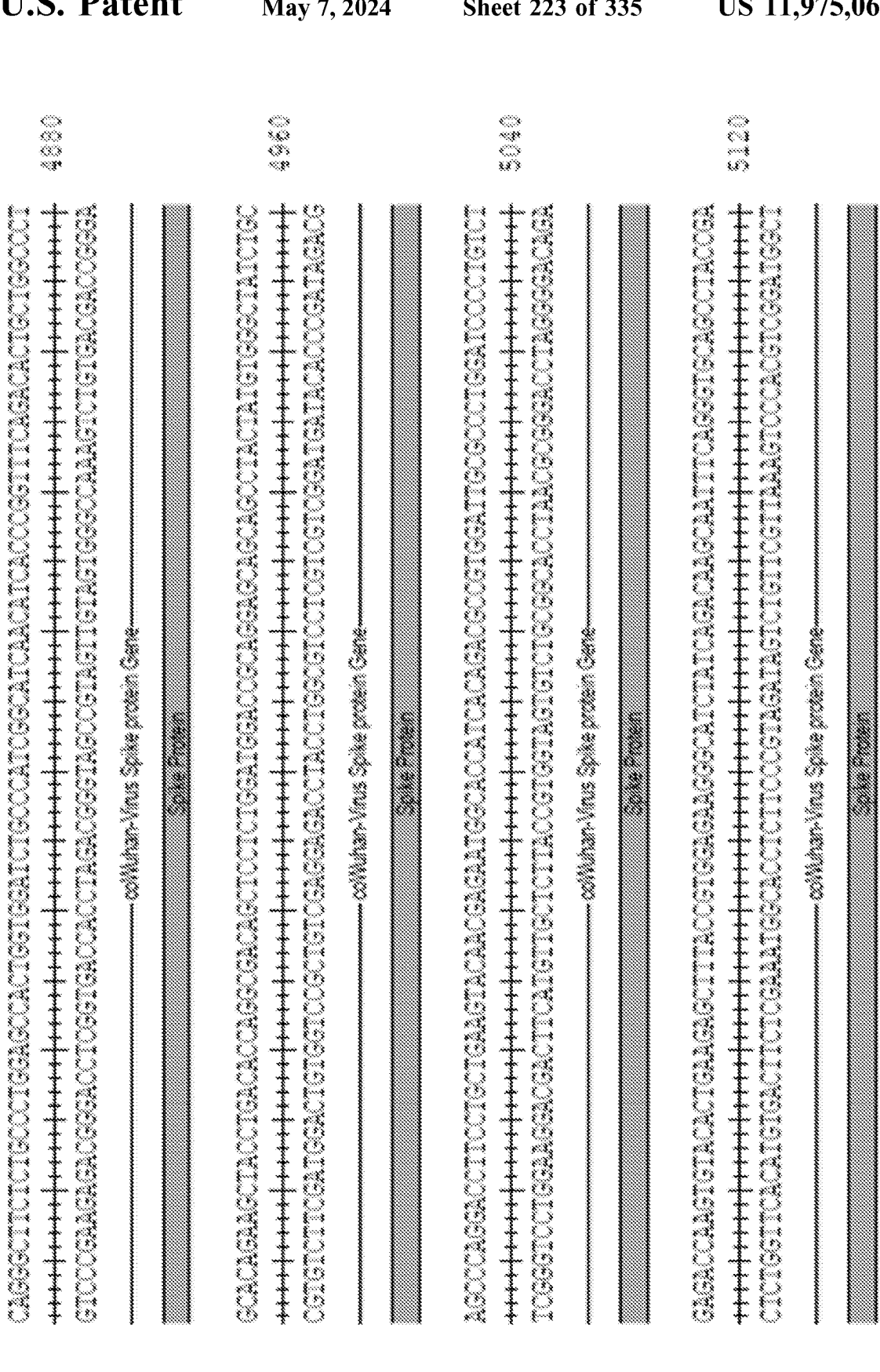
FIG. 20 – continued

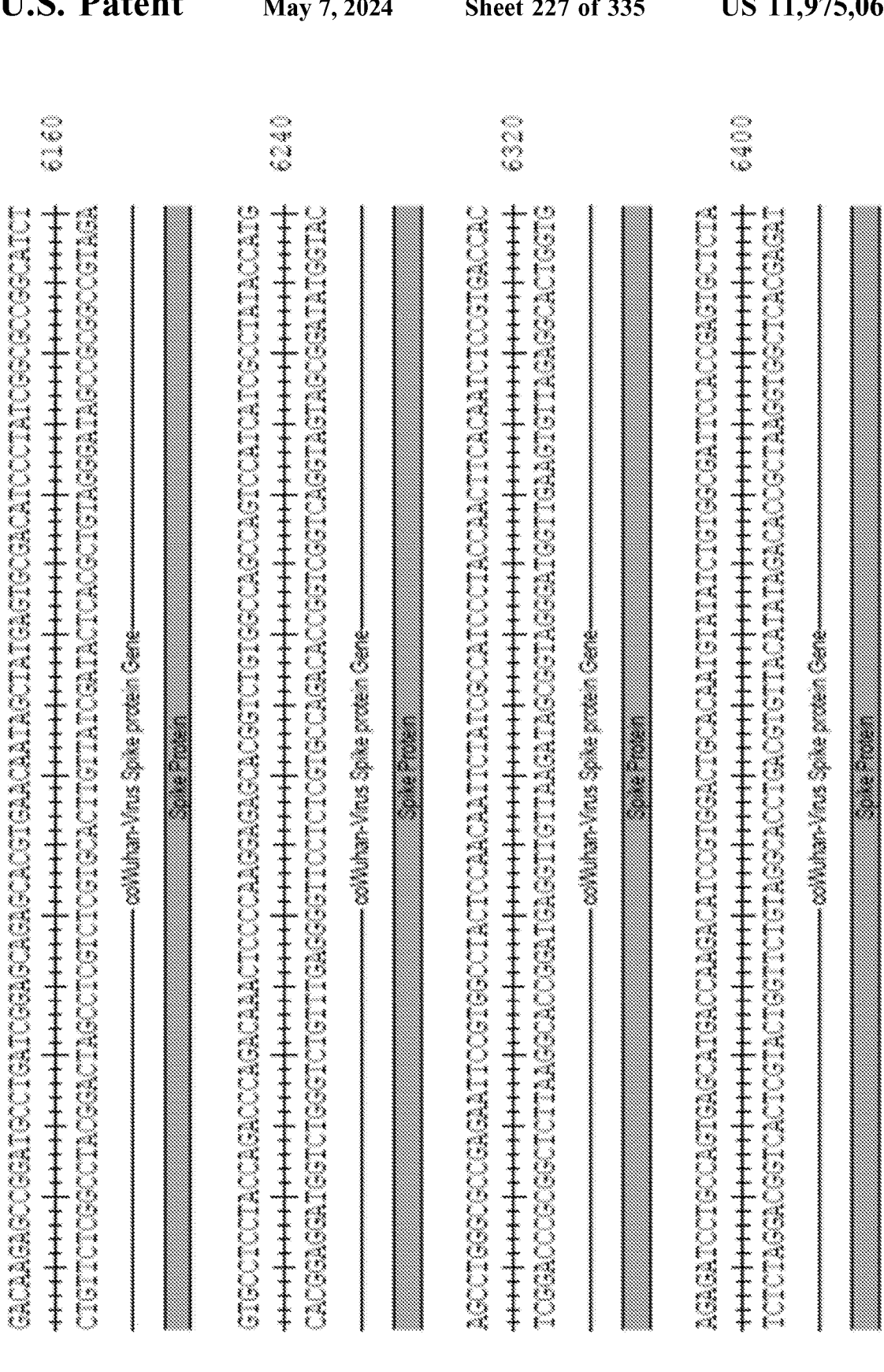
FIG. 20 – continued

FIG. 20 – continued

FIG. 20 – continued

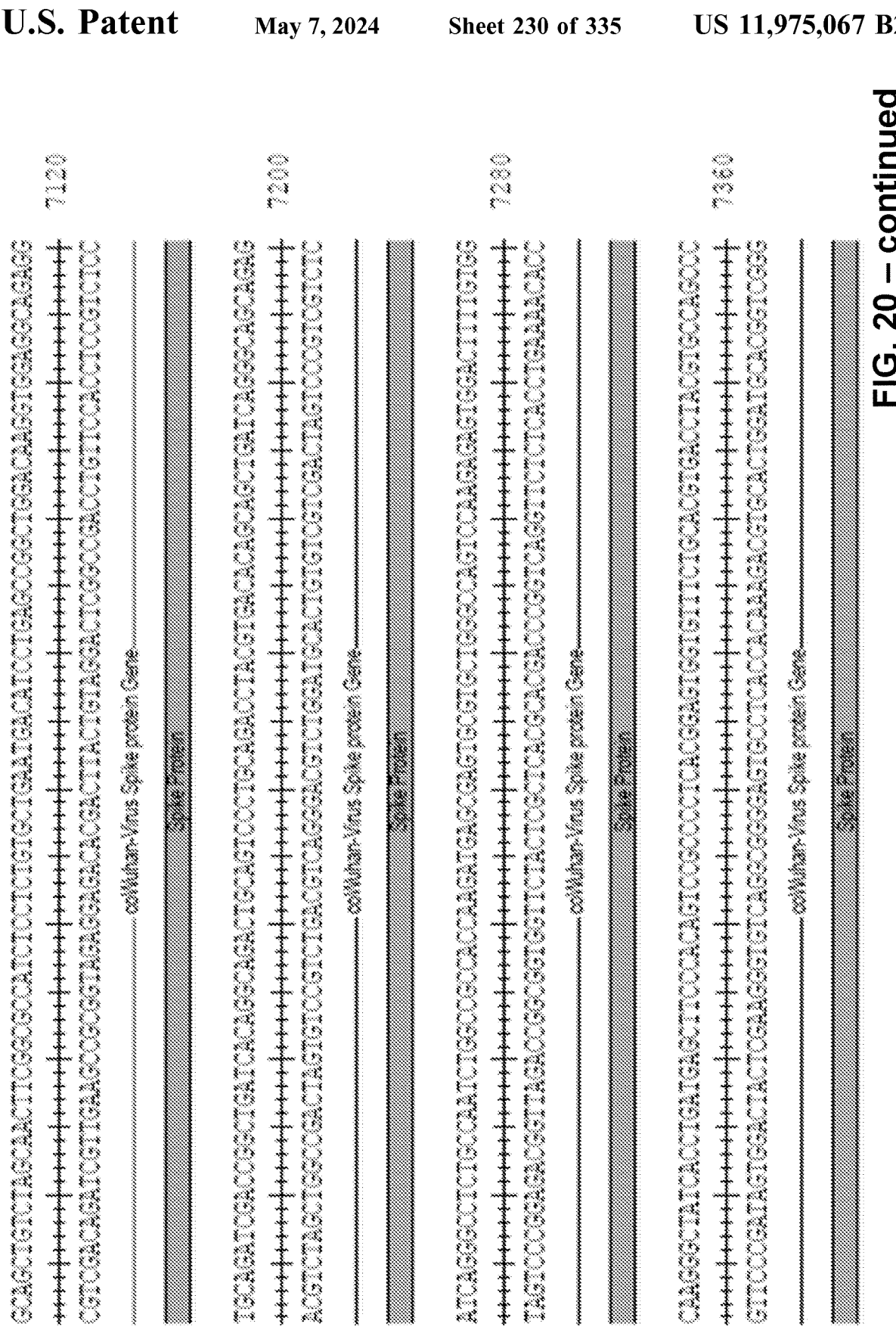
FIG. 20 – continued

FIG. 20 – continued

FIG. 20 – continued

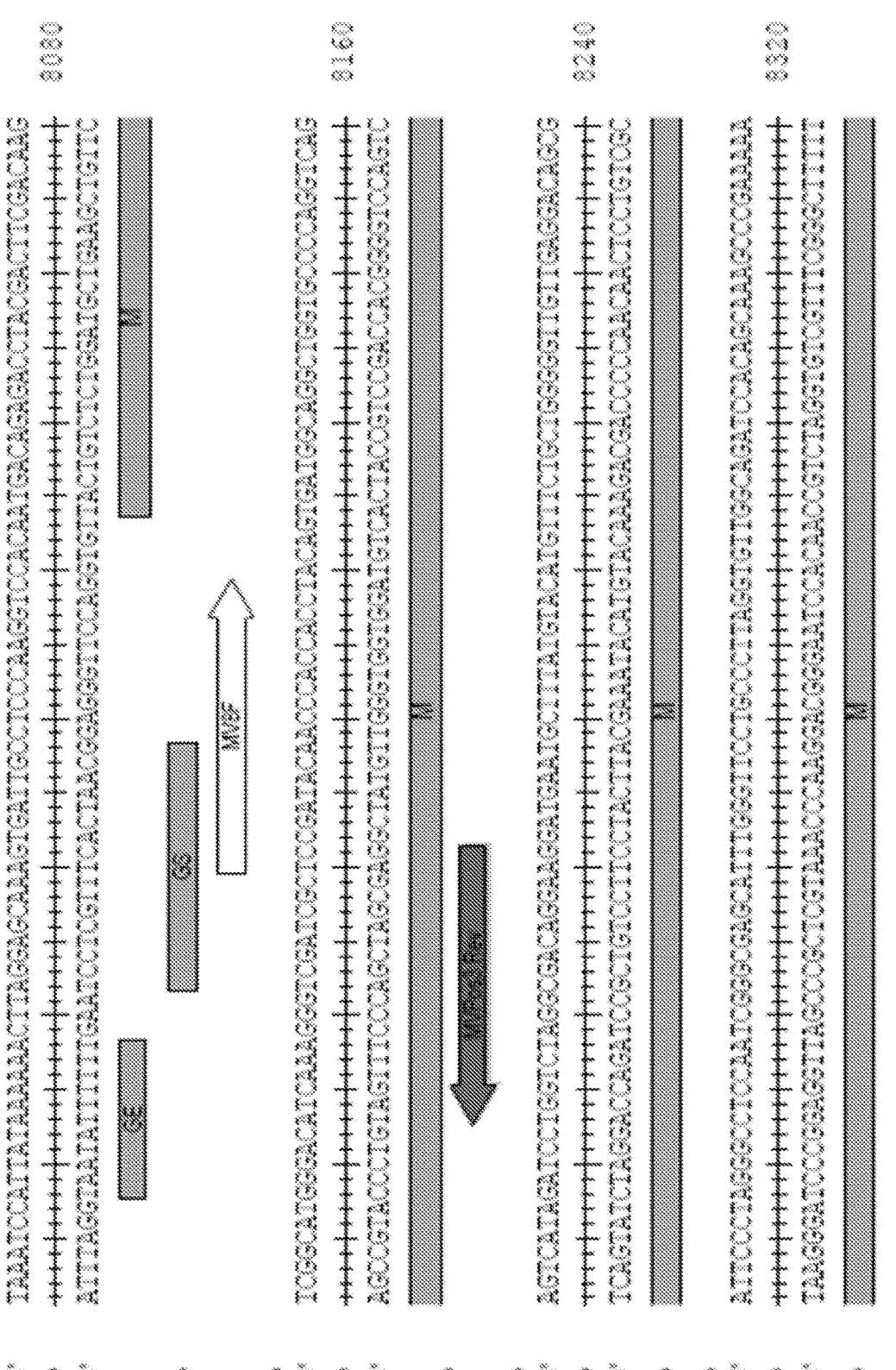
FIG. 20 – continued

FIG. 20 – continued

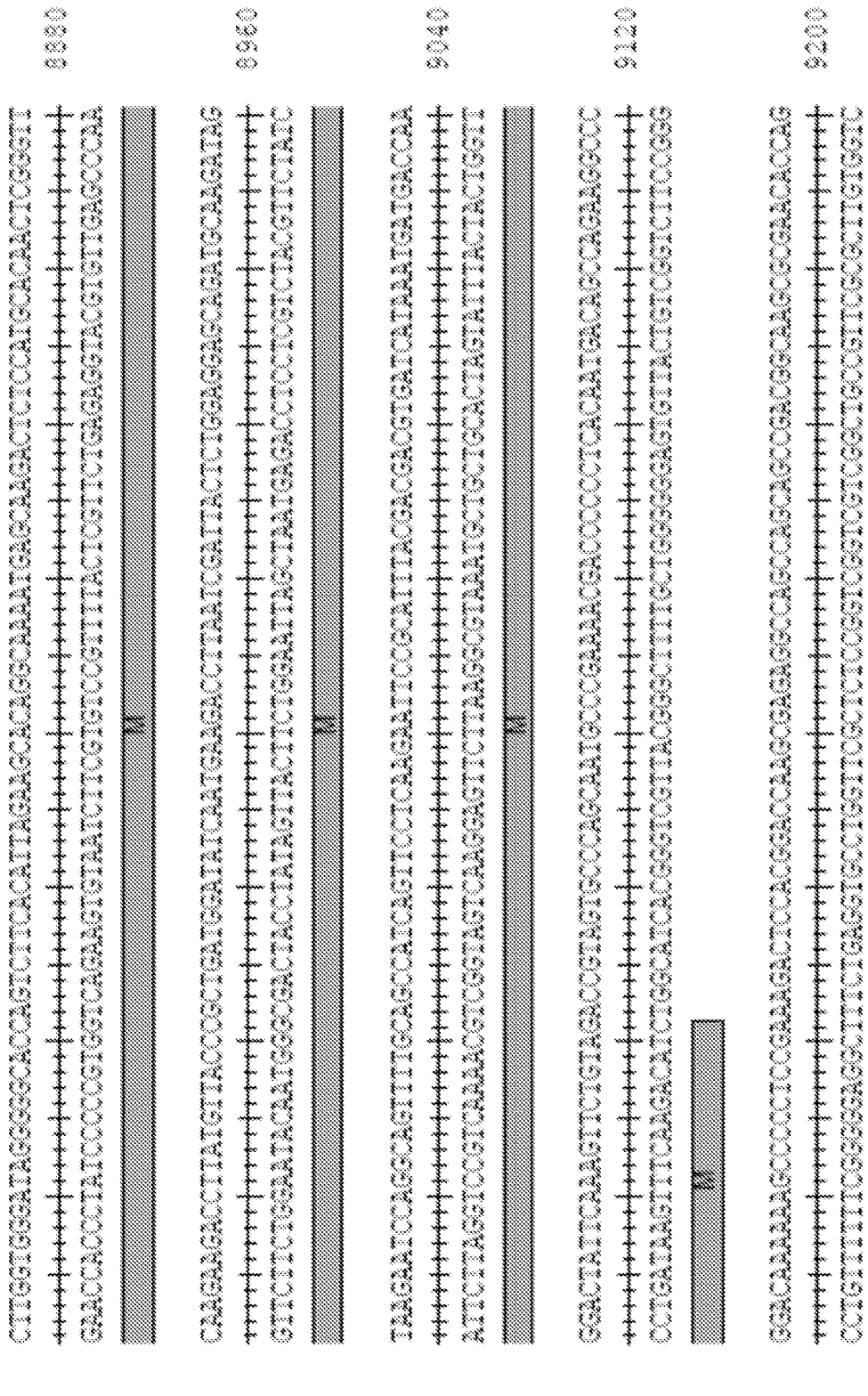
FIG. 20 – continued

FIG. 20 – continued

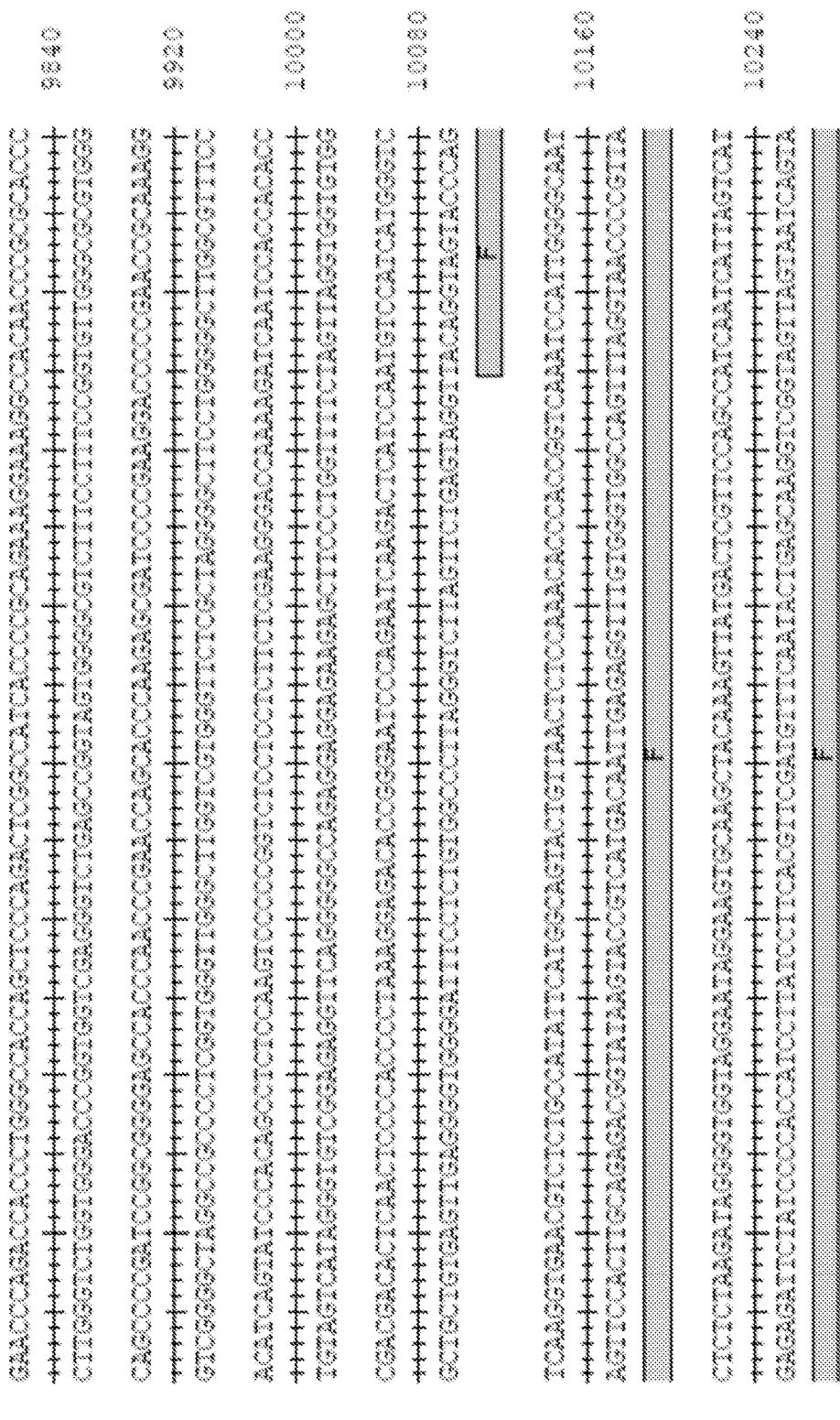
FIG. 20 – continued

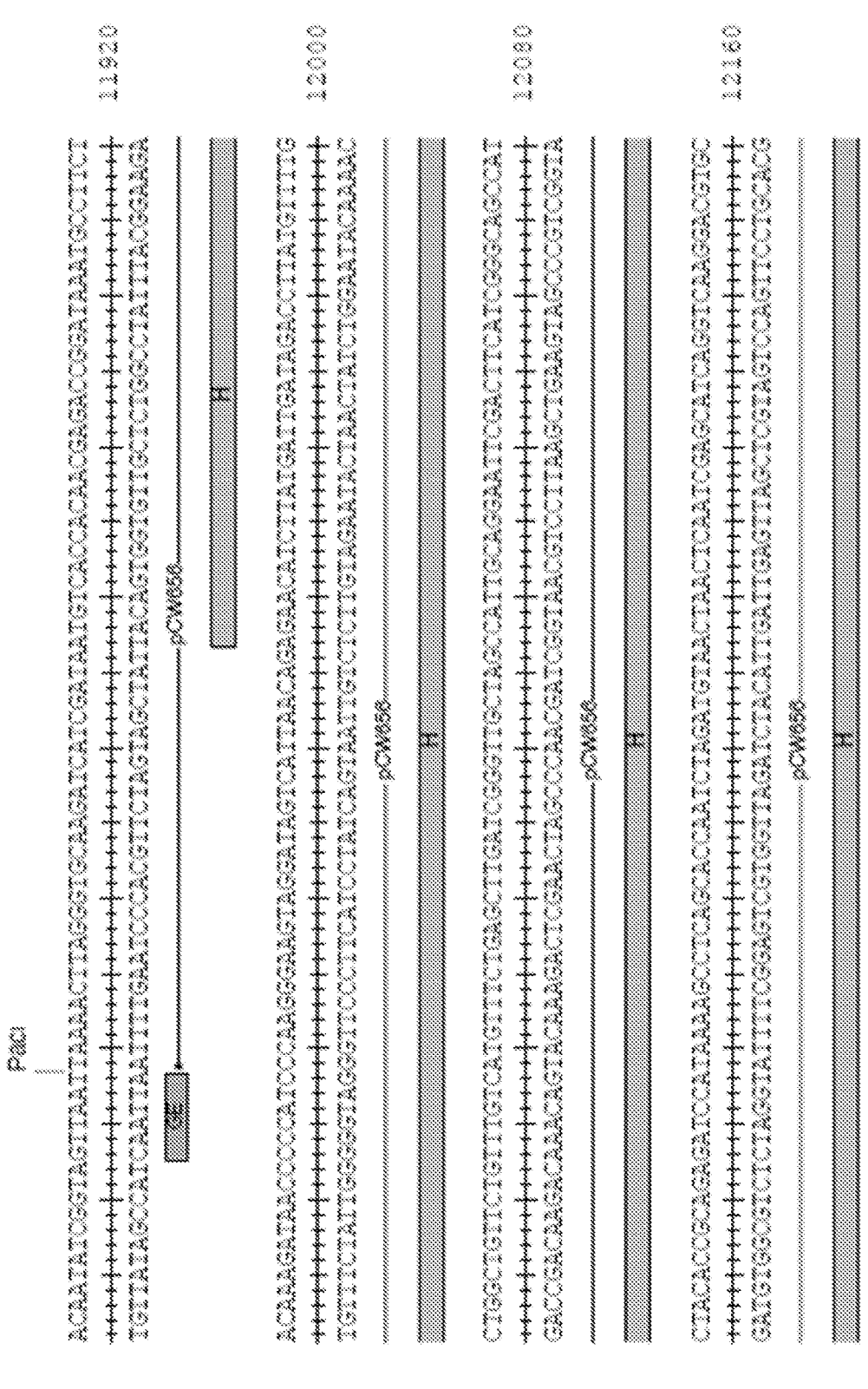
FIG. 20 – continued

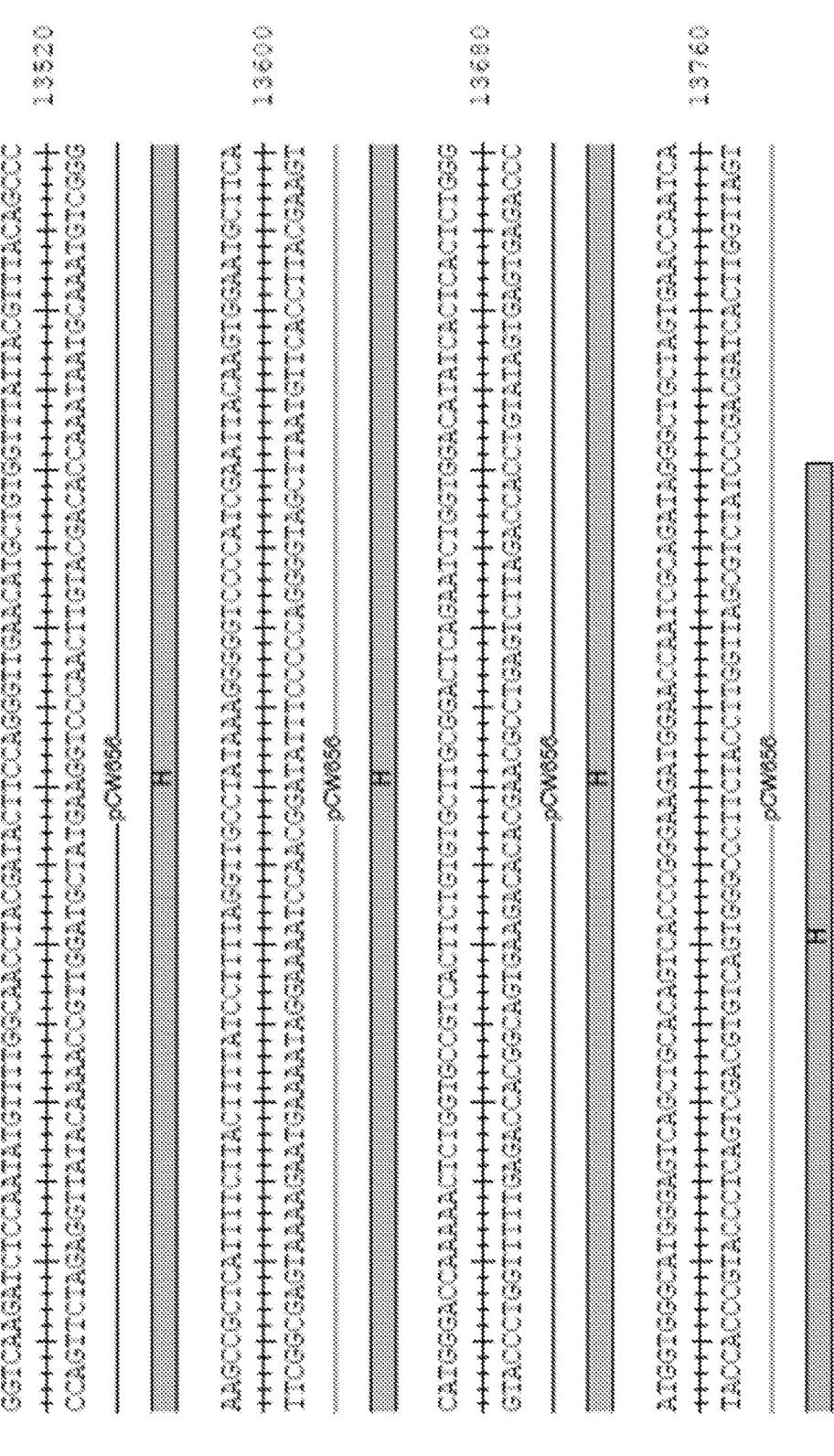
FIG. 20 – continued

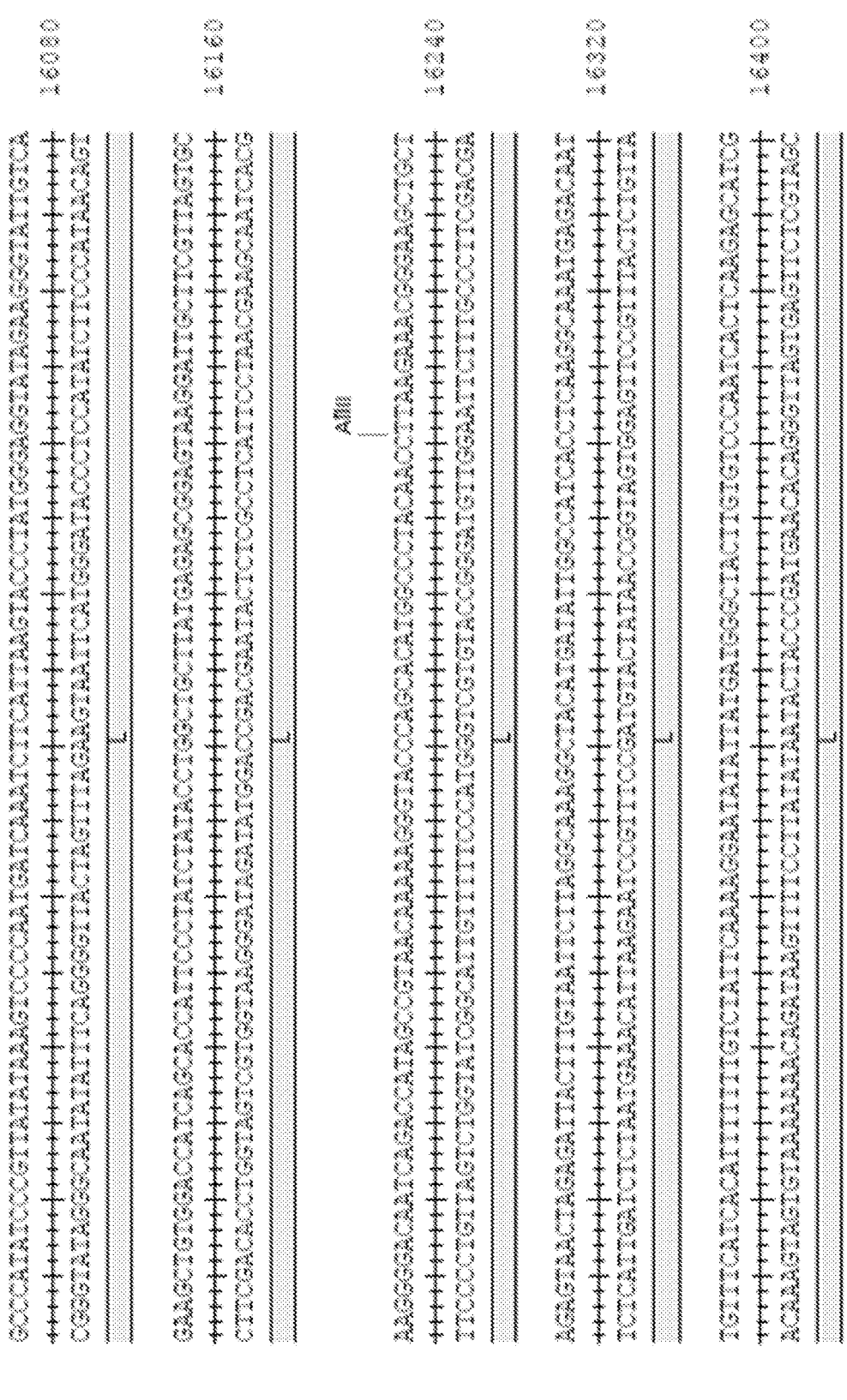
FIG. 20 – continued

FIG. 20 – continued

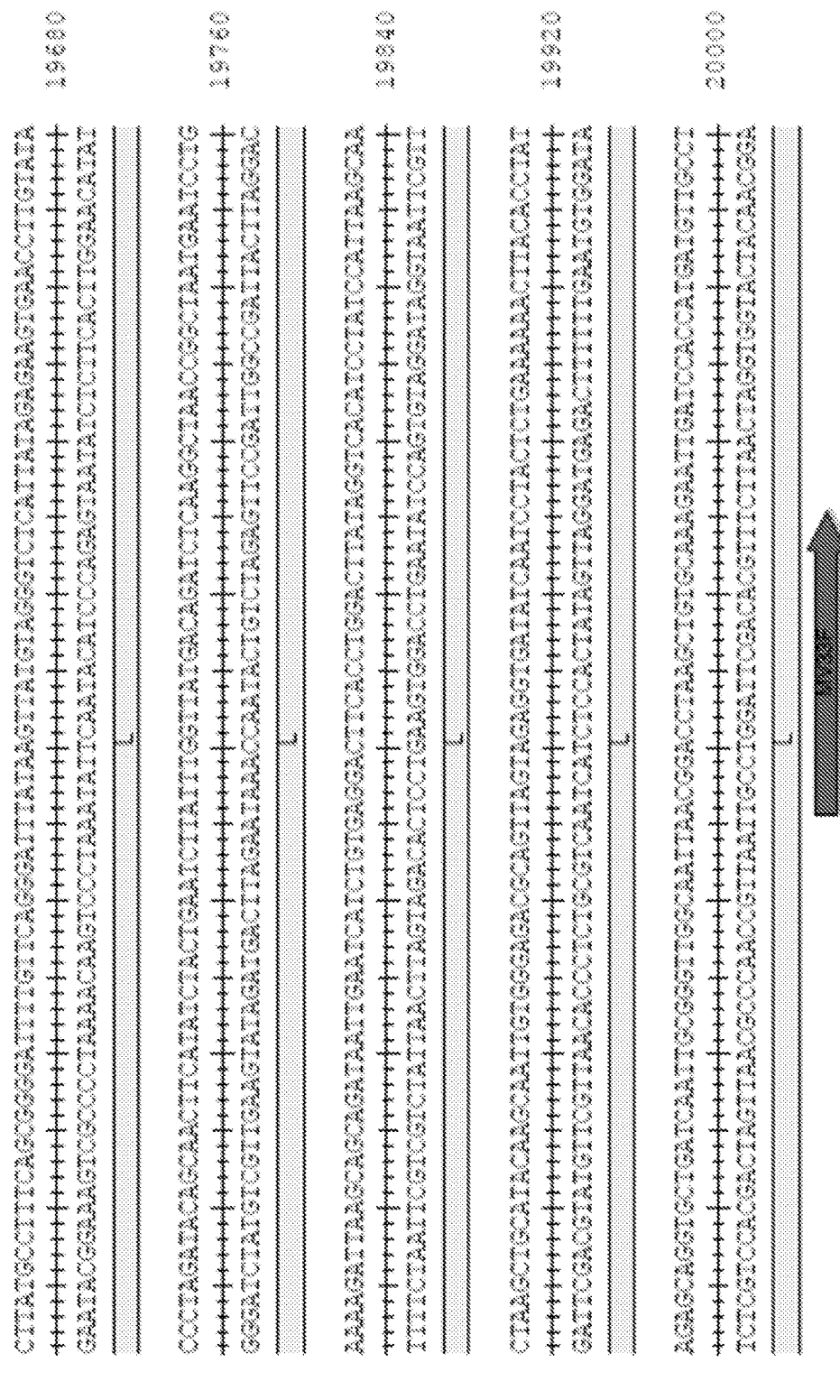
FIG. 20 – continued

FIG. 20 – continued

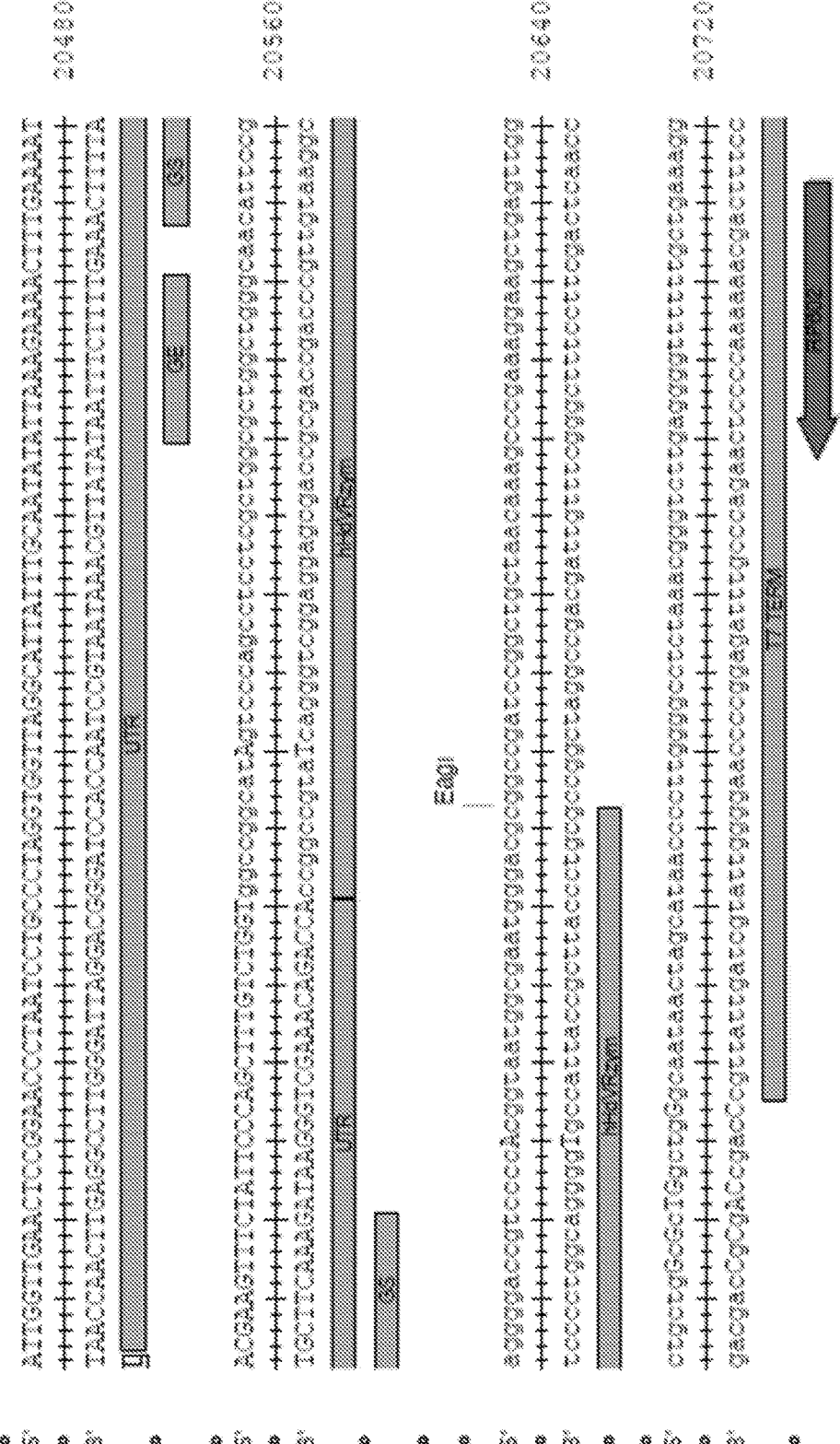
FIG. 20 – continued

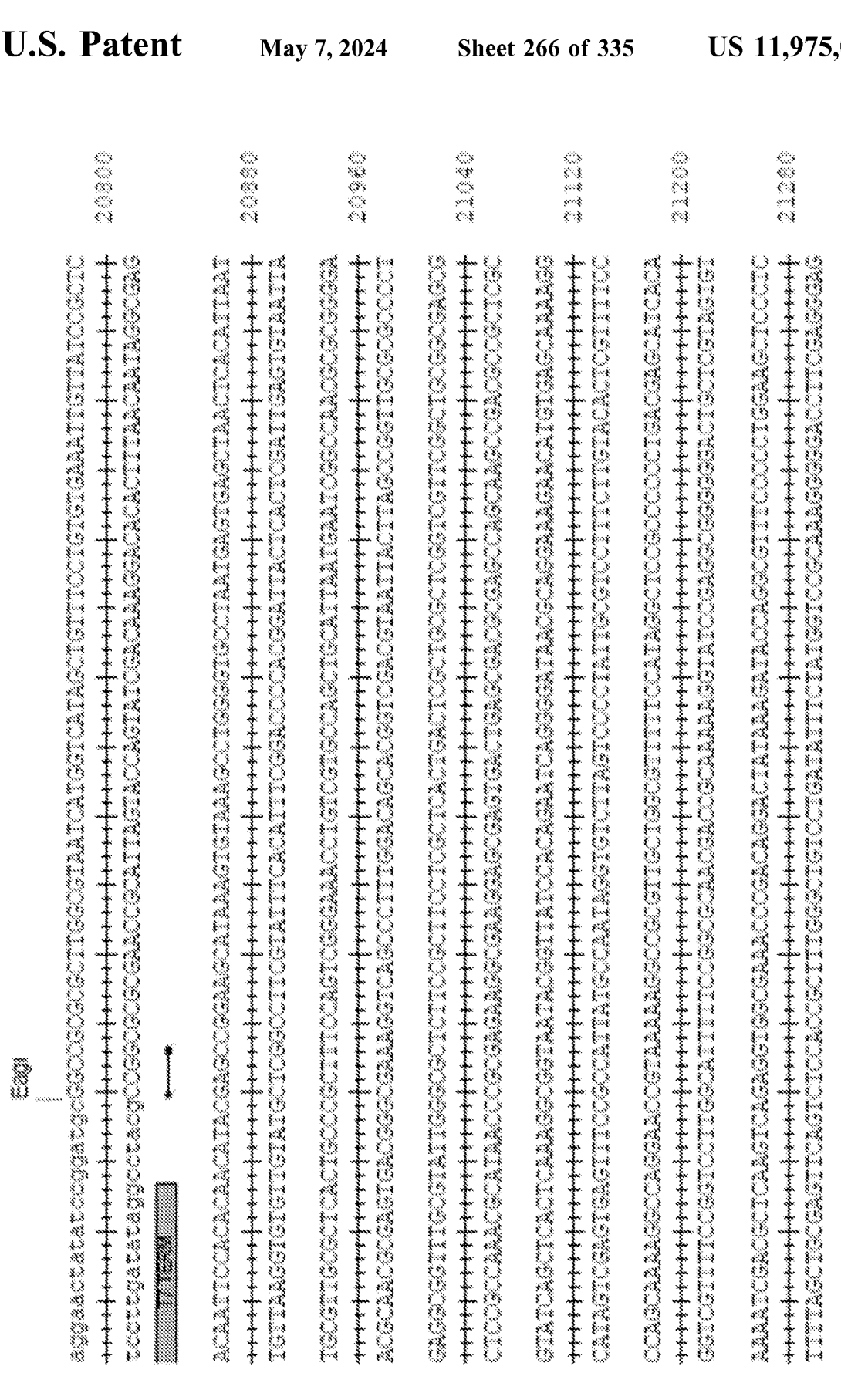
FIG. 20 – continued

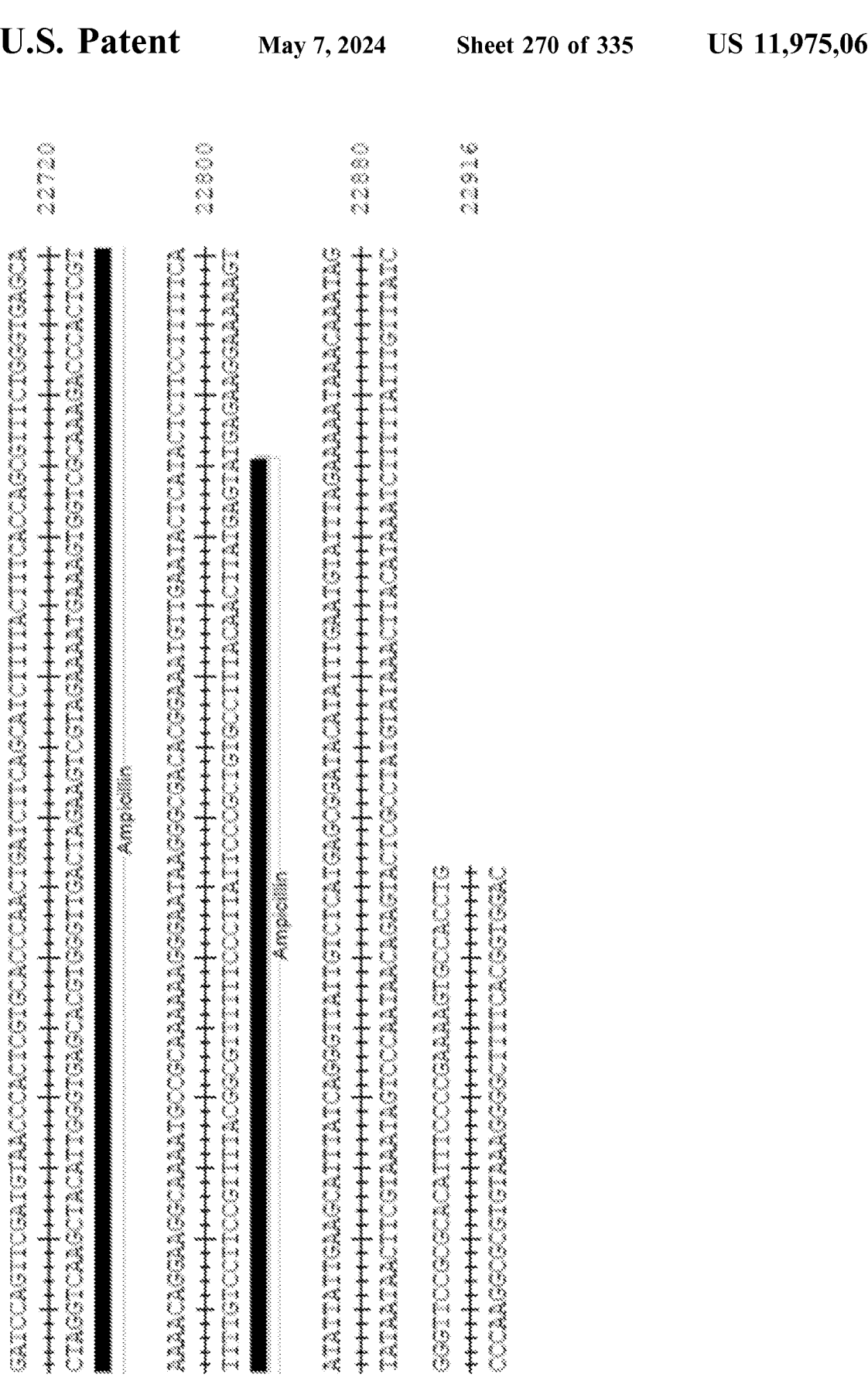
FIG. 20 – continued

FIG. 21 – continued

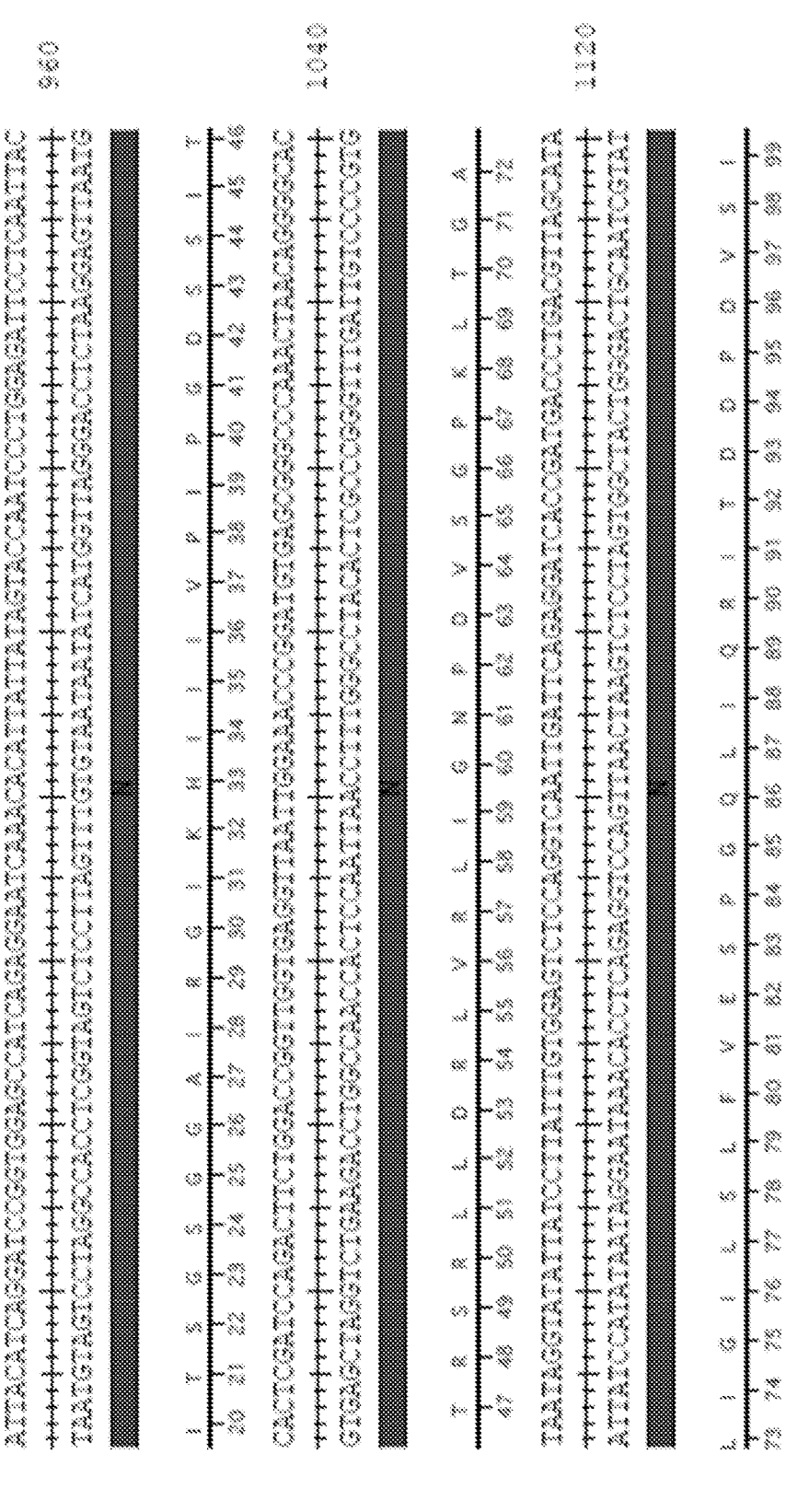
FIG. 21 – continued

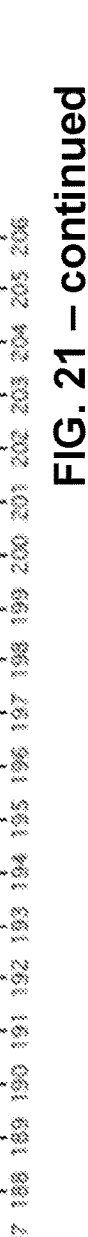
FIG. 21 – continued

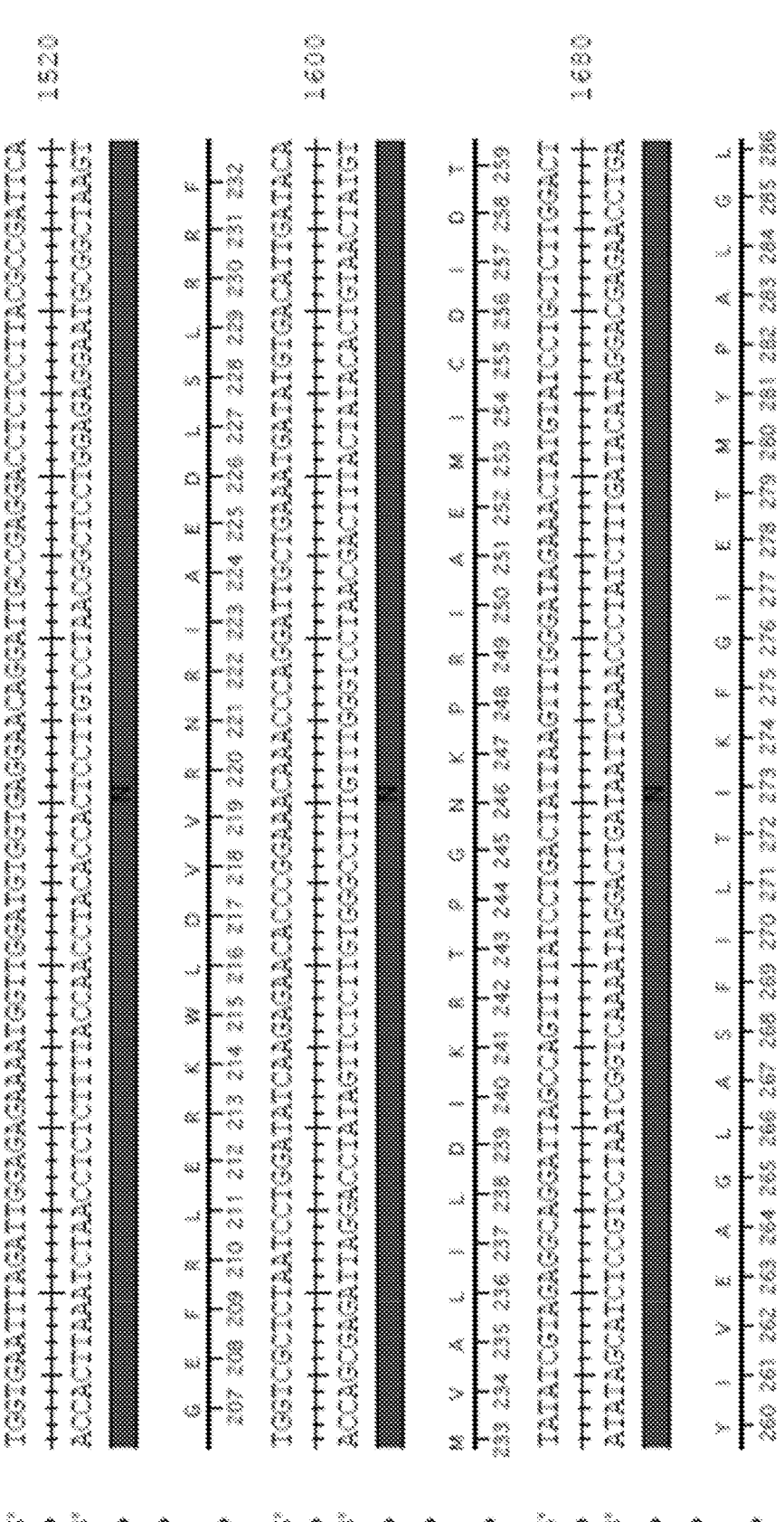
FIG. 21 – continued

FIG. 21 – continued

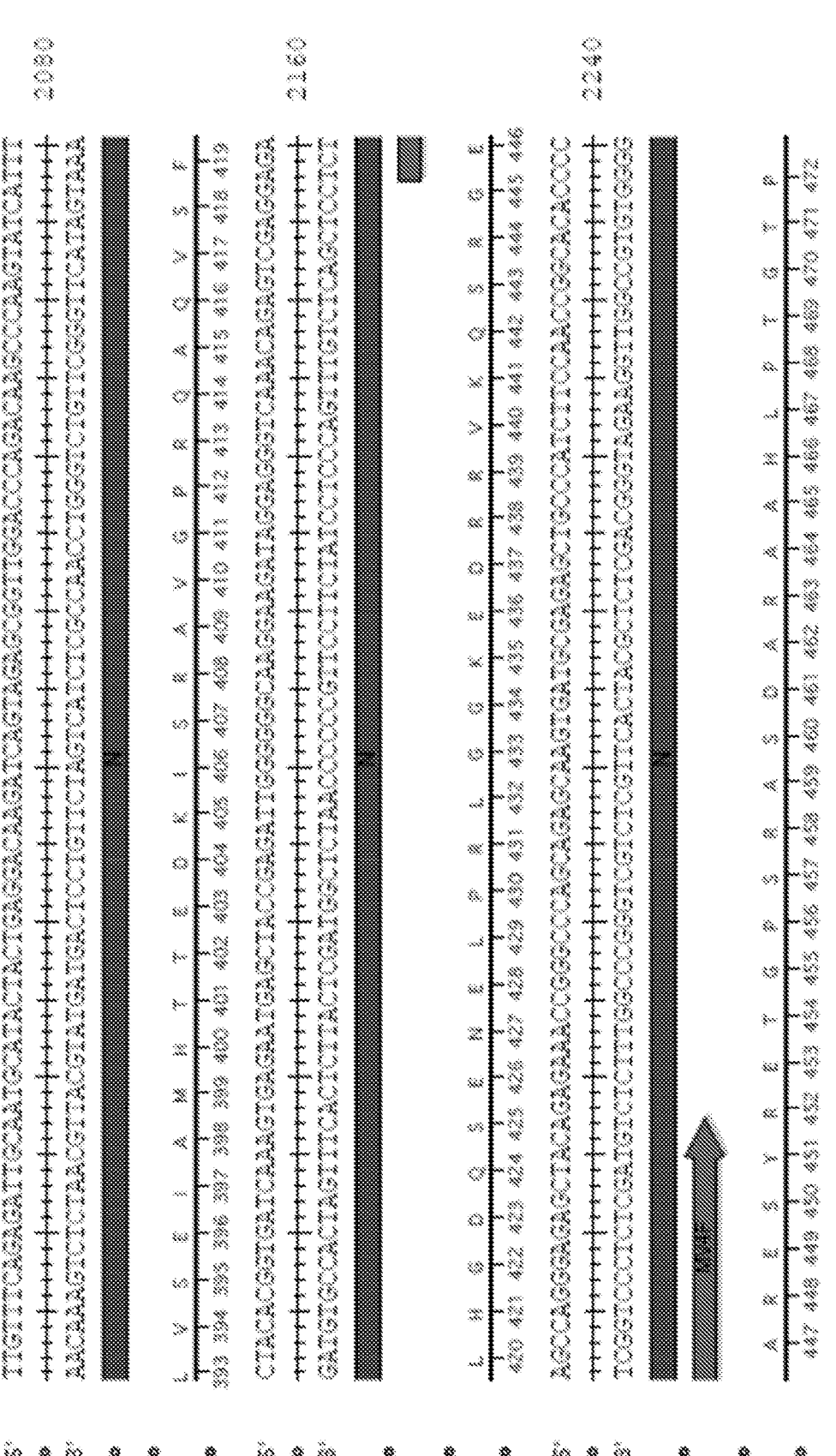
FIG. 21 – continued

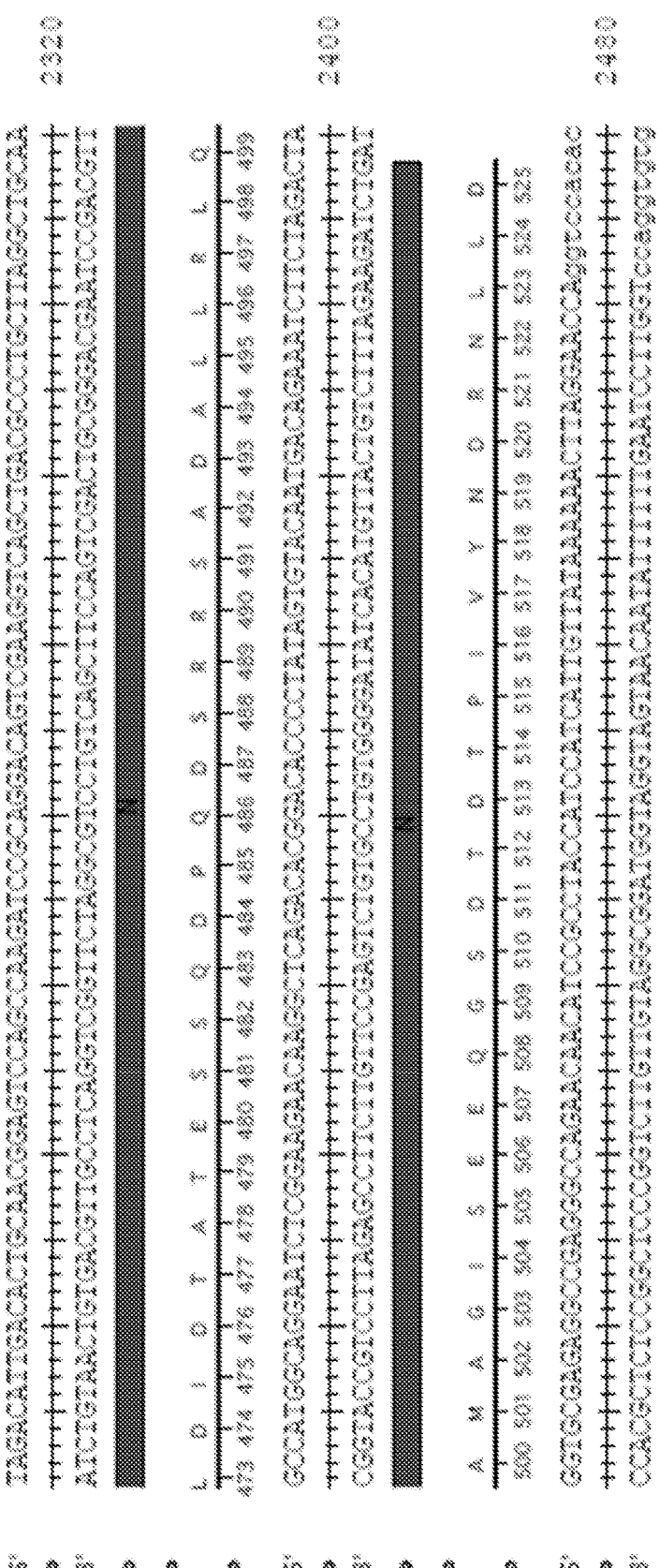
FIG. 21 – continued

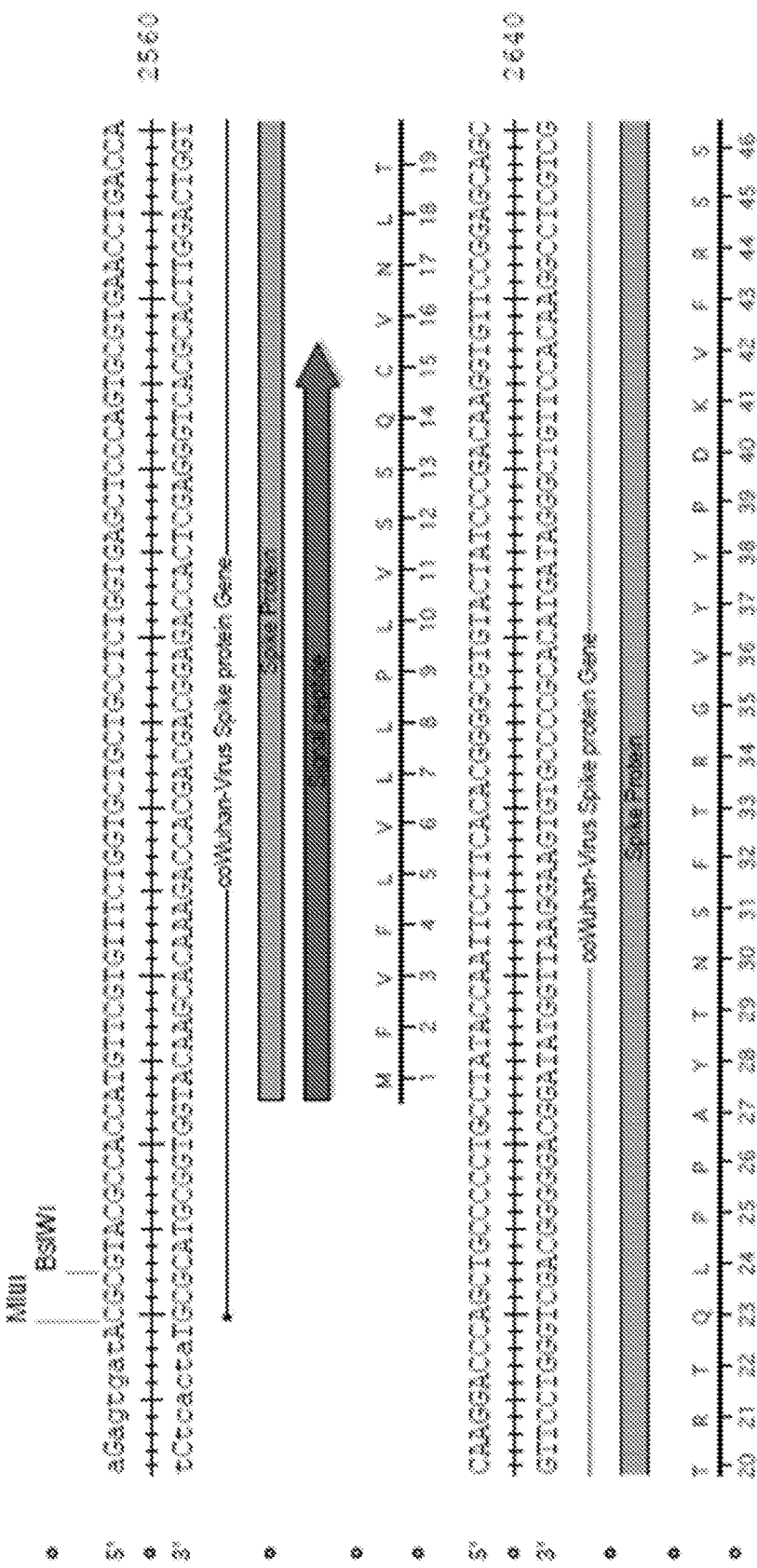
FIG. 21 – continued

FIG. 21 – continued

FIG. 21 – continued

FIG. 21 – continued

FIG. 21 – continued

FIG. 21 – continued

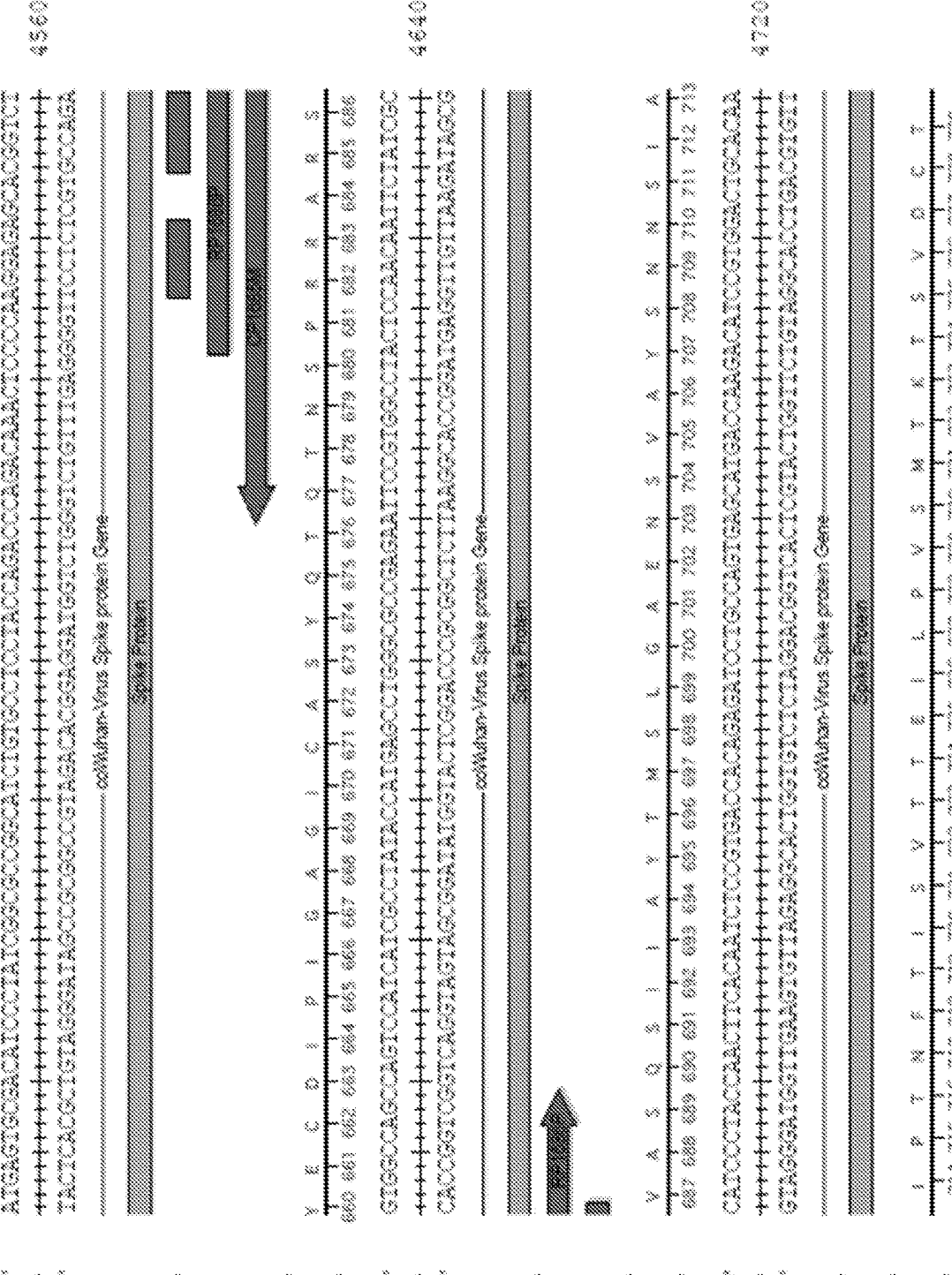
FIG. 21 – continued

FIG. 21 – continued

FIG. 21 – continued

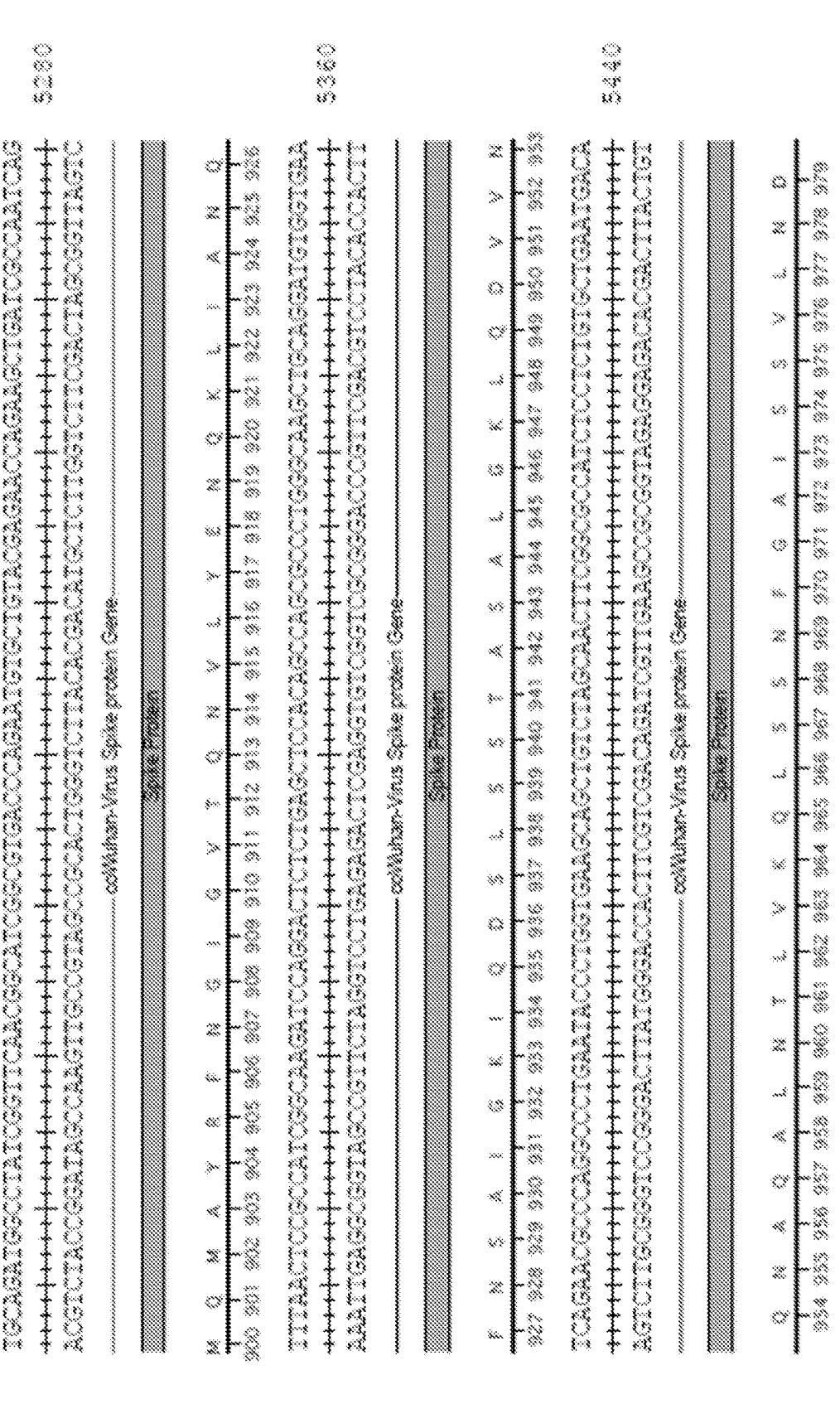
FIG. 21 – continued

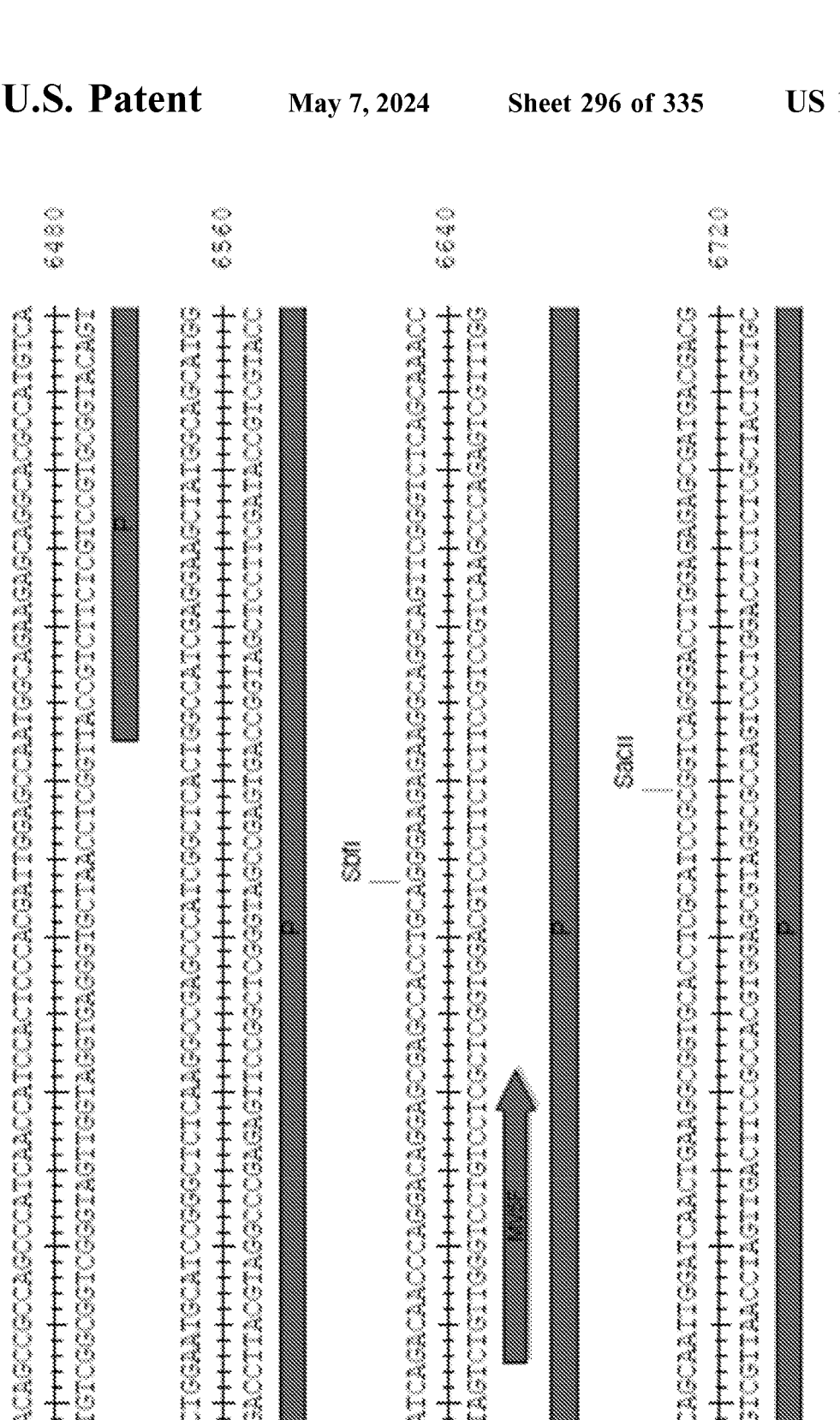
FIG. 21 – continued

FIG. 21 – continued

FIG. 21 – continued

FIG. 21 – continued

FIG. 21 – continued

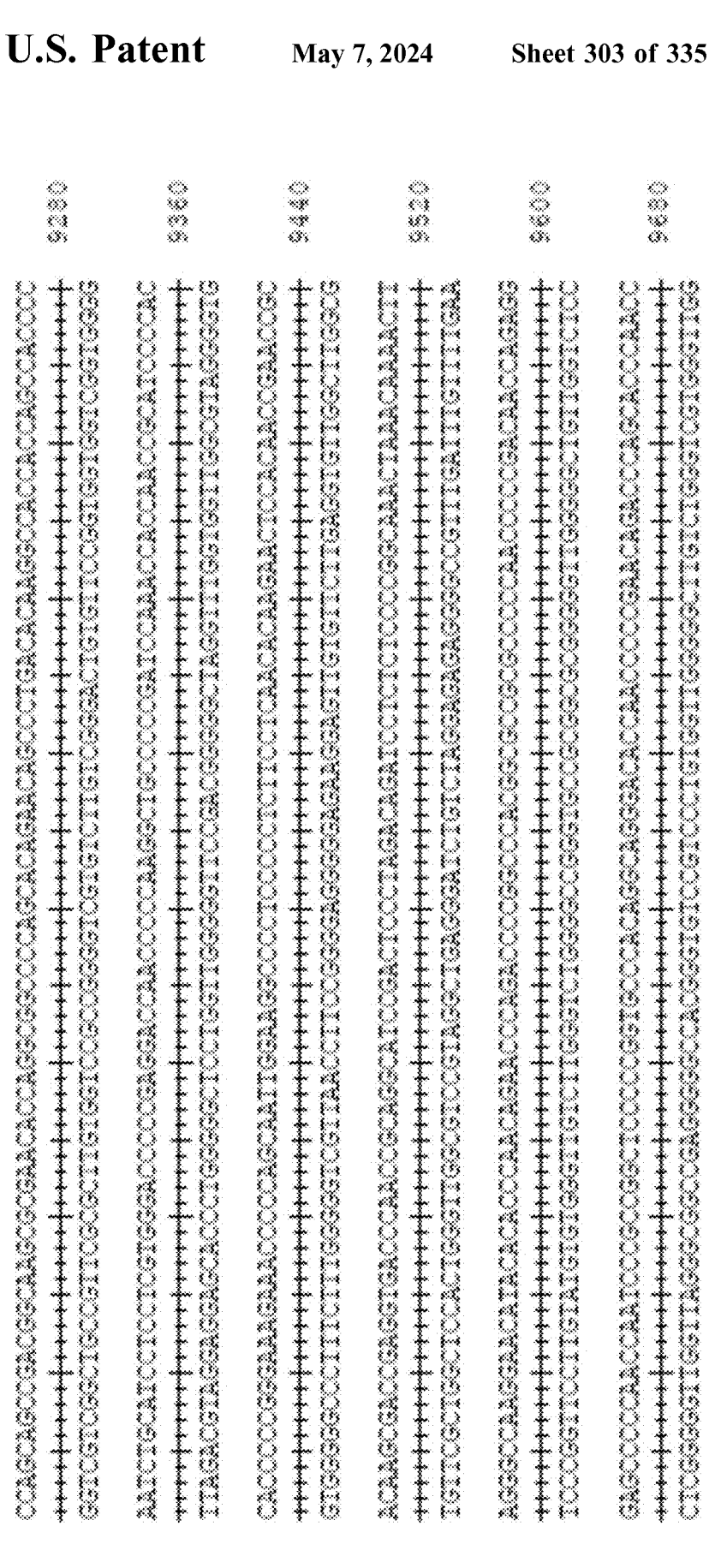
FIG. 21 – continued

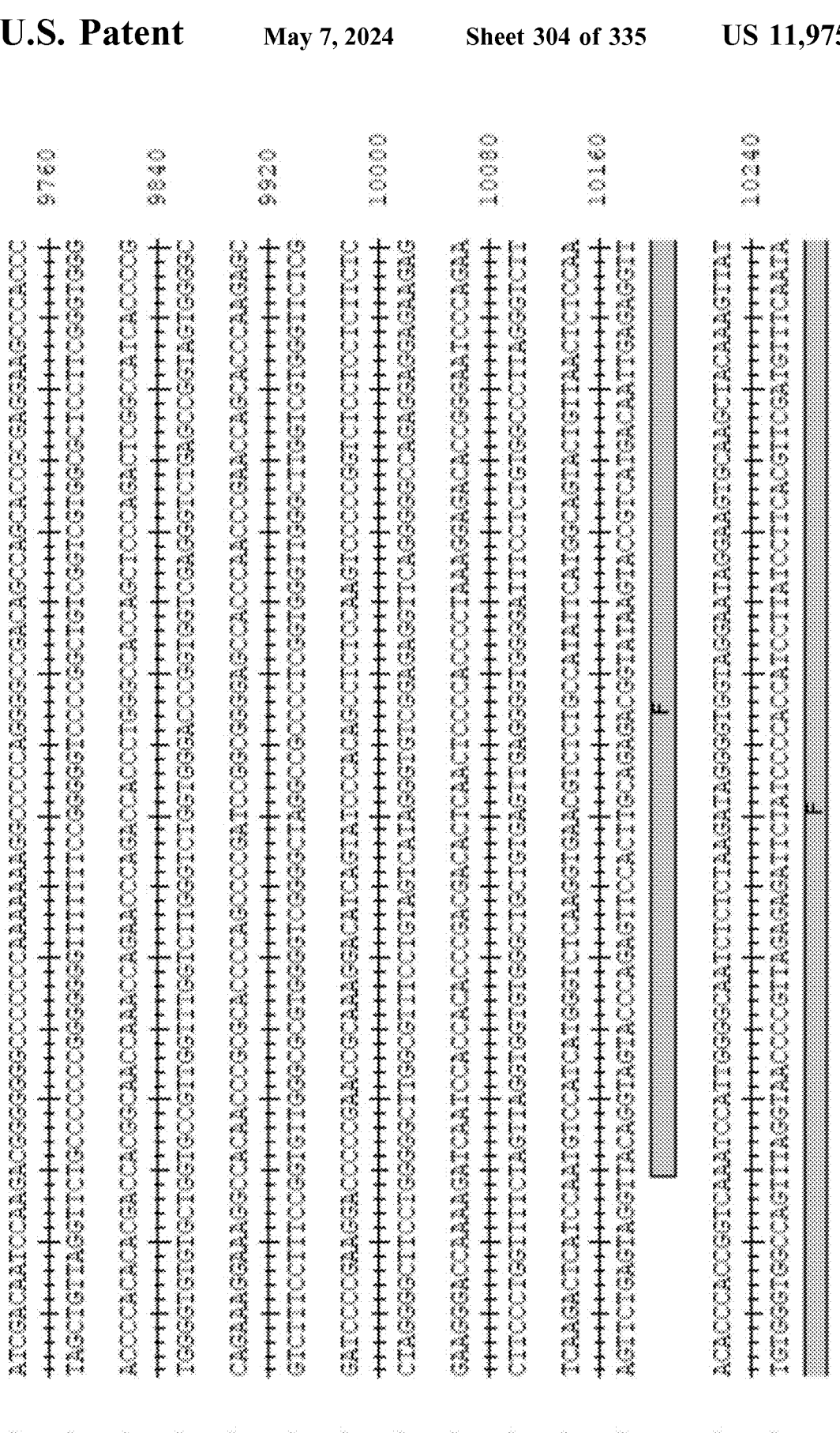
FIG. 21 – continued

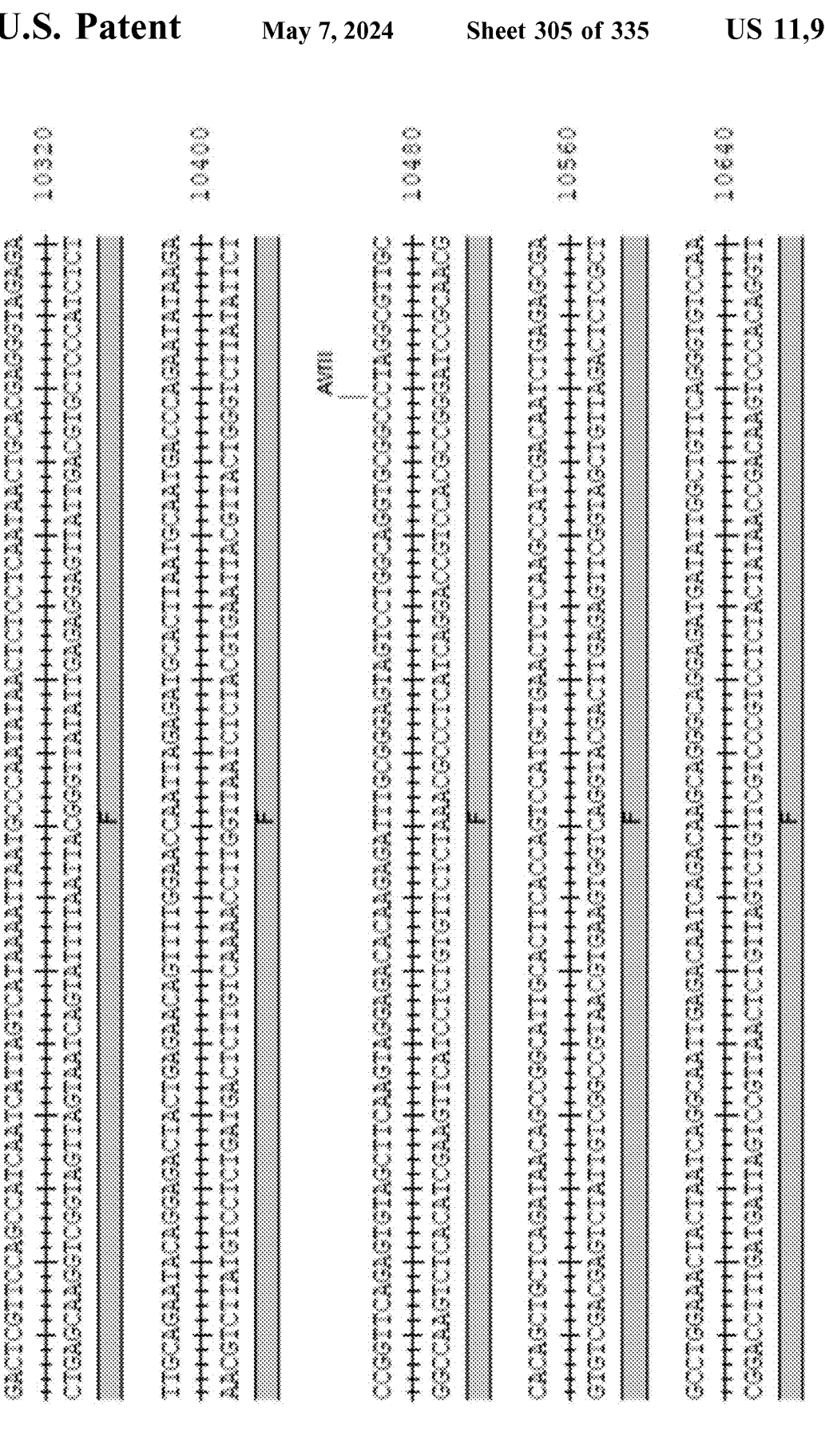
FIG. 21 – continued

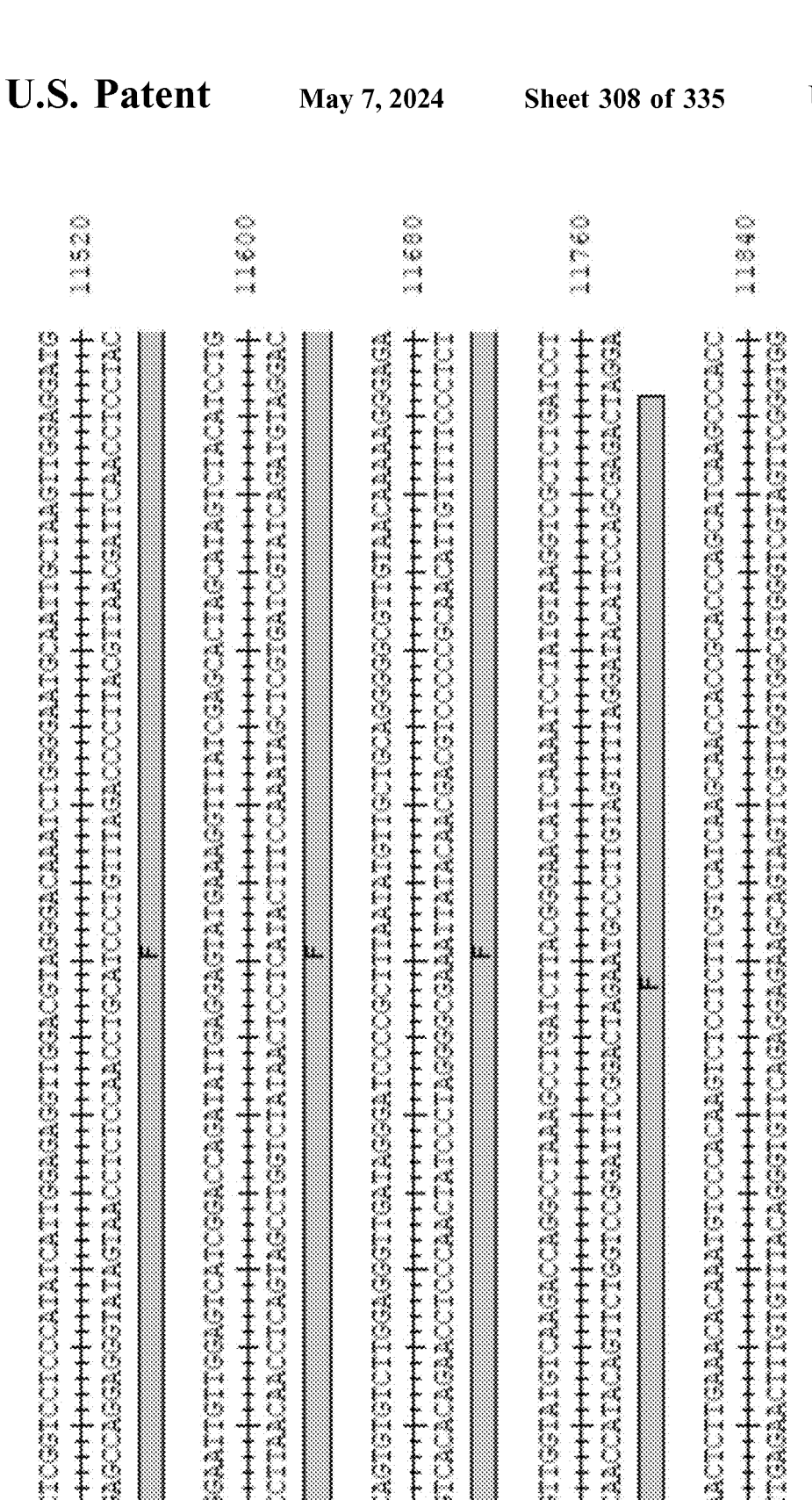
FIG. 21 – continued

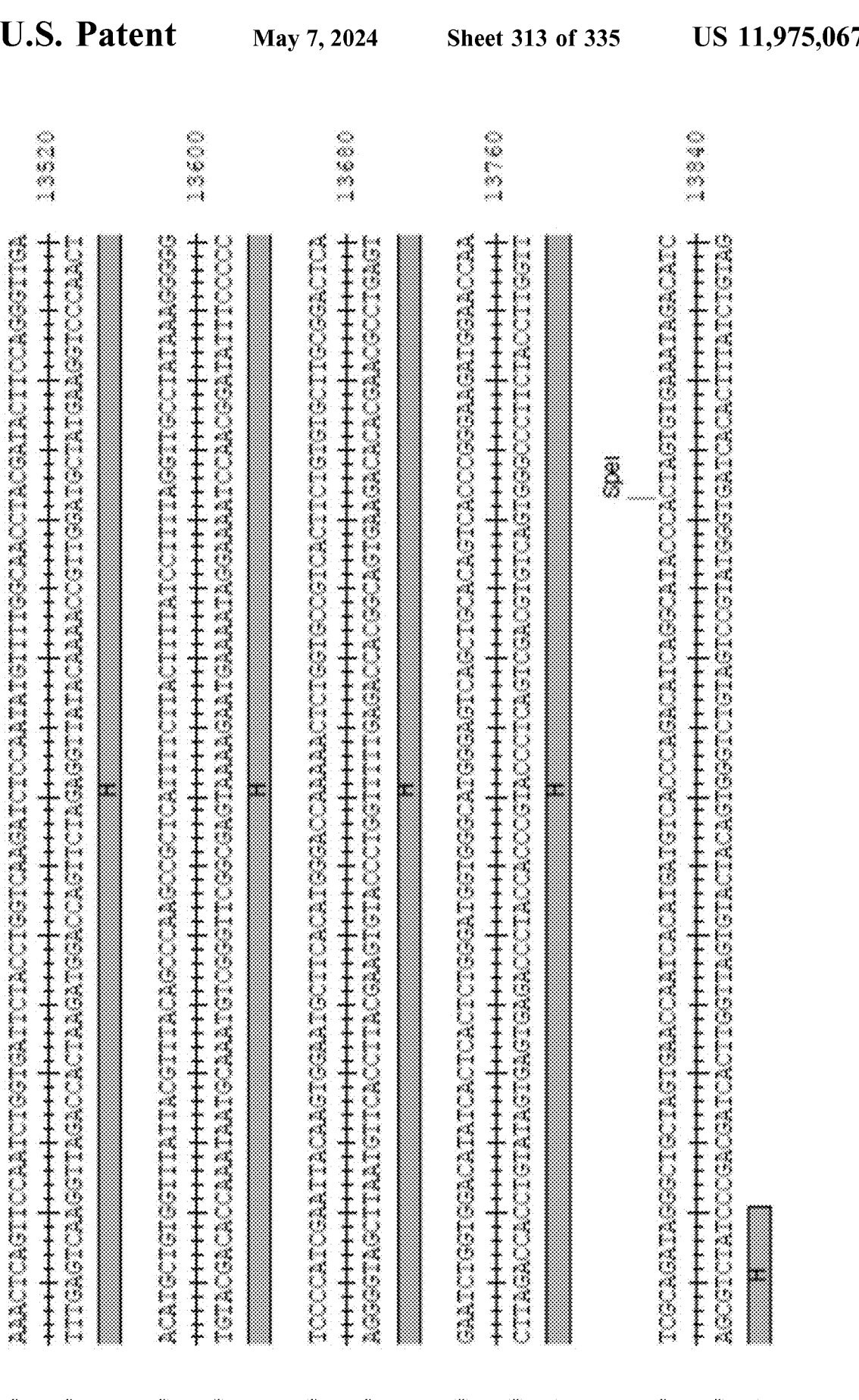
FIG. 21 – continued

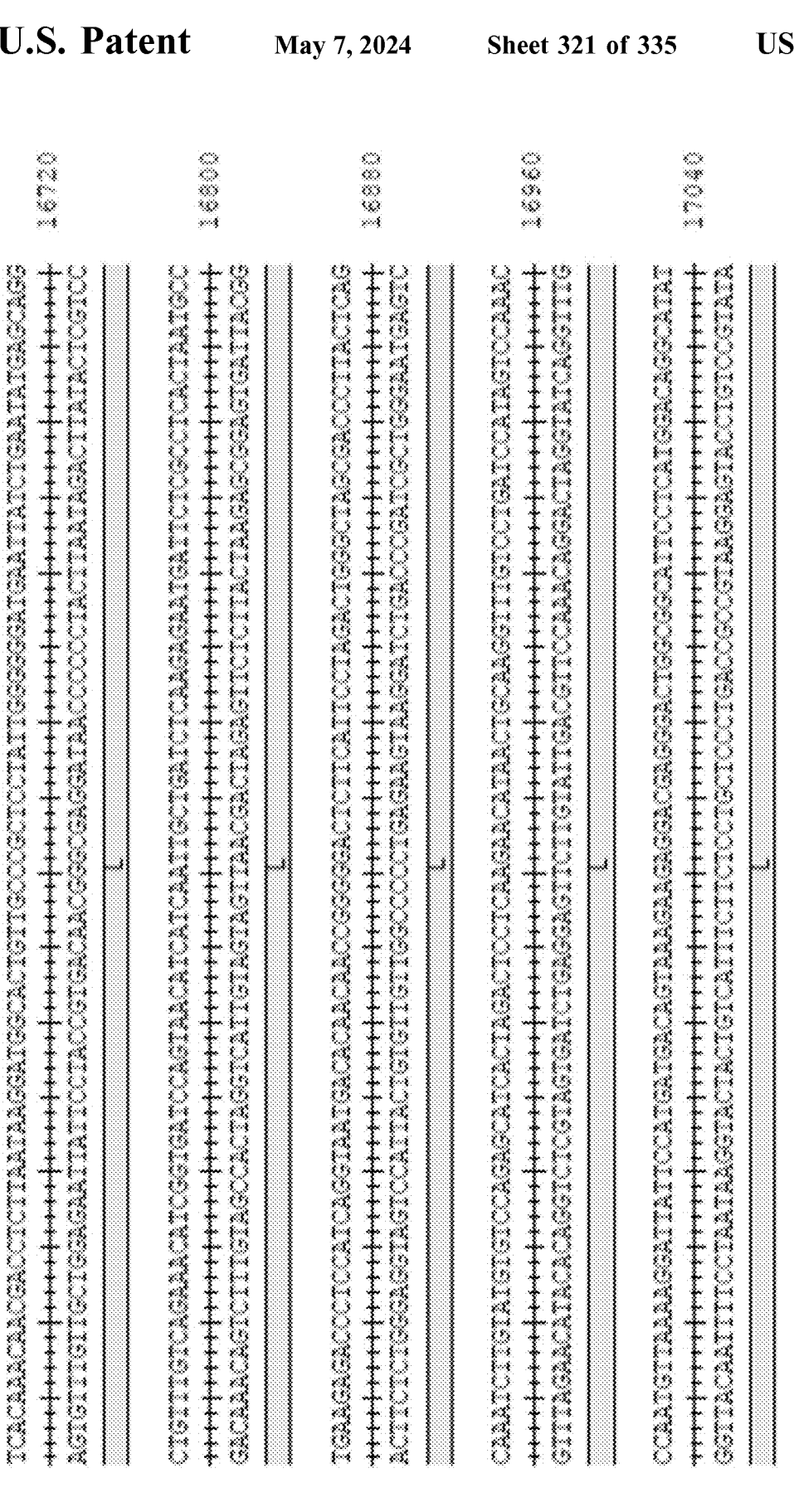
FIG. 21 – continued

FIG. 21 – continued

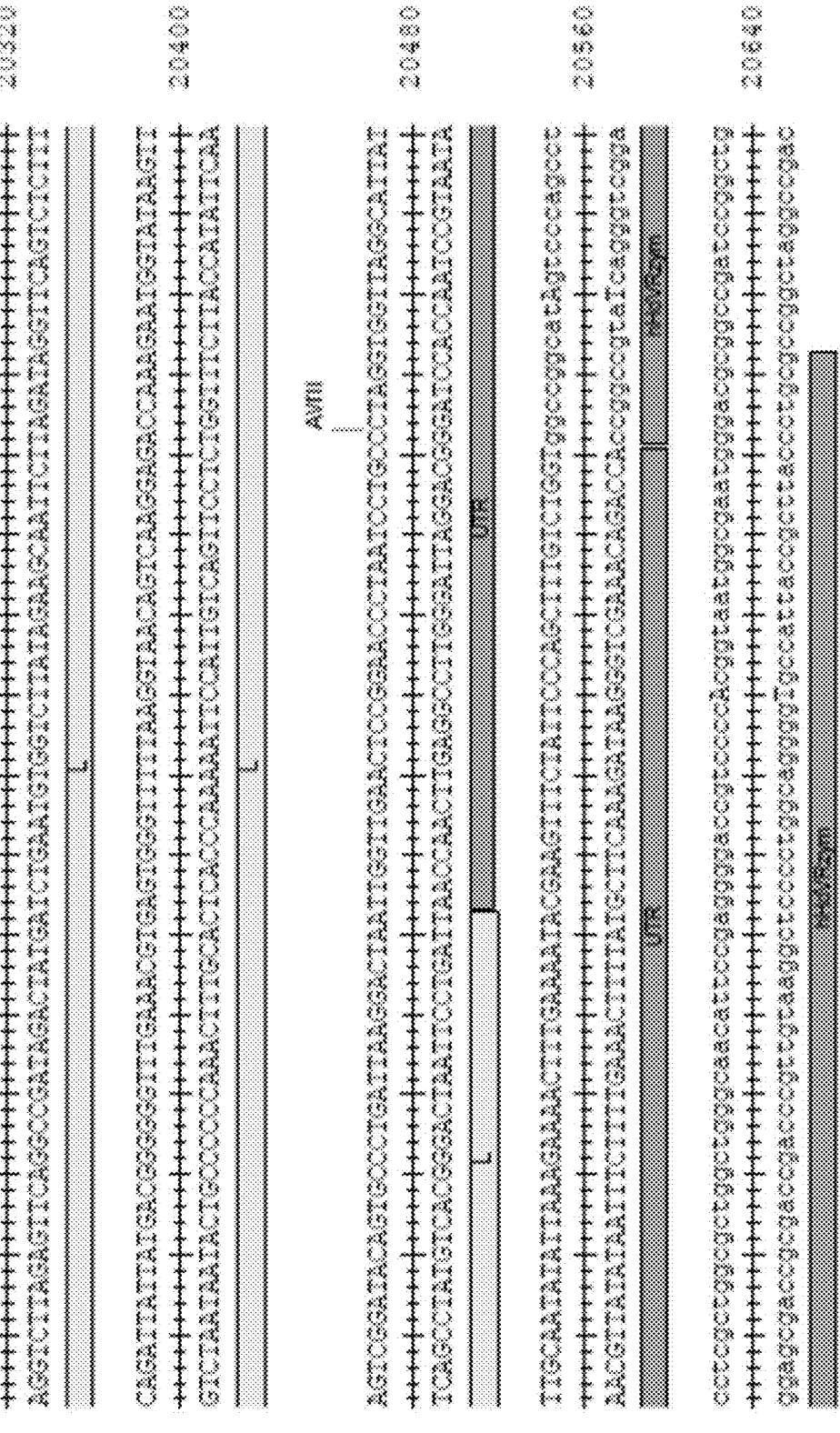
FIG. 21 – continued

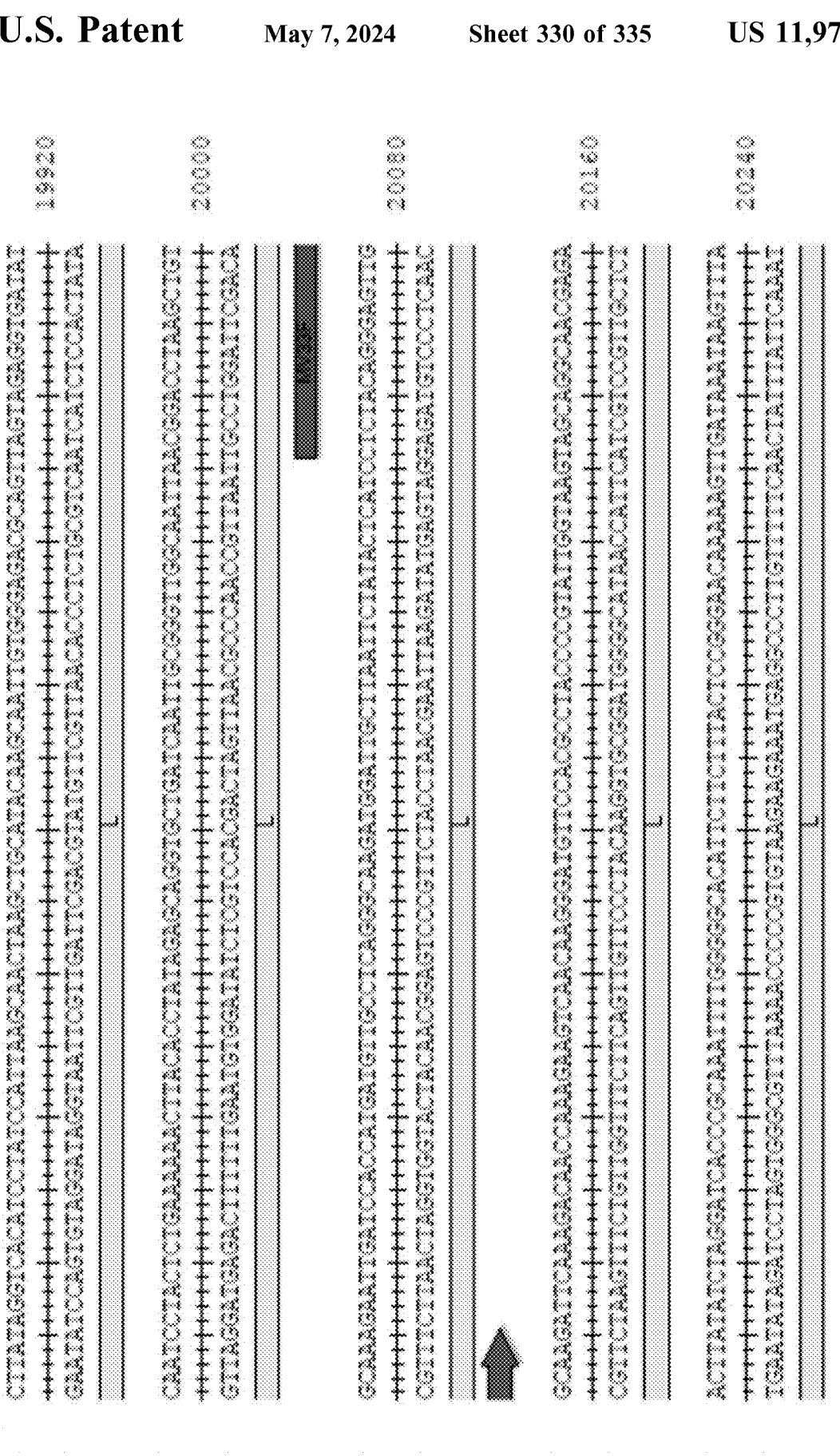
FIG. 21 – continued

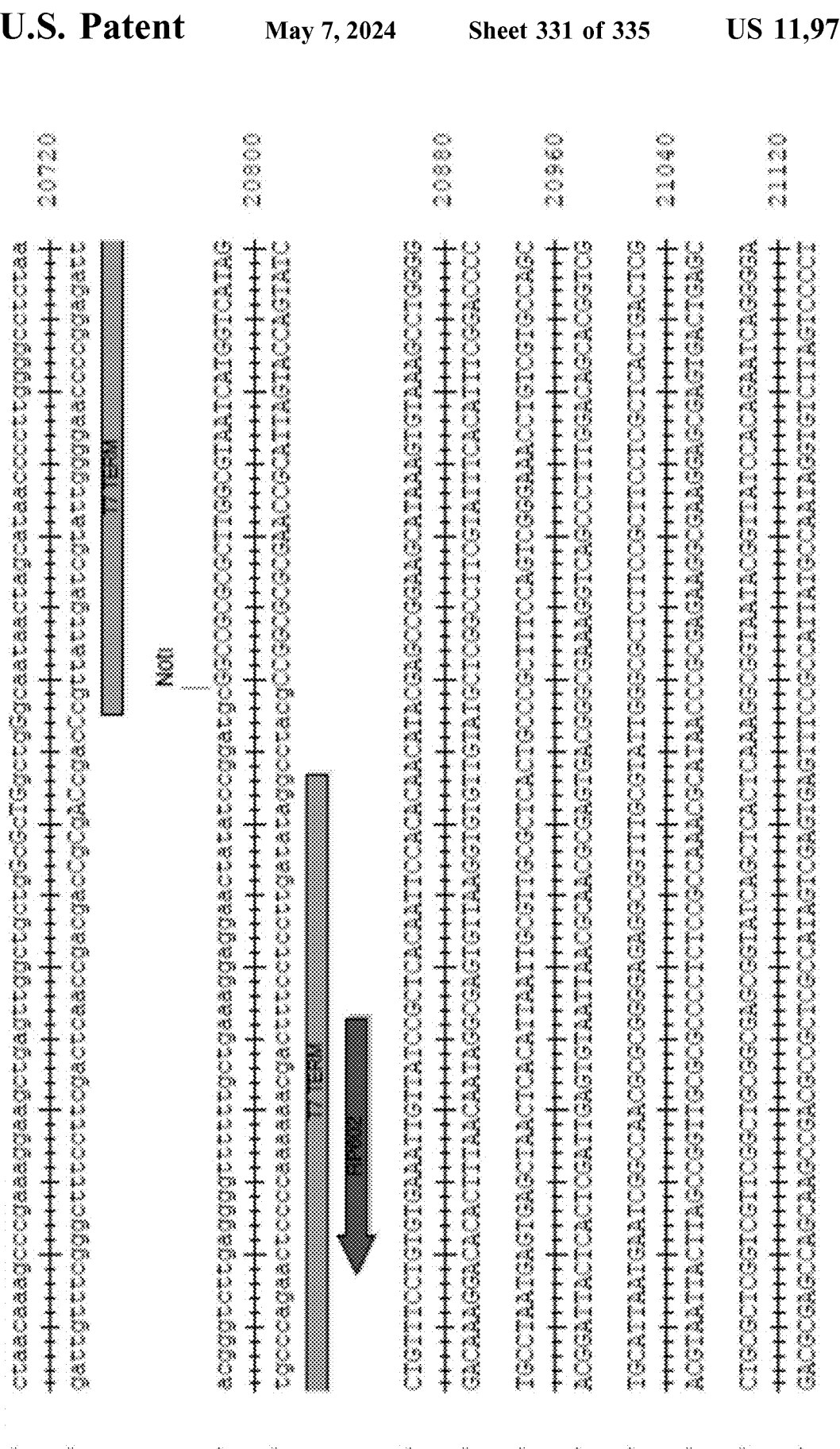
FIG. 21 – continued

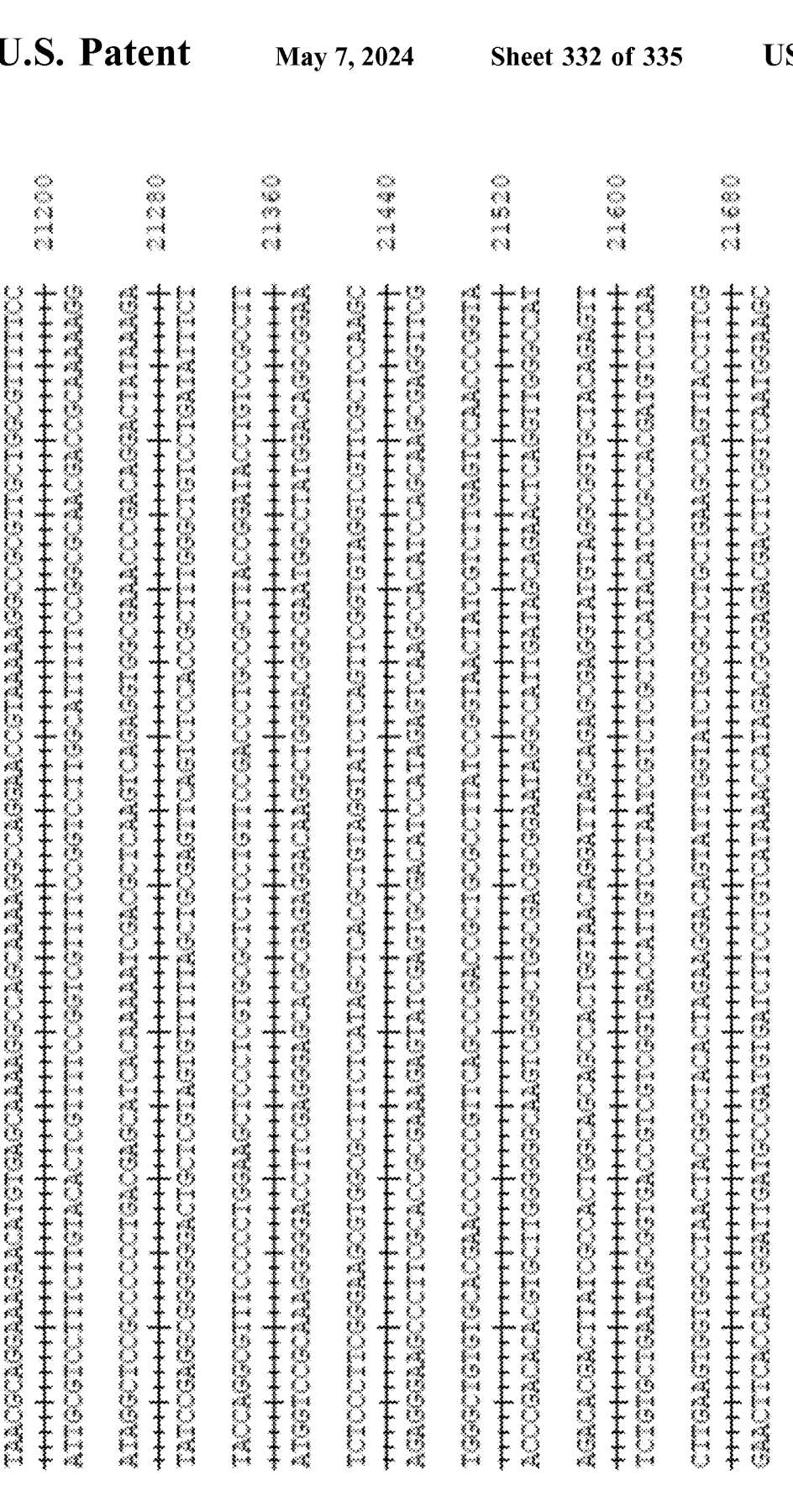
FIG. 21 – continued

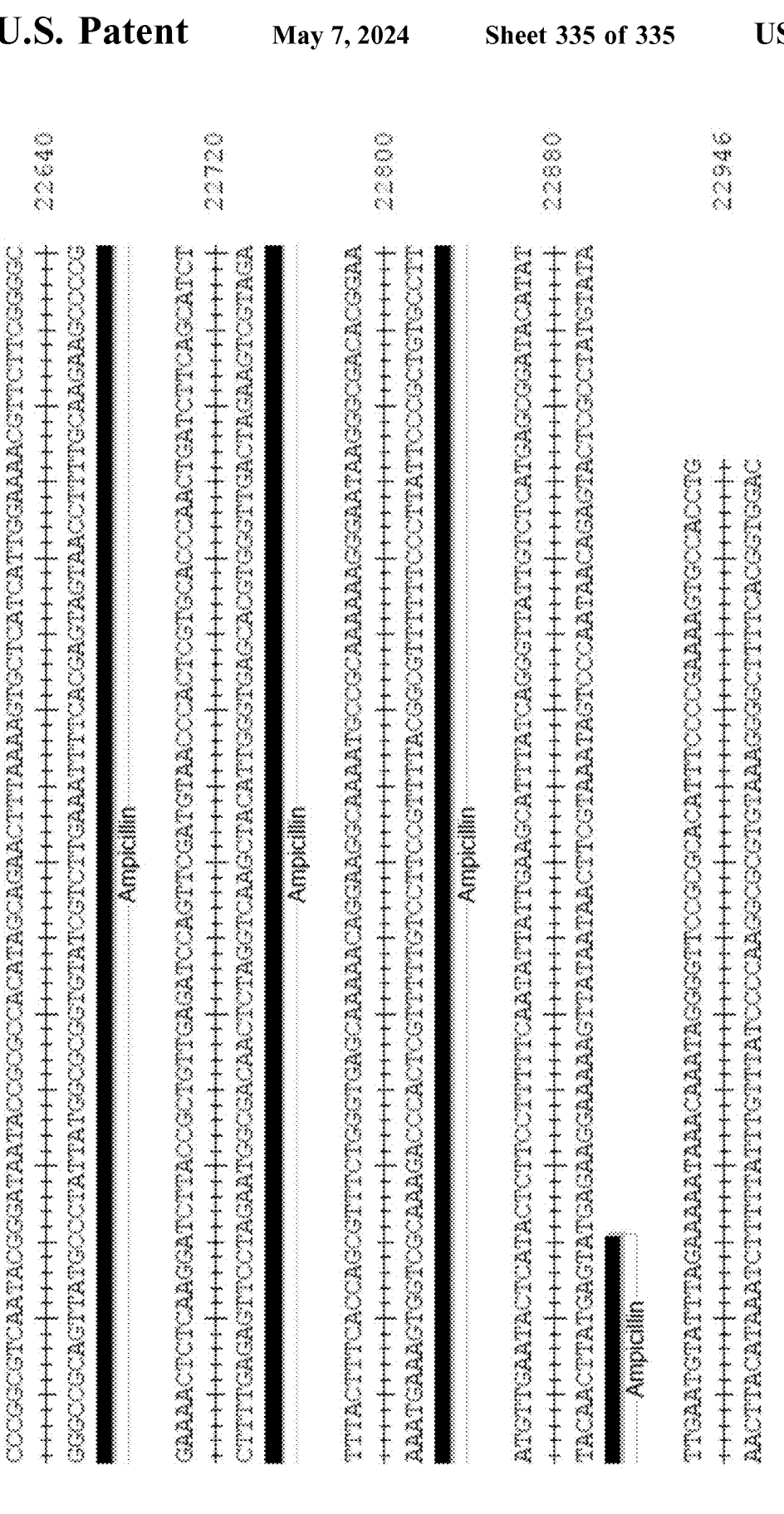
FIG. 21 – continued

CORONAVIRUS DISEASE (COVID-19) VACCINE

CROSS-REFERENCE TO RELATED APPLICATIONS

This application is a divisional of U.S. patent application Ser. No. 17/817,708 filed Aug. 5, 2022, which is a divisional of U.S. patent application Ser. No. 17/193,890 filed Mar. 5, 2021, now U.S. Pat. No. 11,478,543, which claims priority to U.S. Provisional Application No. 62/986,396 filed Mar. 6, 2020 and to U.S. Provisional Application No. 63/017,241 filed Apr. 29, 2020, each of which is herein incorporated by reference in its entirety.

STATEMENT REGARDING FEDERALLY SPONSORED RESEARCH OR DEVELOPMENT

This invention was made with government support under grant no. 1R21AI158044-01 awarded by the National Institute of Health. The government has certain rights in the invention.

REFERENCE TO SEQUENCE LISTING

The Sequence Listing concurrently submitted herewith as a text file named "205961_7055US3_Sequence_Listing.txt," created on Mar. 20, 2023 and having a size of 542,659 bytes is herein incorporated by reference pursuant to 37 C.F.R. § 1.52(e)(5).

BACKGROUND OF THE INVENTION

The recently emerged coronavirus, currently called 2019-nCoV or SARS-CoV-2 virus, is rapidly spreading in China and Asia with over 42,000 cases, 500 deaths and cases in 18 countries as of Feb. 10, 2020. This novel coronavirus is thought to have emerged from a live animal market in Wuhan, China, and has quickly spread in the community with large clusters of human to human transmission. The sequence of several isolates have been determined, and the closest strains are SARS-like bat coronavirus lineages. Little is known about this virus including its susceptibility to anti-viral compounds, ability to replicate in cell lines or host factors regulating replication. Importantly there are no therapeutics available to treat the virus, although investigational studies are underway. Modeling of the current outbreak suggests that the virus could infect >1 billion people and become a yearly epidemic.

A need exists for novel methods for generating vaccines to treat Coronaviruses, in particular, COVID-19. The present invention addresses and satisfies this need.

SUMMARY OF THE INVENTION

In some aspects, the present disclosure provides an isolated nucleic acid encoding a recombinant virus comprising a SARS-CoV-2 spike protein (S) or a portion thereof.

In other aspects, the present disclosure provides a recombinant virus comprising a SARS-CoV-2 spike protein (S) or a portion thereof.

In one aspect, the present disclosure provides a recombinant virus encoded by a nucleic acid described herein. In some embodiments, the nucleic acid encodes a recombinant virus comprising a SARS-CoV-2 spike protein (S) or a portion thereof.

In another aspect, the present disclosure provides a recombinant fusion protein comprising (a) a glycoprotein (G) of a virus or a portion thereof, and (b) a SARS-CoV-2 spike protein (S) or a portion thereof.

In some aspects, the present disclosure provides a vector comprising a nucleic acid described herein. In one embodiment, the nucleic acid encodes a recombinant virus comprising a SARS-CoV-2 spike protein (S) or a portion thereof.

In other aspects, the present disclosure provides a vaccine comprising a recombinant virus comprising a SARS-CoV-2 spike protein (S) or a portion thereof, and a pharmaceutically acceptable carrier.

In one aspect, the present disclosure provides a method of generating an immune response against a SARS-CoV-2 virus in a subject in need thereof, the method comprising administering to the subject an effective amount of a vaccine described herein. In some embodiments, the vaccine comprises a recombinant virus comprising a SARS-CoV-2 spike protein (S) or a portion thereof, and a pharmaceutically acceptable carrier.

In another aspect, the present disclosure provides a method of vaccinating a subject against a SARS-CoV-2 virus, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In other aspects, the present disclosure provides a method of providing immunity against a SARS-CoV-2 virus in a subject, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

In some aspects, the present disclosure provides a method of treating and/or preventing a disease or disorder associated with a SARS-CoV-2 virus in a subject in need thereof, the method comprising administering to the subject an effective amount of the vaccine described herein. In some embodiments, the vaccine comprises a recombinant virus comprising a SARS-CoV-2 spike protein (S) or a portion thereof, and a pharmaceutically acceptable carrier.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1: VSV expressing codon-optimized Covid-S1. The map shows the viral sequence including the plasmids utilized to create the recombinant virus. The sequence is shown in SEQ ID NO: 1 and features are shown in FIG. 7. The sequence and features are also shown in FIG. 17 ("VSV-COVID19-S1-VSVG").

FIG. 7 shows the features of the map shown in FIG. 1.
FIG. 8 shows the features of the map shown in FIG. 2.
FIG. 9 shows the features of the map shown in FIG. 3.
FIG. 10 shows the features of the map shown in FIG. 4.
FIG. 11 shows the features of the map shown in FIG. 5.

FIGS. 16A-16B: FIG. 16A is a presentation showing formulation of BBV151-A vaccine (BBV151-A1 & BBV151-A2) and FIG. 16B is a presentation showing formulation of BBV-151-B vaccine.

FIG. 19 additionally shows the sequences of SEQ ID NOs: 33-106.

DETAILED DESCRIPTION

Definitions

Figure 2:
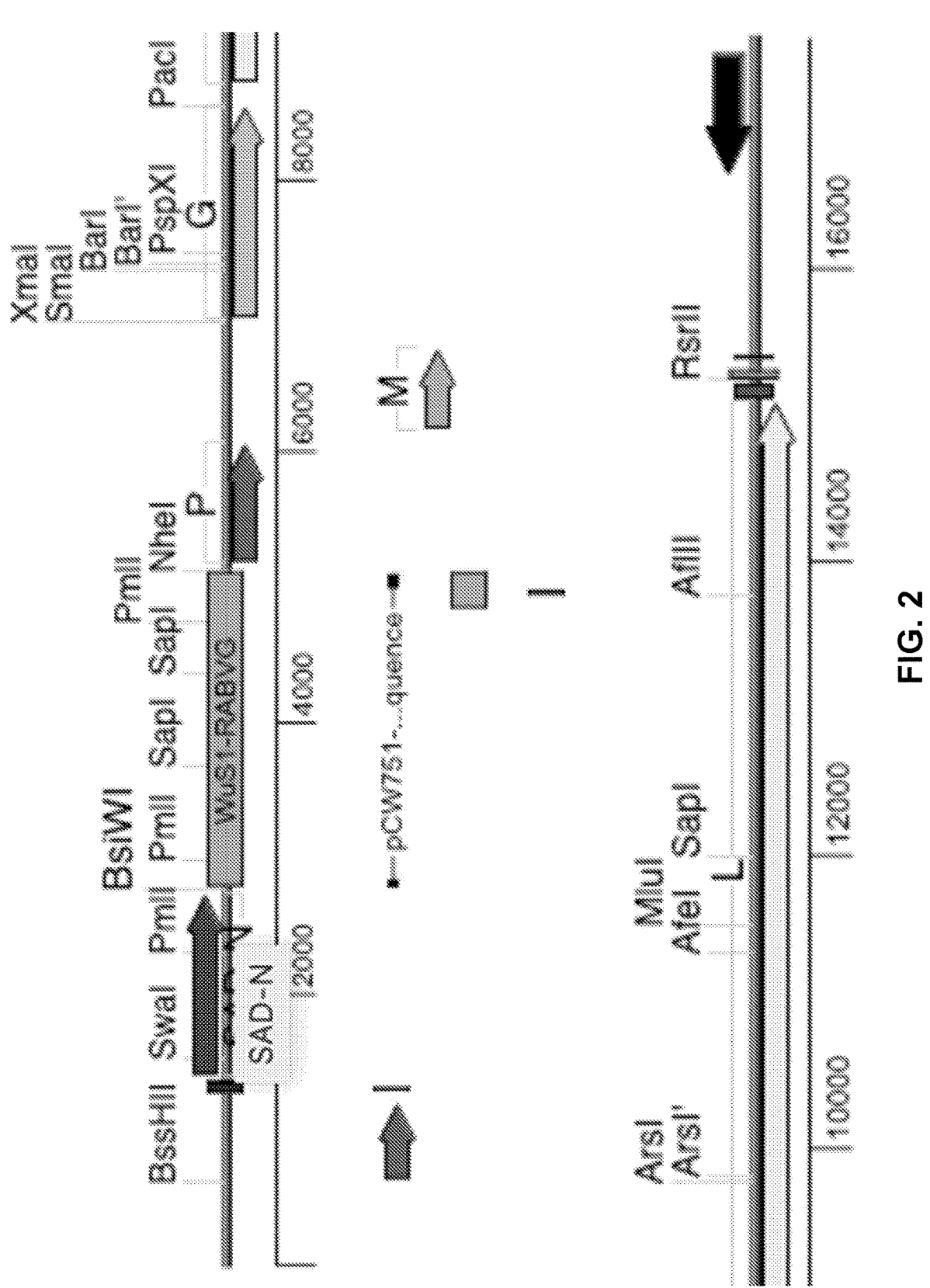
FIG. 2: RABV expressing codon-optimized Covid-S1. The map shows the viral sequence, including the plasmids utilized to create the recombinant virus. The sequence is shown in SEQ ID NO: 2 and features are shown in FIG. 8. The sequence and features are also shown in FIG. 18 ("BNSP333-COVID19-S1-RVG").
Figure 3:
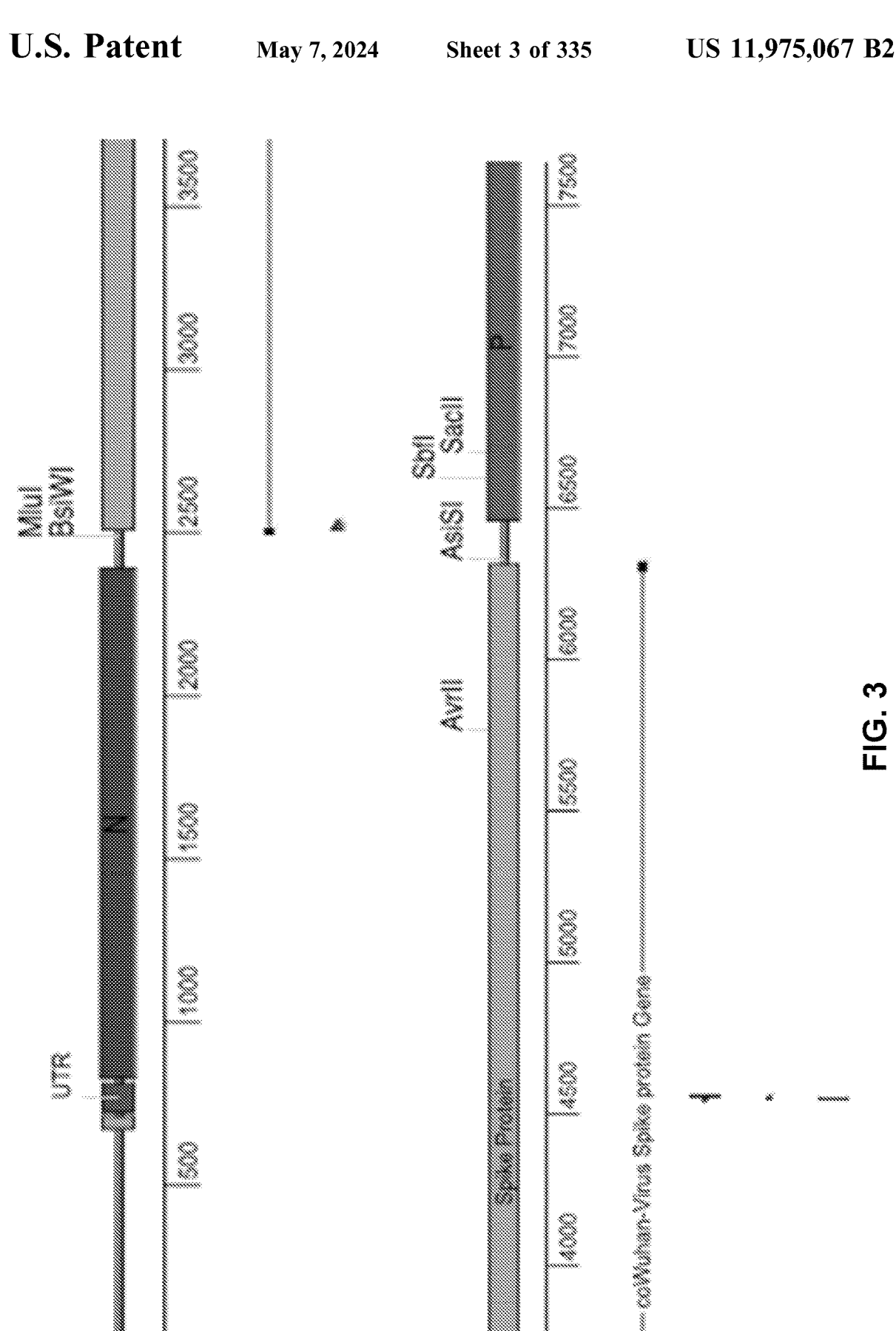
FIG. 3: MV expressing codon-optimized Covid-S from position 2 of the genome. The map shows the viral sequence, including the plasmids utilized to create the recombinant virus. The sequences is shown in SEQ ID NO: 3 and features are shown in FIG. 9. The sequence and features are also shown in FIG. 21 ("MV-coWuhan-S Position 2").
Figure 4:
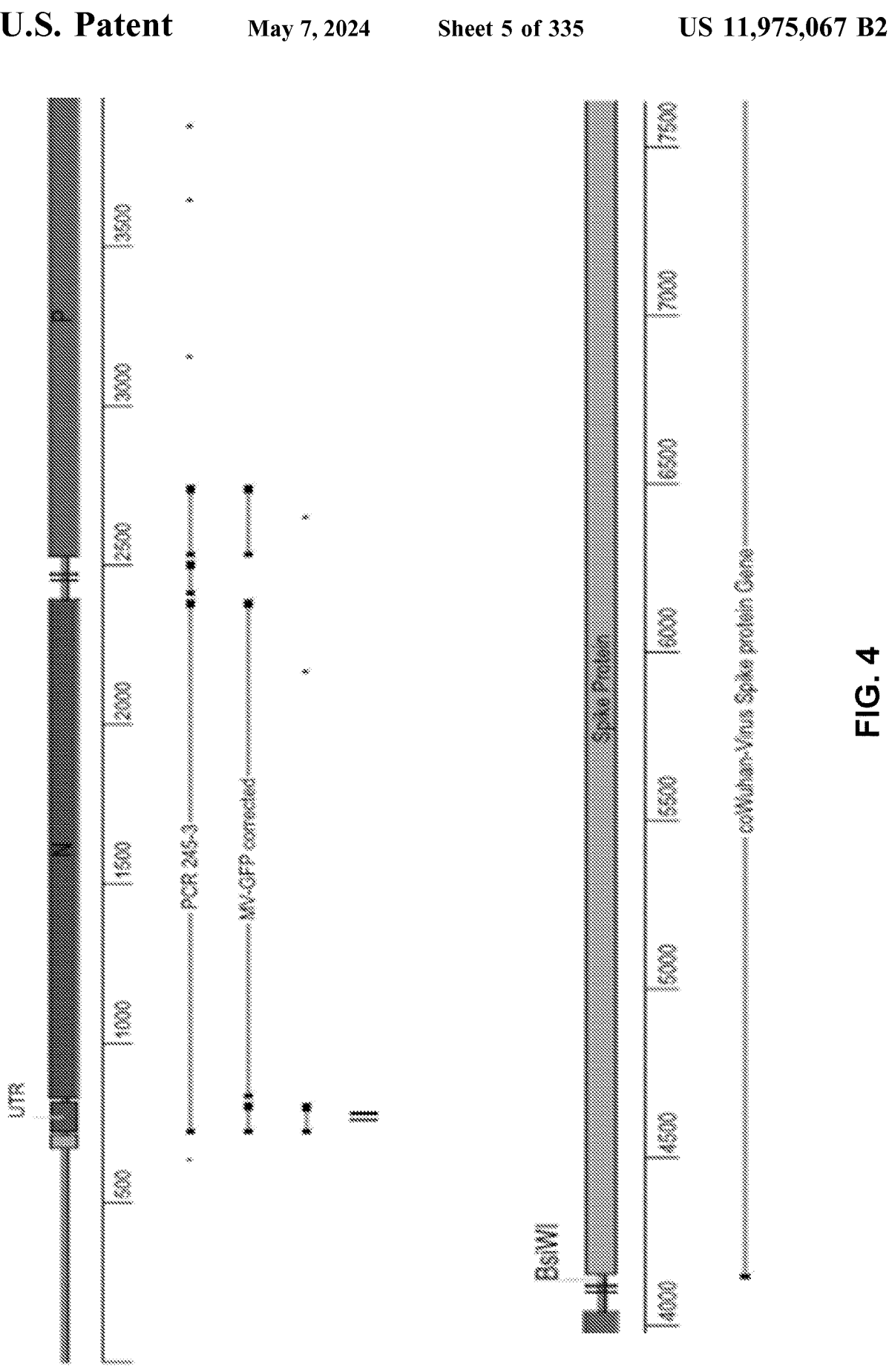
FIG. 4: MV expressing codon-optimized Covid-S from position 3 of the genome. The map shows the viral sequence, including the plasmids utilized to create the recombinant virus. The sequence is shown in SEQ ID NO: 4 and features are shown in FIG. 10. The sequence and features are also depicted in FIG. 20 ("MV Wu S in position 3").
Figure 5:
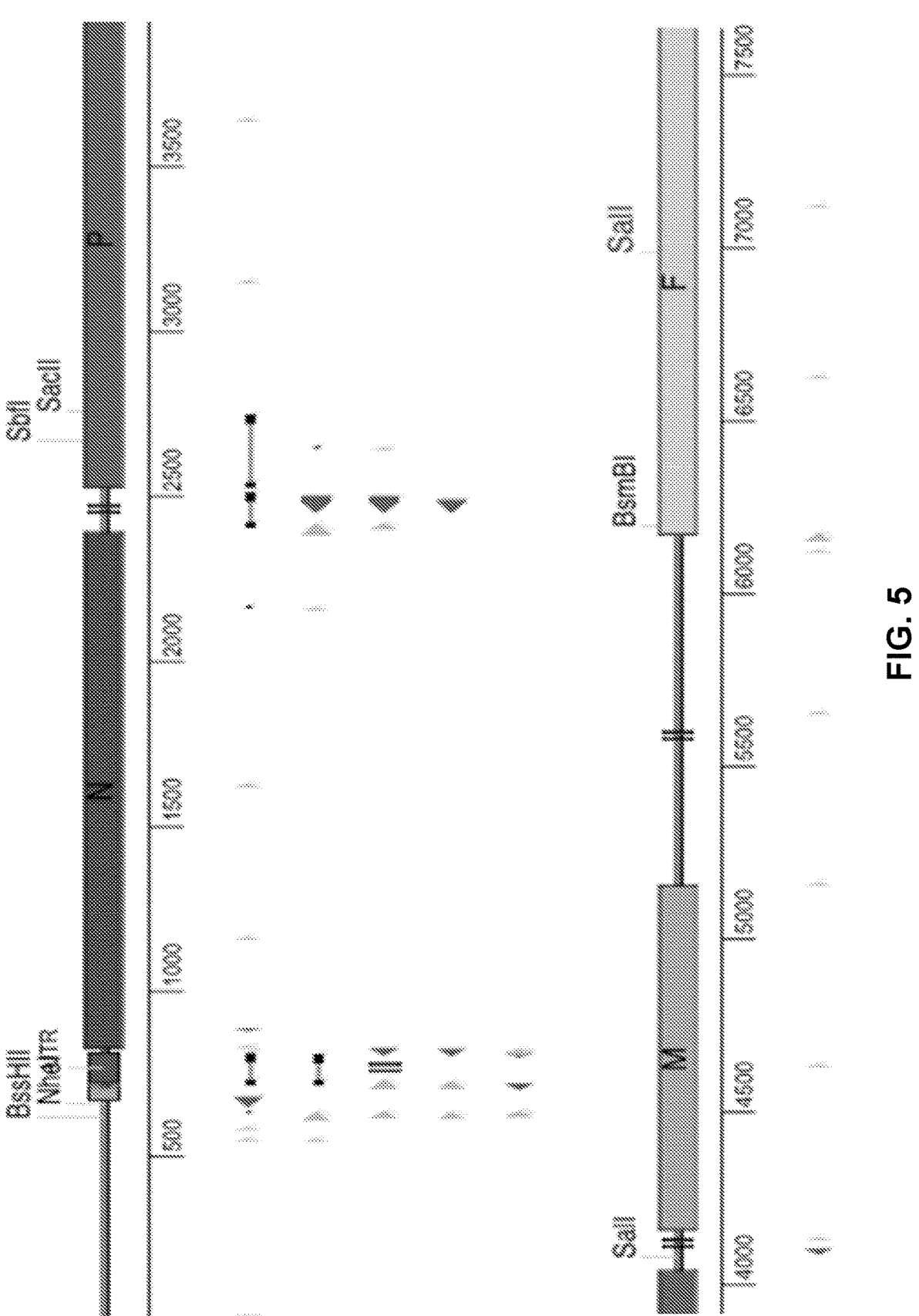
FIG. 5: MV expressing codon-optimized Covid-S from position 6 of the genome. The map shows the viral sequence, including the plasmids utilized to create the recombinant virus. The sequence is shown in SEQ ID NO: 5 and features are shown in FIG. 11. The sequence and features are also depicted in FIG. 19 ("MV WuhanCoV S in position 6").

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

The term "antibody" or "Ab" as used herein, refers to a protein, or polypeptide sequence derived from an immunoglobulin molecule, which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

The term "ameliorating" or "treating" means that the clinical signs and/or the symptoms associated with a disease are lessened as a result of the actions performed. The signs or symptoms to be monitored will be well known to the skilled clinician.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "biological" or "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

As used herein, the terms "control," or "reference" are used interchangeably and refer to a value that is used as a standard of comparison.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

As used herein, the terms "eliciting an immune response" or "immunizing" refer to the process of generating a B cell and/or a T cell response against a heterologous protein.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"Heterologous antigens" used herein to refer to an antigen that is not endogenous to the organism comprising or expressing an antigen. As an example, a virus vaccine vector comprising or expressing a viral or tumor antigen comprises a heterologous antigen. The term "Heterologous protein" as used herein refers to a protein that elicits a beneficial immune response in a subject (i.e. mammal), irrespective of its source.

The term "specifically binds", "selectively binds" or "binding specificity" refers to the ability of the humanized antibodies or binding compounds of the invention to bind to a target epitope with a greater affinity than that which results when bound to a non-target epitope. In certain embodiments, specific binding refers to binding to a target with an affinity that is at least 10, 50, 100, 250, 500, or 1000 times greater than the affinity for a non-target epitope.

As used herein, by "combination therapy" is meant that a first agent is administered in conjunction with another agent.

"In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

"Humoral immunity" or "humoral immune response" both refer to B-cell mediated immunity and are mediated by highly specific antibodies, produced and secreted by B-lymphocytes (B-cells).

"Prevention" refers to the use of a pharmaceutical compositions for the vaccination against a disorder.

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants include, but are not limited to, emulsions (e.g., oil in water (o/w) emulsions), aluminium salts, polyanions, bacterial glycopeptides and slow release agents such as Freund's incomplete.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymers, bacterial ghosts, bacterial polysaccharides, attenuated bacteria, virus like particles, attenuated viruses and ISCOMS.

The term "expression" as used herein is defined as the transcription and/or translation of a particular nucleotide sequence driven by its promoter.

As used herein, the term "expression cassette" means a nucleic acid sequence capable of directing the transcription and/or translation of a heterologous coding sequence. In some embodiments, the expression cassette comprises a promoter sequence operably linked to a sequence encoding a heterologous protein. In some embodiments, the expression cassette further comprises at least one regulatory sequence operably linked to the sequence encoding the heterologous protein.

"Incorporated into" or "encapsulated in" refers to an antigenic peptide and/or nucleic acid molecule that is/are within a delivery vehicle, such as microparticles, bacterial ghosts, attenuated bacteria, virus like particles, attenuated viruses, ISCOMs, liposomes and preferably virosomes.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

"Transform", "transforming", and "transformation" is used herein to refer to a process of introducing an isolated nucleic acid into the interior of an organism.

The term "treatment" as used within the context of the present invention is meant to include therapeutic treatment as well as prophylactic, or suppressive measures for the disease or disorder. As used herein, the term "treatment" and associated terms such as "treat" and "treating" means the reduction of the progression, severity and/or duration of a disease condition or at least one symptom thereof. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

The term "isolated" as used herein with respect to nucleic acids, such as DNA or RNA, refers to molecules separated from other DNAs or RNAs, respectively that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state. The term "isolated" is also used herein to refer to polypeptides, which are isolated from other cellular proteins and is meant to encompass both purified and recombinant polypeptides. An "isolated cell" or "isolated population of cells" is a cell or population of cells that is not present in its natural environment.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

A "mutation" as used therein is a change in a DNA sequence resulting in an alteration from its natural state. The mutation can comprise a deletion and/or insertion and/or duplication and/or substitution of at least one deoxyribonucleic acid base such as a purine (adenine and/or thymine) and/or a pyrimidine (guanine and/or cytosine). Mutations may or may not produce discernible changes in the observable characteristics (phenotype) of an organism.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. As used herein, nucleic acids include but are not limited to, all nucleic acid sequences which are obtained by any means available in the art, including, without limitation, recombinant means, i.e., the cloning of nucleic acid sequences from a recombinant library or a viral genome, using ordinary cloning technology and PCR™, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. There are numerous expression control sequences, including promoters which are native, constitutive, inducible and/or tissue-specific, are known in the art that may be used in the compositions of the invention. "Operably linked" should be construed to include RNA expression and control sequences in addition to DNA expression and control sequences.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence, which is required for expression of a gene product operably linked to the promoter/regulatory sequence. In some instances, this sequence may be the core promoter sequence and in other instances, this sequence may also include an enhancer sequence and other regulatory elements, which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the term "effective amount" or "therapeutically effective amount" means that amount of a composition (e.g., vaccine composition) or active ingredient (e.g., virus like particles (VLPs), virions, viral vectors, antigen, nucleic acid molecule) necessary to achieve an intended result e.g., to produce an intended immunological, pharmacological, therapeutic and/or protective result (e.g., that amount of VLPs, virions, or viral vectors sufficient to induce a measurable immune response, to prevent a particular disease condition, to reduce the severity of and/or ameliorate the disease condition or at least one symptom and/or condition associated therewith).

A "subject" or "patient," as used therein, may be a human or non-human mammal. Non-human mammals include, for example, livestock and pets, such as ovine, bovine, porcine, canine, feline and murine mammals. Preferably, the subject is human. In some embodiments, the subject is a domestic pet or livestock. In some embodiments, the subject is a cat. In some embodiments, the subject is a dog. In some other embodiments, the subject is a ferret.

"Titers" are numerical measures of the concentration of a virus or viral vector compared to a reference sample, where the concentration is determined either by the activity of the virus, or by measuring the number of viruses in a unit volume of buffer. The titer of viral stocks are determined, e.g., by measuring the infectivity of a solution or solutions (typically serial dilutions) of the viruses, e.g., on HeLa cells using the soft agar method (see, Graham & Van Der eb (1973) Virology 52:456-467) or by monitoring resistance conferred to cells, e.g., G418 resistance encoded by the virus or vector, or by quantitating the viruses by UV spectrophotometry (see, Chardonnet & Dales (1970) Virology 40:462-477).

"Vaccination" refers to the process of inoculating a subject with an antigen to elicit an immune response in the subject, that helps to prevent or treat the disease or disorder the antigen is connected with. The term "immunization" is used interchangeably herein with vaccination.

A "vector" is a composition of matter which comprises a nucleic acid and which can be used to deliver the nucleic acid to the interior of a cell. Numerous vectors are known in the art including, but not limited to, linear polynucleotides, polynucleotides associated with ionic or amphiphilic compounds, plasmids, and viruses. In the present disclosure, the term "vector" includes an autonomously replicating virus.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for generating vaccines against a SARS-CoV-2 virus.

The SARS-CoV-2 virus is also referred to herein as 2019-nCoV or 2019 Novel Coronavirus.

Described herein is a vaccine against the SARS-CoV-2 virus that uses a rabies virus-based vector that has proven to be an efficient vector against emerging and re-emerging infectious diseases. It was previously demonstrated that inactivated rabies virus particles containing MERS-CoV spike S1 protein induce potent immune responses against MERS-CoV and RABV and provide protection in animal systems.

The 2019-nCoV vaccine described herein has the following advantages:

- The construct is based on a currently available rabies vaccine product, and therefore will facilitate entry of a vaccine into a clinical phase one study to be prepared within a short time period. Bharat Biotech Ltd (BBIL) produce currently 20 million doses of the RABV vaccine a year.
- The construct can be rapidly scaled, as needed, for additional clinical trials and commercial manufacture.
- The construct can be manufactured at low cost-of-goods. Rabies vaccines have been commercially produced for decades, costs are well known and are inexpensive. The present vaccine uses the same manufacturing process as the current human rabies vaccine. When vaccinating millions of people in resource-limited areas, a low-cost vaccine is a significant advantage
- The vaccine should be safe for all population groups. In some embodiments, the vaccine is based on the killed rabies vaccine backbone since the rabies vaccine has decades of safe use across diverse populations.
- Proof of concept has been demonstrated by protecting in animal models based on challenge studies with the related MERS-CoV in two mouse models and alpacas (camelid).
- Long-term protection is expected since the RABV vaccine often provides life-long protection.
- The vaccine can be produced by an experienced commercial-scale manufacturing partner, Bharat Biotech, who has successfully met WHO pre-qualification standards for other vaccines, and can move quickly into clinical trials and commercial production. Bharat Biotech meets the FDA, EMA, and WHO PQ standards for cGMP.
- Utilises a unique polysaccharide adjuvant, Advax-SM, that has already been extensively tested in human clinical trials, being shown to enhance both humoral and cellular immunity. Most notably, addition of Advax-SM to prototype cGMP whole cell and recombinant spike protein SARS vaccines, not only enhanced neutralising antibody responses and prevented lung viral replication but also completely prevented vaccine-enhanced eosinophilic lung pathology in response to SARS virus exposure.
- Both the RABV vector and the utilized adjuvant can be stabilized and stored at room temperature.

Constructs

In one aspect, the present invention includes an isolated nucleic acid encoding a recombinant virus comprising a SARS-CoV-2 spike protein (S) or a portion thereof. In some embodiments, the virus is a rhabdovirus. In some embodiments, the virus is a rabies virus, a vesicular stomatitis virus (VSV), or a measles virus. In a particular embodiment, the virus is a rabies virus. The nucleic acid can comprises sequences that are codon-optimized for expression in a cell (e.g., a mammalian cell, a human cell).

In one embodiment, the SARS-CoV-2 spike protein (S) or the portion thereof comprises the amino acid sequence as set forth in SEQ ID NO: 28:

MFVFLVLLPLVSSQCVNLTTRTQLPPAYTNSFTRGVYYPDKVFRSSVLHS
TQDLFLPFFSNVTWFHAIHVSGTNGTKRFDNPVLPFNDGVYFASTEKSNI
IRGWIFGTTLDSKTQSLLIVNNATNVVIKVCEFQFCNDPFLGVYYHKNNK
SWMESEFRVYSSANNCTFEYVSQPFLMDLEGKQGNFKNLREFVFKNIDGY
FKIYSKHTPINLVRDLPQGFSALEPLVDLPIGINITRFQTLLALHRSYLT
PGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSF
VIRGDEVRQIAPGQTGKIADYNYKLPDDFTGCVIAWNSNNLDSKVGGNYN
YLYRLFRKSNLKPFERDISTEIYQAGSTPCNGVEGENCYFPLQSYGFQPT
NGVGYQPYRVVVLSFELLHAPATVCGPKKSTNLVKNKCVNFNFNGLTGTG
VLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCL
IGAEHVNNSYECDIPIGAGICASYQTQTNSPR.

In another embodiment, the SARS-CoV-2 spike protein (S) or the portion thereof comprises the amino acid sequence as set forth in SEQ ID NO: 29:

MFVFLVLLPLVSSQCVNLTTRTQLPPAYTNSFTRGVYYPDKVFRSSVLHS
TQDLFLPFFSNVTWFHAIHVSGTNGTKRFDNPVLPFNDGVYFASTEKSNI
IRGWIFGTTLDSKTQSLLIVNNATNVVIKVCEFQFCNDPFLGVYYHKNNK
SWMESEFRVYSSANNCTFEYVSQPFLMDLEGKQGNFKNLREFVFKNIDGY
FKIYSKHTPINLVRDLPQGFSALEPLVDLPIGINITRFQTLLALHRSYLT
PGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASV
YAWNRKRISNCVADYSVLYNSASFSTFKCYGVSPTKLNDLCFTNVYADSF
VIRGDEVRQIAPGQTGKIADYNYKLPDDFTGCVIAWNSNNLDSKVGGNYN
YLYRLFRKSNLKPFERDISTEIYQAGSTPCNGVEGENCYFPLQSYGFQPT
NGVGYQPYRVVVLSFELLHAPATVCGPKKSTNLVKNKCVNFNFNGLTGTG
VLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCL
IGAEHVNNSYECDIPIGAGICASYQTQTNSPRRARSVASQSIIAYTMSLG
AENSVAYSNNSIAIPTNFTISVTTEILPVSMTKTSVDCTMYICGDSTECS
NLLLQYGSFCTQLNRALTGIAVEQDKNTQEVFAQVKQIYKTPPIKDFGGF
NFSQILPDPSKPSKRSFIEDLLFNKVTLADAGFIKQYGDCLGDIAARDLI
CAQKFNGLTVLPPLLTDEMIAQYTSALLAGTITSGWTFGAGAALQIPFAM
QMAYRENGIGVTQNVLYENQKLIANQFNSAIGKIQDSLSSTASALGKLQD
VVNQNAQALNTLVKQLSSNFGAISSVLNDILSRLDKVEAEVQIDRLITGR
LQSLQTYVTQQLIRAAEIRASANLAATKMSECVLGQSKRVDFCGKGYHLM

-continued

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT.

In one embodiment, the SARS-CoV-2 spike protein (S) or the portion thereof comprises the amino acid sequence as set forth in SEQ ID NO: 30:

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGENCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRSVGDEAEDFVEVHLPDVH

NQVSGVDLGLPNWGKYVLLSAGALTALMLIIFLMTCCRRVNRSEPTQHNL

RGTGREVSVTPQSGKIISSWESHKSGGETRL.

In another embodiment, the SARS-CoV-2 spike protein (S) or the portion thereof comprises the amino acid sequence as set forth in SEQ ID NO: 31:

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGENCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPR.

In another embodiment, an N protein (N) or the portion thereof is provided, comprising the amino acid sequence as set forth in SEQ ID NO: 32:

MATLLRSLALFKRNKDKPPITSGSGGAIRGIKHIIIVPIPGDSSITTRSR

LLDRLVRLIGNPDVSGPKLTGALIGILSLFVESPGQLIQRITDDPDVSIR

LLEVVQSDQSQSGLTFASRGTNMEDEADQYFSHDDPISSDQSRFGWFGNK

EISDIEVQDPEGFNMILGTILAQIWVLLAKAVTAPDTAADSELRRWIKYT

QQRRVVGEFRLERKWLDVVRNRIAEDLSLRRFMVALILDIKRTPGNKPRI

AEMICDIDTYIVEAGLASFILTIKFGIETMYPALGLHEFAGELSTLESLM

NLYQQMGETAPYMVILENSIQNKFSAGSYPLLWSYAMGVGVELENSMGGL

NFGRSYFDPAYFRLGQEMVRRSAGKVSSTLASELGITAEDARLVSEIAMH

TTEDKISRAVGPRQAQVSFLHGDQSENELPRLGGKEDRRVKQSRGEARES

YRETGPSRASDARAAHLPTGTPLDIDTATESSQDPQDSRRSADALLRLQA

MAGISEEQGSDTDTPIVYNDRNLLD.

In another embodiment, the SARS-CoV-2 spike protein (S) or the portion thereof is a variant spike polypeptide comprising one or more alterations (e.g., substitution(s), insertion(s), deletion(s), addition(s), modification(s)) in its amino acid sequence relative to the amino acid sequence set forth as SEQ ID NO: 28, 29, 30, or 31.

In other embodiments, the SARS-CoV-2 spike protein (S) or the portion thereof is a variant spike polypeptide comprising, relative to the amino acid sequence set forth as SEQ ID NO: 28, 29, 30, or 31, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the SARS-CoV-2 spike protein (S) or the portion thereof is a variant spike polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 28, 29, 30, or 31.

In another embodiment, the N protein (N) or the portion thereof is a variant N polypeptide comprising one or more alterations (e.g., substitution(s), insertion(s), deletion(s), addition(s), modification(s)) in its amino acid sequence relative to the amino acid sequence set forth as SEQ ID NO: 32.

In other embodiments, the N protein (N) or the portion thereof is a variant N polypeptide comprising, relative to the amino acid sequence set forth as SEQ ID NO: 32, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more alterations.

In one embodiment, the N protein (N) or the portion thereof is a variant N polypeptide comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but not 100%, sequence identity to the amino acid sequence set forth as SEQ ID NO: 32.

In some embodiments, the recombinant virus expresses a full-length SARS-CoV-2 spike protein (S). In some other embodiments, the recombinant virus expresses a portion of the SARS-CoV-2 spike protein (S). In one embodiment, the portion of the SARS-CoV-2 spike protein (S) is a receptor binding site of the SARS-CoV-2 spike protein (S). In another embodiment, the portion of the SARS-CoV-2 spike protein (S) is the 51 domain. In another embodiment, the portion of the SARS-CoV-2 spike protein (S) is the N-terminal 750 amino acids of the SARS-CoV-2 spike protein (S).

In some embodiments, the SARS-CoV-2 spike protein (S) or portion thereof is fused to a glycoprotein (G) or a portion thereof. In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In other embodiments, the portion of the glycoprotein (G) comprises 1 to about 100 amino acids of the ectodomain or a trimerization domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a cell. In some embodiments, the sequence encoding the SARS-CoV-2 spike protein (S) or portion thereof fused to a glycoprotein (G) or portion thereof is codon-optimized for expression in a cell.

In some embodiments, the nucleic acid comprises a sequence encoding at least a portion of the genome of the virus. In some embodiments, the isolated nucleic acid comprises the full-length genome.

In one embodiment, the nucleic acid comprises (a) a sequence encoding at least a portion of the genome of a vesicular stomatitis virus (VSV), and (b) a sequence encoding a protein comprising a SARS-CoV-2 spike protein (S) or a portion thereof. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 1, shown below:

```
CTGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGGCTCC

CTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACAACAC

TCAACCCTATCTCGGTCTATTCTTTTGATTTATAAGGGATTTTGCCGATTTCGGCC

TATTGGTTAAAAAATGAGCTGATTTAACAAAAATTTAACGCGAATTTTAACAAA

ATATTAACGCTTACAATTTCCATTCGCCATTCAGGCTGCGCAACTGTTGGGAAGG

GCGATCGGTGCGGGCCTCTTCGCTATTACGCCAGCTGGCGAAAGGGGGATGTGC

TGCAAGGCGATTAAGTTGGGTAACGCCAGGGTTTTCCCAGTCACGACGTTGTAA

AACGACGGCCAGTGAGcgcgccCTAGTTATTAATAGTAATCAATTACGGGGTCATT

AGTTCATAGCCCATATATGGAGTTCCGCGTTACATAACTTACGGTAAATGGCCCG

CCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATG

GTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAA

ATCAACGGGACTTTCCAAAATGTCGTAACAACTCCGCCCCATTGACGCAAATGG

GCGGTAGGCGTGTACGGTGGGAGGTCTATATAAGCAGAGCTCTCTGGCTAACTA

GAGAACCCACTGCTTACTGGCTTATCGAAATTAATACGACTCACTATAGGGAGA

CCCAAGCTGGCTAGGGTCTTCGTCTGATGAGTCCGTGAGGACGAAACCCGGCGT

ACCGGGTCACGAAGACAAACAAACCATTATTATCATTAAAAGGCTCAGGAGAAA

CTTTAACAGTAATCAAAATGTCTGTTACAGTCAAGAGAATCATTGACAACACAGT

CATAGTTCCAAAACTTCCTGCAAATGAGGATCCAGTGGAATACCCGGCAGATTA
```

-continued

```
CTTCAGAAAATCAAAGGAGATTCCTCTTTACATCAATACTACAAAAAGTTTGTCA
GATCTAAGAGGATATGTCTACCAAGGCCTCAAATCCGGAAATGTATCAATCATA
CATGTCAACAGCTACTTGTATGGAGCATTAAAGGACATCCGGGGTAAGTTGGAT
AAAGATTGGTCAAGTTTCGGAATAAACATCGGGAAAGCAGGGGATACAATCGGA
ATATTTGACCTTGTATCCTTGAAAGCCCTGGACGGCGTACTTCCAGATGGAGTAT
CGGATGCTTCCAGAACCAGCGCAGATGACAAATGGTTGCCTTTGTATCTACTTGG
CTTATACAGAGTGGGCAGAACACAAATGCCTGAATACAGAAAAAAGCTCATGGA
TGGGCTGACAAATCAATGCAAAATGATCAATGAACAGTTTGAACCTCTTGTGCC
AGAAGGTCGTGACATTTTTGATGTGTGGGGAAATGACAGTAATTACACAAAAAT
TGTCGCTGCAGTGGACATGTTCTTCCACATGTTCAAAAAACATGAATGTGCCTCG
TTCAGATACGGAACTATTGTTTCCAGATTCAAAGATTGTGCTGCATTGGCAACAT
TTGGACACCTCTGCAAAATAACCGGAATGTCTACAGAAGATGTAACGACCTGGA
TCTTGAACCGAGAAGTTGCAGATGAAATGGTCCAAATGATGCTTCCAGGCCAAG
AAATTGACAAGGCCGATTCATACATGCCTTATTTGATCGACTTTGGATTGTCTTCT
AAGTCTCCATATTCTTCCGTCAAAAACCCTGCCTTCCACTTCTGGGGGCAATTGA
CAGCTCTTCTGCTCAGATCCACCAGAGCAAGGAATGCCCGACAGCCTGATGACA
TTGAGTATACATCTCTTACTACAGCAGGTTTGTTGTACGCTTATGCAGTAGGATC
CTCTGCCGACTTGGCACAACAGTTTTGTGTTGGAGATAACAAATACACTCCAGAT
GATAGTACCGGAGGATTGACGACTAATGCACCGCCACAAGGCAGAGATGTGGTC
GAATGGCTCGGATGGTTTGAAGATCAAAACAGAAAACCGACTCCTGATATGATG
CAGTATGCGAAAAGAGCAGTCATGTCACTGCAAGGCCTAAGAGAGAAGACAATT
GGCAAGTATGCTAAGTCAGAATTTGACAAATGACCCTATAATTCTCAGATCACCT
ATTATATATTATGCTACATATGAAAAAAACTAACAGATATCATGGATAATCTCAC
AAAAGTTCGTGAGTATCTCAAGTCCTATTCTCGTCTGGATCAGGCGGTAGGAGAG
ATAGATGAGATCGAAGCACAACGAGCTGAAAAGTCCAATTATGAGTTGTTCCAA
GAGGATGGAGTGGAAGAGCATACTAAGCCCTCTTATTTTCAGGCAGCAGATGAT
TCTGACACAGAATCTGAACCAGAAATTGAAGACAATCAAGGTTTGTATGCACCA
GATCCAGAAGCTGAGCAAGTTGAAGGCTTTATACAGGGGCCTTTAGATGACTAT
GCAGATGAGGAAGTGGATGTTGTATTTACTTCGGACTGGAAACAGCCTGAGCTT
GAATCTGACGAGCATGGAAAGACCTTACGGTTGACATCGCCAGAGGGTTTAAGT
GGAGAGCAGAAATCCCAGTGGCTTTCGACGATTAAAGCAGTCGTGCAAAGTGCC
AAATACTGGAATCTGGCAGAGTGCACATTTGAAGCATCGGGAGAAGGGGTCATT
ATGAAGGAGCGCCAGATAACTCCGGATGTATATAAGGTCACTCCAGTGATGAAC
ACACATCCGTCCCAATCAGAAGCAGTATCAGATGTTTGGTCTCTCTCAAAGACAT
CCATGACTTTCCAACCCAAGAAAGCAAGTCTTCAGCCTCTCACCATATCCTTGGA
TGAATTGTTCTCATCTAGAGGAGAGTTCATCTCTGTCGGAGGTGACGGACGAATG
TCTCATAAAGAGGCCATCCTGCTCGGCCTGAGATACAAAAAGTTGTACAATCAG
GCGAGAGTCAAATATTCTCTGTAGACTATGAAAAAAAGTAACAGATATCACGAT
CTAAGTGTTATCCCAATCCATTCATCATGAGTTCCTTAAAGAAGATTCTCGGTCT
GAAGGGGAAAGGTAAGAAATCTAAGAAATTAGGGATCGCACCACCCCCTTATGA
AGAGGACACTAGCATGGAGTATGCTCCGAGCGCTCCAATTGACAAATCCTATTTT
```

-continued

```
GGAGTTGACGAGATGGACACCTATGATCCGAATCAATTAAGATATGAGAAATTC

TTCTTTACAGTGAAAATGACGGTTAGATCTAATCGTCCGTTCAGAACATACTCAG

ATGTGGCAGCCGCTGTATCCCATTGGGATCACATGTACATCGGAATGGCAGGGA

AACGTCCCTTCTACAAAATCTTGGCTTTTTTGGGTTCTTCTAATCTAAAGGCCACT

CCAGCGGTATTGGCAGATCAAGGTCAACCAGAGTATCACACTCACTGCGAAGGC

AGGGCTTATTTGCCACATAGGATGGGGAAGACCCCTCCCATGCTCAATGTACCA

GAGCACTTCAGAAGACCATTCAATATAGGTCTTTACAAGGGAACGATTGAGCTC

ACAATGACCATCTACGATGATGAGTCACTGGAAGCAGCTCCTATGATCTGGGAT

CATTTCAATTCTTCCAAATTTTCTGATTTCAGAGAGAAGGCCTTAATGTTTGGCCT

GATTGTCGAGAAAAAGGCATCTGGAGCGTGGGTCCTGGATTCTATCAGCCACTTC

AAATGAGCTAGTCTAACTTCTAGCTTCTGAACAATCCCCGGTTTACTCAGTCTCT

CCTAATTCCAGCCTCTCGAACAACTAATATCCTGTCTTTTCTATCCCTATGAAAAA

AACTAACAGAGATCGATCTGTTTACGCGTCACTATGAAGTGCCTTTTGTACTTAG

CCTTTTTATTCATTGGGGTGAATTGCAAGTTCACCATAGTTTTTCCACACAACCAA

AAAGGAAACTGGAAAAATGTTCCTTCTAATTACCATTATTGCCCGTCAAGCTCAG

ATTTAAATTGGCATAATGACTTAATAGGCACAGCCATACAAGTCAAAATGCCCA

AGAGTCACAAGGCTATTCAAGCAGACGGTTGGATGTGTCATGCTTCCAAATGGG

TCACTACTTGTGATTTCCGCTGGTATGGACCGAAGTATATAACACAGTCCATCCG

ATCCTTCACTCCATCTGTAGAACAATGCAAGGAAAGCATTGAACAAACGAAACA

AGGAACTTGGCTGAATCCAGGCTTCCCTCCTCAAAGTTGTGGATATGCAACTGTG

ACGGATGCCGAAGCAGTGATTGTCCAGGTGACTCCTCACCATGTGCTGGTTGATG

AATACACAGGAGAATGGGTTGATTCACAGTTCATCAACGGAAAATGCAGCAATT

ACATATGCCCCACTGTCCATAACTCTACAACCTGGCATTCTGACTATAAGGTCAA

AGGGCTATGTGATTCTAACCTCATTTCCATGGACATCACCTTCTTCTCAGAGGAC

GGAGAGCTATCATCCCTGGGAAAGGAGGGCACAGGGTTCAGAAGTAACTACTTT

GCTTATGAAACTGGAGGCAAGGCCTGCAAAATGCAATACTGCAAGCATTGGGGA

GTCAGACTCCCATCAGGTGTCTGGTTCGAGATGGCTGATAAGGATCTCTTTGCTG

CAGCCAGATTCCCTGAATGCCCAGAAGGGTCAAGTATCTCTGCTCCATCTCAGAC

CTCAGTGGATGTAAGTCTAATTCAGGACGTTGAGAGGATCTTGGATTATTCCCTC

TGCCAAGAAACCTGGAGCAAAATCAGAGCGGGTCTTCCAATCTCTCCAGTGGAT

CTCAGCTATCTTGCTCCTAAAAACCCAGGAACCGGTCCTGCTTTCACCATAATCA

ATGGTACCCTAAAATACTTTGAGACCAGATACATCAGAGTCGATATTGCTGCTCC

AATCCTCTCAAGAATGGTCGGAATGATCAGTGGAACTACCACAGAAAGGGAACT

GTGGGATGACTGGGCACCATATGAAGACGTGGAAATTGGACCCAATGGAGTTCT

GAGGACCAGTTCAGGATATAAGTTTCCTTTATACATGATTGGACATGGTATGTTG

GACTCCGATCTTCATCTTAGCTCAAAGGCTCAGGTGTTCGAACATCCTCACATTC

AAGACGCTGCTTCGCAACTTCCTGATGATGAGAGTTTATTTTTTGGTGATACTGG

GCTATCCAAAAATCCAATCGAGCTTGTAGAAGGTTGGTTCAGTAGTTGGAAAAG

CTCTATTGCCTCTTTTTTCTTTATCATAGGGTTAATCATTGGACTATTCTTGGTTCT

CCGAGTTGGTATCCATCTTTGCATTAAATTAAAGCACACCAAGAAAAGACAGAT
```

-continued

```
TTATACAGACATAGAGATGAACCGACTTGGAAAGTAACTCAAATCCTGCTAGGT
ATGAAAAAAACTAACaGATATCACGCTCGAGCGTACGCCACCATGTTCGTGTTTC
TGGTGCTGCTGCCTCTGGTGAGCTCCCAGTGCGTGAACCTGACCACAAGGACCC
AGCTGCCCCTGCCTATACCAATTCCTTCACACGGGGCGTGTACTATCCCGACAA
GGTGTTCCGGAGCAGCGTGCTGCACTCCACACAGGATCTGTTTCTGCCTTTCTTTT
CTAACGTGACCTGGTTCCACGCCATCCACGTGAGCGGCACCAATGGCACAAAGC
GGTTCGACAATCCAGTGCTGCCCTTTAACGATGGCGTGTACTTCGCCTCCACCGA
GAAGTCTAACATCATCAGAGGCTGGATCTTTGGCACCACACTGGACAGCAAGAC
ACAGTCCCTGCTGATCGTGAACAATGCCACCAACGTGGTCATCAAGGTGTGCGA
GTTCCAGTTTTGTAATGATCCATTCCTGGGCGTGTACTATCACAAGAACAATAAG
TCTTGGATGGAGAGCGAGTTTCGCGTGTATTCCTCTGCCAACAATTGCACATTTG
AGTACGTGTCCCAGCCCTTCCTGATGGACCTGGAGGGCAAGCAGGGCAATTTCA
AGAACCTGAGGGAGTTCGTGTTTAAGAATATCGATGGCTACTTCAAAATCTACTC
CAAGCACACCCCAATCAACCTGGTGCGCGACCTGCCACAGGGCTTCTCTGCCCTG
GAGCCACTGGTGGATCTGCCCATCGGCATCAACATCACCCGGTTTCAGACACTGC
TGGCCCTGCACAGAAGCTACCTGACACCAGGCGACAGCTCCTCTGGATGGACCG
CAGGAGCAGCAGCCTACTATGTGGGCTATCTGCAGCCCAGGACCTTCCTGCTGA
AGTACAACGAGAATGGCACCATCACAGACGCCGTGGATTGCGCCCTGGATCCCC
TGTCTGAGACCAAGTGTACACTGAAGAGCTTTACCGTGGAGAAGGGCATCTATC
AGACAAGCAATTTCAGGGTGCAGCCTACCGAGTCCATCGTGCGCTTTCCCAATAT
CACAAACCTGTGCCCTTTTGGCGAGGTGTTCAACGCAACCCGCTTCGCCAGCGTG
TACGCCTGGAATAGGAAGCGCATCTCCAACTGCGTGGCCGACTATTCTGTGCTGT
ACAACAGCGCCTCCTTCTCTACCTTTAAGTGCTATGGCGTGAGCCCCACAAAGCT
GAATGACCTGTGCTTTACCAACGTGTACGCCGATTCCTTCGTGATCAGGGGCGAC
GAGGTGCGCCAGATCGCACCAGGACAGACAGGCAAGATCGCAGACTACAATTAT
AAGCTGCCTGACGATTTCACCGGCTGCGTGATCGCCTGGAACTCTAACAATCTGG
ATAGCAAAGTGGGCGGCAACTACAATTATCTGTACCGGCTGTTTAGAAAGTCTA
ATCTGAAGCCATTCGAGAGGGACATCTCCACAGAAATCTACCAGGCCGGCTCTA
CCCCCTGCAATGGCGTGGAGGGCTTTAACTGTTATTTCCCTCTGCAGAGCTACGG
CTTCCAGCCAACAAACGGCGTGGGCTATCAGCCCTACCGCGTGGTGGTGCTGTCT
TTTGAGCTGCTGCACGCACCTGCAACAGTGTGCGGACCAAAGAAGAGCACCAAT
CTGGTGAAGAACAAGTGCGTGAACTTCAACTTCAACGGACTGACCGGAACAGGC
GTGCTGACCGAGTCCAACAAGAAGTTCCTGCCTTTTCAGCAGTTCGGCAGGGAC
ATCGCAGATACCACAGACGCCGTGCGCGACCCTCAGACCCTGGAGATCCTGGAC
ATCACACCATGCTCCTTCGGCGGCGTGTCTGTGATCACACCAGGCACCAATACAA
GCAACCAGGTGGCCGTGCTGTATCAGGACGTGAATTGTACCGAGGTGCCAGTGG
CAATCCACGCAGATCAGCTGACCCCTACATGGCGGGTGTACTCTACCGGCAGCA
ACGTGTTCCAGACAAGAGCCGGATGCCTGATCGGAGCAGAGCACGTGAACAATA
GCTATGAGTGCGACATCCCTATCGGCGCCGGCATCTGTGCCTCCTACCAGACCCA
GACAAACTCCCCAAGGTCTGTGGGCGATACAGGCCTGTCCAAGAATCCAATCGA
GCTGGTAGAGGGCTGGTTCAGCAGTTGGAAAAGCTCCATCGCCTCCTTTTTCTTT
```

-continued

```
ATCATCGGCCTGATCATCGGACTGTTCCTGGTGCTCCGCGTGGGTATCCACCTGT
GCATCAAGCTGAAGCACACCAAGAAAAGACAGATTTATACAGACATCGAGATGA
ACCGCCTGGGAAAGTGAGCTAGCCAGATTCTTCATGTTTGGACCAAATCAACTTG
TGATACCATGCTCAAAGAGGCCTCAATTATATTTGAGTTTTTAATTTTTATGAAA
AAAACTAACAGCAATCATGGAAGTCCACGATTTTGAGACCGACGAGTTCAATGA
TTTCAATGAAGATGACTATGCCACAAGAGAATTCCTGAATCCCGATGAGCGCAT
GACGTACTTGAATCATGCTGATTACAATTTGAATTCTCCTCTAATTAGTGATGAT
ATTGACAATTTGATCAGGAAATTCAATTCTCTTCCGATTCCCTCGATGTGGGATA
GTAAGAACTGGGATGGAGTTCTTGAGATGTTAACATCATGTCAAGCCAATCCCAT
CTCAACATCTCAGATGCATAAATGGATGGGAAGTTGGTTAATGTCTGATAATCAT
GATGCCAGTCAAGGGTATAGTTTTTTACATGAAGTGGACAAAGAGGCAGAAATA
ACATTTGACGTGGTGGAGACCTTCATCCGCGGCTGGGGCAACAAACCAATTGAA
TACATCAAAAAGGAAAGATGGACTGACTCATTCAAAATTCTCGCTTATTTGTGTC
AAAAGTTTTTGGACTTACACAAGTTGACATTAATCTTAAATGCTGTCTCTGAGGT
GGAATTGCTCAACTTGGCGAGGACTTTCAAAGGCAAAGTCAGAAGAAGTTCTCA
TGGAACGAACATATGCAGGATTAGGGTTCCCAGCTTGGGTCCTACTTTTATTTCA
GAAGGATGGGCTTACTTCAAGAAACTTGATATTCTAATGGACCGAAACTTTCTGT
TAATGGTCAAAGATGTGATTATAGGGAGGATGCAAACGGTGCTATCCATGGTAT
GTAGAATAGACAACCTGTTCTCAGAGCAAGACATCTTCTCCCTTCTAAATATCTA
CAGAATTGGAGATAAAATTGTGGAGAGGCAGGGAAATTTTTCTTATGACTTGATT
AAAATGGTGGAACCGATATGCAACTTGAAGCTGATGAAATTAGCAAGAGAATCA
AGGCCTTTAGTCCCACAATTCCCTCATTTTGAAAATCATATCAAGACTTCTGTTG
ATGAAGGGGCAAAAATTGACCGAGGTATAAGATTCCTCCATGATCAGATAATGA
GTGTGAAAACAGTGGATCTCACACTGGTGATTTATGGATCGTTCAGACATTGGGG
TCATCCTTTTATAGATTATTACACTGGACTAGAAAAATTACATTCCCAAGTAACC
ATGAAGAAAGATATTGATGTGTCATATGCAAAAGCACTTGCAAGTGATTTAGCT
CGGATTGTTCTATTTCAACAGTTCAATGATCATAAAAAGTGGTTCGTGAATGGAG
ACTTGCTCCCTCATGATCATCCCTTTAAAAGTCATGTTAAAGAAAATACATGGCC
CACAGCTGCTCAAGTTCAAGATTTTGGAGATAAATGGCATGAACTTCCGCTGATT
AAATGTTTTGAAATACCCGACTTACTAGACCCATCGATAATATACTCTGACAAAA
GTCATTCAATGAATAGGTCAGAGGTGTTGAAACATGTCCGAATGAATCCGAACA
CTCCTATCCCTAGTAAAAAGGTGTTGCAGACTATGTTGGACACAAAGGCTACCA
ATTGGAAAGAATTTCTTAAAGAGATTGATGAGAAGGGCTTAGATGATGATGATC
TAATTATTGGTCTTAAAGGAAAGGAGAGGGAACTGAAGTTGGCAGGTAGATTTT
TCTCCCTAATGTCTTGGAAATTGCGAGAATACTTTGTAATTACCGAATATTTGAT
AAAGACTCATTTCGTCCCTATGTTTAAAGGCCTGACAATGGCGGACGATCTAACT
GCAGTCATTAAAAAGATGTTAGATTCCTCATCCGGCCAAGGATTGAAGTCATATG
AGGCAATTTGCATAGCCAATCACATTGATTACGAAAAATGGAATAACCACCAAA
GGAAGTTATCAAACGGCCCAGTGTTCCGAGTTATGGGCCAGTTCTTAGGTTATCC
ATCCTTAATCGAGAGAACTCATGAATTTTTTGAGAAAAGTCTTATATACTACAAT
```

```
-continued
GGAAGACCAGACTTGATGCGTGTTCACAACAACACACTGATCAATTCAACCTCC

CAACGAGTTTGTTGGCAAGGACAAGAGGGTGGACTGGAAGGTCTACGGCAAAA

AGGATGGACTATCCTCAATCTACTGGTTATTCAAAGAGAGGCTAAAATCAGAAA

CACTGCTGTCAAAGTCTTGGCACAAGGTGATAATCAAGTTATTTGCACACAGTAT

AAAACGAAGAAATCGAGAAACGTTGTAGAATTACAGGGTGCTCTCAATCAAATG

GTTTCTAATAATGAGAAAATTATGACTGCAATCAAAATAGGGACAGGGAAGTTA

GGACTTTTGATAAATGACGATGAGACTATGCAATCTGCAGATTACTTGAATTATG

GAAAAATACCGATTTTCCGTGGAGTGATTAGAGGGTTAGAGACCAAGAGATGGT

CACGAGTGACTTGTGTCACCAATGACCAAATACCCACTTGTGCTAATATAATGAG

CTCAGTTTCCACAAATGCTCTCACCGTAGCTCATTTTGCTGAGAACCCAATCAAT

GCCATGATACAGTACAATTATTTTGGGACATTTGCTAGACTCTTGTTGATGATGC

ATGATCCTGCTCTTCGTCAATCATTGTATGAAGTTCAAGATAAGATACCGGGCTT

GCACAGTTCTACTTTCAAATACGCCATGTTGTATTTGGACCCTTCCATTGGAGGA

GTGTCGGGCATGTCTTTGTCCAGGTTTTTGATTAGAGCCTTCCCAGATCCCGTAA

CAGAAAGTCTCTCATTCTGGAGATTCATCCATGTACATGCTCGAAGTGAGCATCT

GAAGGAGATGAGTGCAGTATTTGGAAACCCCGAGATAGCCAAGTTTCGAATAAC

TCACATAGACAAGCTAGTAGAAGATCCAACCTCTCTGAACATCGCTATGGGAAT

GAGTCCAGCGAACTTGTTAAAGACTGAGGTTAAAAAATGCTTAATCGAATCAAG

ACAAACCATCAGGAACCAGGTGATTAAGGATGCAACCATATATTTGTATCATGA

AGAGGATCGGCTCAGAAGTTTCTTATGGTCAATAAATCCTCTGTTCCCTAGATTT

TTAAGTGAATTCAAATCAGGCACTTTTTTGGGAGTCGCAGACGGGCTCATCAGTC

TATTTCAAAATTCTCGTACTATTCGGAACTCCTTTAAGAAAAAGTATCATAGGGA

ATTGGATGATTTGATTGTGAGGAGTGAGGTATCCTCTTTGACACATTTAGGGAAA

CTTCATTTGAGAAGGGGATCATGTAAAATGTGGACATGTTCAGCTACTCATGCTG

ACACATTAAGATACAAATCCTGGGGCCGTACAGTTATTGGGACAACTGTACCCC

ATCCATTAGAAATGTTGGGTCCACAACATCGAAAGAGACTCCTTGTGCACCAT

GTAACACATCAGGGTTCAATTATGTTTCTGTGCATTGTCCAGACGGGATCCATGA

CGTCTTTAGTTCACGGGACCATTGCCTGCTTATCTAGGGTCTAAAACATCTGAA

TCTACATCTATTTTGCAGCCTTGGGAAAGGGAAAGCAAAGTCCCACTGATTAAA

AGAGCTACACGTCTTAGAGATGCTATCTCTTGGTTTGTTGAACCCGACTCTAAAC

TAGCAATGACTATACTTTCTAACATCCACTCTTTAACAGGCGAAGAATGGACCAA

AAGGCAGCATGGGTTCAAAAGAACAGGGTCTGCCCTTCATAGGTTTTCGACATCT

CGGATGAGCCATGGTGGGTTCGCATCTCAGAGCACTGCAGCATTGACCAGGTTG

ATGGCAACTACAGACACCATGAGGGATCTGGGAGATCAGAATTTCGACTTTTTAT

TCCAAGCAACGTTGCTCTATGCTCAAATTACCACCACTGTTGCAAGAGACGGATG

GATCACCAGTTGTACAGATCATTATCATATTGCCTGTAAGTCCTGTTTGAGACCC

ATAGAAGAGATCACCCTGGACTCAAGTATGGACTACACGCCCCCAGATGTATCC

CATGTGCTGAAGACATGGAGGAATGGGAAGGTTCGTGGGACAAGAGATAAA

ACAGATCTATCCTTTAGAAGGGAATTGGAAGAATTTAGCACCTGCTGAGCAATC

CTATCAAGTCGGCAGATGTATAGGTTTTCTATATGGAGACTTGGCGTATAGAAAA

TCTACTCATGCCGAGGACAGTTCTCTATTTCCTCTATCTATACAAGGTCGTATTAG
```

-continued

```
AGGTCGAGGTTTCTTAAAAGGGTTGCTAGACGGATTAATGAGAGCAAGTTGCTG
CCAAGTAATACACCGGAGAAGTCTGGCTCATTTGAAGAGGCCGGCCAACGCAGT
GTACGGAGGTTTGATTTACTTGATTGATAAATTGAGTGTATCACCTCCATTCCTTT
CTCTTACTAGATCAGGACCTATTAGAGACGAATTAGAAACGATTCCCCACAAGA
TCCCAACCTCCTATCCGACAAGCAACCGTGATATGGGGGTGATTGTCAGAAATTA
CTTCAAATACCAATGCCGTCTAATTGAAAAGGGAAAATACAGATCACATTATTC
ACAATTATGGTTATTCTCAGATGTCTTATCCATAGACTTCATTGGACCATTCTCTA
TTTCCACCACCCTCTTGCAAATCCTATACAAGCCATTTTTATCTGGGAAAGATAA
GAATGAGTTGAGAGAGCTGGCAAATCTTTCTTCATTGCTAAGATCAGGAGAGGG
GTGGGAAGACATACATGTGAAATTCTTCACCAAGGACATATTATTGTGTCCAGA
GGAAATCAGACATGCTTGCAAGTTCGGGATTGCTAAGGATAATAATAAAGACAT
GAGCTATCCCCCTTGGGGAAGGGAATCCAGAGGGACAATTACAACAATCCCTGT
TTATTATACGACCACCCCTTACCCAAAGATGCTAGAGATGCCTCCAAGAATCCAA
AATCCCCTGCTGTCCGGAATCAGGTTGGGCCAATTACCAACTGGCGCTCATTATA
AAATTCGGAGTATATTACATGGAATGGGAATCCATTACAGGGACTTCTTGAGTTG
TGGAGACGGCTCCGGAGGGATGACTGCTGCATTACTACGAGAAAATGTGCATAG
CAGAGGAATATTCAATAGTCTGTTAGAATTATCAGGGTCAGTCATGCGAGGCGC
CTCTCCTGAGCCCCCCAGTGCCCTAGAAACTTTAGGAGGAGATAAATCGAGATG
TGTAAATGGTGAAACATGTTGGGAATATCCATCTGACTTATGTGACCCAAGGACT
TGGGACTATTTCCTCCGACTCAAAGCAGGCTTGGGGCTTCAAATTGATTTAATTG
TAATGGATATGGAAGTTCGGGATTCTTCTACTAGCCTGAAAATTGAGACGAATGT
TAGAAATTATGTGCACCGGATTTTGGATGAGCAAGGAGTTTTAATCTACAAGACT
TATGGAACATATATTTGTGAGAGCGAAAAGAATGCAGTAACAATCCTTGGTCCC
ATGTTCAAGACGGTCGACTTAGTTCAAACAGAATTTAGTAGTTCTCAAACGTCTG
AAGTATATATGGTATGTAAAGGTTTGAAGAAATTAATCGATGAACCCAATCCCG
ATTGGTCTTCCATCAATGAATCCTGGAAAAACCTGTACGCATTCCAGTCATCAGA
ACAGGAATTTGCCAGAGCAAAGAAGGTTAGTACATACTTTACCTTGACAGGTAT
TCCCTCCCAATTCATTCCTGATCCTTTTGTAAACATTGAGACTATGCTACAAATAT
TCGGAGTACCCACGGGTGTGTCTCATGCGGCTGCCTTAAAATCATCTGATAGACC
TGCAGATTTATTGACCATTAGCCTTTTTTATATGGCGATTATATCGTATTATAACA
TCAATCATATCAGAGTAGGACCGATACCTCCGAACCCCCCATCAGATGGAATTG
CACAAAATGTGGGATCGCTATAACTGGTATAAGCTTTTGGCTGAGTTTGATGGA
GAAAGACATTCCACTATATCAACAGTGTTTAGCAGTTATCCAGCAATCATTCCCG
ATTAGGTGGGAGGCTGTTTCAGTAAAAGGAGGATACAAGCAGAAGTGGAGTACT
AGAGGTGATGGGCTCCCAAAAGATACCCGAACTTCAGACTCCTTGGCCCCAATC
GGGAACTGGATCAGATCTCTGGAATTGGTCCGAAACCAAGTTCGTCTAAATCCAT
TCAATGAGATCTTGTTCAATCAGCTATGTCGTACAGTGGATAATCATTTGAAATG
GTCAAATTTGCGAAGAAACACAGGAATGATTGAATGGATCAATAGACGAATTTC
AAAAGAAGACCGGTCTATACTGATGTTGAAGAGTGACCTACACGAGGAAAACTC
TTGGAGAGATTAAAAAATCATGAGGAGACTCCAAACTTTAAGTATGAAAAAAAC
```

-continued

```
TTTGATCCTTAAGACCCTCTTGTGGTTTTATTTTTTATCTGGTTTTGTGGTCTTCG
TGGGTCGGCATGGCATCTCCACCTCCTCGCGGTCCGACCTGGGCATCCGAAGGA
GGACGCACGTCCACTCGGATGGCTAAGGGAGAGCCAGAAAATAACTAGTGGATC
CGGCTGCTAACAAAGCCCGAAAGGAAGCTGAGTTGGCTGCTGCCACCGCTGAGC
AATAACTAGCATAACCCCTTGGGGCCTCTAAACGGGTCTTGAGGGGTTTTTTGCT
GAAAGtCGCGCTTGGCGTAATCATGGTCATAGCTGTTTCCTGTGTGAAATTGTTAT
CCGCTCACAATTCCACACAACATACGAGCCGGAAGCATAAAGTGTAAAGCCTGG
GGTGCCTAATGAGTGAGCTAACTCACATTAATTGCGTTGCGCTCACTGCCCGCTT
TCCAGTCGGGAAACCTGTCGTGCCAGCTGCATTAATGAATCGGCCAACGCGCGG
GGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTCCATA
GGCTCCGCCCCCTGACGAGCATCACAAAAATCGACGCTCAAGTCAGAGGTGGC
GAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGGC
GGTGCTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAA
GCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAA
TCAGTGAGGCACCTATCTCAGCGATCTGTCTATTTCGTTCATCCATAGTTGCCTGA
CTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCT
CTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCG
ATGTAACCCACTCGTGCACCCAACTGATCTTCAGCATCTTTTACTTTCACCAGCG
```

```
TTTCTGGGTGAGCAAAAACAGGAAGGCAAAATGCCGCAAAAAAGGGAATAAGG

GCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAA

TAAACAAATAGGGGTTCCGCGCACATTTCCCCGAAAAGTGCCAC.
```

In one embodiment, the nucleic acid comprises (a) a sequence encoding at least a portion of the genome of a rabies virus and (b) a sequence encoding a protein comprising a SARS-CoV-2 spike protein (S) or a portion thereof. In some embodiments, the at least a portion of the genome of the rabies virus comprises an N gene and a P gene, and the sequence encoding the protein comprising the SARS-CoV-2 spike protein (S) or portion thereof is inserted into a position between the N gene and P gene. In some embodiments, the protein comprising a SARS-CoV-2 spike protein (S) or a portion thereof is a fusion protein comprising a glycoprotein (G) or a portion thereof and a SARS-CoV-2 spike protein (S) or a portion thereof. In some embodiments, the fusion protein comprises a glycoprotein (G) or portion thereof fused to the S1 domain of a SARS-CoV-2 spike protein (S).

In another embodiment, the nucleic acid comprises the sequence of SEQ ID NO: 2, shown below:

```
CTGACGCGCCCTGTAGCGGCGCATTAAGCGCGGCGGGTGTGGTGGTTACGCGCA

GCGTGACCGCTACACTTGCCAGCGCCCTAGCGCCCGCTCCTTTCGCTTTCTTCCCT

TCCTTTCTCGCCACGTTCGCCGGCTTTCCCCGTCAAGCTCTAAATCGGGGGCTCC

CTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTG

ACGTTGGAGTCCACGTTCTTTAATAGTGGACTCTTGTTCCAAACTGGAACAACAC

TCAACCCTATCTCGGTCTATTCTTTTGATTTATAAGGGATTTTGCCGATTTCGGCC

TATTGGTTAAAAAATGAGCTGATTTAACAAAAATTTAACGCGAATTTTAACAAA

ATATTAACGCTTACAATTTCCATTCGCCATTCAGGCTGCGCAACTGTTGGGAAGG

GCGATCGGTGCGGGCCTCTTCGCTATTACGCCAGCTGGCGAAAGGGGGATGTGC

TGCAAGGCGATTAAGTTGGGTAACGCCAGGGTTTTCCCAGTCACGACGTTGTAA

AACGACGGCCAGTGAGcgcgccCTAGTTATTAATAGTAATCAATTACGGGGTCATT

AGTTCATAGCCCATATATGGAGTTCCGCGTTACATAACTTACGGTAAATGGCCCG

CCTGGCTGACCGCCCAACGACCCCCGCCCATTGACGTCAATAATGACGTATGTTC

CCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCT

ATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATG

GTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAA

ATCAACGGGACTTTCCAAAATGTCGTAACAACTCCGCCCCATTGACGCAAATGG

GCGGTAGGCGTGTACGGTGGGAGGTCTATATAAGCAGAGCTCTCTGGCTAACTA

GAGAACCCACTGCTTACTGGCTTATCGAAATTAATACGACTCACTATAGGGAGA

CCCAAGCTGGCTAGATTAAGCGTCGATGAGTCCGTGAGGACGAAACCCGGCGT

ACCGGGTCACGCTTAACAACCAGATCAAAGAAAAAACAGACATTGTCAATTGCA

AAGCAAAAATGTAACACCCCTACAATGGATGCCGACAAGATTGTATTCAAAGTC

AATAATCAGGTGGTCTCTTTGAAGCCTGAGATTATCGTGGATCAATATGAGTACA

AGTACCCTGCCATCAAAGATTTGAAAAAGCCCTGTATAACCCTAGGAAAGGCTC

CCGATTTAAATAAAGCATACAAGTCAGTTTTGTCAGGCATGAGCGCCGCCAAAC
```

-continued

```
TTAATCCTGACGATGTATGTTCCTATTTGGCAGCGGCAATGCAGTTTTTTGAGGG
GACATGTCCGGAAGACTGGACCAGCTATGGAATTGTGATTGCACGAAAAGGAGA
TAAGATCACCCCAGGTTCTCTGGTGGAGATAAAACGTACTGATGTAGAAGGGAA
TTGGGCTCTGACAGGAGGCATGGAACTGACAAGAGACCCCACTGTCCCTGAGCA
TGCGTCCTTAGTCGGTCTTCTCTTGAGTCTGTATAGGTTGAGCAAAATATCCGGG
CAAAACACTGGTAACTATAAGACAAACATTGCAGACAGGATAGAGCAGATTTTT
GAGACAGCCCCTTTTGTTAAAATCGTGGAACACCATACTCTAATGACAACTCACA
AaATGTGTGCTAATTGGAGTACTATACCAAACTTCAGATTTTTGGCCGGAACCTA
TGACATGTTTTTCTCCCGGATTGAGCATCTATATTCAGCAATCAGAGTGGGCACA
GTTGTCACTGCTTATGAAGACTGTTCAGGACTGGTATCATTTACTGGGTTCATAA
AACAAATCAATCTCACCGCTAGAGAGGCAATACTATATTTCTTCCACAAGAACTT
TGAGGAAGAGATAAGAAGAATGTTTGAGCCAGGGCAGGAGACAGCTGTTCCTCA
CTCTTATTTCATCCACTTCCGTTCACTAGGCTTGAGTGGGAAATCTCCTTATTCAT
CAAATGCTGTTGGTCACGTGTTCAATCTCATTCACTTTGTAGGATGCTATATGGG
TCAAGTCAGATCCCTAAATGCAACGGTTATTGCTGCATGTGCTCCTCATGAAATG
TCTGTTCTAGGGGGCTATCTGGGAGAGGAATTCTTCGGGAAAGGGACATTTGAA
AGAAGATTCTTCAGAGATGAGAAAGAACTTCAAGAATACGAGGCGGCTGAACTG
ACAAAGACTGACGTAGCACTGGCAGATGATGGAACTGTCAACTCTGACGACGAG
GACTACTTTTCAGGTGAAACCAGAAGTCCGGAGGCTGTTTATACTCGAATCATGA
TGAATGGAGGTCGACTAAAGAGATCTCACATACGGAGATATGTCTCAGTCAGTT
CCAATCATCAAGCCCGTCCAAACTCATTCGCCGAGTTTCTAAACAAGACATATTC
GAGTGACTCATAAcatgaaaaaaactaacacccctcccGTACGCCACCATGTTCGTGTTTCTGG
TGCTGCTGCCTCTGGTGAGCTCCCAGTGCGTGAACCTGACCACAAGGACCCAGCT
GCCCCCTGCCTATACCAATTCCTTCACACGGGGCGTGTACTATCCCGACAAGGTG
TTCCGGAGCAGCGTGCTGCACTCCACACAGGATCTGTTTCTGCCTTTCTTTTCTAA
CGTGACCTGGTTCCACGCCATCCACGTGAGCGGCACCAATGGCACAAAGCGGTT
CGACAATCCAGTGCTGCCCTTTAACGATGGCGTGTACTTCGCCTCCACCGAGAAG
TCTAACATCATCAGAGGCTGGATCTTTGGCACCACACTGGACAGCAAGACACAG
TCCCTGCTGATCGTGAACAATGCCACCAACGTGGTCATCAAGGTGTGCGAGTTCC
AGTTTTGTAATGATCCATTCCTGGGCGTGTACTATCACAAGAACAATAAGTCTTG
GATGGAGAGCGAGTTTCGCGTGTATTCCTCTGCCAACAATTGCACATTTGAGTAC
GTGTCCCAGCCCTTCCTGATGGACCTGGAGGGCAAGCAGGGCAATTTCAAGAAC
CTGAGGGAGTTCGTGTTTAAGAATATCGATGGCTACTTCAAAATCTACTCCAAGC
ACACCCCAATCAACCTGGTGCGCGACCTGCCACAGGGCTTCTCTGCCCTGGAGCC
ACTGGTGGATCTGCCCATCGGCATCAACATCACCCGGTTTCAGACACTGCTGGCC
CTGCACAGAAGCTACCTGACACCAGGCGACAGCTCCTCTGGATGGACCGCAGGA
GCAGCAGCCTACTATGTGGGCTATCTGCAGCCCAGGACCTTCCTGCTGAAGTACA
ACGAGAATGGCACCATCACAGACGCCGTGGATTGCGCCCTGGATCCCCTGTCTG
AGACCAAGTGTACACTGAAGAGCTTTACCGTGGAGAAGGGCATCTATCAGACAA
GCAATTTCAGGGTGCAGCCTACCGAGTCCATCGTGCGCTTTCCCAATATCACAAA
CCTGTGCCCTTTTGGCGAGGTGTTCAACGCAACCCGCTTCGCCAGCGTGTACGCC
```

-continued

```
TGGAATAGGAAGCGCATCTCCAACTGCGTGGCCGACTATTCTGTGCTGTACAACA

GCGCCTCCTTCTCTACCTTTAAGTGCTATGGCGTGAGCCCCACAAAGCTGAATGA

CCTGTGCTTTACCAACGTGTACGCCGATTCCTTCGTGATCAGGGGCGACGAGGTG

CGCCAGATCGCACCAGGACAGACAGGCAAGATCGCAGACTACAATTATAAGCTG

CCTGACGATTTCACCGGCTGCGTGATCGCCTGGAACTCTAACAATCTGGATAGCA

AAGTGGGCGGCAACTACAATTATCTGTACCGGCTGTTTAGAAAGTCTAATCTGAA

GCCATTCGAGAGGGACATCTCCACAGAAATCTACCAGGCCGGCTCTACCCCCTG

CAATGGCGTGGAgGGCTTTAACTGTTATTTCCCTCTGCAGAgCTACgGCTTCCAGC

CAACAAACGGCGTGGGCTATCAGCCCTACCGCGTGGTGGTGCTGTCTTTTGAGCT

GCTGCACGCACCTGCAACAGTGTGCGGACCAAAGAAGAGCACCAATCTGGTGAA

GAACAAGTGCGTGAACTTCAACTTCAACGGACTGACCGGAACAGGCGTGCTGAC

CGAGTCCAACAAGAAGTTCCTGCCTTTTCAGCAGTTCGGCAGGGACATCGCAGA

TACCACAGACGCCGTGCGCGACCCTCAGACCCTGGAGATCCTGGACATCACACC

ATGCTCCTTCGGCGGCGTGTCTGTGATCACACCAGGCACCAATACAAGCAACCA

GGTGGCCGTGCTGTATCAGGACGTGAATTGTACCGAGGTGCCAGTGGCAATCCA

CGCAGATCAGCTGACCCCTACATGGCGGGTGTACTCTACCGGCAGCAACGTGTT

CCAGACAAGAGCCGGATGCCTGATCGGAGCAGAGCACGTGAACAATAGCTATG

AGTGCGACATCCCTATCGGCGCCGGCATCTGTGCCTCCTACCAGACCCAGACAA

ACTCCCCAAGGTCTGTGGGAGATGAGGCCGAAGACTTTGTGGAAGTCCACCTGC

CTGATGTGCATAACCAGGTGTCTGGCGTCGACCTGGGACTGCCAAATTGGGGCA

AGTACGTGCTGCTGAGTGCTGGAGCACTGACTGCCCTGATGCTGATCATTTTCCT

GATGACCTGCTGTCGGCGCGTGAACAGAAGTGAGCCCACTCAGCACAATCTGCG

AGGAACCGGGAGAGAAGTGTCAGTCACACCTCAGAGCGGGAAAATCATTAGTA

GTTGGGAATCACATAAAAGCGGGGGCGAGACCAGGCTGTGAGCTAGCCATGAA

AAAAACTAACACCCCTCCTTTCGAACCATCCCAAACATGAGCAAGATCTTTGTCA

ATCCTAGTGCTATTAGAGCCGGTCTGGCCGATCTTGAGATGGCTGAAGAAACTGT

TGATCTGATCAATAGAAATATCGAAGACAATCAGGCTCATCTCCAAGGGGAACC

CATAGAGGTGGACAATCTCCCTGAGGATATGGGGCGACTTCACCTGGATGATGG

AAAATCGCCCAACCATGGTGAGATAGCCAAGGTGGGAGAAGGCAAGTATCGAG

AGGACTTTCAGATGGATGAAGGAGAGGATCCTAGCTTCCTGTTCCAGTCATACCT

GGAAAATGTTGGAGTCCAAATAGTCAGACAAATGAGGTCAGGAGAGAGATTTCT

CAAGATATGGTCACAGACCGTAGAAGAGATTATATCCTATGTCGCGGTCAACTTT

CCCAACCCTCCAGGAAAGTCTTCAGAGGATAAATCAACCCAGACTACTGGCCGA

GAGCTCAAGAAGGAGACAACACCCACTCCTTCTCAGAGAGAAAGCCAATCATCG

AAAGCCAGGATGGCGGCTCAAATTGCTTCTGGCCCTCCAGCCCTTGAATGGTCG

GCTACCAATGAAGAGGATGATCTATCAGTGGAGGCTGAGATCGCTCACCAGATT

GCAGAAAGTTTCTCCAAAAAATATAAGTTTCCCTCTCGATCCTCAGGGATACTCT

TGTATAATTTTGAGCAATTGAAAATGAACCTTGATGATATAGTTAAAGAGGCAA

AAAATGTACCAGGTGTGACCCGTTTAGCCCATGACGGGTCCAAACTCCCCCTAA

GATGTGTACTGGGATGGGTCGCTTTGGCCAACTCTAAGAAATTCCAGTTGTTAGT
```

-continued

```
CGAATCCGACAAGCTGAGTAAAATCATGCAAGATGACTTGAATCGCTATACATC

TTGCTAACCGAACCTCTCCCCTCAGTCCCTCTAGACAATAAAATCCGAGATGTCC

CAAAGTCAACATGAAAAAAACAGGCAACACCACTGATAAAATGAACCTCCTACG

TAAGATAGTGAAAAACCGCAGGGACGAGGACACTCAAAAATCCTCTCCCGCGTC

AGCCCCTCTGGATGACGATGACTTGTGGCTTCCACCCCCTGAATACGTCCCGCTG

AAAGAACTTACAGGCAAGAAGAACATGAGGAACTTTTGTATCAACGGAAGGGTT

AAAGTGTGTAGCCCGAATGGTTACTCGTTCAGGATCCTGCGGCACATTCTGAAAT

CATTCGACGAGATATATTCTGGGAATCATAGGATGATCGGGTTAGTCAAAGTGG

TTATTGGACTGGCTTTGTCAGGATCTCCAGTCCCTGAGGGCCTGAACTGGGTATA

CAAATTGAGGAGAACCTTTATCTTCCAGTGGGCTGATTCCAGGGGCCCTCTTGAA

GGGGAGGAGTTGGAATACTCTCAGGAGATCACTTGGGATGATGATACTGAGTTC

GTCGGATTGCAAATAAGAGTGATTGCAAAACAGTGTCATATCCAGGGCAGAGTC

TGGTGTATCAACATGAACCCGAGAGCATGTCAACTATGGTCTGACATGTCTCTTC

AGACACAAAGGTCCGAAGAGGACAAAGATTCCTCTCTGCTTCTAGAATAATCAG

ATTATATCCCGCAAATTTATCACTTGTTTACCTCTGGAGGAGAGAACATATGGGC

TCAACTCCAACCCTTGGGAGCAATATAACAAAAAACATGTTATGGTGCCATTAA

ACCGCTGCATTTCATCAAAGTCAAGTTGATTACCTTTACATTTTGATCCTCTTGGA

TGTGAAAAAAACTATTAACATCCCTCAAAAGACcccgggAAAGATGGTTCCTCAGG

CTCTCCTGTTTGTACCCCTTCTGGTTTTTCCATTGTGTTTGGGAAATTCCCTATTT

ACACGATACCAGACAAGCTTGGTCCCTGGAGTCCGATTGACATACATCACCTCA

GCTGCCCAAACAATTTGGTAGTGGAGGACGAAGGATGCACCAACCTGTCAGGGT

TCTCCTACATGGAACTTAAAGTTGGATACATCTTAGCCATAAAAGTGAACGGGTT

CACTTGCACAGGCGTTGTGACGGAGGCTGAAACCTACACTAACTTCGTTGGTTAT

GTCACAACCACGTTCAAAAGAAAGCATTTCCGCCCAACACCAGATGCATGTAGA

GCCGCGTACAACTGGAAGATGGCCGGTGACCCCAGATATGAAGAGTCTCTACAC

AATCCGTACCCTGACTACCGCTGGCTTCGAACTGTAAAAACCACCAAGGAGTCT

CTCGTTATCATATCTCCAAGTGTGGCAGATTTGGACCCATATGACAGATCCCTTC

ACTCGAGGGTCTTCCCTAGCGGGAAGTGCTCAGGAGTAGCGGTGTCTTCTACCTA

CTGCTCCACTAACCACGATTACACCATTTGGATGCCCGAGAATCCGAGACTAGG

GATGTCTTGTGACATTTTTACCAATAGTAGAGGGAAGAGAGCATCCAAAGGGAG

TGAGACTTGCGGCTTTGTAGATGAAAGAGGCCTATATAAGTCTTTAAAAGGAGC

ATGCAAACTCAAGTTATGTGGAGTTCTAGGACTTAGACTTATGGATGGAACATG

GGTCTCGATGCAAACATCAAATGAAACCAAATGGTGCCCTCCCGATAAGTTGGT

GAACCTGCACGACTTTCGCTCAGACGAAATTGAGCACCTTGTTGTAGAGGAGTTG

GTCAGGAAGAGAGAGGAGTGTCTGGATGCACTAGAGTCCATCATGACAACCAAG

TCAGTGAGTTTCAGACGTCTCAGTCATTTAAGAAAACTTGTCCCTGGGTTTGGAA

AAGCATATACCATATTCAACAAGACCTTGATGGAAGCCGATGCTCACTACAAGT

CAGTCgagACTTGGAATGAGATCCTCCCTTCAAAAGGGTGTTTAAGAGTTGGGGG

GAGGTGTCATCCTCATGTGAACGGGGTGTTTTTCAATGGTATAATATTAGGACCT

GACGGCAATGTCTTAATCCCAGAGATGCAATCATCCCTCCTCCAGCAACATATGG

AGTTGTTGGAATCCTCGGTTATCCCCCTTGTGCACCCCCTGGCAGACCCGTCTAC
```

-continued

```
CGTTTTCAAGGACGGTGACGAGGCTGAGGATTTTGTTGAAGTTCACCTTCCCGAT

GTGCACAATCAGGTCTCAGGAGTTGACTTGGGTCTCCCGAACTGGGGGAAGTAT

GTATTACTGAGTGCAGGGGCCCTGACTGCCTTGATGTTGATAATTTTCCTGATGA

CATGTTGTAGAAGAGTCAATCGATCAGAACCTACGCAACACAATCTCAGAGGGA

CAGGGAGGGAGGTGTCAGTCACTCCCCAAAGCGGGAAGATCATATCTTCATGGG

AATCACACAAGAGTGGGGGTGAGACCAGACTGTAAttaattaaCGTCCTTTCAACGAT

CCAAGTCcatgaaaaaaactaacacccctcccgtacctagcTTATAAAGTGCTGGGTCATCTAAGCTT

TTCAGTCGAGAAAAAAACATTAGATCAGAAGAACAACTGGCAACACTTCTCAAC

CTGAGACTTACTTCAAGATGCTCGATCCTGGAGAGGTCTATGATGACCCTATTGA

CCCAATCGAGTTAGAGGCTGAACCCAGAGGAACCCCCATTGTCCCCAACATCTT

GAGGAACTCTGACTACAATCTCAACTCTCCTTTGATAGAAGATCCTGCTAGACTA

ATGTTAGAATGGTTAAAAACAGGGAATAGACCTTATCGGATGACTCTAACAGAC

AATTGCTCCAGGTCTTTCAGAGTTTTGAAAGATTATTTCAAGAAGGTAGATTTGG

GTTCTCTCAAGGTGGGCGGAATGGCTGCACAGTCAATGATTTCTCTCTGGTTATA

TGGTGCCCACTCTGAATCCAACAGGAGCCGGAGATGTATAACAGACTTGGCCCA

TTTCTATTCCAAGTCGTCCCCCATAGAGAAGCTGTTGAATCTCACGCTAGGAAAT

AGAGGGCTGAGAATCCCCCAGAGGGAGTGTTAAGTTGCCTTGAGAGGGTTGAT

TATGATAATGCATTTGGAAGGTATCTTGCCAACACGTATTCCTCTTACTTGTTCTT

CCATGTAATCACCTTATACATGAACGCCCTAGACTGGGATGAAGAAAAGACCAT

CCTAGCATTATGGAAAGATTTAACCTCAGTGGACATCGGGAAGGACTTGGTAAA

GTTCAAAGACCAAATATGGGGACTGCTGATCGTGACAAAGGACTTTGTTTACTCC

CAAAGTTCCAATTGTCTTTTTGACAGAAACTACACACTTATGCTAAAAGATCTTT

TCTTGTCTCGCTTCAACTCCTTAATGGTCTTGCTCTCTCCCCCAGAGCCCCGATAC

TCAGATGACTTGATATCTCAACTATGCCAGCTGTACATTGCTGGGGATCAAGTCT

TGTCTATGTGTGGAAACTCCGGCTATGAAGTCATCAAAATATTGGAGCCATATGT

CGTGAATAGTTTAGTCCAGAGAGCAGAAAAGTTTAGGCCTCTCATTCATTCCTTG

GGAGACTTTCCTGTATTTATAAAAGACAAGGTAAGTCAACTTGAAGAGACGTTC

GGTCCCTGTGCAAGAAGGTTCTTTAGGGCTCTGGATCAATTCGACAACATACATG

ACTTGGTTTTTGTGTTTGGCTGTTACAGGCATTGGGGGCACCCATATATAGATTA

TCGAAAGGGTCTGTCAAAACTATATGATCAGGTTCACCTTAAAAAAATGATAGA

TAAGTCCTACCAGGAGTGCTTAGCAAGCGACCTAGCCAGGAGGATCCTTAGATG

GGGTTTTGATAAGTACTCCAAGTGGTATCTGGATTCAAGATTCCTAGCCCGAGAC

CACCCCTTGACTCCTTATATCAAAACCCAAACATGGCCACCCAAACATATTGTAG

ACTTGGTGGGGATACATGGCACAAGCTCCCGATCACGCAGATCTTTGAGATTCC

TGAATCAATGGATCCGTCAGAAATATTGGATGACAAATCACATTCTTTCACCAGA

ACGAGACTAGCTTCTTGGCTGTCAGAAAACCGAGGGGGGCCTGTTCCTAGCGAA

AAAGTTATTATCACGGCCCTGTCTAAGCCGCCTGTCAATCCCCGAGAGTTTCTGA

GGTCTATAGACCTCGGAGGATTGCCAGATGAAGACTTGATAATTGGCCTCAAGC

CAAAGGAACGGGAATTGAAGATTGAAGGTCGATTCTTTGCTCTAATGTCATGGA

ATCTAAGATTGTATTTTGTCATCACTGAAAAACTCTTGGCCAACTACATCTTGCC
```

-continued

```
ACTTTTTGACGCGCTGACTATGACAGACAACCTGAACAAGGTGTTTAAAAAGCT
GATCGACAGGGTCACCGGGCAAGGGCTTTTGGACTATTCAAGGGTCACATATGC
ATTTCACCTGGACTATGAAAAGTGGAACAACCATCAAAGATTAGAGTCAACAGA
GGATGTATTTTCTGTCCTAGATCAAGTGTTTGGATTGAAGAGAGTGTTTTCTAGA
ACACACGAGTTTTTTCAAAAGGCCTGGATCTATTATTCAGACAGATCAGACCTCA
TCGGGTTACGGGAGGATCAAATATACTGCTTAGATGCGTCCAACGGCCCAACCT
GTTGGAATGGCCAGGATGGCGGGCTAGAAGGCTTACGGCAGAAGGGCTGGAGTC
TAGTCAGCTTATTGATGATAGATAGAGAATCTCAAATCAGGAACACAAGAACCA
AAATACTAGCTCAAGGAGACAACCAGGTTTTATGTCCGACATACATGTTGTCGCC
AGGGCTATCTCAAGAGGGGCTCCTCTATGAATTGGAGAGAATATCAAGGAATGC
ACTTTCGATATACAGAGCCGTCGAGGAAGGGGCATCTAAGCTAGGGCTGATCAT
CAAGAAAGAAGAGACCATGTGTAGTTATGACTTCCTCATCTATGGAAAAACCCC
TTTGTTTAGAGGTAACATATTGGTGCCTGAGTCCAAAAGATGGGCCAGAGTCTCT
TGCGTCTCTAATGACCAAATAGTCAACCTCGCCAATATAATGTCGACAGTGTCCA
CCAATGCGCTAACAGTGGCACAACACTCTCAATCTTTGATCAAACCGATGAGGG
ATTTTCTGCTCATGTCAGTACAGGCAGTCTTTCACTACCTGCTATTTAGCCCAATC
TTAAAGGGAAGAGTTTACAAGATTCTGAGCGCTGAAGGGGAGAGCTTTCTCCTA
GCCATGTCAAGGATAATCTATCTAGATCCTTCTTTGGGAGGGATATCTGGAATGT
CCCTCGGAAGATTCCATATACGACAGTTCTCAGACCCTGTCTCTGAAGGGTTATC
CTTCTGGAGAGAGATCTGGTTAAGCTCCCAAGAGTCCTGGATTCACGCGTTGTGT
CAAGAGGCTGGAAACCCAGATCTTGGAGAGAGAACACTCGAGAGCTTCACTCGC
CTTCTAGAAGATCCGACCACCTTAAATATCAGAGGAGGGGCCAGTCCTACCATT
CTACTCAAGGATGCAATCAGAAAGGCTTTATATGACGAGGTGGACAAGGTGGAA
AATTCAGAGTTTCGAGAGGCAATCCTGTTGTCCAAGACCCATAGAGATAATTTTA
TACTCTTCTTAATATCTGTTGAGCCTCTGTTTCCTCGATTTCTCAGTGAGCTATTC
AGTTCGTCTTTTTTGGGAATCCCCGAGTCAATCATTGGATTGATACAAAACTCCC
GAACGATAAGAAGGCAGTTTAGAAAGAGTCTCTCAAAAACTTTAGAAGAATCCT
TCTACAACTCAGAGATCCACGGGATTAGTCGGATGACCCAGACACCTCAGAGGG
TTGGGGGGGTGTGGCCTTGCTCTTCAGAGAGGGCAGATCTACTTAGGGAGATCTC
TTGGGGAAGAAAAGTGGTAGGCACGACAGTTCCTCACCCTTCTGAGATGTTGGG
ATTACTTCCCAAGTCCTCTATTTCTTGCACTTGTGGAGCAACAGGAGGAGGCAAT
CCTAGAGTTTCTGTATCAGTACTCCCGTCCTTTGATCAGTCATTTTTTTCACGAGG
CCCCCTAAAGGGATACTTGGGCTCGTCCACCTCTATGTCGACCCAGCTATTCCAT
GCATGGGAAAAAGTCACTAATGTTCATGTGGTGAAGAGAGCTCTATCGTTAAAA
GAATCTATAAACTGGTTCATTACTAGAGATTCCAACTTGGCTCAAGCTCTAATTA
GGAACATTATGTCTCTGACAGGCCCTGATTTCCCTCTAGAGGAGGCCCCTGTCTT
CAAAAGGACGGGGTCAGCCTTGCATAGGTTCAAGTCTGCCAGATACAGCGAAGG
AGGGTATTCTTCTGTCTGCCCGAACCTCCTCTCTCATATTTCTGTTAGTACAGACA
CCATGTCTGATTTGACCCAAGACGGGAAGAACTACGATTTCATGTTCCAGCCATT
GATGCTTTATGCACAGACATGGACATCAGAGCTGGTACAGAGAGACACAAGGCT
AAGAGACTCTACGTTTCATTGGCACCTCCGATGCAACAGGTGTGTGAGACCCATT
```

-continued

```
GACGACGTGACCCTGGAGACCTCTCAGATCTTCGAGTTTCCGGATGTGTCGAAAA

GAATATCCAGAATGGTTTCTGGGGCTGTGCCTCACTTCCAGAGGCTTCCCGATAT

CCGTCTGAGACCAGGAGATTTTGAATCTCTAAGCGGTAGAGAAAAGTCTCACCA

TATCGGATCAGCTCAGGGGCTCTTATACTCAATCTTAGTGGCAATTCACGACTCA

GGATACAATGATGGAACCATCTTCCCTGTCAACATATACGGCAAGGTTTCCCCTA

GAGACTATTTGAGAGGGCTCGCAAGGGGAGTATTGATAGGATCCTCGATTTGCTT

CTTGACAAGAATGACAAATATCAATATTAATAGACCTCTTGAATTGGTCTCAGGG

GTAATCTCATATATTCTCCTGAGGCTAGATAACCATCCCTCCTTGTACATAATGCT

CAGAGAACCGTCTCTTAGAGGAGAGATATTTTCTATCCCTCAGAAAATCCCCGCC

GCTTATCCAACCACTATGAAAGAAGGCAACAGATCAATCTTGTGTTATCTCCAAC

ATGTGCTACGCTATGAGCGAGAGATAATCACGGCGTCTCCAGAGAATGACTGGC

TATGGATCTTTTCAGACTTTAGAAGTGCCAAAATGACGTACCTATCCCTCATTAC

TTACCAGTCTCATCTTCTACTCCAGAGGGTTGAGAGAAACCTATCTAAGAGTATG

AGAGATAACCTGCGACAATTGAGTTCTTTGATGAGGCAGGTGCTGGGCGGGCAC

GGAGAAGATACCTTAGAGTCAGACGACAACATTCAACGACTGCTAAAAGACTCT

TTACGAAGGACAAGATGGGTGGATCAAGAGGTGCGCCATGCAGCTAGAACCATG

ACTGGAGATTACAGCCCCAACAAGAAGGTGTCCCGTAAGGTAGGATGTTCAGAA

TGGGTCTGCTCTGCTCAACAGGTTGCAGTCTCTACCTCAGCAAACCCGGCCCCTG

TCTCGGAGCTTGACATAAGGGCCCTCTCTAAGAGGTTCCAGAACCCTTTGATCTC

GGGCTTGAGAGTGGTTCAGTGGGCAACCGGTGCTCATTATAAGCTTAAGCCTATT

CTAGATGATCTCAATGTTTTCCCATCTCTCTGCCTTGTAGTTGGGGACGGGTCAG

GGGGGATATCAAGGGCAGTCCTCAACATGTTTCCAGATGCCAAGCTTGTGTTCAA

CAGTCTTTTAGAGGTGAATGACCTGATGGCTTCCGGAACACATCCACTGCCTCCT

TCAGCAATCATGAGGGGAGGAAATGATATCGTCTCCAGAGTGATAGATCTTGAC

TCAATCTGGGAAAAACCGTCCGACTTGAGAAACTTGGCAACCTGGAAATACTTC

CAGTCAGTCCAAAAGCAGGTCAACATGTCCTATGACCTCATTATTTGCGATGCAG

AAGTTACTGACATTGCATCTATCAACCGGATCACCCTGTTAATGTCCGATTTTGC

ATTGTCTATAGATGGACCACTCTATTTGGTCTTCAAAACTTATGGGACTATGCTA

GTAAATCCAAACTACAAGGCTATTCAACACCTGTCAAGAGCGTTCCCCTCGGTCA

CAGGGTTTATCACCCAAGTAACTTCGTCTTTTTCATCTGAGCTCTACCTCCGATTC

TCCAAACGAGGGAAGTTTTTCAGAGATGCTGAGTACTTGACCTCTTCCACCCTTC

GAGAAATGAGCCTTGTGTTATTCAATTGTAGCAGCCCCAAGAGTGAGATGCAGA

GAGCTCGTTCCTTGAACTATCAGGATCTTGTGAGAGGATTTCCTGAAGAAATCAT

ATCAAATCCTTACAATGAGATGATCATAACTCTGATTGACAGTGATGTAGAATCT

TTTCTAGTCCACAAGATGGTTGATGATCTTGAGTTACAGAGGGGAACTCTGTCTA

AAGTGGCTATCATTATAGCCATCATGATAGTTTTCTCCAACAGAGTCTTCAACGT

TTCCAAACCCCTAACTGACCCCTCGTTCTATCCACCGTCTGATCCCAAAATCCTG

AGGCACTTCAACATATGTTGCAGTACTATGATGTATCTATCTACTGCTTTAGGTG

ACGTCCCTAGCTTCGCAAGACTTCACGACCTGTATAACAGACCTATAACTTATTA

CTTCAGAAAGCAAGTCATTCGAGGGAACGTTTATCTATCTTGGAGTTGGTCCAAC
```

```
GACACCTCAGTGTTCAAAAGGGTAGCCTGTAATTCTAGCCTGAGTCTGTCATCTC

ACTGGATCAGGTTGATTTACAAGATAGTGAAGACTACCAGACTCGTTGGCAGCA

TCAAGGATCTATCCAGAGAAGTGGAAAGACACCTTCATAGGTACAACAGGTGGA

TCACCCTAGAGGATATCAGATCTAGATCATCCCTACTAGACTACAGTTGCCTGTG

AACCGGATACTCCTGGAAGCCTGCCCATGCTAAGACTCTTGTGTGATGTATCTTG

AAAAAAACAAGATCCTAAATCTGAACCTTTGGTTGTTTGATTGTTTTTCTCAtttttgtt gtttatttgttaagcgtGGGTCGGCATGGCATCTCCACCTCCTCGCGGTCCGACCTGGGCAT CCGAAGGAGGACGCACGTCCACTCGGATGGCTAAGGGAGagccagaaGGATCCGGC

TGCTAACAAAGCCCGAAAGGAAGCTGAGTTGGCTGCTGCCACCGCTGAGCAATA

ACTAGCATAACCCCTTGGGGCCTCTAAACGGGTCTTGAGGGGTTTTTTGCTGAAA

GtCGCGCTTGGCGTAATCATGGTCATAGCTGTTTCCTGTGTGAAATTGTTATCCGC

TCACAATTCCACACAACATACGAGCCGGAAGCATAAAGTGTAAAGCCTGGGGTG

CCTAATGAGTGAGCTAACTCACATTAATTGCGTTGCGCTCACTGCCCGCTTTCCA

GTCGGGAAACCTGTCGTGCCAGCTGCATTAATGAATCGGCCAACGCGCGGGGAG

AGGCGGTTTGCGTATTGGGCGCTCTTaCGCTTCCTCGCTCACTGACTCGCTGCGCT

CGGTCGTTCGGCTGCGGCGAGCGGTATCAGCTCACTCAAAGGCGGTAATACGGT

TATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAAC

CCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGA

AGCGTGGCGCTTTCTCATAGCTCACGCTGTAGGTATCTCAGTTCGGTGTAGGTCG

TTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCT

ACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCA

GATTACGCGCAGAAAAAAAGGATCTCAAGAAGATCCTTTGATCTTTTCTACGGG

GTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCA

ATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTA

AGTTGGCCGCAGTGTTATCACTCATGGTTATGGCAGCACTGCATAATTCTCTTAC
```

-continued

```
TGTCATGCCATCCGTAAGATGCTTTTCTGTGACTGGTGAGTACTCAACCAAGTCA

TTCTGAGAATAGTGTATGCGGCGACCGAGTTGCTCTTGCCCGGCGTCAATACGGG

ATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCA

GGGTTATTGTCTCATGAGCGGATACATATTTGAATGTATTTAGAAAAATAAACAA

ATAGGGGTTCCGCGCACATTTCCCCGAAAAGTGCCAC.
```

In one embodiment, the nucleic acid comprises a sequence encoding at least a portion of the genome of a measles virus and (b) a sequence encoding a SARS-CoV-2 spike protein (S) or a portion thereof. In some embodiments, the sequence encoding the SARS-CoV-2 spike protein (S) or portion thereof is inserted into position 2, 3, or 6 of the genome of the measles virus.

In one embodiment, the nucleic acid comprises the sequence of SEQ ID NO: 3, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT
```

-continued

```
CAACATGATTCTGGGTACCATCCTAGCCCAAATTTGGGTCTTGCTCGCAAAGGCG
GTTACGGCCCCAGACACGGCAGCTGATTCGGAGCTAAGAAGGTGGATAAAGTAC
ACCCAACAAAGAAGGGTAGTTGGTGAATTTAGATTGGAGAGAAAATGGTTGGAT
GTGGTGAGGAACAGGATTGCCGAGGACCTCTCCTTACGCCGATTCATGGTCGCTC
TAATCCTGGATATCAAGAGAACACCCGGAAACAAACCCAGGATTGCTGAAATGA
TATGTGACATTGATACATATATCGTAGAGGCAGGATTAGCCAGTTTTATCCTGAC
TATTAAGTTTGGGATAGAAACTATGTATCCTGCTCTTGGACTGCATGAATTTGCT
GGTGAGTTATCCACACTTGAGTCCTTGATGAACCTTTACCAGCAAATGGGGGAA
ACTGCACCCTACATGGTAATCCTGGAGAACTCAATTCAGAACAAGTTCAGTGCA
GGATCATACCCTCTGCTCTGGAGCTATGCCATGGGAGTAGGAGTGGAACTTGAA
AACTCCATGGGAGGTTTGAACTTTGGCCGATCTTACTTTGATCCAGCATATTTTA
GATTAGGGCAAGAGATGGTAAGGAGGTCAGCTGGAAAGGTCAGTTCCACATTGG
CATCTGAACTCGGTATCACTGCCGAGGATGCAAGGCTTGTTTCAGAGATTGCAAT
GCATACTACTGAGGACAAGATCAGTAGAGCGGTTGGACCCAGACAAGCCCAAGT
ATCATTTCTACACGGTGATCAAAGTGAGAATGAGCTACCGAGATTGGGGGGCAA
GGAAGATAGGAGGGTCAAACAGAGTCGAGGAGAAGCCAGGGAGAGCTACAGAG
AAACCGGGCCCAGCAGAGCAAGTGATGCGAGAGCTGCCCATCTTCCAACCGGCA
CACCCCTAGACATTGACACTGCAACGGAGTCCAGCCAAGATCCGCAGGACAGTC
GAAGGTCAGCTGACGCCCTGCTTAGGCTGCAAGCCATGGCAGGAATCTCGGAAG
AACAAGGCTCAGACACGGACACCCCTATAGTGTACAATGACAGAAATCTTCTAG
ACTAGGTGCGAGAGGCCGAGGGCCAGAACAACATCCGCCTACCATCCATCATTG
TTATAAAAAACTTAGGAACCAggtccacacaGagtgatACGCGTACGCCACCATGTTCGT
GTTTCTGGTGCTGCTGCCTCTGGTGAGCTCCCAGTGCGTGAACCTGACCACAAGG
ACCCAGCTGCCCCCTGCCTATACCAATTCCTTCACACGGGGCGTGTACTATCCCG
ACAAGGTGTTCCGGAGCAGCGTGCTGCACTCCACACAGGATCTGTTTCTGCCTTT
CTTTTCTAACGTGACCTGGTTCCACGCCATCCACGTGAGCGGCACCAATGGCACA
AAGCGGTTCGACAATCCAGTGCTGCCCTTTAACGATGGCGTGTACTTCGCCTCCA
CCGAGAAGTCTAACATCATCAGAGGCTGGATCTTTGGCACCACACTGGACAGCA
AGACACAGTCCCTGCTGATCGTGAACAATGCCACCAACGTGGTCATCAAGGTGT
GCGAGTTCCAGTTTTGTAATGATCCATTCCTGGGCGTGTACTATCACAAGAACAA
TAAGTCTTGGATGGAGAGCGAGTTTCGCGTGTATTCCTCTGCCAACAATTGCACA
TTTGAGTACGTGTCCCAGCCCTTCCTGATGGACCTGGAGGGCAAGCAGGGCAATT
TCAAGAACCTGAGGGAGTTCGTGTTTAAGAATATCGATGGCTACTTCAAAATCTA
CTCCAAGCACACCCCAATCAACCTGGTGCGCGACCTGCCACAGGGCTTCTCTGCC
CTGGAGCCACTGGTGGATCTGCCCATCGGCATCAACATCACCCGGTTTCAGACAC
TGCTGGCCCTGCACAGAAGCTACCTGACACCAGGCGACAGCTCCTCTGGATGGA
CCGCAGGAGCAGCAGCCTACTATGTGGGCTATCTGCAGCCCAGGACCTTCCTGCT
GAAGTACAACGAGAATGGCACCATCACAGACGCCGTGGATTGCGCCCTGGATCC
CCTGTCTGAGACCAAGTGTACACTGAAGAGCTTTACCGTGGAGAAGGGCATCTA
TCAGACAAGCAATTTCAGGGTGCAGCCTACCGAGTCCATCGTGCGCTTTCCCAAT
ATCACAAACCTGTGCCCTTTTGGCGAGGTGTTCAACGCAACCCGCTTCGCCAGCG
```

-continued

```
TGTACGCCTGGAATAGGAAGCGCATCTCCAACTGCGTGGCCGACTATTCTGTGCT
GTACAACAGCGCCTCCTTCTCTACCTTTAAGTGCTATGGCGTGAGCCCCACAAAG
CTGAATGACCTGTGCTTTACCAACGTGTACGCCGATTCCTTCGTGATCAGGGGCG
ACGAGGTGCGCCAGATCGCACCAGGACAGACAGGCAAGATCGCAGACTACAAT
TATAAGCTGCCTGACGATTTCACCGGCTGCGTGATCGCCTGGAACTCTAACAATC
TGGATAGCAAAGTGGGCGGCAACTACAATTATCTGTACCGGCTGTTTAGAAAGT
CTAATCTGAAGCCATTCGAGAGGGACATCTCCACAGAAATCTACCAGGCCGGCT
CTACCCCCTGCAATGGCGTGGAGGGCTTTAACTGTTATTTCCCTCTGCAGAGCTA
CGGCTTCCAGCCAACAAACGGCGTGGGCTATCAGCCCTACCGCGTGGTGGTGCT
GTCTTTTGAGCTGCTGCACGCACCTGCAACAGTGTGCGGACCAAAGAAGAGCAC
CAATCTGGTGAAGAACAAGTGCGTGAACTTCAACTTCAACGGACTGACCGGAAC
AGGCGTGCTGACCGAGTCCAACAAGAAGTTCCTGCCTTTTCAGCAGTTCGGCAG
GGACATCGCAGATACCACAGACGCCGTGCGCGACCCTCAGACCCTGGAGATCCT
GGACATCACACCATGCTCCTTCGGCGGCGTGTCTGTGATCACACCAGGCACCAAT
ACAAGCAACCAGGTGGCCGTGCTGTATCAGGACGTGAATTGTACCGAGGTGCCA
GTGGCAATCCACGCAGATCAGCTGACCCCTACATGGCGGGTGTACTCTACCGGC
AGCAACGTGTTCCAGACAAGAGCCGGATGCCTGATCGGAGCAGAGCACGTGAAC
AATAGCTATGAGTGCGACATCCCTATCGGCGCCGGCATCTGTGCCTCCTACCAGA
CCCAGACAAACTCCCCAAGGAGAGCACGGTCTGTGGCCAGCCAGTCCATCATCG
CCTATACCATGAGCCTGGGCGCCGAGAATTCCGTGGCCTACTCCAACAATTCTAT
CGCCATCCCTACCAACTTCACAATCTCCGTGACCACAGAGATCCTGCCAGTGAGC
ATGACCAAGACATCCGTGGACTGCACAATGTATATCTGTGGCGATTCCACCGAGT
GCTCTAACCTGCTGCTGCAGTACGGCTCTTTTTGTACCCAGCTGAATAGAGCCCT
GACAGGCATCGCCGTGGAGCAGGACAAGAACACACAGGAGGTGTTCGCCCAGG
TGAAGCAAATCTACAAGACCCCACCCATCAAGGACTTTGGCGGCTTCAACTTCA
GCCAGATCCTGCCCGATCCTAGCAAGCCATCCAAGCGGTCTTTTATCGAGGACCT
GCTGTTCAACAAGGTGACCCTGGCCGATGCCGGCTTCATCAAGCAGTATGGCGA
TTGCCTGGGCGACATCGCCGCCAGAGACCTGATCTGTGCCCAGAAGTTTAATGG
CCTGACCGTGCTGCCTCCACTGCTGACAGATGAGATGATCGCCCAGTACACATCT
GCCCTGCTGGCCGGAACCATCACAAGCGGATGGACCTTCGGCGCAGGAGCCGCC
CTGCAGATCCCCTTTGCCATGCAGATGGCCTATCGGTTCAACGGCATCGGCGTGA
CCCAGAATGTGCTGTACGAGAACCAGAAGCTGATCGCCAATCAGTTTAACTCCG
CCATCGGCAAGATCCAGGACTCTCTGAGCTCCACAGCCAGCGCCCTGGGCAAGC
TGCAGGATGTGGTGAATCAGAACGCCCAGGCCCTGAATACCCTGGTGAAGCAGC
TGTCTAGCAACTTCGGCGCCATCTCCTCTGTGCTGAATGACATCCTGAGCCGGCT
GGACAAGGTGGAGGCAGAGGTGCAGATCGACCGGCTGATCACAGGCAGACTGC
AGTCCCTGCAGACCTACGTGACACAGCAGCTGATCAGGGCAGCAGAGATCAGGG
CCTCTGCCAATCTGGCCGCCACCAAGATGAGCGAGTGCGTGCTGGGCCAGTCCA
AGAGAGTGGACTTTTGTGGCAAGGGCTATCACCTGATGAGCTTCCCACAGTCCGC
CCCTCACGGAGTGGTGTTTCTGCACGTGACCTACGTGCCAGCCCAGGAGAAGAA
```

-continued

```
CTTCACCACAGCACCAGCAATCTGCCACGATGGCAAGGCACACTTTCCTAGGGA
GGGCGTGTTCGTGAGCAACGGCACCCACTGGTTTGTGACACAGCGCAATTTCTAC
GAGCCACAGATCATCACCACAGACAATACATTCGTGTCCGGCAACTGTGACGTG
GTCATCGGCATCGTGAACAATACCGTGTATGATCCTCTGCAGCCAGAGCTGGACT
CTTTTAAGGAGGAGCTGGATAAGTACTTCAAGAATCACACCAGCCCCGACGTGG
ATCTGGGCGACATCTCTGGCATCAATGCCAGCGTGGTGAACATCCAGAAGGAGA
TCGACAGGCTGAACGAGGTGGCCAAGAATCTGAACGAGTCCCTGATCGATCTGC
AGGAGCTGGGCAAGTATGAGCAGTACATCAAGTGGCCCTGGTATATCTGGCTGG
GCTTCATCGCCGGCCTGATCGCCATCGTGATGGTGACCATCATGCTGTGCTGTAT
GACAAGCTGCTGTTCCTGCCTGAAGGGCTGCTGTTCTTGTGGCAGCTGCTGTAAG
TTTGATGAGGACGATAGCGAGCCTGTGCTGAAGGGCGTGAAGCTGCACTACACC
TGATAGCTAGCGATCGCGTGCGAGAGGCCAGAACAACATCCGCCTACCATCCAT
CATTGTTATAAAAAACTTAGGAACCAGGTCCACACAGCCGCCAGCCCATCAACC
ATCCACTCCCACGATTGGAGCCAATGGCAGAAGAGCAGGCACGCCATGTCAAAA
ACGGACTGGAATGCATCCGGGCTCTCAAGGCCGAGCCCATCGGCTCACTGGCCA
TCGAGGAAGCTATGGCAGCATGGTCAGAAATATCAGACAACCCAGGACAGGAG
CGAGCCACCTGCAGGGAAGAGAAGGCAGGCAGTTCGGGTCTCAGCAAACCATG
CCTCTCAGCAATTGGATCAACTGAAGGCGGTGCACCTCGCATCCGCGGTCAGGG
ACCTGGAGAGAGCGATGACGACGCTGAAACTTTGGGAATCCCCCCAAGAAATCT
CCAGGCATCAAGCACTGGGTTACAGTGTTATTACGTTTATGATCACAGCGGTGAA
GCGGTTAAGGGAATCCAAGATGCTGACTCTATCATGGTTCAATCAGGCCTTGATG
GTGATAGCACCCTCTCAGGAGGAGACAATGAATCTGAAAACAGCGATGTGGATA
TTGGCGAACCTGATACCGAGGGATATGCTATCACTGACCGGGGATCTGCTCCCAT
CTCTATGGGGTTCAGGGCTTCTGATGTTGAAACTGCAGAAGGAGGGGAGATCCA
CGAGCTCCTGAGACTCCAATCCAGAGGCAACAACTTTCCGAAGCTTGGGAAAAC
TCTCAATGTTCCTCCGCCCCGGACCCCGGTAGGGCCAGCACTTCCGGGACACCC
ATTAAAAAGGGCACAGACGCGAGATTAGCCTCATTTGGAACGGAGATCGCGTCT
TTATTGACAGGTGGTGCAACCCAATGTGCTCGAAAGTCACCCTCGGAACCATCA
GGGCCAGGTGCACCTGCGGGGAATGTCCCCGAGTGTGTGAGCAATGCCGCACTG
ATACAGGAGTGGACACCCGAATCTGGTACCACAATCTCCCCGAGATCCCAGAAT
AATGAAGAAGGGGGAGACTATTATGATGATGAGCTGTTCTCTGATGTCCAAGAT
ATTAAAACAGCCTTGGCCAAAATACACGAGGATAATCAGAAGATAATCTCCAAG
CTAGAATCACTGCTGTTATTGAAGGGAGAAGTTGAGTCAATTAAGAAGCAGATC
AACAGGCAAAATATCAGCATATCCACCCTGGAAGGACACCTCTCAAGCATCATG
ATCGCCATTCCTGGACTTGGGAAGGATCCCAACGACCCCACTGCAGATGTCGAA
ATCAATCCCGACTTGAAACCCATCATAGGCAGAGATTCAGGCCGAGCACTGGCC
GAAGTTCTCAAGAAACCCGTTGCCAGCCGACAACTCCAAGGAATGACAAATGGA
CGGACCAGTTCCAGAGGACAGCTGCTGAAGGAATTTCAGCTAAAGCCGATCGGG
AAAAAGATGAGCTCAGCCGTCGGGTTTGTTCCTGACACCGGCCCTGCATCACGC
AGTGTAATCCGCTCCATTATAAAAATCCAGCCGGCTAGAGGAGGATCGGAAGCGT
TACCTGATGACTCTCCTTGATGATATCAAAGGAGCCAATGATCTTGCCAAGTTCC
```

-continued

```
ACCAGATGCTGATGAAGATAATAATGAAGTAGCTACAGCTCAACTTACCTGCCA

ACCCCATGCCAGTCGACCCACCTAGTACAACCTAAATCCATTATAAAAAACTTA

GGAGCAAAGTGATTGCCTCCCAAGGTCCACAATGACAGAGACCTACGACTTCGA

CAAGTCGGCATGGGACATCAAAGGGTCGATCGCTCCGATACAACCCACCACCTA

CAGTGATGGCAGGCTGGTGCCCCAGGTCAGAGTCATAGATCCTGGTCTAGGCGA

CAGGAAGGATGAATGCTTTATGTACATGTTTCTGCTGGGGGTTGTTGAGGACAGC

GATTCCCTAGGGCCTCCAATCGGGCGAGCATTTGGGTTCCTGCCCTTAGGTGTTG

GCAGATCCACAGCAAAGCCCGAAAAACTCCTCAAAGAGGCCACTGAGCTTGACA

TAGTTGTTAGACGTACAGCAGGGCTCAATGAAAAACTGGTGTTCTACAACAACA

CCCCACTAACTCTCCTCACACCTTGGAGAAAGGTCCTAACAACAGGGAGTGTCTT

CAACGCAAACCAAGTGTGCAATGCGGTTAATCTGATACCGCTCGATACCCCGCA

GAGGTTCCGTGTTGTTTATATGAGCATCACCCGTCTTTCGGATAACGGGTATTAC

ACCGTTCCTAGAAGAATGCTGGAATTCAGATCGGTCAATGCAGTGGCCTTCAACC

TGCTGGTGACCCTTAGGATTGACAAGGCGATAGGCCCTGGGAAGATCATCGACA

ATACAGAGCAACTTCCTGAGGCAACATTTATGGTCCACATCGGGAACTTCAGGA

GAAAGAAGAGTGAAGTCTACTCTGCCGATTATTGCAAAATGAAAATCGAAAAGA

TGGGCCTGGTTTTTGCACTTGGTGGGATAGGGGGCACCAGTCTTCACATTAGAAG

CACAGGCAAAATGAGCAAGACTCTCCATGCACAACTCGGGTTCAAGAAGACCTT

ATGTTACCCGCTGATGGATATCAATGAAGACCTTAATCGATTACTCTGGAGGAGC

AGATGCAAGATAGTAAGAATCCAGGCAGTTTTGCAGCCATCAGTTCCTCAAGAA

TTCCGCATTTACGACGACGTGATCATAAATGATGACCAAGGACTATTCAAAGTTC

TGTAGACCGTAGTGCCCAGCAATGCCCGAAAACGACCCCCCTCACAATGACAGC

CAGAAGGCCCGGACAAAAAAGCCCCCTCCGAAAGACTCCACGGACCAAGCGAG

AGGCCAGCCAGCAGCCGACGGCAAGCGCGAACACCAGGCGGCCCCAGCACAGA

ACAGCCCTGACACAAGGCCACCACCAGCCACCCCAATCTGCATCCTCCTCGTGG

GACCCCCGAGGACCAACCCCCAAGGCTGCCCCCGATCCAAACCACCAACCGCAT

CCCCACCACCCCCGGGAAAGAAACCCCCAGCAATTGGAAGGCCCCTCCCCCTCT

TCCTCAACACAAGAACTCCACAACCGAACCGCACAAGCGACCGAGGTGACCCAA

CCGCAGGCATCCGACTCCCTAGACAGATCCTCTCTCCCCGGCAAACTAAACAAA

ACTTAGGGCCAAGGAACATACACACCCAACAGAACCCAGACCCCGGCCCACGGC

GCCGCGCCCCAACCCCCGACAACCAGAGGGAGCCCCCAACCAATCCCGCCGGC

TCCCCCGGTGCCCACAGGCAGGGACACCAACCCCCGAACAGACCCAGCACCCAA

CCATCGACAATCCAAGACGGGGGGCCCCCCAAAAAAAGGCCCCCAGGGGCC

GACAGCCAGCACCGCGAGGAAGCCCACCCACCCCACACACGACCACGGCAACC

AAACCAGAACCCAGACCACCCTGGGCCACCAGCTCCCAGACTCGGCCATCACCC

CGCAGAAAGGAAAGGCCACAACCCGCGCACCCCAGCCCCGATCCGGCGGGGAG

CCACCCAACCCGAACCAGCACCCAAGAGCGATCCCCGAAGGACCCCCGAACCGC

AAAGGACATCAGTATCCCACAGCCTCTCCAAGTCCCCCGGTCTCCTCCTCTTCTC

GAAGGGACCAAAAGATCAATCCACCACACCCCGACGACACTCAACTCCCCACCCC

TAAAGGAGACACCGGGAATCCCAGAATCAAGACTCATCCAATGTCCATCATGGG
```

-continued

```
TCTCAAGGTGAACGTCTCTGCCATATTCATGGCAGTACTGTTAACTCTCCAAACA
CCCACCGGTCAAATCCATTGGGGCAATCTCTCTAAGATAGGGGTGGTAGGAATA
GGAAGTGCAAGCTACAAAGTTATGACTCGTTCCAGCCATCAATCATTAGTCATAA
AATTAATGCCCAATATAACTCTCCTCAATAACTGCACGAGGGTAGAGATTGCAG
AATACAGGAGACTACTGAGAACAGTTTTGGAACCAATTAGAGATGCACTTAATG
CAATGACCCAGAATATAAGACCGGTTCAGAGTGTAGCTTCAAGTAGGAGACACA
AGAGATTTGCGGGAGTAGTCCTGGCAGGTGCGGCCCTAGGCGTTGCCACAGCTG
CTCAGATAACAGCCGGCATTGCACTTCACCAGTCCATGCTGAACTCTCAAGCCAT
CGACAATCTGAGAGCGAGCCTGGAAACTACTAATCAGGCAATTGAGACAATCAG
ACAAGCAGGGCAGGAGATGATATTGGCTGTTCAGGGTGTCCAAGACTACATCAA
TAATGAGCTGATACCGTCTATGAACCAACTATCTTGTGATTTAATCGGCCAGAAG
CTCGGGCTCAAATTGCTCAGATACTATACAGAAATCCTGTCATTATTTGGCCCCA
GTTTACGGGACCCCATATCTGCGGAGATATCTATCCAGGCTTTGAGCTATGCGCT
TGGAGGAGACATCAATAAGGTGTTAGAAAAGCTCGGATACAGTGGAGGTGATTT
ACTGGGCATCTTAGAGAGCGGAGGAATAAAGGCCCGGATAACTCACGTCGACAC
AGAGTCCTACTTCATTGTCCTCAGTATAGCCTATCCGACGCTGTCCGAGATTAAG
GGGGTGATTGTCCACCGGCTAGAGGGGTCTCGTACAACATAGGCTCTCAAGAG
TGGTATACCACTGTGCCCAAGTATGTTGCAACCCAAGGGTACCTTATCTCGAATT
TTGATGAGTCATCGTGTACTTTCATGCCAGAGGGGACTGTGTGCAGCCAAAATGC
CTTGTACCCGATGAGTCCTCTGCTCCAAGAATGCCTCCGGGGGTACACCAAGTCC
TGTGCTCGTACACTCGTATCCGGGTCTTTTGGGAACCGGTTCATTTTATCACAAG
GGAACCTAATAGCCAATTGTGCATCAATCCTTTGCAAGTGTTACACAACAGGAA
CGATCATTAATCAAGACCCTGACAAGATCCTAACATACATTGCTGCCGATCACTG
CCCGGTAGTCGAGGTGAACGGCGTGACCATCCAAGTCGGGAGCAGGAGGTATCC
AGACGCTGTGTACTTGCACAGAATTGACCTCGGTCCTCCCATATCATTGGAGAGG
TTGGACGTAGGGACAAATCTGGGGAATGCAATTGCTAAGTTGGAGGATGCCAAG
GAATTGTTGGAGTCATCGGACCAGATATTGAGGAGTATGAAAGGTTTATCGAGC
ACTAGCATAGTCTACATCCTGATTGCAGTGTGTCTTGGAGGGTTGATAGGGATCC
CCGCTTTAATATGTTGCTGCAGGGGGCGTTGTAACAAAAAGGGAGAACAAGTTG
GTATGTCAAGACCAGGCCTAAAGCCTGATCTTACGGGAACATCAAAATCCTATG
TAAGGTCGCTCTGATCCTCTACAACTCTTGAAACACAAATGTCCCACAAGTCTCC
TCTTCGTCATCAAGCAACCACCGCACCCAGCATCAAGCCCACCTGAAATTATCTC
CGGCTTCCCTCTGGCCGAACAATATCGGTAGTTAATTAAAACTTAGGGTGCAAGA
TCATCGATAATGTCACCACAACGAGACCGGATAAATGCCTTCTACAAAGATAAC
CCCCATCCCAAGGGAAGTAGGATAGTCATTAACAGAGAACATCTTATGATTGAT
AGACCTTATGTTTTGCTGGCTGTTCTGTTTGTCATGTTTCTGAGCTTGATCGGGTT
GCTAGCCATTGCAGGAATTCGACTTCATCGGGCAGCCATCTACACCGCAGAGAT
CCATAAAAGCCTCAGCACCAATCTAGATGTAACTAACTCAATCGAGCATCAGGT
CAAGGACGTGCTGACACCACTCTTCAAAATCATCGGTGATGAAGTGGGCCTGAG
GACACCTCAGAGATTCACTGACCTAGTGAAATTAATCTCTGACAAGATTAAATTC
CTTAATCCGGATAGGGAGTACGACTTCAGAGATCTCACTTGGTGTATCAACCCGC
```

-continued

```
CAGAGAGAATCAAATTGGATTATGATCAATACTGTGCAGATGTGGCTGCTGAAG

AGCTCATGAATGCATTGGTGAACTCAACTCTACTGGAGACCAGAACAACCAATC

AGTTCCTAGCTGTCTCAAAGGGAAACTGCTCAGGGCCCACTACAATCAGAGGTC

AATTCTCAAACATGTCGCTGTCCCTGTTAGACTTGTATTTAGGTCGAGGTTACAA

TGTGTCATCTATAGTCACTATGACATCCCAGGGAATGTATGGGGAACTTACCTA

GTGGAAAAGCCTAATCTGAGCAGCAAAAGGTCAGAGTTGTCACAACTGAGCATG

TACCGAGTGTTTGAAGTAGGTGTTATCAGAAATCCGGGTTTGGGGGCTCCGGTGT

TCCATATGACAAACTATCTTGAGCAACCAGTCAGTAATGATCTCAGCAACTGTAT

GGTGGCTTTGGGGGAGCTCAAACTCGCAGCCCTTTGTCACGGGGAAGATTCTATC

ACAATTCCCTATCAGGGATCAGGGAAAGGTGTCAGCTTCCAGCTCGTCAAGCTA

GGTGTCTGGAAATCCCCAACCGACATGCAATCCTGGGTCCCCTTATCAACGGATG

ATCCAGTGATAGACAGGCTTTACCTCTCATCTCACAGAGGTGTTATCGCTGACAA

CCAAGCAAAATGGGCTGTCCCGACAACACGAACAGATGACAAGTTGCGAATGG

AGACATGCTTCCAACAGGCGTGTAAGGGTAAAATCCAAGCACTCTGCGAGAATC

CCGAGTGGGCACCATTGAAGGATAACAGGATTCCTTCATACGGGGTCTTGTCTGT

TGATCTGAGTCTGACAGTTGAGCTTAAAATCAAAATTGCTTCGGGATTCGGGCCA

TTGATCACACACGGTTCAGGGATGGACCTATACAAATCCAACCACAACAATGTG

TATTGGCTGACTATCCCGCCAATGAAGAACCTAGCCTTAGGTGTAATCAACACAT

TGGAGTGGATACCGAGATTCAAGGTTAGTCCCTACCTCTTCACTGTCCCAATTAA

GGAAGCAGGCGAAGACTGCCATGCCCCAACATACCTACCTGCGGAGGTGGATGG

TGATGTCAAACTCAGTTCCAATCTGGTGATTCTACCTGGTCAAGATCTCCAATAT

GTTTTGGCAACCTACGATACTTCCAGGGTTGAACATGCTGTGGTTTATTACGTTT

ACAGCCCAAGCCGCTCATTTTCTTACTTTTATCCTTTTAGGTTGCCTATAAAGGGG

GTCCCCATCGAATTACAAGTGGAATGCTTCACATGGGACCAAAAACTCTGGTGC

CGTCACTTCTGTGTGCTTGCGGACTCAGAATCTGGTGGACATATCACTCACTCTG

GGATGGTGGGCATGGGAGTCAGCTGCACAGTCACCCGGGAAGATGGAACCAATC

GCAGATAGGGCTGCTAGTGAACCAATCACATGATGTCACCCAGACATCAGGCAT

ACCCACTAGTGTGAAATAGACATCAGAATTAAGAAAAACGTAGGGTCCAAGTGG

TTCCCCGTTATGGACTCGCTATCTGTCAACCAGATCTTATACCCTGAAGTTCACCT

AGATAGCCCGATAGTTACCAATAAGATAGTAGCCATCCTGGAGTATGCTCGAGT

CCCTCACGCTTACAGCCTGGAGGACCCTACACTGTGTCAGAACATCAAGCACCG

CCTAAAAAACGGATTTTCCAACCAAATGATTATAAACAATGTGGAAGTTGGGAA

TGTCATCAAGTCCAAGCTTAGGAGTTATCCGGCCCACTCTCATATTCCATATCCA

AATTGTAATCAGGATTTATTTAACATAGAAGACAAAGAGTCAACGAGGAAGATC

CGTGAACTCCTCAAAAAGGGGAATTCGCTGTACTCCAAAGTCAGTGATAAGGTT

TTCCAATGCTTAAGGGACACTAACTCACGGCTTGGCCTAGGCTCCGAATTGAGGG

AGGACATCAAGGAGAAAGTTATTAACTTGGGAGTTTACATGCACAGCTCCCAGT

GGTTTGAGCCCTTTCTGTTTTGGTTTACAGTCAAGACTGAGATGAGGTCAGTGAT

TAAATCACAAACCCATACTTGCCATAGGAGGAGACACACACCTGTATTCTTCACT

GGTAGTTCAGTTGAGTTGCTAATCTCTCGTGACCTTGTTGCTATAATCAGTAAAG
```

-continued

```
AGTCTCAACATGTATATTACCTGACATTTGAACTGGTTTTGATGTATTGTGATGTC
ATAGAGGGGAGGTTAATGACAGAGACCGCTATGACTATTGATGCTAGGTATACA
GAGCTTCTAGGAAGAGTCAGATACATGTGGAAACTGATAGATGGTTTCTTCCCTG
CACTCGGGAATCCAACTTATCAAATTGTAGCCATGCTGGAGCCTCTTTCACTTGC
TTACCTGCAGCTGAGGGATATAACAGTAGAACTCAGAGGTGCTTTCCTTAACCAC
TGCTTTACTGAAATACATGATGTTCTTGACCAAAACGGGTTTTCTGATGAAGGTA
CTTATCATGAGTTAACTGAAGCTCTAGATTACATTTTCATAACTGATGACATACA
TCTGACAGGGGAGATTTTCTCATTTTTCAGAAGTTTCGGCCACCCCAGACTTGAA
GCAGTAACGGCTGCTGAAAATGTTAGGAAATACATGAATCAGCCTAAAGTCATT
GTGTATGAGACTCTGATGAAAGGTCATGCCATATTTTGTGGAATCATAATCAACG
GCTATCGTGACAGGCACGGAGGCAGTTGGCCACCGCTGACCCTCCCCCTGCATG
CTGCAGACACAATCCGGAATGCTCAAGCTTCAGGTGAAGGGTTAACACATGAGC
AGTGCGTTGATAACTGGAAATCTTTTGCTGGAGTGAAATTTGGCTGCTTTATGCC
TCTTAGCCTGGATAGTGATCTGACAATGTACCTAAAGGACAAGGCACTTGCTGCT
CTCCAAAGGGAATGGGATTCAGTTTACCCGAAAGAGTTCCTGCGTTACGACCCTC
CCAAGGGAACCGGGTCACGGAGGCTTGTAGATGTTTTCCTTAATGATTCGAGCTT
TGACCCATATGATGTGATAATGTATGTTGTAAGTGGAGCTTACCTCCATGACCCT
GAGTTCAACCTGTCTTACAGCCTGAAAGAAAAGGAGATCAAGGAAACAGGTAGA
CTTTTTGCTAAAATGACTTACAAAATGAGGGCATGCCAAGTGATTGCTGAAAATC
TAATCTCAAACGGGATTGGCAAATATTTTAAGGACAATGGGATGGCCAAGGATG
AGCACGATTTGACTAAGGCACTCCACACTCTAGCTGTCTCAGGAGTCCCCAAAG
ATCTCAAAGAAAGTCACAGGGGGGGCCAGTCTTAAAAACCTACTCCCGAAGCC
CAGTCCACACAAGTACCAGGAACGTGAGAGCAGCAAAAGGGTTTATAGGGTTCC
CTCAAGTAATTCGGCAGGACCAAGACACTGATCATCCGGAGAATATGGAAGCTT
ACGAGACAGTCAGTGCATTTATCACGACTGATCTCAAGAAGTACTGCCTTAATTG
GAGATATGAGACCATCAGCTTGTTTGCACAGAGGCTAAATGAGATTTACGGATT
GCCCTCATTTTTCCAGTGGCTGCATAAGAGGCTTGAGACCTCTGTCCTGTATGTA
AGTGACCCTCATTGCCCCCCCGACCTTGACGCCCATATCCCGTTATATAAAGTCC
CCAATGATCAAATCTTCATTAAGTACCCTATGGGAGGTATAGAAGGGTATTGTCA
GAAGCTGTGGACCATCAGCACCATTCCCTATCTATACCTGGCTGCTTATGAGAGC
GGAGTAAGGATTGCTTCGTTAGTGCAAGGGGACAATCAGACCATAGCCGTAACA
AAAAGGGTACCCAGCACATGGCCCTACAACCTTAAGAAACGGGAAGCTGCTAGA
GTAACTAGAGATTACTTTGTAATTCTTAGGCAAAGGCTACATGATATTGGCCATC
ACCTCAAGGCAAATGAGACAATTGTTTCATCACATTTTTTGTCTATTCAAAAGG
AATATATTATGATGGGCTACTTGTGTCCCAATCACTCAAGAGCATCGCAAGATGT
GTATTCTGGTCAGAGACTATAGTTGATGAAACAAGGGCAGCATGCAGTAATATT
GCTACAACAATGGCTAAAAGCATCGAGAGAGGTTATGACCGTTACCTTGCATAT
TCCCTGAACGTCCTAAAAGTGATACAGCAAATTCTGATCTCTCTTGGCTTCACAA
TCAATTCAACCATGACCCGGGATGTAGTCATACCCCTCCTCACAAACAACGACCT
CTTAATAAGGATGGCACTGTTGCCCGCTCCTATTGGGGGGATGAATTATCTGAAT
ATGAGCAGGCTGTTTGTCAGAAACATCGGTGATCCAGTAACATCATCAATTGCTG
```

-continued

```
ATCTCAAGAGAATGATTCTCGCCTCACTAATGCCTGAAGAGACCCTCCATCAGGT

AATGACACAACAACCGGGGGACTCTTCATTCCTAGACTGGGCTAGCGACCCTTA

CTCAGCAAATCTTGTATGTGTCCAGAGCATCACTAGACTCCTCAAGAACATAACT

GCAAGGTTTGTCCTGATCCATAGTCCAAACCCAATGTTAAAAGGATTATTCCATG

ATGACAGTAAAGAAGAGGACGAGGGACTGGCGGCATTCCTCATGGACAGGCAT

ATTATAGTACCTAGGGCAGCTCATGAAATCCTGGATCATAGTGTCACAGGGGCA

AGAGAGTCTATTGCAGGCATGCTGGATACCACAAAAGGCTTGATTCGAGCCAGC

ATGAGGAAGGGGGGTTTAACCTCTCGAGTGATAACCAGATTGTCCAATTATGAC

TATGAACAATTCAGAGCAGGGATGGTGCTATTGACAGGAAGAAAGAGAAATGTC

CTCATTGACAAAGAGTCATGTTCAGTGCAGCTGGCGAGAGCTCTAAGAAGCCAT

ATGTGGGCGAGGCTAGCTCGAGGACGGCCTATTTACGGCCTTGAGGTCCCTGAT

GTACTAGAATCTATGCGAGGCCACCTTATTCGGCGTCATGAGACATGTGTCATCT

GCGAGTGTGGATCAGTCAACTACGGATGGTTTTTTGTCCCCTCGGGTTGCCAACT

GGATGATATTGACAAGGAAACATCATCCTTGAGAGTCCCATATATTGGTTCTACC

ACTGATGAGAGAACAGACATGAAGCTTGCCTTCGTAAGAGCCCCAAGTCGATCC

TTGCGATCTGCTGTTAGAATAGCAACAGTGTACTCATGGGCTTACGGTGATGATG

ATAGCTCTTGGAACGAAGCCTGGTTGTTGGCTAGGCAAAGGGCCAATGTGAGCC

TGGAGGAGCTAAGGGTGATCACTCCCATCTCAACTTCGACTAATTTAGCGCATAG

GTTGAGGGATCGTAGCACTCAAGTGAAATACTCAGGTACATCCCTTGTCCGAGTG

GCGAGGTATACCACAATCTCCAACGACAATCTCTCATTTGTCATATCAGATAAGA

AGGTTGATACTAACTTTATATACCAACAAGGAATGCTTCTAGGGTTGGGTGTTTT

AGAAACATTGTTTCGACTCGAGAAAGATACCGGATCATCTAACACGGTATTACA

TCTTCACGTCGAAACAGATTGTTGCGTGATCCCGATGATAGATCATCCCAGGATA

CCCAGCTCCCGCAAGCTAGAGCTGAGGGCAGAGCTATGTACCAACCCATTGATA

TATGATAATGCACCTTTAATTGACAGAGATGCAACAAGGCTATACACCCAGAGC

CATAGGAGGCACCTTGTGGAATTTGTTACATGGTCCACACCCCAACTATATCACA

TTTTAGCTAAGTCCACAGCACTATCTATGATTGACCTGGTAACAAAATTTGAGAA

GGACCATATGAATGAAATTTCAGCTCTCATAGGGGATGACGATATCAATAGTTTC

ATAACTGAGTTTCTGCTCATAGAGCCAAGATTATTCACTATCTACTTGGGCCAGT

GTGCGGCCATCAATTGGGCATTTGATGTACATTATCATAGACCATCAGGGAAATA

TCAGATGGGTGAGCTGTTGTCATCGTTCCTTTCTAGAATGAGCAAAGGAGTGTTT

AAGGTGCTTGTCAATGCTCTAAGCCACCCAAAGATCTACAAGAAATTCTGGCATT

GTGGTATTATAGAGCCTATCCATGGTCCTTCACTTGATGCTCAAAACTTGCACAC

AACTGTGTGCAACATGGTTTACACATGCTATATGACCTACCTCGACCTGTTGTTG

AATGAAGAGTTAGAAGAGTTCACATTTCTCTTGTGTGAAAGCGACGAGGATGTA

GTACCGGACAGATTCGACAACATCCAGGCAAAACACTTATGTGTTCTGGCAGAT

TTGTACTGTCAACCAGGGACCTGCCCACCAATTCGAGGTCTAAGACCGGTAGAG

AAATGTGCAGTTCTAACCGACCATATCAAGGCAGAGGCTATGTTATCTCCAGCA

GGATCTTCGTGGAACATAAATCCAATTATTGTAGACCATTACTCATGCTCCCTGA

CTTATCTCCGGCGAGGATCGATCAAACAGATAAGATTGAGAGTTGATCCAGGAT
```

-continued

```
TCATTTTCGACGCCCTCGCTGAGGTAAATGTCAGTCAGCCAAAGATCGGCAGCA
ACAACATCTCAAATATGAGCATCAAGGCTTTCAGACCCCCACACGATGATGTTG
CAAAATTGCTCAAAGATATCAACACAAGCAAGCACAATCTTCCCATTTCAGGGG
GCAATCTCGCCAATTATGAAATCCATGCTTTCCGCAGAATCGGGTTGAACTCATC
TGCTTGCTACAAAGCTGTTGAGATATCAACATTAATTAGGAGATGCCTTGAGCCA
GGGGAGGACGGCTTGTTCTTGGGTGAGGGATCGGGTTCTATGTTGATCACTTATA
AGGAGATACTTAAACTAAACAAGTGCTTCTATAATAGTGGGGTTTCCGCCAATTC
TAGATCTGGTCAAAGGGAATTAGCACCCTATCCCTCCGAAGTTGGCCTTGTCGAA
CACAGAATGGGAGTAGGTAATATTGTCAAAGTGCTCTTTAACGGGAGGCCCGAA
GTCACGTGGGTAGGCAGTGTAGATTGCTTCAATTTCATAGTTAGTAATATCCCTA
CCTCTAGTGTGGGGTTTATCCATTCAGATATAGAGACCTTGCCTGACAAAGATAC
TATAGAGAAGCTAGAGGAATTGGCAGCCATCTTATCGATGGCTCTGCTCCTGGGC
AAAATAGGATCAATACTGGTGATTAAGCTTATGCCTTTCAGCGGGGATTTTGTTC
AGGGATTTATAAGTTATGTAGGGTCTCATTATAGAGAAGTGAACCTTGTATACCC
TAGATACAGCAACTTCATATCTACTGAATCTTATTTGGTTATGACAGATCTCAAG
GCTAACCGGCTAATGAATCCTGAAAAGATTAAGCAGCAGATAATTGAATCATCT
GTGAGGACTTCACCTGGACTTATAGGTCACATCCTATCCATTAAGCAACTAAGCT
GCATACAAGCAATTGTGGGAGACGCAGTTAGTAGAGGTGATATCAATCCTACTC
TGAAAAAACTTACACCTATAGAGCAGGTGCTGATCAATTGCGGGTTGGCAATTA
ACGGACCTAAGCTGTGCAAAGAATTGATCCACCATGATGTTGCCTCAGGGCAAG
ATGGATTGCTTAATTCTATACTCATCCTCTACAGGGAGTTGGCAAGATTCAAAGA
CAACCAAAGAAGTCAACAAGGGATGTTCCACGCCTACCCCGTATTGGTAAGTAG
CAGGCAACGAGAACTTATATCTAGGATCACCCGCAAATTTTGGGGGCACATTCTT
CTTTACTCCGGGAACAAAAAGTTGATAAATAAGTTTATCCAGAATCTCAAGTCCG
GCTATCTGATACTAGACTTACACCAGAATATCTTCGTTAAGAATCTATCCAAGTC
AGAGAAACAGATTATTATGACGGGGGGTTTGAAACGTGAGTGGGTTTTTAAGGT
AACAGTCAAGGAGACCAAAGAATGGTATAAGTTAGTCGGATACAGTGCCCTGAT
TAAGGACTAATTGGTTGAACTCCGGAACCCTAATCCTGCCCTAGGTGGTTAGGCA
TTATTTGCAATATATTAAAGAAAACTTTGAAAATACGAAGTTTCTATTCCCAGCT
TTGTCTGGTggccggcatAgtcccagcctcctcgctggcgctggctgggcaacattccgaggggaccgtcccc Acgtaa
tggcgaatgggacgcggccgatccggctgctaacaaagcccgaaaggaagctgagttggctgctgGcGcTGgctgGgcaata
actagcataaccccttggggcctctaaacgggtcttgaggggttttttgctgaaaggaggaactatatccggatgcGGCCGCGC
GCTTGGCGTAATCATGGTCATAGCTGTTTCCTGTGTGAAATTGTTATCCGCTCAC
AATTCCACACAACATACGAGCCGGAAGCATAAAGTGTAAAGCCTGGGGTGCCTA
ATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGA
```

```
CAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCT
GACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGC
ACCTATCTCAGCGATCTGTCTATTTCGTTCATCCATAGTTGCCTGACTCCCCGTCG
TGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATA
ATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACACGG
AAATGTTGAATACTCATACTCTTCCTTTTTCAATATTATTGAAGCATTTATCAGGG
TTATTGTCTCATGAGCGGATACATATTTGAATGTATTTAGAAAAATAAACAAATA
GGGGTTCCGCGCACATTTCCCCGAAAAGTGCCACCTG.
```

In another embodiment, the nucleic acid comprises the sequence of SEQ ID NO: 4, shown below:

```
GGACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTT
CCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTAG
GGTGATGGTTCACGTAGTGGGCCATCGCCCTGATAGACGGTTTTTCGCCCTTTGA
CGTTGGAGTCCACGTTCTTTAATAGTGGACTCTTGTTCCAAACTGGAACAACACT
```

-continued

```
CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA

TATGTGACATTGATACATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAGGTCCACACAGCCGCCAGCCCATCAACCATCCA

CTCCCACGATTGGAGCCAATGGCAGAAGAGCAGGCACGCCATGTCAAAAACGG
```

-continued

```
ACTGGAATGCATCCGGGCTCTCAAGGCCGAGCCCATCGGCTCACTGGCCATCGA

GGAAGCTATGGCAGCATGGTCAGAAATATCAGACAACCCAGGACAGGAGCGAG

CCACCTGCAGGGAAGAGAAGGCAGGCAGTTCGGGTCTCAGCAAACCATGCCTCT

CAGCAATTGGATCAACTGAAGGCGGTGCACCTCGCATCCGCGGTCAGGGACCTG

GAGAGAGCGATGACGACGCTGAAACTTTGGGAATCCCCCCAAGAAATCTCCAGG

CATCAAGCACTGGGTTACAGTGTTATTACGTTTATGATCACAGCGGTGAAGCGGT

TAAGGGAATCCAAGATGCTGACTCTATCATGGTTCAATCAGGCCTTGATGGTGAT

AGCACCCTCTCAGGAGGAGACAATGAATCTGAAAACAGCGATGTGGATATTGGC

GAACCTGATACCGAGGGATATGCTATCACTGACCGGGGATCTGCTCCCATCTCTA

TGGGGTTCAGGGCTTCTGATGTTGAAACTGCAGAAGGAGGGGAGATCCACGAGC

TCCTGAGACTCCAATCCAGAGGCAACAACTTTCCGAAGCTTGGGAAAACTCTCA

ATGTTCCTCCGCCCCCGGACCCCGGTAGGGCCAGCACTTCCGGGACACCCATTAA

AAAGGGCACAGACGCGAGATTAGCCTCATTTGGAACGGAGATCGCGTCTTTATT

GACAGGTGGTGCAACCCAATGTGCTCGAAAGTCACCCTCGGAACCATCAGGGCC

AGGTGCACCTGCGGGGAATGTCCCCGAGTGTGTGAGCAATGCCGCACTGATACA

GGAGTGGACACCCGAATCTGGTACCACAATCTCCCCGAGATCCCAGAATAATGA

AGAAGGGGGAGACTATTATGATGATGAGCTGTTCTCTGATGTCCAAGATATTAA

AACAGCCTTGGCCAAAATACACGAGGATAATCAGAAGATAATCTCCAAGCTAGA

ATCACTGCTGTTATTGAAGGGAGAAGTTGAGTCAATTAAGAAGCAGATCAACAG

GCAAAATATCAGCATATCCACCCTGGAAGGACACCTCTCAAGCATCATGATCGC

CATTCCTGGACTTGGGAAGGATCCCAACGACCCCACTGCAGATGTCGAAATCAA

TCCCGACTTGAAACCCATCATAGGCAGAGATTCAGGCCGAGCACTGGCCGAAGT

TCTCAAGAAACCCGTTGCCAGCCGACAACTCCAAGGAATGACAAATGGACGGAC

CAGTTCCAGAGGACAGCTGCTGAAGGAATTTCAGCTAAAGCCGATCGGGAAAAA

GATGAGCTCAGCCGTCGGGTTTGTTCCTGACACCGGCCCTGCATCACGCAGTGTA

ATCCGCTCCATTATAAAATCCAGCCGGCTAGAGGAGGATCGGAAGCGTTACCTG

ATGACTCTCCTTGATGATATCAAAGGAGCCAATGATCTTGCCAAGTTCCACCAGA

TGCTGATGAAGATAATAATGAAGTAGCTACAGCTCAACTTACCTGCCAACCCCAT

GCCAGTCGATCATCCATCATTGTTATAAAAAACTTAGGAACCAggtccacacaGagtgat

ACGCGTACGCCACCATGTTCGTGTTTCTGGTGCTGCTGCCTCTGGTGAGCTCCCA

GTGCGTGAACCTGACCACAAGGACCCAGCTGCCCCCTGCCTATACCAATTCCTTC

ACACGGGGCGTGTACTATCCCGACAAGGTGTTCCGGAGCAGCGTGCTGCACTCC

ACACAGGATCTGTTTCTGCCTTTCTTTTCTAACGTGACCTGGTTCCACGCCATCCA

CGTGAGCGGCACCAATGGCACAAAGCGGTTCGACAATCCAGTGCTGCCCTTTAA

CGATGGCGTGTACTTCGCCTCCACCGAGAAGTCTAACATCATCAGAGGCTGGAT

CTTTGGCACCACACTGGACAGCAAGACACAGTCCCTGCTGATCGTGAACAATGC

CACCAACGTGGTCATCAAGGTGTGCGAGTTCCAGTTTTGTAATGATCCATTCCTG

GGCGTGTACTATCACAAGAACAATAAGTCTTGGATGGAGAGCGAGTTTCGCGTG

TATTCCTCTGCCAACAATTGCACATTTGAGTACGTGTCCCAGCCCTTCCTGATGG

ACCTGGAGGGCAAGCAGGGCAATTTCAAGAACCTGAGGGAGTTCGTGTTTAAGA
```

-continued
```
ATATCGATGGCTACTTCAAAATCTACTCCAAGCACACCCCAATCAACCTGGTGCG

CGACCTGCCACAGGGCTTCTCTGCCCTGGAGCCACTGGTGGATCTGCCCATCGGC

ATCAACATCACCCGGTTTCAGACACTGCTGGCCCTGCACAGAAGCTACCTGACA

CCAGGCGACAGCTCCTCTGGATGGACCGCAGGAGCAGCAGCCTACTATGTGGGC

TATCTGCAGCCCAGGACCTTCCTGCTGAAGTACAACGAGAATGGCACCATCACA

GACGCCGTGGATTGCGCCCTGGATCCCCTGTCTGAGACCAAGTGTACACTGAAG

AGCTTTACCGTGGAGAAGGGCATCTATCAGACAAGCAATTTCAGGGTGCAGCCT

ACCGAGTCCATCGTGCGCTTTCCCAATATCACAAACCTGTGCCCTTTTGGCGAGG

TGTTCAACGCAACCCGCTTCGCCAGCGTGTACGCCTGGAATAGGAAGCGCATCT

CCAACTGCGTGGCCGACTATTCTGTGCTGTACAACAGCGCCTCCTTCTCTACCTTT

AAGTGCTATGGCGTGAGCCCCACAAAGCTGAATGACCTGTGCTTTACCAACGTGT

ACGCCGATTCCTTCGTGATCAGGGGCGACGAGGTGCGCCAGATCGCACCAGGAC

AGACAGGCAAGATCGCAGACTACAATTATAAGCTGCCTGACGATTTCACCGGCT

GCGTGATCGCCTGGAACTCTAACAATCTGGATAGCAAAGTGGGCGGCAACTACA

ATTATCTGTACCGGCTGTTTAGAAAGTCTAATCTGAAGCCATTCGAGAGGGACAT

CTCCACAGAAATCTACCAGGCCGGCTCTACCCCCTGCAATGGCGTGGAGGGCTTT

AACTGTTATTTCCCTCTGCAGAGCTACGGCTTCCAGCCAACAAACGGCGTGGGCT

ATCAGCCCTACCGCGTGGTGGTGCTGTCTTTTGAGCTGCTGCACGCACCTGCAAC

AGTGTGCGGACCAAAGAAGAGCACCAATCTGGTGAAGAACAAGTGCGTGAACTT

CAACTTCAACGGACTGACCGGAACAGGCGTGCTGACCGAGTCCAACAAGAAGTT

CCTGCCTTTTCAGCAGTTCGGCAGGGACATCGCAGATACCACAGACGCCGTGCG

CGACCCTCAGACCCTGGAGATCCTGGACATCACACCATGCTCCTTCGGCGGCGTG

TCTGTGATCACACCAGGCACCAATACAAGCAACCAGGTGGCCGTGCTGTATCAG

GACGTGAATTGTACCGAGGTGCCAGTGGCAATCCACGCAGATCAGCTGACCCCT

ACATGGCGGGTGTACTCTACCGGCAGCAACGTGTTCCAGACAAGAGCCGGATGC

CTGATCGGAGCAGAGCACGTGAACAATAGCTATGAGTGCGACATCCCTATCGGC

GCCGGCATCTGTGCCTCCTACCAGACCCAGACAAACTCCCCAAGGAGAGCACGG

TCTGTGGCCAGCCAGTCCATCATCGCCTATACCATGAGCCTGGGCGCCGAGAATT

CCGTGGCCTACTCCAACAATTCTATCGCCATCCCTACCAACTTCACAATCTCCGT

GACCACAGAGATCCTGCCAGTGAGCATGACCAAGACATCCGTGGACTGCACAAT

GTATATCTGTGGCGATTCCACCGAGTGCTCTAACCTGCTGCTGCAGTACGGCTCT

TTTTGTACCCAGCTGAATAGAGCCCTGACAGGCATCGCCGTGGAGCAGGACAAG

AACACACAGGAGGTGTTCGCCCAGGTGAAGCAAATCTACAAGACCCCACCCATC

AAGGACTTTGGCGGCTTCAACTTCAGCCAGATCCTGCCCGATCCTAGCAAGCCAT

CCAAGCGGTCTTTTATCGAGGACCTGCTGTTCAACAAGGTGACCCTGGCCGATGC

CGGCTTCATCAAGCAGTATGGCGATTGCCTGGGCGACATCGCCGCCAGAGACCT

GATCTGTGCCCAGAAGTTTAATGGCCTGACCGTGCTGCCTCCACTGCTGACAGAT

GAGATGATCGCCCAGTACACATCTGCCCTGCTGGCCGGAACCATCACAAGCGGA

TGGACCTTCGGCGCAGGAGCCGCCCTGCAGATCCCCTTTGCCATGCAGATGGCCT

ATCGGTTCAACGGCATCGGCGTGACCCAGAATGTGCTGTACGAGAACCAGAAGC

TGATCGCCAATCAGTTTAACTCCGCCATCGGCAAGATCCAGGACTCTCTGAGCTC
```

-continued

```
CACAGCCAGCGCCCTGGGCAAGCTGCAGGATGTGGTGAATCAGAACGCCCAGGC

CCTGAATACCCTGGTGAAGCAGCTGTCTAGCAACTTCGGCGCCATCTCCTCTGTG

CTGAATGACATCCTGAGCCGGCTGGACAAGGTGGAGGCAGAGGTGCAGATCGAC

CGGCTGATCACAGGCAGACTGCAGTCCCTGCAGACCTACGTGACACAGCAGCTG

ATCAGGGCAGCAGAGATCAGGGCCTCTGCCAATCTGGCCGCCACCAAGATGAGC

GAGTGCGTGCTGGGCCAGTCCAAGAGAGTGGACTTTTGTGGCAAGGGCTATCAC

CTGATGAGCTTCCCACAGTCCGCCCCTCACGGAGTGGTGTTTCTGCACGTGACCT

ACGTGCCAGCCCAGGAGAAGAACTTCACCACAGCACCAGCAATCTGCCACGATG

GCAAGGCACACTTTCCTAGGGAGGGCGTGTTCGTGAGCAACGGCACCCACTGGT

TTGTGACACAGCGCAATTTCTACGAGCCACAGATCATCACCACAGACAATACAT

TCGTGTCCGGCAACTGTGACGTGGTCATCGGCATCGTGAACAATACCGTGTATGA

TCCTCTGCAGCCAGAGCTGGACTCTTTTAAGGAGGAGCTGGATAAGTACTTCAAG

AATCACACCAGCCCCGACGTGGATCTGGGCGACATCTCTGGCATCAATGCCAGC

GTGGTGAACATCCAGAAGGAGATCGACAGGCTGAACGAGGTGGCCAAGAATCT

GAACGAGTCCCTGATCGATCTGCAGGAGCTGGGCAAGTATGAGCAGTACATCAA

GTGGCCCTGGTATATCTGGCTGGGCTTCATCGCCGGCCTGATCGCCATCGTGATG

GTGACCATCATGCTGTGCTGTATGACAAGCTGCTGTTCCTGCCTGAAGGGCTGCT

GTTCTTGTGGCAGCTGCTGTAAGTTTGATGAGGACGATAGCGAGCCTGTGCTGAA

GGGCGTGAAGCTGCACTACACCTGATAGCTAGCGATCGCCCACCTAGTACAACC

TAAATCCATTATAAAAAACTTAGGAGCAAAGTGATTGCCTCCCAAGGTCCACAA

TGACAGAGACCTACGACTTCGACAAGTCGGCATGGGACATCAAAGGGTCGATCG

CTCCGATACAACCCACCACCTACAGTGATGGCAGGCTGGTGCCCCAGGTCAGAG

TCATAGATCCTGGTCTAGGCGACAGGAAGGATGAATGCTTTATGTACATGTTTCT

GCTGGGGGTTGTTGAGGACAGCGATTCCCTAGGGCCTCCAATCGGGCGAGCATT

TGGGTTCCTGCCCTTAGGTGTTGGCAGATCCACAGCAAAGCCCGAAAAACTCCTC

AAAGAGGCCACTGAGCTTGACATAGTTGTTAGACGTACAGCAGGGCTCAATGAA

AAACTGGTGTTCTACAACAACACCCCACTAACTCTCCTCACACCTTGGAGAAAG

GTCCTAACAACAGGGAGTGTCTTCAACGCAAACCAAGTGTGCAATGCGGTTAAT

CTGATACCGCTCGATACCCCGCAGAGGTTCCGTGTTGTTTATATGAGCATCACCC

GTCTTTCGGATAACGGGTATTACACCGTTCCTAGAAGAATGCTGGAATTCAGATC

GGTCAATGCAGTGGCCTTCAACCTGCTGGTGACCCTTAGGATTGACAAGGCGAT

AGGCCCTGGGAAGATCATCGACAATACAGAGCAACTTCCTGAGGCAACATTTAT

GGTCCACATCGGGAACTTCAGGAGAAAGAAGAGTGAAGTCTACTCTGCCGATTA

TTGCAAAATGAAAATCGAAAAGATGGGCCTGGTTTTTGCACTTGGTGGGATAGG

GGGCACCAGTCTTCACATTAGAAGCACAGGCAAAATGAGCAAGACTCTCCATGC

ACAACTCGGGTTCAAGAAGACCTTATGTTACCCGCTGATGGATATCAATGAAGA

CCTTAATCGATTACTCTGGAGGAGCAGATGCAAGATAGTAAGAATCCAGGCAGT

TTTGCAGCCATCAGTTCCTCAAGAATTCCGCATTTACGACGACGTGATCATAAAT

GATGACCAAGGACTATTCAAAGTTCTGTAGACCGTAGTGCCCAGCAATGCCCGA

AAACGACCCCCCTCACAATGACAGCCAGAAGGCCCGGACAAAAAAGCCCCCTCC
```

-continued

```
GAAAGACTCCACGGACCAAGCGAGAGGCCAGCCAGCAGCCGACGGCAAGCGCG
AACACCAGGCGGCCCCAGCACAGAACAGCCCTGACACAAGGCCACCACCAGCC
ACCCCAATCTGCATCCTCCTCGTGGGACCCCCGAGGACCAACCCCCAAGGCTGC
CCCCGATCCAAACCACCAACCGCATCCCCACCACCCCCGGGAAAGAAACCCCCA
GCAATTGGAAGGCCCCTCCCCCTCTTCCTCAACACAAGAACTCCACAACCGAAC
CGCACAAGCGACCGAGGTGACCCAACCGCAGGCATCCGACTCCCTAGACAGATC
CTCTCTCCCCGGCAAACTAAACAAAACTTAGGGCCAAGGAACATACACACCCAA
CAGAACCCAGACCCCGGCCCACGGCGCCGCGCCCCAACCCCCGACAACCAGAG
GGAGCCCCCAACCAATCCCGCCGGCTCCCCGGTGCCCACAGGCAGGGACACCA
ACCCCCGAACAGACCCAGCACCCAACCATCGACAATCCAAGACGGGGGGCCCC
CCCAAAAAAGGCCCCCAGGGGCCGACAGCCAGCACCGCGAGGAAGCCCACCC
ACCCCACACACGACCACGGCAACCAAACCAGAACCCAGACCACCCTGGGCCACC
AGCTCCCAGACTCGGCCATCACCCCGCAGAAAGGAAAGGCCACAACCCGCGCAC
CCCAGCCCCGATCCGGCGGGGAGCCACCCAACCCGAACCAGCACCCAAGAGCG
ATCCCCGAAGGACCCCCGAACCGCAAAGGACATCAGTATCCCACAGCCTCTCCA
AGTCCCCCGGTCTCCTCCTCTTCTCGAAGGGACCAAAAGATCAATCCACCACACC
CGACGACACTCAACTCCCCACCCCTAAAGGAGACACCGGGAATCCCAGAATCAA
GACTCATCCAATGTCCATCATGGGTCTCAAGGTGAACGTCTCTGCCATATTCATG
GCAGTACTGTTAACTCTCCAAACACCCACCGGTCAAATCCATTGGGGCAATCTCT
CTAAGATAGGGGGGTAGGAATAGGAAGTGCAAGCTACAAAGTTATGACTCGTT
CCAGCCATCAATCATTAGTCATAAAATTAATGCCCAATATAACTCTCCTCAATAA
CTGCACGAGGGTAGAGATTGCAGAATACAGGAGACTACTGAGAACAGTTTTGGA
ACCAATTAGAGATGCACTTAATGCAATGACCCAGAATATAAGACCGGTTCAGAG
TGTAGCTTCAAGTAGGAGACACAAGAGATTTGCGGGAGTAGTCCTGGCAGGTGC
GGCCCTAGGCGTTGCCACAGCTGCTCAGATAACAGCCGGCATTGCACTTCACCA
GTCCATGCTGAACTCTCAAGCCATCGACAATCTGAGAGCGAGCCTGGAAACTAC
TAATCAGGCAATTGAGACAATCAGACAAGCAGGGCAGGAGATGATATTGGCTGT
TCAGGGTGTCCAAGACTACATCAATAATGAGCTGATACCGTCTATGAACCAACT
ATCTTGTGATTTAATCGGCCAGAAGCTCGGGCTCAAATTGCTCAGATACTATACA
GAAATCCTGTCATTATTTGGCCCCAGTTTACGGGACCCCATATCTGCGGAGATAT
CTATCCAGGCTTTGAGCTATGCGCTTGGAGGAGACATCAATAAGGTGTTAGAAA
AGCTCGGATACAGTGGAGGTGATTTACTGGGCATCTTAGAGAGCGGAGGAATAA
AGGCCCGGATAACTCACGTCGACACAGAGTCCTACTTCATTGTCCTCAGTATAGC
CTATCCGACGCTGTCCGAGATTAAGGGGGTGATTGTCCACCGGCTAGAGGGGT
CTCGTACAACATAGGCTCTCAAGAGTGGTATACCACTGTGCCCAAGTATGTTGCA
ACCCAAGGGTACCTTATCTCGAATTTTGATGAGTCATCGTGTACTTTCATGCCAG
AGGGGACTGTGTGCAGCCAAAATGCCTTGTACCCGATGAGTCCTCTGCTCCAAG
AATGCCTCCGGGGGTACACCAAGTCCTGTGCTCGTACACTCGTATCCGGGTCTTT
TGGGAACCGGTTCATTTTATCACAAGGGAACCTAATAGCCAATTGTGCATCAATC
CTTTGCAAGTGTTACAACAGGAACGATCATTAATCAAGACCCTGACAAGATC
CTAACATACATTGCTGCCGATCACTGCCCGGTAGTCGAGGTGAACGGCGTGACC
```

-continued

```
ATCCAAGTCGGGAGCAGGAGGTATCCAGACGCTGTGTACTTGCACAGAATTGAC

CTCGGTCCTCCCATATCATTGGAGAGGTTGGACGTAGGGACAAATCTGGGGAAT

GCAATTGCTAAGTTGGAGGATGCCAAGGAATTGTTGGAGTCATCGGACCAGATA

TTGAGGAGTATGAAAGGTTTATCGAGCACTAGCATAGTCTACATCCTGATTGCAG

TGTGTCTTGGAGGGTTGATAGGGATCCCCGCTTTAATATGTTGCTGCAGGGGCG

TTGTAACAAAAAGGGAGAACAAGTTGGTATGTCAAGACCAGGCCTAAAGCCTGA

TCTTACGGGAACATCAAAATCCTATGTAAGGTCGCTCTGATCCTCTACAACTCTT

GAAACACAAATGTCCCACAAGTCTCCTCTTCGTCATCAAGCAACCACCGCACCC

AGCATCAAGCCCACCTGAAATTATCTCCGGCTTCCCTCTGGCCGAACAATATCGG

TAGTTAATTAAAACTTAGGGTGCAAGATCATCGATAATGTCACCACAACGAGAC

CGGATAAATGCCTTCTACAAAGATAACCCCCATCCCAAGGGAAGTAGGATAGTC

ATTAACAGAGAACATCTTATGATTGATAGACCTTATGTTTTGCTGGCTGTTCTGTT

TGTCATGTTTCTGAGCTTGATCGGGTTGCTAGCCATTGCAGGAATTCGACTTCAT

CGGGCAGCCATCTACACCGCAGAGATCCATAAAAGCCTCAGCACCAATCTAGAT

GTAACTAACTCAATCGAGCATCAGGTCAAGGACGTGCTGACACCACTCTTCAAA

ATCATCGGTGATGAAGTGGGCCTGAGGACACCTCAGAGATTCACTGACCTAGTG

AAATTAATCTCTGACAAGATTAAATTCCTTAATCCGGATAGGGAGTACGACTTCA

GAGATCTCACTTGGTGTATCAACCCGCCAGAGAGAATCAAATTGGATTATGATC

AATACTGTGCAGATGTGGCTGCTGAAGAGCTCATGAATGCATTGGTGAACTCAA

CTCTACTGGAGACCAGAACAACCAATCAGTTCCTAGCTGTCTCAAAGGGAAACT

GCTCAGGGCCCACTACAATCAGAGGTCAATTCTCAAACATGTCGCTGTCCCTGTT

AGACTTGTATTTAGGTCGAGGTTACAATGTGTCATCTATAGTCACTATGACATCC

CAGGGAATGTATGGGGAACTTACCTAGTGGAAAAGCCTAATCTGAGCAGCAAA

AGGTCAGAGTTGTCACAACTGAGCATGTACCGAGTGTTTGAAGTAGGTGTTATCA

GAAATCCGGGTTTGGGGGCTCCGGTGTTCCATATGACAAACTATCTTGAGCAACC

AGTCAGTAATGATCTCAGCAACTGTATGGTGGCTTTGGGGGAGCTCAAACTCGC

AGCCCTTTGTCACGGGGAAGATTCTATCACAATTCCCTATCAGGGATCAGGGAA

AGGTGTCAGCTTCCAGCTCGTCAAGCTAGGTGTCTGGAAATCCCCAACCGACAT

GCAATCCTGGGTCCCCTTATCAACGGATGATCCAGTGATAGACAGGCTTTACCTC

TCATCTCACAGAGGTGTTATCGCTGACAACCAAGCAAAATGGGCTGTCCCGACA

ACACGAACAGATGACAAGTTGCGAATGGAGACATGCTTCCAACAGGCGTGTAAG

GGTAAAATCCAAGCACTCTGCGAGAATCCCGAGTGGGCACCATTGAAGGATAAC

AGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGG

ACCTATACAAATCCAACCACAACAATGTGTATTGGCTGACTATCCCGCCAATGA

AGAACCTAGCCTTAGGTGTAATCAACACATTGGAGTGGATACCGAGATTCAAGG

TTAGTCCCTACCTCTTCACTGTCCCAATTAAGGAAGCAGGCGAAGACTGCCATGC

CCCAACATACCTACCTGCGGAGGTGGATGGTGATGTCAAACTCAGTTCCAATCTG

GTGATTCTACCTGGTCAAGATCTCCAATATGTTTTGGCAACCTACGATACTTCCA

GGGTTGAACATGCTGTGGTTTATTACGTTTACAGCCCAAGCCGCTCATTTTCTTAC
```

-continued

```
TTTTATCCTTTTAGGTTGCCTATAAAGGGGGTCCCCATCGAATTACAAGTGGAAT
GCTTCACATGGGACCAAAAACTCTGGTGCCGTCACTTCTGTGTGCTTGCGGACTC
AGAATCTGGTGGACATATCACTCACTCTGGGATGGTGGGCATGGGAGTCAGCTG
CACAGTCACCCGGGAAGATGGAACCAATCGCAGATAGGGCTGCTAGTGAACCAA
TCACATGATGTCACCCAGACATCAGGCATACCCACTAGTGTGAAATAGACATCA
GAATTAAGAAAAACGTAGGGTCCAAGTGGTTCCCCGTTATGGACTCGCTATCTGT
CAACCAGATCTTATACCCTGAAGTTCACCTAGATAGCCCGATAGTTACCAATAAG
ATAGTAGCCATCCTGGAGTATGCTCGAGTCCCTCACGCTTACAGCCTGGAGGACC
CTACACTGTGTCAGAACATCAAGCACCGCCTAAAAAACGGATTTTCCAACCAAA
TGATTATAAACAATGTGGAAGTTGGGAATGTCATCAAGTCCAAGCTTAGGAGTT
ATCCGGCCCACTCTCATATTCCATATCCAAATTGTAATCAGGATTTATTTAACAT
AGAAGACAAAGAGTCAACGAGGAAGATCCGTGAACTCCTCAAAAAGGGGAATT
CGCTGTACTCCAAAGTCAGTGATAAGGTTTTCCAATGCTTAAGGGACACTAACTC
ACGGCTTGGCCTAGGCTCCGAATTGAGGGAGGACATCAAGGAGAAAGTTATTAA
CTTGGGAGTTTACATGCACAGCTCCCAGTGGTTTGAGCCCTTTCTGTTTTGGTTTA
CAGTCAAGACTGAGATGAGGTCAGTGATTAAATCACAAACCCATACTTGCCATA
GGAGGAGACACACACCTGTATTCTTCACTGGTAGTTCAGTTGAGTTGCTAATCTC
TCGTGACCTTGTTGCTATAATCAGTAAAGAGTCTCAACATGTATATTACCTGACA
TTTGAACTGGTTTTGATGTATTGTGATGTCATAGAGGGGAGGTTAATGACAGAGA
CCGCTATGACTATTGATGCTAGGTATACAGAGCTTCTAGGAAGAGTCAGATACAT
GTGGAAACTGATAGATGGTTTCTTCCCTGCACTCGGGAATCCAACTTATCAAATT
GTAGCCATGCTGGAGCCTCTTTCACTTGCTTACCTGCAGCTGAGGGATATAACAG
TAGAACTCAGAGGTGCTTTCCTTAACCACTGCTTTACTGAAATACATGATGTTCT
TGACCAAAACGGGTTTTCTGATGAAGGTACTTATCATGAGTTAACTGAAGCTCTA
GATTACATTTTCATAACTGATGACATACATCTGACAGGGGAGATTTTCTCATTTTT
CAGAAGTTTCGGCCACCCCAGACTTGAAGCAGTAACGGCTGCTGAAAATGTTAG
GAAATACATGAATCAGCCTAAAGTCATTGTGTATGAGACTCTGATGAAAGGTCA
TGCCATATTTTGTGGAATCATAATCAACGGCTATCGTGACAGGCACGGAGGCAG
TTGGCCACCGCTGACCCTCCCCCTGCATGCTGCAGACACAATCCGGAATGCTCAA
GCTTCAGGTGAAGGGTTAACACATGAGCAGTGCGTTGATAACTGGAAATCTTTTG
CTGGAGTGAAATTTGGCTGCTTTATGCCTCTTAGCCTGGATAGTGATCTGACAAT
GTACCTAAAGGACAAGGCACTTGCTGCTCTCCAAAGGGAATGGGATTCAGTTTA
CCCGAAAGAGTTCCTGCGTTACGACCCTCCCAAGGGAACGGGTCACGGAGGCT
TGTAGATGTTTTCCTTAATGATTCGAGCTTTGACCCATATGATGTGATAATGTATG
TTGTAAGTGGAGCTTACCTCCATGACCCTGAGTTCAACCTGTCTTACAGCCTGAA
AGAAAAGGAGATCAAGGAAACAGGTAGACTTTTTGCTAAAATGACTTACAAAAT
GAGGGCATGCCAAGTGATTGCTGAAAATCTAATCTCAAACGGGATTGGCAAATA
TTTTAAGGACAATGGGATGGCCAAGGATGAGCACGATTTGACTAAGGCACTCCA
CACTCTAGCTGTCTCAGGAGTCCCCAAAGATCTCAAAGAAAGTCACAGGGGGGG
GCCAGTCTTAAAAACCTACTCCCGAAGCCCAGTCCACACAAGTACCAGGAACGT
GAGAGCAGCAAAAGGGTTTATAGGGTTCCCTCAAGTAATTCGGCAGGACCAAGA
```

-continued

```
CACTGATCATCCGGAGAATATGGAAGCTTACGAGACAGTCAGTGCATTTATCAC

GACTGATCTCAAGAAGTACTGCCTTAATTGGAGATATGAGACCATCAGCTTGTTT

GCACAGAGGCTAAATGAGATTTACGGATTGCCCTCATTTTTCCAGTGGCTGCATA

AGAGGCTTGAGACCTCTGTCCTGTATGTAAGTGACCCTCATTGCCCCCCCGACCT

TGACGCCCATATCCCGTTATATAAAGTCCCCAATGATCAAATCTTCATTAAGTAC

CCTATGGGAGGTATAGAAGGGTATTGTCAGAAGCTGTGGACCATCAGCACCATT

CCCTATCTATACCTGGCTGCTTATGAGAGCGGAGTAAGGATTGCTTCGTTAGTGC

AAGGGGACAATCAGACCATAGCCGTAACAAAAAGGGTACCCAGCACATGGCCC

TACAACCTTAAGAAACGGGAAGCTGCTAGAGTAACTAGAGATTACTTTGTAATT

CTTAGGCAAAGGCTACATGATATTGGCCATCACCTCAAGGCAAATGAGACAATT

GTTTCATCACATTTTTTTGTCTATTCAAAAGGAATATATTATGATGGGCTACTTGT

GTCCCAATCACTCAAGAGCATCGCAAGATGTGTATTCTGGTCAGAGACTATAGTT

GATGAAACAAGGGCAGCATGCAGTAATATTGCTACAACAATGGCTAAAAGCATC

GAGAGAGGTTATGACCGTTACCTTGCATATTCCCTGAACGTCCTAAAAGTGATAC

AGCAAATTCTGATCTCTCTTGGCTTCACAATCAATTCAACCATGACCCGGGATGT

AGTCATACCCCTCCTCACAAACAACGACCTCTTAATAAGGATGGCACTGTTGCCC

GCTCCTATTGGGGGATGAATTATCTGAATATGAGCAGGCTGTTTGTCAGAAACA

TCGGTGATCCAGTAACATCATCAATTGCTGATCTCAAGAGAATGATTCTCGCCTC

ACTAATGCCTGAAGAGACCCTCCATCAGGTAATGACACAACAACCGGGGGACTC

TTCATTCCTAGACTGGGCTAGCGACCCTTACTCAGCAAATCTTGTATGTGTCCAG

AGCATCACTAGACTCCTCAAGAACATAACTGCAAGGTTTGTCCTGATCCATAGTC

CAAACCCAATGTTAAAAGGATTATTCCATGATGACAGTAAAGAAGAGGACGAGG

GACTGGCGGCATTCCTCATGGACAGGCATATTATAGTACCTAGGGCAGCTCATG

AAATCCTGGATCATAGTGTCACAGGGGCAAGAGAGTCTATTGCAGGCATGCTGG

ATACCACAAAAGGCTTGATTCGAGCCAGCATGAGGAAGGGGGGTTTAACCTCTC

GAGTGATAACCAGATTGTCCAATTATGACTATGAACAATTCAGAGCAGGGATGG

TGCTATTGACAGGAAGAAAGAGAAATGTCCTCATTGACAAAGAGTCATGTTCAG

TGCAGCTGGCGAGAGCTCTAAGAAGCCATATGTGGGCGAGGCTAGCTCGAGGAC

GGCCTATTTACGGCCTTGAGGTCCCTGATGTACTAGAATCTATGCGAGGCCACCT

TATTCGGCGTCATGAGACATGTGTCATCTGCGAGTGTGGATCAGTCAACTACGGA

TGGTTTTTTGTCCCCTCGGGTTGCCAACTGGATGATATTGACAAGGAAACATCAT

CCTTGAGAGTCCCATATATTGGTTCTACCACTGATGAGAGAACAGACATGAAGCT

TGCCTTCGTAAGAGCCCCAAGTCGATCCTTGCGATCTGCTGTTAGAATAGCAACA

GTGTACTCATGGCTTACGGTGATGATGATAGCTCTTGGAACGAAGCCTGGTTGT

TGGCTAGGCAAAGGGCCAATGTGAGCCTGGAGGAGCTAAGGGTGATCACTCCCA

TCTCAACTTCGACTAATTTAGCGCATAGGTTGAGGGATCGTAGCACTCAAGTGAA

ATACTCAGGTACATCCCTTGTCCGAGTGGCGAGGTATACCACAATCTCCAACGAC

AATCTCTCATTTGTCATATCAGATAAGAAGGTTGATACTAACTTTATATACCAAC

AAGGAATGCTTCTAGGGTTGGGTGTTTTAGAAACATTGTTTCGACTCGAGAAAGA

TACCGGATCATCTAACACGGTATTACATCTTCACGTCGAAACAGATTGTTGCGTG
```

```
ATCCCGATGATAGATCATCCCAGGATACCCAGCTCCCGCAAGCTAGAGCTGAGG
GCAGAGCTATGTACCAACCCATTGATATATGATAATGCACCTTTAATTGACAGAG
ATGCAACAAGGCTATACACCCAGAGCCATAGGAGGCACCTTGTGGAATTTGTTA
CATGGTCCACACCCCAACTATATCACATTTTAGCTAAGTCCACAGCACTATCTAT
GATTGACCTGGTAACAAAATTTGAGAAGGACCATATGAATGAAATTTCAGCTCT
CATAGGGGATGACGATATCAATAGTTTCATAACTGAGTTTCTGCTCATAGAGCCA
AGATTATTCACTATCTACTTGGGCCAGTGTGCGGCCATCAATTGGGCATTTGATG
TACATTATCATAGACCATCAGGGAAATATCAGATGGGTGAGCTGTTGTCATCGTT
CCTTTCTAGAATGAGCAAAGGAGTGTTTAAGGTGCTTGTCAATGCTCTAAGCCAC
CCAAAGATCTACAAGAAATTCTGGCATTGTGGTATTATAGAGCCTATCCATGGTC
CTTCACTTGATGCTCAAAACTTGCACACAACTGTGTGCAACATGGTTTACACATG
CTATATGACCTACCTCGACCTGTTGTTGAATGAAGAGTTAGAAGAGTTCACATTT
CTCTTGTGTGAAAGCGACGAGGATGTAGTACCGGACAGATTCGACAACATCCAG
GCAAAACACTTATGTGTTCTGGCAGATTTGTACTGTCAACCAGGGACCTGCCCAC
CAATTCGAGGTCTAAGACCGGTAGAGAAATGTGCAGTTCTAACCGACCATATCA
AGGCAGAGGCTATGTTATCTCCAGCAGGATCTTCGTGGAACATAAATCCAATTAT
TGTAGACCATTACTCATGCTCCCTGACTTATCTCCGGCGAGGATCGATCAAACAG
ATAAGATTGAGAGTTGATCCAGGATTCATTTTCGACGCCCTCGCTGAGGTAAATG
TCAGTCAGCCAAAGATCGGCAGCAACAACATCTCAAATATGAGCATCAAGGCTT
TCAGACCCCCACACGATGATGTTGCAAAATTGCTCAAAGATATCAACACAAGCA
AGCACAATCTTCCCATTTCAGGGGGCAATCTCGCCAATTATGAAATCCATGCTTT
CCGCAGAATCGGGTTGAACTCATCTGCTTGCTACAAAGCTGTTGAGATATCAACA
TTAATTAGGAGATGCCTTGAGCCAGGGGAGGACGGCTTGTTCTTGGGTGAGGGA
TCGGGTTCTATGTTGATCACTTATAAGGAGATACTTAAACTAAACAAGTGCTTCT
ATAATAGTGGGGTTTCCGCCAATTCTAGATCTGGTCAAAGGGAATTAGCACCCTA
TCCCTCCGAAGTTGGCCTTGTCGAACACAGAATGGGAGTAGGTAATATTGTCAA
AGTGCTCTTTAACGGGAGGCCCGAAGTCACGTGGGTAGGCAGTGTAGATTGCTT
CAATTTCATAGTTAGTAATATCCCTACCTCTAGTGTGGGGTTTATCCATTCAGATA
TAGAGACCTTGCCTGACAAAGATACTATAGAGAAGCTAGAGGAATTGGCAGCCA
TCTTATCGATGGCTCTGCTCCTGGGCAAAATAGGATCAATACTGGTGATTAAGCT
TATGCCTTTCAGCGGGATTTTGTTCAGGGATTTATAAGTTATGTAGGGTCTCATT
ATAGAGAAGTGAACCTTGTATACCCTAGATACAGCAACTTCATATCTACTGAATC
TTATTTGGTTATGACAGATCTCAAGGCTAACCGGCTAATGAATCCTGAAAAGATT
AAGCAGCAGATAATTGAATCATCTGTGAGGACTTCACCTGGACTTATAGGTCAC
ATCCTATCCATTAAGCAACTAAGCTGCATACAAGCAATTGTGGGAGACGCAGTT
AGTAGAGGTGATATCAATCCTACTCTGAAAAAACTTACACCTATAGAGCAGGTG
CTGATCAATTGCGGGTTGGCAATTAACGGACCTAAGCTGTGCAAAGAATTGATC
CACCATGATGTTGCCTCAGGGCAAGATGGATTGCTTAATTCTATACTCATCCTCT
ACAGGGAGTTGGCAAGATTCAAAGACAACCAAAGAAGTCAACAAGGGATGTTC
CACGCCTACCCCGTATTGGTAAGTAGCAGGCAACGAGAACTTATATCTAGGATC
ACCCGCAAATTTTGGGGGCACATTCTTCTTTACTCCGGGAACAAAAAGTTGATAA
```

-continued

```
ATAAGTTTATCCAGAATCTCAAGTCCGGCTATCTGATACTAGACTTACACCAGAA

TATCTTCGTTAAGAATCTATCCAAGTCAGAGAAACAGATTATTATGACGGGGGGT

TTGAAACGTGAGTGGGTTTTTAAGGTAACAGTCAAGGAGACCAAAGAATGGTAT

AAGTTAGTCGGATACAGTGCCCTGATTAAGGACTAATTGGTTGAACTCCGGAAC

CCTAATCCTGCCCTAGGTGGTTAGGCATTATTTGCAATATATTAAAGAAAACTTT

GAAAATACGAAGTTTCTATTCCCAGCTTTGTCTGGTggccggcatAgtcccagcctcctcgctggc gctggctgggcaacattccgaggggaccgtccccAcggtaatggcgaatgggacgcggccgatccggctgctaacaaagcccga aaggaagctgagttggctgctgGcGcTGgctgGgcaataactagcataacccctTgggggcctctaaacgggtcttgaggggttttt tgctgaaaggaggaactatatccggatgcGGCCGCGCGCTTGGCGTAATCATGGTCATAGCTGTTT

CCTGTGTGAAATTGTTATCCGCTCACAATTCCACACAACATACGAGCCGGAAGC

ATAAAGTGTAAAGCCTGGGGTGCCTAATGAGTGAGCTAACTCACATTAATTGCG

TTGCGCTCACTGCCCGCTTTCCAGTCGGGAAACCTGTCGTGCCAGCTGCATTAAT

GAATCGGCCAACGCGCGGGAGAGGCGGTTTGCGTATTGGGCGCTCTTCCGCTT

CCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAA

GAACATGTGAGCAAAAGGCCAGCAAAAGGCCAGGAACCGTAAAAAGGCCGCGT

TGCTGGCGTTTTTCCATAGGCTCCGCCCCCTGACGAGCATCACAAAAATCGACG

CTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATAC

CTGTCCGCCTTTCTCCCTTCGGGAAGCGTGGCGCTTTCTCATAGCTCACGCTGTA

GGTATCTCAGTTCGGTGTAGGTCGTTCGCTCCAAGCTGGGCTGTGTGCACGAACC

CCCCGTTCAGCCCGACCGCTGCGCCTTATCCGGTAACTATCGTCTTGAGTCCAAC

CCGGTAAGACACGACTTATCGCCACTGGCAGCAGCCACTGGTAACAGGATTAGC

AGAGCGAGGTATGTAGGCGGTGCTACAGAGTTCTTGAAGTGGTGGCCTAACTAC

GGCTACACTAGAAGGACAGTATTTGGTATCTGCGCTCTGCTGAAGCCAGTTACCT

TCGGAAAAAGAGTTGGTAGCTCTTGATCCGGCAAACAAACCACCGCTGGTAGCG

GTGGTTTTTTGTTTGCAAGCAGCAGATTACGCGCAGAAAAAAAGGATCTCAAG

AAGATCCTTTGATCTTTTCTACGGGGTCTGACGCTCAGTGGAACGAAAACTCACG

TTAAGGGATTTTGGTCATGAGATTATCAAAAAGGATCTTCACCTAGATCCTTTTA

AATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTC

CTGCAACTTTATCCGCCTCCATCCAGTCTATTAATTGTTGCCGGGAAGCTAGAGT

AAGTAGTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCCTTCGG

TCCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGAC
```

-continued

```
TGGTGAGTACTCAACCAAGTCATTCTGAGAATAGTGTATGCGGCGACCGAGTTG

CTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCG

CTGTTGAGATCCAGTTCGATGTAACCCACTCGTGCACCCAACTGATCTTCAGCAT

CTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAA

GTGCCACCTG.
```

In still another embodiment, the nucleic acid comprises the sequence of SEQ ID NO: 5, shown below:

```
GGACGCGCCCTGTAGCGGCGCATTAAGCGCGGCGGGTGTGGTGGTTACGCGCAG

CGTGACCGCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGA

CGTTGGAGTCCACGTTCTTTAATAGTGGACTCTTGTTCCAAACTGGAACAACACT

CAACCCTATCTCGGTCTATTCTTTTGATTTATAAGGGATTTTGCCGATTTCGGCCT

ATTGGTTAAAAAATGAGCTGATTTAACAAAAATTTAACGCGAATTTTAACAAAA

TATTAACGTTTACAATTTCGCGCCATTCGCCATTCAGGCTGCGCAACTGTTGGGA

AGGGCGATCGGTGCGGGCCTCTTCGCTATTACGCCAGCTGGCGAAAGGGGGATG

TGCTGCAAGGCGATTAAGTTGGGTAACGCCAGGGTTTTCCCAGTCACGACGTTGT

AAAACGACGGCCAGTGCGCGCCGTTAATACGACTCACTATAGGGAGACCCAAGC

TGGCTAGCTTTGTTTGGTCTGATGAGTCCCGTGAGGACGAAACCCGGCGTACCGG

GTCACCAAACAAAGTTGGGTAAGGATAGTTCAATCAATGATCATCTTCTAGTGCA

CTTAGGATTCAAGATCCTATTATCAGGGACAAGAGCAGGATTAGGGATATCCGA

GATGGCCACACTTTTAAGGAGCTTAGCATTGTTCAAAAGAAACAAGGACAAACC

ACCCATTACATCAGGATCCGGTGGAGCCATCAGAGGAATCAAACACATTATTAT

AGTACCAATCCCTGGAGATTCCTCAATTACCACTCGATCCAGACTTCTGGACCGG

TTGGTGAGGTTAATTGGAAACCCGGATGTGAGCGGGCCCAAACTAACAGGGGCA

CTAATAGGTATATTATCCTTATTTGTGGAGTCTCCAGGTCAATTGATTCAGAGGA

TCACCGATGACCCTGACGTTAGCATAAGGCTGTTAGAGGTTGTCCAGAGTGACC

AGTCACAATCTGGCCTTACCTTCGCATCAAGAGGTACCAACATGGAGGATGAGG

CGGACCAATACTTTTCACATGATGATCCAATTAGTAGTGATCAATCCAGGTTCGG

ATGGTTCGGGAACAAGGAAATCTCAGATATTGAAGTGCAAGACCCTGAGGGATT

CAACATGATTCTGGGTACCATCCTAGCCCAAATTTGGGTCTTGCTCGCAAAGGCG

GTTACGGCCCCAGACACGGCAGCTGATTCGGAGCTAAGAAGGTGGATAAAGTAC

ACCCAACAAAGAAGGGTAGTTGGTGAATTTAGATTGGAGAGAAATGGTTGGAT

GTGGTGAGGAACAGGATTGCCGAGGACCTCTCCTTACGCCGATTCATGGTCGCTC

TAATCCTGGATATCAAGAGAACACCCGGAAACAAACCCAGGATTGCTGAAATGA
```

-continued

```
TATGTGACATTGATACATATATCGTAGAGGCAGGATTAGCCAGTTTTATCCTGAC

TATTAAGTTTGGGATAGAAACTATGTATCCTGCTCTTGGACTGCATGAATTTGCT

GGTGAGTTATCCACACTTGAGTCCTTGATGAACCTTTACCAGCAAATGGGGGAA

ACTGCACCCTACATGGTAATCCTGGAGAACTCAATTCAGAACAAGTTCAGTGCA

GGATCATACCCTCTGCTCTGGAGCTATGCCATGGGAGTAGGAGTGGAACTTGAA

AACTCCATGGGAGGTTTGAACTTTGGCCGATCTTACTTTGATCCAGCATATTTTA

GATTAGGGCAAGAGATGGTAAGGAGGTCAGCTGGAAAGGTCAGTTCCACATTGG

CATCTGAACTCGGTATCACTGCCGAGGATGCAAGGCTTGTTTCAGAGATTGCAAT

GCATACTACTGAGGACAAGATCAGTAGAGCGGTTGGACCCAGACAAGCCCAAGT

ATCATTTCTACACGGTGATCAAAGTGAGAATGAGCTACCGAGATTGGGGGGCAA

GGAAGATAGGAGGGTCAAACAGAGTCGAGGAGAAGCCAGGGAGAGCTACAGAG

AAACCGGGCCCAGCAGAGCAAGTGATGCGAGAGCTGCCCATCTTCCAACCGGCA

CACCCCTAGACATTGACACTGCAACGGAGTCCAGCCAAGATCCGCAGGACAGTC

GAAGGTCAGCTGACGCCCTGCTTAGGCTGCAAGCCATGGCAGGAATCTCGGAAG

AACAAGGCTCAGACACGGACACCCCTATAGTGTACAATGACAGAAATCTTCTAG

ACTAGGTGCGAGAGGCCGAGGGCCAGAACAACATCCGCCTACCATCCATCATTG

TTATAAAAAACTTAGGAACCAGGTCCACACAGCCGCCAGCCCATCAACCATCCA

CTCCCACGATTGGAGCCAATGGCAGAAGAGCAGGCACGCCATGTCAAAAACGG

ACTGGAATGCATCCGGGCTCTCAAGGCCGAGCCCATCGGCTCACTGGCCATCGA

GGAAGCTATGGCAGCATGGTCAGAAATATCAGACAACCCAGGACAGGAGCGAG

CCACCTGCAGGGAAGAGAAGGCAGGCAGTTCGGGTCTCAGCAAACCATGCCTCT

CAGCAATTGGATCAACTGAAGGCGGTGCACCTCGCATCCGCGGTCAGGGACCTG

GAGAGAGCGATGACGACGCTGAAACTTTGGGAATCCCCCCAAGAAATCTCCAGG

CATCAAGCACTGGGTTACAGTGTTATTACGTTTATGATCACAGCGGTGAAGCGGT

TAAGGGAATCCAAGATGCTGACTCTATCATGGTTCAATCAGGCCTTGATGGTGAT

AGCACCCTCTCAGGAGGAGACAATGAATCTGAAAACAGCGATGTGGATATTGGC

GAACCTGATACCGAGGGATATGCTATCACTGACCGGGGATCTGCTCCCATCTCTA

TGGGGTTCAGGGCTTCTGATGTTGAAACTGCAGAAGGAGGGGAGATCCACGAGC

TCCTGAGACTCCAATCCAGAGGCAACAACTTTCCGAAGCTTGGGAAAACTCTCA

ATGTTCCTCCGCCCCGGACCCCGGTAGGGCCAGCACTTCCGGGACACCCATTAA

AAAGGGCACAGACGCGAGATTAGCCTCATTTGGAACGGAGATCGCGTCTTTATT

GACAGGTGGTGCAACCCAATGTGCTCGAAAGTCACCCTCGGAACCATCAGGGCC

AGGTGCACCTGCGGGGAATGTCCCCGAGTGTGTGAGCAATGCCGCACTGATACA

GGAGTGGACACCCGAATCTGGTACCACAATCTCCCCGAGATCCCAGAATAATGA

AGAAGGGGAGACTATTATGATGATGAGCTGTTCTCTGATGTCCAAGATATTAA

AACAGCCTTGGCCAAAATACACGAGGATAATCAGAAGATAATCTCCAAGCTAGA

ATCACTGCTGTTATTGAAGGGAGAAGTTGAGTCAATTAAGAAGCAGATCAACAG

GCAAAATATCAGCATATCCACCCTGGAAGGACACCTCTCAAGCATCATGATCGC

CATTCCTGGACTTGGGAAGGATCCCAACGACCCCACTGCAGATGTCGAAATCAA

TCCCGACTTGAAACCCATCATAGGCAGAGATTCAGGCCGAGCACTGGCCGAAGT
```

-continued

```
TCTCAAGAAACCCGTTGCCAGCCGACAACTCCAAGGAATGACAAATGGACGGAC
CAGTTCCAGAGGACAGCTGCTGAAGGAATTTCAGCTAAAGCCGATCGGGAAAAA
GATGAGCTCAGCCGTCGGGTTTGTTCCTGACACCGGCCCTGCATCACGCAGTGTA
ATCCGCTCCATTATAAAATCCAGCCGGCTAGAGGAGGATCGGAAGCGTTACCTG
ATGACTCTCCTTGATGATATCAAAGGAGCCAATGATCTTGCCAAGTTCCACCAGA
TGCTGATGAAGATAATAATGAAGTAGCTACAGCTCAACTTACCTGCCAACCCCAT
GCCAGTCGACCCACCTAGTACAACCTAAATCCATTATAAAAAACTTAGGAGCAA
AGTGATTGCCTCCCAAGGTCCACAATGACAGAGACCTACGACTTCGACAAGTCG
GCATGGGACATCAAAGGGTCGATCGCTCCGATACAACCCACCACCTACAGTGAT
GGCAGGCTGGTGCCCCAGGTCAGAGTCATAGATCCTGGTCTAGGCGACAGGAAG
GATGAATGCTTTATGTACATGTTTCTGCTGGGGGTTGTTGAGGACAGCGATTCCC
TAGGGCCTCCAATCGGGCGAGCATTTGGGTTCCTGCCCTTAGGTGTTGGCAGATC
CACAGCAAAGCCCGAAAAACTCCTCAAAGAGGCCACTGAGCTTGACATAGTTGT
TAGACGTACAGCAGGGCTCAATGAAAAACTGGTGTTCTACAACAACACCCCACT
AACTCTCCTCACACCTTGGAGAAAGGTCCTAACAACAGGGAGTGTCTTCAACGC
AAACCAAGTGTGCAATGCGGTTAATCTGATACCGCTCGATACCCCGCAGAGGTT
CCGTGTTGTTTATATGAGCATCACCCGTCTTTCGGATAACGGGTATTACACCGTT
CCTAGAAGAATGCTGGAATTCAGATCGGTCAATGCAGTGGCCTTCAACCTGCTG
GTGACCCTTAGGATTGACAAGGCGATAGGCCCTGGGAAGATCATCGACAATACA
GAGCAACTTCCTGAGGCAACATTTATGGTCCACATCGGGAACTTCAGGAGAAAG
AAGAGTGAAGTCTACTCTGCCGATTATTGCAAAATGAAAATCGAAAAGATGGGC
CTGGTTTTTGCACTTGGTGGGATAGGGGGCACCAGTCTTCACATTAGAAGCACAG
GCAAAATGAGCAAGACTCTCCATGCACAACTCGGGTTCAAGAAGACCTTATGTT
ACCCGCTGATGGATATCAATGAAGACCTTAATCGATTACTCTGGAGGAGCAGAT
GCAAGATAGTAAGAATCCAGGCAGTTTTGCAGCCATCAGTTCCTCAAGAATTCC
GCATTTACGACGACGTGATCATAAATGATGACCAAGGACTATTCAAAGTTCTGTA
GACCGTAGTGCCCAGCAATGCCCGAAAACGACCCCCCTCACAATGACAGCCAGA
AGGCCCGGACAAAAAGCCCCCTCCGAAAGACTCCACGGACCAAGCGAGAGGC
CAGCCAGCAGCCGACGGCAAGCGCGAACACCAGGCGGCCCCAGCACAGAACAG
CCCTGACACAAGGCCACCACCAGCCACCCCAATCTGCATCCTCCTCGTGGGACCC
CCGAGGACCAACCCCCAAGGCTGCCCCCGATCCAAACCACCAACCGCATCCCCA
CCACCCCGGGAAAGAAACCCCCAGCAATTGGAAGGCCCCTCCCCCTCTTCCTC
AACACAAGAACTCCACAACCGAACCGCACAAGCGACCGAGGTGACCCAACCGC
AGGCATCCGACTCCCTAGACAGATCCTCTCTCCCCGGCAAACTAAACAAAACTT
AGGGCCAAGGAACATACACACCCAACAGAACCCAGACCCCGGCCCACGGCGCC
GCGCCCCAACCCCCGACAACCAGAGGGAGCCCCAACCAATCCCGCCGGCTCC
CCCGGTGCCCACAGGCAGGGACACCAACCCCCGAACAGACCCAGCACCCAACCA
TCGACAATCCAAGACGGGGGGCCCCCCAAAAAAAGGCCCCCAGGGGCCGAC
AGCCAGCACCGCGAGGAAGCCCACCCACCCCCACACACGACCACGGCAACCAAA
CCAGAACCCAGACCACCCTGGGCCACCAGCTCCCAGACTCGGCCATCACCCCGC
AGAAAGGAAAGGCCACAACCCGCGCACCCCAGCCCCGATCCGGCGGGGAGCCA
```

-continued

```
CCCAACCCGAACCAGCACCCAAGAGCGATCCCCGAAGGACCCCCGAACCGCAA

AGGACATCAGTATCCCACAGCCTCTCCAAGTCCCCCGGTCTCCTCCTCTTCTCGA

AGGGACCAAAAGATCAATCCACCACACCCGACGACACTCAACTCCCCACCCCTA

AAGGAGACACCGGGAATCCCAGAATCAAGACTCATCCAATGTCCATCATGGGTC

TCAAGGTGAACGTCTCTGCCATATTCATGGCAGTACTGTTAACTCTCCAAACACC

CACCGGTCAAATCCATTGGGGCAATCTCTCTAAGATAGGGGTGGTAGGAATAGG

AAGTGCAAGCTACAAAGTTATGACTCGTTCCAGCCATCAATCATTAGTCATAAAA

TTAATGCCCAATATAACTCTCCTCAATAACTGCACGAGGGTAGAGATTGCAGAAT

ACAGGAGACTACTGAGAACAGTTTTGGAACCAATTAGAGATGCACTTAATGCAA

TGACCCAGAATATAAGACCGGTTCAGAGTGTAGCTTCAAGTAGGAGACACAAGA

GATTTGCGGGAGTAGTCCTGGCAGGTGCGGCCCTAGGCGTTGCCACAGCTGCTC

AGATAACAGCCGGCATTGCACTTCACCAGTCCATGCTGAACTCTCAAGCCATCG

ACAATCTGAGAGCGAGCCTGGAAACTACTAATCAGGCAATTGAGACAATCAGAC

AAGCAGGGCAGGAGATGATATTGGCTGTTCAGGGTGTCCAAGACTACATCAATA

ATGAGCTGATACCGTCTATGAACCAACTATCTTGTGATTTAATCGGCCAGAAGCT

CGGGCTCAAATTGCTCAGATACTATACAGAAATCCTGTCATTATTTGGCCCCAGT

TTACGGGACCCCATATCTGCGGAGATATCTATCCAGGCTTTGAGCTATGCGCTTG

GAGGAGACATCAATAAGGTGTTAGAAAAGCTCGGATACAGTGGAGGTGATTTAC

TGGGCATCTTAGAGAGCGGAGGAATAAAGGCCCGGATAACTCACGTCGACACAG

AGTCCTACTTCATTGTCCTCAGTATAGCCTATCCGACGCTGTCCGAGATTAAGGG

GGTGATTGTCCACCGGCTAGAGGGGGTCTCGTACAACATAGGCTCTCAAGAGTG

GTATACCACTGTGCCCAAGTATGTTGCAACCCAAGGGTACCTTATCTCGAATTTT

GATGAGTCATCGTGTACTTTCATGCCAGAGGGGACTGTGTGCAGCCAAAATGCCT

TGTACCCGATGAGTCCTCTGCTCCAAGAATGCCTCCGGGGGTACACCAAGTCCTG

TGCTCGTACACTCGTATCCGGGTCTTTTGGGAACCGGTTCATTTTATCACAAGGG

AACCTAATAGCCAATTGTGCATCAATCCTTTGCAAGTGTTACACAACAGGAACG

ATCATTAATCAAGACCCTGACAAGATCCTAACATACATTGCTGCCGATCACTGCC

CGGTAGTCGAGGTGAACGGCGTGACCATCCAAGTCGGGAGCAGGAGGTATCCAG

ACGCTGTGTACTTGCACAGAATTGACCTCGGTCCTCCCATATCATTGGAGAGGTT

GGACGTAGGGACAAATCTGGGGAATGCAATTGCTAAGTTGGAGGATGCCAAGGA

ATTGTTGGAGTCATCGGACCAGATATTGAGGAGTATGAAAGGTTTATCGAGCAC

TAGCATAGTCTACATCCTGATTGCAGTGTGTCTTGGAGGGTTGATAGGGATCCCC

GCTTTAATATGTTGCTGCAGGGGCGTTGTAACAAAAAGGGAGAACAAGTTGGT

ATGTCAAGACCAGGCCTAAAGCCTGATCTTACGGGAACATCAAAATCCTATGTA

AGGTCGCTCTGATCCTCTACAACTCTTGAAACACAAATGTCCCACAAGTCTCCTC

TTCGTCATCAAGCAACCACCGCACCCAGCATCAAGCCCACCTGAAATTATCTCCG

GCTTCCCTCTGGCCGAACAATATCGGTAGTTAATTAAAACTTAGGGTGCAAGATC

ATCGATAATGTCACCACAACGAGACCGGATAAATGCCTTCTACAAAGATAACCC

CCATCCCAAGGGAAGTAGGATAGTCATTAACAGAGAACATCTTATGATTGATAG

ACCTTATGTTTTGCTGGCTGTTCTGTTTGTCATGTTTCTGAGCTTGATCGGGTTGC
```

-continued

```
TAGCCATTGCAGGAATTCGACTTCATCGGGCAGCCATCTACACCGCAGAGATCC

ATAAAAGCCTCAGCACCAATCTAGATGTAACTAACTCAATCGAGCATCAGGTCA

AGGACGTGCTGACACCACTCTTCAAAATCATCGGTGATGAAGTGGGCCTGAGGA

CACCTCAGAGATTCACTGACCTAGTGAAATTAATCTCTGACAAGATTAAATTCCT

TAATCCGGATAGGGAGTACGACTTCAGAGATCTCACTTGGTGTATCAACCCGCCA

GAGAGAATCAAATTGGATTATGATCAATACTGTGCAGATGTGGCTGCTGAAGAG

CTCATGAATGCATTGGTGAACTCAACTCTACTGGAGACCAGAACAACCAATCAG

TTCCTAGCTGTCTCAAAGGGAAACTGCTCAGGGCCCACTACAATCAGAGGTCAA

TTCTCAAACATGTCGCTGTCCCTGTTAGACTTGTATTTAGGTCGAGGTTACAATGT

GTCATCTATAGTCACTATGACATCCCAGGGAATGTATGGGGGAACTTACCTAGTG

GAAAAGCCTAATCTGAGCAGCAAAAGGTCAGAGTTGTCACAACTGAGCATGTAC

CGAGTGTTTGAAGTAGGTGTTATCAGAAATCCGGGTTTGGGGGCTCCGGTGTTCC

ATATGACAAACTATCTTGAGCAACCAGTCAGTAATGATCTCAGCAACTGTATGGT

GGCTTTGGGGGAGCTCAAACTCGCAGCCCTTTGTCACGGGGAAGATTCTATCACA

ATTCCCTATCAGGGATCAGGGAAAGGTGTCAGCTTCCAGCTCGTCAAGCTAGGT

GTCTGGAAATCCCCAACCGACATGCAATCCTGGGTCCCCTTATCAACGGATGATC

CAGTGATAGACAGGCTTTACCTCTCATCTCACAGAGGTGTTATCGCTGACAACCA

AGCAAAATGGGCTGTCCCGACAACACGAACAGATGACAAGTTGCGAATGGAGA

CATGCTTCCAACAGGCGTGTAAGGGTAAAATCCAAGCACTCTGCGAGAATCCCG

AGTGGGCACCATTGAAGGATAACAGGATTCCTTCATACGGGGTCTTGTCTGTTGA

TCTGAGTCTGACAGTTGAGCTTAAAATCAAAATTGCTTCGGGATTCGGGCCATTG

ATCACACACGGTTCAGGGATGGACCTATACAAATCCAACCACAACAATGTGTAT

TGGCTGACTATCCCGCCAATGAAGAACCTAGCCTTAGGTGTAATCAACACATTGG

AGTGGATACCGAGATTCAAGGTTAGTCCCTACCTCTTCACTGTCCCAATTAAGGA

AGCAGGCGAAGACTGCCATGCCCCAACATACCTACCTGCGGAGGTGGATGGTGA

TGTCAAACTCAGTTCCAATCTGGTGATTCTACCTGGTCAAGATCTCCAATATGTTT

TGGCAACCTACGATACTTCCAGGGTTGAACATGCTGTGGTTTATTACGTTTACAG

CCCAAGCCGCTCATTTTCTTACTTTTATCCTTTTAGGTTGCCTATAAAGGGGGTCC

CCATCGAATTACAAGTGGAATGCTTCACATGGGACCAAAAACTCTGGTGCCGTC

ACTTCTGTGTGCTTGCGGACTCAGAATCTGGTGGACATATCACTCACTCTGGGAT

GGTGGGCATGGGAGTCAGCTGCACAGTCACCCGGGAAGATGGAACCAATCGCA

GATAGGGCTGCTAGTGAACCAATCACATGATGTCACCCAGACATCAGGCATACC

CACCATCCATCATTGTTATAAAAAACTTAGGAACCAGGTCCACACAGAGTGATA

CGCGTACGCCACCATGTTCGTGTTTCTGGTGCTGCTGCCTCTGGTGAGCTCCCAG

TGCGTGAACCTGACCACAAGGACCCAGCTGCCCCCTGCCTATACCAATTCCTTCA

CACGGGGCGTGTACTATCCCGACAAGGTGTTCCGGAGCAGCGTGCTGCACTCCA

CACAGGATCTGTTTCTGCCTTTCTTTTCTAACGTGACCTGGTTCCACGCCATCCAC

GTGAGCGGCACCAATGGCACAAAGCGGTTCGACAATCCAGTGCTGCCCTTTAAC

GATGGCGTGTACTTCGCCTCCACCGAGAAGTCTAACATCATCAGAGGCTGGATCT

TTGGCACCACACTGGACAGCAAGACACAGTCCCTGCTGATCGTGAACAATGCCA

CCAACGTGGTCATCAAGGTGTGCGAGTTCCAGTTTTGTAATGATCCATTCCTGGG
```

```
CGTGTACTATCACAAGAACAATAAGTCTTGGATGGAGAGCGAGTTTCGCGTGTA
TTCCTCTGCCAACAATTGCACATTTGAGTACGTGTCCCAGCCCTTCCTGATGGAC
CTGGAGGGCAAGCAGGGCAATTTCAAGAACCTGAGGGAGTTCGTGTTTAAGAAT
ATCGATGGCTACTTCAAAATCTACTCCAAGCACACCCCAATCAACCTGGTGCGCG
ACCTGCCACAGGGCTTCTCTGCCCTGGAGCCACTGGTGGATCTGCCCATCGGCAT
CAACATCACCCGGTTTCAGACACTGCTGGCCCTGCACAGAAGCTACCTGACACC
AGGCGACAGCTCCTCTGGATGGACCGCAGGAGCAGCAGCCTACTATGTGGGCTA
TCTGCAGCCCAGGACCTTCCTGCTGAAGTACAACGAGAATGGCACCATCACAGA
CGCCGTGGATTGCGCCCTGGATCCCCTGTCTGAGACCAAGTGTACACTGAAGAG
CTTTACCGTGGAGAAGGGCATCTATCAGACAAGCAATTTCAGGGTGCAGCCTAC
CGAGTCCATCGTGCGCTTTCCCAATATCACAAACCTGTGCCCTTTTGGCGAGGTG
TTCAACGCAACCCGCTTCGCCAGCGTGTACGCCTGGAATAGGAAGCGCATCTCC
AACTGCGTGGCCGACTATTCTGTGCTGTACAACAGCGCCTCCTTCTCTACCTTTA
AGTGCTATGGCGTGAGCCCCACAAAGCTGAATGACCTGTGCTTTACCAACGTGTA
CGCCGATTCCTTCGTGATCAGGGGCGACGAGGTGCGCCAGATCGCACCAGGACA
GACAGGCAAGATCGCAGACTACAATTATAAGCTGCCTGACGATTTCACCGGCTG
CGTGATCGCCTGGAACTCTAACAATCTGGATAGCAAAGTGGGCGGCAACTACAA
TTATCTGTACCGGCTGTTTAGAAAGTCTAATCTGAAGCCATTCGAGAGGGACATC
TCCACAGAAATCTACCAGGCCGGCTCTACCCCCTGCAATGGCGTGGAGGGCTTT
AACTGTTATTTCCCTCTGCAGAGCTACGGCTTCCAGCCAACAAACGGCGTGGGCT
ATCAGCCCTACCGCGTGGTGGTGCTGTCTTTTGAGCTGCTGCACGCACCTGCAAC
AGTGTGCGGACCAAAGAAGAGCACCAATCTGGTGAAGAACAAGTGCGTGAACTT
CAACTTCAACGGACTGACCGGAACAGGCGTGCTGACCGAGTCCAACAAGAAGTT
CCTGCCTTTTCAGCAGTTCGGCAGGGACATCGCAGATACCACAGACGCCGTGCG
CGACCCTCAGACCCTGGAGATCCTGGACATCACACCATGCTCCTTCGGCGGCGTG
TCTGTGATCACACCAGGCACCAATACAAGCAACCAGGTGGCCGTGCTGTATCAG
GACGTGAATTGTACCGAGGTGCCAGTGGCAATCCACGCAGATCAGCTGACCCCT
ACATGGCGGGTGTACTCTACCGGCAGCAACGTGTTCCAGACAAGAGCCGGATGC
CTGATCGGAGCAGAGCACGTGAACAATAGCTATGAGTGCGACATCCCTATCGGC
GCCGGCATCTGTGCCTCCTACCAGACCCAGACAAACTCCCCAAGGAGAGCACGG
TCTGTGGCCAGCCAGTCCATCATCGCCTATACCATGAGCCTGGGCGCCGAGAATT
CCGTGGCCTACTCCAACAATTCTATCGCCATCCCTACCAACTTCACAATCTCCGT
GACCACAGAGATCCTGCCAGTGAGCATGACCAAGACATCCGTGGACTGCACAAT
GTATATCTGTGGCGATTCCACCGAGTGCTCTAACCTGCTGCTGCAGTACGGCTCT
TTTTGTACCCAGCTGAATAGAGCCCTGACAGGCATCGCCGTGGAGCAGGACAAG
AACACACAGGAGGTGTTCGCCCAGGTGAAGCAAATCTACAAGACCCCACCCATC
AAGGACTTTGGCGGCTTCAACTTCAGCCAGATCCTGCCCGATCCTAGCAAGCCAT
CCAAGCGGTCTTTTATCGAGGACCTGCTGTTCAACAAGGTGACCCTGGCCGATGC
CGGCTTCATCAAGCAGTATGGCGATTGCCTGGGCGACATCGCCGCCAGAGACCT
GATCTGTGCCCAGAAGTTTAATGGCCTGACCGTGCTGCCTCCACTGCTGACAGAT
```

-continued

```
GAGATGATCGCCCAGTACACATCTGCCCTGCTGGCCGGAACCATCACAAGCGGA
TGGACCTTCGGCGCAGGAGCCGCCCTGCAGATCCCCTTTGCCATGCAGATGGCCT
ATCGGTTCAACGGCATCGGCGTGACCCAGAATGTGCTGTACGAGAACCAGAAGC
TGATCGCCAATCAGTTTAACTCCGCCATCGGCAAGATCCAGGACTCTCTGAGCTC
CACAGCCAGCGCCCTGGGCAAGCTGCAGGATGTGGTGAATCAGAACGCCCAGGC
CCTGAATACCCTGGTGAAGCAGCTGTCTAGCAACTTCGGCGCCATCTCCTCTGTG
CTGAATGACATCCTGAGCCGGCTGGACAAGGTGGAGGCAGAGGTGCAGATCGAC
CGGCTGATCACAGGCAGACTGCAGTCCCTGCAGACCTACGTGACACAGCAGCTG
ATCAGGGCAGCAGAGATCAGGGCCTCTGCCAATCTGGCCGCCACCAAGATGAGC
GAGTGCGTGCTGGGCCAGTCCAAGAGAGTGGACTTTTGTGGCAAGGGCTATCAC
CTGATGAGCTTCCCACAGTCCGCCCCTCACGGAGTGGTGTTTCTGCACGTGACCT
ACGTGCCAGCCCAGGAGAAGAACTTCACCACAGCACCAGCAATCTGCCACGATG
GCAAGGCACACTTTCCTAGGGAGGGCGTGTTCGTGAGCAACGGCACCCACTGGT
TTGTGACACAGCGCAATTTCTACGAGCCACAGATCATCACCACAGACAATACAT
TCGTGTCCGGCAACTGTGACGTGGTCATCGGCATCGTGAACAATACCGTGTATGA
TCCTCTGCAGCCAGAGCTGGACTCTTTTAAGGAGGAGCTGGATAAGTACTTCAAG
AATCACACCAGCCCCGACGTGGATCTGGGCGACATCTCTGGCATCAATGCCAGC
GTGGTGAACATCCAGAAGGAGATCGACAGGCTGAACGAGGTGGCCAAGAATCT
GAACGAGTCCCTGATCGATCTGCAGGAGCTGGGCAAGTATGAGCAGTACATCAA
GTGGCCCTGGTATATCTGGCTGGGCTTCATCGCCGGCCTGATCGCCATCGTGATG
GTGACCATCATGCTGTGCTGTATGACAAGCTGCTGTTCCTGCCTGAAGGGCTGCT
GTTCTTGTGGCAGCTGCTGTAAGTTTGATGAGGACGATAGCGAGCCTGTGCTGAA
GGGCGTGAAGCTGCACTACACCTGAGCTAGCGATCGCACTAGTGTGAAATAGAC
ATCAGAATTAAGAAAAACGTAGGGTCCAAGTGGTTCCCCGTTATGGACTCGCTA
TCTGTCAACCAGATCTTATACCCTGAAGTTCACCTAGATAGCCCGATAGTTACCA
ATAAGATAGTAGCCATCCTGGAGTATGCTCGAGTCCCTCACGCTTACAGCCTGGA
GGACCCTACACTGTGTCAGAACATCAAGCACCGCCTAAAAAACGGATTTTCCAA
CCAAATGATTATAAACAATGTGGAAGTTGGGAATGTCATCAAGTCCAAGCTTAG
GAGTTATCCGGCCCACTCTCATATTCCATATCCAAATTGTAATCAGGATTTATTTA
ACATAGAAGACAAAGAGTCAACGAGGAAGATCCGTGAACTCCTCAAAAAGGGG
AATTCGCTGTACTCCAAAGTCAGTGATAAGGTTTTCCAATGCTTAAGGGACACTA
ACTCACGGCTTGGCCTAGGCTCCGAATTGAGGGAGGACATCAAGGAGAAAGTTA
TTAACTTGGGAGTTTACATGCACAGCTCCCAGTGGTTTGAGCCCTTTCTGTTTTGG
TTTACAGTCAAGACTGAGATGAGGTCAGTGATTAAATCACAAACCCATACTTGCC
ATAGGAGGAGACACACACCTGTATTCTTCACTGGTAGTTCAGTTGAGTTGCTAAT
CTCTCGTGACCTTGTTGCTATAATCAGTAAAGAGTCTCAACATGTATATTACCTG
ACATTTGAACTGGTTTTGATGTATTGTGATGTCATAGAGGGGAGGTTAATGACAG
AGACCGCTATGACTATTGATGCTAGGTATACAGAGCTTCTAGGAAGAGTCAGAT
ACATGTGGAAACTGATAGATGGTTTCTTCCCTGCACTCGGGAATCCAACTTATCA
AATTGTAGCCATGCTGGAGCCTCTTTCACTTGCTTACCTGCAGCTGAGGGATATA
ACAGTAGAACTCAGAGGTGCTTTCCTTAACCACTGCTTTACTGAAATACATGATG
```

-continued

```
TTCTTGACCAAAACGGGTTTTCTGATGAAGGTACTTATCATGAGTTAACTGAAGC
TCTAGATTACATTTTCATAACTGATGACATACATCTGACAGGGGAGATTTTCTCA
TTTTTCAGAAGTTTCGGCCACCCCAGACTTGAAGCAGTAACGGCTGCTGAAAATG
TTAGGAAATACATGAATCAGCCTAAAGTCATTGTGTATGAGACTCTGATGAAAG
GTCATGCCATATTTTGTGGAATCATAATCAACGGCTATCGTGACAGGCACGGAG
GCAGTTGGCCACCGCTGACCCTCCCCCTGCATGCTGCAGACACAATCCGGAATG
CTCAAGCTTCAGGTGAAGGGTTAACACATGAGCAGTGCGTTGATAACTGGAAAT
CTTTTGCTGGAGTGAAATTTGGCTGCTTTATGCCTCTTAGCCTGGATAGTGATCTG
ACAATGTACCTAAAGGACAAGGCACTTGCTGCTCTCCAAAGGGAATGGGATTCA
GTTTACCCGAAAGAGTTCCTGCGTTACGACCCTCCCAAGGGAACCGGGTCACGG
AGGCTTGTAGATGTTTTCCTTAATGATTCGAGCTTTGACCCATATGATGTGATAA
TGTATGTTGTAAGTGGAGCTTACCTCCATGACCCTGAGTTCAACCTGTCTTACAG
CCTGAAAGAAAAGGAGATCAAGGAAACAGGTAGACTTTTTGCTAAAATGACTTA
CAAAATGAGGGCATGCCAAGTGATTGCTGAAAATCTAATCTCAAACGGGATTGG
CAAATATTTTAAGGACAATGGGATGGCCAAGGATGAGCACGATTTGACTAAGGC
ACTCCACACTCTAGCTGTCTCAGGAGTCCCCAAAGATCTCAAAGAAAGTCACAG
GGGGGGGCCAGTCTTAAAAACCTACTCCCGAAGCCCAGTCCACACAAGTACCAG
GAACGTGAGAGCAGCAAAAGGGTTTATAGGGTTCCCTCAAGTAATTCGGCAGGA
CCAAGACACTGATCATCCGGAGAATATGGAAGCTTACGAGACAGTCAGTGCATT
TATCACGACTGATCTCAAGAAGTACTGCCTTAATTGGAGATATGAGACCATCAGC
TTGTTTGCACAGAGGCTAAATGAGATTTACGGATTGCCCTCATTTTTCCAGTGGC
TGCATAAGAGGCTTGAGACCTCTGTCCTGTATGTAAGTGACCCTCATTGCCCCCC
CGACCTTGACGCCCATATCCCGTTATATAAAGTCCCCAATGATCAAATCTTCATT
AAGTACCCTATGGGAGGTATAGAAGGGTATTGTCAGAAGCTGTGGACCATCAGC
ACCATTCCCTATCTATACCTGGCTGCTTATGAGAGCGGAGTAAGGATTGCTTCGT
TAGTGCAAGGGGACAATCAGACCATAGCCGTAACAAAAAGGGTACCCAGCACA
TGGCCCTACAACCTTAAGAAACGGGAAGCTGCTAGAGTAACTAGAGATTACTTT
GTAATTCTTAGGCAAAGGCTACATGATATTGGCCATCACCTCAAGGCAAATGAG
ACAATTGTTTCATCACATTTTTTTGTCTATTCAAAAGGAATATATTATGATGGGCT
ACTTGTGTCCCAATCACTCAAGAGCATCGCAAGATGTGTATTCTGGTCAGAGACT
ATAGTTGATGAAACAAGGGCAGCATGCAGTAATATTGCTACAACAATGGCTAAA
AGCATCGAGAGAGGTTATGACCGTTACCTTGCATATTCCCTGAACGTCCTAAAAG
TGATACAGCAAATTCTGATCTCTCTTGGCTTCACAATCAATTCAACCATGACCCG
GGATGTAGTCATACCCCTCCTCACAAACAACGACCTCTTAATAAGGATGGCACT
GTTGCCCGCTCCTATTGGGGGATGAATTATCTGAATATGAGCAGGCTGTTTGTC
AGAAACATCGGTGATCCAGTAACATCATCAATTGCTGATCTCAAGAGAATGATT
CTCGCCTCACTAATGCCTGAAGAGACCCTCCATCAGGTAATGACACAACAACCG
GGGGACTCTTCATTCCTAGACTGGGCTAGCGACCCTTACTCAGCAAATCTTGTAT
GTGTCCAGAGCATCACTAGACTCCTCAAGAACATAACTGCAAGGTTTGTCCTGAT
CCATAGTCCAAACCCAATGTTAAAAGGATTATTCCATGATGACAGTAAAGAAGA
```

-continued

```
GGACGAGGGACTGGCGGCATTCCTCATGGACAGGCATATTATAGTACCTAGGGC

AGCTCATGAAATCCTGGATCATAGTGTCACAGGGGCAAGAGAGTCTATTGCAGG

CATGCTGGATACCACAAAAGGCTTGATTCGAGCCAGCATGAGGAAGGGGGGTTT

AACCTCTCGAGTGATAACCAGATTGTCCAATTATGACTATGAACAATTCAGAGCA

GGGATGGTGCTATTGACAGGAAGAAAGAGAAATGTCCTCATTGACAAAGAGTCA

TGTTCAGTGCAGCTGGCGAGAGCTCTAAGAAGCCATATGTGGGCGAGGCTAGCT

CGAGGACGGCCTATTTACGGCCTTGAGGTCCCTGATGTACTAGAATCTATGCGAG

GCCACCTTATTCGGCGTCATGAGACATGTGTCATCTGCGAGTGTGGATCAGTCAA

CTACGGATGGTTTTTTGTCCCCTCGGGTTGCCAACTGGATGATATTGACAAGGAA

ACATCATCCTTGAGAGTCCCATATATTGGTTCTACCACTGATGAGAGAACAGACA

TGAAGCTTGCCTTCGTAAGAGCCCCAAGTCGATCCTTGCGATCTGCTGTTAGAAT

AGCAACAGTGTACTCATGGGCTTACGGTGATGATGATAGCTCTTGGAACGAAGC

CTGGTTGTTGGCTAGGCAAAGGGCCAATGTGAGCCTGGAGGAGCTAAGGGTGAT

CACTCCCATCTCAACTTCGACTAATTTAGCGCATAGGTTGAGGGATCGTAGCACT

CAAGTGAAATACTCAGGTACATCCCTTGTCCGAGTGGCGAGGTATACCACAATCT

CCAACGACAATCTCTCATTTGTCATATCAGATAAGAAGGTTGATACTAACTTTAT

ATACCAACAAGGAATGCTTCTAGGGTTGGGTGTTTTAGAAACATTGTTTCGACTC

GAGAAAGATACCGGATCATCTAACACGGTATTACATCTTCACGTCGAAACAGAT

TGTTGCGTGATCCCGATGATAGATCATCCCAGGATACCCAGCTCCCGCAAGCTAG

AGCTGAGGGCAGAGCTATGTACCAACCCATTGATATATGATAATGCACCTTTAAT

TGACAGAGATGCAACAAGGCTATACACCCAGAGCCATAGGAGGCACCTTGTGGA

ATTTGTTACATGGTCCACACCCCAACTATATCACATTTTAGCTAAGTCCACAGCA

CTATCTATGATTGACCTGGTAACAAAATTTGAGAAGGACCATATGAATGAAATTT

CAGCTCTCATAGGGGATGACGATATCAATAGTTTCATAACTGAGTTTCTGCTCAT

AGAGCCAAGATTATTCACTATCTACTTGGGCCAGTGTGCGGCCATCAATTGGGCA

TTTGATGTACATTATCATAGACCATCAGGGAAATATCAGATGGGTGAGCTGTTGT

CATCGTTCCTTTCTAGAATGAGCAAAGGAGTGTTTAAGGTGCTTGTCAATGCTCT

AAGCCACCCAAAGATCTACAAGAAATTCTGGCATTGTGGTATTATAGAGCCTATC

CATGGTCCTTCACTTGATGCTCAAAACTTGCACACAACTGTGTGCAACATGGTTT

ACACATGCTATATGACCTACCTCGACCTGTTGTTGAATGAAGAGTTAGAAGAGTT

CACATTTCTCTTGTGTGAAAGCGACGAGGATGTAGTACCGGACAGATTCGACAA

CATCCAGGCAAAACACTTATGTGTTCTGGCAGATTTGTACTGTCAACCAGGGACC

TGCCCACCAATTCGAGGTCTAAGACCGGTAGAGAAATGTGCAGTTCTAACCGAC

CATATCAAGGCAGAGGCTATGTTATCTCCAGCAGGATCTTCGTGGAACATAAATC

CAATTATTGTAGACCATTACTCATGCTCCCTGACTTATCTCCGGCGAGGATCGAT

CAAACAGATAAGATTGAGAGTTGATCCAGGATTCATTTTCGACGCCCTCGCTGAG

GTAAATGTCAGTCAGCCAAAGATCGGCAGCAACAACATCTCAAATATGAGCATC

AAGGCTTTCAGACCCCCACACGATGATGTTGCAAAATTGCTCAAAGATATCAAC

ACAAGCAAGCACAATCTTCCCATTTCAGGGGGCAATCTCGCCAATTATGAAATC

CATGCTTTCCGCAGAATCGGGTTGAACTCATCTGCTTGCTACAAAGCTGTTGAGA

TATCAACATTAATTAGGAGATGCCTTGAGCCAGGGGAGGACGGCTTGTTCTTGG
```

-continued

```
GTGAGGGATCGGGTTCTATGTTGATCACTTATAAGGAGATACTTAAACTAAACA

AGTGCTTCTATAATAGTGGGGTTTCCGCCAATTCTAGATCTGGTCAAAGGGAATT

AGCACCCTATCCCTCCGAAGTTGGCCTTGTCGAACACAGAATGGGAGTAGGTAA

TATTGTCAAAGTGCTCTTTAACGGGAGGCCCGAAGTCACGTGGGTAGGCAGTGT

AGATTGCTTCAATTTCATAGTTAGTAATATCCCTACCTCTAGTGTGGGGTTTATCC

ATTCAGATATAGAGACCTTGCCTGACAAAGATACTATAGAGAAGCTAGAGGAAT

TGGCAGCCATCTTATCGATGGCTCTGCTCCTGGGCAAAATAGGATCAATACTGGT

GATTAAGCTTATGCCTTTCAGCGGGGATTTTGTTCAGGGATTTATAAGTTATGTA

GGGTCTCATTATAGAGAAGTGAACCTTGTATACCCTAGATACAGCAACTTCATAT

CTACTGAATCTTATTTGGTTATGACAGATCTCAAGGCTAACCGGCTAATGAATCC

TGAAAAGATTAAGCAGCAGATAATTGAATCATCTGTGAGGACTTCACCTGGACT

TATAGGTCACATCCTATCCATTAAGCAACTAAGCTGCATACAAGCAATTGTGGGA

GACGCAGTTAGTAGAGGTGATATCAATCCTACTCTGAAAAAACTTACACCTATA

GAGCAGGTGCTGATCAATTGCGGGTTGGCAATTAACGGACCTAAGCTGTGCAAA

GAATTGATCCACCATGATGTTGCCTCAGGGCAAGATGGATTGCTTAATTCTATAC

TCATCCTCTACAGGGAGTTGGCAAGATTCAAAGACAACCAAAGAAGTCAACAAG

GGATGTTCCACGCCTACCCCGTATTGGTAAGTAGCAGGCAACGAGAACTTATATC

TAGGATCACCCGCAAATTTTGGGGGCACATTCTTCTTTACTCCGGGAACAAAAAG

TTGATAAATAAGTTTATCCAGAATCTCAAGTCCGGCTATCTGATACTAGACTTAC

ACCAGAATATCTTCGTTAAGAATCTATCCAAGTCAGAGAAACAGATTATTATGAC

GGGGGGTTTGAAACGTGAGTGGGTTTTTAAGGTAACAGTCAAGGAGACCAAAGA

ATGGTATAAGTTAGTCGGATACAGTGCCCTGATTAAGGACTAATTGGTTGAACTC

CGGAACCCTAATCCTGCCCTAGGTGGTTAGGCATTATTTGCAATATATTAAAGAA

AACTTTGAAAATACGAAGTTTCTATTCCCAGCTTTGTCTGGTggccggcatAgtcccagcct cctcgctggcgctggctgggcaacattccgaggggaccgtccccAcggtaatggcgaatgggacgcggccgatccggctgctaa caaagcccgaaaggaagctgagttggctgctgGcGcTGgctgGgcaataactagcataacccctTgggCCTctaaacgggtct tgaggggttttttgctgaaaggaggaactatatccggatgcGGCCGCGCGCTTGGCGTAATCATGGTCATA

GCTGTTTCCTGTGTGAAATTGTTATCCGCTCACAATTCCACACAACATACGAGCC

GGAAGCATAAAGTGTAAAGCCTGGGGTGCCTAATGAGTGAGCTAACTCACATTA

ATTGCGTTGCGCTCACTGCCCGCTTTCCAGTCGGGAAACCTGTCGTGCCAGCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGT
```

-continued

```
CCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTA

ACTACGGCTACACTAGAAGGACAGTATTTGGTATCTGCGCTCTGCTGAAGCCAGT

TACCTTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAGGATCT

CAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTAT

TTCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAA

GTGGTCCTGCAACTTTATCCGCCTCCATCCAGTCTATTAATTGTTGCCGGGAAGC

TAGAGTAAGTAGTTCGCCAGTTAATAGTTTGCGCAACGTTGTTGCCATTGCTACA

GGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCT

CCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACC

GAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTT

CAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCT

TCCTTTTTCAATATTATTGAAGCATTTATCAGGGTTATTGTCTCATGAGCGGATAC

ATATTTGAATGTATTTAGAAAAATAAACAAATAGGGGTTCCGCGCACATTTCCCC

GAAAAGTGCCACCTG.
```

In one embodiment, the nucleic acid comprises the sequence of SEQ ID NO: 6, shown below (RABV vector: Coravax V1-China (RABVG-E31)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC
```

```
TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT
```

-continued

```
GGGCGGCAACTACAATTATCTGTACCGGCTGTTTAGAAAGTCTAATCTGAAGCCA
TTCGAGAGGGACATCTCCACAGAAATCTACCAGGCCGGCTCTACCCCCTGCAAT
GGCGTGGAgGGCTTTAACTGTTATTTCCCTCTGCAGAgCTACgGCTTCCAGCCAAC
AAACGGCGTGGGCTATCAGCCCTACCGCGTGGTGGTGCTGTCTTTTGAGCTGCTG
CACGCACcTGCAACAGTGTGCGGACCAAAGAAGAGCACCAATCTGGTGAAGAAC
AAGTGCGTGAACTTCAACTTCAACGGACTGACCGGAACAGGCGTGCTGACCGAG
TCCAACAAGAAGTTCCTGCCTTTTCAGCAGTTCGGCAGGGACATCGCAGATACC
ACAGACGCCGTGCGCGACCCTCAGACCCTGGAGATCCTGGACATCACACCATGC
TCCTTCGGCGGCGTGTCTGTGATCACACCAGGCACCAATACAAGCAACCAGGTG
GCCGTGCTGTATCAGGACGTGAATTGTACCGAGGTGCCAGTGGCAATCCACGCA
GATCAGCTGACCCCTACATGGCGGGTGTACTCTACCGGCAGCAACGTGTTCCAG
ACAAGAGCCGGATGCCTGATCGGAGCAGAGCACGTGAACAATAGCTATGAGTGC
GACATCCCTATCGGCGCCGGCATCTGTGCCTCCTACCAGACCCAGACAAACTCCC
CAAGGTCTGTGGGAGATGAGGCCGAAGACTTTGTGGAAGTCCACCTGCCTGATG
TGCATAACCAGGTGTCTGGCGTCGACCTGGGACTGCCAAATTGGGGCAAGTACG
TGCTGCTGAGTGCTGGAGCACTGACTGCCCTGATGCTGATCATTTTCCTGATGAC
CTGCTGTCGGCGCGTGAACAGAAGTGAGCCCACTCAGCACAATCTGCGAGGAAC
CGGGAGAGAAGTGTCAGTCACACCTCAGAGCGGGAAAATCATTAGTAGTTGGGA
ATCACATAAAAGCGGGGCGAGACCAGGCTGTGAGCTAGCCATGAAAAAAACT
AACACCCCTCCTTTCGAACCATCCCAAACATGAGCAAGATCTTTGTCAATCCTAG
TGCTATTAGAGCCGGTCTGGCCGATCTTGAGATGGCTGAAGAAACTGTTGATCTG
ATCAATAGAAATATCGAAGACAATCAGGCTCATCTCCAAGGGGAACCCATAGAG
GTGGACAATCTCCCTGAGGATATGGGGCGACTTCACCTGGATGATGGAAAATCG
CCCAACCATGGTGAGATAGCCAAGGTGGGAGAAGGCAAGTATCGAGAGGACTTT
CAGATGGATGAAGGAGAGGATCCTAGCTTCCTGTTCCAGTCATACCTGGAAAAT
GTTGGAGTCCAAATAGTCAGACAAATGAGGTCAGGAGAGAGATTTCTCAAGATA
TGGTCACAGACCGTAGAAGAGATTATATCCTATGTCGCGGTCAACTTTCCCAACC
CTCCAGGAAAGTCTTCAGAGGATAAATCAACCCAGACTACTGGCCGAGAGCTCA
AGAAGGAGACAACACCCACTCCTTCTCAGAGAGAAAGCCAATCATCGAAAGCCA
GGATGGCGGCTCAAATTGCTTCTGGCCCTCCAGCCCTTGAATGGTCGGCTACCAA
TGAAGAGGATGATCTATCAGTGGAGGCTGAGATCGCTCACCAGATTGCAGAAAG
TTTCTCCAAAAAATATAAGTTTCCCTCTCGATCCTCAGGGATACTCTTGTATAATT
TTGAGCAATTGAAAATGAACCTTGATGATATAGTTAAAGAGGCAAAAAATGTAC
CAGGTGTGACCCGTTTAGCCCATGACGGGTCCAAACTCCCCCTAAGATGTGTACT
GGGATGGGTCGCTTTGGCCAACTCTAAGAAATTCCAGTTGTTAGTCGAATCCGAC
AAGCTGAGTAAAATCATGCAAGATGACTTGAATCGCTATACATCTTGCTAACCG
AACCTCTCCCCTCAGTCCCTCTAGACAATAAAATCCGAGATGTCCCAAAGTCAAC
ATGAAAAAAACAGGCAACACCACTGATAAAATGAACCTCCTACGTAAGATAGTG
AAAAACCGCAGGGACGAGGACACTCAAAAATCCTCTCCCGCGTCAGCCCCTCTG
GATGACGATGACTTGTGGCTTCCACCCCCTGAATACGTCCCGCTGAAAGAACTTA
```

-continued

```
CAGGCAAGAAGAACATGAGGAACTTTTGTATCAACGGAAGGGTTAAAGTGTGTA

GCCCGAATGGTTACTCGTTCAGGATCCTGCGGCACATTCTGAAATCATTCGACGA

GATATATTCTGGGAATCATAGGATGATCGGGTTAGTCAAAGTGGTTATTGGACTG

GCTTTGTCAGGATCTCCAGTCCCTGAGGGCCTGAACTGGGTATACAAATTGAGGA

GAACCTTTATCTTCCAGTGGGCTGATTCCAGGGGCCCTCTTGAAGGGGAGGAGTT

GGAATACTCTCAGGAGATCACTTGGGATGATGATACTGAGTTCGTCGGATTGCA

AATAAGAGTGATTGCAAAACAGTGTCATATCCAGGGCAGAGTCTGGTGTATCAA

CATGAACCCGAGAGCATGTCAACTATGGTCTGACATGTCTCTTCAGACACAAAG

GTCCGAAGAGGACAAAGATTCCTCTCTGCTTCTAGAATAATCAGATTATATCCCG

CAAATTTATCACTTGTTTACCTCTGGAGGAGAGAACATATGGGCTCAACTCCAAC

CCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAAA

CTATTAACATCCCTCAAAAGACcccgggAAAGATGGTTCCTCAGGCTCTCCTGTTTG

TACCCCTTCTGGTTTTTCCATTGTGTTTTGGGAAATTCCCTATTTACACGATACCA

GACAAGCTTGGTCCCTGGAGTCCGATTGACATACATCACCTCAGCTGCCCAAAC

AATTTGGTAGTGGAGGACGAAGGATGCACCAACCTGTCAGGGTTCTCCTACATG

GAACTTAAAGTTGGATACATCTTAGCCATAAAAGTGAACGGGTTCACTTGCACA

GGCGTTGTGACGGAGGCTGAAACCTACACTAACTTCGTTGGTTATGTCACAACCA

CGTTCAAAAGAAAGCATTTCCGCCCAACACCAGATGCATGTAGAGCCGCGTACA

ACTGGAAGATGGCCGGTGACCCCAGATATGAAGAGTCTCTACACAATCCGTACC

CTGACTACCGCTGGCTTCGAACTGTAAAAACCACCAAGGAGTCTCTCGTTATCAT

ATCTCCAAGTGTGGCAGATTTGGACCCATATGACAGATCCCTTCACTCGAGGGTC

TTCCCTAGCGGGAAGTGCTCAGGAGTAGCGGTGTCTTCTACCTACTGCTCCACTA

ACCACGATTACACCATTTGGATGCCCGAGAATCCGAGACTAGGGATGTCTTGTG

ACATTTTTACCAATAGTAGAGGGAAGAGAGCATCCAAAGGGAGTGAGACTTGCG

GCTTTGTAGATGAAAGAGGCCTATATAAGTCTTTAAAAGGAGCATGCAAACTCA

AGTTATGTGGAGTTCTAGGACTTAGACTTATGGATGGAACATGGGTCTCGATGCA

AACATCAAATGAAACCAAATGGTGCCCTCCCGATAAGTTGGTGAACCTGCACGA

CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG
```

-continued

```
AGTGGGGGTGAGACCAGACTGTAAttaattaaCGTCCTTTCAACGATCCAAGTCcatgaaa aaaactaacaccccccgtacctagcTTATAAAGTGCTGGGTCATCTAAGCTTTTCAGTCGAGA

AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG

GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCCATAGAGAAGCTGTTGAATCTCACGCTAGGAAATAGAGGGCTGAG

AATCCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGGAAGGACTTGGTAAAGTTCAAAGACC

AAATATGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC

CTGTATTTATAAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGGCACCCATATATAGATTATCGAAAGGGTC

TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG

GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA
```

-continued

```
GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA

AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT

AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA

GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGGTGT

GGCCTTGCTCTTCAGAGAGGGCAGATCTACTTAGGGAGATCTCTTGGGGAAGAA

AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA

AGTCACTAATGTTCATGTGGTGAAGAGAGCTCTATCGTTAAAAGAATCTATAAAC

TGGTTCATTACTAGAGATTCCAACTTGGCTCAAGCTCTAATTAGGAACATTATGT

CTCTGACAGGCCCTGATTTCCCTCTAGAGGAGGCCCCTGTCTTCAAAAGGACGGG

GTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTT

GACCCAAGACGGGAAGAACTACGATTTCATGTTCCAGCCATTGATGCTTTATGCA

CAGACATGGACATCAGAGCTGGTACAGAGAGACACAAGGCTAAGAGACTCTAC

GTTTCATTGGCACCTCCGATGCAACAGGTGTGTGAGACCCATTGACGACGTGACC

CTGGAGACCTCTCAGATCTTCGAGTTTCCGGATGTGTCGAAAAGAATATCCAGAA

TGGTTTCTGGGGCTGTGCCTCACTTCCAGAGGCTTCCCGATATCCGTCTGAGACC

AGGAGATTTTGAATCTCTAAGCGGTAGAGAAAAGTCTCACCATATCGGATCAGC

TCAGGGGCTCTTATACTCAATCTTAGTGGCAATTCACGACTCAGGATACAATGAT

GGAACCATCTTCCCTGTCAACATATACGGCAAGGTTTCCCCTAGAGACTATTTGA
```

-continued

```
GAGGGCTCGCAAGGGGAGTATTGATAGGATCCTCGATTTGCTTCTTGACAAGAA

TGACAAATATCAATATTAATAGACCTCTTGAATTGGTCTCAGGGGTAATCTCATA

TATTCTCCTGAGGCTAGATAACCATCCCTCCTTGTACATAATGCTCAGAGAACCG

TCTCTTAGAGGAGAGATATTTTCTATCCCTCAGAAAATCCCCGCCGCTTATCCAA

CCACTATGAAAGAAGGCAACAGATCAATCTTGTGTTATCTCCAACATGTGCTACG

CTATGAGCGAGAGATAATCACGGCGTCTCCAGAGAATGACTGGCTATGGATCTT

TTCAGACTTTAGAAGTGCCAAAATGACGTACCTATCCCTCATTACTTACCAGTCT

CATCTTCTACTCCAGAGGGTTGAGAGAAACCTATCTAAGAGTATGAGAGATAAC

CTGCGACAATTGAGTTCTTTGATGAGGCAGGTGCTGGGCGGGCACGGAGAAGAT

ACCTTAGAGTCAGACGACAACATTCAACGACTGCTAAAAGACTCTTTACGAAGG

ACAAGATGGGTGGATCAAGAGGTGCGCCATGCAGCTAGAACCATGACTGGAGAT

TACAGCCCCAACAAGAAGGTGTCCCGTAAGGTAGGATGTTCAGAATGGGTCTGC

TCTGCTCAACAGGTTGCAGTCTCTACCTCAGCAAACCCGGCCCCTGTCTCGGAGC

TTGACATAAGGGCCCTCTCTAAGAGGTTCCAGAACCCTTTGATCTCGGGCTTGAG

AGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGGATAT

CAAGGGCAGTCCTCAACATGTTTCCAGATGCCAAGCTTGTGTTCAACAGTCTTTT

AGAGGTGAATGACCTGATGGCTTCCGGAACACATCCACTGCCTCCTTCAGCAATC

ATGAGGGGAGGAAATGATATCGTCTCCAGAGTGATAGATCTTGACTCAATCTGG

GAAAAACCGTCCGACTTGAGAAACTTGGCAACCTGGAAATACTTCCAGTCAGTC

CAAAAGCAGGTCAACATGTCCTATGACCTCATTATTTGCGATGCAGAAGTTACTG

ACATTGCATCTATCAACCGGATCACCCTGTTAATGTCCGATTTTGCATTGTCTATA

GATGGACCACTCTATTTGGTCTTCAAAACTTATGGGACTATGCTAGTAAATCCAA

ACTACAAGGCTATTCAACACCTGTCAAGAGCGTTCCCCTCGGTCACAGGGTTTAT

CACCCAAGTAACTTCGTCTTTTTCATCTGAGCTCTACCTCCGATTCTCCAAACGA

GGGAAGTTTTTCAGAGATGCTGAGTACTTGACCTCTTCCACCCTTCGAGAAATGA

GCCTTGTGTTATTCAATTGTAGCAGCCCCAAGAGTGAGATGCAGAGAGCTCGTTC

CTTGAACTATCAGGATCTTGTGAGAGGATTTCCTGAAGAAATCATATCAAATCCT

TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG
```

-continued

```
AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAtttttgttgtttatttgttaagcgt.
```

In another embodiment, the nucleic acid comprises the sequence of SEQ ID NO: 7, shown below (RABV vector: Coravax V1-South Africa (RABVG-E31)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG
```

```
-continued
TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCaagGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGCGAGACCAGGCTGTGAGCTAGCCATGAAAAAAACT

AACACCCCTCCTTTCGAACCATCCCAAACATGAGCAAGATCTTTGTCAATCCTAG

TGCTATTAGAGCCGGTCTGGCCGATCTTGAGATGGCTGAAGAAACTGTTGATCTG

ATCAATAGAAATATCGAAGACAATCAGGCTCATCTCCAAGGGGAACCCATAGAG

GTGGACAATCTCCCTGAGGATATGGGCGACTTCACCTGGATGATGGAAAATCG

CCCAACCATGGTGAGATAGCCAAGGTGGGAGAAGGCAAGTATCGAGAGGACTTT
```

-continued

```
CAGATGGATGAAGGAGAGGATCCTAGCTTCCTGTTCCAGTCATACCTGGAAAAT

GTTGGAGTCCAAATAGTCAGACAAATGAGGTCAGGAGAGAGATTTCTCAAGATA

TGGTCACAGACCGTAGAAGAGATTATATCCTATGTCGCGGTCAACTTTCCCAACC

CTCCAGGAAAGTCTTCAGAGGATAAATCAACCCAGACTACTGGCCGAGAGCTCA

AGAAGGAGACAACACCCACTCCTTCTCAGAGAGAAAGCCAATCATCGAAAGCCA

GGATGGCGGCTCAAATTGCTTCTGGCCCTCCAGCCCTTGAATGGTCGGCTACCAA

TGAAGAGGATGATCTATCAGTGGAGGCTGAGATCGCTCACCAGATTGCAGAAAG

TTTCTCCAAAAAATATAAGTTTCCCTCTCGATCCTCAGGGATACTCTTGTATAATT

TTGAGCAATTGAAAATGAACCTTGATGATATAGTTAAAGAGGCAAAAAATGTAC

CAGGTGTGACCCGTTTAGCCCATGACGGGTCCAAACTCCCCCTAAGATGTGTACT

GGGATGGGTCGCTTTGGCCAACTCTAAGAAATTCCAGTTGTTAGTCGAATCCGAC

AAGCTGAGTAAAATCATGCAAGATGACTTGAATCGCTATACATCTTGCTAACCG

AACCTCTCCCCTCAGTCCCTCTAGACAATAAAATCCGAGATGTCCCAAAGTCAAC

ATGAAAAAAACAGGCAACACCACTGATAAAATGAACCTCCTACGTAAGATAGTG

AAAAACCGCAGGGACGAGGACACTCAAAAATCCTCTCCCGCGTCAGCCCCTCTG

GATGACGATGACTTGTGGCTTCCACCCCCTGAATACGTCCCGCTGAAAGAACTTA

CAGGCAAGAAGAACATGAGGAACTTTTGTATCAACGGAAGGGTTAAAGTGTGTA

GCCCGAATGGTTACTCGTTCAGGATCCTGCGGCACATTCTGAAATCATTCGACGA

GATATATTCTGGGAATCATAGGATGATCGGGTTAGTCAAAGTGGTTATTGGACTG

GCTTTGTCAGGATCTCCAGTCCCTGAGGGCCTGAACTGGGTATACAAATTGAGGA

GAACCTTTATCTTCCAGTGGGCTGATTCCAGGGGCCCTCTTGAAGGGGAGGAGTT

GGAATACTCTCAGGAGATCACTTGGGATGATGATACTGAGTTCGTCGGATTGCA

AATAAGAGTGATTGCAAAACAGTGTCATATCCAGGGCAGAGTCTGGTGTATCAA

CATGAACCCGAGAGCATGTCAACTATGGTCTGACATGTCTCTTCAGACACAAAG

GTCCGAAGAGGACAAAGATTCCTCTCTGCTTCTAGAATAATCAGATTATATCCCG

CAAATTTATCACTTGTTTACCTCTGGAGGAGAGAACATATGGGCTCAACTCCAAC

CCTTGGGAGCAATATAACAAAAAACATGTTATGGTGCCATTAAACCGCTGCATTT

CATCAAAGTCAAGTTGATTACCTTTACATTTTGATCCTCTTGGATGTGAAAAAAA

CTATTAACATCCCTCAAAAGACcccgggAAAGATGGTTCCTCAGGCTCTCCTGTTTG

TACCCCTTCTGGTTTTTCCATTGTGTTTTGGGAAATTCCCTATTTACACGATACCA

GACAAGCTTGGTCCCTGGAGTCCGATTGACATACATCACCTCAGCTGCCCAAAC

AATTTGGTAGTGGAGGACGAAGGATGCACCAACCTGTCAGGGTTCTCCTACATG

GAACTTAAAGTTGGATACATCTTAGCCATAAAAGTGAACGGGTTCACTTGCACA

GGCGTTGTGACGGAGGCTGAAACCTACACTAACTTCGTTGGTTATGTCACAACCA

CGTTCAAAAGAAAGCATTTCCGCCCAACACCAGATGCATGTAGAGCCGCGTACA

ACTGGAAGATGGCCGGTGACCCCAGATATGAAGAGTCTCTACACAATCCGTACC

CTGACTACCGCTGGCTTCGAACTGTAAAAACCACCAAGGAGTCTCTCGTTATCAT

ATCTCCAAGTGTGGCAGATTTGGACCCATATGACAGATCCCTTCACTCGAGGGTC

TTCCCTAGCGGGAAGTGCTCAGGAGTAGCGGTGTCTTCTACCTACTGCTCCACTA

ACCACGATTACACCATTTGGATGCCCGAGAATCCGAGACTAGGGATGTCTTGTG
```

-continued

```
ACATTTTTACCAATAGTAGAGGGAAGAGAGCATCCAAAGGGAGTGAGACTTGCG

GCTTTGTAGATGAAAGAGGCCTATATAAGTCTTTAAAAGGAGCATGCAAACTCA

AGTTATGTGGAGTTCTAGGACTTAGACTTATGGATGGAACATGGGTCTCGATGCA

AACATCAAATGAAACCAAATGGTGCCCTCCCGATAAGTTGGTGAACCTGCACGA

CTTTCGCTCAGACGAAATTGAGCACCTTGTTGTAGAGGAGTTGGTCAGGAAGAG

AGAGGAGTGTCTGGATGCACTAGAGTCCATCATGACAACCAAGTCAGTGAGTTT

CAGACGTCTCAGTCATTTAAGAAAACTTGTCCCTGGGTTTGGAAAAGCATATACC

ATATTCAACAAGACCTTGATGGAAGCCGATGCTCACTACAAGTCAGTCgagACTT

GGAATGAGATCCTCCCTTCAAAAGGGTGTTTAAGAGTTGGGGGGAGGTGTCATC

CTCATGTGAACGGGGTGTTTTTCAATGGTATAATATTAGGACCTGACGGCAATGT

CTTAATCCCAGAGATGCAATCATCCCTCCTCCAGCAACATATGGAGTTGTTGGAA

TCCTCGGTTATCCCCCTTGTGCACCCCCTGGCAGACCCGTCTACCGTTTTCAAGG

ACGGTGACGAGGCTGAGGATTTTGTTGAAGTTCACCTTCCCGATGTGCACAATCA

GGTCTCAGGAGTTGACTTGGGTCTCCCGAACTGGGGGAAGTATGTATTACTGAGT

GCAGGGGCCCTGACTGCCTTGATGTTGATAATTTTCCTGATGACATGTTGTAGAA

GAGTCAATCGATCAGAACCTACGCAACACAATCTCAGAGGGACAGGGAGGGAG

GTGTCAGTCACTCCCCAAAGCGGGAAGATCATATCTTCATGGGAATCACACAAG

AGTGGGGGTGAGACCAGACTGTAAttaattaaCGTCCTTTCAACGATCCAAGTCcatgaaa aaaactaacaccccccgtacctagcTTATAAAGTGCTGGGTCATCTAAGCTTTTCAGTCGAGA

AAAAAACATTAGATCAGAAGAACAACTGGCAACACTTCTCAACCTGAGACTTAC

TTCAAGATGCTCGATCCTGGAGAGGTCTATGATGACCCTATTGACCCAATCGAGT

TAGAGGCTGAACCCAGAGGAACCCCCATTGTCCCCAACATCTTGAGGAACTCTG

ACTACAATCTCAACTCTCCTTTGATAGAAGATCCTGCTAGACTAATGTTAGAATG

GTTAAAAACAGGGAATAGACCTTATCGGATGACTCTAACAGACAATTGCTCCAG

GTCTTTCAGAGTTTTGAAAGATTATTTCAAGAAGGTAGATTTGGGTTCTCTCAAG

GTGGGCGGAATGGCTGCACAGTCAATGATTTCTCTCTGGTTATATGGTGCCCACT

CTGAATCCAACAGGAGCCGGAGATGTATAACAGACTTGGCCCATTTCTATTCCAA

GTCGTCCCCCATAGAGAAGCTGTTGAATCTCACGCTAGGAAATAGAGGGCTGAG

AATCCCCCCAGAGGGAGTGTTAAGTTGCCTTGAGAGGGTTGATTATGATAATGC

ATTTGGAAGGTATCTTGCCAACACGTATTCCTCTTACTTGTTCTTCCATGTAATCA

CCTTATACATGAACGCCCTAGACTGGGATGAAGAAAAGACCATCCTAGCATTAT

GGAAAGATTTAACCTCAGTGGACATCGGGAAGGACTTGGTAAAGTTCAAAGACC

AAATATGGGACTGCTGATCGTGACAAAGGACTTTGTTTACTCCCAAAGTTCCAA

TTGTCTTTTTGACAGAAACTACACACTTATGCTAAAAGATCTTTTCTTGTCTCGCT

TCAACTCCTTAATGGTCTTGCTCTCTCCCCCAGAGCCCCGATACTCAGATGACTT

GATATCTCAACTATGCCAGCTGTACATTGCTGGGGATCAAGTCTTGTCTATGTGT

GGAAACTCCGGCTATGAAGTCATCAAAATATTGGAGCCATATGTCGTGAATAGT

TTAGTCCAGAGAGCAGAAAAGTTTAGGCCTCTCATTCATTCCTTGGGAGACTTTC

CTGTATTTATAAAAGACAAGGTAAGTCAACTTGAAGAGACGTTCGGTCCCTGTGC

AAGAAGGTTCTTTAGGGCTCTGGATCAATTCGACAACATACATGACTTGGTTTTT

GTGTTTGGCTGTTACAGGCATTGGGGGCACCCATATATAGATTATCGAAAGGGTC
```

-continued

```
TGTCAAAACTATATGATCAGGTTCACCTTAAAAAAATGATAGATAAGTCCTACCA

GGAGTGCTTAGCAAGCGACCTAGCCAGGAGGATCCTTAGATGGGGTTTTGATAA

GTACTCCAAGTGGTATCTGGATTCAAGATTCCTAGCCCGAGACCACCCCTTGACT

CCTTATATCAAAACCCAAACATGGCCACCCAAACATATTGTAGACTTGGTGGGG

GATACATGGCACAAGCTCCCGATCACGCAGATCTTTGAGATTCCTGAATCAATGG

ATCCGTCAGAAATATTGGATGACAAATCACATTCTTTCACCAGAACGAGACTAG

CTTCTTGGCTGTCAGAAAACCGAGGGGGGCCTGTTCCTAGCGAAAAAGTTATTAT

CACGGCCCTGTCTAAGCCGCCTGTCAATCCCCGAGAGTTTCTGAGGTCTATAGAC

CTCGGAGGATTGCCAGATGAAGACTTGATAATTGGCCTCAAGCCAAAGGAACGG

GAATTGAAGATTGAAGGTCGATTCTTTGCTCTAATGTCATGGAATCTAAGATTGT

ATTTTGTCATCACTGAAAAACTCTTGGCCAACTACATCTTGCCACTTTTTGACGCG

CTGACTATGACAGACAACCTGAACAAGGTGTTTAAAAAGCTGATCGACAGGGTC

ACCGGGCAAGGGCTTTTGGACTATTCAAGGGTCACATATGCATTTCACCTGGACT

ATGAAAAGTGGAACAACCATCAAAGATTAGAGTCAACAGAGGATGTATTTTCTG

TCCTAGATCAAGTGTTTGGATTGAAGAGAGTGTTTTCTAGAACACACGAGTTTTT

TCAAAAGGCCTGGATCTATTATTCAGACAGATCAGACCTCATCGGGTTACGGGA

GGATCAAATATACTGCTTAGATGCGTCCAACGGCCCAACCTGTTGGAATGGCCA

GGATGGCGGGCTAGAAGGCTTACGGCAGAAGGGCTGGAGTCTAGTCAGCTTATT

GATGATAGATAGAGAATCTCAAATCAGGAACACAAGAACCAAAATACTAGCTCA

AGGAGACAACCAGGTTTTATGTCCGACATACATGTTGTCGCCAGGGCTATCTCAA

GAGGGGCTCCTCTATGAATTGGAGAGAATATCAAGGAATGCACTTTCGATATAC

AGAGCCGTCGAGGAAGGGGCATCTAAGCTAGGGCTGATCATCAAGAAAGAAGA

GACCATGTGTAGTTATGACTTCCTCATCTATGGAAAAACCCCTTTGTTTAGAGGT

AACATATTGGTGCCTGAGTCCAAAAGATGGGCCAGAGTCTCTTGCGTCTCTAATG

ACCAAATAGTCAACCTCGCCAATATAATGTCGACAGTGTCCACCAATGCGCTAA

CAGTGGCACAACACTCTCAATCTTTGATCAAACCGATGAGGGATTTTCTGCTCAT

GTCAGTACAGGCAGTCTTTCACTACCTGCTATTTAGCCCAATCTTAAAGGGAAGA

GTTTACAAGATTCTGAGCGCTGAAGGGGAGAGCTTTCTCCTAGCCATGTCAAGG

ATAATCTATCTAGATCCTTCTTTGGGAGGGATATCTGGAATGTCCCTCGGAAGAT

TCCATATACGACAGTTCTCAGACCCTGTCTCTGAAGGGTTATCCTTCTGGAGAGA

GATCTGGTTAAGCTCCCAAGAGTCCTGGATTCACGCGTTGTGTCAAGAGGCTGGA

AACCCAGATCTTGGAGAGAGAACACTCGAGAGCTTCACTCGCCTTCTAGAAGAT

CCGACCACCTTAAATATCAGAGGAGGGGCCAGTCCTACCATTCTACTCAAGGAT

GCAATCAGAAAGGCTTTATATGACGAGGTGGACAAGGTGGAAAATTCAGAGTTT

CGAGAGGCAATCCTGTTGTCCAAGACCCATAGAGATAATTTTATACTCTTCTTAA

TATCTGTTGAGCCTCTGTTTCCTCGATTTCTCAGTGAGCTATTCAGTTCGTCTTTTT

TGGGAATCCCCGAGTCAATCATTGGATTGATACAAAACTCCCGAACGATAAGAA

GGCAGTTTAGAAAGAGTCTCTCAAAAACTTTAGAAGAATCCTTCTACAACTCAG

AGATCCACGGGATTAGTCGGATGACCCAGACACCTCAGAGGGTTGGGGGGTGT

GGCCTTGCTCTTCAGAGAGGGCAGATCTACTTAGGGAGATCTCTTGGGGAAGAA
```

-continued

```
AAGTGGTAGGCACGACAGTTCCTCACCCTTCTGAGATGTTGGGATTACTTCCCAA

GTCCTCTATTTCTTGCACTTGTGGAGCAACAGGAGGAGGCAATCCTAGAGTTTCT

GTATCAGTACTCCCGTCCTTTGATCAGTCATTTTTTTCACGAGGCCCCCTAAAGG

GATACTTGGGCTCGTCCACCTCTATGTCGACCCAGCTATTCCATGCATGGGAAAA

AGTCACTAATGTTCATGTGGTGAAGAGAGCTCTATCGTTAAAAGAATCTATAAAC

TGGTTCATTACTAGAGATTCCAACTTGGCTCAAGCTCTAATTAGGAACATTATGT

CTCTGACAGGCCCTGATTTCCCTCTAGAGGAGGCCCCTGTCTTCAAAAGGACGGG

GTCAGCCTTGCATAGGTTCAAGTCTGCCAGATACAGCGAAGGAGGGTATTCTTCT

GTCTGCCCGAACCTCCTCTCTCATATTTCTGTTAGTACAGACACCATGTCTGATTT

GACCCAAGACGGGAAGAACTACGATTTCATGTTCCAGCCATTGATGCTTTATGCA

CAGACATGGACATCAGAGCTGGTACAGAGAGACACAAGGCTAAGAGACTCTAC

GTTTCATTGGCACCTCCGATGCAACAGGTGTGTGAGACCCATTGACGACGTGACC

CTGGAGACCTCTCAGATCTTCGAGTTTCCGGATGTGTCGAAAAGAATATCCAGAA

TGGTTTCTGGGGCTGTGCCTCACTTCCAGAGGCTTCCCGATATCCGTCTGAGACC

AGGAGATTTTGAATCTCTAAGCGGTAGAGAAAAGTCTCACCATATCGGATCAGC

TCAGGGGCTCTTATACTCAATCTTAGTGGCAATTCACGACTCAGGATACAATGAT

GGAACCATCTTCCCTGTCAACATATACGGCAAGGTTTCCCCTAGAGACTATTTGA

GAGGGCTCGCAAGGGGAGTATTGATAGGATCCTCGATTTGCTTCTTGACAAGAA

TGACAAATATCAATATTAATAGACCTCTTGAATTGGTCTCAGGGGTAATCTCATA

TATTCTCCTGAGGCTAGATAACCATCCCTCCTTGTACATAATGCTCAGAGAACCG

TCTCTTAGAGGAGAGATATTTTCTATCCCTCAGAAAATCCCCGCCGCTTATCCAA

CCACTATGAAAGAAGGCAACAGATCAATCTTGTGTTATCTCCAACATGTGCTACG

CTATGAGCGAGAGATAATCACGGCGTCTCCAGAGAATGACTGGCTATGGATCTT

TTCAGACTTTAGAAGTGCCAAAATGACGTACCTATCCCTCATTACTTACCAGTCT

CATCTTCTACTCCAGAGGGTTGAGAGAAACCTATCTAAGAGTATGAGAGATAAC

CTGCGACAATTGAGTTCTTTGATGAGGCAGGTGCTGGGCGGGCACGGAGAAGAT

ACCTTAGAGTCAGACGACAACATTCAACGACTGCTAAAAGACTCTTTACGAAGG

ACAAGATGGGTGGATCAAGAGGTGCGCCATGCAGCTAGAACCATGACTGGAGAT

TACAGCCCCAACAAGAAGGTGTCCCGTAAGGTAGGATGTTCAGAATGGGTCTGC

TCTGCTCAACAGGTTGCAGTCTCTACCTCAGCAAACCCGGCCCCTGTCTCGGAGC

TTGACATAAGGGCCCTCTCTAAGAGGTTCCAGAACCCTTTGATCTCGGGCTTGAG

AGTGGTTCAGTGGGCAACCGGTGCTCATTATAAGCTTAAGCCTATTCTAGATGAT

CTCAATGTTTTCCCATCTCTCTGCCTTGTAGTTGGGGACGGGTCAGGGGGATAT

CAAGGGCAGTCCTCAACATGTTTCCAGATGCCAAGCTTGTGTTCAACAGTCTTTT

AGAGGTGAATGACCTGATGGCTTCCGGAACACATCCACTGCCTCCTTCAGCAATC

ATGAGGGAGGAAATGATATCGTCTCCAGAGTGATAGATCTTGACTCAATCTGG

GAAAAACCGTCCGACTTGAGAAACTTGGCAACCTGGAAATACTTCCAGTCAGTC

CAAAAGCAGGTCAACATGTCCTATGACCTCATTATTTGCGATGCAGAAGTTACTG

ACATTGCATCTATCAACCGGATCACCCTGTTAATGTCCGATTTTGCATTGTCTATA

GATGGACCACTCTATTTGGTCTTCAAAACTTATGGGACTATGCTAGTAAATCCAA

ACTACAAGGCTATTCAACACCTGTCAAGAGCGTTCCCCTCGGTCACAGGGTTTAT
```

```
CACCCAAGTAACTTCGTCTTTTTCATCTGAGCTCTACCTCCGATTCTCCAAACGA

GGGAAGTTTTTCAGAGATGCTGAGTACTTGACCTCTTCCACCCTTCGAGAAATGA

GCCTTGTGTTATTCAATTGTAGCAGCCCCAAGAGTGAGATGCAGAGAGCTCGTTC

CTTGAACTATCAGGATCTTGTGAGAGGATTTCCTGAAGAAATCATATCAAATCCT

TACAATGAGATGATCATAACTCTGATTGACAGTGATGTAGAATCTTTTCTAGTCC

ACAAGATGGTTGATGATCTTGAGTTACAGAGGGGAACTCTGTCTAAAGTGGCTA

TCATTATAGCCATCATGATAGTTTTCTCCAACAGAGTCTTCAACGTTTCCAAACC

CCTAACTGACCCCTCGTTCTATCCACCGTCTGATCCCAAAATCCTGAGGCACTTC

AACATATGTTGCAGTACTATGATGTATCTATCTACTGCTTTAGGTGACGTCCCTA

GCTTCGCAAGACTTCACGACCTGTATAACAGACCTATAACTTATTACTTCAGAAA

GCAAGTCATTCGAGGGAACGTTTATCTATCTTGGAGTTGGTCCAACGACACCTCA

GTGTTCAAAAGGGTAGCCTGTAATTCTAGCCTGAGTCTGTCATCTCACTGGATCA

GGTTGATTTACAAGATAGTGAAGACTACCAGACTCGTTGGCAGCATCAAGGATC

TATCCAGAGAAGTGGAAAGACACCTTCATAGGTACAACAGGTGGATCACCCTAG

AGGATATCAGATCTAGATCATCCCTACTAGACTACAGTTGCCTGTGAACCGGATA

CTCCTGGAAGCCTGCCCATGCTAAGACTCTTGTGTGATGTATCTTGAAAAAAACA

AGATCCTAAATCTGAACCTTTGGTTGTTTGATTGTTTTTCTCAtttttgttgtttatttgttaagcgt.
```

In some embodiments, the nucleic acid comprises the sequence of SEQ ID NO: 8, shown below (RABV vector: Coravax V2-China (RABVG-E51)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT
```

-continued

```
AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccgtacgCCACCATGTTCGTGTTTCTGGTGCTGCTGC

CTCTGGTGAGCTCCCAGTGCGTGAACCTGACCACAAGGACCCAGCTGCCCCCTG

CCTATACCAATTCCTTCACACGGGGCGTGTACTATCCCGACAAGGTGTTCCGGAG

CAGCGTGCTGCACTCCACACAGGATCTGTTTCTGCCTTTCTTTTCTAACGTGACCT

GGTTCCACGCCATCCACGTGAGCGGCACCAATGGCACAAAGCGGTTCGACAATC

CAGTGCTGCCCTTTAACGATGGCGTGTACTTCGCCTCCACCGAGAAGTCTAACAT

CATCAGAGGCTGGATCTTTGGCACCACACTGGACAGCAAGACACAGTCCCTGCT

GATCGTGAACAATGCCACCAACGTGGTCATCAAGGTGTGCGAGTTCCAGTTTTGT

AATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGACCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAAGATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGGAGGGCTTTAACTGTTATTTCCCTCTGCAGAGCTACGGCTTCCAGCCAAC

AAACGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT
```

-continued

```
GGCCGTGCTGTATcAGGACGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAGAATCAAGCGTGATTCCTCTGGTCCATCCACTGGCAGATCCCTCCACAGTGTT

CAAAGACGGAGATGAGGCCGAAGACTTTGTGGAAGTCCACCTGCCTGATGTGCA

TAACCAGGTGTCTGGCGTCGACCTGGGACTGCCAAATTGGGGCAAGTACGTGCT

GCTGAGTGCTGGAGCACTGACTGCCCTGATGCTGATCATTTTCCTGATGACCTGC

TGTCGGCGCGTGAACAGAAGTGAGCCCACTCAGCACAATCTGCGAGGAACCGGG

AGAGAAGTGTCAGTCACACCTCAGAGCGGGAAAATCATTAGTAGTTGGGAATCA

CATAAAAGCGGGGGCGAGACCAGGCTGTGAgctagcCATGAAAAAAACTAACACCC

CTCCTTTCGAACCATCCCAAACATGAGCAAGATCTTTGTCAATCCTAGTGCTATT

AGAGCCGGTCTGGCCGATCTTGAGATGGCTGAAGAAACTGTTGATCTGATCAAT

AGAAATATCGAAGACAATCAGGCTCATCTCCAAGGGGAACCCATAGAGGTGGAC

AATCTCCCTGAGGATATGGGGCGACTTCACCTGGATGATGGAAAATCGCCCAAC

CATGGTGAGATAGCCAAGGTGGGAGAAGGCAAGTATCGAGAGGACTTTCAGATG

GATGAAGGAGAGGATCCTAGCTTCCTGTTCCAGTCATACCTGGAAAATGTTGGA

GTCCAAATAGTCAGACAAATGAGGTCAGGAGAGAGATTTCTCAAGATATGGTCA

CAGACCGTAGAAGAGATTATATCCTATGTCGCGGTCAACTTTCCCAACCCTCCAG

GAAAGTCTTCAGAGGATAAATCAACCCAGACTACTGGCCGAGAGCTCAAGAAGG

AGACAACACCCACTCCTTCTCAGAGAGAAAGCCAATCATCGAAAGCCAGGATGG

CGGCTCAAATTGCTTCTGGCCCTCCAGCCCTTGAATGGTCGGCTACCAATGAAGA

GGATGATCTATCAGTGGAGGCTGAGATCGCTCACCAGATTGCAGAAAGTTTCTCC

AAAAAATATAAGTTTCCCTCTCGATCCTCAGGGATACTCTTGTATAATTTTGAGC

AATTGAAAATGAACCTTGATGATATAGTTAAAGAGGCAAAAAATGTACCAGGTG

TGACCCGTTTAGCCCATGACGGGTCCAAACTCCCCCTAAGATGTGTACTGGGATG

GGTCGCTTTGGCCAACTCTAAGAAATTCCAGTTGTTAGTCGAATCCGACAAGCTG

AGTAAAATCATGCAAGATGACTTGAATCGCTATACATCTTGCTAACCGAACCTCT

CCCCTCAGTCCCTCTAGACAATAAAATCCGAGATGTCCCAAAGTCAACATGAAA

AAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGAC

GATGACTTGTGGCTTCCACCCCCTGAATACGTCCCGCTGAAAGAACTTACAGGCA

AGAAGAACATGAGGAACTTTTGTATCAACGGAAGGGTTAAAGTGTGTAGCCCGA

ATGGTTACTCGTTCAGGATCCTGCGGCACATTCTGAAATCATTCGACGAGATATA

TTCTGGGAATCATAGGATGATCGGGTTAGTCAAAGTGGTTATTGGACTGGCTTTG

TCAGGATCTCCAGTCCCTGAGGGCCTGAACTGGGTATACAAATTGAGGAGAACC

TTTATCTTCCAGTGGGCTGATTCCAGGGGCCCTCTTGAAGGGGAGGAGTTGGAAT

ACTCTCAGGAGATCACTTGGGATGATGATACTGAGTTCGTCGGATTGCAAATAA

GAGTGATTGCAAAACAGTGTCATATCCAGGGCAGAGTCTGGTGTATCAACATGA

ACCCGAGAGCATGTCAACTATGGTCTGACATGTCTCTTCAGACACAAAGGTCCG

AAGAGGACAAAGATTCCTCTCTGCTTCTAGAATAATCAGATTATATCCCGCAAAT
```

-continued

```
TTATCACTTGTTTACCTCTGGAGGAGAGAACATATGGGCTCAACTCCAACCCTTG

GGAGCAATATAACAAAAAACATGTTATGGTGCCATTAAACCGCTGCATTTCATC

AAAGTCAAGTTGATTACCTTTACATTTTGATCCTCTTGGATGTGAAAAAAACTAT

TAACATCCCTCAAAAGACcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa caccoctcccgtacctagcTTATAAAGTGCTGGGTCATCTAAGCTTTTCAGTCGAGAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC
```

-continued

```
GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG
```

-continued

```
CACAACACTCTCAATCTTTGATCAAACCGATGAGGGATTTTCTGCTCATGTCAGT
ACAGGCAGTCTTTCACTACCTGCTATTTAGCCCAATCTTAAAGGGAAGAGTTTAC
AAGATTCTGAGCGCTGAAGGGGAGAGCTTTCTCCTAGCCATGTCAAGGATAATC
TATCTAGATCCTTCTTTGGGAGGGATATCTGGAATGTCCCTCGGAAGATTCCATA
TACGACAGTTCTCAGACCCTGTCTCTGAAGGGTTATCCTTCTGGAGAGAGATCTG
GTTAAGCTCCCAAGAGTCCTGGATTCACGCGTTGTGTCAAGAGGCTGGAAACCC
AGATCTTGGAGAGAGAACACTCGAGAGCTTCACTCGCCTTCTAGAAGATCCGAC
CACCTTAAATATCAGAGGAGGGGCCAGTCCTACCATTCTACTCAAGGATGCAAT
CAGAAAGGCTTTATATGACGAGGTGGACAAGGTGGAAAATTCAGAGTTTCGAGA
GGCAATCCTGTTGTCCAAGACCCATAGAGATAATTTTATACTCTTCTTAATATCT
GTTGAGCCTCTGTTTCCTCGATTTCTCAGTGAGCTATTCAGTTCGTCTTTTTTGGG
AATCCCCGAGTCAATCATTGGATTGATACAAAACTCCCGAACGATAAGAAGGCA
GTTTAGAAAGAGTCTCTCAAAAACTTTAGAAGAATCCTTCTACAACTCAGAGATC
CACGGGATTAGTCGGATGACCCAGACACCTCAGAGGGTTGGGGGGGTGTGGCCT
TGCTCTTCAGAGAGGGCAGATCTACTTAGGGAGATCTCTTGGGGAAGAAAAGTG
GTAGGCACGACAGTTCCTCACCCTTCTGAGATGTTGGGATTACTTCCCAAGTCCT
CTATTTCTTGCACTTGTGGAGCAACAGGAGGAGGCAATCCTAGAGTTTCTGTATC
AGTACTCCCGTCCTTTGATCAGTCATTTTTTTCACGAGGCCCCCTAAAGGGATAC
TTGGGCTCGTCCACCTCTATGTCGACCCAGCTATTCCATGCATGGGAAAAAGTCA
CTAATGTTCATGTGGTGAAGAGAGCTCTATCGTTAAAAGAATCTATAAACTGGTT
CATTACTAGAGATTCCAACTTGGCTCAAGCTCTAATTAGGAACATTATGTCTCTG
ACAGGCCCTGATTTCCCTCTAGAGGAGGCCCCTGTCTTCAAAAGGACGGGGTCA
GCCTTGCATAGGTTCAAGTCTGCCAGATACAGCGAAGGAGGGTATTCTTCTGTCT
GCCCGAACCTCCTCTCTCATATTTCTGTTAGTACAGACACCATGTCTGATTTGACC
CAAGACGGGAAGAACTACGATTTCATGTTCCAGCCATTGATGCTTTATGCACAGA
CATGGACATCAGAGCTGGTACAGAGAGACACAAGGCTAAGAGACTCTACGTTTC
ATTGGCACCTCCGATGCAACAGGTGTGTGAGACCCATTGACGACGTGACCCTGG
AGACCTCTCAGATCTTCGAGTTTCCGGATGTGTCGAAAAGAATATCCAGAATGGT
TTCTGGGGCTGTGCCTCACTTCCAGAGGCTTCCCGATATCCGTCTGAGACCAGGA
GATTTTGAATCTCTAAGCGGTAGAGAAAAGTCTCACCATATCGGATCAGCTCAG
GGGCTCTTATACTCAATCTTAGTGGCAATTCACGACTCAGGATACAATGATGGAA
CCATCTTCCCTGTCAACATATACGGCAAGGTTTCCCCTAGAGACTATTTGAGAGG
GCTCGCAAGGGAGTATTGATAGGATCCTCGATTTGCTTCTTGACAAGAATGACA
AATATCAATATTAATAGACCTCTTGAATTGGTCTCAGGGGTAATCTCATATATTC
TCCTGAGGCTAGATAACCATCCCTCCTTGTACATAATGCTCAGAGAACCGTCTCT
TAGAGGAGAGATATTTTCTATCCCTCAGAAAATCCCCGCCGCTTATCCAACCACT
ATGAAAGAAGGCAACAGATCAATCTTGTGTTATCTCCAACATGTGCTACGCTATG
AGCGAGAGATAATCACGGCGTCTCCAGAGAATGACTGGCTATGGATCTTTTCAG
ACTTTAGAAGTGCCAAAATGACGTACCTATCCCTCATTACTTACCAGTCTCATCT
TCTACTCCAGAGGGTTGAGAGAAACCTATCTAAGAGTATGAGAGATAACCTGCG
```

-continued

```
ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAttttttgttgtttatttgttaagcgt.
```

In other embodiments, the nucleic acid comprises the sequence of SEQ ID NO: 9, shown below (RABV vector: Coravax V2 South Africa (S1-RABVG-E51)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA
```

```
-continued
AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacaccccctcccgtacgCCACCATGTTCGTGTTTCTGGTGCTGCTGC

CTCTGGTGAGCTCCCAGTGCGTGAACTTCACCACAAGGACCCAGCTGCCCCCTGC

CTATACCAATTCCTTCACACGGGGCGTGTACTATCCCGACAAGGTGTTCCGGAGC

AGCGTGCTGCACTCCACACAGGATCTGTTTCTGCCTTTCTTTTCTAACGTGACCTG

GTTCCACGCCATCCACGTGAGCGGCACCAATGGCACAAAGCGGTTCGCCAATCC

AGTGCTGCCCTTTAACGATGGCGTGTACTTCGCCTCCACCGAGAAGTCTAACATC

ATCAGAGGCTGGATCTTTGGCACCACACTGGACAGCAAGACACAGTCCCTGCTG

ATCGTGAACAATGCCACCAACGTGGTCATCAAGGTGTGCGAGTTCCAGTTTTGTA

ATGATCCATTCCTGGGCGTGTACTATCACAAGAACAATAAGTCTTGGATGGAGA

GCGAGTTTCGCGTGTATTCCTCTGCCAACAATTGCACATTTGAGTACGTGTCCCA

GCCCTTCCTGATGGACCTGGAGGGCAAGCAGGGCAATTTCAAGAACCTGAGGGA

GTTCGTGTTTAAGAATATCGATGGCTACTTCAAAATCTACTCCAAGCACACCCCA

ATCAACCTGGTGCGCGGCCTGCCACAGGGCTTCTCTGCCCTGGAGCCACTGGTGG

ATCTGCCCATCGGCATCAACATCACCCGGTTTCAGACACTGCTGGCCCTGCACAG

AAGCTACCTGACACCAGGCGACAGCTCCTCTGGATGGACCGCAGGAGCAGCAGC

CTACTATGTGGGCTATCTGCAGCCCAGGACCTTCCTGCTGAAGTACAACGAGAAT

GGCACCATCACAGACGCCGTGGATTGCGCCCTGGATCCCCTGTCTGAGACCAAG

TGTACACTGAAGAGCTTTACCGTGGAGAAGGGCATCTATCAGACAAGCAATTTC

AGGGTGCAGCCTACCGAGTCCATCGTGCGCTTTCCCAATATCACAAACCTGTGCC
```

-continued

```
CTTTTGGCGAGGTGTTCAACGCAACCCGCTTCGCCAGCGTGTACGCCTGGAATAG

GAAGCGCATCTCCAACTGCGTGGCCGACTATTCTGTGCTGTACAACAGCGCCTCC

TTCTCTACCTTTAAGTGCTATGGCGTGAGCCCCACAAAGCTGAATGACCTGTGCT

TTACCAACGTGTACGCCGATTCCTTCGTGATCAGGGGCGACGAGGTGCGCCAGA

TCGCACCAGGACAGACAGGCAATATCGCAGACTACAATTATAAGCTGCCTGACG

ATTTCACCGGCTGCGTGATCGCCTGGAACTCTAACAATCTGGATAGCAAAGTGG

GCGGCAACTACAATTATCTGTACCGGCTGTTTAGAAAGTCTAATCTGAAGCCATT

CGAGAGGGACATCTCCACAGAAATCTACCAGGCCGGCTCTACCCCCTGCAATGG

CGTGAAGGGCTTTAACTGTTATTTCCCTCTGCAGAGCTACGGCTTCCAGCCAACA

TATGGCGTGGGCTATCAGCCCTACCGCGTGGTGGTGCTGTCTTTTGAGCTGCTGC

ACGCACCTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGGCGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAGAATCAAGCGTGATTCCTCTGGTCCATCCACTGGCAGATCCCTCCACAGTGTT

CAAAGACGGAGATGAGGCCGAAGACTTTGTGGAAGTCCACCTGCCTGATGTGCA

TAACCAGGTGTCTGGCGTCGACCTGGGACTGCCAAATTGGGGCAAGTACGTGCT

GCTGAGTGCTGGAGCACTGACTGCCCTGATGCTGATCATTTTCCTGATGACCTGC

TGTCGGCGCGTGAACAGAAGTGAGCCCACTCAGCACAATCTGCGAGGAACCGGG

AGAGAAGTGTCAGTCACACCTCAGAGCGGGAAAATCATTAGTAGTTGGGAATCA

CATAAAAGCGGGGCGAGACCAGGCTGTGAgctagcCATGAAAAAAACTAACACCC

CTCCTTTCGAACCATCCCAAACATGAGCAAGATCTTTGTCAATCCTAGTGCTATT

AGAGCCGGTCTGGCCGATCTTGAGATGGCTGAAGAAACTGTTGATCTGATCAAT

AGAAATATCGAAGACAATCAGGCTCATCTCCAAGGGGAACCCATAGAGGTGGAC

AATCTCCCTGAGGATATGGGGCGACTTCACCTGGATGATGGAAAATCGCCCAAC

CATGGTGAGATAGCCAAGGTGGGAGAAGGCAAGTATCGAGAGGACTTTCAGATG

GATGAAGGAGAGGATCCTAGCTTCCTGTTCCAGTCATACCTGGAAAATGTTGGA

GTCCAAATAGTCAGACAAATGAGGTCAGGAGAGAGATTTCTCAAGATATGGTCA

CAGACCGTAGAAGAGATTATATCCTATGTCGCGGTCAACTTTCCCAACCCTCCAG

GAAAGTCTTCAGAGGATAAATCAACCCAGACTACTGGCCGAGAGCTCAAGAAGG

AGACAACACCCACTCCTTCTCAGAGAGAAAGCCAATCATCGAAAGCCAGGATGG

CGGCTCAAATTGCTTCTGGCCCTCCAGCCCTTGAATGGTCGGCTACCAATGAAGA

GGATGATCTATCAGTGGAGGCTGAGATCGCTCACCAGATTGCAGAAAGTTTCTCC

AAAAAATATAAGTTTCCCTCTCGATCCTCAGGGATACTCTTGTATAATTTTGAGC

AATTGAAAATGAACCTTGATGATATAGTTAAAGAGGCAAAAAATGTACCAGGTG
```

-continued

```
TGACCCGTTTAGCCCATGACGGGTCCAAACTCCCCCTAAGATGTGTACTGGGATG

GGTCGCTTTGGCCAACTCTAAGAAATTCCAGTTGTTAGTCGAATCCGACAAGCTG

AGTAAAATCATGCAAGATGACTTGAATCGCTATACATCTTGCTAACCGAACCTCT

CCCCTCAGTCCCTCTAGACAATAAAATCCGAGATGTCCCAAAGTCAACATGAAA

AAAACAGGCAACACCACTGATAAAATGAACCTCCTACGTAAGATAGTGAAAAAC

CGCAGGGACGAGGACACTCAAAAATCCTCTCCCGCGTCAGCCCCTCTGGATGAC

GATGACTTGTGGCTTCCACCCCCTGAATACGTCCCGCTGAAAGAACTTACAGGCA

AGAAGAACATGAGGAACTTTTGTATCAACGGAAGGGTTAAAGTGTGTAGCCCGA

ATGGTTACTCGTTCAGGATCCTGCGGCACATTCTGAAATCATTCGACGAGATATA

TTCTGGGAATCATAGGATGATCGGGTTAGTCAAAGTGGTTATTGGACTGGCTTTG

TCAGGATCTCCAGTCCCTGAGGGCCTGAACTGGGTATACAAATTGAGGAGAACC

TTTATCTTCCAGTGGGCTGATTCCAGGGGCCCTCTTGAAGGGGAGGAGTTGGAAT

ACTCTCAGGAGATCACTTGGGATGATGATACTGAGTTCGTCGGATTGCAAATAA

GAGTGATTGCAAAACAGTGTCATATCCAGGGCAGAGTCTGGTGTATCAACATGA

ACCCGAGAGCATGTCAACTATGGTCTGACATGTCTCTTCAGACACAAAGGTCCG

AAGAGGACAAAGATTCCTCTCTGCTTCTAGAATAATCAGATTATATCCCGCAAAT

TTATCACTTGTTTACCTCTGGAGGAGAGAACATATGGGCTCAACTCCAACCCTTG

GGAGCAATATAACAAAAAACATGTTATGGTGCCATTAAACCGCTGCATTTCATC

AAAGTCAAGTTGATTACCTTTACATTTTGATCCTCTTGGATGTGAAAAAAACTAT

TAACATCCCTCAAAAGACcccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT

GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT
```

```
-continued
CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGG

GGGTGAGACCAGACTGTAAttaattaaCGTCCTTTCAACGATCCAAGTCcatgaaaaaaactaa cacccctcccgtacctagcTTATAAAGTGCTGGGTCATCTAAGCTTTTCAGTCGAGAAAAA

ACATTAGATCAGAAGAACAACTGGCAACACTTCTCAACCTGAGACTTACTTCAA

GATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAGTTATTATCACGGCC

CTGTCTAAGCCGCCTGTCAATCCCCGAGAGTTTCTGAGGTCTATAGACCTCGGAG

GATTGCCAGATGAAGACTTGATAATTGGCCTCAAGCCAAAGGAACGGGAATTGA
```

-continued
```
AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC

CAAGACGGGAAGAACTACGATTTCATGTTCCAGCCATTGATGCTTTATGCACAGA
```

```
CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCCAGATGCCAAGCTTGTGTTCAACAGTCTTTTAGAGG

TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG
```

-continued

```
CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCC

TAAATCTGAACCTTTGGTTGTTTGATTGTTTTTCTCAtttttgttgtttatttgttaagcgt.
```

In one embodiment, the nucleic acid comprises the sequence of SEQ ID NO: 10, shown below (RABV vector: Coravax V3-China (S1-VSVG-E26)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacacccctcccGTACGCCACCATGTTCGTGTTTCTGGTGCTGCT

GCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG
```

```
-continued
AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAGGGCTTTAACTGTTATTTCCCTCTGCAGAGCTACGGCTTCCAGCCAA

CAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGA

ACAAGTGCGTGAACTTCAACTTCAACGGACTGACCGGAACAGGCGTGCTGACCG

AGTCCAACAAGAAGTTCCTGCCTTTTCAGCAGTTCGGCAGGGACATCGCAGATA

CCACAGACGCCGTGCGCGACCCTCAGACCCTGGAGATCCTGGACATCACACCAT

GCTCCTTCGGCGGCGTGTCTGTGATCACACCAGGCACCAATACAAGCAACCAGG

TGGCCGTGCTGTATCAGGACGTGAATTGTACCGAGGTGCCAGTGGCAATCCACG

CAGATCAGCTGACCCCTACATGGCGGGTGTACTCTACCGGCAGCAACGTGTTCC

AGACAAGAGCCGGATGCCTGATCGGAGCAGAGCACGTGAACAATAGCTATGAGT

GCGACATCCCTATCGGCGCCGGCATCTGTGCCTCCTACCAGACCCAGACAAACTC

CCCAAGGTCTGTGGGCGATACAGGCCTGTCCAAGAATCCAATCGAGCTGGTAGA

GGGCTGGTTCAGCAGTTGGAAAAGCTCCATCGCCTCCTTTTTCTTTATCATCGGC

CTGATCATCGGACTGTTCCTGGTGCTCCGCGTGGGTATCCACCTGTGCATCAAGC

TGAAGCACACCAAGAAAAGACAGATTTATACAGACATCGAGATGAACCGCCTGG

GAAAGTGAGCTAGCCATGAAAAAAACTAACACCCCTCCTTTCGAACCATCCCAA

ACATGAGCAAGATCTTTGTCAATCCTAGTGCTATTAGAGCCGGTCTGGCCGATCT
```

```
TGAGATGGCTGAAGAAACTGTTGATCTGATCAATAGAAATATCGAAGACAATCA
GGCTCATCTCCAAGGGGAACCCATAGAGGTGGACAATCTCCCTGAGGATATGGG
GCGACTTCACCTGGATGATGGAAAATCGCCCAACCATGGTGAGATAGCCAAGGT
GGGAGAAGGCAAGTATCGAGAGGACTTTCAGATGGATGAAGGAGAGGATCCTA
GCTTCCTGTTCCAGTCATACCTGGAAAATGTTGGAGTCCAAATAGTCAGACAAAT
GAGGTCAGGAGAGAGATTTCTCAAGATATGGTCACAGACCGTAGAAGAGATTAT
ATCCTATGTCGCGGTCAACTTTCCCAACCCTCCAGGAAAGTCTTCAGAGGATAAA
TCAACCCAGACTACTGGCCGAGAGCTCAAGAAGGAGACAACACCCACTCCTTCT
CAGAGAGAAAGCCAATCATCGAAAGCCAGGATGGCGGCTCAAATTGCTTCTGGC
CCTCCAGCCCTTGAATGGTCGGCTACCAATGAAGAGGATGATCTATCAGTGGAG
GCTGAGATCGCTCACCAGATTGCAGAAAGTTTCTCCAAAAAATATAAGTTTCCCT
CTCGATCCTCAGGGATACTCTTGTATAATTTTGAGCAATTGAAAATGAACCTTGA
TGATATAGTTAAAGAGGCAAAAAATGTACCAGGTGTGACCCGTTTAGCCCATGA
CGGGTCCAAACTCCCCCTAAGATGTGTACTGGGATGGGTCGCTTTGGCCAACTCT
AAGAAATTCCAGTTGTTAGTCGAATCCGACAAGCTGAGTAAAATCATGCAAGAT
GACTTGAATCGCTATACATCTTGCTAACCGAACCTCTCCCCTCAGTCCCTCTAGA
CAATAAAATCCGAGATGTCCCAAAGTCAACATGAAAAAAACAGGCAACACCACT
GATAAAATGAACCTCCTACGTAAGATAGTGAAAAACCGCAGGGACGAGGACACT
CAAAAATCCTCTCCCGCGTCAGCCCCTCTGGATGACGATGACTTGTGGCTTCCAC
CCCCTGAATACGTCCCGCTGAAAGAACTTACAGGCAAGAAGAACATGAGGAACT
TTTGTATCAACGGAAGGGTTAAAGTGTGTAGCCCGAATGGTTACTCGTTCAGGAT
CCTGCGGCACATTCTGAAATCATTCGACGAGATATATTCTGGGAATCATAGGATG
ATCGGGTTAGTCAAAGTGGTTATTGGACTGGCTTTGTCAGGATCTCCAGTCCCTG
AGGGCCTGAACTGGGTATACAAATTGAGGAGAACCTTTATCTTCCAGTGGGCTG
ATTCCAGGGGCCCTCTTGAAGGGGAGGAGTTGGAATACTCTCAGGAGATCACTT
GGGATGATGATACTGAGTTCGTCGGATTGCAAATAAGAGTGATTGCAAAACAGT
GTCATATCCAGGGCAGAGTCTGGTGTATCAACATGAACCCGAGAGCATGTCAAC
TATGGTCTGACATGTCTCTTCAGACACAAAGGTCCGAAGAGGACAAAGATTCCT
CTCTGCTTCTAGAATAATCAGATTATATCCCGCAAATTTATCACTTGTTTACCTCT
GGAGGAGAGAACATATGGGCTCAACTCCAACCCTTGGGAGCAATATAACAAAAA
ACATGTTATGGTGCCATTAAACCGCTGCATTTCATCAAAGTCAAGTTGATTACCT
TTACATTTTGATCCTCTTGGATGTGAAAAAAACTATTAACATCCCTCAAAAGACcc
cgggAAAGATGGTTCCTCAGGCTCTCCTGTTTGTACCCCTTCTGGTTTTTCCATTGT
GTTTTGGGAAATTCCCTATTTACACGATACCAGACAAGCTTGGTCCCTGGAGTCC
GATTGACATACATCACCTCAGCTGCCCAAACAATTTGGTAGTGGAGGACGAAGG
ATGCACCAACCTGTCAGGGTTCTCCTACATGGAACTTAAAGTTGGATACATCTTA
GCCATAAAAGTGAACGGGTTCACTTGCACAGGCGTTGTGACGGAGGCTGAAACC
TACACTAACTTCGTTGGTTATGTCACAACCACGTTCAAAAGAAAGCATTTCCGCC
CAACACCAGATGCATGTAGAGCCGCGTACAACTGGAAGATGGCCGGTGACCCCA
GATATGAAGAGTCTCTACACAATCCGTACCCTGACTACCGCTGGCTTCGAACTGT
```

```
AAAAACCACCAAGGAGTCTCTCGTTATCATATCTCCAAGTGTGGCAGATTTGGAC

CCATATGACAGATCCCTTCACTCGAGGGTCTTCCCTAGCGGGAAGTGCTCAGGA

GTAGCGGTGTCTTCTACCTACTGCTCCACTAACCACGATTACACCATTTGGATGC

CCGAGAATCCGAGACTAGGGATGTCTTGTGACATTTTTACCAATAGTAGAGGGA

AGAGAGCATCCAAAGGGAGTGAGACTTGCGGCTTTGTAGATGAAAGAGGCCTAT

ATAAGTCTTTAAAAGGAGCATGCAAACTCAAGTTATGTGGAGTTCTAGGACTTA

GACTTATGGATGGAACATGGGTCTCGATGCAAACATCAAATGAAACCAAATGGT

GCCCTCCCGATAAGTTGGTGAACCTGCACGACTTTCGCTCAGACGAAATTGAGC

ACCTTGTTGTAGAGGAGTTGGTCAGGAAGAGAGAGGAGTGTCTGGATGCACTAG

AGTCCATCATGACAACCAAGTCAGTGAGTTTCAGACGTCTCAGTCATTTAAGAAA

ACTTGTCCCTGGGTTTGGAAAAGCATATACCATATTCAACAAGACCTTGATGGAA

GCCGATGCTCACTACAAGTCAGTCgagACTTGGAATGAGATCCTCCCTTCAAAAG

GGTGTTTAAGAGTTGGGGGAGGTGTCATCCTCATGTGAACGGGGTGTTTTTCAA

TGGTATAATATTAGGACCTGACGGCAATGTCTTAATCCCAGAGATGCAATCATCC

CTCCTCCAGCAACATATGGAGTTGTTGGAATCCTCGGTTATCCCCCTTGTGCACC

CCCTGGCAGACCCGTCTACCGTTTTCAAGGACGGTGACGAGGCTGAGGATTTTGT

TGAAGTTCACCTTCCCGATGTGCACAATCAGGTCTCAGGAGTTGACTTGGGTCTC

CCGAACTGGGGGAAGTATGTATTACTGAGTGCAGGGGCCCTGACTGCCTTGATG

TTGATAATTTTCCTGATGACATGTTGTAGAAGAGTCAATCGATCAGAACCTACGC

AACACAATCTCAGAGGGACAGGGAGGGAGGTGTCAGTCACTCCCCAAAGCGGG

AAGATCATATCTTCATGGGAATCACACAAGAGTGGGGGTGAGACCAGACTGTAA ttaattaaCGTCCTTTCAACGATCCAAGTCcatgaaaaaaactaacaccccctcccgtacctagcTTATAAA

GTGCTGGGTCATCTAAGCTTTTCAGTCGAGAAAAAAACATTAGATCAGAAGAAC

AACTGGCAACACTTCTCAACCTGAGACTTACTTCAAGATGCTCGATCCTGGAGAG

GTCTATGATGACCCTATTGACCCAATCGAGTTAGAGGCTGAACCCAGAGGAACC

CCCATTGTCCCCAACATCTTGAGGAACTCTGACTACAATCTCAACTCTCCTTTGA

TAGAAGATCCTGCTAGACTAATGTTAGAATGGTTAAAAACAGGGAATAGACCTT

ATCGGATGACTCTAACAGACAATTGCTCCAGGTCTTTCAGAGTTTTGAAAGATTA

TTTCAAGAAGGTAGATTTGGGTTCTCTCAAGGTGGGCGGAATGGCTGCACAGTC

AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT
```

```
AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA

TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGGATACATGGCACAAGCTCCCGATC

ACGCAGATCTTTGAGATTCCTGAATCAATGGATCCGTCAGAAATATTGGATGACA

AATCACATTCTTTCACCAGAACGAGACTAGCTTCTTGGCTGTCAGAAAACCGAGG

GGGGCCTGTTCCTAGCGAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC

GACATACATGTTGTCGCCAGGGCTATCTCAAGAGGGGCTCCTCTATGAATTGGAG

AGAATATCAAGGAATGCACTTTCGATATACAGAGCCGTCGAGGAAGGGGCATCT

AAGCTAGGGCTGATCATCAAGAAAGAAGAGACCATGTGTAGTTATGACTTCCTC

ATCTATGGAAAAACCCCTTTGTTTAGAGGTAACATATTGGTGCCTGAGTCCAAAA

GATGGGCCAGAGTCTCTTGCGTCTCTAATGACCAAATAGTCAACCTCGCCAATAT

AATGTCGACAGTGTCCACCAATGCGCTAACAGTGGCACAACACTCTCAATCTTTG

ATCAAACCGATGAGGGATTTTCTGCTCATGTCAGTACAGGCAGTCTTTCACTACC

TGCTATTTAGCCCAATCTTAAAGGGAAGAGTTTACAAGATTCTGAGCGCTGAAG

GGGAGAGCTTTCTCCTAGCCATGTCAAGGATAATCTATCTAGATCCTTCTTTGGG

AGGGATATCTGGAATGTCCCTCGGAAGATTCCATATACGACAGTTCTCAGACCCT

GTCTCTGAAGGGTTATCCTTCTGGAGAGATCTGGTTAAGCTCCCAAGAGTCCT

GGATTCACGCGTTGTGTCAAGAGGCTGGAAACCCAGATCTTGGAGAGAGAACAC

TCGAGAGCTTCACTCGCCTTCTAGAAGATCCGACCACCTTAAATATCAGAGGAG

GGGCCAGTCCTACCATTCTACTCAAGGATGCAATCAGAAAGGCTTTATATGACG

AGGTGGACAAGGTGGAAAATTCAGAGTTTCGAGAGGCAATCCTGTTGTCCAAGA

CCCATAGAGATAATTTTATACTCTTCTTAATATCTGTTGAGCCTCTGTTTCCTCGA

TTTCTCAGTGAGCTATTCAGTTCGTCTTTTTTGGGAATCCCCGAGTCAATCATTGG
```

-continued

```
ATTGATACAAAACTCCCGAACGATAAGAAGGCAGTTTAGAAAGAGTCTCTCAAA

AACTTTAGAAGAATCCTTCTACAACTCAGAGATCCACGGGATTAGTCGGATGAC

CCAGACACCTCAGAGGGTTGGGGGGGTGTGGCCTTGCTCTTCAGAGAGGGCAGA

TCTACTTAGGGAGATCTCTTGGGGAAGAAAAGTGGTAGGCACGACAGTTCCTCA

CCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCA

GTCATTTTTTTCACGAGGCCCCCTAAAGGGATACTTGGGCTCGTCCACCTCTATG

TCGACCCAGCTATTCCATGCATGGGAAAAAGTCACTAATGTTCATGTGGTGAAG

AGAGCTCTATCGTTAAAAGAATCTATAAACTGGTTCATTACTAGAGATTCCAACT

TGGCTCAAGCTCTAATTAGGAACATTATGTCTCTGACAGGCCCTGATTTCCCTCT

AGAGGAGGCCCCTGTCTTCAAAAGGACGGGGTCAGCCTTGCATAGGTTCAAGTC

TGCCAGATACAGCGAAGGAGGGTATTCTTCTGTCTGCCCGAACCTCCTCTCTCAT

ATTTCTGTTAGTACAGACACCATGTCTGATTTGACCCAAGACGGGAAGAACTACG

ATTTCATGTTCCAGCCATTGATGCTTTATGCACAGACATGGACATCAGAGCTGGT

ACAGAGAGACACAAGGCTAAGAGACTCTACGTTTCATTGGCACCTCCGATGCAA

CAGGTGTGTGAGACCCATTGACGACGTGACCCTGGAGACCTCTCAGATCTTCGA

GTTTCCGGATGTGTCGAAAAGAATATCCAGAATGGTTTCTGGGGCTGTGCCTCAC

TTCCAGAGGCTTCCCGATATCCGTCTGAGACCAGGAGATTTTGAATCTCTAAGCG

GTAGAGAAAAGTCTCACCATATCGGATCAGCTCAGGGGCTCTTATACTCAATCTT

AGTGGCAATTCACGACTCAGGATACAATGATGGAACCATCTTCCCTGTCAACATA

TACGGCAAGGTTTCCCCTAGAGACTATTTGAGAGGGCTCGCAAGGGGAGTATTG

ATAGGATCCTCGATTTGCTTCTTGACAAGAATGACAAATATCAATATTAATAGAC

CTCTTGAATTGGTCTCAGGGGTAATCTCATATATTCTCCTGAGGCTAGATAACCA

TCCCTCCTTGTACATAATGCTCAGAGAACCGTCTCTTAGAGGAGAGATATTTTCT

ATCCCTCAGAAAATCCCCGCCGCTTATCCAACCACTATGAAAGAAGGCAACAGA

TCAATCTTGTGTTATCTCCAACATGTGCTACGCTATGAGCGAGAGATAATCACGG

CGTCTCCAGAGAATGACTGGCTATGGATCTTTTCAGACTTTAGAAGTGCCAAAAT

GACGTACCTATCCCTCATTACTTACCAGTCTCATCTTCTACTCCAGAGGGTTGAG

AGAAACCTATCTAAGAGTATGAGAGATAACCTGCGACAATTGAGTTCTTTGATG

AGGCAGGTGCTGGGCGGGCACGGAGAAGATACCTTAGAGTCAGACGACAACATT

CAACGACTGCTAAAAGACTCTTTACGAAGGACAAGATGGGTGGATCAAGAGGTG

CGCCATGCAGCTAGAACCATGACTGGAGATTACAGCCCCAACAAGAAGGTGTCC

CGTAAGGTAGGATGTTCAGAATGGGTCTGCTCTGCTCAACAGGTTGCAGTCTCTA

CCTCAGCAAACCCGGCCCCTGTCTCGGAGCTTGACATAAGGGCCCTCTCTAAGA

GGTTCCAGAACCCTTTGATCTCGGGCTTGAGAGTGGTTCAGTGGGCAACCGGTGC

TCATTATAAGCTTAAGCCTATTCTAGATGATCTCAATGTTTTCCCATCTCTCTGCC

TTGTAGTTGGGGACGGGTCAGGGGGGATATCAAGGGCAGTCCTCAACATGTTTC

CAGATGCCAAGCTTGTGTTCAACAGTCTTTTAGAGGTGAATGACCTGATGGCTTC

CGGAACACATCCACTGCCTCCTTCAGCAATCATGAGGGGAGGAAATGATATCGT

CTCCAGAGTGATAGATCTTGACTCAATCTGGGAAAAACCGTCCGACTTGAGAAA

CTTGGCAACCTGGAAATACTTCCAGTCAGTCCAAAAGCAGGTCAACATGTCCTAT
```

```
GACCTCATTATTTGCGATGCAGAAGTTACTGACATTGCATCTATCAACCGGATCA

CCCTGTTAATGTCCGATTTTGCATTGTCTATAGATGGACCACTCTATTTGGTCTTC

AAAACTTATGGGACTATGCTAGTAAATCCAAACTACAAGGCTATTCAACACCTGT

CAAGAGCGTTCCCCTCGGTCACAGGGTTTATCACCCAAGTAACTTCGTCTTTTTC

ATCTGAGCTCTACCTCCGATTCTCCAAACGAGGGAAGTTTTTCAGAGATGCTGAG

TACTTGACCTCTTCCACCCTTCGAGAAATGAGCCTTGTGTTATTCAATTGTAGCA

GCCCCAAGAGTGAGATGCAGAGAGCTCGTTCCTTGAACTATCAGGATCTTGTGA

GAGGATTTCCTGAAGAAATCATATCAAATCCTTACAATGAGATGATCATAACTCT

GATTGACAGTGATGTAGAATCTTTTCTAGTCCACAAGATGGTTGATGATCTTGAG

TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```

In one embodiment, the nucleic acid comprises the sequence of SEQ ID NO: 11, shown below (RABV vector: Coravax V3-South Africa (S1-VSVG-E26)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG
```

-continued

```
AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGACTC

ATAAcatgaaaaaaactaacacccctcccGTACGCCACCATGTTCGTGTTTCTGGTGCT

GCTGCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA
```

-continued

```
CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAAGGTCTGTGGGCGATACAGGCCTGTCCAAGAATCCAATCGAGCTGGTAGAG

GGCTGGTTCAGCAGTTGGAAAAGCTCCATCGCCTCCTTTTTCTTTATCATCGGCCT

GATCATCGGACTGTTCCTGGTGCTCCGCGTGGGTATCCACCTGTGCATCAAGCTG

AAGCACACCAAGAAAAGACAGATTTATACAGACATCGAGATGAACCGCCTGGG

AAAGTGAGCTAGCCATGAAAAAAACTAACACCCCTCCTTTCGAACCATCCCAAA

CATGAGCAAGATCTTTGTCAATCCTAGTGCTATTAGAGCCGGTCTGGCCGATCTT

GAGATGGCTGAAGAAACTGTTGATCTGATCAATAGAAATATCGAAGACAATCAG

GCTCATCTCCAAGGGGAACCCATAGAGGTGGACAATCTCCCTGAGGATATGGGG

CGACTTCACCTGGATGATGGAAAATCGCCCAACCATGGTGAGATAGCCAAGGTG

GGAGAAGGCAAGTATCGAGAGGACTTTCAGATGGATGAAGGAGAGGATCCTAG

CTTCCTGTTCCAGTCATACCTGGAAAATGTTGGAGTCCAAATAGTCAGACAAATG

AGGTCAGGAGAGAGATTTCTCAAGATATGGTCACAGACCGTAGAAGAGATTATA

TCCTATGTCGCGGTCAACTTTCCCAACCCTCCAGGAAAGTCTTCAGAGGATAAAT

CAACCCAGACTACTGGCCGAGAGCTCAAGAAGGAGACAACACCCACTCCTTCTC

AGAGAGAAAGCCAATCATCGAAAGCCAGGATGGCGGCTCAAATTGCTTCTGGCC

CTCCAGCCCTTGAATGGTCGGCTACCAATGAAGAGGATGATCTATCAGTGGAGG

CTGAGATCGCTCACCAGATTGCAGAAAGTTTCTCCAAAAAATATAAGTTTCCCTC

TCGATCCTCAGGGATACTCTTGTATAATTTTGAGCAATTGAAAATGAACCTTGAT

GATATAGTTAAAGAGGCAAAAAATGTACCAGGTGTGACCCGTTTAGCCCATGAC

GGGTCCAAACTCCCCCTAAGATGTGTACTGGGATGGGTCGCTTTGGCCAACTCTA

AGAAATTCCAGTTGTTAGTCGAATCCGACAAGCTGAGTAAAATCATGCAAGATG

ACTTGAATCGCTATACATCTTGCTAACCGAACCTCTCCCCTCAGTCCCTCTAGAC

AATAAAATCCGAGATGTCCCAAAGTCAACATGAAAAAAACAGGCAACACCACT

GATAAAATGAACCTCCTACGTAAGATAGTGAAAAACCGCAGGGACGAGGACACT

CAAAAATCCTCTCCCGCGTCAGCCCCTCTGGATGACGATGACTTGTGGCTTCCAC

CCCCTGAATACGTCCCGCTGAAAGAACTTACAGGCAAGAAGAACATGAGGAACT

TTTGTATCAACGGAAGGGTTAAAGTGTGTAGCCCGAATGGTTACTCGTTCAGGAT

CCTGCGGCACATTCTGAAATCATTCGACGAGATATATTCTGGGAATCATAGGATG

ATCGGGTTAGTCAAAGTGGTTATTGGACTGGCTTTGTCAGGATCTCCAGTCCCTG

AGGGCCTGAACTGGGTATACAAATTGAGGAGAACCTTTATCTTCCAGTGGGCTG

ATTCCAGGGGCCCTCTTGAAGGGGAGGAGTTGGAATACTCTCAGGAGATCACTT

GGGATGATGATACTGAGTTCGTCGGATTGCAAATAAGAGTGATTGCAAAACAGT

GTCATATCCAGGGCAGAGTCTGGTGTATCAACATGAACCCGAGAGCATGTCAAC
```

```
TATGGTCTGACATGTCTCTTCAGACACAAAGGTCCGAAGAGGACAAAGATTCCT

CTCTGCTTCTAGAATAATCAGATTATATCCCGCAAATTTATCACTTGTTTACCTCT

GGAGGAGAGAACATATGGGCTCAACTCCAACCCTTGGGAGCAATATAACAAAAA

ACATGTTATGGTGCCATTAAACCGCTGCATTTCATCAAAGTCAAGTTGATTACCT

TTACATTTTGATCCTCTTGGATGTGAAAAAAACTATTAACATCCCTCAAAAGACCC cgggAAAGATGGTTCCTCAGGCTCTCCTGTTTGTACCCCTTCTGGTTTTTCCATTGT

GTTTTGGGAAATTCCCTATTTACACGATACCAGACAAGCTTGGTCCCTGGAGTCC

GATTGACATACATCACCTCAGCTGCCCAAACAATTTGGTAGTGGAGGACGAAGG

ATGCACCAACCTGTCAGGGTTCTCCTACATGGAACTTAAAGTTGGATACATCTTA

GCCATAAAAGTGAACGGGTTCACTTGCACAGGCGTTGTGACGGAGGCTGAAACC

TACACTAACTTCGTTGGTTATGTCACAACCACGTTCAAAAGAAAGCATTTCCGCC

CAACACCAGATGCATGTAGAGCCGCGTACAACTGGAAGATGGCCGGTGACCCCA

GATATGAAGAGTCTCTACACAATCCGTACCCTGACTACCGCTGGCTTCGAACTGT

AAAAACCACCAAGGAGTCTCTCGTTATCATATCTCCAAGTGTGGCAGATTTGGAC

CCATATGACAGATCCCTTCACTCGAGGGTCTTCCCTAGCGGGAAGTGCTCAGGA

GTAGCGGTGTCTTCTACCTACTGCTCCACTAACCACGATTACACCATTTGGATGC

CCGAGAATCCGAGACTAGGGATGTCTTGTGACATTTTTACCAATAGTAGAGGGA

AGAGAGCATCCAAAGGGAGTGAGACTTGCGGCTTTGTAGATGAAAGAGGCCTAT

ATAAGTCTTTAAAAGGAGCATGCAAACTCAAGTTATGTGGAGTTCTAGGACTTA

GACTTATGGATGGAACATGGGTCTCGATGCAAACATCAAATGAAACCAAATGGT

GCCCTCCCGATAAGTTGGTGAACCTGCACGACTTTCGCTCAGACGAAATTGAGC

ACCTTGTTGTAGAGGAGTTGGTCAGGAAGAGAGAGGAGTGTCTGGATGCACTAG

AGTCCATCATGACAACCAAGTCAGTGAGTTTCAGACGTCTCAGTCATTTAAGAAA

ACTTGTCCCTGGGTTTGGAAAAGCATATACCATATTCAACAAGACCTTGATGGAA

GCCGATGCTCACTACAAGTCAGTCgagACTTGGAATGAGATCCTCCCTTCAAAAG

GGTGTTTAAGAGTTGGGGGGAGGTGTCATCCTCATGTGAACGGGGTGTTTTTCAA

TGGTATAATATTAGGACCTGACGGCAATGTCTTAATCCCAGAGATGCAATCATCC

CTCCTCCAGCAACATATGGAGTTGTTGGAATCCTCGGTTATCCCCCTTGTGCACC

CCCTGGCAGACCCGTCTACCGTTTTCAAGGACGGTGACGAGGCTGAGGATTTTGT

TGAAGTTCACCTTCCCGATGTGCACAATCAGGTCTCAGGAGTTGACTTGGGTCTC

CCGAACTGGGGGAAGTATGTATTACTGAGTGCAGGGGCCCTGACTGCCTTGATG

TTGATAATTTTCCTGATGACATGTTGTAGAAGAGTCAATCGATCAGAACCTACGC

AACACAATCTCAGAGGGACAGGGAGGGAGGTGTCAGTCACTCCCCAAAGCGGG

AAGATCATATCTTCATGGGAATCACACAAGAGTGGGGGTGAGACCAGACTGTAAttaa ttaaCGTCCTTTCAACGATCCAAGTCcatgaaaaaaactaacacccctcccgtacctagc

TTATAAAGTGCTGGGTCATCTAAGCTTTTCAGTCGAGAAAAAAACATTAGATCAGAAGAA

CAACTGGCAACACTTCTCAACCTGAGACTTACTTCAAGATGCTCGATCCTGGAGAG

GTCTATGATGACCCTATTGACCCAATCGAGTTAGAGGCTGAACCCAGAGGAACC

CCCATTGTCCCCAACATCTTGAGGAACTCTGACTACAATCTCAACTCTCCTTTGA

TAGAAGATCCTGCTAGACTAATGTTAGAATGGTTAAAAACAGGGAATAGACCTT
```

-continued

```
ATCGGATGACTCTAACAGACAATTGCTCCAGGTCTTTCAGAGTTTTGAAAGATTA

TTTCAAGAAGGTAGATTTGGGTTCTCTCAAGGTGGGCGGAATGGCTGCACAGTC

AATGATTTCTCTCTGGTTATATGGTGCCCACTCTGAATCCAACAGGAGCCGGAGA

TGTATAACAGACTTGGCCCATTTCTATTCCAAGTCGTCCCCCATAGAGAAGCTGT

TGAATCTCACGCTAGGAAATAGAGGGCTGAGAATCCCCCAGAGGGAGTGTTAA

GTTGCCTTGAGAGGGTTGATTATGATAATGCATTTGGAAGGTATCTTGCCAACAC

GTATTCCTCTTACTTGTTCTTCCATGTAATCACCTTATACATGAACGCCCTAGACT

GGGATGAAGAAAAGACCATCCTAGCATTATGGAAAGATTTAACCTCAGTGGACA

TCGGGAAGGACTTGGTAAAGTTCAAAGACCAAATATGGGGACTGCTGATCGTGA

CAAAGGACTTTGTTTACTCCCAAAGTTCCAATTGTCTTTTTGACAGAAACTACAC

ACTTATGCTAAAAGATCTTTTCTTGTCTCGCTTCAACTCCTTAATGGTCTTGCTCT

CTCCCCCAGAGCCCCGATACTCAGATGACTTGATATCTCAACTATGCCAGCTGTA

CATTGCTGGGGATCAAGTCTTGTCTATGTGTGGAAACTCCGGCTATGAAGTCATC

AAAATATTGGAGCCATATGTCGTGAATAGTTTAGTCCAGAGAGCAGAAAAGTTT

AGGCCTCTCATTCATTCCTTGGGAGACTTTCCTGTATTTATAAAAGACAAGGTAA

GTCAACTTGAAGAGACGTTCGGTCCCTGTGCAAGAAGGTTCTTTAGGGCTCTGGA

TCAATTCGACAACATACATGACTTGGTTTTTGTGTTTGGCTGTTACAGGCATTGG

GGGCACCCATATATAGATTATCGAAAGGGTCTGTCAAAACTATATGATCAGGTTC

ACCTTAAAAAAATGATAGATAAGTCCTACCAGGAGTGCTTAGCAAGCGACCTAG

CCAGGAGGATCCTTAGATGGGTTTTGATAAGTACTCCAAGTGGTATCTGGATTC

AAGATTCCTAGCCCGAGACCACCCCTTGACTCCTTATATCAAAACCCAAACATGG

CCACCCAAACATATTGTAGACTTGGTGGGGATACATGGCACAAGCTCCCGATC

ACGCAGATCTTTGAGATTCCTGAATCAATGGATCCGTCAGAAATATTGGATGACA

AATCACATTCTTTCACCAGAACGAGACTAGCTTCTTGGCTGTCAGAAAACCGAGG

GGGGCCTGTTCCTAGCGAAAAAGTTATTATCACGGCCCTGTCTAAGCCGCCTGTC

AATCCCCGAGAGTTTCTGAGGTCTATAGACCTCGGAGGATTGCCAGATGAAGAC

TTGATAATTGGCCTCAAGCCAAAGGAACGGGAATTGAAGATTGAAGGTCGATTC

TTTGCTCTAATGTCATGGAATCTAAGATTGTATTTTGTCATCACTGAAAAACTCTT

GGCCAACTACATCTTGCCACTTTTTGACGCGCTGACTATGACAGACAACCTGAAC

AAGGTGTTTAAAAAGCTGATCGACAGGGTCACCGGGCAAGGGCTTTTGGACTAT

TCAAGGGTCACATATGCATTTCACCTGGACTATGAAAAGTGGAACAACCATCAA

AGATTAGAGTCAACAGAGGATGTATTTTCTGTCCTAGATCAAGTGTTTGGATTGA

AGAGAGTGTTTTCTAGAACACACGAGTTTTTTCAAAAGGCCTGGATCTATTATTC

AGACAGATCAGACCTCATCGGGTTACGGGAGGATCAAATATACTGCTTAGATGC

GTCCAACGGCCCAACCTGTTGGAATGGCCAGGATGGCGGGCTAGAAGGCTTACG

GCAGAAGGGCTGGAGTCTAGTCAGCTTATTGATGATAGATAGAGAATCTCAAAT

CAGGAACACAAGAACCAAAATACTAGCTCAAGGAGACAACCAGGTTTTATGTCC

GACATACATGTTGTCGCCAGGGCTATCTCAAGAGGGGCTCCTCTATGAATTGGAG

AGAATATCAAGGAATGCACTTTCGATATACAGAGCCGTCGAGGAAGGGGCATCT

AAGCTAGGGCTGATCATCAAGAAAGAAGAGACCATGTGTAGTTATGACTTCCTC

ATCTATGGAAAAACCCCTTTGTTTAGAGGTAACATATTGGTGCCTGAGTCCAAAA
```

-continued

```
GATGGGCCAGAGTCTCTTGCGTCTCTAATGACCAAATAGTCAACCTCGCCAATAT

AATGTCGACAGTGTCCACCAATGCGCTAACAGTGGCACAACACTCTCAATCTTTG

ATCAAACCGATGAGGGATTTTCTGCTCATGTCAGTACAGGCAGTCTTTCACTACC

TGCTATTTAGCCCAATCTTAAAGGGAAGAGTTTACAAGATTCTGAGCGCTGAAG

GGGAGAGCTTTCTCCTAGCCATGTCAAGGATAATCTATCTAGATCCTTCTTTGGG

AGGGATATCTGGAATGTCCCTCGGAAGATTCCATATACGACAGTTCTCAGACCCT

GTCTCTGAAGGGTTATCCTTCTGGAGAGAGATCTGGTTAAGCTCCCAAGAGTCCT

GGATTCACGCGTTGTGTCAAGAGGCTGGAAACCCAGATCTTGGAGAGAGAACAC

TCGAGAGCTTCACTCGCCTTCTAGAAGATCCGACCACCTTAAATATCAGAGGAG

GGGCCAGTCCTACCATTCTACTCAAGGATGCAATCAGAAAGGCTTTATATGACG

AGGTGGACAAGGTGGAAAATTCAGAGTTTCGAGAGGCAATCCTGTTGTCCAAGA

CCCATAGAGATAATTTTATACTCTTCTTAATATCTGTTGAGCCTCTGTTTCCTCGA

TTTCTCAGTGAGCTATTCAGTTCGTCTTTTTTGGGAATCCCCGAGTCAATCATTGG

ATTGATACAAAACTCCCGAACGATAAGAAGGCAGTTTAGAAAGAGTCTCTCAAA

AACTTTAGAAGAATCCTTCTACAACTCAGAGATCCACGGGATTAGTCGGATGAC

CCAGACACCTCAGAGGGTTGGGGGGGTGTGGCCTTGCTCTTCAGAGAGGGCAGA

TCTACTTAGGGAGATCTCTTGGGGAAGAAAAGTGGTAGGCACGACAGTTCCTCA

CCCTTCTGAGATGTTGGGATTACTTCCCAAGTCCTCTATTTCTTGCACTTGTGGAG

CAACAGGAGGAGGCAATCCTAGAGTTTCTGTATCAGTACTCCCGTCCTTTGATCA

GTCATTTTTTTCACGAGGCCCCCTAAAGGGATACTTGGGCTCGTCCACCTCTATG

TCGACCCAGCTATTCCATGCATGGGAAAAAGTCACTAATGTTCATGTGGTGAAG

AGAGCTCTATCGTTAAAAGAATCTATAAACTGGTTCATTACTAGAGATTCCAACT

TGGCTCAAGCTCTAATTAGGAACATTATGTCTCTGACAGGCCCTGATTTCCCTCT

AGAGGAGGCCCCTGTCTTCAAAAGGACGGGGTCAGCCTTGCATAGGTTCAAGTC

TGCCAGATACAGCGAAGGAGGGTATTCTTCTGTCTGCCCGAACCTCCTCTCTCAT

ATTTCTGTTAGTACAGACACCATGTCTGATTTGACCCAAGACGGGAAGAACTACG

ATTTCATGTTCCAGCCATTGATGCTTTATGCACAGACATGGACATCAGAGCTGGT

ACAGAGAGACACAAGGCTAAGAGACTCTACGTTTCATTGGCACCTCCGATGCAA

CAGGTGTGTGAGACCCATTGACGACGTGACCCTGGAGACCTCTCAGATCTTCGA

GTTTCCGGATGTGTCGAAAAGAATATCCAGAATGGTTTCTGGGGCTGTGCCTCAC

TTCCAGAGGCTTCCCGATATCCGTCTGAGACCAGGAGATTTTGAATCTCTAAGCG

GTAGAGAAAAGTCTCACCATATCGGATCAGCTCAGGGGCTCTTATACTCAATCTT

AGTGGCAATTCACGACTCAGGATACAATGATGGAACCATCTTCCCTGTCAACATA

TACGGCAAGGTTTCCCCTAGAGACTATTTGAGAGGGCTCGCAAGGGGAGTATTG

ATAGGATCCTCGATTTGCTTCTTGACAAGAATGACAAATATCAATATTAATAGAC

CTCTTGAATTGGTCTCAGGGGTAATCTCATATATTCTCCTGAGGCTAGATAACCA

TCCCTCCTTGTACATAATGCTCAGAGAACCGTCTCTTAGAGGAGAGATATTTTCT

ATCCCTCAGAAAATCCCCGCCGCTTATCCAACCACTATGAAAGAAGGCAACAGA

TCAATCTTGTGTTATCTCCAACATGTGCTACGCTATGAGCGAGAGATAATCACGG

CGTCTCCAGAGAATGACTGGCTATGGATCTTTTCAGACTTTAGAAGTGCCAAAAT
```

-continued
```
GACGTACCTATCCCTCATTACTTACCAGTCTCATCTTCTACTCCAGAGGGTTGAG

AGAAACCTATCTAAGAGTATGAGAGATAACCTGCGACAATTGAGTTCTTTGATG

AGGCAGGTGCTGGGCGGGCACGGAGAAGATACCTTAGAGTCAGACGACAACATT

CAACGACTGCTAAAAGACTCTTTACGAAGGACAAGATGGGTGGATCAAGAGGTG

CGCCATGCAGCTAGAACCATGACTGGAGATTACAGCCCCAACAAGAAGGTGTCC

CGTAAGGTAGGATGTTCAGAATGGGTCTGCTCTGCTCAACAGGTTGCAGTCTCTA

CCTCAGCAAACCCGGCCCCTGTCTCGGAGCTTGACATAAGGGCCCTCTCTAAGA

GGTTCCAGAACCCTTTGATCTCGGGCTTGAGAGTGGTTCAGTGGGCAACCGGTGC

TCATTATAAGCTTAAGCCTATTCTAGATGATCTCAATGTTTTCCCATCTCTCTGCC

TTGTAGTTGGGGACGGGTCAGGGGGGATATCAAGGGCAGTCCTCAACATGTTTC

CAGATGCCAAGCTTGTGTTCAACAGTCTTTTAGAGGTGAATGACCTGATGGCTTC

CGGAACACATCCACTGCCTCCTTCAGCAATCATGAGGGGAGGAAATGATATCGT

CTCCAGAGTGATAGATCTTGACTCAATCTGGGAAAAACCGTCCGACTTGAGAAA

CTTGGCAACCTGGAAATACTTCCAGTCAGTCCAAAAGCAGGTCAACATGTCCTAT

GACCTCATTATTTGCGATGCAGAAGTTACTGACATTGCATCTATCAACCGGATCA

CCCTGTTAATGTCCGATTTTGCATTGTCTATAGATGGACCACTCTATTTGGTCTTC

AAAACTTATGGGACTATGCTAGTAAATCCAAACTACAAGGCTATTCAACACCTGT

CAAGAGCGTTCCCCTCGGTCACAGGGTTTATCACCCAAGTAACTTCGTCTTTTTC

ATCTGAGCTCTACCTCCGATTCTCCAAACGAGGGAAGTTTTTCAGAGATGCTGAG

TACTTGACCTCTTCCACCCTTCGAGAAATGAGCCTTGTGTTATTCAATTGTAGCA

GCCCCAAGAGTGAGATGCAGAGAGCTCGTTCCTTGAACTATCAGGATCTTGTGA

GAGGATTTCCTGAAGAAATCATATCAAATCCTTACAATGAGATGATCATAACTCT

GATTGACAGTGATGTAGAATCTTTTCTAGTCCACAAGATGGTTGATGATCTTGAG

TTACAGAGGGGAACTCTGTCTAAAGTGGCTATCATTATAGCCATCATGATAGTTT

TCTCCAACAGAGTCTTCAACGTTTCCAAACCCCTAACTGACCCCTCGTTCTATCC

ACCGTCTGATCCCAAAATCCTGAGGCACTTCAACATATGTTGCAGTACTATGATG

TATCTATCTACTGCTTTAGGTGACGTCCCTAGCTTCGCAAGACTTCACGACCTGT

ATAACAGACCTATAACTTATTACTTCAGAAAGCAAGTCATTCGAGGGAACGTTTA

TCTATCTTGGAGTTGGTCCAACGACACCTCAGTGTTCAAAAGGGTAGCCTGTAAT

TCTAGCCTGAGTCTGTCATCTCACTGGATCAGGTTGATTTACAAGATAGTGAAGA

CTACCAGACTCGTTGGCAGCATCAAGGATCTATCCAGAGAAGTGGAAAGACACC

TTCATAGGTACAACAGGTGGATCACCCTAGAGGATATCAGATCTAGATCATCCCT

ACTAGACTACAGTTGCCTGTGAACCGGATACTCCTGGAAGCCTGCCCATGCTAA

GACTCTTGTGTGATGTATCTTGAAAAAAACAAGATCCTAAATCTGAACCTTTGGT

TGTTTGATTGTTTTTCTCAttttttgttgtttatttgttaagcgt.
```

In one embodiment, the nucleic acid comprises the sequence of SEQ ID NO: 12, shown below (RABV vector: Coravax V4-China (S1-RABVG-T2A-P)):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA
```

-continued

```
GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGACTCA

TAAcatgaaaaaaactaacacccccccgtacgGCCACCATGTTCGTGTTTCTGGTGCTG

CTGCCTCTGGTGAGCTCCCAGTGCGTGAACCTGACCACAAGGACCCAGCTGCCCCC

TGCCTATACCAATTCCTTCACACGGGGCGTGTACTATCCCGACAAGGTGTTCCGG

AGCAGCGTGCTGCACTCCACACAGGATCTGTTTCTGCCTTTCTTTTCTAACGTGAC

CTGGTTCCACGCCATCCACGTGAGCGGCACCAATGGCACAAAGCGGTTCGACAA

TCCAGTGCTGCCCTTTAACGATGGCGTGTACTTCGCCTCCACCGAGAAGTCTAAC

ATCATCAGAGGCTGGATCTTTGGCACCACACTGGACAGCAAGACACAGTCCCTG

CTGATCGTGAACAATGCCACCAACGTGGTCATCAAGGTGTGCGAGTTCCAGTTTT

GTAATGATCCATTCCTGGGCGTGTACTATCACAAGAACAATAAGTCTTGGATGGA

GAGCGAGTTTCGCGTGTATTCCTCTGCCAACAATTGCACATTTGAGTACGTGTCC

CAGCCCTTCCTGATGGACCTGGAGGGCAAGCAGGGCAATTTCAAGAACCTGAGG

GAGTTCGTGTTTAAGAATATCGATGGCTACTTCAAAATCTACTCCAAGCACACCC

CAATCAACCTGGTGCGCGACCTGCCACAGGGCTTCTCTGCCCTGGAGCCACTGGT

GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC
```

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAGGGCTTTAACTGTTATTTCCCTCTGCAGAGCTACGGCTTCCAGCCAA

CAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGA

ACAAGTGCGTGAACTTCAACTTCAACGGACTGACCGGAACAGGCGTGCTGACCG

AGTCCAACAAGAAGTTCCTGCCTTTTCAGCAGTTCGGCAGGGACATCGCAGATA

CCACAGACGCCGTGCGCGACCCTCAGACCCTGGAGATCCTGGACATCACACCAT

GCTCCTTCGGCGGCGTGTCTGTGATCACACCAGGCACCAATACAAGCAACCAGG

TGGCCGTGCTGTATCAGGACGTGAATTGTACCGAGGTGCCAGTGGCAATCCACG

CAGATCAGCTGACCCCTACATGGCGGGTGTACTCTACCGGCAGCAACGTGTTCC

AGACAAGAGCCGGATGCCTGATCGGAGCAGAGCACGTGAACAATAGCTATGAGT

GCGACATCCCTATCGGCGCCGGCATCTGTGCCTCCTACCAGACCCAGACAAACTC

CCCAAGGTCTGTGGGAGATGAGGCCGAAGACTTTGTGGAAGTCCACCTGCCTGA

TGTGCATAACCAGGTGTCTGGCGTCGACCTGGGACTGCCAAATTGGGGCAAGTA

CGTGCTGCTGAGTGCTGGAGCACTGACTGCCCTGATGCTGATCATTTTCCTGATG

ACCTGCTGTCGGCGCGTGAACAGAAGTGAGCCCACTCAGCACAATCTGCGAGGA

ACCGGGAGAGAAGTGTCAGTCACACCTCAGAGCGGGAAAATCATTAGTAGTTGGGAAT

CACATAAAAGCGGGGCGAGACCAGGCTGggatccggctccggcgagggcaggggaag tctactaacatgcggggacgtggaggaaaatcccggccccATGAGCAAGATCTTTGTC

AATCCTAGTGCTATTAGAGCCGGTCTGGCCGATCTTGAGATGGCTGAAGAAACTGTTG

ATCTGATCAATAGAAATATCGAAGACAATCAGGCTCATCTCCAAGGGGAACCCATAGA

GGTGGACAATCTCCCTGAGGATATGGGCGACTTCACCTGGATGATGGAAAATCGCCC

AACCATGGTGAGATAGCCAAGGTGGGAGAAGGCAAGTATCGAGAGGACTTTCAGAT

GGATGAAGGAGAGGATCCTAGCTTCCTGTTCCAGTCATACCTGGAAAATGTTGG

AGTCCAAATAGTCAGACAAATGAGGTCAGGAGAGAGATTTCTCAAGATATGGTC

ACAGACCGTAGAAGAGATTATATCCTATGTCGCGGTCAACTTTCCCAACCCTCCA

GGAAAGTCTTCAGAGGATAAATCAACCCAGACTACTGGCCGAGAGCTCAAGAAG

GAGACAACACCCACTCCTTCTCAGAGAGAAAGCCAATCATCGAAAGCCAGGATG

GCGGCTCAAATTGCTTCTGGCCCTCCAGCCCTTGAATGGTCGGCTACCAATGAAG

AGGATGATCTATCAGTGGAGGCTGAGATCGCTCACCAGATTGCAGAAAGTTTCT

CCAAAAAATATAAGTTTCCCTCTCGATCCTCAGGGATACTCTTGTATAATTTTGA

```
GCAATTGAAAATGAACCTTGATGATATAGTTAAAGAGGCAAAAAATGTACCAGG

TGTGACCCGTTTAGCCCATGACGGGTCCAAACTCCCCCTAAGATGTGTACTGGGA

TGGGTCGCTTTGGCCAACTCTAAGAAATTCCAGTTGTTAGTCGAATCCGACAAGC

TGAGTAAAATCATGCAAGATGACTTGAATCGCTATACATCTTGCTAACCGAACCT

CTCCCCTCAGTCCCTCTAGACAATAAAATCCGAGATGTCCCAAAGTCAACATGA

AAAAAACAGGCAACACCACTGATAAAATGAACCTCCTACGTAAGATAGTGAAAA

ACCGCAGGGACGAGGACACTCAAAAATCCTCTCCCGCGTCAGCCCCTCTGGATG

ACGATGACTTGTGGCTTCCACCCCCTGAATACGTCCCGCTGAAAGAACTTACAGG

CAAGAAGAACATGAGGAACTTTTGTATCAACGGAAGGGTTAAAGTGTGTAGCCC

GAATGGTTACTCGTTCAGGATCCTGCGGCACATTCTGAAATCATTCGACGAGATA

TATTCTGGGAATCATAGGATGATCGGGTTAGTCAAAGTGGTTATTGGACTGGCTT

TGTCAGGATCTCCAGTCCCTGAGGGCCTGAACTGGGTATACAAATTGAGGAGAA

CCTTTATCTTCCAGTGGGCTGATTCCAGGGGCCCTCTTGAAGGGGAGGAGTTGGA

ATACTCTCAGGAGATCACTTGGGATGATGATACTGAGTTCGTCGGATTGCAAATA

AGAGTGATTGCAAAACAGTGTCATATCCAGGGCAGAGTCTGGTGTATCAACATG

AACCCGAGAGCATGTCAACTATGGTCTGACATGTCTCTTCAGACACAAAGGTCC

GAAGAGGACAAAGATTCCTCTCTGCTTCTAGAATAATCAGATTATATCCCGCAAA

TTTATCACTTGTTTACCTCTGGAGGAGAGAACATATGGGCTCAACTCCAACCCTT

GGGAGCAATATAACAAAAAACATGTTATGGTGCCATTAAACCGCTGCATTTCAT

CAAAGTCAAGTTGATTACCTTTACATTTTGATCCTCTTGGATGTGAAAAAAACTA

TTAACATCCCTCAAAAGACCcccgggAAAGATGGTTCCTCAGGCTCTCCTGTTTGTAC

CCCTTCTGGTTTTTCCATTGTGTTTTGGGAAATTCCCTATTTACACGATACCAGAC

AAGCTTGGTCCCTGGAGTCCGATTGACATACATCACCTCAGCTGCCCAAACAATT

TGGTAGTGGAGGACGAAGGATGCACCAACCTGTCAGGGTTCTCCTACATGGAAC

TTAAAGTTGGATACATCTTAGCCATAAAAGTGAACGGGTTCACTTGCACAGGCGT

TGTGACGGAGGCTGAAACCTACACTAACTTCGTTGGTTATGTCACAACCACGTTC

AAAAGAAAGCATTTCCGCCCAACACCAGATGCATGTAGAGCGCGTACAACTGG

AAGATGGCCGGTGACCCCAGATATGAAGAGTCTCTACACAATCCGTACCCTGAC

TACCGCTGGCTTCGAACTGTAAAAACCACCAAGGAGTCTCTCGTTATCATATCTC

CAAGTGTGGCAGATTTGGACCCATATGACAGATCCCTTCACTCGAGGGTCTTCCC

TAGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG
```

-continued

```
TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGGGGG

TGAGACCAGACTGTAAttaattaaCGTCCTTTCAACGATCCAAGTCcatgaaaaaaa ctaacacccctcccgtacctagcTTATAAAGTGCTGGGTCATCTAAGCTTTTCAGTC

GAGAAAAAAACATTAGATCAGAAGAACAACTGGCAACACTTCTCAACCTGAGACTTA

CTTCAAGATGCTCGATCCTGGAGAGGTCTATGATGACCCTATTGACCCAATCGAGTT

AGAGGCTGAACCCAGAGGAACCCCCATTGTCCCCAACATCTTGAGGAACTCTGACTA

CAATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC

CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG
```

-continued

```
GATTGCCAGATGAAGACTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT

CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCTCATATTTCTGTTAGTACAGACACCATGTCTGATTTGACC
```

-continued

```
CAAGACGGGAAGAACTACGATTTCATGTTCCAGCCATTGATGCTTTATGCACAGA
CATGGACATCAGAGCTGGTACAGAGAGACACAAGGCTAAGAGACTCTACGTTTC
ATTGGCACCTCCGATGCAACAGGTGTGTGAGACCCATTGACGACGTGACCCTGG
AGACCTCTCAGATCTTCGAGTTTCCGGATGTGTCGAAAAGAATATCCAGAATGGT
TTCTGGGGCTGTGCCTCACTTCCAGAGGCTTCCCGATATCCGTCTGAGACCAGGA
GATTTTGAATCTCTAAGCGGTAGAGAAAAGTCTCACCATATCGGATCAGCTCAG
GGGCTCTTATACTCAATCTTAGTGGCAATTCACGACTCAGGATACAATGATGGAA
CCATCTTCCCTGTCAACATATACGGCAAGGTTTCCCCTAGAGACTATTTGAGAGG
GCTCGCAAGGGAGTATTGATAGGATCCTCGATTTGCTTCTTGACAAGAATGACA
AATATCAATATTAATAGACCTCTTGAATTGGTCTCAGGGGTAATCTCATATATTC
TCCTGAGGCTAGATAACCATCCCTCCTTGTACATAATGCTCAGAGAACCGTCTCT
TAGAGGAGAGATATTTTCTATCCCTCAGAAAATCCCCGCCGCTTATCCAACCACT
ATGAAAGAAGGCAACAGATCAATCTTGTGTTATCTCCAACATGTGCTACGCTATG
AGCGAGAGATAATCACGGCGTCTCCAGAGAATGACTGGCTATGGATCTTTTCAG
ACTTTAGAAGTGCCAAAATGACGTACCTATCCCTCATTACTTACCAGTCTCATCT
TCTACTCCAGAGGGTTGAGAGAAACCTATCTAAGAGTATGAGAGATAACCTGCG
ACAATTGAGTTCTTTGATGAGGCAGGTGCTGGGCGGGCACGGAGAAGATACCTT
AGAGTCAGACGACAACATTCAACGACTGCTAAAAGACTCTTTACGAAGGACAAG
ATGGGTGGATCAAGAGGTGCGCCATGCAGCTAGAACCATGACTGGAGATTACAG
CCCCAACAAGAAGGTGTCCCGTAAGGTAGGATGTTCAGAATGGGTCTGCTCTGC
TCAACAGGTTGCAGTCTCTACCTCAGCAAACCCGGCCCCTGTCTCGGAGCTTGAC
ATAAGGGCCCTCTCTAAGAGGTTCCAGAACCCTTTGATCTCGGGCTTGAGAGTGG
TTCAGTGGGCAACCGGTGCTCATTATAAGCTTAAGCCTATTCTAGATGATCTCAA
TGTTTTCCCATCTCTCTGCCTTGTAGTTGGGGACGGGTCAGGGGGGATATCAAGG
GCAGTCCTCAACATGTTTCCAGATGCCAAGCTTGTGTTCAACAGTCTTTTAGAGG
TGAATGACCTGATGGCTTCCGGAACACATCCACTGCCTCCTTCAGCAATCATGAG
GGGAGGAAATGATATCGTCTCCAGAGTGATAGATCTTGACTCAATCTGGGAAAA
ACCGTCCGACTTGAGAAACTTGGCAACCTGGAAATACTTCCAGTCAGTCCAAAA
GCAGGTCAACATGTCCTATGACCTCATTATTTGCGATGCAGAAGTTACTGACATT
GCATCTATCAACCGGATCACCCTGTTAATGTCCGATTTTGCATTGTCTATAGATG
GACCACTCTATTTGGTCTTCAAAACTTATGGGACTATGCTAGTAAATCCAAACTA
CAAGGCTATTCAACACCTGTCAAGAGCGTTCCCCTCGGTCACAGGGTTTATCACC
CAAGTAACTTCGTCTTTTTCATCTGAGCTCTACCTCCGATTCTCCAAACGAGGGA
AGTTTTTCAGAGATGCTGAGTACTTGACCTCTTCCACCCTTCGAGAAATGAGCCT
TGTGTTATTCAATTGTAGCAGCCCCAAGAGTGAGATGCAGAGAGCTCGTTCCTTG
AACTATCAGGATCTTGTGAGAGGATTTCCTGAAGAAATCATATCAAATCCTTACA
ATGAGATGATCATAACTCTGATTGACAGTGATGTAGAATCTTTTCTAGTCCACAA
GATGGTTGATGATCTTGAGTTACAGAGGGGAACTCTGTCTAAAGTGGCTATCATT
ATAGCCATCATGATAGTTTTCTCCAACAGAGTCTTCAACGTTTCCAAACCCCTAA
CTGACCCCTCGTTCTATCCACCGTCTGATCCCAAAATCCTGAGGCACTTCAACAT
```

-continued
ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCCTAA

ATCTGAACCTTTGGTTGTTTGATTGTTTTTCTCAtttttgttgtttatttgttaagcgt

In one embodiment, the nucleic acid comprises the sequence of SEQ ID NO: 13, shown below (RABV vector: Coravax V4 South Africa):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAaATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAcatgaaaaaaactaacaccccctcccgtacgGCCACCATGTTCGTGTTTCTG

GTGCTGCTGCCTCTGGTGAGCTCCCAGTGCGTGAACTTCACCACAAGGACCCAGCTGC

-continued
```
CCCCTGCCTATACCAATTCCTTCACACGGGGCGTGTACTATCCCGACAAGGTGTTCCG

GAGCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC

CCAGAATCAAGCGTGATTCCTCTGGTCCATCCACTGGCAGATCCCTCCACAGTGT

TCAAAGACGGAGATGAGGCCGAAGACTTTGTGGAAGTCCACCTGCCTGATGTGC

ATAACCAGGTGTCTGGCGTCGACCTGGGACTGCCAAATTGGGGCAAGTACGTGC

TGCTGAGTGCTGGAGCACTGACTGCCCTGATGCTGATCATTTTCCTGATGACCTG

CTGTCGGCGCGTGAACAGAAGTGAGCCCACTCAGCACAATCTGCGAGGAACCGG
```

-continued

```
GAGAGAAGTGTCAGTCACACCTCAGAGCGGGAAAATCATTAGTAGTTGGGAATCACAT

AAAAGCGGGGGCGAGACCAGGCTGggatccggctccggcgagggcaggggaagtctac taacatgcggggacgtggaggaaaatcccggccccATGAGCAAGATCTTTGTCAATCC

TAGTGCTATTAGAGCCGGTCTGGCCGATCTTGAGATGGCTGAAGAAACTGTTGATCTG

ATCAATAGAAATATCGAAGACAATCAGGCTCATCTCCAAGGGGAACCCATAGAGGTGG

ACAATCTCCCTGAGGATATGGGGCGACTTCACCTGGATGATGGAAAATCGCCCAACCA

TGGTGAGATAGCCAAGGTGGGAGAAGGCAAGTATCGAGAGGACTTTCAGATGG

ATGAAGGAGAGGATCCTAGCTTCCTGTTCCAGTCATACCTGGAAAATGTTGGAGT

CCAAATAGTCAGACAAATGAGGTCAGGAGAGAGATTTCTCAAGATATGGTCACA

GACCGTAGAAGAGATTATATCCTATGTCGCGGTCAACTTTCCCAACCCTCCAGGA

AAGTCTTCAGAGGATAAATCAACCCAGACTACTGGCCGAGAGCTCAAGAAGGAG

ACAACACCCACTCCTTCTCAGAGAGAAAGCCAATCATCGAAAGCCAGGATGGCG

GCTCAAATTGCTTCTGGCCCTCCAGCCCTTGAATGGTCGGCTACCAATGAAGAGG

ATGATCTATCAGTGGAGGCTGAGATCGCTCACCAGATTGCAGAAAGTTTCTCCAA

AAAATATAAGTTTCCCTCTCGATCCTCAGGGATACTCTTGTATAATTTTGAGCAA

TTGAAAATGAACCTTGATGATATAGTTAAAGAGGCAAAAAATGTACCAGGTGTG

ACCCGTTTAGCCCATGACGGGTCCAAACTCCCCCTAAGATGTGTACTGGGATGG

GTCGCTTTGGCCAACTCTAAGAAATTCCAGTTGTTAGTCGAATCCGACAAGCTGA

GTAAAATCATGCAAGATGACTTGAATCGCTATACATCTTGCTAACCGAACCTCTC

CCCTCAGTCCCTCTAGACAATAAAATCCGAGATGTCCCAAAGTCAACATGAAAA

AAACAGGCAACACCACTGATAAAATGAACCTCCTACGTAAGATAGTGAAAAACC

GCAGGGACGAGGACACTCAAAAATCCTCTCCCGCGTCAGCCCCTCTGGATGACG

ATGACTTGTGGCTTCCACCCCCTGAATACGTCCCGCTGAAAGAACTTACAGGCAA

GAAGAACATGAGGAACTTTTGTATCAACGGAAGGGTTAAAGTGTGTAGCCCGAA

TGGTTACTCGTTCAGGATCCTGCGGCACATTCTGAAATCATTCGACGAGATATAT

TCTGGGAATCATAGGATGATCGGGTTAGTCAAAGTGGTTATTGGACTGGCTTTGT

CAGGATCTCCAGTCCCTGAGGGCCTGAACTGGGTATACAAATTGAGGAGAACCT

TTATCTTCCAGTGGGCTGATTCCAGGGGCCCTCTTGAAGGGGAGGAGTTGGAATA

CTCTCAGGAGATCACTTGGGATGATGATACTGAGTTCGTCGGATTGCAAATAAG

AGTGATTGCAAAACAGTGTCATATCCAGGGCAGAGTCTGGTGTATCAACATGAA

CCCGAGAGCATGTCAACTATGGTCTGACATGTCTCTTCAGACACAAAGGTCCGA

AGAGGACAAAGATTCCTCTCTGCTTCTAGAATAATCAGATTATATCCCGCAAATT

TATCACTTGTTTACCTCTGGAGGAGAGAACATATGGGCTCAACTCCAACCCTTGG

GAGCAATATAACAAAAACATGTTATGGTGCCATTAAACCGCTGCATTTCATCA

AAGTCAAGTTGATTACCTTTACATTTTGATCCTCTTGGATGTGAAAAAAACTATT

AACATCCCTCAAAAGACCccgggAAAGATGGTTCCTCAGGCTCTCCTGTTTGTACC

CCTTCTGGTTTTTCCATTGTGTTTTGGGAAATTCCCTATTTACACGATACCAGACA

AGCTTGGTCCCTGGAGTCCGATTGACATACATCACCTCAGCTGCCCAAACAATTT

GGTAGTGGAGGACGAAGGATGCACCAACCTGTCAGGGTTCTCCTACATGGAACT

TAAAGTTGGATACATCTTAGCCATAAAAGTGAACGGGTTCACTTGCACAGGCGTT
```

```
GTGACGGAGGCTGAAACCTACACTAACTTCGTTGGTTATGTCACAACCACGTTCA

AAAGAAAGCATTTCCGCCCAACACCAGATGCATGTAGAGCCGCGTACAACTGGA

AGATGGCCGGTGACCCCAGATATGAAGAGTCTCTACACAATCCGTACCCTGACT

ACCGCTGGCTTCGAACTGTAAAAACCACCAAGGAGTCTCTCGTTATCATATCTCC

AAGTGTGGCAGATTTGGACCCATATGACAGATCCCTTCACTCGAGGGTCTTCCCT

AGCGGGAAGTGCTCAGGAGTAGCGGTGTCTTCTACCTACTGCTCCACTAACCAC

GATTACACCATTTGGATGCCCGAGAATCCGAGACTAGGGATGTCTTGTGACATTT

TTACCAATAGTAGAGGGAAGAGAGCATCCAAAGGGAGTGAGACTTGCGGCTTTG

TAGATGAAAGAGGCCTATATAAGTCTTTAAAAGGAGCATGCAAACTCAAGTTAT

GTGGAGTTCTAGGACTTAGACTTATGGATGGAACATGGGTCTCGATGCAAACAT

CAAATGAAACCAAATGGTGCCCTCCCGATAAGTTGGTGAACCTGCACGACTTTC

GCTCAGACGAAATTGAGCACCTTGTTGTAGAGGAGTTGGTCAGGAAGAGAGAGG

AGTGTCTGGATGCACTAGAGTCCATCATGACAACCAAGTCAGTGAGTTTCAGAC

GTCTCAGTCATTTAAGAAAACTTGTCCCTGGGTTTGGAAAAGCATATACCATATT

CAACAAGACCTTGATGGAAGCCGATGCTCACTACAAGTCAGTCgagACTTGGAAT

GAGATCCTCCCTTCAAAAGGGTGTTTAAGAGTTGGGGGGAGGTGTCATCCTCATG

TGAACGGGGTGTTTTTCAATGGTATAATATTAGGACCTGACGGCAATGTCTTAAT

CCCAGAGATGCAATCATCCCTCCTCCAGCAACATATGGAGTTGTTGGAATCCTCG

GTTATCCCCCTTGTGCACCCCCTGGCAGACCCGTCTACCGTTTTCAAGGACGGTG

ACGAGGCTGAGGATTTTGTTGAAGTTCACCTTCCCGATGTGCACAATCAGGTCTC

AGGAGTTGACTTGGGTCTCCCGAACTGGGGGAAGTATGTATTACTGAGTGCAGG

GGCCCTGACTGCCTTGATGTTGATAATTTTCCTGATGACATGTTGTAGAAGAGTC

AATCGATCAGAACCTACGCAACACAATCTCAGAGGGACAGGGAGGGAGGTGTC

AGTCACTCCCCAAAGCGGGAAGATCATATCTTCATGGGAATCACACAAGAGTGGGGGT

GAGACCAGACTGTAAttaattaaCGTCCTTTCAACGATCCAAGTCcatgaaaaaaact aacaccccteccgtacctagcTTATAAAGTGCTGGGTCATCTAAGCTTTTCAGTCGAG

AAAAAAACATTAGATCAGAAGAACAACTGGCAACACTTCTCAACCTGAGACTTACTTC

AAGATGCTCGATCCTGGAGAGGTCTATGATGACCCTATTGACCCAATCGAGTTAGAG

GCTGAACCCAGAGGAACCCCCATTGTCCCCAACATCTTGAGGAACTCTGACTAC

AATCTCAACTCTCCTTTGATAGAAGATCCTGCTAGACTAATGTTAGAATGGTTAA

AAACAGGGAATAGACCTTATCGGATGACTCTAACAGACAATTGCTCCAGGTCTTT

CAGAGTTTTGAAAGATTATTTCAAGAAGGTAGATTTGGGTTCTCTCAAGGTGGGC

GGAATGGCTGCACAGTCAATGATTTCTCTCTGGTTATATGGTGCCCACTCTGAAT

CCAACAGGAGCCGGAGATGTATAACAGACTTGGCCCATTTCTATTCCAAGTCGTC

CCCCATAGAGAAGCTGTTGAATCTCACGCTAGGAAATAGAGGGCTGAGAATCCC

CCCAGAGGGAGTGTTAAGTTGCCTTGAGAGGGTTGATTATGATAATGCATTTGGA

AGGTATCTTGCCAACACGTATTCCTCTTACTTGTTCTTCCATGTAATCACCTTATA

CATGAACGCCCTAGACTGGGATGAAGAAAAGACCATCCTAGCATTATGGAAAGA

TTTAACCTCAGTGGACATCGGGAAGGACTTGGTAAAGTTCAAAGACCAAATATG

GGGACTGCTGATCGTGACAAAGGACTTTGTTTACTCCCAAAGTTCCAATTGTCTT

TTTGACAGAAACTACACACTTATGCTAAAAGATCTTTTCTTGTCTCGCTTCAACTC
```

-continued

```
CTTAATGGTCTTGCTCTCTCCCCCAGAGCCCCGATACTCAGATGACTTGATATCT

CAACTATGCCAGCTGTACATTGCTGGGGATCAAGTCTTGTCTATGTGTGGAAACT

CCGGCTATGAAGTCATCAAAATATTGGAGCCATATGTCGTGAATAGTTTAGTCCA

GAGAGCAGAAAAGTTTAGGCCTCTCATTCATTCCTTGGGAGACTTTCCTGTATTT

ATAAAAGACAAGGTAAGTCAACTTGAAGAGACGTTCGGTCCCTGTGCAAGAAGG

TTCTTTAGGGCTCTGGATCAATTCGACAACATACATGACTTGGTTTTTGTGTTTGG

CTGTTACAGGCATTGGGGGCACCCATATATAGATTATCGAAAGGGTCTGTCAAA

ACTATATGATCAGGTTCACCTTAAAAAAATGATAGATAAGTCCTACCAGGAGTG

CTTAGCAAGCGACCTAGCCAGGAGGATCCTTAGATGGGGTTTTGATAAGTACTCC

AAGTGGTATCTGGATTCAAGATTCCTAGCCCGAGACCACCCCTTGACTCCTTATA

TCAAAACCCAAACATGGCCACCCAAACATATTGTAGACTTGGTGGGGATACAT

GGCACAAGCTCCCGATCACGCAGATCTTTGAGATTCCTGAATCAATGGATCCGTC

AGAAATATTGGATGACAAATCACATTCTTTCACCAGAACGAGACTAGCTTCTTGG

CTGTCAGAAAACCGAGGGGGGCCTGTTCCTAGCGAAAAAGTTATTATCACGGCC

CTGTCTAAGCCGCCTGTCAATCCCCGAGAGTTTCTGAGGTCTATAGACCTCGGAG

GATTGCCAGATGAAGCTTGATAATTGGCCTCAAGCCAAAGGAACGGGAATTGA

AGATTGAAGGTCGATTCTTTGCTCTAATGTCATGGAATCTAAGATTGTATTTTGTC

ATCACTGAAAAACTCTTGGCCAACTACATCTTGCCACTTTTTGACGCGCTGACTA

TGACAGACAACCTGAACAAGGTGTTTAAAAAGCTGATCGACAGGGTCACCGGGC

AAGGGCTTTTGGACTATTCAAGGGTCACATATGCATTTCACCTGGACTATGAAAA

GTGGAACAACCATCAAAGATTAGAGTCAACAGAGGATGTATTTTCTGTCCTAGA

TCAAGTGTTTGGATTGAAGAGAGTGTTTTCTAGAACACACGAGTTTTTTCAAAAG

GCCTGGATCTATTATTCAGACAGATCAGACCTCATCGGGTTACGGGAGGATCAA

ATATACTGCTTAGATGCGTCCAACGGCCCAACCTGTTGGAATGGCCAGGATGGC

GGGCTAGAAGGCTTACGGCAGAAGGGCTGGAGTCTAGTCAGCTTATTGATGATA

GATAGAGAATCTCAAATCAGGAACACAAGAACCAAAATACTAGCTCAAGGAGA

CAACCAGGTTTTATGTCCGACATACATGTTGTCGCCAGGGCTATCTCAAGAGGGG

CTCCTCTATGAATTGGAGAGAATATCAAGGAATGCACTTTCGATATACAGAGCC

GTCGAGGAAGGGGCATCTAAGCTAGGGCTGATCATCAAGAAAGAAGAGACCAT

GTGTAGTTATGACTTCCTCATCTATGGAAAAACCCCTTTGTTTAGAGGTAACATA

TTGGTGCCTGAGTCCAAAAGATGGGCCAGAGTCTCTTGCGTCTCTAATGACCAAA

TAGTCAACCTCGCCAATATAATGTCGACAGTGTCCACCAATGCGCTAACAGTGG

CACAACACTCTCAATCTTTGATCAAACCGATGAGGGATTTTCTGCTCATGTCAGT

ACAGGCAGTCTTTCACTACCTGCTATTTAGCCCAATCTTAAAGGGAAGAGTTTAC

AAGATTCTGAGCGCTGAAGGGGAGAGCTTTCTCCTAGCCATGTCAAGGATAATC

TATCTAGATCCTTCTTTGGGAGGGATATCTGGAATGTCCCTCGGAAGATTCCATA

TACGACAGTTCTCAGACCCTGTCTCTGAAGGGTTATCCTTCTGGAGAGAGATCTG

GTTAAGCTCCCAAGAGTCCTGGATTCACGCGTTGTGTCAAGAGGCTGGAAACCC

AGATCTTGGAGAGAGAACACTCGAGAGCTTCACTCGCCTTCTAGAAGATCCGAC

CACCTTAAATATCAGAGGAGGGGCCAGTCCTACCATTCTACTCAAGGATGCAAT
```

```
CAGAAAGGCTTTATATGACGAGGTGGACAAGGTGGAAAATTCAGAGTTTCGAGA

GGCAATCCTGTTGTCCAAGACCCATAGAGATAATTTTATACTCTTCTTAATATCT

GTTGAGCCTCTGTTTCCTCGATTTCTCAGTGAGCTATTCAGTTCGTCTTTTTTGGG

AATCCCCGAGTCAATCATTGGATTGATACAAAACTCCCGAACGATAAGAAGGCA

GTTTAGAAAGAGTCTCTCAAAAACTTTAGAAGAATCCTTCTACAACTCAGAGATC

CACGGGATTAGTCGGATGACCCAGACACCTCAGAGGGTTGGGGGGGTGTGGCCT

TGCTCTTCAGAGAGGGCAGATCTACTTAGGGAGATCTCTTGGGGAAGAAAAGTG

GTAGGCACGACAGTTCCTCACCCTTCTGAGATGTTGGGATTACTTCCCAAGTCCT

CTATTTCTTGCACTTGTGGAGCAACAGGAGGAGGCAATCCTAGAGTTTCTGTATC

AGTACTCCCGTCCTTTGATCAGTCATTTTTTTCACGAGGCCCCCTAAAGGGATAC

TTGGGCTCGTCCACCTCTATGTCGACCCAGCTATTCCATGCATGGGAAAAAGTCA

CTAATGTTCATGTGGTGAAGAGAGCTCTATCGTTAAAAGAATCTATAAACTGGTT

CATTACTAGAGATTCCAACTTGGCTCAAGCTCTAATTAGGAACATTATGTCTCTG

ACAGGCCCTGATTTCCCTAGAGGAGGCCCCTGTCTTCAAAAGGACGGGGTCA

GCCTTGCATAGGTTCAAGTCTGCCAGATACAGCGAAGGAGGGTATTCTTCTGTCT

GCCCGAACCTCCTCTCATATTTCTGTTAGTACAGACACCATGTCTGATTTGACC

CAAGACGGGAAGAACTACGATTTCATGTTCCAGCCATTGATGCTTTATGCACAGA

CATGGACATCAGAGCTGGTACAGAGAGACACAAGGCTAAGAGACTCTACGTTTC

ATTGGCACCTCCGATGCAACAGGTGTGTGAGACCCATTGACGACGTGACCCTGG

AGACCTCTCAGATCTTCGAGTTTCCGGATGTGTCGAAAAGAATATCCAGAATGGT

TTCTGGGGCTGTGCCTCACTTCCAGAGGCTTCCCGATATCCGTCTGAGACCAGGA

GATTTTGAATCTCTAAGCGGTAGAGAAAAGTCTCACCATATCGGATCAGCTCAG

GGGCTCTTATACTCAATCTTAGTGGCAATTCACGACTCAGGATACAATGATGGAA

CCATCTTCCCTGTCAACATATACGGCAAGGTTTCCCCTAGAGACTATTTGAGAGG

GCTCGCAAGGGAGTATTGATAGGATCCTCGATTTGCTTCTTGACAAGAATGACA

AATATCAATATTAATAGACCTCTTGAATTGGTCTCAGGGGTAATCTCATATATTC

TCCTGAGGCTAGATAACCATCCCTCCTTGTACATAATGCTCAGAGAACCGTCTCT

TAGAGGAGAGATATTTTCTATCCCTCAGAAAATCCCCGCCGCTTATCCAACCACT

ATGAAAGAAGGCAACAGATCAATCTTGTGTTATCTCCAACATGTGCTACGCTATG

AGCGAGAGATAATCACGGCGTCTCCAGAGAATGACTGGCTATGGATCTTTTCAG

ACTTTAGAAGTGCCAAAATGACGTACCTATCCCTCATTACTTACCAGTCTCATCT

TCTACTCCAGAGGGTTGAGAGAAACCTATCTAAGAGTATGAGAGATAACCTGCG

ACAATTGAGTTCTTTGATGAGGCAGGTGCTGGGCGGGCACGGAGAAGATACCTT

AGAGTCAGACGACAACATTCAACGACTGCTAAAAGACTCTTTACGAAGGACAAG

ATGGGTGGATCAAGAGGTGCGCCATGCAGCTAGAACCATGACTGGAGATTACAG

CCCCAACAAGAAGGTGTCCCGTAAGGTAGGATGTTCAGAATGGGTCTGCTCTGC

TCAACAGGTTGCAGTCTCTACCTCAGCAAACCCGGCCCCTGTCTCGGAGCTTGAC

ATAAGGGCCCTCTCTAAGAGGTTCCAGAACCCTTTGATCTCGGGCTTGAGAGTGG

TTCAGTGGGCAACCGGTGCTCATTATAAGCTTAAGCCTATTCTAGATGATCTCAA

TGTTTTCCCATCTCTCTGCCTTGTAGTTGGGGACGGGTCAGGGGGGATATCAAGG

GCAGTCCTCAACATGTTTCCAGATGCCAAGCTTGTGTTCAACAGTCTTTTAGAGG
```

-continued

```
TGAATGACCTGATGGCTTCCGGAACACATCCACTGCCTCCTTCAGCAATCATGAG

GGGAGGAAATGATATCGTCTCCAGAGTGATAGATCTTGACTCAATCTGGGAAAA

ACCGTCCGACTTGAGAAACTTGGCAACCTGGAAATACTTCCAGTCAGTCCAAAA

GCAGGTCAACATGTCCTATGACCTCATTATTTGCGATGCAGAAGTTACTGACATT

GCATCTATCAACCGGATCACCCTGTTAATGTCCGATTTTGCATTGTCTATAGATG

GACCACTCTATTTGGTCTTCAAAACTTATGGGACTATGCTAGTAAATCCAAACTA

CAAGGCTATTCAACACCTGTCAAGAGCGTTCCCCTCGGTCACAGGGTTTATCACC

CAAGTAACTTCGTCTTTTTCATCTGAGCTCTACCTCCGATTCTCCAAACGAGGGA

AGTTTTTCAGAGATGCTGAGTACTTGACCTCTTCCACCCTTCGAGAAATGAGCCT

TGTGTTATTCAATTGTAGCAGCCCCAAGAGTGAGATGCAGAGAGCTCGTTCCTTG

AACTATCAGGATCTTGTGAGAGGATTTCCTGAAGAAATCATATCAAATCCTTACA

ATGAGATGATCATAACTCTGATTGACAGTGATGTAGAATCTTTTCTAGTCCACAA

GATGGTTGATGATCTTGAGTTACAGAGGGGAACTCTGTCTAAAGTGGCTATCATT

ATAGCCATCATGATAGTTTTCTCCAACAGAGTCTTCAACGTTTCCAAACCCCTAA

CTGACCCCTCGTTCTATCCACCGTCTGATCCCAAAATCCTGAGGCACTTCAACAT

ATGTTGCAGTACTATGATGTATCTATCTACTGCTTTAGGTGACGTCCCTAGCTTCG

CAAGACTTCACGACCTGTATAACAGACCTATAACTTATTACTTCAGAAAGCAAGT

CATTCGAGGGAACGTTTATCTATCTTGGAGTTGGTCCAACGACACCTCAGTGTTC

AAAAGGGTAGCCTGTAATTCTAGCCTGAGTCTGTCATCTCACTGGATCAGGTTGA

TTTACAAGATAGTGAAGACTACCAGACTCGTTGGCAGCATCAAGGATCTATCCA

GAGAAGTGGAAAGACACCTTCATAGGTACAACAGGTGGATCACCCTAGAGGATA

TCAGATCTAGATCATCCCTACTAGACTACAGTTGCCTGTGAACCGGATACTCCTG

GAAGCCTGCCCATGCTAAGACTCTTGTGTGATGTATCTTGAAAAAAACAAGATCCTAA

ATCTGAACCTTTGGTTGTTTGATTGTTTTCTCAttttttgttgtttatttgttaagcgt
```

In one embodiment, the nucleic acid comprises the sequence of SEQ ID NO: 14, shown below (RABV vector: Coravax V5 China):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT
```

-continued

```
TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC
```

-continued

```
CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggccaccATGTTC

GTGTTTCTGGTGCTGCTGCCTCTGGTGAGCTCCCAGTGCGTGAACCTGACCACAA

GGACCCAGCTGCCCCCTGCCTATACCAATTCCTTCACACGGGGCGTGTACTATCC

CGACAAGGTGTTCCGGAGCAGCGTGCTGCACTCCACACAGGATCTGTTTCTGCCT

TTCTTTTCTAACGTGACCTGGTTCCACGCCATCCACGTGAGCGGCACCAATGGCA

CAAAGCGGTTCGACAATCCAGTGCTGCCCTTTAACGATGGCGTGTACTTCGCCTC

CACCGAGAAGTCTAACATCATCAGAGGCTGGATCTTTGGCACCACACTGGACAG

CAAGACACAGTCCCTGCTGATCGTGAACAATGCCACCAACGTGGTCATCAAGGT

GTGCGAGTTCCAGTTTTGTAATGATCCATTCCTGGGCGTGTACTATCACAAGAAC

AATAAGTCTTGGATGGAGAGCGAGTTTCGCGTGTATTCCTCTGCCAACAATTGCA

CATTTGAGTACGTGTCCCAGCCCTTCCTGATGGACCTGGAGGGCAAGCAGGGCA

ATTTCAAGAACCTGAGGGAGTTCGTGTTTAAGAATATCGATGGCTACTTCAAAAT

CTACTCCAAGCACACCCCAATCAACCTGGTGCGCGACCTGCCACAGGGCTTCTCT

GCCCTGGAGCCACTGGTGGATCTGCCCATCGGCATCAACATCACCCGGTTTCAGA

CACTGCTGGCCCTGCACAGAAGCTACCTGACACCAGGCGACAGCTCCTCTGGAT

GGACCGCAGGAGCAGCAGCCTACTATGTGGGCTATCTGCAGCCCAGGACCTTCC

TGCTGAAGTACAACGAGAATGGCACCATCACAGACGCCGTGGATTGCGCCCTGG

ATCCCCTGTCTGAGACCAAGTGTACACTGAAGAGCTTTACCGTGGAGAAGGGCA

TCTATCAGACAAGCAATTTCAGGGTGCAGCCTACCGAGTCCATCGTGCGCTTTCC

CAATATCACAAACCTGTGCCCTTTTGGCGAGGTGTTCAACGCAACCCGCTTCGCC

AGCGTGTACGCCTGGAATAGGAAGCGCATCTCCAACTGCGTGGCCGACTATTCT

GTGCTGTACAACAGCGCCTCCTTCTCTACCTTTAAGTGCTATGGCGTGAGCCCCA

CAAAGCTGAATGACCTGTGCTTTACCAACGTGTACGCCGATTCCTTCGTGATCAG

GGGCGACGAGGTGCGCCAGATCGCACCAGGACAGACAGGCAAGATCGCAGACT

ACAATTATAAGCTGCCTGACGATTTCACCGGCTGCGTGATCGCCTGGAACTCTAA

CAATCTGGATAGCAAAGTGGGCGGCAACTACAATTATCTGTACCGGCTGTTTAG

AAAGTCTAATCTGAAGCCATTCGAGAGGGACATCTCCACAGAAATCTACCAGGC

CGGCTCTACCCCCTGCAATGGCGTGGAgGGCTTTAACTGTTATTTCCCTCTGCAGA gCTACgGCTTCCAGCCAACAAACGGCGTGGGCTATCAGCCCTACCGCGTGGTGGT

GCTGTCTTTTGAGCTGCTGCACGCACCTGCAACAGTGTGCGGACCAAAGAAGAGC

ACCAATCTGGTGAAGAACAAGTGCGTGAACTTCAACTTCAACGGACTGACCGGA

ACAGGCGTGCTGACCGAGTCCAACAAGAAGTTCCTGCCTTTTCAGCAGTTCGGC

AGGGACATCGCAGATACCACAGACGCCGTGCGCGACCCTCAGACCCTGGAGATC

CTGGACATCACACCATGCTCCTTCGGCGGCGTGTCTGTGATCACACCAGGCACCA
```

-continued

```
ATACAAGCAACCAGGTGGCCGTGCTGTATCAGGACGTGAATTGTACCGAGGTGC

CAGTGGCAATCCACGCAGATCAGCTGACCCCTACATGGCGGGTGTACTCTACCG

GCAGCAACGTGTTCCAGACAAGAGCCGGATGCCTGATCGGAGCAGAGCACGTGA

ACAATAGCTATGAGTGCGACATCCCTATCGGCGCCGGCATCTGTGCCTCCTACCA

GACCCAGACAAACTCCCCAAGGTCTgtgggaGATGAGGCCGAAGACTTTGTGGAAG

TCCACCTGCCTGATGTGCATAACCAGGTGTCTGGCGTCGACCTGGGACTGCCAAA

TTGGGGCAAGTACGTGCTGCTGAGTGCTGGAGCACTGACTGCCCTGATGCTGATC

ATTTTCCTGATGACCTGCTGTCGGCGCGTGAACAGAAGTGAGCCCACTCAGCAC

AATCTGCGAGGAACCGGGAGAGAAGTGTCAGTCACACCTCAGAGCGGGAAAAT

CATTAGTAGTTGGGAATCACATAAAAGCGGGGGCGAGACCAGGCTGggatccggctccggcga gggcaggggaagtctactaacatgcggggacgtggaggaaaatcccggccccATGGTTCCTCA

GGCTCTCCTGTTTGTACCCCTTCTGGTTTTTCCATTGTGTTTTGGGAAATTCCCTATTTACAC

GATACCAGACAAGCTTGGTCCCTGGAGTCCGATTGACATACATCACCTCAGCTGC

CCAAACAATTTGGTAGTGGAGGACGAAGGATGCACCAACCTGTCAGGGTTCTCC

TACATGGAACTTAAAGTTGGATACATCTTAGCCATAAAAGTGAACGGGTTCACTT

GCACAGGCGTTGTGACGGAGGCTGAAACCTACACTAACTTCGTTGGTTATGTCAC

AACCACGTTCAAAAGAAAGCATTTCCGCCCAACACCAGATGCATGTAGAGCCGC

GTACAACTGGAAGATGGCCGGTGACCCCAGATATGAAGAGTCTCTACACAATCC

GTACCCTGACTACCGCTGGCTTCGAACTGTAAAAACCACCAAGGAGTCTCTCGTT

ATCATATCTCCAAGTGTGGCAGATTTGGACCCATATGACAGATCCCTTCACTCGA

GGGTCTTCCCTAGCGGGAAGTGCTCAGGAGTAGCGGTGTCTTCTACCTACTGCTC

CACTAACCACGATTACACCATTTGGATGCCCGAGAATCCGAGACTAGGGATGTC

TTGTGACATTTTTACCAATAGTAGAGGGAAGAGAGCATCCAAAGGGAGTGAGAC

TTGCGGCTTTGTAGATGAAAGAGGCCTATATAAGTCTTTAAAAGGAGCATGCAA

ACTCAAGTTATGTGGAGTTCTAGGACTTAGACTTATGGATGGAACATGGGTCTCG

ATGCAAACATCAAATGAAACCAAATGGTGCCCTCCCGATAAGTTGGTGAACCTG

CACGACTTTCGCTCAGACGAAATTGAGCACCTTGTTGTAGAGGAGTTGGTCAGG

AAGAGAGAGGAGTGTCTGGATGCACTAGAGTCCATCATGACAACCAAGTCAGTG

AGTTTCAGACGTCTCAGTCATTTAAGAAAACTTGTCCCTGGGTTTGGAAAAGCAT

ATACCATATTCAACAAGACCTTGATGGAAGCCGATGCTCACTACAAGTCAGTCga gACTTGGAATGAGATCCTCCCTTCAAAAGGGTGTTTAAGAGTTGGGGGGAGGTGT

CATCCTCATGTGAACGGGGTGTTTTTCAATGGTATAATATTAGGACCTGACGGCA

ATGTCTTAATCCCAGAGATGCAATCATCCCTCCTCCAGCAACATATGGAGTTGTT

GGAATCCTCGGTTATCCCCCTTGTGCACCCCCTGGCAGACCCGTCTACCGTTTTC

AAGGACGGTGACGAGGCTGAGGATTTTGTTGAAGTTCACCTTCCCGATGTGCAC

AATCAGGTCTCAGGAGTTGACTTGGGTCTCCCGAACTGGGGGAAGTATGTATTAC

TGAGTGCAGGGGCCCTGACTGCCTTGATGTTGATAATTTTCCTGATGACATGTTG

TAGAAGAGTCAATCGATCAGAACCTACGCAACACAATCTCAGAGGGACAGGGA

GGGAGGTGTCAGTCACTCCCCAAAGCGGGAAGATCATATCTTCATGGGAATCAC

ACAAGAGTGGGGGTGAGACCAGACTGTAAgctagcTTATAAAGTGCTGGGTCATCT
```

-continued

```
AAGCTTTTCAGTCGAGAAAAAAACATTAGATCAGAAGAACAACTGGCAACACTT

CTCAACCTGAGACTTACTTCAAGATGCTCGATCCTGGAGAGGTCTATGATGACCC

TATTGACCCAATCGAGTTAGAGGCTGAACCCAGAGGAACCCCCATTGTCCCCAA

CATCTTGAGGAACTCTGACTACAATCTCAACTCTCCTTTGATAGAAGATCCTGCT

AGACTAATGTTAGAATGGTTAAAAACAGGGAATAGACCTTATCGGATGACTCTA

ACAGACAATTGCTCCAGGTCTTTCAGAGTTTTGAAAGATTATTTCAAGAAGGTAG

ATTTGGGTTCTCTCAAGGTGGGCGGAATGGCTGCACAGTCAATGATTTCTCTCTG

GTTATATGGTGCCCACTCTGAATCCAACAGGAGCCGGAGATGTATAACAGACTT

GGCCCATTTCTATTCCAAGTCGTCCCCCATAGAGAAGCTGTTGAATCTCACGCTA

GGAAATAGAGGGCTGAGAATCCCCCCAGAGGGAGTGTTAAGTTGCCTTGAGAGG

GTTGATTATGATAATGCATTTGGAAGGTATCTTGCCAACACGTATTCCTCTTACTT

GTTCTTCCATGTAATCACCTTATACATGAACGCCCTAGACTGGGATGAAGAAAAG

ACCATCCTAGCATTATGGAAAGATTTAACCTCAGTGGACATCGGGAAGGACTTG

GTAAAGTTCAAAGACCAAATATGGGGACTGCTGATCGTGACAAAGGACTTTGTT

TACTCCCAAAGTTCCAATTGTCTTTTTGACAGAAACTACACACTTATGCTAAAAG

ATCTTTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCC

ATATGTCGTGAATAGTTTAGTCCAGAGAGCAGAAAAGTTTAGGCCTCTCATTCAT

TCCTTGGGAGACTTTCCTGTATTTATAAAAGACAAGGTAAGTCAACTTGAAGAGA

CGTTCGGTCCCTGTGCAAGAAGGTTCTTTAGGGCTCTGGATCAATTCGACAACAT

ACATGACTTGGTTTTTGTGTTTGGCTGTTACAGGCATTGGGGCACCCATATATA

GATTATCGAAAGGGTCTGTCAAAACTATATGATCAGGTTCACCTTAAAAAAATG

ATAGATAAGTCCTACCAGGAGTGCTTAGCAAGCGACCTAGCCAGGAGGATCCTT

AGATGGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG
```

-continued

```
AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT

AATTTTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTTT

TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG
```

-continued
```
GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTTC

TCATTTTTGTTGTTTATTTGTTAAGCGT.
```

In one embodiment, the nucleic acid comprises the sequence of SEQ ID NO: 15, shown below (RABV vector: Coravax V5 South Africa):

ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCACTCCTTCTCAGAGAGAAAGC

CAATCATCGAAAGCCAGGATGGCGGCTCAAATTGCTTCTGGCCCTCCAGCCCTTG

```
-continued
AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggccaccATGTTC

GTGTTTCTGGTGCTGCTGCCTCTGGTGAGCTCCCAGTGCGTGAACTTCACCACAA

GGACCCAGCTGCCCCCTGCCTATACCAATTCCTTCACACGGGGCGTGTACTATCC

CGACAAGGTGTTCCGGAGCAGCGTGCTGCACTCCACACAGGATCTGTTTCTGCCT

TTCTTTTCTAACGTGACCTGGTTCCACGCCATCCACGTGAGCGGCACCAATGGCA

CAAAGCGGTTCGCCAATCCAGTGCTGCCCTTTAACGATGGCGTGTACTTCGCCTC

CACCGAGAAGTCTAACATCATCAGAGGCTGGATCTTTGGCACCACACTGGACAG

CAAGACACAGTCCCTGCTGATCGTGAACAATGCCACCAACGTGGTCATCAAGGT

GTGCGAGTTCCAGTTTTGTAATGATCCATTCCTGGGCGTGTACTATCACAAGAAC

AATAAGTCTTGGATGGAGAGCGAGTTTCGCGTGTATTCCTCTGCCAACAATTGCA

CATTTGAGTACGTGTCCCAGCCCTTCCTGATGGACCTGGAGGGCAAGCAGGGCA

ATTTCAAGAACCTGAGGGAGTTCGTGTTTAAGAATATCGATGGCTACTTCAAAAT

CTACTCCAAGCACACCCCAATCAACCTGGTGCGCGGCCTGCCACAGGGCTTCTCT

GCCCTGGAGCCACTGGTGGATCTGCCCATCGGCATCAACATCACCCGGTTTCAGA

CACTGCTGGCCCTGCACAGAAGCTACCTGACACCAGGCGACAGCTCCTCTGGAT

GGACCGCAGGAGCAGCAGCCTACTATGTGGGCTATCTGCAGCCCAGGACCTTCC

TGCTGAAGTACAACGAGAATGGCACCATCACAGACGCCGTGGATTGCGCCCTGG

ATCCCCTGTCTGAGACCAAGTGTACACTGAAGAGCTTTACCGTGGAGAAGGGCA

TCTATCAGACAAGCAATTTCAGGGTGCAGCCTACCGAGTCCATCGTGCGCTTTCC
```

-continued

```
CAATATCACAAACCTGTGCCCTTTTGGCGAGGTGTTCAACGCAACCCGCTTCGCC
AGCGTGTACGCCTGGAATAGGAAGCGCATCTCCAACTGCGTGGCCGACTATTCT
GTGCTGTACAACAGCGCCTCCTTCTCTACCTTTAAGTGCTATGGCGTGAGCCCCA
CAAAGCTGAATGACCTGTGCTTTACCAACGTGTACGCCGATTCCTTCGTGATCAG
GGGCGACGAGGTGCGCCAGATCGCACCAGGACAGACAGGCAATATCGCAGACT
ACAATTATAAGCTGCCTGACGATTTCACCGGCTGCGTGATCGCCTGGAACTCTAA
CAATCTGGATAGCAAAGTGGGCGGCAACTACAATTATCTGTACCGGCTGTTTAG
AAAGTCTAATCTGAAGCCATTCGAGAGGGACATCTCCACAGAAATCTACCAGGC
CGGCTCTACCCCCTGCAATGGCGTGAAGGGCTTTAACTGTTATTTCCCTCTGCAG
AGCTACGGCTTCCAGCCAACATATGGCGTGGGCTATCAGCCCTACCGCGTGGTG
GTGCTGTCTTTTGAGCTGCTGCACGCACCTGCAACAGTGTGCGGACCAAAGAAG
AGCACCAATCTGGTGAAGAACAAGTGCGTGAACTTCAACTTCAACGGACTGACC
GGAACAGGCGTGCTGACCGAGTCCAACAAGAAGTTCCTGCCTTTTCAGCAGTTC
GGCAGGGACATCGCAGATACCACAGACGCCGTGCGCGACCCTCAGACCCTGGAG
ATCCTGGACATCACACCATGCTCCTTCGGCGGCGTGTCTGTGATCACACCAGGCA
CCAATACAAGCAACCAGGTGGCCGTGCTGTATCAGGGCGTGAATTGTACCGAGG
TGCCAGTGGCAATCCACGCAGATCAGCTGACCCCTACATGGCGGGTGTACTCTA
CCGGCAGCAACGTGTTCCAGACAAGAGCCGGATGCCTGATCGGAGCAGAGCACG
TGAACAATAGCTATGAGTGCGACATCCCTATCGGCGCCGGCATCTGTGCCTCCTA
CCAGACCCAGACAAACTCCCCAGAATCAAGCGTGATTCCTCTGGTCCATCCACTG
GCAGATCCCTCCACAGTGTTCAAAGACGGAGATGAGGCCGAAGACTTTGTGGAA
GTCCACCTGCCTGATGTGCATAACCAGGTGTCTGGCGTCGACCTGGGACTGCCAA
ATTGGGGCAAGTACGTGCTGCTGAGTGCTGGAGCACTGACTGCCCTGATGCTGAT
CATTTTCCTGATGACCTGCTGTCGGCGCGTGAACAGAAGTGAGCCCACTCAGCAC
AATCTGCGAGGAACCGGGAGAGAAGTGTCAGTCACACCTCAGAGCGGGAAAAT
CATTAGTAGTTGGGAATCACATAAAAGCGGGGGCGAGACCAGGCTGggatccggctccggcga
gggcaggggaagtctactaacatgcggggacgtggaggaaaatcccggccccATGGTTCCTCA
GGCTCTCCTGTTTGTACCCCTTCTGGTTTTTCCATTGTGTTTTGGGAAATTCCCTATTTACAC
GATACCAGACAAGCTTGGTCCCTGGAGTCCGATTGACATACATCACCTCAGCTGC
CCAAACAATTTGGTAGTGGAGGACGAAGGATGCACCAACCTGTCAGGGTTCTCC
TACATGGAACTTAAAGTTGGATACATCTTAGCCATAAAAGTGAACGGGTTCACTT
GCACAGGCGTTGTGACGGAGGCTGAAACCTACACTAACTTCGTTGGTTATGTCAC
AACCACGTTCAAAAGAAAGCATTTCCGCCCAACACCAGATGCATGTAGAGCCGC
GTACAACTGGAAGATGGCCGGTGACCCCAGATATGAAGAGTCTCTACACAATCC
GTACCCTGACTACCGCTGGCTTCGAACTGTAAAAACCACCAAGGAGTCTCTCGTT
ATCATATCTCCAAGTGTGGCAGATTTGGACCCATATGACAGATCCCTTCACTCGA
GGGTCTTCCCTAGCGGGAAGTGCTCAGGAGTAGCGGTGTCTTCTACCTACTGCTC
CACTAACCACGATTACACCATTTGGATGCCCGAGAATCCGAGACTAGGGATGTC
TTGTGACATTTTTACCAATAGTAGAGGGAAGAGAGCATCCAAAGGGAGTGAGAC
TTGCGGCTTTGTAGATGAAAGAGGCCTATATAAGTCTTTAAAAGGAGCATGCAA
```

-continued

```
ACTCAAGTTATGTGGAGTTCTAGGACTTAGACTTATGGATGGAACATGGGTCTCG
ATGCAAACATCAAATGAAACCAAATGGTGCCCTCCCGATAAGTTGGTGAACCTG
CACGACTTTCGCTCAGACGAAATTGAGCACCTTGTTGTAGAGGAGTTGGTCAGG
AAGAGAGAGGAGTGTCTGGATGCACTAGAGTCCATCATGACAACCAAGTCAGTG
AGTTTCAGACGTCTCAGTCATTTAAGAAAACTTGTCCCTGGGTTTGGAAAAGCAT
ATACCATATTCAACAAGACCTTGATGGAAGCCGATGCTCACTACAAGTCAGTCga
gACTTGGAATGAGATCCTCCCTTCAAAAGGGTGTTTAAGAGTTGGGGGGAGGTGT
CATCCTCATGTGAACGGGGTGTTTTTCAATGGTATAATATTAGGACCTGACGGCA
ATGTCTTAATCCCAGAGATGCAATCATCCCTCCTCCAGCAACATATGGAGTTGTT
GGAATCCTCGGTTATCCCCCTTGTGCACCCCCTGGCAGACCCGTCTACCGTTTTC
AAGGACGGTGACGAGGCTGAGGATTTTGTTGAAGTTCACCTTCCCGATGTGCAC
AATCAGGTCTCAGGAGTTGACTTGGGTCTCCCGAACTGGGGGAAGTATGTATTAC
TGAGTGCAGGGGCCCTGACTGCCTTGATGTTGATAATTTTCCTGATGACATGTTG
TAGAAGAGTCAATCGATCAGAACCTACGCAACACAATCTCAGAGGGACAGGGA
GGGAGGTGTCAGTCACTCCCCAAAGCGGGAAGATCATATCTTCATGGGAATCAC
ACAAGAGTGGGGGTGAGACCAGACTGTAAgctagcTTATAAAGTGCTGGGTCATCT
AAGCTTTTCAGTCGAGAAAAAAACATTAGATCAGAAGAACAACTGGCAACACTT
CTCAACCTGAGACTTACTTCAAGATGCTCGATCCTGGAGAGGTCTATGATGACCC
TATTGACCCAATCGAGTTAGAGGCTGAACCCAGAGGAACCCCCATTGTCCCCAA
CATCTTGAGGAACTCTGACTACAATCTCAACTCTCCTTTGATAGAAGATCCTGCT
AGACTAATGTTAGAATGGTTAAAAACAGGGAATAGACCTTATCGGATGACTCTA
ACAGACAATTGCTCCAGGTCTTTCAGAGTTTTGAAAGATTATTTCAAGAAGGTAG
ATTTGGGTTCTCTCAAGGTGGGCGGAATGGCTGCACAGTCAATGATTTCTCTCTG
GTTATATGGTGCCCACTCTGAATCCAACAGGAGCCGGAGATGTATAACAGACTT
GGCCCATTTCTATTCCAAGTCGTCCCCCATAGAGAAGCTGTTGAATCTCACGCTA
GGAAATAGAGGGCTGAGAATCCCCCCAGAGGGAGTGTTAAGTTGCCTTGAGAGG
GTTGATTATGATAATGCATTTGGAAGGTATCTTGCCAACACGTATTCCTCTTACTT
GTTCTTCCATGTAATCACCTTATACATGAACGCCCTAGACTGGGATGAAGAAAG
ACCATCCTAGCATTATGGAAAGATTTAACCTCAGTGGACATCGGGAAGGACTTG
GTAAAGTTCAAAGACCAAATATGGGGACTGCTGATCGTGACAAAGGACTTTGTT
TACTCCCAAAGTTCCAATTGTCTTTTTGACAGAAACTACACACTTATGCTAAAAG
ATCTTTTCTTGTCTCGCTTCAACTCCTTAATGGTCTTGCTCTCTCCCCCAGAGCCC
CGATACTCAGATGACTTGATATCTCAACTATGCCAGCTGTACATTGCTGGGGATC
AAGTCTTGTCTATGTGTGGAAACTCCGGCTATGAAGTCATCAAAATATTGGAGCC
ATATGTCGTGAATAGTTTAGTCCAGAGAGCAGAAAAGTTTAGGCCTCTCATTCAT
TCCTTGGGAGACTTTCCTGTATTTATAAAAGACAAGGTAAGTCAACTTGAAGAGA
CGTTCGGTCCCTGTGCAAGAAGGTTCTTTAGGGCTCTGGATCAATTCGACAACAT
ACATGACTTGGTTTTTGTGTTTGGCTGTTACAGGCATTGGGGGCACCCATATATA
GATTATCGAAAGGGTCTGTCAAAACTATATGATCAGGTTCACCTTAAAAAAATG
ATAGATAAGTCCTACCAGGAGTGCTTAGCAAGCGACCTAGCCAGGAGGATCCTT
AGATGGGGTTTTGATAAGTACTCCAAGTGGTATCTGGATTCAAGATTCCTAGCCC
```

-continued

```
GAGACCACCCCTTGACTCCTTATATCAAAACCCAAACATGGCCACCCAAACATA

TTGTAGACTTGGTGGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT

CTCCTAGCCATGTCAAGGATAATCTATCTAGATCCTTCTTTGGGAGGGATATCTG

GAATGTCCCTCGGAAGATTCCATATACGACAGTTCTCAGACCCTGTCTCTGAAGG

GTTATCCTTCTGGAGAGAGATCTGGTTAAGCTCCCAAGAGTCCTGGATTCACGCG

TTGTGTCAAGAGGCTGGAAACCCAGATCTTGGAGAGAGAACACTCGAGAGCTTC

ACTCGCCTTCTAGAAGATCCGACCACCTTAAATATCAGAGGAGGGGCCAGTCCT

ACCATTCTACTCAAGGATGCAATCAGAAAGGCTTTATATGACGAGGTGGACAAG

GTGGAAAATTCAGAGTTTCGAGAGGCAATCCTGTTGTCCAAGACCCATAGAGAT

AATTTTATACTCTTCTTAATATCTGTTGAGCCTCTGTTTCCTCGATTTCTCAGTGA

GCTATTCAGTTCGTCTTTTTTGGGAATCCCCGAGTCAATCATTGGATTGATACAA

AACTCCCGAACGATAAGAAGGCAGTTTAGAAAGAGTCTCTCAAAAACTTTAGAA

GAATCCTTCTACAACTCAGAGATCCACGGGATTAGTCGGATGACCCAGACACCT

CAGAGGGTTGGGGGGGTGTGGCCTTGCTCTTCAGAGAGGGCAGATCTACTTAGG

GAGATCTCTTGGGGAAGAAAAGTGGTAGGCACGACAGTTCCTCACCCTTCTGAG

ATGTTGGGATTACTTCCCAAGTCCTCTATTTCTTGCACTTGTGGAGCAACAGGAG

GAGGCAATCCTAGAGTTTCTGTATCAGTACTCCCGTCCTTTGATCAGTCATTTTTT
```

```
-continued
TCACGAGGCCCCCTAAAGGGATACTTGGGCTCGTCCACCTCTATGTCGACCCAGC

TATTCCATGCATGGGAAAAAGTCACTAATGTTCATGTGGTGAAGAGAGCTCTATC

GTTAAAAGAATCTATAAACTGGTTCATTACTAGAGATTCCAACTTGGCTCAAGCT

CTAATTAGGAACATTATGTCTCTGACAGGCCCTGATTTCCCTCTAGAGGAGGCCC

CTGTCTTCAAAAGGACGGGGTCAGCCTTGCATAGGTTCAAGTCTGCCAGATACA

GCGAAGGAGGGTATTCTTCTGTCTGCCCGAACCTCCTCTCTCATATTTCTGTTAGT

ACAGACACCATGTCTGATTTGACCCAAGACGGGAAGAACTACGATTTCATGTTCC

AGCCATTGATGCTTTATGCACAGACATGGACATCAGAGCTGGTACAGAGAGACA

CAAGGCTAAGAGACTCTACGTTTCATTGGCACCTCCGATGCAACAGGTGTGTGA

GACCCATTGACGACGTGACCCTGGAGACCTCTCAGATCTTCGAGTTTCCGGATGT

GTCGAAAAGAATATCCAGAATGGTTTCTGGGGCTGTGCCTCACTTCCAGAGGCTT

CCCGATATCCGTCTGAGACCAGGAGATTTTGAATCTCTAAGCGGTAGAGAAAAG

TCTCACCATATCGGATCAGCTCAGGGGCTCTTATACTCAATCTTAGTGGCAATTC

ACGACTCAGGATACAATGATGGAACCATCTTCCCTGTCAACATATACGGCAAGG

TTTCCCCTAGAGACTATTTGAGAGGGCTCGCAAGGGGAGTATTGATAGGATCCTC

GATTTGCTTCTTGACAAGAATGACAAATATCAATATTAATAGACCTCTTGAATTG

GTCTCAGGGGTAATCTCATATATTCTCCTGAGGCTAGATAACCATCCCTCCTTGT

ACATAATGCTCAGAGAACCGTCTCTTAGAGGAGAGATATTTTCTATCCCTCAGAA

AATCCCCGCCGCTTATCCAACCACTATGAAAGAAGGCAACAGATCAATCTTGTG

TTATCTCCAACATGTGCTACGCTATGAGCGAGAGATAATCACGGCGTCTCCAGAG

AATGACTGGCTATGGATCTTTTCAGACTTTAGAAGTGCCAAAATGACGTACCTAT

CCCTCATTACTTACCAGTCTCATCTTCTACTCCAGAGGGTTGAGAGAAACCTATC

TAAGAGTATGAGAGATAACCTGCGACAATTGAGTTCTTTGATGAGGCAGGTGCT

GGGCGGGCACGGAGAAGATACCTTAGAGTCAGACGACAACATTCAACGACTGCT

AAAAGACTCTTTACGAAGGACAAGATGGGTGGATCAAGAGGTGCGCCATGCAGC

TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA
```

-continued

```
GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTC

TCATTTTTGTTGTTTATTTGTTAAGCGT.
```

In one embodiment, the nucleic acid comprises the sequence of SEQ ID NO: 16, shown below (RABV vector: Coravax V6 China):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA
```

-continued

```
CTGACGTAGCACTGGCAGATGATGGAACTGTCAACTCTGACGACGAGGACTACT
TTTCAGGTGAAACCAGAAGTCCGGAGGCTGTTTATACTCGAATCATGATGAATG
GAGGTCGACTAAAGAGATCTCACATACGGAGATATGTCTCAGTCAGTTCCAATC
ATCAAGCCCGTCCAAACTCATTCGCCGAGTTTCTAAACAAGACATATTCGAGTGA
CTCATAAGAAGTTGAATAACAAAATGCCGGAAATCTACGGATTGTGTATATCCA
TCATGAAAAAAACTAACACCCCTCCTTTCGAACCATCCCAAACATGAGCAAGAT
CTTTGTCAATCCTAGTGCTATTAGAGCCGGTCTGGCCGATCTTGAGATGGCTGAA
GAAACTGTTGATCTGATCAATAGAAATATCGAAGACAATCAGGCTCATCTCCAA
GGGGAACCCATAGAGGTGGACAATCTCCCTGAGGATATGGGCGACTTCACCTG
GATGATGGAAAATCGCCCAACCATGGTGAGATAGCCAAGGTGGGAGAAGGCAA
GTATCGAGAGGACTTTCAGATGGATGAAGGAGAGGATCCTAGCTTCCTGTTCCA
GTCATACCTGGAAAATGTTGGAGTCCAAATAGTCAGACAAATGAGGTCAGGAGA
GAGATTTCTCAAGATATGGTCACAGACCGTAGAAGAGATTATATCCTATGTCGCG
GTCAACTTTCCCAACCCTCCAGGAAAGTCTTCAGAGGATAAATCAACCCAGACT
ACTGGCCGAGAGCTCAAGAAGGAGACAACACCCACTCCTTCTCAGAGAGAAAGC
CAATCATCGAAAGCCAGGATGGCGGCTCAAATTGCTTCTGGCCCTCCAGCCCTTG
AATGGTCGGCTACCAATGAAGAGGATGATCTATCAGTGGAGGCTGAGATCGCTC
ACCAGATTGCAGAAAGTTTCTCCAAAAAATATAAGTTTCCCTCTCGATCCTCAGG
GATACTCTTGTATAATTTTGAGCAATTGAAAATGAACCTTGATGATATAGTTAAA
GAGGCAAAAAATGTACCAGGTGTGACCCGTTTAGCCCATGACGGGTCCAAACTC
CCCCTAAGATGTGTACTGGGATGGGTCGCTTTGGCCAACTCTAAGAAATTCCAGT
TGTTAGTCGAATCCGACAAGCTGAGTAAAATCATGCAAGATGACTTGAATCGCT
ATACATCTTGCTAACCGAACCTCTCCCCTCAGTCCCTCTAGACAATAAAATCCGA
GATGTCCCAAAGTCAACATGAAAAAAACAGGCAACACCACTGATAAAATGAAC
CTCCTACGTAAGATAGTGAAAAACCGCAGGGACGAGGACACTCAAAAATCCTCT
CCCGCGTCAGCCCCTCTGGATGACGATGACTTGTGGCTTCCACCCCCTGAATACG
TCCCGCTGAAAGAACTTACAGGCAAGAAGAACATGAGGAACTTTTGTATCAACG
GAAGGGTTAAAGTGTGTAGCCCGAATGGTTACTCGTTCAGGATCCTGCGGCACA
TTCTGAAATCATTCGACGAGATATATTCTGGGAATCATAGGATGATCGGGTTAGT
CAAAGTGGTTATTGGACTGGCTTTGTCAGGATCTCCAGTCCCTGAGGGCCTGAAC
TGGGTATACAAATTGAGGAGAACCTTTATCTTCCAGTGGGCTGATTCCAGGGGCC
CTCTTGAAGGGGAGGAGTTGGAATACTCTCAGGAGATCACTTGGGATGATGATA
CTGAGTTCGTCGGATTGCAAATAAGAGTGATTGCAAAACAGTGTCATATCCAGG
GCAGAGTCTGGTGTATCAACATGAACCCGAGAGCATGTCAACTATGGTCTGACA
TGTCTCTTCAGACACAAAGGTCCGAAGAGGACAAAGATTCCTCTCTGCTTCTAGA
ATAATCAGATTATATCCCGCAAATTTATCACTTGTTTACCTCTGGAGGAGAGAAC
ATATGGGCTCAACTCCAACCCTTGGGAGCAATATAACAAAAAACATGTTATGGT
GCCATTAAACCGCTGCATTTCATCAAAGTCAAGTTGATTACCTTTACATTTTGATC
CTCTTGGATGTGAAAAAAACTATTAACATCCCTCAAAAGACCcccgggAAAGATGGT
TCCTCAGGCTCTCCTGTTTGTACCCCTTCTGGTTTTTCCATTGTGTTTTGGGAAATT
```

-continued

```
CCCTATTTACACGATACCAGACAAGCTTGGTCCCTGGAGTCCGATTGACATACAT
CACCTCAGCTGCCCAAACAATTTGGTAGTGGAGGACGAAGGATGCACCAACCTG
TCAGGGTTCTCCTACATGGAACTTAAAGTTGGATACATCTTAGCCATAAAAGTGA
ACGGGTTCACTTGCACAGGCGTTGTGACGGAGGCTGAAACCTACACTAACTTCGT
TGGTTATGTCACAACCACGTTCAAAAGAAAGCATTTCCGCCCAACACCAGATGC
ATGTAGAGCCGCGTACAACTGGAAGATGGCCGGTGACCCCAGATATGAAGAGTC
TCTACACAATCCGTACCCTGACTACCGCTGGCTTCGAACTGTAAAAACCACCAAG
GAGTCTCTCGTTATCATATCTCCAAGTGTGGCAGATTTGGACCCATATGACAGAT
CCCTTCACTCGAGGGTCTTCCCTAGCGGGAAGTGCTCAGGAGTAGCGGTGTCTTC
TACCTACTGCTCCACTAACCACGATTACACCATTTGGATGCCCGAGAATCCGAGA
CTAGGGATGTCTTGTGACATTTTTACCAATAGTAGAGGGAAGAGAGCATCCAAA
GGGAGTGAGACTTGCGGCTTTGTAGATGAAAGAGGCCTATATAAGTCTTTAAAA
GGAGCATGCAAACTCAAGTTATGTGGAGTTCTAGGACTTAGACTTATGGATGGA
ACATGGGTCTCGATGCAAACATCAAATGAAACCAAATGGTGCCCTCCCGATAAG
TTGGTGAACCTGCACGACTTTCGCTCAGACGAAATTGAGCACCTTGTTGTAGAGG
AGTTGGTCAGGAAGAGAGAGGAGTGTCTGGATGCACTAGAGTCCATCATGACAA
CCAAGTCAGTGAGTTTCAGACGTCTCAGTCATTTAAGAAAACTTGTCCCTGGGTT
TGGAAAAGCATATACCATATTCAACAAGACCTTGATGGAAGCCGATGCTCACTA
CAAGTCAGTCgagACTTGGAATGAGATCCTCCCTTCAAAAGGGTGTTTAAGAGTTG
GGGGGAGGTGTCATCCTCATGTGAACGGGGTGTTTTTCAATGGTATAATATTAGG
ACCTGACGGCAATGTCTTAATCCCAGAGATGCAATCATCCCTCCTCCAGCAACAT
ATGGAGTTGTTGGAATCCTCGGTTATCCCCCTTGTGCACCCCCTGGCAGACCCGT
CTACCGTTTTCAAGGACGGTGACGAGGCTGAGGATTTTGTTGAAGTTCACCTTCC
CGATGTGCACAATCAGGTCTCAGGAGTTGACTTGGGTCTCCCGAACTGGGGAA
GTATGTATTACTGAGTGCAGGGGCCCTGACTGCCTTGATGTTGATAATTTTCCTG
ATGACATGTTGTAGAAGAGTCAATCGATCAGAACCTACGCAACACAATCTCAGA
GGGACAGGGAGGGAGGTGTCAGTCACTCCCCAAAGCGGGAAGATCATATCTTCA
TGGGAATCACACAAGAGTGGGGGTGAGACCAGACTGTAAttaattaaCGTCCTTTCAA
CGATCCAAGTCcatgaaaaaaactaacacccctcccgtacgaccATGTTCGTGTTTCTGGT
GCTGCTGCCTCTGGTGAGCTCCCAGTGCGTGAACCTGACCACAAGGACCCAGCTGCCCCC
TGCCTATACCAATTCCTTCACACGGGGCGTGTACTATCCCGACAAGGTGTTCCGG
AGCAGCGTGCTGCACTCCACACAGGATCTGTTTCTGCCTTTCTTTTCTAACGTGAC
CTGGTTCCACGCCATCCACGTGAGCGGCACCAATGGCACAAAGCGGTTCGACAA
TCCAGTGCTGCCCTTTAACGATGGCGTGTACTTCGCCTCCACCGAGAAGTCTAAC
ATCATCAGAGGCTGGATCTTTGGCACCACACTGGACAGCAAGACACAGTCCCTG
CTGATCGTGAACAATGCCACCAACGTGGTCATCAAGGTGTGCGAGTTCCAGTTTT
GTAATGATCCATTCCTGGGCGTGTACTATCACAAGAACAATAAGTCTTGGATGGA
GAGCGAGTTTCGCGTGTATTCCTCTGCCAACAATTGCACATTTGAGTACGTGTCC
CAGCCCTTCCTGATGGACCTGGAGGGCAAGCAGGGCAATTTCAAGAACCTGAGG
GAGTTCGTGTTTAAGAATATCGATGGCTACTTCAAAATCTACTCCAAGCACACCC
CAATCAACCTGGTGCGCGACCTGCCACAGGGCTTCTCTGCCCTGGAGCCACTGGT
```

-continued

```
GGATCTGCCCATCGGCATCAACATCACCCGGTTTCAGACACTGCTGGCCCTGCAC

AGAAGCTACCTGACACCAGGCGACAGCTCCTCTGGATGGACCGCAGGAGCAGCA

GCCTACTATGTGGGCTATCTGCAGCCCAGGACCTTCCTGCTGAAGTACAACGAG

AATGGCACCATCACAGACGCCGTGGATTGCGCCCTGGATCCCCTGTCTGAGACC

AAGTGTACACTGAAGAGCTTTACCGTGGAGAAGGGCATCTATCAGACAAGCAAT

TTCAGGGTGCAGCCTACCGAGTCCATCGTGCGCTTTCCCAATATCACAAACCTGT

GCCCTTTTGGCGAGGTGTTCAACGCAACCCGCTTCGCCAGCGTGTACGCCTGGAA

TAGGAAGCGCATCTCCAACTGCGTGGCCGACTATTCTGTGCTGTACAACAGCGCC

TCCTTCTCTACCTTTAAGTGCTATGGCGTGAGCCCCACAAAGCTGAATGACCTGT

GCTTTACCAACGTGTACGCCGATTCCTTCGTGATCAGGGGCGACGAGGTGCGCC

AGATCGCACCAGGACAGACAGGCAAGATCGCAGACTACAATTATAAGCTGCCTG

ACGATTTCACCGGCTGCGTGATCGCCTGGAACTCTAACAATCTGGATAGCAAAGT

GGGCGGCAACTACAATTATCTGTACCGGCTGTTTAGAAAGTCTAATCTGAAGCCA

TTCGAGAGGGACATCTCCACAGAAATCTACCAGGCCGGCTCTACCCCCTGCAAT

GGCGTGGAgGGCTTTAACTGTTATTTCCCTCTGCAGAgCTACgGCTTCCAGCCAAC

AAACGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAAC

AAGTGCGTGAACTTCAACTTCAACGGACTGACCGGAACAGGCGTGCTGACCGAG

TCCAACAAGAAGTTCCTGCCTTTTCAGCAGTTCGGCAGGGACATCGCAGATACC

ACAGACGCCGTGCGCGACCCTCAGACCCTGGAGATCCTGGACATCACACCATGC

TCCTTCGGCGGCGTGTCTGTGATCACACCAGGCACCAATACAAGCAACCAGGTG

GCCGTGCTGTATCAGGACGTGAATTGTACCGAGGTGCCAGTGGCAATCCACGCA

GATCAGCTGACCCCTACATGGCGGGTGTACTCTACCGGCAGCAACGTGTTCCAG

ACAAGAGCCGGATGCCTGATCGGAGCAGAGCACGTGAACAATAGCTATGAGTGC

GACATCCCTATCGGCGCCGGCATCTGTGCCTCCTACCAGACCCAGACAAACTCCC

CAAGGTCTGTGGGAGATGAGGCCGAAGACTTTGTGGAAGTCCACCTGCCTGATG

TGCATAACCAGGTGTCTGGCGTCGACCTGGGACTGCCAAATTGGGGCAAGTACG

TGCTGCTGAGTGCTGGAGCACTGACTGCCCTGATGCTGATCATTTTCCTGATGAC

CTGCTGTCGGCGCGTGAACAGAAGTGAGCCCACTCAGCACAATCTGCGAGGAAC

CGGGAGAGAAGTGTCAGTCACACCTCAGAGCGGGAAAATCATTAGTAGTTGGGA

ATCACATAAAAGCGGGGGCGAGACCAGGCTGggatccggctccggcgagggcaggg-
gaagtctact aacatgcgggacgtggaggaaaatcccggccccATGCTCGATCCTGGAGAGGTCTAT-
GATGACCC

TATTGACCCAATCGAGTTAGAGGCTGAACCCAGAGGAACCCCCATTGTCCCCAA

CATCTTGAGGAACTCTGACTACAATCTCAACTCTCCTTTGATAGAAGATCCTGCT

AGACTAATGTTAGAATGGTTAAAAACAGGGAATAGACCTTATCGGATGACTCTA

ACAGACAATTGCTCCAGGTCTTTCAGAGTTTTGAAAGATTATTTCAAGAAGGTAG

ATTTGGGTTCTCTCAAGGTGGGCGGAATGGCTGCACAGTCAATGATTTCTCTCTG

GTTATATGGTGCCCACTCTGAATCCAACAGGAGCCGGAGATGTATAACAGACTT

GGCCCATTTCTATTCCAAGTCGTCCCCCATAGAGAAGCTGTTGAATCTCACGCTA
```

```
GGAAATAGAGGGCTGAGAATCCCCCCAGAGGGAGTGTTAAGTTGCCTTGAGAGG

GTTGATTATGATAATGCATTTGGAAGGTATCTTGCCAACACGTATTCCTCTTACTT

GTTCTTCCATGTAATCACCTTATACATGAACGCCCTAGACTGGGATGAAGAAAG

ACCATCCTAGCATTATGGAAAGATTTAACCTCAGTGGACATCGGGAAGGACTTG

GTAAAGTTCAAAGACCAAATATGGGGACTGCTGATCGTGACAAAGGACTTTGTT

TACTCCCAAAGTTCCAATTGTCTTTTTGACAGAAACTACACACTTATGCTAAAAG

ATCTTTTCTTGTCTCGCTTCAACTCCTTAATGGTCTTGCTCTCTCCCCCAGAGCCC

CGATACTCAGATGACTTGATATCTCAACTATGCCAGCTGTACATTGCTGGGGATC

AAGTCTTGTCTATGTGTGGAAACTCCGGCTATGAAGTCATCAAAATATTGGAGCC

ATATGTCGTGAATAGTTTAGTCCAGAGAGCAGAAAAGTTTAGGCCTCTCATTCAT

TCCTTGGGAGACTTTCCTGTATTTATAAAAGACAAGGTAAGTCAACTTGAAGAGA

CGTTCGGTCCCTGTGCAAGAAGGTTCTTTAGGGCTCTGGATCAATTCGACAACAT

ACATGACTTGGTTTTTGTGTTTGGCTGTTACAGGCATTGGGGCACCCATATATA

GATTATCGAAAGGGTCTGTCAAAACTATATGATCAGGTTCACCTTAAAAAAATG

ATAGATAAGTCCTACCAGGAGTGCTTAGCAAGCGACCTAGCCAGGAGGATCCTT

AGATGGGGTTTTGATAAGTACTCCAAGTGGTATCTGGATTCAAGATTCCTAGCCC

GAGACCACCCCTTGACTCCTTATATCAAAACCCAAACATGGCCACCCAAACATA

TTGTAGACTTGGTGGGGATACATGGCACAAGCTCCCGATCACGCAGATCTTTGA

GATTCCTGAATCAATGGATCCGTCAGAAATATTGGATGACAAATCACATTCTTTC

ACCAGAACGAGACTAGCTTCTTGGCTGTCAGAAAACCGAGGGGGGCCTGTTCCT

AGCGAAAAAGTTATTATCACGGCCCTGTCTAAGCCGCCTGTCAATCCCCGAGAG

TTTCTGAGGTCTATAGACCTCGGAGGATTGCCAGATGAAGACTTGATAATTGGCC

TCAAGCCAAAGGAACGGGAATTGAAGATTGAAGGTCGATTCTTTGCTCTAATGT

CATGGAATCTAAGATTGTATTTTGTCATCACTGAAAAACTCTTGGCCAACTACAT

CTTGCCACTTTTTGACGCGCTGACTATGACAGACAACCTGAACAAGGTGTTTAAA

AAGCTGATCGACAGGGTCACCGGGCAAGGGCTTTTGGACTATTCAAGGGTCACA

TATGCATTTCACCTGGACTATGAAAAGTGGAACAACCATCAAAGATTAGAGTCA

ACAGAGGATGTATTTTCTGTCCTAGATCAAGTGTTTGGATTGAAGAGAGTGTTTT

CTAGAACACACGAGTTTTTTCAAAAGGCCTGGATCTATTATTCAGACAGATCAGA

CCTCATCGGGTTACGGGAGGATCAAATATACTGCTTAGATGCGTCCAACGGCCC

AACCTGTTGGAATGGCCAGGATGGCGGGCTAGAAGGCTTACGGCAGAAGGGCTG

GAGTCTAGTCAGCTTATTGATGATAGATAGAGAATCTCAAATCAGGAACACAAG

AACCAAAATACTAGCTCAAGGAGACAACCAGGTTTTATGTCCGACATACATGTT

GTCGCCAGGGCTATCTCAAGAGGGGCTCCTCTATGAATTGGAGAGAATATCAAG

GAATGCACTTTCGATATACAGAGCCGTCGAGGAAGGGGCATCTAAGCTAGGGCT

GATCATCAAGAAAGAAGAGACCATGTGTAGTTATGACTTCCTCATCTATGGAAA

AACCCCTTTGTTTAGAGGTAACATATTGGTGCCTGAGTCCAAAAGATGGGCCAG

AGTCTCTTGCGTCTCTAATGACCAAATAGTCAACCTCGCCAATATAATGTCGACA

GTGTCCACCAATGCGCTAACAGTGGCACAACACTCTCAATCTTTGATCAAACCGA

TGAGGGATTTTCTGCTCATGTCAGTACAGGCAGTCTTTCACTACCTGCTATTTAGC

CCAATCTTAAAGGGAAGAGTTTACAAGATTCTGAGCGCTGAAGGGGAGAGCTTT
```

-continued

```
CTCCTAGCCATGTCAAGGATAATCTATCTAGATCCTTCTTTGGGAGGGATATCTG
GAATGTCCCTCGGAAGATTCCATATACGACAGTTCTCAGACCCTGTCTCTGAAGG
GTTATCCTTCTGGAGAGAGATCTGGTTAAGCTCCCAAGAGTCCTGGATTCACGCG
TTGTGTCAAGAGGCTGGAAACCCAGATCTTGGAGAGAGAACACTCGAGAGCTTC
ACTCGCCTTCTAGAAGATCCGACCACCTTAAATATCAGAGGAGGGGCCAGTCCT
ACCATTCTACTCAAGGATGCAATCAGAAAGGCTTTATATGACGAGGTGGACAAG
GTGGAAAATTCAGAGTTTCGAGAGGCAATCCTGTTGTCCAAGACCCATAGAGAT
AATTTTATACTCTTCTTAATATCTGTTGAGCCTCTGTTTCCTCGATTTCTCAGTGA
GCTATTCAGTTCGTCTTTTTTGGGAATCCCCGAGTCAATCATTGGATTGATACAA
AACTCCCGAACGATAAGAAGGCAGTTTAGAAAGAGTCTCTCAAAAACTTTAGAA
GAATCCTTCTACAACTCAGAGATCCACGGGATTAGTCGGATGACCCAGACACCT
CAGAGGGTTGGGGGGGTGTGGCCTTGCTCTTCAGAGAGGGCAGATCTACTTAGG
GAGATCTCTTGGGGAAGAAAAGTGGTAGGCACGACAGTTCCTCACCCTTCTGAG
ATGTTGGGATTACTTCCCAAGTCCTCTATTTCTTGCACTTGTGGAGCAACAGGAG
GAGGCAATCCTAGAGTTTCTGTATCAGTACTCCCGTCCTTTGATCAGTCATTTTTT
TCACGAGGCCCCCTAAAGGGATACTTGGGCTCGTCCACCTCTATGTCGACCCAGC
TATTCCATGCATGGGAAAAAGTCACTAATGTTCATGTGGTGAAGAGAGCTCTATC
GTTAAAAGAATCTATAAACTGGTTCATTACTAGAGATTCCAACTTGGCTCAAGCT
CTAATTAGGAACATTATGTCTCTGACAGGCCCTGATTTCCCTCTAGAGGAGGCCC
CTGTCTTCAAAAGGACGGGGTCAGCCTTGCATAGGTTCAAGTCTGCCAGATACA
GCGAAGGAGGGTATTCTTCTGTCTGCCCGAACCTCCTCTCTCATATTTCTGTTAGT
ACAGACACCATGTCTGATTTGACCCAAGACGGGAAGAACTACGATTTCATGTTCC
AGCCATTGATGCTTTATGCACAGACATGGACATCAGAGCTGGTACAGAGAGACA
CAAGGCTAAGAGACTCTACGTTTCATTGGCACCTCCGATGCAACAGGTGTGTGA
GACCCATTGACGACGTGACCCTGGAGACCTCTCAGATCTTCGAGTTTCCGGATGT
GTCGAAAAGAATATCCAGAATGGTTTCTGGGGCTGTGCCTCACTTCCAGAGGCTT
CCCGATATCCGTCTGAGACCAGGAGATTTTGAATCTCTAAGCGGTAGAGAAAAG
TCTCACCATATCGGATCAGCTCAGGGGCTCTTATACTCAATCTTAGTGGCAATTC
ACGACTCAGGATACAATGATGGAACCATCTTCCCTGTCAACATATACGGCAAGG
TTTCCCCTAGAGACTATTTGAGAGGGCTCGCAAGGGGAGTATTGATAGGATCCTC
GATTTGCTTCTTGACAAGAATGACAAATATCAATATTAATAGACCTCTTGAATTG
GTCTCAGGGTAATCTCATATATTCTCCTGAGGCTAGATAACCATCCCTCCTTGT
ACATAATGCTCAGAGAACCGTCTCTTAGAGGAGAGATATTTTCTATCCCTCAGAA
AATCCCCGCCGCTTATCCAACCACTATGAAAGAAGGCAACAGATCAATCTTGTG
TTATCTCCAACATGTGCTACGCTATGAGCGAGAGATAATCACGGCGTCTCCAGAG
AATGACTGGCTATGGATCTTTTCAGACTTTAGAAGTGCCAAAATGACGTACCTAT
CCCTCATTACTTACCAGTCTCATCTTCTACTCCAGAGGGTTGAGAGAAACCTATC
TAAGAGTATGAGAGATAACCTGCGACAATTGAGTTCTTTGATGAGGCAGGTGCT
GGGCGGGCACGGAGAAGATACCTTAGAGTCAGACGACAACATTCAACGACTGCT
AAAAGACTCTTTACGAAGGACAAGATGGGTGGATCAAGAGGTGCGCCATGCAGC
```

```
TAGAACCATGACTGGAGATTACAGCCCCAACAAGAAGGTGTCCCGTAAGGTAGG

ATGTTCAGAATGGGTCTGCTCTGCTCAACAGGTTGCAGTCTCTACCTCAGCAAAC

CCGGCCCCTGTCTCGGAGCTTGACATAAGGGCCCTCTCTAAGAGGTTCCAGAACC

CTTTGATCTCGGGCTTGAGAGTGGTTCAGTGGGCAACCGGTGCTCATTATAAGCT

TAAGCCTATTCTAGATGATCTCAATGTTTTCCCATCTCTCTGCCTTGTAGTTGGGG

ACGGGTCAGGGGGGATATCAAGGGCAGTCCTCAACATGTTTCCAGATGCCAAGC

TTGTGTTCAACAGTCTTTTAGAGGTGAATGACCTGATGGCTTCCGGAACACATCC

ACTGCCTCCTTCAGCAATCATGAGGGGAGGAAATGATATCGTCTCCAGAGTGAT

AGATCTTGACTCAATCTGGGAAAAACCGTCCGACTTGAGAAACTTGGCAACCTG

GAAATACTTCCAGTCAGTCCAAAAGCAGGTCAACATGTCCTATGACCTCATTATT

TGCGATGCAGAAGTTACTGACATTGCATCTATCAACCGGATCACCCTGTTAATGT

CCGATTTTGCATTGTCTATAGATGGACCACTCTATTTGGTCTTCAAAACTTATGGG

ACTATGCTAGTAAATCCAAACTACAAGGCTATTCAACACCTGTCAAGAGCGTTCC

CCTCGGTCACAGGGTTTATCACCCAAGTAACTTCGTCTTTTTCATCTGAGCTCTAC

CTCCGATTCTCCAAACGAGGGAAGTTTTTCAGAGATGCTGAGTACTTGACCTCTT

CCACCCTTCGAGAAATGAGCCTTGTGTTATTCAATTGTAGCAGCCCCAAGAGTGA

GATGCAGAGAGCTCGTTCCTTGAACTATCAGGATCTTGTGAGAGGATTTCCTGAA

GAAATCATATCAAATCCTTACAATGAGATGATCATAACTCTGATTGACAGTGATG

TAGAATCTTTTCTAGTCCACAAGATGGTTGATGATCTTGAGTTACAGAGGGGAAC

TCTGTCTAAAGTGGCTATCATTATAGCCATCATGATAGTTTTCTCCAACAGAGTC

TTCAACGTTTCCAAACCCCTAACTGACCCCTCGTTCTATCCACCGTCTGATCCCA

AAATCCTGAGGCACTTCAACATATGTTGCAGTACTATGATGTATCTATCTACTGC

TTTAGGTGACGTCCCTAGCTTCGCAAGACTTCACGACCTGTATAACAGACCTATA

ACTTATTACTTCAGAAAGCAAGTCATTCGAGGGAACGTTTATCTATCTTGGAGTT

GGTCCAACGACACCTCAGTGTTCAAAAGGGTAGCCTGTAATTCTAGCCTGAGTCT

GTCATCTCACTGGATCAGGTTGATTTACAAGATAGTGAAGACTACCAGACTCGTT

GGCAGCATCAAGGATCTATCCAGAGAAGTGGAAAGACACCTTCATAGGTACAAC

AGGTGGATCACCCTAGAGGATATCAGATCTAGATCATCCCTACTAGACTACAGTT

GCCTGTGAACCGGATACTCCTGGAAGCCTGCCCATGCTAAGACTCTTGTGTGATG

TATCTTGAAAAAAACAAGATCCTAAATCTGAACCTTTGGTTGTTTGATTGTTTTTC

TCATTTTTGTTGTTTATTTGTTAAGCGT.
```

In one embodiment, the nucleic acid comprises the sequence of SEQ ID NO: 17, shown below (RABV vector: Coravax V6 South Africa):

```
ACGCTTAACAACCAGATCAAAGAAAAAACAGACATTGTCAATTGCAAAGCAAAA

ATGTAACACCCCTACAATGGATGCCGACAAGATTGTATTCAAAGTCAATAATCA

GGTGGTCTCTTTGAAGCCTGAGATTATCGTGGATCAATATGAGTACAAGTACCCT

GCCATCAAAGATTTGAAAAAGCCCTGTATAACCCTAGGAAAGGCTCCCGATTTA

AATAAAGCATACAAGTCAGTTTTGTCAGGCATGAGCGCCGCCAAACTTAATCCT

GACGATGTATGTTCCTATTTGGCAGCGGCAATGCAGTTTTTTGAGGGGACATGTC
```

-continued

CGGAAGACTGGACCAGCTATGGAATTGTGATTGCACGAAAAGGAGATAAGATCA

CCCCAGGTTCTCTGGTGGAGATAAAACGTACTGATGTAGAAGGGAATTGGGCTC

TGACAGGAGGCATGGAACTGACAAGAGACCCCACTGTCCCTGAGCATGCGTCCT

TAGTCGGTCTTCTCTTGAGTCTGTATAGGTTGAGCAAAATATCCGGGCAAAACAC

TGGTAACTATAAGACAAACATTGCAGACAGGATAGAGCAGATTTTTGAGACAGC

CCCTTTTGTTAAAATCGTGGAACACCATACTCTAATGACAACTCACAAAATGTGT

GCTAATTGGAGTACTATACCAAACTTCAGATTTTTGGCCGGAACCTATGACATGT

TTTTCTCCCGGATTGAGCATCTATATTCAGCAATCAGAGTGGGCACAGTTGTCAC

TGCTTATGAAGACTGTTCAGGACTGGTATCATTTACTGGGTTCATAAAACAAATC

AATCTCACCGCTAGAGAGGCAATACTATATTTCTTCCACAAGAACTTTGAGGAAG

AGATAAGAAGAATGTTTGAGCCAGGGCAGGAGACAGCTGTTCCTCACTCTTATTT

CATCCACTTCCGTTCACTAGGCTTGAGTGGGAAATCTCCTTATTCATCAAATGCT

GTTGGTCACGTGTTCAATCTCATTCACTTTGTAGGATGCTATATGGGTCAAGTCA

GATCCCTAAATGCAACGGTTATTGCTGCATGTGCTCCTCATGAAATGTCTGTTCT

AGGGGGCTATCTGGGAGAGGAATTCTTCGGGAAAGGGACATTTGAAAGAAGATT

CTTCAGAGATGAGAAAGAACTTCAAGAATACGAGGCGGCTGAACTGACAAAGA

CTGACGTAGCACTGGCAGATGATGGAACTGTCAACTCTGACGACGAGGACTACT

TTTCAGGTGAAACCAGAAGTCCGGAGGCTGTTTATACTCGAATCATGATGAATG

GAGGTCGACTAAAGAGATCTCACATACGGAGATATGTCTCAGTCAGTTCCAATC

ATCAAGCCCGTCCAAACTCATTCGCCGAGTTTCTAAACAAGACATATTCGAGTGA

CTCATAAGAAGTTGAATAACAAAATGCCGGAAATCTACGGATTGTGTATATCCA

TCATGAAAAAAACTAACACCCCTCCTTTCGAACCATCCCAAACATGAGCAAGAT

CTTTGTCAATCCTAGTGCTATTAGAGCCGGTCTGGCCGATCTTGAGATGGCTGAA

GAAACTGTTGATCTGATCAATAGAAATATCGAAGACAATCAGGCTCATCTCCAA

GGGGAACCCATAGAGGTGGACAATCTCCCTGAGGATATGGGGCGACTTCACCTG

GATGATGGAAAATCGCCCAACCATGGTGAGATAGCCAAGGTGGGAGAAGGCAA

GTATCGAGAGGACTTTCAGATGGATGAAGGAGAGGATCCTAGCTTCCTGTTCCA

GTCATACCTGGAAAATGTTGGAGTCCAAATAGTCAGACAAATGAGGTCAGGAGA

GAGATTTCTCAAGATATGGTCACAGACCGTAGAAGAGATTATATCCTATGTCGCG

GTCAACTTTCCCAACCCTCCAGGAAAGTCTTCAGAGGATAAATCAACCCAGACT

ACTGGCCGAGAGCTCAAGAAGGAGACAACACCCCACTCCTTCTCAGAGAGAAAGC

CAATCATCGAAAGCCAGGATGGCGGCTCAAATTGCTTCTGGCCCTCCAGCCCTTG

AATGGTCGGCTACCAATGAAGAGGATGATCTATCAGTGGAGGCTGAGATCGCTC

ACCAGATTGCAGAAAGTTTCTCCAAAAAATATAAGTTTCCCTCTCGATCCTCAGG

GATACTCTTGTATAATTTTGAGCAATTGAAAATGAACCTTGATGATATAGTTAAA

GAGGCAAAAAATGTACCAGGTGTGACCCGTTTAGCCCATGACGGGTCCAAACTC

CCCCTAAGATGTGTACTGGGATGGGTCGCTTTGGCCAACTCTAAGAAATTCCAGT

TGTTAGTCGAATCCGACAAGCTGAGTAAAATCATGCAAGATGACTTGAATCGCT

ATACATCTTGCTAACCGAACCTCTCCCCTCAGTCCCTCTAGACAATAAAATCCGA

GATGTCCCAAAGTCAACATGAAAAAAACAGGCAACACCACTGATAAAATGAAC

CTCCTACGTAAGATAGTGAAAAACCGCAGGGACGAGGACACTCAAAAATCCTCT

```
CCCGCGTCAGCCCCTCTGGATGACGATGACTTGTGGCTTCCACCCCCTGAATACG

TCCCGCTGAAAGAACTTACAGGCAAGAAGAACATGAGGAACTTTTGTATCAACG

GAAGGGTTAAAGTGTGTAGCCCGAATGGTTACTCGTTCAGGATCCTGCGGCACA

TTCTGAAATCATTCGACGAGATATATTCTGGGAATCATAGGATGATCGGGTTAGT

CAAAGTGGTTATTGGACTGGCTTTGTCAGGATCTCCAGTCCCTGAGGGCCTGAAC

TGGGTATACAAATTGAGGAGAACCTTTATCTTCCAGTGGGCTGATTCCAGGGGCC

CTCTTGAAGGGGAGGAGTTGGAATACTCTCAGGAGATCACTTGGGATGATGATA

CTGAGTTCGTCGGATTGCAAATAAGAGTGATTGCAAAACAGTGTCATATCCAGG

GCAGAGTCTGGTGTATCAACATGAACCCGAGAGCATGTCAACTATGGTCTGACA

TGTCTCTTCAGACACAAAGGTCCGAAGAGGACAAAGATTCCTCTCTGCTTCTAGA

ATAATCAGATTATATCCCGCAAATTTATCACTTGTTTACCTCTGGAGGAGAGAAC

ATATGGGCTCAACTCCAACCCTTGGGAGCAATATAACAAAAAACATGTTATGGT

GCCATTAAACCGCTGCATTTCATCAAAGTCAAGTTGATTACCTTTACATTTTGATC

CTCTTGGATGTGAAAAAAACTATTAACATCCCTCAAAAGACCccgggAAAGATGGT

TCCTCAGGCTCTCCTGTTTGTACCCCTTCTGGTTTTTCCATTGTGTTTTGGGAAATT

CCCTATTTACACGATACCAGACAAGCTTGGTCCCTGGAGTCCGATTGACATACAT

CACCTCAGCTGCCCAAACAATTTGGTAGTGGAGGACGAAGGATGCACCAACCTG

TCAGGGTTCTCCTACATGGAACTTAAAGTTGGATACATCTTAGCCATAAAAGTGA

ACGGGTTCACTTGCACAGGCGTTGTGACGGAGGCTGAAACCTACACTAACTTCGT

TGGTTATGTCACAACCACGTTCAAAAGAAAGCATTTCCGCCCAACACCAGATGC

ATGTAGAGCCGCGTACAACTGGAAGATGGCCGGTGACCCCAGATATGAAGAGTC

TCTACACAATCCGTACCCTGACTACCGCTGGCTTCGAACTGTAAAAACCACCAAG

GAGTCTCTCGTTATCATATCTCCAAGTGTGGCAGATTTGGACCCATATGACAGAT

CCCTTCACTCGAGGGTCTTCCCTAGCGGGAAGTGCTCAGGAGTAGCGGTGTCTTC

TACCTACTGCTCCACTAACCACGATTACACCATTTGGATGCCCGAGAATCCGAGA

CTAGGGATGTCTTGTGACATTTTTACCAATAGTAGAGGGAAGAGAGCATCCAAA

GGGAGTGAGACTTGCGGCTTTGTAGATGAAAGAGGCCTATATAAGTCTTTAAAA

GGAGCATGCAAACTCAAGTTATGTGGAGTTCTAGGACTTAGACTTATGGATGGA

ACATGGGTCTCGATGCAAACATCAAATGAAACCAAATGGTGCCCTCCCGATAAG

TTGGTGAACCTGCACGACTTTCGCTCAGACGAAATTGAGCACCTTGTTGTAGAGG

AGTTGGTCAGGAAGAGAGAGGAGTGTCTGGATGCACTAGAGTCCATCATGACAA

CCAAGTCAGTGAGTTTCAGACGTCTCAGTCATTTAAGAAAACTTGTCCCTGGGTT

TGGAAAAGCATATACCATATTCAACAAGACCTTGATGGAAGCCGATGCTCACTA

CAAGTCAGTCgagACTTGGAATGAGATCCTCCCTTCAAAAGGGTGTTTAAGAGTTG

GGGGGAGGTGTCATCCTCATGTGAACGGGGTGTTTTTCAATGGTATAATATTAGG

ACCTGACGGCAATGTCTTAATCCCAGAGATGCAATCATCCCTCCTCCAGCAACAT

ATGGAGTTGTTGGAATCCTCGGTTATCCCCCTTGTGCACCCCCTGGCAGACCCGT

CTACCGTTTTCAAGGACGGTGACGAGGCTGAGGATTTTGTTGAAGTTCACCTTCC

CGATGTGCACAATCAGGTCTCAGGAGTTGACTTGGGTCTCCCGAACTGGGGGAA

GTATGTATTACTGAGTGCAGGGGCCCTGACTGCCTTGATGTTGATAATTTTCCTG
```

```
ATGACATGTTGTAGAAGAGTCAATCGATCAGAACCTACGCAACACAATCTCAGA

GGGACAGGGAGGGAGGTGTCAGTCACTCCCCAAAGCGGGAAGATCATATCTTCA

TGGGAATCACACAAGAGTGGGGGTGAGACCAGACTGTAAttaattaaCGTCCTTTCAA

CGATCCAAGTCcatgaaaaaaactaacacccctcccgtacgaccATGTTCGTGTTTCTGGT

GCTGCTGCCTCTGGTGAGCTCCCAGTGCGTGAACTTCACCACAAGGACCCAGCTGCCCCCT

GCCTATACCAATTCCTTCACACGGGGCGTGTACTATCCCGACAAGGTGTTCCGGA

GCAGCGTGCTGCACTCCACACAGGATCTGTTTCTGCCTTTCTTTTCTAACGTGACC

TGGTTCCACGCCATCCACGTGAGCGGCACCAATGGCACAAAGCGGTTCGCCAAT

CCAGTGCTGCCCTTTAACGATGGCGTGTACTTCGCCTCCACCGAGAAGTCTAACA

TCATCAGAGGCTGGATCTTTGGCACCACACTGGACAGCAAGACACAGTCCCTGC

TGATCGTGAACAATGCCACCAACGTGGTCATCAAGGTGTGCGAGTTCCAGTTTTG

TAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCC

AGCCCTTCCTGATGGACCTGGAGGGCAAGCAGGGCAATTTCAAGAACCTGAGGG

AGTTCGTGTTTAAGAATATCGATGGCTACTTCAAAATCTACTCCAAGCACACCCC

AATCAACCTGGTGCGCGGCCTGCCACAGGGCTTCTCTGCCCTGGAGCCACTGGTG

GATCTGCCCATCGGCATCAACATCACCCGGTTTCAGACACTGCTGGCCCTGCACA

GAAGCTACCTGACACCAGGCGACAGCTCCTCTGGATGGACCGCAGGAGCAGCAG

CCTACTATGTGGGCTATCTGCAGCCCAGGACCTTCCTGCTGAAGTACAACGAGA

ATGGCACCATCACAGACGCCGTGGATTGCGCCCTGGATCCCCTGTCTGAGACCA

AGTGTACACTGAAGAGCTTTACCGTGGAGAAGGGCATCTATCAGACAAGCAATT

TCAGGGTGCAGCCTACCGAGTCCATCGTGCGCTTTCCCAATATCACAAACCTGTG

CCCTTTTGGCGAGGTGTTCAACGCAACCCGCTTCGCCAGCGTGTACGCCTGGAAT

AGGAAGCGCATCTCCAACTGCGTGGCCGACTATTCTGTGCTGTACAACAGCGCCT

CCTTCTCTACCTTTAAGTGCTATGGCGTGAGCCCCACAAAGCTGAATGACCTGTG

CTTTACCAACGTGTACGCCGATTCCTTCGTGATCAGGGGCGACGAGGTGCGCCA

GATCGCACCAGGACAGACAGGCAATATCGCAGACTACAATTATAAGCTGCCTGA

CGATTTCACCGGCTGCGTGATCGCCTGGAACTCTAACAATCTGGATAGCAAAGTG

GGCGGCAACTACAATTATCTGTACCGGCTGTTTAGAAAGTCTAATCTGAAGCCAT

TCGAGAGGGACATCTCCACAGAAATCTACCAGGCCGGCTCTACCCCCTGCAATG

GCGTGAAGGGCTTTAACTGTTATTTCCCTCTGCAGAGCTACGGCTTCCAGCCAAC

ATATGGCGTGGGCTATCAGCCCTACCGCGTGGTGGTGCTGTCTTTTGAGCTGCTG

CACGCACCTGCAACAGTGTGCGGACCAAAGAAGAGCACCAATCTGGTGAAGAA

CAAGTGCGTGAACTTCAACTTCAACGGACTGACCGGAACAGGCGTGCTGACCGA

GTCCAACAAGAAGTTCCTGCCTTTTCAGCAGTTCGGCAGGGACATCGCAGATAC

CACAGACGCCGTGCGCGACCCTCAGACCCTGGAGATCCTGGACATCACACCATG

CTCCTTCGGCGGCGTGTCTGTGATCACACCAGGCACCAATACAAGCAACCAGGT

GGCCGTGCTGTATCAGGGCGTGAATTGTACCGAGGTGCCAGTGGCAATCCACGC

AGATCAGCTGACCCCTACATGGCGGGTGTACTCTACCGGCAGCAACGTGTTCCA

GACAAGAGCCGGATGCCTGATCGGAGCAGAGCACGTGAACAATAGCTATGAGTG

CGACATCCCTATCGGCGCCGGCATCTGTGCCTCCTACCAGACCCAGACAAACTCC
```

-continued

```
CCAGAATCAAGCGTGATTCCTCTGGTCCATCCACTGGCAGATCCCTCCACAGTGT

TCAAAGACGGAGATGAGGCCGAAGACTTTGTGGAAGTCCACCTGCCTGATGTGC

ATAACCAGGTGTCTGGCGTCGACCTGGGACTGCCAAATTGGGGCAAGTACGTGC

TGCTGAGTGCTGGAGCACTGACTGCCCTGATGCTGATCATTTTCCTGATGACCTG

CTGTCGGCGCGTGAACAGAAGTGAGCCCACTCAGCACAATCTGCGAGGAACCGG

GAGAGAAGTGTCAGTCACACCTCAGAGCGGGAAAATCATTAGTAGTTGGGAATCACATA

AAAGCGGGGCGAGACCAGGCTGggatccggctccggcgagggcaggggaagtctactaacat gcggggacgtggaggaaaatcccggccccATGCTCGATCCTGGAGAGGTCTATGATGACCCTAT

TGACCCAATCGAGTTAGAGGCTGAACCCAGAGGAACCCCCATTGTCCCCAACAT

CTTGAGGAACTCTGACTACAATCTCAACTCTCCTTTGATAGAAGATCCTGCTAGA

CTAATGTTAGAATGGTTAAAAACAGGGAATAGACCTTATCGGATGACTCTAACA

GACAATTGCTCCAGGTCTTTCAGAGTTTTGAAAGATTATTTCAAGAAGGTAGATT

TGGGTTCTCTCAAGGTGGGCGGAATGGCTGCACAGTCAATGATTTCTCTCTGGTT

ATATGGTGCCCACTCTGAATCAACAGGAGCCGGAGATGTATAACAGACTTGGC

CCATTTCTATTCCAAGTCGTCCCCCATAGAGAAGCTGTTAATCTCACGCTAGGA

AATAGAGGGCTGAGAATCCCCCCAGAGGGAGTGTTAAGTTGCCTTGAGAGGGTT

GATTATGATAATGCATTTGGAAGGTATCTTGCCAACACGTATTCCTCTTACTTGTT

CTTCCATGTAATCACCTTATACATGAACGCCCTAGACTGGGATGAAGAAAAGAC

CATCCTAGCATTATGGAAAGATTTAACCTCAGTGGACATCGGGAAGGACTTGGT

AAAGTTCAAAGACCAAATATGGGGACTGCTGATCGTGACAAAGGACTTTGTTTA

CTCCCAAAGTTCCAATTGTCTTTTTGACAGAAACTACACACTTATGCTAAAAGAT

CTTTTCTTGTCTCGCTTCAACTCCTTAATGGTCTTGCTCTCTCCCCAGAGCCCCG

ATACTCAGATGACTTGATATCTCAACTATGCCAGCTGTACATTGCTGGGGATCAA

GTCTTGTCTATGTGTGGAAACTCCGGCTATGAAGTCATCAAAATATTGGAGCCAT

ATGTCGTGAATAGTTTAGTCCAGAGAGCAGAAAAGTTTAGGCCTCTCATTCATTC

CTTGGGAGACTTTCCTGTATTTATAAAAGACAAGGTAAGTCAACTTGAAGAGAC

GTTCGGTCCCTGTGCAAGAAGGTTCTTTAGGGCTCTGGATCAATTCGACAACATA

CATGACTTGGTTTTTGTGTTTGGCTGTTACAGGCATTGGGGGCACCCATATATAG

ATTATCGAAAGGGTCTGTCAAAACTATATGATCAGGTTCACCTTAAAAAAATGAT

AGATAAGTCCTACCAGGAGTGCTTAGCAAGCGACCTAGCCAGGAGGATCCTTAG

ATGGGGTTTTGATAAGTACTCCAAGTGGTATCTGGATTCAAGATTCCTAGCCCGA

GACCACCCCTTGACTCCTTATATCAAAACCCAAACATGGCCACCCAAACATATTG

TAGACTTGGTGGGGATACATGGCACAAGCTCCCGATCACGCAGATCTTTGAGA

TTCCTGAATCAATGGATCCGTCAGAAATATTGGATGACAAATCACATTCTTTCAC

CAGAACGAGACTAGCTTCTTGGCTGTCAGAAAACCGAGGGGGCCTGTTCCTAG

CGAAAAAGTTATTATCACGGCCCTGTCTAAGCCGCCTGTCAATCCCCGAGAGTTT

CTGAGGTCTATAGACCTCGGAGGATTGCCAGATGAAGACTTGATAATTGGCCTC

AAGCCAAAGGAACGGGAATTGAAGATTGAAGGTCGATTCTTTGCTCTAATGTCA

TGGAATCTAAGATTGTATTTTGTCATCACTGAAAAACTCTTGGCCAACTACATCT

TGCCACTTTTTGACGCGCTGACTATGACAGACAACCTGAACAAGGTGTTTAAAAA
```

-continued

```
GCTGATCGACAGGGTCACCGGGCAAGGGCTTTTGGACTATTCAAGGGTCACATA

TGCATTTCACCTGGACTATGAAAAGTGGAACAACCATCAAAGATTAGAGTCAAC

AGAGGATGTATTTTCTGTCCTAGATCAAGTGTTTGGATTGAAGAGAGTGTTTTCT

AGAACACACGAGTTTTTTCAAAAGGCCTGGATCTATTATTCAGACAGATCAGACC

TCATCGGGTTACGGGAGGATCAAATATACTGCTTAGATGCGTCCAACGGCCCAA

CCTGTTGGAATGGCCAGGATGGCGGGCTAGAAGGCTTACGGCAGAAGGGCTGGA

GTCTAGTCAGCTTATTGATGATAGATAGAGAATCTCAAATCAGGAACACAAGAA

CCAAAATACTAGCTCAAGGAGACAACCAGGTTTTATGTCCGACATACATGTTGTC

GCCAGGGCTATCTCAAGAGGGGCTCCTCTATGAATTGGAGAGAATATCAAGGAA

TGCACTTTCGATATACAGAGCCGTCGAGGAAGGGGCATCTAAGCTAGGGCTGAT

CATCAAGAAAGAAGAGACCATGTGTAGTTATGACTTCCTCATCTATGGAAAAAC

CCCTTTGTTTAGAGGTAACATATTGGTGCCTGAGTCCAAAAGATGGGCCAGAGTC

TCTTGCGTCTCTAATGACCAAATAGTCAACCTCGCCAATATAATGTCGACAGTGT

CCACCAATGCGCTAACAGTGGCACAACACTCTCAATCTTTGATCAAACCGATGA

GGGATTTTCTGCTCATGTCAGTACAGGCAGTCTTTCACTACCTGCTATTTAGCCCA

ATCTTAAAGGGAAGAGTTTACAAGATTCTGAGCGCTGAAGGGGAGAGCTTTCTC

CTAGCCATGTCAAGGATAATCTATCTAGATCCTTCTTTGGGAGGGATATCTGGAA

TGTCCCTCGGAAGATTCCATATACGACAGTTCTCAGACCCTGTCTCTGAAGGGTT

ATCCTTCTGGAGAGAGATCTGGTTAAGCTCCCAAGAGTCCTGGATTCACGCGTTG

TGTCAAGAGGCTGGAAACCCAGATCTTGGAGAGAGAACACTCGAGAGCTTCACT

CGCCTTCTAGAAGATCCGACCACCTTAAATATCAGAGGAGGGCCAGTCCTACC

ATTCTACTCAAGGATGCAATCAGAAAGGCTTTATATGACGAGGTGGACAAGGTG

GAAAATTCAGAGTTTCGAGAGGCAATCCTGTTGTCCAAGACCCATAGAGATAAT

TTTATACTCTTCTTAATATCTGTTGAGCCTCTGTTTCCTCGATTTCTCAGTGAGCT

ATTCAGTTCGTCTTTTTTGGGAATCCCCGAGTCAATCATTGGATTGATACAAAAC

TCCCGAACGATAAGAAGGCAGTTTAGAAAGAGTCTCTCAAAAACTTTAGAAGAA

TCCTTCTACAACTCAGAGATCCACGGGATTAGTCGGATGACCCAGACACCTCAG

AGGGTTGGGGGGTGTGGCCTTGCTCTTCAGAGAGGGCAGATCTACTTAGGGAG

ATCTCTTGGGGAAGAAAAGTGGTAGGCACGACAGTTCCTCACCCTTCTGAGATGT

TGGGATTACTTCCCAAGTCCTCTATTTCTTGCACTTGTGGAGCAACAGGAGGAGG

CAATCCTAGAGTTTCTGTATCAGTACTCCCGTCCTTTGATCAGTCATTTTTTTCAC

GAGGCCCCCTAAAGGGATACTTGGGCTCGTCCACCTCTATGTCGACCCAGCTATT

CCATGCATGGGAAAAGTCACTAATGTTCATGTGGTGAAGAGAGCTCTATCGTT

AAAAGAATCTATAAACTGGTTCATTACTAGAGATTCCAACTTGGCTCAAGCTCTA

ATTAGGAACATTATGTCTCTGACAGGCCCTGATTTCCCTCTAGAGGAGGCCCCTG

TCTTCAAAAGGACGGGGTCAGCCTTGCATAGGTTCAAGTCTGCCAGATACAGCG

AAGGAGGGTATTCTTCTGTCTGCCCGAACCTCCTCTCTCATATTTCTGTTAGTACA

GACACCATGTCTGATTTGACCCAAGACGGGAAGAACTACGATTTCATGTTCCAGC

CATTGATGCTTTATGCACAGACATGGACATCAGAGCTGGTACAGAGAGACACAA

GGCTAAGAGACTCTACGTTTCATTGGCACCTCCGATGCAACAGGTGTGTGAGACC

CATTGACGACGTGACCCTGGAGACCTCTCAGATCTTCGAGTTTCCGGATGTGTCG
```

-continued

```
AAAAGAATATCCAGAATGGTTTCTGGGGCTGTGCCTCACTTCCAGAGGCTTCCCG
ATATCCGTCTGAGACCAGGAGATTTTGAATCTCTAAGCGGTAGAGAAAAGTCTC
ACCATATCGGATCAGCTCAGGGGCTCTTATACTCAATCTTAGTGGCAATTCACGA
CTCAGGATACAATGATGGAACCATCTTCCCTGTCAACATATACGGCAAGGTTTCC
CCTAGAGACTATTTGAGAGGGCTCGCAAGGGGAGTATTGATAGGATCCTCGATT
TGCTTCTTGACAAGAATGACAAATATCAATATTAATAGACCTCTTGAATTGGTCT
CAGGGGTAATCTCATATATTCTCCTGAGGCTAGATAACCATCCCTCCTTGTACAT
AATGCTCAGAGAACCGTCTCTTAGAGGAGAGATATTTTCTATCCCTCAGAAAATC
CCCGCCGCTTATCCAACCACTATGAAAGAAGGCAACAGATCAATCTTGTGTTATC
TCCAACATGTGCTACGCTATGAGCGAGAGATAATCACGGCGTCTCCAGAGAATG
ACTGGCTATGGATCTTTTCAGACTTTAGAAGTGCCAAAATGACGTACCTATCCCT
CATTACTTACCAGTCTCATCTTCTACTCCAGAGGGTTGAGAGAAACCTATCTAAG
AGTATGAGAGATAACCTGCGACAATTGAGTTCTTTGATGAGGCAGGTGCTGGGC
GGGCACGGAGAAGATACCTTAGAGTCAGACGACAACATTCAACGACTGCTAAAA
GACTCTTTACGAAGGACAAGATGGGTGGATCAAGAGGTGCGCCATGCAGCTAGA
ACCATGACTGGAGATTACAGCCCCAACAAGAAGGTGTCCCGTAAGGTAGGATGT
TCAGAATGGGTCTGCTCTGCTCAACAGGTTGCAGTCTCTACCTCAGCAAACCCGG
CCCCTGTCTCGGAGCTTGACATAAGGGCCCTCTCTAAGAGGTTCCAGAACCCTTT
GATCTCGGGCTTGAGAGTGGTTCAGTGGGCAACCGGTGCTCATTATAAGCTTAAG
CCTATTCTAGATGATCTCAATGTTTTCCCATCTCTCTGCCTTGTAGTTGGGGACGG
GTCAGGGGGATATCAAGGGCAGTCCTCAACATGTTTCCAGATGCCAAGCTTGT
GTTCAACAGTCTTTTAGAGGTGAATGACCTGATGGCTTCCGGAACACATCCACTG
CCTCCTTCAGCAATCATGAGGGGAGGAAATGATATCGTCTCCAGAGTGATAGAT
CTTGACTCAATCTGGGAAAAACCGTCCGACTTGAGAAACTTGGCAACCTGGAAA
TACTTCCAGTCAGTCCAAAAGCAGGTCAACATGTCCTATGACCTCATTATTTGCG
ATGCAGAAGTTACTGACATTGCATCTATCAACCGGATCACCCTGTTAATGTCCGA
TTTTGCATTGTCTATAGATGGACCACTCTATTTGGTCTTCAAAACTTATGGGACTA
TGCTAGTAAATCCAAACTACAAGGCTATTCAACACCTGTCAAGAGCGTTCCCCTC
GGTCACAGGGTTTATCACCCAAGTAACTTCGTCTTTTTCATCTGAGCTCTACCTCC
GATTCTCCAAACGAGGGAAGTTTTTCAGAGATGCTGAGTACTTGACCTCTTCCAC
CCTTCGAGAAATGAGCCTTGTGTTATTCAATTGTAGCAGCCCCAAGAGTGAGATG
CAGAGAGCTCGTTCCTTGAACTATCAGGATCTTGTGAGAGGATTTCCTGAAGAAA
TCATATCAAATCCTTACAATGAGATGATCATAACTCTGATTGACAGTGATGTAGA
ATCTTTTCTAGTCCACAAGATGGTTGATGATCTTGAGTTACAGAGGGGAACTCTG
TCTAAAGTGGCTATCATTATAGCCATCATGATAGTTTTCTCCAACAGAGTCTTCA
ACGTTTCCAAACCCCTAACTGACCCCTCGTTCTATCCACCGTCTGATCCCAAAAT
CCTGAGGCACTTCAACATATGTTGCAGTACTATGATGTATCTATCTACTGCTTTA
GGTGACGTCCCTAGCTTCGCAAGACTTCACGACCTGTATAACAGACCTATAACTT
ATTACTTCAGAAAGCAAGTCATTCGAGGGAACGTTTATCTATCTTGGAGTTGGTC
CAACGACACCTCAGTGTTCAAAAGGGTAGCCTGTAATTCTAGCCTGAGTCTGTCA
```

```
                                  -continued
TCTCACTGGATCAGGTTGATTTACAAGATAGTGAAGACTACCAGACTCGTTGGCA

GCATCAAGGATCTATCCAGAGAAGTGGAAAGACACCTTCATAGGTACAACAGGT

GGATCACCCTAGAGGATATCAGATCTAGATCATCCCTACTAGACTACAGTTGCCT

GTGAACCGGATACTCCTGGAAGCCTGCCCATGCTAAGACTCTTGTGTGATGTATC

TTGAAAAAAACAAGATCCTAAATCTGAACCTTTGGTTGTTTGATTGTTTTTCTCAT

TTTTGTTGTTTATTTGTTAAGCGT.
```

In one embodiment, the nucleic acid comprises the sequence of SEQ ID NO: 18, shown below (VSV vector: Convac V1 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTCCA

AAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAGAGGA

TATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT
```

```
GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG
```

-continued

```
ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCTCGAGCGTACGCCACCATGTTCGTGTTTCTGGTGCTG

CTGCCTCTGGTGAGCTCCCAGTGCGTGAACCTGACCACAAGGACCCAGCTGCCC

CCTGCCTATACCAATTCCTTCACACGGGGCGTGTACTATCCCGACAAGGTGTTCC

GGAGCAGCGTGCTGCACTCCACACAGGATCTGTTTCTGCCTTTCTTTTCTAACGT

GACCTGGTTCCACGCCATCCACGTGAGCGGCACCAATGGCACAAAGCGGTTCGA

CAATCCAGTGCTGCCCTTTAACGATGGCGTGTACTTCGCCTCCACCGAGAAGTCT

AACATCATCAGAGGCTGGATCTTTGGCACCACACTGGACAGCAAGACACAGTCC

CTGCTGATCGTGAACAATGCCACCAACGTGGTCATCAAGGTGTGCGAGTTCCAGT

TTTGTAATGATCCATTCCTGGGCGTGTACTATCACAAGAACAATAAGTCTTGGAT

GGAGAGCGAGTTTCGCGTGTATTCCTCTGCCAACAATTGCACATTTGAGTACGTG

TCCCAGCCCTTCCTGATGGACCTGGAGGGCAAGCAGGGCAATTTCAAGAACCTG

AGGGAGTTCGTGTTTAAGAATATCGATGGCTACTTCAAAATCTACTCCAAGCACA

CCCCAATCAACCTGGTGCGCGACCTGCCACAGGGCTTCTCTGCCCTGGAGCCACT

GGTGGATCTGCCCATCGGCATCAACATCACCCGGTTTCAGACACTGCTGGCCCTG

CACAGAAGCTACCTGACACCAGGCGACAGCTCCTCTGGATGGACCGCAGGAGCA

GCAGCCTACTATGTGGGCTATCTGCAGCCCAGGACCTTCCTGCTGAAGTACAACG

AGAATGGCACCATCACAGACGCCGTGGATTGCGCCCTGGATCCCCTGTCTGAGA

CCAAGTGTACACTGAAGAGCTTTACCGTGGAGAAGGGCATCTATCAGACAAGCA

ATTTCAGGGTGCAGCCTACCGAGTCCATCGTGCGCTTTCCCAATATCACAAACCT

GTGCCCTTTTGGCGAGGTGTTCAACGCAACCCGCTTCGCCAGCGTGTACGCCTGG

AATAGGAAGCGCATCTCCAACTGCGTGGCCGACTATTCTGTGCTGTACAACAGC

GCCTCCTTCTCTACCTTTAAGTGCTATGGCGTGAGCCCCACAAAGCTGAATGACC

TGTGCTTTACCAACGTGTACGCCGATTCCTTCGTGATCAGGGGCGACGAGGTGCG

CCAGATCGCACCAGGACAGACAGGCAAGATCGCAGACTACAATTATAAGCTGCC

TGACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA
```

-continued

```
ATGGCGTGGAGGGCTTTAACTGTTATTTCCCTCTGCAGAGCTACGGCTTCCAGCC

AACAAACGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGACGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAAGGTCTGTGGGCGATACAGGCCTGTCCAAGAATCCAATCGAGCTGGT

AGAGGGCTGGTTCAGCAGTTGGAAAAGCTCCATCGCCTCCTTTTTCTTTATCATC

GGCCTGATCATCGGACTGTTCCTGGTGCTCCGCGTGGGTATCCACCTGTGCATCA

AGCTGAAGCACACCAAGAAAAGACAGATTTATACAGACATCGAGATGAACCGC

CTGGGAAAGTGAGCTAGCCAGATTCTTCATGTTTGGACCAAATCAACTTGTGATA

CCATGCTCAAAGAGGCCTCAATTATATTTGAGTTTTTAATTTTTATGAAAAAAAC

TAACAGCAATCATGGAAGTCCACGATTTTGAGACCGACGAGTTCAATGATTTCA

ATGAAGATGACTATGCCACAAGAGAATTCCTGAATCCCGATGAGCGCATGACGT

ACTTGAATCATGCTGATTACAATTTGAATTCTCCTCTAATTAGTGATGATATTGAC

AATTTGATCAGGAAATTCAATTCTCTTCCGATTCCCTCGATGTGGGATAGTAAGA

ACTGGGATGGAGTTCTTGAGATGTTAACATCATGTCAAGCCAATCCCATCTCAAC

ATCTCAGATGCATAAATGGATGGGAAGTTGGTTAATGTCTGATAATCATGATGCC

AGTCAAGGGTATAGTTTTTTACATGAAGTGGACAAAGAGGCAGAAATAACATTT

GACGTGGTGGAGACCTTCATCCGCGGCTGGGGCAACAAACCAATTGAATACATC

AAAAAGGAAAGATGGACTGACTCATTCAAAATTCTCGCTTATTTGTGTCAAAGT

TTTTGGACTTACACAAGTTGACATTAATCTTAAATGCTGTCTCTGAGGTGGAATT

GCTCAACTTGGCGAGGACTTTCAAAGGCAAAGTCAGAAGAAGTTCTCATGGAAC

GAACATATGCAGGATTAGGGTTCCCAGCTTGGGTCCTACTTTTATTTCAGAAGGA

TGGGCTTACTTCAAGAAACTTGATATTCTAATGGACCGAAACTTTCTGTTAATGG

TCAAAGATGTGATTATAGGGAGGATGCAAACGGTGCTATCCATGGTATGTAGAA

TAGACAACCTGTTCTCAGAGCAAGACATCTTCTCCCTTCTAAATATCTACAGAAT

TGGAGATAAAATTGTGGAGAGGCAGGGAAATTTTTCTTATGACTTGATTAAAAT

GGTGGAACCGATATGCAACTTGAAGCTGATGAAATTAGCAAGAGAATCAAGGCC

TTTAGTCCCACAATTCCCTCATTTTGAAAATCATATCAAGACTTCTGTTGATGAA

GGGGCAAAAATTGACCGAGGTATAAGATTCCTCCATGATCAGATAATGAGTGTG

AAAACAGTGGATCTCACACTGGTGATTTATGGATCGTTCAGACATTGGGTCATC

CTTTTATAGATTATTACACTGGACTAGAAAAATTACATTCCCAAGTAACCATGAA

GAAAGATATTGATGTGTCATATGCAAAAGCACTTGCAAGTGATTTAGCTCGGATT

GTTCTATTTCAACAGTTCAATGATCATAAAAAGTGGTTCGTGAATGGAGACTTGC

TCCCTCATGATCATCCCTTTAAAAGTCATGTTAAAGAAAATACATGGCCCACAGC
```

```
TGCTCAAGTTCAAGATTTTGGAGATAAATGGCATGAACTTCCGCTGATTAAATGT

TTTGAAATACCCGACTTACTAGACCCATCGATAATATACTCTGACAAAAGTCATT

CAATGAATAGGTCAGAGGTGTTGAAACATGTCCGAATGAATCCGAACACTCCTA

TCCCTAGTAAAAAGGTGTTGCAGACTATGTTGGACACAAAGGCTACCAATTGGA

AAGAATTTCTTAAAGAGATTGATGAGAAGGGCTTAGATGATGATGATCTAATTA

TTGGTCTTAAAGGAAAGGAGAGGGAACTGAAGTTGGCAGGTAGATTTTTCTCCC

TAATGTCTTGGAAATTGCGAGAATACTTTGTAATTACCGAATATTTGATAAAGAC

TCATTTCGTCCCTATGTTTAAAGGCCTGACAATGGCGGACGATCTAACTGCAGTC

ATTAAAAAGATGTTAGATTCCTCATCCGGCCAAGGATTGAAGTCATATGAGGCA

ATTTGCATAGCCAATCACATTGATTACGAAAAATGGAATAACCACCAAAGGAAG

TTATCAAACGGCCCAGTGTTCCGAGTTATGGGCCAGTTCTTAGGTTATCCATCCT

TAATCGAGAGAACTCATGAATTTTTTGAGAAAAGTCTTATATACTACAATGGAAG

ACCAGACTTGATGCGTGTTCACAACAACACACTGATCAATTCAACCTCCCAACG

AGTTTGTTGGCAAGGACAAGAGGGTGGACTGGAAGGTCTACGGCAAAAAGGAT

GGACTATCCTCAATCTACTGGTTATTCAAAGAGAGGCTAAAATCAGAAACACTG

CTGTCAAAGTCTTGGCACAAGGTGATAATCAAGTTATTTGCACACAGTATAAAAC

GAAGAAATCGAGAAACGTTGTAGAATTACAGGGTGCTCTCAATCAAATGGTTTC

TAATAATGAGAAAATTATGACTGCAATCAAAATAGGGACAGGGAAGTTAGGACT

TTTGATAAATGACGATGAGACTATGCAATCTGCAGATTACTTGAATTATGGAAAA

ATACCGATTTTCCGTGGAGTGATTAGAGGGTTAGAGACCAAGAGATGGTCACGA

GTGACTTGTGTCACCAATGACCAAATACCCACTTGTGCTAATATAATGAGCTCAG

TTTCCACAAATGCTCTCACCGTAGCTCATTTTGCTGAGAACCCAATCAATGCCAT

GATACAGTACAATTATTTTGGGACATTTGCTAGACTCTTGTTGATGATGCATGAT

CCTGCTCTTCGTCAATCATTGTATGAAGTTCAAGATAAGATACCGGGCTTGCACA

GTTCTACTTTCAAATACGCCATGTTGTATTTGGACCCTTCCATTGGAGGAGTGTC

GGGCATGTCTTTGTCCAGGTTTTTGATTAGAGCCTTCCCAGATCCCGTAACAGAA

AGTCTCTCATTCTGGAGATTCATCCATGTACATGCTCGAAGTGAGCATCTGAAGG

AGATGAGTGCAGTATTTGGAAACCCCGAGATAGCCAAGTTTCGAATAACTCACA

TAGACAAGCTAGTAGAAGATCCAACCTCTCTGAACATCGCTATGGGAATGAGTC

CAGCGAACTTGTTAAAGACTGAGGTTAAAAAATGCTTAATCGAATCAAGACAAA

CCATCAGGAACCAGGTGATTAAGGATGCAACCATATATTTGTATCATGAAGAGG

ATCGGCTCAGAAGTTTCTTATGGTCAATAAATCCTCTGTTCCCTAGATTTTTAAGT

GAATTCAAATCAGGCACTTTTTTGGGAGTCGCAGACGGGCTCATCAGTCTATTTC

AAAATTCTCGTACTATTCGGAACTCCTTTAAGAAAAAGTATCATAGGGAATTGGA

TGATTTGATTGTGAGGAGTGAGGTATCCTCTTTGACACATTTAGGGAAACTTCAT

TTGAGAAGGGGATCATGTAAAATGTGGACATGTTCAGCTACTCATGCTGACACA

TTAAGATACAAATCCTGGGGCCGTACAGTTATTGGGACAACTGTACCCCATCCAT

TAGAAATGTTGGGTCCACAACATCGAAAAGAGACTCCTTGTGCACCATGTAACA

CATCAGGGTTCAATTATGTTTCTGTGCATTGTCCAGACGGGATCCATGACGTCTT

TAGTTCACGGGGACCATTGCCTGCTTATCTAGGGTCTAAAACATCTGAATCTACA
```

-continued
```
TCTATTTTGCAGCCTTGGGAAAGGGAAAGCAAAGTCCCACTGATTAAAAGAGCT

ACACGTCTTAGAGATGCTATCTCTTGGTTTGTTGAACCCGACTCTAAACTAGCAA

TGACTATACTTTCTAACATCCACTCTTTAACAGGCGAAGAATGGACCAAAAGGC

AGCATGGGTTCAAAAGAACAGGGTCTGCCCTTCATAGGTTTTCGACATCTCGGAT

GAGCCATGGTGGGTTCGCATCTCAGAGCACTGCAGCATTGACCAGGTTGATGGC

AACTACAGACACCATGAGGGATCTGGGAGATCAGAATTTCGACTTTTTATTCCAA

GCAACGTTGCTCTATGCTCAAATTACCACCACTGTTGCAAGAGACGGATGGATCA

CCAGTTGTACAGATCATTATCATATTGCCTGTAAGTCCTGTTTGAGACCCATAGA

AGAGATCACCCTGGACTCAAGTATGGACTACACGCCCCCAGATGTATCCCATGT

GCTGAAGACATGGAGGAATGGGGAAGGTTCGTGGGGACAAGAGATAAAACAGA

TCTATCCTTTAGAAGGGAATTGGAAGAATTTAGCACCTGCTGAGCAATCCTATCA

AGTCGGCAGATGTATAGGTTTTCTATATGGAGACTTGGCGTATAGAAAATCTACT

CATGCCGAGGACAGTTCTCTATTTCCTCTATCTATACAAGGTCGTATTAGAGGTC

GAGGTTTCTTAAAAGGGTTGCTAGACGGATTAATGAGAGCAAGTTGCTGCCAAG

TAATACACCGGAGAAGTCTGGCTCATTTGAAGAGGCCGGCCAACGCAGTGTACG

GAGGTTTGATTTACTTGATTGATAAATTGAGTGTATCACCTCCATTCCTTTCTCTT

ACTAGATCAGGACCTATTAGAGACGAATTAGAAACGATTCCCCACAAGATCCCA

ACCTCCTATCCGACAAGCAACCGTGATATGGGGGTGATTGTCAGAAATTACTTCA

AATACCAATGCCGTCTAATTGAAAAGGGAAAATACAGATCACATTATTCACAAT

TATGGTTATTCTCAGATGTCTTATCCATAGACTTCATTGGACCATTCTCTATTTCC

ACCACCCTCTTGCAAATCCTATACAAGCCATTTTTATCTGGGAAAGATAAGAATG

AGTTGAGAGAGCTGGCAAATCTTTCTTCATTGCTAAGATCAGGAGAGGGGTGGG

AAGACATACATGTGAAATTCTTCACCAAGGACATATTATTGTGTCCAGAGGAAA

TCAGACATGCTTGCAAGTTCGGGATTGCTAAGGATAATAATAAAGACATGAGCT

ATCCCCCTTGGGGAAGGGAATCCAGAGGGACAATTACAACAATCCCTGTTTATT

ATACGACCACCCCTTACCCAAAGATGCTAGAGATGCCTCCAAGAATCCAAAATC

CCCTGCTGTCCGGAATCAGGTTGGGCCAATTACCAACTGGCGCTCATTATAAAAT

TCGGAGTATATTACATGGAATGGGAATCCATTACAGGGACTTCTTGAGTTGTGGA

GACGGCTCCGGAGGGATGACTGCTGCATTACTACGAGAAAATGTGCATAGCAGA

GGAATATTCAATAGTCTGTTAGAATTATCAGGGTCAGTCATGCGAGGCGCCTCTC

CTGAGCCCCCCAGTGCCCTAGAAACTTTAGGAGGAGATAAATCGAGATGTGTAA

ATGGTGAAACATGTTGGGAATATCCATCTGACTTATGTGACCCAAGGACTTGGG

ACTATTTCCTCCGACTCAAAGCAGGCTTGGGGCTTCAAATTGATTTAATTGTAAT

GGATATGGAAGTTCGGGATTCTTCTACTAGCCTGAAAATTGAGACGAATGTTAG

AAATTATGTGCACCGGATTTTGGATGAGCAAGGAGTTTAATCTACAAGACTTAT

GGAACATATATTTGTGAGAGCGAAAAGAATGCAGTAACAATCCTTGGTCCCATG

TTCAAGACGGTCGACTTAGTTCAAACAGAATTTAGTAGTTCTCAAACGTCTGAAG

TATATATGGTATGTAAAGGTTTGAAGAAATTAATCGATGAACCCAATCCCGATTG

GTCTTCCATCAATGAATCCTGGAAAAACCTGTACGCATTCCAGTCATCAGAACAG

GAATTTGCCAGAGCAAAGAAGGTTAGTACATACTTTACCTTGACAGGTATTCCCT

CCCAATTCATTCCTGATCCTTTTGTAAACATTGAGACTATGCTACAAATATTCGG
```

-continued

```
AGTACCCACGGGTGTGTCTCATGCGGCTGCCTTAAAATCATCTGATAGACCTGCA

GATTTATTGACCATTAGCCTTTTTTATATGGCGATTATATCGTATTATAACATCAA

TCATATCAGAGTAGGACCGATACCTCCGAACCCCCCATCAGATGGAATTGCACA

AAATGTGGGGATCGCTATAACTGGTATAAGCTTTTGGCTGAGTTTGATGGAGAA

AGACATTCCACTATATCAACAGTGTTTAGCAGTTATCCAGCAATCATTCCCGATT

AGGTGGGAGGCTGTTTCAGTAAAAGGAGGATACAAGCAGAAGTGGAGTACTAG

AGGTGATGGGCTCCCAAAAGATACCCGAACTTCAGACTCCTTGGCCCCAATCGG

GAACTGGATCAGATCTCTGGAATTGGTCCGAAACCAAGTTCGTCTAAATCCATTC

AATGAGATCTTGTTCAATCAGCTATGTCGTACAGTGGATAATCATTTGAAATGGT

CAAATTTGCGAAGAAACACAGGAATGATTGAATGGATCAATAGACGAATTTCAA

AAGAAGACCGGTCTATACTGATGTTGAAGAGTGACCTACACGAGGAAAACTCTT

GGAGAGATTAAAAAATCATGAGGAGACTCCAAACTTTAAGTATGAAAAAAACTT

TGATCCTTAAGACCCTCTTGTGGTTTTATTTTTATCTGGTTTTGTGGTCTTCGT.
```

In another embodiment, the nucleic acid comprises the sequence of SEQ ID NO: 19, shown below (VSV vector: Convac V1 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTCCAA

AACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTGCAGTG

GACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT
```

-continued

```
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
```

-continued

```
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCCACCATGTTCGTGTTTCTGGTGCTGCTGCCTC
TGGTGAGCTCCCAGTGCGTGAACTTCACCACAAGGACCCAGCTGCCCCCTGCCTA
TACCAATTCCTTCACACGGGGCGTGTACTATCCCGACAAGGTGTTCCGGAGCAGC
GTGCTGCACTCCACACAGGATCTGTTTCTGCCTTTCTTTTCTAACGTGACCTGGTT
CCACGCCATCCACGTGAGCGGCACCAATGGCACAAAGCGGTTCGCCAATCCAGT
GCTGCCCTTTAACGATGGCGTGTACTTCGCCTCCACCGAGAAGTCTAACATCATC
AGAGGCTGGATCTTTGGCACCACACTGGACAGCAAGACACAGTCCCTGCTGATC
GTGAACAATGCCACCAACGTGGTCATCAAGGTGTGCGAGTTCCAGTTTTGTAATG
ATCCATTCCTGGGCGTGTACTATCACAAGAACAATAAGTCTTGGATGGAGAGCG
AGTTTCGCGTGTATTCCTCTGCCAACAATTGCACATTTGAGTACGTGTCCCAGCC
CTTCCTGATGGACCTGGAGGGCAAGCAGGGCAATTTCAAGAACCTGAGGGAGTT
CGTGTTTAAGAATATCGATGGCTACTTCAAAATCTACTCCAAGCACACCCCAATC
AACCTGGTGCGCGGCCTGCCACAGGGCTTCTCTGCCCTGGAGCCACTGGTGGATC
TGCCCATCGGCATCAACATCACCCGGTTTCAGACACTGCTGGCCCTGCACAGAA
GCTACCTGACACCAGGCGACAGCTCCTCTGGATGGACCGCAGGAGCAGCAGCCT
ACTATGTGGGCTATCTGCAGCCCAGGACCTTCCTGCTGAAGTACAACGAGAATG
GCACCATCACAGACGCCGTGGATTGCGCCCTGGATCCCCTGTCTGAGACCAAGT
GTACACTGAAGAGCTTTACCGTGGAGAAGGGCATCTATCAGACAAGCAATTTCA
GGGTGCAGCCTACCGAGTCCATCGTGCGCTTTCCCAATATCACAAACCTGTGCCC
TTTTGGCGAGGTGTTCAACGCAACCCGCTTCGCCAGCGTGTACGCCTGGAATAGG
```

-continued

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAA

GTGAGCTAGCCAGATTCTTCATGTTTGGACCAAATCAACTTGTGATACCATGCTC

AAAGAGGCCTCAATTATATTTGAGTTTTTAATTTTTATGAAAAAAACTAACAGCA

ATCATGGAAGTCCACGATTTTGAGACCGACGAGTTCAATGATTTCAATGAAGAT

GACTATGCCACAAGAGAATTCCTGAATCCCGATGAGCGCATGACGTACTTGAAT

CATGCTGATTACAATTTGAATTCTCCTCTAATTAGTGATGATATTGACAATTTGAT

CAGGAAATTCAATTCTCTTCCGATTCCCTCGATGTGGGATAGTAAGAACTGGGAT

GGAGTTCTTGAGATGTTAACATCATGTCAAGCCAATCCCATCTCAACATCTCAGA

TGCATAAATGGATGGGAAGTTGGTTAATGTCTGATAATCATGATGCCAGTCAAG

GGTATAGTTTTTTACATGAAGTGGACAAAGAGGCAGAAATAACATTTGACGTGG

TGGAGACCTTCATCCGCGGCTGGGGCAACAAACCAATTGAATACATCAAAAAGG

AAAGATGGACTGACTCATTCAAAATTCTCGCTTATTTGTGTCAAAAGTTTTTGGA

CTTACACAAGTTGACATTAATCTTAAATGCTGTCTCTGAGGTGGAATTGCTCAAC

TTGGCGAGGACTTTCAAAGGCAAAGTCAGAAGAAGTTCTCATGGAACGAACATA

TGCAGGATTAGGGTTCCCAGCTTGGGTCCTACTTTTATTTCAGAAGGATGGGCTT

ACTTCAAGAAACTTGATATTCTAATGGACCGAAACTTTCTGTTAATGGTCAAAGA

TGTGATTATAGGGAGGATGCAAACGGTGCTATCCATGGTATGTAGAATAGACAA

CCTGTTCTCAGAGCAAGACATCTTCTCCCTTCTAAATATCTACAGAATTGGAGAT

AAAATTGTGGAGAGGCAGGGAAATTTTTCTTATGACTTGATTAAAATGGTGGAA

-continued

```
CCGATATGCAACTTGAAGCTGATGAAATTAGCAAGAGAATCAAGGCCTTTAGTC
CCACAATTCCCTCATTTTGAAAATCATATCAAGACTTCTGTTGATGAAGGGGCAA
AAATTGACCGAGGTATAAGATTCCTCCATGATCAGATAATGAGTGTGAAAACAG
TGGATCTCACACTGGTGATTTATGGATCGTTCAGACATTGGGGTCATCCTTTTAT
AGATTATTACACTGGACTAGAAAAATTACATTCCCAAGTAACCATGAAGAAAGA
TATTGATGTGTCATATGCAAAAGCACTTGCAAGTGATTTAGCTCGGATTGTTCTA
TTTCAACAGTTCAATGATCATAAAAAGTGGTTCGTGAATGGAGACTTGCTCCCTC
ATGATCATCCCTTTAAAAGTCATGTTAAAGAAAATACATGGCCCACAGCTGCTCA
AGTTCAAGATTTTGGAGATAAATGGCATGAACTTCCGCTGATTAAATGTTTTGAA
ATACCCGACTTACTAGACCCATCGATAATATACTCTGACAAAAGTCATTCAATGA
ATAGGTCAGAGGTGTTGAAACATGTCCGAATGAATCCGAACACTCCTATCCCTA
GTAAAAAGGTGTTGCAGACTATGTTGGACACAAAGGCTACCAATTGGAAAGAAT
TTCTTAAAGAGATTGATGAGAAGGGCTTAGATGATGATGATCTAATTATTGGTCT
TAAAGGAAAGGAGAGGGAACTGAAGTTGGCAGGTAGATTTTTCTCCCTAATGTC
TTGGAAATTGCGAGAATACTTTGTAATTACCGAATATTTGATAAAGACTCATTTC
GTCCCTATGTTTAAAGGCCTGACAATGGCGGACGATCTAACTGCAGTCATTAAAA
AGATGTTAGATTCCTCATCCGGCCAAGGATTGAAGTCATATGAGGCAATTTGCAT
AGCCAATCACATTGATTACGAAAAATGGAATAACCACCAAAGGAAGTTATCAAA
CGGCCCAGTGTTCCGAGTTATGGGCCAGTTCTTAGGTTATCCATCCTTAATCGAG
AGAACTCATGAATTTTTTGAGAAAAGTCTTATATACTACAATGGAAGACCAGACT
TGATGCGTGTTCACAACAACACACTGATCAATTCAACCTCCCAACGAGTTTGTTG
GCAAGGACAAGAGGGTGGACTGGAAGGTCTACGGCAAAAAGGATGGACTATCC
TCAATCTACTGGTTATTCAAAGAGAGGCTAAAATCAGAAACACTGCTGTCAAAG
TCTTGGCACAAGGTGATAATCAAGTTATTTGCACACAGTATAAAACGAAGAAAT
CGAGAAACGTTGTAGAATTACAGGGTGCTCTCAATCAAATGGTTTCTAATAATGA
GAAAATTATGACTGCAATCAAAATAGGGACAGGGAAGTTAGGACTTTTGATAAA
TGACGATGAGACTATGCAATCTGCAGATTACTTGAATTATGGAAAAATACCGATT
TTCCGTGGAGTGATTAGAGGGTTAGAGACCAAGAGATGGTCACGAGTGACTTGT
GTCACCAATGACCAAATACCCACTTGTGCTAATATAATGAGCTCAGTTTCCACAA
ATGCTCTCACCGTAGCTCATTTTGCTGAGAACCCAATCAATGCCATGATACAGTA
CAATTATTTTGGGACATTTGCTAGACTCTTGTTGATGATGCATGATCCTGCTCTTC
GTCAATCATTGTATGAAGTTCAAGATAAGATACCGGGCTTGCACAGTTCTACTTT
CAAATACGCCATGTTGTATTTGGACCCTTCCATTGGAGGAGTGTCGGGCATGTCT
TTGTCCAGGTTTTTGATTAGAGCCTTCCCAGATCCCGTAACAGAAAGTCTCTCAT
TCTGGAGATTCATCCATGTACATGCTCGAAGTGAGCATCTGAAGGAGATGAGTG
CAGTATTTGGAAACCCCGAGATAGCCAAGTTTCGAATAACTCACATAGACAAGC
TAGTAGAAGATCCAACCTCTCTGAACATCGCTATGGGAATGAGTCCAGCGAACT
TGTTAAAGACTGAGGTTAAAAAATGCTTAATCGAATCAAGACAAACCATCAGGA
ACCAGGTGATTAAGGATGCAACCATATATTTGTATCATGAAGAGGATCGGCTCA
GAAGTTTCTTATGGTCAATAAATCCTCTGTTCCCTAGATTTTTAAGTGAATTCAAA
TCAGGCACTTTTTTGGGAGTCGCAGACGGGCTCATCAGTCTATTTCAAAATTCTC
```

-continued

```
GTACTATTCGGAACTCCTTTAAGAAAAAGTATCATAGGGAATTGGATGATTTGAT

TGTGAGGAGTGAGGTATCCTCTTTGACACATTTAGGGAAACTTCATTTGAGAAGG

GGATCATGTAAAATGTGGACATGTTCAGCTACTCATGCTGACACATTAAGATACA

AATCCTGGGGCCGTACAGTTATTGGGACAACTGTACCCCATCCATTAGAAATGTT

GGGTCCACAACATCGAAAAGAGACTCCTTGTGCACCATGTAACACATCAGGGTT

CAATTATGTTTCTGTGCATTGTCCAGACGGGATCCATGACGTCTTTAGTTCACGG

GGACCATTGCCTGCTTATCTAGGGTCTAAAACATCTGAATCTACATCTATTTTGC

AGCCTTGGGAAAGGGAAAGCAAAGTCCCACTGATTAAAAGAGCTACACGTCTTA

GAGATGCTATCTCTTGGTTTGTTGAACCCGACTCTAAACTAGCAATGACTATACT

TTCTAACATCCACTCTTTAACAGGCGAAGAATGGACCAAAAGGCAGCATGGGTT

CAAAAGAACAGGGTCTGCCCTTCATAGGTTTTCGACATCTCGGATGAGCCATGGT

GGGTTCGCATCTCAGAGCACTGCAGCATTGACCAGGTTGATGGCAACTACAGAC

ACCATGAGGGATCTGGGAGATCAGAATTTCGACTTTTTATTCCAAGCAACGTTGC

TCTATGCTCAAATTACCACCACTGTTGCAAGAGACGGATGGATCACCAGTTGTAC

AGATCATTATCATATTGCCTGTAAGTCCTGTTTGAGACCCATAGAAGAGATCACC

CTGGACTCAAGTATGGACTACACGCCCCCAGATGTATCCCATGTGCTGAAGACA

TGGAGGAATGGGGAAGGTTCGTGGGGACAAGAGATAAAACAGATCTATCCTTTA

GAAGGGAATTGGAAGAATTTAGCACCTGCTGAGCAATCCTATCAAGTCGGCAGA

TGTATAGGTTTTCTATATGGAGACTTGGCGTATAGAAAATCTACTCATGCCGAGG

ACAGTTCTCTATTTCCTCTATCTATACAAGGTCGTATTAGAGGTCGAGGTTTCTTA

AAAGGGTTGCTAGACGGATTAATGAGAGCAAGTTGCTGCCAAGTAATACACCGG

AGAAGTCTGGCTCATTTGAAGAGGCCGGCCAACGCAGTGTACGGAGGTTTGATT

TACTTGATTGATAAATTGAGTGTATCACCTCCATTCCTTTCTCTTACTAGATCAGG

ACCTATTAGAGACGAATTAGAAACGATTCCCCACAAGATCCCAACCTCCTATCC

GACAAGCAACCGTGATATGGGGGTGATTGTCAGAAATTACTTCAAATACCAATG

CCGTCTAATTGAAAAGGGAAAATACAGATCACATTATTCACAATTATGGTTATTC

TCAGATGTCTTATCCATAGACTTCATTGGACCATTCTCTATTTCCACCACCCTCTT

GCAAATCCTATACAAGCCATTTTTATCTGGGAAAGATAAGAATGAGTTGAGAGA

GCTGGCAAATCTTTCTTCATTGCTAAGATCAGGAGAGGGGTGGGAAGACATACA

TGTGAAATTCTTCACCAAGGACATATTATTGTGTCCAGAGGAAATCAGACATGCT

TGCAAGTTCGGGATTGCTAAGGATAATAATAAAGACATGAGCTATCCCCCTTGG

GGAAGGGAATCCAGAGGGACAATTACAACAATCCCTGTTTATTATACGACCACC

CCTTACCCAAAGATGCTAGAGATGCCTCCAAGAATCCAAAATCCCCTGCTGTCCG

GAATCAGGTTGGGCCAATTACCAACTGGCGCTCATTATAAAATTCGGAGTATATT

ACATGGAATGGGAATCCATTACAGGGACTTCTTGAGTTGTGGAGACGGCTCCGG

AGGGATGACTGCTGCATTACTACGAGAAAATGTGCATAGCAGAGGAATATTCAA

TAGTCTGTTAGAATTATCAGGGTCAGTCATGCGAGGCGCCTCTCCTGAGCCCCCC

AGTGCCCTAGAAACTTTAGGAGGAGATAAATCGAGATGTGTAAATGGTGAAACA

TGTTGGGAATATCCATCTGACTTATGTGACCCAAGGACTTGGGACTATTTCCTCC

GACTCAAAGCAGGCTTGGGGCTTCAAATTGATTTAATTGTAATGGATATGGAAGT
```

-continued

```
TCGGGATTCTTCTACTAGCCTGAAAATTGAGACGAATGTTAGAAATTATGTGCAC

CGGATTTTGGATGAGCAAGGAGTTTTAATCTACAAGACTTATGGAACATATATTT

GTGAGAGCGAAAAGAATGCAGTAACAATCCTTGGTCCCATGTTCAAGACGGTCG

ACTTAGTTCAAACAGAATTTAGTAGTTCTCAAACGTCTGAAGTATATATGGTATG

TAAAGGTTTGAAGAAATTAATCGATGAACCCAATCCCGATTGGTCTTCCATCAAT

GAATCCTGGAAAAACCTGTACGCATTCCAGTCATCAGAACAGGAATTTGCCAGA

GCAAAGAAGGTTAGTACATACTTTACCTTGACAGGTATTCCCTCCCAATTCATTC

CTGATCCTTTTGTAAACATTGAGACTATGCTACAAATATTCGGAGTACCCACGGG

TGTGTCTCATGCGGCTGCCTTAAAATCATCTGATAGACCTGCAGATTTATTGACC

ATTAGCCTTTTTTATATGGCGATTATATCGTATTATAACATCAATCATATCAGAGT

AGGACCGATACCTCCGAACCCCCCATCAGATGGAATTGCACAAAATGTGGGGAT

CGCTATAACTGGTATAAGCTTTTGGCTGAGTTTGATGGAGAAAGACATTCCACTA

TATCAACAGTGTTTAGCAGTTATCCAGCAATCATTCCCGATTAGGTGGGAGGCTG

TTTCAGTAAAAGGAGGATACAAGCAGAAGTGGAGTACTAGAGGTGATGGGCTCC

CAAAAGATACCCGAACTTCAGACTCCTTGGCCCCAATCGGGAACTGGATCAGAT

CTCTGGAATTGGTCCGAAACCAAGTTCGTCTAAATCCATTCAATGAGATCTTGTT

CAATCAGCTATGTCGTACAGTGGATAATCATTTGAAATGGTCAAATTTGCGAAGA

AACACAGGAATGATTGAATGGATCAATAGACGAATTTCAAAAGAAGACCGGTCT

ATACTGATGTTGAAGAGTGACCTACACGAGGAAAACTCTTGGAGAGATTAAAAA

ATCATGAGGAGACTCCAAACTTTAAGTATGAAAAAAACTTTGATCCTTAAGACC

CTCTTGTGGTTTTTATTTTTTATCTGGTTTTGTGGTCTTCGT.
```

35

In some embodiments, the nucleic acid comprises the sequence of SEQ ID NO: 20, shown below (VSV vector: Convac V2 China):

```
ACGAAGACAAACAAACCATTATTATCATTAAAAGGCTCAGGAGAAACTTTAACAGTAAT-
CAA

AATGTCTGTTACAGTCAAGAGAATCATTGACAACACAGTCATAGTTCCAA

AACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC
```

-continued

```
AAGGCCGATTCATACATGCCTTATTTGATCGACTTTGGATTGTCTTCTAAGTCTCC
ATATTCTTCCGTCAAAAACCCTGCCTTCCACTTCTGGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
```

-continued
```
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCTCGAGCGTACGCCACCATGTTCGTGTTTCTGGTGCTG
CTGCCTCTGGTGAGCTCCCAGTGCGTGAACCTGACCACAAGGACCCAGCTGCCC
CCTGCCTATACCAATTCCTTCACACGGGGCGTGTACTATCCCGACAAGGTGTTCC
GGAGCAGCGTGCTGCACTCCACACAGGATCTGTTTCTGCCTTTCTTTTCTAACGT
GACCTGGTTCCACGCCATCCACGTGAGCGGCACCAATGGCACAAAGCGGTTCGA
CAATCCAGTGCTGCCCTTTAACGATGGCGTGTACTTCGCCTCCACCGAGAAGTCT
AACATCATCAGAGGCTGGATCTTTGGCACCACACTGGACAGCAAGACACAGTCC
CTGCTGATCGTGAACAATGCCACCAACGTGGTCATCAAGGTGTGCGAGTTCCAGT
TTTGTAATGATCCATTCCTGGGCGTGTACTATCACAAGAACAATAAGTCTTGGAT
GGAGAGCGAGTTTCGCGTGTATTCCTCTGCCAACAATTGCACATTTGAGTACGTG
TCCCAGCCCTTCCTGATGGACCTGGAGGGCAAGCAGGGCAATTTCAAGAACCTG
AGGGAGTTCGTGTTTAAGAATATCGATGGCTACTTCAAAATCTACTCCAAGCACA
```

CCCCAATCAACCTGGTGCGCGACCTGCCACAGGGCTTCTCTGCCCTGGAGCCACT

GGTGGATCTGCCCATCGGCATCAACATCACCCGGTTTCAGACACTGCTGGCCCTG

CACAGAAGCTACCTGACACCAGGCGACAGCTCCTCTGGATGGACCGCAGGAGCA

GCAGCCTACTATGTGGGCTATCTGCAGCCCAGGACCTTCCTGCTGAAGTACAACG

AGAATGGCACCATCACAGACGCCGTGGATTGCGCCCTGGATCCCCTGTCTGAGA

CCAAGTGTACACTGAAGAGCTTTACCGTGGAGAAGGGCATCTATCAGACAAGCA

ATTTCAGGGTGCAGCCTACCGAGTCCATCGTGCGCTTTCCCAATATCACAAACCT

GTGCCCTTTTGGCGAGGTGTTCAACGCAACCCGCTTCGCCAGCGTGTACGCCTGG

AATAGGAAGCGCATCTCCAACTGCGTGGCCGACTATTCTGTGCTGTACAACAGC

GCCTCCTTCTCTACCTTTAAGTGCTATGGCGTGAGCCCCACAAAGCTGAATGACC

TGTGCTTTACCAACGTGTACGCCGATTCCTTCGTGATCAGGGGCGACGAGGTGCG

CCAGATCGCACCAGGACAGACAGGCAAGATCGCAGACTACAATTATAAGCTGCC

TGACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA

ATGGCGTGGAGGGCTTTAACTGTTATTTCCCTCTGCAGAGCTACGGCTTCCAGCC

AACAAACGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGACGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAAGGTCTGTGGGAGATGAGGCCGAAGACTTTGTGGAAGTCCACCTGCC

TGATGTGCATAACCAGGTGTCTGGCGTCGACCTGGGACTGCAAATTGGGGCAA

GTACGTGCTGCTGAGTGCTGGAGCACTGACTGCCCTGATGCTGATCATTTTCCTG

ATGACCTGCTGTCGGCGCGTGAACAGAAGTGAGCCCACTCAGCACAATCTGCGA

GGAACCGGGAGAGAAGTGTCAGTCACACCTCAGAGCGGGAAAATCATTAGTAGT

TGGGAATCACATAAAAGCGGGGGCGAGACCAGGCTGTGAGCTAGCCAGATTCTT

CATGTTTGGACCAAATCAACTTGTGATACCATGCTCAAAGAGGCCTCAATTATAT

TTGAGTTTTTAATTTTTATGAAAAAAACTAACAGCAATCATGGAAGTCCACGATT

TTGAGACCGACGAGTTCAATGATTTCAATGAAGATGACTATGCCACAAGAGAAT

TCCTGAATCCCGATGAGCGCATGACGTACTTGAATCATGCTGATTACAATTTGAA

TTCTCCTCTAATTAGTGATGATATTGACAATTTGATCAGGAAATTCAATTCTCTTC

CGATTCCCTCGATGTGGGATAGTAAGAACTGGGATGGAGTTCTTGAGATGTTAAC

ATCATGTCAAGCCAATCCCATCTCAACATCTCAGATGCATAAATGGATGGGAAG

TTGGTTAATGTCTGATAATCATGATGCCAGTCAAGGGTATAGTTTTTTACATGAA

-continued

```
GTGGACAAAGAGGCAGAAATAACATTTGACGTGGTGGAGACCTTCATCCGCGGC

TGGGGCAACAAACCAATTGAATACATCAAAAAGGAAAGATGGACTGACTCATTC

AAAATTCTCGCTTATTTGTGTCAAAAGTTTTTGGACTTACACAAGTTGACATTAA

TCTTAAATGCTGTCTCTGAGGTGGAATTGCTCAACTTGGCGAGGACTTTCAAAGG

CAAAGTCAGAAGAAGTTCTCATGGAACGAACATATGCAGGATTAGGGTTCCCAG

CTTGGGTCCTACTTTTATTTCAGAAGGATGGGCTTACTTCAAGAAACTTGATATT

CTAATGGACCGAAACTTTCTGTTAATGGTCAAAGATGTGATTATAGGGAGGATG

CAAACGGTGCTATCCATGGTATGTAGAATAGACAACCTGTTCTCAGAGCAAGAC

ATCTTCTCCCTTCTAAATATCTACAGAATTGGAGATAAAATTGTGGAGAGGCAGG

GAAATTTTTCTTATGACTTGATTAAAATGGTGGAACCGATATGCAACTTGAAGCT

GATGAAATTAGCAAGAGAATCAAGGCCTTTAGTCCCACAATTCCCTCATTTTGAA

AATCATATCAAGACTTCTGTTGATGAAGGGGCAAAAATTGACCGAGGTATAAGA

TTCCTCCATGATCAGATAATGAGTGTGAAAACAGTGGATCTCACACTGGTGATTT

ATGGATCGTTCAGACATTGGGGTCATCCTTTTATAGATTATTACACTGGACTAGA

AAAATTACATTCCCAAGTAACCATGAAGAAAGATATTGATGTGTCATATGCAAA

AGCACTTGCAAGTGATTTAGCTCGGATTGTTCTATTTCAACAGTTCAATGATCAT

AAAAAGTGGTTCGTGAATGGAGACTTGCTCCCTCATGATCATCCCTTTAAAAGTC

ATGTTAAAGAAAATACATGGCCCACAGCTGCTCAAGTTCAAGATTTTGGAGATA

AATGGCATGAACTTCCGCTGATTAAATGTTTTGAAATACCCGACTTACTAGACCC

ATCGATAATATACTCTGACAAAAGTCATTCAATGAATAGGTCAGAGGTGTTGAA

ACATGTCCGAATGAATCCGAACACTCCTATCCCTAGTAAAAAGGTGTTGCAGACT

ATGTTGGACACAAAGGCTACCAATTGGAAAGAATTTCTTAAAGAGATTGATGAG

AAGGGCTTAGATGATGATGATCTAATTATTGGTCTTAAAGGAAAGGAGAGGGAA

CTGAAGTTGGCAGGTAGATTTTTCTCCCTAATGTCTTGGAAATTGCGAGAATACT

TTGTAATTACCGAATATTTGATAAAGACTCATTTCGTCCCTATGTTTAAAGGCCT

GACAATGGCGGACGATCTAACTGCAGTCATTAAAAAGATGTTAGATTCCTCATCC

GGCCAAGGATTGAAGTCATATGAGGCAATTTGCATAGCCAATCACATTGATTAC

GAAAAATGGAATAACCACCAAAGGAAGTTATCAAACGGCCCAGTGTTCCGAGTT

ATGGGCCAGTTCTTAGGTTATCCATCCTTAATCGAGAGAACTCATGAATTTTTG

AGAAAAGTCTTATATACTACAATGGAAGACCAGACTTGATGCGTGTTCACAACA

ACACACTGATCAATTCAACCTCCCAACGAGTTTGTTGGCAAGGACAAGAGGGTG

GACTGGAAGGTCTACGGCAAAAAGGATGGACTATCCTCAATCTACTGGTTATTC

AAAGAGAGGCTAAAATCAGAAACACTGCTGTCAAAGTCTTGGCACAAGGTGATA

ATCAAGTTATTTGCACACAGTATAAAACGAAGAAATCGAGAAACGTTGTAGAAT

TACAGGGTGCTCTCAATCAAATGGTTTCTAATAATGAGAAAATTATGACTGCAAT

CAAAATAGGGACAGGGAAGTTAGGACTTTTGATAAATGACGATGAGACTATGCA

ATCTGCAGATTACTTGAATTATGGAAAAATACCGATTTTCCGTGGAGTGATTAGA

GGGTTAGAGACCAAGAGATGGTCACGAGTGACTTGTGTCACCAATGACCAAATA

CCCACTTGTGCTAATATAATGAGCTCAGTTTCCACAAATGCTCTCACCGTAGCTC

ATTTTGCTGAGAACCCAATCAATGCCATGATACAGTACAATTATTTTGGGACATT

TGCTAGACTCTTGTTGATGATGCATGATCCTGCTCTTCGTCAATCATTGTATGAAG
```

-continued

```
TTCAAGATAAGATACCGGGCTTGCACAGTTCTACTTTCAAATACGCCATGTTGTA

TTTGGACCCTTCCATTGGAGGAGTGTCGGGCATGTCTTTGTCCAGGTTTTTGATTA

GAGCCTTCCCAGATCCCGTAACAGAAAGTCTCTCATTCTGGAGATTCATCCATGT

ACATGCTCGAAGTGAGCATCTGAAGGAGATGAGTGCAGTATTTGGAAACCCCGA

GATAGCCAAGTTTCGAATAACTCACATAGACAAGCTAGTAGAAGATCCAACCTC

TCTGAACATCGCTATGGGAATGAGTCCAGCGAACTTGTTAAAGACTGAGGTTAA

AAAATGCTTAATCGAATCAAGACAAACCATCAGGAACCAGGTGATTAAGGATGC

AACCATATATTTGTATCATGAAGAGGATCGGCTCAGAAGTTTCTTATGGTCAATA

AATCCTCTGTTCCCTAGATTTTTAAGTGAATTCAAATCAGGCACTTTTTTGGGAGT

CGCAGACGGGCTCATCAGTCTATTTCAAAATTCTCGTACTATTCGGAACTCCTTT

AAGAAAAAGTATCATAGGGAATTGGATGATTTGATTGTGAGGAGTGAGGTATCC

TCTTTGACACATTTAGGGAAACTTCATTTGAGAAGGGGATCATGTAAAATGTGGA

CATGTTCAGCTACTCATGCTGACACATTAAGATACAAATCCTGGGGCCGTACAGT

TATTGGGACAACTGTACCCCATCCATTAGAAATGTTGGGTCCACAACATCGAAA

AGAGACTCCTTGTGCACCATGTAACACATCAGGGTTCAATTATGTTTCTGTGCAT

TGTCCAGACGGGATCCATGACGTCTTTAGTTCACGGGACCATTGCCTGCTTATC

TAGGGTCTAAAACATCTGAATCTACATCTATTTTGCAGCCTTGGGAAAGGGAAA

GCAAAGTCCCACTGATTAAAAGAGCTACACGTCTTAGAGATGCTATCTCTTGGTT

TGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCAGATGTATCCCATGTGCTGAAGACATGGAGGAATGGGGAAGG

TTCGTGGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC

TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG
```

-continued

```
CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.
```

In other embodiments, the nucleic acid comprises the sequence of SEQ ID NO: 21, shown below (VSV vector: Convac V2 South Africa):

```
ACGAAGACAAACAAACCATTATTATCATTAAAAGGCTCAGGAGAAACTTTAACAGTAATCA

AAATGTCTGTTACAGTCAAGAGAATCATTGACAACACAGTCATAGTTCCAAA

ACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG
```

-continued

```
GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC
```

-continued

```
TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCTCGAGCGTACGCCACCATGTTCGTGTTTCTGGTGCTG

CTGCCTCTGGTGAGCTCCCAGTGCGTGAACTTCACCACAAGGACCCAGCTGCCCC
```

-continued
```
CTGCCTATACCAATTCCTTCACACGGGGCGTGTACTATCCCGACAAGGTGTTCCG

GAGCAGCGTGCTGCACTCCACACAGGATCTGTTTCTGCCTTTCTTTTCTAACGTG

ACCTGGTTCCACGCCATCCACGTGAGCGGCACCAATGGCACAAAGCGGTTCGCC

AATCCAGTGCTGCCCTTTAACGATGGCGTGTACTTCGCCTCCACCGAGAAGTCTA

ACATCATCAGAGGCTGGATCTTTGGCACCACACTGGACAGCAAGACACAGTCCC

TGCTGATCGTGAACAATGCCACCAACGTGGTCATCAAGGTGTGCGAGTTCCAGTT

TTGTAATGATCCATTCCTGGGCGTGTACTATCACAAGAACAATAAGTCTTGGATG

GAGAGCGAGTTTCGCGTGTATTCCTCTGCCAACAATTGCACATTTGAGTACGTGT

CCCAGCCCTTCCTGATGGACCTGGAGGGCAAGCAGGGCAATTTCAAGAACCTGA

GGGAGTTCGTGTTTAAGAATATCGATGGCTACTTCAAAATCTACTCCAAGCACAC

CCCAATCAACCTGGTGCGCGGCCTGCCACAGGGCTTCTCTGCCCTGGAGCCACTG

GTGGATCTGCCCATCGGCATCAACATCACCCGGTTTCAGACACTGCTGGCCCTGC

ACAGAAGCTACCTGACACCAGGCGACAGCTCCTCTGGATGGACCGCAGGAGCAG

CAGCCTACTATGTGGGCTATCTGCAGCCCAGGACCTTCCTGCTGAAGTACAACGA

GAATGGCACCATCACAGACGCCGTGGATTGCGCCCTGGATCCCCTGTCTGAGAC

CAAGTGTACACTGAAGAGCTTTACCGTGGAGAAGGGCATCTATCAGACAAGCAA

TTTCAGGGTGCAGCCTACCGAGTCCATCGTGCGCTTTCCCAATATCACAAACCTG

TGCCCTTTTGGCGAGGTGTTCAACGCAACCCGCTTCGCCAGCGTGTACGCCTGGA

ATAGGAAGCGCATCTCCAACTGCGTGGCCGACTATTCTGTGCTGTACAACAGCG

CCTCCTTCTCTACCTTTAAGTGCTATGGCGTGAGCCCCACAAAGCTGAATGACCT

GTGCTTTACCAACGTGTACGCCGATTCCTTCGTGATCAGGGGCGACGAGGTGCGC

CAGATCGCACCAGGACAGACAGGCAATATCGCAGACTACAATTATAAGCTGCCT

GACGATTTCACCGGCTGCGTGATCGCCTGGAACTCTAACAATCTGGATAGCAAA

GTGGGCGGCAACTACAATTATCTGTACCGGCTGTTTAGAAAGTCTAATCTGAAGC

CATTCGAGAGGGACATCTCCACAGAAATCTACCAGGCCGGCTCTACCCCCTGCA

ATGGCGTGAAGGGCTTTAACTGTTATTTCCCTCTGCAGAGCTACGGCTTCCAGCC

AACATATGGCGTGGGCTATCAGCCCTACCGCGTGGTGGTGCTGTCTTTTGAGCTG

CTGCACGCACCTGCAACAGTGTGCGGACCAAAGAAGAGCACCAATCTGGTGAAG

AACAAGTGCGTGAACTTCAACTTCAACGGACTGACCGGAACAGGCGTGCTGACC

GAGTCCAACAAGAAGTTCCTGCCTTTTCAGCAGTTCGGCAGGGACATCGCAGAT

ACCACAGACGCCGTGCGCGACCCTCAGACCCTGGAGATCCTGGACATCACACCA

TGCTCCTTCGGCGGCGTGTCTGTGATCACACCAGGCACCAATACAAGCAACCAG

GTGGCCGTGCTGTATCAGGGCGTGAATTGTACCGAGGTGCCAGTGGCAATCCAC

GCAGATCAGCTGACCCCTACATGGCGGGTGTACTCTACCGGCAGCAACGTGTTC

CAGACAAGAGCCGGATGCCTGATCGGAGCAGAGCACGTGAACAATAGCTATGA

GTGCGACATCCCTATCGGCGCCGGCATCTGTGCCTCCTACCAGACCCAGACAAA

CTCCCCAGAATCAAGCGTGATTCCTCTGGTCCATCCACTGGCAGATCCCTCCACA

GTGTTCAAAGACGGAGATGAGGCCGAAGACTTTGTGGAAGTCCACCTGCCTGAT

GTGCATAACCAGGTGTCTGGCGTCGACCTGGGACTGCCAAATTGGGGCAAGTAC

GTGCTGCTGAGTGCTGGAGCACTGACTGCCCTGATGCTGATCATTTTCCTGATGA

CCTGCTGTCGGCGCGTGAACAGAAGTGAGCCCACTCAGCACAATCTGCGAGGAA
```

-continued

```
CCGGGAGAGAAGTGTCAGTCACACCTCAGAGCGGGAAAATCATTAGTAGTTGGG

AATCACATAAAAGCGGGGGCGAGACCAGGCTGTGAGCTAGCCAGATTCTTCATG

TTTGGACCAAATCAACTTGTGATACCATGCTCAAAGAGGCCTCAATTATATTTGA

GTTTTTAATTTTTATGAAAAAAACTAACAGCAATCATGGAAGTCCACGATTTTGA

GACCGACGAGTTCAATGATTTCAATGAAGATGACTATGCCACAAGAGAATTCCT

GAATCCCGATGAGCGCATGACGTACTTGAATCATGCTGATTACAATTTGAATTCT

CCTCTAATTAGTGATGATATTGACAATTTGATCAGGAAATTCAATTCTCTTCCGA

TTCCCTCGATGTGGGATAGTAAGAACTGGGATGGAGTTCTTGAGATGTTAACATC

ATGTCAAGCCAATCCCATCTCAACATCTCAGATGCATAAATGGATGGGAAGTTG

GTTAATGTCTGATAATCATGATGCCAGTCAAGGGTATAGTTTTTTACATGAAGTG

GACAAAGAGGCAGAAATAACATTTGACGTGGTGGAGACCTTCATCCGCGGCTGG

GGCAACAAACCAATTGAATACATCAAAAAGGAAAGATGGACTGACTCATTCAAA

ATTCTCGCTTATTTGTGTCAAAAGTTTTTGGACTTACACAAGTTGACATTAATCTT

AAATGCTGTCTCTGAGGTGGAATTGCTCAACTTGGCGAGGACTTTCAAAGGCAA

AGTCAGAAGAAGTTCTCATGGAACGAACATATGCAGGATTAGGGTTCCCAGCTT

GGGTCCTACTTTTATTTCAGAAGGATGGGCTTACTTCAAGAAACTTGATATTCTA

ATGGACCGAAACTTTCTGTTAATGGTCAAAGATGTGATTATAGGGAGGATGCAA

ACGGTGCTATCCATGGTATGTAGAATAGACAACCTGTTCTCAGAGCAAGACATCT

TCTCCCTTCTAAATATCTACAGAATTGGAGATAAAATTGTGGAGAGGCAGGGAA

ATTTTTCTTATGACTTGATTAAAATGGTGGAACCGATATGCAACTTGAAGCTGAT

GAAATTAGCAAGAGAATCAAGGCCTTTAGTCCCACAATTCCCTCATTTTGAAAAT

CATATCAAGACTTCTGTTGATGAAGGGGCAAAAATTGACCGAGGTATAAGATTC

CTCCATGATCAGATAATGAGTGTGAAAACAGTGGATCTCACACTGGTGATTTATG

GATCGTTCAGACATTGGGGTCATCCTTTTATAGATTATTACACTGGACTAGAAAA

ATTACATTCCCAAGTAACCATGAAGAAAGATATTGATGTGTCATATGCAAAAGC

ACTTGCAAGTGATTTAGCTCGGATTGTTCTATTTCAACAGTTCAATGATCATAAA

AAGTGGTTCGTGAATGGAGACTTGCTCCCTCATGATCATCCCTTTAAAAGTCATG

TTAAAGAAAATACATGGCCCACAGCTGCTCAAGTTCAAGATTTTGGAGATAAAT

GGCATGAACTTCCGCTGATTAAATGTTTTGAAATACCCGACTTACTAGACCCATC

GATAATATACTCTGACAAAAGTCATTCAATGAATAGGTCAGAGGTGTTGAAACA

TGTCCGAATGAATCCGAACACTCCTATCCCTAGTAAAAAGGTGTTGCAGACTATG

TTGGACACAAAGGCTACCAATTGGAAAGAATTTCTTAAAGAGATTGATGAGAAG

GGCTTAGATGATGATGATCTAATTATTGGTCTTAAAGGAAAGGAGAGGGAACTG

AAGTTGGCAGGTAGATTTTCTCCCTAATGTCTTGGAAATTGCGAGAATACTTTG

TAATTACCGAATATTTGATAAAGACTCATTTCGTCCCTATGTTTAAAGGCCTGAC

AATGGCGGACGATCTAACTGCAGTCATTAAAAAGATGTTAGATTCCTCATCCGGC

CAAGGATTGAAGTCATATGAGGCAATTTGCATAGCCAATCACATTGATTACGAA

AAATGGAATAACCACCAAAGGAAGTTATCAAACGGCCCAGTGTTCCGAGTTATG

GGCCAGTTCTTAGGTTATCCATCCTTAATCGAGAGAACTCATGAATTTTTTGAGA

AAAGTCTTATATACTACAATGGAAGACCAGACTTGATGCGTGTTCACAACAACA
```

```
CACTGATCAATTCAACCTCCCAACGAGTTTGTTGGCAAGGACAAGAGGGTGGAC
TGGAAGGTCTACGGCAAAAAGGATGGACTATCCTCAATCTACTGGTTATTCAAA
GAGAGGCTAAAATCAGAAACACTGCTGTCAAAGTCTTGGCACAAGGTGATAATC
AAGTTATTTGCACACAGTATAAAACGAAGAAATCGAGAAACGTTGTAGAATTAC
AGGGTGCTCTCAATCAAATGGTTTCTAATAATGAGAAAATTATGACTGCAATCAA
AATAGGGACAGGGAAGTTAGGACTTTTGATAAATGACGATGAGACTATGCAATC
TGCAGATTACTTGAATTATGGAAAAATACCGATTTTCCGTGGAGTGATTAGAGGG
TTAGAGACCAAGAGATGGTCACGAGTGACTTGTGTCACCAATGACCAAATACCC
ACTTGTGCTAATATAATGAGCTCAGTTTCCACAAATGCTCTCACCGTAGCTCATT
TTGCTGAGAACCCAATCAATGCCATGATACAGTACAATTATTTTGGGACATTTGC
TAGACTCTTGTTGATGATGCATGATCCTGCTCTTCGTCAATCATTGTATGAAGTTC
AAGATAAGATACCGGGCTTGCACAGTTCTACTTTCAAATACGCCATGTTGTATTT
GGACCCTTCCATTGGAGGAGTGTCGGGCATGTCTTTGTCCAGGTTTTTGATTAGA
GCCTTCCCAGATCCCGTAACAGAAAGTCTCTCATTCTGGAGATTCATCCATGTAC
ATGCTCGAAGTGAGCATCTGAAGGAGATGAGTGCAGTATTTGGAAACCCCGAGA
TAGCCAAGTTTCGAATAACTCACATAGACAAGCTAGTAGAAGATCCAACCTCTCT
GAACATCGCTATGGGAATGAGTCCAGCGAACTTGTTAAAGACTGAGGTTAAAAA
ATGCTTAATCGAATCAAGACAAACCATCAGGAACCAGGTGATTAAGGATGCAAC
CATATATTTGTATCATGAAGAGGATCGGCTCAGAAGTTTCTTATGGTCAATAAAT
CCTCTGTTCCCTAGATTTTTAAGTGAATTCAAATCAGGCACTTTTTTGGGAGTCGC
AGACGGGCTCATCAGTCTATTTCAAAATTCTCGTACTATTCGGAACTCCTTTAAG
AAAAAGTATCATAGGGAATTGGATGATTTGATTGTGAGGAGTGAGGTATCCTCTT
TGACACATTTAGGGAAACTTCATTTGAGAAGGGGATCATGTAAAATGTGGACAT
GTTCAGCTACTCATGCTGACACATTAAGATACAAATCCTGGGGCCGTACAGTTAT
TGGGACAACTGTACCCCATCCATTAGAAATGTTGGGTCCACAACATCGAAAAGA
GACTCCTTGTGCACCATGTAACACATCAGGGTTCAATTATGTTTCTGTGCATTGTC
CAGACGGGATCCATGACGTCTTTAGTTCACGGGACCATTGCCTGCTTATCTAGG
GTCTAAAACATCTGAATCTACATCTATTTTGCAGCCTTGGGAAAGGGAAAGCAA
AGTCCCACTGATTAAAAGAGCTACACGTCTTAGAGATGCTATCTCTTGGTTTGTT
GAACCCGACTCTAAACTAGCAATGACTATACTTTCTAACATCCACTCTTTAACAG
GCGAAGAATGGACCAAAAGGCAGCATGGGTTCAAAAGAACAGGGTCTGCCCTTC
ATAGGTTTTCGACATCTCGGATGAGCCATGGTGGGTTCGCATCTCAGAGCACTGC
AGCATTGACCAGGTTGATGGCAACTACAGACACCATGAGGGATCTGGGAGATCA
GAATTTCGACTTTTTATTCCAAGCAACGTTGCTCTATGCTCAAATTACCACCACTG
TTGCAAGAGACGGATGGATCACCAGTTGTACAGATCATTATCATATTGCCTGTAA
GTCCTGTTTGAGACCCATAGAAGAGATCACCCTGGACTCAAGTATGGACTACAC
GCCCCCAGATGTATCCCATGTGCTGAAGACATGGAGGAATGGGGAAGGTTCGTG
GGGACAAGAGATAAAACAGATCTATCCTTTAGAAGGGAATTGGAAGAATTTAGC
ACCTGCTGAGCAATCCTATCAAGTCGGCAGATGTATAGGTTTTCTATATGGAGAC
TTGGCGTATAGAAAATCTACTCATGCCGAGGACAGTTCTCTATTTCCTCTATCTAT
ACAAGGTCGTATTAGAGGTCGAGGTTTCTTAAAAGGGTTGCTAGACGGATTAAT
```

```
GAGAGCAAGTTGCTGCCAAGTAATACACCGGAGAAGTCTGGCTCATTTGAAGAG

GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT

ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG

GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC
```

-continued

```
TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTATC

TGGTTTTGTGGTCTTCGT.
```

In one embodiment, the nucleic acid comprises the sequence of SEQ ID NO: 22, shown below (VSV vector: Convac V3 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT
```

-continued

```
GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA

TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC
```

-continued

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGTTCGTGTTTCTGGTGCTGCTGCCTCT

GGTGAGCTCCCAGTGCGTGAACCTGACCACAAGGACCCAGCTGCCCCCTGCCTA

TACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGACAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGACCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAAGATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGGAGGGCTTTAACTGTTATTTCCCTCTGCAGAGCTACGGCTTCCAGCCAACAAA

CGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

-continued
GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGACGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGGATCCGGCTACATCCCCGAGGCCCCCAGAGACGGCCAGGCCTACGTG

CGGAAGGACGGCGAGTGGGTACTGctcagcaccttcctgggcAGCAGTTGGAAAAGCTCCA

TCGCCTCCTTTTTCTTTATCATCGGCCTGATCATCGGACTGTTCCTGGTGCTCCGC

GTGGGTATCCACCTGTGCATCAAGCTGAAGCACACCAAGAAAAGACAGATTTAT

ACAGACATCGAGATGAACCGACTTGGAAAGTAAGCTAGCCAGATTCTTCATGTT

TGGACCAAATCAACTTGTGATACCATGCTCAAAGAGGCCTCAATTATATTTGAGT

TTTTAATTTTTATGAAAAAAACTAACAGCAATCATGGAAGTCCACGATTTTGAGA

CCGACGAGTTCAATGATTTCAATGAAGATGACTATGCCACAAGAGAATTCCTGA

ATCCCGATGAGCGCATGACGTACTTGAATCATGCTGATTACAATTTGAATTCTCC

TCTAATTAGTGATGATATTGACAATTTGATCAGGAAATTCAATTCTCTTCCGATTC

CCTCGATGTGGGATAGTAAGAACTGGGATGGAGTTCTTGAGATGTTAACATCAT

GTCAAGCCAATCCCATCTCAACATCTCAGATGCATAAATGGATGGGAAGTTGGTT

AATGTCTGATAATCATGATGCCAGTCAAGGGTATAGTTTTTTACATGAAGTGGAC

AAAGAGGCAGAAATAACATTTGACGTGGTGGAGACCTTCATCCGCGGCTGGGGC

AACAAACCAATTGAATACATCAAAAAGGAAAGATGGACTGACTCATTCAAAATT

CTCGCTTATTTGTGTCAAAAGTTTTTGGACTTACACAAGTTGACATTAATCTTAAA

TGCTGTCTCTGAGGTGGAATTGCTCAACTTGGCGAGGACTTTCAAAGGCAAAGTC

AGAAGAAGTTCTCATGGAACGAACATATGCAGGATTAGGGTTCCCAGCTTGGGT

CCTACTTTTATTTCAGAAGGATGGGCTTACTTCAAGAAACTTGATATTCTAATGG

ACCGAAACTTTCTGTTAATGGTCAAAGATGTGATTATAGGGAGGATGCAAACGG

TGCTATCCATGGTATGTAGAATAGACAACCTGTTCTCAGAGCAAGACATCTTCTC

CCTTCTAAATATCTACAGAATTGGAGATAAAATTGTGGAGAGGCAGGGAAATTT

TTCTTATGACTTGATTAAAATGGTGGAACCGATATGCAACTTGAAGCTGATGAAA

TTAGCAAGAGAATCAAGGCCTTTAGTCCCACAATTCCCTCATTTTGAAAATCATA

TCAAGACTTCTGTTGATGAAGGGGCAAAAATTGACCGAGGTATAAGATTCCTCC

ATGATCAGATAATGAGTGTGAAAACAGTGGATCTCACACTGGTGATTTATGGAT

CGTTCAGACATTGGGGTCATCCTTTTATAGATTATTACACTGGACTAGAAAAATT

ACATTCCCAAGTAACCATGAAGAAAGATATTGATGTGTCATATGCAAAAGCACT

TGCAAGTGATTTAGCTCGGATTGTTCTATTTCAACAGTTCAATGATCATAAAAAG

TGGTTCGTGAATGGAGACTTGCTCCCTCATGATCATCCCTTTAAAAGTCATGTTA

AAGAAAATACATGGCCCACAGCTGCTCAAGTTCAAGATTTTGGAGATAAATGGC

ATGAACTTCCGCTGATTAAATGTTTTGAAATACCCGACTTACTAGACCCATCGAT

AATATACTCTGACAAAAGTCATTCAATGAATAGGTCAGAGGTGTTGAAACATGT

-continued

```
CCGAATGAATCCGAACACTCCTATCCCTAGTAAAAAGGTGTTGCAGACTATGTTG

GACACAAAGGCTACCAATTGGAAAGAATTTCTTAAAGAGATTGATGAGAAGGGC

TTAGATGATGATGATCTAATTATTGGTCTTAAAGGAAAGGAGAGGGAACTGAAG

TTGGCAGGTAGATTTTTCTCCCTAATGTCTTGGAAATTGCGAGAATACTTTGTAA

TTACCGAATATTTGATAAAGACTCATTTCGTCCCTATGTTTAAAGGCCTGACAAT

GGCGGACGATCTAACTGCAGTCATTAAAAAGATGTTAGATTCCTCATCCGGCCA

AGGATTGAAGTCATATGAGGCAATTTGCATAGCCAATCACATTGATTACGAAAA

ATGGAATAACCACCAAAGGAAGTTATCAAACGGCCCAGTGTTCCGAGTTATGGG

CCAGTTCTTAGGTTATCCATCCTTAATCGAGAGAACTCATGAATTTTTTGAGAAA

AGTCTTATATACTACAATGGAAGACCAGACTTGATGCGTGTTCACAACAACACA

CTGATCAATTCAACCTCCCAACGAGTTTGTTGGCAAGGACAAGAGGGTGGACTG

GAAGGTCTACGGCAAAAAGGATGGACTATCCTCAATCTACTGGTTATTCAAAGA

GAGGCTAAAATCAGAAACACTGCTGTCAAAGTCTTGGCACAAGGTGATAATCAA

GTTATTTGCACACAGTATAAAACGAAGAAATCGAGAAACGTTGTAGAATTACAG

GGTGCTCTCAATCAAATGGTTTCTAATAATGAGAAAATTATGACTGCAATCAAA

TAGGGACAGGGAAGTTAGGACTTTTGATAAATGACGATGAGACTATGCAATCTG

CAGATTACTTGAATTATGGAAAAATACCGATTTTCCGTGGAGTGATTAGAGGGTT

AGAGACCAAGAGATGGTCACGAGTGACTTGTGTCACCAATGACCAAATACCCAC

TTGTGCTAATATAATGAGCTCAGTTTCCACAAATGCTCTCACCGTAGCTCATTTTG

CTGAGAACCCAATCAATGCCATGATACAGTACAATTATTTTGGGACATTTGCTAG

ACTCTTGTTGATGATGCATGATCCTGCTCTTCGTCAATCATTGTATGAAGTTCAAG

ATAAGATACCGGGCTTGCACAGTTCTACTTTCAAATACGCCATGTTGTATTTGGA

CCCTTCCATTGGAGGAGTGTCGGGCATGTCTTTGTCCAGGTTTTTGATTAGAGCC

TTCCCAGATCCCGTAACAGAAAGTCTCTCATTCTGGAGATTCATCCATGTACATG

CTCGAAGTGAGCATCTGAAGGAGATGAGTGCAGTATTTGGAAACCCCGAGATAG

CCAAGTTTCGAATAACTCACATAGACAAGCTAGTAGAAGATCCAACCTCTCTGA

ACATCGCTATGGGAATGAGTCCAGCGAACTTGTTAAAGACTGAGGTTAAAAAAT

GCTTAATCGAATCAAGACAAACCATCAGGAACCAGGTGATTAAGGATGCAACCA

TATATTTGTATCATGAAGAGGATCGGCTCAGAAGTTTCTTATGGTCAATAAATCC

TCTGTTCCCTAGATTTTTAAGTGAATTCAAATCAGGCACTTTTTTGGGAGTCGCA

GACGGGCTCATCAGTCTATTTCAAAATTCTCGTACTATTCGGAACTCCTTTAAGA

AAAAGTATCATAGGGAATTGGATGATTTGATTGTGAGGAGTGAGGTATCCTCTTT

GACACATTTAGGGAAACTTCATTTGAGAAGGGGATCATGTAAAATGTGGACATG

TTCAGCTACTCATGCTGACACATTAAGATACAAATCCTGGGGCCGTACAGTTATT

GGGACAACTGTACCCCATCCATTAGAAATGTTGGGTCCACAACATCGAAAAGAG

ACTCCTTGTGCACCATGTAACACATCAGGGTTCAATTATGTTTCTGTGCATTGTCC

AGACGGGATCCATGACGTCTTTAGTTCACGGGGACCATTGCCTGCTTATCTAGGG

TCTAAAACATCTGAATCTACATCTATTTTGCAGCCTTGGGAAAGGGAAAGCAAA

GTCCCACTGATTAAAAGAGCTACACGTCTTAGAGATGCTATCTCTTGGTTTGTTG

AACCCGACTCTAAACTAGCAATGACTATACTTTCTAACATCCACTCTTTAACAGG
```

-continued

```
CGAAGAATGGACCAAAAGGCAGCATGGGTTCAAAAGAACAGGGTCTGCCCTTCA

TAGGTTTTCGACATCTCGGATGAGCCATGGTGGGTTCGCATCTCAGAGCACTGCA

GCATTGACCAGGTTGATGGCAACTACAGACACCATGAGGGATCTGGGAGATCAG

AATTTCGACTTTTTATTCCAAGCAACGTTGCTCTATGCTCAAATTACCACCACTGT

TGCAAGAGACGGATGGATCACCAGTTGTACAGATCATTATCATATTGCCTGTAAG

TCCTGTTTGAGACCCATAGAAGAGATCACCCTGGACTCAAGTATGGACTACACG

CCCCCAGATGTATCCCATGTGCTGAAGACATGGAGGAATGGGGAAGGTTCGTGG

GGACAAGAGATAAAACAGATCTATCCTTTAGAAGGGAATTGGAAGAATTTAGCA

CCTGCTGAGCAATCCTATCAAGTCGGCAGATGTATAGGTTTTCTATATGGAGACT

TGGCGTATAGAAAATCTACTCATGCCGAGGACAGTTCTCTATTTCCTCTATCTAT

ACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAG

GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT

ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG

GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC
```

-continued

```
ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTATC

TGGTTTTGTGGTCTTCGT.
```

In another embodiment, the nucleic acid comprises the sequence of SEQ ID NO: 23, shown below (VSV vector: Convac V3 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT
```

-continued

```
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
```

-continued

```
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
GTATCCATCTTTGCATTAAATTAAAGCACACCAAGAAAAGACAGATTTATACAG
ACATAGAGATGAACCGACTTGGAAAGTAACTCAAATCCTGCTAGGTATGAAAAA
AACTAACaGATATCACGCtcgagGCCACCATGTTCGTGTTTCTGGTGCTGCTGCCTCT
GGTGAGCTCCCAGTGCGTGAACTTCACCACAAGGACCCAGCTGCCCCCTGCCTAT
ACCAATTCCTTCACACGGGGCGTGTACTATCCCGACAAGGTGTTCCGGAGCAGC
GTGCTGCACTCCACACAGGATCTGTTTCTGCCTTTCTTTTCTAACGTGACCTGGTT
CCACGCCATCCACGTGAGCGGCACCAATGGCACAAAGCGGTTCGCCAATCCAGT
GCTGCCCTTTAACGATGGCGTGTACTTCGCCTCCACCGAGAAGTCTAACATCATC
AGAGGCTGGATCTTTGGCACCACACTGGACAGCAAGACACAGTCCCTGCTGATC
GTGAACAATGCCACCAACGTGGTCATCAAGGTGTGCGAGTTCCAGTTTTGTAATG
ATCCATTCCTGGGCGTGTACTATCACAAGAACAATAAGTCTTGGATGGAGAGCG
AGTTTCGCGTGTATTCCTCTGCCAACAATTGCACATTTGAGTACGTGTCCCAGCC
CTTCCTGATGGACCTGGAGGGCAAGCAGGGCAATTTCAAGAACCTGAGGGAGTT
CGTGTTTAAGAATATCGATGGCTACTTCAAAATCTACTCCAAGCACACCCCAATC
AACCTGGTGCGCGGCCTGCCACAGGGCTTCTCTGCCCTGGAGCCACTGGTGGATC
TGCCCATCGGCATCAACATCACCCGGTTTCAGACACTGCTGGCCCTGCACAGAA
GCTACCTGACACCAGGCGACAGCTCCTCTGGATGGACCGCAGGAGCAGCAGCCT
ACTATGTGGGCTATCTGCAGCCCAGGACCTTCCTGCTGAAGTACAACGAGAATG
GCACCATCACAGACGCCGTGGATTGCGCCCTGGATCCCCTGTCTGAGACCAAGT
GTACACTGAAGAGCTTTACCGTGGAGAAGGGCATCTATCAGACAAGCAATTTCA
GGGTGCAGCCTACCGAGTCCATCGTGCGCTTTCCCAATATCACAAACCTGTGCCC
TTTTGGCGAGGTGTTCAACGCAACCCGCTTCGCCAGCGTGTACGCCTGGAATAGG
AAGCGCATCTCCAACTGCGTGGCCGACTATTCTGTGCTGTACAACAGCGCCTCCT
TCTCTACCTTTAAGTGCTATGGCGTGAGCCCCACAAAGCTGAATGACCTGTGCTT
```

```
TACCAACGTGTACGCCGATTCCTTCGTGATCAGGGGCGACGAGGTGCGCCAGAT

CGCACCAGGACAGACAGGCAATATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGAAGGGCTTTAACTGTTATTTCCCTCTGCAGAGCTACGGCTTCCAGCCAACATA

TGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGGCGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGGGATCCGGCTACATCCCCGAGGCCCCAGAGACGGCCAGGCCTACGTGCGG

AAGGACGGCGAGTGGGTACTGctcagcaccttcctgggcAGCAGTTGGAAAAGCTCCATCG

CCTCCTTTTTCTTTATCATCGGCCTGATCATCGGACTGTTCCTGGTGCTCCGCGTG

GGTATCCACCTGTGCATCAAGCTGAAGCACACCAAGAAAAGACAGATTTATACA

GACATCGAGATGAACCGACTTGGAAAGTAAGCTAGCCAGATTCTTCATGTTTGG

ACCAAATCAACTTGTGATACCATGCTCAAAGAGGCCTCAATTATATTTGAGTTTT

TAATTTTTATGAAAAAAACTAACAGCAATCATGGAAGTCCACGATTTTGAGACC

GACGAGTTCAATGATTTCAATGAAGATGACTATGCCACAAGAGAATTCCTGAAT

CCCGATGAGCGCATGACGTACTTGAATCATGCTGATTACAATTTGAATTCTCCTC

TAATTAGTGATGATATTGACAATTTGATCAGGAAATTCAATTCTCTTCCGATTCC

CTCGATGTGGGATAGTAAGAACTGGGATGGAGTTCTTGAGATGTTAACATCATGT

CAAGCCAATCCCATCTCAACATCTCAGATGCATAAATGGATGGGAAGTTGGTTA

ATGTCTGATAATCATGATGCCAGTCAAGGGTATAGTTTTTTACATGAAGTGGACA

AAGAGGCAGAAATAACATTTGACGTGGTGGAGACCTTCATCCGCGGCTGGGGCA

ACAAACCAATTGAATACATCAAAAAGGAAAGATGGACTGACTCATTCAAAATTC

TCGCTTATTTGTGTCAAAAGTTTTTGGACTTACACAAGTTGACATTAATCTTAAAT

GCTGTCTCTGAGGTGGAATTGCTCAACTTGGCGAGGACTTTCAAAGGCAAAGTC

AGAAGAAGTTCTCATGGAACGAACATATGCAGGATTAGGGTTCCCAGCTTGGGT

CCTACTTTTATTTCAGAAGGATGGGCTTACTTCAAGAAACTTGATATTCTAATGG

ACCGAAACTTTCTGTTAATGGTCAAAGATGTGATTATAGGGAGGATGCAAACGG

TGCTATCCATGGTATGTAGAATAGACAACCTGTTCTCAGAGCAAGACATCTTCTC

CCTTCTAAATATCTACAGAATTGGAGATAAAATTGTGGAGAGGCAGGGAAATTT

TTCTTATGACTTGATTAAAATGGTGGAACCGATATGCAACTTGAAGCTGATGAAA

TTAGCAAGAGAATCAAGGCCTTTAGTCCCACAATTCCCTCATTTTGAAAATCATA
```

```
-continued
TCAAGACTTCTGTTGATGAAGGGGCAAAAATTGACCGAGGTATAAGATTCCTCC

ATGATCAGATAATGAGTGTGAAAACAGTGGATCTCACACTGGTGATTTATGGAT

CGTTCAGACATTGGGGTCATCCTTTTATAGATTATTACACTGGACTAGAAAAATT

ACATTCCCAAGTAACCATGAAGAAAGATATTGATGTGTCATATGCAAAAGCACT

TGCAAGTGATTTAGCTCGGATTGTTCTATTTCAACAGTTCAATGATCATAAAAAG

TGGTTCGTGAATGGAGACTTGCTCCCTCATGATCATCCCTTTAAAAGTCATGTTA

AAGAAAATACATGGCCCACAGCTGCTCAAGTTCAAGATTTTGGAGATAAATGGC

ATGAACTTCCGCTGATTAAATGTTTTGAAATACCCGACTTACTAGACCCATCGAT

AATATACTCTGACAAAAGTCATTCAATGAATAGGTCAGAGGTGTTGAAACATGT

CCGAATGAATCCGAACACTCCTATCCCTAGTAAAAAGGTGTTGCAGACTATGTTG

GACACAAAGGCTACCAATTGGAAAGAATTTCTTAAAGAGATTGATGAGAAGGGC

TTAGATGATGATGATCTAATTATTGGTCTTAAAGGAAAGGAGAGGGAACTGAAG

TTGGCAGGTAGATTTTTCTCCCTAATGTCTTGGAAATTGCGAGAATACTTTGTAA

TTACCGAATATTTGATAAAGACTCATTTCGTCCCTATGTTTAAAGGCCTGACAAT

GGCGGACGATCTAACTGCAGTCATTAAAAAGATGTTAGATTCCTCATCCGGCCA

AGGATTGAAGTCATATGAGGCAATTTGCATAGCCAATCACATTGATTACGAAAA

ATGGAATAACCACCAAAGGAAGTTATCAAACGGCCCAGTGTTCCGAGTTATGGG

CCAGTTCTTAGGTTATCCATCCTTAATCGAGAGAACTCATGAATTTTTTGAGAAA

AGTCTTATATACTACAATGGAAGACCAGACTTGATGCGTGTTCACAACAACACA

CTGATCAATTCAACCTCCCAACGAGTTTGTTGGCAAGGACAAGAGGGTGGACTG

GAAGGTCTACGGCAAAAAGGATGGACTATCCTCAATCTACTGGTTATTCAAAGA

GAGGCTAAAATCAGAAACACTGCTGTCAAAGTCTTGGCACAAGGTGATAATCAA

GTTATTTGCACACAGTATAAAACGAAGAAATCGAGAAACGTTGTAGAATTACAG

GGTGCTCTCAATCAAATGGTTTCTAATAATGAGAAAATTATGACTGCAATCAAA

TAGGGACAGGGAAGTTAGGACTTTTGATAAATGACGATGAGACTATGCAATCTG

CAGATTACTTGAATTATGGAAAAATACCGATTTTCCGTGGAGTGATTAGAGGGTT

AGAGACCAAGAGATGGTCACGAGTGACTTGTGTCACCAATGACCAAATACCCAC

TTGTGCTAATATAATGAGCTCAGTTTCCACAAATGCTCTCACCGTAGCTCATTTTG

CTGAGAACCCAATCAATGCCATGATACAGTACAATTATTTTGGGACATTTGCTAG

ACTCTTGTTGATGATGCATGATCCTGCTCTTCGTCAATCATTGTATGAAGTTCAAG

ATAAGATACCGGGCTTGCACAGTTCTACTTTCAAATACGCCATGTTGTATTTGGA

CCCTTCCATTGGAGGAGTGTCGGGCATGTCTTTGTCCAGGTTTTTGATTAGAGCC

TTCCCAGATCCCGTAACAGAAAGTCTCTCATTCTGGAGATTCATCCATGTACATG

CTCGAAGTGAGCATCTGAAGGAGATGAGTGCAGTATTTGGAAACCCCGAGATAG

CCAAGTTTCGAATAACTCACATAGACAAGCTAGTAGAAGATCCAACCTCTCTGA

ACATCGCTATGGGAATGAGTCCAGCGAACTTGTTAAAGACTGAGGTTAAAAAAT

GCTTAATCGAATCAAGACAAACCATCAGGAACCAGGTGATTAAGGATGCAACCA

TATATTTGTATCATGAAGAGGATCGGCTCAGAAGTTTCTTATGGTCAATAAATCC

TCTGTTCCCTAGATTTTTAAGTGAATTCAAATCAGGCACTTTTTTGGGAGTCGCA

GACGGGCTCATCAGTCTATTTCAAAATTCTCGTACTATTCGGAACTCCTTTAAGA

AAAAGTATCATAGGGAATTGGATGATTTGATTGTGAGGAGTGAGGTATCCTCTTT
```

-continued

```
GACACATTTAGGGAAACTTCATTTGAGAAGGGGATCATGTAAAATGTGGACATG

TTCAGCTACTCATGCTGACACATTAAGATACAAATCCTGGGGCCGTACAGTTATT

GGGACAACTGTACCCCATCCATTAGAAATGTTGGGTCCACAACATCGAAAAGAG

ACTCCTTGTGCACCATGTAACACATCAGGGTTCAATTATGTTTCTGTGCATTGTCC

AGACGGGATCCATGACGTCTTTAGTTCACGGGGACCATTGCCTGCTTATCTAGGG

TCTAAAACATCTGAATCTACATCTATTTTGCAGCCTTGGGAAAGGGAAAGCAAA

GTCCCACTGATTAAAAGAGCTACACGTCTTAGAGATGCTATCTCTTGGTTTGTTG

AACCCGACTCTAAACTAGCAATGACTATACTTTCTAACATCCACTCTTTAACAGG

CGAAGAATGGACCAAAAGGCAGCATGGGTTCAAAAGAACAGGGTCTGCCCTTCA

TAGGTTTTCGACATCTCGGATGAGCCATGGTGGGTTCGCATCTCAGAGCACTGCA

GCATTGACCAGGTTGATGGCAACTACAGACACCATGAGGGATCTGGGAGATCAG

AATTTCGACTTTTTATTCCAAGCAACGTTGCTCTATGCTCAAATTACCACCACTGT

TGCAAGAGACGGATGGATCACCAGTTGTACAGATCATTATCATATTGCCTGTAAG

TCCTGTTTGAGACCCATAGAAGAGATCACCCTGGACTCAAGTATGGACTACACG

CCCCCAGATGTATCCCATGTGCTGAAGACATGGAGGAATGGGGAAGGTTCGTGG

GGACAAGAGATAAAACAGATCTATCCTTTAGAAGGGAATTGGAAGAATTTAGCA

CCTGCTGAGCAATCCTATCAAGTCGGCAGATGTATAGGTTTTCTATATGGAGACT

TGGCGTATAGAAAATCTACTCATGCCGAGGACAGTTCTCTATTTCCTCTATCTAT

ACAAGGTCGTATTAGAGGTCGAGGTTTCTTAAAAGGGTTGCTAGACGGATTAAT

GAGAGCAAGTTGCTGCCAAGTAATACACCGGAGAAGTCTGGCTCATTTGAAGAG

GCCGGCCAACGCAGTGTACGGAGGTTTGATTTACTTGATTGATAAATTGAGTGTA

TCACCTCCATTCCTTTCTCTTACTAGATCAGGACCTATTAGAGACGAATTAGAAA

CGATTCCCCACAAGATCCCAACCTCCTATCCGACAAGCAACCGTGATATGGGGG

TGATTGTCAGAAATTACTTCAAATACCAATGCCGTCTAATTGAAAAGGGAAAAT

ACAGATCACATTATTCACAATTATGGTTATTCTCAGATGTCTTATCCATAGACTTC

ATTGGACCATTCTCTATTTCCACCACCCTCTTGCAAATCCTATACAAGCCATTTTT

ATCTGGGAAAGATAAGAATGAGTTGAGAGAGCTGGCAAATCTTTCTTCATTGCT

AAGATCAGGAGAGGGGTGGGAAGACATACATGTGAAATTCTTCACCAAGGACAT

ATTATTGTGTCCAGAGGAAATCAGACATGCTTGCAAGTTCGGGATTGCTAAGGAT

AATAATAAAGACATGAGCTATCCCCCTTGGGGAAGGGAATCCAGAGGGACAATT

ACAACAATCCCTGTTTATTATACGACCACCCCTTACCCAAAGATGCTAGAGATGC

CTCCAAGAATCCAAAATCCCCTGCTGTCCGGAATCAGGTTGGGCCAATTACCAA

CTGGCGCTCATTATAAAATTCGGAGTATATTACATGGAATGGGAATCCATTACAG

GGACTTCTTGAGTTGTGGAGACGGCTCCGGAGGGATGACTGCTGCATTACTACG

AGAAAATGTGCATAGCAGAGGAATATTCAATAGTCTGTTAGAATTATCAGGGTC

AGTCATGCGAGGCGCCTCTCCTGAGCCCCCAGTGCCCTAGAAACTTTAGGAGG

AGATAAATCGAGATGTGTAAATGGTGAAACATGTTGGGAATATCCATCTGACTT

ATGTGACCCAAGGACTTGGGACTATTTCCTCCGACTCAAAGCAGGCTTGGGCTT

CAAATTGATTTAATTGTAATGGATATGGAAGTTCGGGATTCTTCTACTAGCCTGA

AAATTGAGACGAATGTTAGAAATTATGTGCACCGGATTTTGGATGAGCAAGGAG
```

-continued

TTTTAATCTACAAGACTTATGGAACATATATTTGTGAGAGCGAAAAGAATGCAGT

AACAATCCTTGGTCCCATGTTCAAGACGGTCGACTTAGTTCAAACAGAATTTAGT

AGTTCTCAAACGTCTGAAGTATATATGGTATGTAAAGGTTTGAAGAAATTAATCG

ATGAACCCAATCCCGATTGGTCTTCCATCAATGAATCCTGGAAAAACCTGTACGC

ATTCCAGTCATCAGAACAGGAATTTGCCAGAGCAAAGAAGGTTAGTACATACTT

TACCTTGACAGGTATTCCCTCCCAATTCATTCCTGATCCTTTTGTAAACATTGAGA

CTATGCTACAAATATTCGGAGTACCCACGGGTGTGTCTCATGCGGCTGCCTTAAA

ATCATCTGATAGACCTGCAGATTTATTGACCATTAGCCTTTTTTATATGGCGATTA

TATCGTATTATAACATCAATCATATCAGAGTAGGACCGATACCTCCGAACCCCCC

ATCAGATGGAATTGCACAAAATGTGGGGATCGCTATAACTGGTATAAGCTTTTG

GCTGAGTTTGATGGAGAAAGACATTCCACTATATCAACAGTGTTTAGCAGTTATC

CAGCAATCATTCCCGATTAGGTGGGAGGCTGTTTCAGTAAAAGGAGGATACAAG

CAGAAGTGGAGTACTAGAGGTGATGGGCTCCCAAAAGATACCCGAACTTCAGAC

TCCTTGGCCCCAATCGGGAACTGGATCAGATCTCTGGAATTGGTCCGAAACCAA

GTTCGTCTAAATCCATTCAATGAGATCTTGTTCAATCAGCTATGTCGTACAGTGG

ATAATCATTTGAAATGGTCAAATTTGCGAAGAAACACAGGAATGATTGAATGGA

TCAATAGACGAATTTCAAAAGAAGACCGGTCTATACTGATGTTGAAGAGTGACC

TACACGAGGAAAACTCTTGGAGAGATTAAAAAATCATGAGGAGACTCCAAACTT

TAAGTATGAAAAAAACTTTGATCCTTAAGACCCTCTTGTGGTTTTTATTTTTTATC

TGGTTTTGTGGTCTTCGT.

In some embodiments, the nucleic acid comprises the sequence of SEQ ID NO: 24, shown below (VSV vector: Convac V4 China):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

-continued
```
ATATTCTTCCGTCAAAAACCCTGCCTTCCACTTCTGGGGGCAATTGACAGCTCTT
CTGCTCAGATCCACCAGAGCAAGGAATGCCCGACAGCCTGATGACATTGAGTAT
ACATCTCTTACTACAGCAGGTTTGTTGTACGCTTATGCAGTAGGATCCTCTGCCG
ACTTGGCACAACAGTTTTGTGTTGGAGATAACAAATACACTCCAGATGATAGTAC
CGGAGGATTGACGACTAATGCACCGCCACAAGGCAGAGATGTGGTCGAATGGCT
CGGATGGTTTGAAGATCAAAACAGAAAACCGACTCCTGATATGATGCAGTATGC
GAAAAGAGCAGTCATGTCACTGCAAGGCCTAAGAGAGAAGACAATTGGCAAGT
ATGCTAAGTCAGAATTTGACAAATGACCCTATAATTCTCAGATCACCTATTATAT
ATTATGCTACATATGAAAAAAACTAACAGATATCATGGATAATCTCACAAAAGT
TCGTGAGTATCTCAAGTCCTATTCTCGTCTGGATCAGGCGGTAGGAGAGATAGAT
GAGATCGAAGCACAACGAGCTGAAAAGTCCAATTATGAGTTGTTCCAAGAGGAT
GGAGTGGAAGAGCATACTAAGCCCTCTTATTTTCAGGCAGCAGATGATTCTGAC
ACAGAATCTGAACCAGAAATTGAAGACAATCAAGGTTTGTATGCACCAGATCCA
GAAGCTGAGCAAGTTGAAGGCTTTATACAGGGGCCTTTAGATGACTATGCAGAT
GAGGAAGTGGATGTTGTATTTACTTCGGACTGGAAACAGCCTGAGCTTGAATCTG
ACGAGCATGGAAAGACCTTACGGTTGACATCGCCAGAGGGTTTAAGTGGAGAGC
AGAAATCCCAGTGGCTTTCGACGATTAAAGCAGTCGTGCAAAGTGCCAAATACT
GGAATCTGGCAGAGTGCACATTTGAAGCATCGGGAGAAGGGGTCATTATGAAGG
AGCGCCAGATAACTCCGGATGTATATAAGGTCACTCCAGTGATGAACACACATC
CGTCCCAATCAGAAGCAGTATCAGATGTTTGGTCTCTCAAAGACATCCATGAC
TTTCCAACCCAAGAAAGCAAGTCTTCAGCCTCTCACCATATCCTTGGATGAATTG
TTCTCATCTAGAGGAGAGTTCATCTCTGTCGGAGGTGACGGACGAATGTCTCATA
AAGAGGCCATCCTGCTCGGCCTGAGATACAAAAAGTTGTACAATCAGGCGAGAG
TCAAATATTCTCTGTAGACTATGAAAAAAAGTAACAGATATCACGATCTAAGTGT
TATCCCAATCCATTCATCATGAGTTCCTTAAAGAAGATTCTCGGTCTGAAGGGGA
AAGGTAAGAAATCTAAGAAATTAGGGATCGCACCACCCCCTTATGAAGAGGACA
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAACTAACA
GAGATCGATCTGTTTACGCGTGCCACCATGTTCGTGTTTCTGGTGCTGCTGCCTCT
GGTGAGCTCCCAGTGCGTGAACCTGACCACAAGGACCCAGCTGCCCCCTGCCTA
```

-continued

```
TACCAATTCCTTCACACGGGGCGTGTACTATCCCGACAAGGTGTTCCGGAGCAGC

GTGCTGCACTCCACACAGGATCTGTTTCTGCCTTTCTTTTCTAACGTGACCTGGTT

CCACGCCATCCACGTGAGCGGCACCAATGGCACAAAGCGGTTCGACAATCCAGT

GCTGCCCTTTAACGATGGCGTGTACTTCGCCTCCACCGAGAAGTCTAACATCATC

AGAGGCTGGATCTTTGGCACCACACTGGACAGCAAGACACAGTCCCTGCTGATC

GTGAACAATGCCACCAACGTGGTCATCAAGGTGTGCGAGTTCCAGTTTTGTAATG

ATCCATTCCTGGGCGTGTACTATCACAAGAACAATAAGTCTTGGATGGAGAGCG

AGTTTCGCGTGTATTCCTCTGCCAACAATTGCACATTTGAGTACGTGTCCCAGCC

CTTCCTGATGGACCTGGAGGGCAAGCAGGGCAATTTCAAGAACCTGAGGGAGTT

CGTGTTTAAGAATATCGATGGCTACTTCAAAATCTACTCCAAGCACACCCCAATC

AACCTGGTGCGCGACCTGCCACAGGGCTTCTCTGCCCTGGAGCCACTGGTGGATC

TGCCCATCGGCATCAACATCACCCGGTTTCAGACACTGCTGGCCCTGCACAGAA

GCTACCTGACACCAGGCGACAGCTCCTCTGGATGGACCGCAGGAGCAGCAGCCT

ACTATGTGGGCTATCTGCAGCCCAGGACCTTCCTGCTGAAGTACAACGAGAATG

GCACCATCACAGACGCCGTGGATTGCGCCCTGGATCCCCTGTCTGAGACCAAGT

GTACACTGAAGAGCTTTACCGTGGAGAAGGGCATCTATCAGACAAGCAATTTCA

GGGTGCAGCCTACCGAGTCCATCGTGCGCTTTCCCAATATCACAAACCTGTGCCC

TTTTGGCGAGGTGTTCAACGCAACCCGCTTCGCCAGCGTGTACGCCTGGAATAGG

AAGCGCATCTCCAACTGCGTGGCCGACTATTCTGTGCTGTACAACAGCGCCTCCT

TCTCTACCTTTAAGTGCTATGGCGTGAGCCCCACAAAGCTGAATGACCTGTGCTT

TACCAACGTGTACGCCGATTCCTTCGTGATCAGGGGCGACGAGGTGCGCCAGAT

CGCACCAGGACAGACAGGCAAGATCGCAGACTACAATTATAAGCTGCCTGACGA

TTTCACCGGCTGCGTGATCGCCTGGAACTCTAACAATCTGGATAGCAAAGTGGGC

GGCAACTACAATTATCTGTACCGGCTGTTTAGAAAGTCTAATCTGAAGCCATTCG

AGAGGGACATCTCCACAGAAATCTACCAGGCCGGCTCTACCCCCTGCAATGGCG

TGGAGGGCTTTAACTGTTATTTCCCTCTGCAGAGCTACGGCTTCCAGCCAACAAA

CGGCGTGGGCTATCAGCCCTACCGCGTGGTGGTGCTGTCTTTTGAGCTGCTGCAC

GCACCTGCAACAGTGTGCGGACCAAAGAAGAGCACCAATCTGGTGAAGAACAA

GTGCGTGAACTTCAACTTCAACGGACTGACCGGAACAGGCGTGCTGACCGAGTC

CAACAAGAAGTTCCTGCCTTTTCAGCAGTTCGGCAGGGACATCGCAGATACCAC

AGACGCCGTGCGCGACCCTCAGACCCTGGAGATCCTGGACATCACACCATGCTC

CTTCGGCGGCGTGTCTGTGATCACACCAGGCACCAATACAAGCAACCAGGTGGC

CGTGCTGTATCAGGACGTGAATTGTACCGAGGTGCCAGTGGCAATCCACGCAGA

TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAAGggatcc
```

-continued ggctccggcgagggcaggggaagtctactaacatgcggggacgtggaggaaaatcccggcccc
ATGAAGTGCCTTTTGTACTTAGCCTTTTTATTCATTGGGGTGAATTGCAAGTTCACCATAGTTT
TTCCACACAACCAAAAAGGAAACTGGAAAAATGTTCCTTCTAATTACCATTATTG
CCCGTCAAGCTCAGATTTAAATTGGCATAATGACTTAATAGGCACAGCCATACA
AGTCAAAATGCCCAAGAGTCACAAGGCTATTCAAGCAGACGGTTGGATGTGTCA
TGCTTCCAAATGGGTCACTACTTGTGATTTCCGCTGGTATGGACCGAAGTATATA
ACACAGTCCATCCGATCCTTCACTCCATCTGTAGAACAATGCAAGGAAAGCATT
GAACAAACGAAACAAGGAACTTGGCTGAATCCAGGCTTCCCTCCTCAAAGTTGT
GGATATGCAACTGTGACGGATGCCGAAGCAGTGATTGTCCAGGTGACTCCTCAC
CATGTGCTGGTTGATGAATACACAGGAGAATGGGTTGATTCACAGTTCATCAAC
GGAAAATGCAGCAATTACATATGCCCCACTGTCCATAACTCTACAACCTGGCATT
CTGACTATAAGGTCAAAGGGCTATGTGATTCTAACCTCATTTCCATGGACATCAC
CTTCTTCTCAGAGGACGGAGAGCTATCATCCCTGGGAAAGGAGGGCACAGGGTT
CAGAAGTAACTACTTTGCTTATGAAACTGGAGGCAAGGCCTGCAAAATGCAATA
CTGCAAGCATTGGGGAGTCAGACTCCCATCAGGTGTCTGGTTCGAGATGGCTGAT
AAGGATCTCTTTGCTGCAGCCAGATTCCCTGAATGCCCAGAAGGGTCAAGTATCT
CTGCTCCATCTCAGACCTCAGTGGATGTAAGTCTAATTCAGGACGTTGAGAGGAT
CTTGGATTATTCCCTCTGCCAAGAAACCTGGAGCAAAATCAGAGCGGGTCTTCCA
ATCTCTCCAGTGGATCTCAGCTATCTTGCTCCTAAAAACCCAGGAACCGGTCCTG
CTTTCACCATAATCAATGGTACCCTAAAATACTTTGAGACCAGATACATCAGAGT
CGATATTGCTGCTCCAATCCTCTCAAGAATGGTCGGAATGATCAGTGGAACTACC
ACAGAAAGGGAACTGTGGGATGACTGGGCACCATATGAAGACGTGGAAATTGG
ACCCAATGGAGTTCTGAGGACCAGTTCAGGATATAAGTTTCCTTTATACATGATT
GGACATGGTATGTTGGACTCCGATCTTCATCTTAGCTCAAAGGCTCAGGTGTTCG
AACATCCTCACATTCAAGACGCTGCTTCGCAACTTCCTGATGATGAGAGTTTATT
TTTTGGTGATACTGGGCTATCCAAAAATCCAATCGAGCTTGTAGAAGGTTGGTTC
AGTAGTTGGAAAAGCTCTATTGCCTCTTTTTTCTTTATCATAGGGTTAATCATTGG
ACTATTCTTGGTTCTCCGAGTTGGTATCCATCTTTGCATTAAATTAAAGCACACCA
AGAAAAGACAGATTTATACAGACATAGAGATGAACCGACTTGGAAAGTAAgCTA
GCCAGATTCTTCATGTTTGGACCAAATCAACTTGTGATACCATGCTCAAAGAGGC
CTCAATTATATTTGAGTTTTTAATTTTTATGAAAAAAACTAACAGCAATCATGGA
AGTCCACGATTTTGAGACCGACGAGTTCAATGATTTCAATGAAGATGACTATGCC
ACAAGAGAATTCCTGAATCCCGATGAGCGCATGACGTACTTGAATCATGCTGATT
ACAATTTGAATTCTCCTCTAATTAGTGATGATATTGACAATTTGATCAGGAAATT
CAATTCTCTTCCGATTCCCTCGATGTGGGATAGTAAGAACTGGGATGGAGTTCTT
GAGATGTTAACATCATGTCAAGCCAATCCCATCTCAACATCTCAGATGCATAAAT
GGATGGAAGTTGGTTAATGTCTGATAATCATGATGCCAGTCAAGGGTATAGTTT
TTTACATGAAGTGGACAAAGAGGCAGAAATAACATTTGACGTGGTGGAGACCTT
CATCCGCGGCTGGGGCAACAAACCAATTGAATACATCAAAAAGGAAAGATGGA
CTGACTCATTCAAAATTCTCGCTTATTGTGTCAAAAGTTTTTGGACTTACACAAG
TTGACATTAATCTTAAATGCTGTCTCTGAGGTGGAATTGCTCAACTTGGCGAGGA -continued

```
CTTTCAAAGGCAAAGTCAGAAGAAGTTCTCATGGAACGAACATATGCAGGATTA

GGGTTCCCAGCTTGGGTCCTACTTTTATTTCAGAAGGATGGGCTTACTTCAAGAA

ACTTGATATTCTAATGGACCGAAACTTTCTGTTAATGGTCAAAGATGTGATTATA

GGGAGGATGCAAACGGTGCTATCCATGGTATGTAGAATAGACAACCTGTTCTCA

GAGCAAGACATCTTCTCCCTTCTAAATATCTACAGAATTGGAGATAAAATTGTGG

AGAGGCAGGGAAATTTTTCTTATGACTTGATTAAAATGGTGGAACCGATATGCA

ACTTGAAGCTGATGAAATTAGCAAGAGAATCAAGGCCTTTAGTCCCACAATTCC

CTCATTTTGAAAATCATATCAAGACTTCTGTTGATGAAGGGGCAAAAATTGACCG

AGGTATAAGATTCCTCCATGATCAGATAATGAGTGTGAAAACAGTGGATCTCAC

ACTGGTGATTTATGGATCGTTCAGACATTGGGGTCATCCTTTTATAGATTATTAC

ACTGGACTAGAAAAATTACATTCCCAAGTAACCATGAAGAAAGATATTGATGTG

TCATATGCAAAAGCACTTGCAAGTGATTTAGCTCGGATTGTTCTATTTCAACAGT

TCAATGATCATAAAAAGTGGTTCGTGAATGGAGACTTGCTCCCTCATGATCATCC

CTTTAAAAGTCATGTTAAAGAAAATACATGGCCCACAGCTGCTCAAGTTCAAGA

TTTTGGAGATAAATGGCATGAACTTCCGCTGATTAAATGTTTTGAAATACCCGAC

TTACTAGACCCATCGATAATATACTCTGACAAAAGTCATTCAATGAATAGGTCAG

AGGTGTTGAAACATGTCCGAATGAATCCGAACACTCCTATCCCTAGTAAAAAGG

TGTTGCAGACTATGTTGGACACAAAGGCTACCAATTGGAAAGAATTTCTTAAAG

AGATTGATGAGAAGGGCTTAGATGATGATGATCTAATTATTGGTCTTAAAGGAA

AGGAGAGGGAACTGAAGTTGGCAGGTAGATTTTTCTCCCTAATGTCTTGGAAATT

GCGAGAATACTTTGTAATTACCGAATATTTGATAAAGACTCATTTCGTCCCTATG

TTTAAAGGCCTGACAATGGCGGACGATCTAACTGCAGTCATTAAAAAGATGTTA

GATTCCTCATCCGGCCAAGGATTGAAGTCATATGAGGCAATTTGCATAGCCAATC

ACATTGATTACGAAAAATGGAATAACCACCAAAGGAAGTTATCAAACGGCCCAG

TGTTCCGAGTTATGGGCCAGTTCTTAGGTTATCCATCCTTAATCGAGAGAACTCA

TGAATTTTTTGAGAAAAGTCTTATATACTACAATGGAAGACCAGACTTGATGCGT

GTTCACAACAACACACTGATCAATTCAACCTCCCAACGAGTTTGTTGGCAAGGA

CAAGAGGGTGGACTGGAAGGTCTACGGCAAAAAGGATGGACTATCCTCAATCTA

CTGGTTATTCAAAGAGAGGCTAAAATCAGAAACACTGCTGTCAAAGTCTTGGCA

CAAGGTGATAATCAAGTTATTTGCACACAGTATAAAACGAAGAAATCGAGAAAC

GTTGTAGAATTACAGGGTGCTCTCAATCAAATGGTTTCTAATAATGAGAAAATTA

TGACTGCAATCAAAATAGGGACAGGGAAGTTAGGACTTTTGATAAATGACGATG

AGACTATGCAATCTGCAGATTACTTGAATTATGGAAAAATACCGATTTTCCGTGG

AGTGATTAGAGGGTTAGAGACCAAGAGATGGTCACGAGTGACTTGTGTCACCAA

TGACCAAATACCCACTTGTGCTAATATAATGAGCTCAGTTTCCACAAATGCTCTC

ACCGTAGCTCATTTTGCTGAGAACCCAATCAATGCCATGATACAGTACAATTATT

TTGGGACATTTGCTAGACTCTTGTTGATGATGCATGATCCTGCTCTTCGTCAATCA

TTGTATGAAGTTCAAGATAAGATACCGGGCTTGCACAGTTCTACTTTCAAATACG

CCATGTTGTATTTGGACCCTTCCATTGGAGGAGTGTCGGGCATGTCTTTGTCCAG

GTTTTTGATTAGAGCCTTCCCAGATCCCGTAACAGAAAGTCTCTCATTCTGGAGA
```

-continued

```
TTCATCCATGTACATGCTCGAAGTGAGCATCTGAAGGAGATGAGTGCAGTATTTG

GAAACCCCGAGATAGCCAAGTTTCGAATAACTCACATAGACAAGCTAGTAGAAG

ATCCAACCTCTCTGAACATCGCTATGGGAATGAGTCCAGCGAACTTGTTAAAGAC

TGAGGTTAAAAAATGCTTAATCGAATCAAGACAAACCATCAGGAACCAGGTGAT

TAAGGATGCAACCATATATTTGTATCATGAAGAGGATCGGCTCAGAAGTTTCTTA

TGGTCAATAAATCCTCTGTTCCCTAGATTTTTAAGTGAATTCAAATCAGGCACTTT

TTTGGGAGTCGCAGACGGGCTCATCAGTCTATTTCAAAATTCTCGTACTATTCGG

AACTCCTTTAAGAAAAAGTATCATAGGGAATTGGATGATTTGATTGTGAGGAGT

GAGGTATCCTCTTTGACACATTTAGGGAAACTTCATTTGAGAAGGGGATCATGTA

AAATGTGGACATGTTCAGCTACTCATGCTGACACATTAAGATACAAATCCTGGG

GCCGTACAGTTATTGGGACAACTGTACCCCATCCATTAGAAATGTTGGGTCCACA

ACATCGAAAGAGACTCCTTGTGCACCATGTAACACATCAGGGTTCAATTATGTT

TCTGTGCATTGTCCAGACGGGATCCATGACGTCTTTAGTTCACGGGGACCATTGC

CTGCTTATCTAGGGTCTAAAACATCTGAATCTACATCTATTTTGCAGCCTTGGGA

AAGGGAAAGCAAAGTCCCACTGATTAAAAGAGCTACACGTCTTAGAGATGCTAT

CTCTTGGTTTGTTGAACCCGACTCTAAACTAGCAATGACTATACTTTCTAACATCC

ACTCTTTAACAGGCGAAGAATGGACCAAAAGGCAGCATGGGTTCAAAAGAACA

GGGTCTGCCCTTCATAGGTTTTCGACATCTCGGATGAGCCATGGTGGGTTCGCAT

CTCAGAGCACTGCAGCATTGACCAGGTTGATGGCAACTACAGACACCATGAGGG

ATCTGGGAGATCAGAATTTCGACTTTTTATTCCAAGCAACGTTGCTCTATGCTCA

AATTACCACCACTGTTGCAAGAGACGGATGGATCACCAGTTGTACAGATCATTAT

CATATTGCCTGTAAGTCCTGTTTGAGACCCATAGAAGAGATCACCCTGGACTCAA

GTATGGACTACACGCCCCCAGATGTATCCCATGTGCTGAAGACATGGAGGAATG

GGGAAGGTTCGTGGGACAAGAGATAAAACAGATCTATCCTTTAGAAGGGAATT

GGAAGAATTTAGCACCTGCTGAGCAATCCTATCAAGTCGGCAGATGTATAGGTTT

TCTATATGGAGACTTGGCGTATAGAAAATCTACTCATGCCGAGGACAGTTCTCTA

TTTCCTCTATCTATACAAGGTCGTATTAGAGGTCGAGGTTTCTTAAAAGGGTTGC

TAGACGGATTAATGAGAGCAAGTTGCTGCCAAGTAATACACCGGAGAAGTCTGG

CTCATTTGAAGAGGCCGGCCAACGCAGTGTACGGAGGTTTGATTTACTTGATTGA

TAAATTGAGTGTATCACCTCCATTCCTTTCTCTTACTAGATCAGGACCTATTAGAG

ACGAATTAGAAACGATTCCCCACAAGATCCCAACCTCCTATCCGACAAGCAACC

GTGATATGGGGTGATTGTCAGAAATTACTTCAAATACCAATGCCGTCTAATTGA

AAAGGGAAAATACAGATCACATTATTCACAATTATGGTTATTCTCAGATGTCTTA

TCCATAGACTTCATTGGACCATTCTCTATTTCCACCACCCTCTTGCAAATCCTATA

CAAGCCATTTTTATCTGGGAAAGATAAGAATGAGTTGAGAGAGCTGGCAAATCT

TTCTTCATTGCTAAGATCAGGAGAGGGGTGGGAAGACATACATGTGAAATTCTTC

ACCAAGGACATATTATTGTGTCCAGAGGAAATCAGACATGCTTGCAAGTTCGGG

ATTGCTAAGGATAATAATAAAGACATGAGCTATCCCCCTTGGGGAAGGGAATCC

AGAGGGACAATTACAACAATCCCTGTTTATTATACGACCACCCCTTACCCAAAG

ATGCTAGAGATGCCTCCAAGAATCCAAAATCCCCTGCTGTCCGGAATCAGGTTG

GGCCAATTACCAACTGGCGCTCATTATAAAATTCGGAGTATATTACATGGAATGG
```

-continued

```
GAATCCATTACAGGGACTTCTTGAGTTGTGGAGACGGCTCCGGAGGGATGACTG

CTGCATTACTACGAGAAAATGTGCATAGCAGAGGAATATTCAATAGTCTGTTAG

AATTATCAGGGTCAGTCATGCGAGGCGCCTCTCCTGAGCCCCCCAGTGCCCTAGA

AACTTTAGGAGGAGATAAATCGAGATGTGTAAATGGTGAAACATGTTGGGAATA

TCCATCTGACTTATGTGACCCAAGGACTTGGGACTATTTCCTCCGACTCAAAGCA

GGCTTGGGGCTTCAAATTGATTTAATTGTAATGGATATGGAAGTTCGGGATTCTT

CTACTAGCCTGAAAATTGAGACGAATGTTAGAAATTATGTGCACCGGATTTTGGA

TGAGCAAGGAGTTTTAATCTACAAGACTTATGGAACATATATTTGTGAGAGCGA

AAAGAATGCAGTAACAATCCTTGGTCCCATGTTCAAGACGGTCGACTTAGTTCAA

ACAGAATTTAGTAGTTCTCAAACGTCTGAAGTATATATGGTATGTAAAGGTTTGA

AGAAATTAATCGATGAACCCAATCCCGATTGGTCTTCCATCAATGAATCCTGGAA

AAACCTGTACGCATTCCAGTCATCAGAACAGGAATTTGCCAGAGCAAAGAAGGT

TAGTACATACTTTACCTTGACAGGTATTCCCTCCCAATTCATTCCTGATCCTTTTG

TAAACATTGAGACTATGCTACAAATATTCGGAGTACCCACGGGTGTGTCTCATGC

GGCTGCCTTAAAATCATCTGATAGACCTGCAGATTTATTGACCATTAGCCTTTTTT

ATATGGCGATTATATCGTATTATAACATCAATCATATCAGAGTAGGACCGATACC

TCCGAACCCCCCATCAGATGGAATTGCACAAAATGTGGGGATCGCTATAACTGG

TATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAG

GAGGATACAAGCAGAAGTGGAGTACTAGAGGTGATGGGCTCCCAAAAGATACC

CGAACTTCAGACTCCTTGGCCCCAATCGGGAACTGGATCAGATCTCTGGAATTGG

TCCGAAACCAAGTTCGTCTAAATCCATTCAATGAGATCTTGTTCAATCAGCTATG

TCGTACAGTGGATAATCATTTGAAATGGTCAAATTTGCGAAGAAACACAGGAAT

GATTGAATGGATCAATAGACGAATTTCAAAAGAAGACCGGTCTATACTGATGTT

GAAGAGTGACCTACACGAGGAAAACTCTTGGAGAGATTAAAAAATCATGAGGA

GACTCCAAACTTTAAGTATGAAAAAAACTTTGATCCTTAAGACCCTCTTGTGGTT

TTTATTTTTTATCTGGTTTTGTGGTCTTCGT.
```

In other embodiments, the nucleic acid comprises the sequence of SEQ ID NO: 25, shown below (VSV vector: Convac V4 South Africa):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG
```

```
ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGGAAGACCCCTCCCATGCTCAATGTACCAGAGCACTTC
```

-continued

```
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCTCCTAATTCC
AGCCTCTCGAACAACTAATATCCTGTCTTTTCTATCCCTATGAAAAAAACTAACA
GAGATCGATCTGTTTACGCGTGCCACCATGTTCGTGTTTCTGGTGCTGCTGCCTCT
GGTGAGCTCCCAGTGCGTGAACTTCACCACAAGGACCCAGCTGCCCCCTGCCTAT
ACCAATTCCTTCACACGGGGCGTGTACTATCCCGACAAGGTGTTCCGGAGCAGC
GTGCTGCACTCCACACAGGATCTGTTTCTGCCTTTCTTTTCTAACGTGACCTGGTT
CCACGCCATCCACGTGAGCGGCACCAATGGCACAAAGCGGTTCGCCAATCCAGT
GCTGCCCTTTAACGATGGCGTGTACTTCGCCTCCACCGAGAAGTCTAACATCATC
AGAGGCTGGATCTTTGGCACCACACTGGACAGCAAGACACAGTCCCTGCTGATC
GTGAACAATGCCACCAACGTGGTCATCAAGGTGTGCGAGTTCCAGTTTTGTAATG
ATCCATTCCTGGGCGTGTACTATCACAAGAACAATAAGTCTTGGATGGAGAGCG
AGTTTCGCGTGTATTCCTCTGCCAACAATTGCACATTTGAGTACGTGTCCCAGCC
CTTCCTGATGGACCTGGAGGGCAAGCAGGGCAATTTCAAGAACCTGAGGGAGTT
CGTGTTTAAGAATATCGATGGCTACTTCAAAATCTACTCCAAGCACACCCCAATC
AACCTGGTGCGCGGCCTGCCACAGGGCTTCTCTGCCCTGGAGCCACTGGTGGATC
TGCCCATCGGCATCAACATCACCCGGTTTCAGACACTGCTGGCCCTGCACAGAA
GCTACCTGACACCAGGCGACAGCTCCTCTGGATGGACCGCAGGAGCAGCAGCCT
ACTATGTGGGCTATCTGCAGCCCAGGACCTTCCTGCTGAAGTACAACGAGAATG
GCACCATCACAGACGCCGTGGATTGCGCCCTGGATCCCCTGTCTGAGACCAAGT
GTACACTGAAGAGCTTTACCGTGGAGAAGGGCATCTATCAGACAAGCAATTTCA
GGGTGCAGCCTACCGAGTCCATCGTGCGCTTTCCCAATATCACAAACCTGTGCCC
TTTTGGCGAGGTGTTCAACGCAACCCGCTTCGCCAGCGTGTACGCCTGGAATAGG
AAGCGCATCTCCAACTGCGTGGCCGACTATTCTGTGCTGTACAACAGCGCCTCCT
TCTCTACCTTTAAGTGCTATGGCGTGAGCCCCACAAAGCTGAATGACCTGTGCTT
TACCAACGTGTACGCCGATTCCTTCGTGATCAGGGGCGACGAGGTGCGCCAGAT
CGCACCAGGACAGACAGGCAATATCGCAGACTACAATTATAAGCTGCCTGACGA
TTTCACCGGCTGCGTGATCGCCTGGAACTCTAACAATCTGGATAGCAAAGTGGGC
GGCAACTACAATTATCTGTACCGGCTGTTTAGAAAGTCTAATCTGAAGCCATTCG
AGAGGGACATCTCCACAGAAATCTACCAGGCCGGCTCTACCCCCTGCAATGGCG
TGAAGGGCTTTAACTGTTATTTCCCTCTGCAGAGCTACGGCTTCCAGCCAACATA
TGGCGTGGGCTATCAGCCCTACCGCGTGGTGGTGCTGTCTTTTGAGCTGCTGCAC
GCACCTGCAACAGTGTGCGGACCAAAGAAGAGCACCAATCTGGTGAAGAACAA
GTGCGTGAACTTCAACTTCAACGGACTGACCGGAACAGGCGTGCTGACCGAGTC
CAACAAGAAGTTCCTGCCTTTTCAGCAGTTCGGCAGGGACATCGCAGATACCAC
AGACGCCGTGCGCGACCCTCAGACCCTGGAGATCCTGGACATCACACCATGCTC
CTTCGGCGGCGTGTCTGTGATCACACCAGGCACCAATACAAGCAACCAGGTGGC
CGTGCTGTATCAGGGCGTGAATTGTACCGAGGTGCCAGTGGCAATCCACGCAGA
```

```
TCAGCTGACCCCTACATGGCGGGTGTACTCTACCGGCAGCAACGTGTTCCAGAC

AAGAGCCGGATGCCTGATCGGAGCAGAGCACGTGAACAATAGCTATGAGTGCGA

CATCCCTATCGGCGCCGGCATCTGTGCCTCCTACCAGACCCAGACAAACTCCCCA

AGGTCTGTGGGCGATACAGGCCTGTCCAAGAATCCAATCGAGCTGGTAGAGGGC

TGGTTCAGCAGTTGGAAAAGCTCCATCGCCTCCTTTTTCTTTATCATCGGCCTGAT

CATCGGACTGTTCCTGGTGCTCCGCGTGGGTATCCACCTGTGCATCAAGCTGAAG

CACACCAAGAAAAGACAGATTTATACAGACATCGAGATGAACCGCCTGGGAAAGggatcc ggctccggcgagggcaggggaagtctactaacatgcggggacgtggaggaaaatcccggcccc

ATGAAGTGCCTTTTGTACTTAGCCTTTTTATTCATTGGGGTGAATTGCAAGTTCACCATAGTTT

TTCCACACAACCAAAAAGGAAACTGGAAAAATGTTCCTTCTAATTACCATTATTG

CCCGTCAAGCTCAGATTTAAATTGGCATAATGACTTAATAGGCACAGCCATACA

AGTCAAAATGCCCAAGAGTCACAAGGCTATTCAAGCAGACGGTTGGATGTGTCA

TGCTTCCAAATGGGTCACTACTTGTGATTTCCGCTGGTATGGACCGAAGTATATA

ACACAGTCCATCCGATCCTTCACTCCATCTGTAGAACAATGCAAGGAAAGCATT

GAACAAACGAAACAAGGAACTTGGCTGAATCCAGGCTTCCCTCCTCAAAGTTGT

GGATATGCAACTGTGACGGATGCCGAAGCAGTGATTGTCCAGGTGACTCCTCAC

CATGTGCTGGTTGATGAATACACAGGAGAATGGGTTGATTCACAGTTCATCAAC

GGAAAATGCAGCAATTACATATGCCCCACTGTCCATAACTCTACAACCTGGCATT

CTGACTATAAGGTCAAAGGGCTATGTGATTCTAACCTCATTTCCATGGACATCAC

CTTCTTCTCAGAGGACGGAGAGCTATCATCCCTGGGAAAGGAGGGCACAGGGTT

CAGAAGTAACTACTTTGCTTATGAAACTGGAGGCAAGGCCTGCAAAATGCAATA

CTGCAAGCATTGGGGAGTCAGACTCCCATCAGGTGTCTGGTTCGAGATGGCTGAT

AAGGATCTCTTTGCTGCAGCCAGATTCCCTGAATGCCCAGAAGGGTCAAGTATCT

CTGCTCCATCTCAGACCTCAGTGGATGTAAGTCTAATTCAGGACGTTGAGAGGAT

CTTGGATTATTCCCTCTGCCAAGAAACCTGGAGCAAAATCAGAGCGGGTCTTCCA

ATCTCTCCAGTGGATCTCAGCTATCTTGCTCCTAAAAACCCAGGAACCGGTCCTG

CTTTCACCATAATCAATGGTACCCTAAAATACTTTGAGACCAGATACATCAGAGT

CGATATTGCTGCTCCAATCCTCTCAAGAATGGTCGGAATGATCAGTGGAACTACC

ACAGAAAGGGAACTGTGGGATGACTGGGCACCATATGAAGACGTGGAAATTGG

ACCCAATGGAGTTCTGAGGACCAGTTCAGGATATAAGTTTCCTTTATACATGATT

GGACATGGTATGTTGGACTCCGATCTTCATCTTAGCTCAAAGGCTCAGGTGTTCG

AACATCCTCACATTCAAGACGCTGCTTCGCAACTTCCTGATGATGAGAGTTTATT

TTTTGGTGATACTGGGCTATCCAAAAATCCAATCGAGCTTGTAGAAGGTTGGTTC

AGTAGTTGGAAAAGCTCTATTGCCTCTTTTTTCTTTATCATAGGGTTAATCATTGG

ACTATTCTTGGTTCTCCGAGTTGGTATCCATCTTTGCATTAAATTAAAGCACACCA

AGAAAAGACAGATTTATACAGACATAGAGATGAACCGACTTGGAAAGTAAgCTA

GCCAGATTCTTCATGTTTGGACCAAATCAACTTGTGATACCATGCTCAAAGAGGC

CTCAATTATATTTGAGTTTTTAATTTTTATGAAAAAAACTAACAGCAATCATGGA

AGTCCACGATTTTGAGACCGACAGAGTTCAATGATTTCAATGAAGATGACTATGCC

ACAAGAGAATTCCTGAATCCCGATGAGCGCATGACGTACTTGAATCATGCTGATT
```

-continued

```
ACAATTTGAATTCTCCTCTAATTAGTGATGATATTGACAATTTGATCAGGAAATT

CAATTCTCTTCCGATTCCCTCGATGTGGGATAGTAAGAACTGGGATGGAGTTCTT

GAGATGTTAACATCATGTCAAGCCAATCCCATCTCAACATCTCAGATGCATAAAT

GGATGGGAAGTTGGTTAATGTCTGATAATCATGATGCCAGTCAAGGGTATAGTTT

TTTACATGAAGTGGACAAAGAGGCAGAAATAACATTTGACGTGGTGGAGACCTT

CATCCGCGGCTGGGGCAACAAACCAATTGAATACATCAAAAAGGAAAGATGGA

CTGACTCATTCAAAATTCTCGCTTATTTGTGTCAAAAGTTTTTGGACTTACACAAG

TTGACATTAATCTTAAATGCTGTCTCTGAGGTGGAATTGCTCAACTTGGCGAGGA

CTTTCAAAGGCAAAGTCAGAAGAAGTTCTCATGGAACGAACATATGCAGGATTA

GGGTTCCCAGCTTGGGTCCTACTTTTATTTCAGAAGGATGGGCTTACTTCAAGAA

ACTTGATATTCTAATGGACCGAAACTTTCTGTTAATGGTCAAAGATGTGATTATA

GGGAGGATGCAAACGGTGCTATCCATGGTATGTAGAATAGACAACCTGTTCTCA

GAGCAAGACATCTTCTCCCTTCTAAATATCTACAGAATTGGAGATAAAATTGTGG

AGAGGCAGGGAAATTTTTCTTATGACTTGATTAAAATGGTGGAACCGATATGCA

ACTTGAAGCTGATGAAATTAGCAAGAGAATCAAGGCCTTTAGTCCCACAATTCC

CTCATTTTGAAAATCATATCAAGACTTCTGTTGATGAAGGGGCAAAAATTGACCG

AGGTATAAGATTCCTCCATGATCAGATAATGAGTGTGAAAACAGTGGATCTCAC

ACTGGTGATTTATGGATCGTTCAGACATTGGGGTCATCCTTTTATAGATTATTAC

ACTGGACTAGAAAAATTACATTCCCAAGTAACCATGAAGAAAGATATTGATGTG

TCATATGCAAAAGCACTTGCAAGTGATTTAGCTCGGATTGTTCTATTTCAACAGT

TCAATGATCATAAAAAGTGGTTCGTGAATGGAGACTTGCTCCCTCATGATCATCC

CTTTAAAAGTCATGTTAAAGAAAATACATGGCCCACAGCTGCTCAAGTTCAAGA

TTTTGGAGATAAATGGCATGAACTTCCGCTGATTAAATGTTTTGAAATACCCGAC

TTACTAGACCCATCGATAATATACTCTGACAAAAGTCATTCAATGAATAGGTCAG

AGGTGTTGAAACATGTCCGAATGAATCCGAACACTCCTATCCCTAGTAAAAAGG

TGTTGCAGACTATGTTGGACACAAAGGCTACCAATTGGAAAGAATTTCTTAAAG

AGATTGATGAGAAGGGCTTAGATGATGATGATCTAATTATTGGTCTTAAAGGAA

AGGAGAGGGAACTGAAGTTGGCAGGTAGATTTTTCTCCCTAATGTCTTGGAAATT

GCGAGAATACTTTGTAATTACCGAATATTTGATAAAGACTCATTTCGTCCCTATG

TTTAAAGGCCTGACAATGGCGGACGATCTAACTGCAGTCATTAAAAAGATGTTA

GATTCCTCATCCGGCCAAGGATTGAAGTCATATGAGGCAATTTGCATAGCCAATC

ACATTGATTACGAAAAATGGAATAACCACCAAAGGAAGTTATCAAACGGCCCAG

TGTTCCGAGTTATGGGCCAGTTCTTAGGTTATCCATCCTTAATCGAGAGAACTCA

TGAATTTTTTGAGAAAAGTCTTATATACTACAATGGAAGACCAGACTTGATGCGT

GTTCACAACAACACACTGATCAATTCAACCTCCCAACGAGTTTGTTGGCAAGGA

CAAGAGGGTGGACTGGAAGGTCTACGGCAAAAAGGATGGACTATCCTCAATCTA

CTGGTTATTCAAAGAGAGGCTAAAATCAGAAACACTGCTGTCAAAGTCTTGGCA

CAAGGTGATAATCAAGTTATTTGCACACAGTATAAAACGAAGAAATCGAGAAAC

GTTGTAGAATTACAGGGTGCTCTCAATCAAATGGTTTCTAATAATGAGAAAATTA

TGACTGCAATCAAAATAGGGACAGGGAAGTTAGGACTTTTGATAAATGACGATG

AGACTATGCAATCTGCAGATTACTTGAATTATGGAAAAATACCGATTTTCCGTGG
```

```
AGTGATTAGAGGGTTAGAGACCAAGAGATGGTCACGAGTGACTTGTGTCACCAA

TGACCAAATACCCACTTGTGCTAATATAATGAGCTCAGTTTCCACAAATGCTCTC

ACCGTAGCTCATTTTGCTGAGAACCCAATCAATGCCATGATACAGTACAATTATT

TTGGGACATTTGCTAGACTCTTGTTGATGATGCATGATCCTGCTCTTCGTCAATCA

TTGTATGAAGTTCAAGATAAGATACCGGGCTTGCACAGTTCTACTTTCAAATACG

CCATGTTGTATTTGGACCCTTCCATTGGAGGAGTGTCGGGCATGTCTTTGTCCAG

GTTTTTGATTAGAGCCTTCCCAGATCCCGTAACAGAAAGTCTCTCATTCTGGAGA

TTCATCCATGTACATGCTCGAAGTGAGCATCTGAAGGAGATGAGTGCAGTATTTG

GAAACCCCGAGATAGCCAAGTTTCGAATAACTCACATAGACAAGCTAGTAGAAG

ATCCAACCTCTCTGAACATCGCTATGGGAATGAGTCCAGCGAACTTGTTAAAGAC

TGAGGTTAAAAAATGCTTAATCGAATCAAGACAAACCATCAGGAACCAGGTGAT

TAAGGATGCAACCATATATTTGTATCATGAAGAGGATCGGCTCAGAAGTTTCTTA

TGGTCAATAAATCCTCTGTTCCCTAGATTTTTAAGTGAATTCAAATCAGGCACTTT

TTTGGGAGTCGCAGACGGGCTCATCAGTCTATTTCAAAATTCTCGTACTATTCGG

AACTCCTTTAAGAAAAAGTATCATAGGGAATTGGATGATTTGATTGTGAGGAGT

GAGGTATCCTCTTTGACACATTTAGGGAAACTTCATTTGAGAAGGGGATCATGTA

AAATGTGGACATGTTCAGCTACTCATGCTGACACATTAAGATACAAATCCTGGG

GCCGTACAGTTATTGGGACAACTGTACCCCATCCATTAGAAATGTTGGGTCCACA

ACATCGAAAAGAGACTCCTTGTGCACCATGTAACACATCAGGGTTCAATTATGTT

TCTGTGCATTGTCCAGACGGGATCCATGACGTCTTTAGTTCACGGGGACCATTGC

CTGCTTATCTAGGGTCTAAAACATCTGAATCTACATCTATTTTGCAGCCTTGGGA

AAGGGAAAGCAAAGTCCCACTGATTAAAAGAGCTACACGTCTTAGAGATGCTAT

CTCTTGGTTTGTTGAACCCGACTCTAAACTAGCAATGACTATACTTTCTAACATCC

ACTCTTTAACAGGCGAAGAATGGACCAAAAGGCAGCATGGGTTCAAAAGAACA

GGGTCTGCCCTTCATAGGTTTTCGACATCTCGGATGAGCCATGGTGGGTTCGCAT

CTCAGAGCACTGCAGCATTGACCAGGTTGATGGCAACTACAGACACCATGAGGG

ATCTGGGAGATCAGAATTTCGACTTTTTATTCCAAGCAACGTTGCTCTATGCTCA

AATTACCACCACTGTTGCAAGAGACGGATGGATCACCAGTTGTACAGATCATTAT

CATATTGCCTGTAAGTCCTGTTTGAGACCCATAGAAGAGATCACCCTGGACTCAA

GTATGGACTACACGCCCCCAGATGTATCCCATGTGCTGAAGACATGGAGGAATG

GGGAAGGTTCGTGGGGACAAGAGATAAAACAGATCTATCCTTTAGAAGGGAATT

GGAAGAATTTAGCACCTGCTGAGCAATCCTATCAAGTCGGCAGATGTATAGGTTT

TCTATATGGAGACTTGGCGTATAGAAAATCTACTCATGCCGAGGACAGTTCTCTA

TTTCCTCTATCTATACAAGGTCGTATTAGAGGTCGAGGTTTCTTAAAAGGGTTGC

TAGACGGATTAATGAGAGCAAGTTGCTGCCAAGTAATACACCGGAGAAGTCTGG

CTCATTTGAAGAGGCCGGCCAACGCAGTGTACGGAGGTTTGATTTACTTGATTGA

TAAATTGAGTGTATCACCTCCATTCCTTTCTCTTACTAGATCAGGACCTATTAGAG

ACGAATTAGAAACGATTCCCCACAAGATCCCAACCTCCTATCCGACAAGCAACC

GTGATATGGGGTGATTGTCAGAAATTACTTCAAATACCAATGCCGTCTAATTGA

AAAGGGAAAATACAGATCACATTATTCACAATTATGGTTATTCTCAGATGTCTTA
```

-continued
```
TCCATAGACTTCATTGGACCATTCTCTATTTCCACCACCCTCTTGCAAATCCTATA

CAAGCCATTTTTATCTGGGAAAGATAAGAATGAGTTGAGAGAGCTGGCAAATCT

TTCTTCATTGCTAAGATCAGGAGAGGGGTGGGAAGACATACATGTGAAATTCTTC

ACCAAGGACATATTATTGTGTCCAGAGGAAATCAGACATGCTTGCAAGTTCGGG

ATTGCTAAGGATAATAATAAAGACATGAGCTATCCCCCTTGGGGAAGGGAATCC

AGAGGGACAATTACAACAATCCCTGTTTATTATACGACCACCCCTTACCCAAAG

ATGCTAGAGATGCCTCCAAGAATCCAAAATCCCCTGCTGTCCGGAATCAGGTTG

GGCCAATTACCAACTGGCGCTCATTATAAAATTCGGAGTATATTACATGGAATGG

GAATCCATTACAGGGACTTCTTGAGTTGTGGAGACGGCTCCGGAGGGATGACTG

CTGCATTACTACGAGAAAATGTGCATAGCAGAGGAATATTCAATAGTCTGTTAG

AATTATCAGGGTCAGTCATGCGAGGCGCCTCTCCTGAGCCCCCCAGTGCCCTAGA

AACTTTAGGAGGAGATAAATCGAGATGTGTAAATGGTGAAACATGTTGGGAATA

TCCATCTGACTTATGTGACCCAAGGACTTGGGACTATTTCCTCCGACTCAAAGCA

GGCTTGGGGCTTCAAATTGATTTAATTGTAATGGATATGGAAGTTCGGGATTCTT

CTACTAGCCTGAAAATTGAGACGAATGTTAGAAATTATGTGCACCGGATTTTGGA

TGAGCAAGGAGTTTTAATCTACAAGACTTATGGAACATATATTTGTGAGAGCGA

AAAGAATGCAGTAACAATCCTTGGTCCCATGTTCAAGACGGTCGACTTAGTTCAA

ACAGAATTTAGTAGTTCTCAAACGTCTGAAGTATATATGGTATGTAAAGGTTTGA

AGAAATTAATCGATGAACCCAATCCCGATTGGTCTTCCATCAATGAATCCTGGAA

AAACCTGTACGCATTCCAGTCATCAGAACAGGAATTTGCCAGAGCAAAGAAGGT

TAGTACATACTTTACCTTGACAGGTATTCCCTCCCAATTCATTCCTGATCCTTTTG

TAAACATTGAGACTATGCTACAAATATTCGGAGTACCCACGGGTGTGTCTCATGC

GGCTGCCTTAAAATCATCTGATAGACCTGCAGATTTATTGACCATTAGCCTTTTTT

ATATGGCGATTATATCGTATTATAACATCAATCATATCAGAGTAGGACCGATACC

TCCGAACCCCCCATCAGATGGAATTGCACAAAATGTGGGGATCGCTATAACTGG

TATAAGCTTTTGGCTGAGTTTGATGGAGAAAGACATTCCACTATATCAACAGTGT

TTAGCAGTTATCCAGCAATCATTCCCGATTAGGTGGGAGGCTGTTTCAGTAAAAG

GAGGATACAAGCAGAAGTGGAGTACTAGAGGTGATGGGCTCCCAAAAGATACC

CGAACTTCAGACTCCTTGGCCCCAATCGGGAACTGGATCAGATCTCTGGAATTGG

TCCGAAACCAAGTTCGTCTAAATCCATTCAATGAGATCTTGTTCAATCAGCTATG

TCGTACAGTGGATAATCATTTGAAATGGTCAAATTTGCGAAGAAACACAGGAAT

GATTGAATGGATCAATAGACGAATTTCAAAAGAAGACCGGTCTATACTGATGTT

GAAGAGTGACCTACACGAGGAAAACTCTTGGAGAGATTAAAAAATCATGAGGA

GACTCCAAACTTTAAGTATGAAAAAAACTTTGATCCTTAAGACCCTCTTGTGGTT

TTTATTTTTTATCTGGTTTTGTGGTCTTCGT.
```

In one embodiment, the nucleic acid comprises the sequence of SEQ ID NO: 26, shown below (VSV vector: Convac V5 China):

```
ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC
```

-continued
```
CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAAACAGAAAACCGACTCCTGATATGATGCAGTATGC

GAAAAGAGCAGTCATGTCACTGCAAGGCCTAAGAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA
```

```
CTAGCATGGAGTATGCTCCGAGCGCTCCAATTGACAAATCCTATTTTGGAGTTGA
CGAGATGGACACCTATGATCCGAATCAATTAAGATATGAGAAATTCTTCTTTACA
GTGAAAATGACGGTTAGATCTAATCGTCCGTTCAGAACATACTCAGATGTGGCA
GCCGCTGTATCCCATTGGGATCACATGTACATCGGAATGGCAGGGAAACGTCCC
TTCTACAAAATCTTGGCTTTTTTGGGTTCTTCTAATCTAAAGGCCACTCCAGCGGT
ATTGGCAGATCAAGGTCAACCAGAGTATCACACTCACTGCGAAGGCAGGGCTTA
TTTGCCACATAGGATGGGGAAGACCCCTCCCATGCTCAATGTACCAGAGCACTTC
AGAAGACCATTCAATATAGGTCTTTACAAGGGAACGATTGAGCTCACAATGACC
ATCTACGATGATGAGTCACTGGAAGCAGCTCCTATGATCTGGGATCATTTCAATT
CTTCCAAATTTTCTGATTTCAGAGAGAAGGCCTTAATGTTTGGCCTGATTGTCGA
GAAAAAGGCATCTGGAGCGTGGGTCCTGGATTCTATCAGCCACTTCAAATGAGC
TAGTCTAACTTCTAGCTTCTGAACAATCCCCGGTTTACTCAGTCTCCTAATTCC
AGCCTCTCGAACAACTAATATCCTGTCTTTTCTATCCCTATGAAAAAAACTAACA
GAGATCGATCTGTTTACGCGTCACTATGAAGTGCCTTTTGTACTTAGCCTTTTTAT
TCATTGGGGTGAATTGCAAGTTCACCATAGTTTTTCCACACAACCAAAAAGGAA
ACTGGAAAAATGTTCCTTCTAATTACCATTATTGCCCGTCAAGCTCAGATTTAAA
TTGGCATAATGACTTAATAGGCACAGCCATACAAGTCAAAATGCCCAAGAGTCA
CAAGGCTATTCAAGCAGACGGTTGGATGTGTCATGCTTCCAAATGGGTCACTACT
TGTGATTTCCGCTGGTATGGACCGAAGTATATAACACAGTCCATCCGATCCTTCA
CTCCATCTGTAGAACAATGCAAGGAAAGCATTGAACAAACGAAACAAGGAACTT
GGCTGAATCCAGGCTTCCCTCCTCAAAGTTGTGGATATGCAACTGTGACGGATGC
CGAAGCAGTGATTGTCCAGGTGACTCCTCACCATGTGCTGGTTGATGAATACACA
GGAGAATGGGTTGATTCACAGTTCATCAACGGAAAATGCAGCAATTACATATGC
CCCACTGTCCATAACTCTACAACCTGGCATTCTGACTATAAGGTCAAAGGGCTAT
GTGATTCTAACCTCATTTCCATGGACATCACCTTCTTCTCAGAGGACGGAGAGCT
ATCATCCCTGGGAAAGGAGGGCACAGGGTTCAGAAGTAACTACTTTGCTTATGA
AACTGGAGGCAAGGCCTGCAAAATGCAATACTGCAAGCATTGGGGAGTCAGACT
CCCATCAGGTGTCTGGTTCGAGATGGCTGATAAGGATCTCTTTGCTGCAGCCAGA
TTCCCTGAATGCCCAGAAGGGTCAAGTATCTCTGCTCCATCTCAGACCTCAGTGG
ATGTAAGTCTAATTCAGGACGTTGAGAGGATCTTGGATTATTCCCTCTGCCAAGA
AACCTGGAGCAAAATCAGAGCGGGTCTTCCAATCTCTCCAGTGGATCTCAGCTAT
CTTGCTCCTAAAAACCCAGGAACCGGTCCTGCTTTCACCATAATCAATGGTACCC
TAAAATACTTTGAGACCAGATACATCAGAGTCGATATTGCTGCTCCAATCCTCTC
AAGAATGGTCGGAATGATCAGTGGAACTACCACAGAAAGGGAACTGTGGGATG
ACTGGGCACCATATGAAGACGTGGAAATTGGACCCAATGGAGTTCTGAGGACCA
GTTCAGGATATAAGTTTCCTTTATACATGATTGGACATGGTATGTTGGACTCCGA
TCTTCATCTTAGCTCAAAGGCTCAGGTGTTCGAACATCCTCACATTCAAGACGCT
GCTTCGCAACTTCCTGATGATGAGAGTTTATTTTTTGGTGATACTGGGCTATCCA
AAAATCCAATCGAGCTTGTAGAAGGTTGGTTCAGTAGTTGGAAAAGCTCTATTGC
CTCTTTTTTCTTTATCATAGGGTTAATCATTGGACTATTCTTGGTTCTCCGAGTTG
```

-continued

```
GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGAAGTGCCTGTTGTACTTAGCCTTCC

TGTTCATCGGGGTGAATTGCCGCTTTCCCAATATCACAAACCTGTGCCCTTTTGG

CGAGGTGTTCAACGCAACCCGCTTCGCCAGCGTGTACGCCTGGAATAGGAAGCG

CATCTCCAACTGCGTGGCCGACTATTCTGTGCTGTACAACAGCGCCTCCTTCTCT

ACCTTTAAGTGCTATGGCGTGAGCCCCACAAAGCTGAATGACCTGTGCTTTACCA

ACGTGTACGCCGATTCCTTCGTGATCAGGGGCGACGAGGTGCGCCAGATCGCAC

CAGGACAGACAGGCAAGATCGCAGACTACAATTATAAGCTGCCTGACGATTTCA

CCGGCTGCGTGATCGCCTGGAACTCTAACAATCTGGATAGCAAAGTGGGCGGCA

ACTACAATTATCTGTACCGGCTGTTTAGAAAGTCTAATCTGAAGCCATTCGAGAG

GGACATCTCCACAGAAATCTACCAGGCCGGCTCTACCCCCTGCAATGGCGTGGA

GGGCTTTAACTGTTATTTCCCTCTGCAGAGCTACGGCTTCCAGCCAACAAACGGC

GTGGGCTATCAGCCCTACCGCGTGGTGGTGCTGTCTTTTGAGCTGCTGCACGCAC

CTGCAACAGTGTGCGGACCAAAGAAGAGCACCAATCTGGTGAAGAACAAGTGC

GTGAACTTCAAcggCTCTGGATCCGGCTACATCCCCGAGGCCCCCAGAGACGGCC

AGGCCTACGTGCGGAAGGACGGCGAGTGGGTACTGctcagcaccttcctgggcAGCAGTTG

GAAAAGCTCCATCGCCTCCTTTTTCTTTATCATCGGCCTGATCATCGGACTGTTCC

TGGTGCTCCGCGTGGGTATCCACCTGTGCATCAAGCTGAAGCACACCAAGAAAA

GACAGATTTATACAGACATCGAGATGAACCGACTTGGAAAGTAAGCTAGCCAGA

TTCTTCATGTTTGGACCAAATCAACTTGTGATACCATGCTCAAAGAGGCCTCAAT

TATATTTGAGTTTTTAATTTTTATGAAAAAAACTAACAGCAATCATGGAAGTCCA

CGATTTTGAGACCGACGAGTTCAATGATTTCAATGAAGATGACTATGCCACAAG

AGAATTCCTGAATCCCGATGAGCGCATGACGTACTTGAATCATGCTGATTACAAT

TTGAATTCTCCTCTAATTAGTGATGATATTGACAATTTGATCAGGAAATTCAATT

CTCTTCCGATTCCCTCGATGTGGGATAGTAAGAACTGGGATGGAGTTCTTGAGAT

GTTAACATCATGTCAAGCCAATCCCATCTCAACATCTCAGATGCATAAATGGATG

GGAAGTTGGTTAATGTCTGATAATCATGATGCCAGTCAAGGGTATAGTTTTTTAC

ATGAAGTGGACAAAGAGGCAGAAATAACATTTGACGTGGTGGAGACCTTCATCC

GCGGCTGGGGCAACAAACCAATTGAATACATCAAAAAGGAAAGATGGACTGAC

TCATTCAAAATTCTCGCTTATTTGTGTCAAAAGTTTTTGGACTTACACAAGTTGAC

ATTAATCTTAAATGCTGTCTCTGAGGTGGAATTGCTCAACTTGGCGAGGACTTTC

AAAGGCAAAGTCAGAAGAAGTTCTCATGGAACGAACATATGCAGGATTAGGGTT

CCCAGCTTGGGTCCTACTTTTATTTCAGAAGGATGGGCTTACTTCAAGAAACTTG

ATATTCTAATGGACCGAAACTTTCTGTTAATGGTCAAAGATGTGATTATAGGGAG

GATGCAAACGGTGCTATCCATGGTATGTAGAATAGACAACCTGTTCTCAGAGCA

AGACATCTTCTCCCTTCTAAATATCTACAGAATTGGAGATAAAATTGTGGAGAGG

CAGGGAAATTTTTCTTATGACTTGATTAAAATGGTGGAACCGATATGCAACTTGA

AGCTGATGAAATTAGCAAGAGAATCAAGGCCTTTAGTCCCACAATTCCCTCATTT

TGAAAATCATATCAAGACTTCTGTTGATGAAGGGGCAAAAATTGACCGAGGTAT

AAGATTCCTCCATGATCAGATAATGAGTGTGAAAACAGTGGATCTCACACTGGT
```

-continued

```
GATTTATGGATCGTTCAGACATTGGGGTCATCCTTTTATAGATTATTACACTGGA

CTAGAAAAATTACATTCCCAAGTAACCATGAAGAAAGATATTGATGTGTCATAT

GCAAAAGCACTTGCAAGTGATTTAGCTCGGATTGTTCTATTTCAACAGTTCAATG

ATCATAAAAAGTGGTTCGTGAATGGAGACTTGCTCCCTCATGATCATCCCTTTAA

AAGTCATGTTAAAGAAAATACATGGCCCACAGCTGCTCAAGTTCAAGATTTTGG

AGATAAATGGCATGAACTTCCGCTGATTAAATGTTTTGAAATACCCGACTTACTA

GACCCATCGATAATATACTCTGACAAAAGTCATTCAATGAATAGGTCAGAGGTG

TTGAAACATGTCCGAATGAATCCGAACACTCCTATCCCTAGTAAAAAGGTGTTGC

AGACTATGTTGGACACAAAGGCTACCAATTGGAAAGAATTTCTTAAAGAGATTG

ATGAGAAGGGCTTAGATGATGATGATCTAATTATTGGTCTTAAAGGAAAGGAGA

GGGAACTGAAGTTGGCAGGTAGATTTTTCTCCCTAATGTCTTGGAAATTGCGAGA

ATACTTTGTAATTACCGAATATTTGATAAAGACTCATTTCGTCCCTATGTTTAAAG

GCCTGACAATGGCGGACGATCTAACTGCAGTCATTAAAAAGATGTTAGATTCCTC

ATCCGGCCAAGGATTGAAGTCATATGAGGCAATTTGCATAGCCAATCACATTGA

TTACGAAAAATGGAATAACCACCAAAGGAAGTTATCAAACGGCCCAGTGTTCCG

AGTTATGGGCCAGTTCTTAGGTTATCCATCCTTAATCGAGAGAACTCATGAATTT

TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG

AATTACAGGGTGCTCTCAATCAAATGGTTTCTAATAATGAGAAAATTATGACTGC

AATCAAAATAGGGACAGGGAAGTTAGGACTTTTGATAAATGACGATGAGACTAT

GCAATCTGCAGATTACTTGAATTATGGAAAAATACCGATTTTCCGTGGAGTGATT

AGAGGGTTAGAGACCAAGAGATGGTCACGAGTGACTTGTGTCACCAATGACCAA

ATACCCACTTGTGCTAATATAATGAGCTCAGTTTCCACAAATGCTCTCACCGTAG

CTCATTTTGCTGAGAACCCAATCAATGCCATGATACAGTACAATTATTTTGGGAC

ATTTGCTAGACTCTTGTTGATGATGCATGATCCTGCTCTTCGTCAATCATTGTATG

AAGTTCAAGATAAGATACCGGGCTTGCACAGTTCTACTTTCAAATACGCCATGTT

GTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCC

ATGTACATGCTCGAAGTGAGCATCTGAAGGAGATGAGTGCAGTATTTGGAAACC

CCGAGATAGCCAAGTTTCGAATAACTCACATAGACAAGCTAGTAGAAGATCCAA

CCTCTCTGAACATCGCTATGGGAATGAGTCCAGCGAACTTGTTAAAGACTGAGGT

TAAAAAATGCTTAATCGAATCAAGACAAACCATCAGGAACCAGGTGATTAAGGA

TGCAACCATATATTTGTATCATGAAGAGGATCGGCTCAGAAGTTTCTTATGGTCA

ATAAATCCTCTGTTCCCTAGATTTTTAAGTGAATTCAAATCAGGCACTTTTTTGGG

AGTCGCAGACGGGCTCATCAGTCTATTTCAAAATTCTCGTACTATTCGGAACTCC

TTTAAGAAAAAGTATCATAGGGAATTGGATGATTTGATTGTGAGGAGTGAGGTA

TCCTCTTTGACACATTTAGGGAAACTTCATTTGAGAAGGGGATCATGTAAAATGT
```

-continued

```
GGACATGTTCAGCTACTCATGCTGACACATTAAGATACAAATCCTGGGGCCGTAC

AGTTATTGGGACAACTGTACCCCATCCATTAGAAATGTTGGGTCCACAACATCGA

AAAGAGACTCCTTGTGCACCATGTAACACATCAGGGTTCAATTATGTTTCTGTGC

ATTGTCCAGACGGGATCCATGACGTCTTTAGTTCACGGGACCATTGCCTGCTTA

TCTAGGGTCTAAAACATCTGAATCTACATCTATTTTGCAGCCTTGGGAAAGGGAA

AGCAAAGTCCCACTGATTAAAAGAGCTACACGTCTTAGAGATGCTATCTCTTGGT

TTGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCCAGATGTATCCCATGTGCTGAAGACATGGAGGAATGGGGAAGG

TTCGTGGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC

TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA
```

-continued

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA

GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.

In other embodiments, the nucleic acid comprises the sequence of SEQ ID NO: 27, shown below (VSV vector: Convac V5 South Africa):

ACGAAGACAAACAAACCATTATTATCATTAAAAGGCTCAGGAGAAACTTTAACA

GTAATCAAAATGTCTGTTACAGTCAAGAGAATCATTGACAACACAGTCATAGTTC

CAAAACTTCCTGCAAATGAGGATCCAGTGGAATACCCGGCAGATTACTTCAGAA

AATCAAAGGAGATTCCTCTTTACATCAATACTACAAAAAGTTTGTCAGATCTAAG

AGGATATGTCTACCAAGGCCTCAAATCCGGAAATGTATCAATCATACATGTCAA

CAGCTACTTGTATGGAGCATTAAAGGACATCCGGGGTAAGTTGGATAAAGATTG

GTCAAGTTTCGGAATAAACATCGGGAAAGCAGGGGATACAATCGGAATATTTGA

CCTTGTATCCTTGAAAGCCCTGGACGGCGTACTTCCAGATGGAGTATCGGATGCT

TCCAGAACCAGCGCAGATGACAAATGGTTGCCTTTGTATCTACTTGGCTTATACA

GAGTGGGCAGAACACAAATGCCTGAATACAGAAAAAAGCTCATGGATGGGCTG

ACAAATCAATGCAAAATGATCAATGAACAGTTTGAACCTCTTGTGCCAGAAGGT

CGTGACATTTTTGATGTGTGGGGAAATGACAGTAATTACACAAAAATTGTCGCTG

CAGTGGACATGTTCTTCCACATGTTCAAAAAACATGAATGTGCCTCGTTCAGATA

CGGAACTATTGTTTCCAGATTCAAAGATTGTGCTGCATTGGCAACATTTGGACAC

CTCTGCAAAATAACCGGAATGTCTACAGAAGATGTAACGACCTGGATCTTGAAC

CGAGAAGTTGCAGATGAAATGGTCCAAATGATGCTTCCAGGCCAAGAAATTGAC

AAGGCCGATTCATACATGCCTTATTTGATCGACTTTGGATTGTCTTCTAAGTCTCC

ATATTCTTCCGTCAAAAACCCTGCCTTCCACTTCTGGGGGCAATTGACAGCTCTT

CTGCTCAGATCCACCAGAGCAAGGAATGCCCGACAGCCTGATGACATTGAGTAT

-continued

```
ACATCTCTTACTACAGCAGGTTTGTTGTACGCTTATGCAGTAGGATCCTCTGCCG

ACTTGGCACAACAGTTTTGTGTTGGAGATAACAAATACACTCCAGATGATAGTAC

CGGAGGATTGACGACTAATGCACCGCCACAAGGCAGAGATGTGGTCGAATGGCT

CGGATGGTTTGAAGATCAAACAGAAAACCGACTCCTGATATGATGCAGTATGC

GAAAAGAGCAGTCATGTCACTGCAAGGCCTAAGAGAAGACAATTGGCAAGT

ATGCTAAGTCAGAATTTGACAAATGACCCTATAATTCTCAGATCACCTATTATAT

ATTATGCTACATATGAAAAAAACTAACAGATATCATGGATAATCTCACAAAAGT

TCGTGAGTATCTCAAGTCCTATTCTCGTCTGGATCAGGCGGTAGGAGAGATAGAT

GAGATCGAAGCACAACGAGCTGAAAAGTCCAATTATGAGTTGTTCCAAGAGGAT

GGAGTGGAAGAGCATACTAAGCCCTCTTATTTTCAGGCAGCAGATGATTCTGAC

ACAGAATCTGAACCAGAAATTGAAGACAATCAAGGTTTGTATGCACCAGATCCA

GAAGCTGAGCAAGTTGAAGGCTTTATACAGGGGCCTTTAGATGACTATGCAGAT

GAGGAAGTGGATGTTGTATTTACTTCGGACTGGAAACAGCCTGAGCTTGAATCTG

ACGAGCATGGAAAGACCTTACGGTTGACATCGCCAGAGGGTTTAAGTGGAGAGC

AGAAATCCCAGTGGCTTTCGACGATTAAAGCAGTCGTGCAAAGTGCCAAATACT

GGAATCTGGCAGAGTGCACATTTGAAGCATCGGGAGAAGGGGTCATTATGAAGG

AGCGCCAGATAACTCCGGATGTATATAAGGTCACTCCAGTGATGAACACACATC

CGTCCCAATCAGAAGCAGTATCAGATGTTTGGTCTCTCAAAGACATCCATGAC

TTTCCAACCCAAGAAAGCAAGTCTTCAGCCTCTCACCATATCCTTGGATGAATTG

TTCTCATCTAGAGGAGAGTTCATCTCTGTCGGAGGTGACGGACGAATGTCTCATA

AAGAGGCCATCCTGCTCGGCCTGAGATACAAAAAGTTGTACAATCAGGCGAGAG

TCAAATATTCTCTGTAGACTATGAAAAAAAGTAACAGATATCACGATCTAAGTGT

TATCCCAATCCATTCATCATGAGTTCCTTAAAGAAGATTCTCGGTCTGAAGGGGA

AAGGTAAGAAATCTAAGAAATTAGGGATCGCACCACCCCCTTATGAAGAGGACA

CTAGCATGGAGTATGCTCCGAGCGCTCCAATTGACAAATCCTATTTTGGAGTTGA

CGAGATGGACACCTATGATCCGAATCAATTAAGATATGAGAAATTCTTCTTTACA

GTGAAAATGACGGTTAGATCTAATCGTCCGTTCAGAACATACTCAGATGTGGCA

GCCGCTGTATCCCATTGGGATCACATGTACATCGGAATGGCAGGGAAACGTCCC

TTCTACAAAATCTTGGCTTTTTTGGGTTCTTCTAATCTAAAGGCCACTCCAGCGGT

ATTGGCAGATCAAGGTCAACCAGAGTATCACACTCACTGCGAAGGCAGGGCTTA

TTTGCCACATAGGATGGGAAGACCCCTCCCATGCTCAATGTACCAGAGCACTTC

AGAAGACCATTCAATATAGGTCTTTACAAGGGAACGATTGAGCTCACAATGACC

ATCTACGATGATGAGTCACTGGAAGCAGCTCCTATGATCTGGGATCATTTCAATT

CTTCCAAATTTTCTGATTTCAGAGAGAAGGCCTTAATGTTTGGCCTGATTGTCGA

GAAAAAGGCATCTGGAGCGTGGGTCCTGGATTCTATCAGCCACTTCAAATGAGC

TAGTCTAACTTCTAGCTTCTGAACAATCCCCGGTTTACTCAGTCTCTCCTAATTCC

AGCCTCTCGAACAACTAATATCCTGTCTTTTCTATCCCTATGAAAAAAACTAACA

GAGATCGATCTGTTTACGCGTCACTATGAAGTGCCTTTTGTACTTAGCCTTTTTAT

TCATTGGGGTGAATTGCAAGTTCACCATAGTTTTTCCACACAACCAAAAAGGAA

ACTGGAAAAATGTTCCTTCTAATTACCATTATTGCCCGTCAAGCTCAGATTTAAA
```

-continued

```
TTGGCATAATGACTTAATAGGCACAGCCATACAAGTCAAAATGCCCAAGAGTCA

CAAGGCTATTCAAGCAGACGGTTGGATGTGTCATGCTTCCAAATGGGTCACTACT

TGTGATTTCCGCTGGTATGGACCGAAGTATATAACACAGTCCATCCGATCCTTCA

CTCCATCTGTAGAACAATGCAAGGAAAGCATTGAACAAACGAAACAAGGAACTT

GGCTGAATCCAGGCTTCCCTCCTCAAAGTTGTGGATATGCAACTGTGACGGATGC

CGAAGCAGTGATTGTCCAGGTGACTCCTCACCATGTGCTGGTTGATGAATACACA

GGAGAATGGGTTGATTCACAGTTCATCAACGGAAAATGCAGCAATTACATATGC

CCCACTGTCCATAACTCTACAACCTGGCATTCTGACTATAAGGTCAAAGGGCTAT

GTGATTCTAACCTCATTTCCATGGACATCACCTTCTTCTCAGAGGACGGAGAGCT

ATCATCCCTGGGAAAGGAGGGCACAGGGTTCAGAAGTAACTACTTTGCTTATGA

AACTGGAGGCAAGGCCTGCAAAATGCAATACTGCAAGCATTGGGGAGTCAGACT

CCCATCAGGTGTCTGGTTCGAGATGGCTGATAAGGATCTCTTTGCTGCAGCCAGA

TTCCCTGAATGCCCAGAAGGGTCAAGTATCTCTGCTCCATCTCAGACCTCAGTGG

ATGTAAGTCTAATTCAGGACGTTGAGAGGATCTTGGATTATTCCCTCTGCCAAGA

AACCTGGAGCAAAATCAGAGCGGGTCTTCCAATCTCTCCAGTGGATCTCAGCTAT

CTTGCTCCTAAAAACCCAGGAACCGGTCCTGCTTTCACCATAATCAATGGTACCC

TAAAATACTTTGAGACCAGATACATCAGAGTCGATATTGCTGCTCCAATCCTCTC

AAGAATGGTCGGAATGATCAGTGGAACTACCACAGAAAGGGAACTGTGGGATG

ACTGGGCACCATATGAAGACGTGGAAATTGGACCCAATGGAGTTCTGAGGACCA

GTTCAGGATATAAGTTTCCTTTATACATGATTGGACATGGTATGTTGGACTCCGA

TCTTCATCTTAGCTCAAAGGCTCAGGTGTTCGAACATCCTCACATTCAAGACGCT

GCTTCGCAACTTCCTGATGATGAGAGTTTATTTTTTGGTGATACTGGGCTATCCA

AAAATCCAATCGAGCTTGTAGAAGGTTGGTTCAGTAGTTGGAAAAGCTCTATTGC

CTCTTTTTTCTTTATCATAGGGTTAATCATTGGACTATTCTTGGTTCTCCGAGTTG

GTATCCATCTTTGCATTAAATTAAAGCACACCAAGAAAAGACAGATTTATACAG

ACATAGAGATGAACCGACTTGGAAAGTAACTCAAATCCTGCTAGGTATGAAAAA

AACTAACaGATATCACGCtcgagGCCACCATGAAGTGCCTGTTGTACTTAGCCTTCC

TGTTCATCGGGGTGAATTGCCGCTTTCCCAATATCACAAACCTGTGCCCTTTTGG

CGAGGTGTTCAACGCAACCCGCTTCGCCAGCGTGTACGCCTGGAATAGGAAGCG

CATCTCCAACTGCGTGGCCGACTATTCTGTGCTGTACAACAGCGCCTCCTTCTCT

ACCTTTAAGTGCTATGGCGTGAGCCCCACAAAGCTGAATGACCTGTGCTTTACCA

ACGTGTACGCCGATTCCTTCGTGATCAGGGGCGACGAGGTGCGCCAGATCGCAC

CAGGACAGACAGGCAATATCGCAGACTACAATTATAAGCTGCCTGACGATTTCA

CCGGCTGCGTGATCGCCTGGAACTCTAACAATCTGGATAGCAAAGTGGGCGGCA

ACTACAATTATCTGTACCGGCTGTTTAGAAAGTCTAATCTGAAGCCATTCGAGAG

GGACATCTCCACAGAAATCTACCAGGCCGGCTCTACCCCCTGCAATGGCGTGAA

GGGCTTTAACTGTTATTTCCCTCTGCAGAGCTACGGCTTCCAGCCAACATATGGC

GTGGGCTATCAGCCCTACCGCGTGGTGGTGCTGTCTTTTGAGCTGCTGCACGCAC

CTGCAACAGTGTGCGGACCAAAGAAGAGCACCAATCTGGTGAAGAACAAGTGC

GTGAACTTCAAcggCTCTGGATCCGGCTACATCCCCGAGGCCCCCAGAGACGGCC

AGGCCTACGTGCGGAAGGACGGCGAGTGGGTACTGctcagcaccttcctgggcAGCAGTTG
```

-continued

```
GAAAAGCTCCATCGCCTCCTTTTTCTTTATCATCGGCCTGATCATCGGACTGTTCC

TGGTGCTCCGCGTGGGTATCCACCTGTGCATCAAGCTGAAGCACACCAAGAAAA

GACAGATTTATACAGACATCGAGATGAACCGACTTGGAAAGTAAGCTAGCCAGA

TTCTTCATGTTTGGACCAAATCAACTTGTGATACCATGCTCAAAGAGGCCTCAAT

TATATTTGAGTTTTTAATTTTTATGAAAAAAACTAACAGCAATCATGGAAGTCCA

CGATTTTGAGACCGACGAGTTCAATGATTTCAATGAAGATGACTATGCCACAAG

AGAATTCCTGAATCCCGATGAGCGCATGACGTACTTGAATCATGCTGATTACAAT

TTGAATTCTCCTCTAATTAGTGATGATATTGACAATTTGATCAGGAAATTCAATT

CTCTTCCGATTCCCTCGATGTGGGATAGTAAGAACTGGGATGGAGTTCTTGAGAT

GTTAACATCATGTCAAGCCAATCCCATCTCAACATCTCAGATGCATAAATGGATG

GGAAGTTGGTTAATGTCTGATAATCATGATGCCAGTCAAGGGTATAGTTTTTTAC

ATGAAGTGGACAAAGAGGCAGAAATAACATTTGACGTGGTGGAGACCTTCATCC

GCGGCTGGGGCAACAAACCAATTGAATACATCAAAAAGGAAAGATGGACTGAC

TCATTCAAAATTCTCGCTTATTTGTGTCAAAAGTTTTTGGACTTACACAAGTTGAC

ATTAATCTTAAATGCTGTCTCTGAGGTGGAATTGCTCAACTTGGCGAGGACTTTC

AAAGGCAAAGTCAGAAGAAGTTCTCATGGAACGAACATATGCAGGATTAGGGTT

CCCAGCTTGGGTCCTACTTTTATTTCAGAAGGATGGGCTTACTTCAAGAAACTTG

ATATTCTAATGGACCGAAACTTTCTGTTAATGGTCAAAGATGTGATTATAGGGAG

GATGCAAACGGTGCTATCCATGGTATGTAGAATAGACAACCTGTTCTCAGAGCA

AGACATCTTCTCCCTTCTAAATATCTACAGAATTGGAGATAAAATTGTGGAGAGG

CAGGGAAATTTTTCTTATGACTTGATTAAAATGGTGGAACCGATATGCAACTTGA

AGCTGATGAAATTAGCAAGAGAATCAAGGCCTTTAGTCCCACAATTCCCTCATTT

TGAAAATCATATCAAGACTTCTGTTGATGAAGGGGCAAAAATTGACCGAGGTAT

AAGATTCCTCCATGATCAGATAATGAGTGTGAAAACAGTGGATCTCACACTGGT

GATTTATGGATCGTTCAGACATTGGGGTCATCCTTTTATAGATTATTACACTGGA

CTAGAAAAATTACATTCCCAAGTAACCATGAAGAAAGATATTGATGTGTCATAT

GCAAAAGCACTTGCAAGTGATTTAGCTCGGATTGTTCTATTTCAACAGTTCAATG

ATCATAAAAAGTGGTTCGTGAATGGAGACTTGCTCCCTCATGATCATCCCTTTAA

AAGTCATGTTAAAGAAAATACATGGCCCACAGCTGCTCAAGTTCAAGATTTTGG

AGATAAATGGCATGAACTTCCGCTGATTAAATGTTTTGAAATACCCGACTTACTA

GACCCATCGATAATATACTCTGACAAAAGTCATTCAATGAATAGGTCAGAGGTG

TTGAAACATGTCCGAATGAATCCGAACACTCCTATCCCTAGTAAAAAGGTGTTGC

AGACTATGTTGGACACAAAGGCTACCAATTGGAAAGAATTTCTTAAAGAGATTG

ATGAGAAGGGCTTAGATGATGATGATCTAATTATTGGTCTTAAAGGAAAGGAGA

GGGAACTGAAGTTGGCAGGTAGATTTTTCTCCCTAATGTCTTGGAAATTGCGAGA

ATACTTTGTAATTACCGAATATTTGATAAAGACTCATTTCGTCCCTATGTTTAAAG

GCCTGACAATGGCGGACGATCTAACTGCAGTCATTAAAAAGATGTTAGATTCCTC

ATCCGGCCAAGGATTGAAGTCATATGAGGCAATTTGCATAGCCAATCACATTGA

TTACGAAAAATGGAATAACCACCAAAGGAAGTTATCAAACGGCCCAGTGTTCCG

AGTTATGGGCCAGTTCTTAGGTTATCCATCCTTAATCGAGAGAACTCATGAATTT
```

-continued

```
TTTGAGAAAAGTCTTATATACTACAATGGAAGACCAGACTTGATGCGTGTTCACA

ACAACACACTGATCAATTCAACCTCCCAACGAGTTTGTTGGCAAGGACAAGAGG

GTGGACTGGAAGGTCTACGGCAAAAAGGATGGACTATCCTCAATCTACTGGTTA

TTCAAAGAGAGGCTAAAATCAGAAACACTGCTGTCAAAGTCTTGGCACAAGGTG

ATAATCAAGTTATTTGCACACAGTATAAAACGAAGAAATCGAGAAACGTTGTAG

AATTACAGGGTGCTCTCAATCAAATGGTTTCTAATAATGAGAAAATTATGACTGC

AATCAAAATAGGGACAGGGAAGTTAGGACTTTTGATAAATGACGATGAGACTAT

GCAATCTGCAGATTACTTGAATTATGGAAAAATACCGATTTTCCGTGGAGTGATT

AGAGGGTTAGAGACCAAGAGATGGTCACGAGTGACTTGTGTCACCAATGACCAA

ATACCCACTTGTGCTAATATAATGAGCTCAGTTTCCACAAATGCTCTCACCGTAG

CTCATTTTGCTGAGAACCCAATCAATGCCATGATACAGTACAATTATTTTGGGAC

ATTTGCTAGACTCTTGTTGATGATGCATGATCCTGCTCTTCGTCAATCATTGTATG

AAGTTCAAGATAAGATACCGGGCTTGCACAGTTCTACTTTCAAATACGCCATGTT

GTATTTGGACCCTTCCATTGGAGGAGTGTCGGGCATGTCTTTGTCCAGGTTTTTG

ATTAGAGCCTTCCCAGATCCCGTAACAGAAAGTCTCTCATTCTGGAGATTCATCC

ATGTACATGCTCGAAGTGAGCATCTGAAGGAGATGAGTGCAGTATTTGGAAACC

CCGAGATAGCCAAGTTTCGAATAACTCACATAGACAAGCTAGTAGAAGATCCAA

CCTCTCTGAACATCGCTATGGGAATGAGTCCAGCGAACTTGTTAAAGACTGAGGT

TAAAAAATGCTTAATCGAATCAAGACAAACCATCAGGAACCAGGTGATTAAGGA

TGCAACCATATATTTGTATCATGAAGAGGATCGGCTCAGAAGTTTCTTATGGTCA

ATAAATCCTCTGTTCCCTAGATTTTTAAGTGAATTCAAATCAGGCACTTTTTTGGG

AGTCGCAGACGGGCTCATCAGTCTATTTCAAAATTCTCGTACTATTCGGAACTCC

TTTAAGAAAAGTATCATAGGGAATTGGATGATTTGATTGTGAGGAGTGAGGTA

TCCTCTTTGACACATTTAGGGAAACTTCATTTGAGAAGGGGATCATGTAAAATGT

GGACATGTTCAGCTACTCATGCTGACACATTAAGATACAAATCCTGGGGCCGTAC

AGTTATTGGGACAACTGTACCCCATCCATTAGAAATGTTGGGTCCACAACATCGA

AAAGAGACTCCTTGTGCACCATGTAACACATCAGGGTTCAATTATGTTTCTGTGC

ATTGTCCAGACGGGATCCATGACGTCTTTAGTTCACGGGGACCATTGCCTGCTTA

TCTAGGGTCTAAAACATCTGAATCTACATCTATTTTGCAGCCTTGGGAAAGGGAA

AGCAAAGTCCCACTGATTAAAAGAGCTACACGTCTTAGAGATGCTATCTCTTGGT

TTGTTGAACCCGACTCTAAACTAGCAATGACTATACTTTCTAACATCCACTCTTTA

ACAGGCGAAGAATGGACCAAAAGGCAGCATGGGTTCAAAAGAACAGGGTCTGC

CCTTCATAGGTTTTCGACATCTCGGATGAGCCATGGTGGGTTCGCATCTCAGAGC

ACTGCAGCATTGACCAGGTTGATGGCAACTACAGACACCATGAGGGATCTGGGA

GATCAGAATTTCGACTTTTTATTCCAAGCAACGTTGCTCTATGCTCAAATTACCA

CCACTGTTGCAAGAGACGGATGGATCACCAGTTGTACAGATCATTATCATATTGC

CTGTAAGTCCTGTTTGAGACCCATAGAAGAGATCACCCTGGACTCAAGTATGGA

CTACACGCCCCAGATGTATCCCATGTGCTGAAGACATGGAGGAATGGGGAAGG

TTCGTGGGGACAAGAGATAAAACAGATCTATCCTTTAGAAGGGAATTGGAAGAA

TTTAGCACCTGCTGAGCAATCCTATCAAGTCGGCAGATGTATAGGTTTTCTATAT

GGAGACTTGGCGTATAGAAAATCTACTCATGCCGAGGACAGTTCTCTATTTCCTC
```

-continued

```
TATCTATACAAGGTCGTATTAGAGGTCGAGGTTTCTTAAAAGGGTTGCTAGACGG

ATTAATGAGAGCAAGTTGCTGCCAAGTAATACACCGGAGAAGTCTGGCTCATTT

GAAGAGGCCGGCCAACGCAGTGTACGGAGGTTTGATTTACTTGATTGATAAATT

GAGTGTATCACCTCCATTCCTTTCTCTTACTAGATCAGGACCTATTAGAGACGAA

TTAGAAACGATTCCCCACAAGATCCCAACCTCCTATCCGACAAGCAACCGTGAT

ATGGGGGTGATTGTCAGAAATTACTTCAAATACCAATGCCGTCTAATTGAAAAG

GGAAAATACAGATCACATTATTCACAATTATGGTTATTCTCAGATGTCTTATCCA

TAGACTTCATTGGACCATTCTCTATTTCCACCACCCTCTTGCAAATCCTATACAAG

CCATTTTTATCTGGGAAAGATAAGAATGAGTTGAGAGAGCTGGCAAATCTTTCTT

CATTGCTAAGATCAGGAGAGGGGTGGGAAGACATACATGTGAAATTCTTCACCA

AGGACATATTATTGTGTCCAGAGGAAATCAGACATGCTTGCAAGTTCGGGATTG

CTAAGGATAATAATAAAGACATGAGCTATCCCCCTTGGGGAAGGGAATCCAGAG

GGACAATTACAACAATCCCTGTTTATTATACGACCACCCCTTACCCAAAGATGCT

AGAGATGCCTCCAAGAATCCAAAATCCCCTGCTGTCCGGAATCAGGTTGGGCCA

ATTACCAACTGGCGCTCATTATAAAATTCGGAGTATATTACATGGAATGGGAATC

CATTACAGGGACTTCTTGAGTTGTGGAGACGGCTCCGGAGGGATGACTGCTGCA

TTACTACGAGAAAATGTGCATAGCAGAGGAATATTCAATAGTCTGTTAGAATTAT

CAGGGTCAGTCATGCGAGGCGCCTCTCCTGAGCCCCCCAGTGCCCTAGAAACTTT

AGGAGGAGATAAATCGAGATGTGTAAATGGTGAAACATGTTGGGAATATCCATC

TGACTTATGTGACCCAAGGACTTGGGACTATTTCCTCCGACTCAAAGCAGGCTTG

GGGCTTCAAATTGATTTAATTGTAATGGATATGGAAGTTCGGGATTCTTCTACTA

GCCTGAAAATTGAGACGAATGTTAGAAATTATGTGCACCGGATTTTGGATGAGC

AAGGAGTTTTAATCTACAAGACTTATGGAACATATATTTGTGAGAGCGAAAAGA

ATGCAGTAACAATCCTTGGTCCCATGTTCAAGACGGTCGACTTAGTTCAAACAGA

ATTTAGTAGTTCTCAAACGTCTGAAGTATATATGGTATGTAAAGGTTTGAAGAAA

TTAATCGATGAACCCAATCCCGATTGGTCTTCCATCAATGAATCCTGGAAAAACC

TGTACGCATTCCAGTCATCAGAACAGGAATTTGCCAGAGCAAAGAAGGTTAGTA

CATACTTTACCTTGACAGGTATTCCCTCCCAATTCATTCCTGATCCTTTTGTAAAC

ATTGAGACTATGCTACAAATATTCGGAGTACCCACGGGTGTGTCTCATGCGGCTG

CCTTAAAATCATCTGATAGACCTGCAGATTTATTGACCATTAGCCTTTTTTATATG

GCGATTATATCGTATTATAACATCAATCATATCAGAGTAGGACCGATACCTCCGA

ACCCCCCATCAGATGGAATTGCACAAAATGTGGGATCGCTATAACTGGTATAA

GCTTTTGGCTGAGTTTGATGGAGAAAGACATTCCACTATATCAACAGTGTTTAGC

AGTTATCCAGCAATCATTCCCGATTAGGTGGGAGGCTGTTTCAGTAAAAGGAGG

ATACAAGCAGAAGTGGAGTACTAGAGGTGATGGGCTCCCAAAAGATACCCGAAC

TTCAGACTCCTTGGCCCCAATCGGGAACTGGATCAGATCTCTGGAATTGGTCCGA

AACCAAGTTCGTCTAAATCCATTCAATGAGATCTTGTTCAATCAGCTATGTCGTA

CAGTGGATAATCATTTGAAATGGTCAAATTTGCGAAGAAACACAGGAATGATTG

AATGGATCAATAGACGAATTTCAAAAGAAGACCGGTCTATACTGATGTTGAAGA
```

-continued
GTGACCTACACGAGGAAAACTCTTGGAGAGATTAAAAAATCATGAGGAGACTCC

AAACTTTAAGTATGAAAAAAACTTTGATCCTTAAGACCCTCTTGTGGTTTTTATTT

TTTATCTGGTTTTGTGGTCTTCGT.

In another aspect, the invention provides an isolated nucleic acid encoding a recombinant fusion protein comprising (a) a glycoprotein (G) of a virus or a portion thereof, and (b) a SARS-CoV-2 spike protein (S) or a portion thereof. In some embodiments, the virus is a rhabdovirus. In some embodiments, the virus is a rabies virus or a vesicular stomatitis virus (VSV). In a particular embodiment, the virus is a rabies virus.

In one embodiment, the portion of the SARS-CoV-2 spike protein (S) is a receptor binding site of the SARS-CoV-2 spike protein (S). In another embodiment, the portion of the SARS-CoV-2 spike protein (S) is the S1 domain. In another embodiment, the portion of the SARS-CoV-2 spike protein (S) is the N-terminal 750 amino acids of the SARS-CoV-2 spike protein (S).

In some embodiments, the glycoprotein (G) comprises a mutation substituting arginine with glutamic acid at position 333. In some embodiments, the portion of glycoprotein (G) comprises an ectodomain, a cytoplasmic domain, and a transmembrane domain. In some embodiments, the portion of the glycoprotein (G) comprises 31 amino acids of the ectodomain. In some embodiments, the glycoprotein (G) comprises 31 amino acids of the ectodomain and the full-length cytoplasmic domain.

In some embodiments, the sequence encoding the SARS-CoV-2 spike protein (S) or portion thereof is codon-optimized for expression in a human cell. In some embodiments, the sequence encoding the SARS-CoV-2 spike protein (S) or portion thereof fused to a glycoprotein (G) or portion thereof is codon-optimized for expression in a human cell.

Figure 18:
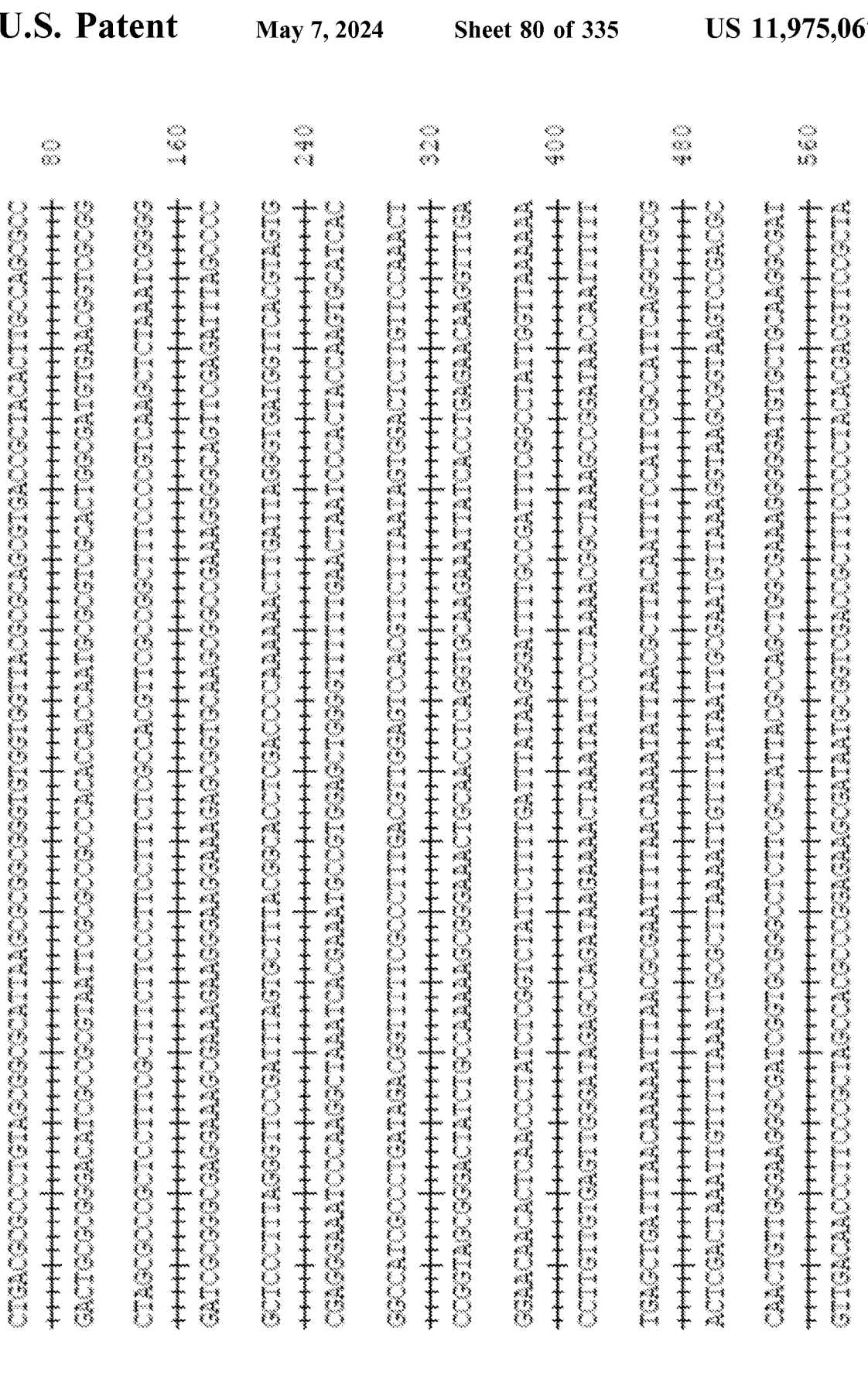
FIG. 18 shows the sequence (SEQ ID NO: 2) and features of "BNSP333-COVID19-S1-RVG".
Figure 19:
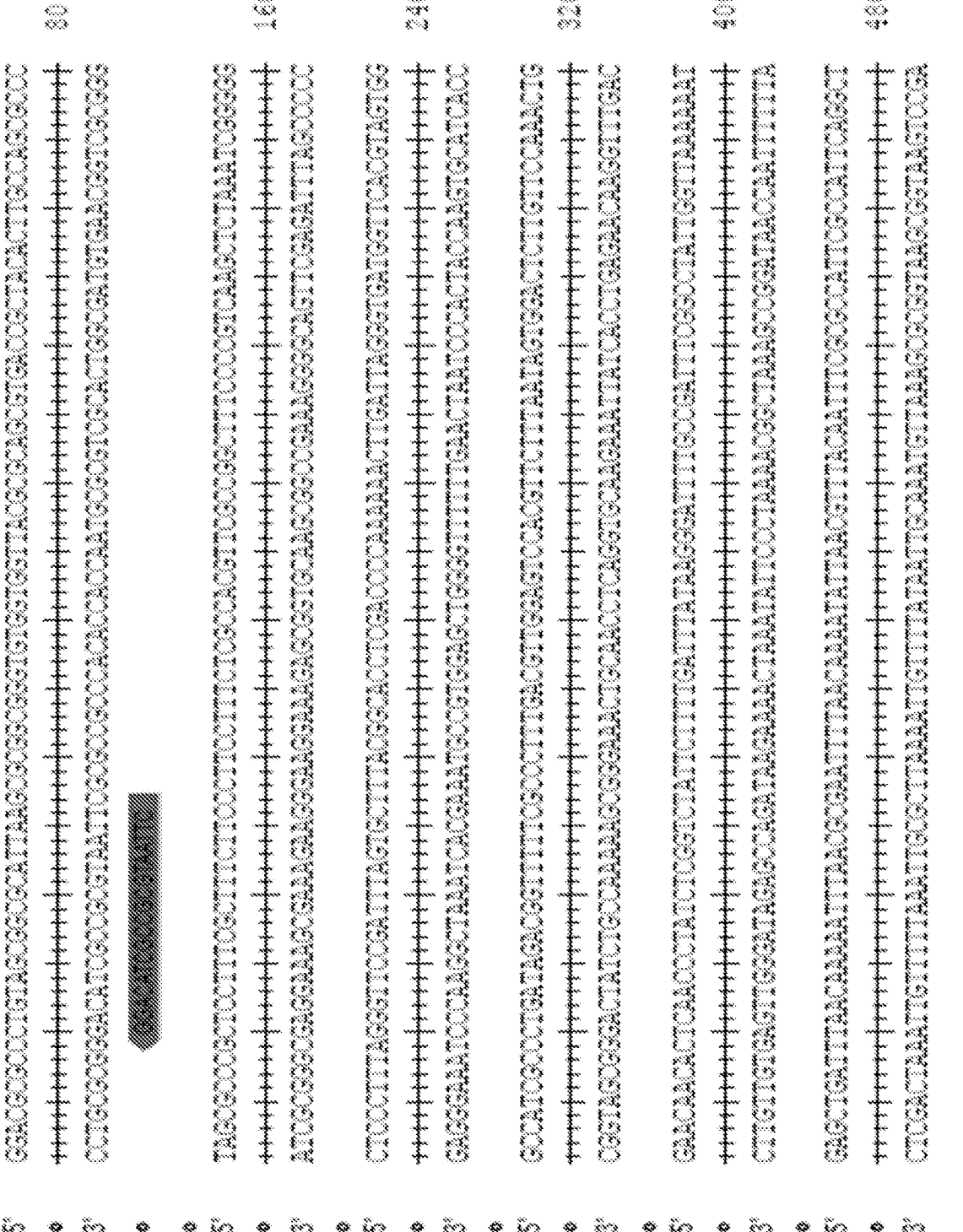
FIG. 19 shows the sequence (SEQ ID NO: 5) and features of "MV WuhanCoV S in position 6".
Figure 20:
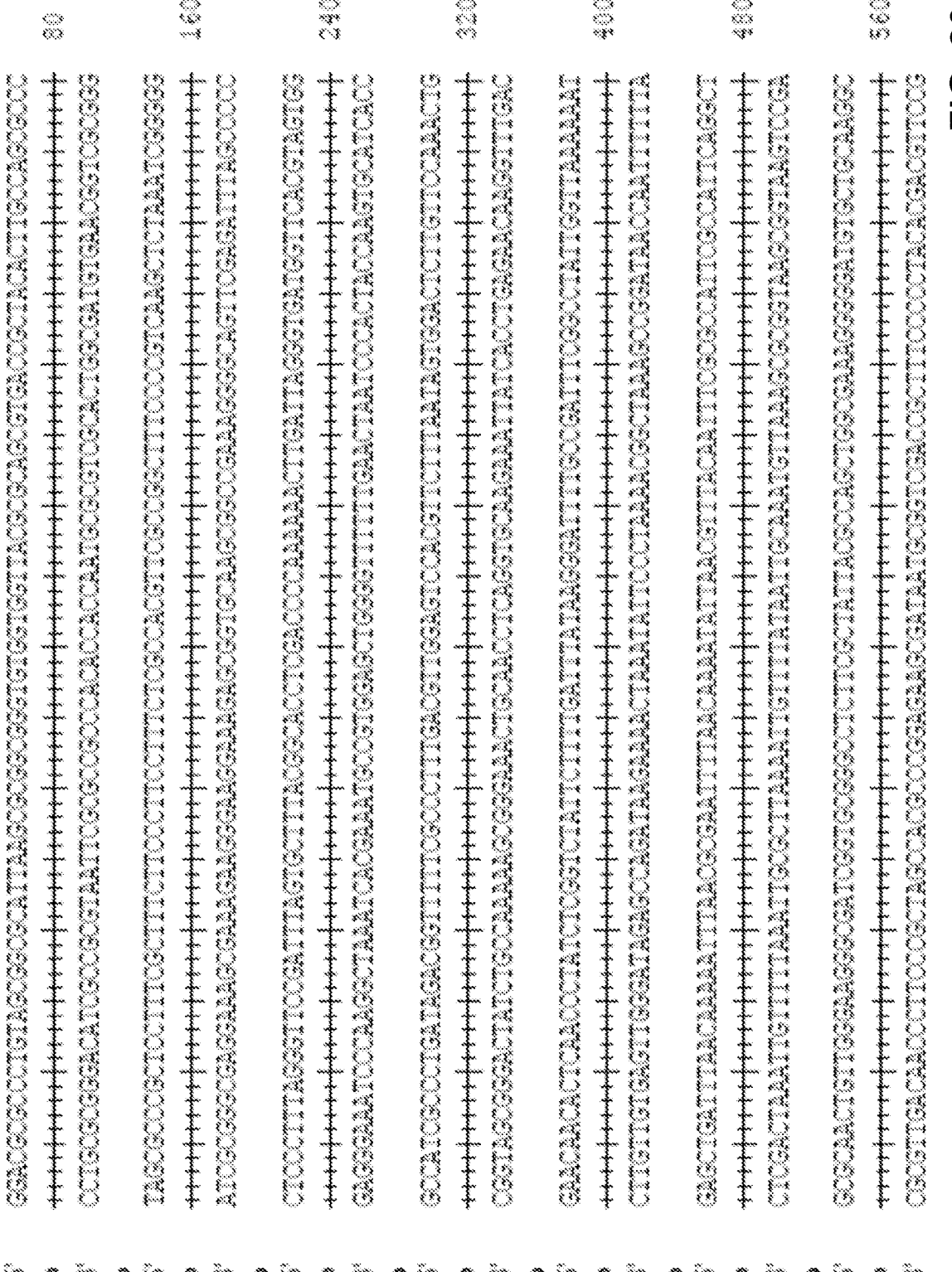
FIG. 20 shows the sequence (SEQ ID NO: 4) and features of "MV Wu S in position 3".
Figure 21:
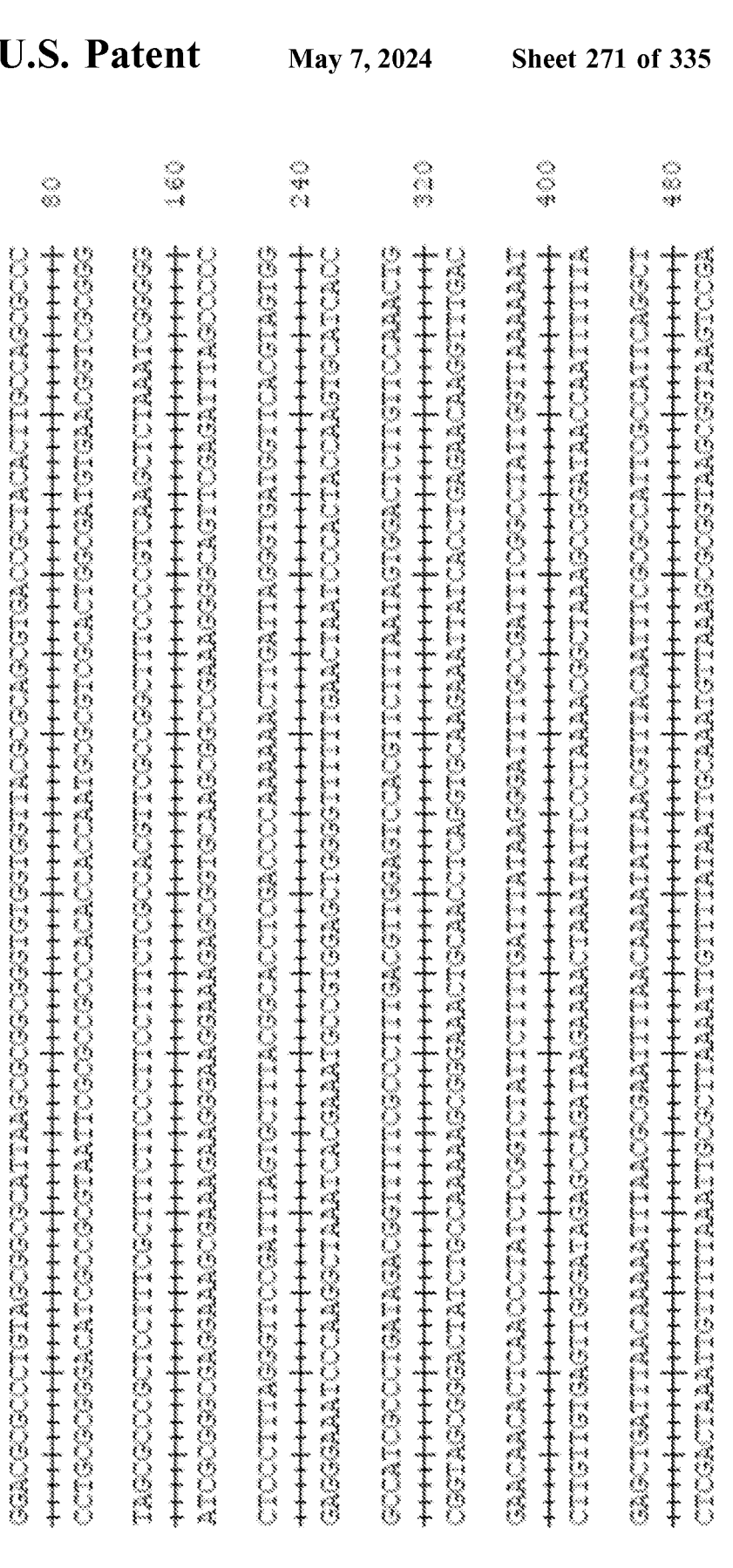
FIG. 21 shows the sequence (SEQ ID NO: 3) and features of "MV-coWuhan-S Position 2".

In some embodiments, the recombinant fusion protein comprises the sequence of the S1 domain of the SARS-CoV-2 spike protein (S) fused to a rabies glycoprotein (G) or portion thereof, shown as element "WuS1-RABVG" in "BNSP333-COVID19-S1-RVG" in FIG. 18.

Figure 17:
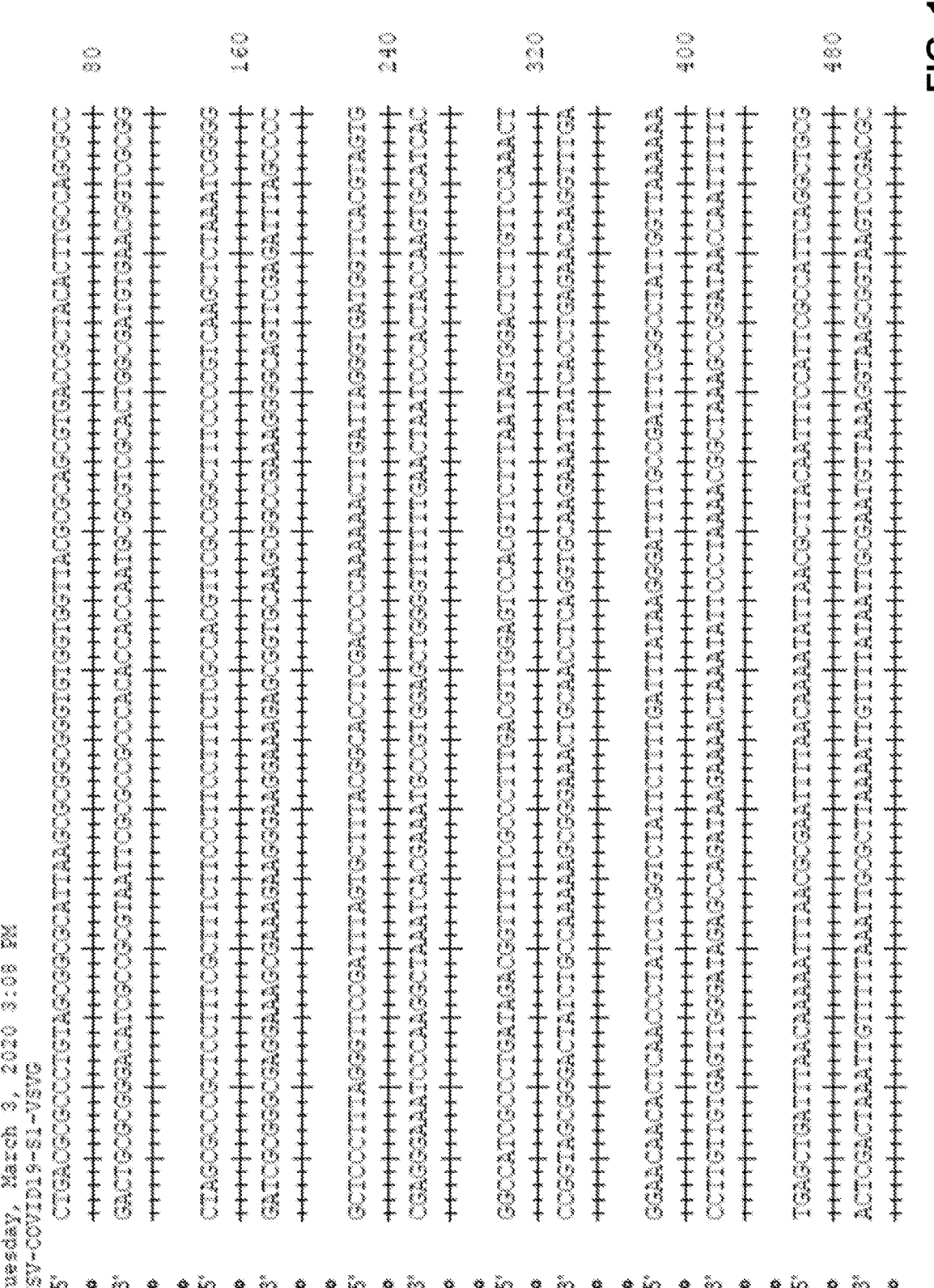
FIG. 17 shows the sequence (SEQ ID NO: 1) and features of "VSV-COVID19-S1-VSVG.

In some embodiments, the recombinant fusion protein comprises the sequence of the S1 domain of the SARS-CoV-2 spike protein (S) fused to a VSV glycoprotein (G) or portion thereof, shown as element "WuhanS-coVSV-G-tail" in "VSV-COVID19-S1-VSVG" in FIG. 17.

In other aspects, the present invention provides nucleic acid molecules having double-stranded, single-stranded, and/or combinations of double- and single-stranded regions as well as full or partial complements of any of the sequences of the present disclosure.

In some aspects, the present disclosure provides the following sequences, or complements thereof:

| SEQ ID NO: | Sequence |
|---|---|
| 34 | ATGTGCT...GCGATTA AT...TA |
| 35 | TGTGCTG...ATTAAG TGT...AAG |
| 36 | GTTTTCCCAGTCACGAC |
| 37 | AAAcgacgGcCagtgGaattCCGTTAATACGACTCACTATAGG AAA...GG |
| 38 | ggtTGCGCGCCGTT...GACTCACTATAGG ggtT...AGG |
| 39 | gaGagCgcgcatCGaaaTTAATACGACTCACTATA ga...TA |
| 40 | GagacGTaCGCGtaaT...ACGACTCACTATAGGG Gaga...GGG |
| 41 | TAATAC...ATAGGG TAAT...GGG |
| 42 | gtGtcgtctcgCgcgtgcggCcgcGCTAGCCAGCTTGGGTCTCCCT |
| 43 | gtGtCGTctCt...GGGTAAGGATA gtGtCGTctCtG...GGGTAAGGATA |
| 44 | gtGtgGTctCtG...AGGATAGTTCA<br>gtGtgGTctCtGGTC...GGTAAGGATAGTTCA |
| 45 | gAgaaGGTTTgAgaacgcgTctcGGTACGCCGGGTTT |
| 46 | tgTCaCGGATATCCATCCTGCTCTTGTCCtgTCC |
| 47 | cAgtccaccGgtgTCaCGGATATCCCTAATCCTGCT |
| 48 | GGATTAGGGATATCCGAGATGGCCACACTT |
| 49 | AAGTGTGGCCATCTCGGATATCCCTAATCCTGCTCT |
| 50 | TGGCCACACTTTTAAGGAGCT |
| 51 | CCACCGGATCCTGATGTAAT |
| 52 | CTGGCCTTACCTTCGCATCA |

| SEQ ID NO: | Sequence |
|---|---|
| 53 | AGGATTAGCCAGTTTTATCCTGACT |
| 54 | AGAAGCCAG...GAGCTACA |
| 55 | gt...A gtgtGcgatcgcgtGCgagaGGCCAGAACAACA |
| 56 | gTGtacGcgtTCc...GCCAGAACAACA<br>gTGtacGcgtTCcTgacG...gagaGGCCAGAACAACA |
| 57 | GTGtGcGgccgctaTaGcgTAAGTTTTTTATAACAATGGTGtGcGgccgctaTaGcgatcTCCTAAGTTTTTTATAACAATG |
| 58 | GtgTGcgGccgTTATAACAATGGtgTGcgGccgctataaCgcgtTTCCTAAGTTTTTATAACAATG |
| 59 | gtGtgcgGccgctaTaAcGTAAGTTTTTTATAACAATGgtGtgcgGccgctaTaAcGcGtTTCCTAAGTTTTTTATAACAATG |
| 60 | GACAACCCAGGACAGGAGC |
| 61 | ACTCTCAATGTTCCTCCGCC |
| 62 | GCCATTCCTGGACTTGGGAA |
| 63 | gtgtgcGGccgcAGGTTGTACTAGGTGGGTC |
| 64 | AGTGATTGCCTCCCAAGGTC |
| 65 | TGAG...TTCG TGAGC...TTTCG |
| 66 | tcTCTGTAGACCGTAGTGCCCA |
| 67 | CAACCCCGACAACCAGAG |
| 68 | CACCCCTAAAGGAGACACCG |
| 69 | gtgtgAa...TCTCAA gtgtgAagacttcatg...CATCATGGGTCTCAA |
| 70 | GAGCGAGC...AAACTACT |
| 71 | CCCAAGTATGTTGCAACCCA |
| 72 | TCGAGCACTAGCATAGTCTACA |
| 73 | gTGTtctaGATCAGAGCGACCTTACATAGGA |
| 74 | GtgtcgtctctATGTCACCACAACGAGACCG Gtg...CG |
| 75 | CTTGATCGGGTTGCTAGCCA |
| 76 | CCAGGGAATGTATGGGGAA |
| 77 | ATGCTTCCAACAGGCGTGTA |
| 78 | GTTGCCTATAAAGGGGGTCCC |
| 79 | GGGGTCC...AATTACA GG...CA |
| 80 | gtgttCCATCTTgtgttCtagaCTATATTGGTTCCATCTT |
| 81 | gcagAgaCgcgtctTTTTTTATAACAATGgcagAgaCgcgtcTTTTATAACAATG |
| 82 | gcTataaCgcgtatcTTTTTTATAACAATGgcTataaCgcgtaTTTTATAACAATG |
| 83 | TATCACTCTGTGTTTTATAACAATGTATCACTCTGTTTTATAACAATG |
| 84 | GTATGCTCGAGTCCCTCACG |
| 85 | TCTCTCGTGACCTTGTTGCT |
| 86 | ACGGCTGCTGAAAATGTTAGG |
| 87 | AGTTCA...AGCCT AGTTC...GCCT |
| 88 | AGGCTTGAGACCTCTGTCCT |

-continued

| SEQ ID NO: | Sequence |
|---|---|
| 89 | ATGAAACAAGGGCAGCATGC |
| 90 | AGAAGAGGACGAGGGACTGG |
| 91 | CGGGTT...ATGAT CGGG...TGAT |
| 92 | TTGTTGCGTGATCCCGATGA |
| 93 | TCAATGCTCTAAGCCACCCA |
| 94 | TCGGCAGCAACAACATCTCA |
| 95 | CCCTACCTCTAGTGTGGGGT |
| 96 | ACGGACCTAAGCTGTGCAAA |
| 97 | CTcgcgAt...ATCCTGCC CTcgcgAtcGcCTAATTG...CGGAACCCTAATCCTGCC |
| 98 | GCCCTAGGTGGTTAGGCATTA |
| 99 | CctTaCCCAaCTTTGTtTGGTGGCCGGCATAGTCCCAGCCT |
| 100 | TCAGCAAAAACCCCTCA |
| 101 | GgttGcgCGCATCCGGATATAGTTCCTCCTTTGgTT |
| 102 | gaccatgattAcGCcaGCGGCCGCATCCGGATAT |
| 103 | AGCGGATAACAATTTCACACAGGA |
| 104 | TATTACCGCCTTTGAGTGAGCTGA |
| 105 | CTTTTTACGGTTCCTGGCCT |
| 106 | ACATTTCCCCGAAAAGTGC |

Pharmaceutical Compositions and Formulations.

The vaccine of the invention may be formulated as a pharmaceutical composition. In some embodiments, the vaccine contains a live virus. In some embodiments, the vaccine contains deactivated viral particles. In some embodiments, the virus is a recombinant virus encoded by any one of the nucleic acid constructs as described herein.

Such a pharmaceutical composition may be in a form suitable for administration to a subject (i.e. mammal), or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In one embodiment, the pharmaceutical compositions useful for practicing the method of the invention may comprise an adjuvant. Non-limiting examples of suitable adjuvants are Freund's complete adjuvant, Freund's incomplete adjuvant, Quil A, Detox, ISCOMs or squalene. In one embodiment, the adjuvant is an ADVAX™ adjuvant. In another embodiment, the adjuvant comprises Sepivac SWE™ adjuvant. In another embodiment, the adjuvant is monophosphoryl Lipid A (MPLA) (PHAD®) in squalene. In one embodiment, the adjuvant is MPLA 3D(6-acyl) PHAD® in 2% squalene. In one embodiment, the adjuvant increases or induces a Th-1 type immune response. The pharmaceutical composition or vaccine composition can comprise any one or more of the adjuvants described herein.

In some embodiments, the adjuvant comprises inulin e.g., delta inulin (e.g., delta inulin manufactured under current Good Manufacturing Practices is referred to in the art as Advax).

In one embodiment, the adjuvant comprises a delta inulin polysaccharide formulated with the TLR9 agonist (e.g., CpG oligodeoxynucleotides (CpG ODN)). In some embodiments, the adjuvant is Advax-SM™ (Vaxine Pty Ltd, Bedford Park, Australia).

In some embodiments, the adjuvant comprises a mixture of an oil component and a surfactant component.

In one embodiment, the composition may be an oil/surfactant dispersion or an oil/surfactant solution.

In other embodiments, the adjuvant comprises an emulsion e.g., an oil in water (o/w) emulsion.

In one embodiment, the composition includes an oil component which is formed from one or more oil(s).

In another embodiment, the oil(s) and the surfactant(s) in the composition are metabolizable (biodegradable) and biocompatible.

In some embodiments, the composition further comprises component(s) in addition to the oil and surfactant components.

In other embodiments, the proportions of the oil component and the surfactant component can vary. In some embodiments, an oil-in-water emulsion comprises oil droplets (e.g., submicron oil droplets as determined by e.g., dynamic light scattering (DLS)) when mixed with a volume of an aqueous material (e.g., water). In other embodiments, the oil droplets have an average diameter of less than about 300 nm when mixed with a volume of an aqueous material (e.g., water), illustratively, about 50 to about 290 nm, about 60 to about 280 nm, about 70 to about 270 nm, about 80 to about 260 nm, about 90 to about 250 nm, about 100 to about 240 nm, about 110 to about 230 nm, about 120 to about 220 nm, about 130 to about 210 nm, and about 140 to about 200 nm. In some embodiments, the oil droplets have an average diameter of about 160 nm (e.g., 160±10 nm), about 155 nm (e.g., 155±10 nm), about 142 nm (e.g., 142±5 nm), about 120 nm (e.g., 120±40 nm), or about 100 nm (e.g., 10±20 nm). In some embodiments, the oil droplets have an average diameter of about 142 nm (e.g., 142±5 nm).

In one embodiment, the total oil component is about 50% to about 90% by volume of the adjuvant composition. In another embodiment, the total oil component is no more than about 50%, no more than about 55%, no more than about 60%, no more than about 65%, no more than about 70%, no more than about 75%, no more than about 80%, no more than about 85%, or no more than about 90% by volume of the adjuvant composition.

In some embodiments, the oil comprises a terpenoid (e.g., a branched, unsaturated terpenoid).

In one embodiment, the oil comprises squalene.

In another embodiment, the oil comprises a saturated analog to squalene. In one embodiment, saturated analog to squalene is squalane.

In one embodiment, the adjuvant comprises a squalene oil in water emulsion. In another embodiment, the squalene in water emulsion comprises one or more non-ionic surfactants and/or other oils and/or stabilizers.

In other embodiments, the adjuvant comprises about 7 mgs to about 13 mgs, about 8 mgs to about 12 mgs, about 8 mgs to about 11 mgs, about 9 mgs to about 10 mgs, about 9.5 mgs to about 9.75 mgs of squalene (e.g., (mgs of squalene per 0.25 ml) or in 0.5 ml vaccine dose)). In one embodiment, the adjuvant comprises about 8.6 mgs, 9.75 mgs, 10.75 mgs, or 12.5 mgs of squalene.

In another embodiment, the adjuvant is a squalene in water emulsion comprising about 7 to about 13 mgs of squalene (e.g., (mgs of squalene per 0.25 ml) or in 0.5 ml vaccine dose)), illustratively, about 7 to about 13 mgs, about 8 to about 12 mgs, about 8 to about 11 mgs, about 9 to about 10 mgs, about 9.5 to about 9.75 mgs of squalene (e.g., (mgs per 0.25 ml) or in 0.5 ml vaccine dose)). In one embodiment, the adjuvant is a squalene in water emulsion comprising about 9.75 mgs of squalene (e.g., (mgs of squalene per 0.25 ml) or in 0.5 ml vaccine dose)).

In other embodiments, the oil component comprises one or more tocopherols (e.g., α, β, γ, δ, ξ, tocopherol). In one embodiment, the tocopherol is D-α-tocopherol and/or DL-α-tocopherol. In another embodiment, the α-tocopherol is DL-α-tocopherol. In other embodiments, the oil component of the adjuvant is an oil combination comprising squalene and a tocopherol (e.g. DL-α-tocopherol).

In some embodiments, the surfactant component comprises an ionic, a non-ionic, or a zwitterionic surfactant, and any combination thereof. In one embodiment, the surfactant component comprises only non-ionic surfactant(s).

Examples of surfactants include, but are not limited to, the polyoxyethylene sorbitan esters surfactants (e.g., Tweens, polysorbates, such as, e.g., polysorbate 80 (e.g., Tween™ 80), copolymers of ethylene oxide, propylene oxide, butylene oxide), sorbitan esters (e.g., sorbitan trioleate (e.g., Span™ 85), sorbitan monolaurate), and polyoxyethylene lauryl ether (e.g., Emulgen 104P), octoxynols (e.g., Triton X-100, IGEPAL CA-630/NP-40), phospholipids (e.g., lecithin), and Brij surfactants (e.g., polyoxyl 4 lauryl ether (Brij 30)).

In some embodiments, the surfactant in the composition (% by volume of the oil/surfactant composition) is no more than about: 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10%.

In one embodiment, the surfactant component consists of a mixture of polysorbate 80 (e.g., Tween™ 80) and sorbitan trioleate (e.g., Span™ 85). In another embodiment, the surfactant component consists of a mixture of polysorbate 80 (e.g., Tween™ 80) and sorbitan trioleate (e.g., Span™ 85) in a volume ratio having more sorbitan trioleate (e.g., Span™ 85) than polysorbate 80 (e.g., Tween™ 80). In some embodiments, the surfactant component consists of a mixture of polysorbate 80 (e.g., Tween™ 80) and sorbitan trioleate (e.g., Span™ 85) in a volume ratio that achieves a HLB of about 8. In some embodiments, the surfactant component consists of a mixture (e.g., (mgs of squalene per 0.25 ml) or in 0.5 ml vaccine dose)) of about 1.175 mgs polysorbate 80 (e.g., Tween™ 80) and about 1.175 mgs sorbitan trioleate (e.g., Span™ 85).

In other embodiments, the aqueous component (e.g., water) further comprises one or more components e.g. solutes/salts/buffers. In one embodiment, the salts (e.g., sodium salts) form a pH buffer (e.g. citrate, phosphate). In another embodiments, one or more buffers include, but are not limited to, a citrate buffer, phosphate buffer (e.g., phosphate buffered saline, ammonium phosphate), a Tris buffer, a borate buffer, a succinate buffer, or a histidine buffer. In some embodiment, a buffered aqueous component comprises about 1 to about 20 mM of total buffer.

In other embodiments, the pH of the aqueous component is buffered at about pH 5.5 to about pH 8.0, illustratively, about pH 6.1 to about pH 7.9, about pH 6.2 to about pH 7.8, about pH 6.3 to about pH 7.7, about pH 6.4 to about pH 7.6, about pH 6.5 to about pH 7.5, about pH 6.6 to about pH 7.4, about pH 6.7 to about pH 7.3, about pH 6.8 to about pH 7.2, and about pH 6.9 to about pH 7.1. In one embodiment, the pH of the aqueous component is buffered at about pH: 5.7, 6.0, 6.5, 6.8, or 7.2. In another embodiment, the pH of the aqueous component is buffered at about pH 6.0 to about pH 6.5. In other embodiments, the buffer is 10 mM citrate buffer with a pH of about 6.5.

In other embodiments, the adjuvant is a squalene in water emulsion comprising (e.g., (mgs of squalene per 0.25 ml) or in 0.5 ml vaccine dose)) about 9.75 mgs squalene, 1.175 mgs polysorbate 80 (e.g., Tween™ 80), 1.175 mgs sorbitan trioleate (e.g., Span™ 85), citrate buffer, and a pH of about 6.5.

In some embodiments, an adjuvant of the present disclosure is co-formulated or co-administered with the vaccine.

In other embodiments, an adjuvant of the present disclosure is not co-formulated or co-administered with the vaccine.

Pharmaceutical compositions that are useful in the methods of the invention may be suitably developed for inhalation, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

The composition of the invention may comprise a preservative from about 0.005% to 2.0% by total weight of the composition. The preservative is used to prevent spoilage in the case of exposure to contaminants in the environment.

Administration/Dosing

The regimen of administration of the compositions of the present invention may affect what constitutes an effective amount. For example, the vaccines, polypeptides, and/or the nucleic acids of the invention may be administered to the subject (i.e. mammal) in a single dose, in several divided dosages, as well as staggered dosages may be administered daily or sequentially, or the dose may be continuously infused, or may be a bolus injection. Further, the dosages may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat the disease in the subject. An effective amount of the composition necessary to achieve the intended result will vary and will depend on factors such as the disease to be treated or prevented, the age, sex, weight, condition, general health and prior medical history of the subject being treated, and like factors well-known in the medical arts. In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the composition and the heterologous protein to be expressed, and the particular therapeutic effect to be achieved.

In some embodiments, the vaccine administered may be in an amount that will depend e.g., on the subject to be treated, the capacity of the subject's immune system to develop the desired immune response, and/or the degree of protection desired.

In other embodiments, the administration of the vaccines of the present invention can be in accordance with any suitable vaccination schedule, e.g., day 0, one month, four months, and twelve months from day 0. In other embodiments, the vaccines described herein may also be given in a single dose schedule, or a multiple dose schedule in which a primary course of vaccination may be with 1-10 separate doses, followed by other doses given at subsequent time intervals required to maintain and/or reinforce the immune response, for example, at 1-4 months for a second dose, and if needed, a subsequent dose(s) after several months. In some embodiment, other examples of suitable immunization schedules include, but are not limited to: (i) 0, 1 month and 6 months, (ii) 0, 7 days and 1 month, (iii) 0 and 1 month, (iv) 0 and 6 months, (v) 0, 1 month and 2 months, or other schedules sufficient to elicit the desired immune responses expected to confer protective immunity, and/or reduce disease symptoms, or reduce severity of disease.

In one embodiment, the administration of the vaccines of the present can be in accordance with any suitable vaccination schedule and/or dosage(s) effective to produce an antigen-specific immune response. In some embodiments, an antigen-specific immune response comprises a B and/or T cell response. In other embodiments, the antigen-specific immune response comprises administration of a single dose (no booster dose). In some embodiments, a second (booster) dose of the vaccine may be administered. In other embodiments, additional doses may be administered.

In some embodiments, the administration of the vaccines of the present can be in accordance with any suitable vaccination schedule and/or dosage(s) effective such that the subjects exhibit a seroconversion rate of at least 60%, at least 70%, at least 80%, at least 85%, at least 90%, or at least 95% following the first dose or the second (booster) dose of the vaccine.

In other embodiments, the administration of the vaccines of the present can be in accordance with any suitable vaccination schedule and/or dosage(s) effective to produce an antigen-specific immune response in the subject, wherein the anti-antigen antibody titer produced in the subject is increased by at least 1 log relative to a control.

In some embodiments, the control is an anti-antigen antibody titer produced in a subject who has not been administered a vaccine of the present disclosure. In other embodiments, the control is a titer produced in a subject that has been administered a live attenuated or inactivated vaccine; a recombinant or purified protein vaccine; or a virus-like particle vaccine.

In one embodiment, the titer produced in the subject is increased by 1-3 log relative to the control. In another embodiment, the titer produced in a subject is increased at least 2 times relative to the control. In other embodiments, the titer produced in the subject is increased at least 3, 4, 5, 10 or more times relative to the control. In one embodiment, the titer produced in the subject is increased at least 10 times relative to a control. In another embodiment, the titer produced in the subject is increased 2-10 times relative to a control.

In some embodiments, the vaccine of the present disclosure is administered to a subject in an effective amount (e.g., an amount effective to induce an immune response). In some embodiments, the effective amount is a dose equivalent to an at least 2-fold, at least 4-fold, at least 10-fold, at least 100-fold, at least 1000-fold reduction in the standard of care dose of a recombinant protein vaccine, wherein the anti-antigen antibody titer produced in the subject is equivalent to an anti-antigen antibody titer produced in a control subject administered the standard of care dose of a recombinant protein vaccine, a purified protein vaccine, a live attenuated vaccine, an inactivated vaccine, or a VLP vaccine. In some embodiments, the effective amount is a dose equivalent to 2-1000-fold reduction in the standard of care dose of a recombinant protein vaccine, a purified protein vaccine, a live attenuated vaccine, an inactivated vaccine, or a VLP vaccine.

In other embodiments, the effective amount of the vaccine administered comprises a total dose of about 0.1 µg to about 1000 µg of the vaccine or active ingredient (e.g., VLP, virion, viral vector, antigen, or nucleic acid molecule), illustratively, about 1 µg to about 900 µg, about 5 µg to about 700 µg, about 10 µg to about 500 µg, about 15 µg to about 300 µg, about 20 µg to about 200 µg, and about 25 µg to about 100 µg. In some embodiments, the effective amount is a total dose of about 25 µg, about 50 µg, or about 100 µg. In other embodiments, the effective amount is a total dose of not less than (NLT) about 1 µg, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg. In other embodiments, the effective amount is a total dose of about 0.1 µg to about 10 µg.

In some embodiments, doses of the vaccine are based on quantification of DNase-resistant particles (DRPs). In one embodiment, DRPs are equivalent to encapsidated vector genomes. In some embodiments, the subject receives at least one dose (e.g., a first dose at time zero) of the vaccine of about $10^5$ to $10^{20}$ about DRPs, illustratively, about $10^6$ to $10^{18}$, about $10^7$ to $10^{17}$, about $10^8$ to $10^{16}$, about $10^9$ to $10^{15}$, about $10^{10}$ to $10^{14}$, and about $10^{11}$ to $10^{13}$ DRPs. In other embodiments, the subject receives at least one dose (e.g., a first does at time zero) of at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, at least about $10^{16}$, at least about $10^{17}$, at least about $10^{18}$, at least about $10^{19}$, or at least about $10^{20}$ DRPs.

In some embodiments, the effective amount is a dose administered to the subject a total of one, two, three, four, five, or more times.

In some embodiments, the efficacy or effectiveness of a vaccine of the present disclosure is equal to or greater than about 60%. Vaccine efficacy or effectiveness may be assessed using e.g., standard analyses and protocols known in the art. In one embodiment, the efficacy or effectiveness of the vaccine is at least about 60%, at least about 65%, at least about 70%, at least about 75%, at least about 80%, at least about 85%, or at least about 90%.

In some embodiments, the vaccine immunizes the subject against a coronavirus (e.g., SARS-CoV-2 virus) for up to 6 months, 1 year or 2 years. In some embodiments, the vaccine immunizes the subject against a coronavirus (e.g., SARS-CoV-2 virus) for at least about 6 months, at least about 1 year, at least about 2 years, at least about 3 years, at least about 4 years, or about 5 years to about 10 years, or more.

Routes of Administration

One skilled in the art will recognize that although more than one route can be used for administration, a particular route can provide a more immediate and more effective reaction than another route. Routes of administration of any of the compositions of the invention include inhalation, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, electroporation and topical administration.

Kits

In some embodiments a kit is provided for treating, preventing, or ameliorating an a given disease, disorder or condition, or a symptom thereof, as described herein wherein the kit comprises: a) a compound or compositions as described herein; and optionally b) an additional agent or therapy as described herein. The kit can further include instructions or a label for using the kit to treat, prevent, or ameliorate the disease, disorder or condition. In yet other embodiments, the invention extends to kits assays for a given disease, disorder or condition, or a symptom thereof, as described herein. Such kits may, for example, contain the reagents from PCR or other nucleic acid hybridization technology (microarrays) or reagents for immunologically based detection techniques (e.g., ELISpot, ELISA).

Methods of Treatment

In one aspect, the invention includes a method of generating an immune response against a SARS-CoV-2 virus in a subject in need thereof. In another aspect, a method of vaccinating a subject against a SARS-CoV-2 virus is provided. In yet another aspect, a method of providing immunity against a SARS-CoV-2 virus in a subject is provided. In still another aspect, a method of treating and/or preventing a disease or disorder associated with SARS-CoV-2 virus in a subject in need thereof. In some embodiments, the method comprises administering to the subject an effective amount of a recombinant virus as described herein. In some embodiments, the method comprises administering to the subject an effective amount of a vaccine described herein.

In some embodiments, the disease or disorder associated with the SARS-CoV-2 virus is a respiratory disease. In some embodiments, the disease or disorder associated with the SARS-CoV-2 virus is coronavirus disease. In some embodiments, the disease or disorder associated with the SARS-CoV-2 virus is COVID-19.

Pharmaceutical compositions comprising the vaccine of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the vaccine of the invention may be carried out in any convenient manner known to those of skill in the art. The vaccine of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally.

Subjects to which administration of the pharmaceutical compositions of the invention is contemplated include, but are not limited to, humans and other primates, mammals, and birds, including commercially relevant mammals and birds such as cattle, pigs, horses, sheep, chicken, ducks, cats, dogs, and ferrets.

In some embodiments, the subject is a domesticated animal. In some embodiments, the subject is a domestic pet. In some embodiments, the animal is a captive animal, e.g., an animal maintained in an exhibit or in a zoological park. In some embodiments, the animal is livestock. In some embodiments, the subject is an animal susceptible to infection with SARS-CoV-2 and can be a reservoir for the SARS-CoV-2 virus. In some embodiments, the subject is a feline. In some other embodiments, the subject is a canine. In some embodiments, the subject is a member of the Mustelidae family, such as a weasel, polecat, stoat, marten, mink, badger, otter, or ferret. In some embodiments, the subject is a cat. In some other embodiments, the subject is a dog. In some embodiments, the subject is a ferret.

In one aspect, a method of preventing SARS-CoV-2 infection or providing immunity to SARS-CoV-2 in a subject is provided, the method comprising administering to a subject a SARS-CoV-2 vaccine described herein, wherein the subject is a domestic pet selected from a cat, a dog, and a ferret. In particular, felines and ferrets have been identified as a potential host for SARS-CoV-2 (J. Shi et al., Science 10.1126/science.abb7015 (2020)). Cats are one of the most favored pets of the USA's citizens. In the United States, one in three households owns a pet cat, with an average of 2.2 cats per cat-owning household. However, pet cats are only a part of the total cat population in the country, which is estimated to be around 76.5 million.

Currently, rabies vaccination is recommended for cats, dogs, and ferrets. CDC guidelines recommend that all dogs, cats, and ferrets should be vaccinated and revaccinated against rabies according to product label directions (www.cdc.gov/rabies/specific groups/20 veterinarians/vaccination.html). If a previously vaccinated animal is overdue for a booster, it should be revaccinated. Immediately following the booster, the animal is considered currently vaccinated and should be placed on a vaccination schedule according to the labeled duration of the vaccine used.

The existing RABV vaccine for cats, dogs, or ferrets can be replaced with a rabies virus-based SARS-CoV-2 vaccine to induce protection from both diseases. Thus, in one aspect, a method of providing immunity to rabies and a SARS-CoV-2 associated disease in a subject is provided, wherein the subject is a cat, dog, or ferret. The method includes the step of administering to the subject a vaccine comprising a rabies virus-based SARS-CoV-2 vaccine. In another aspect, a vaccine for cats, dogs, or ferrets is provided, the vaccine comprising a rabies virus-based SARS-CoV-2 vaccine. In some embodiments, the vaccine comprises a recombinant rabies virus comprising a SARS-CoV-2 spike protein (S) or a portion thereof. In some embodiments, the vaccine comprises a recombinant rabies virus comprising a fusion of (a) a glycoprotein (G) of a virus or a portion thereof, and (b) a SARS-CoV-2 spike protein (S) or a portion thereof. In some embodiments, the vaccine comprises an inactivated virus. In particular embodiments, the vaccine comprises an adjuvant. In some embodiments, the vaccine is formulated for administration to a cat. In some other embodiments, the vaccine is formulated for administration to a dog. In still other embodiments, the vaccine is formulated for administration to a ferret.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Green, M. R. & Sambrook, J., Cold Spring Harbor Laboratory Press, 2012); "Oligonucleotide Synthesis, a practical approach" (Paselk R. A., edited by Gait, M. J., IRL Press, Oxford, 1984); "Culture of Animal Cells: A Manual of Basic Technique and Specialized Applications, Sixth Edition" (Freshney, R. I., John Wiley & Sons, Inc., 2010); "Methods in Enzymology" (Vol. 152, Guide to Molecular Cloning Techniques, Berger and Kimmel, Eds., San Diego: Academic Press, Inc., 1987); "Handbook of Experimental Immunology" (Herzenberg L. A., Weir, D. M., Blackwell, C., Wiley, 1997); "Gene Transfer Vectors for Mammalian Cells" (Miller and Calos, eds., Cold Spring Harbor Laboratory, Cold Spring Harbor, 1987); "Short Protocols in Molecular Biology" (Ausubel, F. M., et al., ed., John Wiley & Sons, 2002); "Polymerase Chain Reaction: Principles, Applications and Troubleshooting" (Babar, M. E., publisher VDM Verlag Dr. Müller, 2011); "Current Protocols in Immunology" (Colligan, J. E., et al., ed., Greene Pub. Associates and Wiley-Interscience, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1

RABV, VSV, and MV Expressing Covid S or Covid-S1

The materials and methods employed in Examples 1-5 are now described.
Generation of RABV-, VSV-, and MV-Based Vaccines Against COVID-19
The SARS-CoV-2 spike protein (S) was used in generating the vaccines against COVID-19 described herein. SARS-CoV-2 causes Convid-19. The S1 domain (receptor binding site of the S protein) was incorporated into the Genome of rabies virus (RABV) and vesicular stomatitis virus (VSV). For both constructs part of their native G protein was used to promote the incorporation of the S1 domain. The full-length SARS-CoV-2 S was found to interfere with viral growth (VSV or RABV G) making it almost impossible to produce the vaccine; thus the S1 domain was used instead.

Three measles virus (MV)-based vaccine expressing full-length SARS-CoV-2 spike protein (S) were also prepared. These three viruses express the SARS-CoV-2 spike protein (S) from position 2, 3, or 6 of the genome. Previous research indicates that for measles virus the position a foreign gene is expressed is important for MV replication and immunogenicity of the trans-gene. However this depends on the antigen, so three different viruses were prepared.
Testing of RABV-, VSV-, and MV-Based Vaccines Against COVID-19 in Animals
In the next phase, the vaccines are tested in animals. The receptor for both viruses is believed to be ACE 2. The model that will be used is a hamster or mice (transgenic expressing ACE2 or wildtype infected with an Adenovirus expressing ACE2).

Both live and killed viruses are tested. After immunization mice or hamster are challenged with the SARS-CoV-2 (Convid-19).
Immunological Parameters of the 2019-nCoV Vaccine.
The parameters of the induced humoral and cellular immune responses will be studied after i.m. inoculation of mice (including 2019-nCoV challenge), and non-human primate (NHP) (immunogenicity). ELISA and virus neutralization assays (VNA) will be utilized to analyze the humoral immune response. These assays are developed for mice and NHP and, based on the limited space, only briefly described below. Previous experience will be used in the development of such assays especially in the field of coronaviruses ELISA Assay for Detection of 2019-nCoV S1 and Vector RABV G-Specific Humoral Responses.

Preparation of highly purified antigens against 2019-nCoV S1 or RABV G. Purification of the HA-tagged soluble protein from the supernatant of transfected 293T cells is carried out as described previously for MERS-CoV (17). Purified proteins can be prepared in the mg range sufficient for large numbers of assay plates. Approximately 10-20 mg of purified RABV G is produced on a regular basis in the Schnell laboratory.

To determine antibody responses to the 2019-nCoV S or RABV G, an indirect ELISA will be developed utilizing purified S1 or G protein (26) and unpublished. Sera from vaccinated mice or NHP will be used at different dilutions to determine the EC50 over time. Serum IgM and IgG antibodies (total IgM, IgG, IgG1, IgG2 for NHP, IgG2c and IgG1 for B6) to each vaccine antigen will be measured by a qualified ELISA that is well established in the Thomas Jefferson University (TJU) laboratories. Prior to performing the ELISA assays, we will qualify the assay for each vaccine antigen. Our ELISA platform will be standardized to measure serum IgG specific for the vaccine antigens by characterizing assay variability, determining the limit of quantitation, defining the positive and negative quality control ranges, and defining assay acceptance criteria. TJU has substantial experience in qualifying and performing ELISA assays using this platform and plan to use it for future clinical studies as well. Assays will be transferred for the human clinical samples to a contractor via IQVIA.

Virus Neutralization assays (VNA) for RABV are well established in the TJU laboratory (12, 27, 28) for mouse, monkey, and human sera. Use of an internal WHO standard, allows determining the international unit (I.U.) achieved by the immunization. The presence of 0.5 I.U or more in the sera is considered a correlate of protection from rabies. VNA for MERS-CoV are established at the University of Maryland in the Frieman lab. Dr. Frieman has a virus sample from CDC from the Washington St patient. He is also recreating multiple strains using his infectious clone and synthesizing full genomes.

Cellular Responses

Most likely, humoral responses are the key for protection based on previous studies of coronaviruses but as a research part, frequencies and cytokine expression profiles of vaccine antigen-specific T cells will be measured in splenocytes or cryopreserved NHP PBMCs using a qualified 13-color ICS assay. In order to assess potential for durable antibody responses, antigen specific IgG+ ELISPOT analysis will be performed to detect antibody-secreting plasma cells in the bone marrow 28 days post-boost immunization.

The results of the experiments are now described.
RABV, VSV, and MV Expressing Covid S or Covid-S1

VSV expressing codon-optimized Covid-S1, RABV expressing codon-optimized Covid-S1, and MV expressing codon-optimized Covid-S from positions 2, 3, and 6 of the genome were generated (FIGS. 1-5; FIGS. 17-21).

Figure 6:
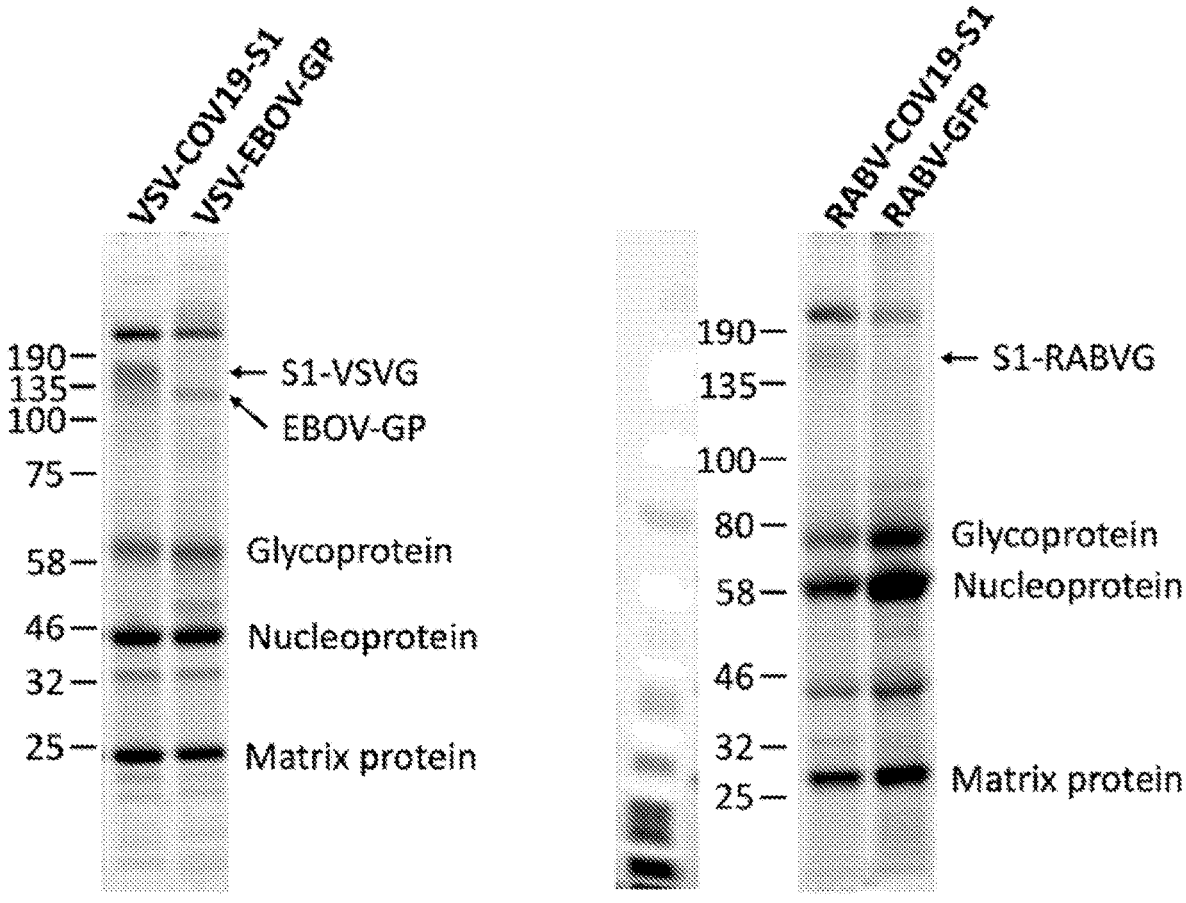
FIG. 6: Characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 S1 protein is indicated. The controls show VSV and RABV virions.

FIG. 6 shows characterization of RABV (RABV-COV19-S1) and VSV (VSV-COV19-S1) expressing a chimeric S1-G fusion protein. SDS-PAGE analysis of purified virions after sucrose gradient purification. Letters indicate the positions of the VSV or RABV L, G, N, P, and M proteins. Numbers to the left indicate the sizes of the molecular mass standards. The Covid-19 S1 protein is indicated. The controls show VSV and RABV virions.

Example 2

A Rabies Vaccine Based Bivalent Vaccine Against 2019-nCoV

Technologies developed for MERS-CoV and SARS-CoV can be transferred to the 2019-nCov. Most vaccine design has focused on the major immunodominant antigen, the Spike (S) protein located on the surface of the virion, which serves as the ligand for the MERS-CoV receptor dipeptidyl peptidase 4 (DPP4, also known as CD26) (1). Similar to MERS-CoV S 2019-nCoV S is a transmembrane glycoprotein that is likely cleaved by the furin protease into S1 and S2 domains as MERS-CoV S (2). Without intending to be bound by theory, it is believed that, as for other coronaviruses such as MERS-CoV, virus neutralizing antibodies (VNA), which are produced in response to infection or vaccination with MERS-CoV S, will neutralize virus infection in vitro and protect lungs from infection in mouse models of disease (3-6).

Described herein is a Rhabdovirus-based vaccine that offers a combination of features that could prove desirable for an effective 2019-nCoV vaccine. Rhabdovirus-vectored vaccine candidates have been developed for several human pathogens (7). More recently both RABV and VSV have been successfully utilized as Ebola virus (EBOV) vaccines and both approaches are either close to clinical trials (RABV) or have already completed phase 2 clinical trials (VSV) (8, 9). Chemically inactivated RABV vaccines are widely used and safe for humans; approximately 100 million doses of inactivated RABV vaccines are administered to humans every year, demonstrating an excellent safety profile (10). Both live and chemically inactivated RABV vaccines are shown to be safe for animals. In a proof of concept study both live-attenuated as well as inactivated RABV-EBOV have been utilized successfully against EBOV and this vaccine enters a phase 1 clinical trial in 2020. (11-14). Construction of an attenuated RABV 2019-CoV based on the well-characterized MERS-CoV vaccine (FIGS. 12 and (15)).

Figure 12:
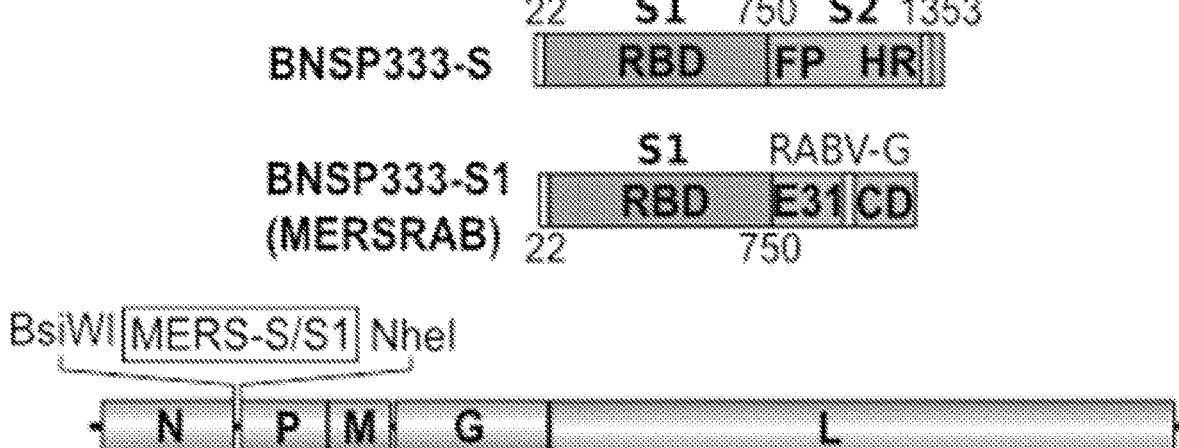
FIG. 12: Schematic illustration of the 2019-nCoV vaccine constructs used in this study. Spike protein cDNA is inserted between the N and P genes of the SAD-B19-derived RABV virus vaccine vector BNSP333. The BNSP333-S1-G construct expresses a chimeric protein that contains the entire 51 domain fused to the C-terminal part of the RABV G glycoprotein (amino acids 428-524), which encompasses the entire cytoplasmic domain (CD), the transmembrane domain (TM), plus 31 amino acids of the ectodomain (E31) of RABV G. Different structural elements of the spike protein are indicated in the full length construct: signal peptide (SP), receptor-binding domain (RBD), fusion peptide (FP), heptad repeat regions 1 and 2 (HR1 and HR2), transmembrane domain (TM), and cytoplasmic domain (CD).

The nucleotide sequence encoding 2019-nCoV S1 protein was inserted into the cBNSP333 vector (FIG. 12; FIG. 18 "BNSP333-COVID19-S1-RVG"). 2019-nCoV S is a glycoprotein anchored in the membrane of the 2019-nCoV virions that projects from the surface of the virus to act as a ligand to susceptible cells, and is therefore a major immunogen. The BNSP333 vaccine vector utilized is derived from the attenuated RABV strain SAD-B19 (16). Several modifications were introduced into the parent strain to increase safety and maximize expression of foreign genes. It was previously shown that foreign genes can be stably introduced into this vector (14, 17-20). Moreover, it was shown that expression of foreign antigens from a position between the RABV N and P gene, as well as codon optimization for human cells of the target gene, results in the highest expression level of the foreign antigen (14). Additionally, replacing the arginine with glutamic acid at position 333 (333R->333E) within the RABV glycoprotein (G) further reduces the pathogenicity of the already highly attenuated vector (19). This improved vector was successfully used to generate candidate vaccines against several emerging zoonotic viral diseases like EBOV and Henipaviruses (14, 21). However, expression of full length CoV S was found to inhibit expression of RABV G protein and reduces viral titers dramatically. However, expression of 51 fused to the C-terminal part of RABV G resulted in strong incorporation of RABV G-MERS-CoV-S1 fusion protein. The RABV G-2019-nCoV-S1 vaccine is similar to the MERS-CoV 331-S1=MERSRAB) expressing the N-terminal 750 aa of 2019-nCoV S fused to a truncated RABV glycoprotein, which comprises 31 aa of the ectodomain (ED) of RABV G and the complete CD and the transmembrane domain of RABV G to allow chimeric glycoprotein incorporation into RABV virions. The chimeric 2019-nCoV S1/RABV G protein utilizes the original 2019-CoV ER translocation sequence (SS) and is generated by PCR of codon optimized cDNA fragments (FIG. 12).

All the following results are presented from previous studies with the MERS construct (MERSRAB). For MERSRAB, infectious virus was recovered. The new virus expressing the S1 fragment grew to similar titers of roughly 108 FFU/mL as the control virus BNSP333 on Vero cells, which are approved for human vaccine production. The BNSP333 RABV expressing the S1 was entitled MERSRAB and the animal efficacy studies listed below resulted from this constructs. The RABV-based MERSRAB vaccine proved efficacious in three different animal models: mice transduced with an Ad5 virus expressing human hDPP4 (the receptor for MERS-CoV), CRISPR-CASc mice expressing human hDPP4 and Alpacas (camelid).

MERSRAB is immunogenic in mice and protects against challenge with MERS-CoV. To analyze the immunogenicity of the MERSRAB (FIG. 12 and FIG. 13), we immunized 4 groups of BALB/c mice (5 mice per group) with 10 μg of the control virus FILORAB1 (Ebola virus vaccine, group 1), 10 μg of MERSRAB (groups 2 and 3), or PBS (group 4) at day 0, 7, and 21 post-inoculations. We followed the immune response against RABV G and MERS-CoV S by antigen-specific ELISAs. The antigen-specific IgG responses increased over time and after each immunization; they reached high antibody levels against both RABV G and MERS-CoV S after the third inoculations. MERS-CoV-S specific immune responses were only detected in groups 2 and 3, but RABV G specific IgG was detected in groups 1-3. None of the animals of group 4, which were mock immunized, demonstrated immune responses against RABV G or MERS-CoV S protein, confirming the specificity of the ELISAs assays. Whereas the RABV G-specific ELISA titers are known to predict protection against RABV challenge (22-24), the protective abilities of the MERS-CoV S-directed antibodies are unknown. Therefore VNA was performed against MERS-CoV of sera on day 35 of the immunized mice of all four groups. Low levels of MERS-CoV neutralizing antibodies were detected in the sera of mice from group 1 (FILORAB1) or mock (PBS) immunized mice (group 4), but the sera of mice immunized with MERSRAB (group 2 and 3) neutralized MERS-CoV at serum dilutions between 1:1280 and 1:5120. This demonstrates a high level of anti-MERS-CoV neutralizing antibody produced in the BNSP333-S1 vaccinated mice.

Figure 13:
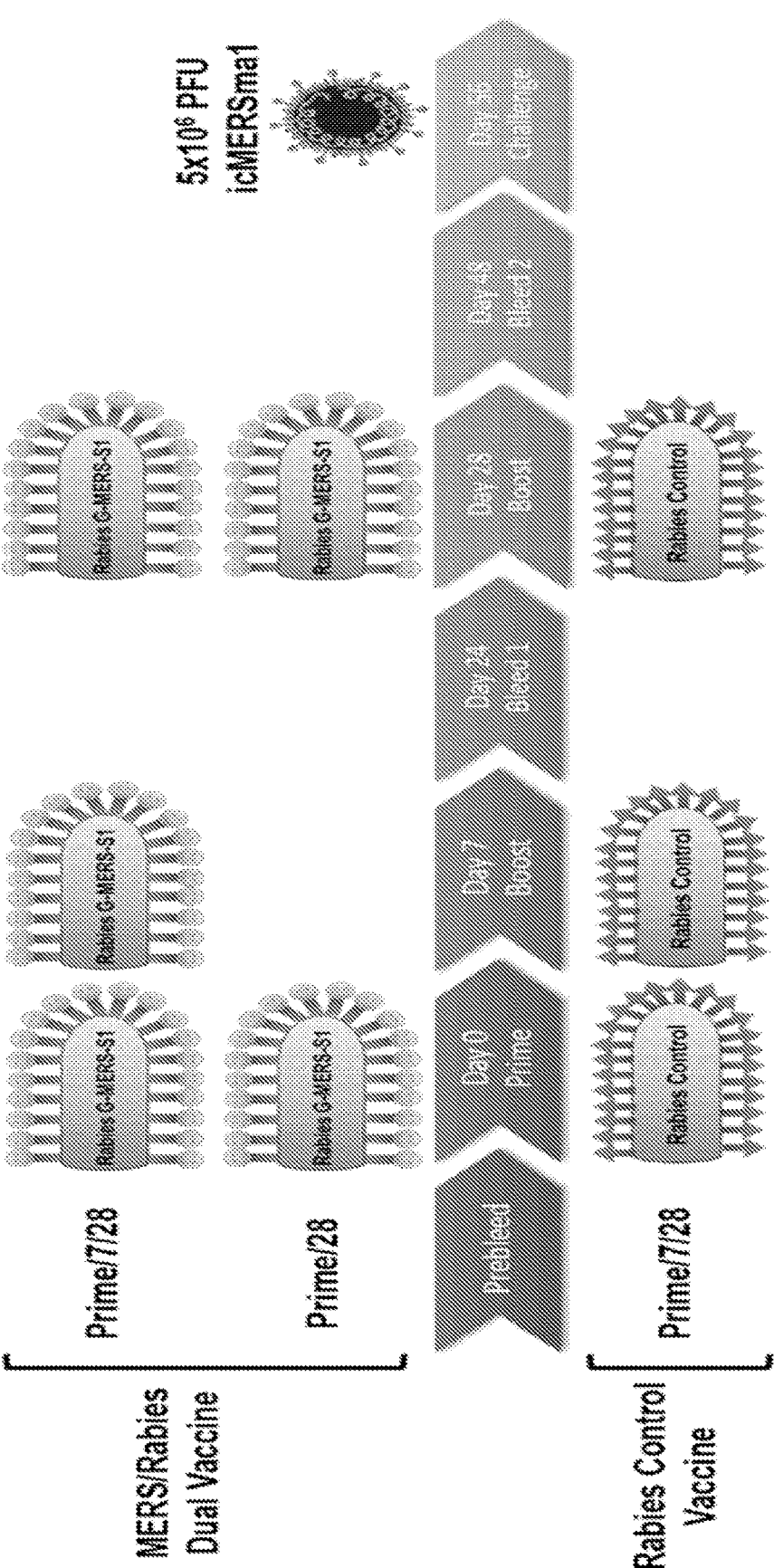
FIG. 13: Schematic illustration of the MERSRAB immunization schedule and challenge with MERS-CoV. Two and three immunization were analyzed with the deactivated vaccine.

Efficacy testing of the RABV-MERS vaccine was performed using the adenovirus-hDPP4 transduced mouse model (25). All four groups of mice were transduced, and after five days, mice in groups 1, 2, and 4 were challenged intranasally (IN) with MERS-CoV at 1×10$^5$ pfu/mouse (strain Jordan-n3/2012). Four days after the challenge, the mice were euthanized, and their lungs were dissected, homogenized, and assayed for viral load by qRT-PCR and a viral plaque assay. For BNSP333-S1 immunized mice, both genomic and mRNA were reduced to background levels similar to those found in mice not transduced by the Ad5-expressing hDPP4. Moreover, the immunization with BNSP333-S1 reduced the viral load in the lungs to a level below detection of the assay. In the next step the RABV based vaccine MERSRAB was tested in the CRISPR-CAS generated transgenic mouse model (mice expressing human hDPP4). Transgenic mice in groups of 10 mice were immunized with 10 μg of the control virus FILORAB (Empty vector, group Rabies control vaccine), 10 μg of MERSRAB (MERS/Rabies dual vaccine), at day 0, 7, and 28 or only at day 0 and 28 (FIG. 13). The immune response against RABV G and MERS-CoV S was followed by antigen-specific ELISAs. The antigen-specific IgG responses increased over time and after each immunization; they reached high antibody levels against both RABV G and MERS-CoV S after the second or third immunization. MERS-CoV-S specific immune responses were only detected in groups 1 and 2 (MERS-Rabies), but RABV G specific IgG was detected in all three groups.

Figures 14A, 14B, 14C:
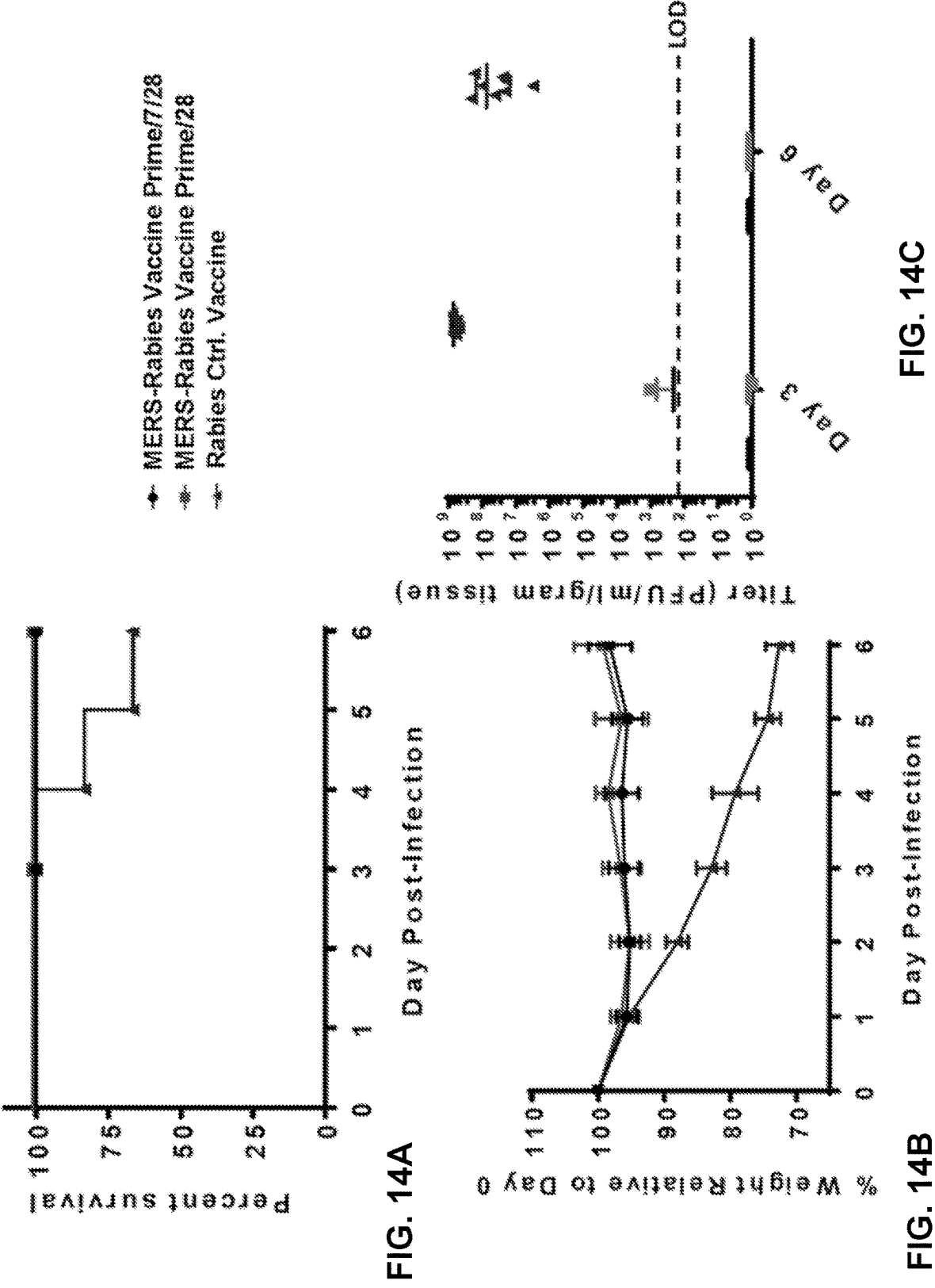
FIGS. 14A-14C: Two or three inoculation with MERSRAB protect animals from weight loss and vaccine induce immune responses control the MERS-CoV challenge viruses to undetectable levels. Animals were immunized and challenge as outlined in FIG. 13.

Whereas the RABV G-specific ELISA titers are known to predict protection against RABV challenge (22-24), the protective abilities of the MERS-CoV S-directed antibodies are not well characterized. The transgenic mice were therefore challenged with pathogenic MERS-CoV at day 56. As shown in FIG. 14A all immunized mice survived the infection whereas 40% of the mock immunized animals succumbed to the infection. As shown all mice, which received one or two inoculation with the MERSRAB were protected from weight-loss completely. Moreover, immunization did reduce viral loads to undetectable levels (FIGS. 14A-14C) whereas the MERS-CoV replicated to very high levels in empty vector immunized animals (FIG. 14C). This can also be seen in FIG. 15. Two or three inoculations with MERSRAB protect animals from viral replication in the lung and MERS-CoV antigen in lungs of immunized mice is detected at day three after challenge, no antigen is detected at day six. In contrast, the lung tissue of animal immunized with the vector only, large amount of tissue damage and viral antigen can be detected at both time points consistent with the viral load shown in FIGS. 14A-14C.

Figure 15:
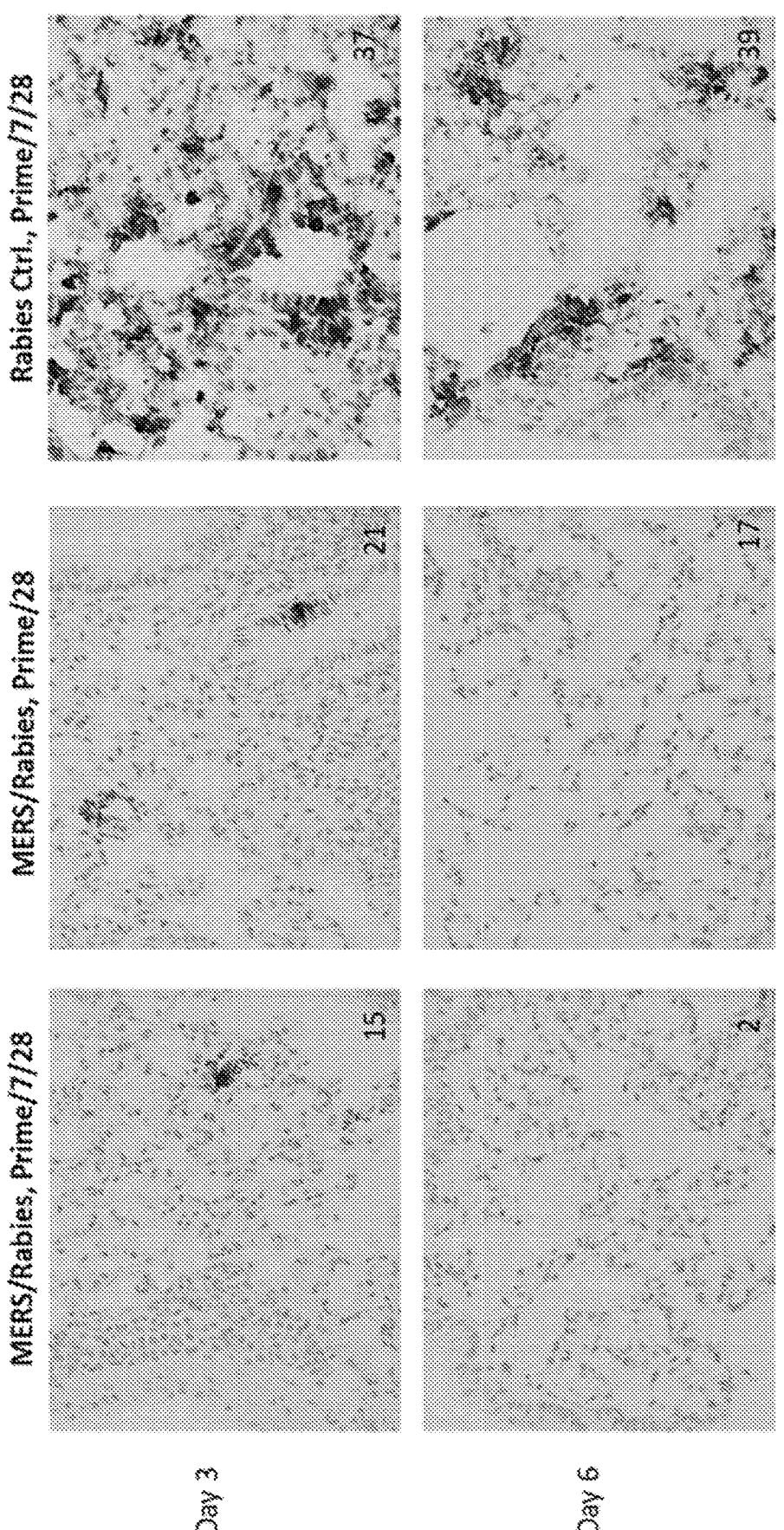
FIG. 15: Two or three inoculation with MERSRAB protect animals from viral replication in the lung. The figure shows that only small amounts of MERS-CoV antigen is detected in lungs of immunized mice at day three after challenge, and no antigen is detected at day six. In contrast, in the lung tissue of animal immunized with the rabies virus vector only large amount of tissue damage and viral antigen can be detected at both time points consistent with the viral load shown in FIG. 14.
Figure 16A:
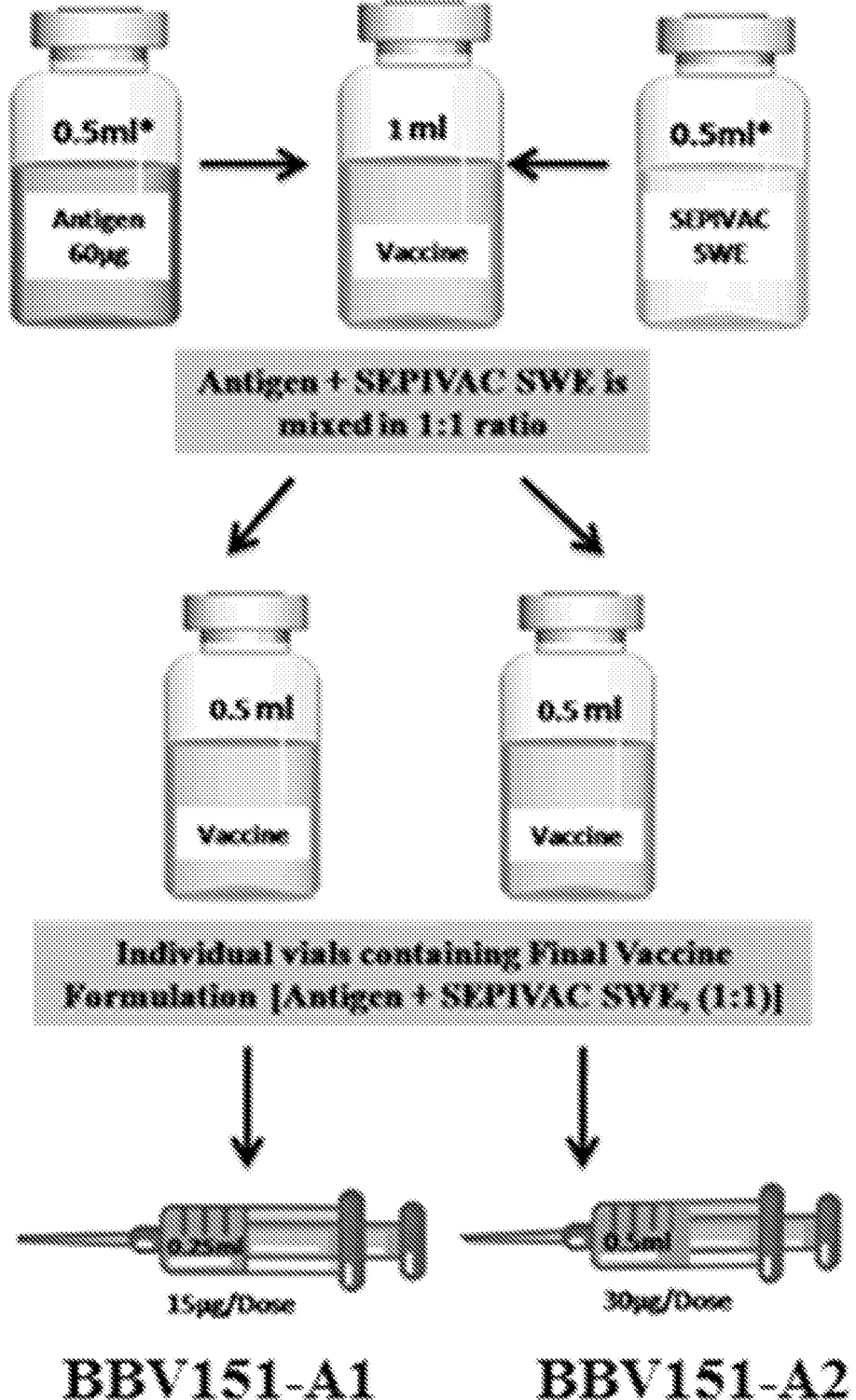

Lastly, to determine the potential of preventing transmission from host species to humans, the next study tested if the MERSRAB vaccine was efficacious in Camelids. In brief, a group of five Alpacas were immunized with 107 foci forming units (ffu) of live MERSRAB i.m., or intranasally or immunized i.m. with 100 μg or 300 μg of the inactivated MERSRAB vaccine. After 56 days the animals were challenged with MERS-CoV intranasally and nasal swabs were taken over time to analyse viral shedding. No disease was detected after immunization with either the live or the killed MERSRAB vaccine. As shown in FIG. 15, two inoculations with 100 or 300 μg resulted in almost complete suppression of viral shedding from the infected animals.

Inactivated RABV has a 30-year long history as an efficient and safe vaccine. Taken together, the results presented above clearly indicate that a vaccine based on deactivated RABV particles is a strong candidate against 2019-nCoV infection.

Furthermore, the use of an adjuvant might allow clinical benefit after just one vaccination. Appropriate adjuvant selection is likely be critical to design of a safe and effective nCoV vaccine. Notably, vaccine-enhanced eosinophilic lung disease was seen to be exacerbated when SARS vaccines were formulated with aluminium salt adjuvants whereas it was completely prevented when the same SARS vaccines were formulated with Advax-SM adjuvant, which is a formulation of polysaccharide particles combined with a potent TLR9 agonist. The addition of Advax to a broad range of vaccines results in significant benefits including enhanced protection associated with higher antibody titers, increased B cell receptor affinity maturation, IgG subtype diversification, enhanced memory CD4 and CD8 T cell responses and antigen dose sparing. Advax adjuvant have been shown to provide protective immunity with a single dose in neonatal pups. A particular advantage of Advax adjuvants is that they have already been shown to be safe and well tolerated in human clinical trials in combination with many different antigens thereby facilitating rapid translation of successful vaccines from preclinical studies to human trials.

Adjuvants increase the immunity of vaccines and can also change the antibody isotype. It was previously shown for a rabies virus platform that the addition of MPLA in squalene (PHAD®) increased both the total humoral responses as well as the Th1/TH2 bias. For most viral vaccines, it has been shown that a TH1-bias is beneficial. It has been demonstrated a TH1 bias is necessary for robust protection against EBOV by the FILORAB1 vaccine. For the 2019-nCoV vaccine, the MPLA 3D(6-acyl)PHAD® in 2% Squalene can be used as well as an adjuvant with the potential to increase immunity and induce TH1 responses (e.g., CpG-Oligodeoxynucleotide).

Example 3

Preclinical Studies

The following describes preclinical studies to test the 2019-nCoV vaccine:

1) Most critical is the ability to test efficacy in animal models (small animal and NHP), which will be performed in parallel to the proposed Phase 1 clinical trial to evaluate safety and immunogenicity and potential adverse effects such as enhancement of infection after vaccination. Because 2019-nCoV and the SARS-CoV seem to utilize the same receptor the human ACE2 transgenic mice may be a suitable model for 2019-nCoV, however evaluation of this model has not been characterized and experiments to confirm the model are in the planning stages. NHP animal modelling is expected to start in mid-March 2020. Cynomolgus monkeys, African Green monkeys, common marmosets, and rhesus monkeys will be evaluated for disease development following intratracheal, small-particle aerosol, or large-particle aerosol. The IRF-Frederick has experience with MERS, ebola virus, nipah virus and cowpox aerosol models. The unique positron emission tomography with computed tomography (PET/CT will be incorporated into the animal model to measure disease progression since the nonhuman primate model is expected to be sublethal. CT has been used previously to demonstrate vaccine efficacy and to complement small molecule countermeasure efficacy tests (www.ncbi.nlm.nih.gov/pubmed/26218507 and www.ncbi.nlm.nih.gov/pmc/articles/PMC5640857/). CT has also been used to evaluated a MERS monoclonal antibody in the rhesus monkey model of MERS and to evaluate disease progression in the common marmoset model of MERS (www.ncbi.nlm.nih.gov/pubmed/26828465 and www.ncbi.nlm.nih.gov/pubmed/26342468)

2) Characterization of the 2019-nCoV vaccine by biochemical and virological assay at TJU 3) Recovery of the vaccine at BBIL under GLP 4) Establish VNA against the 2019-nCoV strain. Establish pseudotype VNA assay for BSL2

5) ELISA for 2019-nCoV S—similar to the previously developed ELISA for MERS-CoV S.

6) Formulation of the vaccine and adjuvant.

Example 4

Clinical Studies

The following describes clinical studies to test the 2019-nCoV vaccine:

Based on the information from preclinical studies, efficacy in animal models will be performed in parallel to the proposed Phase 1 clinical trial to evaluate safety and immunogenicity in human subjects. Of note, our previous discussion (pre-IND) with the FDA for a similar killed rabies-virus based vaccine against EBOV was agreed not to require a toxicity study based on the safety history of deactivated rabies vaccines applied to more than 100 million people. The phase 1 study, if successful, would be followed by a Phase 2 clinical trial to increase the upper end of the age spectrum (since older persons have most severe 2019 nCoV disease) and to expand the cohort size to obtain statistically valid data related to the immune response.

Target populations: Healthy U.S. adults 18 through 55 years of age, inclusive.

Clinical Trial Design: Phase 1 Clinical Trial.

The Phase 1 trial is a randomized, observer-blinded, dose-escalation study to evaluate the safety, reactogenicity, and immunogenicity of the inactivated rabies virus (RABV) based 2019-nCoV vaccine candidates (RABV-nCoV). The clinical trial will be performed at a single site at the University of Maryland, Baltimore, in healthy adults 18 through 55 years of age. Enrolment will proceed in a staged fashion. We will being with 8 subjects in cohort 1. If no pausing rules are met by day 8 following the first dose of vaccine, then cohort 2 can begin immediately after full enrolment of Cohort 1, with no pausing. Cohorts 3 and 4 will proceed simultaneously after review of day 8 data in cohort 2 (assuming no halting rules are met. Importantly, we will include a single dose arm with adjuvant that will commence simultaneously with the 100 µg group (so groups 3 and 4 will be enrolled together after safety data available from all of group 2 through day 8). The study consists of four cohorts totaling 64 subjects (2 rabies vaccine controls and 14 investigational vaccines in each cohort). All study injections will be administered by the intramuscular (IM) route. Treatment assignments are outlined in Table 1.

TABLE 1

Treatment Assignment for the Phase I Ranging Safety Study of the nCoVRAB Vaccine

| Cohort | Sample size | Vaccine | Dose | Timing |
|---|---|---|---|---|
| 1 | 14 | nCoVRAB | 25 µg | Days 0 and 28 |
| 2 | 14 | nCoVRAB | 50 µg | Days 0 and 28 |
| 3 | 14 | nCOVRAB | 100 µg | Days 0 and 28 |
| 4 | 14 | nCoVRAB and adjuvant AdVax ® | 50 µg | Days 0-single dose |
| Control | 8 (2 in each cohort above) | RabAvert © (Rabies Vaccine) | — | Days 0 and 28 (According to label) |

Primary Objective: To assess the safety and tolerability of a 2-dose schedule of the unadjuvanted nCoVRAB and a 1-dose schedule of the adjuvanted vaccine candidates delivered IM at 0 and 28 days.

Secondary Objective: To evaluate the immunogenicity of the nCoVRAB vaccine candidates delivered IM at 0 and 28 days (or day 0 for adjuvanted) at escalating dose levels at Days 0, 28, 56, 120 (with primary measure at day 56 for unadjuvanted and day 28 for adjuvanted). Primary Endpoints: The number and percentage of study participants who experience any study injection-associated adverse events, solicited systemic events, or serious adverse events at the following time points:
  Solicited events for 7 days after each study injection.
  Unsolicited events through 28 days after the last study injection (Day 56).
  Serious adverse events (SAEs) for 56 days and at Days 56 and 120 and 365 per a scripted interview.
  Number of participants with early discontinuation of study injections and reason for discontinuation.
Secondary Endpoints: Immunogenicity as Measured by ELISA to 2019-nCoV and Rabies GP.
  nCoV S1- and nCoV 51 and RABV G specific serum IgG ELISA titers per time point through Day 120: geometric mean antibody titers (GMT) and percentage of subjects seroconverting (4-fold rise over baseline).
- nCoV and rabies neutralizing antibody titers through Day 120: GMT and percentage of subjects seroconverting (4-fold rise over baseline); for rabies, percentage of subjects with titers >0.5 IU/ml (correlate of protection).

Exploratory (Future Studies)

- Antigen-specific serum IgM, IgA and IgG subclasses (selected time-points).
- T cell responses (Th1, Th2 and Th17 cytokines and chemokines post vaccination).
- B cell responses (magnitude of antigen-specific plasmablasts and memory B cells post vaccination).
- IgG avidity.

Phase 2 Clinical Trial

This clinical trial is proposed as a Phase 2, randomized, observer-blinded, single antigen level study to evaluate the safety and immunogenicity of a two Dose Rabies-Vectored nCoVRAB Vaccine (or a one dose adjuvanted regimen). Given the demographics of the current NCoV outbreak, we will expand the upper age to 70 years. Volunteers will be assessed before the injection and days 1, 3, 7, 14, and 28 after the vaccine for safety, reactogenicity, and immunogenicity. The clinical trial will be performed in healthy adults meeting all inclusion criteria and no exclusion criteria at 2 sites in the US—Baltimore, MD and one additional site. total of 200 adults will be consecutively enrolled into groups, stratified by age. All study injections will be administered by the intramuscular (IM) route. Treatment assignments are outlined in Table 2 below.

TABLE 2

Treatment Assignment for the First Dose Ranging Safety Study of the nCoVRAB Vaccine*

| Group | Number of Participants | Study Injections | Antigen Dose* | Dosing Schedule |
|---|---|---|---|---|
| 1 | 180 | nCoVRAB, Liquid | x µg determined in phase 1) | Days 0 and 28 Or one inoculation |
| 2 | 20 | RabAvert | TBD | Days 0 and 28 |

*The overall antigen dose, the relative concentration of the antigen component used for this study will depend upon the outcome of the Phase 1 clinical trial.

Primary Objective: To assess the safety and tolerability of a leading nCoVRAB vaccine candidates delivered IM at 0 and 28 days.

Secondary Objective: To evaluate the immunogenicity of the nCoVRAB vaccine candidates delivered IM at 0 and 28 days at Days 7, 14, 28, 35, 42, 56, 90, 120, 180, and 365.

Primary Endpoints: The number and percentage of study participants who experience any study injection-associated adverse events or serious adverse events at the following time point:

- Solicited events for 7 days after each study injection.
- Unsolicited events through 28 days after the last study injection (Day 56).
- Serious adverse events (SAEs) for 56 days and at Days 56 and 120 and 365 per a scripted interview.
- Number of participants with early discontinuation of study injections and reason for discontinuation.

Secondary Endpoints/Exploratory endpoints see above (Phase 1 Clinical Trial.)

Example 5

Manufacturing

In the setting of the public health emergency of 2019 Novel Coronavirus (2019-nCoV or SARS-CoV-2), considerations for the development of a 2019-nCoV vaccine must balance manufacturing speed and technical feasibility with clinical safety and immunogenicity considerations. Ultimately, the manufacturing must be scalable, and the delivery simple in order to reach the maximum number of people in the shortest period of time. A collaborator, Bharat Biotech Ltd (BBIL) is a large vaccine manufacturer with the ability to scale production of such a vaccine to millions of doses rapidly. Relying on an existing technology to maximize feasibility and speed of development is the best approach to achieving this goal.

BBIL experience in positioning licensed vaccines for International supplies is summarized in the table below.

Experience in Manufacture and Scale-Up/Infrastructures and Facilities

BBIL has several facilities for the manufacturing of Viral, Bacterial and recombinant Drug Substance. BBIL is the largest viral vaccine manufacturer in India. For the manufacturing of viral vaccines, it possesses expertise in the utilization of Vero, MDCK cell lines and platforms like Cell factories, Micro carriers and fermenters. There are 5 viral bulk manufacturing facilities including a pilot plant, these facilities have capabilities ranging from 50 L to 1000 L fermentation and purification by TFF, Gel permeation and Affinity chromatography. These automated facilities can produce up to 500 million doses of vaccines.

BBIL also has capabilities of manufacturing recombinant and bacterial drug substances and these are manufactured in 6 facilities including one pilot plant, BBIL expertise ranges from usage of recombinant *E. coli*, Yeast, Toxins producing bacteria such as, Diphtheria, tetanus and Whole cell bacteria viz pertussis and Cholera. These organisms are processed from 50 L to 1500 L fermenters and subsequent purifications are carried out using either Ion Exchange, Gel permeation chromatography's.

For Drug Product, all bulk product is either filled in vials, PFS or BFS ranging from 0.5 ML to 25 ml capacities in filling machine having capacity from 50-300 vials per min. Keeping in view, of the various products manufactured and also the products to be manufactured in future, BBIL has a Developmental QC Lab, which in involved in the development and validation of different assays and a Strong QC department for routine batch testing and release of all vaccines and biotherapeutics.

Manufacturing capacity: Approximately, 500 million doses of vaccines and 4 million units of Bio-therapeutics are manufactured per year. About 20-30% of the vaccines are supplied to GAVI countries.

With a strong QC department, BBIL manufacture, test and release following vaccines and biotherapeutics. Apart from the facilities available at BBIL, in case of Emergency situation, higher manufacturing capacities of 5,000 L, at BSL3/Ag+ facility is available at BIOVET, Bengaluru.

Example 6

CORAVAX (rDNA-BBV151)

To evaluate the reactogenicity and safety of BBV151 (inactivated rabies vector platform Corona Virus) vaccine administered via the intramuscular route, a dose escalation study of an intramuscular inactivated rabies vector platform Corona Virus Vaccine (rDNA-BBV151) in healthy volunteers will be performed.

CORAVAX (rDNA-BBV151) is an adjuvanted rabies vectored Corona virus vaccine, that express the S1 domain of the SARSCoV-2 spike (S) protein fused to part of the N terminal domain of the RABV glycoprotein (G) and is incorporated in RABV particles. CORAVAX (rDNA-BBV151) vaccine has two presentations.

TABLE 1

Coronavirus Vaccine (rDNA)-BBVI51 composition
Dosage form: Liquid (Injection for Intramuscular route)

| | | Each dose of 0.5 ml contains |
|---|---|---|
| | I | Active ingredient | Quantity |
| Composition: | | Coronavirus Vaccine (rDNA) BBVI51 | NLT 15 (or) 30 mcg |
| | | Inactive ingredients | |
| | | 2-Phenoxyethanol (2-PE)-I.P. | 2.5 mg |
| | | Phosphate Buffered Saline | Qs to 0.25 mL |
| | II | Adjuvant | |
| | | SEPIVAC SWE-Oil in water (O/W) emulsion* | 0.25 ml |

PRESENTATION 1 (BBV151-A)—Ingredients I and II will be provided as two separate vials (each 0.5 mL) and these two vials (A and B) will be mixed at the time of administration. The final reconstituted 1.0 mL volume is equivalent to 2 doses. BBV151-A presentation has two vaccine formulations with a variation in the dosage strength of active ingredient (Figure XA):
BBV151-A1: BBV151-A1 formulation has 15 mcg of the active ingredient.
BBV151-A2: BBV151-A2 formulation has 30 mcg of the active ingredient.
PRESENTATION 2 (BBV151-B): Ingredients I and II will be mixed together, before itself and will be provided as a single vial (0.5 mL dose volume). BBV151-B presentation has only one formulation (Figure XB):
BBV151-B: BBV151-B formulation has 30 mcg of the active ingredient.

The study is designed to evaluate the safety, reactogenicity, and immunogenicity of four groups of healthy volunteers who receive either vaccine or placebo.

Group 1 (BBV151-A1): In this group, 15 participants will be recruited and administered with BBV151-A1 vaccine formulation on day 0 and day 28 via intramuscular route.
Group 2 (BBV151-A2): In this group, 15 participants will be recruited and administered with BBV151-A2 vaccine formulation on day 0 and day 28 via intramuscular route.
Group 3 (BBV151-B): In this group, 15 participants will be recruited and administered with BBV151-B vaccine formulation on day 0 via intramuscular route.

Data will be un-blinded to the third-party bio-statistician and an interim analysis will be performed at day 42 for Immunogenicity and Safety. nAb titer of the COVID-19 virus will be assessed by the MNT/PRNT assay and evaluate the immunogenicity in terms of GMT of vaccine comparison with the placebo group. Serum samples will be assessed for nAb. Binding antibody titer against spike protein of SARS-CoV-2 virus will be assessed for serum samples by using ELISA. Cell Mediated Immunity will be assessed from the subset of the study population.

The GMT will be calculated for neutralization titers in each vaccine group (one dose and two doses) separately. A two-sided 95% confidence interval (CI) for the GMT will be calculated from a 95% CI for the mean of $\log_{10}$-transformed titer, using a normal approximation for the distribution of $\log_{10}$ (titer). The ratio of GMTs in the two vaccine groups (GMT with two doses/GMT with one dose) and the corresponding 95% CI will also be presented. The two-sided 95% CI for the GMT ratio will be calculated from a 95% CI for the difference in means of $\log_{10}$ (titer). The two vaccine groups will be compared using a two-sided two-sample t-test on the means of $\log_{10}$-transformed titers, at the 5% significance level.

To evaluate the humoral immune responses of BBV151, GMT and four-fold seroconversion rate (SCR) of neutralizing antibodies (NAb's) by MNT/PRNT assays across the three groups, from baseline to days 28±2, 42±2, 90±7 and 180±7, will be performed.

To compare the humoral responses between single dose group and double dose group, GMT and four-fold seroconversion rate (SCR) of neutralizing antibodies (NAb's) by MNT/PRNT assays across the three groups, from baseline to days 28+2, 42±2, 90±7 and 180±7.

To evaluate the immune responses against spike protein of SARS-CoV-2 virus and Rabies vector, GMT and four-fold seroconversion rate of binding antibodies (bAb's) IgA and IgG against spike protein across the three groups, from baseline to days 28+2, 42±2, 90±7 and 180±7, will be determined. Immune response (binding/or neutralization) to the vector will be assessed by ELISA from baseline to days 28+2, 42±2, 90±7 and 180±7.

To evaluate the safety of the vaccine in terms of assessing adverse event of special interest (AESI), the occurrence of AESI will be monitored and documented throughout the study duration.

REFERENCES

1. Raj V S, Mou H, Smits S L, Dekkers D H, Muller M A, Dijkman R, Muth D, Demmers J A, Zaki A, Fouchier R A, Thiel V, Drosten C, Rottier P J, Osterhaus A D, Bosch B J, Haagmans B L. Dipeptidyl peptidase 4 is a functional receptor for the emerging human coronavirus-EMC. Nature. 2013; 495(7440):251-4. doi: 10.1038/nature12005. PubMed PMID: 23486063
2. Burkard C, Verheije M H, Wicht O, van Kasteren S I, van Kuppeveld F J, Haagmans B L, Pelkmans L, Rottier P J, Bosch B J, de Haan C A. Coronavirus cell entry occurs through the endo-/lysosomal pathway in a proteolysis-dependent manner. PLoS pathogens. 2014; 10(11): e1004502. doi: 10.1371/journal.ppat.1004502. PubMed PMID: 25375324; PMCID: PMC422306
3. Volz A, Kupke A, Song F, Jany S, Fux R, Shams-Eldin H, Schmidt J, Becker C, Eickmann M, Becker S, Sutter G. Protective Efficacy of Recombinant Modified Vaccinia Virus Ankara Delivering Middle East Respiratory Syndrome Coronavirus Spike Glycoprotein. J Virol. 2015; 89(16):8651-6. doi: 10.1128/JVI.00614-15. PubMed PMID: 26018172; PMCID: PMC4524222
4. Ma C, Wang L, Tao X, Zhang N, Yang Y, Tseng C T, Li F, Zhou Y, Jiang S, Du L. Searching for an ideal vaccine candidate among different MERS coronavirus receptor-binding fragments—the importance of immunofocusing in subunit vaccine design. Vaccine. 2014; 32(46):6170-6. doi: 10.1016/j.vaccine.2014.08.086. PubMed PMID: 25240756; PMCID: PMC4194190
5. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular therapy Methods & clinical development. 2014; 1:14046. doi: 10.1038/mtm.2014.46. PubMed PMID: 26015984; PMCID: 4362357
6. Muthumani K, Falzarano D, Reuschel E L, Tingey C, Flingai S, Villarreal D O, Wise M, Patel A, Izmirly A, Aljuaid A, Seliga A M, Soule G, Morrow M, Kraynyak K A, Khan A S, Scott D P, Feldmann F, LaCasse R, Meade-White K, Okumura A, Ugen K E, Sardesai N Y, Kim J J, Kobinger G, Feldmann H, Weiner D B. A synthetic consensus anti-spike protein DNA vaccine induces protective immunity against Middle East respiratory syndrome coronavirus in nonhuman primates. Sci Transl Med. 2015; 7(301):301ra132. doi: 10.1126/scitranslmed.aac7462. PubMed PMID: 26290414; PMCID: PMC4573558
7. Pfaller C K, Cattaneo R, Schnell M J. Reverse genetics of Mononegavirales: How they work, new vaccines, and new cancer therapeutics. Virology. 2015; 479-480:331-44. doi: 10.1016/j.virol.2015.01.029. PubMed PMID: 25702088; PMCID: 4557643
8. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015; 212 Suppl 2:S414-24. doi: 10.1093/infdis/jiv251. PubMed PMID: 26063224; PMCID: 4564550
9. Huttner A, Dayer J A, Yerly S, Combescure C, Auderset F, Desmeules J, Eickmann M, Finckh A, Goncalves A R, Hooper J W, Kaya G, Krahling V, Kwilas S, Lemaitre B, Matthey A, Silvera P, Becker S, Fast P E, Moorthy V, Kieny M P, Kaiser L, Siegrist C A, Consortium V S-E. The effect of dose on the safety and immunogenicity of the VSV Ebola candidate vaccine: a randomised double-blind, placebo-controlled phase 1/2 trial. Lancet Infect Dis. 2015; 15(10):1156-66. doi: 10.1016/S1473-3099(15) 00154-1. PubMed PMID: 26248510
10. WHO. Rabies, Fact Sheet #99. 2015.
11. Blaney J E, Marzi A, Willet M, Papaneri A B, Wirblich C, Feldmann F, Holbrook M, Jahrling P, Feldmann H, Schnell M J. Antibody quality and protection from lethal Ebola virus challenge in nonhuman primates immunized with rabies virus based bivalent vaccine. PLoS pathogens. 2013; 9(5):e1003389. doi: 10.1371/journal.ppat.1003389. PubMed PMID: 23737747; PMCID: 3667758.
12. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/JVI.00558-11. PubMed PMID: 21849459; PMCID: 3187516.
13. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or live-attenuated bivalent vaccines that confer protection against rabies and Ebola viruses. J Virol. 2011; 85(20):10605-16. Epub 2011/08/19. doi: 10.1128/JVI.00558-11. PubMed PMID: 21849459; PMCID: 3187516.
14. Willet M, Kurup D, Papaneri A, Wirblich C, Hooper J W, Kwilas S A, Keshwara R, Hudacek A, Beilfuss S, Rudolph G, Pommerening E, Vos A, Neubert A, Jahrling P, Blaney J E, Johnson R F, Schnell M J. Preclinical Development of Inactivated Rabies Virus-Based Polyvalent Vaccine Against Rabies and Filoviruses. J Infect Dis. 2015. doi: 10.1093/infdis/jiv251. PubMed PMID: 26063224
15. Wirblich C, Coleman C M, Kurup D, Abraham T S, Bernbaum J G, Jahrling P B, Hensley L E, Johnson R F, Frieman M B, Schnell M J. One-Health: a Safe, Efficient, Dual-Use Vaccine for Humans and Animals against Middle East Respiratory Syndrome Coronavirus and Rabies Virus. Journal of virology. 2017; 91(2). Epub 2016/11/04. doi: 10.1128/JVI.02040-16. PubMed PMID: 27807241; PMCID: PMC5215356
16. Conzelmann K K, Cox J H, Schneider L G, Thiel H J. Molecular cloning and complete nucleotide sequence of the attenuated rabies virus SAD B19. Virology. 1990; 175(2):485-99. PubMed PMID: 2139267
17. Kurup D, Wirblich C, Feldmann H, Marzi A, Schnell M J. Rhabdoviral-Based Vaccine Platforms against Henipaviruses. J Virol. 2014. doi: 10.1128/JVI.02308-14. PubMed PMID: 25320306
18. Hudacek A W, Al-Saleem F H, Willet M, Eisemann T, Mattis J A, Simpson L L, Schnell M J. Recombinant rabies virus particles presenting botulinum neurotoxin antigens elicit a protective humoral response in vivo. Molecular Therapy—Methods & Clinical Development. 2014; 1
19. McGettigan J P, Pomerantz R J, Siler C A, McKenna P M, Foley H D, Dietzschold B, Schnell M J. Second-generation rabies virus-based vaccine vectors expressing human immunodeficiency virus type 1 gag have greatly reduced pathogenicity but are highly immunogenic. J Virol. 2003; 77(1):237-44. Epub 2002/12/13. PubMed PMID: 12477829; PMCID: 140592.
20. McGettigan J P, Naper K, Orenstein J, Koser M, McKenna P M, Schnell M J.
Functional human immunodeficiency virus type 1 (HIV-1) Gag-Pol or HIV-1 Gag-Pol and env expressed from a single rhabdovirus-based vaccine vector genome. J Virol. 2003; 77(20):10889-99. Epub 2003/09/27. PubMed PMID: 14512539; PMCID: 224996
21. Kurup D, Wirblich C, Feldmann H, Marzi A, Schnell M J. Rhabdovirus-based vaccine platforms against henipaviruses. J Virol. 2015; 89(1):144-54. doi: 10.1128/JVI.02308-14. PubMed PMID: 25320306; PMCID: 4301098

22. Servat A, Feyssaguet M, Blanchard I, Morize J L, Schereffer J L, Boue F, Cliquet F. A quantitative indirect ELISA to monitor the effectiveness of rabies vaccination in domestic and wild carnivores. J Immunol Methods. 2007; 318(1-2):1-10. doi: 10.1016/j.jim.2006.07.026. PubMed PMID: 17166510
23. Wasniewski M, Cliquet F. Evaluation of ELISA for detection of rabies antibodies in domestic carnivores. J Virol Methods. 2012; 179(1):166-75. doi: 10.1016/j.jviromet.2011.10.019. PubMed PMID: 22080853
24. Wasniewski M, Guiot A L, Schereffer J L, Tribout L, Mahar K, Cliquet F. Evaluation of an ELISA to detect rabies antibodies in orally vaccinated foxes and raccoon dogs sampled in the field. J Virol Methods. 2013; 187(2):264-70. doi: 10.1016/j.jviromet.2012.11.022. PubMed PMID: 23201293
25. Zhao J, Li K, Wohlford-Lenane C, Agnihothram S S, Fett C, Gale M J, Jr., Baric R S, Enjuanes L, Gallagher T, McCray P B, Jr., Perlman S. Rapid generation of a mouse model for Middle East respiratory syndrome. Proc Natl Acad Sci USA. 2014; 111(13):4970-5. Epub 2014/03/07. doi: 10.1073/pnas.1323279111. PubMed PMID: 24599590; PMCID: 3977243
26. Blaney J E, Wirblich C, Papaneri A B, Johnson R F, Myers C J, Juelich T L, Holbrook M R, Freiberg A N, Bernbaum J G, Jahrling P B, Paragas J, Schnell M J. Inactivated or Live-Attenuated Bivalent Vaccines that Confer Protection against Rabies and Ebola Viruses. PLoS Pathog, under review. 2011
27. Johnson R F, Kurup D, Hagen K R, Fisher C, Keshwara R, Papaneri A, Perry D L, Cooper K, Jahrling P B, Wang J T, Ter Meulen J, Wirblich C, Schnell M J. An Inactivated Rabies Virus-Based Ebola Vaccine, FILORAB1, Adjuvanted With Glucopyranosyl Lipid A in Stable Emulsion Confers Complete Protection in Nonhuman Primate Challenge Models. The Journal of infectious diseases. 2016; 214(suppl 3):S342-S54. doi: 10.1093/infdis/jiw231. PubMed PMID: 27456709; PMCID: PMC5050469
28. Papaneri A B, Wirblich C, Marissen W E, Schnell M J. Alanine scanning of the rabies virus glycoprotein antigenic site III using recombinant rabies virus: implication for post-exposure treatment. Vaccine. 2013; 31(49):5897-902. Epub 2013/10/15. doi: 10.1016/j.vaccine.2013.09.038. PubMed PMID: 24120673
29. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan GVJA, Prasad S, Rao T S, Boslego J, Bhan M K, Group I R V. Efficacy of a monovalent human-bovine (116E) rotavirus vaccine in Indian children in the second year of life. Vaccine. 2014; 32 Suppl 1:A110-6. doi: 10.1016/j.vaccine.2014.04.079. PubMed PMID: 25091663; PMCID: 25091663
30. Bhandari N, Rongsen-Chandola T, Bavdekar A, John J, Antony K, Taneja S, Goyal N, Kawade A, Kang G, Rathore S S, Juvekar S, Muliyil J, Arya A, Shaikh H, Abraham V, Vrati S, Proschan M, Kohberger R, Thiry G, Glass R, Greenberg H B, Curlin G, Mohan K, Harshavardhan G V, Prasad S, Rao T S, Boslego J, Bhan M K. Efficacy of a monovalent human-bovine (116E) rotavirus vaccine in Indian infants: a randomised, double-blind, placebo-controlled trial. Lancet. 2014; 383(9935):2136-43. Epub 2014/03/19. doi: 10.1016/s0140-6736(13) 62630-6. PubMed PMID: 24629994; PMCID: PMC4532697
31. Bhandari N, Sharma P, Taneja S, Kumar T, Rongsen-Chandola T, Appaiahgari M B, Mishra A, Singh S, Vrati S. A dose-escalation safety and immunogenicity study of live attenuated oral rotavirus vaccine 116E in infants: a randomized, double-blind, placebo-controlled trial. J Infect Dis. 2009; 200(3):421-9. Epub 2009/06/24. doi: 10.1086/600104. PubMed PMID: 19545211
32. Bhandari N, Sharma P, Glass R I, Ray P, Greenberg H, Taneja S, Saksena M, Rao C D, Gentsch J R, Parashar U, Maldonado Y, Ward R L, Bhan M K. Safety and immunogenicity of two live attenuated human rotavirus vaccine candidates, 116E and I321, in infants: results of a randomised controlled trial. Vaccine. 2006; 24(31-32):5817-23. Epub 2006/06/01. doi: 10.1016/j.vaccine.2006.05.001. PubMed PMID: 16735085
33. Mohan V K, Varanasi V, Singh A, Pasetti M F, Levine M M, Venkatesan R, Ella K M. Safety and immunogenicity of a Vi polysaccharide-tetanus toxoid conjugate vaccine (Typbar-TCV) in healthy infants, children, and adults in typhoid endemic areas: a multicenter, 2-cohort, open-label, double-blind, randomized controlled phase 3 study. Clinical infectious diseases: an official publication of the Infectious Diseases Society of America. 2015; 61(3):393-402. Epub 2015/04/15. doi: 10.1093/cid/civ295. PubMed PMID: 25870324
34. Shakya M, Colin-Jones R, Theiss-Nyland K, Voysey M, Pant D, Smith N, Liu X, Tonks S, Mazur O, Farooq Y G, Clarke J, Hill J, Adhikari A, Dongol S, Karkey A, Bajracharya B, Kelly S, Gurung M, Baker S, Neuzil K M, Shrestha S, Basnyat B, Pollard A J. Phase 3 Efficacy Analysis of a Typhoid Conjugate Vaccine Trial in Nepal. New England Journal of Medicine. 2019; 381(23):2209-18. doi: 10.1056/NEJMoa1905047
35. Voysey M, Pollard A J. Seroefficacy of Vi Polysaccharide—Tetanus Toxoid Typhoid Conjugate Vaccine (Typbar TCV). Clinical Infectious Diseases. 2018; 67(1):18-24. doi: 10.1093/cid/cix1145
36. Jin C, Gibani MINI, Moore M, Juel H B, Jones E, Meiring J, Harris V, Gardner J, Nebykova A, Kerridge S A, Hill J, Thomaides-Brears H, Blohmke C J, Yu L-M, Angus B, Pollard A J. Efficacy and immunogenicity of a Vi-tetanus toxoid conjugate vaccine in the prevention of typhoid fever using a controlled human infection model of *Salmonella Typhi*: a randomised controlled, phase 2b trial. The Lancet. 2017; 390(10111):2472-80. doi: doi.org/10.1016/S0140-6736(17)32149-9
37. Vadrevu K M, Potula V, Khalatkar V, Mahantshetty N S, Shah A, Ella R. Persistence of Immune Responses With an Inactivated Japanese Encephalitis Single-Dose Vaccine, JENVAC and Interchangeability With a Live-Attenuated Vaccine. The Journal of Infectious Diseases. 2019. doi: 10.1093/infdis/jiz672
38. Singh A, Mitra M, Sampath G, Venugopal P, Rao J V, Krishnamurthy B, Gupta M K, Sri Krishna S, Sudhakar B, Rao N B, Kaushik Y, Gopinathan K, Hegde N R, Gore M M, Krishna Mohan V, Ella K M. A Japanese Encephalitis Vaccine From India Induces Durable and Cross-protective Immunity Against Temporally and Spatially Wide-ranging Global Field Strains. The Journal of Infectious Diseases. 2015; 212(5):715-25. doi: 10.1093/infdis/jiv023

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A recombinant fusion protein comprising (a) a glycoprotein (G) of a virus or a portion thereof, and (b) a SARS-CoV-2 spike protein (S) or a portion thereof, wherein the SARS-CoV-2 spike protein (S) comprises the amino acid sequence of SEQ ID NO: 28, 29, 30, or 31.

2. A vaccine comprising the recombinant fusion protein of claim 1, and a pharmaceutically acceptable carrier.

3. The vaccine of claim 2, further comprising an adjuvant.

4. The vaccine of claim 3, wherein the adjuvant is MPLA 3D(6-acyl) in 2% squalene.

5. A method of generating an immune response against a SARS-CoV-2 virus in a subject in need thereof, the method comprising administering to the subject an effective amount of the vaccine of claim 2.

6. A method of vaccinating a subject against a SARS-CoV-2 virus, the method comprising administering to the subject an effective amount of the vaccine of claim 2.

7. A method of providing immunity against a SARS-CoV-2 virus in a subject, the method comprising administering to the subject an effective amount of the vaccine of claim 2.

8. A method of treating and/or preventing a disease or disorder associated with a SARS-CoV-2 virus in a subject in need thereof, the method comprising administering to the subject an effective amount of the vaccine of claim 2.

9. The recombinant fusion protein of claim 1, wherein the SARS-CoV-2 spike protein (S) comprises the amino acid sequence of SEQ ID NO: 28.

10. The recombinant fusion protein of claim 1, wherein the SARS-CoV-2 spike protein (S) comprises the amino acid sequence of SEQ ID NO: 29.

11. The recombinant fusion protein of claim 1, wherein the SARS-CoV-2 spike protein (S) comprises the amino acid sequence of SEQ ID NO: 30.

12. The recombinant fusion protein of claim 1, wherein the SARS-CoV-2 spike protein (S) comprises the amino acid sequence of SEQ ID NO: 31.

* * * * *

SEQUENCE LISTING

```
Sequence total quantity: 106
SEQ ID NO: 1              moltype = DNA  length = 17189
FEATURE                   Location/Qualifiers
misc_feature              1..17189
                          note = VSV-COVID19-S1-VSVG
source                    1..17189
                          mol_type = other DNA
                          organism = synthetic construct
SEQUENCE: 1
ctgacgcgcc ctgtagcggc gcattaagcg cggcgggtgt ggtggttacg cgcagcgtga  60
ccgctacact tgccagcgcc ctagcgcccg ctcctttcgc tttcttccct tcctttctcg  120
ccacgttcgc cggctttccc cgtcaagctc taaatcgggg gctcccttta gggttccgat  180
ttagtgcttt acggcacctc gaccccaaaa aacttgatta gggtgatggt tcacgtagtg  240
ggccatcgcc ctgatagacg gtttttcgcc ctttgacgtt ggagtccacg ttctttaata  300
gtggactctt gttccaaact ggaacaacac tcaaccctat ctcggtctat tcttttgatt  360
tataagggat tttgccgatt tcggcctatt ggttaaaaaa tgagctgatt taacaaaaat  420
ttaacgcgaa ttttaacaaa atattaacgc ttacaatttc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgccctagt tattaatagt aatcaattac ggggtcatta  660
gttcatagcc catatatgga gttccgcgtt acataactta cggtaaatgg cccgcctggc  720
tgaccgccca acgacccccg cccattgacg tcaataatga cgtatgttcc catagtaacg  780
ccaataggga ctttccattg acgtcaatgg gtggagtatt tacggtaaac tgcccacttg  840
gcagtacatc aagtgtatca tatgccaagt acgcccccta ttgacgtcaa tgacggtaaa  900
tggcccgcct ggcattatgc ccagtacatg accttatggg actttcctac ttggcagtac  960
atctacgtat tagtcatcgc tattaccatg gtgatgcggt tttggcagta catcaatggg  1020
cgtggatagc ggtttgactc acggggattt ccaagtctcc accccattga cgtcaatggg  1080
agtttgtttt ggcaccaaaa tcaacgggac tttccaaaat gtcgtaacaa ctccgcccca  1140
ttgacgcaaa tgggcggtag gcgtgtacgg tgggaggtct atataagcag agctctctgg  1200
ctaactagag aacccactgc ttactggctt atcgaaatta atacgactca ctatagggag  1260
acccaagctg gctagggtct tcgtctgatg agtccgtgag gacgaaaccc ggcgtaccgg  1320
gtcacgaaga caaacaaacc attattatca ttaaaaggct caggagaaac tttaacagta  1380
atcaaaatgt ctgttacagt caagagaatc attgacaaca cagtcatagt tccaaaactt  1440
cctgcaaatg aggatccagt ggaatacccg gcagattact tcagaaaatc aaaggagatt  1500
cctctttaca tcaatactac aaaaagtttg tcagatctaa gaggatatgt ctaccaaggc  1560
ctcaaatccg gaaatgtatc aatcatacat gtcaacagct acttgtatgg agcattaaag  1620
gacatccggg gtaagttgga taaagattgg tcaagtttcg gaataaacat cgggaaagca  1680
ggggatacaa tcggaatatt tgaccttgta tccttgaaag ccctggacgg cgtacttcca  1740
gatggagtat cggatgcttc cagaaccagc gcagatgaca aatggttgcc tttgtatcta  1800
cttggcttat acagagtggg cagaacacaa atgcctgaat acagaaaaaa gctcatggat  1860
gggctgacaa atcaatgcaa aatgatcaat gaacagtttg aacctcttgt gccagaaggt  1920
cgtgacattt ttgatgtgtg gggaaatgac agtaattaca caaaaattgt cgctgcagtg  1980
gacatgttct tccacatgtt caaaaaacat gaatgtgcct cgttcagata cggaactatt  2040
gtttccagat tcaaagattg tgctgcattg gcaacatttg gacacctctg caaaataacc  2100
ggaatgtcta cagaagatgt aacgacctgg atcttgaacc gagaagttgc agatgaaatg  2160
gtccaaatga tgcttccagg ccaagaaatt gacaaggccg attcatacat gccttatttg  2220
atcgactttg gattgtcttc taagtctcca tattcttccg tcaaaaaccc tgccttccac  2280
ttctgggggc aattgacagc tcttctgctc agatccacca gagcaaggaa tgcccgacag  2340
cctgatgaca ttgagtatac atctcttact acagcaggtt tgttgtacgc ttatgcagta  2400
ggatcctctg ccgacttggc acaacagttt tgtgttggag ataacaaata cactccagat  2460
gatagtaccg gaggattgac gactaatgca ccgccacaag gcagagatgt ggtcgaatgg  2520
ctcggatggt ttgaagatca aaacagaaaa ccgactcctg atatgatgca gtatgcgaaa  2580
agagcagtca tgtcactgca aggcctaaga gagaagacaa ttggcaagta tgctaagtca  2640
gaatttgaca aatgacccta taattctcag atcacctatt atatattatg ctacatatga  2700
aaaaaactaa cagatatcat ggataatctc acaaaagttc gtgagtatct caagtcctat  2760
tctcgtctgg atcaggcggt aggagagata gatgagatcg aagcacaacg agctgaaaag  2820
tccaattatg agttgttcca agaggatgga gtggaagagc atactaagcc ctcttatttt  2880
caggcagcag atgattctga cacagaatct gaaccagaaa ttgaagacaa tcaaggtttg  2940
tatgcaccag atccagaagc tgagcaagtt gaaggcttta tacaggggcc tttagatgac  3000
tatgcagatg aggaagtgga tgttgtattt acttcggact ggaaacagcc tgagcttgaa  3060
tctgacgagc atggaaagac cttacggttg acatcgccag agggtttaag tggagagcag  3120
aaatcccagt ggctttcgac gattaaagca gtcgtgcaaa gtgccaaata ctggaatctg  3180
gcagagtgca catttgaagc atcgggagaa ggggtcatta tgaaggagcg ccagataact  3240
ccggatgtat ataaggtcac tccagtgatg aacacacatc cgtcccaatc agaagcagta  3300
tcagatgttt ggtctctctc aaagacatcc atgactttcc aacccaagaa agcaagtctt  3360
cagcctctca ccatatcctt ggatgaattg ttctcatcta gaggagagtt catctctgtc  3420
ggaggtgacg gacgaatgtc tcataaagag gccatcctgc tcggcctgag atacaaaaag  3480
ttgtacaatc aggcgagagt caaatattct ctgtagacta tgaaaaaaag taacagatat  3540
cacgatctaa gtgttatccc aatccattca tcatgagttc cttaaagaag attctcggtc  3600
tgaaggggaa aggtaagaaa tctaagaaat tagggatcgc accacccccct tatgaagagg  3660
```

```
acactagcat ggagtatgct ccgagcgctc caattgacaa atcctatttt ggagttgacg   3720
agatggacac ctatgatccg aatcaattaa gatatgagaa attcttcttt acagtgaaaa   3780
tgacggttag atctaatcgt ccgttcagaa catactcaga tgtggcagcc gctgtatccc   3840
attgggatca catgtacatc ggaatggcag ggaaacgtcc cttctacaaa atcttggctt   3900
ttttggggttc ttctaatcta aaggccactc cagcggtatt ggcagatcaa ggtcaaccag   3960
agtatcacac tcactgcgaa ggcagggctt atttgccaca taggatgggg aagacccctc   4020
ccatgctcaa tgtaccagag cacttcagaa gaccattcaa tataggtctt tacaagggaa   4080
cgattgagct cacaatgacc atctacgatg atgagtcact ggaagcagct cctatgatct   4140
gggatcattt caattcttcc aaattttctg atttcagaga gaaggcctta atgtttggcc   4200
tgattgtcga gaaaaaggca tctggagcgt gggtcctgga ttctatcagc cacttcaaat   4260
gagctagtct aacttctagc ttctgaacaa tccccggttt actcagtctc tcctaattcc   4320
agcctctcga acaactaata tcctgtcttt tctatcccta tgaaaaaaac taacagagat   4380
cgatctgttt acgcgtcact atgaagtgcc ttttgtactt agccttttta ttcattgggg   4440
tgaattgcaa gttcaccata gttttccac acaaccaaaa aggaaactgg aaaaatgttc   4500
cttctaatta ccattattgc ccgtcaagct cagatttaaa ttggcataat gacttaatag   4560
gcacagccat acaagtcaaa atgcccaaga gtcacaaggc tattcaagca gacggttgga   4620
tgtgtcatgc ttccaaatgg gtcactactt gtgatttccg ctggtatgga ccgaagtata   4680
taacacagtc catccgatcc ttcactccat ctgtagaaca atgcaaggaa agcattgaac   4740
aaacgaaaca aggaacttgg ctgaatccag gcttccctcc tcaaagttgt ggatatgcaa   4800
ctgtgacgga tgccgaagca gtgattgtcc aggtgactcc tcaccatgtg ctggttgatg   4860
aatacacagg agaatgggtt gattcacagt tcatcaacgg aaaatgcagc aattacatat   4920
gccccactgt ccataactct acaacctggc atttgacta taaggtcaaa gggctatgtg   4980
attctaacct catttccatg gacatcacct tcttctcaga ggacggagag ctatcatccc   5040
tgggaaagga gggcacaggg ttcagaagta actactttgc ttatgaaact ggaggcaagg   5100
cctgcaaaat gcaatactgc aagcattggg gagtcagact cccatcaggt gtctggttcg   5160
agatggctga taaggatctc tttgctgcag ccagattccc tgaatgccca gaagggtcaa   5220
gtatctctgc tccatctcag acctcagtgg atgtaagtct aattcaggac gttgagagga   5280
tcttggatta ttccctctgc caagaaacct ggagcaaaat cagagcgggt cttccaatct   5340
ctccagtgga tctcagctat cttgctccta aaaacccagg aaccggtcct gctttcacca   5400
taatcaatgg taccctaaaa tactttgaga ccagatacat cagtcgat attgctgctc   5460
caatcctctc aagaatggtc ggaatgatca gtgaactac cacagaaagg gaactgtggg   5520
atgactgggc accatatgaa gacgtggaaa ttggacccaa tggagttctg aggaccagtt   5580
caggatataa gtttcctta tacatgattg gacatggtat gttggactcc gatcttcatc   5640
ttagctcaaa ggctcaggtg ttcgaacatc ctcacattca agacgctgct tcgcaactct   5700
ctgatgatga gagtttattt tttggtgata ctgggctatc caaaaatcca atcgagcttg   5760
tagaaggttg gttcagtagt tggaaaagct ctattgcctc ttttttcttt atcatagggt   5820
taatcattgg actattcttg gttctccgag ttggtatcca tctttgcatt aaattaaagc   5880
acaccaagaa aagacagatt tatacagaca tagagatgaa ccgactttga aagtaactca   5940
aatcctgcta ggtatgaaaa aaactaacag atatcacgct cgagcgtacg ccaccatgtt   6000
cgtgttttctg tgtgctgctgc ctctggtgag ctcccagtgc gtgaacctga ccacaaggac   6060
ccagctgccc cctgcctata ccaattcctt cacacggggc gtgtactatc ccgacaaggt   6120
gttccggagc agcgtgctgc actccacaca ggatctgttt ctgcctttct tttctaacgt   6180
gacctggttc cacgccatcc agctgagcgg caccaatggc acaaagcggt tcgacaatcc   6240
agtgctgccc tttaacgatg gcgtgtactt cgcctccacc gagaagtcta acatcatcag   6300
aggctggatc tttggcacca cactggacag caagacacag tccctgctga tcgtgaacaa   6360
tgccaccaac gtggtcatca aggtgtgcga gttccagttt tgtaatgatc cattcctggg   6420
cgtgtactat cacaagaaca ataagtcttg gatggagagc gagtttcgcg tgtattcctc   6480
tgccaacaat tgcacatttg agtacgtgtc ccagcccttc ctgatggacc tggagggcaa   6540
gcagggcaat ttcaagaacc tgagggagtt cgtgtttaag aatatcgatg gctacttcaa   6600
aatctactcc aagcacaccc caatcaacct ggtgcgcgac ctgccacagg gcttctctgc   6660
cctgcagcca ctggtggatc tgcccatcgg catcaacatc accgggtttc agacactgtt   6720
ggccctgcac agaagctacc tgacaccagg cgacagctcc tctggatgga ccgcaggagc   6780
agcagcctac tatgtgggct atctgcagcc caggaccttc ctgctgaagt acaacgagaa   6840
tggcaccatc acagacgccg tggattgcgc cctggatccc ctgtctgaga ccaagtgtac   6900
actgaagagc tttaccgtgg agaagggcat ctatcagaca agcaatttca gggtgcagcc   6960
taccgagtcc atcgtgcgct ttcccaatat cacaaacctg tgcccttttg gcgaggtgtt   7020
caacgcaacc cgcttcgcca gcgtatacgc ctggaatagg aagcgcatct ccaactgcgt   7080
ggccgactat tctgtgctgt acaacagcgc ctccttctct acctttaagt gctatggcgt   7140
gagccccaca aagctgaatg acctgtgctt taccaacgtg tacgccgatt ccttcgtgat   7200
caggggcgac gaggtgcgcc agatcgcacc aggacagaca ggcaagatcg cagactacaa   7260
ttataagctg cctgacgatt tcaccggctg cgtgatcgcc tggaactcta caatctggga   7320
tagcaaagtg ggcggcaact acaattatct gtaccggctg tttagaaagt ctaatctgaa   7380
gccattcgag agggacatct ccacagaaat ctaccaggcc ggctctaccc cctgcaatgg   7440
cgtggagggc tttaactgtt atttccctct gcagagctac ggcttccaac caacaaacgg   7500
cgtgggctat cagccctacc gcgtggtggt gctgtctttt gagctgctgc acgcacctgc   7560
aacagtgtgc ggaccaaaga gagcaccaa tctggtgaag aacaagtgcg tgaacttcaa   7620
cttcaacgga ctgaccggaa caggcgtgct gaccgagtcc aacaagaagt tcctgccttt   7680
tcagcagttc ggcagggaca tcgcagatac cacagacgcc gtgcgcgacc ctcagaccct   7740
ggagatcctg gacatcacac catgctcctt cggcggcgtg tctgtgatca caccaggcac   7800
caatacaagc aaccaggtgg ccgtgctgta tcaggacgtg aattgtaccg aggtgccagt   7860
ggcaatccac gcagatcagc tgacccctac atggcgggtg tactctaccg gcagcaacgt   7920
gttccagaca gagaccggat gcctgatcgg agcagagcac gtgaacaata gctatgagtg   7980
cgacatccct atcggcgccg gcatctgtgc ctcctaccag acccagacaa actccccaag   8040
gtctgtggga gatacaggcc tgtccaagaa tccaatcgag ctggtagagg gctggttcag   8100
cagttggaaa agctccatcg cctccttttt ctttatcatc ggcctgatca tcggactgtt   8160
cctggtgctc cgcgtgggta tccacctgtg catcaagctg aagcacacca agaaaagaca   8220
gatttataca gacatcgaga tgaaccgcct gggaaagtga gctagccaga ttcttcatgt   8280
ttggaccaaa tcaacttgtg ataccatgct caaagaggcc tcaattatat ttgagttttt   8340
aatttttatg aaaaaaacta acagcaatca tggaagtcca cgattttgag accgacgagt   8400
```

```
tcaatgattt caatgaagat gactatgcca caagagaatt cctgaatccc gatgagcgca   8460
tgacgtactt gaatcatgct gattacaatt tgaattctcc tctaattagt gatgatattg   8520
acaatttgat caggaaattc aattctcttc cgattccctc gatgtgggat agtaagaact   8580
gggatggagt tcttgagatg ttaacatcat gtcaagccaa tcccatctca acatctcaga   8640
tgcataaatg gatgggaagt tggttaatgt ctgataatca tgatgccagt caagggtata   8700
gttttttaca tgaagtggac aaagaggcag aaataacatt tgacgtggtg gagaccttca   8760
tccgcggctg gggcaacaaa ccaattgaat acatcaaaaa ggaaagatgg actgactcat   8820
tcaaaattct cgcttatttg tgtcaaaagt ttttggactt acacaagttg acattaatct   8880
taaatgctgt ctctgaggtg gaattgctca acttggcgag gactttcaaa ggcaaagtca   8940
gaagaagttc tcatggaacg aacatatgca ggattagggt tcccagcttg ggtcctactt   9000
ttatttcaga aggatgggct tacttcaaga aacttgatat tctaatggac cgaaactttc   9060
tgttaatggt caaagatgtg attataggga ggatgcaaac ggtgctatcc atggtatgta   9120
gaatagacaa cctgttctca gagcaagaca tcttctccct tctaaatatc tacagaattg   9180
gagataaaat tgtggagagg cagggaaatt tttcttatga cttgattaaa atggtggaac   9240
cgatatgcaa cttgaagctg atgaaattag caagagaatc aaggccttta gtcccacaat   9300
tccctcattt tgaaaatcat atcaagactt ctgttgatga aggggcaaaa attgaccgag   9360
gtataagatt cctccatgat cagataatga gtgtgaaaac agtggatctc acactggtga   9420
tttatggatc gttcagacat tggggtcatc ttttataga ttattacact ggactagaaa   9480
aattacattc ccaagtaacc atgaagaaag atattgatgt gtcatatgca aaagcacttg   9540
caagtgattt agctcggatt gttctatttc aacagttcaa tgatcataaa aagtggttcg   9600
tgaatggaga cttgctccct catgatcatc cctttaaaag tcatgttaaa gaaaatacat   9660
ggcccacagc tgctcaagtt caagattttg gagataaatg gcatgaactt ccgctgatta   9720
aatgttttga ataccccgac ttactagacc catcgataat atactctgac aaaagtcatt   9780
caatgaatag gtcagaggtg ttgaaacatg tccgatgaa tccgaacact cctatcccta   9840
gtaaaaaggt gttgcagact atgttggaca caaaggctac caattggaaa gaatttctta   9900
aagagattga tgaaagggc ttagatgatg atgatccaat tattggtctt aaaggaaagg   9960
agagggaact gaagttggca ggtagatttt tctccctaat gtcttggaaa ttgcgagaat  10020
actttgtaat taccgaatat ttgataaaga ctcatttcgt ccctatgttt aaaggcctga  10080
caatggcgga cgatctaact gcagtcatta aaaagatgtt agattcctca tccggccaag  10140
gattgaagtc atatgaggca atttgcatag ccaatcacat tgattacgaa aatggaata  10200
accaccaaag gaagttatca aacggcccag tgttccgagt tatgggccag ttcttaggtt  10260
atccatcctt aatcgagaga actcatgaat tttttgagaa aagtcttata tactacaatg  10320
gaagaccaga cttgatgcgt gttcacaaca acacactgat caattcaacc tcccaacgag  10380
tttgttggca aggacaagag ggtggactgg aaggtctacg gcaaaaagga tggactatcc  10440
tcaatctact ggttattcaa agagaggcta aaatcagaaa cactgctgtc aaagtcttgg  10500
cacaaggtga taatcaagtt atttgcacac agtataaaac gaagaaatcg agaacgttg   10560
tagaattaca gggtgctctc aatcaaatgg tttctaataa tgagaaaatt atgactgcaa  10620
tcaaaatagg gacagggaag ttaggacttt tgataaatga cgatgagact atgcaatctg  10680
cagattactt gaattatgga aaaataccga ttttccgtgg agtgattaga gggttagaga  10740
ccaagagatg gtcacgagtg acttgtgtca ccaatgacca aatacccact tgtgctaata  10800
taatgagctc agtttccaca aatgctctca ccgtagctca ttttgctgag aacccaatca  10860
atgccatgat acagtacaat tattttggga catttgctag actcttgttg atgatgcatg  10920
atcctgctct tcgtcaatca ttgtatgaag ttcaagataa gataccggtc ttgcacagtt  10980
ctactttcaa atacgccatg ttgtatttgg accttccat tggaggagtg tcgggcatgt  11040
ctttgtccag gttttgatt agagccttcc cagatcccgt aacagaaagt ctctcattct  11100
ggagattcat ccatgtacat gctcgaagtg agcatctgaa ggagatgagt gcagtatttg  11160
gaaaccccga gatagccaag tttcgaataa ctcacataga caagctagta gaagatccaa  11220
cctctctgaa catcgctatg ggaatgagtc cagcgaactt gttaaagact gaggttaaaa  11280
aatgcttaat cgaatcaaga caaaccatca ggaaccaggt gattaaggat gcaaccatat  11340
atttgtatca tgaagaggat cggctcagaa gttttcttatg tcaataaaat cctctgttcc  11400
ctagatttttt aagtgaattc aaatcaggca cttttttggg agtcgcagac gggctcatca  11460
gtctatttca aaattctcgt actattcgga actcctttaa gaaaaagtat cataggaat   11520
tggatgattt gattgtgagg agtgaggtat cctctttgac acatttaggg aaacttcatt  11580
tgagaagggg atcatgtaaa atgtggacat gttcagctac tcatgctgac acattaagat  11640
acaaatcctg gggccgtaca gttattggga caactgtacc ccatccatta gaaatgttgg  11700
gtccacaaca tcgaaaagag actccttgtg caccatgtaa cacatcaggg ttcaattatg  11760
tttctgtgca ttgtccagac gggatccatg acgtctttag ttcacgggga ccattgcctg  11820
cttatcctagg gtctaaaaca tctgaatcta catctatttt gcagcttggg aaagggaaa   11880
gcaaagtccc actgattaaa agagctacac gtcttagaga tgctatctct tggtttgttg  11940
aacccgactc taaactagca atgactatac tttctaacat ccactctttta acaggcgaag  12000
aatggaccaa aaggcagcat gggttcaaaa gaacagggtc tgcccttcat aggttttcga  12060
catctcggat gagccatggt gggttcgcat ctcagagcac tgcagcattg accaggttga  12120
tggcaactac agacaccatg agggatctgg gagatcagaa tttcgacttt ttattccaag  12180
caacgttgct ctatgctcaa attaccacca ctgttgcaga agacgatgg atcaccagtt  12240
gtacagatca ttatcatatt gcctgtaagt cctgtttgag acccatagaa gagatcacc   12300
tggactcaag tatggactac acgccccag atgtatccca tgtgctgaag acatggagga  12360
atggggaagg ttcgtgggga caagagataa acagatcta tcctttagaa gggaattgga  12420
agaatttagc acctgctgag caatcctatc aagtcggcag atgtataggt tttctatatg  12480
gagacttgtg gtatagaaaa tctactcatg ccgaggacga ttctctattt cctctatcta  12540
tacaaggtcg tattagaggt cgaggtttct taaagggtt gctagacgga ttaatgagag  12600
caagttgctg ccaagtaata caccggagaa gtctggctca tttgaagagg ccggccaacg  12660
cagtgtacga aggtttgatt tacttgattg ataaattgag tgtatcacct ccattccttt  12720
ctcttactag atcaggacct attagagacg aattagaaac gattcccac aagatcccaa  12780
cctcctatcc gacaagcaac cgtgatatgg gggtgattgt cagaaattac ttcaaatacc  12840
aatgccgtct aattgaaaag ggaaaatca gatcacatta ttcacaatta tggttattct  12900
cagatgtctt atccatagac ttcattggac cattctctat ttccaccacc ctcttgcaaa  12960
tcctatacaa gccatttta tctgggaaag ataagaatga gttgagagag ctggcaaatc  13020
tttcttcatt gctaagatca ggagagggt gggaagacat acatgtgaaa ttcttcacca  13080
aggacatatt attgtgtcca gaggaaatca gacatgcttg caagttcggg attgctaagg  13140
```

```
ataataataa agacatgagc tatccccctt ggggaaggga atccagaggg acaattacaa   13200
caatccctgt ttattatacg accaccectt acccaaagat gctagagatg cctccaagaa   13260
tccaaaatcc cctgctgtcc ggaatcaggt tgggccaatt accaactggc gctcattata   13320
aaattcggag tatattacat ggaatgggaa tccattacag ggacttcttg agttgtggag   13380
acggctccgg agggatgact gctgcattac tacgagaaga tgtgcatagc agaggaaatat   13440
tcaatagtct gttagaatta tcagggtcag tcatgcgagg cgcctctcct gagccccccca   13500
gtgccctaga aactttagga ggagataaat cgagatgtgt aaatggtgaa acatgttggg   13560
aatatccatc tgacttatgt gacccaagga cttgggacta tttcctccga ctcaaagcag   13620
gcttggggct tcaaattgat ttaattgtaa tggatatgga agttcgggat tcttctacta   13680
gcctgaaaat tgagacgaat gttagaaatt atgtgcaccg gattttggat gagcaaggag   13740
ttttaatcta caagacttat ggaacatata tttgtgagag cgaaaagaat gcagtaacaa   13800
tccttggtcc catgttcaag acggtcgact tagttcaaac agaatttagt agttctcaaa   13860
cgtctgaagt atatatggta tgtaaaggtt tgaagaaatt aatcgatgaa cccaatcccg   13920
attggtcttc catcaatgaa tcctggaaaa acctgtacgc attccagtca tcagaacagg   13980
aatttgccag agcaaagaag gttagtacat actttacctt gacaggtatt ccctcccaat   14040
tcattcctga tccttttgta aacattgaga ctatgctaca aatattcgga gtacccacgg   14100
gtgtgtctca tgcggctgcc ttaaaatcat ctgatagacc tgcagattta ttgaccatta   14160
gccttttta tatggcgatt atatcgtatt ataacatcaa tcatatcaga gtaggaccga   14220
tacctccgaa cccccccatca gatgaattgc cacaaaatgt ggggatcgct ataactggta   14280
taagctttg gctgagtttg atggagaaag acattccact atatcaacag tgtttagcag   14340
ttatccagca atcattcccg attaggtggg aggctgtttc agtaaaagga ggatacaagc   14400
agaagtggag tactagaggt gatgggctcc caaaagatac ccgaacttca gactccttgg   14460
ccccaatcgg gaactggatc agatctctgg aattggtccg aaaccaagtt cgtctaaatc   14520
cattcaatga gatcttgttc aatcagctat gtcgtacagt ggataatcat ttgaaatggt   14580
caaatttgcg aagaaacaca ggaatgattg aatggatcaa tagacgaatt tcaaaagaag   14640
accggtctat actgatgttg aagagtgacc tacacgagga aaactcttgg agagattaaa   14700
aaatcatgag gagactccaa actttaagta tgaaaaaaac tttgatcctt aagaccctct   14760
tgtggttttt attttttatc tggttttgtg gtcttcgtgg gtcggcatgg catctccacc   14820
tcctcgcggt ccgacctggg catccgaagg aggacgcacg tccactcgga tggctaaggg   14880
agagccagaa aataactagt ggatccggct gctaacaaag cccgaaagga agctgagttg   14940
gctgctgcca ccgctgagca ataactagca taaccccttg gggcctctaa acgggtcttg   15000
aggggttttt tgctgaaagt cgcgcttggc gtaatcatgg tcatagctgt ttcctgtgtg   15060
aaattgttat ccgctcacaa ttccacacaa catacgagcc ggaagcataa agtgtaaagc   15120
ctggggtgcc taatgagtga gctaactcac attaattgcg ttgcgctcac tgcccgcttt   15180
ccagtcggga aacctgtcgt gccagctgca ttaatgaatc ggccaacgcg cggggagagg   15240
cggtttgcgt attgggcgct cttccgcttc ctcgctcact gactcgctgc gctcggtcgt   15300
tcggctgcgg cgagcggtat cagctcactc aaaggcggta atacggttat ccacagaatc   15360
aggggataac gcaggaaaga acatgtgagc aaaaggccag caaaaggcca ggaaccgtaa   15420
aaaggccgcg ttgctggcgt ttttccatag gctccgcccc cctgacgagc atcacaaaaa   15480
tcgacgctca agtcagaggt ggcgaaaccc gacaggacta taaagatacc aggcgtttcc   15540
ccctggaagc tccctcgtgc gctctcctgt tccgaccctg ccgcttaccg gatacctgtc   15600
cgccttttct ccttcgggaa gcgtggcgct ttctcatagc tcacgctgta ggtatctcag   15660
ttcggtgtag gtcgttcgct ccaagctggg ctgtgtgcac gaaccccccg ttcagcccga   15720
ccgctgcgcc ttatccggta actatcgtct tgagtccaac ccggtaagac acgacttatc   15780
gccactggca gcagccactg gtaacaggat tagcagagcg aggtatgtag gcggtgctac   15840
agagttcttg aagtggtggc ctaactacgg ctacactaga aggacagtat ttggtatctg   15900
cgctctgctg aagccagtta ccttcggaaa aagagttggt agctcttgat ccggcaaaca   15960
aaccaccgct ggtagcggtg gtttttttgt ttgcaagcag cagattacgc gcagaaaaaa   16020
aggatctcaa gaagatcctt tgatcttttc tacggggtct gacgctcagt ggaacgaaaa   16080
ctcacgttaa gggattttgg tcatgagatt atcaaaaagg atcttcacct agatcctttt   16140
aaattaaaaa tgaagtttta aatcaatcta agtatatat gagtaaactt ggtctgacag   16200
ttaccaatgc ttaatcagtg aggcacctat ctcagcgatc tgtctatttc gttcatccat   16260
agttgcctga ctccccgtcg tgtagataac tacgatacgg gagggcttac catctggccc   16320
cagtgctgca atgataccgc gagacccacg ctcaccggct ccagatttat cagcaataaa   16380
ccagccagcc ggaagggccg agcgcagaag tggtcctgca actttatccg cctccatcca   16440
gtctattaat tgttgccggg aagctagagt aagtagttcg ccagttaata gtttgcgcaa   16500
cgttgttgcc attgctacag gcatcgtggt gtcacgctcg tcgtttggta tggcttcatt   16560
cagctccggt tcccaacgat caaggcgagt tacatgatcc cccatgttgt gcaaaaaagc   16620
ggttagctcc ttcggtcctc cgatcgttgt cagaagtaag ttggccgcag tgttatcact   16680
catggttatg gcagcactgc ataattctct tactgtcatg ccatccgtaa gatgcttttc   16740
tgtgactggt gagtactcaa ccaagtcatt ctgagaatag tgtatgcggc gaccgagttg   16800
ctcttgcccg gcgtcaatac gggataatac cgcgccacat agcagaactt taaaagtgct   16860
catcattgga aaacgttctt cggggcgaaa actctcaagg atcttaccgc tgttgagatc   16920
cagttcgatg taacccactc gtgcacccaa ctgatcttca gcatctttta ctttcaccag   16980
cgtttctggg tgagcaaaaa caggaaggca aaatgccgca aaaaagggaa taagggcgac   17040
acggaaatgt tgaatactca tactcttcct ttttcaatat tattgaagca tttatcaggg   17100
ttattgtctc atgagcggat acatatttga atgtatttag aaaaataaac aatagggggt   17160
tccgcgcaca tttccccgaa aagtgccac                                     17189

SEQ ID NO: 2         moltype = DNA   length = 17611
FEATURE              Location/Qualifiers
misc_feature         1..17611
                     note = BNSP333-COVID19-S1-RVG
source               1..17611
                     mol_type = other DNA
                     organism = synthetic construct
SEQUENCE: 2
ctgacgcgcc ctgtagcggc gcattaagcg cggcgggtgt ggtggttacg cgcagcgtga   60
ccgctacact tgccagcgcc ctagcgcccg ctcctttcgc tttcttccct tcctttctcg  120
```

```
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccctagt tattaatagt aatcaattac gggтgтсатта   660
gttcatagcc catatatgga gttccgcgtt acataactta cggtaaatgg cccgcctggc    720
tgaccgccca acgacccccg cccattgacg tcaataatga cgtatgttcc catagtaacg    780
ccaataggga ctttccattg acgtcaatgg gtggagtatt tacggtaaac tgcccacttg    840
gcagtacatc aagtgtatca tatgccaagt acgcccccta ttgacgtcaa tgacggtaaa    900
tggcccgcct ggcattatgc ccagtacatg actttaccac ttggcagtac                960
atctacgtat tagtcatcgc tattaccatg gtgatgcggt tttggcagta catcaatggg   1020
cgtggatagc ggtttgactc acggggattt ccaagtctcc accccattga cgtcaatggg   1080
agtttgtttt ggcaccaaaa tcaacgggac tttccaaaat gtcgtaacaa ctccgcccca   1140
ttgacgcaaa tgggcggtag gcgtgtacgg tgggaggtct atataagcag agctctctgg   1200
ctaactagag aacccactgc ttactggctt atcgaaatta atacgactca ctatagggag   1260
acccaagctg gctagattaa gcgtctgatg agtccgtgag gacgaaaccc ggcgtaccgg   1320
gtcacgctta acaccagat caaagaaaa acagacattg tcaattgcaa agcaaaaatg   1380
taacacccct aaatggatc ccgacaagat tgtattcaa caataatc aggtggtctc   1440
tttgaagcct gagattatcg tgatcaata tgagtacaag taccctgcca tcaaagattt   1500
gaaaaagccc tgtataaccc taggaaaggc tcccgattta aataaagcat aaagtcagt   1560
tttgtcagga atgagcgccg ccaaacttaa tcctgacgat gtatgttcct аттттggсаgс   1620
ggcaatgcag ttttttgagg ggacatgtcc ggaagctgg accagctatg gaatttgtat   1680
tgcacgaaaa ggagataaga tcaccccagg ttctctggtg gagataaaac gtactgatgt   1740
agaagggaat tgggctctga caggaggcat ggaactgaca agagacccca ctgtccctga   1800
gcatgcgtcc ttagtcggtc тттстсттgаg tctgtatagg ttgagcaaaa tatccgggca   1860
aaacactggt aactataaga caaacattgc agacaggata gagcagattt ttgagacagc   1920
cccttttgtt aaaatcgtgg aacaccatac tctaatgaca actcacaaaa tgtgtgctaa   1980
ttggagtact ataccaaact tcagatttt ggccggaacc tatgcatgt tttttctccg   2040
gattgagcat ctatattcag caatcagagt gggcacagtt gtcactgctt atgaagactg   2100
ttcaggactg gtatcattta ctgggttcat aaaacaaatc aatctcaccg ctagagaggc   2160
aatactatat ttcttccaca agaactttga ggaagagata agaagaatgt ttgagccagg   2220
gcaggagaca gctgttcctc actcttattt catccacтттс cgttcactag gcttgagtgg   2280
gaaatctcct tattcatcaa atgctgttgg tcacgtgttc aatctcattc actttgtagg   2340
atgctatatg ggtcaagtca gatccctaaa tgcaacggtt attgctgcat gtgctcctca   2400
tgaaatgtct gttctagggg gctatctggg agaggaattc ttcgggaaag ggacatttga   2460
aagaagattc ttcagagatg agaaagaact tcaagaatac gaggcggctg aactgacaaa   2520
gactgacgta gcactggcag atgatggaac tgtcaactct gacgacgagg actacttttc   2580
aggtgaaacc agagtccgg aggctgttta tactcgaatc atgatgaatg gaggtcgact   2640
aaagagatct cacatacgga gatatgtctc agtcagttcc aatcatccaa ccgtccaaa    2700
ctcattcgcc gagtttctaa acaagacata ttcgagtgac tcataacatg ааааааааста   2760
acacccctcc cgtacgccac catgttcgtg tttctggtgc tgctgcctct ggtgagctcc    2820
cagtgcgtga acctgaccac aaggaccag ctgcccctg cctataccaa ttccttcaca    2880
cggggctgtg actatcccga caaggtgttc cggagcaggc tgctgcactc cacacaggat    2940
ctgtttctgc ctttctttc taacgtgacc tggttccacg ccatcacgt gagcggcacc    3000
aatggcacaa agcggttcga caatccagtg ctgcccttta acgatggcgt gtacttcgcc   3060
tccaccgaga agtctaacat catcagaggc tggatctttg gcaccacact ggacagcaag    3120
acacagtccc tgctgatcgt gaacaatgcc accaacgtgg tcatcaaggt gtgcgagttc    3180
cagтттттgта atgatccatt cctgggcgtg tactatcaca agaacaataa gtcttggatg    3240
gagagcgagt ttcgcgtgta ttcctctgcc aacaattgca catttgagta cgtgtcccag    3300
cccttcctga tggacctgga gggcaagcag ggcaattca agaacctgag ggagttcgtg    3360
tttaagaata tcgatggcta cttcaaaatc tactccaagc acaccccaat caacctggtg    3420
cgcgacctgc cacagggctt ctctgccctg gagccactgg tggatctgcc catcggcatc    3480
aacatcaccc ggtttcagac actgctggcc ctgcacagaa gctacctgac accaggcgac    3540
agctcctctg gatggaccgc aggagcagca gcctactatg tgggctatct gcagcccagg    3600
accttcctgc tgaagtacaa cgagaatggc accatccaca cgccgtggaa ttgcgccctg    3660
gatcccctgt ctgagaccaa gтgтасактa aagagcttta ccgtggagaa gggcatctat    3720
cagacaagca atttcagggt gcagcctacc agtccatcg tgcgctttcc caatatcaca    3780
aacctgtgcc cttttggcga ggtgttcaac gcaacccgct tcgccagcgt tacgcctgg    3840
aataggaagc gcatctccaa ctgcgtggcc gactattctg tgctgtacaa cagcgcctcc    3900
ttctctacct ttaagtgcta tggcgtgagc cccacaagct tggatttcct gtgctttacc    3960
aacgtgtacg ccgatccctt cgtgatcagg ggcgacgagg tgcgccagat cgcaccagga    4020
cagacaggca agatcgcaga ctacaattat aagcgcctg acgatttcac cggctgcgtg    4080
atcgcctgga actctaacaa tctggatagc aaagtgggcg gcaactacaa ttatctgtac    4140
cggctgttta gaaagtctaa tctgaagcca ttcgagaggg acatctccac agaaatctac    4200
caggccggct ctacccctg caatggcgtg gagggcttta actgttatt ccctctgcag    4260
agctacggct tccagccaac aaacggcgtg ggctatcagc cctaccgcgt ggtggtgctg    4320
tcttttgagc tgctgcacgc acctgcaaca gtgtgcggac caagaagag caccaatctg    4380
gtgaagaaca gtgcgtgaa cttcaactc aacggactga ccggaacagg cgtgctgacc    4440
gagtccaaca agaagttcct gcctttcag cagttcggca gggacatcgc agataccaca    4500
gatgcagtcc gagacctca gacctggaca tcacaccatg ctccttcgga    4560
ggcgtgtctg tgatcacacc aggcaccaat acaagcaacc aggtggccgt gctgtatcag    4620
gacgtgaatt gtaccgaggt gccagtggca atccacgcag atcagctgac ccctacatgg    4680
cgggtgtact ctaccggcag caacgtgttc cagacaagag ccggatgcct gatcggagca    4740
gagcacgtga acaatagcta tgagtgcgac atccctatcg cgccggcat ctgtgcctcc    4800
taccagaccc agacaaactc cccaaggtct gtgggagatg aggccgaaga ctttgtggaa    4860
```

```
gtccacctgc ctgatgtgca taaccaggtg tctggcgtcg acctgggact gccaaattgg   4920
ggcaagtacg tgctgctgag tgctggagca ctgactgccc tgatgctgat catttttcctg  4980
atgacctgct gtcggcgcgt gaacagaagt gagcccactc agcacaatct gcgaggaacc   5040
gggagagaag tgtcagtcac acctcagagc gggaaaatca ttagtagttg gaatcacat    5100
aaaagcgggg gcgagaccag gctgtgagct agccatgaaa aaaactaaca cccctcctt   5160
cgaaccatcc caaacatgag caagatcttt gtcaatccta gtgctattag agccggtctg   5220
gccgatcttg agatggctga agaaactgtt gatctgatca atagaaatat cgaagacaat   5280
caggctcatc tccaagggga acccatagag gtggacaatc tccctgagga tatggggcga   5340
cttcacctgg atgatggaaa atcgcccaac catggtgaga tagccaaggt gggagaaggc   5400
aagtatcgag aggactttca gatggatgaa ggagaggatc ctagcttcct gttccagtca   5460
tacctggaaa atgttggagt ccaaatagtc agacaaatga ggtcaggaga gagatttctc   5520
aagatatggt cacagaccgt agaagagatt atatcctatg tcgcggtcaa ctttcccaac   5580
cctccaggaa agtcttcaga ggataaatca acccagacta ctggccgaga gctcaagaag   5640
gagacaacac ccactccttc tcagagagaa agccaatcat cgaaagccag gatgcgggct   5700
caaattgctt ctggccctcc agccttgaa tggtcggcta ccaatgaaga ggatgatcta    5760
tcagtggagg ctgagatcgc tcaccagatt gcagaaagtt tctccaaaaa atataagttt   5820
ccctctcgat cctcagggat actcttgtat aattttgagc aattgaaaat gaaccttgat   5880
gatatagtta aagaggcaaa aaatgtacca ggtgtgaccc gtttagccca tgacgggtcc   5940
aaactccccc taagatgtgt actgggatgg gtcgctttgg ccaactctaa gaaattccag   6000
ttgttagtcg aatccgacaa gctgagtaaa atcatgcaag atgacttgaa tcgctataca   6060
tcttgctaac cgaacctctc ccctcagtcc ctctagacaa taaaatccga gatgtcccaa   6120
agtcaacatg aaaaaaatag gcaacaccac tgataaaatg aacctcctac gtaagatagt   6180
gaaaaaccgc agggacgagg acactcaaaa atcctctccc gcgtcagccc ctctggatga   6240
cgatgacttg tggcttccac cccctgaata cgtcccgctg aaagaactta caggcaagaa   6300
gaacatgagg aactttgta tcaacggaag ggttaaagtg tgtagcccga atggttactc    6360
gttcaggatc ctgcggcaca ttctgaaatc attcgacgag atatattctg ggaatcatag   6420
gatgatcggg ttagtcaaag tggttattgg actggctttg tcaggatctc cagtccctga   6480
gggcctgaac tgggtataca aattgaggag aacctttatc ttccagtggg ctgattccag   6540
gggccctctt gaaggggagg agttggaata ctctcaggag atcacttggg atgatgatac   6600
tgagttcgtc ggattgcaaa taagagtgat tgcaaaacag tgtcatatcc agggcagagt   6660
ctggtgtatc aacatgaacc cgagagcatg tcaactatgg tctgacatgt ctcttcagac   6720
acaaaggtcc gaagaggaca aagattcctc tctgcttcta gaataatcag attatatccc   6780
gcaaatttat cacttgttta cctctggagg agagaacata tgggctcaac tccaaccctt   6840
gggagcaata taacaaaaaa catgttatgg tgccattaaa ccgctgcatt tcatcaaagt   6900
caagttgatt acctttacat tttgatcctc ttggatgtga aaaaaactat taacatccgt   6960
caaaagaccc cgggaaagat ggttcctcag gctctcctgt ttgtaccct tctggttttt     7020
ccattgtgtt ttgggaaatt ccctatttac acgataccag acaagcttgg tccctggagt   7080
ccgattgaca tacatcacct cagctgccca aacaatttgg tagtggagga cgaaggatgc   7140
accaacctgt cagggttctc ctacatggaa cttaaagttg gatacatctt agccataaaa   7200
gtgaacgggt tcacttgcac aggcgttgtg acggaggctg aaacctacac taacttcgtt   7260
ggttatgtca caaccacgtt caaaagaaag catttccgcc caacaccaga tgcatgtaga   7320
gccgcgtaca actggaagat ggccggtgac cccagatatg aagagtctct acacaatccg   7380
taccctgact accgctggct tcgaactgta aaaaccacca aggagtctct cgttatcata   7440
tctccaagtg tggcagattt ggacccatat gacagatccc ttcactcgag ggtcttccct   7500
agcgggaagt gctcaggagt agcggtgtct tctacctact gctccactaa ccacgattac   7560
accatttgga tgcccgagaa tccgagacta gggatgtctt gtgacatttt taccaatagt   7620
agagggagga gagcatccaa agggagtgag acttgcggct ttgtagatga aagaggccta   7680
tataagtctt taaaaggagc atgcaaactc aagttatgtg gagttctagg acttagactt   7740
atggatggaa catgggtctc gatgcaaaca tcaaatgaaa ccaaatggtg ccctcccgat   7800
aagttggtga acctgcacga ctttcgctca gacgaaattg agcaccttgt tgtagaggag   7860
ttggtcagga agagagga gtgtctggat gcactagagt ccatcatgac aaccaagtca    7920
gtgagtttca gacgtctcag tcatttaaga aaacttgtcc ctgggtttgg aaaagcatat   7980
accatattca acaagacctt gatggaagcc gatgctcact acaagtcagt cgagacttgg   8040
aatgagatcc tcccttcaaa agggtgttta agagttgggg ggaggtgtca tcctcatgtg   8100
aacggggtgt ttttcaatgg tataatatta ggacctgacg gcaatgtctt aatcccagag   8160
atgcaatcat ccctcctcca gcaacatatg gagttgttgg aatcctcggt tatcccctt    8220
gtgcaccccc tggcagaccc gtctaccgtt ttcaaggacg tgacgaggc tgaggatttt   8280
gttgaagttc accttcccga tgtgcacaat caggtctcag gagttgactt gggtctcccg   8340
aactggggga agtatgtatt actgagtgca ggggccctga ctgccttgat gttgataatt   8400
ttcctgatga catgttgtag aagagtcaat cgatcagaac ctacgcaaca caatctcaga   8460
gggacaggga gggaggtgtc agtcactccc aaagcgggga agatcatatc ttcatgggaa   8520
tcacacaaga gtgggggtga gaccagactg taattaatta acgtcctttc aacgatccaa   8580
gtccatgaaa aaaactaaca cccctcccgt acctagctta taaagtgctg ggtcatctaa   8640
gcttttcagt cgagaaaaaa acattagatc agaagaacca ttctcaacct  8700
gagacttact tcaagatgct cgatcctgga gaggtctatg atgacccat tgacccaatc    8760
gagttagagg ctgaacccag aggaaccccc attgtcccca acatcttgag gaactctgac   8820
tacaatctca actctccttt gatagaagat cctgctagac taatgttaga atggttaaa    8880
acagggaata gaccttatcg gatgactcta acagacaatt gctccaggtc tttcagagtt   8940
ttgaaagatt atttcaagaa ggtagatttg ggttctctca aggtgggcgg aatgctgca    9000
cagtcaatga tttctctctg gttatatggt gccactctg aatccaacag agccggaga     9060
tgtataacag acttggccca tttctattcc aagtcgtccc ccatagagaa gctgttgaat   9120
ctcacgctag gaaatagagg gctgagaatc ccccagagg gagtgttaag ttgccttgag    9180
agggttgatt atgataatgc atttggaagg tatcttgcca acacgtattc ctcttacttg   9240
ttcttccatg taatcaccct atacatgaac aagccctgaa aaagaccatc                9300
ctagcattat ggaaagattt aacctcagtg gacatcggga aggacttggt aaagttcaaa   9360
gaccaaatat ggggactgct gatcgtgaca aaggactttg tttactccca aagttccaat   9420
tgtctttttg acagaaacta cacttatgct ctaaagatc ttttcttgtc tcgcttcaac    9480
tccttaatgg tcttgctctc tccccagag ccccgatact cagatgactt gatatctcaa    9540
ctatgccagc tgtacattgc tggggatcaa gtcttgtcta tgtgtggaaa ctccggctat   9600
```

```
gaagtcatca aaatattgga gccatatgtc gtgaatagtt tagtccagag agcagaaaag   9660
tttaggcctc tcattcattc cttgggagac tttcctgtat ttataaaaga caaggtaagt   9720
caacttgaag agacgttcgg tccctgtgca agaaggttct ttagggctct ggatcaattc   9780
gacaacatac atgacttggt ttttgtgttt ggctgttaca ggcattgggg gcacccatat   9840
atagattatc gaaagggtct gtcaaaacta tatgatcagg ttcaccttaa aaaaatgata   9900
gataagtcct accaggagtg cttagcaagc gacctagcca ggaggatcct tagatggggt  9960
tttgataagt actccaagtg gtatctggat tcaagattcc tagcccgaga ccaccccttg  10020
actccttata tcaaaaccca aacatggcca cccaaacata ttgtagactt ggtggggggat 10080
acatggcaca agctcccgat cacgcagatc tttgagattc ctgaatcaat ggatccgtca  10140
gaaatattgg atgacaaatc acattctttc accagaacga gactagcttc ttggctgtca  10200
gaaaaccgag gggggcctgt tcctagcgaa aaagttatta tcacggccct gtctaagccg  10260
cctgtcaatc cccgagagtt tctgaggtct atagacctcg gaggattgcc agatgaagac  10320
ttgataattg gcctcaagcc aaaggaacgg gaattgaaga ttgaaggtcg attctttgct  10380
ctaatgtcat ggaatctaag attgtatttt gtcatcactg aaaaactctt ggccaactac  10440
atcttgccac ttttttgacgc gctgactatg acagacaacc tgaacaaggt gtttaaaaag  10500
ctgatcgaca gggtcaccgg gcaagggctt tggactattc aagggtcac atatgcattt  10560
cacctggact atgaaaagtg gaacaaccat caaagattag agtcaacaga ggatgtattt  10620
tctgtcctag atcaagtgtt tggattgaag agagtgtttt ctagaacaca cgagttttct  10680
caaaaggcct ggatctatta ttcagacaga tcagacctca tcgggttacg ggaggatcaa  10740
atatactgct tagatgcgtc caacggccca acctgttgga atggccagga tggcgggcta  10800
gaaggcttac ggcagaaggg ctggagtcta gtcagcttat tgatgataga tagagaatct  10860
caaatcagga acacaagaac caaaatacta gctcaaggag acaaccaggt tttatgtccg  10920
acatacatgt tgtcgccagg gctatctcaa gaggggctcc tctatgaatt ggagagaata  10980
tcaaggaatg cactttcgat atacagagcc gtcgaggaag gggcatctaa gctagggctg  11040
atcatcaaga aagaagagac catgtgtagt tatgacttcc tcatctatgg aaaaaccct   11100
ttgtttagag gtaacatatt ggtgcctgag tccaaaagat ggccagagt ctcttgctc    11160
tctaatgacc aaaatagtca acctcgccaat ataatgtcga cagtgtccac caatgcgcta  11220
acagtggcac aacactctca atctttgatc aaaccgatga gggattttct gctcatgtca  11280
gtacaggcag tctttcacta cctgctattt agcccaatct taaagggaag agtttacaag  11340
attctgagcg ctgaagggga gagctttctc ctagccatgt caaggataat ctatctagat  11400
ccttctttgg gagggatatc tggaatgtcc ctcggaagat tccatatacg acagttctca  11460
gaccctgtct ctgaagggtt atccttctgg agagagatct ggttaagctc ccaagagtcc  11520
tggattcacg cgttgtgtca agaggctgga aacccagatc ttggagagag aacactcgag  11580
agcttcactc gccttctaga agatccgacc accttaaata tcagaggagg ggccagtcct  11640
accattctac tcaaggatgc aatcagaaag gctttatatg acgaggtgga caaggtggaa  11700
aattcagagt ttcgagaggc aatcctgttg tccaagaccc atagagataa ttttatactc  11760
ttcttaatat ctgttgagcc tctgtttcct cgatttctca gtgagctatt cagttcgtct  11820
tttttgggaa tccccgagtc aatcattgga ttgatacaaa actcccgaac gataagaagg  11880
cagtttagaa agagtctctc aaaaactta gaagaatcct tctacaactc agatcgatc    11940
gggattagtc ggatgaccca gacacctcag agggttgggg gggtgtggcc ttgctcttca  12000
gagagggcag atctacttag ggagatctct tggggaagaa aagtggtagg cacgacagtt  12060
cctcacccctt ctgagatgtt gggattactt cccaagtcct ctatttcttg cacttgtgga  12120
gcaacaggag gaggcaatcc tagagtttct gtatcagtac tcccgtcctt tgatcagtca  12180
ttttttttcac gaggcccctt aaaggggatac ttgggctcgt ccacctctat gtcgacccag  12240
ctattccatg catgggaaaa agtcactaat gttcatgtgg tgaagagagc tctatcgtta  12300
aaagaatcta taaactggtt cattactaga gattccaact tggctcaagc tctaattagg  12360
aacattatgt ctctgacagg ccctgatttc cctctagagg aggcccctgt cttcaaaagg  12420
acggggtcag ccttgcatag gttcaagtct gccagatca gcgaaggagg gtattcttct   12480
gtctgcccga acctcctctc tcatatttct gttagtacag acaccatgtc tgatttgacc  12540
caagacggga agaactacga tttcatgttc cagccattga tgctttatgc acagacatgg  12600
acatcagagc tggtacagag agacacaagg ctaagagact ctacgtttca ttggcacctc  12660
cgatgcaaca ggtgtgtgag acccattgac gacgtgaccc tggagacctc tcagatcttc  12720
gagtttccgg atgtgtcgaa aagaatatcc agaatggttt ctggggctgt gcctcacttc  12780
cagaggcttc ccgatatccg tctgagacca ggagattttg aatctctaag cggtagagaa  12840
aagtctcacc atatcggatc agctcagggg ctcttatact caatcttagt ggcaattcac  12900
gactcaggat acaatgatgg aaccatcttc cctgtcaaca tatacggcaa ggtttcccct  12960
agagactatt tgagagggct cgcaagggga gtattgatag gatcctcgat ttgcttcttg  13020
acaagaatga caaatatcaa tattaataga cctcttgaat tggtctcagg ggtaatctca  13080
tatattctcc tgaggctaga taaccatccc tccttgtaca taatgctcag agaaccgtct  13140
cttagaggag agatattttc tatccctcag aaaatccccg ccgcttatcc aaccactatg  13200
aaagaaggca acagatcaat cttgtgttat ctccaacatg tgctacgcta tgagcgagag  13260
ataatcacgg cgtctccaga gaatgactgg ctatggatct tttcagactt agaagtgcc   13320
aaaatgacgt acctatccct cattacttac cagtctcatc ttctactcca gagggttgag  13380
agaaacctat ctaagagtat gagagataac ctgcggacaat tgagttcttt gatgaggcag  13440
gtgctgggcg ggcacggaga agatacctta gagtcagacg acaacattca acgactgcta  13500
aaagactctt tacgaaggac aagatgggtg gatcaagagg tgcgccatgc agctagaacc  13560
atgactggaa attacagccc caacaagaag gtgtcccgta aggtaggatg ttcagaatgg  13620
gtctgctctg ctcaacaggt tgcagtctct acctcagcaa acccggcccc tgtctcggag  13680
cttgacataa gggccctctc taagaggttc cagaaccctt tgatctcgga cttgagagtg  13740
gttcagtggg caaccggtgc tcattataag cttaagccta ttctagatga tctcaatgtt  13800
ttcccatctc tctgccttgt agttgggac gggtcagggg ggatatcaag ggcagtcctc  13860
aacatgtttc cagatgccaa gcttgtgttc aacagtcttt tagaggtgaa tgacctgatg  13920
gcttccggaa cacatccact gcctccttca gcaatcatga gggaggaaaa tgatatcgtc  13980
tccagatga tagatcttga ctcaatctgg gaaaaaccgt ccgacttgag aaacttggca   14040
acctggaaat acttccagtc agtccaaaag caggtcaaca tgtcctatga cctcattatt  14100
tgcgatgcag aagttactga cattgcatct atcaaccgga tcacccttgt aatgtccgat  14160
tttgcattgt ctatagatgg accactctat ttggtcttca aaacttatgg gactatgcta  14220
gtaaatccaa actacaaggc tattcaacac ctgtcaagag cgttccccctc ggtcacaggg  14280
tttatcaccc aagtaacttc gtcttttttca tctgagctct acctccgatt ctccaaaacga  14340
```

```
gggaagtttt tcagagatgc tgagtacttg acctcttcca cccttcgaga aatgagcctt  14400
gtgttattca attgtagcag ccccaagagt gagatgcaga gagctcgttc cttgaactat  14460
caggatcttg tgagaggatt tcctgaagaa atcatatcaa atccttacaa tgagatgatc  14520
ataactctga ttgacagtga tgtagaatct ttttctagtcc acaagatggt tgatgatctt  14580
gagttacaga ggggaactct gtctaaagtg gctatcatta tagccatcat gatagttttc  14640
tccaacagag tcttcaacgt ttccaaaccc ctaactgacc cctcgttcta tccaccgtct  14700
gatcccaaaa tcctgaggca cttcaacata tgttgcagta ctatgatgta tctatctact  14760
gctttaggtg acgtccctag cttcgcaaga cttcacgacc tgtataacag acctataact  14820
tattacttca gaaagcaagt cattcgaggg aacgtttatc tatcttggag ttggtccaac  14880
gacacctcag tgttcaaaag ggtagcctgt aattctagcc tgagtctgtc atctcactgg  14940
atcaggttga tttacaagat agtgaagact accagactcg ttggcagcat caaggatcta  15000
tccagagaag tggaaagaca ccttcatagg tacaacaggt ggatcaccct agaggatatc  15060
agatctagat catccctact agactacagt tgcctgtgaa ccggatactc ctggaagcct  15120
gcccatgcta agactcttgt gtgatgtatc ttgaaaaaaa caagatccta aatctgaacc  15180
tttggttgtt tgattgtttt tctcattttt gttgtttatt tgttaagcgt gggtcggcat  15240
ggcatctcca cctcctcgcg gtccgacctg ggcatccgaa ggaggacgca cgtccactcg  15300
gatggctaag ggagagccag aaggatccgg ctgctaacaa agcccgaaag gaagctgagt  15360
tggctgctgc caccgctgag caataactag cataacccct tggggcctct aaacgggtct  15420
tgaggggttt tttgctgaaa gtcgcgcttg gcgtaatcat ggtcatagct gtttcctgtg  15480
tgaaattgtt atccgctcac aattccacac aacatacgag ccggaagcat aaagtgtaaa  15540
gcctggggtg cctaatgagt gagctaactc acattaattg cgttgcgctc actgcccgct  15600
ttccagtcgg gaaacctgtc gtgccagctg cattaatgaa tcggccaacg cgcggggaga  15660
ggcggtttgc gtattgggcg ctcttacgct tcctcgctca ctgactcgct gcgctcggtc  15720
gttcggctgc ggcgagcggt atcagctcac tcaaaggcgg taatacggtt atccacagaa  15780
tcaggggata acgcaggaaa gaacatgtga gcaaaaggcc agcaaaaggc caggaaccgt  15840
aaaaaggccg cgttgctggc gtttttccat aggctccgcc cccctgacga gcatcacaaa  15900
aatcgacgct caagtcagag gtggcgaaac ccgacaggac tataaagata ccaggcgttt  15960
ccccctggaa gctccctcgt gcgctctcct gttccgaccc tgccgcttac cggatacctg  16020
tccgcctttc tcccttcggg aagcgtggcg ctttctcata gctcacgctg taggtatctc  16080
agttcggtgt aggtcgttcg ctccaagctg ggctgtgtgc acgaaccccc cgttcagccc  16140
gaccgctgcg ccttatccgg taactatcgt cttgagtcca acccggtaag acacgactta  16200
tcgccactgg cagcagccac tggtaacagg attagcagag cgaggtatgt aggcggtgct  16260
acagagttct tgaagtggtg gcctaactac ggctacacta gaaggacagt atttggtatc  16320
tgcgctctgc tgaagccagt taccttcgga aaaagagttg gtagctcttg atccggcaaa  16380
caaaccaccg ctggtagcgg tggttttttt gtttgcaagc agcagattac gcgcagaaaa  16440
aaaggatctc aagaagatcc tttgatcttt tctacggggt ctgacgctca gtggaacgaa  16500
aactcacgtt aagggatttt ggtcatgaga ttatcaaaaa ggatcttcac ctagatcctt  16560
ttaaattaaa aatgaagttt taaatcaatc taaagtatat atgagtaaac ttggtctgac  16620
agttaccaat gcttaatcag tgaggcacct atctcagcga tctgtctatt tcgttcatcc  16680
atagttgcct gactccccgt cgtgtagata actacgatac gggagggctt accatctggc  16740
cccagtgctg caatgatacc gcgagaccca cgctcaccgg ctccagattt atcagcaata  16800
aaccagccag ccggaagggc cgagcgcaga agtggtcctg caactttatc cgcctccatc  16860
cagtctatta attgttgccg ggaagctaga gtaagtagtt cgccagttaa tagtttgcgc  16920
aacgttgttg ccattgctac aggcatcgtg gtgtcacgct cgtcgtttgg tatggcttca  16980
ttcagctccg gttcccaacg atcaaggcga gttacatgat cccccatgtt gtgcaaaaaa  17040
gcggttagct ccttcggtcc tccgatcgtt gtcagaagta agttggccgc agtgttatca  17100
ctcatggtta tggcagcact gcataattct cttactgtca tgccatccgt aagatgcttt  17160
tctgtgactg gtgagtactc aaccaagtca ttctgagaat agtgtatgcg gcgaccgagt  17220
tgctcttgcc cggcgtcaat acgggataat accgcgccac atagcagaac tttaaaagtg  17280
ctcatcattg gaaaacgttc ttcggggcga aaactctcaa ggatcttacc gctgttgaga  17340
tccagttcga tgtaacccac tcgtgcaccc aactgatctt cagcatcttt tactttcacc  17400
agcgtttctg ggtgagcaaa aacaggaagg caaaatgccg caaaaaaggg aataagggcg  17460
acacggaaat gttgaatact catactcttc ctttttcaat attattgaag catttatcag  17520
ggttattgtc tcatgagcgg atacatattt gaatgtattt agaaaaataa acaaataggg  17580
gttccgcgca catttccccg aaaagtgcca c                                 17611

SEQ ID NO: 3            moltype = DNA  length = 22946
FEATURE                 Location/Qualifiers
misc_feature            1..22946
                        note = MV-coWuhan-S Position 2
source                  1..22946
                        mol_type = other DNA
                        organism = synthetic construct
SEQUENCE: 3
ggacgcgccc tgtagcggcg cattaagcgc ggcgggtgtg gtggttacgc gcagcgtgac  60
cgctacactt gccagcgccc tagcgcccgc tcctttcgct ttcttccctt cctttctcgc  120
cacgttcgcc ggctttcccc gtcaagctct aaatcggggg ctccctttag ggttccgatt  180
tagtgcttta cggcacctcg accccaaaaa acttgattag ggtgatggtt cacgtagtgg  240
gccatcgccc tgatagacgg tttttcgccc tttgacgttg gagtccacgt tctttaatag  300
tggactcttg ttccaaactg gaacaacact caaccctatc tcggtctatt cttttgattt  360
ataagggatt ttgccgattt cggcctattg gttaaaaaat gagctgattt aacaaaaatt  420
taacgcgaat tttaacaaaa tattaacgtt tacaatttcg cgccattcgc cattcaggct  480
gcgcaactgt tgggaagggc gatcggtgcg ggcctcttcg ctattacgcc agctggcgaa  540
agggggatgt gctgcaaggc gattaagttg ggtaacgcca gggttttccc agtcacgacg  600
ttgtaaaacg acggccagtg cgcgccgtta atacgactca ctatagggag acccaagctg  660
gctagctttg tttggtctga tgagtcccgt gaggacgaaa cccggcgtac cgggtcacca  720
aacaaagttg ggtaaggata gttcaatcaa tgatcatctt ctagtgcact taggattcaa  780
gatcctatta tcagggacaa gagcaggatt agggatatcc gagatggcca cactttttaag  840
gagcttagca ttgttcaaaa gaaacaagga caaaccaccc attacatcag gatccggtgg  900
```

```
agccatcaga ggaatcaaac acattattat agtaccaatc cctggagatt cctcaattac   960
cactcgatcc agacttctgg accggttggt gaggttaatt ggaaacccgg atgtgagcgg  1020
gcccaaacta acaggggcac taataggtat attatcctta tttgtggagt ctccaggtca  1080
attgattcag aggatcaccg atgaccctga cgttagcata aggctgttag aggttgtcca  1140
gagtgaccag tcacaatctg gccttacctt cgcatcaaga ggtaccaaca tggaggatga  1200
ggcggaccaa tacttttcac atgatgatcc aattagtagt gatcaatcca ggttcggatg  1260
gttcgggaac aaggaaatct cagatattga agtgcaagac cctgagggat tcaacatgat  1320
tctgggtacc atcctagccc aaatttgggt cttgctcgca aaggcggtta cggcccccaga  1380
cacggcagct gattcggagc taagaaggtg gataaagtac acccaacaaa gaagggtagt  1440
tggtgaattt agattggaga gaaaatggtt ggatgtggtg aggaacagga ttgccgagga  1500
cctctcctta cgccgattca tggtcgctct aatcctggat atcaagagaa cacccggaaa  1560
caaacccagg attgctgaaa tgatatgtga cattgataca tatatcgtag aggcaggatt  1620
agccagtttt atcctgacta ttaagtttgg gatagaaact atgtatcctg ctcttggact  1680
gcatgaattt gctggtgagt tatccacact tgagtccttg atgaaccttt accagcaaat  1740
gggggaaact gcaccctaca tggtaatcct ggagaactca attcagaaca agttcagtgc  1800
aggatcatac cctctgctct ggagctatgc catgggagta ggagtggaac ttgaaaactc  1860
catgggaggt ttgaactttg gccgatctta ctttgatcca gcatatttta gattagggca  1920
agagatggta aggaggtcag ctggaaaggt cagttccaca ttggcatctg aactcggtat  1980
cactgccgag gatgcaaggc ttgtttcaga gattgcaatg catactactg aggacaagat  2040
cagtagagcg gttggaccca gacaagccca agtatcattt ctacacggtg atcaaagtga  2100
gaatgagcta ccgagattgg ggggcaagga agataggagg gtcaaacaga gtcgaggaga  2160
agccagggag agctacagag aaaccggggcc cagcagagca agtgatgcga gagctgccca  2220
tcttccaacc ggcacacccc tagacattga cactgcaacg gagtccagcc aagatccgca  2280
ggacagtcga aggtcagctg acgccctgct taggctgcaa gccatggcag gaatctcgga  2340
agaacaaggc tcagacacgg acaccccatat agtgtacaat gacagaaatc ttctagacta  2400
ggtgcgagag gccgagggcc agaacaacat ccgcctacca tccatcattg ttataaaaaa  2460
cttaggaacc aggtccacac agagtgatac gcgtacgacc ccatgttcgt gtttctggtg  2520
ctgctgcctc tggtgagctc ccagtgcgtg aacctgacca caaggaccca gctgcccct  2580
gcctatacca attccttcac acgggcgtg tactatcccg acaaggtgtt ccggagcagc  2640
gtgctgcact ccacacagga tctgtttctg ccttttcttt ctaacgtgac ctggttccac  2700
gccatccacg tgagcggcac caatggcaca aagcggttcg acaatccagt gctgcccttt  2760
aacgatggcg tgtacttcgc ctccaccgag aagtctaaca tcatcagagg ctggatcttt  2820
ggcaccacac tggacagcaa gacacagtcc ctgctgatcg tgaacaatgc caccaacgtg  2880
gtcatcaagg tgtgcgagtt ccagtttttgt aatgatccat tcctgggcgt gtactatcac  2940
aagaacaata agtcttggat ggagagcgag tttcgcgtgt attcctctgc caacaattgc  3000
acatttgagt acgtgtccca gccccttcctg atggacctgg agggcaagca gggcaatttc  3060
aagaacctga gggagttcgt gtttaagaat atcgatggct acttcaaaat ctactccaag  3120
cacaccccaa tcaacctggt gcgcgacctg ccacagggct ctctgcccct ggagccactg  3180
gtggatctgc ccatcggcat caacatcacc cggtttcaga cactgctggc cctgcacaga  3240
agctacctga caccaggcga cagctcctct ggatggaccg caggagcagc agcctactat  3300
gtgggctatc tgcagcccag gaccttcctg ctgaagtaca acgagaatgg caccatcaca  3360
gacgccgtgg attgcgccct ggatccctg tctgagacca agtgtacact gaagagcttt  3420
accgtggaga agggcatcta tcagacaagc aatttcaggg ttcagcctac cgagtccatc  3480
gtgcgctttc caatatcac aaacctgtgc cctttggcg aggtgttcaa cgcaacccgc  3540
ttcgccagcg tgtacgcctg gaataggaag cgcatctcca actgcgtggc cgactattct  3600
gtgctgtaca acagcgcctc cttctctacc tttaagtgct atggcgtgag ccccacaaag  3660
ctgaatgacc tgtgctttac caacgtgtac gccgattcct tcgtgatcag gggcgacgag  3720
gtgcgccaga tcgcaccagg acagacaggc aagatcgcag actacaatta taagctgcct  3780
gacgatttca ccggctgcgt gatcgcctgg aactctaaca atctggatag caaagtgggc  3840
ggcaactaca attatctgta ccggctgttt agaaagtcta atctgaagcc attcgagagg  3900
gacatctcca cagaaatcta ccaggccggc tctaccccct gcaatggcgt ggggcttt  3960
aactgttatt tccctctgca gagctacggc ttccagccaa caaacggcgt gggctatcag  4020
ccctaccgcg tggtggtgct gtcttttgag ctgctgcacg caccctgcaac agtgtgcgga  4080
ccaaagaaga gcaccaatct ggtgaagaac aagtgcgtga acttcaactt caacggactg  4140
accggaacag gcgtgctgac cgagtccaac aagaagttcc tgccttttca gcagttcggc  4200
agggacatcg cagataccac agacgccgtg cgcgaccctc agaccctgga gatcctggac  4260
atcacaccat gctccttcgg cggcgtgtct gtgatcacac caggcaccaa tacaagcaac  4320
caggtggccg tgctgtatca ggacgtgaat tgtaccgagg tgccagtggc aatccacgca  4380
gatcagctga cccctacatg gcgggtgtac tctaccggca gcaacgtgtt ccagacaaga  4440
gccggatgcc tgatcggagc agagcacgtg aacaatagct atgagtgcga catccctatc  4500
ggcgccggca tctgtgcctc ctaccagacc cagacaaact ccccaaggag agcacggtct  4560
gtggccagca gtccatcat cgcctatacc atgagcctgg gcgccgagaa ttccgtggcc  4620
tactccaaca attctatcgc catccctacc aacttcacaa tctccgtgac cacagagatc  4680
ctgccagtga gcatgaccaa gacatccgtg gactgcacaa tgtatatctg tggcgattca  4740
accgagtgct ctaacctgct gctgcagtac ggctcttttt gtacccagct gaatagagcc  4800
ctgacaggca tcgccgtgga gcaggacaag aacacacagg aggtgttcgc ccaggtgaag  4860
caaatctaca agacccccacc catcaaggac tttggcggct tcaacttcag ccagatcctg  4920
cccgatccta gcaagcccatc caagcggtct tttatcgagg acctgctgtt caacaaggtg  4980
accctggccg atgccggctt catcaagcag tatggcgatt gcctgggcga catcgccgcc  5040
agagacctga tctgtgccca gaagtttaat ggcctgaccg tgctgcctcc actgctgaca  5100
gatgagatga tcgcccagta cacatctgcc ctgctggccg gaaccatcac aagcggatgg  5160
accttcggcg caggagccgc cctgcagatc cccttgtgcca tgcagatggc ctatcggttc  5220
aacggcatcg gcgtgaccca gaatgtgctg tacgagaacc agaagctgat cgccaatcag  5280
tttaactccg ccatcggcaa gatccaggac tctctgagct ccaccgccag cgccctgggc  5340
aagctgcagg atgtggtgaa tcagaacgcc caggccctga acaccctggt gaagcagctg  5400
tctagcaact tcggcgccat ctcctctgtg ctgaatgaca tcctgagccg gctggacaag  5460
gtggaggcag aggtgcagat cgaccggctg atcacaggca gactgcagtc cctgcagacc  5520
tacgtgacac agcagctgat cagggcagca gagatcaggg cctctgccaa tctggccgcc  5580
accaagatga gcgagtgcgt gctgggccag tccaagagag tggactttgt ggcaagggc  5640
```

```
tatcacctga tgagcttccc acagtccgcc cctcacggag tggtgtttct gcacgtgacc    5700
tacgtgccag cccaggagaa gaacttcacc acagcaccag caatctgcca cgatggcaag    5760
gcacactttc ctagggaggg cgtgttcgtg agcaacggca cccactggtt tgtgacacag    5820
cgcaatttct acgagccaca gatcatcacc acagacaata cattcgtgtc cggcaactgt    5880
gacgtggtca tcggcatcgt gaacaatacc gtgtatgatc tctgcagcc agagctggac    5940
tcttttaagg aggagctgga taagtacttc aagaatcaca ccagccccga cgtggatctg    6000
ggcgacatct ctggcatcaa tgccagcgtg gtgaacatcc agaaggagat cgacaggctg    6060
aacgaggtgg ccaagaatct gaacgagtcc ctgatcgatc tgcaggagct gggcaagtat    6120
gagcagtaca tcaagtggcc ctggtatatc tggctgggct tcatcgccgg cctgatcgtg    6180
atcgtgatgg tgaccatcat gctgtgctgt atgacaagct gctgttcctg cctgaagggc    6240
tgctgttctt gtggcagctg ctgtaagttt gatgaggacg atagcgagcc tgtgctgaag    6300
ggcgtgaagc tgcactacac ctgatagcta gcgatcgcgt gcgagaggcc agaacaacat    6360
ccgcctacca tccatcattg ttataaaaaa cttaggaacc aggtccacac agccgccagc    6420
ccatcaacca tccactccca cgattggagc caatggcaga agagcaggca cgccatgtca    6480
aaaacggact ggaatgcatc cgggctctca aggccgagcc catcggctca ctggccatcg    6540
aggaagctat ggcagcatgg tcagaaatat cagacaaccc aggacaggag cgagccacct    6600
gcagggaaga gaaggcaggc agttcgggtc tcagcaaacc atgcctctca gcaattggat    6660
caactgaagg cggtgcacct cgcatccgcg gtcagggacc tggagagagc gatgacgacg    6720
ctgaaacttt gggaatcccc ccaagaaatc tccaggcatc aagcactggg ttacagtgtt    6780
attacgttta tgatcacagc ggtgaagcgg ttaagggaat ccaagatgct gactctatca    6840
tggttcaatc aggccttgat ggtgatagca ccctctcagg aggagacaat gaatctgaaa    6900
acagcagtgt ggatattggc gaacctgata ccgagggata tgctatcact gaccggggat    6960
ctgctcccat ctctatgggg ttcagggctt ctgatgttga aactgcagaa ggaggggaga    7020
tccacgagct cctgagactc caatccgagg gcaacaactt tccgaagctt gggaaaaactc    7080
tcaatgttcc tccgccccg gaccccgta gggccagcac ttccgggaca cccattaaaa    7140
agggcacaga cgcgagatta gcctcatttg gaacggagat cgcgtcttta ttgacaggtg    7200
gtgcaaccca atgtgctcga aagtcaccct cggaaccatc agggccaggt gcacctgcgg    7260
ggaatgtccc cgagtgtgtg agcaatgccg cactgataca ggagtggaca cccgaatctg    7320
gtaccacaat ctccccgaga tcccagaata atgaagaagg gggagactat tatgatgatg    7380
agctgttctc tgatgtccaa gatattaaaa cagccttcgc caaaatacac gaggataatc    7440
agaagatata ctccaagcta gaatcactgc tgttattgaa gggagaagtt gagtcaatta    7500
agaagcagat caacaggcaa aatatcagca tatccaccct ggaaggacac ctctcaagca    7560
tcatgatcgc cattcctgga cttgggaagg atcccaacga ccccactgca gatgtcgaaa    7620
tcaatcccga cttgaaaccc atcataggca gagattcagg ccgagcactg gccgaagttc    7680
tcaagaaacc cgttgccagc cgacaactcc aaggaatgac aaatggacgg accagttcca    7740
gaggacagct gctgaaggaa tttcagctaa agccgatcgg gaaaaagatg agctcagccg    7800
tcgggttttgt tcctgacacc ggccctgcat cacgcagtgt aatccgctcc attataaaat    7860
ccagccggct agaggaggat cggaagcgtt acctgatgac tctccttgat gatatcaaag    7920
gagccaatga tcttgccaag ttccaccaga tgctgatgaa gataataatg aagtagctac    7980
agctcaactt acctgccaac cccatgccag tcgacccacc tagtacaacc taaatccatt    8040
ataaaaaact taggagcaaa gtgattgcct ccaaggtcc acaatgacag agacctacga    8100
cttcgacaag tcggcatggg acatcaaagg gtcgatcgct ccgatacaac ccaccaccta    8160
cagtggggc aggctggtgc cccaggtcag agtcatagat cctggtctag gcgacaggaa    8220
ggatgaatgc tttatgtaca tgtttctgct ggggggttgtt gaggacacgc attccctagg    8280
gcctccaatc gggcgagcat ttgggttcct gcccttaggt gttggcagat ccacagcaaa    8340
gccccgaaaaa ctcctcaaag aggccactga gcttgacata gttgttagac gtacagcagg    8400
gctcaatgaa aaactggtgt tctacaacaa cacccacta actctcctca caccttggag    8460
aaaggtccta acaacaggga gtgtcttcaa cgcaaaccaa gtgtgcaatg cggttaatct    8520
gataccgctc gatacccgc agaggttccg tgttgttat atgagcatca cccgtctttc    8580
ggataacggg tattacaccg ttcctagaag aatgctggaa ttcagatcgg tcaatgcagt    8640
ggccttcaac ctgctggtga cccttaggat tgacaaggcg ataggccctg ggaagatcat    8700
cgacaataca gagcaacttc ctgaggcaac atttatggtc cacatcggga acttcaggag    8760
aaagaagagt gaagtctact ctgccgatta ttgcaaaatg aaaatcgaaa agatgggcct    8820
ggttttgca cttggtggga taggggcac cagtcttcac attagaagca caggcaaaat    8880
gagcagact ctccatgcac aactcgggtt caagaagacc ttatgttacc cgctgatga    8940
tatcaatgaa gaccttaatc gattactctg gaggagcaga tgcaagatag taagaatcca    9000
ggcagttttg cagccatcag ttcctcaaga attccgcatt tacgacgacg tgatcataaa    9060
tgatgaccaa ggactattca aagttctgta gaccgtagtg cccagcaatg cccgaaaacg    9120
acccccctca caatgacagc agaaggccc ggacaaaaaa gcccctccg aaagactcca    9180
cggaccaagc gagaggccag ccagcagccg acggcaagcg cgaacaccag gcggcccag    9240
cacagaacag ccctgacaca aggccaccac cagccacccc aatctgcatc ctcctcgtgg    9300
gaccccgag gaccaacccc caaggctgcc cccgatccaa accaccaacc gcatcccac    9360
cacccccggg aaagaaaccc ccagcaattg gaaggcccct ccccctcttc ctcaacacaa    9420
gaactccaca accgaacgc acaagcgacc gaggtgacca accgcaggc atccgactcc    9480
ctagacagat cctctctccc cggcaaacta aacaaaactt agggccaagg aacatacaca    9540
cccaacagaa cccagacccc ggccacggc ccgcgcccc caaccccga caaccagagg    9600
gagccccaa ccaatcccgc cggctcccc ggtgcccaca gcagggaca ccaacccccg    9660
aacagaccca gcacccaacc atcgacaatc caagacgggg gggcccccc aaaaaaaggc    9720
ccccagggc cgacagccag caccgcgagg aagcccaccc acccccacaa ccgaccacgg    9780
aaccaaacca gaaccagac cacccctgggc caccagctcc cagactcggc catcaccccg    9840
cagaaaggaa aggccacaac ccgcgcaccc cagcccgat ccggcgggga gccacccaac    9900
ccgaaccagc acccaagagc gatccccgaa ggaccccga accgcaaagg acatcagtat    9960
cccacagcct ctccaagtcc cccggtctcc tcctcttctc gaagggacca aaagatcaat    10020
ccaccacacc cgacgacact caactcccca ccctaaaagg agacaccggg aatcccagaa    10080
tcaagactca tccaatgtcc atcatgggtc tcaaggtgaa cgtctctgcc atattcatgg    10140
cagtactgtt aactctccaa acacccaccg gtcaaatcca ttggggcaat ctctctaaga    10200
tagggtggt aggaatagga agtgcaagct acaaagttat gactcgttcc agccatcaat    10260
cattagtcat aaaaattaatg cccaatataa ctctcctcaa taactgcacg agggtagaga    10320
ttgcagaata caggagacta ctgagaacag ttttggaacc aattagagat gcacttaatg    10380
```

```
caatgaccca gaatataaga ccggttcaga gtgtagcttc aagtaggaga cacaagagat   10440
ttgcgggagt agtcctggca ggtgcggccc taggcgttgc cacagctgct cagataacag   10500
ccggcattgc acttccaccag tccatgctga actctcaagc catcgacaat ctgagagcga   10560
gcctggaaac tactaatcag gcaattgaga caatcagaca agcagggcag gagatgatat   10620
tggctgttca gggtgtccaa gactacatca ataatgagct gataccgtct atgaaccaac   10680
tatcttgtga tttaatcggc cagaagctcg ggctcaaatt gctcagatac tatacagaaa   10740
tcctgtcatt atttggcccc agtttacggg accccatatc tgcggagata tctatccagg   10800
ctttgagcta tgcgcttgga ggagacatca ataaggtgtt agaaaagctc ggatacagtg   10860
gaggtgattt actgggcatc ttagagagcg gaggaataaa ggcccggata actcacgtcg   10920
acacagagtc ctacttcatt gtcctcagta tagcctatcc gacgctgtcc gagattaagg   10980
gggtgattgt ccaccggcta gagggggtct cgtacaacat aggctctcaa gagtggtata   11040
ccactgtgcc caagtatgtt gcaacccaag ggtaccttat ctcgaatttt gatgagtcat   11100
cgtgtacttt catgccagag gggactgtgt gcagccaaaa tgccttgtac ccgatgagtc   11160
ctctgctcca agaatgcctc cgggggtaca ccaagtcctg tgctcgtaca ctcgtatccg   11220
ggtcttttgg gaaccggttc attttatcac aagggaacct aatagccaat tgtgcatcaa   11280
tcctttgcaa gtgttacaca acaggaacga tcattaatca agaccctgac aagatcctaa   11340
catacattgc tgccgatcac tgcccggtag tcgaggtgaa cggcgtgacc atccaagtcg   11400
ggagcaggag gtatccagac gctgtgtact tgcacagaat tgacctcggt cctcccatat   11460
cattggagag gttggacgta gggacaaatc tggggaatgc aattgctaag ttggaggatg   11520
ccaaggaatt gttggagtca tcggaccaga tattgaggag tatgaaaggt ttatcgagca   11580
ctagcatagt ctacatcctg attgcagtgt gtcttggagg gttgatagg atccccgctt   11640
taatatgttg ctgcagggg cgtttgtaaca aaaagggaga acaagttggt atgtcaagac   11700
caggcctaaa gcctgatctt acgggaacat caaaatccta tgtaaggtcg ctctgatcct   11760
ctacaactct tgaaacacaa atgtcccaca agtctcctct tcgtcatcaa gcaaccaccg   11820
cacccagcat caagcccacc tgaaattatc tccggcttcc ctctggccga acaatatcgg   11880
tagttaatta aaacttaggg tgcaagatca tcgataagtc caccacaacg agaccggata   11940
aatgccttct acaaagataa ccccccatccc aagggaagta ggatagtcat taacagaaaa   12000
catcttatga ttgatagacc ttatgttttg ctggctgttc tgtttgtcat gtttctgagc   12060
ttgatcgggt tgctagccat tgcaggaatt cgacttcatc gggcagccat ctacaccgca   12120
gagatccata aaagcctcag caccaatcta gatgtaacta actcaatcga gcatcaggtc   12180
aaggacgtgc tgacaccact cttcaaaatc atcggtgatg aagtgggcct gaggacacct   12240
cagagattca ctgacctagt gaaattaatc tctgacaaga ttaaaattcct taatccggat   12300
agggagtacg acttcagaga tctcacttgg tgtatcaacc cgccagagag aatcaaattg   12360
gattatgatc aatactgtgc agatgtggct gctgaagagc tcatgaatgc attggtgaac   12420
tcaactctac tggagaccag aacaaccaat cagttcctag ctgtctcaaa gggaaactgc   12480
tcagggccca ctacaatcag aggtcaattc tcaaacatgt cgctgtccct gttagacttg   12540
tatttaggtc gaggttacaa tgtgtcatct atagtcacta tgacatccca gggaatgtat   12600
gggggaactt acctagtgga aaagcctaat ctgagcagca aaaggtcaga gttgtcacaa   12660
ctgagcatgt accgagtgtt tgaagtaggt gttatcagaa atccgggttt ggggctccg   12720
gtgttccata tgacaaacta tcttgagcaa ccagtcagta atgatctcag caactgtatg   12780
gtggctttgg gggagctcaa actcgcagcc ctttgtcacg gggaagattc tatcacaatt   12840
ccctatcagg gatcagggaa aggtgtcagc ttccagctcg tcaagctagg tgtctggaaa   12900
tccccaacc atcaatc ctgggtcccc ttatcaacgg atgtcacgg atagacagg   12960
ctttacctct catctcacag aggtgttatc gctgacaacc aagcaaaatg gctgtcccg   13020
acaacacgaa cagatgacaa gttgcgaatg gagacatgct tccaacaggc gtgtaagggt   13080
aaaatccaag cactctgcga gaatcccgag tgggcaccat tgaaggataa caggattcct   13140
tcatacgggg tcttgtctgt tgatctgagt ctgacagttg agcttaaaat caaaattgct   13200
tcgggattcg ggccattgat cacacacggt tcagggatgg acctatacaa atccaaccac   13260
aacaatgtgt attggctgac tatcccgcca atgaagaacc tagccttagg tgtaatcaac   13320
acattggagt ggatacccga gattcaaggtt agtcccctacc tcttcactgt cccaattaag   13380
gaagcaggcg aagactgcca tgccccaaca tacctacctg cggaggtgga tggtgatgtc   13440
aaactcagtt ccaatctggt gattctacct ggtcaagatc tccaatatgt tttggcaacc   13500
tacgatactt ccaggttga acatgctgtg gtttattacg tttacagccc aagccgctca   13560
ttttcttact tttatccttt taggttgcct ataaggggg tccccatcga attcaagtg   13620
gaatgcttca catgggacca aaaactctgg tgccgtcact tctgtgtgct tgcggactca   13680
gaatctggtg gacatatcac tcactctggg atggtgggca tgggagtcag ctgcacagtc   13740
acccgggaag atgaaccaa tcgcagatag ggctgctagt gaaccaatca catgatgtca   13800
cccagacatc aggcataccc actagtgtga aatagacatc agaattaaga aaaacgtagg   13860
gtccaagtgg ttccccgtta tggactcgct atctgtcaac cagatcttat accctgaagt   13920
tcacctagat agcccgatag ttaccaataa gatagtagcc atcctggagt atgctcgagt   13980
ccctcacgct tacagcctgg aggacccgtac actgtgtcag aacatcaagc accgcctaaa   14040
aaacggattt tccaaccaaa tgattataaa caatgtggaa gttgggaatg tcatcaagtc   14100
caagcttagg agttatccgg cccactctca tattccatat ccaaattgta atcaggattt   14160
atttaacata gaagacaaag agtcaacgag gaagatccgt aaagggaa   14220
ttcgctgtac tccaaagtca gtgataaggt tttccaatgc ttaagggaca ctaactcacg   14280
gcttggccta ggctccgaat tgagggagga catcaaggag aaagttatta acttgggagt   14340
ttacatgcac agctcccagt ggtttgagcc ctttctgttt tggtttacag tcaagactga   14400
gatgaggtca gtgattaaat cacaaaccca tacttgccat aggaaggagac acacacctgt   14460
attcttcact ggtagttcag ttgagttgct aatctctcgt gaccttgttg ctataatcag   14520
taaagagtct caacatgtat attacctgac attgaactg gttttgatgt attgtgatgt   14580
catagagggg aggttaatga cagagaccgc tatgactatt gatgctaggt atacagagct   14640
tctaggaaga gtcagataca tgtggaaact gatagatggt ttcttccctg cactcggaa   14700
tccaacttat caaattgtag ccatgctgga gcctctttca cttgcttacc tgcagctgag   14760
ggatataaca gtagaactca gaggtgcttt ccttaaccac tgctttactg aaatacatga   14820
tgttcttgac caaaacgggg tttctgatga aggtactat catgagttaa ctgaagctct   14880
agattacatt ttcataactg atgacataca tctgacaggg gagattttct cattttttcag   14940
aagtttcggc cacccagac ttgaagcagt aacggctgct gaaaatgtta ggaaatacat   15000
gaatcagcct aaagtcattg tgtatgagac tctgatgaaa ggtcatgcca tattttgtgg   15060
aatcataatc aacggctatc gtgacaggca cggaggcagt tggccaccgc tgaccctccc   15120
```

```
cctgcatgct gcagacacaa tccggaatgc tcaagcttca ggtgaagggt taacacatga    15180
gcagtgcgtt gataactgga aatcttttgc tggagtgaaa tttggctgct ttatgcctct    15240
tagcctggat agtgatctga caatgtacct aaaggacaag gcacttgctg ctctccaaag    15300
ggaatgggat tcagtttacc cgaaagagtt cctgcgttac gaccctccca agggaaccgg    15360
gtcacggagg cttgtagatg ttttccttaa tgattcgagc tttgacccat atgatgtgat    15420
aatgtatgtt gtaagtggag cttaccttcca tgaccctgag ttcaacctgt cttacagcct    15480
gaaagaaaag gagatcaagg aaacaggtag acttttttgct aaaatgactt acaaaatgag    15540
ggcatgccaa gtgattgctg aaaatctaat ctcaaacggg attggcaaat attttaagga    15600
caatgggatg gccaaggatg agcacgattt gactaaggca ctccacactc tagctgtctc    15660
aggagtcccc aaagatctca aagaaagtca caggggggg ccagtcttaa aaacctactc    15720
ccgaagccca gtccacacaa gtaccaggaa cgtgagagca gcaaaagggt ttataggggtt    15780
ccctcaagta attcggcagg accaagacac tgatcatccg gagaatatgg aagcttacga    15840
gacagtcagt gcatttatca cgactgatct caagaagtac tgccttaatt ggagatatga    15900
gaccatcagc ttgtttgcac agaggctaaa tgagatttac ggattgccct cattttttcca    15960
gtggctgcat aagaggcttg agacctctgt cctgtatgta agtgaccctc attgccccc    16020
cgaccttgac gcccatatcc cgttatataa agtcccaat gatcaaatct tcattaagta    16080
ccctatggga ggtatagaag ggtattgtca gaagctgtgg accatcagca ccattcccta    16140
tctatacctg gctgcttatg agagcggagt aaggattgct tcgttagtgc aaggggacaa    16200
tcagaccata gccgtaacaa aaagggtacc cagcacatgg ccctacaacc ttaagaaacg    16260
ggaagctgct agagtaacta gagattactt tgtaattctt aggcaaaggc tacatgatat    16320
tggccatcac ctcaaggcaa atgagacaat tgtttcatca cattttttg tctattcaaa    16380
aggaatatat tatgatgggc tacttgtgtc ccaatcactc aagagcatcg caagatgtgt    16440
attctggtca gagactatag ttgatgaaac aagggcagca tgcagtaata ttgctacaac    16500
aatggctaaa agcatcgaga gaggttatga ccgttacctt gcatattccc tgaacgtcct    16560
aaaagtgata cagcaaattc tgatctctct tggcttcaca atcaattcaa ccatgacccg    16620
ggatgtagtc ataccctcc tcacaaacaa cgacctctta ataaggatgg cactgttgcc    16680
cgctcctatt gggggggatga attatctgaa tatgagcagg ctgtttgtca gaaacatcgg    16740
tgatccagta acatcatcaa ttgctgatct caagagaatg attctcgcct cactaatgcc    16800
tgaagagacc ctccatcagg taatgacaca acaaccgggg gactcttcat tcctagactg    16860
ggctagcgac ccttactcag caaatcttgt atgtgtccaa agcatcacta gactcctcaa    16920
gaacataact gcaaggtttg tcctgatcca tagtccaaac ccaatgttaa aaggattatt    16980
ccatgatgac agtaaagaag aggacgaggg actggcggca ttcctcatgg acaggcatat    17040
tatagtacct agggcagctc atgaaatcct ggatcatagt gtcacagggg caagagagtc    17100
tattgcaggc atgctggata ccacaaaagg cttgattcga gccagcatga ggaaggggg    17160
tttaacctct cgagtgataa ccagattgtc caattatgac tatgaacaat tcagagcagg    17220
gatggtgcta ttgacaggaa gaaagagaaa tgtcctcatt gacaaagagt catgttcagt    17280
gcagctggcg agagctctaa gaagccatat gtgggcgagg ctagctcgag gacggccctat    17340
ttacggcctt gaggtccctg atgtactaga atctatgcga ggccacccta ttcggcgtca    17400
tgagacatgt gtcatctgcg agtgtggatc agtcaactac ggatggttt ttgtccccctc    17460
gggttgccaa ctggatgata ttgacaagga acatcatcc ttgagagtcc catatattgg    17520
ttctaccact gatgagagaa cagacatgaa gcttgccttc gtaagagccc caagtcgatc    17580
cttgcgatct gctgttagaa tagcaacagt gtactcatgg gcttacgtg atgatgatag    17640
ctcttggaac gaagccttgggt tgttggctag gcaaaggggcc aatgtgagcc tggaggagct    17700
aagggtgatc actcccatct caacttcgac taatttagcg cataggttga gggatcgtag    17760
cactcaagtg aaatactcag gtacatccct tgtccgagtg gcgaggtata ccacaatctc    17820
caacgacaat ctctcatttg tcatatcaga taagaaggtt gatactaact ttatataccga    17880
acaaggaatg cttctagggt tgggtgtttt agaaacattg tttcgactcg agaaagatac    17940
cggatcatct aacacggtat tacatcttca cgtcgaaaca gattgttgcg tgatcccgat    18000
gatagatcat cccaggatac ccagctcccg caagctagag ctgagggcag agctatgtac    18060
caacccattg atatatgata atgcacctt aattgacaga gatgcaacaa ggctatacac    18120
ccagagccat aggaggcacc ttgtggaatt tgttacatga tccacacccc aactatatca    18180
catttagct aagtccacag cactatctat gattgacctg gtaacaaaat ttgagaagga    18240
ccatatgaat gaaatttcag ctctccatagg ggatgacgat atcaatagtt tcataactga    18300
gtttctgctc atagagccaa gattattcac tatctacttg ggccagtgtg cggccatcaa    18360
ttgggcattt gatgtacatt atcatagacc atcagggaaa tatcagatgg gtgagctgtt    18420
gtcatcgttc ctttctagaa tgagcaaagg agtgtttaag gtgcttgtca atgctcaag    18480
ccacccaaag atctacaaga aattctggca ttgtgggtatt atagagccta tccatggtcc    18540
ttcacttgat gctcaaaact tgcacacaac tgtgtgcaac atggtttaca catgctatat    18600
gacctacctc gacctgttgt tgaatgaaga gttagaagag ttcacatttc tcttgtgtga    18660
aagcgacgag gatgtagtac cggacagatt cgacaacatc caggcaaaac acttatgtgt    18720
tctggcagat ttgtactgtc aaccaggggac ctgcccacca attcgaggtc taagaccggt    18780
agagaaatgt gcagttctaa ccgaccatat caaggcagag gctatgttat ctccagcagg    18840
atcttcgtgg aacataaatc caattattgt agaccattac tcatgctccc tgacttatct    18900
ccggcgagga tcgatcaaac agataagatt gagagttgat ccaggattca ttttcgacgc    18960
cctcgctgag gtaaatgtca gtcagccaaa gatcggcagc aacaacatct caaatatgag    19020
catcaaggct ttcagacccc cacacgatga tgttgcaaaa ttgctcaaag atatcaacac    19080
aagcaagcac aatcttccca tttcaggggg caatctcgcc aattatgaaa tccatgcttt    19140
ccgcagaatc gggttgaact catctgcttg ctacaaagct gttgagatat caacattaat    19200
taggagtcag cttgagccag gggagggacgg cttgttcttg ggtgaggcgt cgggttctat    19260
gttgatcact tataaggaga tacttaaact aaacaagtgc ttctataata gtgggggtttc    19320
cgccaattct agatcggtc aaagggaatt agcaccctat ccctccgaag ttggccttgt    19380
cgaacacaga atgggagtag gtaatattgt caaagtgctc tttaacggga ggcccgaagt    19440
cacgtgggta ggcagtgtag attgcttcaa tttcatagtt agtaatatcc ctacctag    19500
tgtgggggttt atccattcag atatagagac cttgcctgac aaagatacta tagagaagct    19560
agaggaattg gcagccatct tatcgatggc tctgctcctg ggcaaaaatag gatcaatact    19620
ggtgattaag cttatgcctt tcagctggga ttttgttcag ggatttataa gttatggatgg    19680
gtctcattat agagaagtga accttgtata ccctagatac agcaacttca tatctactga    19740
atcttatttg gttatgacag atcctcaaggc taaccggcta atgaatcctg aaaagattaa    19800
gcagcagata attgaatcat ctgtgaggac ttcacctgga cttataggtc acatcctatc    19860
```

```
cattaagcaa ctaagctgca tacaagcaat tgtgggagac gcagttagta gaggtgatat  19920
caatcctact ctgaaaaaac ttacacctat agagcaggtg ctgatcaatt gcgggttggc  19980
aattaacgga cctaagctgt gcaaagaatt gatccaccat gatgttgcct cagggcaaga  20040
tggattgctt aattctatac tcatcctcta cagggagttg gcaagattca aagacaacca  20100
aagaagtcaa caagggatgt tccacgccta ccccgtattg gtaagtagca ggcaacgaga  20160
acttatatct aggatcaccc gcaaattttg ggggcacatt cttctttact ccgggaacaa  20220
aaagttgata aataagttta tccagaatct caagtccggc tatctgatac tagacttaca  20280
ccagaatatc ttcgttaaga atctatccaa gtcagagaaa cagattatta tgacgggggg  20340
tttgaaacgt gagtgggttt ttaaggtaac agtcaaggag accaaagaat ggtataagtt  20400
agtcggatac agtgccctga ttaaggacta attggttgaa ctccggaacc ctaatcctgc  20460
cctaggtggt taggcattat ttgcaatata ttaaagaaaa ctttgaaaat acgaagtttc  20520
tattcccagc tttgtctggt ggccggcata gtcccagcct cctcgctggc gctggctggg  20580
caacattccg aggggaccgt ccccacggta atggcgaatg ggacgcggcc gatccggctg  20640
ctaacaaagc ccgaaaggaa gctgagttgg ctgctggcgc tggctgggca ataactagca  20700
taaccccttg gggcctctaa acgggtcttg aggggttttt tgctgaaagg aggaactata  20760
tccggatgcg gccgcgcgct tggcgtaatc atggtcatag ctgtttcctg tgtgaaattg  20820
ttatccgctc acaattccac acaacatacg agccggaagc ataaagtgta aagcctgggg  20880
tgcctaatga gtgagctaac tcacattaat tgcgttgcgc tcactgcccg ctttccagtc  20940
gggaaacctg tcgtgccagc tgcattaatg aatcggccaa cgcgcgggga gaggcggttt  21000
gcgtattggg cgctcttccg cttcctcgct cactgactcg ctgcgctcgg tcgttcggct  21060
gcggcgagcg gtatcagctc actcaaaggc ggtaatacgg ttatccacag aatcagggga  21120
taacgcagga aagaacatgt gagcaaaagg ccagcaaaag gccaggaacc gtaaaaaggc  21180
cgcgttgctg gcgtttttcc ataggctccg cccccctgac gagcatcaca aaaatcgacg  21240
ctcaagtcag aggtggcgaa acccgacagg actataaaga taccaggcgt ttccccctgg  21300
aagctccctc gtgcgctctc ctgttccgac cctgccgctt accggatacc tgtccgcctt  21360
tctcccttcg ggaagcgtgg cgctttctca tagctcacgc tgtaggtatc tcagttcggt  21420
gtaggtcgtt cgctccaagc tgggctgtgt gcacgaaccc cccgttcagc ccgaccgctg  21480
cgccttatcc ggtaactatc gtcttgagtc caacccggta agacacgact tatcgccact  21540
ggcagcagcc actggtaaca ggattagcag agcgaggtat gtaggcggtg ctacagagtt  21600
cttgaagtgg tggcctaact acggctacac tagaaggaca gtatttggta tctgcgctct  21660
gctgaagcca gttaccttcg gaaaaagagt tggtagctct tgatccggca aacaaaccac  21720
cgctggtagc ggtggttttt ttgtttgcaa gcagcagatt acgcgcagaa aaaaaggatc  21780
tcaagaagat cctttgatct tttctacggg gtctgacgct cagtggaacg aaaactcacg  21840
ttaagggatt ttggtcatga gattatcaaa aaggatcttc acctagatcc ttttaaatta  21900
aaaatgaagt tttaaatcaa tctaaagtat atatgagtaa acttggtctg acagttacca  21960
atgcttaatc agtgaggcac ctatctcagc gatctgtcta tttcgttcat ccatagttgc  22020
ctgactcccc gtcgtgtaga taactacgat acgggagggc ttaccatctg gccccagtgc  22080
tgcaatgata ccgcgagacc cacgctcacc ggctccagat ttatcagcaa taaaccagcc  22140
agccggaagg gccgagcgca gaagtggtcc tgcaacttta tccgcctcca tccagtctat  22200
taattgttgc cgggaagcta gagtaagtag ttcgccagtt aatagtttgc gcaacgttgt  22260
tgccattgct acaggcatcg tggtgtcacg ctcgtcgttt ggtatggctt cattcagctc  22320
cggttcccaa cgatcaaggc gagttacatg atcccccatg ttgtgcaaaa aagcggttag  22380
ctccttcggt cctccgatcg ttgtcagaag taagttggcc gcagtgttat cactcatggt  22440
tatggcagca ctgcataatt ctcttactgt catgccatcc gtaagatgct tttctgtgac  22500
tggtgagtac tcaaccaagt cattctgaga atagtgtatg cggcgaccga gttgctcttg  22560
cccggcgtca atacgggata ataccgcgcc acatagcaga actttaaaag tgctcatcat  22620
tggaaaacgt tcttcggggc gaaaactctc aaggatctta ccgctgttga gatccagttc  22680
gatgtaaccc actcgtgcac ccaactgatc ttcagcatct tttactttca ccagcgtttc  22740
tgggtgagca aaaacaggaa ggcaaaatgc cgcaaaaaag ggaataaggg cgacacggaa  22800
atgttgaata ctcatactct tcctttttca atattattga agcatttatc agggttattg  22860
tctcatgagc ggatacatat ttgaatgtat ttagaaaaat aaacaaatag gggttccgcg  22920
cacatttccc cgaaaagtgc cacctg                                      22946

SEQ ID NO: 4            moltype = DNA  length = 22916
FEATURE                 Location/Qualifiers
misc_feature            1..22916
                        note = MV Wu S in position 3
source                  1..22916
                        mol_type = other DNA
                        organism = synthetic construct
SEQUENCE: 4
ggacgcgccc tgtagcggcg cattaagcgc ggcgggtgtg gtggttacgc gcagcgtgac  60
cgctacactt gccagcgccc tagcgcccgc tcctttcgct ttcttccctt cctttctcgc  120
cacgttcgcc ggctttcccc gtcaagctct aaatcggggg ctccctttag ggttccgatt  180
tagtgcttta cggcacctcg accccaaaaa acttgattag ggtgatggtt cacgtagtgg  240
gccatcgccc tgatagacgg tttttcgccc tttgacgttg gagtccacgt tctttaatag  300
tggactcttg ttccaaactg gaacaacact caaccctatc tcggtctatt cttttgattt  360
ataagggatt ttgccgattt cggcctattg gttaaaaaat gagctgattt aacaaaaatt  420
taacgcgaat tttaacaaaa tattaacgtt tacaatttcg cgccattcgc cattcaggct  480
gcgcaactgt tgggaagggc gatcggtgcg ggcctcttcg ctattacgcc agctggcgaa  540
agggggatgt gctgcaaggc gattaagttg ggtaacgcca gggttttccc agtcacgacg  600
ttgtaaaacg acggccagtg cgcgccgtta atacgactca ctatagggag acccaagctg  660
gctagctttg tttggtctga tgagtcccgt gaggacgaaa cccggcgtac cgggtcacca  720
aacaaagttg ggtaaggata gttcaatcaa tgatcatctt ctagtgcact taggattcaa  780
gatcctatta tcagggacaa gagcaggatt agggatatcc gagatggcca cactttaag  840
gagcttagca ttgttcaaaa gaaacaagga caaaccaccc attacatcag gatccggtgg  900
agccatcaga ggaatcaaac acattattat agtaccaatc cctggagatt cctcaattac  960
cactcgatcc agacttctgg accggttggt gaggttaatt ggaaacccgg atgtgagcgg  1020
gcccaaacta acaggggcac taataggtat attatcctta tttgtggagt ctccaggtca  1080
```

```
attgattcag aggatcaccg atgaccctga cgttagcata aggctgttag aggttgtcca    1140
gagtgaccag tcacaatctg gccttacctt cgcatcaaga ggtaccaaca tggaggatga    1200
ggcggaccaa tacttttcac atgatgatcc aattagtagt gatcaatcca ggttcggatg    1260
gttcgggaac aaggaaatct cagatattga agtgcaagac cctgagggat tcaacatgat    1320
tctgggtacc atcctagccc aaatttgggt cttgctcgca aaggcggtta cggcccccaga   1380
cacgcgcagct gattcggagc taagaaggtg gataaagtac acccaacaaa gaagggtagt   1440
tggtgaattt agattggaga gaaaatggtt ggatgtggtg aggaacagga ttgccgagga    1500
cctctcctta cgccgattca tggtcgtctct aatcctggat atcaagagaa cacccggaaa   1560
caaacccagg attgctgaaa tgatatgtga cattgataca tatatcgtag aggcaggatt    1620
agccagtttt atcctgacta ttaagttttgg gatagaaact atgtatcctg ctcttggact   1680
gcatgaattt gctggtgagt tatccacact tgagtccttg atgaaccttt accagcaaat    1740
gggggaaact gcaccctaca tggtaatcct ggagaactca attcagaaca agttcagtgc    1800
aggatcatac cctctgctct ggagctatgc catgggagta ggagtggaac ttgaaaactc    1860
catgggaggt ttgaactttg gccgatctta ctttgatccg gcatatttta gattagggca    1920
agagatggta aggaggtcag ctggaaaggt cagttccaca ttggcatctg aactcggtat    1980
cactgccgag gatgcaaggc ttgtttcaga gattgcaatg catactactg aggacaagat    2040
cagtagagcg gttggaccca gacaagccca agtatcattt ctacacgtg atcaaagtga    2100
gaatgagcta ccgagattgg ggggcaagga agataggagg gtcaaacaga gtcgaggaga    2160
agccagggag agctacagag aaaccggggcc cagcagagca agtgatgcga gagctgccca   2220
tcttccaacc ggcacacccc tagacattga cactgcaacg gagtccagcc aagatccgca    2280
ggacagtcga aggtcagctg acgccctgct taggctgcaa gccatggcag gaatctcgga    2340
agaacaaggc tcagacacgg acaccccctat agtgtacaat gacagaaatc ttctagacta    2400
ggtgcgagag gccgagggcc agaacaacat ccgcctacca tccatcattg ttataaaaaa    2460
cttaggaacc aggtccacac agccgccagc ccatcaacca tccactccca cgattggagc    2520
caatggcaga agagcaggca cgccatgtca aaaacggact ggaatgcatc cgggctctca    2580
aggccgagcc catcggctca ctggcatcg aggaagctat ggcagcatgg tcagaaatat    2640
cagacaaccc aggacaggag cgagccacct gcagggaaga gaaggcaggc agttcgggtc    2700
tcagcaaacc atgcctctca gcaattggat caactgaagg cggtgcacct cgcatccgcg    2760
gtcagggacc tggagagagc gatgacgacg ctgaaacttt gggaatcccc caagaaatc    2820
tccaggcatc aagcactggg ttacagtgtt attacgttta tgatcacagc ggtgaagcgg    2880
ttaagggaat ccaagatgct gactctatca tggttcaatc aggccttgat ggtgatagca    2940
ccctctcagg aggagacaat gaatctgaaa acagcgatgt ggatattggc gaacctgata    3000
ccgagggata tgctatcact gaccgggat ctgctcccat ctctatgggg ttcagggctt    3060
ctgatgtga aactgcagaa ggaggggaa tccacgagct cctgagactc caatccagag    3120
gcaacaactt tccgaagctt gggaaaactc tcaatgttcc tccgccccg gaccccggta    3180
gggccagcac ttccgggaca cccattaaaa agggcacaga cgcgagatta gcctcatttg    3240
gaacggagat cgcgtcttta ttgacaggtg gtgcaaccca atgtgctcga agtcaccct    3300
cggaaccatc agggccaggt gcacctgcgg ggaatgtccc cgagtgtgtg agcaatgccg    3360
cactgataca ggagtggaca cccgaatctg gtaccacaat ctccccgaga tcccagaata   3420
atgaagaagg gggagactat tatgatgatg agctgttctc tgatgtccaa gatattaaaa    3480
cagccttggc caaaatacac gaggataatc agaagataat ctccaagcta gaatcactgc    3540
tgttattgaa gggagaagtt gagtcaatta agaagcagat caacaggcaa aatatcagca    3600
tatccaccct ggaaggacac ctctcaagca tcatgatgac cattcctgga cttgggaagg    3660
atcccaacga ccccactgca gatgtcgaaa tcaatcccga cttgaaaccc atcataggca    3720
gagattcagg ccgagcactg gccgaagttc tcaagaaacc cgttgccagc cgacaactcc    3780
aaggaatgac aaatggacgg accagttcca gaggacagct gctgaaggaa tttcagctaa    3840
agccgatcgg gaaaaagatg agctcagccg tcgggttttgt tcctgacaga ggccctgcat   3900
cacgcagtgt aatccgctcc attataaat ccagccggct agaggaggat cggaagcgtt    3960
acctgatgac tctccttgat gatatcaaag gagccaatga tcttgccaag ttccaccaga    4020
tgctgatgaa gataataatg aagtagctac agctcaactt acctgccaac ccatgccaag    4080
tcgatcatcc atcattgtta taaaaaactt aggaaccagg tccacacaga tgatacgcg    4140
tacgccacca tgttcgtgtt tctggtgctg ctgcctctgg tgagctccca gtgcgtgaac    4200
ctgaccacaa ggaccaggct gccccctgcc tataccaatt ccttcacacg gggcgtgtac    4260
tatcccgaca aggtgttccg gagcagcgtg ctgcactcca cacaggatct gtttctgcct    4320
ttcttttcta acgtgacctg gttccacgcc atccacgtga gcggcaccaa tggcacaaag    4380
cggttcgaca atccagtgct gccctttaac gatggcgtgt acttcgcctc caccgagaag    4440
tctaacatca tcagaggctg gatctttggc accacactgg acagcaagac acagtccctg    4500
ctgatcgtga caatgccac caacgtggtc atcaaggtgt gcgagttcca gttttgtaat    4560
gatccattcc tgggcgtgta ctatcacaag aacaataagt ctggatgga gagcgagttt    4620
cgcgtgtatt cctctgccaa caattgcaca tttgagtacg tgtcccagcc cttcctgatg    4680
gacctggagg gcaagcaggg caatttcaag aacctgaggg agttcgtgtt taagaatatc    4740
gatggctact tcaaaatcta ctccaagcac accccaatca acctggtgcg cgacctgcca    4800
cagggcttct ctgccctgga gccactggtg gatctgccca tcggcatcaa catcacccgg    4860
tttcagacac tgctggccct gcacagaagc tacctgaccc caggcgacag ctccagcgga    4920
tggaccgcag gagcagcagc ctactatgtg ggctatctgc agcccaggac cttcctgctg    4980
aagtacaacg agaatggcac catcacagac gccgtggatt gcgccctgga tccctgtct    5040
gagaccaagt gtacactgaa gagctttacc gtggagaagg gcatctatca gacaagcaat    5100
ttcagggtgc agcctaccga gtccatcgtg cgctttccca atatcacaaa cctgtgccct    5160
tttggcgagg tgttcaacgc aacccgcttc gccagcgtgt acgcctggaa taggaagcgc    5220
atctccaact gcgtggccga ctattctgtg ctgtacaaca gcgcctcctt ctctaccttt    5280
aagtgctatg gcgtggagccc cacaaagctg aatgacctgt gctttaccaa cgtgtacgcc    5340
gattccttcg tgatcagggg cgacgaggtg cgccagatcg caccaggaca gacaggcaag    5400
atcgcagact acaattataa gctgcctgac gatttcaccg gctgcgtgat cgcctggaac    5460
tctaacaatc tggatagcaa agtgggcggc aactacaatt atctgtaccg gctgtttaga    5520
aagtctaatc tgaagccatt cgagagggac atctccacac aaatctacca ggccggctct    5580
accccctgca atggcgtgga gggctttaac tgttatttcc ctctgcagag ctacggcttc    5640
cagccaacaa acggcgtggg ctatcagccc taccgcgtgg tggtgctgtc ttttgagctg    5700
ctgcacgcac ctgcaacagt gtgcggacca aagaagagca ccaatctggt gaagaacaag    5760
tgcgtgaact tcaacttcaa cggactgacc ggaacaggcg tgctgaccga gtccaacaag    5820
```

-continued

```
aagttcctgc cttttcagca gttcggcagg gacatcgcag ataccacaga cgccgtgcgc   5880
gaccctcaga ccctggagat cctggacatc acaccatgct ccttcggcgg cgtgtctgtg   5940
atcacaccag gcaccaatac aagcaaccag gtggccgtgc tgtatcagga cgtgaattgt   6000
accgaggtgc cagtggcaat ccacgcagat cagctgaccc ctacatggcg ggtgtactct   6060
accggcagca acgtgttcca gacaagagcc ggatgcctga tcggagcaga gcacgtgaac   6120
aatagctatg agtgcgacat ccctatcggc gccggcatct gtgcctccta ccagacccag   6180
acaaactccc caaggagagc acggtctgtg gccagccagt ccatcatcgc ctataccatg   6240
agcctgggcg ccgagaattc cgtggcctac tccaacaatt ctatcgccat ccctaccaac   6300
ttcacaatct ccgtgaccac agagatcctg ccagtgacca tgaccaagac atccgtggac   6360
tgcacaatgt atatctgtgg cgattccacc gagtgctcta acctgctgct gcagtacggc   6420
tcttttttgta cccagctgaa tagagccctg acaggcatcg ccgtggagca ggacaagaac   6480
acacaggagg tgttcgccca ggtgaagcaa atctacaaga ccccacccat caaggacttt   6540
ggcggcttca acttcagcca gatcctgccc gatcctagca agccatccaa gcggtctttt   6600
atcgaggacc tgctgttcaa caaggtgacc ctggccgatg ccggcttcat caagcagtat   6660
ggcgattgcc tgggcgacat cgccgccaga gacctgatct gtgcccagaa gtttaatggc   6720
ctgaccgtgc tgcctccact gctgacagat gagatgatcg cccagtacac atctgccctg   6780
ctggccggaa ccatcacaag cggatggacc ttcggcgcag gagccgccct gcagatcccc   6840
tttgccatgc agatggccta tcggttcaac ggcatcggcg tgacccagaa tgtgctgtac   6900
gagaaccaga agctgatcgc caatcagttt aactccgcca tcggcaagat ccaggactct   6960
ctgagctcca cagccagcgc cctgggcaag ctgcaggatg tggtgaatca gaacgcccag   7020
gccctgaata ccctggtgaa gcagctgtct agcaacttcg cgccatctc ctctgtgctg   7080
aatgacatcc tgagccggct ggacaaggtg gaggcagagg tcagatcga ccggctgatc   7140
acaggcagac tgcagtccct gcagacctac gtgacacagc agctgatcag ggcagcagag   7200
atcagggcct ctgccaatct ggccgccacc aagatgagcg agtgcgtgct gggccagtcc   7260
aagagagtgg actttgtgg caagggctat cacctgatga gcttcccaca gtccgcccct   7320
cacggagtgg tgttctgca cgtgacctac gtgccagccc aggagaagaa cttcaccaca   7380
gcaccagcaa tctgccacga tgcaaggca cactttccta ggagggcgt gttcgtgagc   7440
aacggcaccc actggtttgt gacacagcgc aattttctacg agccacagat catcaccaca   7500
gacaatacat tcgtgtccgg caactgtgac gtggtcatcg gcatcgtgaa caataccgtg   7560
tatgatcctc tgcagccaga gctggactct tttaaggagg tggataa gtacttcaag   7620
aatcacacca gccccgacgt ggatctgggc gacatctctg gcatcaatgc cagccgtggtg   7680
aacatccaga aggagatcga caggctgaac gaggtggcca agaatctgaa cgagtccctg   7740
atcgatctgc aggagctggg caagtatgag cagtacatca agtgggcctg gtatatctgg   7800
ctgggcttca tcgccggcct gatcgccatc gtgatggtga tcatgctgct gtgctgtatg   7860
acaagctgct gttcctgcct gaagggctgc tgttcttgtg gcagctgctg taagtttgat   7920
gaggacgata gcgagcctgt gctgaagggc gtgaagctgc actacacctg atagctagcg   7980
atcgccacc tagtacaacc taaatccatt ataaaaaact taggagcaaa gtgattgcct   8040
cccaaggtcc acaatgacag agacctacga cttcgacaag tcggcatggg acatcaaagg   8100
gtcgatcgct ccgatacaac ccaccaccta cagtgatggc aggctggtgc cccaggtcag   8160
agtcatagat cctggtctag gcgacaggaa ggatgaatga tttatgtaca tgtttctgct   8220
ggggggttgtt gaggacagcg attccctagg gcctccaatc gggcgagcat ttgggttcct   8280
gcccttaggt gttggcagat ccacagcaaa gcccgaaaaa ctcctcaaag aggccactga   8340
gcttgacata gttgttagac gacagcagg gctcaatgaa aaactggtgt tctacaacaa   8400
caccccacta actctcctca caccttggag aaaggtccta acaacaggga gtgtcttcaa   8460
cgcaaaccaa gtgtgcaatg cggttaatct gataccgctc gataccccgc agaggttccg   8520
tgttgtttat atgagcatca cccgtctttc ggataacggg tattcaccg ttcctagaag   8580
aatgctggaa ttcagatcgg tcaatgcagt ggccttcaac ctgctggtga ccccttaggat   8640
tgacaaggcg ataggccctg ggaagatcat cgacaataca gagcaacttc ctgaggcaac   8700
atttatggtc cacatcggga acttcaggag aaagaagagt gaagtctact ctgccgatta   8760
ttgcaaaatg aaaatcgaaa agatgggcct ggttttgca cttggtggga taggggcac   8820
cagtcttcac attagaagca caggcaaaat gagcaagact ctccatgcac aactcgggtt   8880
caagaagacc ttatgttacc cgctgatgga tatcaatgaa gaccttaatc gattactctg   8940
gaggagcaga tgcaagatag taagaatcca ggcagttttg cagccatcag ttcctcaaga   9000
attccgcatt tacgacgcg tgatcataaa tgatgaccaa ggactattca aagttctgta   9060
gaccgtagtg cccagcaatg cccgaaaacg accccctca caatgacagc cagaaggccc   9120
ggacaaaaaa gccccctccg aaagactcca cggaccaagc gagaggccag ccagcagccg   9180
acggcaagcg cgaacaccag gcggcccag cacagaacag ccctgacaca aggccaccac   9240
cagccacccc aatctgcatc ctcctcgtgg gaccccgag gaccaacccc caaggctgcc   9300
cccgatccaa accaccaacc gcatcccac caccccggg aaagaaaccc ccagcaattg   9360
gaaggcccct cccccctcttc ctcaacacaa gaactccaca accgaaccgc acaagcgacc   9420
gaggtgaccc aaccgcaggc atccgactcc ctagacagat cctctctccc cggcaaacta   9480
aacaaaactt agggccaagg aacatacaca cccaacagaa cccagacccc ggcccacggc   9540
gccgcgcccc caacccccga caaccagagg gagcccccaa ccaatcccgc cggctccccc   9600
ggtgcccaca ggcagggaca ccaaccccg aacagaccca gccccaacc atcgacaatc   9660
caagacgggg ggccccccc aaaaaaggc ccccagggc cgacagccag caccgcgagg   9720
aagcccaccc acccccaaca cgaccacggc aaccaaacca gaacccagac caccctgggc   9780
caccagctcc cagactcggc catcaccccg cagaaaggaa aggccacaac ccgcgcaccc   9840
cagccccgat ccggcggga gccaccaaac ccgaaccagc acccaagagc gatcccgaa   9900
ggaccccga accgcaaagg acatcagtat cccaagcct ctccaagtcc cccgtctcc   9960
tcctcttctc gaagggacca aaagatcaat ccaccacacc cgacgacact caactcccca  10020
ccctaaagg agacaccggg aatcccgaaa tcaagactca tccaatgtcc atcatgggtc  10080
tcaaggtgaa cgtctctgcc atattcatgg cagtactgtt aactctccaa acacccaccg  10140
gtcaaatcca ttggggcaat ctctctaaga taggggtggt aggaatagga agtgcaagct  10200
acaaagttat gactcgttcc agccatcaat cattagtcat aaaattaatg cccaatataa  10260
ctctcctcaa taactgcacg aggggtagaga ttgcagaata caggagacta ctgagaacag  10320
ttttggaacc aattagagat gcacttaatg caatgcccca gaatataaga ccggttcaga  10380
gtgtagcttc aagtaggaga cacaagagat ttgcgggagt agtcctggca ggtcgggccc  10440
taggcgttgc cacacagctgct cagataacag ccggcattgc acttcaccag tccatgctga  10500
actctcaagc catcgcacaat ctgagagcga gcctggaaac tactaatcag gcaattgaga  10560
```

```
caatcagaca agcagggcag gagatgatat tggctgttca gggtgtccaa gactacatca  10620
ataatgagct gataccgtct atgaaccaac tatcttgtga tttaatcggc cagaagctcg  10680
ggctcaaatt gctcagatac tatacagaaa tcctgtcatt atttggcccc agtttacggg  10740
accccatatc tgcggagata tctatccagg ctttgagcta tgcgcttgga ggagacatca  10800
ataaggtgtt agaaaagctc ggatacagtg gaggtgattt actgggcatc ttagagagcg  10860
gaggaataaa ggcccggata actcacgtcg acacagagtc ctacttcatt gtcctcagta  10920
tagcctatcc gacgctgtcc gagattaagg gggtgattgt ccaccggcta gaggggtct   10980
cgtacaacat aggctctcaa gagtggtata ccactgtgcc caagtatgtt gcaacccaag  11040
ggtaccttat ctcgaatttt gatgagtcat cgtgtacttt catgccagag gggactgtgt  11100
gcagccaaaa tgccttgtac ccgatgagtc ctctgctcca agaatgcctc cgggggtaca  11160
ccaagtcctg tgctcgtaca ctcgtatccg ggtctttggg aaccggttc  attttatcac  11220
aagggaacct aatagccaat tgtgcatcaa tcctttgcaa gtgttacaca acaggaacga  11280
tcattaatca agaccctgac aagatcctaa catacattgc tgccgatcac tgcccggtag  11340
tcgaggtgaa cggcgtgacc atccaagtcg ggagcaggag gtatccagac gctgtgtact  11400
tgcacagaat tgacctcggt cctcccatat cattggagag gttggacgta ggacaaaatc  11460
tggggaatgc aattgctaag ttggaggatg ccaaggaatt gttggagtca tcggaccaga  11520
tattgaggag tatgaaaggt ttatcgagca ctagcatagt ctacatcctg attgcagtgt  11580
gtcttggagg gttgataggg atccccgctt taatatgttc ctgcaggggg cgttgtaaca  11640
aaaagggaga acaagttggt atgtcaagac caggcctaaa gcctgatctt acgggaacat  11700
caaaatccta tgtaaggtcg ctctgatcct ctacaactct tgaaacacaa atgtcccaca  11760
agtctcctct tcgtcatcaa gcaaccaccg cacccagcat caagcccacc tgaaattatc  11820
tccggcttcc ctctgccga  aacaatatcgg tagttaatta aaacttaggg tgcaagatca  11880
tcgataatgt caccacaacg agaccggata aatgccttct acaaagataa ccccccatccc  11940
aagggaagta ggatagtcat taacagaaa  catcttatga ttgatagacc ttatgttttg  12000
ctggctgttc tgtttgtcat gtttctgagc ttgatcgggt tgctagccat tgcaggaatt  12060
cgacttcatc gggcagccat ctacaccgca gagatccata aaagcctcag caccaatcta  12120
gatgtaacta actcaatcga tcatcaggtc aaggacgtgc tgacaccact cttcaaaatc  12180
atcggtgatg aagtgggcct gaggacacct cagagattca ctgacctagt gaaattaatc  12240
tctgacaaga ttaaattcct taatccggat agggagtacg acttcagaga tctcacttgg  12300
tgtatcaacc cgcagagag  aatcaaattg gattatgatc aatactgtgc agatgtgcct  12360
gctgaagagc tcatgaatgc attggtgaac tcaactctac tggagaccag aacaaccaat  12420
cagttcctag ctgtctcaaa gggaaactgc tcagggccca ctacaatcag aggtcaattc  12480
tcaaacatgt cgctgtccct gttagacttg tatttaggtc gaggttacaa tgtgtcatct  12540
atagtcacta tgcatcccca gggaatgtat gggggaactt acctagtgga aaagcctaat  12600
ctgagcagca aaaggtcaga gttgtcacaa ctgagcatgt accgagtgtt tgaagtaggt  12660
gttatcagaa atccgggttt gggggctccg tgttccata  tgacaaacta tcttgagcaa  12720
ccagtcagta atgatctcag caactgtatg gtggctttgg gggagctcaa actcgcagcc  12780
ctttgtcacg gggaagattc tatcacaatt ccctatcagg gatcagggaa aggtgtcagc  12840
ttccagctcg tcaagctagg tgtctggaaa tccccaaccg acatgcaatc ctgggtcccc  12900
ttatcaacgg atgatccagt gatagacagg ctttacctct catctcacag aggtgttatc  12960
gctgacaacc aagcaaaatg ggctgtcccg acaacacgaa cagatgacaa gttgcgaatg  13020
gagacatgct tccaacaggc gtgtaagggt aaaatccaag cactctgcga gaatcccgag  13080
tgggcaccat tgaaggataa caggattcct tcatacggga tcttgtctgt tgatctgagt  13140
ctgacagttg agcttaaaat caaaattgct tcgggattcg ggccattgat cacacacggt  13200
tcagggatgg acctatacaa atccaaccac aacaatgtgt attggctgac tatcccgcca  13260
atgaagaacc tagccttagg tgtaatcaac acattggagt ggataccgag attcaaggtt  13320
agtcccctacc tcttcactgt cccaattaag gaagcaggcg aagactgcca tgccccaaca  13380
tacctacctg cggaggtgga tgatgatgtc aaactcagtt ccaatctggt gattctacct  13440
ggtcaagatc tccaatatgt tttggcaacc tacgatactt ccagggttga acatgctgtg  13500
gtttattacg tttacagccc aagccgctca ttttcttact tttatccttt taggttgcct  13560
ataaaggggt tccccatcga attacaagtg gaatgcttca catggggacca aaaactcttg  13620
tgccgtcact tctgtgtgct tgcggactca gaatctggtg gacatatcac tcactctggg  13680
atggtgggca tgggagtcag ctgcacagtc acccgggaag atggaaccaa tcgcagatag  13740
ggctgctagt gaaccaatca catgatgtca cccagacatc aggcatatccc actagtgtga  13800
aatagacatc agaattaaga aaaacgtagg gtccaagtgg ttccccgtta tggactcgct  13860
atctgtcaac cagatcttat accctgaagt tcacctagat agcccgatag ttaccaataa  13920
gatagtagcc atcctggagt atgctcgagt ccctcacgct tacagcctgg aggccctac   13980
actgtgtcag aacatcaagc accgcctaaa aaacggattt tccaaccaaa tgattataaa  14040
caatgtggaa gttgggaatg tcatcaagtc caagcttagg agttatccgg cccactctca  14100
tattccatat ccaaattgta atcaggattt atttaacata gaagacaaag agtcaacgaa  14160
gaagatccgt gaactcctca aaagggaa ttcgctgtac tccaaagtca gtgataaggt  14220
tttccaatgc ttaagggaca ctaactcacg gcttggccta ggctccgaat tgagggagga  14280
catcaaggag aaagttatta acttgggagt ttacatgcac agctcccagt ggtttgagcc  14340
ctttctgttt tggtttacag tcaagactga gtgatggtca gtgattaaat cacaaaccga  14400
tacttgccat aggaggagac acacacctgt attcttcact ggtagttcag ttgagttgct  14460
aatctctcgt gaccttgttg ctataatcag taaagagtct caacatgtat attacctgac  14520
atttgaactg gttttgatgt attgtgatgt catagagggg aggttaatga cagagaccgc  14580
tatgactatt gatgctaggt atacagagct tctaggaaga gtcagataca tgtggaaact  14640
gatagatgat tcttccctg  cactcggaa  tccaacttat caaattgtag ccatgctgga  14700
gcctctttca cttgcttacc tgcagctgag ggatataaca gtagaactca gaggtgcttt  14760
ccttaaccac tgctttactg aaatacgatga tgttcttgac caaaacgggt tttctgatga  14820
aggtacttat catgagttaa ctgaagctct agattacatt tcataactg  atgacataca  14880
tctgacaggg gagatttctct cattttttcag aagtttcggc cacccagac  ttgaagcagt  14940
aacggctgct gaaaatgtta ggaaatacat gaatcagcct aaagtcattg tgtatgagac  15000
tctgatgaaa ggtcatgcca tattttgtgg aatcataatc aacggctatc gtgcaggca   15060
cggaggcagt tggccaccgc tgaccctccc cctgcatgct gcagacacaa tccgaatgc   15120
tcaagcttca ggtgaagggt taacacatga gcagtcgctt gataactgga atcttttgc   15180
tggagtgaaa tttggctgct ttatgcctct agcctggat  agtgatctga caatgtacct  15240
aaaggacaag gcacttgctg ctctccaaag ggaatgggat tcagtttacc cgaaagagtt  15300
```

```
cctgcgttac gaccctccca agggaaccgg gtcacggagg cttgtagatg ttttccttaa   15360
tgattcgagc tttgacccat atgatgtgat aatgtatgtt gtaagtggag cttacctcca   15420
tgaccctgag ttcaacctgt cttacagcct gaaagaaaag gagatcaagg aaacaggtag   15480
acttttttgct aaaatgactt acaaaatgag ggcatgccaa gtgattgctg aaaatctaat   15540
ctcaaacggg attggcaaat attttaagga caatgggatg gccaaggatg agcacgattt   15600
gactaaggca ctccacactc tagctgtctc aggagtcccc aaagatctca agaaaagtca   15660
caggggggg ccagtcttaa aaacctactc ccgaagccca gtccacacaa gtaccaggaa   15720
cgtgagagca gcaaagggt ttatagggtt ccctcaagta attcggcagg accaagacac   15780
tgatcatccg gagaatatgg aagcttacga gacagtcagt gcatttatca cgactgatct   15840
caagaagtac tgccttaatt ggagatatga gaccatcagc ttgtttgcac agaggctaaa   15900
tgagatttac ggattgccct catttttcca gtggctgcat aagaggcttg agacctctgt   15960
cctgtatgta agtgaccctc attgcccccc cgaccttgac gcccatatcc cgttatataa   16020
agtccccaat gatcaaatct tcattaagta ccctatggga ggtatagaag ggtattgtca   16080
gaagctgtgg accatcagca ccattcccta tctataccg gctgcttatg agagcggagt   16140
aaggattgct tcgttagtgc aaggggacaa tcagaccata gccgtaacaa aaagggtacc   16200
cagcacatgg ccctacaacc ttaagaaacg ggaagctgct agagtaacta gagattactt   16260
tgtaattctt aggcaaaggc tacatgatat tggccatcca ctcaaggcaa atgagacaat   16320
tgtttcatca catttttttg tctattcaaa aggaatatat tatgatgggc tacttgtgtc   16380
ccaatcactc aagagcatcg caagatgtgt attctggtca gagactatag ttgatgaaac   16440
aagggcagca tgcagtaata ttgctacaac aatggctaaa agcatcgaga gaggttatga   16500
ccgttacctt gcatattccc tgaacgtcct aaaagtgata cagcaaattc tgatctctct   16560
tggcttcaca atcaattcaa ccatgacccg ggatgtagtc ataccctcc tcacaaacaa   16620
cgacctctta ataaggatgg cactgttgcc cgctcctatt gggggatga attatctgaa   16680
tatgagcagg ctgtttgtca gaaacatcgg tgatccagta acatcatcaa ttgctgatct   16740
caagagaatg attctcgcct cactaatgcc tgaagagacc ctccatcagg taatgacaca   16800
acaaccgggg gactcttcat tcctagactg ggctagcgaa cctttactgag caaatcttgt   16860
atgtgtccag agcatcacta gactcctcaa gaacataact gcaaggtttg tcctgatcca   16920
tagtccaaac ccaatgttaa aaggattatt ccatgatgac agtaaagaag aggacgaggg   16980
actggcggca ttcctcatgg acaggcatat tatagtacct agggcagctc atgaaatcct   17040
ggatcatagt gtcacagggg caagagagtc tattgcagtc atgctggata ccacaaaagg   17100
cttgattcga gccagcatga gggaaggggg tttaacctct cgagtgataa ccagattgtc   17160
caattatgac tatgaacaat tcagagcagg gatggtgcta ttgacaggaa gaaagagaaa   17220
tgtcctcatt gacaaagagt catgttcagt gcagctggcg agagctctaa gaagccatat   17280
gtgggcgagg ctagctcgag gacggcctat ttacggcctt gaggtccctg atgtactaga   17340
atctatgcga ggccaccta ttcggcgtca tgagacatgt gtcatctgcg agtgtggatc   17400
agtcaactac ggatggtttt ttgtcccctc gggttgccaa ctggatgata ttgacaagga   17460
aacatcatcc ttgagagtcc catatattgg ttctaccact gatgagagaa cagacatgaa   17520
gcttgccttc gtaagagccc caagtcgatc cttgcgatct gctgttagaa tagcaacagt   17580
gtactcatgg gcttacgtg atgatgatag ctcttgaac gaagcctggt tgttggctag   17640
gcaaagggcc aatgtgagcc tggaggagct aaggtgatc actcccatct caacttcgac   17700
taatttagcg cataggttga gggatcgtag cactcaagtg aaatactcag gtacatccct   17760
tgtccgagtg gcgaggtata ccacaatctc caacgacaat ctctcatttg tcatatcaga   17820
taagaaggtt gatactaact ttatatacca acaaggaagg cttctagggt tgggtgtttt   17880
agaaacattg tttcgactcg agaaagatac cggatcatct aacacggtat tacatcttca   17940
cgtcgaaaca gattgttgcg tgatcccgat gatagatcat cccgggatac ccagctcccg   18000
caagctagag ctgagggcag agctatgtac caacccattg atatatgata atgcacctttt   18060
aattgagaag gatgcaacaa ggctatacac ccagagccat aggaggcacc ttgtggaatt   18120
tgttacatgg tccacacccc aactatatca catttttagct aagtccacag cactatctat   18180
gattgacctg gtaacaaaat ttgagaagga ccatatgaat gaaatttcag ctctcatagg   18240
ggatgacgat atcaatagtt tcataactga gtttctgctc atagagccaa gattattcac   18300
tatctacttg ggccagtgtg cggccatcaa ttgggcattt gatgtacatt atcatagacc   18360
atcagggaaa tatcagatgg gtgagctgtt gtcatcgttc cttttctagaa tgagcaaagg   18420
agtgtttaag gtgcttgtca atgctctaag ccacccaaag atctacaaga aattctggca   18480
ttgtggtatt atagagccta tccatggtcc ttcacttgat gctcaaaact tgcacacaac   18540
tgtgtgcaac atgtttaca catgctatat gacctaccctc gacctgttgt gaatgaaga   18600
gttagaagag ttcacatttc tcttgtgtga aagcgacgag gatgtagtac cggacagatt   18660
cgacaacatc caggcaaaac acttatgtgt tctggcagat ttgtactgtc aaccagggac   18720
ctgcccacca attcgaggtc taagaccggt agagaaatgt gcagttctaa ccgaccatat   18780
caaggcagag gctatgttat ctccagcagg atcttcgtgg aacataaatc caattattgt   18840
agaccattac tcatgctccc tgacttatct ccggcaggaa tcgatcaaac agataagatt   18900
gagagttgat ccaggattca ttttcgacgc cctcgctgag gtaaatgtca gtcagccaaa   18960
gatcggcagc aacaacatct caaatatgag catcaaggct ttcagacccc cacacgatga   19020
tgttgcaaaa ttgctcaaag atatcaacac aagcaagcac aatcttccca tttcagggggg   19080
caatctcgcc aattatgaaa tccatgcttt ccgcagcagc gggttgaact catctgcttg   19140
ctacaaagct gttgagatat caacattaat taggagatgc cttgagccag gggaggacgg   19200
cttgttcttg ggtgagggat cgggttctat gttgatcact tataaggaga tacttaaact   19260
aaacaagtgc ttctataata gtgggggttc cgccaattct agatctggtc aaagggaatt   19320
agcaccctat ccctccgaag ttggccttgt cgaacacaga atgggagtag gtaatattgt   19380
caaagtgctc tttaacggga gcccgaagt cacgtcggta ggcagtgtag attgcttcaa   19440
tttcatagtt agtaatatcc ctaccctag tgtgggggttt atccattcag atatagagac   19500
cttgcctgac aaagatacta tagagaagct agaggggaattg gcagccatct tatcgatggc   19560
tctgctcctgg ggcaaaatag gatcaatact ggtgattaag cttatgcctt tcagcgggga   19620
ttttgttcag ggatttataa gttatgtagg gtctcattat agagaagtga accttgtata   19680
catatac gacaacttca tatctactga atcttatttg gttatgacag atctcaaggc   19740
taaccggcta atgaatcctg aaaagattaa gcagcagata attgaatcat ctgtgaggac   19800
ttcacctgga cttataggtc acatcctatc cattaagcaa ctaagctgca tacaagcaat   19860
tgtgggagac gcagttagta gaggtgatat caatcctact ctgaaaaaac ttacacctat   19920
agagcaggtg ctgatcaatt gcgggttggc aattaacgga cctaagctgt gcaaagaatt   19980
gatccaccat gatgttgcct cagggcaaga tggattgctt aattctatac tcatcctcta   20040
```

```
cagggagttg gcaagattca aagacaacca aagaagtcaa caagggatgt tccacgccta  20100
ccccgtattg gtaagtagca ggcaacgaga acttatatct aggatcaccc gcaaattttg  20160
ggggcacatt cttctttact ccgggaacaa aaagttgata aataagttta tccagaatct  20220
caagtccggc tatctgatac tagacttaca ccagaatatc ttcgttaaga atctatccaa  20280
gtcagagaaa cagattatta tgacgggggg tttgaaacgt gagtgggttt ttaaggtaac  20340
agtcaaggag accaaagaat ggtataagtt agtcggatac agtgccctga ttaaggacta  20400
attggttgaa ctccggaacc ctaatcctgc cctaggtggt taggcattat ttgcaatata  20460
ttaaagaaaa ctttgaaaat acgaagtttc tattcccagc tttgtctggt ggccggcata  20520
gtcccagcct cctcgctggc gctggctggg caacattccg aggggaccgt ccccacggta  20580
atggcgaatg ggacgcgggcc gatccggctg ctaacaaagc ccgaaaggaa gctgagttga  20640
ctgctggcgc tggctgggca ataactagca taacccttg gggcctctaa acgggtcttg  20700
aggggttttt tgctgaaagg aggaactata tccggatgcg gccgcgcgct tggcgtaatc  20760
atggtcatag ctgtttcctg tgtgaaattg ttatccgctc acaattccac acaacatacg  20820
agccggaagc ataaagtgta aagcctgggg tgcctaatga gtgagctaac tcacattaat  20880
tgcgttgcgc tcactgcccg ctttccagtc gggaaacctg tcgtgccagc tgcattaatg  20940
aatcggccaa cgcgcgggga gaggcggttt gcgtattggg cgctcttccg cttcctcgct  21000
cactgactcg ctgcgctcgg tcgttcggct gcggcgagcg tatcagctc actcaaaggc  21060
ggtaatacgg ttatccacag aatcagggga taacgcagga aagaacatgt gagcaaaagg  21120
ccagcaaaag gccaggaacc gtaaaaaggc cgcgttgctg gcgtttttcc ataggctccg  21180
ccccctgac gagcatcaca aaaatcgacg ctcaagtcag aggtggcgaa acccgacagg  21240
actataaaga taccaggcgt tttccctgg aagctccctc gtgcgctctc ctgttccgac  21300
cctgccgctt accggatacc tgtccgcctt tctccccttcg ggaagcgtgg cgctttctca  21360
tagctcacgc tgtaggtatc tcagttcggt gtaggtcgtt cgctccaagc tgggctgtgt  21420
gcacgaaccc cccgttcagc ccgaccgctg cgccttatcc ggtaactatc gtcttgagtc  21480
caacccggta agacacgact tatcgccact ggcagcagcc actggtaaca ggattagcag  21540
agcgaggtat gtaggcggtg ctacagagtt cttgaagtgg tggcctaact acggctacac  21600
tagaaggaca gtatttggta tctgcgctct gctgaagcca gttaccttcg aaaaagagt  21660
tggtagctct tgatccggca aacaaaccac cgctggtagc ggtggttttt tgtttgcaa  21720
gcagcagatt acgcgcagaa aaaaaggatc tcaagaagat cctttgatct tttctacggg  21780
gtctgacgct cagtggaacg aaaactcacg ttaagggatt ttggtcatga gattatcaaa  21840
aaggatcttc acctagatcc ttttaaatta aaaatgaagt tttaaatcaa tctaaagtat  21900
atatgagtaa acttggtctg acagttacca atgcttaatc agtgaggcac ctatctcagc  21960
gatctgtcta tttcgttcat ccatagttgc ctgactcccc gtcgtgtaga taactacgat  22020
acgggagggc ttaccatctg gccccagtgc tgcaatgata ccgcgagacc cacgctcacc  22080
ggctccagat ttatcagcaa taaaccagcc agccggaagg gccgagcgca gaagtggtcc  22140
tgcaacttta tccgcctcca tccagtctat taattgttgc cgggaagcta gagtaagtag  22200
ttcgccagtt aatagtttgc gcaacgttgt tgccattgct acaggcatcg tggtgtcacg  22260
ctcgtcgttt ggtatggctt cattcagctc cggttcccaa cgatcaaggc gagttacatg  22320
atccccatg ttgtgcaaaa aagcggttag ctccttcggt cctccgatcg ttgtcagaag  22380
taagttggcc gcagtgttat cactcatggt tatggcagca ctgcataatt ctcttactgt  22440
catgccatcc gtaagatgct tttctgtgac tggtgagtac tcaaccaagt cattctgaga  22500
atagtgtatg cggcgaccga gttgctcttg cccggcgtca atacgggata ataccgcgcc  22560
acatagcaga actttaaaag tgctcatcat tggaaaacgt tcttcgggc gaaaactctc  22620
aaggatctta ccgctgttga gatccagttc gatgtaaccc actcgtgcac ccaactgatc  22680
ttcagcatct tttactttca ccagcgtttc tgggtgagca aaaacaggaa ggcaaaatgc  22740
cgcaaaaaag gaataaggg cgacacgaa atgttaata ctcatactct ccttttttca  22800
atattattga agcatttatc agggttattg tctcatgagc ggatacatat ttgaatgtat  22860
ttagaaaaat aaacaaatag ggttccgcg cacatttccc cgaaaagtgc cacctg       22916

SEQ ID NO: 5            moltype = DNA   length = 22916
FEATURE                 Location/Qualifiers
misc_feature            1..22916
                        note = MV WuhanCoV S in position 6
source                  1..22916
                        mol_type = other DNA
                        organism = synthetic construct
SEQUENCE: 5
ggacgcgccc tgtagcggcg cattaagcgc ggcgggtgtg gtggttacgc gcagcgtgac    60
cgctacactt gccagcgccc tagcgcccgc tcctttcgct ttcttccctt cctttctcgc   120
cacgttcgcc ggctttcccc gtcaagctct aaatcggatt ctcccttag ggttccgatt   180
tagtgcttta cggcacctcg accccaaaaa acttgattag ggtgatggtt cacgtagtgg   240
gccatcgccc tgatagacgg ttttcgccc tttgacgttg gagtccacgt tctttaatag   300
tggactcttg ttccaaactg gaacaacact caacccctatc tcggtctatt cttttgattt   360
ataagggatt ttgccgattt cggcctattg gttaaaaaat gagctgattt aacaaaaatt   420
taacgcgaat tttaacaaaa tattaacgtt tacaatttcg cctcattcgc cattcaggct   480
gcgcaactgt tgggaaggc gatcggtgcg ggcctcttcg ctattacgcc agctggcgaa   540
agggggatgt gctgcaaggc gattaagttg gtaacgcca gggttttccc agtcacgacg   600
ttgtaaaacg acggccagtg cgcgccgtta atacgactca ctataggag cccaagctg   660
gctagctttg tttggtctga tgagtcccgt gaggacgaaa cccggcgtac cgggtcacca   720
aacaaagttg ggtaaggata gttcaatcaa tgatcatctt ctagtgcact taggattcaa   780
gatcctatta tcagggacaa gagcaggatt gggagatcc gagatggcca cactttttaag   840
gagcttagca ttgttcaaaa gaaacaagga caaaccaccc attacatcag gatcggtgg   900
agccatcaga ggaatcaaac acattattat agtaccaatc cctggagatt cctcaattac   960
cactcgatcc agacttctgg accggttggt gaggttaatt gaaaaccgga atgagcgg    1020
gcccaaacta acagggcac taataggtat attatccta tttgtggagt ctccaggtca   1080
attgattcag aggatcaccg atgacccctga cgttagcata aggctgttag aggttgtcca   1140
gagtgaccag tcacaatctg gccttacctt cgcatcaaga ggtaccaaca tggaggatga   1200
gcggaccaa tactttcac atgatgatcc aattagtagt gatcaatcca ggttcggatg   1260
gttcgggaac aaggaaatct cagatattga agtgcaagac cctgagggat tcaacatgat   1320
```

```
tctgggtacc atcctagccc aaatttgggt cttgctcgca aaggcggtta cggccccaga    1380
cacggcagct gattcggagc taagaaggtg gataaagtac acccaacaaa gaagggtagt    1440
tggtgaattt agattggaga gaaaatggtt ggatgtggtg aggaacagga ttgccgagga    1500
cctctcctta cgccgattca tggtcgctct aatcctggat atcaagagaa cacccggaaa    1560
caaacccagg attgctgaaa tgatatgtga cattgataca tatatcgtag aggcaggatt    1620
agccagtttt atcctgacta ttaagtttgg gatagaaact atgtatcctg ctcttggact    1680
gcatgaattt gctggtgagt tatccacact tgagtccttg atgaaccttt accagcaaat    1740
gggggaaact gcaccctaca tggtaatcct ggagaactca attcagaaca agttcagtgc    1800
aggatcatac cctctgctct ggagctatgc catgggagta ggagtggaac ttgaaaactc    1860
catgggaggt ttgaactttg gccgatctta ctttgatcca gcatatttta gattagggca    1920
agagatggta aggaggtcag ctggaaaggt cagttccaca ttggcatctg aactcggtat    1980
cactgccgag gatgcaaggc ttgtttcaga gattgcaatg catactactg aggacaagat    2040
cagtagagcg gttggaccca gacaagccca agtatcattt ctacacggtg atcaaagtga    2100
gaatgagcta ccgagattgg ggggcaagga agataggagg gtcaaacaga gtcgaggaga    2160
agccagggag agctacagag aaaccgggcc cagcagagca agtgatgcga gagctgccca    2220
tcttccaacc ggcacacccc tagacattga cactgcaacg gagtccagcc aagatccgca    2280
ggacagtcga aggtcagctg acgccctgct taggctgcaa gccatggcag gaatctcgga    2340
agaacaaggc tcagacacgg cacccctat agtgtacaat gacagaaatc ttctagacta    2400
ggtgcgagag gccgagggcc agaacaacat ccgcctacca tccatcattg ttataaaaaa    2460
cttaggaacc aggtccacac agccgccagc ccatcaacca tccactccca cgattggagc    2520
caatggcaga agagcaggca cgccatgtca aaaacggact ggaatgcatc cgggctctca    2580
aggccgagcc catcggctca ctggccatcg aggaagctat ggcagcatgg tcagaaatat    2640
cagacaaccc aggacaggag cgagccacct gcagggaaga gaaggcaggc agttcgggtc    2700
tcagcaaacc atgcctctca gcaattggat caactgaagg cggtgcacct cgcatccgcg    2760
gtcagggacc tggagagagc gatgacgacg ctgaaacttt gggaatcccc caagaaatc     2820
tccaggcatc aagcactggg ttacagtgtt attacgttta tgatcacagc ggtgaagcgg    2880
ttaagggaat ccaagatgct gactctatca tggttcaatc aggccttgat ggtgatagca    2940
ccctctcagg aggagacaat gaatctgaaa acagcgatgt ggatattggc gaacctgata    3000
ccgagggata tgctatcact gaccgggat ctgctcccat ctctatgggg ttcagggctt     3060
ctgatgttga aactgcagaa ggaggggaga tccacgagct cctgagactc caatccagag    3120
gcaacaactt tccgaagctt gggaaaactc tcaatgttcc tccgccccg gaccccggta     3180
gggccagcac ttccgggaca cccattaaaa agggcacaga cgcgagatta gcctcatttg    3240
gaacggagat cgcgtctta ttgacaggtg gtgcaaccca atgtgctcga aagtcaccct      3300
cggaaccatc agggccaggt gcacctgcgg ggaatgtccc ccgagtgtgtg agcaatgccg    3360
cactgataca ggagtggaca cccgaatctg gtaccacaat ctccccgaga tcccagaata    3420
atgaagaagg gggagactat tatgatgatg agctgttctc tgatgtccaa gatattaaaa    3480
cagccttggc caaaatacac gaggataatc agaagataat ctccaagcta gaatcactgc    3540
tgttattgaa gggagaagtt gagtcaatta agaagcagat caacaggcaa aatatcagca    3600
tatccaccct ggaaggacac ctctcaagca tcatgatcgc cattcctgga cttgggaagg    3660
atcccaacga ccccactgca gatgtcgaaa tcaatcccga cttgaaaccc atcataggca    3720
gagattcagg ccgagcactg gccgaagttc tcaagaaacc cgttgccagc cgacaactcc    3780
aaggaatgac aaatggacgg accagttcca gaggacagct gctgaaggaa tttcagctaa    3840
agccgatcgg gaaaaagatg agctcagccg tcgggttttgt tcctgacaga ggccctgcat    3900
cacgcagtgt aatccgctcc attataaaat ccagccggct agaggaggat cggaagcgtt    3960
acctgatgac tctccttgat gatatcaaag agccaatga tcttgccaag ttccaccaga     4020
tgctgatgaa gataataatg aagtagctac agctcaactt acctgccaac ccatgccag     4080
tcgacccacc tagtacaacc taaatccatt ataaaaact taggagcaaa gtgattgcct     4140
cccaaggtcc acaatgacag agacctacga cttcgacaag tcggcatggg acatcaaagg    4200
gtcgatcgct ccgatacaac ccaccaccta cagtgatggc aggctggtgc cccaggtcag    4260
agtcatagat cctggtctag cgacaggaa ggatgaatgc tttatgtaca tgtttctgct     4320
gggggttgtt gaggacgcg attccctagg gcctccaatc gggcgagcat ttgggttcct    4380
gcccttaggt gttggcagat ccacagcaaa gcccgaaaaa ctcctcaaag aggccactga    4440
gcttgacata gttgttagac gtacagcagg gctcaatgaa aaactggtgt ctacaacaa     4500
cacccactca actctcctca caccttggag aaaggtccta caacaggga gtgtcttcaa     4560
cgcaaaccaa gtgtgcaatg cggttaatct gatccgctc gatacccgc agaggttccg      4620
tgttgtttat atgagcatca cccgtctttc ggataacggg tattacaccg ttcctagaag    4680
aatgctggaa ttcagatcgg tcaatgcagt ggccttcaac ctgctggtga cccttaggat    4740
tgacaaggcg ataggccctg gaagatcat cgacaataca gagcaacttc ctgaggcaac     4800
atttatggtc cacatcggga acttcaggag aaagaagagt gaagtctact ctgccgatta    4860
ttgcaaaatg aaaatcggga agatgggcct ggtttttgca cttggtggga tagggggcac    4920
cagtcttcac attagaagca caggcaaaat gagcaagact ctccatgcac aactcggggtt   4980
caagaagacc ttatgttacc cgctgatgga tatcaatgaa gaccttaatc gattactctg    5040
gaggagcaga tgcaagatag taagaatcca ggcagttttg cagccatcag ttcctctcaaga  5100
attccgcatt tacgacgacg tgatcataaa tgatgaccaa agcattattca aagttctgta   5160
gaccgtagtg cccagcaatg cccgaaaacg accccctca caatgacagc cagaaggccc     5220
ggacaaaaaa gccccctccg aaagactcca ggaccaagc gagaggccag ccagcagccg     5280
acggcaagcc cgaacaccag gcggcccag cacagaacag ccctgacaca aggccaccac     5340
cagccacccc aatctgcatc ctcctcgtgg gacccccgag gaccaccccc caaggctgcc    5400
cccgatccaa accaccaacc gcatccccac cacccccgg aaagaaaccc ccagcaattg     5460
gaaggcccct cccctctctc ctcaacacaa gaactccaca accgaaccgc acaagcgacc    5520
gaggtgaccc aaccgcaggc atccgactcc ctagacagat cctctctccc cggcaaacta   5580
aacaaaactt agggccaagg aacatacaca cccaacagaa cccagacccc ggcccacggc    5640
gccgcgcccc caaccccga aaccagagg gagcccccaa ccaatcccgc cggctccccc      5700
ggtgcccaca gcaggaca ccaacccccg aacagacccc aacccaaatc atcgacaatc      5760
caagacgggg gggcccccc aaaaaaaggc cccaggggc cgacagccag caccgcgagg     5820
aagcccaccc accccacaca cgaccacggc aaccaaacca gaaccagac cacccctgggc   5880
caccagctcc cagactcggc catcacccg cagaaaggaa aggccacaac ccgcgcaccc    5940
cagccccgat ccggcgggga gccacccaac ccgaaccagc acccaagagc gatccccgaa    6000
ggaccccga accgcaaagg acatcagtat cccacagcct ctccaagtcc cccggtctcc   6060
```

```
tcctcttctc gaagggacca aaagatcaat ccaccacacc cgacgacact caactcccca    6120
cccctaaagg agacaccggg aatcccagaa tcaagactca tccaatgtcc atcatgggtc    6180
tcaaggtgaa cgtctctgcc atattcatgg cagtactgtt aactctccaa acacccaccg    6240
gtcaaatcca ttggggcaat ctctctaaga tagggggtggt aggaatagga agtgcaagct    6300
acaaagttat gactcgttcc agccatcaat cattagtcat aaaattaatg cccaatataa    6360
ctctcctcaa taactgcacg agggtagaga ttgcagaata caggagacta ctgagaacag    6420
ttttggaacc aattagagat gcacttaatg caatgaccca gaatataaga ccggttcaga    6480
gtgtagcttc aagtaggaga cacaagagat ttgcgggagt agtcctggca ggtgcggccc    6540
taggcgttgc cacagctgct cagataacag ccggcattgc acttcaccag tccatgctga    6600
actctcaagc catcgacaat ctgagagcga gcctggaaac tactaatcag gcaattgaga    6660
caatcagaca agcagggcag gagatgatat tggctgttca gggtgtccaa gactacatca    6720
ataatgagct gataccgtct atgaaccaac tatcttgtga tttaatcggc cagaagctcg    6780
ggctcaaatt gctcagatac tatacagaaa tcctgtcatt atttggcccc agtttacggg    6840
accccatatc tgcggagata tctatccagg ctttgagcta tgcgcttgga ggagacatca    6900
ataaggtgtt agaaaagctc ggatacagtg gaggtgattt actgggcatc ttagagagcg    6960
gaggaataaa ggcccggata actcacgtcg acacagagtc ctacttcatt gtcctcagta    7020
tagcctatcc gacgctgtcc gagattaagg gggtgattgt ccaccggcta gagggggtct    7080
cgtacaacat aggctctcaa gagtggtata ccactgtgcc caagtatgtt gcaacccaag    7140
ggtaccttat ctcgaattt tgatgagtcat cgtgtacttt catgccagag ggactgtgt     7200
gcagccaaaa tgccttgtac ccgatgagtc ctctgctcca agaatgcctc cggggggtaca   7260
ccaagtcctg tgctcgtaca ctcgtatccg ggtcttttgg gaaccggttc attttatcac    7320
aagggaacct aatagccaat tgtgcatcaa tcctttgcaa gtgttacaca acaggaacga    7380
tcattaatca agaccctgac aagatcctaa catacattgc tgccgatcac tgccggtag    7440
tcgaggtgaa cggcgtgacc atccaagtcg ggagcaggag gtatccagac gctgtgtact    7500
tgcacagaat tgacctcggt cctcccatat cattggagag gttggacgta gggacaaatc    7560
tgggggaatgc aattgctaag ttggaggatg ccaaggaatt gttggagtca tcggaccaga    7620
tattgaggag tatgaaaggt ttatcgagca ctagcatagt ctacatcctg attgcagtgt    7680
gtcttggagg gttgataggg atccccgctt taatatgttg ctgcagggg cgttgtaaca    7740
aaaagggaga acaagttggt atgtcaagac caggcctaaa gcctgatctt acgggaacat    7800
caaaatccta tgtaaggtcg ctctgatcct ctacaactct tgaaacacaa atgtcccaca    7860
agtctcctct tcgtcatcaa gcaaccaccg caccccagcat caagcccacc tgaaattatc    7920
tccggcttcc ctctggccga acaatatcgg tagttaatta aaacttaggg tgcaagatca    7980
tcgataatgt caccacaacg agaccggata aatgccttct acaaagataa ccccccatccc    8040
aagggaagta ggatagtcat taacagagaa catcttatga ttgatagacc ttatgttttg    8100
ctggctgttc tgtttgtcat gtttctgagc ttgatcgggt tgctagccat tgcaggaatt    8160
cgacttcatc gggcagccat ctacaccgca gagatccata aaagcctcag caccaatcta    8220
gatgtaacta actcaatcga gcatcaggtc aaggacgtgc tgacaccact cttcaaaatc    8280
atcggtgatg aagtgggcct gaggacacct cagagattca ctgacctagt gaaattaatc    8340
tctgacaaga ttaaattcct taatccggat agggagtacg acttcagaga tctcacttgg    8400
tgtatcaacc cgccagagag aatcaaattg gattatgatc aatactgtgc agatgtggct    8460
gctgaagagc tcatgaatgc cattggtgaac tcaactctac tggagaccag aacaaccaat    8520
cagttcctag ctgtctcaaa gggaaactgc tcagggccca ctacaatcag aggtcaattc    8580
tcaaacatgt cgctgtccct gttagacttg tatttaggtc gaggttacaa tgtgtcatct    8640
atagtcacta tgcatatccca ggggaatgtat gggggaactt acctagtgga aaagcctaat    8700
ctgagcagca aaaggtcaga gttgtcacaa ctgagcatgt accgagtgtt tgaagtaggt    8760
gttatcagaa atcggggttt gggggctccg tgttccata tgacaaacta tcttgagcaa    8820
ccagtcagta atgatctcag caactgtatg gtggcttttg gggagctcaa actcgcagcc    8880
ctttgtcacg gggaagattc tatcacaatt ccctatcagg gatcaggaa aggtgtcagc    8940
ttccagctcg tcaagctagg tgtctggaaa tccccaaccg acatgcaatc ctgggtcccc    9000
ttatcaacga atgatccagt gatagacagg ctttacctct catctcacag aggtgttatc    9060
gctgacaacc aagcaaaatg ggctgtcccg acaacacgaa cagatgacaa gttgcgaatg    9120
gagacatgct tccaacaggc gtgtaagggt aaaatccaag cactctgcga gaatcccgag    9180
tgggcaccat tgaaggataa caggattcct tcatacgggg tcttgtcgt tgatctgagt    9240
ctgacagttg agcttaaaat caaaattgct tcgggattcg ggccattgat cacacacggt    9300
tcagggatgg acctatacaa atccaaccac aacaatgtgt attggctgac tatcccgcca    9360
atgaagaacc tagccttagg tgtaatcaac acattggagt ggataccgag attcaaggtt    9420
agtccctacc tcttcactgt cccaattaag gaagcaggcg aagactgcca tgccccaaca    9480
tacctacctg cggaggtgga tggtgatgtc aaactcagtt ccaatctggt gattctacct    9540
ggtcaagatc tccaatatgt tttggcaacc tacgatactt ccagggttga acatgctgtg    9600
gtttattacg tttacagccc aagccgctca ttttcttact tttatccttt taggttgcct    9660
ataaagggggg tccccatcga attacaagtg gaatgcttca catggaccaa aaaactctgg    9720
tgccgtcact tctgtgtgct tgcggactca gaatctggtg gacatatcac tcactctggg    9780
atggtgggca tgggagtcag ctgcacagtc acccgggaag atggaaccaa tcgcagatag    9840
ggctgctagt gaaccaatca catgatgtca cccagacatc aggcatactc accatccatc    9900
attgttataa aaaacttagg aaccaggtcc acacagagtg atacgcgtac gccaccatgt    9960
tcgtgttttct ggtgctgctg cctctggtga gctcccagtg cgtgaacctg accacaagga   10020
cccagctgcc ccctgcctat accaattcct tcacacgggg cgtgtactat cccgacaagg   10080
tgttccggag cagcgtgctg cactccacac aggatctgtt tgccttttc ttttctaacg   10140
tgacctggtt ccacgccatc cacgtgagcg gcaccaatgg cacaaagcgg ttcgacaatc   10200
cagtgctgcc ctttaacgat ggcgtgtact cgcctccac cgagaagtct aacatcatca   10260
gaggctggat ctttggcacc acactggaca gcaagacaca gtccctgctg atcgtgaaca   10320
atgccaccaa cgtggtcatc aaggtgtgcg agttccagtt ttgtaatgat ccattcctgg   10380
gcgtgtacta tcacaagaac aataagtctt ggatggagag cgagtttcgc gtgtattcct   10440
ctgccaacaa ttgcacattt gagtacgtgt cccagccctt cctgatggac ctggagggca   10500
agcagggcaa tttcaagaac ctgagggagt tcgtgtttaa gaatatcgat ggctacttca   10560
aaatctactc caagcacacc ccaatcaacc tggtgcgcga cctgccacag gcttctctg    10620
ccctggagcc actggtggat ctgcccatcg gcatcaacat cacccggttt cagacactgc   10680
tggccctgca cagaagctac ctgacaccag cgcagactc ctctggatgg accgcaggag   10740
cagcagccta ctatgtgggc tatctgcagc ccaggacctt cctgctgaag tacaacgaga   10800
```

```
atggcaccat cacagacgcc gtggattgcg ccctggatcc cctgtctgag accaagtgta  10860
cactgaagag ctttaccgtg gagaagggca tctatcagac aagcaatttc agggtgcagc  10920
ctaccgagtc catcgtgcgc tttcccaata tcacaaacct gtgcccttttt ggcgaggtgt  10980
tcaacgcaac ccgcttcgcc agcgtgtacg cctggaatag gaagcgcatc tccaactgcg  11040
tggccgacta ttctgtgctg tacaacagcg cctccttctc tacctttaag tgctatggcg  11100
tgagccccac aaaagctgaat gacctgtgct ttaccaacgt gtacgccgat tccttcgtga  11160
tcaggggcga cgaggtgcgc cagatcgcac caggacagag aggcaagatc gcagactaca  11220
attataagct gcctgacgat ttcaccggct gcgtgatcgc ctggaactct aacaatctgg  11280
atagcaaagt gggcggcaac tacaattatc tgtaccggct gtttagaaag tctaatctga  11340
agccattcga gagggacatc tccacagaaa tctaccaggc cggctctacc ccctgcaatg  11400
gcgtggaggg ctttaactgt tatttccctc tgcagagcta cggcttccag ccaacaaacg  11460
gcgtgggcta tcagccctac cgcgtggtgg tgctgtcttt tgagctgctg cacgcacctg  11520
caacagtgtg cggaccaaag aagagcacca atctggtgaa gaacaagtgc gtgaacttca  11580
acttcaacgg actgaccgga acaggcgtgc tgaccgagtc caacaagaag ttcctgcctt  11640
ttcagcagtt cggcagggac atcgcagata ccacagacgc cgtgcgcgac cctcagaccc  11700
tggagatcct ggacatcaca ccatgctcct tcggcggcgt gtctgtgatc acaccaggca  11760
ccaatacaag caaccaggtg gccgtgctgt atcaggacgt gaattgtacc gaggtgccag  11820
tggcaatcca cgcagatcag ctgacccgta catggccgggt gtactctacc ggcagcaacg  11880
tgttccagac aagagccgga tgcctgatcg gagcagagca cgtgaacaat agctatgagt  11940
gcgacatccc tatcggcgcc ggcatctgtg cctcctacca gacccagaca aactccccaa  12000
ggagagcacg gtctgtggcc agccagtcca tcatcgccta taccatgagc ctgggcgccg  12060
agaattccgt ggcctactcc aacaattcta tcgccatccc taccaacttc acaatctccg  12120
tgaccacaga gatcctgcca gtgagcatga ccaagacatc cgtggactgc acaatgtata  12180
tctgtggcga ttcaccgag tgctctaacc tgctgctgca gtacgcctct ttttgtaccc  12240
agctgaatag agccctgaca ggcatcgccg tggagcagga caagaacaca caggaggtgt  12300
tcgcccaggt gaagcaaatc tacaagaccc cacccatcaa ggactttgag ggcttcaact  12360
tcagccagat cctgcccgat cctagcaagc atcccaagcg gtcttttatc gaggacctgc  12420
tgttcaacaa ggtgaccctg gccgatgccg gcttcatcaa gcagtatggc gattgcctgg  12480
gcgacatcgc cgccagagac ctgatctgtg cccagaagtt taatggcctg accgtgctgc  12540
ctccactgct gacagatgag atgatcgccc agtacacatc tgccctgctg gccggaacca  12600
tcacaagcgg atggaccttc ggcgcaggag ccgccctgca gatccccttt gccatgcaga  12660
tggcctatcg gttcaacggc atcggcgtga cccagaatgt gctgtacgag aaccagaagc  12720
tgatcgccaa tcagtttaac tccgccatcg gcaagatcca ggactctctg agctccacag  12780
ccagcgccct gggcaagctg caggatgtgg tgaatcaaga cgccaggcc ctgaataccc  12840
tggtgaagca gctgtctagc aacttcggcg ccatctcctc tgtgctgaat gacatcctga  12900
gccggctgga caaggtggag gcagaggtgc agatcgaccg gctgatcaca ggcagactgc  12960
agtccctgca gacctacgtg acacagcagc tgatcagggc agcagagatc agggcctctg  13020
ccaatctggc cgccaccaag atgagcgagt gcgtgctggg ccagtcccaag agagtggact  13080
tttgtggcaa gggctatcac ctgatgagct cccacagtc cgcccctcac ggagtggtgt  13140
ttctgcacgt gacctacgtg ccagcccagg agaagaactt caccacagca ccagcaatct  13200
gccacgatgg caaggcacac tttcctaggg agggcgtgtt cgtgagcaac ggcacccact  13260
ggtttgtgac acagcgcaat ttctacgagc cacagatcat caccacagac aatacattcg  13320
tgtccggcaa ctgtgacgtg gtcatcggca tcgtgaacaa taccgtgat gatcctctgc  13380
agccagagct ggactctttt aaggaggagc tggataagta cttcaagaat cacaccagcc  13440
ccgacgtgga tctgggcgac atctctggca tcaatgccag cgtggtgaac atccagaagg  13500
agatcgacag gctgaacgag gtggccaaga atctgaacga gtccctgatc gatctgcagg  13560
agctggcgcaa gtatgagcag tacatcaagt ggccctgta tatctgctg ggcttcatcg  13620
ccggcctgat cgccatccgt atggtgacca tcatgctgtg ctgtatgaca agctgctgtt  13680
cctgcctgaa gggctgctgt tcttgtggca gctgctgtaa gtttgatgag gacgatagcg  13740
agcctgtgct gaagggcgtg aagctgcact acacctgagc tagcgatcgc actagtgtga  13800
aatagacatc agaattaaga aaaacgtagg tccaagtgg ttccccgtta tggactcgat  13860
atctgtcaac cagatcttat accctgaagt tcacctagat agcccgatag ttaccaataa  13920
gatagtagcc atcctggagt atgctcgagt ccctcacgct tacagcctgg aggacccctac  13980
actgtgtcag aacatcaagc accgcctaaa aaacggattt tccaaccaaa tgattataaa  14040
caattggaa gttgggaatg tcatcaagtc caagcttagg agttatccgg cccactctca  14100
tattccatat ccaaattgta atcaggattt atttaacata gaagacaaag agtcaacgag  14160
gaagatccgt gaactcctca aaaagggaa ttcgctgtac tccaaagtca gtgataaggt  14220
tttccaatgc ttaagggaca ctaactcacg gcttggccta ggctccgaat tgagggagga  14280
catcaaggag aaagttatta acttgggagt ttacatgcac agctcccagt ggtttgagcc  14340
ctttctgttt tggtttacag tcaagactga gatgaggtca gtgattaaat cacaaaccca  14400
tacttgccat aggaggagac acacaccgt attcttcact ggtagttcag ttgagttgct  14460
aatctctcgt gaccttgttg ctataatcag taaagagtct caacatgtat attacctgac  14520
atttgaactg gttttgatgt attgtgatgt catagagggg aggttaatga cagagaccgc  14580
tatgactatt atgctaggt atacagagct tctaggaaga gtcagataca tgtggaaact  14640
gatagatgct tcttcccctg cactcggaaa tccaacttat caaattgtag ccatgctgga  14700
gcctcttttca cttgcttacc tgcagctgag ggatataaca gtagaactca gaggtgcttt  14760
ccttaaccac tgctttactg aaatacatga tgttcttgac caaacgggt tttctgatga  14820
aggtacttat catgagttaa ctgaagctct agattacatt ttcataactg atgacataca  14880
tctgacaggg gagatttct cattttttcag aagtttcggc caccccagac ttgaagcagt  14940
aacggctgct gaaaatgtta ggaaatacat gaatcagcct aaagtcattg tgtatgagac  15000
tctgatgaaa ggtcatgcca tattttgtgg aatcataatc aacggctatc gtgacaggca  15060
cggaggcagt tggccaccgc tgaccctccc cctgcatgct gcagacacaa tccggaatgc  15120
tcaagcttca ggtgaagggt taacacatga gcagtgcgtt gataactgga atcttttgc  15180
tggagtgaaa tttggctgct ttatgcctct tagcctgggc agtgatctga caatgtacct  15240
aaaggacaag gcacttgctg ctctccaaag ggaatgggat tcagtttacc cgaaagagtt  15300
cctgcgttac gaccctccca agggaaccgg gtcacggagg cttgtagatg ttttccttaa  15360
tgattcgagc tttgacccat atgatgtgat aatgtatgtt gtaagtggag cttacctcca  15420
tgaccctgag ttcaacctgt cttacagcct gaaagaaaag gagatcaagg aaacaggtag  15480
acttttgct aaaatgactt acaaaatgag ggcatgccaa gtgattgctg aaaatctaat  15540
```

```
ctcaaacggg attggcaaat attttaagga caatgggatg gccaaggatg agcacgattt    15600
gactaaggca ctccacactc tagctgtctc aggagtcccc aaagatctca aagaaagtca    15660
cagggggggg ccagtcttaa aaacctactc ccgaagccca gtccacacaa gtaccaggaa    15720
cgtgagagca gcaaaagggt ttatagggtt ccctcaagta attcggcagg accaagacac    15780
tgatcatccg gagaatatgg aagcttacga gacagtcagt gcatttatca cgactgatct    15840
caagaagtac tgccttaatt ggagatatga gaccatcagc ttgtttgcac agaggctaaa    15900
tgagatttac ggattgccct cattttccaa gtggctgcat aagaggcttg agacctctgt    15960
cctgtatgta agtgaccctc attgccccc  cgaccttgac gcccatatcc cgttatataa    16020
agtccccaat gatcaaatct tcattaagta ccctatggga ggtatagaag ggtattgtca    16080
gaagctgtgg accatcagca ccattcccta tctatacctg gctgcttatg agagcggagt    16140
aaggattgct tcgttagtgc aaggggacaa tcagaccata gccgtaacaa aaagggtacc    16200
cagcacatgg ccctacaacc ttaagaaacg ggaagctgct agagtaacta gagattactt    16260
tgtaattctt aggcaaaggc tacatgatat tggccatcac ctcaaggcaa atgagacaat    16320
tgtttcatca cattttttg  tctattcaaa aggaatatat tatgatgggc tacttgtgtc    16380
ccaatcactc aagagcatcg caagatgtgt attctggtca gagactatag ttgatgaaac    16440
aagggcagca tgcagtaata ttgctacaac aatggctaaa agcatcgaga gaggttatga    16500
ccgttacctt gcatattccc tgaacgtcct aaaagtgata cagcaaattc tgatctctct    16560
tggcttcaca atcaattcaa ccatgacccg ggatgtagtc ataccctcc  tcacaaacaa    16620
cgacctctta ataaggatgg cactgttgcc cgctcctatt gggggagatga attatctgaa    16680
tatgagcagg ctgtttgtca gaaacatcgg tgatccagta acatcatcaa ttgctgatct    16740
caagagaatg attctcgcct cactaatgcc tgaagagacc ctccatcagg taatgacaca    16800
acaaccgggg gactcttcat tcctagactg ggctagcgac ccttactcag caaatcttgg    16860
atgtgtccag agcatcacta gactcctcaa gaacataact gcaaggtttg tcctgatcca    16920
tagtccaaac ccaatgttaa aaggattatt ccatgatgac agtaaagaag aggacgaggg    16980
actggcggca ttcctcatgg acaggcatat tatagtacct agggcagctc atgaaatcct    17040
ggatcatagt gtcacagggg caagagagtc tattgcagtc ttggtgata  ccacaaaagg    17100
cttgattcga gccagcatga ggaagggggg tttaacctct cgagtgataa ccagattgtc    17160
caattatgac tatgaacaat tcagagcagg atggtgcta  ttgacaggaa gaaagagaaa    17220
tgtcctcatt gacaaagagt catgttcagt gcagctggcg agagctctaa gaagccatat    17280
gtgggcgagg ctagctcgag gacggcctat ttacggcctt gaggtccctg atgtactaga    17340
atctatgcga ggccaccta ttcggcgtca tgagacatgt gtcatctgcg agtgtggatc    17400
agtcaactac ggatggtttt ttgtcccctc gggttgccaa ctggatgata ttgacaagga    17460
aacatcatcc ttgagagtcc catatattgg ttctaccact gatgagagaa cagacatgaa    17520
gcttgcctct gtaagagccc caagtcgatc cttgcattct gctgttaagaa tagcaacagt    17580
gtactcatgg gcttacggtg atgatgatag ctcttggaac gaagcctggt tgttggctag    17640
gcaaagggcc aatgtgagcc tggaggagct aaggggtgatc actcccatct caacttcgac    17700
taatttagcg cataggttga gggatcgtag cactcaagtg aaatactcag gtacatccct    17760
tgtccgagtg gcgaggtata ccacaatctc caacgacaat ctctcatttg tcatatcaga    17820
taaagaggtt gatactaact ttatatacca acaaggaagt ttctagggt tgggtgtttt    17880
agaaacattg tttcgactcg agaaagatac cggatcatct aacacggtat tacatcttca    17940
cgtcgaaaca gattgttgcg tgatcccgat gatagatcat cccaggatac ccagctcccg    18000
caagctagag ctgagggcag agctatgtac caacccattg atatatgata atgcacctt    18060
aattgacaga gatgcaacaa ggctatacac ccagagccac ttgtggaatt  ttgtggaatt    18120
tgttacatgg tccacacccc aactatatca cattttagct aagtccacag cactatctat    18180
gattgacctg gtaacaaaat ttgagaagga ccatatgaat gaaatttcag ctctcatagg    18240
ggatgacgat atcaatagtt tcataactga gtttctgctc atagagccaa gattattcac    18300
tatctacttg ggccagtgtg cggccatcaa ttgggcattt gatgtacatt atcatagacc    18360
atcagggaaa tatcagatgg gtgagctgtt gtcatcgttc ctttctagaa tgagcaaagg    18420
agtgtttaag gtgcttgtca atgctctaag ccacccaaag atctacaaga aattctggca    18480
ttgtggtatt atagagccta tccatggtcc ttcacttgat gctcaaaact tgcacacaac    18540
tgtgtgcaac atggtttaca catgctatat gacctacctc gacctgttgt tgaatgaaga    18600
gttagaagag ttcacatttc tcttgtgtga aagcgacgag gatgtagtac cggacagatt    18660
cgacaacatc caggcaaaac acttatgtgt tctggcagat ttgtactgtc aaccagggac    18720
ctgcccacca attcgaggtc taagaccggt agagaaatgt gcagttctaa ccgaccatat    18780
caaggcagag gctatgttat ctccagcagg atcttcgttg aacataaatc caattattgt    18840
agaccattac tcatgctccc tgacttatct ccggcgagga tcgatcaaac agataagatt    18900
gagagttgat ccaggattca ttttcgacgc ccctcgctgag gtaaatgtca gtcagccaaa    18960
gatcggcagc aacaacatct caaatatgag catcaaggct ttcagacccc cacacgatga    19020
tgttgcaaaa ttgctcaaag atatcaacac aagcaagcac aatcttccca tttcaggggg    19080
caatctcgcc aattatgaaa tccatgcttt ccgcagaatc gggttgaact catctgcttg    19140
ctacaaagct gttgagatat caacattaat taggagatgc cttgagccag gggaggacgg    19200
cttgttcttg ggtgagggat cgggttctat gttgatcact tataaggaga tacttaaact    19260
aaacaagtgc ttctataata gtgggggttc cgccaattct agatctggtc aaagggaatt    19320
agcacctat ccctccgaag ttggccttgt cgaacacaga atgggagtag gtaatattgt    19380
caaagtgctc tttaacggga ggcccgaagt cacgtgggta ggcagtgtag attgcttcaa    19440
tttcatagtt agtaatatcc ctaccctag  tgtggggttt atccattcag atatagagac    19500
cttgcctgac aaagatacta gagaagct  agaggaattg gcagccatct tatcgatggc    19560
tctgctcctg ggcaaaatag gatcaatact ggtgattaag cttatgcctt tcagcgggga    19620
ttttgttcag ggattttataa gttatgtagg gtctcattat agagaagtga accttgtata    19680
ccctagatac agcaacttca tatctactga atcttatttg gttatgacag atctcaaggc    19740
taaccggcta atgaatcctg aaaagattaa gcagcagata attgaatcat ctgtgaggac    19800
ttcacctgga cttataggtc acatcctatc cattaagcaa ctaagctgca tacaagcaat    19860
tgtgggagac gcagttagta gaggtgatat caatcctact ctgaaaaaac ttacctat    19920
agagcagtg ctgatcaatt gcgggttggc aattaacgga cctaagctgt gaaagaatt    19980
gatccaccat gatgttgcct cagggcaaga tggattgctt aattctatac tcatcctcta    20040
cagggagttg gcaagattca aagacaacca agaagtcaa caagggatgt tccacgccta    20100
cccgtattg  gtaagtagca ggcaacgaga acttatatct aggatcaccc gcaaattttg    20160
ggggcacatt cttctttact ccgggaacaa aaagttgata aataagttta tccagaatct    20220
caagtccggc tatctgatac tagacttaca ccagaatatc ttcgttaaga atctatccaa    20280
```

```
gtcagagaaa cagattatta tgacgggggg tttgaaacgt gagtgggttt taaggtaac    20340
agtcaaggag accaaagaat ggtataagtt agtcggatac agtgccctga ttaaggacta   20400
attggttgaa ctccggaacc ctaatcctgc cctaggtggt taggcattat ttgcaatata   20460
ttaaagaaaa ctttgaaaat acgaagtttc tattcccagc tttgtctggt ggccggcata   20520
gtcccagcct cctcgctggc gctggctggg caacattccg aggggaccgt cccacggta    20580
atggcgaatg ggacgcggcc gatccggctg ctaacaaagc ccgaaaggaa gctgagttgg   20640
ctgctggcgc tggctgggca ataactagca taaccccttg gggcctctaa acgggtcttg   20700
agggggttttt tgctgaaagg aggaactata tccggatgcg gccgcgcgct tggcgtaatc  20760
atggtcatag ctgtttcctg tgtgaaattg ttatccgctc acaattccac acaacatacg   20820
agccggaagc ataaagtgta aagcctgggg tgcctaatga gtgagctaac tcacattaat   20880
tgcgttgcgc tcactgcccg ctttccagtc gggaaacctg tcgtgccagc tgcattaatg   20940
aatcggccaa cgcgcgggga gaggcggttt gcgtattggg cgctcttccg cttcctcgct   21000
cactgactcg ctgcgctcgg tcgttcggct gcggcgagcg gtatcagctc actcaaaggc   21060
ggtaatacgg ttatccacag aatcagggga taacgcagga aagaacatgt gagcaaaagg   21120
ccagcaaaag gccaggaacc gtaaaaaggc cgcgttgctg cgttttttcc ataggctccg   21180
cccccctgac gagcatcaca aaaatcgacg ctcaagtcag aggtggcgaa acccgacagg   21240
actataaaga taccaggcgt ttccccctgg aagctccctc gtgcgctctc ctgttccgac   21300
cctgccgctt accggatacc tgtccgcctt tctcccttcg ggaagcgtgg cgctttctca   21360
tagctcacgc tgtaggtatc tcagttcggt gtaggtcgtt cgctccaagc tgggctgtgt   21420
gcacgaaccc cccgttcagc ccgaccgctg cgccttatcc ggtaactatc gtcttgagtc   21480
caacccggta agacacgact tatcgccact ggcagcagcc actggtaaca ggattagcag   21540
agcgaggtat gtaggcggtg ctacagagtt cttgaagtgg tggcctaact acggctacac   21600
tagaaggaca gtatttggta tctgcgctct gctgaagcca gttaccttcg aaaaagagt    21660
tggtagctct tgatccggca aacaaaccac cgctggtagc ggtggttttt tgtttgcaa    21720
gcagcagatt acgcgcagaa aaaaggatc tcaagaagat cctttgatct tttctacggg    21780
gtctgacgct cagtggaacg aaaactcacg ttaagggatt ttggtcatga gattatcaaa   21840
aaggatcttc acctagatcc ttttaaatta aaaatgaagt tttaaatcaa tctaaagtat   21900
atatgagtaa acttggtctg acagttacca atgcttaatc agtgaggcac ctatctcagc   21960
gatctgtcta tttcgttcat ccatagttgc ctgactcccc gtcgtgtaga taactacgat   22020
acgggagggc ttaccatctg gccccagtgc tgcaatgata ccgcgagacc cacgctcacc   22080
ggctccagat ttatcagcaa taaaccagcc agccggaagg gccgagcgca gaagtggtcc   22140
tgcaacttta tccgcctcca tccagtctat taattgttgc cgggaagcta gagtaagtag   22200
ttcgccagtt aatagtttgc gcaacgttgt tgccattgct acaggcatcg tggtgtcacg   22260
ctcgtcgttt ggtatggctt cattcagctc cggttcccaa cgatcaaggc gagttacatg   22320
atcccccatg ttgtgcaaaa aagcggttag ctccttcggt cctccgatcg ttgtcagaag   22380
taagttggcc gcagtgttat cactcatggt tatggcagca ctgcataatt ctcttactgt   22440
catgccatcc gtaagatgct tttctgtgac tggtgagtac tcaaccaagt cattctgaga   22500
atagtgtatg cggcgaccga gttgctcttg cccggcgtca atacgggata taccgcgcc    22560
acatagcaga actttaaaag tgctcatcat tggaaaacgt tcttcggggc gaaaactctc   22620
aaggatctta ccgctgttga gatccagttc gatgtaaccc actcgtgcac ccaactgatc   22680
ttcagcatct tttactttca ccagcgtttc tgggtgagca aaaacaggaa ggcaaaatgc   22740
cgcaaaaaag ggaataaggg cgacacgaaa atgttgaata ctcatactct tcctttttca   22800
atattattga agcatttatc agggttattg tctcatgagc ggatacatat ttgaatgtat   22860
ttagaaaaat aaacaaatag gggttccgcg cacatttccc cgaaaagtgc cacctg       22916

SEQ ID NO: 6              moltype = DNA   length = 13907
FEATURE                   Location/Qualifiers
misc_feature              1..13907
                          note = RABV vector: Coravax V1-China (RABVG-E31)
source                    1..13907
                          mol_type = other DNA
                          organism = synthetic construct
SEQUENCE: 6
acgcttaaca accagatcaa agaaaaaaca gacattgtca attgcaaagc aaaaatgtaa   60
caccccctaca atggatgccg acaagattgt attcaaagtc aataatcagg tggtctcttt  120
gaagcctgag attatcgtgg atcaatatga gtacaagtac cctgccatca aagatttgaa  180
aaagccctgt ataaccctag gaaaggctcc cgatttaaat aaagcataca agtcagttt    240
gtcaggcatg agcgccgcca aacttaatcc tgacgatgta tgttcctatt tggcagcggc   300
aatgcagttt ttgagggga catgtccgga agactggacc agctatgaa ttgtgattgc     360
acgaaaagga gataagatca ccccaggttc tctggtaggg ataaaacgta ctgatgtaga   420
agggaattgg gctctgacag gaggcatgga actgacaaga gaccccactg tccctgagca   480
tgcgtcctta gtcggtcttc tcttgagtct gtataggttg agcaaaatat ccgggcaaaa   540
cactggtaac tataagacaa acattgcaga caggatagag cagattttg agacagcccc    600
ttttgttaaa atcgtggaac accatactct aatgacaact gtgctaattg                660
gagtactata ccaaacttca gattttggc cggaacctat gacatgtttt tctcccggat    720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttcacaagaa actttgagga agataaatgttg agcagggca              900
ggagacagct gttcctcact cttatttcat ccacttccgt tcactaggct tgagtgggaa   960
atctccttat tcatcaaatg ctgttggtca cgtgttcaat ctcattcact tgtaggatg    1020
ctatatgggg caagtcagat ccctaaatgc aacggttatt gctgcatgtg ctcctcatga  1080
aatgtctgtt ctaggggct atctgggaga ggaattcttc gggaagggga catttgaaag   1140
aagattcttc agagatgaga agaaacttca agaatacgcc cgcgctgaac tgacaaagac   1200
tgacgtagca ctggcagtca tgaactgt caactctgac gacgagact acttttcagg     1260
tgaaccagga agtccggagg ctgtttatac tcgaatcatg atgaatggag gtcgactaaa   1320
gagatctcac atacggagat atgtctcagt cagttccaat catcaagccc gtccaaactc   1380
attcgccgag tttctaaaca agacattc gagtgactca taacatgaaa aaactaaca    1440
cccctcccgt acgccaccat gttcgtgttt ctggtgctgc tgcctctggt gagctcccag   1500
tgcgtgaacc tgaccacaag gacccagctg cccccctgcc ataccaattc cttcacacgg   1560
```

```
ggcgtgtact atcccgacaa ggtgttccgg agcagcgtgc tgcactccac acaggatctg 1620
tttctgcctt tcttttctaa cgtgacctgg ttccacgcca tccacgtgag cggcaccaat 1680
ggcacaaagc ggttcgacaa tccagtgctg ccctttaacg atggcgtgta cttcgcctcc 1740
accgagaagt ctaacatcat cagaggctgg atctttggca ccacactgga cagcaagaca 1800
cagtccctgc tgatcgtgaa caatgccacc aacgtggtca tcaaggtgtg cgagttccag 1860
ttttgtaatg atccattcct gggcgtgtac tatcacaaga acaataagtc ttggatggag 1920
agcgagtttc gcgtgtattc ctctgccaac aattgcacat tgagtacgt gtcccagccc 1980
ttcctgatgg acctggaggg caagcagggc aatttcaaga acctgaggga gttcgtgttt 2040
aagaatatcg atggctactt caaaatctac tccaagcaca ccccaatcaa cctggtgcgc 2100
gacctgccac agggcttctc tgccctggag ccactggtgg atctgcccat cggcatcaac 2160
atcacccggt tcagacact gctggccctg cacagaagct acctgacacc aggcgacagc 2220
tcctctggat ggaccgcagg agcagcagcc tactatgtgg gctatctgca gcccaggacc 2280
ttcctgctga agtacaacga gaatggcacc atcacagacg ccgtggattg cgccctggat 2340
cccctgtctg agaccaagtg tacactgaag agcttaccg tggagaaggg catctatcag 2400
acaagcaatt tcagggtgca gcctaccgag tccatcctgc gctttcccaa tatcacaaac 2460
ctgtgcccttt tggcgaggt gttcaacgca acccgcttcg ccagcgtgta cgcctggaat 2520
aggaagcgca tctccaactg cgtggccgac tattctgtgc tgtacaacag cgcctccttc 2580
tctacctta agtgctatgg cgtsagccc acaaagctga atgacctgtg ctttaccaac 2640
gtgtacgccg attccttcgt gatcagggcgc gacgaggtgc gccagatcgc accaggacag 2700
acaggcaaga tcgcagacta caattataag ctgcctgacg atttcaccgg ctgcgtgatc 2760
gcctggaact ctaacaatct ggatagcaaa gtgggcggca actacaatta tctgtaccgg 2820
ctgtttagaa agtctaatct gaagccattc gagagggaca tctccacaga aatctaccag 2880
gccggctcta ccccctgcaa tggcgtggag ggctttaact gttatttccc tctgcagagc 2940
tacggcttcc agccaacaaa cggcgtgggc tatcagccct accgcgtggt ggtgctgtct 3000
tttgagctgc tgcacgcacc tgcaacagtg tgcggaccaa agaagagcac caatctggtg 3060
aagaacaagt gcgtgaactt caacttcaac ggactggtgc taagccaggt gctgaccgag 3120
tccaacaaga agttcctgcc ttttcagcag ttcggcaggg acatcgcaga taccacagac 3180
gccgtgcgcg accctcagac cctggagatc ctggacatca ccatgctc cttcggcggc 3240
gtgtctgtga tcacaccagg caccaataca agcaaccagg tggccgtgct gtatcaggac 3300
gtgaattgta ccgaggtgcc agtggcaatc cacgcagatc agctgaccc tacatgcgag 3360
gtgtactcta ccggcagcaa cgtgttccag acaagagccg gatgcctgat cggagcagag 3420
cacgtgaaca atagctatga gtgcgacatc cctatcggcg ccggcatctg tgcctcctac 3480
cagacccaga caaactcccc aaggtctgtg ggagatgagg ccgaagactt tgtggaagtc 3540
cacctgcctg atgtgcataa ccaggtgtct ggcgtcgacc tgggactgcc aaattgggc 3600
aagtacgtgc tgctgagtgc tggagcactg actgccctga tgctgatcat tttcctgatg 3660
acctgctgtc ggcgcgtgaa cagaagtgag cccactcagc acaatctgcg aggaaccggg 3720
agagaagtgt cagtcacacc tcagagcggg aaaatcatta gtagttggga atcacataaa 3780
agcggggcg agaccaggct gtgagctagc catgaaaaaa actaacaccc ctcctttcga 3840
accatcccaa acatgagcaa gatctttgtc aatcctagtg ctattagagc cggtctggcc 3900
gatcttgaga tggctgaaga aactgttgat ctgatcaata gaaatatcga agacaatcag 3960
gctcatctcc aaggggaacc catagaggtg gacaatctcc ctgaggatat ggggcgactt 4020
cacctggatg atggaaaatc gcccaaccat ggtgagatag ccaaggtggg agaaggcaag 4080
tatcggaagg acttcagat ggatgaagga gagatcctca gcttcctgct ccagtcatac 4140
ctggaaaatg ttggagtcca aatagtcaga caaatgaggt cagagagag atttctcaag 4200
atatggtcac agaccgtaga agagattata tcctatgtcg cggtcaactt tccaacccct 4260
ccaggaaagt cttcagagga taaatcaacc cagactactg gccgagagct caagaaggag 4320
acaacaccca ctccttctca gagagaaagc caatcatcga aagccaggat ggcggctcaa 4380
attgcttctg gccctccagc ccttgaatgg tcggctacca atgaagagga tgatctatca 4440
gtggaggctg agatcgctca ccagattgca gaaagtttct ccaaaaaata taagtttccc 4500
tctcgatcct cagggatact cttgtataat tttgagcaat tgaaaatgaa ccttgatgat 4560
atagttaaag aggcaaaaaa tgtaccaggt gtgacccgtt tagcccatga cgggtccaaa 4620
ctccccctaa gatgtgtact gggatgggtc gctttggcca actctaagaa attccagttg 4680
ttagtcgaat ccgacaagct gagtaaaatc atgcaagatg acttgaatcg ctatacatct 4740
tgctaaccga acctctcccc tcagtccctc tagacaataa atccgagat gtcccaaagt 4800
caacatgaaa aaaacaggca acaccactga taaaatgaac ctcctacgta agatagtgaa 4860
aaaccgcagg gacgaggaca ctcaaaaatc ctctcccgcg tcagcccctc tggatgacga 4920
tgacttgtgg cttccacccc ctgaatacg cccgctgaaa gaacttacag gcaagaagaa 4980
catgaggaac ttttgtatca acggaagggt taaagtgtgt agcccgaatg gttactcgtt 5040
caggatcctg cggcacattc tgaaatcatt cgacgagata tattctggga atcataggat 5100
gatcgggtta gtcaaagtgg ttattggact ggctttgtca ggatctccag tccctgaggg 5160
cctgaactgg gtatacaaat tgaggagaac ctttatcttc cagtgggctg attccagggg 5220
ccctcttgaa ggggaggagt tggaatactc tcaggagatc acttgggatg atgatactga 5280
gttcgtcgga ttgcaaataa gagtgattgc aaaacagtgt catatccagg gcagagtctg 5340
gtgtatcaac atgaacccga gcatgtca actatgtctc ttcagacaca gacaccatgg 5400
aaggtccgaa gaggacaaag attcctctct gcttctagaa taatcagatt atatcccgca 5460
aatttatcac ttgtttacct ctggaggaga aacatatgg gctcaactcc aacccttggg 5520
agcaatataa caaaaaacat gttatggtgc cattaaaccg ctgcatttca tcaaagtcaa 5580
gttgattacc tttacatttt gatcctcttg gatgtgaaaa aaactattaa catccctcaa 5640
aagaccccgg gaaagatggt tcctcaggct ctcctgtttg taccccttct ggttttcca 5700
ttgtgttttg ggaaattccc tatttacacg ataccagaca agcttggtcc ctggagtccg 5760
attgacatac atcacctcag ctgcccaaac aatttggtag tggaggacga aggatgcacc 5820
aacctgtcag ggttctccta catggaactt aaagttggat acatcttagc cataaaagtg 5880
aacggggttca cttgcacagg cgttgtgacg gaggctgaaa cctacactaa cttcgttggt 5940
tatgtcacaa ccacgttcaa aagaaagcat tccgccgatg atgtagagcc 6000
gcgtacaact ggaagatggc cgtgaccccc agatatgaag agtctctaca caatccgtac 6060
cctgactacc gctggcttcg aactgtaaaa accaccaagg agtctctcgt tatcatatct 6120
ccaagtgtgg cagatttgga cccatatgac agatcccttc actcgagggt cttccctagc 6180
gggaagtgct caggagtagc ggtgtcttct acctactgct ccactaacca cgattacacc 6240
atttggatgc ccgagaatcc gagactaggg atgtcttgtg acatttttac caatagtaga 6300
```

```
gggaagagag catccaaagg gagtgagact tgcggctttg tagatgaaag aggcctatat  6360
aagtctttaa aaggagcatg caaactcaag ttatgtggag ttctaggact tagacttatg  6420
gatggaacat gggtctcgat gcaaacatca aatgaaacca aatggtgccc tcccgataag  6480
ttggtgaacc tgcacgactt tcgctcagac gaaattgagc accttgttgt agaggagttg  6540
gtcaggaaga gagaggagtg tctgatgca ctagagtcca tcatgacaac caagtcagtg  6600
agtttcagac gtctcagtca tttaagaaaa cttgtccctg ggtttggaaa agcatatacc  6660
atattcaaca agaccttgat ggaagccgat gctcactaca agtcagtcga gacttggaat  6720
gagatcctcc cttcaaaagg gtgtttaaga gttgggggga ggtgtcatcc tcatgtgaac  6780
ggggtgtttt tcaatggtat aatattagga cctgacggca atgtcttaat cccagagatg  6840
caatcatccc tcctccagca acatatggag ttgttggaat cctcggttat ccccttgtg  6900
cacccctgg cagacccgtc taccgttttc aaggacggtg acgaggctga ggattttgtt  6960
gaagttcacc ttcccgatgt gcacaatcag gtctcaggag ttgacttggg tctcccgaac  7020
tgggggaagt atgtattact gagtgcaggg gccctgactg cttgatgtt gataatttc  7080
ctgatgacat gttgtagaag agtcaatcga tcagaaccta cgcaacacaa tctcagaggg  7140
acagggaggg aggtgtcagt cactcccaa agcgggaaga tcatatcttc atgggaatca  7200
cacaagagtg ggggtgagac cagactgtaa ttaattaacg tccttcaac gatccaagtc  7260
catgaaaaaa actaacaccc ctcccgtacc tagcttataa agtgctgggt catctaagct  7320
tttcagtcga gaaaaaaaca ttagatcaga agaacaactg gcaacacttc tcaacctgag  7380
acttacttca agatgctcga tcctggagag gtctatgatg acctattga cccaatcgag  7440
ttagaggctg aacccagagg aaccccatt gtccccaaca tcttgaggaa ctctgactac  7500
aatctcaact ctcctttgat agaagatcct gctagactaa tgttagaatg gttaaaaaca  7560
gggaatagac cttatcggat gactctaaca gacaattgct ccaggtcttc cagagttttg  7620
aaagattatt tcaagaaggt agatttgggt tctctcaagg tgggcggaat ggctgcacag  7680
tcaatgattt ctctctggtt atatggtgcc cactctgaat ccaacaggag ccggagatgt  7740
ataacagact tggcccattt ctattccaag tcgtcccca tagagaagct gttgaatctc  7800
acgctaggaa atagagggct gagaatcccc ccagagggag tgttaagttg ccttgagagg  7860
gttgattatg ataatgcatt tggaaggtat cttgccaaca cgtattcctc ttacttgttc  7920
ttccatgtaa tcaccttata catgaacgcc ctagactggg atgaagaaaa gaccatccta  7980
gcattatgga aagatttaac ctcagtggac atcgggaagg acttggtaaa gttcaaagac  8040
caaatatggg gactgctgat cgtgacaaag gactttgttt actcccaaag ttccaattgt  8100
cttttgaca gaaactacac acttatgcta aaagatcttt tcttgtctcg cttcaactcc  8160
ttaatggtct tgctctctcc cccagagccc cgatactcag atgacttgat atctcaacta  8220
tgccagctgt acattgctgg ggatcaagtc ttgtctatgt gtggaaactc cggctatgaa  8280
gtcatcaaaa tattggagcc atatgtcgtg aatagtttag tccagagagc agaaaagttt  8340
aggcctctca ttcattcctt gggagacttt cctgtatttta taaaagacaa ggtaagtcaa  8400
cttgaagaga cgttcggtcc ctgtgcaaga aggttcttta gggctctgga tcaattcgac  8460
aacatacatg acttggtttt tgtgtttggc tgttacaggc attgggggca cccatatata  8520
gattatcgaa agggtctgtc aaaactatat gatcaggttc accttaaaaa aatgatagat  8580
aagtcctacc aggagtgctt agcaagcgac ctagccagga ggatccttag atgggggttt  8640
gataagtact ccaagtggta tctggattca agattcctag cccgagacca ccccttgact  8700
ccttatatca aaacccaaac atggccaccc aaacatattg tagacttggt gggggataca  8760
tggcacaagc tcccgatcac gcagatcttt gagattcctg aatcaatgga tccgtcagaa  8820
atattggatg acaaatgaca ttcttttcacc agaacgagac tagcttcttg gctgtcagaa  8880
aaccgagggg ggcctgttcc tagcgaaaaa gttattatca cggccctgtc taagccgcct  8940
gtcaatcccc gagagtttct gaggtctata gacctcggag gattgccaga tgaagacttg  9000
ataattggcc tcaagccaaa ggaacgggaa ttgaagattg aaggtcgatt ctttgctcta  9060
atgtcatgga atctaagatt gtatttttgtc atcactgaaa aactcttggc caactacatc  9120
ttgccacttt ttgacgcgct gactatgaca gacaacctga acaaggtgtt taaaaagctg  9180
atcgacaggg tcaccgggca agggcttttg gactattcaa gggtcacata tgcatttcac  9240
ctggactatg aaaagtggaa caaccatcaa agattagagt caacagagga tgtattttct  9300
gtcctagatc aagtgtttgg attgaagaga gtgttttcta gaacacacga gtttttttcaa  9360
aaggcctgga tctattattc agacagatca gacctcatcg ggttacggga ggatcaaata  9420
tactgcttag atgcgtccaa cggcccaacc tgttggaatg gccaggatgg cgggctagaa  9480
ggcttacggg agaagggctg gagtctagtc agcttattga tgatagatag agaatctcaa  9540
atcaggaaca caagaaccaa aatactagct caaggagaca accaggtttt atgtccgaca  9600
tacatgttgt cgccagggct atctcaagag gggctcctct atgaattgga gagaatatca  9660
aggaatgcac tttcgatata cagagccgtc gaggaagggg catctaagct agggctgatc  9720
atcaagaaag aagagaccat gtgtagttat gacttcctca tctatggaaa aaccccctttg  9780
tttagaggta acatattggt gcctgagtcc aaaagatggg ccagagtctc ttgcgtctct  9840
aatgaccaaa tagtcaacct cgccaatata atgtcgacag tgtccaccaa tgcgctaaca  9900
gtggcacaac actctcaatc tttgatcaaa ccgatgaggg attttctgct catgtcagta  9960
caggcagtct ttcactacct gctatttagc ccaatcttaa aggaagagt ttacaagatt 10020
ctgagcgctg aagggggagag cttttctccta gccatgtcaa ggataatcta tctagatcct 10080
tctttgggag ggatatctgg aatgtccctc ggaagattcc atatacgaca gttctcagac 10140
cctgtctctg aagggttatc cttctggaga gagatctggt taagctccca agagtcctgg 10200
attcacgcgt tgtgtcaaga ggctggaaac ccagatcttg agagagaac actcgagagc 10260
tcactcgcg ttcagaaga tccgaccacc ttaaatatca gaggaggggc cagtcctacc 10320
attctactca aggatgcaat cagaaaggct ttatatgacg aggtggacaa ggtggaaaat 10380
tcagagtttc gagaggcaat cctgttgtcc aagacccata gagataattt tatactcttc 10440
ttaatatctg ttgagcctct gttcctctcga tttctcagtg agctattcag ttcgtctttt 10500
ttgggaatcc ccgagtcaat cattggattg atacaaaact cccgaacgat aagaaggcag 10560
tttagaaaga gtctctcaaa aactttagaa gaatccttct acaactcaga gatccacggg 10620
attagtcgga tgacccagac acctcagagg gttggggggg tgtggccttg ctcttcagag 10680
agggcagatc tacttaggga gatcttttg ggaagaaaaag tgtaggcac gacagttcct 10740
cacccttctg agatgttggg attacttccc aagtcctcta tttcttgcac ttgtggagca 10800
acaggaggag gcaatcctag agtttctgta tcagtactcc cgtcctttga tcagtcattt 10860
ttttcacgag gccccctaaa gggatacttg ggctcgtcca cctctatgtc gacccagcta 10920
ttccatgcat gggaaaaagt cactaatgtt catgtggtga agagagctct atcgttaaaa 10980
gaatctataa actggttcat tactagagat tccaacttgg ctcaagctct aattaggaac 11040
```

```
attatgtctc tgacaggccc tgatttccct ctagaggagg cccctgtctt caaaaggacg    11100
gggtcagcct tgcataggtt caagtctgcc agatacagcg aaggagggta ttcttctgtc    11160
tgcccgaacc tcctctctca tatttctgtt agtacagaca ccatgtctga tttgacccaa    11220
gacgggaaga actacgattt catgttccag ccattgatgc tttatgcaca gacatggaca    11280
tcagagctgg tacagagaga cacaaggcta agagactcca cgtttcattg gcacctccga    11340
tgcaacaggt gtgtgagacc cattgacgac gtgaccctgg agacctctca gatcttcgag    11400
tttccggatg tgtcgaaaag aatatccaga atggtttctg gggctgtgcc tcacttccag    11460
aggcttcccg atatccgtct gagaccagga gattttgaat ctctaagcgg tagagaaaag    11520
tctcaccata tcggatcagc tcaggggctc ttatactcaa tcttagtggc aattcacgac    11580
tcaggataca atgatggaac catcttccct gtcaacatat acggcaaggt ttcccctaga    11640
gactatttga gagggctcgc aaggggagta ttgataggac cctcgatttg cttcttgaca    11700
agaatgacaa atatcaatat taatagacct cttgaattgg tctcagggct aatctctcatat   11760
attctcctca ggctagataa ccatccctcc ttgtacataa tgctcagaga accgtctctt    11820
agaggagaga tattttctat ccctcagaaa atccccgccg cttatccaac cactatgaaa    11880
gaaggcaaca gatcaatctt gtgttatctc aacatgtgc tacgctatga gcgagagata    11940
atcacgcgct ctcagagaa tgactggcta tggatctttt cagactttag aagtgccaaa    12000
atgacgtacc tatccctcat tacttaccag tctcatcttc tactccagag ggttgagaga    12060
aacctatcta agagtatgag agataacctg cgacaattga gttctttgat gaggcaggtg    12120
ctgggcgggc acgagaaga taccttagag tcagacgaca acattcaacg actgctaaaa    12180
gactctttac gaaggacaag atgggtggat caagaggtgc gccatgcagc tagaaccatg    12240
actggagatt acagccccaa caagaaggtg tcccgtaagg taggatgttc agaatgggtc    12300
tgctctgtctc aacaggttgc agtctctacc cggcccctgt ctcggagctt    12360
gacataaggg ccctctctaa gaggttccag aacccttga tctcgggctt gagagtggtt    12420
cagtgggcaa ccggtgctca ttataagctt aagcctattc tagatgatct caatgttttc    12480
ccatctctct gccttgtagt tggggacggg tcaggggga tatcaagggc agtcctcaac    12540
atgtttccag atgccaagct tgtgttcaac agtcttttta aggtgaatga cctgatggct    12600
tccggaacac atccactgcc tccttcagca atcatgaggg gaggaaatga tatcgtctcc    12660
agagtgatga tcttgactc aatctgggaa aaaccgtccg acttgagaaa cttggcaacc    12720
tggaaatact tccagtcagt ccaaaagcag gtcaacatgt cctatgacct cattatttgc    12780
gatgcagaag ttactgacat tgcatctatc aaccggatca ccctgttaat gtccgattt    12840
gcattgtcta tagatggacc actctatttg gtcttcaaaa cttatgggac tatgctagta    12900
aatccaaact acaaggctat tcaacacctg tcaagagcgt tcccctcggt cacagggttt    12960
atcacccaag taacttcgtc ttttttcatct gagctctacc tccgattctc caaacgaggg    13020
aagttttttca gagatgctga gtacttgacc tcttccaagg ttcgagaaat gagccttgtg    13080
ttattcaatt gtagcagccc caagagtgag atgcagagag ctcgttcctt gaactatcag    13140
gatcttgtga gaggatttcc tgaagaaatc atatcaaatc cttacaatga gatgatcata    13200
actctgattg acagtgatgt agaatctttt ctagtccaca gatggttga tgatcttgag    13260
ttacagaggg gaactctgtc taagtggct atcattatag ccatcatgat agttttctcc    13320
aacagagtct tcaacgtttc caaacccta actgaccct cgttctatcc accgtctgat    13380
cccaaaatcc tgaggcactt caacatatgt tgcagtacta tgatgtatct atctactgct    13440
ttaggtgacg tccctagctt cgcaagactt cacgacctgt ataacagacc tataactat    13500
tacttcagaa agcaagtcat tcgagggaac gtttatctat cttggagttg gtccaacgac    13560
acctcagtgt tcaaaagggt agcctgtaat tctagcctga tcactggatc    13620
aggttgattt acaagatagt gaagactacc agactcgttg gcagcatcaa ggatctatcc    13680
agagaagtgg aaagacacct tcataggtac aacaggtgga tcaccctaga ggatatcaga    13740
tctagatcat ccctactaga ctacgttgc ctgtgaaccg gatactcctg gaagcctgcc    13800
catgctaaga ctcttgtgtg atgtatcttg aaaaaaacaa gatcctaaat ctgaaccttt    13860
ggttgtttga ttgttttct cattttttgtt gtttattgt taagcgt                   13907
```

| SEQ ID NO: 7 | moltype = DNA   length = 13907 |
|---|---|
| FEATURE | Location/Qualifiers |
| misc_feature | 1..13907 |
| | note = RABV vector: Coravax V1-South Africa (RABVG-E31) |
| source | 1..13907 |
| | mol_type = other DNA |
| | organism = synthetic construct |

```
SEQUENCE: 7
acgcttaaca accagatcaa agaaaaaaca gacattgtca attgcaaagc aaaaatgtaa      60
caccctaca atggatgccg acaagattgt attcaaagtc aataatcagg tggtctcttt     120
gaagcctgag attatcgtgg atcaatatga gtacaagtac cctgccatca aagatttgaa     180
aaagcccctgt ataaccctag gaaaggctcc cgatttaaat aaagcataca agtcagtttt    240
gtcaggcatg agcgccgcca aacttaatcc tgacgatgta tgttcctatt ggcagcggc     300
aatgcagttt tttgaggga catgtccgga agactggacc agctatggaa ttgtgattgc     360
acgaaaagga gataagatca ccccaggttc tctggtgaga ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttttg agacagcccc    600
ttttgttaaa atcgtgaac accatactct aatgacaact cacaaagtgt gtctaattg      660
gagtactata ccaaacttca gatttttggc cggaacctat gacatgtttt tctcccggat    720
tgagcatcta tattcagcaa tcagagtgag cacagttgtc actgcttatg aagactgttc    780
aggactggta tcatttactg ggttcataaa acaaatcaat ctcaccgcta gagaggcaat    840
actatatttc ttccacaaga actttgagga agagataaga gaatgtttg agccagggca    900
ggagacagct gttcctcact cttatttcat ccacttccgt tcactaggct tgagtgggaa     960
atctccttat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctagggggct atctgggaga ggaattcttc gggaagggg cattttgaaag   1140
aagattcttc agagatgaga aagaactcca agaatacgag cgcggtgaac tgacaaagac    1200
tgacgtagca ctggcagatg atggaactgt caactctgac gacgaggact acttttcagg    1260
tgaaaccaga gtccggagg ctgttttatac tcgaatcatg atgaatggag tcgactaaa    1320
```

```
gagatctcac atacggagat atgtctcagt cagttccaat catcaagccc gtccaaactc 1380
attcgccgag tttctaaaca agacatattc gagtgactca taacatgaaa aaaactaaca 1440
cccctcccgt acgccaccat gttcgtgttt ctggtgctgc tgcctctggt gagctcccag 1500
tgcgtgaact tcaccacaag gacccagctg cccccctgcct ataccaattc cttcacacgg 1560
ggcgtgtact atcccgacaa ggtgttccgg agcagcgtgc tgcactccac acaggatctg 1620
tttctgcctt tcttttctaa cgtgacctgc ttccacgcca tccacgtgag cggcaccaat 1680
ggcacaaagc ggttcgccaa tccagtgctg ccctttaacg atggcgtgta cttcgcctcc 1740
accgagaagt ctaacatcat cagaggctgg atctttggca ccacactgga cagcaagaca 1800
cagtccctgc tgatcgtgaa caatgccacc aacgtggtca tcaaggtgtg cgagttccag 1860
ttttgtaatg atccattcct gggcgtgtac tatcacaaga acaataagtc ttggatggag 1920
agcgagtttc gcgtgtattc ctctgccaac aattgcacat ttgagtacgt gtcccagccc 1980
ttcctgatgg acctggaggg caagcagggc aatttcaaga acctgaggga gttcgtgttt 2040
aagaatatcg atggctactt caaaatctac tccaagcaca ccccaatcaa cctggtgcgc 2100
ggcctgccac agggcttctc tgccctggag ccactggtgg atctgcccat cggcatcaac 2160
atcacccggt ttcagacact gctggccctg cacagaagct acctgacacc aggcgacagc 2220
tcctctggat ggaccgcagg agcagcagcc tactatgtgg gctatctgca gcccaggacc 2280
ttcctgctga agtacaacga gaatggcacc atcacagacg ccgtggattg cgccctggat 2340
cccctgtctg agaccaagtg tacactgaag agctttaccg tggagaaggg catctatcag 2400
acaagcaatt tcagggtgca gcctaccgag tccatcgtgc gctttcccaa tatcacaaac 2460
ctgtgccctt tggcgaggt gttcaacgca acccgcttcg ccagcgtgta cgcctggaat 2520
aggaagcgca tctccaactg cgtggccgac tattctgtgc tgtacaacag cgcctccttc 2580
tctaccttta agtgctatgg cgtgagcccc acaaagctga atgacctgtg ctttaccaac 2640
gtgtacgccg attccttcgt gatcagggc gacgaggtgc gccagatcgc caccaggacg 2700
acaggcaata tcgcagacta caattataag ctgcctgacg atttcaccgg ctgcgtgatc 2760
gcctggaact ctaacaatct ggatagcaaa gtgggcggca actacaatta tctgtaccgg 2820
ctgtttagaa agtctaatct gaagccattc gagagggaca tctccacaga aatctaccag 2880
gccggctcta ccccctgcaa tggcgtgaag ggctttaact gttatttccc tctgcagagc 2940
tacggcttcc agccaacata tggcgtgggc tatcagccct accgcgtggt ggtgctgtct 3000
tttgagctgc tgcacgcacc tgcaacagtg tgcggaccaa agaagagcac caatctggtg 3060
aagaacaagt gcgtgaactt caacttcaac ggactgaccg gaaccggcgt gctgaccgag 3120
tccaacaaga agttcctgcc ttttcagcag ttcggcaggg acatcgcaga taccacagac 3180
gccgtgcgcg accctcagac cctggagatc ctggacatca ccatgctc cttcggcggc 3240
gtgtctgtga tcacaccagg caccaataca agcaaccagg tggccgtgct gtatcagggc 3300
gtgaattgta ccgaggtgcc agtggcaatc cacgcagatc agctgaccc tactggcgg 3360
gtgtactcta ccggcagcaa cgtgttccag acaagaagcg gatgcctgat cggagcaggc 3420
cacgtgaaca atagctatga gtgcgacatc cctatcggcg ccggcatctg tgcctcctac 3480
cagacccaga caaactcccc aaggtctgtg ggagatgagg ccgaagactt tgtggaagtc 3540
cacctgcctg atgtgcataa ccaggtgtct ggcgtcgacc tgggactgcc aaattggggc 3600
aagtacgtgc tgctgagtgc tggagcactg actgccctga tgctgatcat tttcctgatg 3660
acctgctgtc ggcgcgtgaa cagaagtgag cccactcagc acaatctgcg aggaaccggg 3720
agagaagtgt cagtcacacc tcagagcggg aaaatcatta gtagttggga atcacataaa 3780
agcggggcg agaccaggct gtgagctagc atgaaaaaa actaacaccc ctccttttcga 3840
accatcccaa acatgagcaa gatctttgtc aatcctagtg ctattagagc cggtctggcc 3900
gatcttgaga tggctgaaga aactgttgat ctgatcaata gaaatatcga agacaatcag 3960
gctcatctcc aagggaacc catagaggtg gacaatctcc ctgaggatat ggggcgactt 4020
cacctggatg atggaaaatc gcccaaccat ggtgagatag ccaaggtggg agaaggcaag 4080
tatcgagagg actttcagat ggatgaagga gaggatctca gcttcctgtt ccagtcatac 4140
ctggaaaatg ttggagtcca aatagtcaga caaatgaggt caggagagag atttctcaag 4200
atatggtcac agaccgtaga agagattata tcctatgtcg cggtcaactt tcccaaccct 4260
ccaggaaagt cttcagagga taaatcaacc cagactactg gccgagagct caagaaggag 4320
acaacaccca ctccttctca gagagaaagc caatcatcga agccaggat ggcggctcaa 4380
attgcttctg gccctccagc ccttgaatgg tcgctacca atgaagagga tgatctatca 4440
gtggaggctg agatcgctca ccagattgca gaaagtttct ccaaaaaata taagtttccc 4500
tctcgatcct cagggatact cttgtataat tttgagcaat tgaaaatgaa ccttgatgat 4560
atagttaaag aggcaaaaaa tgtaccaggt gtgacccgtt tagcccatga cgggtccaaa 4620
ctccccctaa gatgtgtact gggatggtc gctttggcca actctaagaa attccagttg 4680
ttagtcgaat ccgacaagct gagtaaaatc atgcaagatg acttgaatcg ctatacatct 4740
tgctaaccga acctctcccc tcagtccctc tagacaataa atccgagat gtcccaaagt 4800
caacatgaaa aaaacaggca acaccactga taaaatgaac ctcctacgta agatagtgaa 4860
aaaccgcagg gacgaggaca ctcaaaaatc ctctcccgcg tcagcccctc tggatgacga 4920
tgacttgtgg cttccacccc ctgaatacgt cccgctgaaa gaacttacag gcaagaagaa 4980
catgaggaac ttttgtatca acggaagggt taaagtgtgt agcccgaatg gttactcgtt 5040
caggatcctg cggcacattc tgaaatcatt cgacgagata tattctggga atcataggat 5100
gatcgggtta gtcaaagtgg ttattggact ggctttgtca ggatctccag tccctgaggg 5160
cctgaactgg gtatacaaat tgaggagaac ctttatcttc cagtgggctg attccagggg 5220
ccctcttgaa gggggagagt tggaatactc tcaggagatc acttgggatg atgatactga 5280
gttcgtcgga ttgcaaataa gagtgattgc aaaacagtgt catatccagg gcagagtctg 5340
gtgtatcaac atgaaccga gagcatgtca actatgtctc gacatgtctc ttcagacaca 5400
aaggtccgaa gaggacaaag attcctctct gcttctagaa taatcagatt atatcccgca 5460
aatttatcac ttgttaccct ctggaggaga aacatatgg gctcaactcc aacccttggg 5520
agcaatataa caaaaacat gttatggtgc cattaaaccg ctgcatttca tcaaagtcaa 5580
gttgattacc tttacatttt gatcctcttg gatgtgaaaa aaactattaa catccctcaa 5640
aagacccgg gaaagatggt tcctcaggct ctcctgtttg tacccttct ggttttcca 5700
tttttgtggg ggaaattccc tatttacacg ataccagaca agcttggtcc ctggagtccg 5760
attgacatac atcaacctcag ctgcccaaac aatttggtag tggaggacga aggatgcacc 5820
aacctgtcag ggttctccta catgaacttt aaagttggat acatcttagc cataaaagtg 5880
aacgggttca cttgcacagg cgttgtgacg gaggctgaaa cctacactaa cttcgttggt 5940
tatgtcacaa ccacgttcaa aagaaagcat ttccgcccaa caccagatgc atgtagagcc 6000
gcgtacaact ggaagatggc cggtgacccc agatatgaag agtctctaca caatccgtac 6060
```

```
cctgactacc gctggcttcg aactgtaaaa accaccaagg agtctctcgt tatcatatct   6120
ccaagtgtgg cagatttgga cccatatgac agatcccttc actcgagggt cttccctagc   6180
gggaagtgct caggagtagc ggtgtcttct acctactgct ccactaacca cgattacacc   6240
atttggatgc ccgagaatcc gagactaggg atgtcttgtg acattttttac caatagtaga   6300
gggaagagag catccaaagg gagtgaagac tgccggcttg tagatgaaag aggcctatat   6360
aagtctttaa aaggagcatg caaactcaag ttatgtggag ttctaggact tagacttatg   6420
gatgaaacat gggtctcgat gcaaacatca aatgaaacca aatggtgccc tcccgataag   6480
ttggtgaacc tgcacgactt tcgctcagac gaaattgagc accttgttgt agaggagtta   6540
gtcaggaaga gagaggagtg tctggatgca ctagagtcca tcatgacaac caagtcagtg   6600
agtttcagac gtctcagtca tttaagaaaa cttgtccctg ggtttggaaa agcatatacc   6660
atattcaaca agaccttgat ggaagccgat gctcactaca agtcagtcga gacttggaat   6720
gagatcctcc cttcaaaagg gtgtttaaga gttgggggga ggtgtcatcc tcatgtgaac   6780
ggggtgtttt tcaatggtat aatattagga cctgacggca atgtcttaat cccagagatg   6840
caatcatccc tcctccagca acatatggag ttgttggaat cctcggttat ccccccttgtg   6900
cacccctgg cagacccgtc taccgttttc aaggacggtg acgaggctga ggattttgtt   6960
gaagttcacc ttcccgatgt gcacaatcag gtctcaggag ttgacttggg tctcccgaac   7020
tgggggaagt atgtattact gagtgcaggg gccctgactg ccttgatgtt gataattttc   7080
ctgatgacat gttgtagaag agtcaatcga tcagaaccta cgcaacacaa tctcagaggg   7140
acagggaggg aggtgtcagt cactcccaa agcgggaaga tcatatcttc atgggaatca   7200
cacaagagtg gggtgagac cagactgtaa ttaattaacg tcctttcaac gatccaagtc   7260
catgaaaaaa actaacaccc ctcccgtacc tagcttataa agtgctgggt catctaagct   7320
tttcagtcga gaaaaaaaca ttagatcaga agaacaactg gcaacactc tcaacctgag   7380
acttacttca agatgctcga tcctggagag gtctatgatg accctattga cccaatcgag   7440
ttagaggctg aacccagagg aaccccccatt gtccccaaca tcttgaggaa ctctgactac   7500
aatctcaact ctcctttgat agaagatcct gctagactaa tgttagaatg gttaaaaaca   7560
gggaatagac cttatcggat gactctaaca gacaattgct ccaggtcttt cagagttttg   7620
aaagattatt tcaagaaggt agatttgggt tctctcaagg tgggcggaat ggctgcacag   7680
tcaatgattt ctctctggtt atatggtgcc cactctgaat ccaacaggag ccggagatgt   7740
ataacagact tgcccccattt ctattccaag tcgtccccca tagagaagct gttgaatctc   7800
acgctaggaa atagagggct gagaatcccc ccagagggag ttaagttg ccttgagagg   7860
gttgattatg ataatgcatt tggaaggtat cttgccaaca cgtattcctc ttacttgttc   7920
ttccatgtaa tcaccttata catgaacgcc ctagactggg atgaagaaaa gaccatccta   7980
gcattatgga aagatttaac ctcagtggac atcgggaagg acttggtaaa gttcaaagac   8040
caaatatggg gactgctgat cgtgacaaag gactttgttt actcccaaag ttccaattgt   8100
cttttttgaca gaaactacac acttatgcta aaagatcttt tcttgtctcg cttcaactcc   8160
ttaatggtct tgctctctcc cccagagccc cgatactcag atgacttgat atctcaacta   8220
tgccagctgt acattgctgg ggatcaagtc ttgtctatgt gtggaaactc cggctatgaa   8280
gtcatcaaaa tattggagcc atatgtcgtg aatagtttag tccagagagc agaaaagttt   8340
aggcctctca ttcattcctt gggagacttt cctgtatta taaaagacaa ggtaagtcaa   8400
cttgaagaga cgtccggtcc ctgtgcaaga aggttcttta gggctctgga tcaattcgac   8460
aacatacatg acttggtttt tgtgtttggc tgttacaggc attggggggca cccatatata   8520
gattatcgaa agggtctgtc aaaactatat gatcaggttc accttaaaaa aatgatagat   8580
aagtcctacc aggagtgctt agcaagcgac ctagccagga ggatccttag atgggggtttt   8640
gataagtact ccaagtggta tctggattca agattcctag cccgagacca cccccttgact   8700
ccttatatca aaacccaaac atggccaccc aaacatattg tagacttggt gggggataca   8760
tggcacaagc tcccgatcac gcagatcttt gagattcctg aatcaatgga tccgtcagaa   8820
atattggatg acaaatcaca ttcctttcacc agaacgagac tagcttcttg gctgtcagaa   8880
aaccgagggg ggcctgttcc tagcgaaaaa gttattatca cggccctgtc taagccgcct   8940
gtcaatcccc gagagtttct gaggtctata gacctcggag gattgccaga tgaagacttg   9000
ataattggcc tcaagccaaa ggaacgggaa ttgaagattg aaggtcgatt ctttgctcta   9060
atgtcatgga atctaagatt gtatttttgtc atcactgaaa aactcttggc caactacatc   9120
ttgccacttt ttgacgcgct gactatgaca gacaacctga acaaggtgtt taaaaagctg   9180
atcgacaggg tcaccgggca agggcttttg gactattcaa gggtcacata tgcatttcac   9240
ctggactatg aaaagtggaa caaccatcaa agattagagt caacagagga tgtatttttct   9300
gtcctagatc aagtgtttgg attgaagaga gtgtttttttca gaacacacga gttttttcaa   9360
aaggcctgga tctattattc agacagatca gacctcatcg ggttacggga ggatcaaata   9420
tactgcttag atgcgtccaa cggcccaacc tgttggaatg gccaggatgg cgggctagaa   9480
ggcttacggc agaagggctg gagtctagtc agcttattga tgatagatag agaatctcaa   9540
atcaggaaca caagaaccaa aatactagct caaggagaca accaggtttt atgtccgaca   9600
tacatgttgt cgccagggct atctcaagag gggctcctct atgaattgga gagaatatca   9660
aggaatgcac tttcgatata cagagccgtc gaggaagggg catctaagct agggctgatc   9720
atcaagaaag aagagaccat gtgtagttat gacttcctca tctatggaaa aaccccctttg   9780
tttagaggta acatattggt gcctgagtcc aaaagatggg ccagagtctc ttgcgtctct   9840
aatgaccaaa tagtcaacct cgccaatata atgtcgacag tgtccaccaa tgcctcaaca   9900
gtggcacaac actctcaatc tttgatcaaa ccgatgaggg attttctgct catgtcagta   9960
caggcagtct ttcactacct gctatttagc ccaatcttaa agggaagagt ttacaagatt  10020
ctgagcgctc aaggggagag cttttctccta gccatgtcaa ggataatcta tctagatcct  10080
tctttgggag ggatatctgg aatgtccctc ggaagattcc atatacgaca gttctcagac  10140
cctgtctctg aagggttatc cttctggaga gatctgtt taagctccca agagtcctga  10200
attcacgcgt tgtgtcaaga ggctggaaac ccagatcttg agagagaac actcgagagc  10260
ttcactcgcc ttcagaaaga tccgaccacc ttaaatatca gaggagggc cagtcctacc  10320
attctactca aggatgcaat cagaaaggct ttatatgacg aggtggacaa ggtggaaaat  10380
tcagagttttc gagaggcaat cctgttgtcc aagacccata gagataattt tatactcttc  10440
ttaatatctg ttgagcctct gttctcctcga tttctcagtg agctattcag ttcgtctttt  10500
ttgggaatcc ccgagtcaat cattggattg atacaaaact cccgaacgat aagaaggcag  10560
tttagaaaga gtctctcaaa aactttagaa gaatccttct acaactcaga gatccacggg  10620
attagtcgga tgacccagac acctcagagg gttgggggga tgtggccttg ctcttcgaga  10680
agggcagatc tacttaggga gatctcttgg ggaagaaaag tggtaggcac gacagttcct  10740
cacccttctg agatgttggg attacttccc aagtcctcta tttcttgcac ttgtggagca  10800
```

```
acaggaggag gcaatcctag agtttctgta tcagtactcc cgtcctttga tcagtcattt   10860
ttttcacgag gcccctaaa gggatacttg ggctcgtcca cctctatgtc gacccagcta   10920
ttccatgcat gggaaaaagt cactaatgtt catgtggtga agagagctct atcgttaaaa   10980
gaatctataa actggttcat tactagagat tccaacttgg ctcaagctct aattaggaac   11040
attatgtctc tgacaggccc tgatttccct ctagaggagg ccctgtctt caaaaggacg   11100
gggtcagcct tgcataggtt caagtctgcc agatacagcg aaggagggta ttcttctgtc   11160
tgcccgaacc tcctctctca tatttctgtt agtacagaca ccatgtctga tttgacccaa   11220
gacgggaaga actacgattt catgttccag ccattgatgc tttatgcaca gacatggaca   11280
tcagagctgg tacagagaga cacaaggcta agagactca cgtttcattg gcacctccga   11340
tgcaacaggt gtgtgagacc cattgacgac gtgaccctgg agacctctca gatcttcgag   11400
tttccggatg tgtcgaaaag aatatcccaga atggtttctg gggctgtgcc tcacttccag   11460
aggcttcccg atatccgtct gagaccagga gattttgaat ctctaagcgg tagagaaaag   11520
tctccaccata tcggatcagc tcaggggctc ttatactcaa tcttagtggc aattcacgac   11580
tcaggataca atgatggaac catcttccct gtcaacatat acggcaaggt ttcccctaga   11640
gactatttga gagggctcgc aaggggagta ttgataggaa cctcgatttg cttcttgaca   11700
agaatgacaa atatcaatat taatagacct cttgaattgg tctcagggt aatctcatat   11760
attctcctga ggctagataa ccatccctcc ttgtacataa tgctcagaga accgtctctt   11820
agaggagaga tatttctat ccctcagaaa atccccgccg cttatccaac cactatgaaa   11880
gaaggcaaca gatcaatctt gtgttatctc caacatgtgc tacgctatga gcgagagata   11940
atcacggcgt ctccagagaa tgactggcta tggatctttt cagactttag aagtgccaaa   12000
atgacgtacc tatccctcat tacttaccag tctcatcttc tactccagag ggttgagaga   12060
aacctatcta agagtatgag agataacctg cgacaattga gttctttgat gaggcaggtg   12120
ctgggcgggc acgagaaga taccttagag tcagacgaca acattcaacg actgctaaaa   12180
gactcttta gaaggacaag atgggtggat caagaggtgc gccatgcagc tagaaccatg   12240
actggagatt acagccccaa caagaaggtg tcccgtaagg taggatgttc agaatgggtc   12300
tgctctgctc aacaggttgc agtctctacc tcagcaaacc cggcccctgt cctcggagctt   12360
gacataaggg ccctctctaa gaggttccga aaccctttga tctcgggctt gagagtggtt   12420
cagtgggcaa ccggtgctca ttataagctt aagcctattc tagatgatct caatgttttc   12480
ccatctctct gccttgtagt tggggacggg tcaggggga tatcaagggc agtcctcaac   12540
atgtttccag atgccaagct tgtgttcaac agtcttttag aggtgaatga cctgatggct   12600
tccggaacac atccactgcc tccttcagca atcatgaggg gaggaaatga tatcgtctcc   12660
agagtgatag atcttgactc aatctgggaa aaaccgtccg acttgagaaa cttggcaacc   12720
tggaaatact tccagtcagt ccaaaagcag gtcaacatgt cctatgacct cattatttgc   12780
gatgcagaag ttactgacat tgcatctatc aaccgatca ccctgttaat gtccgattt   12840
gcattgtcta tagatggacc actctatttg gtcttcaaaa cttatgggac tatgctagta   12900
aatccaaact acaaggctat tcaacacctg tcaagagcgt tccctcggt cacagggttt   12960
atcacccaag taacttcgtc ttttttcatct gagctctacc tccgattctc caacgagg   13020
aagttttttca gagatgctga gtacttgacc tcttccaccc ttcgagaaat gagccttgtg   13080
ttattcaatt gtagcagccc caagagtgag atgcagagag ctcgttcctt gaactatcag   13140
gatcttgtga gaggatttcc tgaagaaatc atatccaaatc cttacaatga gatgatcata   13200
actctgattg acagtgatgt agaatctttt ctagtccaca agatggttga tgatcttgag   13260
ttacagaggg gaactctgtc taaagtggct atcattatag ccatcatgat agtttctctcc   13320
aacagatct tcaacgttc caaaccccta actgaccct cgttctatcc accgtctgat   13380
cccaaaatcc tgaggcactt caacatatgt tgcagtacta tgatgtatct atctactgct   13440
ttaggtgacg tccctagctt cgcaagactt cacgacctgt ataacagacc tataacttat   13500
tacttcagaa agcaagtcat tcgagggaac gtttatctat cttggagttg gtccaacgac   13560
acctcagtgt tcaaaagggt agcctgtaat tctagcctga gtctgtcatc tcactggatc   13620
aggttgattt acaagatagt gaagactacc agactcgttg gcagcatcaa ggatctatcc   13680
agagaagtgg aaagacacct tcataggtac aacaggtgga tccctctaga ggatatcaga   13740
tctagatcat ccctactaga ctacagttgc ctgtgaaccg gatactcctg gaagcctgcc   13800
catgctaaga ctcttgtgtg atgtatcttg aaaaaaacaa gatcctaaat ctgaaccttt   13860
ggttgtttga ttgttttttct cattttttgtt gtttattttgt taagcgt              13907

SEQ ID NO: 8          moltype = DNA  length = 13958
FEATURE              Location/Qualifiers
misc_feature         1..13958
                     note = RABV vector: Coravax V2-China (RABVG-E51)
source               1..13958
                     mol_type = other DNA
                     organism = synthetic construct
SEQUENCE: 8
acgcttaaca accagatcaa agaaaaaaca gacattgtca attgcaaagc aaaaatgtaa     60
caccccctaca atggatgccg acaagattgt attcaaagtc aataatcagg tggtctcttt    120
gaagcctgag attatcgtgg atcaaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaaa ttgtgattgc    360
acgaaaagga gataagatca cccccaggttc tctggtggag ataaaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttgt agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cactgcttatg aagactgttc                 780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctcctat tcatcaaatg ctgttggtca cgtgttcaat ctcattcact ttgtaggatg   1020
ctatatgggt caagtcagat ccctaaatgc aacggttatt gctgcatgtg ctcctcatga   1080
```

-continued

```
aatgtctgtt ctaggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acgccaccat gttcgtgttt ctggtgctgc tgcctctggt gagctcccag    1500
tgcgtgaacc tgaccacaag gacccagctg cccctgcct ataccaattc cttcacacgg     1560
ggcgtgtact atcccgacaa ggtgttccgg agcagcgtgc tgcactccac acaggatctg    1620
tttctgcctt tcttttctaa cgtgacctgg ttccacgcca tccacgtgag cggcaccaat    1680
ggcacaaagc ggttcgacaa tccagtgctg ccctttaacg atggcgtgta cttcgcctcc    1740
accgagaagt ctaacatcat cagaggctgg atctttggca ccacactgga cagcaagaca    1800
cagtccctgc tgatcgtgaa caatgccacc aacgtggtca tcaaggtgtg cgagttccag    1860
ttttgtaatg atccattcct gggcgtgtac tatcacaaga acaataagtc ttggatggag    1920
agcgagtttc gcgtgtattc ctctgccaac aattgcacat ttgagtacgt gtcccagccc    1980
ttcctgatgg acctggaggg caagcagggc aatttcaaga acctgaggga gttcgtgttt    2040
aagaaatatcg atggctactt caaaatctac tccaagcaca cccaatcaa cctggtgcgc    2100
gacctgccac agggcttctc tgccctggag ccactggtgg atctgcccat cggcatcaac    2160
atcacccggt ttcagacact gctggccctg cacagaagct acctgacacc aggcgacagc    2220
tcctctggat ggaccgcagg agcagcagcc tactatgtgg gctatctgca gcccaggacc    2280
ttcctgctga agtacaacga gaatggcacc atcacagacg ccgtggattg cgccctggat    2340
ccctgtctg agaccaagtg tacactgaag agctttccgg tggagaaggg catctatcag    2400
acaagcaatt tcagggtgca gcctaccgag tccatcgtgc gctttcccaa tatcacaaac    2460
ctgtgccctt ttggcgaggt gttcaacgca acccgcttcg ccagcgtgta cgcctggaat    2520
aggaagcgca ctccaactg cgtggccgac tattctgtgc tgtacaacag cgcctccttc    2580
tctaccttta agtgctatgg cgtcagcccc acaaagctga atgacctgtg ctttaccaac    2640
gtgtacgccg attccttcgt gatcagggc gacgaggtgg gccagatcgc accaggacag    2700
acaggcaaga tcgcagacta caattataag ctgcctgacg atttcaccgg ctgcgtgatc    2760
gcctggaact ctaacaatct ggatagcaaa gtgggcggca actacaatta tctgtaccgg    2820
ctgtttagaa agtctaatct gaagccattc gagagggaca tctccacaga aatctaccag    2880
gccggctcta cccctgcaa tggcgtggag ggctttaact gttatttccc tctgcagagc     2940
tacggcttcc agccaacaaa cggcgtgggc tatcagccct accgcgtggt ggtgctgtct    3000
tttgagctgc tgcacgcacc tgcaacagtg tgcggaccaa agaagagcac caatctggtg    3060
aagaacaagt gcgtgaactt caacttcaac ggactgaccg gaacaggcgt gctgaccgag    3120
tccaacaaga agttcctgcc ttttcagcag ttcggcaggg acatcgcaga taccacagac    3180
gccgtgcgcg accctcagac cctggagatc ctggacatca ccatgctc cttcggcggc     3240
gtgtctgtga tcacaccagg caccaataca agcaaccagg tggccgtgct gtatcaggac    3300
gtgaattgta ccgaggtgcc agtggcaatc cacgcagatc agctgaccc ctacatggcgg    3360
gtgtactcta ccggcagcaa cgtgttccag acaagagccg gatgcctgat cggagcagag    3420
cacgtgaaca atagctatga gtgcgacatc cctatcggcg ccggcatctg tgcctcctac    3480
cagacccaga caaactcccc agaatcaagc gtgattcctc tggtccatcc actggcagat    3540
ccctccacag tgttcaaaga cggagatgag gccgaagact ttgtggaagt ccacctgcct    3600
gatgtgcata accaggtgtc tggcgtcgac ctgggactgc caaattgggg caagtacgtg    3660
ctgctgagtg ctggagcact gactgccctg atgctgatca ttttcctgat gacctgctgt    3720
cggcgcgtga acagaagtga gcccactcag cacaatctgc gaggaaccgg gagagaagtg    3780
tcagtcacac ctcagagcgg gaaaatcatt agtagttggg aatcacataa aagcggggc     3840
gagaccaggc tgtgagctag ccatgaaaaa aactaacacc cctccttcg aaccatccca     3900
aacatgagca agatctttgt caatcctagt gctattagag ccggtctggc cgatcttgag    3960
atggctgaag aaactgttga tctgatcaat agaaatatcg aagacaatca ggctcatctc    4020
caaggggaac ccatagaggt ggacaatctc cctgaggata tggggcgact tcacctggat    4080
gatggaaaat cgcccaacca tggtgagata gccaaggtgg gagaaggcaa gtatcgagag    4140
gactttcaga tggatgaagg agaggatcct agcttcctgt tccagtcata cctgaaaat     4200
gttggagtcc aaatagtcag acaaatgagg tcaggagaga gatttctcaa gatatggtca    4260
cagaccgtag aagagattat atcctatgtc gcggtcaact ttcccaaccc tccaggaaag    4320
tcttcagaga ataaatcaac cagactactt ggccgagagc tcaagaagga gcaacaccc    4380
actccttctc agagagaaag ccaatcatcg aaagcagga tggcggctca aattgcttct    4440
ggccctccag cccttgaatg gtcggctacc aatgaagagg atgatctatc agtggaggct    4500
gagatcgctc accagattgc agaaagtttc tccaaaaaat ataagtttcc ctctcgatcc    4560
tcaggatac tcttgtataa ttttgagcaa ttgaaaatga accttgatga tatagttaaa     4620
gaggcaaaaa atgtaccagg tgtgaccgt ttagcccatg acgggtccaa actcccccta    4680
agatgtgtac tgggatgggt cgctttggcc aactctaaga aattccagtt gttagtcgaa    4740
tccgacaagc tgagtaaaat catgcaagat gacttgaatc gctatacatc ttgctaaccg    4800
aacctctccc ctcagtccct ctagacaata aaatccgaga tgtcccaaag tcaacatgaa    4860
aaaaacaggc aacaccactg ataaaatgaa cctcctacgt aagatagtga aaaaccgcag    4920
ggacgaggac actcaaaaat cctctcccgc gtcagcccct ctggatgacg atgacttgtg    4980
gcttccaccc cctgaatacg tcccgctgaa agaacttaca gcaagaaga acatgaggaa     5040
cttttgtatc aacggaaggg ttaaagtgtg tagcccgaat ggttactcgt tcaggatcct    5100
gcggcacatt ctgaaatcat tcgacgagat atattctggg aatcataga tgatcgggtt    5160
agtcaaagtg gttattggac tggctttgtc aggatctcca gtccctgagg gcctgaactg    5220
ggtatacaaa ttgaggagaa cctttatctt ccagtgggct gattcagggg gccctcttga    5280
agggaggag ttgaaatact ctcaggagat cacttgggat gatgatactg agttcgtcgg     5340
attgcaaata agagtgattg caaaacagtg tcatatccag gcagagtct ggtgtatcaa     5400
catgaacccg agagcatgtc aactatggtc tgacatgtct cttcagacac aaaggtccga    5460
agaggacaaa gattcctctc tgcttctaga ataatcagat tatatcccgc aaatttatca    5520
cttgtttacc tctggaggag agaacatatg ggctcaactc caaccttgg gagcaatata     5580
acaaaaaaca tgttatggtg ccattaaacc gctgcattc atcaaagtca agttgattac      5640
ctttacattt tgatcctctt ggatgtgaaa aaaactatta acatccctca aaagaccccg    5700
ggaaagatgg ttcctcaggc tctcctgttt gtacccttc tggttttcc attgtgtttt      5760
gggaaattcc ctatttacac gataccagac aagcttggtc cctggagtcc gattgacata    5820
```

```
catcacctca gctgcccaaa caatttggta gtggaggacg aaggatgcac caacctgtca   5880
gggttctcct acatggaact taaagttgga tacatcttag ccataaaagt gaacgggttc   5940
acttgcacag gcgttgtgac ggaggctgaa acctacacta acttcgttgg ttatgtcaca   6000
accacgttca aagaaagca tttccgccca acaccagatg catgtagagc cgcgtacaac   6060
tggaagatgg ccggtgaccc cagatatgaa gagtctctac acaatccgta ccctgactac   6120
cgctggcttc gaactgtaaa aaccaccaag gagtctctcg ttatcatatc tccaagtgtg   6180
gcagatttgg acccatatga cagatccctt cactcgaggg tcttccctag cgggaagtgc   6240
tcaggagtag cggtgtcttc tacctactgc tccactaacc acgattacac catttggatg   6300
cccgagaatc cgagactagg gatgtcttgt gacatttta ccaatagtag agggaagaga   6360
gcatccaaag ggagtgagac ttgcggcttt gtagatgaaa gaggcctata taagtcttta   6420
aaaggagcat gcaaactcaa gttatgtgga gttctaggac ttagacttat ggatggaaca   6480
tgggtctcga tgcaaacatc aaatgaaacc aatggtgcc ctcccgataa gttggtgaac   6540
ctgcacgact ttcgctcaga cgaaattgag caccttgttg tagaggagtt ggtcaggaag   6600
agagaggagt gtctggatgc actagagtcc atcatgacaa ccaagtcagt gagttttcaga   6660
cgtctcagtc atttaagaaa acttgtccct gggtttggaa aagcatatac catattcaac   6720
aagaccttga tggaagccga tgctcactac aagtcagtcg agacttggaa tgagatcctc   6780
ccttcaaaag ggtgtttaag agttgggggg aggtgtcatc ctcatgtgaa cggggtgttt   6840
ttcaatggta taattattagg acctgacggg aatgtcttaa tcccagagat gcaatcatcc   6900
ctcctccagc aacatatgga gttgttggaa tcctcggtta tccccccttgt gcacccctg    6960
gcagacccgt ctaccgtttt caaggacggt gacgaggctg aggattttgt tgaagttcac   7020
cttcccgatg tgcacaatca ggtctcagga gttgacttgg gtctcccgaa ctgggggaag   7080
tatgttattac tgagtgcagg ggccctgact gccttgatga tgataattt cctgatgaca   7140
tgttgtagaa gagtcaatcg atcagaacct acgaacaca atctcagagg gacagggagg   7200
gaggtgtcag tcactcccca aagcgggaag atcatatctt catgggaatc acacaagagt   7260
gggggtgaga ccagactgta attaattaac gtcctttcaa cgatccaagt ccatgaaaaa   7320
aactaacacc cctcccgtac ctagcttata aagtgctggg tcatctaagc ttttcagtcg   7380
agaaaaaaac attagatcag aagaacaact ggcaacactt ctcaacctga gacttacttc   7440
aagatgctcg atcctggaga ggtctatgat gaccctattg acccaatcga gttagaggct   7500
gaacccagag gaacccccat tgtccccaac atcttgagga actctgacta caatctcaac   7560
tctcctttga tagaagatcc tgctagacta atgttagaat ggtaaaaac agggaataga   7620
ccttatcgga tgactctaac agacaattgc tccaggtctt tcagagtttt gaaagattat   7680
ttcaagaagg tagatttggg ttctctcaag gtgggcggaa tggctgcaca gtcaatgatt   7740
tctctctggt tatatggtgc ccactctgaa tccaacagga gccggagatg tataacagac   7800
ttggcccatt tctattccaa gtcgtccccc atagagaagc tgttgaatct cacgctagga   7860
aatagagggc tgaaatccc cccagaggga gtgttaagtt gccttgagag ggttgattat   7920
gataatgcat ttgaaggta tcttgccaac acgtattcct cttacttgtt cttccatgta   7980
atcacccttat acatgaacgc cctagactgg gatgaagaaa agaccatcct agcattatgg   8040
aaagatttaa cctcagtgga catcgggaag gacttggtaa agttcaaaga ccaaatatgg   8100
ggactgctga tcgtgacaaa ggactttgtt tactcccaaa gttccaattg tctttttgac   8160
agaaactaca cacttatgct aaaagatctt ttccttgtctc gcttcaactc cttaatggtc   8220
ttgctctctc ccccagagcc ccgatactca gatgacttga tatctcaact atgccagctg   8280
tacattgctg gggatcaagt cttgtctatg tgtggaaact ccggctatga agtcatcaaa   8340
atattggagc catatgtcgt gaatagttta gtccagagag cagaaaagtt taggcctctc   8400
attcattcct tgggagactt tcctgtattt ataaaagaca aggtaagtca acttgaagag   8460
acgttcggtc cctgtgcaag aaggttcttt agggctctgg atcaattcga caacatacat   8520
gacttggttt ttgtgtttgg ctgttacagg cattgggggc acccatatat agattatcga   8580
aagggtctgt caaaactata tgatcaggtt caccttaaaa aaatgataga taagtcctac   8640
caggagtgct tagcaagcga cctagccagg aggatcctta gatgggggttt tgataagtac   8700
tccaagtggt atctggattc aagattccta gcccgagacc acccccttgac tccttatatc   8760
aaaacccaaa catggccacc caaacatatt gtagacttgg tgggggatac atggcacaag   8820
ctcccgatca cgcagatctt tgagattcct gaatcaatgg atccgtcaga aatattggat   8880
gacaaatcac attcttttcac cagaacgaga ctagcttctt ggctgtcaga aaaccgaggg   8940
gggcctgttc ctagcgaaaa agttattatc acggccctgt ctaagccgcc tgtcaatccc   9000
cgagagtttc tgaggtctat agacctcgga ggattgccag atgaagactt gataattggc   9060
ctcaagccaa aggaacggga attgaagatt gaaggtcgat tctttgctct aatgtcatgg   9120
aatctaagat tgtatttttgt catcactgaa aaactcttgg ccaactacat cttgccactt   9180
tttgacgcgc tgactatgac agacaacctg aacaaggtgt ttaaaaagct gatcgacagg   9240
gtcaccgggc aagggctttt ggactattca agggtcacat atgcatttca cctgactctat   9300
gaaaagtgga acaaccatca aagattagag tcaacagagg atgtatttc tgtcctagat   9360
caagtgtttg gattgaagag agtgttttct agaacacacg agttttttca aaaggcctgg   9420
atctattatt cagacagatc agacctcatc gggttacggg aggatcaaat atactgctta   9480
gatgcgtcca acgcccaac ctgttggaat ggccaggatg gcgggctaga aggcttacgg   9540
cagaagggct ggagtctagt cagcttattg atgatagata gagaatctca aatcaggaac   9600
acaagaacca aaatactagc tcaaggaaca aaccaggttt tatgtccgac atacatgttg   9660
tcgccagggc tatctcaaga ggggctcctc tatgaattga gagaatatc aaggaatgca   9720
ctttcgatat acagagccgt cgaggaaggg gcatctaagc tagggctgat catcaagaaa   9780
gaagagacca tgtgtagtta tgacttcctc atctatggaa aaacccctctt gtttagaggt   9840
aacatattgg tgcctgagtc caaaagatgg gccagagcct cttgcgtctc taatgaccaa   9900
atagtcaacc tcgccaatat aatgtcgaca gtgtccacca atgccgtaac agtggcacaa   9960
cactctcaat ctttgatcaa accgatgagg gattttctgc tcatgtcagt acaggcagtg  10020
tttcactacc tgctatttag cccaatcctta aagggaagag tttacaagat tctgagcgct  10080
gaaggggaga gctttctcct agccatgtca aggataatct atctagatcc ttctttggga  10140
gggatatctg gaatgtccct cggaagattc catatacgac agttctcaga ccctgtctct  10200
gaagggtat ccttctggag agatctggc ttaagctcc aagagtcctg gattcacgcg  10260
ttgtgtcaag aggctggaaa cccagatctt ggagagagaa cactcgagag cttcactcgc  10320
cttctagaag atccgaccac cttaaatatc agaggagggg ccagtccta cattctactc  10380
aaggatgcaa tcgaaaaggc tttatatgac gaggtggaca aggtggaaaa ttcagagttt  10440
cgagaggcaa tcctgttgtc caagacccat agagataatt ttatactctt cttaatatct  10500
gttgagcctc tgtttcctcg attctcagt gagctattca gttcgtcttt tttgggaatc  10560
```

```
cccgagtcaa tcattggatt gatacaaaac tcccgaacga taagaaggca gtttagaaag    10620
agtctctcaa aaactttaga agaatccttc tacaactcag agatccacgg gattagtcgg    10680
atgacccaga cacctcagag ggttgggggg gtgtggcctt gctcttcaga gagggcagat    10740
ctacttaggg agatctcttg gggaagaaaa gtggtaggca cgacagttcc tcacccttct    10800
gagatgttgg gattacttcc caagtcctct atttcttgca cttgtggagc aacaggagga    10860
ggcaatccta gagtttctgt atcagtactc ccgtcctttg atcagtcatt tttttcacga    10920
ggccccctaa agggatactt gggctcgtcc acctctatgt cgacccagct attccatgca    10980
tgggaaaaag tcactaatgt tcatgtggtg aagagagctc tatcgttaaa agaatctata    11040
aactggttca ttactagaga ttccaacttg gctcaagctc taattaggaa cattatgtct    11100
ctgacaggcc ctgatttccc tctagaggag gcccctgtct tcaaaaggac ggggtcagcc    11160
ttgcataggt tcaagtctgc cagatacagc gaaggagggt attcttctgt ctgcccgaac    11220
ctcctctctc atatttctgt tagtacagac accatgtctg atttgaccca agacgggaag    11280
aactacgatt tcatgttcca gccattgatg ctttatgcac agacatggac atcagagctg    11340
gtacagagag acacaaggct aagagactct acgtttcatt ggcacctccg atgcaacagg    11400
tgtgtgagac ccattgacga cgtgaccctc gagacctctc agatcttcga gtttccggat    11460
gtgtcgaaaa gaatatccag aatggtttct ggggctgtgc ctcacttcca gaggcttccc    11520
gatatccgtc tgagaccagg agattttgaa tctctaagcg gtagagaaaa gtctcaccat    11580
atcggatcag ctcaggggct ctatactca atcttagtcg caattcacga ctcaggatac    11640
aatgatggaa ccatcttccc tgtcaacata tacggcaagg tttcccctag agactatttg    11700
agagggctcg caaggggagt attgatagga tcctcgattt gcttcttgac aagaatgaca    11760
aatatcaata ttaatagacc tcttgaattg gtctcagggg taatctcata tattctcctg    11820
aggctagata accatccctc gttgtacata atgctcaaga aaccgtctct tagaggagag    11880
atattttcta tccctcagaa aatccccgcc gcttatccaa ccactatgaa agaaggcaac    11940
agatcaatct tgtgttatct ccaacatgtg ctacgctatg agcgagagat aatcacggcg    12000
tctccagaga atgactggct atggatcttt tcagacttta gaagtgccaa aatgacgtac    12060
ctatccctca ttacttacca gtctcatctt ctactccaga gggttgagag aaacctatct    12120
aagagtatga gagataacct gcgacaattg agttctttga tgaggcaggt gctgggcggg    12180
cacggagaag ataccttaga gtcagacgac aacattcaac gactgctaaa agactcttta    12240
cgaaggacaa gatgggtgga tcaagaggtg cgccatgcag ctagaaccat gactggagat    12300
tacagcccca acaagaaggt gtcccgtaag gtaggatgtt cagaatgggt ctgctctgct    12360
caacaggttg cagtctctac ctcagcaaac ccggcccctg tctcggagct tgacataagg    12420
gccctctcta agaggttcca gaaccctttg atctcgggct tgagagtggt tcagtgggca    12480
accggtgctc attataagct taagcctatt ctagatgatc tcaatgtttt cccatctctc    12540
tgccttgtag ttggggacgg gtcagggggg atatcaaggg cagtcctcaa catgtttcca    12600
gatgccaagc ttgtgttcaa cagtcttttta gaggtgaga acctgatggc ttccggaaca    12660
catccactgc ctccttcagc aatcatgagg ggaggaaatg atatcgtctc cagagtgata    12720
gatcttgact caatctggga aaaaccgtcc gacttgagaa acttggcaac ctggaaatac    12780
ttccagtcag tccaaaagca ggtcaacatg tcctatgacc tcattatttg cgatgcagaa    12840
gttactgaca ttgcatctat caaccggatc accctgttaa tgtccgattt tgcattgtct    12900
atagatggac cactctattt ggtcttcaaa acttatggga ctatgctagt aaatccaaac    12960
tacaaggcta ttcaacacct gtcaagagcg ttccctcgg tcacagggtt tatcacccaa    13020
gtaacttcgt ctttttcatc tgagctctac ctccgattct ccaaacgagg gaagttttc    13080
agagatgctg agtacttgac ctcttccacc cttcgagaaa tgagccttgt gttattcaat    13140
tgtagcagcc ccaagagtga gatgcagaga gctcgttcct tgaactatca ggatcttgtg    13200
agaggatttc ctgaagaaat catatcaaat ccttacaatg agatgatcat aactctgatt    13260
gacagtgatg tagaatcttt tctagtccac aagatggttg atgatcttga gttacagagg    13320
ggaactctgt ctaaagtggc tatcattata gccatcatga gtttttctc caacagagtc    13380
ttcaacgttt ccaaacccct aactgacccc tcgttctatc caccgtctga tcccaaaatc    13440
ctgaggcact tcaacatatg ttgcagtact atgatgtatc tatctactgc tttaggtgac    13500
gtccctagct tcgcaagact tcacgacctg tataacagac ctataactta ttacttcaga    13560
aagcagtca ttcgagggaa cgtttatcta tcttggaagt ggtccaacga cacctcagtg    13620
ttcaaaaggg tagcctgtaa ttctagcctg agtctgtcat ctcactggat caggttgatt    13680
tacaagatag tgaagactac cagactcgtt ggcagcatca aggatctatc cagagaagtg    13740
gaaagacacc ttcataggta caacaggtgg atcaccctag aggatatcag atctagatca    13800
tccctactag actacagttg cctgtgaacc ggatatctct ggaagcctgc ccatgctaag    13860
actcttgtgt gatgtatctt gaaaaaaca agatcctaaa tctgaacctt tggttgtttg    13920
attgttttttc tcattttgt tgtttatttg ttaagcgt                            13958
SEQ ID NO: 9             moltype = DNA  length = 13958
FEATURE                  Location/Qualifiers
misc_feature             1..13958
                         note = RABV vector: Coravax V2 South Africa (S1-RABVG-E51)
source                   1..13958
                         mol_type = other DNA
                         organism = synthetic construct
SEQUENCE: 9
acgcttaaca accagatcaa agaaaaaaca gacattgtca attgcaaagc aaaaatgtaa      60
caccctaca atggatgccg acaagattgt attcaaagtc aataatcagg tggtctcttt     120
gaagcctgag attatcgtgg atcaatatga gtacaagtac cctgccatca aagatttgaa     180
aaagccctgt ataaccctag gaaaggctcc cgatttaaat aaagcataca agtcagtttt     240
gtcaggcatg agcgccgcca aacttaatcc tgacgatgta tgttcctatt tggcagcggc     300
aatgcagttt tttgagggga catgtccgga agactggacc agctatgaa ttgtgattgc     360
acgaaaagga gataagatca cccaggttc tctggtggag ataaaacgta ctgatgtaga     420
agggaattgg gctctgacag gaggcatgga actgacagga gccccactg tccctgagca     480
tgcgtccta gtcggtcttc tcttgagtct gtataggttg agcaaaatat ccggccaaaa     540
cactggtaac tataagacaa acattgcaga caggatagag cagattttttg agacagcccc     600
tttgttaaa atcgtggaac accatactct aatgacaact cacaaaatgt gtgctaattg     660
gagtactata ccaaacttca gatttttggc cggaaccta gacatgtttt tctcccggat     720
tgagcatcta tattcagcaa tcagagtggg cacagttgtc actgcttatg aagactgttc     780
```

-continued

```
aggactggta tcatttactg ggttcataaa acaaatcaat ctcaccgcta gagaggcaat        840
actatatttc ttccacaaga actttgagga agagataaga agaatgtttg agccagggca        900
ggagacagct gttcctcact ctttatttcat ccacttccgt tcactaggct tgagtgggaa       960
atctccttat tcatcaaatg ctgttggtca cgtgttcaat ctcattcact ttgtaggatg       1020
ctatatgggt caagtcagat ccctaaatgc aacggttatt gctgcatgtg ctcctcatga       1080
aatgtctgtt ctaggggggct atctgggaga ggaattcttc gggaaaggga catttgaaag      1140
aagattcttc agagatgaga aagaacttca agaatacgag gcggctgaac tgacaaagac       1200
tgacgtagca ctggcagatg atggaactgt caactctgac gacgaggact actttcagg        1260
tgaaaccaga agtccggagg ctgtttatac tcgaatcagt atgaatggag gtcgactaaa       1320
gagatctcac atacggagat atgtctcagt cagttccaat catcaagccc gtccaaactc       1380
attcgccgag tttctaaaca agacatattc gagtgactca taacatgaaa aaaactaaca       1440
cccctcccgt acgccaccat gttcgtgttt ctggtgctgc tgcctctggt gagctcccag       1500
tgcgtgaact tcaccacaag gacccagctg cccctgcct ataccaattc cttcacaggg        1560
ggcgtgtact atcccgacaa ggtgttccgg agcagcgtgc tgcactccac acaggatctg       1620
tttctgcctt tcttttctaa cgtgacctgg ttccacgcca tccacgtgag cggcaccaat       1680
ggcacaaagc ggttcgccaa tccagtgctg ccctttaacg atggcgtgta cttcgcctcc       1740
accgagaagt ctaacatcat cagaggctgg atctttggca ccacactgga cagcaagaca       1800
cagtccctgc tgatcgtgaa caatgccacc aacgtgtgca tcaaggtgtg cgagttccag       1860
ttttgtaatg atccattcct gggcgtgtac tatcacaaga acaataagtc ttggatggag       1920
agcgagtttc gcgtgtattc ctctgccaac aattgcacat ttgagtacgt gtcccagccc       1980
ttcctgatgg acctggaggg caagcagggc aatttcaaga acctgaggga gttcgtgttt       2040
aagaatatcg atggctactt caaaatctac tccaagcaca ccccaatcaa cctggtgcgg       2100
ggcctgccac agggcttctc tgccctggag ccactggtgg atctgcccat cggcatcaac       2160
atcacccggt tcagacactg ctggcctg cacagaagct acctgacacc aggcgacagc         2220
tcctctggat ggaccgcagg agcagcagcc tactatgtgg gctatctgca gcccaggacc       2280
ttcctgctga agtacaacga gaatggcacc atcacagacg ccgtgactg cgccctggat        2340
cccctgtctg agaccaagtg tacactgaag agctttaccg tggagaaggg catctatcag       2400
acaagcaatt tcagggtgca gcctaccgag tccatcgtgc gctttcccaa tatcacaaac       2460
ctgtgcccctt ttggcgaggt gttcaacgca acccgcttcg ccagcgtgta cgcctggaat      2520
aggaagcgca tctccaactg cgtgccgac tattctgtgc tgtacaacag cgcctccttc        2580
tctaccttta gtgctatgg cgtgagcccc acaaagctga atgacctgtg ctttaccaac        2640
gtgtacgccg attccttcgt gatcaggggc gacgaggtgc gccagatcgc accaggacag       2700
acaggcaata tcgcagacta caattataag ctgcctgacg atttcaccgg ctgcgtgatc       2760
gcctggaact ctaacaatct ggatagcaaa gtgggcggca actacaatta tctgtaccgg       2820
ctgtttagaa agtctaatct gaagccattc gagagggaca tctccacaga aatctaccag       2880
gccggctcta cccctgcaa tggcgtgaag ggctttaact gttatttccc tctgcagagc        2940
tacggcttcc agccaacata tggcgtgggc tatcagccct accgcgtggt ggtgctgtct       3000
tttgagctgc tgcacgcacc tgcaacagtg tgcggaccaa agaagagcac caatctggtg       3060
aagaacaagt gcgtgaactt caacttcaac ggactgaccg gaaccggtgt gctgaccgag       3120
tccaacaaga agttcctgcc ttttcagcag ttcggcaggg acatcgcaga taccacagac       3180
gccgtgcgcg accctcagac cctggagatc ctggacatca ccatgctc cttcggcggc        3240
gtgtctgtga tcaccaggg caccaataca agcaaccagg tggccgtgct gtatcagggc       3300
gtgaattgta ccgaggtgcc agtggcaatc cacgcagatc agctgacccc tacatggcgg       3360
gtgtactcta ccggcagcaa cgtgttccag acaagagccg gatgcctgat cggagcagag       3420
cacgtgaaca atagctatga gtgcgacatc cctatcggcg ccggcatctg tgcctcctac       3480
cagacccaga caaactcccc agaatcaagc gtgattcctc tggtccatcc actggcagat       3540
ccctccacag tgttcaaaga cggagatgga gccgaagact ttgtggaagt ccacctgcct       3600
gatgtgcata accaggtgtc tggcgtcgac ctgggactgc caaattgggg caagtacgtg       3660
ctgctgagtg ctggagcact gactgccctg atgctgatca ttttcctgat gacctgctgt       3720
cggcgcgtga acagaagtga gcccactcag cacaatctgc gaggaaccgg gagagaagtg       3780
tcagtcacac ctcagagcgg gaaaatcatt agtagttggg aatcacataa aagcgggggc       3840
gagaccaggc tgtgagctag ccatgaaaaa aactaacacc cctcctttcg aaccatccca       3900
aacatgagca agatctttgt caatcctagt gctattagag ccggtctggc cgatcttgag       3960
atggctgaag aaactgttga tctgatcaat agaaatatcg aagacaatca ggctcatctc       4020
caaggggaac ccatagaggt ggacaatctc cctgaggata tggggcgact tcacctggat       4080
gatgggaaaat cgcccaacca tggtgagata gccaaggtgg agaaggcaa gtatcgagag       4140
gactttcaga tggatgaagg agaggatcct agcttcctgt tccagtcata cctgaaaat        4200
gttggagtcc aaatagtcag acaaatgagg tcaggagaga gatttctcaa gatatggtca       4260
cagaccgtag aagagattat atcctatgtc gcggtcaact ttcccaaccc tccaggaaag       4320
tcttcagagg ataaatcaac ccagactact ggccgagagc tcaagaagga gacaacaccc       4380
actccttctc agagagaaag ccaatcatcg aaagccagga tggcggctca aattgcttct       4440
ggccctccag cccttgaatg gtcggctacc aatgaagagg atgatctatc agtggaggct       4500
gagatcgctc accagattgc agaaagtttc tccaaaaaat ataagtttcc ctctcgatcc       4560
tcaggatac tcttgtataa ttttgagcaa ttgaaaatga accttgata tagttaaa          4620
gaggcaaaaa atgtaccagg tgtgacccgt ttagcccatg acgggtccaa actcccccta       4680
agatgtgtac tgggatgggt cgctttggcc aactctaaga aattccagtt gttagtcgaa       4740
tccgacaagc tgagtaaaat catgcaagat gacttgaatc gctatacatc ttgctaaccg       4800
aacctctccc ctcagtccct ctagacaata aaatccgaga tgtccaaag tcaacatgaa        4860
aaaaacaggc aaccactg ataaaatgaa cctcctacgt aagatagtga aaaaccgcag         4920
ggacgaggac actcaaaaat cctctcccgc gtcagcccct ctggatgacg atgacttgtg       4980
gcttccaccc cctgaatacg tcccgctgaa agaacttaca ggcaagaaga acatgaggaa       5040
cttttgtatc aacggaaggg ttaaagtgtg tagcccgaat ggttactcgt tcaggatcct       5100
gcggcacatt ctgaaatcat tcgacagat atattctggg aatcatagga tgatcgggtt       5160
agtcaaagtg gttattggac tggcttttgt aggatctcca gtccctgagg gcctgaactg       5220
ggtatacaaa ttgaggagaa cctttatctt ccagtgggct gattcagggg ccctccttga       5280
agggggagga ttggaatact ctcaggagat cacttgggat gatgatactg agttcgtcgg       5340
attgcaaata gagtgattg caaaacagtg tcatatccag gcagagtct ggtgtatcaa        5400
catgaacccg agagcatgtc aactatggtc tgacatgtct cttcagacac aaaggtccga       5460
agaggacaaa gattcctctc tgcttctaga ataatcagat tatatcccgc aaatttatca       5520
```

```
cttgtttacc tctggaggag agaacatatg ggctcaactc caacccttgg gagcaatata   5580
acaaaaaaca tgttatggtg ccattaaacc gctgcatttc atcaaagtca agttgattac   5640
ctttacattt tgatcctctt ggatgtgaaa aaaactatta acatccctca aaagaccccg   5700
ggaaagatgg ttcctcaggc tctcctgttt gtacccttcc tggttttttcc attgtgtttt   5760
gggaaattcc ctatttacac gataccagac aagcttggtc cctggagtcc gattgacata   5820
catcacctca gctgcccaaa caatttggta gtggaggacg aaggatgcac caacctgtca   5880
gggttctcct acatggaact taaagttgga tacatcttag ccataaaagt gaacgggttc   5940
acttgcacag gcgttgtgac ggaggctgaa acctacacta acttcgttgg ttatgtcaca   6000
accacgttca aaagaaagca tttccgccca acaccagatg catgtagagc cgcgtacaac   6060
tggaagatgg ccggtgaccc cagatatgaa gagtctctac acaatccgta ccctgactac   6120
cgctggcttc gaactgtaaa aaccaccaag gagtctctcg ttatcatatc tccaagtgtg   6180
gcagatttgg acccatatga cagatccctt cactcgaggg tcttccctag cgggaagtgc   6240
tcaggagtag cggtgtcttc tacctactgc tccactaacc acgattacac catttggatg   6300
cccgagaatc cgagactagg gatgtcttgt gacatttta ccaatagtag agggaagaga   6360
gcatccaaag ggagtgagac ttgcggcttt gtagatgaaa gaggcctata taagtcttta   6420
aaaggagcat gcaaactcaa gttatgtgga gttctaggac ttagacttat ggatggaaca   6480
tgggtctcga tgcaaacatc aaatgaaacc aaatggtgcc ctcccgataa gttggtgaac   6540
ctgcacgact ttcgctcaga cgaaattgag caccttgttg tagaggagtt ggtcaggaag   6600
agagaggagt gtctggatgc actagagtcc atcatgacaa ccaagtcagt gagtttcaga   6660
cgtctcagtc atttaagaaa acttgtccct gggtttggaa aagcatatac catattcaac   6720
aagaccttga tggaagccga tgctcactac aagtcagtcg agacttggaa tgagatcctc   6780
ccttcaaaag ggtgtttaag agttgggggg aggtgtcatc ctcatgtgaa ctgggggtgttt   6840
ttcaatggta taatattagg acctgacggc aatgtcttaa tcccagagat gcaatcatcc   6900
ctcctccagc aacatatgga gttgttgaaa tcctcggtta tccccttgt gcaccccctg   6960
gcagaccgt ctaccgtttt caaggacggt gacgaggctg aggattttgt tgaagttcac   7020
cttccgatg tgcacaatca ggtctcagga gttgacttgg gtctcccgac ctgggggaag   7080
tatgtattac tgagtgcagg ggccctgact gccttgatgt tgataatttt cctgatgaca   7140
tgttgtagaa gagtcaatcg atcagaacct acgcaacaca atctcagagg gacagggagg   7200
gaggtgtcag tcactcccca aagcgggaag atcatatctt catgggaatc acacaagagt   7260
ggggggtgaga ccagactgta attaattaac gtcctttcaa cgatccaagt ccatgaaaaa   7320
aactaacacc cctcccgtac ctagcttata aagtgctggg tcatctaagc ttttcagtcg   7380
agaaaaaaac attagatcag aagaacaact ggcaacactt ctcaacctga gacttacttc   7440
aagatgctcg atcctggaga ggtctatgat gaccctattg acccaatcga gttagaggct   7500
gaacccagag gaacccccat tgtccccaac atctgagga aatctgacta caatctcaac   7560
tctcctttga tagaagatcc tgctagacta atgttagaat ggttaaaaac agggaataga   7620
ccttatcgga tgactctaac agacaattgc tccaggtctt tcagagtttt gaaagattat   7680
ttcaagaagg tagatttggg ttctctcaag gtgggcggaa tggctgcaca gtcaatgatt   7740
tctctctggt tatatggtgc ccactctgaa tccaacagga gccggagatg tataacagac   7800
ttggccatt tctattccaa gtcgtccccc atagagaagc tgttgaatct cacgctagga   7860
aatagagggc tgagaatccc cccagaggga gtgttaagtt gccttgagag ggttgattat   7920
gataatgcat ttgaaggta tcttgccaac acgtattcct cttacttgtt cttccatgta   7980
atcacctat acatgaacgc cctagactgg gatgaagaaa agaccatcct agcattatgg   8040
aaagatttaa cctcagtgga catcgggaag gacttggtaa agttcaaaga ccaaatatgg   8100
ggactgctga tcgtgacaaa ggactttgtt tactcccaaa gttccaattg tcttttttgac   8160
agaaactaca cacttatgct aaaagatctt ttcttgtctc gcttcaactc cttaatggtc   8220
ttgctctctc ccccagagcc ccgatactca gatgacttga tatctcaact atgccagctg   8280
tacattgctg gggatcaagt cttgtctatg tgtggaaact ccggctatga agtcatcaaa   8340
atattggagc catatgtcgt gaatagttta gtccagagag cagaaaagtt taggcctctc   8400
attcattcct tgggagactt tcctgtattt ataaaagaca aggtaagtca acttgaaagg   8460
acgttcggtc cctgtgcaag aaggttcttt agggctctgg atcaattcga caacatacat   8520
gacttggtttt ttgtgtttgg ctgttacagg cattgggggc acccatatat agattatcga   8580
aagggtctgt caaaactata tgatcaggtt cacttaaaaa aatgatagaa taagtcctac   8640
caggagtgct tagcaagcga cctagccagg aggatcctta gatgggggttt tgataagtac   8700
tccaagtggt atctggattc aagattccta gcccgagacc accccttgac tccttatatc   8760
aaaacccaaa catggccacc caaacatatt gtagacttgg tggggggatac atggcacaag   8820
ctcccgatca cgcagatctt tgagattcct gaatcaatgg atccgtcaga aatattggat   8880
gacaaatcac attctttcac cagaacgaga ctagcttctt ggctgtcaga aaaccgaggg   8940
gggcctgttc ctagcgaaaa agttattatc acggccctgt ctaagccgcc tgtcaatccc   9000
cgagagtttc tgaggtctat agacctcgga ggattgccag atgaagactt gataattgac   9060
ctcaagccaa aggaacggga attgaagatt gaaggtcgat tctttgtctc aatgtcatgg   9120
aatctaagat tgtattttgt catcactgaa aaactcttgg ccaactacat cttgccactt   9180
tttgacgcgc tgactatgac agacaacctg aacaaggtgt ttaaaaagct gatcgacagg   9240
gtcaccgggc aagggctttt ggactattca agggtcacat atgcatttca cctggactat   9300
gaaaagtgaa acaaccatca aagattagag tcaacagagg atgtatttc tgtcctagat   9360
caagtgtttg gattgaagag agtgttttct agaacacacg agttttttca aaaggcctga   9420
atctattatt cagacagatc agacctcatc ggggttacggg aggatcaaat atactgctta   9480
gatgcgtcca acgcccaac ctgttggaat ggccaggatg cgggctaga aggcttacgg   9540
cagaagggct ggagtctagt cagcttattg atgatagata gagaatctca aatcaggaac   9600
acaagaacca aaatactagc tcaaggagac aaccaggttt tatgtccgac atacatgtgg   9660
tcgccagggc tatctcaaga ggggctcctc tatgaattgg agagaatatc aaggaatgca   9720
ctttcgatat acagagccgt cgaggaaggg gcatctaagc tagggctgat catcaagaaa   9780
gaagagacca tgtgtagtta tgacttcctc atctatggaa aaaccccttt gtttagaggt   9840
aacatattgg tgcctgagtc caaaagatgg gccagagtct cttgcgtctc taatgaccaa   9900
atagtcaacc tcgccaatat aatgtcgaca gtgtccacca atgcgtaac agtggcacaa   9960
cactctcaat ctttgatcaa accgatgagg gattttctgc tcatgtcagt acaggcagtc  10020
tttcactacc tgctatttag cccaatcttaa agggaagag tttacaagat tctgagcgct  10080
gaaggggaga gctttctcct agccatgtca aggataatct atctagatcc ttctttggga  10140
gggatatctg aatgtccct cggaagattc catatacgac agttctcaga ccctgtctct  10200
gaagggttat ccttctggag agagatctgg ttaagctccc aagagtcctg gattcacgcg  10260
```

```
ttgtgtcaag aggctggaaa cccagatctt ggagagagaa cactcgagag cttcactcgc   10320
cttctagaag atccgaccac cttaaatatc agaggagggg ccagtcctac cattctactc   10380
aaggatgcaa tcagaaaggc tttatatgac gaggtggaca aggtggaaaa ttcagagttt   10440
cgagaggcaa tcctgttgtc caagacccat agagataatt ttatactctt cttaatatct   10500
gttgagcctc tgtttcctcg atttctcagt gagctattca gttcgtcttt tttgggaatc   10560
cccgagtcaa tcattggatt gatacaaaac tcccgaacga taagaaggca gtttagaaag   10620
agtctctcaa aaactttaga agaatccttc tacaactcag agatccacgg gattagtcgg   10680
atgacccaga cacctcagag ggttgggggg gtgtggcctt gctcttcaga gagggcagat   10740
ctacttaggg agatctcttg gggaagaaaa gtggtaggca cgacagttcc tcacccttcc   10800
gagatgttgg gattacttcc caagtcctct atttcttgca cttgtggagc aacaggagga   10860
ggcaatccta gagtttctgt atcagtactc ccgtcctttg atcagtcatt ttttttcacga   10920
ggcccccctaa agggatactt gggctcgtcc acctctatgt cgacccagct attccatgca   10980
tgggaaaaag tcactaatgt tcatgtggtg aagagagctc tatcgttaaa agaatctata   11040
aactggttca ttactagaga ttccaacttg gctcaagctc taattaggaa cattatgtct   11100
ctgacaggcc ctgatttccc tctagaggag gcccctgtct tcaaaaggac ggggtcagcc   11160
ttgcataggt tcaagtctgc cagatacagc gaaggaggt attcttctgt ctgcccgaac   11220
ctcctctctc atatttctgt tagtacagac accatgtctg atttgaccca agacgggaag   11280
aactacgatt tcatgttcca gccattgatg ctttatgcac agacatgcac atcagagctg   11340
gtacagagag acacaaggct aagagactct acgtttcatt ggcacctccg atgcaacagg   11400
tgtgtgagac ccattgacga cgtgaccctg gagacctctc agatcttcga gttccggat    11460
gtgtcgaaaa gaatatccag aatggtttct ggggctgtgc ctcacttcca gaggcttccc   11520
gatatccgtc tgagaccagg agattttgaa tctctaagcg gtagagaaaa gtctccaccat  11580
atcggatcag ctcaggggct cttatactca atcttagtgg caattcacga ctcaggatac   11640
aatgatggaa ccatcttccc tgtcaacata tacggcaagg tttcccctag agactatttg   11700
agagggctcg caagggagt attgatagga tcctcgattt gcttcttgac aagaatgaca   11760
aatatcaata ttaatagacc tcttgaattg gtctcaggga taatctcata tattctcctg   11820
aggctagata accatccctc cttgtacata atgctcagaa accgtctctc tagaggagag   11880
atattttcta tccctcagaa aatccccgcc gcttatccaa ccactatgaa agaaggcaac   11940
agatcaatcc tgtgttatct ccaacatgtg ctacgctatg agcgagagat aatcacggcg   12000
tctccagaga atgactggct atggatcttt tcagacttga gaagtgccaa aatgacgtac   12060
ctatccctca ttacttacca gtctcatctt ctactccaga gggttgagag aaacctatct   12120
aagagtatga gagataacct gcgacaattg agttctttga tgaggcaggt gctgggcggg   12180
cacggagaag ataccttaga gtcagacgac aacattcaac gactgctaaa agactcttta   12240
cgaaggacaa gatgggtgga tcaagaggtg cgccatgcag ctagaaccat gactggagat   12300
tacagcccca acaagaaggt gtcccgtaag gtaggatgtt cagaatggg ctgctctgct    12360
caacaggttg cagtctctac ctcagcaaac ccggcccctg tctcggagct tgacataagg   12420
gccctctcta agaggttcca gaacccttg atctcgggct tgagagtggt tcagtgggca    12480
accggtgctc attataagct taagcctatt ctagatgatc tcaatgtttt cccatctctc   12540
tgccttgtag ttggggacgg gtcaggggg atatcaaggg cagtcctcaa catgtttcca     12600
gatgccaagc ttgtgttcaa cagtcttta gaggtgaatg acctgatggc ttccggaaca    12660
catccactgc ctccttcagc aatcatgagg ggaggaaatg atatcgtctc cagagtgata   12720
gatcttgact caatctggga aaaaccgtcc gacttgagaa acttggcaac ctggaaatac   12780
ttccagtcag tccaaaagca ggtcaacatg tcctatgacc tcattatttg cgatgcagaa   12840
gttactgaca ttgcatctat caaccggatc accctgttaa tgtccgattt tgcattgtct   12900
atagatggac cactctattt ggtcttcaaa acttatggga ctatgctagt aaatccaaac   12960
tacaaggcta ttcaacacct gtcaagagcg ttccctcgg tcacagggtt tatcacccaa    13020
gtaacttcgt cttttcatc tgagctctac ctccgattct ccaaacgagg gaagttttc     13080
agatgctgc agtacttgac ctcttccacc cttcgagaaa tgagccttgt gttattcaat    13140
tgtagcagcc ccaagagtga gatgcagaga gctcgttcct tgaactatca ggatcttgtg   13200
agaggatttc ctgaagaaat catatcaaat ccttacaatg agatgatcat aactctgatt   13260
gacagtgatg tagaatcttt tctagtccac aagatggttg atgatcttga gttacagagg   13320
ggaactctgt ctaaagtggc tatcattata gccatcatga tagttttctc caacagagtc   13380
ttcaacgttt ccaaacccct aactgacccc tcgttctatc caccgtctga tcccaaaatc   13440
ctgaggcact tcaacatatg ttgcagtact atgatgtatc tatctactgc tttaggtgac   13500
gtccctagct tcgcaagact tcacgacctg tataacagac ctataactta ttacttcaga   13560
aagcaagtca ttcgagggaa cgtttatcta tcttggagtt ggtccaacga cacctcagtg   13620
ttcaaaaggg tagcctgtaa ttctagcctg agtctgtcat ctcactggat caggttgatt   13680
tacaagatag tgaagactac cagactcgtt ggcagcatca aggatctatc cagagaagtg   13740
gaaagacacc ttcataggta caacgatgtg atcaccctag aggatatcga atctagatca   13800
tccctactag actacagttg cctgtgaacc ggatactcct ggaagcctcc ccatgctaag   13860
actcttgtgt gatgtatctt gaaaaaaaca agatcctaaa tctgaacctt tggttgtttg   13920
attgtttttc tcatttttgt tgtttatttg ttaagcgt                           13958
```

```
SEQ ID NO: 10           moltype = DNA   length = 13826
FEATURE                 Location/Qualifiers
misc_feature            1..13826
                        note = RABV vector: Coravax V3-China (S1-VSVG-E26)
source                  1..13826
                        mol_type = other DNA
                        organism = synthetic construct SEQUENCE: 10
acgcttaaca accagatcaa agaaaaaaca gacattgtca attgcaaagc aaaaatgtaa    60
cacccctaca atggatgccg acaagattgt attcaaagtc aataatcagg tggtctcttt   120
gaagcctgag attatcgtgg atcaaatatga gtacaagtac cctgccatca aagatttgaa   180
aaagcccgt ataaccctag gaaaggctcc cgatttaaat aaagcataca agtcagtttt    240
gtcaggcatg agcgccgcca aacttaatcc tgacgatgta tgttcctatt tggcagcggc   300
aatgcagttt tttgagggga catgtccgga agactggacc agctatgaa ttgtgattgc     360
acgaaaagga gataagatca ccccaggttc tctggtggag ataaaacgta ctgatgtaga   420
agggaattgg gctctgacag gaggcatgga actgacaaga gaccccactg tccctgagca   480
```

```
tgcgtcctta gtcggtcttc tcttgagtct gtataggttg agcaaaatat ccgggcaaaa   540
cactggtaac tataagacaa acattgcaga caggatagag cagattttg agacagcccc   600
ttttgttaaa atcgtggaac accatactct aatgacaact cacaaaatgt gtgctaattg   660
gagtactata ccaaacttca gattttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga gagataaga agaatgtttg agccagggca   900
ggagacagct gttcctcact cttatttcat ccacttccgt tcactaggct tgagtgggaa   960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctagggggct atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag gtcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaacc tgaccacaag gacccagctg ccccctgcct ataccaattc cttcacaagg  1560
ggcgtgtact atcccgacaa ggtgttccgg agcagcgtgc tgcactccac acaggatctg  1620
tttctgcctt tcttttctaa cgtgacctgg ttccacgcca tccacgtgag cggcaccaat  1680
ggcacaaagc ggttcgacaa tccagtgctg cccttttaacg atgcgtgta cttcgcctcc  1740
accgagaagt ctaacatcat cagaggctgg atctttggca ccacactgga cagcaagaca  1800
cagtccctgc tgatcgtgaa caatgccacc aacgtgtca tcaaggtgtg cgagttccag  1860
ttttgtaatg atccattcct gggcgtgtac tatcacaaga acaataagtc ttggatggag  1920
agcgagtttc gcgtgtattc ctctgccaac aattgcacat ttgagtacgt gtcccagccc  1980
ttcctgatgg acctggaggg caagcagggc aatttcaaga acctgagga gttcgtgttt  2040
aagaatatcg atggctactt caaaatctac tccaagcaca ccccaatcaa cctggtgcgc  2100
gacctgccac agggcttctc tgccctggag ccactggtgg atctgcccat cggcatcaac  2160
atcacccggt tcagacact gctggccctg cacagaagct acctgacacc aggcgacagc  2220
tcctctggat ggaccgcagg agcagcagcc tactatgtgg gctatctgca gcccaggacc  2280
ttcctgctga gtacaacga gaatggcacc atcacagacg ccgtggattg cgccctggat  2340
cccctgtctg agaccaagtg tacactgaag agctttaccg tggagaaggg catctatcag  2400
acaagcaatt tcagggtgca gcctaccgag tccatcgtgc gctttccaa tatcacaaac  2460
ctgtgccctt ttggcgaggt gttcaacgca acccgcttcg ccagcgtgta cgcctggaat  2520
aggaagcgca tctccaactg cgtggccgac tattctgtgc tgtacaacag cgcctccttc  2580
tctaccttta gtgctatgg cgtgagcccc acaaagctga atgacctgtg ctttaccaac  2640
gtgtacgccg attccttcgt gatcagggc gacgaggtgc gccagatcgc accaggacag  2700
acaggcaaga tcgcagacta caattataag ctgcctgacg attcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta ccccctgcaa tggcgtggag ggctttaact gttatttccc tctgcagagc  2940
tacggcttcc agccaacaaa cggcgtgggc tatcagccct accgcgtggt ggtgctgtct  3000
tttgagctgc tgcacgcacc tgcaacagtg tgcggaccaa agaagagcac caatctgtgg  3060
aagaacaagt gcgtgaactt caacttcaac ggactgaccg gaacaggcgt gctgaccgag  3120
tccaacaaga agttcctgcc ttttcagcag ttcggcaggg acatcgcaga taccacagac  3180
gccgtgcgcg accctcagac cctggagatc ctggacatca ccatgctc cttcggcggc  3240
gtgtctgtga tcacaccagg caccaataca agcaaccagg tcgccgtgct gtatcaggac  3300
gtgaattgta ccgaggtgcc agtggcaatc cacgcagatc agctgacccc tacatgcgg  3360
gtgtactcta ccggcagcaa cgtgttccag acaagagccg gatgcctgat cggagcagag  3420
cacgtgaaca atagctatga gtgcgacatc cctatcggcg ccggcatctg tgcctcctac  3480
cagaccccaga caaactcccc aaggtctgtg ggcgatacag gcctgtccaa gaatccaatc  3540
gagctggtag agggctggtt cagcagttgg aaaagctcca tcgcctcctt ttctcttat  3600
atcggcctga tcatcggact gttcctggtg ctccgcgtgg gtatccacct gtgcatcaag  3660
ctgaagcaca ccaagaaaag acagatttat acagacatcg agatgaaccg cctgggaaag  3720
tgagctagcc atgaaaaaaa ctaacacccc tcctttcgaa ccatcccaaa catgagcaag  3780
atctttgtca atcctagtgc tattagagcc ggtctggccg atcttgagat ggctgaagaa  3840
actgttgatc tgatcaatag aaatatcgaa gacaatcagg ctcatctcca agggaaccc  3900
atagaggtgg acaatctccc tgaggatatg ggcgacttc acctggatga tggaaaatcg  3960
cccaaccatg gtgagatagc caaggtggga gaaggcaagt atcgagagga cttttcagatg  4020
gatgaaggag aggatcctag cttcctgttc cagtcatacc tggaaaatgt tggagtccaa  4080
atagtcagac aaatgaggtc aggagagaga tttctcaaga tatggtcaca gaccgtagaa  4140
gagattatat cctatgtcgc ggtcaacttt cccaaccctc aggaaagtc ttcagaggat  4200
aaatcaaccc agactactgg ccgagagctc aagaaggaga caacacccac tccttctcag  4260
agagaagcc aatcatcgaa agccaggatg gcggctcaga ttgcttctgg ccctccaaca  4320
cttgaatggt cggctaccaa tgaagaggat gatctatcag tggaggctga gatcgctcac  4380
cagattgcag aaagtttctc caaaaaatat aagtttccct ctcgatcctc agggatactc  4440
ttgtataatt tgagcaatt gaaaatgaac cttgatgata tagttaaaga ggcaaaaaat  4500
gtaccaggtg tgacccgttt agcccatgac gggtccaaac tccccctaag atgtgtactg  4560
ggatgggtcg ctttggccaa ctctaagaaa ttccagttgt tagtcgaatc cgacaagctg  4620
agtaaaatca tgcaagatga cttgaatcgc tatacatctt gctaaccgaa cctctcccct  4680
cagtccctct agacaataaa atccgagatg tcccaaagtc aacatgaaaa aaacaggcaa  4740
caccactgat aaaatgaacc tcctacgtaa gatagtgaaa aaccgcaggg acgaggacac  4800
tcaaaaatcc tctcccgcgt cagcccctct ggatgacgat gacttgtggc ttccaccccc  4860
tgaatacgtc ccgctgaaag aacttacagg caagaagaac atgaggaact tttgtatcaa  4920
cggaagggtt aaagtgtgta gcccgaatgg ttactcgttc aggatcctgc ggcacattct  4980
gaaatcattc gacgagatat attctgggaa tcataggatg atcgggttag tcaaagtggt  5040
tattggactg gctttgtcag gatctccagt ccctgagggc ctgaactggg tatacaaatt  5100
gaggagaacc tttatcttcc agtgggctga ttccagggc cctcttgaag ggaggagtt  5160
ggaatactct caggagatca cttgggatga tgatactgag ttcgtcggat tgcaaataag  5220
```

```
agtgattgca aaacagtgtc atatccaggg cagagtctgg tgtatcaaca tgaacccgag   5280
agcatgtcaa ctatggtctg acatgtctct tcagacacaa aggtccgaag aggacaaaga   5340
ttcctctctg cttctagaat aatcagatta tatcccgcaa atttatcact tgtttacctc   5400
tggaggagag aacatatggg ctcaactcca acccttggga gcaatataac aaaaaacatg   5460
ttatggtgcc attaaaacgc tgcatttcat caaagtcaag ttgattacct ttacattttg   5520
atcctcttgg atgtgaaaaa aactattaac atccctcaaa agaccccggg aaagatggtt   5580
cctcaggctc tcctgtttgt accccttctg gttttccat tgtgtttggg gaaattccct    5640
atttacacga taccagacaa gcttggtccc tggagtccga ttgacataca tcacctcagc   5700
tgcccaaaca atttggtagt ggaggacgaa ggatgcacca acctgtcagg gttctcctac   5760
atggaactta aagttggata catcttagcc ataaaagtga acgggttcac ttgcacaggc   5820
gttgtgacgg aggctgaaac ctacactaac ttcgttggtt atgtcacaac cacgttcaaa   5880
agaaagcatt tccgcccaac accagatgca tgtagagccg cgtacaactg gaagatggcc   5940
ggtgacccca gatatgaaga gtctctacac aatccgtacc ctgactaccg ctggcttcga   6000
actgtaaaaa ccaccaagga gtctctcgtt atcatatctc caagtgtggc agatttggac   6060
ccatatgaca gatcccttca ctcgagggtc ttccctagcg ggaagtgctc aggagtagcg   6120
gtgtcttcta cctactgctc cactaaccac gattacacca tttggatgcc cgagaatccg   6180
agactaggga tgtcttgtga catttttacc aatagtgagg gaagagagc atccaaaggg    6240
agtgagactt gcggctttgt agatgaaaga ggctatata agtctttaaa aggagcatgc    6300
aaactcaagt tatgtggagt tctaggactt agacttatgg atggaacatg ggtctctgatg  6360
caaacatcaa atgaaaccaa atggtgccct cccgataagt tggtgaacct gcacgacttt   6420
cgctcagacg aaattgagca ccttgttgta gaggagttgg tcaggaagag agaggagtgt   6480
ctggatgcac tagagtccat catgacaacc aagtcagtga gtttcagacg tctcagtcat   6540
ttaagaaaac ttgtccctgg gtttggaaaa gcatatacca tattcaacaa gaccttgatg   6600
gaagccgatg ctcactacaa gtcagtcgag acttggaatg agatcctccc ttcaaaaggg   6660
tgtttaagag ttggggggag gtgtcatcct catgtgaacg gggtgttttt caatggtata   6720
atattaggac ctgacggcaa tgtcttaatc ccagagatgc aatcatccct cctccagcaa   6780
catatggagt tgttggaatc ctcggttatc ccccttgtgc accccctggc agacccgtct   6840
accgttttca aggacggtga cgaggctgag gattttgttg aagttcacct tcccgatgtg   6900
cacaatcagg tctcaggagt tgacttgggt ctcccgaact gggggaagta tgtattactg   6960
agtgcagggg ccctgactgc cttgatgttg ataattttcc tgatgacatg ttgtagaaga   7020
gtcaatcgat cagaacctac gcaacacaat ctcagaggga cagggaggga ggtgtcagtc   7080
actcccaaa gcgggaagat catatcttca tgggaatcac acaagagtgg gggtgagacc     7140
agactgtaat taattaacgt cctttcaacg atccaagtcc atgaaaaaaa ctaacacccc   7200
tcccgtacct agcttataaa gtgctgggtc atctaagctt ttcagtcgag aaaaaaacat   7260
tagatcagaa gaacaactgg caacacttct caacctgaga cttacttcaa gatgctcgat   7320
cctggagagg tctatgatga ccctattgac ccaatcgagt tagaggctga acccagagga   7380
accccattg tccccaacat cttgaggaac tctgactaca atctcaactc tcctttgata    7440
gaagatcctg ctagactaat gttagaatgg ttaaaaacag gaatagacc ttatcggatg    7500
actctaacag acaattgctc caggtctttc agagttttga aagattattt caagaaggta   7560
gatttgggtt ctctcaaggt gggcggaatg gctgcacaca caatgatttc tctctggtta   7620
tatggtgccc actctgaatc caacaggagc cggagatgta taacagactt ggcccatttc   7680
tattccaagt cgtcccccat agagaagctg ttgaatctca cgctaggaaa tagagggctg   7740
agaatcccc cagagggagt gttaagttgc cttgagaggg ttgattatga taatgcattt   7800
ggaaggtatc ttgccaacac gtattcctct tacttgttct tccatgtaat caccttatac   7860
atgaacgccc tagactggga tgaagaaaag accatcctag cattatgaa agatttaacc    7920
tcagtggaca tcgggaagga cttggtaaag ttcaaagacc aaatatgggg actgctgatc   7980
gtgacaaagg actttgttta ctcccaaagt tccaattgtc tttttgacag aaactacaca   8040
cttatgctaa aagatctttt cttgtctcgc ttcaactcct taatggtctt gctctctccc   8100
ccagagcccc gatactcaga tgacttgata tctcaactat gccagctgta cattgctggg   8160
gatcaagtct tgtctatgtg tggaaactcc ggctatgaag tcatcaaaat attggagcca   8220
tatgtcgtga atagtttagt ccagagagca gaaaagttta ggcctctcat tcattccttg   8280
ggagactttc ctgtatttat aaaagacaag gtaagtcaac ttgaagagac gttcggtccc   8340
tgtgcaagaa ggttctttag ggctctggat caattcgaca acatacatga cttggttttt   8400
gtgtttggct gttacaggca ttgggggcac ccatatatag attatcgaaa gggtctgtca   8460
aaactatatg atcaggttca ccttaaaaaa atgatagata agtcctacca ggagtgctta   8520
gcaagcgacc tagccaggag gatccttaga tggggttttg ataagtactc caagtggtat   8580
ctggattcaa gattcctagc ccgagaccac cccttgactc cttatatcaa acccaaaaca   8640
tggccacccca aacatattgt agacttggtg ggggatacat ggcacaagct cccgatcacg   8700
cagatcttg agattcctga atcaatggat ccgtcagaaa tattggatga caaatcacat   8760
tctttcacca gaacgagact agcttcttgg ctgtcagaaa accgaggggg gcctgttcct   8820
agcgaaaaag ttattatcac ggccctgtct aagccgcctg tcaatccccg agagtttctg   8880
aggtctatag acctcggagg attgccagat gaagacttga taattggcct caagccaaag   8940
gaacgggaat tgaagattga aggtcgattc tttgctctaa tgtcatggaa tctaagattg   9000
tattttgtca tcactgaaaa actccttgcc aactacatct tgccacttttt ctgacgcgtg   9060
actatgacag acaacctgaa caaggtgttt aaaaagctga tcgacagggt caccgggcaa   9120
gggcttttgg actattcaag ggtcacatat gcatttcacc tggactatga aaagtggaac   9180
aaccatcaaa gattagagtc aacagaggat gtattttctg tcctgataca agtgtttgga   9240
ttgaagagag tgttttctag aacacgag tttttcaaa aggcctggat ctattattca    9300
gacagatcag acctcatcgg gttacgggag gatcaaatat actgcttaga tgacgtccaac   9360
ggcccaacct gttggaatgg ccaggatggc gggctagaag gcttacggca gaagggctgg   9420
agtctagtca gcttattgat gatagataga gaatctcaaa tcaggaacac aagaaccaaa   9480
atactagctc aaggagacaa ccaggttta tgtccgacat acatgttgtc gccagggcta    9540
tctcaagagg ggctcctcta tgaattggag agaaatcaa ggaatgcact ttcgatatac    9600
agagccgtcg aggaaggggc atctaagcta gggctgatca tcaagaaaga aggaaccatg   9660
tgtagttatg acttcctcat ctatggaaaa acccctttgt ttagaggtaa catattggtg   9720
cctgagtcca aaagatgggc cagagtctct tgcgtctcta atgacccaaat agtcaacctc   9780
gccaatataa tgtcgacagt gtccaccaat gcgctaacag tggcacaaca ctctcaatct   9840
ttgatcaaac cgatgagga ttttctgctc atgtcagtac aggcagtctt tcactacctg   9900
ctatttagcc caatcttaaa gggaagagtt tacaagattc tgagcgctga aggggagagc   9960
```

```
tttctcctag ccatgtcaag gataatctat ctagatcctt ctttgggagg gatatctgga    10020
atgtccctcg gaagattcca tatacgacga ttctcagacc ctgtctctga agggttatcc    10080
ttctggagag agatctggtt aagctcccaa gagtcctgga ttcacgcgtt gtgtcaagag    10140
gctgaaacc cagatcttgg agagagaaca ctcgagagct tcactcgcct tctagaagat    10200
ccgaccacct taaatatcag aggaggggcc agtcctacca ttctactcaa ggatgcaatc    10260
agaaaggctt tatatgacga ggtggacaag gtggaaaatt cagagtttcg agaggcaatc    10320
ctgttgtcca agaccatag agataatttt atactcttct taatatctgt tgagcctctg    10380
tttcctcgat ttctcagtga gctattcagt tcgtcttttt tgggaatccc cgagtcaatc    10440
attggattga tacaaaactc ccgaacgata agaaggcagt ttagaaagag tctctcaaaa    10500
actttagaag aatccttcta caactcagag atccacggga ttagtcggat gacccagaca    10560
cctcagaggg ttggggggt gtggccttgc tcttcagaga gggcagatct acttagggag    10620
atctcttggg gaagaaaagt ggtaggcacg acagttcctc accttctga gatgttggga    10680
ttacttccca agtcctctat ttcttgcact tgtggagcaa caggaggagg caatcctaga    10740
gttctgtat cagtactccc gtcctttgat cagtcatttt tttcacgagg cccctaaag    10800
ggatacttgg gctcgtccac ctctatgtcg acccagctat tccatgcatg ggaaaaagtc    10860
actaatgttc atgtggtgaa gagagctcta tcgttaaaag aatctataaa ctggttcatt    10920
actagagatt ccaacttggc tcaagctcta attaggaaca ttatgtctct gacaggccc    10980
gatttccctc tagaggaggc ccctgtcttc aaaaggacgg gctcagcctt gcataggttc    11040
aagtctgcca gatacagcga aggagggtat tcttctgtct gcccgaacct cctctctcat    11100
atttctgtta gtacagacac catgtctgat ttgacccaag acgggaagaa ctacgatttc    11160
atgttccagc cattgatgct ttatgcacag acatggacat cagagctggt acagagagac    11220
acaaggctaa gagactctac gtttcattgg cacctccgat gcaacaggtg tgtgagaccc    11280
attgacgacg tgaccctgga gacctctcag atcttgagt ttccggatgt gtcgaaaaga    11340
atatccagaa tggtttctgg ggctgtgcct cactccaga ggcttcccga tatccgtctg    11400
agaccaggag attttgaatc tctaagcggt agagaaaagt ctcaccatat cggatcagct    11460
caggggctct tatactcaat cttagtgca attcacgact caggatacaa tgatgaacc    11520
atcttccctg tcaacatata cggcaaggtt tcccctagag actatttgag agggctcgca    11580
aggggagtat tgataggatc ctcgatttgc ttcttgacaa gaatgacaaa tatcaatatt    11640
aatagacctc ttgaattggt ctcaggggta atctcatata ttctcctgag gctagataac    11700
catccctcct tgtacataat gctcagagaa ccgtctctta gggagagat attttctatc    11760
cctcagaaaa tccccgccgc ttatccaacc actatgaaag aaggcaacag atcaatcttg    11820
tgttatctcc aacatgtgct acgctatgag cgagagataa tcacggcgtc tccagagaat    11880
gactggctat ggatcttttc agactttaga agtgccaaaa tgacgtacct atccctcatt    11940
acttaccagt ctcatcttct actccagagg gttgagagaa aatcatctaa gagtatgaca    12000
gataacctgc gacaattgag ttctttgatg aggcaggtgc tgggcgggca cggagaagat    12060
accttagagt cagacgacaa cattcaacga ctgctaaaag actcttacg aaggacaaga    12120
tgggtggatc aagaggtgcg ccatgcagct agaaccatga ctggagatta cagccccaac    12180
aagaaggtgt cccgtaaggt aggatgttca gaatgggtct gctctgctca acaggttgca    12240
gtctctacct cagcaaaccc ggcccctgtc tcggagcttg acataagggc cctctctaag    12300
aggttccaga acccttttgat ctcgggcttg agagtggttc agtgggcaac cggtgctcat    12360
tataagctta agcctattct agatgatctc aatgttttcc catctctctg ccttgtagtt    12420
ggggacgggt caggggggat atcaagggca gtcctcaaca tgtttccaga tgccaagctt    12480
gtgttcaaca gtctttaga ggtgaatgac ctgatgcgtt ccggaacaca tccactgcct    12540
ccttcagcaa tcatgagggg aggaaatgat atcgtctcca gagtgataga tcttgactca    12600
atctgggaaa aacgtccga cttgagaaac ttggcaaccct ggaaatactt ccagtcagtc    12660
caaaagcagg tcaacatgtc ctatgacctc attatttgcg atgcagaagt tactgacatt    12720
gcatctatca accggatcac cctgttaatg tccgattttg cattgtctat agatgaccca    12780
ctctatttgg tcttcaaaac ttatgggact atgctagtaa atccaaacta caaggctatt    12840
caacacctgt caagagcgtt ccctcgtc acagggttta tcacccaagt aacttcgtct    12900
ttttcatctg agctctacct ccgattctcc aaacagggga agtttttcag agatgctgag    12960
tacttgacct cttccaccct tcgagaaatg agccttgtgt tattcaattg tagcagccgc    13020
aagagtgaga tgcagagagc tcgttccttg aactatcagg atcttgtgag aggatttcct    13080
gaagaaatca tatcaaatcc ttacaatgag atgatcataa ctctgattga cagtgatgta    13140
gaatcttttc tagtccacaa gatggttgat gatcttgagt acagagggg aactctgtct    13200
aaagtggcta tcattatagc catcatgata gttttctcca acagagtgt caacgtttcc    13260
aaaccctaa ctgacccctc gttctatcca ccgtctgatc ccaaaatcct gaggcacttc    13320
aacatatgtt gcagtactat gatgtatcta tctactgctt taggtgacgt ccctagcttc    13380
gcaagacttc acgacctgta taacagacct ataacttatt acttcagaaa gcaagtcatt    13440
cgagggaacg tttatctatc ttggagttgg tccaacgaca cctcagtgt caaaagggta    13500
gcctgtaatt ctagcctgag tctgtcatct cactggatca ggttgattta caagatagtg    13560
aagactacca gactcgttgg cagcatcaag gatctatcca gagaagtgga aagacaccctt    13620
cataggtaca caggtggat caccctagag gatatcagat ctagatcatc cctactagac    13680
tacagttgcc tgtgaaccgg atactcctgg aagcctgccc atgctaagac tcttgtgtga    13740
tgtatcttga aaaaaacaag atcctaaatc tgaaccttg gttgtttgat tgttttctc    13800
atttttgttg tttatttgtt aagcgt                                         13826

SEQ ID NO: 11       moltype = DNA   length = 13826
FEATURE             Location/Qualifiers
misc_feature        1..13826
                    note = RABV vector: Coravax V3-South Africa (S1-VSVG-E26)
source              1..13826
                    mol_type = other DNA
                    organism = synthetic construct
SEQUENCE: 11
acgcttaaca accagatcaa agaaaaaaca gacattgtca attgcaaagc aaaaatgtaa     60
caccccctaca atggatgccg acaagattgt attcaaagtc aataatcagg tggtctcttt    120
gaagcctgag attatcgtgg atcaatatga gtacaagtac cctgccatca agatttgaa    180
aaagccctgt ataaccctag gaaaggctcc cgatttaaat aaagcataca agtcagtttt    240
gtcaggcatg agcgccgcca aacttaatcc tgacgatgta tgttcctatt ggcagcggc    300
```

```
aatgcagttt tttgagggga catgtccgga agactggacc agctatgaa ttgtgattgc    360
acgaaaagga gataagatca ccccaggttc tctggtggag ataaaacgta ctgatgtaga   420
agggaattgg gctctgacag gaggcatgga actgacaaga gacccactg tccctgagca    480
tgcgtcctta gtcggtcttc tcttgagtct gtataggttg agcaaaatat ccgggcaaaa   540
cactggtaac tataagacaa acattgcaga caggatagag cagattttg agacagccc    600
ttttgttaaa atcgtggaac accatactct aatgacaact cacaaaatgt gtgctaattg   660
gagtactata ccaaacttca gattttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagataaga agaatgtttg agccagggca   900
ggagacagct gttcctcact cttatttcat ccacttccgt tcactaggct tgagtgggaa   960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctagggggct atctgggaga ggaattcttc gggaaaggga cattgaaag   1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag gtcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccaccat gttcgtgttt ctggtgctgc tgcctctggt gagctcccag  1500
tgcgtgaact tcaccacaag gacccagctg cccctgcct ataccaattc cttcacacgg   1560
ggcgtgtact atcccgacaa ggtgttccgg agcagcgtgc tgcactccac acaggatctg  1620
tttctgcctt tcttttctaa cgtgacctgg ttccacgcca tccacgtgag cggcaccaat  1680
ggcacaaagc ggttcgccaa tccagtgctg ccctttaacg atgcgtgta cttcgcctcc   1740
accgagaagt ctaacatcat cagaggctgg atctttggca ccacactgga cagcaagaca  1800
cagtccctgc tgatcgtgaa caatgccacc aacgtgtca tcaaggtgtg cgagttccag   1860
ttttgtaatg atccattcct gggcgtgtac tatcacaaga acaataagtc ttggatggag  1920
agcgagtttc gcgtgtattc ctctgccaac aattgcacat ttgagtacgt gtcccagccc  1980
ttcctgatgg acctggaggg caagcagggc aatttcaaga acctgaggga gttcgtgttt  2040
aagaatatcg atggctactt caaaatctac tccaagcaca ccccaatcaa cctggtgcgc  2100
ggcctgccac agggcttctc tgccctggag ccactggtgg atctgcccat cggcatcaac  2160
atcacccggt tcagacact gctggccctg cacagaagct acctgacacc aggcgacagc   2220
tcctctggat ggaccgcagg agcagcagcc tactatgtgg gctatctgca gcccaggacc  2280
ttcctgctga agtacaacga gaatggcacc atcacagacc cgtggattg cgccctggat   2340
ccccctgtctg agaccaagtg tacactgaag agctttaccg tggagaaggg catctatcag  2400
acaagcaatt tcagggtgca gcctaccgag tccatcgtgc gctttcccaa tatcacaaac  2460
ctgtgcccctt ttggcgaggt gttcaacgca acccgcttcg ccagcgtgta cgcctggaat  2520
aggaagcgca tctccaactg cgtggccgac tattctgtgc tgtacaacag cgcctccttc  2580
tctaccttta agtgctatgg cgtgagcccc acaaagctga atgacctgtg ctttaccaac  2640
gtgtacgccg attccttcgt gatcagggc gacgaggtgc gccagatcgc accaggacag   2700
acaggcaata tcgcagacta caattataag ctgcctgacg atttcaccgg ctgcgtgatc  2760
gcctggaact ctaacaatct ggatagcaaa gtgggcggca actacaatta tctgtaccgg  2820
ctgtttagaa agtctaatct gaagccattc gagagggaca tctccacaga aatctaccag  2880
gccggctcta ccccctgcaa tggcgtgaag ggctttaact gttatttccc tctgcagagc  2940
tacggcttcc agccaacata tggcgtgggc tatcagccct accgcgtggt ggtgctgtct  3000
tttgagctgc tgcacgcacc tgcaacagtg tgcggaccaa agaagagcac caatctggtg  3060
aagaacaagt gcgtgaactt caacttcaac ggactgaccg gaaccggcgt gctgaccgag  3120
tccaacaaga agttcctgcc ttttcagcag ttcggcaggg acatcgcaga taccacagac  3180
gccgtgcgcg accctcagac cctggagatc ctggacatca ccatgctc cttcggcggc   3240
gtgtctgtga tcacaccagg caccaataca agcaaccagg tggccgtgct gtatcaggc    3300
gtgaattgta ccgaggtgcc agtggcaatc cacgcagatc agctgaccc tacatggcg    3360
gtgtactcta ccggcagcaa cgtgttccag acaagagccg gatgcctgat cggagcagag  3420
cacgtgaaca atagctatga gtgcgacatc cctatcggcg ccggcatctg tgcctcctac  3480
cagacccaga caaactcccc aagtgtctgtg ggcgatacag gcctgtccaa gaatccaatc  3540
gagctggtag agggctggtt cagcagttgg aaaagctcca tcgcctcctt tttctttat    3600
atcggcctga tcatcggact gttcctggtg ctccgcgtgg gtatccacct gtgcatcaag  3660
ctgaagcaca ccaagaaaag acagatttat acagacatcg agatgaaccg cctgggaaag  3720
tgagctagcc atgaaaaaaa ctaacacccc tcctttcgaa ccatcccaaa catgagcaag  3780
atctttgtca atcctagtgc tattagagcc ggtctggccg atcttgagat ggctgaagaa  3840
actgttgatc tgatcaatag aaatatcgaa gacaatcagg ctcatctcca agggaaccc    3900
atagaggtgg acaatctccc tgaggatatg ggcgacttc acctggatga tggaaaatcg   3960
cccaaccatg gtgagatagc caaggtggga gaaggcaagt atcgagagga ctttcagatg  4020
gatgaaggag aggatcctag cttcctgttc cagtcatacc tggaaaatgt tggagtccaa  4080
atagtcgac aaatgaggtc aggagagaga tttctcaaga tatggtcaca gaccgtagaa  4140
gagattatat cctatgtcgc ggtcaacttt cccaaccctc caggaaagtc ttcagaggat  4200
aaatcaaccc agactactgg ccgagagctc aagaaggaga caacacccac tccttctcag  4260
agagaaagcc aatcatcgaa agccaggatg gcggctcaaa ttgcttctgg ccctccagcc  4320
cttgaatggt cggctaccaa tgaagaggat gatctcatcag tggaggctga gatcgctcac  4380
cagattgcag aaagtttctc caaaaaatat aagtttccct ctcgatcctc agggatactc  4440
ttgtataatt ttgagcaatt gaaaatgaac cttgatgata tagttaaaga ggcaaaaaat  4500
gtaccaggtg tgacccgttt agcccatgac gggtccaaac tcccctaag atgtgtactg    4560
ggatgggtcg ctttggccaa ctctaagaaa ttccagttgt tagtcgaatc cgacaagctg  4620
agtaaaatca tgcaagatga cttgaatcgc tatacatctt gctaaccgaa cctctcccct  4680
cctctcc cagtcccctct agacaataaa atccgagatg tcccaaagtc aacatgaaaa aaacaggcaa  4740
caccactgat aaaatgaacc tcctacgtaa gatagtgaaa aaccgcaggg acgaggacac  4800
tcaaaaatcc tctcccgcgt cagcccctct ggatgacgat gacttgtggc ttccaccccc  4860
tgaatacgtc ccgctgaaag aacttacagg caagaagaac atgaggaact tttgtatcaa  4920
cggaagggt aaagtgtgta gcccgaatgg ttactcgttc aggatcctgc ggcacattct   4980
gaaatcattc gacgagatat attctgggaa tcataggatg atcgggttag tcaaagtggt  5040
```

```
tattggactg gctttgtcag gatctccagt ccctgagggc ctgaactggg tatacaaatt   5100
gaggagaacc tttatcttcc agtgggctga ttccagggc cctcttgaag gggaggagtt   5160
ggaatactct caggagatca cttgggatga tgatactgag ttcgtcggat tgcaaataag   5220
agtgattgca aaacagtgtc atatccaggg cagagtctgg tgtatcaaca tgaacccgag   5280
agcatgtcaa ctatggtctg acatgtctct tcagacacaa aggtccgaag aggacaaaga   5340
ttcctctctg cttctagaat aatcagatta tatcccgcaa atttatcact tgtttacctc   5400
tggaggagag aacatatggg ctcaactcca acccttggga gcaatataac aaaaaacatg   5460
ttatggtgcc attaaaccgc tgcatttcat caaagtcaag ttgattacct ttacattttg   5520
atcctcttgg atgtgaaaaa aactattaac atccctcaaa agaccccggg aaagatggtt   5580
cctcaggctc tcctgtttgt acccccttctg gtttttccat tgtgttttgg gaaattccct   5640
atttacacga taccagacaa gcttggtccc tggagtccga ttgacataca tcacctcagc   5700
tgcccaaaca atttggtagt ggaggacgaa ggatgcacca acctgtcagg ttctcctac    5760
atggaactta aagttggata catcttagcc ataaaagtga acgggttcac ttgcacaggc   5820
gttgtgacgg aggctgaaac ctacactaac ttcgttgtt atgtcacaac cacgttcaaa    5880
agaaagcatt tccgcccaac accagatgca tgtagagccg cgtacaactg gaagatggcc   5940
ggtgacccca gatatgaaga gtctctacac aatccgtacc ctgactaccg ctggcttcga   6000
actgtaaaaa ccaccaagga gtctctcgtt atcatatctc caagtgtggc agatttggac   6060
ccatatgaca gatcccttca ctcgagggtc ttccctagcg ggaagtgctc aggagtagcg   6120
gtgtcttcta cctactgctc cactaaccac gattacacca tttggatgcc cgagaatccg   6180
agactaggga tgtcttgtga cattttttacc aatagtagag ggaagagagc atccaaaggg   6240
agtgagactt gcgggctttgt agatgaaaga ggcctatata agtctttaaa aggagcatgc   6300
aaactcaagt tatgtggagt tctaggactt agacttatgg aggaacatg ggtctcgatg     6360
caaacatcaa atgaaaccaa atggtgccct cccgataagt tggtgaacct gcacgacttt   6420
cgctcagacg aaattgagca ccttgttgta gaggagttgg tcaggaagag agaggagtgt   6480
ctggatgcac tagagtccat catgacaacc aagtcagtga gtttcagacg tctcagtcat   6540
ttaagaaaac ttgtccctgg gttttgaaaa gcatatacca tattcaacaa gaccttgatg   6600
gaagccgatg ctcactacaa gtcagtcgag acttggaatg agatcctccc ttcaaaaggg   6660
tgtttaagag ttgggggggag tgtcatcct catgtgaacg gggtgttttt caatggtata   6720
atattaggac ctgacggcaa tgtcttaatc ccagagatgc aatcatccct cctccagcaa    6780
catatggagt tgttggaatc tcggttatc ccccttgtgc accccctggc agacccgtct     6840
accgttttca aggacggtga cgaggctgag gattttgttg aagttcacct tcccgatgtg    6900
cacaatcagg tctcaggagt tgacttgggt ctcccgaact gggggaagta tgtattactg   6960
agtgcagggg ccctgactgc cttgatgttg ataatttttcc tgatgacatg ttgtagaaga  7020
gtcaatcgat cagaacctac gcaacacaat ctcagaggga cagggaggga ggtgtcagtc    7080
actcccaaa gcgggaagat catatcttca tgggaatcac acaagagtgg gggtgagacc     7140
agactgtaat taattaacgt cctttcaacg atccaagtcc atgaaaaaaa ctaacaccc    7200
tcccgtacct agcttataaa gtgctgggtc atctaagctt ttcagtcgag aaaaaaacat   7260
tagatcagaa gaacaactgg caacacttct caacctgaga cttacttcaa gatgctcgat   7320
cctggaagga tctatgatga cccctattgac ccaatcgagt tagaggctga acccagagga  7380
accccccattg tccccaacat cttgaggaac tctgactaca atctcaactc tccttttgata 7440
gaagatcctg ctagactaat gttagaatgg ttaaaaacag ggaatagacc ttatcggatg    7500
actctaacag acaattgctc caggtctttc agagtttttga aagattattt caagaaggta   7560
gatttggtt ctctcaaggt gggcggaatg gctgcacagt caattgatttc tctctggtta    7620
tatggtgccc actctgaatc caacaggagc cggagatgta taacagactt ggcccatttc    7680
tattccaagt cgtcccccat agagaagctg ttgaatctca cgctaggaaa tagagggctg   7740
agaatccccc cagagggagt gttaagttgc cttgagaggg ttgattatga taatgcattt    7800
ggaaggtatc ttgccaacac gtattcctct tacttgttct tccatgtaat caccttatac    7860
atgaacgccc tagactggga tgaagaaaag accatcctag cattatgaa agatttaacc     7920
tcagtggaca tcgggaagga cttggtaaag ttcaaagacc aaatatgggg actgctgatc    7980
gtgacaaagg actttgttta ctcccaaagt tccaattgtc ttttttgacag aaactacaca    8040
cttatgctaa aagatctttt cttgtctcgc ttcaactcct taatggtctt gctctctcca    8100
ccagagcccc gatactcaga tgacttgata tctcaactat gccagctgta cattgctggg    8160
gatcaagtct tgtctatgtg tggaaactcc ggctatgaag tcatcaaaat attggagcca    8220
tatgtcgtga atagtttagt ccagagagca gaaaagttta ggcctctcat tcattccttg    8280
ggagactttc ctgtatttat aaaaagacaag gtaagtcaac ttgaagagac ttcggtccc   8340
tgtgcaagaa ggttcttttag ggctctggat caattcgaca acatacatga cttggttttt   8400
gtgtttggct gttacaggca ttgggggcac ccatatatag attatcgaaa gggtctgtca    8460
aaactatatg atcaggttca ccttaaaaaa atgatagata agtcctacca ggagtgctta    8520
gcaagcgacc tagccaggag gatccttaga tggggttttg ataagtactc caagtggtat   8580
ctggattcaa gattcctagc ccgagaccac cccttgactc cttatatcaa aacccaaaca   8640
tggccaccca aacatattgt agacttggtg ggggatacat ggcacaagct cccgatcacg    8700
cagatctttg agattcctga atcaatggat ccgtcagaaa tattggatga caaatcacat   8760
tctttcacca gaacgagact agcttcttgg ctgtcagaaa accgagggggg gcctgttcct   8820
agcgaaaaag ttattatcac ggccctgtct aagccgctc tcaatcccg agagttttctg   8880
aggtctatag acctcggagg attgccagat gaagacttga taattggcct caagccaaag    8940
gaacgggaat tgaagattga aggtcgattc tttgctctaa tgtcatggaa tctaagattg    9000
tattttgtca tcactgaaaa actcttgccc aactacatct tgccacttt tgacgcgctg     9060
actatgacag acaacctgaa caaggtgttt aaaaagctga tcgacagggt cacogggcaa   9120
gggcttttgg actattcaag ggtcacatat gcatttcacc tggactatga aagtgcaac    9180
aaccatcaaa gattagagtc aacagaggat gtattttctg tcctagatca agtgtttgga   9240
ttgaagagag tgttttctag aacacacgag tttttttcaaa aggcctggat ctattattca   9300
gacagatcag acctcatcgg gttacgggag atcaaatat actgcttaga tcgtccaac    9360
ggcccaacct gttggaatgg ccaggatggc gggctagaaa gcttacgca gaagggctgg   9420
agtctgtca gcttattgat gatagataga tcaggaacac aagaaccaaa                9480
atactagctc aaggagacaa ccaggttta tgtccgacat acatgttgtc gccagggcta    9540
tctcaagagg ggctcctcta tgaattggag agaatatcaa ggaatgcact ttcgatatac    9600
agagccgtcg aggaagggc atctaagcta gggctgatca tcaagaaaga agagaccatg   9660
tgtagttatg acttcctcat ctatggaaaa acccccttgt ttagaggtaa catattggtg    9720
cctgagtcca aagatgggc cagagtctct tgcgtctcta atgaccaaat agtcaacctc    9780
```

```
gccaatataa tgtcgacagt gtccaccaat gcgctaacag tggcacaaca ctctcaatct   9840
ttgatcaaac cgatgaggga ttttctgctc atgtcagtac aggcagtctt tcactacctg   9900
ctatttagcc caatcttaaa gggaagagtt tacaagattc tgagcgctga aggggagagc   9960
tttctcctag ccatgtcaag gataatctat ctagatcctt ctttgggagg gatatctgga  10020
atgtccctcg gaagattcca tatacgacag ttctcagacc ctgtctctga agggttatcc  10080
ttctggagag agatctggtt aagctcccaa gagtcctgga ttcacgcgtt gtgtcaagag  10140
gctggaaacc cagatcttgg agagagaaca ctcgagagct tcactcgcct tctagaagat  10200
ccgaccacct taaatatcag aggaggggcc agtcctacca ttctactcaa ggatgcaatc  10260
agaaaggctt tatatgacga ggtggacaag gtggaaaatt cagagtttcg agaggcaatc  10320
ctgttgtcca agacccatag agataatttt atactcttct taatatctgt tgagcctctg  10380
tttcctcgat ttctcagtga gctattcagt tcgtcttttt tgggaatccc cgagtcaatc  10440
attggattga tacaaaactc ccgaacgata agaaggcagt ttagaaagag tctctcaaaa  10500
actttagaag aatccttcta caactcagag atccacggga ttagtcggat gacccagaca  10560
cctcagaggg ttgggggggt gtggccttgc tcttcagaga gggcagatct acttagggag  10620
atctcttggg gaagaaaagt ggtaggcacg acagttcctc acccttctga gatgttggga  10680
ttacttccca agtcctctat ttcttgcact tgtggagcaa caggaggagg caatcctaga  10740
gtttctgtat cagtactccc gtcctttgat cagtcatttt tttcacgagg cccctaaag   10800
ggatacttgg gctcgtccac ctctatgtcg acccagctat tccatgcatg ggaaaaagtc  10860
actaatgttc atgtggtgaa gagagctcta tcgttaaaag aatctataaa ctggttcatt  10920
actagagatt ccaacttggc tcaagctcta attaggaaca ttatgtctct gacaggccct  10980
gatttccctc tagaggaggc ccctgtcttc aaaaggacgg ggtcagcctt gcataggttc  11040
aagtcgcca gatacagcga aggagggtat tcttctgtct gcccgaacct cctctctcat  11100
atttctgtta gtacagacac catgtctgat ttgacccaag acgggaagaa ctacgatttc  11160
atgttccagc cattgatgct ttatgcacag acatggacat cagagctggt acagagagac  11220
acaaggctaa gagactctac gtttcattgg cacctccgat gcaacaggtg tgtgagaccc  11280
attgacgacg tgaccctgga gacctctcag atcttcgatt ttccggatgt gtcgaaaaga  11340
atatccagaa tggtttctgg ggctgtgcct cacttccaga ggcttcccga tatccgtctg  11400
agaccaggag atttttgaatc tctaagcggt agagaaaagt ctcaccatat cggatcagct  11460
caggggctct tatactcaat cttagtggca attcacgact caggatacaa tgatggaacc  11520
atcttccctg tcaacatata cggcaaggtt tcccctagag actatttgag agggctcgca  11580
agggagtat tgataggatc ctcgatttgc ttcttgacaa gaatgacaaa tatcaatatt  11640
aatagacctc ttgaattggt tcagggggta atctcatata ttctcctgag gctagataac  11700
catccctcct tgtacataat gctcagagaa ccgtctctta gaggagagat attttctatc  11760
cctcagaaaa tccccgccgc ttatccaacc actatgaagg aaggcaacag atcaatcttg  11820
tgttatctcc aacatgtgct acgctatgag cgagagataa tcacggcgtc tccagagaat  11880
gactggctat ggatcttttc agacttttaga agtgccaaaa tgacgtacct atccctcatt  11940
acttaccagt ctcatcttct actccagagg gttgagagaa acctatctaa gagtatgaga  12000
gataacctgc gacaattgag ttctttgatg aggcaggtgc tgggcgggca cggagaagat  12060
aaccttagagt cagacgacaa cattcaacga ctgctaaaag actctttacg aaggacaaga  12120
tgggtggatc aagaggtgcg ccatgcagct agaaccatga ctggagatta cagccccaac  12180
aagaaggtgt cccgtaaggt aggatgttca gaatgggtct gctctgctca acaggttgca  12240
gtctctacct cagcaaaccc ggcccctgtc tcggagcttg acataaggc cctctctaag  12300
aggttccaga acccttttgat ctcgggcttg agagtgctc agtagggcaa cggtgctcat  12360
tataagctta agcctattct agatgatctc aatgttttcc catctctctg ccttgtagtt  12420
ggggacgggt caggggggat atcaagggca gtcctcaaca tgtttccaga tgccaagctt  12480
gtgttcaaca gtcttttaga ggtgaatgac ctgatggctt ccggaacaca tccactgcct  12540
ccttcagcaa tcatgagggg aggaaatgat atcgtctcga gtgataga tcttgactca  12600
atctgggaaa aaccgtccga cttgagaaac ttggcaacct ggaaatactt ccagtcagtc  12660
caaaagcagg tcaacatgtc ctatgacctc attatttgcg atgcagaagt tactgacatt  12720
gcatctatca accggatcac cctgttaatg tccgattttg cattgtctat agatggacca  12780
ctctattgg tcttcaaaac ttatgggact atgctagtaa atccaaacta caaggctatt  12840
caacacctgt caagagcgtt cccctcggtc acagggttta tcacccaagt aacttcgtct  12900
ttttcatctg agctctacct ccgattctcc aaacgaggga gtttttcag agatgctgag  12960
tacttgacct cttccaccct tcgagaaatg agccttgtgt tattcaattg tagcagcccc  13020
aagagtgaga tgcagagagc tcgttccttg aactatcagg atcttgtgag aggatttcct  13080
gaagaatca tatcaaatcc ttacaatgag atgatcataa ctctgattga cagtgatgta  13140
gaatcttttc tagtccacaa gatggttgat gatcttgagt tacagagggg aactctgtct  13200
aaagtggcta tcattatagc catcatgata gttttctcca acagtcttt caacgtttcc  13260
aaaccctaa ctgaccccctc gttctatcca ccgtctgatc ccaaaatcct gaggcacttc  13320
aacatatgtt gcagtactat gatgtatcta tctactgctt taggtgacgt ccctagcttc  13380
gcaagacttc acgacctgta taacagacct ataacttatt acttcagaaa gcaagtcatt  13440
cgagggaacg tttatctatc ttggagttgg tccaacgaca cctcagtgtt caaagggta   13500
gcctgtaatt ctagcctgag tctgtcatct cactggatca ggttgattta caagatagtg  13560
aagactacca gactcgttgg cagcatcaag gatctatcca gagaagtgga aagcaccctt  13620
cataggtaca acaggtggat caccctagag gatatcagat ctagatcatc cctactagac  13680
tacagttgcc tgtgaaccgg atactcctgg aagcctgccc atgctaagac tcttgtgtga  13740
tgtatcttga aaaaaacaag atcctaaatc tgaaccttttg gttgtttgat tgtttttctc  13800
attttgttg tttatttgtt aagcgt                                        13826

SEQ ID NO: 12        moltype = DNA   length = 13926
FEATURE              Location/Qualifiers
misc_feature         1..13926
                     note = RABV vector: Coravax V4-China (S1-RABVG-T2A-P)
source               1..13926
                     mol_type = other DNA
                     organism = synthetic construct
SEQUENCE: 12
acgcttaaca accagatcaa agaaaaaaca gacattgtca attgcaaagc aaaaatgtaa   60
caccctaca atggatgccg acaagattgt attcaaagtc aataatcagg tggtctcttt  120
```

```
gaagcctgag attatcgtgg atcaatatga gtacaagtac cctgccatca aagatttgaa    180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaa ttgtgattgc     360
acgaaaagga gataagatca ccccaggttc tctggtggga ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagattttg agacagcccc     600
ttttgttaaa atcgtggaac accatactct aatgacaact tcaaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctcctat tcatcaaatg ctgttggtca cgtgttcaat ctcattcact ttgtaggatg    1020
ctatatgggt caagtcagat ccctaaatgc aacggttatt gctgcatgtg ctcctcatga    1080
aatgtctgtt ctaggggggct atctgggaga ggaattcttc gggaaaggga catttgaaag    1140
aagattcttc agagatgaga aagaacttca agaatacgag gcggctgaac tgacaaagac    1200
tgacgtagca ctggcagatg atggaactgt caactctgac gacgaggact acttttcagg    1260
tgaaaccaga agtccggagg ctgtttatac tcgaatcatg atgaatggag gtcgactaaa    1320
gagatctcac atacggagat atgtctcagt cagttccaat catcaagccc gtccaaactc    1380
attcgccgag tttctaaaca agacatattc gagtgactca taacatgaaa aaaactaaca    1440
cccctcccgt acggccacca tgttcgtgtt tctggtgctg ctgcctctgg tgagctccca    1500
gtgcgtgaac ctgaccacaa ggacccagct gccccctgcc tataccaatt ccttcacacg    1560
gggcgtgtac tatcccgaca aggtgttccg gagcagcgtg ctgcactcca cacaggatct    1620
gtttctgcct ttcttttcta acgtgacctg gttccacgcc atccacgtga gcggcaccaa    1680
tggcacaaag cggttcgaca atccagtgct gccctttaac gatgcgtgt acttcgcctc     1740
caccgagaag tctaacatca tcagaggctg gatcttggc accacactgg acagcaagac     1800
acagtccctg ctgatcgtga acaatgccac caacgtggtc atcaaggtgt gcgagttcca    1860
gttttgtaat gatccattcc tgggcgtgta ctatcacaag aacaataagt cttggatgga    1920
gagcgagttt cgcgtgtatt cctctgccaa caattgcaca tttgagtacg tgtcccagcc    1980
cttcctgatg gacctggagg gcaagcaggg caatttcaag aacctgaggg agttcgtgtt    2040
taagaatatc gatggctact tcaaaatcta ctccaagcac accccaatca acctggtgcg    2100
cgacctgcca cagggcttct ctgccctgga gccactggtg gatctgccca tcggcatcaa    2160
catcacccgg tttcagacac tgctggcct gcacagaagc tacctgacac caggcgacag     2220
ctcctctgga tggaccgcag gagcagcagc ctactatgtg ggctatctgc agcccaggac    2280
cttcctgctg aagtacaacg agaatggcac catcacagac gccgtggatt gcgccctgga    2340
tccccctgtct gagaccaagt gtacactgaa gagctttacc gtggagaagg gcatctatca    2400
gacaagcaat ttcagggtgc agcctaccga gtccatcgtg cgcttcccca atatccaaaa    2460
cctgtgccct tttggcgagg tgttcaacgc aacccgcttc gccagcgtgt acgcctggaa    2520
taggaagcgc atctccaact gcgtggccga ctattctgtg ctgtacaaca cgcctcctt     2580
ctctaccttt aagtgctatg gcgtgagccc cacaaagctg aatgacctgt gctttaccaa    2640
cgtgtacgcc gattccttcg tgatcagggg cgacgaggtg cgccagatcg caccaggaca    2700
gacaggcaag atcgcagact acaattataa gctgcctgac gatttcaccg gctgcgtgat    2760
cgcctggaac tctaacaatc tggatagcaa agtgggcggc aactacaatt atctgtaccg    2820
gctgtttaga aagtctaatc tgaagccatt cgagagggac atctccacag aaatctacca    2880
ggccggctct acccccctgca atggcgtgga gggctttaac tgttatttcc ctctgcagag    2940
ctacggcttc cagccaacaa acggcgtggg ctatcagccc taccgcgtgg tggtgctgtc    3000
ttttgagctg ctgcacgcac ctgcaacagt gtgcggacca agaagagca ccaatctggt     3060
gaagaacaag tgcgtgaact tcaacttcaa cggactgacc ggaacaggcg tgctgaccga    3120
gtccaacaag aagttcctgc cttttcagca gttcggcagg gacatcgcag ataccacaga    3180
cgccgtgcgc gaccctcaga ccctggagat cctggacatc acaccatgct ccttcggcgg    3240
cgtgtctgtg atcacaccag gcaccaatac aagcaaccag gtggccgtgc tgtatcagga    3300
cgtgaattgt accgaggtgc cagtggcaat ccacgcagat cagctgaccc ctacatggcg    3360
ggtgtactct accggcagca acgtgttcca gacaagagcc ggatgcctga tcggagcaga    3420
gcacgtgaac aatagctatg agtgcgacat ccctatcggc ccggcatct gtgcctccta     3480
ccagacccag acaaactccc caaggtctgt gggagatgag gccgaagact tgtggaagt     3540
ccacctgcct gatgtgcata accaggtgtc tggcgtcgac ctgggactgc aaattgggga    3600
caagtacgtg ctgctgagtg ctggagcact gactgccctg atgctgatca tttcctgat    3660
gacctgctgt cggcgcgtga acaagaagtga gcccactcag cacaatctgc gaggaaccga    3720
gagagaagtg tcagtcacac ctcagagcgg gaaaatcatt agtagttggg aatcacataa    3780
aagcggggc gagaccaggc tgggatccgg ctccggcgag ggcagggaa gtctactaac      3840
atgcggggac gtggaggaaa atcccggccc catgagcaag atctttgtca atcctagtgc    3900
tattagacc ggtctggccg atcttgagat ggctgaagaa actgttgatc tgatcaattag    3960
aaatatcgaa gacaatcagg ctcatctcca aggggaaccc atagaggtgg acaatctccc    4020
tgaggatatg gggcgacttc acctggatga tggaaatcg cccaaccatg gtgagatagc    4080
caaggtggga gaaggcaagt atcgagagga ctttcagatg gatgaaggag aggatcctag    4140
cttcctgtc cagtcatacc tggaaaatgt tggagtccaa atagtcagac aaatgaggtc    4200
aggagagaga tttctcaaga tatggtcaca gaccgtagga gagattatat cctatgtcgc    4260
ggtcaacttt cccaaccctc caggaaagtc ttcagaggat aaatcaaccc agactactgg    4320
ccgagagctc aagaaggaga caacacccac tccttctcag agagaaagcc aatcatcgaa    4380
agccaggatg gcggctcaaa ttgcttctgg ccctccagcc cttgaatggt cggctaccaa    4440
tgaagaggat gatctatcag tggaggctga gatcgctcac cagattgcag aaagtttctc    4500
caaaaaatat aagtttccct ctcgatcctc agggatactc ttgtataatt ttgagcaatt    4560
gaaaatgaac cttgatgata tagttaaaga ggcaaaaaat gtaccaggtg tgacccgttt    4620
agcccatgac gggtccaaac tcccctaag atgtgtactg ggatgggtcg ctttggccaa    4680
ctctaagaaa ttccagttgt tagtcgaatc cgacaagctc agtaaaatca tgcaagatga    4740
cttgaatcgc tatacatctt gctaaccgaa cctctcccct cagtccctct agacaataaa    4800
atccgagatg tcccaaagtc aacatgaaaa aaacaggcaa caccactgat aaaatgaacc    4860
```

```
tcctacgtaa gatagtgaaa aaccgcaggg acgaggacac tcaaaaatcc tctcccgcgt   4920
cagcccctct ggatgacgat gacttgtggc ttccacccc  tgaatacgtc ccgctgaaag   4980
aacttacagg caagaagaac atgaggaact tttgtatcaa cggaagggtt aaagtgtgta   5040
gcccgaatgg ttactcgttc aggatcctgc ggcacattct gaaatcattc gacgagatat   5100
attctgggaa tcataggatg atcgggttag tcaaagtggt tattggactg gcttttgtcag  5160
gatctccagt ccctgagggc ctgaactggg tatacaaatt gaggagaacc tttatcttcc   5220
agtgggctga ttccagggc  cctcttgaag gggaggagtt ggaatactct caggagatca   5280
cttgggatga tgatactgag ttcgtcggat tgcaaataag agtgattgca aaacagtgtc   5340
atatccaggg cagagtctgg tgtatcaaca tgaacccgag agcatgtcaa ctatggtctg   5400
acatgtctct tcagacacaa aggtccgaag aggacaaaga ttcctctctg cttctagaat   5460
aatcagatta tatcccgcaa atttatcact tgtttacctc tggaggagag aacatatggg   5520
ctcaactcca acccttggga gcaatataac aaaaaacatg ttatggtgcc attaaaccgc   5580
tgcatttcat caaagtcaag ttgattacct ttacattttg atcctcttgg atgtgaaaaa   5640
aactattaac atccctcaaa agaccccggg aaagatggtt cctcaggctc tcctgtttgt   5700
acccctctg  gttttccat  tgtgttttgg gaaattccct atttacacga taccagacaa   5760
gcttggtccc tggagtccga ttgacataca tcacctcagc tgcccaaaca atttggtagt   5820
ggaggacgaa ggatgcacca acctgtcagg gttctcctac atggaactta agttggata   5880
catcttagcc ataaaagtga acgggttcac ttgcacaggc gttgtgacgg aggctgaaac   5940
ctacactaac ttcgttggtt atgtcacaac cacgttcaaa agaaagcatt tccgcccaac   6000
accagatgca tgtagagccg cgtacaactg gaagatggcc ggtgacccca gatatgaaga   6060
gtctctacac aatccgtacc ctgactaccg ctggcttcga actgtaaaaa ccaccaagga   6120
gtctctcgtt atcatatctc caagtgtggc agatttggac ccatatgaca gatcccttca   6180
ctcgagggtc ttccctagcg ggaagtgctc aggagtagcc gtgtcttcta cctactgctc   6240
cactaaccac gattacacca tttgatgcc  cgagaatccg agactaggga tgtcttgtga   6300
catttttacc aatagtagag ggaagagagc atccaaaggg agtgagactt gcggctttgt   6360
agatgaaaga ggctatatat agtctttaaa aggagcatgc aaactcaagt tatgtggagt   6420
tctaggactt agacttatgg atggaacatg ggtctcgatg caaacatcaa atgaaaccaa   6480
atggtgccct cccgataagt tggtgaacct gcacgacttt cgctcagacg aaattgagca   6540
ccttgttgta gaggagttgg tcaggaagag agaggagtgt ctggatgcac tagagtccat   6600
catgacaacc aagtcagtga gtttcagacg tctcagtcat ttaagaaaac ttgtccctgg   6660
gtttggaaaa gcatataccc tattcaacaa gaccttgatg gaagccgatg ctcactacaa   6720
gtcagtcgag acttggaatg agatcctccc ttcaaagggt tgtttaagag ttgggggggag   6780
gtgtcatcct catgtgaacg gggtgttttt caatggtata atattaggac ctgacggcaa   6840
tgtcttaatc ccagagatgc aatcatccct cctccagcaa catatggagt tgttggaatc   6900
ctcggttatc cccccttgtgc acccccctggc agaccgtct  accgttttca aggacggtga   6960
cgaggctgag gatttttgttg aagttcacct tcccgatgtg cacaatcagg tctcaggagt   7020
tgacttgggt ctcccgaact ggggggaagta tgtattactg agtgcagggg ccctgactgc   7080
cttgatgttg ataattttcc tgatgacatg ttgtagaaga gtcaatcgat cagaacctac   7140
gcaacaacaat ctcagaggga cagggaggga ggtgtcagtc actccccaaa gcgggaagat   7200
catatcttca tgggaatcac acaagagtgg gggtgagacc agactgtaat taattaacgt   7260
cctttcaacg atccaagtcc atgaaaaaaa ctaacacccc tcccgtacct agcttataaa   7320
gtgctgggtc atctaagctt ttcagtcgag aaaaaaacat tagatcagaa gaacaactgg   7380
caacacttct caacctgaga cttacttcaa gatgctcgat cctggagagg tctatgatga   7440
ccctattgac ccaatcgagt tagaggctga acccagagga accccattg  tccccaacat   7500
cttgaggaac tctgactaca atctcaactc tccttgata  gaagatcctg ctagactaat   7560
gttagaatgg ttaaaacag  ggaatagacc ttatcggatg actctaacag acaattgctc   7620
caggtctttc agagttttga aagattattt caagaaggta gatttgggtt ctctcaaggt   7680
gggcggaatg gctgcacagt caatgatttc tctctggtta tatggtgccc actctgaatc   7740
caacaggagc cggagatgta taacagactt ggcccatttc tattccaagt cgtcccccat   7800
agagaagctg ttgaatctca cgctaggaaa tagagggctg agaatccccc cagagggagt   7860
gttaagttgc cttgagaggg ttgattatga taatgcattt ggaaggtatc ttgccaacac   7920
gtattcctct tacttgttct tccatgtaat caccttatac atgaacgccc tagactggga   7980
tgaagaaaag accatcctag cattatgaa  agatttaacc tcagtggaca tcgggaagga   8040
cttggtaaag ttcaaagacc aaatatgggg actgctgatc gtgacaaagg actttgttta   8100
ctcccaaagt tccaattgtc ttttttgacag aaactacaca cttatgctaa aagatctttt   8160
cttgtctcgc ttcaactcct taatggtctt gctctctccc ccagagcccc gatactcaga   8220
tgacttgata tctcaactat gccagctgta cattgctggg gatcaagtct tgtctatgtg   8280
tggaaactcc ggctatgaag tcatcaaaat attggagcca tatgtcgtga atagtttagt   8340
ccagagagca gaaaagttta ggcctctcat tcattccttg ggagactttc ctgtatttat   8400
aaaaagacaag gtaagtcaac ttgaagagac gttcggtccc tgtgcaagaa ggttctttag   8460
ggctctggat caattcgaca acatacatga cttggttttt gtgtttggct gttacaggca   8520
ttgggggcac ccatatatag attatcgaaa gggtctgtca aaactatatg atcaggttca   8580
ccttaaaaaa atgatagata agtcctacca ggagtgctta gcaagcgacc tagccaggag   8640
gatccttaga tgggggttttg ataagtactc caagtggtat ctggattcaa gattcaggag   8700
ccgagaccac cccttgactc cttatatcaa aacccaaaca tggccaccca acatattgt    8760
agacttggtg ggggatacat ggcacaagct cccgatcacg cagatctttg agattcctga   8820
atcaatggat ccgtcagaaa tattggatga caaatcacat tctttcacca gaacgagact   8880
agcttcttgg ctgtcagaaa accgaggggg gcctgttcct agcgaaaaag ttattatcac   8940
gccctgtct  aagccgcctg tcaatcccg  agagttttctg aggtctatag acctcggagg   9000
attgccagat gaagacttga taattggcct caagccaaag gaacgggaat tgaagattga   9060
aggtcgattc tttgctctaa tgtcatgaa  tctaagattg tattttgtca tcactgaaaa   9120
actcttggcc aactacatct tgccactttt tgacgcgctg actatgacag acaacctgaa   9180
caaggtgttt aaaaagctga tcgacagggt caccgggcaa gggcttttgg actattcaag   9240
gtcacatat  gcatttcacc tggactatga aaagtgaac aaccatcaaa gattagagtc   9300
aacagaggat gtattttctg tcctagatca agtgtttgga ttgaagagag tgttttctag   9360
aacacacgag tttttttcaaa aggcctggat ctattattca gacagatcag acctcatcgg   9420
gttacgggag gatcaaatat actgcttaga tgcgtccaac ggcccaacct gttgaatgg    9480
ccaggatggc gggctagaag gcttacggca gaaggggctgg agtctagtca gcttattgat   9540
gatagataga gaatctcaaa tcaggaacac aagaaccaaa atactagctc aaggagacaa   9600
```

```
ccaggtttta tgtccgacat acatgttgtc gccagggcta tctcaagagg ggctcctcta    9660
tgaattggag agaatatcaa ggaatgcact ttcgatatac agagccgtcg aggaagtggc    9720
atctaagcta gggctgatca tcaagaaaga agagaccatg tgtagttatg acttcctcat    9780
ctatggaaaa accccttgt ttagaggtaa catattggtg cctgagtcca aaagatgggc    9840
cagagtctct tgcgtctcta atgaccaaat agtcaacctc gccaatataa tgtcgacagt    9900
gtccaccaat gcgctaacag tggcacaaca ctctcaatct ttgatcaaac cgatgaggga    9960
ttttctgctc atgtcagtac aggcagtctt tcactacctg ctatttagcc caatcttaaa   10020
gggaagagtt tacaagattc tgagcgctga aggggagagc tttctcctag ccatgtcaag   10080
gataatctat ctagatcctt ctttgggagg atatctgga atgtccctcg gaagattcca   10140
tatacgacag ttctcagacc ctgtctctga agggttatcc ttctggagag agatctggtt   10200
aagctcccaa gagtcctgga ttcacgcgtt gtgtcaagag gctggaaacc cagatcttgg   10260
agagagaaca ctcgagagct tcactcgcct tctagaagat ccgaccacct taaatatcag   10320
aggagggcc agtcctacca ttctactcaa ggatgcaatc agaaaggctt tatatgacga   10380
ggtggacaag gtggaaaatt cagagtttcg agaggcaatc ctgttgtcca agaccactag   10440
agataaattt atactcttct taatatcgt tgagcctctg tttcctcgat ttctcagtga   10500
gctattcagt tcgtcttttt tgggaatccc cgagtcaatc attggattga tacaaaactc   10560
ccgaacgata agaaggcagt ttagaaagag tctctcaaaa actttagaag aatccttcta   10620
caactcagag atccacggga ttagtcggat gacccagaca cctcagaggg ttgggggggt   10680
gtggccttgc tcttcagaga gggcagatct acttagggag atctcttggg gaagaaaagt   10740
ggtaggcacg acagttcctc acccttctga gatgttggga ttacttccca agtcctctat   10800
ttcttgcact tgtggagcaa caggaggagg caatcctaga gttctgtat cagtactccc   10860
gtcctttgat cagtcatttt tttcacgagg ccccctaaag ggatacttgg gctcgtccac   10920
ctctatgtcg acccagctat tccatgcatg ggaaaaagtc actaatgttc atgtggtgaa   10980
gagagctcta tcgttaaaag aatctataaa ctggttcatt actagagatt ccaacttggc   11040
tcaagctcta attaggaaca ttatgtctct gacaggccct gatttccctc tagaggaggc   11100
ccctgtcttc aaaaggacgg ggtcagcctt gcataggttc aagtctgcca gatacagcga   11160
aggagggtat tcttctgtct gcccgaacct cctctctcat atttctgtta gtacagacac   11220
catgtctgat ttgacccaag acgggaagaa ctacgatttc atgttccagc cattgatgct   11280
ttatgcacag acatggacat cagagctggt acagagagac acaaggctaa gagactctac   11340
gtttcattgg cacctccgat gcaacaggtg tgtgagaccc attgacgacg tgaccctgaa   11400
gacctctcag atcttcgagt ttccggatgt gtcgaaaaga atatccagaa tggtttctgg   11460
ggctgtgcct cacttccaga ggcttcccga tatccgtctg agaccaggag attttgaatc   11520
tctaagcggt agagaaaagt ctcaccatat cggatcagct caggggctct tatactcaat   11580
cttagtggca attcacgact caggatacaa tgatgaacc atcttccctg tcaacatata   11640
cggcaaggtt tcccctagag actatttgag agggctcgca aggggagtat tgataggatc   11700
ctcgatttgc ttcttgacaa gaatgacaaa tatcaatatt aatagacctc ttgaattggt   11760
ctcagggggta atctcatata ttctcctgag gctagataac catccctcct tgtacataat   11820
gctcagagaa ccgtctctta gaggagagat atttttcatc cctcagaaaa tccccgccgc   11880
ttatccaacc actatgaaag aaggcaacag atcaatcttg tgttatctcc aacatgtgct   11940
acgctatgag cgagagataa tcacggcgtc tccagaaat gactggctat ggatctttc   12000
agactttaga agtgccaaaa tgacgtacct atccctcatt acttaccagt ctcatcttct   12060
actccagagg gttgagagaa acctatctaa gagtatgaga gataacctgc gacaattgag   12120
ttctttgatg aggcaggtgc tgggcgggca cggagaagat acctagagt cagacgacaa   12180
cattcaacga ctgctaaaag actctttacg aaggacaaga tgggtggatc aagaggtgcg   12240
ccatgcagct agaaccatga ctggagatta cagcccaac aagaaggtgt cccgtaaggt   12300
aggatgttca gaatgggtct gctctgctca acaggttgca gtctctacct cagcaaaccc   12360
ggccctgtc tcggagcttg acataagggc cctctctaag aggttccaga acccttgat   12420
ctcgggcttg agagtggttc agtgggcaac cggtgctcat tataagctta agcctattct   12480
agatgatctc aatgttttcc catctctctg ccttgtagtt ggggacgggt caggggggat   12540
atcaaggca gtcctcaaca tgtttccaga tgccaagctt gtgttcaaca gtcttttaga   12600
ggtgaatgac ctgatggctt ccggaacaca tccactgcct ccttcagcaa tcatgaggag   12660
aggaaatgat atcgtctcca gagtgataga tcttgactca atctgggaaa accgtccga   12720
cttgagaaac ttggcaacct ggaaatactt ccagtcagtc caaaagcagg tcaacatgtc   12780
ctatgacctc attatttgcg atgcagaagt tactgacatt gcatctatca accggatcac   12840
cctgttaatg tccgattttg cattgtctat agatggacca ctctatttgg tcttcaaaac   12900
ttatgggact atgctagtaa atccaaacta caaggctatt caacaccctgt caagagcgtt   12960
cccctcggtc acagggttta tcacccaagt aacttcgtct ttttcatctg agctctacct   13020
ccgattctcc aaacgaggga gtttttcag agatgctgag tacttgacct cttccacccct   13080
tcgagaaatg agccttgtgt tattcaattg tagcagcccc aagagtgaga tgcagagag   13140
tcgttccttg aactatcagg atccttgtgag aggatttcct gaagaaatca tatcaaatcc   13200
ttacaatgag atgatcataa ctctgattga cagtgatgta gaatctttc tagtccacaa   13260
gatggttgat gatcttgagt tacagagggg aactctgtct aaagtggcta tcattatagc   13320
catcatgata gttttctcca acagtgtctt caacgtttcc aaacccctaa ctgaccctc   13380
gttctatcca ccgtctgatc ccaaaatcct gaggcactca acatatgtt gcagtactat   13440
gatgtatcta tctactgctt taggtgacgt ccctagcttc gcaagacttc acgacctgta   13500
taacagacct ataacttatt acttcagaaa gcaagtcatt cgaggggaacg tttatctatc   13560
ttggagttgg tccaacgaca cctcagtgtt caaaagggta gcctgtaatt ctagcctgag   13620
tctgtcatct cactggatca ggttgattta caagatagtg aagactacca gactcgttgg   13680
cagcatcaag gatctatcca gagaagtgga aagcacctt cataggtaca acaggtggtt   13740
caccctagag gatatcagat ctagatcatc cctactagac tacagttgcc tgtgaaccgg   13800
atactcctgg aagcctgccc atgctaagac tcttgtgtga tgtatcttga aaaaaacaag   13860
atcctaaatc tgaaccttg gttgtttgat tgttttctc attttgttg tttatttgtt   13920
aagcgt                                                              13926
```

| SEQ ID NO: 13 | moltype = DNA length = 13977 |
|---|---|
| FEATURE | Location/Qualifiers |
| misc_feature | 1..13977 |
| | note = RABV vector: Coravax V4 South Africa |
| source | 1..13977 |

```
                  mol_type = other DNA
                  organism = synthetic construct
SEQUENCE: 13
acgcttaaca accagatcaa agaaaaaaca gacattgtca attgcaaagc aaaaatgtaa    60
caccccTaca atggatgccg acaagattgt attcaaagtc aataatcagg tggtctcttt   120
gaagcctgag attatcgtgg atcaatatga gtacaagtac cctgccatca aagatttgaa   180
aaagccctgt ataaccctag gaaaggctcc cgatttaaat aaagcataca agtcagtttt   240
gtcaggcatg agcgccgcca aacttaatcc tgacgatgta tgttcctatt tggcagcggc   300
aatgcagttt tttgagggga catgtccgga agactgacc agctatggaa ttgtgattgc   360
acgaaaagga gataagatca ccccaggttc tctggtggag ataaaacgta ctgatgtaga   420
agggaattgg gctctgacag gaggcatgga actgacaaga gaccccactg tccctgagca   480
tgcgtccttA gtcggtcttc tcttgagtct gtataggttg agcaaaatat ccgggcaaaa   540
cactggtaac tataagacaa acattgcaga caggatagag cagattttTg agacagcccc   600
ttttgttaaa atcgtggaac accatactct aatgacaact cacaaaatgt gtgctaattg   660
gagtactata ccaaacttca gatttttggc cggaacctat gacatgtttt tctcccggat   720
tgagcatcta tattcagcaa tcagagtggg cacagttgtc actgcttatg aagactgttc   780
aggactggta tcatttactg ggttcataaa acaaatcaat ctcaccgcta gagaggcaat   840
actatatttc ttccacaaga actttgagga agagtaaga agaatgtttg agccagggca   900
ggagacagct gttcctcact cttatttcat ccacttccgt tcactaggct tgagtgggaa   960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctaggggcT atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact acttttcagg  1260
tgaaaccaga agtccggagg ctgtttatac tcgaatcatg atgaatggag tcgactaaa  1320
gagatctcac atacggagat atgtctcagt cagttccaat catcaagccc gtccaaactc  1380
attcgccgag tttctaaaca agacatattc gagtgactca taacatgaaa aaaactaaca  1440
cccctcccgt acgccacca tgttcgtgtt tctggtgctg ctgcctctgg tgagctccca  1500
gtgcgtgaac ttcaccacaa ggacccagct gcccctgcc tataccaatt ccttcacacg  1560
gggcgtgtac tatcccgaca aggtgttccg gagcagcgtg ctgcactcca cacaggatct  1620
gtttctgcct ttctttttct acgtgacctg gttccacgcc atccacgtgg cggcaccaa  1680
tggcacaaag cggttcgcca atccagtgct gcccttTaac gatggcgtgt acttcgcctc  1740
caccgagaag tctaacatca tcagaggctg gatctttggc accacactgg acagcaagac  1800
acagtccctg ctgatcgtga acaatgccac caacgtggtc atcaaggtgt gcgagttcca  1860
gttTtgtaat gatccattcc tgggcgtgta ctatcacaag aacactaagt cttggatgga  1920
gagcgagttt cgcgtgtatt cctctgccaa caattgcaca tttgagtacg tgtcccagcc  1980
cttcctgatg gacctggagg gcaagcaggg caatttcaag aacctgaggg agttcgtgtt  2040
taagaatatc gatggctact tcaaaatcta ctccaagcac accccaatca acctggtgcg  2100
cggcctgcca cagggcttct ctgcctgga gccactggtg gatctgccca tcggcatcaa  2160
catcacccgg tttcagacac tgctggccct gcacagaagc tacctgacac caggcgacag  2220
ctcctctgga tggaccgcag gagcagcagc ctactatgtg ggctatctgc agcccaggac  2280
cttcctgctg aagtacaacg agaatggcac catcacagac gccgtggatt gcgccctgga  2340
tcccctgtct gagaccaagt gtacactgaa gagctttacc gtggaGaagg gcatctatca  2400
gacaagcaat ttcagggtgc agcctaccga gtccatcgtg cgctttccca atatcacaaa  2460
cctgtgccct tttggcgagg tgttcaacgc aacccgcttc gccagcgtgt acgcctggaa  2520
taggaagcgc atctccaact gcgtggccga ctattctgtg ctgtacaaca cgcctcctt   2580
ctctaccttt aagtctatg gcgtgagccc cacaaagctg aatgacctgt gctttaccaa  2640
cgtgtacgcc gattccttcg tgatcagggg cgacgaggtg cgccagatcg caccaggaca  2700
gacaggcaat atcgcagact acaattataa gctgcctgac gatttcaccg gctgcgtgat  2760
cgcctggaac tctaacaatc tggatagcaa agtgggcggc aactacaatt atctgtaccg  2820
gctgtttaga aagtctaatc tgaagccatt cgagagggac atctccacag aaatctacca  2880
ggccggctct accccctgca atggcgtgaa gggctttaac tgttatttcc ctctgcagag  2940
ctacggcttc cagccaacat atggcgtggg ctatcagccc taccgcgtgg tggtgctgtc  3000
ttttgagctg ctgcacgcac ctgcaacagt gtgcggacca aagaagagca ccatctggt  3060
gaagaacaag tgcgtgaact tcaacttcaa cggactgacc ggaacaggcg tgctgaccga  3120
gtccaacaag aagttcctgc cttttcagca gttcggcagg gacatcgcag ataccacaga  3180
cgccgtgcgc gaccctcaga ccctggagat cctggacatc acaccatgct ccttcggcgg  3240
cgtgtctgtg atcacaccag gcaccaatac aagcaaccag gtggccgtgc tgtatcaggg  3300
cgtgaattgt accgaggtgc cagtggcaat ccacgcagat cagctgaccc ctacatgccg  3360
ggtgtactct accggcagca acgtgttcca gacaagagcc ggatgcctga tcggagcaga  3420
gcacgtgaac aatagctatg agtgcgacat ccctatcggc gccggcatct gtgcctccta  3480
ccagacccag acaaactccc agaatcaag cgtgattcct ctggtccatc cactggcaga  3540
tcctccacac gtgttcaaag acggagtga ggccgaagac ttTgtggaag tccacctgcc  3600
tgatgtgcat aaccaggtgt ctggcgtcga cctgggacgt ggcaagtacg gctctgctt   3660
gctgctgagt gctggagcac tgactgcct gatgctgatc attttcctga tgacctgctg  3720
tcggcgcgtg aacagaagtg agcccactca gcacaatctg cgaggaaccg ggagagaagt  3780
gtcagtcaca cctcagagcg gaaaatcat tagtagttgg gaatcacata aaagcggggg  3840
cgagaccagg ctgggatccg gctccggcga gggcagggga agtctactaa catgcgggga  3900
cgtggaggaa aatcccggcc catgagcaa gatctttgtc aatccagtg ctattagaC   3960
cggtctggcc gatcttgaga tggctgaaga actgtttgat ctgatcaata gaaatatcga  4020
agacaatcag gctcatctcc aaggggaacc catagaggtg gacaatctcc ctgaggatat  4080
ggggcgactt cacctggatg atggaaaat gcccaaccat ggtgagatag ccaaggtggg  4140
agaaggcaag tatcgagagg actttcagat ggatgaagga gagaTccta gcttcctgtt  4200
ccagtcatac ctggaaaatg ttggagtcca aatagtcaga caggagagga aagagaggaC  4260
atttctcaag atatggtcac agaccgtaga agagattata tcctatgtcg cggtcaactt  4320
tcccaaccct ccaggaaagt cttcagagga taaatcaacc cagactactg gccgagagct  4380
caagaaggag acaacacccca ctccttctca gagagaaagc caatcatcga aagccaggat  4440
ggcggctcaa attgcttctg gcctccagc ccttgaatgg tcggctacca atgaagagga  4500
tgatctatca gtggaggctg agatcgctca ccagattgca gaaagtttct ccaaaaaata  4560
```

```
taagtttccc tctcgatcct cagggatact cttgtataat tttgagcaat tgaaaatgaa   4620
ccttgatgat atagttaaag aggcaaaaaa tgtaccaggt gtgacccgtt tagcccatga   4680
cgggtccaaa ctcccctaa gatgtgtact gggatgggtc gctttggcca actctaagaa    4740
attccagttg ttagtcgaat ccgacaagct gagtaaaatc atgcaagatg acttgaatcg   4800
ctatacatct tgctaaccga acctctcccc tcagtccctc tagacaataa aatccgagat   4860
gtcccaaagt caacatgaaa aaaacaggca acaccactga taaaatgaac ctcctactga   4920
agatagtgaa aaaccgcagg gacgaggaca ctcaaaaatc ctctcccgcg tcagcccctc   4980
tggatgacga tgacttgtgg cttccacccc ctgaatacgt cccgctgaaa gaacttacag   5040
gcaagaagaa catgaggaac ttttgtatca acggaagggt taaagtgtgt agcccgaatg   5100
gttactcgtt caggatcctg cggcacattc tgaaatcatt cgacgagata tattctggga   5160
atcataggat gatcgggtta gtcaaagtgg ttattggact ggctttgtca ggatctccag   5220
tccctgaggg cctgaactgg gtatacaaat tgaggagaac ctttatcttc cagtgggctg   5280
attccagggg ccctcttgaa ggggaggagt tggaatactc tcaggagatc acttgggatg   5340
atgatactga gttcgtcgga ttgcaaataa gagtgattgc aaaacagtgt catatccagg   5400
gcagagtctg tgtatcaac atgaacccga gagcatgtca actatggtct gacatgtctc    5460
ttcagacaca aaggtccgaa gaggacaaag attcctctct gcttctagaa taatcagatt   5520
atatcccgca aatttatcac ttgtttacct ctggaggaga gaacatatgg gctcaactcc   5580
aacccttggg agcaatataa caaaaaacat gttatggtgc cattaaaccg ctgcatttca   5640
tcaaagtcaa gttgattacc tttacatttt gatcctcttg gatgtgaaaa aaactattaa   5700
catccctcaa aagaccccgg gaaagatggt tcctcaggct ctcctgtttg tacccttct    5760
ggtttttcca ttgtgttttg ggaaattccc tatttacacg ataccagaca agcttggtcc   5820
ctggagtccg attgacatac atcacctcag ctgcccaaac aatttggtag tggaggacga   5880
aggatgcacc aacctgtcag ggttctccta catggaactt aaagttggat acatcttagc   5940
cataaaagtg aacgggttca cttgcacagg cgttgtgacg gaggctgaaa cctacactaa   6000
cttcgttggt tatgtcacaa ccacgttcaa aagaaagcat ttccgcccaa caccagatgc   6060
atgtagagcc gcgtacaact ggaagtaggc cggtgacccc agatatgaag agtctctaca   6120
caatccgtac cctgactacc gctgcgttcg aactgtaaaa accaccaagg agtctctcgt   6180
tatcatatct ccaagtgtgg cagatttgga cccatgac agatcccttc actcgagggt      6240
cttccctagc gggaagtgct caggagtagc ggtgtcttct acctactgct ccactaacca   6300
cgattacacc atttggatgc ccgagaatcc gagactaggc atgtcttgtg acatttttac   6360
caatagtaga gggagagag catccaaagg gagtgagact tgcggctttg tagatgaaag    6420
aggcctatat aagtctttaa aaggagcatg caaactcaag ttatgtggag ttctaggact   6480
tagacttatg gatggaacat gggtctcgat gcaaacatca aatgaaacca aatggtgccc   6540
tcccgataag ttggtgaacc tgcacgactt tcgctcgaac gaaattgacg accttgttgt   6600
agaggagttg gtcaggaaga gagaggagtg tctggatgca ctagagtcca tcatgacaac   6660
caagtcagtg agtttcagac gtctcagtca tttaagaaaa cttgtccctg ggtttggaaa   6720
agcatatacc atattcaaca agaccttgat ggaagccgat gctcactaca agtcagtcga   6780
gacttggaat gagatcctcc cttcaaaagg gtgtttaaga gttgggggga ggtgtcatcc   6840
tcatgtgaac gggtgttttt tcaatggtat aattattaga cctgacggca atgtcttaat   6900
cccagagatg caatcatccc tcctccagca acatatggag ttgttggaat cctcggttat   6960
ccccttgtg cacccctgg cagacccgtc taccgttttc aaggacggtg acgaggctga     7020
ggattttgtt gaagttcacc ttcccgatgt gcacaatcag gtctcaggag ttgacttggg   7080
tctcccgaac tgggggaagt atgtattact gagtgcaggg gccctgactg ccttgatgtt   7140
gataatttc ctgatgacat gttgtagaag agtcaatcga tcagaaccta cgcaacacaa    7200
tctcagaggg acaggaggg aggtgtcagt cactccccaa agcgggaaga tcatatcttc    7260
atgggaatca cacaagagtg ggggtgagac cagactgtaa ttaattaacg tccttcaac   7320
gatccaagtc catgaaaaaa actaacaccc ctcccgtacc tagcttataa agtgctgggt   7380
catctaagct tttcagtcga gaaaaaaaca ttagatcaga agaacaactg gcaacacttc   7440
tcaacctgag acttacttca agatgctcga tcctggagag gtctatgatg acctattga   7500
cccaatcgag ttagaggctg aacccagagg aaccccatt gtcccccaaca tcttgaggaa   7560
ctctgactac aatctcaact ctcctttgat agaagatcct gctagactaa tgttagaatg   7620
gttaaaaaca gggaatagac cttatcggat gactctaaca gacaattgct ccaggtcttt   7680
cagagtttg aaagattatt tcaagaaggt agatttgggt tctctcaagg tgggcggaat    7740
ggctgcacag tcaatgattt ctctctggtt atatggtgcc cactctgaat ccaacaggag   7800
ccggagatgt ataacagact tggcccattt ctattccaag tcgtccccca tagagaagct   7860
gttgaatctc acgctaggaa atagagggct gagaatcccc ccagagggag tgttaagttg   7920
ccttgagagg gttgattatg ataatgcatt tggaaggtat cttgccaaca cgtattcctc   7980
ttacttgttc ttccatgtaa tcaccttata catgaacgcc ctagactggg atgaagaaaa   8040
gaccatccta gcattatgga aagatttaac ctcagtggac ctgggaaagg acttggtaaa   8100
gttcaaagac caaatatggg gactgctgat cgtgacaaag gactttgttt actcccaaag   8160
ttccaattgt ctttttgaca gaaactacac acttatgcta aaagatcttt tcttgtctcg   8220
cttcaactcc ttaatggtct tgctctctcc cccagagccc cgatactcag atgacttgat   8280
atctcaacta tgccagctgt acattgctgg ggatcaagtc ttgtctatgt gtggaaactc   8340
cggctatgaa gtcatcaaaa tattggagcc atatgtcgtg aatagtttag tccagagagc   8400
agaaaagttt aggcctctca ttcattcctt gggagacttt cctgtattta taaaagacaa   8460
ggtaagtcaa cttgaagaga cgttcggtcc ctgtgcaaga aggttcttta gggctctgga   8520
tcaattcgac aacatacatg acttggtttt tgtgtttggc tgttacaggc attggggca    8580
cccatatata gattatcgaa agggtctgtc aaaactatat gatcaggttc accttaaaaa   8640
aatgatagat aagtcctacc ggagtgcttt agcaagcgac ctagccagga ggatccttag   8700
atgggggtttt gataagtact ccaagtggta tctggattca agattcctag cccgagacca   8760
cccccttgact ccttatatca aaacccaaac atggccaccc aaacatattg tagacttggt   8820
ggggggataca tggcacaagc tcccgatcac gcagatcttt gagattcctg aatcaatgga   8880
tccgtcagaa atattggatg acaaatcaca ttctttcacc agaacgagac tagcttcttg   8940
gctgtcagaa aaccgagggg ggcctgttcc tagcgaaaaa gttattatca cggccctgtc   9000
taagccgcct gtcaatcccc gagagttct gaggtctata gacctcggag gattgccaga    9060
tgaagacttg ataattggcc tcaagccaaa ggaacgggaa ttgaagattg aagtcgatt    9120
ctttgctcta atgtcatgga atctaagatt gtattttgtc atcactgaaa aactcttggc   9180
caactacatc ttgccacttt ttgacgcgct gactatgaca gacaacctga acaaggtgtt   9240
taaaaagctg atcgacaggg tcaccgggca agggcttttg gactattcaa gggtcacata   9300
```

```
tgcatttcac ctggactatg aaaagtggaa caaccatcaa agattagagt caacagagga   9360
tgtattttct gtcctagatc aagtgtttgg attgaagaga gtgttttcta gaacacacga   9420
gttttttcaa aaggcctgga tctattattc agacagatca gacctcatcg ggttacggga   9480
ggatcaaata tactgcttag atgcgtccaa cggcccaacc tgttggaatg gccaggatgg   9540
cgggctagaa ggcttacggc agaagggctg gagtctagtc agcttattga tgatagatag   9600
agaatctcaa atcaggaaca caagaaccaa aatactagct caaggagaca accaggtttt   9660
atgtccgaca tacatgttgt cgccagggct atctcaagag gggctcctct atgaattgga   9720
gagaatatca aggaatgcac tttcgatata cagagccgtc gaggaagggg catctaagct   9780
agggctgatc atcaagaaag aagagaccat gtgtagttat gacttcctca tctatggaaa   9840
aaccccttg tttagaggta acatattggt gcctgagtcc aaaagatggg ccagagtctc   9900
ttgcgtctct aatgaccaaa tagtcaacct cgccaatata atgtcgacag tgtccaccaa   9960
tgcgctaaca gtggcacaac actctcaatc tttgatcaaa ccgatgaggg attttctgct  10020
catgtcagta caggcagtct ttcactacct gctatttagc ccaatcttaa agggaagagt  10080
ttacaagatt ctgagcgctg aagggagag ctttctccta gccatgtcaa ggataatcta  10140
tctagatcct tctttgggag ggatatctgg aatgtccctc ggaagattcc atatacgaca  10200
gttctcagac cctgtctctg aagggttatc cttctggaga gagatctggt taagctccca  10260
agagtcctgg attcacgcgt tgtgtcaaga ggctggaaac ccagatcttg gagagagaac  10320
actcgagagc ttcactcgcc ttctagaaga tccgaccacc ttaaatatca gaggaggggc  10380
cagtcctacc attctactca aggatgcaat cagaaaggct ttatatgacg aggtggacaa  10440
ggtgaaaat tcagagtttc gagaggcaat cctgttgtcc aagacccata gagataattt  10500
tatactcttc ttaatatctg ttgagcctct gtttcctcga tttctcagtg agctattcag  10560
ttcgtcttt ttgggaatcc ccgagtcaat cattggattg atacaaaact cccgaacgat  10620
aagaaggcag tttagaaaga gtctctcaaa aactttagaa gaatccttct acaactcaga  10680
gatccacggg attagtcgga tgacccagac acctcagagg gttggggggg tgtggccttg  10740
ctcttcagag agggcagatc tacttaggga gatctcttgg ggaagaaaag tggtaggcac  10800
gacagttcct caccctctg agatgtttgg attacttccc aagtcctcta tttcttgcac  10860
ttgtggagca acaggaggag gcaatcctag agtttctgta tcagtactcc cgtcctttga  10920
tcagtcattt ttttcacgag gcccctaaa gggatacttg ggctcgtcca cctctatgtc  10980
gacccagcta ttccatgcat gggaaaaagt cactaatgtt catgtggtga agagagctct  11040
atcgttaaa gaatctataa actgttcat tactagagat tccaacttgg ctcaagctct  11100
aattaggaac attatgtctc tgacaggccc tgatttccct ctagaggagg ccctgtctt  11160
caaaaggacg gggtcagcct tgcataggtt caagtctgcc agatacagcg aaggagggta  11220
ttcttctgtc tgcccgaacc tcctctctca tatttctgtt agtacagaca ccatgtctga  11280
tttgacccaa gacgggaaga actacgattt catgttccag tccattgatgc tttatgcaaa  11340
gacatggaca tcagagctgg tacagagaga cacaaggcta agagactcta cgtttcattg  11400
gcacctccga tgcaacaggt gtgtgagacc cattgacgac gtgaccctgg agacctctca  11460
gatcttcgag tttccggatg tgtcgaaaag aatatccaga atggttctg gggctgtgcc  11520
tcacttccag aggcttcccg atatccgtct gagaccagga gattttgaat ctctaagcgg  11580
tagagaaaag tctcaccata tcggatcagc tcagggggctc ttatactcaa tcttagtggc  11640
aattcacgac tcaggataca atgatgaac catcttccct gtcaacatat acggcaaggt  11700
ttcccctaga gactatttga gagggctcgc aaggggagta ttgataggat cctcgatttg  11760
cttcttgaca agaatgacaa atatcaatat taatagacct cttgaattgg tctcaggggt  11820
aatctcatat atttctcctga ggctagataa ccatccctcc ttgtacataa tgctcagaga  11880
accgtctctt agaggagaga tatttctcat ccctcagaaa atcccgccg cttatccaac  11940
cactatgaaa gaaggcaaca gatcaatctt gtgttatctc caacatgtgc tacgctatga  12000
gcgagagata atcacggcgt ctccagagaa tgactggcta tggatctttt cagactttag  12060
aagtgccaaa atgactgtacc tatccctcat tacttaccag tctcatcttc tactccagag  12120
ggttgagaga aacctatcta agagtatgag agataaactg cgacaattga gttctttgat  12180
gaggcaggtg ctgggcggc acggagaaga taccttagag tcagacgaca acattcaacg  12240
actgctaaaa gactctttac gaaggacaag atgggtggat caagaggtgc gccatgcagc  12300
tagaaccatg actggagatt acagcccaa caagaaggtg tcccgtaagg taggatgttc  12360
agaatgggtc tgctctgctc aacaggttgc agtctctacc tcagcaaacc cggcccctgt  12420
ctcggagctt gacataaggg ccctctctaa gaggttccag aacccttga tctcgggctt  12480
gagagtggtt cagtgggcaa ccggtgctca ttataagctt aagcctattc tagatgatct  12540
caatgttttc tcatctctct gccttgtagt tggggacggg tcaggggga tatcaagggc  12600
agtcctcaac atgtttccag atgccaagct tgtgttcaac agtcttttag aggtgaatga  12660
cctgatggct tccggaacac atccactgcc tccttcagca atcatgaggg gaggaaatga  12720
tatcgtctcc agagtgatag atcttgactc aatctgggaa aaaccgtccg acttgagaaa  12780
cttggcaacc tggaaatact tccagtcagt ccaaaagcag gtcaacatgt cctatgacct  12840
cattatttgc gatgcagaag ttactgacat tgcatctatc aaccggatca ccctgttaat  12900
gtccgatttt gcattgtcta tagatggacc actctatttg gtcttcaaaa cttatgggac  12960
tatgctagta aatccaaact acaaggctat tcaacacctg tcaagagcgt tcccctcggt  13020
cacagggttt atcacccaag taacttcgtc ttttttcatct gagctctacc tccgattctc  13080
caaacgaggg aagttttttca gagatgctga gtacttgacc tcttccaccc ttcagaaat  13140
gagccttgtg ttattcaatt gtagcagccc caagagtgag atgcagagag ctcgttcctt  13200
gaactatcag gatcttgtga gaggatttcc tgaagaaatc atatcaaatc cttacaatga  13260
gatgatcata actctgattg acagtgatgt agaatctttt ctagtccaca agatggttga  13320
tgatcttgag ttacagaggg gaactctgtc taagtggct atcattatag ccatcatgat  13380
agttttctcc aacagagtct tcaacgttc caaaccccta actgaccct cgttctatcc  13440
accgtctgat cccaaaatcc tgaggcactt caacatatgt gcagtacta tgatgtatct  13500
atctactgct ttaggtgacg tccctagctt cgcaagactt cacgaccgtg ataacagacc  13560
tataacttat tacttcagaa agcaagtcat tcgagggaac gttatctat cttggagttg  13620
gtccaacgac acctcagtgt tcaaaagggt agcctgtaat tctagcctga gtctgtcatc  13680
tcactggata aggttgattt acaagatagt gaagactcgttg gcagcatcaa  13740
ggatctatcc agagaagtgg aaagacacct tcataggtac aacaggtgga tcaccctaga  13800
ggatatcaga tctagatcat ccctactaga ctacagttgc ctgtgaaccg gatactcctg  13860
gaagcctgcc catgctaaga ctcttgtgtg atgtatcttg aaaaaacaa gatcctaaat  13920
ctgaaccttt ggttgtttga ttgttttct cattttgtt gtttattgt taagcgt      13977
```

| SEQ ID NO: 14 | moltype = DNA   length = 13923 |
|---|---|
| FEATURE | Location/Qualifiers |
| misc_feature | 1..13923 |
| | note = RABV vector: Coravax V5 China |
| source | 1..13923 |
| | mol_type = other DNA |
| | organism = synthetic construct |

SEQUENCE: 14
acgcttaaca accagatcaa agaaaaaaca gacattgtca attgcaaagc aaaaatgtaa 60
cacccctaca atggatgccg acaagattgt attcaaagtc aataatcagg tggtctcttt 120
gaagcctgag attatcgtgg atcaatatga gtacaagtac cctgccatca aagatttgaa 180
aaagccctgt ataaccctag gaaaggctcc cgatttaaat aaagcataca agtcagtttt 240
gtcaggcatg agcgccgcca aacttaatcc tgacgatgta tgttcctatt tggcagcggc 300
aatgcagttt tttgagggga catgtccgga agactggacc agctatggaa ttgtgattgc 360
acgaaaagga gataagatca ccccaggttc tctggtggag ataaaacgta ctgatgtaga 420
agggaattgg gctctgacag gaggcatgga actgacaaga gaccccactg tccctgagca 480
tgcgtcctta gtcggtcttc tcttgagtct gtataggttg agcaaaatat ccgggcaaaa 540
cactggtaac tataagacaa acattgcaga caggatagag cagatttttg agacagcccc 600
ttttgttaaa atcgtggaac accatactct aatgacaact cacaaaatgt gtgctaattg 660
gagtactata ccaaacttca gatttttggc cggaacctat gacatgtttt tctcccggat 720
tgagcatcta tattcagcaa tcagagtggg cacagttgtc actgcttatg aagactgttc 780
aggactggta tcatttactg ggttcataaa acaaatcaat ctcaccgcta gagaggcaat 840
actatatttc ttccacaaga actttgagga agagataaga agaatgtttg agccagggca 900
ggagacagct gttcctcact cttatttcat ccacttccgt tcactaggct tgagtgggaa 960
atctccttat tcatcaaatg ctgttggtca cgtgttcaat ctcattcact ttgtaggatg 1020
ctatatgggt caagtcagat ccctaaatgc aacggttatt gctgcatgtg ctcctcatga 1080
aatgtctgtt ctagggggct atctgggaga ggaattcttc gggaaaggga catttgaaag 1140
aagattcttc agagatgaga aagaacttca agaatacgag gcggctgaac tgacaaagac 1200
tgacgtagca ctggcagatg atggaactgt caactctgac gacgaggact acttttcagg 1260
tgaaaccaga agtccggagg ctgtttatac tcgaatcatg atgaatggag gtcgactaaa 1320
gagatctcac atacggagat atgtctcagt cagttccaat catcaagccc gtccaaactc 1380
attcgccgag tttctaaaca agacatattc gagtgactca taagaagttg aataacaaaa 1440
tgccggaaat ctacggattg tgtatatcca tcatgaaaaa aactaacacc cctcctttcg 1500
aaccatccca aacatgagca agatctttgt caatcctagt gctattagag ccggtctggc 1560
cgatcttgag atggctgaag aaactgttga tctgatcaat agaaatatcg aagacaatca 1620
ggctcatctc caaggggaac ccatagaggt ggacaatctc cctgaggata tggggcgact 1680
tcacctggat gatggaaaat cgcccaacca tggtgagata gccaaggtgg gagaaggcaa 1740
gtatcgagag gactttcaga tggatgaagg agaggatcct agcttcctgt tccagtcata 1800
cctggaaaat gttggagtcc aaatagtcag acaaatgagg tcaggagaga gatttctcaa 1860
gatatggtca cagaccgtag aagagattat atcctatgtc gcggtcaact ttcccaaccc 1920
tccaggaaag tcttcagagg ataaatcaac ccagactact ggccgagagc tcaagaagga 1980
gacaacaccc actccttctc agagagaaag ccaatcatcg aaagccagga tggcggctca 2040
aattgcttct ggccctccag cccttgaatg gtcggctacc aatgaagagg atgatctatc 2100
agtggaggct gagatcgctc accagattgc agaaagtttc tccaaaaaat ataagtttcc 2160
ctctcgatcc tcagggatac tcttgtataa ttttgagcaa ttgaaaatga accttgatga 2220
tatagttaaa gaggcaaaaa atgtaccagg tgtgacccgt ttagcccatg acgggtccaa 2280
actcccccta agatgtgtac tgggatgggt cgctttggcc aactctaaga aattccagtt 2340
gttagtcgaa tccgacaagc tgagtaaaat catgcaagat gacttgaatc gctatacatc 2400
ttgctaaccg aacctctccc ctcagtccct ctagacaata aaatccgaga tgtcccaaag 2460
tcaacatgaa aaaaacaggc aacaccactg ataaaatgaa cctcctacgt aagatagtga 2520
aaaaccgcag ggacgaggac actcaaaaat cctctcccgc gtcagcccct ctggatgacg 2580
atgacttgtg gcttccaccc cctgaatacg tcccgctgaa agaacttaca ggcaagaaga 2640
acatgaggaa cttttgtatc aacggaaggg ttaaagtgtg tagcccgaat ggttactcgt 2700
tcaggatcct gcggcacatt ctgaaatcat tcgacgagat atattctggg aatcatagga 2760
tgatcgggtt agtcaaagtg gttattggac tggctttgtc aggatctcca gtccctgagg 2820
gcctgaactg ggtatacaaa ttgaggagaa cctttatctt ccagtgggct gattccaggg 2880
gccctcttga aggggaggag ttggaatact ctcaggagat cacttgggat gatgatactg 2940
agttcgtcgg attgcaaata agagtgattg caaaacagtg tcatatccag ggcagagtct 3000
ggtgtatcaa catgaacccg agagcatgtc aactatggtc tgacatgtct cttcagacac 3060
aaaggtccga agaggacaaa gattcctctc tgcttctaga ataatcagat tatatcccgc 3120
aaatttatca cttgtttacc tctggaggag agaacatatg ggctcaactc caacccttgg 3180
gagcaatata acaaaaaaca tgttatggtg ccattaaacc gctgcatttc atcaaagtca 3240
agttgattac ctttacattt tgatcctctt ggatgtgaaa aaaactatta acatccctca 3300
aaagaccccg ggccaccatg ttcgtgtttc tggtgctgct gcctctggtg agctcccagt 3360
gcgtgaacct gaccacaagg acccagctgc cccctgccta taccaattcc ttcacacggg 3420
gcgtgtacta tcccgacaag gtgttccgga gcagcgtgct gcactccaca caggatctgt 3480
ttctgccttt cttttctaac gtgacctggt tccacgccat ccacgtgagc ggcaccaatg 3540
gcacaaagcg gttcgacaat ccagtgctgc cctttaacga tggcgtgtac ttcgcctcca 3600
ccgagaagtc taacatcatc agaggctgga tctttggcac cacactggac agcaagacac 3660
agtccctgct gatcgtgaac aatgccacca acgtggtcat caaggtgtgc gagttccagt 3720
tttgtaatga tccattcctg ggcgtgtact atcacaagaa caataagtct tggatggaga 3780
gcgagtttcg cgtgtattcc tctgccaaca attgcacatt tgagtacgtg tcccagccct 3840
tcctgatgga cctggagggc aagcagggca atttcaagaa cctgagggag ttcgtgttta 3900
agaatatcga tggctacttc aaaatctact ccaagcacac ccccaatcaac ctggtgcgcg 3960
acctgccaca gggcttctct gccctggagc cactggtgga tctgcccatc ggcatcaaca 4020
tcacccggtt tcagacactg ctggccctgc acagaagcta cctgacacca ggcgacagct 4080
cctctggatg gaccgcagga gcagcagcct actatgtggg ctatctgcag cccaggacct 4140
tcctgctgaa gtacaacgag aatggcacca tcacagacgc cgtggattgc gccctggatc 4200
ccctgtctga gaccaagtgt acactgaaga gctttaccgt ggagaagggc atctatcaga 4260

```
caagcaattt cagggtgcag cctaccgagt ccatcgtgcg ctttcccaat atcacaaacc   4320
tgtgcccttt tggcgaggtg ttcaacgcaa cccgcttcgc cagcgtgtac gcctggaata   4380
ggaagcgcat ctccaactgc gtggccgact atttctgtgct gtacaacagc gcctccttct   4440
ctaccttaa gtgctatggc gtgagcccca caaagctgaa tgacctgtgc tttaccaacg   4500
tgtacgccga ttccttcgtg atcagggcg acgaggtgcg ccagatccga ccaggacaga   4560
caggcaagat cgcagactac aattataagc tgcctgacga tttcaccggc tgcgtgatcg   4620
cctggaactc taacaatctg gatagcaaag tgggcggcaa ctacaattat ctgtaccggc   4680
tgtttagaaa gtctaatctg aagccattcg agggggacat ctccacagaa atctaccagg   4740
ccggctctac ccctgcaat ggcgtggagg gctttaactg ttatttccct ctgcagagct   4800
acggcttcca gccaacaaac ggcgtgggct atcagcccta ccgcgtggtg gtgctgtctt   4860
ttgagctgct gcacgcacct gcaacagtgt gcggaccaaa gaagagcacc aatctggtga   4920
agaacaagtg cgtgaacttc aacttcaacg gactgaccgg aacaggcgtg ctgaccgagt   4980
ccaacaagaa gttcctgcct tttcagcagt tcggcaggga catcgcagat accacagacg   5040
ccgtgcgcga ccctcagacc ctggagatcc tggacatcac accatgctcc ttcggcggca   5100
tgtctgtgat cacaccaggc accaatacaa gcaaccaggt ggccgtgctg tatcaggacg   5160
tgaattgtac cgaggtgcca gtggcaatcc acgcagatca gctgacccct acatggcggg   5220
tgtactctac cggcagcaac gtgttccaga caagagccgg atgcctgatc ggagcagagc   5280
acgtgaacaa tagctatgag tgcgacatcc ctatccggcc cggcatctgt gcctcctacc   5340
agacccagac aaactcccca aggtctgtgg gagatgaggc cgaagacttt gtggaagtcc   5400
acctgcctga tgtgcataac caggtgtctg cgctcgacct gggactgcca aattggggca   5460
agtacgtgct gctgagtgct ggagcactga ctgccctgat gctgatcatt ttcctgatga   5520
cctgctgtcg gcgcgtgaac agaagtgagc ccactcagca caatctggca ggaaccggga   5580
gagaagtgtc agtcacacct cagagcggga aaatcattag tagttgggaa tcacataaaa   5640
gcgggggcga gaccaggctg ggatccggct ccggcgaggg caggggaagt ctactaacat   5700
gcggggacgt ggaggaaaat cccggcccca tggttcctca ggctctcctg tttgtacccc   5760
ttctggtttt tccattgtgt tttgggaaat tcccctattta cacgatacca gacaagctgg   5820
gtccctggag tccgattgac atacatcacc tcagctgccc aaacaatttg gtagtggagg   5880
acgaaggatg caccaacctg tcagggttct cctacatgga acttaaagtt ggatacatct   5940
tagccataaa agtgaacggg ttcacttgca caggcgttgt gacggaggct gaaacctaca   6000
ctaacttcgt tggttatgtc acaaccacgt tcaaaagaaa gcatttccgc ccaaccaccag   6060
atgcatgtag agccgcgtac aactggaaga tggccggtga ccccagatat gaagagtctc   6120
tacacaatcc gtaccctgac taccgctggc ttcgaactgt aaaaaccacc aaggagtctc   6180
tcgttatcat atctccaagt gtggcagatt tggacccata tgcagatcc cttcactcga   6240
gggtcttccc tagcgggaag tgctcaggag tagcggtgtc ttctacctac tgctccacta   6300
accacgatta caccattggg atgcccgaga atccgagact agggatgtct tgtgacattt   6360
ttaccaatag tagagggaag agagcatcca aagggagtga gacttgcggc tttgtagatg   6420
aaagaggcct atataagtct ttaaaggag catgcaaact caagtatgt ggagttctag   6480
gacttagact tatggatgga acatgggtct cgatgcaaac atcaaatgaa accaaatggt   6540
gccctcccga taagttggtg aacctgcacg actttcgctc agacgaaatt gagcaccttg   6600
ttgtagagga gttggtcagg aagagagagg agtgtctgga tgcactagag tccatcatga   6660
caaccaagtc agtgagtttc agacgtctca gtcatttaag aaaacttgtc cctgggtttg   6720
gaaaagcata taccatattc aacaagacct tgatggaagc cgatgctcac tacaagtcag   6780
tcgagacttg gaatgagatc ctcccttcaa aagggtgtt aagagttgag ggaggtgctc   6840
atcctcatgt gaacgggtg ttttttcaatg gtataatatt aggacctgac ggcaatgtct   6900
taatcccaga gatgcaatca tccctcctcc agcaacatat ggagttgttg aatcctcgg   6960
ttatcccct tgtgcaccc ctggcagacc cgtctaccg tttcaaggac ggtgacgagg   7020
ctgaggattt tgttgaagtt caccttcccg atgtgcaa tcaggtctca ggagttgact   7080
tgggtctccc gaactgggg aagtatgtat tactgagtgc aggggccctg actgccttga   7140
tgttgataat tttcctgatg acatgttgta gaagagtcaa tcgatcagaa cctacgcaac   7200
acaatctcag agggacaggg agggaggtgt cagtcactcc ccaaagcggg aagatcatat   7260
cttcatggga atcacacaag agtgggggtg agaccagact gtaagctagc ttataaagtg   7320
ctgggtcatc taagcttttc agtcgagaaa aaaacattag atcagaagaa caactggcaa   7380
cacttctcaa cctgagactt acttcaagat gctcgatcct ggagaggtct atgatgaccc   7440
tattgaccca atcgagttag aggctgaacc cagaggaacc cccattgtcc caacatcttt   7500
gaggaactct gactacaatc tcaactctcc tttgataga gatcctgcta gactaattgt   7560
agaatggtta aaaacaggga atagaccta tcggatgact ctaacagaca attgctccag   7620
gtctttcaga gttttgaaag attatttcaa gaaggtagat ttgggttctc tcaaggtggg   7680
cggaatggct gcacagtcaa tgatttctct ctggttatat ggtgcccact ctgaatccaa   7740
caggagccgg agatgtataa cagacttggc ccatttctat tccaagtcgt cccccataga   7800
gaagctgttg aatctcacgc taggaaatag agggctgaga atcccccag agggagtgtt   7860
aagttgcctt gagagggttg attatgataa tgcatttgga aggtatcttg ccaacacgta   7920
ttcctcttac ttgttcttcc atgtaatcac cttatacatg aacgcctag actgggatga   7980
agaaaagacc atcctagcat tatggaaaga tttaaccta gtggacatcg ggaaggactt   8040
ggtaaagttc aaagaccaaa tatggggact gctgatcgta acaaaggact ttgtttactc   8100
ccaaagttcc aattgtcttt ttgacagaaa ctacacactt atgctaaaag atctttctt   8160
gtctcgcttc aactccttaa tggtcttgct ctctcccca gagccccgat actcagatga   8220
cttgatatct caactatgcc agctgtacat tgctggggat caagtcttgt ctatgtgtgg   8280
aaactccggc tatgaagtca tcaaaatatt ggagccatat gtcgtgaata gtttagtcca   8340
gagagcagaa aagtttaggc ctctcattca ttccttggga gactttcctg tatttataaa   8400
agacaaggta agtcaacttg aagagacgtt cggtccctgt gcaagaaggt tctttagggc   8460
tctggatcaa ttcgacaaca tacatgactt ggttttttgtg tttggctgtt acaggcattg   8520
ggggcaccca tatatagatt atcgaaaggg ctgtcaaaa ctatatgatc aggttcacct   8580
taaaaaaaatg atagataagt cctaccagga gtgcttagca agcgacctag ccaggaggat   8640
ccttagatgg ggttttgata agtactccaa gtggtatctg gattcaagat tcctagccg   8700
agaccacccc ttgactcctt atatcaaaac ccaaacatgg ccaccaaac atattgtaga   8760
cttggtgggg gatacatggc acaagctccc gatcacgcag atctttgaga ttcctgaatc   8820
aatggatccg tcagaaatat tggatgacaa atcacattct ttcaccagaa cgagactagc   8880
ttcttggctg tcagaaaacc gagggggggcc tgttcctagc gaaaagtta ttatcacggc   8940
cctgtctaag ccgcctgtca atccccgaga gtttctgagg tctatagacc tcggaggatt   9000
```

```
gccagatgaa gacttgataa ttggcctcaa gccaaggaa cgggaattga agattgaagg   9060
tcgattcttt gctctaatgt catggaatct aagattgtat tttgtcatca ctgaaaaact   9120
cttggccaac tacatcttgc cactttttga cgcgctgact atgacagaca acctgaacaa   9180
ggtgtttaaa aagctgatcg acagggtcac cgggcaaggg cttttggact attcaagggt   9240
cacatatgca tttcacctgg actatgaaaa gtggaacaac catcaaagat tagagtcaac   9300
agaggatgta ttttctgtcc tagatcaagt gtttggattg aagagagtgt tttctagaac   9360
acacgagttt tttcaaaagg cctgatcta ttattcagac agatcagacc tcatcgggtt   9420
acgggaggat caaatatact gcttagatgc gtccaacggc ccaacctgtt ggaatggcca   9480
ggatggcggg ctagaaggct tacggcagaa gggctggagt ctagtcagct tattgatgat   9540
agatagagaa tctcaaaata ggaacacaag aaccaaaata ctagctcaag gagacaacca   9600
ggttttatgt ccgacataca tgttgtcgcc agggctatct caagaggggc tcctctatga   9660
attggagaga atatcaagga atgcactttc gatatacaga gccgtcgagg aaggggcatc   9720
taagctaggg ctgatcatca agaaagaaga gaccatgtgt agttatgact tcctcatcta   9780
tggaaaaacc cctttgttta gaggtaacat attggtgcct gagtccaaaa gatgggccag   9840
agtctcttgc gtctctaatg accaaatagt caacctcgcc aatataatgt cgacagtgtc   9900
caccaatgcg ctaacagtgg cacaacactc tcaatctttg atcaaaccga tgagggattt   9960
tctgctcatg tcagtacagg cagtctttca ctacctgcta tttagcccaa tcttaaaggg  10020
aagagtttac aagattctga gcgctgaagg ggagagcttt ctcctagcca tgtcaaggat  10080
aatctatccta gatccttctt tgggagggat atctggaatg tccctcggaa gattccatat  10140
acgacagttc tcagaccctg tctctgaagg gttatccttc tggagagaga tctggttaag  10200
ctcccaagag tcctggattc acgcgttgtg tcaagaggct ggaaacccag atcttggaga  10260
gagaacactc gagagcttca ctcgccttct agaagatccg actaccttaa atatcagagg  10320
aggggccagt cctaccattc tactcaagga tgcaatcaga aaggctttat atgacgaggt  10380
ggacaaggtg gaaaattcag agtttcgaga ggcaatcctt ttgtccaaga cccatagaga  10440
taattttata ctcttcttaa tatctgttga gcctctgttt cctcgatttc tcagtgagct  10500
attcagttcg tcttttttgg gaatcccga gtcaatcatt ggattgatac aaaactcccg  10560
aacgataaga aggcagttta gaaagagtct ctcaaaaact ttagaagaat ccttctacaa  10620
ctcagagatc cacgggatta gtcggatgac ccagacacct cagagggttg ggggggtgtg  10680
gccttgctct tcagagaggg cagatctact tagggagatc tcttgggaa gaaaagtggt  10740
aggcacgaca gttcctcacc cttctgagat gttgggatta cttcccaagt cctctatttc  10800
ttgcacttgt ggagcaacag gaggaggcaa tcctagagtt tctgtatcag tactcccgtc  10860
ctttgatcag tcattttttt cacgaggccc cctaaaggga tacttgggct cgtccacctc  10920
tatgtcgacc cagctattcc atgcatggga aaaagtcact aatgttcatg tggtgaagag  10980
agctctatcg ttaaaagaat ctataaactg gttcattact agagattcca acttggctca  11040
agctctaatt aggaacatta tgtctctgac aggccctgat ttccctctag aggaggcccc  11100
tgtcttcaaa aggacggggt cagccttgca taggttcaag tctgccagat acagcgaagg  11160
agggtattct tctgtctgcc cgaacctcct ctctcatatt tctgttagta cagacaccat  11220
gtctgatttg acccaagacg ggaagaacta cgatttcatg ttccagccat tgatgcttta  11280
tgcacagaca tggacatcag agctgggtaca gagagacaca aggctaagag actctacgtt  11340
tcattggcac ctccgatgca acaggtgtgt gagacccatt gacgacgtga ccctgggagac  11400
ctctcagatc ttcgagtttc cggatgtgtc gaaaagaata tccagaatgg tttctggggc  11460
tgtgcctcac ttccagaggc ttcccgatat ccgtctgaga ccaggagatt ttgaatctct  11520
aagcgggtaga gaaaagtctc accatatcgg atcagctcag ggctcttat actcaatctt  11580
agtggcaatt cacgactcag gatacaatga tggaaccatc ttccctgtca acatatacgg  11640
caaggttttcc cctagagact atttgagagg gctcgcaagg ggagtattga taggatcctc  11700
gatttgcttc ttgacaagaa tgacaaatat caatattaat agacctcttg aattggtctc  11760
aggggtaatc tcatatattc tcctgaggct agataaccat ccctccttgt acataatgct  11820
cagagaaccg tctcttagag gagagatatt ttctatccct cagaaaatcc ccgccgctta  11880
tccaaccact atgaaagaag gcaacagatc aatcttgtgt tatctccaac atgtgctacg  11940
ctatgagcga gagataatca cggcgtctcc agagaatgac tggctatgga tcttttcaga  12000
ctttagaagt gccaaaatga cgtacctatc cctcattact taccagtctc atcttctact  12060
ccagagggtt gagagaaacc tatctaagag tatgagagat aacctgcgac aattgagttc  12120
tttgatgagg caggtgctgg gcgggcacgg agaagatacc ttagagtcag acgcaaacat  12180
tcaacgactg ctaaaagact ctttacgaag gacaagatgg gtggatcaag aggtgcgcca  12240
tgcagctaga accatgactg gagattacag ccccaacaag aaggtgtcc gtaaggtagg  12300
atgttcagaa tgggtctgct ctgctcaaca ggttgcagtc tctacctcag caaacccggc  12360
ccctgtctcg gagcttgaca taagggcccct ctctaagagg ttccagaacc ctttgatctc  12420
gggcttgaga gtggttcagt gggcaaccgg tgctcattat aagcttaagc ctattctaga  12480
tgatctcaat gttttcccat ctctctgcct tgtagttggg gacgggtcag ggggatatc  12540
aagggcagtc ctcaacatgt ttcagatgc caagcttgtg ttcaacagtc ttttagaggt  12600
gaatgacctg atggcttccg gaacacatcc actgcctcct tcagcaatca tgaggggagg  12660
aaatgatatc gtctccagag tgatagatct tgactcaatc tgggaaaaac cgtccgactt  12720
gagaaacttg gcaacctgga aatacttcca gtcagtccaa agcaggtca acatgtccta  12780
tgacctcatt atttgcgatg cagaagttac tgacattgca tctatcaacc ggatcaccct  12840
gttaatgtcc gattttgcat tgtctataga tggaccactc tatttggtct tcaaaactta  12900
tgggactatg ctagtaaatc caaactacaa ggctattcaa cacctgtcaa gagcgttccc  12960
ctcggtcaca gggtttatca cccaagtaac ttcgtctttt tcatctgagc tctacctccg  13020
attctccaaa cgagggaagt ttttcagaga tgctgagtac ttgacctctt ccaccctccg  13080
agaaatgagc cttgtgttat tcaattgtag cagcccccaag agtgagatgc agagagctcg  13140
ttccttgaac tatcaggatc ttgtgagagg atttcctgaa gaaatcatat caaatcctta  13200
caatgagatg atcataactc tgattgacag tgatgtagaa tcttttcag tccacaagat  13260
ggttgatgat cttgagttac agaggggaac tctgtctaaa gtggctatca ttatagccat  13320
catgatagtt ttctccaaca gagtcttcaa cgtttcaaaa ccctaactg accccctcgtt  13380
ctatccaccg tctgatccca aaatcctgag gcacttcaaa atatgttgca gtactatgat  13440
gtatctatct actgctttag gtgacgtccc tagcttcgca agacttcacg acctgtataa  13500
cagacctata acttattact tcagaaagca agtcattcga gggaacgttt atctatcttg  13560
gagttggtcc aacgacacct cagtgttcaa aagggtagcc tgtaattcta gcctgagtct  13620
gtcatctcac tggatcaggt tgatttacaa gatagtgaag actaccagac tcgttggcag  13680
catcaaggat ctatccagag aagtggaaag acaccttcat aggtacaaca ggtggatcac  13740
```

```
cctagaggat atcagatcta gatcatccct actagactac agttgcctgt gaaccggata    13800
ctcctggaag cctgcccatg ctaagactct tgtgtgatgt atcttgaaaa aaacaagatc    13860
ctaaatctga acctttggtt gtttgattgt ttttctcatt tttgttgttt atttgttaag    13920
cgt                                                                  13923

SEQ ID NO: 15           moltype = DNA   length = 13974
FEATURE                 Location/Qualifiers
misc_feature            1..13974
                        note = RABV vector: Coravax V5 South Africa
source                  1..13974
                        mol_type = other DNA
                        organism = synthetic construct
SEQUENCE: 15
acgcttaaca accagatcaa agaaaaaaca gacattgtca attgcaaagc aaaaatgtaa      60
caccccctaca atggatgccg acaagattgt attcaaagtc aataatcagg tggtctcttt    120
gaagcctgag attatcgtgg atcaatatga gtacaagtac cctgccatca agatttgaa     180
aaagccctgt ataaccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaa ttgtgattgc    360
acgaaaagga gataagatca ccccaggttc tctggtggag ataaaacgta ctgatgtaga    420
agggaattgg gctctgacag gaggcatgga actgacaaga gaccccactg tccctgagca    480
tgcgtcctta gtcggtcttc tcttgagtct gtataggtta agcaaaatat ccgggcaaaa    540
cactggtaac tataagacaa acattgcaga caggatagag cagattttg agacagcccc    600
ttttgttaaa atcgtggaac accatactct aatgacaact cacaaaatgt gtgctaattg    660
gagtactata ccaaacttca gatttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga agaatgtttg agccagggca    900
ggagacagct gttcctcact cttatttcat ccacttccgt tcactaggct tgagtgggaa    960
atctccttat tcatcaaatg ctgttggtca cgtgttcaat ctcattcact ttgtaggatg   1020
ctatatgggt caagtcagat ccctaaatgc aacggttatt gctgcatgtg ctcctcatga   1080
aatgtctgtt ctagggggct atctgggaga ggaattcttc gggaaaggga catttgaaag   1140
aagattcttc agagatgaga aagaacttca agaatacgag gcggctgaac tgacaaagac   1200
tgacgtagca ctggcagatg atggaactgt caactctgac gacgaggact actttttcagg   1260
tgaaaccaga agtccggagg ctgtttatac tcgaatcatg atgaatggag gtcgactaga   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctcctttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caaggggaac ccatagaggt ggacaatctc cctgaggata tggggcgact   1680
tcacctggat gatgaaaat cgcccaacca tggtgagata gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtccggctacc aatgaagagg atgatctatc   2100
agtggaggct gagatcgctc accagattgc agaaagtttc tccaaaaaat ataagttttcc   2160
ctctcgatcc tcaggatac tcttgtataa ttttgagcaa ttgaaaatga accttgatga   2220
tatagttaaa gaggcaaaaa atgtaccagg tgtgacccgt ttagcccatg acggggtcaa   2280
actcccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgca cctcctacgt aagatagtga   2520
aaaaccgcag ggacgaggac actcaaaaat cctctcccgc gtcagcccct ctggatgacg   2580
atgacttgtg gcttccaccc cctgaatacg tcccgctgaa agaacttaca ggcaagaaga   2640
acatgaggaa ctttgtatc aacggaaggg ttaaagtgtg tagcccgaat ggttactcgt   2700
tcaggatcct gcggcacatt ctgaaatcat tcgacgaat atattctggg aatcatagga   2760
tgatcgggtt agtcaaagtg gttattggac tggctttgtc aggatctcca gtccctgagg   2820
gcctgaactg ggtatacaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaacagtg tcatatccag gcagagtcct   3000
ggtgtatcaa catgaacccg agacatgtc aactatggtc tacatgtct cttcagacac   3060
aaaggtccga agaggacaaa gattcctctc tgcttctaga ataatcagat tatatcccgc   3120
aaatttatca cttgtttacc tctggaggag agaacatatg ggctcaactc caaccccttgg   3180
gagcaatata acaaaaaaca tgttatggtg ccattaaacc gctgcatttc atcaaagtca   3240
agttgattac ctttacattt tgatcctctt ggatgtgaaa aaaactatta acatccctca   3300
aaagaccccg ggccaccatg ttcgtgtttc tggtgctgct gcctctggtg agctcccagt   3360
gcgtgaactt caccacaagg acccagctgc ccctgcta taccaattcc ttcacacggg   3420
gcgtgtacta cccgacaag gtgttccgga gcagcgtgct gcactccaca caggatctgt   3480
ttctgccttt cttttctaac gtgacctggt tccacgccat ccacgtgagc ggcaccaatg   3540
gcacaaagcg gttcgccaat ccagtgctgc ctttaacga tggcgtgtac ttcgcctcca   3600
ccgagaagcg taacatcatc agaggctgga tcttttggca cactggac acaagacac   3660
agtccctgct gatcgtgaac aatgccacca acgtggtcat caaggtgtgc gagttccagt   3720
tttgtaatga tccattcctg ggcgtgtact atcacaagaa caataagtct tggatggaga   3780
gcgagtttcg cgtgtattcc tctgccaaca attgcacatt tgagtacgtg tcccagccct   3840
tcctgatgga cctgggggc aagcaggca atttcaagaa cctgagggag ttcgtgttta   3900
agaatatcga tggctacttc aaaatctact ccaagcacac cccaatcaac ctggtgcgcg   3960
```

-continued

```
gcctgccaca gggcttctct gccctggagc cactggtgga tctgcccatc ggcatcaaca   4020
tcacccggtt tcagacactg ctggccctgc acagaagcta cctgacacca ggcgacagct   4080
cctctggatg gaccgcagga gcagcagcct actatgtggg ctatctgcag cccaggacct   4140
tcctgctgaa gtacaacgag aatggcacca tcacagacgc cgtggattgc gccctggatc   4200
ccctgtctga gaccaagtgt acactgaaga gctttaccgt ggagaagggc atctatcaga   4260
caagcaattt cagggtgcag cctaccgagt ccatcgtgcg ctttcccaat atcacaaacc   4320
tgtgcccttt tggcgaggtg ttcaacgcaa cccgcttcgc cagcgtgtac gcctggaata   4380
ggaagcgcat ctccaactgc gtggccgact attctgtgct gtacaacagc gcctccttct   4440
ctaccttaa gtgctatggc gtgagcccca caaagctgaa tgacctgtgc tttaccaacg   4500
tgtacgccga ttccttcgtg atcaggggcg acgaggtgcg ccagatcgca ccaggacaga   4560
caggcaatat cgcagactac aattataagc tgcctgacga tttcaccggc tgcgtgatcg   4620
cctgaactc taacaatctg gatagcaaag tgggcggcaa ctacaattat ctgtaccggc   4680
tgtttagaaa gtcaatctg aagccattcg agagggacat ctccacagaa atctaccagg   4740
ctcgtctac cccctgcaat ggcgtgaagg gctttaactg ttattcccct ctgcagagct   4800
acggcttcca gccaacatat ggcgtgggct atcagcccta ccgcgtggtg gtgctgtctt   4860
ttgagctgct gcacgcacct gcaacagtgt gcggaccaaa gaagagcacc aatctggtga   4920
agaacaagtg cgtgaacttc aacttcaacg gactgaccgg aacaggcgtg ctgaccgagt   4980
ccaacaagaa gttcctgcct tttcagcagt tcggcaggga catcgcagat accacagacg   5040
ccgtgcgcga ccctcagacc ctggagatcc tggacatcac accatgctcc ttcggcggca   5100
tgtctgtgat cacaccaggc accaatacaa gcaaccaggt ggccgtgctg tatcagggcg   5160
tgaattgtac cgaggtgcca gtggcaatcc acgcagatca gctgaccccct acatggcggg   5220
tgtactctac cggcagcaac gtgttccaga caagagccgg atgcctgatc ggacagcagc   5280
acgtgaacaa tagctatgag tgcgacatcc ctatcggcgc cggcatctgt gcctcctacc   5340
agacccagac aaaactcccca gaatcaagcg tgattcctct ggtccatcca ctggcagatc   5400
cctccacagt gttcaaagac ggagatgagg ccgaagactt tgtggaagtc cacctgcctg   5460
atgtgcataa ccaggtgtct ggcgtcgacc tgggactgcc aaattgggc aagtacgtgc   5520
tgctgagtgc tggagcactg actgccctga tgctgatcat tttcctgatg acctgctgtc   5580
ggcgcgtgaa cagaagtgag cccactcagc acaatctgcg aggaaccggg agagaagtgt   5640
cagtcacacc tcagagcggg aaaatcatta gtagttggga atcacataaa agcggggcg   5700
agaccaggct gggatccggc tccggcgagg gcaggggaag tctactaaca tgcgggacg   5760
tggaggaaaa tcccggcccc atggttcctc aggctctcct gtttgtaccc cttctggttt   5820
ttccattgtg ttttgggaaa ttccctattt acacgatacc agacaagctt ggtccctgga   5880
gtccgattga catacatcac ctcagctgcc caaacaattt ggtagtggag gacgaaggat   5940
gcaccaacct gtcagggttc tcctacatgg aacttaaagt tggatacatc ttagccataa   6000
aagtgaacgg gttcacttgc acaggcgttg tgacggaggc tgaaacctac actaacttcg   6060
ttggttatgt cacaaccacg ttcaaaagaa agcatttccg cccaacacca gatgcatgta   6120
gagccgcgta caactggaag atggccgtg accccagata tgaagagtct ctacacaatc   6180
cgtaccctga ctaccgctgg cttcgaactg taaaaccac caaggagtct ctcgttatca   6240
tatctccaag tgtggcagat ttggacccat atgacagatc ccttcactcg agggtcttcc   6300
ctagcgggaa gtgctcagga gtagcggtgt cttctaccta ctgctccact aaccacgatt   6360
acaccatttg gatgcccgag aatccgagac tagggatgtc ttgtgacatt tttaccaata   6420
gtagagggaa gagagcatcc aaagggagtg agacttgcgg ctttgtagat gaaagaggcc   6480
tatataagtc tttaaaagga gcatgcaaac tcaagttatg tggagttcta ggacttagac   6540
ttatggatgg aacatgggtc tcgatgcaaa catcaaatga aaccaaatgg tgccctcccg   6600
ataagttggt gaacctgcac gactttcgct cagacgaaat tgagcacctt gttgtagagg   6660
agttggtcag gaagagagag gagtgtctgg atgcactaga gtccatcatg acaaccaagt   6720
cagtgagttt cagacgtctc agtcatttaa gaaaacttct ccctgggttt cggaaaagcat   6780
ataccatatt caacaagacc ttgatggaag ccgatgctca ctacaagtca gtcgagactt   6840
ggaatgagat cctccccttca aaagggtgtt taagagttgg ggagaggtgt catcctcatg   6900
tgaacgggt gtttttcaat ggtataatat taggacctga cggcaatgtc ttaatcccag   6960
agatgcaatc atccctcctc cagcaacata tggagttgtt ggaatcctcg gttatcccct   7020
ttgtgcaccc cctggcagac ccgtctaccg tttttcaagga cggtgacgag gctgaggatt   7080
ttgttgaagt tcacctttcccc gatgtgcaca atcaggtctc aggagttgac ttgggtctcc   7140
cgaactgggg gaagtatgta ttactgagtg caggggccct gactgccttg atgttgataa   7200
ttttcctgat gacatgttgt agaagagtca atcgatcaga acctacgcaa cacaatctca   7260
gagggacagg gagggaggtg tcagtcactc cccaaagcgg gaagatcata tcttcatggg   7320
aatcacacaa gagtggggt gagaccagac tgtaagctag cttataaagt gctgggtcat   7380
ctaagctttt cagtcgagaa aaaaacatta gatcagaaga acaactggca acacttctca   7440
acctgagact tacttcaaga tgctcgatcc tggaaggtc tatgatgacc ctattgaccc   7500
aatcagagtta gaggctgaac ccagaggaac ccccattgtc cccaacatct tgaggaactc   7560
tgactacaat ctcaactctc ctttgataga agatcctgct agactaatgt tagaatggtt   7620
aaaaacaggg aatagacctt atcggatgac tctaacagac aattgctcca ggtctttcag   7680
agttttgaaa gattatttca agaaggtaga tttgggttct ctcaaggtgg gcggaatggc   7740
tgcacagtca atgatttctc tctggttata tggtgcccac tgtgaatcca acgaggagcg   7800
gagatgtata acagacttgg cccatttcta ttccaagtcg tcccccatag agaagctgtt   7860
gaatctcacg ctaggaaata gagggctgag aatcccccca gagggagtgt taagttgcct   7920
tgagagggtt gattatgata atgcatttgg aaggtatctt gccaacacgt attcctctta   7980
cttgttcttc catgtaatca cctatacat gaacgcccta gactgggatg aagaaaagac   8040
catcctagca ttatggaaag atttaacctc agtggacatc gggaaggact tggtaaagtt   8100
caaagaccaa atatggggac tgctgatcgt gacaaaggac tttgtttact cccaaagttc   8160
caattgtctt tttgacagaa actacacact tatgctaaaa gatcttttct tgtctcgctt   8220
caactcctta atggtcttgc tctctcccc agagccccga tactcagatg acttgatatc   8280
tcaactatgc cagctgtaca ttgctgggga tcaagtcttg tctatgtgtg aaactccgg   8340
ctatgaagtc atcaaaaatat tggagccata tgtcgtgaat agttagtcc agagagcgaa   8400
aaagtttagg cctctcattc attccttggg agactttcct gtatttataa agacaaggt   8460
aagtcaactt gaagagacgt tcggtccctg tgcaagaagg ttctttaggg ctctggatca   8520
attcgacaac atacatgact tggttttgt gtttggctgt tacaggcatt gggggcaccc   8580
atatatatgat tatcgaaagg gtctgtcaaa actatatgat caggttcacc ttaaaaaat   8640
gatagataag tcctaccagg agtgcttagc aagcgaccta gccaggagga tccttagatg   8700
```

```
gggttttgat aagtactcca agtggtatct ggattcaaga ttcctagccc gagaccaccc   8760
cttgactcct tatatcaaaa cccaaacatg gccaccaaaa catattgtag acttggtggg   8820
ggatacatgg cacaagctcc cgatcacgca gatctttgag attcctgaat caatggatcc   8880
gtcagaaata ttggatgaca aatcacattc tttcaccaga acgagactag cttcttggct   8940
gtcagaaaac cgaggggggc ctgttcctag cgaaaaagtt attatcacgg ccctgtctaa   9000
gccgcctgtc aatccccgag agtttctgag gtctatagac ctcggaggat tgccagatga   9060
agacttgata attggcctca agccaaagga acgggaattg aagattgaag gtcgattctt   9120
tgctctaatg tcatggaatc taagattgta ttttgtcatc actgaaaaac tcttggccaa   9180
ctacatcttg ccactttttg acgcgctgac tatgacagac aacctgaaca aggtgtttaa   9240
aaagctgatc gacagggtca ccgggcaagg gcttttggac tattcaaggg tcacatatgc   9300
atttcacctg gactatgaaa agtggaacaa ccatcaaaga ttagagtcaa cagaggatgt   9360
attttctgtc ctagatcaag tgtttggatt gaagagagtg ttttctagaa cacacgagtt   9420
ttttcaaaag gcctggatct attattcaga cagatcagac ctcatcgggt tacgggagga   9480
tcaaatatac tgcttagatg cgtccaacgg cccaacctgt tggaatggcc aggatggcgg   9540
gctagaaggc ttacggcaga agggctggag tctagtcagc ttattgatga tagatagaga   9600
atctcaaatc aggaacacaa gaaccaaaat actagctcaa ggagacaacc aggttttatg   9660
tccgacatac atgttgtcgc cagggctatc tcaagagggg ctcctctatg aattggagag   9720
aatatcaagg aatgcacttt cgatatacag agccgtcgag gaaggggcat ctaagctagg   9780
gctgatcatc aagaaagaag agaccatgtg tagttatgac ttcctcatct atggaaaaac   9840
cccttttgttt agaggtaaca tattggtgcc tgagtccaaa agatgggcca gagtctcttg   9900
cgtctctaat gaccaaatag tcaacctcgc caatataatg tcgacagtgt ccaccaatgc   9960
gctaacagtg gcacaacact ctcaatcttt gatcaaaccg atgagggatt ttctgctcat  10020
gtcagtacag gcagtctttc actacctgct atttagccca atcttaaagg gaagagttta  10080
caagattctg agcgctgaag gggagagctt tctcctagcc atgtcaagga taatctatct  10140
agatccttct ttgggaggga tatctggaat gtccctcgga agattccata tacgacagtt  10200
ctcagaccct gtctctgaag ggttatcctt ctggaagaga atctggttaa gctcccaaga  10260
gtcctggatt cacgcgttgt gtcaagaggc tggaaaccca gatcttggag agagaacact  10320
cgagagcttc actcgccttc tagaagatcc gaccaccta aatatcagag gaggggccag  10380
tcctaccatt ctactcaagg atgcaatcag aaaggcttta tatgacgagg tggacaaggt  10440
ggaaaattca gagtttcgag aggcaaatcc tgttgtccaag acccatagag ataattttat  10500
actcttctta atatctgttg agcctctgtt tcctcgattt ctcagtgagc tattcagttc  10560
gtctttttg ggaatccccg agtcaatcat tggattgata caaaactccc gaacgataag  10620
aaggcagttt agaaagagtc tctcaaaaac tttagaagaa tccttctaca actcagagat  10680
ccacgggatt agtcggatga cccagacacc tcagagggt ggggggggtgt ggccttgctc  10740
ttcagagagg gcagatctac ttagggagat ctcttgggga agaaaagtgg taggcacgac  10800
agttcctcac ccttctgaga tgttgggatt acttcccaag tcctctattt cttgcacttg  10860
tggagcaaca ggaggaggca atcctagagt ttctgtatca gtactcccgt cctttgatca  10920
gtcatttttt tcacgaggcc ccctcaaaggg atacttgggc tcgtccacct ctatgtcgac  10980
ccagctattc catgcatggg aaaaagtcac taatgttcat gtggtgaaga gagctctatc  11040
gttaaaagaa tctataaact ggttcattac tagagattcc aacttggctc aagctctaat  11100
taggaacatt atgtctctga caggccctga tttccctcta gaggaggccc ctgtcttcaa  11160
aaggacggg tcagccttgc ataggttcaa gtctgccaga tacagcgaag agggtattc  11220
ttctgtctgc ccgaacctcc tctctcatat ttctgttagt acagacacca tgtctgattt  11280
gacccaagac gggaagaact acgatttcat gttccagcca ttgatgcttt atgcacagac  11340
atggacatca gagctggtac agagagacac aaggctaaga gactctacgt ttcattggca  11400
cctccgatgc aacaggtgtg tgagacccat tgacgacgtg accctggaga cctctcagat  11460
cttcgagttt ccggatgtgt cgaaaagaat atccagaatg gtttctgggg ctgtgcctca  11520
cttccagagg cttcccgata tccgtctgag accaggagat tttgaatctc taagcggtag  11580
agaaaagtct caccatatcg gatcagctca ggggctcttta tactcaatct tagtggcaat  11640
tcacgactca ggatacaatg atggaaccat cttccctgtc aacatatacg gcaaggtttc  11700
ccctagagac tatttgagag ggctcgcaag gggagtattg ataggatctc cgatttgctt  11760
cttgacaaga atgacaaata tcaatattaa tagacctctt gaattggtct cagggggtaat  11820
ctcatatatt ctcctgaggc tagataacca tccctccttg tacataatgc tcagagaacc  11880
gtctcttaga ggagagatat tttctatccc tcagaaaatc cccgccgctt atccaaccac  11940
tatgaaagaa ggcaacagat caatcttgtg ttatctccaa catgtgctac gctatgagcg  12000
agagataatc acggcgtctc cagagaatga ctggctatgg atcttttcag acttagaag  12060
tgccaaaatg acgtacctat ccctcattac ttaccagtct catcttctac tccagagggt  12120
tgagagaaac ctatctaaga gtatgagaga taacctgcga caattgagtt ctttgatgag  12180
gcaggtgctg ggcgggcacg gagaagatac cttagagtca gacgacaaca ttcaacgact  12240
gctaaaagac tctttacgaa ggacaagatg ggtggatcaa gaggtgcgcc atgcagctag  12300
aaccatgact ggagattaca gccccaacaa gaaggtgtcc cgtaaggtag gatgttcaga  12360
atgggtctgc tctgctcaac aggttgcagt tctctacctca gcaaaccgg cctgtctc  12420
ggagcttgac ataagggccc tctctaagag gttccagaac ccttttgatct cgggcttgag  12480
agtggttcag tgggcaaccg gtgctcatta taagcttaag cctattctag atgatctcaa  12540
tgttttccca tctctctgcc ttgtagtgg ggacgggtca gggggggatat caagggcagt  12600
cctcaacatg tttccagatg ccaagcttgt gttcaacagt cttttagagg tgaatgacct  12660
gatggcttcc ggaacacatc cactgcctcc ttcagcaatc atgagggggag gaaatgatat  12720
cgtctccaga gtgatagatc ttgactcaat ctgggaaaaa ccgtccgact tgagaaactt  12780
ggcaacctgg aaatacttcc agtcagtcaa aaagcaggtc aacatgtcct atgacctcat  12840
tatttgcgat gcagaagtta ctgacattgc atctatcaac cggatcaccc tgttaatgtc  12900
cgatttgca ttgtctatag atggaccact ctatttggtc ttcaaaactt atgggactat  12960
gctagtaaat ccaaactaca aggctattca acacctgtca agagcgttcc cctcggtcac  13020
agggtttatc acccaagtaa cttcgtcttt ttcatctgag ctctacctcc gattctccaa  13080
acgagggaag ttttcagag atgctgagta cttgacctct cggcgaaatgag  13140
ccttgtgtta ttcaattgta gcagcccaa gagtgagatg cagagagctc gttccttgaa  13200
ctatcaggat cttgtgagag atttcctga agaaatcata tcaaatcctt acaatgagat  13260
gatcataact ctgattgaca gtgatgtaga atcttttcta gtccacaaga tggttgatga  13320
tcttgagtta cagaggggaa ctctgtctaa agtggctatc attatagcca tcatgatagt  13380
tttctccaac agagtcttca acgtttccaa accccctaact gaccccctcgt tctatccacc  13440
```

```
gtctgatccc aaaatcctga ggcacttcaa catatgttgc agtactatga tgtatctatc    13500
tactgcttta ggtgacgtcc ctagcttcgc aagacttcac gacctgtata acagacctat    13560
aacttattac ttcagaaagc aagtcattcg agggaacgtt tatctatctt ggagttggtc    13620
caacgacacc tcagtgttca aaagggtagc ctgtaattct agcctgagtc tgtcatctca    13680
ctggatcagg ttgatttaca agatagtgaa gactaccaga ctcgttggca gcatcaagga    13740
tctatccaga gaagtggaaa gacaccttca taggtacaac aggtggatca ccctagagga    13800
tatcagatct agatcatccc tactagacta cagttgcctg tgaaccggat actcctggaa    13860
gcctgcccat gctaagactc ttgtgtgatg tatcttgaaa aaaacaagat cctaaatctg    13920
aacctttggt tgtttgattg ttttttctcat ttttgttgtt tatttgttaa gcgt         13974

SEQ ID NO: 16          moltype = DNA   length = 13881
FEATURE                Location/Qualifiers
misc_feature           1..13881
                       note = RABV vector: Coravax V6 China
source                 1..13881
                       mol_type = other DNA
                       organism = synthetic construct
SEQUENCE: 16
acgcttaaca accagatcaa agaaaaaaca gacattgtca attgcaaagc aaaaatgtaa     60
caccnctaca atgatgccg acaagattgt attcaaagtc aataatcagg tggtctcttt    120
gaagcctgag attatcgtgg atcaatatga gtacaagtac cctgccatca aagatttgaa    180
aaagccctgt ataacccctag gaaaggctcc cgatttaaat aaagcataca agtcagtttt    240
gtcaggcatg agcgccgcca aacttaatcc tgacgatgta tgttcctatt tggcagcggc    300
aatgcagttt tttgagggga catgtccgga agactggacc agctatgaa ttgtgattgc    360
acgaaaagga gataagatca ccccaggttc tctggtggga ataaaacgta ctgatgtaga    420
agggaattgg gctctgacag gaggcatgga actgacaaga gaccccactg tccctgagca    480
tgcgtcctta gtcggtcttc tcttgagtct gtataggttg agcaaaatat ccgggcaaaa    540
cactggtaac tataagacaa acattgcaga caggatagag cagatttttg agacagcccc    600
ttttgttaaa atcgtggaac accatactct aatgacaact cacaaaatgt gtgctaattg    660
gagtactata ccaaacttca gattttttggc cggaacctat gacatgtttt tctcccggat    720
tgagcatcta tattcagcaa tcagagtggg cacagttgtc actgcttatg aagactgttc    780
aggactggta tcatttactg ggttcataaa acaaatcaat ctcaccgcta gagaggcaat    840
actatatttc ttccacaaga actttgagga agagataaga gaatgtttg agccagggca    900
ggagacagct gttcctcact cttatttcat ccacttccgt tcactaggct tgagtgggaa    960
atctccttat tcatcaaatg tcgttggtca cgtgttcaat ctcattcact ttgtaggatg   1020
ctatatgggt caagtcagat ccctaaatgc aacggttatt gctgcatgtg ctcctcatga   1080
aatgtctgtt ctaggggct atctgggaga ggaattcttc gggaaggga catttgaaag   1140
aagattcttc agagatgaga agaacttca agaatacgag cggctgaac tgacaaagac   1200
tgacgtagca ctggcagatg atggaactgt caactctgac gacgaggact actttttcagg   1260
tgaaaccaga agtccggagg ctgtttatac tcgaatcatg atgaatggag tcgactaaa   1320
gagatctcac atacggagat atgtctcagt cagttccaat catcaagccc gtccaaactc   1380
attcgccgag tttctaaaca agacatattc gagtgactca taagaagttg aataacaaaa   1440
tgccggaaat ctacggattg tgtatatcca tcatgaaaaa aactaacacc cctccttcg   1500
aaccatccca aacatgagca agatctttgt caatcctagt gctattagag ccggtctggc   1560
cgatcttgag atggctgaag aaactgttga tctgatcaat agaaatatcg aagacaatca   1620
ggctcatctc caagggaac ccatagaggt ggacaatctc cctgaggata tggggcgact   1680
tcacctggat gatggaaaat cgcccaacca tggtgagaga gccaaggtgg gagaaggcaa   1740
gtatcgagag gactttcaga tggatgaagg agaggatcct agcttcctgt tccagtcata   1800
cctggaaaat gttggagtcc aaatagtcag acaaatgagg tcaggagaga gatttctcaa   1860
gatatggtca cagaccgtag aagagattat atcctatgtc gcggtcaact ttcccaaccc   1920
tccaggaaag tcttcagagg ataaatcaac ccagactact ggccgagagc tcaagaagga   1980
gacaacaccc actccttctc agagagaaag ccaatcatcg aaagccagga tggcggctca   2040
aattgcttct ggccctccag cccttgaatg gtcggctacc aatgaagagg atgatctatc   2100
agtggaggct gagatcgctc accagattgc agaaagtttc tccaaaaaat ataagtttcc   2160
ctctcgatcc tcaggggatac tcttgtataa ttttgagcaa ttgaaaatga accttttgatga   2220
tatagtaaaa gaggcaaaaa atgtaccagg tgtgacccgt ttagcccatg acgggtccaa   2280
actccccta agatgtgtac tgggatgggt cgctttggcc aactctaaga aattccagtt   2340
gttagtcgaa tccgacaagc tgagtaaaat catgcaagat gacttgaatc gctatacatc   2400
ttgctaaccg aacctctccc ctcagtccct ctagacaata aaatccgaga tgtcccaaag   2460
tcaacatgaa aaaaacaggc aacaccactg ataaaatgaa cctcctacgt aagatagtaa   2520
aaaaccgcag ggacgaggac actcaaaaat cctctcccgc gtcagccct ctggatgacg   2580
atgacttgtg gcttccaccc cctgaatacg tcccgctgaa agaacttaca ggcaagaaga   2640
acatgaggaa cttttgtatc aacggaaggg ttaaagtgtg tagcccgaat ggttactcgt   2700
tcaggatcct gcggcacatt ctgaaatcat tcgacgagat atattctggg aatcataga   2760
tgatcgggtt agtcaaagtg gttattgac tggcttgtc aggatctcca gtccctgagg   2820
gcctgaactg gtatacaaaa ttgaggagaa cctttatctt ccagtgggct gattccaggg   2880
gccctcttga aggggaggag ttggaatact ctcaggagat cacttgggat gatgatactg   2940
agttcgtcgg attgcaaata agagtgattg caaaacagtg tcatatccag gcagagtct   3000
ggtgtatcaa catgaacccg agagcatgtc aactatggtc tgacatgtct cttcagacac   3060
aaaggtccga agaggacaaa gattcctctc tgcttctaga ataatcagat tatatcccgc   3120
aaatttatca cttgtttacc tctggaggag agaacatatg gctcaactc caaccccttgg   3180
gagcaatata acaaaaaaca tgttatggtg ccattaaacc gctgcatttc atcaaagtca   3240
agttgattac cttttacattt tgatcctctt ggatgtgaaa aaaactatta acatccctca   3300
aaagaccccg ggaaagatgg ttcctcaggc tctcctgttt gtacccttc tggtttttcc   3360
attgtgttttt gggaaattcc ctatttacac gataccagac aagcccgtc cctgagtcc   3420
gattgacata catcacctca gctgcccaaa caatttggta gtggaggacg aaggatgcac   3480
caacctgtca gggttctcct acatggaact taaagttgga tacatcttag ccataaaagt   3540
gaacgggttc acttgcacag gcgttgtgac ggaggctgaa acctacacta acttcgttgg   3600
ttatgtcaca accacgttca aaagaaagca tttccgccca acaccagatg catgtagagc   3660
```

```
cgcgtacaac tggaagatgg ccggtgaccc cagatatgaa gagtctctac acaatccgta  3720
ccctgactac cgctggcttc gaactgtaaa aaccaccaag gagtctctcg ttatcatatc  3780
tccaagtgtg gcagatttgg acccatatga cagatccctt cactcgaggg tcttccctag  3840
cgggaagtgc tcaggagtag cggtgtcttc tacctactgc tccactaacc acgattacac  3900
catttggatg cccgagaatc cgagactagg gatgtccttgt gacatttta ccaatagtag  3960
agggaagaga gcatccaaag ggagtgagac ttgcggcttt gtagatgaaa gaggcctata  4020
taagtcttta aaaggagcat gcaaactcaa gttatgtgga gttctaggac ttagacttat  4080
ggatggaaca tgggtctcga tgcaaacatc aaatgaaacc aaatggtgcc ctcccgataa  4140
gttggtgaac ctgcacgact ttcgctcaga cgaaattgag caccttgttg tagaggagtt  4200
ggtcaggaag agagaggagt gtctggatgc actagagtcc atcatgacaa ccaagtcagt  4260
gagtttcaga cgtctcagtc atttaagaaa acttgtccct gggtttggaa aagcatatac  4320
catattcaac aagaccttga tggaagccga tgctcactac aagtcagtcg agacttggaa  4380
tgagatcctc ccttcaaaag ggtgtttaag agttgggggg aggtgtcatc ctcatgtgaa  4440
cgggggtgttt ttcaatggta taatattagg acctgacggc aatgtcttaa tcccagagat  4500
gcaatcatcc ctcctccagc aacatatgga gttgttggaa tcctcggtta tcccccttgt  4560
gcaccccctg gcagaccgt ctaccgtttt caaggacggt gacgaggctg aggattttgt  4620
tgaagttcac cttcccgatg tgcacaatca ggtctcagga gttgacttgg gtctcccgaa  4680
ctgggggaag tatgtattac tgagtgcagg ggccctgact gccttgatgt tgataatttt  4740
cctgatgaca tgttgtagaa gagtcaatcg atcagaacct acgcaacaca atctcagagg  4800
gacagggagg gaggtgtcag tcactcccca aagcgggaag atcatatctt catgggaatc  4860
acacaagagt gggggtgaga ccagactgta attaattaac gtccttttcaa cgatccaagt  4920
ccataaaaaa aactaacacc cctcccgtac gaccatgtcc gtgttttctgg tgctgctgcc  4980
tctggtgagc tcccagtgcg tgaacctgac cacaaggacc cagctgcccc ctgcctatac  5040
caattccttc acacggggcg tgtactatcc cgacaaggtg ttccgagca gcgtgctgca  5100
ctccacacag gatctgtttc tgcctttctt ttctaacgtg acctggttcc acgccatcca  5160
cgtgagcggc accaatgca caaagcggtt cgacaatcca gtgtcgccct ttaacgatgg  5220
cgtgtacttc gcctccaccg agaagtctaa catcatcaga ggctggatct ttggcaccac  5280
actgacagc aagacacagt ccctgctgat cgtgaacaat gccaccaacg tggtcatcaa  5340
ggtgtgcgag ttccagtttt gtaatgatcc attcctgggc gtgtactatc acaagaacaa  5400
taagtcttgg atggagagcg agtttcgcgt gtattcctct gccaacaact gcacattga  5460
gtacgtgtcc cagcccttcc tgatggacct ggagggcaag cagggcaatt tcaagaacct  5520
gagggagttc gtgtttaaga atatcgatgg ctacttcaaa atctactcca agcacacccc  5580
aatcaacctg gtgcgcgacc tgccacaggg cttttctgcc ctggagccac tggtggatct  5640
gccctcggc atcaacatca cccggttca gacactgctg gcctgcaca gaagctacct  5700
gacaccaggc gacagctcct ctggatggac cgcaggagca gcagctact atgtgggcta  5760
tctgcagccc aggaccttcc tgctgaagta caacgagaat ggcaccatca cagacgccgt  5820
ggattgcgc ctggatcccc tgtctgagac caagtgtaca ctgaagagct ttaccgtgga  5880
gaagggcatc tatcagacaa gcaatttcag ggtgcagcct accgagtcca tcgtgcgctt  5940
tcccaatatc acaaacctgt gccctttgg cgaggtgttc aacgcaaccc gcttcgcag  6000
cgtgtacgcc tggaatagga agcgcatctc caactgcgtg gccgactatt ctgtgctgta  6060
caacagcgcc tccttctcta cctttaagtg ctatggcgtg agccccacaa agctgaatga  6120
cctgtgcttt accaacgtgt acgccgattc cttcgtgatc aggggcgacg aggtgcgcca  6180
gatcgcacca ggacagacag gcaagatcgc agactacaat tataagctgc ctgacgattt  6240
caccggctgc gtgatcgcct ggaactctaa caatctggat agcaaagtgg cggcaacta  6300
caattatctg taccggctgt ttagaaagtc taatctgaag ccattcgaga gggacatctc  6360
cacagaaatc taccaggccg gctctacccc ctgcaatggc gtggagggct ttaactgtta  6420
tttccctctg cagagctacg gcttccagcc aacaaacggc gtgggctatc agccctaccg  6480
cgtggtggtg ctgtctttg agctgctgca cgccacctgca acagtgtgcg gaccaaagaa  6540
gagcaccaat ctggtgaaga caagtgcgt gaacttcaac ttcaacggac tgaccggaac  6600
aggcgtgctg accgagtcca caagaagtt cctgcctttt cagcagttcg gcagggacat  6660
cgcagatacc acagacgccg tgcgcagacc tcagaccctg gagatcctgg acatcaccac  6720
atgctccttc ggcggcgtgt ctgtgatcac accaggcacc aatacaagca accaggtggc  6780
cgtgctgtat caggacgtga attgtaccga ggtgccagtg gcaatccacg cagatcagct  6840
gacccctaca tggcgggtgt actctaccgg cagcaacgtg ttccagacaa gagccggatg  6900
cctgatcgga cagagcacg tgaacaatag ctatgagtgc gacatcccta tcggcgccgg  6960
catctgtgcc tcctaccaga cccagacaaa ctcccccaagg tctgtgggag atgaggccga  7020
agactttgtg gaagtccacc tgcctgatgt gcataaccag gtgtctggcg tcgacctggg  7080
actgccaaat tggggcaagt acgtgctgct gagtgctgga gcactgactg ccctgatgct  7140
gatcattttc ctgatgacct gctgtcggcg cgtgaacaga agtgagccca ctcagcacaa  7200
tctgcgagga accgggagag aagtgtcagt cacacctcag agcgggaaaa tcattagtag  7260
ttgggaatca cataaaagcg ggggcgagac caggctggga tccggctccg gcgagggcag  7320
gggaagtcta ctaacatgcg gggacgtgga ggaaaatccc ggccccatgc tcgatcctgg  7380
agaggtctat gatgacccta ttgacccaat cgagttagag gctgaaccca gagaaccccc  7440
cattgtcccc aacatcttga gaactctga ctacaatcc aactctcctt tgatagaaga  7500
tcctgctaga ctaatgttag aatggttaaa aacagggaat agaccttatc ggatgactct  7560
aacagacaat tgctccaggt cttttcagagt ttgaaagat tatttcaaga aggtagattt  7620
gggttctctc aaggtgggcg gaatggctgc acagtcaatg atttctctct ggttatatgg  7680
tgcccactct gaatccaaca ggagccggag atgtataaca gacttggccc atttctattc  7740
caagtcgtcc cccatagaga agctgttgaa tctcacgcta gggaaatagag ggctggaaat  7800
cccccccagag ggagtgttaa gttgccttga gagggttgat tatgataatg catttggaag  7860
gtatcttgcc aacacgtatt cctcttactt gttcttccat gtaatcacct tatacatgaa  7920
cgccctagac tgggatgaag aaaagaccat cctagcatta tggaaagatt taacctcagt  7980
ggacatcggg aaggacttgg taaagttcaa agaccaaata tggggactgc tgatcgtgac  8040
aaaggactt gttactccc aaagttccaa ttgtcttttt acacacttat  8100
gctaaaagat cttttcttgt ctcgcttcaa ctccttaatg gtcttgctct ctcccccaga  8160
gccccgatac tcagatgact tgatatctca actatgccag ctgtacattg ctggggatca  8220
agtcttgtct atgtgtggaa actccggcta tgaagtcatc aaaatattgg agccatatgt  8280
cgtgaatagt ttagtccaga gagcagaaaa gtttaggcct ctcattcatt ccttgggaga  8340
ctttcctgta tttataaaag acaaggtaag tcaacttgaa gagacgttcg gtccctgtgc  8400
```

```
aagaaggttc tttagggctc tggatcaatt cgacaacata catgacttgg tttttgtgtt   8460
tggctgttac aggcattggg ggcacccata tatagattat cgaaagggtc tgtcaaaact   8520
atatgatcag gttcacctta aaaaaatgat agataagtcc taccaggagt gcttagcaag   8580
cgacctagcc aggaggatcc ttagatgggg ttttgataag tactccaagt ggtatctgga   8640
ttcaagattc ctagcccgag accaccccct gactcctat atcaaaaccc aaacatggcc    8700
acccaaacat attgtagact tggtggggga tacatggcac aagctcccga tcacgcagat   8760
ctttgagatt cctgaatcaa tggatccgtc agaaatattg gatgacaaat cacattcttt   8820
caccagaacg agactagctt cttggctgtc agaaaaccga ggggggcctg ttcctagcga   8880
aaaagttatt atcacgqccc tgtctaagcc gcctgtcaat ccccgagagt ttctgaggtc   8940
tatagacctc ggaggattgc cagatgaaga cttgataatt ggcctcaagc caaaggaacg   9000
ggaattgaag attgaaggtc gattctttgc tctaatgtca tggaatctaa gattgtattt   9060
tgtcatcact gaaaaactct tggccaacta catcttgcca cttttgacg cgctgactat    9120
gacagacaac ctgaacaagg tgtttaaaaa gctgatcgac agggtcaccg ggcaagggct   9180
tttggactat tcaagggtca catatgcatt tcacctggac tatgaaaagt ggaacaacca   9240
tcaaagatta gagtcaacag aggatgtatt ttctgtccta gatcaagtgt ttggattgaa   9300
gagagtgttt tctagaacac acgagttttt tcaaaaggcc tggatctatt attcagacag   9360
atcagacctc atcgggttac gggaggatca aatatactgc ttagatgcgt ccaacggccc   9420
aacctgttgg aatggccagg atggcgggct agaaggctta cggcagaagg gctggagtct   9480
agtcagctta ttgatgatag atagagaatc tcaaatcagg aacacaagaa ccaaaatact   9540
agctcaagga gacaaccagg ttttatgtcc gacatacatg ttgtcgccag ggctatctca   9600
agaggggctc ctctatgaat tggagagaat atcaaggaat gcactttcga tatacagagc   9660
cgtcgaggaa ggggcatcta agctagggct gatcatcaag aaagaagaga catgtgtag   9720
ttatgacttc ctcatctatg gaaaaacccc tttgtttaga ggtaacatat tggtgcctga   9780
gtccaaaaga tgggccagag tctcttgcgt ctctaatgac caaatagtca acctcgccaa   9840
tataatgtcg acagtgtcca ccaatgcgct aacagtggca caacactctc aatctttgat   9900
caaaccgatg agggattttc tgctcatgtc agtacagqca gtctttcact acctgctatt   9960
tagcccaatc ttaaagggaa gagtttacaa gattctgagc gctgaagggg agagcttttct  10020
cctagccatg tcaaggataa tctatctaga tccttctttg ggaggqatat ctggaatgtc   10080
cctcggaaga ttccatatac gacagttctc agaccctgtc tctgaagggt tatccttctg   10140
gagagagatc tggttaagct cccaagagtc ctggattcac gcgttgtgtc aagaggctgg   10200
aaacccagat cttggagaga gaacactcga gagcttcact cgccttctag aagatccgac   10260
caccttaaat atcagaggag gggccagtcc taccattcta ctcaaggatg caatcagaaa   10320
ggctttatat gacgaggtgg acaaggtgga aaattcagag tttcgagagg caatcctgtt   10380
gtccaagacc catagagata atttttatact cttcttaata tctgttgagc ctctgtttcc   10440
tcgatttctc agtgagctat tcagttcgtc tttttttggga atccccgagt caatcattgg   10500
attgatacaa aactcccgaa cgataagaag gcagtttaga aagagtctct caaaaacttt   10560
agaagaatcc ttctacaact cagagatcca cgggattagt cggatgaccc agacacctca   10620
gagggttggg ggggtgtgggc cttgctcttc agagagggca gatctactta gggagatctc   10680
ttgggqaaga aaagtggtag gcacgacagt tcctcacct tctgagatgt tgqgattact   10740
tcccaagtcc tctatttctt gcacttgtgg agcaacagga ggaggcaatc ctagagtttc   10800
tgtatcagta ctcccgtcct ttgatcagtc attttttttca cgaggccccc taagggata   10860
cttgggctcg tccacctcta tgtcgaccca gctattccat gcatgggaaa aagtcactaa   10920
tgttcatgtg gtgaagagag ctctatcgtt aaaagaatct ataaactggt tcattactag   10980
agattccaac ttggctcaag ctctaattag gaacattatg tctctgacag gccctgattt   11040
ccctctagag gaggccctg tcttcaaaag gacggggtca gccttgcata ggttcaagtc   11100
tgccagatac agcgaaggag ggtattcttc tgtctgcccg aacctcctct ctcatatttc   11160
tgttagtaca gacaccatgt ctgatttgac ccaagacggg aagaactacg atttcatgtt   11220
ccagccattg atgctttatg cacagacatg gacatcagag ctggtacaga gagacacaag   11280
gctaagagac tctacgtttc attggcacct ccgatgcaac aggtgtgtga gacccattga   11340
cgacgtgacc ctggagacct ctcagatctt cgagtttccg gatgtgtcga aaagaatatc   11400
cagaatggtt tctggggctg tgcctcactt ccagaggctt cccgatatcc gtctgagacc   11460
aggagatttt gaatctctaa gcggtagaga aaagtctcac catatcggat cagctcaggg   11520
gctcttatac tcaatcttag tggcaattca cgactcagga tacaatgatg gaaccatctt   11580
ccctgtcaac atatacggca aggtttcccc tagagactat ttgagagggc tcgcaagggg   11640
agtattgata gaatcctcga tttgcttctt gacaagaatg acaaatatca atattaatag   11700
acctcttgaa ttggtctcag gggtaatctc atatattctc ctgaggctag ataaccatcc   11760
ctccttgtac ataatgctca gagaaccgtc tcttagagga gagatatttt ctatccctca   11820
gaaaatcccc gccgcttatc caaccactat gaaagaaggc aacagatcaa tcttgtgtta   11880
tctccaacat gtgctacgct atgagcgaga gataatcacg gcgtctccag agaatgactg   11940
gctatggatc ttttcagact ttagaagtgc caaaatgacg tacctatccc tcattactta   12000
ccagtctcat cttctactcc agaggggttga gagaaaccta tctaagagta tgagagataa   12060
cctgcgacaa ttgagttctt tgatgaggca ggtgctgggc gggcacggag aagatacctt   12120
agagtcagac gacaacattc aacgactgct aaaagactct ttacgaagga caagatgggt   12180
ggatcaagag gtgcgccatg cagctagaac catgactgga gattacagcc ccaacaagaa   12240
ggtgtcccgt aaggtaggat gttcagaatg ggtctgctct gctcaacagg ttgcagtctc   12300
tacctcagca aacccggccc ctgtctcgga gcttgacata agggccctct ctaagaggtt   12360
ccagaaccct tgatctcgg gcttgagagt ggttcagtgg gcaaccggtg ctcattataa   12420
gcttaagcct attctagatg atctcaatgt tttcccatct ctctgccttg tagttgggga   12480
cgggtcaggg gggatatcaa gggcagtcct caacatgttt ccagatgcca agcttgtgtt   12540
caacagtctt ttagaggtga atgacctgat ggcttccgga acacatccac tgcctccttc    12600
agcaatcatg agggaggaa atgatatcgt ctccagagtg atagatcttg actcaatctg   12660
ggaaaaaccg tccgacttga gaaacttggc aacctgaaa tacttccagt cagtccaaaa   12720
gcaggtcaac atgtcctatg acctcattat ttgcgatgca gaagttactg acattgcatc   12780
tatcaaccgt tctcaccctg taatgtccga ttttgcattg tctatagatg gaccactcta   12840
tttggtcttc aaaacttatg ggactatgct agtaaatcca aactacaagg ctattcaaca   12900
cctgtcaaga gcgttcccct cggtcacagg gtttatcacc caagtaactt cgtcttttttc   12960
atctgagctc tacctccgat tctccaaacg agggaagttt tcagagatgc tgagtactt   13020
gacctcttcc accttcgag aaatgagcct tgtgttattc aattgtagca gcccaagag   13080
tgagatgcag agagctcgtt ccttgaacta tcaggatctt gtgagaggat ttcctgaaga   13140
```

```
aatcatatca aatccttaca atgagatgat cataactctg attgacagtg atgtagaatc  13200
ttttctagtc cacaagatgg ttgatgatct tgagttacag aggggaactc tgtctaaagt  13260
ggctatcatt atagccatca tgatagtttt ctccaacaga gtcttcaacg tttccaaacc  13320
cctaactgac ccctcgttct atccaccgtc tgatcccaaa atcctgaggc acttcaacat  13380
atgttgcagt actatgatgt atctatctac tgctttaggt gacgtcccta gcttcgcaag  13440
acttcacgac ctgtataaca gacctataac ttattacttc agaaagcaag tcattcgagg  13500
gaacgtttat ctatcttgga gttggtccaa cgacacctca gtgttcaaaa gggtagcctg  13560
taattctagc ctgagtctgt catctcactg gatcaggttg atttacaaga tagtgaagac  13620
taccagactc gttggcagca tcaaggatct atccagagaa gtggaaagac accttcatag  13680
gtacaacagg tggatcaccc tagaggatat cagatctaga tcatccctac tagactacag  13740
ttgcctgtga accggatact cctggaagcc tgcccatgct aagactcttg tgtgatgtat  13800
cttgaaaaaa acaagatcct aaatctgaac ctttggttgt ttgattgttt ttctcatttt  13860
tgttgtttat ttgttaagcg t                                            13881

SEQ ID NO: 17           moltype = DNA  length = 13932
FEATURE                 Location/Qualifiers
misc_feature            1..13932
                        note = RABV vector: Coravax V6 South Africa
source                  1..13932
                        mol_type = other DNA
                        organism = synthetic construct
SEQUENCE: 17
acgcttaaca accagatcaa agaaaaaaca gacattgtca attgcaaagc aaaaatgtaa  60
cacccctaca atggatgccg acaagattgt attcaaagtc aataatcagg tggtctcttt  120
gaagcctgag attatcgtgg atcaatatga gtacaagtac cctgccatca aagatttgaa  180
aaagccctgt ataaccctag gaaaggctcc cgatttaaat aaagcataca agtcagtttt  240
gtcaggcatg agcgccgcca aacttaatcc tgacgatgta tgttcctatt tggcagcggc  300
aatgcagttt tttgagggga catgtccgga agactggacc agctatggaa ttgtgattgc  360
acgaaaagga gataagatca ccccaggttc tctggtggag ataaaacgta ctgatgtaga  420
agggaattgg gctctgacag gaggcatgga actgacaaga gaccccactg tccctgagca  480
tgcgtcctta gtcggtcttc tcttgagtct gtataggttg agcaaaatat ccgggcaaaa  540
cactggtaac tataagacaa acattgcaga caggatagag cagatttttg agacagcccc  600
ttttgttaaa atcgtggaac accatactct aatgacaact cacaaaatgt gtgctaattg  660
gagtactata ccaaacttca gatttttggc cggaacctat gacatgtttt tctcccggat  720
tgagcatcta tattcagcaa tcagagtggg cacagttgtc actgcttatg aagactgttc  780
aggactggta tcatttactg ggttcataaa acaaatcaat ctcaccgcta gagaggcaat  840
actatatttc ttccacaaga actttgagga agagataaga agaatgtttg agccagggca  900
ggagacagct gttcctcact cttatttcat ccacttccgt tcactaggct tgagtgggaa  960
atctccttat tcatcaaatg ctgttggtca cgtgttcaat ctcattcact ttgtaggatg  1020
ctatatgggt caagtcagat ccctaaatgc aacggttatt gctgcatgtg ctcctcatga  1080
aatgtctgtt ctagggggct atctgggaga ggaattcttc gggaaaggga catttgaaag  1140
aagattcttc agagatgaga aagaacttca agaatacgag gcggctgaac tgacaaagac  1200
tgacgtagca ctggcagatg atggaactgt caactctgac gacgaggact actttcagg  1260
tgaaaccaga agtccggagg ctgtttatac tcgaatcatg atgaatggag gtcgactaaa  1320
gagatctcac atacggagat atgtctcagt cagttccaat catcaagccc gtccaaactc  1380
attcgccgag tttctaaaca agacatattc gagtgactca taagaagttg aataacaaaa  1440
tgccggaaat ctacggattg tgtatatcca tcatgaaaaa aactaacacc cctcctttcg  1500
aaccatccca aacatgagca agatctttgt caatcctagt gctattagag ccggtctggc  1560
cgatcttgag atggctgaag aaactgttga tctgatcaat agaaatatcg aagacaatca  1620
ggctcatctc caaggggaac ccatagaggt ggacaatctc cctgaggata tggggcgact  1680
tcacctggat gatggaaaat cgcccaacca tggtgagata gccaaggtgg gagaaggcaa  1740
gtatcgagag gactttcaga tggatgaagg agaggatcct agcttcctgt tccagtcata  1800
cctggaaaat gttggagtcc aaatagtcag acaaatgagg tcaggagaga gatttctcaa  1860
gatatggtca cagaccgtag aagagattat atcctatgtc gcggtcaact ttcccaaccc  1920
tccaggaaag tcttcagagg ataaatcaac ccagactact ggccgagagc tcaagaagga  1980
gacaacaccc actccttctc agagagaaag ccaatcatcg aaagccagga tggcggctca  2040
aattgcttct ggccctccag cccttgaatg gtcggctacc aatgaagagg atgatctatc  2100
agtggaggct gagatcgctc accagattgc agaaagtttc tccaaaaaat ataagtttcc  2160
ctctcgatcc tcagggatac tcttgtataa ttttgagcaa ttgaaaatga accttgatga  2220
tatagttaaa gaggcaaaaa atgtaccagg tgtgacccgt ttagcccatg acgggtccaa  2280
actcccccta agatgtgtac tgggatgggt cgctttggcc aactctaaga aattccagtt  2340
gttagtcgaa tccgacaagc tgagtaaaat catgcaagat gacttgaatc gctatacatc  2400
ttgctaaccg aacctctccc ctcagtccct ctagacaata aaatccgaga tgtcccaaag  2460
tcaacatgaa aaaaacaggc aacaccactg ataaaatgaa cctcctacgt aagatagtga  2520
aaaaccgcag ggacgaggac actcaaaaat cctctcccgc gtcagcccct ctggatgacg  2580
atgacttgtg gcttccaccc cctgaatacg tcccgctgaa agaacttaca ggcaagaaga  2640
acatgaggaa cttttgtatc aacggaaggg ttaaagtgtg tagcccgaat ggttactcgt  2700
tcaggatcct gcggcacatt ctgaaatcat tcgacgagat atattctggg aatcatagga  2760
tgatcgggtt agtcaaagtg gttattggac tggctttgtc aggatctcca gtccctgagg  2820
gcctgaactg ggtatacaaa ttgaggagaa cctttatctt ccagtgggct gattccaggg  2880
gccctcttga aggggaggag ttggaatact ctcaggagat cacttgggat gatgatactg  2940
agttcgtcgg attgcaaata agagtgattg caaaacagtg tcatatccag ggcagagtct  3000
ggtgtatcaa catgaacccg agagcatgtc aactatggtc tgacatgtct cttcagacac  3060
aaaggtccga agaggacaaa gattcctctc tgcttctaga ataatcagat tatatcccgc  3120
aaatttatca cttgtttacc tctggaggag agaacatatg ggctcaactc caacccttgg  3180
gagcaatata acaaaaaaca tgttatggtg ccattaaacc gctgcatttc atcaaagtca  3240
agttgattac ctttacattt tgatcctctt ggatgtgaaa aaaactatta acatccctca  3300
aaagaccccg ggaaagatgg ttcctcaggc tctcctgttt gtacccctc tggttttcc  3360
attgtgtttt gggaaattcc ctatttacac gataccagac aagcttggtc cctggagtcc  3420
```

```
gattgacata catcacctca gctgcccaaa caatttggta gtggaggacg aaggatgcac  3480
caacctgtca gggttctcct acatggaact taaagttgga tacatcttag ccataaaagt  3540
gaacgggttc acttgcacag gcgttgtgac ggaggctgaa acctacacta acttcgttgg  3600
ttatgtcaca accacgttca aaagaaagca tttccgccca acaccagatg catgtagagc  3660
cgcgtacaac tggaagatgg ccggtgaccc cagatatgaa gagtctctac acaatccgta  3720
ccctgactac cgctggcttc gaactgtaaa aaccaccaag gagtctctcg ttatcatatc  3780
tccaagtgtg gcagatttgg acccatatga cagatccctt cactcgaggg tcttccctag  3840
cgggaagtgc tcaggagtag cggtgtcttc tacctactgc tccactaacc acgattacac  3900
catttggatg cccgagaatc cgagactagg gatgtcttgt gacattttta ccaatagtag  3960
agggaagaga gcatccaaag ggagtgagac ttgcggcttt gtagatgaaa gaggcctata  4020
taagtcttta aaaggagcat gcaaactcaa gttatgtgga gttctaggac ttagacttat  4080
ggatggaaca tgggtctcga tgcaaacatc aaatgaaacc aaatggtgcc ctcccgataa  4140
gttggtgaac ctgcacgact ttcgctcaga cgaaattgag caccttgttg tagaggagtt  4200
ggtcaggaag agagaggagt gtcggatgc actagagtcc atcatgacaa ccaagtcagt  4260
gagtttcaga cgtctcagtc atttaagaaa acttgtccct gggtttggaa aagcatatac  4320
catattcaac aagaccttga tggaagccga tgctcactac aagtcagtcg agacttggaa  4380
tgagatcctc ccttcaaaag ggtgtttaag agttggggg aggtgtcatc ctcatgtgaa  4440
cggggtgttt ttcaatggta taatattagg acctgacggc aatgtcttaa tcccagagat  4500
gcaatcatcc ctcctccagc aacatatgga gttgttggaa tcctcggtta tcccccttgt  4560
gcaccccctg gcagaccctg ctaccgtttt caaggacggt gacgaggctg aggattttgt  4620
tgaagttcac cttcccgatg tgcacaatca ggtctcagga gttgacttgg gtctcccgaa  4680
ctgggggaag tatgtattac tgagtgcagg ggccctgact gcctgatgt tgataatttt  4740
cctgatgaca tgttgtagaa gagtcaatcg atcagaacct acgcaacaca atctcagagg  4800
gacagggagg gaggtgtcag tcactcccca aagcgggaag atcatatctt catgggaatc  4860
acacaagagt ggggtgaga ccagactgta attaattaac gtcctttcaa cgatccaagt  4920
ccatgaaaaa aactaacacc cctcccgtac gaccatgttc gtgtttctgg tgctgctgcc  4980
tctggtgagc tcccagtgcg tgaacttcac cacaaggacc cagctgcccc ctgcctatac  5040
caattccttc acacggggcg tgtactatcc cgacaagtg ttccgagca gcgtgctgca  5100
ctccacacag gatctgtttc tgcctttctt ttctaacgtg acctggttcc acgccatcca  5160
cgtgagcggc accaatggca caaagcggtt gccaatcca gtgctgccct ttaacgatgg  5220
cgtgtacttc gcctccaccg agaagtctaa catcatcaga gctggatct ttggcaccac  5280
actggacagc aagacacagt ccctgctgat cgtgaacaat gccaccaacg tggtcatcaa  5340
ggtgtgcgag ttccagtttt gtaatgatcc attcctgggc gtgtactatc acaagaacaa  5400
taagtcttgg atggagagcg agtttcgcgt gtattcctct gccaacaatt gcacatttga  5460
gtacgtgtcc cagcccttcc tgatggacct ggagggcaag cagggcaatt tcaagaacct  5520
gagggagttc gtgtttaaga atatcgatgg ctacttcaaa atctactcca agcacacccc  5580
aatcaacctg gtgcgcggcc tgccacaggg cttctctgcc ctggagccac tggtggatct  5640
gcccatcggc atcaacatca cccggtttca gacactgctg gccctgcaca gaagctacct  5700
gacaccaggc gacagctcct ctggatggac cgcaggacga gcagcctact atgtgggcta  5760
tctgcagccc aggaccttcc tgctgaagta caacgagaat ggcaccatca cagacgccgt  5820
ggattgcgcc ctggatcccc tgtctgagac caagtgtaca ctgaagagct ttaccgtgga  5880
gaagggcatc tatcagacaa gcaatttcag ggtgcagcct accgagtcca tcgtgcgctt  5940
tcccaatatc acaaacctgt gcccttttg cgaggtgttc aacgcaaccc gcttcgccag  6000
cgtgtacgcc tggaatagga gcgcatctc caactgcgtg gccgactatt ctgtgctgta  6060
caacagcgcc tccttctcta cctttaagtg ctatggcgtg agcccacaa agctgaatga  6120
cctgtgcttt accaacgtgt acgccgattc cttcgtgatc agggcgacg aggtgcgcca  6180
gatcgcacca ggacagacag gcaatatcgc agactacaat tataagctgc ctgacgattt  6240
caccggctgc gtgatcgcct ggaactctaa caatctggat agcaaagtgg cggcaacta  6300
caattatctg taccggctgt ttagaaagtc taatctgaag ccattcgaga gggacatctc  6360
cacagaaatc taccaggccg gctctacccc ctgcaatggc gtgaagggct ttaactgtta  6420
tttccctctg cagagctacg gcttccagcc aacatatggc gtggctatc agccctaccg  6480
cgtggtggtg ctgtctttg agctgctgca cgcacctgca acagtgtgcg gaccaaagaa  6540
gagcaccaat ctggtgaaga caagtgcgt gaacttcaac ttcaacggac tgaccggaac  6600
aggcgtgctg accgagtcca acaagaagtt cctgcctttt cagcagttcg cagggacat  6660
cgcagatacc acagacgccg tgcgcgaccc tcagaccctg gagatcctgg acatcacacc  6720
atgctccttc ggcggcgtgt ctgtgatcac accaggcacc aatacaagca accaggtggc  6780
cgtgctgtat cagggcgtga attgtaccga ggtgccagtg gcaatccacg cagatcagct  6840
gacccctaca tggcggtgt actctaccgg cagcaacgtg ttccagacaa gagccggatg  6900
cctgatcgga gcagagcacg tgaacaatag ctatgagtgc gacatcccta tcggcgccgg  6960
catctgtgcc tcctaccaga cccagacaaa ctcccccaga tcaagcgtga ttcctctgtg  7020
ccatccactg gcagatccct ccacagtgtt caaagacgga gatgaggccg aagactttgt  7080
ggaagtccac ctgcctgatg tgcataacca ggtgtctggc gtcgacctgg gactgccaaa  7140
ttgggggcaag tacgtgctgc tgagtgctgg agcactgact gccctgatgc tgatcatttt  7200
cctgatgcca tgctgtcggc gcgtgaacag aagtgagccc actcagcaca tctgcagg  7260
aaccgggaga gaagtgtcag tcacacctca gagcgggaaa atcattagta gttgggaatc  7320
acataaaagc gggggcgaga ccaggctggg atccggctcc ggcagggca ggggaagtct  7380
actaacatgc ggggacgtgg aggaaaatcc cggcccatg ctcgatcctg agagtgtcta  7440
tgatgaccct attgacccaa tcgagttaga ggctgaactg agaggaaccc ccattgtccc  7500
caactcttg aggaactctg actacaatct caactctcct ttgatagaag atcctgctga  7560
actaatgtta gaatggttaa aaacagggaa tagaccttat cggatgactc taacagacaa  7620
ttgctccagg tcttttcagag ttttgaaaga ttatttcaag aaggtagatt tgggttctct  7680
caaggtgggc ggaatggctg cacagtcaat gatttctctc tggttatatg gtgcccactc  7740
tgaatccaac aggagccgga gatgtataac agacttggcc catttctatt ccaagtcgtc  7800
cccatagag aagctgttga atctcacgct aggaaataga gctgagaa tccccccaga  7860
gggagtgtta agttgccttg agaggggtga ttatgataat gcatttggaa ggtatcttgc  7920
caacacgtat tcctcttact tgttcttcca tgtaatcacc ttatcatga acgccctaga  7980
ctgggatgaa gaaagaccaa tcctagcatt atggaaagat ttaacctcag tggacatcgg  8040
gaaggacttg gtaaagttca aagaccaaat atggggactg ctgatcgtga caaaggcttt  8100
tgtttactcc caaagttcca attgtctttt tgacagaaac tacacactta tgctaaaaga  8160
```

```
tcttttcttg tctcgcttca actccttaat ggtcttgctc tctccccag agccccgata    8220
ctcagatgac ttgatatctc aactatgcca gctgtacatt gctggggatc aagtcttgtc   8280
tatgtgtgga aactccggct atgaagtcat caaaatattg gagccatatg tcgtgaatag   8340
tttagtccga agagcagaaa agtttaggcc tctcattcat tccttgggag actttcctgt   8400
atttataaaa gacaaggtaa gtcaacttga agagacgttc ggtccctgtg caagaaggtt   8460
ctttagggct ctggatcaat tcgacaacat acatgacttg gttttttgtgt ttggctgtta   8520
caggcattgg gggcacccat atatagatta tcgaaagggt ctgtcaaaac tatatgatca   8580
ggttcacctt aaaaaaatga tagataagtc ctaccaggag tgcttagcaa gcgacctagc   8640
caggaggatc cttagatggg gttttgataa gtactccaag tggtatctgg attcaagatt   8700
cctagcccga gaccaccct tgactcctta tatcaaaacc caaacatggc cacccaaaca   8760
tattgtagac ttggtggggg atacatggca caagctcccg atcacgcaga tctttgagat   8820
tcctgaatca atggatccgt cagaaatatt ggatgacaaa tcacattctt tcaccagaac   8880
gagactagct tcttggctgt cagaaaaccg agggggggcct gttcctagcg aaaaagttat   8940
tatcacggcc ctgtctaagc cgcctgtcaa tccccgagag tttctgaggt ctatagacct   9000
cggaggattg ccagatgaag acttgataat tggcctcaag ccaaaggaac gggaattgaa   9060
gattgaaggt cgattctttg ctctaatgtc atggaatcta agattgtatt ttgtcatcac   9120
tgaaaaactc ttggccaact acatcttgcc acttttttgac gcgctgacta tgacagacaa   9180
cctgaacaag gtgttttaaaa agctgaatcga cagggtcacc gggcaagggc ttttggacta   9240
ttcaagggtc acatatgcat ttcacctgga ctatgaaaag tggaacaacc atcaaagatt   9300
agagtcaaca gaggatgtat tttctgtcct agatcaagtg tttggattga agagagtgtt   9360
ttctagaaca cacgagtttt ttcaaaaggc ctggatctat tattcagaca gatcagacct   9420
catcgggtta cgggaggatc aaatatactg cttagatgcg tccaacggcc caacctgttg   9480
gaatggccag gatggcgggc tagaaggctt acggcagaag ggctggagtc tagtcagctt   9540
attgatgata gatagagaat ctcaaatcag gaacacaaga accaaaatac tagctcaagg   9600
agacaaccag gttttatgtc cgacatacat gttgtcgcca gggctatctc aagagggggct   9660
cctctatgaa ttggagagaa tatcaaggaa tgcactttcg atatacagag ccgtcgagga   9720
aggggcatct aagctagggc tgatcatcaa gaaagaagag accatgtgta gttatgactt   9780
cctcatctat ggaaaaaccc ctttgtttag aggtaacata ttggtgcctg agtccaaaag   9840
atgggccaga gtctcttgcg tctctaatga ccaaatagtc aacctcgcca atataatgtc   9900
gacagtgtcc accaatgcgc taacagtggc acaaccactct caatctttga tcaaaccgat   9960
gagggatttt ctgctcatgt cagtacaggc agtctttcac tacctgctat ttagcccaat  10020
cttaaaggga agagtttaca agattctgag cgctgaaggg gagagctttc tcctagccat  10080
gtcaaggata atctatctag atccttcttt gggagggata tctggaatgt ccctcggaag  10140
attccatata cgacagttct cagaccctgt ctctgaaggg ttatccttct ggagagagat  10200
ctggttaagc tcccaagagt cctggattca cgcgttgtgt caagaggctg gaaacccaga  10260
tcttggagag agaacactcg agagcttcac tcgccttcta gaagatccga ccaccttaaa  10320
tatcagagga gggggccagtc ctaccattct actcaaggat gcaatcagaa aggctttata  10380
tgacgaggtg gacaaggtgg aaaattcaga gtttcgagag gcaatcctgt tgtccaagac  10440
ccatagagat aattttatac tcttcttaat atctgttgag cctctgtttc ctcgatttct  10500
cagtgagcta ttcagttcgt ctttttttggg aatccccgag tcaatcattg gattgataca  10560
aaactcccga acgataagaa ggcagtttag aaagagtctc tcaaaaactt tagaagaatc  10620
cttctacaac tcagagatcc acgggattag tcggatgacc cagacacctc agagggttgg  10680
ggggtgtgg ccttgctctt cagagagggc agatctactt cttggggaag cttggggaag  10740
aaaagtggta ggcacgacag ttcctcaccc ttctgagatg ttgggattac ttccaagtc  10800
ctctatttct tgcacttgtg gagcaacagg aggaggcaat cctagagttt ctgtatcagt  10860
actcccgtcc tttgatcagt cattttttttc acgaggcccc ctaaagggat acttgggctc  10920
gtccaactct atgtcgaccc aagctattcca tgcatggaaa aaagtcacta atgttcatgt  10980
ggtgaagaga gctctatcgt taaaagaatc tataaactgg ttcattacta gagattccaa  11040
cttggctcaa gctctaatta ggaacattat gtctctgaca ggccctgatt ccctctaga  11100
ggaggcccct gtcttcaaaa ggacggggtc agccttgcat aggttcaagt ctgccagata  11160
cagcgaagga gggtattctt ctgtctgccc gaacctcctc tctcatattt ctgttagtac  11220
agacaccatg tctgatttga cccaagacgg gaagaactac gatttcatgt tccagccatt  11280
gatgctttat gcacagacat ggcatcaga gctggtacag agagacacaa ggctaagaga  11340
ctctacgttt cattggcacc tccgatgcaa caggtgtgtg agaccccattg acgacgtgac  11400
cctggagacc tctcagatct tcgagtttcc ggatgtgtcg aaaagaatat ccagaatggt  11460
ttctggggct gtgcctcact tccagaggct tcccgatatc cgtctgagac caggagattt  11520
tgaatctcta agcggtagag aaaagtctca ccatatcgga tcagctcagg ggctcttata  11580
ctcaatctta gtgcaattc acgactcagg atacaatgat ggaaccatct tccctgtcaa  11640
catatacggc aaggttttccc ctagagacta tttgagaggg ctcgcaaggg gagtattgat  11700
aggatcctcg atttgcttct tgacaagaat gacaaatatc aatattaata gacctcttga  11760
attggtctca gggtaatct catatattct cctgaggcta gataaccatc cctccttgta  11820
cataatgctc agagaaccgt ctcttagagg agagatattt tctatccctc agaaaatccc  11880
cgccgcttat ccaaccacta tgaaagaagg caacagatca atcttgtgtt atctccaaca  11940
tgtgctacgc tatgagcgag agataatcac gcgtctccca gagaatgact ggctatggat  12000
cttttcagac tttagaagtg ccaaaatgac gtacctatcc ctcattactt accagtctca  12060
tcttctactc cagagggttg agagaaacct atctaagagt atgagagata acctgcgaca  12120
attgagttct ttgatgaggc aggtgctggg cgggcacgga gaagatacct tagagtcaga  12180
cgacaacatt caacgactgc taaaagactc tttacgaagg acaagatggg tggatcaaga  12240
ggtgcgccat gcagctagaa ccatgactgg agattacgac cccaacaaga aggtgtcccg  12300
taaggtagga tgttcagaat gggtctgctc tgctcaacag gttgcagtct ctacctcagc  12360
aaacccggcc cctgtctcgg agcttgacat aaggggccctc tctaagaggt tccagaaccc  12420
tttgatctcg ggcttgagag tggttcagtg ggcaaccggt gctcattata agcttaagcc  12480
tattctagat gatctcaatg ttttcccatc tctctgcctt gtagtgggggg acgggtcagg  12540
ggggatatca agggcagtcc tcaacatgtt tccagatgcc aagcttgtgt tcaacagtct  12600
tttagaggtg aatgacctga tggcttccgg aacacatcca ctgcctcctt cagcaatcat  12660
gagggggagga aatgatatcg tctccagagt gatagatctt gactcaatct gggaaaaacc  12720
gtccgacttg agaaacttgg caacctggaa atacttccag tcagtcccaaa agcaggtcaa  12780
catgtcctat gacctcatta tttgcgatgc agaagttact gacattgcat ctatcaaccg  12840
gatcacccctg ttaatgtccg attttgcatt gtctatagat ggaccactct atttggtctt  12900
```

```
caaaacttat gggactatgc tagtaaatcc aaactacaag gctattcaac acctgtcaag  12960
agcgttcccc tcggtcacag ggtttatcac ccaagtaact tcgtcttttt catctgagct  13020
ctacctccga ttctccaaac gagggaagtt tttcagagat gctgagtact tgacctcttc  13080
cacccttcga gaaatgagcc ttgtgttatt caattgtagc agccccaaga gtgagatgca  13140
gagagctcgt tccttgaact atcaggatct tgtgagagga tttcctgaag aaatcatatc  13200
aaatccttac aatgagatga tcataactct gattgacagt gatgtagaat cttttctagt  13260
ccacaagatg gttgatgatc ttgagttaca gaggggaact ctgtctaaag tggctatcat  13320
tatagccatc atgatagttt tctccaacag agtcttcaac gtttccaaac ccctaactga  13380
cccctcgttc tatccaccgt ctgatcccaa aatcctgagg cacttcaaca tatgttgcag  13440
tactatgatg tatctatcta ctgctttagg tgacgtccct agcttcgcaa gacttcacga  13500
cctgtataac agacctataa cttattactt cagaaagcaa gtcattcgag ggaacgttta  13560
tctatcttgg agttggtcca acgacacctc agtgttcaaa agggtagcct gtaattctag  13620
cctgagtctg tcatctcact ggatcaggtt gatttacaag atagtgaaga ctaccagact  13680
cgttggcagc atcaaggatc tatccagaga agtggaaaga caccttcata ggtacaacag  13740
gtggatcacc ctagaggata tcagatctag atcatcccta ctagactaca gttgcctgtg  13800
aaccggatac tcctggaagc ctgcccatgc taagactctt gtgtgatgta tcttgaaaaa  13860
aacaagatcc taaatctgaa cctttggttg tttgattgtt tttctcattt ttgttgttta  13920
tttgttaagc gt                                                      13932

SEQ ID NO: 18          moltype = DNA  length = 13475
FEATURE                Location/Qualifiers
misc_feature           1..13475
                       note = VSV vector: Convac V1 China
source                 1..13475
                       mol_type = other DNA
                       organism = synthetic construct
SEQUENCE: 18
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc acccccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtcactatg aagtgccttt tgtacttagc ctttttattc attggggtga  3120
```

```
attgcaagtt caccatagtt tttccacaca accaaaaagg aaactggaaa aatgttcctt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatgaccg aagtatataa    3360
cacagtccat ccgatccttc attccatctg tagaacagtc caaggaaagc attgaacaaa   3420
cgaaacaagg aacttggctg aatccaggct tccctcctca aagttgtgga tatgcaactg   3480
tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720
gaaaggaggg cacagggttc agaagtaact actttgctta tgaaactgga ggcaaggcct   3780
gcaaaatgca atactgcaag cattgggag tcagactccc atcaggtgtc tggttcgaga    3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg gacccaatgg agttctgagg accagttcag   4260
gatataagtt tccttatac atgattggac atggtatgtt ggactccgat cttcatctta    4320
gctcaaaggc tcaggtgttc gaacatcctc acattcaaga cgctgcttcg caacttcctg   4380
atgatgagag tttattttt ggtgatactg ggctatccaa aaatccaatc gagcttgtag    4440
aaggttggtt cagtagttgg aaaagctcta ttgcctcttt tttctttatc ataggggttaa   4500
tcattggact attcttggtt ctccgagttg gtatccatct ttgcattaaa ttaaagcaca   4560
ccaagaaaag acagatttat acagacatag agatgaaccg acttgaaaag taactcaaat   4620
cctgctaggt atgaaaaaaa ctaacagata tcacgctgcg gcgtacgcca ccatgttcgt   4680
gtttctggtg ctgctgcctc tggtgagctc ccagtgcgtg aacctgacca caaggaccca   4740
gctgccccct gcctatacca attccttcac acggggcgtg tactatcccg acaaggtgtt   4800
ccggagcagc gtgctgcact ccacacagga tctgtttctg ccttctttt ctaacgtgac    4860
ctggttccac gccatccacg tgagcggcac caatggcaca aagcggttcg acaatccgat   4920
gctgcccttt aacgatgcg tgtacttcgc ctccaccgag aagtctaaca tcatcagagg    4980
ctggatcttt ggcaccacac tggacagcaa gacacagtcc ctgctgatcg tgaacaatgc   5040
caccaacgtg gtcatcaagg tgtgcgagtt ccagttttgt aatgatccat tcctgggcgt   5100
gtactatcac aagaacaata agtcttggat ggagagcgag tttcgcgtgt attcctctgc   5160
caacaattgc acatttgagt acgtgtccca gcccttcctg atggacctgg agggcaagca   5220
gggcaatttc aagaacctga gggagttcgt gtttaagaat atcgatggct acttcaaaat   5280
ctactccaag cacaccccaa tcaacctggt gcgcgacctg ccacagggct tctctgccct   5340
ggagccactg gtggatctgc ccatcggcat caacatcacc cggtttcaga cactgctggc   5400
cctgcacaga agctacctga caccaggcga cagctcctcc ggatggaccg caggagcagt   5460
agcctactat gtgggctatc tgcagcccag gaccttcctg ctgaagtaca acgagaatgc   5520
caccatcaca gacgccgtgg attgcgccct ggatccctg tctgagacca agtgtacact    5580
gaagagcttt accgtggaga agggcatcta tcagacaagc aatttcaggg tgcagcctac   5640
cgagtccatc gtgcgctttc ccaatatcac aaacctgtgc cctttggcg aggtgttcaa    5700
cgcaacccgc ttcgcagcg tgtacgcctg gaataggaag cgcatctcca actgcgtggc   5760
cgactattct gtgctgtaca acagcgcctc cttctctacc tttaagtgct atggcgtgag   5820
ccccacaaag ctgaatgacc tgtgctttac caacgtgtac gccgattcct tcgtgatcag   5880
gggcgacgag gtgcgccaga tcgcaccagg acagacggc aagatcgcag actacaatta    5940
taagctgcct gacgatttca ccggctgcgt gatcgcctgg aactctaaca atctggatag   6000
caaagtgggc ggcaactaca attatctgta ccggctgttt agaaagtcta atctgaagcc   6060
attcgagagg gacatctcca cagaaatcta ccaggccggc tctaccccct gcaatggcgt   6120
ggagggcttt aactgttatt tccctctgca gagctacggc ttccagccaa caaacggcgt   6180
gggctatcag ccctaccgcg tggtggtgct gtcttttgag ctgctgcacg cacctgcaac   6240
agtgtgcgga ccaaagaaga gcaccaatct ggtgaagaac aagtgcgtga acttcaactt   6300
caacggactg accggaacag gcgtgctgac cgagtccaac aagaagttcc tgccttttca   6360
gcagttcggc agggacatcg cagataccac agacgccgtg cgcgaccctc agacccctga   6420
gatcctggac atcacaccat gctccttcgg cggcgtgtct gtgatcacac caggcaccaa   6480
tacaagcaac caggtggccg tgctgtatca ggactgtgaat tgtaccgagg tgccagtggc   6540
aatccacgca gatcagctga cccctacatg gcgggtgtac tctaccggca gcaacgtgtt   6600
ccagacaaga gccgatgcc tgatcggagc agagcacgtg aacaatagct atgagtgcga    6660
catccctatc ggccgggca tctgtgcctc ctaccagaca cagacaaact cccccaggtc   6720
tgtgggcgat acaggcctgt ccaagaatcc aatcgagctg gtagagggct ggtcagcag    6780
ttggaaaagc tccatcgcct cctttttctt tatcatcggc ctgatcatcg gactgttcct   6840
ggtgctccgc gtgggtatcc acctgtgcat caagctgaag cacaccaaga aagacagat    6900
ttatacagac atcgagatga accgcctggg aaagtgcatt ccagattc ttcatgtttg    6960
gaccaaatca acttgtgata ccatgctcaa agaggcctca attatatttg agttttaat    7020
ttttatgaaa aaaactaaca gcaatcatgg aagtccacga ttttgagacc gacgagttca   7080
atgatttcaa tgaagatgac tatgccacaa gagaattcct gaatcccgat gagcgcatga   7140
cgtacttgaa tcatgctgat tacaatttga attctcctct aattagtagt gatattgaca   7200
atttgatcag gaaattcaat tctcttcga ttccctcgat gtgggatagt aagaactgga    7260
atggagttct tgagatgtta acatcatgtc aagccaatcc catctcaaca tctcagatgc   7320
ataaatggat gggaagttgg ttaatgtctg ataatcatga tgccagtcaa gggtatagtt   7380
ttttacatga agtggacaaa gaggcagaaa taacatttga cgtggtggag accttcatcc   7440
gcggctgggg caacaaacca attgaataca tcaaaaaggg aagatggact gactcattca   7500
aaattctcgc ttatttgtgt caaaagtttt tggacttaca caagttgaca ttaatcttaa   7560
atgctgtctc tgaggtggaa ttgctcaact tggcgaggac tttcaaaggc aaagtcagaa   7620
gaagttctca tggaacgaac atatgcagga ttagggttcc cagcttggt cctactttta    7680
tttcagaagg atgggcttac ttcaagaaac ttgatattct aatggaccga acttttctgt   7740
taatggtcaa agatgtgatt atagggagga tgcaacggt gctatccatg gtatgtagaa    7800
tagacaacct gttctcagag caagacatct tctccctctt aaatatctac agaattggag   7860
```

```
ataaaattgt ggagaggcag ggaaattttt cttatgactt gattaaaatg gtggaaccga   7920
tatgcaactt gaagctgatg aaattagcaa gagaatcaag gccttagtc ccacaattcc    7980
ctcattttga aaatcatatc aagacttctg ttgatgaagg ggcaaaaatt gaccgaggta   8040
taagattcct ccatgatcag ataatgagtg tgaaaacagt ggatctcaca ctggtgattt   8100
atggatcgtt cagacattgg ggtcatcctt ttatagatta ttacactgga ctagaaaaat   8160
tacattccca agtaaccatg aagaaagata ttgatgtgtc atatgcaaaa gcacttgcaa   8220
gtgatttagc tcggattgtt ctatttcaac agttcaatga tcataaaaag tggttcgtga   8280
atggagactt gctccctcat gatcatccct ttaaaagtca tgttaaagaa aatacatggc   8340
ccacagctgc tcaagttcaa gattttggag ataaatggca tgaacttccg ctgattaaat   8400
gttttgaaat acccgactta ctagacccat cgataatata ctctgacaaa agtcattcaa   8460
tgaataggtc agaggtgttg aaacatgtcc gaatgaatcc gaacactcct atccctagta   8520
aaaaggtgtt gcagactatg ttggacacaa aggctaccaa ttggaaagaa tttcttaaag   8580
agattgatga aagggcttta gatgatgatg atctaattat tggtcttaaa ggaaaggaga   8640
gggaactgaa gttggcaggt agattttct ccctaagtgc ttggaaattg cgagaatact    8700
ttgtaattac cgaatatttg ataaagactc atttcgtccc tatgtttaaa ggcctgacaa   8760
tggcggacga tctaactgca gtcattaaaa agatgttaga ttcctcatcc ggccaaggat   8820
tgaagtcata tgaggcaatt tgcatagcca atcacattga ttacgaaaaa tggaataacc   8880
accaaaggaa gttatcaaac ggcccagtgt tccgagttat gggccagttc ttaggttatc   8940
catccttaat cgagagaact catgaatttt ttgagaaaag tcttatatac tacaatggaa   9000
gaccagactt gatgcgtgtt cacaacaaca cactgatcaa ttcaacctcc caacgagttt   9060
gttggcaaga caagagggt ggactggaag gtctacggca aaaaggatgg actatcctca    9120
atctactggt tattcaaaga gaggctaaaa tcagaaacac tgctgtcaaa gtcttggcac   9180
aaggtgataa tcaagttatt tgcacacagt ataaaacgaa gaaatcgaga aacgttgtag   9240
aattacaggg tgctctcaat caaatggttt ctaataatga gaaaattatg actgcaatca   9300
aaataggac agggaagtta ggacttttga taaatgacga tgagactatg caatctgcag    9360
attacttgaa ttatggaaaa ataccgattt tccgtggagt gattagaggg ttagagacca   9420
agagatggtc acgagtgact tgtgtcacca atgaccaaat acccacttgt gctaatataa   9480
tgagctcagt ttccacaaat gctctcaccg tagctcattt tgctgagaac ccaatcaatg   9540
ccatgataca gtacaattat tttgggacat ttgctagact cttgttgatg atgcatgatc   9600
ctgctcttcg tcaatcattg tatgaagttc aagataagat accggcttg cacagttcta    9660
ctttcaaata cgccatgttg tatttggacc cttccattgg aggagtgtcg ggcatgtctt   9720
tgtccaggtt tttgattaga gccttccag atcccgtaac agaaagtctc tcattctgga    9780
gattcatcca tgtacatgct cgaagtgagc atctgaagga gatgagtgca gtatttgaa    9840
accccgagat agccaagttt cgaataactc acatagacaa gctagtagaa gatccaacct   9900
ctctgaacat cgctatggga atgagtccag cgaacttgtt aaagactgag gttaaaaaat   9960
gcttaatcga atcaagacaa accatcagga accaggtgat taaggatgca accatatatt  10020
tgtatcatga gaggatcgg ctcagaagtt tcttatggtc aataaatcct ctgttcccta   10080
gattttttaag tgaattcaaa tcaggcactt tttgggagt cgcagacggg ctcatcagtc   10140
tatttcaaaa ttctcgtact attcggaact cctttaagaa aagtatcat agggaattgg    10200
atgatttgat tgtgaggagt gaggtatcct ctttgacaca tttagggaaa cttcatttga   10260
gaagggatc atgtaaaatg tggacatgtt cagctactca tgctgacaca ttaagataca   10320
aatcctgggg ccgtacagtt attgggacaa ctgtacccca tccattagaa atgtgggtc    10380
cacaacatcg aaaagagact ccttgtgcac catgtaaccac atcagggttc aattatgttt   10440
ctgtgcattg tccagacggg atccatgacg tctttagttc acggggacca ttgcctgctt   10500
atctagggtc taaaacatct gaatctacat ctattttgca gccttgggaa agggaaagca   10560
aagtcccact gattaaaaga gctacacgtc ttagagatgc tatctcttgg tttgttgaac   10620
ccgactctaa actagcaatg actatacttt ctaacatcca ctctttaaca ggcgaagaat   10680
ggaccaaaag gcagcatggg ttcaaaagaa cagggtctgc ccttcatagg ttttcgacat   10740
ctcggatgag ccatggtggg ttcgcatctc agagcactgc agcattgacc aggttgatgg   10800
caactacaga caccatgagg gatctggag atcagaattt cgacttttta ttccaagcaa    10860
cgttgctcta tgctcaaatt accaccactg ttgcaagaga cggatgatc accagttgta    10920
cagatcatta tcatattgcc tgtaagtcct gtttgagacc catagaagag atcaccctgg   10980
actcaagtat ggactacacg ccccccagatg tatccatgt gctgaagaca tggaggaatg   11040
gggaaggttc gtgggacaa gagataaaac agatctatcc tttagaaggg aattggaaga    11100
atttgacacc tgctgagcaa tcctatcaag tcggcagatg tataggtttt ctatatggag   11160
acttggcgta tagaaaatct actcatgccg aggacagttc tctatttcct ctatctatac   11220
aagtcgtat tagaggtcga ggtttcttaa aagggttgct agacggatta atgagagcaa    11280
gttgctgcca agtaatacac cggagaagtc tggctcattt gaagaggccg gccaacgcag   11340
tgtacggagg tttgatttac ttgattgata aattgagtgt atcacctcca ttccttttctc   11400
ttactagatc aggacctatt agagacgaat tagaaacgat tcccacaag atcccaacct    11460
cctatccgac aagcaaccgt gatatggggg tgattgtcag aaattacttc aaataccaat   11520
gccgtcaat tgaaaaggga aaatacagat cacattattc acaattatgg ttattctcag    11580
atgtcttatc catagacttc attggaccat tctctatttc caccaccctc ttgcaaatcc   11640
tatacaagcc attttatct gggaaagata agaatagtt gagagagctg gcaaatcttt     11700
cttcattgct aagatcagga gaggggtggg aagacataca tgtgaaattc ttccaccaagg  11760
acatattatt gtgtccagag gaaatcagac atgcttgcaa gttcgggatt gctaaggata   11820
ataataaaga catgagctat ccccttggg aaggaatc cagagggaca attacaacaa      11880
tccctgttta ttatacgacc accccttacc caaagatgct agagatgcct ccaagaatcc   11940
aaaatcccct gctgtccgga atcaggttgg gccaattacc aactggtgct cattataaaa   12000
ttcggagtat attacatgga atgggaatcc attacaggga cttcttgagt tgtggagacg   12060
gctccggagg gatgactgct gcattactac gagaaaatgt gcatagcaga ggaatattca   12120
atagtctgtt agaattatca gggtcagtca tgcgaggcgc ctctcctgag ccccccagtg   12180
ccctagaaac tttaggagga gataaatcga gatgtgtaaa tggtgaaaca tgttgggaat   12240
atccgtcctg cttatgtgac ccaaggactt gggactattc cctccgactc aaagcaggct   12300
tggggcttca aattgattta attgtaatgg atatggaagt tcgggattct tctactagcc   12360
tgaaaattga gacgaatgtt agaaattatg tgcaccggat tttggatgag caaggagttt   12420
taatctacaa gacttatgga acatatattt gtgagagcga aaagaatgca gtaacaatcc   12480
ttggtccat gttcaagacg gtcgacttag ttcaaacaga atttagtagt tctcaaacgt    12540
ctgaagtata tatggtatgt aaaggtttga agaaattaat cgatgaaccc aatcccgatt   12600
```

```
ggtcttccat caatgaatcc tggaaaaacc tgtacgcatt ccagtcatca gaacaggaat  12660
ttgccagagc aaagaaggtt agtacatact ttaccttgac aggtattccc tcccaattca  12720
ttcctgatcc tttttgtaaac attgagacta tgctacaaat attcggagta cccacgggtg  12780
tgtctcatgc ggctgcctta aaatcatctg atagacctgc agatttattg accattagcc  12840
ttttttatat ggcgattata tcgtattata acatcaatca tatcagagta ggaccgatac  12900
ctccgaaccc cccatcagat ggaattgcac aaaatgtggg gatcgctata actggtataa  12960
gcttttggct gagtttgatg gagaaagaca ttccactata tcaacagtgt ttagcagtta  13020
tccagcaatc attcccgatt aggtgggagg ctgtttcagt aaaaggagga tacaagcaga  13080
agtggagtac tagaggtgat gggctcccaa aagatacccg aacttcagac tcctttggcc  13140
caatcgggaa ctggatcaga tctctggaat tggtccgaaa ccaagtcgt ctaaatccat  13200
tcaatgagat cttgttcaat cagctatgtc gtacagtgga taatcatttg aaatggtcaa  13260
atttgcgaag aaacacagga atgattgaat ggatcaatag acgaatttca aaagaagacc  13320
ggtctatact gatgttgaag agtgacctac acgaggaaaa ctcttggaga gattaaaaaa  13380
tcatgaggag actccaaact ttaagtatga aaaaacttt gatccttaag accctcttgt   13440
ggttttttatt ttttatctgg ttttgtggtc ttcgt                            13475

SEQ ID NO: 19         moltype = DNA  length = 13469
FEATURE               Location/Qualifiers
misc_feature          1..13469
                      note = VSV vector: Convac V1 South Africa
source                1..13469
                      mol_type = other DNA
                      organism = synthetic construct
SEQUENCE: 19
acgaagacaa acaaaccatt attatcatta aaaggctcag gagaaacttt aacagtaatc    60
aaaatgtctg ttacagtcaa gagaatcatt gacaacacag tcatagttcc aaaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact gtatggagc attaaaggac  300
atccgggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaagct catggatggg  540
ctgacaaatc aatgcaaaat gatcaatgaa cagtttgaac ctcttgtgcc agaaggtcgt  600
gacattttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca agattgtgc tgcattggca acatttggac acctctgcaa ataaccgga  780
atgtctacag aagatgtaac gacctggatc ttgaaccgag aagttgcaga tgaaatggtc  840
caaatgatgc ttccaggcca agaaattgac aaggccgatt catcatgc ttatttgatc  900
gactttggat tgtcttctaa gtctccatat tcttccgtca aaaaccctgc cttccacttc  960
tggggggcaat tgacagctct tctgctcaga tccaccagag caaggaatgc ccgacagcct  1020
gatgacattg agtatacatc tcttactaca gcaggttttgt tgtacgctta tgcagtagga  1080
tcctctgccg acttggcaca acagttttgt gttggagata acaaatacac tccagatgat  1140
agtaccggag gattgacgac taatgcaccg ccaaaggca gagatgtggt cgaatgctc  1200
ggatggtttg aagatcaaaa cagaaaaccg actcctgata tgatgcagta tgcgaaaaga  1260
gcagtcatgt cactgcaagg cctaagagag aagacaattg caagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatgagtg aagagcata ctaagccctc ttatttttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga acagcctga gcttgaatct  1740
gacgagcatg gaaagacctt acggttgaca tcgccagagg gttaagtgg agagcagaaa  1800
tcccagtgc tttcgacgat taaagcagtc gtgcaaagtg caaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagagcc atcctgctcg gcctgagata caaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
agggggaagg taagaaatct aagaaattag ggatcgcacc cccccttat gaagaggaca  2340
ctagcatgga gtatgctccg agcgctccaa ttgacaaatc ctattttgga gttgacggaa  2400
tggacaccta tgatccgaat caattaagat atgagaaatt cttcttaca gtgaaaatga  2460
cggttagatc taatcgtccg ttcagaacat actcagatgt ggcagccgct gtatcccatt  2520
gggatcacat gtacatcgga atggcaggga acgtccctt ctacaaaatc ttggctttttt  2580
tgggttctct taatctaaag gccactccag cggtattggc agatcaaggt caaccagagt  2640
atcacactca ctgcgaaggc agggcttatt tgccacatag gatgggaag accctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt cagagagaa ggccttaatg tttggcctga  2880
ttgtcgagaa aaaggcatct ggagcgtggg tcctggattc tatcagccac ttcaaatgag  2940
ctagtcaac ttctagcttc tgaacaatcc ccggttact cagtctctcc taattcaag  3000
ctctcgaaca actaatatcc tgtcttttct atccctatga aaaaaactaa cagagatcga  3060
tctgtttacg cgtcactatg aagtgccttt tgtacttagc ctttttattc attggggtga  3120
attgcaagtt caccatagtt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
```

```
gtcatgcttc caaatgggtc actacttgtg atttccgctg gtatggaccg aagtatataa 3360
cacagtccat ccgatccttc actccatctg tagaacaatg caaggaaagc attgaacaaa 3420
cgaaacaagg aacttggctg aatccaggct tccctcctca aagttgtgga tatgcaactg 3480
tgacggatgc cgaagcagtg attgtccagg tgactcctca ccatgtgctg gttgatgaat 3540
acacaggaga atgggttgat tcacagttca tcaacggaaa atgcagcaat tacatatgcc 3600
ccactgtcca taactctaca acctggcatt ctgactataa ggtcaaaggg ctatgtgatt 3660
ctaacctcat ttcatggac atcaccttct tctcagagga cggagagcta tcatccctgg 3720
gaaaggaggg cacagggttc agaagtaact actttgctta tgaaactgga ggcaaggcct 3780
gcaaaatgca atactgcaag cattgggag tcagactccc atcaggtgtc tggttcgaga 3840
tggctgataa ggatctcttt gctgcagcca gattcctga atgcccagaa gggtcaagta 3900
tctctgctcc atctcagacc tcagtggatg taagtctaat tcaggacgtt gagaggatct 3960
tggattattc cctctgccaa gaaacctgga gcaaaatcag agcgggtctt ccaatctctc 4020
cagtggatct cagctatctt gctcctaaaa acccaggaac cggtcctgct ttcaccataa 4080
tcaatggtac cctaaaatac tttgagacca gatcatcag agtcgatatt gctgctccaa 4140
tcctctcaag aatggtcgga atgatcagtg gaactaccac agaaagggaa ctgtgggatg 4200
actgggcacc atatgaagac gtggaaattg gacccaatgg agttctgagg accagttcag 4260
gatataagtt tccttttatac atgattggac atggtatgtt ggactccgat cttcatctta 4320
gctcaaaggc tcaggtgttc gaacatcctc acattcaaga cgctgcttcg caacttcctg 4380
atgatgagag tttatttttt ggtgatactg ggctatccaa aaatccaatc gagcttgtag 4440
aaggttggtt cagtagttgg aaaagctcta ttgcctcttt tttctttatc atagggttaa 4500
tcattggact attcttggtt ctccgagttg gtatccatct ttgcattaaa ttaaagcaca 4560
ccaagaaaag acagatttat acagacatag agatgaaccg acttggaaag taactcaaat 4620
cctgctaggt atgaaaaaaa ctaacagata tcacgaccga gccaccatgt tcgtgttttct 4680
ggtgctgctg cctctggtga gctcccagtg cgtgaacttc accacaagga cccagctgcc 4740
ccctgcctat accaattcct tcacacgggg cgtgtactat cccgacaagg tgttccggag 4800
cagcgtgctg cactccacac aggatctgtt tctgccttc ttttctaacg tgaccctggtt 4860
ccacgccatc cacgtgagcg gcaccaatgg cacaaagcgg ttcgccaatc cagtgctgcc 4920
ctttaacgat ggcgtgtact cgcctccac cgagaagtct aacatcatca gaggctggat 4980
cttggcacc acactggaca gcaagacaca gtccctgctg atcgtgaaca atgccaccaa 5040
cgtggtcatc aaggtgtgcg agttccagtt tgtaatgat ccattcctgg gcgtgtacta 5100
tcacaagaac aataagtctt ggatggagag cgagtttcgc gtgtattcct ctgccaacaa 5160
ttgcacattt gagtacgtgt cccagccctt cctgatggac ctggagggca gcagggcaa 5220
tttcaagaac ctgagggagt tcgtgtttaa gaatatcgat ggctacttca aaatctactc 5280
caagcacacc ccaatcaacc tggtgcgcgg cctgccacag ggctctctg ccctgagagcc 5340
actggtggat ctgcccatcg gcatcaacat cacccggttt cagacactgc tggccctgca 5400
cagaagctac ctgacaccag gcgacagctc ctctggatgg accgcaggag cagcagccta 5460
ctatgtgggc tatctgcagc ccaggacctt cctgctgaag tacaacgaga atggcaccat 5520
cacagacgcc gtggattgcg ccctggatcc cctgtctgag accaagtgta cactgaagag 5580
ctttaccgtg gagaagggca tctatcagac aagcaatttc agggtgcagc taccgagtc 5640
catcgtcgcg tttcccaata tcacaaacct gtgccctttt ggcgaggtgt tcaacgcaac 5700
ccgcttcgcc agcgtgtacg cctggaatag gaagcgcatc tccaactgcg tggccgacta 5760
ttctgtgctg tacaacagcg cctccttctc tacctttaag tgctatggcg tgagcccac 5820
aaagctgaat gacctgtgct ttaccaacgt gtacgccgat tcctcgtga tcagggggca 5880
cgaggtgcgc cagatcgcac caggacagac aggcaatatc gcagactaca attataagct 5940
gcctgacgat ttcaccggct gcgtgatcgc ctggaactct aacaatctgg atagcaaagt 6000
gggcggcaac tacaattatc tgtaccggct gtttagaaag tctaatctga gccattcga 6060
gagggcatc tccacagaaa tctaccaggc cggctctacc ccctgcaatg gcgtgaaggg 6120
ctttaactgt tatttccctc tgcagagcta cggcttccag ccaacatatg gcgtgggcta 6180
tcagccctac cgcgtggtgg tgctgtcttt tgagctgctg cacgcacctg caacagtgtg 6240
cggaccaaaa aagagcacca atctggtgaa gaacaagtgc gtgaacttca cttcaacgg 6300
actgaccgga acaggcgtgc tgaccgagtc caacaagaag ttcctgcctt ttcagcagtt 6360
cggcagggac atcgcagata ccacagacgc cgtgcgcgca cctcagaccc tggagatcct 6420
ggacatcaca ccatgctcct tcggcggcgt gtctgtgatc acaccaggca ccaatacaag 6480
caaccaggtg gccgtgctgt atcagggcgt gaattgtacc gaggtgccag tggcaatcca 6540
cgcagatcag ctgaccccta catgggggt gtactctacc ggcagcaacg tgttccagac 6600
aagagccgga tgcctgatcg gagcagagca cgtgaacaat agctatgagt gcgacatccc 6660
tatcggcgcc ggcatctgtg cctcctacca gacccagaca aactcccaa ggtctgtggg 6720
cgatacaggc ctgtccaaga tccaatcga gctggtagag ggctggttca gcagttggaa 6780
aagctccatc gcctccttt tctttatcat cggcctgatc atcggactgt tcctggtgct 6840
ccgcgtgggt atccacctgt gcatcaagct gaagcacacc aagaaaagac agatttatac 6900
agacatcgag atgaaccgcc tgggaaagtg agctagccag attcttcatg tttgaccaa 6960
atcaacttgt gataccatgc tcaaagaggc ctcaattata tttgagtttt taattttat 7020
gaaaaaaact aacagcaatc atgaagtcc acgatttga gaccgacgag ttcaatgatt 7080
tcaatgaaga tgactatgcc acaagagaat tcctgaatcc cgatgagcc atgacgtact 7140
tgaatcatgc tgattacaat tgaattctc ctctaattga tgatgatatt gacaatttga 7200
tcaggaaatt caattctctt ccgattccct cgatgtggga tagtaagaac tgggatggag 7260
ttcttgagat gttaacatca tgtcaagcca atcccatctc aacatctcag atgcataaat 7320
ggatgggaag ttggttaatg tctgataatc atgatgccag tcaagggtat agttttttac 7380
atgaagtgga caaagaggca gaaataacat tgacgtggt ggagaccttc atccgcggct 7440
ggggcaacaa accaattgaa tacatcaaaa aggaagatg gactgactca ttcaaaattc 7500
tcgcttattt gtgtcaaaag ttttttggact tacacaagtt gacattaatc ttaaatgctg 7560
tctctgaggt ggaattgctc aacttggcga ggactttcaa aggcaaagtc agaagaagtt 7620
ctcatggaac gaacatatgc aggattaggg ttccagcgtt gggtcctact tttatttcag 7680
aaggatggggc ttacttcaag aaacttgata ttccatcga ccgaaactt ctgttaatgg 7740
tcaaagatgt gattagggg aggatgcaaa cggtgctatc catggtatgt agaatagaca 7800
acctgttctc agagcaagac atcttctccc ttctaaatat ctacagaatt ggagataaaa 7860
ttgtggagag gcagggaaat tttcttatg acttgattaa aatggtggaa ccgatatgca 7920
acttgaagct gatgaaatta gcaagagaat caaggccttt agtcccacaa ttccctcatt 7980
ttgaaaatca tatcaagact tctgttgatg aagggggcaaa aattgaccga ggtataagat 8040
```

```
tcctccatga tcagataatg agtgtgaaaa cagtggatct cacactggtg atttatggat   8100
cgttcagaca ttgggggtcat ccttttatag attattacac tggactagaa aaattacatt   8160
cccaagtaac catgaagaaa gatattgatg tgtcatatgc aaaagcactt gcaagtgatt   8220
tagctcggat tgttctattt caacagttca atgatcataa aaagtggttc gtgaatggag   8280
acttgctccc tcatgatcat cccttttaaaa gtcatgttaa agaaaataca tggcccacag   8340
ctgctcaagt tcaagatttt ggagataaat ggcatgaact tccgctgatt aaatgttttg   8400
aaataccccga cttactagac ccatcgataa tatactctga caaaagtcat tcaatgaata   8460
ggtcagaggt gttgaaacat gtccgaatga atccgaacac tcctatccct agtaaaaagg   8520
tgttgcagac tatgttggac acaaaggcta ccaattggaa agaatttctt aaagagattg   8580
atgagaaggg cttagatgat gatgatctaa ttattggtct taaaggaaag gagagggaac   8640
tgaagttggc aggtagattt ttctccctaa tgtcttggaa attgcagaaa actttgtaa    8700
ttaccgaata tttgataaag actcatttcg tccctatgtt taaaggcctg acaatggcgg   8760
acgatctaac tgcagtcatt aaaaagatgt tagattcctc atccgccaa ggattgaagt    8820
catatgaggc aatttgcata gccaatcaca ttgattacga aaaatggaat aaccaccaaa   8880
ggaagttatc aaacgcccca gtgttccgag ttatgggcca gttcttaggt tatccatcct   8940
taatcgagag aactcatgaa ttttttgaga aaagtcttat atactacaat ggaagaccag   9000
acttgatgcg tgttcacaac aacacactga tcaattcaac ctcccaacga gtttgttggc   9060
aaggacaaga gggtggactg gaaggtctac ggcaaaaagg attggactat ctcaatctac   9120
tggttattca aagagaggct aaaatcagaa acactgctgt caaagtcttg gcacaaggtg   9180
ataatcaagt tatttgcaca cagtataaaa cgaagaaatc gagaaacgtt gtagaattac   9240
agggtgctct caatcaaatg gtttctaata atgaaaaat tatgactgca atcaaaatag    9300
ggacagggaa gttaggactt ttgataaatg acgatgaact atgcaatct gcagattact    9360
tgaattatgg aaaaataccg atttttccgtg gagtgattag agggttagag accaagagat   9420
ggtcacgagt gacttgtgtc accaatgacc aaataccccac ttgtgctaat ataatgagct   9480
cagtttccac aaatgctctc accgtagctc attttgctga aacccaatc aatgccatga    9540
tacagtacaa ttatttgggg acatttgcta gactcttgtt gatgatgcat gatcctgctc   9600
ttcgtcaatc attgtatgaa gttcaagata gataccgggg cttgcacagt tctactttca   9660
aatacgccat gttgtatttg gacccttcca ttggaggagt gtcgggcatg tcttttgtcca   9720
ggttttttgat tagagccttc ccagatcccg taacagaaag tctctcattc tggagattca   9780
tccatgtaca tgctcgaagt gagcatctga aggagatgag tgcagtattt ggaaacccccg   9840
agatagccaa gttcgaata actcacatag acaagctagt agaagatcca acctctctga    9900
acatcgctat gggaatgagt ccagcgaact tgttaaagac tgaggttaaa aatgcttaa   9960
tcgaatcaag acaaaccatc aggaaccagg tgattaagga tgcaaccata tatttgtatc  10020
atgaagagga tcggctcaga agttctttat ggtcaataaa tcctctgttc cctagatttt  10080
taagtgaatt caaatcaggc acttttttgg gagtcgcaga cgggctccatc agtctatttc  10140
aaaaattctcg tactattcgg aactcctttta agaaaaagta tcatagggaa ttggatgatt  10200
tgattgtgag gagtgaggta tcctcttga cacatttagg gaaacttcat ttgagaaggg   10260
gatcatgtaa aatgtggaca tgttcagcta ctcatgccatt cacattaaga tacaaatcctt 10320
gggccgtac agttattggg acaactgtac cccatccatt agaaatgttg ggtccacaac    10380
atcgaaaaga gactccttgt gcaccatgta acacatcagg gttcaattat gtttctgtgc   10440
attgtccaga cgggatccat gacgtcttta gttcacgggg accattgcct gcttatctag   10500
ggtctaaaac atctgaatct acatctattt tgcagccttg ggaaagggaa agcaaagtcc   10560
cactgattaa aagagctaca cgtcttagag atgctatctc ttgggtttgtt gaacccgact   10620
ctaaactagc aatgactata cttttctaaca tccactcttt aacaggcgaa gaatggacca   10680
aaaggcagca tgggttcaaa agaacagggt ctgcccttca taggttttcg acatctcgga   10740
tgagccatgt tgggttcgca tctcagagca ctgcagcatt gaccaggttg atggcaacta   10800
cagacaccat gaggggatctg ggagatcaga atttcgatt tttattccaa gcaacgttgc   10860
tctatgctca aattaccacc actgttgcaa gagacggatg gatcaccagt tgtacagatc   10920
attatcatat tgcctgtaag tcctgttttga gacccataga agagatcacc ctggactcaa   10980
gtatggacta cacgccccca gatgtatccc atgtgctgaa gacatggagg aatgggggaag  11040
gttcgtgggg acaagagata aaacagatct atcctttaga agggaattggg aagaatttag   11100
cacctgctga gcaatcctat caagtcggca gatgtatagg ttttctatat ggagacttgg   11160
cgtatagaaa atctactcat gccgaggaca gttctctatt tcctctatct atacaaggtc   11220
gtattagagg tcgaggttttc ttaaaagggt tgctagacgg attaatgaga gcaagttgct   11280
gccaagtaat acaccggaga agtctggctc atttgaagag gccggccaac gcagtgtacg   11340
gaggttttgat ttacttgatt gataaattga gtgtatcacc tccattcctt tctcttacta   11400
gatcaggacc tattagagac gaattagaaa cgattcccca caagatccca acctcctatc   11460
cgacaagcaa ccgtgatatg ggggtgattg tcagaaatta cttcaaatac caatgccgtc   11520
taattgaaaa gggaaaatac agatcacatt atttcacaatt atggttattc tcagatgtct   11580
tatccataga cttcattgga ccattctcta tttccaccac cctccttgcaa atcctataca   11640
agccatttt atctgggaaa gataagaatg agttgagaga gctggcaaat ctttcttcat    11700
tgctaagatc aggagagggg tgggaagaca tacatgtgaa attcttcacc aaggacatat   11760
tattgtgtcc agaggaaatc agacatgctt gcaagttcgg gattgctaag gataataata   11820
aagacatgag ctatccccct tggggaaggg aatccagagg gacaattaca acaatccctg   11880
tttattatac gaccacccct tacccaaaga tgctagagat gcctccaaga atccaaaatc   11940
ccctgctgtc cggaatcagg ttgggccaat taccaactgg cgctcattat aaaattcgga   12000
gtatattaca tggaatggga atccattaca gggacttctt gagttgtgga gacggctccg   12060
gagggatgac tgctgcatta ctacgagaaa atgtgcatag cagaggaata ttcaatagtc   12120
tgttagaatt atcagggtca gtcatgcgag cgcctctcc tgagccccc agtgccctag    12180
aaactttagg aggagataaa tcgagatgtg taaatggtga aacatgttgg gaatatccat   12240
ctgacttatg tgacccaagg acttgggact atttcctccg actcaaagca ggcttggggc   12300
ttcaaattga tttaattgta atggatatgg aagttcggga ttcttctact agcctgaaaa   12360
ttgagacgaa tgttagaaat tatgtgcacc ggattttgga tgagcaagga gttttaatct   12420
acaagactta tggaacatat atttgtgaga gcgaaaagaa tgcagtaaca atccttggtc   12480
ccatgttcaa gacggtcgac ttagttcaaa cagaatttag tagttctcaa acgtctgaag   12540
tatatatggt atgtaaaggt ttgaagaaat taatcgatga acccaatccc gattggtctt   12600
ccatcaatga atcctggaaa aacctgtacg cattccagtc atcagaacag gaatttgcca   12660
gagcaaagaa ggttagtaca tactttacct tgacaggtat tccctcccaa ttcattcctg   12720
atccttttgt aaacattgag actatgctac aaatattcgg agtacccacg ggtgtgtctc   12780
```

```
atgcggctgc cttaaaatca tctgatagac ctgcagattt attgaccatt agccttttt  12840
atatggcgat tatatcgtat tataacatca atcatatcag agtaggaccg atacctccga 12900
accccccatc agatggaatt gcacaaaatg tggggatcgc tataactggt ataagctttt 12960
ggctgagttt gatggagaaa gacattccac tatatcaaca gtgtttagca gttatccagc 13020
aatcattccc gattaggtgg gaggctgttt cagtaaaagg aggatacaag cagaagtgga 13080
gtactagagg tgatgggctc ccaaaagata cccgaacttc agactccttg gccccaatcg 13140
ggaactggat cagatctctg gaattggtcc gaaaccaagt tcgtctaaat ccattcaatg 13200
agatcttgtt caatcagcta tgtcgtacag tggataatca tttgaaatgg tcaaatttgc 13260
gaagaaacac aggaatgatt gaatggatca atagacgaat ttcaaaagaa gaccggtcta 13320
tactgatgtt gaagagtgac ctacacgagg aaaactcttg gagagattaa aaatcatga  13380
ggagactcca aactttaagt atgaaaaaaa ctttgatcct taagaccctc ttgtggtttt 13440
tattttttat ctggttttgt ggtcttcgt                                   13469

SEQ ID NO: 20          moltype = DNA  length = 13556
FEATURE                Location/Qualifiers
misc_feature           1..13556
                       note = VSV vector: Convac V2 China
source                 1..13556
                       mol_type = other DNA
                       organism = synthetic construct
SEQUENCE: 20
acgaagacaa acaaaccatt attatcatta aaaggctcag gagaaacttt aacagtaatc 60
aaaatgtctg ttacagtcaa gagaatcatt gacaacacag tcatagttcc aaaacttcct 120
gcaaatgagg atccagtgga atacccggca gattacttca gaaaatcaaa ggagattcct 180
ctttacatca atactacaaa aagtttgtca gatctaagag gatatgtcta ccaaggcctc 240
aaatccggaa atgtatcaat catacatgtc aacagctact tgtatggagc attaaaggac 300
atccggggta agttggataa agattggtca agtttcggaa taaacatcgg gaaagcaggg 360
gatacaatcg gaatatttga ccttgtatcc ttgaaagccc tggacggcgt acttccagat 420
ggagtatcgg atgcttccag aaccagcgca gatgacaaat ggttgccttt gtatctactt 480
ggcttataca gagtgggcag aacacaaatg cctgaataca gaaaaaagct catggatggg 540
ctgacaaatc aatgcaaaat gatcaatgaa cagtttgaac ctcttgtgcc agaaggtcgt 600
gacatttttg atgtgtgggg aaatgacagt aattacacaa aaattgtcgc tgcagtggac 660
atgttcttcc acatgttcaa aaaacatgaa tgtgcctcgt tcagatacgg aactattgtt 720
tccagattca aagattgtgc tgcattggca acatttggac acctctgcaa aataaccgga 780
atgtctacag aagatgtaac gacctggatc ttgaaccgag aagttgcaga tgaaatggtc 840
caaatgatgc ttccaggcca agaaattgac aaggccgatt catacatgcc ttatttgatc 900
gactttggat tgtcttctaa gtctccatat tcttccgtca aaaaccctgc cttccacttc 960
tgggggcaat tgacagctct tctgctcaga tccaccagag caaggaatgc ccgacagcct 1020
gatgacattg agtatacatc tcttactaca gcaggtttgt tgtacgctta tgcagtagga 1080
tcctctgccg acttggcaca acagttttgt gttggagata acaaatacac tccagatgat 1140
agtaccggag gattgacgac taatgcaccg ccacaaggca gagatgtggt cgaatggctc 1200
ggatggtttg aagatcaaaa cagaaaaccg actcctgata tgatgcagta tgcgaaaaga 1260
gcagtcatgt cactgcaagg cctaagagag aagacaattg gcaagtatgc taagtcagaa 1320
tttgacaaat gaccctataa ttctcagatc acctattata tattatgcta catatgaaaa 1380
aaactaacag atatcatgga taatctcaca aaagttcgtg agtatctcaa gtcctattct 1440
cgtctggatc aggcggtagg agagatagat gagatcgaag cacaacgagc tgaaaagtcc 1500
aattatgagt tgttccaaga ggatggagtg gaagagcata ctaagccctc ttattttcag 1560
gcagcagatg attctgacac agaatctgaa ccagaaattg aagacaatca aggtttgtat 1620
gcaccagatc cagaagctga gcaagttgaa ggctttatac aggggccttt agatgactat 1680
gcagatgagg aagtggatgt tgtatttact tcggactgga aacagcctga gcttgaatct 1740
gacgagcatg gaaagacctt acggttgaca tcgccagagg gtttaagtgg agagcagaaa 1800
tcccagtggc tttcgacgat taaagcagtc gtgcaaagtg ccaaatactg gaatctggca 1860
gagtgcacat ttgaagcatc gggagaaggg gtcattatga aggagcgcca gataactccg 1920
gatgtatata aggtcactcc agtgatgaac acacatccgt cccaatcaga agcagtatca 1980
gatgtttggt ctctctcaaa gacatccatg actttccaac ccaagaaagc aagtcttcag 2040
cctctcacca tatccttgga tgaattgttc tcatctagag gagagttcat ctctgtcgga 2100
ggtgacggac gaatgtctca taaagaggcc atcctgctcg gcctgagata caaaaagttg 2160
tacaatcagg cgagagtcaa atattctctg tagactatga aaaaaagtaa cagatatcac 2220
gatctaagtg ttatcccaat ccattcatca tgagttcctt aaagaagatt ctcggtctga 2280
aggggaaagg taagaaatct aagaaattag ggatcgcacc acccccttat gaagaggaca 2340
ctagcatgga gtatgctccg agcgctccaa ttgacaaatc ctattttgga gttgacgaga 2400
tggacaccta tgatccgaat caattaagat atgagaaatt cttctttaca gtgaaaatga 2460
cggttagatc taatcgtccg ttcagaacat actcagatgt ggcagccgct gtatcccatt 2520
gggatcacat gtacatcgga atggcaggga aacgtccctt ctacaaaatc ttggcttttt 2580
tgggttcttc taatctaaag gccactccag cggtattggc agatcaaggt caaccagagt 2640
atcacactca ctgcgaaggc agggcttatt tgccacatag gatggggaag acccctccca 2700
tgctcaatgt accagagcac ttcagaagac cattcaatat aggtctttac aagggaacga 2760
ttgagctcac aatgaccatc tacgatgatg agtcactgga agcagctcct atgatctggg 2820
atcatttcaa ttcttccaaa ttttctgatt tcagagagaa ggccttaatg tttggcctga 2880
ttgtcgagaa aaaggcatct ggagcgtggg tcctggattc tatcagccac ttcaaatgag 2940
ctagtctaac ttctagcttc tgaacaatcc ccggtttact cagtctctcc taattccagc 3000
ctctcgaaca actaatatcc tgtcttttct atccctatga aaaaaactaa cagagatcga 3060
tctgtttacg cgtcactatg aagtgccttt tgtacttagc ctttttattc attggggtga 3120
attgcaagtt caccatagtt tttccacaca accaaaaagg aaactggaaa aatgttcctt 3180
ctaattacca ttattgcccg tcaagctcag atttaaattg gcataatgac ttaataggca 3240
cagccataca agtcaaaatg cccaagagtc acaaggctat tcaagcagac ggttggatgt 3300
gtcatgcttc caaatgggtc actacttgtg atttccgctg gtatggaccg aagtatataa 3360
cacagtccat ccgatccttc actccatctg tagaacaatg caaggaaagc attgaacaaa 3420
cgaaacaagg aacttggctg aatccaggct tccctcctca aagttgtgga tatgcaactg 3480
```

```
tgacggatgc cgaagcagtg attgtccagg tgactcctca ccatgtgctg gttgatgaat    3540
acacaggaga atgggttgat tcacagttca tcaacggaaa atgcagcaat tacatatgcc    3600
ccactgtcca taactctaca acctggcatt ctgactataa ggtcaaaggg ctatgtgatt    3660
ctaacctcat ttccatggac atcaccttct tctcagagga cggagagcta tcatccctgg    3720
gaaaggaggg cacagggttc agaagtaact actttgctta tgaaactgga ggcaaggcct    3780
gcaaaatgca atactgcaag cattgggag tcagactccc atcaggtgtc tggttcgaga    3840
tggctgataa ggatctcttt gctgcagcca gattccctga atgcccagaa gggtcaagta    3900
tctctgctcc atctcagacc tcagtggatg taagtctaat tcaggacgtt gagaggatct    3960
tggattattc cctctgccaa gaaacctgga gcaaaatgca agcgggtctt ccaatctctc    4020
cagtggatct cagctatctt gctcctaaaa acccaggaac cggtcctgct ttcaccataa    4080
tcaatggtac cctaaaatac tttgagacca gatacatcag agtcgatatt gctgctccaa    4140
tcctctcaag aatggtcgga atgatcagtg gaactaccac agaaagggaa ctgtgggatg    4200
actgggcacc atatgaagac gtggaaattg acccaatgg agttctgagg accagttcag    4260
gatataagtt tcctttatac atgattggac atggtatgtt ggactccgat cttcatctta    4320
gctcaaaggc tcaggtgttc gaacatcctc acattcaaga cgctgcttcg caacttcctg    4380
atgatgagag tttatttttt ggtgatactg gctatccaa aaatccaatc gagcttgtag    4440
aaggttggtt cagtagttgg aaaagctcta ttgcctcttt tttctttatc ataggttaa    4500
tcattggact attcttggtt ctccgagttg gtatccatct ttgcattaaa ttaaagcaca    4560
ccaagaaaag acagatttat acagacatag atgatgaaccg acttggaaag taactcaaat    4620
cctgctaggt atgaaaaaaa ctaacagata tcacgctcga gcgtacgcca ccatgttcgt    4680
gtttctggtg ctgctgcctc tggtgagctc ccagtgcgtg aacctgacca caaggaccca    4740
gctgccccct gcctatacca attccttcac acggggcgtg tactatcccg acaaggtgtt    4800
ccggagcagc gtgctgcact ccacacagga tctgtttctg cctttctttt ctaacgtgac    4860
ctggttccac gccatccacg tgagcggcac caatggcaca aagcggttcg acaatccagt    4920
gctgccctt aacgatggcg tgtacttcgc ctccaccgag aagtctaaca tcatcagagg    4980
ctggatcttt ggcaccacac tggacagcaa gacacagtcc ctgctgatcg tgaacaatgc    5040
caccaacgtg gtcatcaagg tgtgcgagtt ccagttttgt aatgatccat tcctgggcgt    5100
gtactatcac aagaacaata agtcttggat ggagagcgag tttcgcgtgt attcctctgc    5160
caacaattgc acatttgagt acgtgtccca gcccttcctg atggacctgg agggcaagca    5220
gggcaatttc aagaacctga gggagttcgt gtttaagaat atcgatggct acttcaaaat    5280
ctactccaag cacaccccaa tcaacctggt gcgcgacctg ccacagggct tctctgccct    5340
ggagccactg gtggatctgc catcggcat caacatcacc cggtttcaga cactgctggc    5400
cctgcacaga agctacctga caccaggcga cagctcctct ggatgaccg caggagcagc    5460
agcctactat gtgggctatc tgcagcccag gaccttcctg ctgaagtaca acgagaatgg    5520
caccatcaca gacgccgtgg attgcgccct ggatcccctg tctgagacca gtgtacact    5580
gaagagcttt accgtggaga agggcatcta tcagacaagc aatttcaggg tgcagcctac    5640
cgagtccatc gtgcgctttc caatatcac aaacctgtgc ccttttggcg aggtgttcaa    5700
cgcaaccgc ttcgccagcg tgtacgcctg aataggaag cgcatctcca actgcgtggc    5760
cgactattct gtgctgtaca acagcgcctc ctttctctacc tttaagtgct atggcgtgag    5820
ccccacaaag ctgaatgacc tgtgcttac caacgtgtac gccgattcct tcgtgatcag    5880
gggcgacgag gtgcgccaga tcgcaccagg acagacaggc aagatcgcag actacaatta    5940
taagctgcct gacgatttca ccggctgcgt gatcgcctgg aactctaaca tctggatag    6000
caaagtgggc ggcaactaca attatctgta ccggctgttt agaaagtcta atctgaagcc    6060
attcgagagg gacatctcca cagaaatcta ccaggccggc tctaccccct gcaatgcgt    6120
ggagggcttt aactgttatt tccctctgca gagctacggc ttccagccaa caacggcgt    6180
gggctatcag ccctaccgcg tggtggtgct gtcttttgag ctgctgcacg cacctgcaac    6240
agtgtgcgga ccaaagaaga gcaccaatct ggtgaagaac aagtgcgtga acttcaactt    6300
caacggactg accggaacag gcgtgctgac cgagtccaac aagaagttcc tgccttttca    6360
gcagttcggc agggacatcg cagataccac agacgccgtg cgcgaccctc agaccctgga    6420
gatcctggac atcaccacat gctccttcgg cggcgtgtct gtgatcacac aggcaccaa    6480
tacaagcaac caggtggccg tgctgtatca ggacgtgaat tgtaccgagg tgccagtggc    6540
aatccacgca gatcagctga cccctacatg gcgggtgtac tctaccggca gcaacgtgtt    6600
ccagacaaga gccggatgcc tgatcggagc agagcacgtg aacaatagct atgagtgcga    6660
catccctatc ggcgccggca tctgtgcctc ctaccagacc cagacaaact ccccaaggtc    6720
tgtgggagat gaggccgaag actttgtgga agtccacctg cctgatgtgc ataaccaggt    6780
gtctggcgtc gacctgggac tgccaaattg gggcaagtac gtgctgctga gtgctggagc    6840
actgactgcc ctgatgctga tcattttcct gatgacctgc tgtcggcgcg tgaacagaag    6900
tgagcccact cagcacaatc tgcgaggaac cgggagagaa gtgtcagtca cctcagag    6960
cgggaaaatc attagtagtt gggaatcaca taaaagcggg ggcagaccag ggctgtgagc    7020
tagccagatt cttcatgttt ggaccaaatc aacttgtgat accatgctca aagaggcctc    7080
aattatattt gagttttaa ttttatgaa aaaaactaac agcaatcatg gaagtccacg    7140
attttgagac cgacgagttc aatgatttca tgaagatgac ctatgccaca agagaattcc    7200
tgaatcccga tgagcgcatg acgtacttga atcatgctga ttacaatttg aattctcctc    7260
taattagtga tgatattgac aatttgatca ggaaattcaa ttctcttccg attccctcga    7320
tgtgggatag taagaactgg gatggagttc ttgagatgtt aacatcatgt caagccaatc    7380
ccatctcaac atctcagatg cataaatgga tgggaagttg gttaatgtct gataatcatg    7440
atgccagtca agggtatagt ttttacatg aagtggacaa agaggcagaa ataacatttg    7500
acgtggtgga gaccttcatc cgcggctggg gcaacaaacc aattgaatac atcaaaaagg    7560
aaagatggac tgactcattc aaaattctcg ttcattgtg tcaaaagttt ttggacttac    7620
acaagttgac attaatctta aatgctgtct ctgaggtgga attgctcaac ttggcgagga    7680
ctttcaaagg caaagtcaga agaagttctc atggaacgaa catatgcagg attagggttc    7740
ccagcttggg tcctacttt atttcagaag gatgggctta cttcaagaaa cttgatattc    7800
taatggaccg aaactttctg ttaatggtca aagatgtgat tataggagg atgcaaacgg    7860
tgctatccat ggtatgtaga ataacaacc tgttctcaga caagacatc ttctccttc    7920
taaatatcta cagaattgga gataaaattg tggagaggca gggaaatttt tcttatgact    7980
tgattaaaat ggtggaaccg atatgcaact tgaagctgat gaaattagca agagaatcaa    8040
ggcctttagt cccacaattc cctcattttg aaaatcatat caagcttct gttgatgaag    8100
gggcaaaaat tgaccgaggt ataagattcc tccatgatca gataatgagt gtgaaaacag    8160
tggatctcac actggtgatt tatggatcgt tcagacattg gggtcatcct tttatagatt    8220
```

```
attacactgg actagaaaaa ttacattccc aagtaaccat gaagaaagat attgatgtgt   8280
catatgcaaa agcacttgca agtgatttag ctcggattgt tctatttcaa cagttcaatg   8340
atcataaaaa gtggttcgtg aatggagact tgctccctca tgatcatccc tttaaaagtc   8400
atgttaaaga aaatacatgg cccacagctg ctcaagttca agattttgga gataaatggc   8460
atgaacttcc gctgattaaa tgttttgaaa tacccgactt actagaccca tcgataatat   8520
actctgacaa aagtcattca atgaataggc cagaggtgtt gaaacatgtc cgaatgaatc   8580
cgaacactcc tatccctagt aaaaaggtgt tgcagactat gttggacaca aaggctacca   8640
attggaaaga atttcttaaa gagattgatg agaagggctt agatgatgat gatctaatta   8700
ttggtcttaa aggaaaggag agggaactga agttggcagg tagattttc tccctaatgt    8760
cttggaaatt gcgagaatac tttgtaatta ccgaatattt gataaagact catttcgtcc   8820
ctatgtttaa aggcctgaca atggcggacg atctaactgc agtcattaaa aagatgttag   8880
attcctcatc cggccaagga ttgaagtcat atgaggcaat tgcatagcc aatcacattg     8940
attacgaaaa atggaataac caccaaagga agttatcaaa cggcccagtg ttccgagtta   9000
tgggccagtt cttaggttat ccatccttaa tcgagagaac tcatgaattt tttgagaaaa   9060
gtcttatata ctacaatgga agaccagact tgatgcgtgt tcacaacaac acactgatca   9120
attcaacctc ccaacgagtt tgttggcaag gacaagaggg tggactgaa ggtctacggc     9180
aaaaaggatg gactatcctc aatctactgg ttattcaaag agaggctaaa atcagaaaca   9240
ctgctgtcaa agtcttggca caaggtgata atcaagttat ttgcacacag tataaaacga   9300
agaaatcgag aaacgttgta gaattacagg gtgctctcaa tcaaatggtt tctaataatg   9360
agaaaattat gactgcaatc aaaataggga cagggaagtt aggactttg ataaatgacg     9420
atgagactat gcaatctgca gattacttga attatgaaa aataccgatt ttccgtggag     9480
tgattagagg gttagagacc aagagatggt cacgagtgac ttgtgtcacc aatgaccaaa   9540
tacccacttg tgctaatata atgagctcag tttccacaaa tgctctcacc gtagctcatt   9600
ttgctgagaa cccaatcaat gccatgatac agtacaatta ttttgggaca tttgctagac   9660
tcttgttgat gatgcatgat cctgctcttc gtcaatcatt gtatgaagtt caagataaga   9720
taccgggctt gcacagttct actttgcaaat acgccatgtt gtatttggac ccttccattg   9780
gaggagtgtc gggcatgtct ttgtccaggt ttttgattag agccttccca gatcccgtaa    9840
cagaaagtct ctcattctgg agattcatcc atgtacatgc tcgaagtgag catctgaagg    9900
agatgagtgc agtatttgga aaccccgaga tagccaagtt tcgaataact cacatagaca    9960
agctagtaga agatccaacc tctctgaaca tcgctatgga aatgagtcca gcgaacttgt   10020
taaagactga ggttaaaaaa tgcttaatcg aatcaagaca aaccatcagg aaccaggtga   10080
ttaaggatgc aaccatatat ttgtatcatg aagaggatcg gctcagaagt ttcttatggt   10140
caataaaatcc tctgttccct agattttaa gtgaattcaa atcaggcact ttttttggag    10200
tcgcagacgg gctcatcagt ctatttcaaa attctcgtac tattcggaac tccttttaaga  10260
aaaagtatca tagggaattg gatgatttga ttgtgaggag tgaggtatcc tctttgacac   10320
atttagggaa acttcatttg agaagggat catgtaaaat gtggacatgt tcagctactc    10380
atgctgacac attaagatac aaatcctggg gccgtacagt tattgggaca actgtaccc     10440
atccattaga aatgttgggt ccacaacatc gaaaagagac tccttgtgca ccatgtaaca   10500
catcagggtt caattatgtt tctgtgcatt gtccagacgg gatccatgac gtcttttagtt  10560
cacgggacc attgcctgct tatctagggt ctaaaacatc tgaatctaca tctattttgc    10620
agccttggga aagggaaagc aaagtcccac tgattaaaag agctacacgt cttagagatg   10680
ctatctcttg gtttgttgaa cccgactcta aactagcaat gactatactt tctaacatcc   10740
actcttaac aggcgaagaa tggaccaaaa ggcagcatgg gttcaaaaga acagggtctg     10800
cccttcatag gttttcgaca tctcggatga gccatggtgg gttcgcatct cagagcactg   10860
cagcattgac caggttgatg gcaactacag acaccatgag ggatctggga gatcagaatt   10920
tcgacttttt attccaagca acgttgctct atgctcaaat taccaccact gttgcaagag   10980
acggatggat caccagttgt acagatcatt atcatattgc ctgtaagtcc tgtttggagac  11040
ccatagaaga gatcacccctg gactcaagta tggactacag gccccagat gtatcccatg    11100
tgctgaaggac atggaggaat ggggaaggtt cgtggggaca agagataaaa cagatctatc   11160
ctttagaagg gaattggaag aatttagcac ctgctgagca atcctatcaa gtcggcagat   11220
gtataggttt tctatatgga gacttggcgt atagaaaatc tactcatgcc gaggacagtt   11280
ctctatttcc tctatctata caaggtcgta ttagaggtcg aggtttctta aaagggttgc   11340
tagacggatt aatgagagca agttgctgcc aagtaataca ccggagaagt ctggctcatt   11400
tgaagaggcc ggccaacgca gtgtacgag gtttgattta cttgattgat aaattgagtg     11460
tatccctcc attcctttct cttactagat caggacctat tagagacgaa ttagaaacga    11520
ttccccacaa gatcccaacc tcctatccga caagcaaccg tgatatgggg gtgattgtca   11580
gaaattactt caaataccaa tgccgtcaa ttgaaaaggg aaaatacaga tcacattatt    11640
cacaattatg gttattctca gatgtcttat ccatagactt cattggacca ttctctatt    11700
ccaccaccct cttgcaaatc ctatacaagc cattttatc tgggaaagat aagaatgagt   11760
tgagagagct ggcaaatctt tcttcattgc taagatcagg agagggtgg gaagacatac     11820
atgtgaaatt cttcaccaag gacatatat tgtgtccaga ggaaatcaga catgcttgca    11880
agttcggat tgctaaggat aataataaag acatgagcta tcccccttgg ggaagggaat   11940
ccagagggac aattacaaca atccctgttt attatacgac caccccttac ccaaagatgc    12000
tagagatgcc tccaagaatc caaaatcccc tgctgtccga aatcaggttg ggccaattac   12060
caactggcgc tcattataaa attcggagta tattacatgg aatgggaatc cattacaggg   12120
acttcttgag ttgtggagac ggctccggag ggatgactgc tgcattacta cgagaaaatg   12180
tgcatagcag aggaatattc aatagtcgt tagaattatc agggtcagtc atgcgaggcg    12240
cctctcctga gccccccagt gccctagaaa ctttaggagg agataaatcg agatgtgtaa   12300
atggtgaaac atgttgggaa tatcctctg acttatgtga cccaaggact tgggactatt   12360
tcctccgact caaagcaggc ttggggcttc aaattgattt aattgtaatg gatatgaag    12420
ttcgggattc ttctactagc ctgaaaattg agacgaatgt tagaaattat gtgcaccgga   12480
ttttggatga gcaaggagtt ttaatctaca gacttatgg aacatatatt tgtgagagcg   12540
aaaagaatgc agtaacaatc cttggtccca tgttcaagac ggtcgactta gttcaaacag   12600
aatttagtag ttctcaaacg tctgaagtat atatgtatg taaaggtttg aagaaattaa   12660
tcgatgaacc caatcccgat tggtcttcca tcaatgaatc ctggaaaaac ctgtacgcat   12720
tccagtcatc agaacaggaa tttgccagag caaagaaggt tagtacatac tttacccttga  12780
caggtatttcc ctcccaattc attcctgatc tttttgtaaa cattgagact atgctacaaa  12840
tattcggagt acccacgggt gtgtctcatg cggctgcctt aaaatcatct gatagacctg   12900
cagatttatt gaccattagc cttttttata tggcgattat atcgtattat aacatcaatc   12960
```

-continued

```
atatcagagt aggaccgata cctccgaacc ccccatcaga tggaattgca caaaatgtgg   13020
ggatcgctat aactggtata agcttttggc tgagtttgat ggagaaagac attccactat   13080
atcaacagtg tttagcagtt atccagcaat cattcccgat taggtgggag gctgtttcag   13140
taaaaggagg atacaagcag aagtggagta ctagaggtga tgggctccca aaagataccc   13200
gaacttcaga ctccttggcc ccaatcggga actggatcga atctctgaga ttggtccgaa   13260
accaagttcg tctaaatcca ttcaatgaga tcttgttcaa tcagctatgt cgtacagtgg   13320
ataatcattt gaaatggtca aatttgcgaa gaaacacagg aatgattgaa tggatcaata   13380
gacgaatttc aaaagaagac cggtctatac tgatgttgaa gagtgaccta cacgaggaaa   13440
actcttggag agattaaaaa atcatgagga gactccaaac tttaagtatg aaaaaaactt   13500
tgatccttaa gaccctcttg tggttttat tttttatctg gttttgtggt cttcgt        13556

SEQ ID NO: 21          moltype = DNA   length = 13607
FEATURE                Location/Qualifiers
misc_feature           1..13607
                       note = VSV vector: Convac V2 South Africa
source                 1..13607
                       mol_type = other DNA
                       organism = synthetic construct
SEQUENCE: 21
acgaagacaa acaaaccatt attatcatta aaaggctcag gagaaacttt aacagtaatc     60
aaaatgtctg ttacagtcaa gagaatcatt gacaacacag tcatagttcc aaaacttcct   120
gcaaatgagg atccagtgga atacccggca gattacttca gaaaatcaaa ggagattcat   180
ctttacatca atactacaaa aagtttgtca gatctaagag gatatgtcta ccaaggcctc   240
aaatccggaa atgtatcaat catacatgtc aacagctact tgtatggagc attaaaggac   300
atccgggta agttggataa agattggtca agtttcggaa taaacatcgg gaaagcaggg   360
gatacaatcg gaatatttga ccttgtatcc ttgaaagccc ttgacggact acttccagat   420
ggagtatcgg atgcttccag aaccagcgca gatgacaaat ggttgccttt gtatctactt   480
ggcttataca gagtgggcag aacacaaatg cctgaataca gaaaaaagct catggatggg   540
ctgacaaatc aatgcaaaat gatcaatgaa cagtttgaac ctcttgtgcc agaaggtcgt   600
gacattttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca acatttggac acctctgcaa ataaccgga   780
atgtctacag aagatgtaac gacctggatc ttgaaccgag aagttgcaga tgaaatggtc   840
caaatgatgc ttccaggcca agaaattgac aaggccgatt catacatgcc ttatttgatc   900
gactttggat tgtcttctaa gtctccatat tcttccgtca aaaaccctgc cttccacttc   960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggcctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aagttcgtg agtatctcaa gtcctattct  1440
cgtctggatc aggcggtagg agagatagat gagatcgaag cacaacgagc tgaaaagtcc  1500
aattatgagt tgttccaaga ggatggagtg aagagcata ctaagccctc ttatttttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga acagcctga gcttgaatct  1740
gacgagcatg gaaagacctt acggttgaca tcgccagagg gttaagtgg agagcagaaa  1800
tcccagtggc tttcgacgat taaagcagtc gtgcaaagtg ccaaatactg gaatctggca  1860
gagtgcacat ttgaagcatc ggggagaggg gtcattatga aggagcgcca gataactccg  1920
gatgtatata aggtcactcc agtgatgaac acacatccgt cccaatcaga agcagtatca  1980
gatgtttggt ctctctcaaa gacatccatg acttttcaac ccaagaaagc aagtcttcag  2040
cctctcacca tatccttgga tgaattgttc tcatctagag gagagttcat ctctgtcgga  2100
ggtgacggac gaatgtctca taagagggcc atcctgctcg gcctgagata caaaaagttg  2160
tacaatcagg cgagagtcaa atattctctg tagactatga aaaaagtaa cagatatcac  2220
gatctaagtg ttatcccaat ccattcatca tgagttcctt aaagaagatt ctcggtctga  2280
aggggaaagg taagaaatct aagaaattag ggatcgcacc accccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga acgtcccctt ctacaaaatc ttggcttttt  2580
tgggttcttc taatctaaag gccactccag cggtattggc agatcaaggt caaccagagt  2640
atcacactca ctgcgaaggc agggcttatt tgccacataa gatggggaag accccctcca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggcttaatg tttggcctga  2880
ttgtcgagaa aaaggcatct ggagcgtggg tcctggattc tagcaccac ttcaaatgag  2940
ctagtctaac ttctagcttc tgaacaatcc ccggttact cagtctctcc taattccagc  3000
ctctcgaaca actaatatcc tgtcttttct atccctatga aaaaaactaa cagagatcga  3060
tctgtttacg cgtcactatg aagtgccttt tgtacttagc cttttattc attggggtga  3120
attgcaagtt caccatagtt tttccacaca accaaaaagg aaactggaaa atgttcctt   3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc actccatctg tagaacaatg caaggaaagc attgaacaaa  3420
cgaaacaagg aacttggctg aatccaggct ccctcctca agttgtggga tatgcaactg  3480
tgacggatgc cgaagcagtg attgtccagg tgactcctca ccatgtgctg gttgatgaat  3540
acacaggaga atgggttgat tcacagttca ttcaacgaaa atgcagcaat tacatatgcc  3600
```

```
ccactgtcca taactctaca acctggcatt ctgactataa ggtcaaaggg ctatgtgatt 3660
ctaacctcat ttccatggac atcaccttct tctcagagga cggagagcta tcatccctgg 3720
gaaaggaggg cacagggttc agaagtaact actttgctta tgaaactgga ggcaaggcct 3780
gcaaaatgca atactgcaag cattgggag tcagactccc atcaggtgtc tggttcgaga 3840
tggctgataa ggatctcttt gctgcagcca gattccctga atgcccagaa gggtcaagta 3900
tctctgctcc atctcagacc tcagtggatg taagtctaat tcaggacgtt gagaggatct 3960
tggattattc cctctgccaa gaaacctgga gcaaaatcag agcgggtctt ccaatctctc 4020
cagtggatct cagctatctt gctcctaaaa acccaggaac cggtcctgct ttcaccataa 4080
tcaatggtac cctaaaatac tttgagacca gatacatcag agtcgatatt gctgctccaa 4140
tcctctcaag aatggtcgga atgatcagtg gaactaccac agaaagggaa ctgtgggatg 4200
actgggcacc atatgaagac gtggaaattg gacccaatgg agttctgagg accagttcag 4260
gatataagtt tcctttatac atgattggac atggtatgtt ggactccgat cttcatctta 4320
gctcaaaggc tcaggtgttc gaacatcctc acattcaaga cgctgcttcg caacttcctg 4380
atgatgagag tttatttttt ggtgatactg ggctatccaa aaatccaatc gagcttgtag 4440
aaggttggtt cagtagttgg aaaagctcta ttgcctcttt tttctttatc ataggggttaa 4500
tcattggact attcttggtt ctccgagttg gtatccatct ttgcattaaa ttaaaagcaca 4560
ccaagaaaag acagatttat acagacatag agatgaaccg acttggaaag taactcaaat 4620
cctgctaggt atgaaaaaaa ctaacagata tcacgctcga gcgtacgcca ccatgttcgt 4680
gtttctggtg ctgctgcctc tggtgagctc ccagtgcgtg aacttcacca caaggaccca 4740
gctgccccct gcctatacca attccttcac acggggcgtg tactatcccg acaaggtgtt 4800
ccggagcagc gtgctgcact ccacacagga tctgtttctg cctttctttt ctaacgtgac 4860
ctggttccac gccatccacg tgagcggcac caatggcaca aagcggttcg ccaatccagt 4920
gctgcccttt aacgatggcg tgtacttcgc ctccaccgag aagtctaaca tcatcagagg 4980
ctggatcttt ggcaccacac tggacagcaa gacacagtcc ctgctgatcg tgaacaatgc 5040
caccaacgtg tcatcaagg tgtgcgagtt ccagttttgt aatgatccat tcctgggcgt 5100
gtactatcac aagaacaata agtcttggat ggagagcgaa ttcgcgtgt attcctctgc 5160
caacaattgc acatttgagt acgtgtccca gcccttcctg atggacctgg agggcaagca 5220
gggcaatttc aagaacctga gggagttcgt gtttaagaat atcgatggct acttcaaaat 5280
ctactccaag cacacccca tcaacctggt gcgcggcctg ccacagggct tctctgccct 5340
ggagccactg gtgatccgc catcggcat caacatcacc cggtttcaga cactgctggc 5400
cctgcacaga agctacctga caccaggcga cagctcctct ggatggaccg caggagcagc 5460
agcctactat gtgggctatc tgcagcccag gaccttcctg ctgaagtaca cgagaatgg 5520
caccatcaca gacgccgtgg attgcgccct ggatccctg tctgagacca agtgtacact 5580
gaagagcttt accgtggaga agggcatcta tcagacaagc aatttcaggg tgcagcctac 5640
cgagtccatc gtgcgctttc ccaatatcac aaacctgtgc ccttttggcg aggtgttcaa 5700
cgcaaccgc ttcgccagcg tgtacgcctg gaataggaag cgcatctcca actgcgtggc 5760
cgactattct gtgctgtaca acagcgcctc cttctctacc tttaagtgct atggcgtgag 5820
ccccacaaag ctgaatgacc tgtgctttac caacgtgtac gccgattcct tcgtgatcag 5880
gggcgacgag gtgcgccaga tcgcaccagg acagacaggc aatatccgcag actacaatta 5940
taagctgcct gacgatttca ccggctgcgt gatcgcctgg aactctaaca atctggatag 6000
caaagtgggc ggcaactaca attatctgta ccggctgtt agaaagtcta atctgaagcc 6060
attcgagagg gacatctcca cagaaatcta ccaggccggc tctacccct gcaatggcgt 6120
gaagggcttt aactgttatt tccctctgca gagctacggc ttccagccaa catatggcgt 6180
gggctatcag ccctaccgcg tggtggtgct gtcttttgag ctgctgcacg cacctgcaac 6240
agtgtgcgga ccaaagaaga gcaccaatct ggtgaagaac aagtgcgtga acttcaactt 6300
caacggactg accggaacag gcgtgctgac cgagtccaac aagaagttcc tgcctttca 6360
gcagttcggc agggacatcg cagataccac agacgccgtg cgcgaccctc agaccctgga 6420
gatcctggac atcacaccat gctccttcgg cggcgtgtct gtgatcacac caggcaccaa 6480
tacaagcaac caggtggccg tgctgtatca gggcgtgaat tgtaccgagg tgccagtggc 6540
aatccacgca gatcagctga cccctacatg gcgggtgtac tctaccggca gcaacgtgtt 6600
ccagacaaga gccggatgcc tgatcggagc agagcacgtg aacaatagct atgagtgcga 6660
catccctatc ggcgccggca tctgtgcctc ctaccagacc cagacaaact ccccagaatc 6720
aagcgtgatt cctctggtcc atccactggc agatcccc acagtgttca agacggaga 6780
tgaggccgaa gactttgtgg aagtccacct gcctgatgtg cataaccagg tgtctggcgt 6840
cgacctggga ctgccaaatt ggggcaagta cgtgctgctg agtgctggga cactgactgc 6900
cctgatgctg atcattttcc tgatgacctg ctgtcggcgc gtgaacagaa gtgagcccac 6960
tcagcacaat ctgcgaggaa ccgggagaga agtgtcagtc acacctcaga gcgggaaaat 7020
cattagtagt tgggaatcac ataaaagcgg gcgcagacc aggctgtgag ctagccagat 7080
tcttcatgtt tggaccaaat caacttgtga taccatgctc aaagaggcct caattatatt 7140
tgagtttta attttatga aaaaactaa cagcaatcat ggaagtccac gattttgaga 7200
ccgacgagtt caatgatttc aatgaagatg actatgccac aagagaattc ctgaatcccg 7260
atgagcgcat gacgtacttg aatcatgctg attacaattt gaattctcct ctaattagtg 7320
atgatattga caattttgatc aggaaattca attctcttcc gattccctcg atgtgggata 7380
gtaagaactg ggatgagttt cttgaagtgt taacatcatc tcaagccaat cccatctcaa 7440
catctcagat gcataaatgg atgggaagtt ggttaatgtc tgataatcat gatgccagtc 7500
aagggtatag tttttacat gaagtggaca agaggcaga aataacattt gacgtggtgg 7560
agaccttcat ccgcggctgg ggcaacaaac aattgaata tcaaaaag gaaagatgga 7620
ctgactcatt caaaattctc gcttatttgt gtcaaaagtt tttggactta cacaagttga 7680
cattaatctt aaatgctgtc tctgaggtgg aattgctcaa cttggcgagg actttcaaag 7740
gcaaagtcag aagaagttct catgaacga acatatgcag gattgggtt cccagcttgg 7800
gtcctacttt tatttcagaa ggatgggctt acttcaagaa acttgatatt ctaatggacc 7860
gaaactttct gttaatggtc aaagatgtga ttataggag gatgcaaacg gtgctatcca 7920
tggtatgtag aatagacaac ctgttctcag agcaagacat cttctccctt ctaaatatct 7980
acagaattgg agataaaatt gtgggagagt agggaaattt ttcttatgac ttgattaaaa 8040
tggtggaacc gatatgcaac ttgaagctga tgaaattagc aagagaatca aggccttag 8100
tcccacaatt ccctcatttt gaaaatcata tcaagacttc tgttgatgaa ggggcaaaaa 8160
ttgaccgagg tataagattc ctccatgatc agataatgag tgtgaaaaca gtggatctca 8220
cactggtgat ttatggatcg ttcagacatt ggggtcatca ttttatagat tattcactg 8280
gactagaaaa attacattcc caagtaacca tgaagaaaga tattgatgtg tcatatgcaa 8340
```

```
aagcacttgc aagtgattta gctcggattg ttctatttca acagttcaat gatcataaaa   8400
agtggttcgt gaatgagaac ttgctccctc atgatcatcc ctttaaaagt catgttaaag   8460
aaaatacatg gcccacagct gctcaagttc aagattttgg agataaatgg catgaacttc   8520
cgctgattaa atgttttgaa atacccgact tactagaccc atcgataata tactctgaca   8580
aaagtcattc aatgaatagg tcagaggtgt tgaaacatgt ccgaatgaat ccgaacactc   8640
ctatccctag taaaaaggtg ttgcagacta tgttggacac aaaggctacc aattggaaag   8700
aatttcttaa agagattgat gagaagggct tagatgatga tgatctaatt attggtctta   8760
aaggaaagga gagggaactg aagttggcag gtagattttt ctccctaatg tcttggaaat   8820
tgcgagaata ctttgtaatt accgaatatt tgataaagac tcatttcgtc cctatgttta   8880
aaggcctgac aatggcggac gatctaactg cagtcattaa aaagatgtta gattcctcat   8940
ccggccaagg attgaagtca tatgaggcaa tttgcatagc caatcacatt gattacgaaa   9000
aatgaataa ccaccaaagg aagttatcaa acggcccagt gttccgagtt atgggccagt   9060
tcttaggtta tccatcctta atcgagagaa ctcatgaatt ttttgagaaa agtcttatat   9120
actacaatgg aagaccagac ttgatgcgtg ttcacaacaa cacactgatc aattcaacct   9180
cccaacgagt ttgttggcaa ggacaagagg gtggactgga aggtctacgg caaaaaggat   9240
ggactatcct caatctactg gttattcaaa gagaggctaa aatcagaaac actgctgtca   9300
aagtcttggc acaaggtgat aatcaagtta tttgcacaca gtataaaacg aagaaatcga   9360
gaaacgttgt agaattacag ggtgctctca atcaaatggt ttctaataat gagaaaatta   9420
tgactgcaat caaaataggg acagggaagt taggacttt gataaatgac gatgagacta   9480
tgcaatctgc agattacttg aattatggaa aaataccgat tttccgtgga gtgattagag   9540
ggttagagac caagagatgg tcacgagtga cttgtgtcac caatgaccaa atacccactt   9600
gtgctaatat aatgagctca gttccacaa atgctctcac cgtagctcat tttgctgaga   9660
acccaatcaa tgccatgata cagtacaatt attttgggac atttgctaga ctcttgttga   9720
tgatgcatga tcctgctctt cgtcaatcat tgtatgaagt tcaagataag ataccgggct   9780
tgcacagttc tactttcaaa tacgccatgt tgtatttgga cccttccatt ggaggagtgt   9840
cgggcatgtc tttgtccagg tttttgatta gagccttccc agatcccgta acagaaagtc   9900
tctcattctg gagattcatc catgtacatg ctcgaagtga gcatcgaag gagatgagtg   9960
cagtatttgg aaaccccgag atagccaagt ttcgaataac tcacatagac aagctagtag  10020
aagatccaac ctctctgaac atcgctatgg gaatgagtcc agcgaacttg ttaaagactg  10080
aggttaaaaa atgcttaatc gaatcaagac aaaccatcag gaaccaggtg attaaggatg  10140
caaccatata tttgtatcat gaagaggatc ggctcagaag tttcttatgg tcaataaatc  10200
ctctgttccc tagattttta agtgaattca aatcaggcac ttttttggga gtcgcagacg  10260
ggctcatcag tctatttcaa aattctcgta ctattcggaa ctcctttaag aaaaagtatc  10320
atagggaatt ggatgatttg attgtgagga gtgaggtatc ctctttgaca catttaggga  10380
aacttcattt gagaagggga tcatgtaaaa tgtgaacatg ttcagctact catgctgaca  10440
cattaagata caaatcctgg ggccgtacag ttattgggac aactgtaccc catccattag  10500
aaatgttggg tccacaacat cgaaaagaga ctccttgtgc accatgtaac acatcagggt  10560
tcaattatgt ttctgtgcat tgtccagacg ggatccatga cgtctttagt tcacggggac  10620
cattgcctgc ttatctaggg tctaaaacat ctgaatctac atctattttg cagccttggg  10680
aaagggaaa caaagtccca ctgattaaaa gagctacacg tcttagagat gctatctctt  10740
ggtttgttga acccgactct aaactagcaa tgactatact ttctaacatc cactctttaa  10800
caggcgaaga atggaccaaa aggcagcatg ggttcaaaag aacagggtct gcccttcata  10860
ggttttcgac atctcggatg agccatggtg ggttcgcatc tcagagcact gcagcattga  10920
ccaggttgat ggcaactaca gacaccatga gggatctggg agatcagaat ttcgactttt  10980
tattccaagc aacgttgctc tatgctcaaa ttaccaccac tgttcaagaa gacgatgga  11040
tcaccagttg tacagatcat tatcatattg cctgtaagtc ctgtttgaga cccatagaag  11100
agatcaccct ggactcaagt atggactaca cgccccccaga tgtatcccat gtgctgaaga  11160
catgaggaa tggggaaggt tcgtgggac aagagataaa acagatctat cctttagaag  11220
ggaattggaa gaatttagca cctgctgagc aatcctatca agtcggcaga tgtataggtt  11280
ttctatatgg agacttggcg tatagaaaat ctactcatgc cgaggacagt tctctatttc  11340
ctctatctat acaaggtcgt attagaggtc gaggttttct aaaaggggttg ctagacgagt  11400
taatgagagc aagttgctgc caagtaatac accggagaag tctggctcat ttgaaggagc  11460
cggcaacgc agtgtacgga ggtttgattt acttgattga taaattgagt gtatcacctc  11520
cattcctttc tcttactaga tcaggaccta ttagagacga attagaaacg attcccacaa  11580
agatcccac ctcctatccg acaagcaacc gtgatatggg ggtgattgtc agaaattact  11640
tcaaatacca atgccgtcta attgaaaagg gaaaatacga atcacattat tcacaattat  11700
ggttattctc agatgtctta tccatagact tcattggacc attctctatt tccaccaccc  11760
tcttgcaaat cctatacaag ccatttttat ctgggaaaga taagaatgag ttgagagagc  11820
tggcaaatct ttcttcattg ctaagatcag gagaggggtg ggaagacata catgtgaaat  11880
tcttcaccaa ggacatatta ttgtgtccag aggaaatcag acatgcttgc aagttcggga  11940
ttgctaagga taataataaa gacatgagct atccccttg gggaagggaa tccagaggga  12000
caattacaac aatccctgtt tattatacga ccaccccctta cccaaagatg ctagagatgc  12060
ctccaagaat ccaaaatccc ctgctgtccg gaatcaggtt gggccaatta ccaactggcg  12120
ctcattataa aattcggagt tcattacatg gaatggaaat ccattcacagg gacttcttga  12180
gttgtggaga cggctccgga gggatgactg ctgcattact acgagaaaat gtgcatagca  12240
gaggaatatt caatagtctg ttagaattat cagggtcagt catgcgaggc gcctctcctg  12300
agccccccag tgccctagaa actttaggag gagataaatc gagatgtgta aatggtgaaa  12360
catgttggga atatccatct gacttatgtg acccaaggac ttgggactta ttcctccgac  12420
tcaaagcag cttggggctt caaattgatt taattgtaat ggatatggaa gttcgggatt  12480
cttctactag cctgaaaatt gagacgaatg ttagaaatta tgtgcaccgg attttggatg  12540
agcaaggagt tttaatctac aagacttatg gaacatatat ttgtgagagc gaaaagaatg  12600
cagtaacaat ccttggtccc atgttcaaga cggtcgactt agttcaaaca gaatttgta  12660
gttctcaaac gtctcgaagta tatatggtat gtaaaggttt gaagaaatta atcgatgaac  12720
ccgatcccga ttggtcttcc atcaatgaat cctggaaaaa cctgtacgca ttccagtcat  12780
cagaacagga atttgccaga gcaaagaagg ttagtacata ctttacccttg acaggtattc  12840
cctcccaatt cattcctgat ccttttgtaa acattgagac tatgctacaa atattcggag  12900
tacccacggg tgtgtctcat gcggctgcct taaaatcatc tgatagacct gcagatttat  12960
tgaccattag ccttttttat atggcgatta tatcgtatta taacatcaat catatcagag  13020
taggaccgat acctccgaac ccccatcag atggaattgc acaaaatgtg gggatcgcta  13080
```

```
taactggtat aagcttttgg ctgagtttga tggagaaaga cattccacta tatcaacagt  13140
gtttagcagt tatccagcaa tcattcccga ttaggtggga ggctgtttca gtaaaaggag  13200
gatacaagca gaagtggagt actagaggtg atgggctccc aaaagatacc cgaacttcag  13260
actccttggc cccaatcggg aactggatca gatctctgga attggtccga aaccaagttc  13320
gtctaaatcc attcaatgag atcttgttca atcagctatg tcgtacagtg gataatcatt  13380
tgaaatggtc aaatttgcga agaaacacag gaatgattga atggatcaat agacgaattt  13440
caaaagaaga ccggtctata ctgatgttga agagtgacct acacgaggaa aactcttgga  13500
gagattaaaa aatcatgagg agactccaaa ctttaagtat gaaaaaaact ttgatcctta  13560
agaccctctt gtggttttta ttttttatct ggttttgtgg tcttcgt               13607

SEQ ID NO: 22          moltype = DNA  length = 13506
FEATURE                Location/Qualifiers
misc_feature           1..13506
                       note = VSV vector: Convac V3 China
source                 1..13506
                       mol_type = other DNA
                       organism = synthetic construct
SEQUENCE: 22
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc accccctat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtcactatg aagtgccttt tgtacttagc ctttttattc attggggtga  3120
attgcaagtt caccatagtt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc actccatctg tagaacaatg caaggaaagc attgaacaaa  3420
cgaaacaagg aacttggctg aatccaggct tccctcctca aagttgtgga tatgcaactg  3480
tgacggatgc cgaagcagtg attgtccagg tgactcctca ccatgtgctg gttgatgaat  3540
acacaggaga atgggttgat tcacagttca tcaacggaaa atgcagcaat tacatatgcc  3600
ccactgtcca taactctaca acctggcatt ctgactataa ggtcaaaggg ctatgtgatt  3660
```

```
ctaacctcat ttccatggac atcacctcct tctcagagga cggagagcta tcatccctgg   3720
gaaaggaggg cacagggttc agaagtaact actttgctta tgaaactgga ggcaaggcct   3780
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctccagac tcagtggatg taagtctaat tcaggacgtt gagaggatct   3960
tggattattc cctctgccaa gaaacctgga gcaaaatcag agcgggtctt ccaatctctc   4020
cagtggatct cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaagggaa ctgtgggatg   4200
actgggcacc atatgaagac gtggaaattg gacccaatgg agttctgagg accagttcag   4260
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttattttt ggtgatactg gctatccaa aaatccaatc gagcttgtag   4440
aaggttggtt cagtagttgg aaaagctcta ttgcctcttt tttctttatc ataggggtaa   4500
tcattggact attcttggtt ctccgagttg gtatccatct ttgcattaaa ttaaagcaca   4560
ccaagaaaag acagatttat acagacatag agatgaaccg acttggaaag taactcaaat   4620
cctgctaggt atgaaaaaaa ctaacagata tcacgctcga ggccaccatg ttcgtgtttc   4680
tggtgctgct gcctctgagt agctcccagt gcgtgaacct gaccacaagg acccagctgc   4740
cccctgccta taccaattcc ttcacacggg gcgtgtacta tcccgacaag gtgttccgga   4800
gcagcgtgct gcactccaca caggatcgtt ttctgccttt cttttctaac gtgacctggt   4860
tccacgccat ccacgtgagc ggcaccaatg gcacaaagcg gttcgacaat ccagtgctgc   4920
cctttaacga tggcgtgtac ttcgcctcca ccgagaagtc taacatcatc agaggctgga   4980
tctttggcac cacactggac agcaagacac agtccctgct gatcgtgaac aatgccacca   5040
acgtggtcat caaggtgtgc gagttccagt tttgtaatga tccattcctg ggcgtgtact   5100
atcacaagaa caataagtct tggatggaga gcgagtttcg cgtgtattcc tctgccaaca   5160
attgcacatt tgagtacgtg tcccagccct tcctgatgga cctggagggc aagcagggca   5220
atttcaagaa cctgagggag ttcgtgttta agaatatcga tggctacttc aaaatctact   5280
ccaagcacac cccaatcaac ctggtgcgcg acctgccaca gggcttctct gccctggagc   5340
cactggtgga tctgcccatc ggcatcaaca tcacccggtt tcagacactg ctggcctgc   5400
acagaagcta cctgacacca ggcgacagct cctctggatg gacagcagga gcagcagcct   5460
actatgtggg ctatctgcag cccaggacct tcctgctgaa gtacaacgag aatggccacca   5520
tcacagacgc cgtggattgc gccctggatc ccctgtctga gaccaagtgt acactgaaga   5580
gctttaccgt ggagaagggc atctatcaga caagcaattt cagggtgcag cctaccgagt   5640
ccatcgtgcg cttttcccaat atcacaaacc tgtgcccttt tggcgaggtg ttcaacgcaa   5700
cccgcttcgc cagcgtgtac gcctggaata ggaagcgcat ctccaactgc gtggccgact   5760
attctgtgct gtacaacagc gcctccttct ctaccttta gtgctatggc gtgagcccca   5820
caaagctgaa tgacctgtgc tttaccaacg tgtacgccga ttccttcgtg atcaggggcg   5880
acgaggtgcg ccagatcgca ccaggacaga caggcaagat cgcagactac aattataagc   5940
tgcctgacga tttcaccggc tgcgtgatcg cctggaactc taacaatctg gatagcaaag   6000
tgggcggcaa ctacaattat ctgtaccggc tgtttagaaa gtctaatctg aagccattcg   6060
agagggacat ctccacagaa atctaccagg ccggctctac ccctgcaat ggcgtggagg   6120
gctttaactg ttatttccct ctgcagagct acggcttcca gccaacaaac ggcgtgggct   6180
atcagcccta ccgcgtggtg gtgctgtctt ttgagctgct gcacgcacct gcaacagtga   6240
gcggaccaaa gaagagcacc aatctggtga agaacaagtg cgtgaacttc aacttcaacg   6300
gactgaccgg aacaggcgtg ctgaccgagt ccaacaagaa gttcctgcct tttcagcagt   6360
tcggcaggga catcgcagat accacagacg ccgtgcgcga ccctcagacc ctggagatcc   6420
tggacatcac accatgctcc ttcggcgcg tgtctgtgat cacaccaggc accaatacaa   6480
gcaaccaggt ggccgtgctg tatcaggacg tgaattgtac cgaggtgcca gtggcaatcc   6540
acgcagatca gctgaccccct acatggcggg tgtactctac cggcagcaac gtgttccaga   6600
caagagccgg atgcctgatc ggagcagagc acgtgaacaa tagctatgag tcgacatcc   6660
ctatcggcgc cggcatctgt gcctcctacc agacccagac aaactcccca aggtctggat   6720
ccggctacat cccgaggcc cccagagacg gccaggccta cgtgcggaag gacggcgagt   6780
gggtactgct cagcaccttc ctgggcagca gttggaaaag ctccatcgcc tccttttct   6840
ttatcatcgg cctgatcatc ggactgttcc tggtgctccg cgtgggtatc cacctgtgca   6900
tcaagctgaa gcacaccaag aaaagacaga tttatacaga catcgagatg aaccgacttg   6960
gaaagtaagc tagccagatt cttcatgttt ggaccaaatc aacttgtgat accatgctca   7020
aagaggcctc aattatattt gagtttttaa tttttatgaa aaaaactaac agcaatcatg   7080
gaagtccacg attttgagac cgacgagttc aatgatttca tgaagatga ctatgccaca   7140
agagaattcc tgaatcccga tgagcgcatg acgtacttga atcatgctga ttacaatttg   7200
aattctcctc taattagtga tgatattgac aatttgatca ggaaattcaa ttctcttccg   7260
attccctcga tgtgggatag taagaactgg gatggagttc ttgagatgtt aacatcatgt   7320
caagccaatc ccatctcaac atctcagatg cataaatgga tgggaagttg gttaatgtct   7380
gataatcatg atgccagtca agggtatagt ttttacatgt aagtggacaa agaggcagaa   7440
ataacatttg acgtggttgga gaccttcatc cgcgcgtgga gcaacaaacc aattgaatac   7500
atcaaaaagg aaagatggac tgactcattc aaaattctcg cttatttgtg tcaaaagttt   7560
ttggacttac acaagttgac attaatctta aatgctgtct ctgaggtgga attgctcaac   7620
ttggcgagga ctttcaaagg caagtcaga agaagttctc atggaacgaa catatgcagg   7680
attagggttc ccagctgggt tcctactttt atttcagaag gatggcta cttcaagaaa   7740
cttgatattc taatggaccg aaactttctg ttaatggtca aagtgtgat tatagggagg   7800
atgcaaacgg tgctatccat ggtatgtaga atagacaacc tgttctcaga gcaagacatc   7860
ttctcccttc taaatatcta cagaattgga gataaaattg tggagaggca gggaaatttt   7920
tcttatgact tgattaaaat ggtggaaccg atatgcaact gaagctgat gaaattagca   7980
agagaatcaa ggcctttagt cccacaattc cctcattttg aaaatcatat caagacttct   8040
agtggtgaag gggcaaaaat tgaccgaggt ataagattcc tccatgatca gataatgagt   8100
gtgaaaacag tggatctcac actggtgatt tatggatcgt tcagacattg gggtcatcct   8160
tttatagatt attacactgg actagaaaaa ttacattccc aagtaaccat gaagaaagat   8220
attgatgtgt catatgcaaa agcacttgca agtgatttag ctcggattgt tctatttcaa   8280
cagttcaatg atcataaaaa gtggttcgtg aatgagact tgctccctca tgatcatccc   8340
tttaaaagtc atgttaaaga aaatacatgg cccacagctg ctcaagttca agattttgga   8400
```

```
gataaatggc atgaacttcc gctgattaaa tgttttgaaa tacccgactt actagaccca   8460
tcgataatat actctgacaa aagtcattca atgaataggt cagaggtgtt gaaacatgtc   8520
cgaatgaatc cgaacactcc tatccctagt aaaaaggtgt tgcagactat gttggacaca   8580
aaggctacca attggaaaga atttcttaaa gagattgatg agaagggctt agatgatgat   8640
gatctaatta ttggtcttaa aggaaaggag agggaactga agttggcagg tagattttc    8700
tccctaatgt cttggaaatt gcgagaatac tttgtaatta ccgaatattt gataaagact   8760
catttcgtcc ctatgtttaa aggcctgaca atggcggacg atctaactgc agtcattaaa   8820
aagatgttag attcctcatc cggccaagga ttgaagtcat atgaggcaat ttgcatagcc   8880
aatcacattg attacgaaaa atggaataac caccaaagga agttatcaaa cggcccagtg   8940
ttccgagtta tgggccagtt cttaggttat ccatccttaa tcgagagaac tcatgaattt   9000
tttgagaaaa gtcttatata ctacaatgga agaccagact tgatgcgtgt tcacaacaac   9060
acactgatca attcaacctc caacgagtt tgttggcaag acaagaggg tggactggaa     9120
ggtctacggc aaaaaggatg gactatcctc aatctactgg ttattcaaag agaggctaaa   9180
atcagaaaca ctgctgtcaa agtcttggca caaggtgata atcaagttat ttgcacacag   9240
tataaaacga agaaatcgag aaacgttgta gaattacgag gtgctctcaa tcaaatggtt   9300
tctaataatg agaaaattat gactgcaatc aaaatagga cagggaagtt aggacttttg     9360
ataaatgacg atgagactat gcaatctgca gattacttga attatggaaa aataccgatt   9420
ttccgtggag tgattagagg gttagagacc aagagatggt cacgagtgac ttgtgtcacc   9480
aatgaccaaa tacccacttg tgctaatata atgagctcag tttccacaaa tgctctcacc   9540
gtagctcatt ttgctgagaa cccaatcaat gccatgatac agtacaatta ttttgggaca   9600
tttgctagac tcttgttgat gatgcatgat cctgctcttc gtcaatcatt gtatgaagtt   9660
caagataaga taccgggctt gcacagttct acttttcaaat acgccatgtt gtatttggac   9720
ccttccattg gaggagtgtc gggcatgtct ttgtccaggt ttttgattag agccttccca   9780
gatcccgtaa cagaaagtct ctcattctgg agattcatcc atgtacatgc tcgaagtgag   9840
catctgaagg agatgagtgc agtatttgga aaccccgaga tagccaagtt tcgaataact   9900
cacatagaca agctagtaga agatccaacc tctctgaaca tcgctatggg aatgagtcca   9960
gcgaacttgt taaagactga ggttaaaaaa tgcttaatcg aatcaagaca aaccatcagg  10020
aaccaggtga ttaaggatgc aaccatatat ttgtatcatg aagaggatcg gctcagaagt  10080
ttcttatggt caataaatcc tctgttccct agatttttaa gtgaattcaa atcaggcact  10140
ttttgggag tcgcagacgg gctcatcagt ctatttcaaa attctcgtac tattcggaac   10200
tccttaagaa aaagtatca tagggaattg gatgattga ttgtgaggag tgaggtatcc     10260
tctttgacac atttagggaa acttcatttg agaaggggat catgtaaaat gtggacatgt  10320
tcagctactc atgctgacac attaagatac aaatcctggg gccgtacagt tattgggaca  10380
actgtacccc atccattaga aatgttgggt ccacaacatc gaaaagagac tccttgtgca  10440
ccatgtaaca catcagggtt caattatgtt tctgtgcatt gtccagacgg gatccatgac  10500
gtctttagtt cacggggacc attgcctgct tatctagggt ctaaaacatc tgaatctaca  10560
tctattttgc agccttggga aagggaaagc aaagtcccac tgattaaaag agctacacgt  10620
cttagagatg ctatctcttg gtttgttgaa cccgactcta aactagcaat gactatactt  10680
tctaacatcc actctttaac aggcgaagaa tggaccaaaa gcagcatgg gttcaaaaga   10740
acagggtctg cccttcatag gttttcgaca tctcggatga gccatggtgg gttcgcatct  10800
cagagcactg cagcattgac caggttgatg gcaactacag acaccatgag ggatctggga  10860
gatcagaatt tcgactttt attccaagca acgttgctct atgctcaaat taccaccact  10920
gttgcaagag acggatggat caccagttgt acagatcatt atcatattgc tcgtaagtcc  10980
tgtttgagac ccatagaaga gatcaccctg gactcaagta tggactacac gcccccagat  11040
gtatcccatg tgctgaagac atggaggaat ggggaaggtt cgtggggaca agagataaaa  11100
cagatctatc ctttagaagg gaattggaag aatttagcac tgctgagca atcctatcaa   11160
gtcggcagat gtataggttt tctatatgga gacttggcgt ataaaaatc tactcatgcc   11220
gaggacagtt ctctatttcc tctatctata caaggtcgta ttagaggtcg aggttttctta 11280
aaagggttgc tagacggatt aatgagagca agttgctgcc aagtaataca ccggagaagt  11340
ctggctcatt tgaagaggcc ggccaacgca gtgtacggag gtttgattta cttgattgat  11400
aaattggtg tatcacctcc attccttttct cttactagat caggacctat tagagacgaa   11460
ttagaaacga ttccccacaa gatcccaacc tcctatccga caagcaaccg tgatatgggg  11520
gtgattgtca gaaattactt caaataccaa tgccgtctaa ttgaaaaggg aaaatacaga  11580
tcacattatt cacaattatg gttattctca gatgtcttat ccatagactt cattggacca  11640
ttctctatttt ccaccaccct cttgcaaatc ctatacaagc attttttatc tgggaaagat 11700
aagaatgagt tgagagagct ggcaaatctt tcttcattgc taagatcagg agaggggtg    11760
gaagacatac atgtgaaatt cttccaccaag gacatattat tgtgtccaga ggaaatcaga  11820
catgcttgca agtcgggat tgctaaggat aataataaag acatgagcta tccccccttgg  11880
ggaagggaat ccagagggac aattacaaca atccctgttt attatacgac cacccccttac 11940
ccaaagatgc tagagatgcc tccaagaatc caaaatcccc tgctgtccgg aatcaggttg  12000
ggccaattac caactggcgc tcattataaa attcggagta tattcatgg aatgggaatc   12060
cattacaggg acttcttgag ttgtggagac ggctccggag ggatgactgc tgcattacta  12120
cgagaaaatg tgcatagcag aggaatattc aatagtctgt tagaattatc agggtcagtc  12180
atgcgaggtg cctctcctga gcccccagt gccctagaaa cttaggagg agataaatcg     12240
agatgtgtaa atggtgaaac atgttgggaa tatccatctg acttatgtga cccaaggact   12300
tgggactatt tcctccgact caaagcaggc ttggggcttc aaattgattt aattgtaatg   12360
gatatggaag ttcgggattc ttctactagc ctgaaaattg agacgaatgt tagaaattat   12420
gtgcaccgga tttttggatga gcaaggagtt ttaatctaca agacttatgg aacatatatt   12480
tgtgagacg agtaacaatc cttggtccca tgttcaagac ggtcgactta               12540
gttcaaacag aatttagtag ttctcaaacg tctgaagtat atatggtatg taaggtttg    12600
aagaaattaa tcgatgaacc caatcccgat tggtcttcca tcaatgaatc ctggaaaaac  12660
ctgtacgcat ccagtcatc agaacaggaa tttgccagag caagaaggt tagtacatac    12720
tttaccttga caggtattcc ctcccaattc attcctgatc cttttgtaaa cattgagact  12780
atgctacaaa tattcggagc tgtgtctcatg cggctgcctt aaaatcattc                 12840
gatagacctg cagattatt gaccattagc cttttttata tggcgattat atcgtattat   12900
aacatcaatc atatcagagt aggaccgata cctccgaacc cccatcaga tggaattgca    12960
caaaatgtgg ggatcgctat aactggtata agcttttggc tgagtttgat ggagaaagac  13020
attccactat atcaacagtg tttagcagtt atccagcaat cattccccgat taggtgggag  13080
gctgtttcag taaaaggagg atacaagcag aagtggagta ctagaggtga tgggctccca  13140
```

```
aaagataccc gaacttcaga ctccttggcc ccaatcggga actggatcag atctctggaa   13200
ttggtccgaa accaagttcg tctaaatcca ttcaatgaga tcttgttcaa tcagctatgt   13260
cgtacagtgg ataatcattt gaaatggtca aatttgcgaa gaaacacagg aatgattgaa   13320
tggatcaata gacgaatttc aaaagaagac cggtctatac tgatgttgaa gagtgaccta   13380
cacgaggaaa actcttggag agattaaaaa atcatgagga gactccaaac tttaagtatg   13440
aaaaaaactt tgatccttaa gaccctcttg tggttttat ttttatctg gttttgtggt      13500
cttcgt                                                               13506

SEQ ID NO: 23          moltype = DNA  length = 13503
FEATURE                Location/Qualifiers
misc_feature           1..13503
                       note = VSV vector: Convac V3 South Africa
source                 1..13503
                       mol_type = other DNA
                       organism = synthetic construct
SEQUENCE: 23
acgaagacaa acaaaccatt attatcatta aaaggctcag gagaaacttt aacagtaatc   60
aaaatgtctg ttacagtcaa gagaatcatt gacaacacag tcatagttcc aaaacttcct   120
gcaaatgagg atccagtgga ataccccgca gattacttca gaaaatcaaa ggagattcct   180
ctttacatca atactacaaa aagtttgtca gatctaagag gatatgtcta ccaaggcctc   240
aaatccggaa atgtatcaat catacatgtc aacagctact gtatggagc attaaaggac    300
atccgggta agttggataa agattggtca agttccgaca taaacatcgg gaaagcaggg    360
gatacaatcg gaatatttga ccttgtatcc ttgaaagccc tggacggcgt acttccagat   420
ggagtatcgg atgcttccag aaccagcgca gatgacaaat ggttgccttt gtatctactt   480
ggcttataca gagtgggcag aacacaaatg cctgaataca gaaaaagct catggatggg     540
ctgacaaatc aatgcaaaat gatcaatgaa cagtttgaac ctcttgtgcc agaaggtcgt   600
gacattttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca acatttggac acctctgcaa ataaccgga     780
atgtctacag aagatgtaac gacctggatc ttgaaccgaa aagttgcaga tgaaatggtc   840
caaatgatgc ttccaggcca agaaattgac aaggccgatt catacatgcc ttatttgatc   900
gactttggat tgtcttctaa gtctccatat tcttccgtca aaaaccctgc cttccacttc   960
tgggggcaat tgcagctctc tctgctcaga tccaccagag caaggaatgc ccgacagcct   1020
gatgcattg agtatacatc tcttactaca gcaggtttgt tgtacgctta tgcagtagga   1080
tcctctgccg acttggcaca acagttttgt gttggagata acaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg gcaagtatgc taagtcagaa   1320
tttgacaaat gacccctataa ttctcagatc acctattata tttatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatgagtg gaagagcata ctaagccctc ttatttcag    1560
gcagcagatg attctgacac agaatctgaa ccagaaattg aagacaatca aggtttgtat   1620
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga ggagcgcca gataactccg      1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagtttcat ctctgtcgtg   2100
ggtgacggac gaatgtctca taaagaggcc atcctgctcg gcctgagata caaaaagttg   2160
tacaatcagg cgagagtcaa atattctctg tagactatga aaaaagtaa cagatatcac   2220
gatctaagtg ttatcccaat ccattcatca tgagttcctt aaagaagatt ctcggtctga   2280
aggggaaagg taagaaatct aagaaattag ggatcgcacc accccccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtccctt ctacaaaatc ttggcttttt      2580
tgggttcttc taatcgaaag gccactccag cggtattggc agatcaaggt caaccagagt   2640
atcacactca ctgcgaaggc agggcttatt tgccacatag gatggggaag acccctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctgattc tatcagccac ttcaaatgag   2940
ctagtctaac ttctagcttc tgaacaatcc ccgttact cagtctctcc taattccagc       3000
ctctcgaaca actaatatcc tgtctttct atccctatga aaaaactaa cagagatcga    3060
tctgttttcg cgtcactatg aagtgccttt tgtacttagc cttttattc attggggtga    3120
attgcaagtt caccatagtt tttcacacaca accaaaaggt aaactggaaa atgttcttc   3180
ctaattacca ttattgcccg tcaagctcag atttaaattg gcataatgac ttaatagggca   3240
cagccataca agtcaaaatg cccaagagtc acaaggctat tcaagcagac ggttggatgt   3300
gtcatgcttc caaatgggtc actacttgtg atttccgctg gtatgaccg aagtatataa    3360
cacagtccat ccgatccttc actccatctg tagaacaatg caaggaaagc attgaacaaa   3420
cgaaaaagg aacttggctg aatcaggct ccattcaggt agcagttaac   3480
tgacggatgc cgaagcagtg attgtccagg tgactcctca ccatgtgctg gttgatgaat   3540
acacaggaga atgggttgat tcacagttca tcaacgaaaa atgcagcaat tacatatgcc   3600
ccactgtcca taactctaca acctggcatt ctgactataa ggtcaaaggg ctatgtgatt   3660
ctaacctcat ttccatggac atcaccttct ctcagagga cggagagcta tcatccctgg   3720
gaaggaggg cacagggttc agaagtaact actttgctta tgaaactgga ggcaaggcct   3780
```

```
gcaaaatgca atactgcaag cattggggag tcagactccc atcaggtgtc tggttcgaga  3840
tggctgataa ggatctcttt gctgcagcca gattccctga atgcccagaa gggtcaagta  3900
tctctgctcc atctcagacc tcagtggatg taagtctaat tcaggacgtt gagaggatct  3960
tggattattc cctctgccaa gaaacctgga gcaaaatcag agcgggtctt ccaatctctc  4020
cagtggatct cagctatctt gctcctaaaa acccaggaac cggtcctgct ttcaccataa  4080
tcaatggtac cctaaaatac tttgagacca gatacatcga agtcgatatt gctgctccaa  4140
tcctctcaag aatggtcgga atgatcagtg gaactaccac agaaagggaa ctgtgggatg  4200
actgggcacc atatgaagac gtggaaattg gacccaatgg agttctgagg accagttcag  4260
gatataagtt tccttatac atgattggac atggtatgtt ggactccgat cttcatctta  4320
gctcaaaggc tcaggtgttc gaacatcctc acattcaaga cgctgcttcg caacttcctg  4380
atgatgagag tttatttttt ggtgatactg ggctatccaa aaatccaatc gagcttgtag  4440
aaggttggtt cagtagttgg aaaagctcta ttgcctcttt tttctttatc ataggggttaa  4500
tcattggact attcttggtt ctccgagttg gtatccatct ttgcattaaa ttaaagcaca  4560
ccaagaaaag acagatttat acagacatag agatgaaccg acttggaaag taactcaaat  4620
cctgctaggt atgaaaaaaa ctaacagata tcacgctcga ggccaccatg ttcgtgtttc  4680
tggtgctgct gcctctggtg agctcccagt gcgtgaactt caccacaagg acccagctgc  4740
ccctgcct a taccaattcc ttcacacggg gcgtgtacta tcccgacaag gtgttccgga  4800
gcagcgtgct gcactccaca caggatctgt ttctgccttt cttttctaac gtgacctggt  4860
tccacgccat ccacgtgagc ggcaccaatg tgcacaaagcg gttcgccaat ccagtgctgc  4920
cctttaacga tggcgtgtac ttcgcctcca ccgagaagtc taacatcatc agaggctgga  4980
tctttggcac cacactggac agcaagacac agtccctgct gatcgtgaac aatgccacca  5040
acgtggtcat caaggtgtgc gagttccagt tttgtaatga tccattcctg ggcgtgtact  5100
atcacaagaa caataagtct tggatggaga gcgagtttcg cgtgtattcc tctgccaaca  5160
attgcacatt tgagtacgtg tcccagcccct tcctgatgga cctggagggc aagcagggca  5220
atttcaagaa cctgagggag ttcgtgttta agaatatcga tggctactt c aaaatctact  5280
ccaagcacac cccaatcaac ctggtgcgcg acctgccaca gggcttctct gccctggagc  5340
cactggtgga tctgcccatc ggcatcaaca tcacccggtt tcagacactg ctggccctgc  5400
acagaagcta cctgacacca ggcgacagct cctctggatg gaccgcagga gcagcagcct  5460
actatgtggg ctatctgcag cccaggacct tcctgctgaa gtacaacgag aatggcacca  5520
tcacagacgc cgtggattgc gccctggatc ccctgtctga gccaagtgt acactgaaga  5580
gctttaccgt ggagaagggc atctatcaga caagcaattt cagggtgcag cctaccgagt  5640
ccatcgtgcg ctttcccaat atcacaaacc tgtgcccttt tggcgaggtg ttcaacgcaa  5700
cccgcttcgc cagcgtgtac gcctggaata ggaagcgcat ctccaactgc gtggccgact  5760
attctgtgct gtacaacagc gcctccttct ctacctttaa gtgctatggc gtgagcccta  5820
caaagctgaa tgacctgtgc tttaccaacg tgtacgccga ttccttcgtg atcaggggcg  5880
acgaggtgcg ccagatcgca ccaggacaga caggcaatat cgcagactac aattataagc  5940
tgcctgacga tttccaccgc tgcgtgatcg cctggaactc taacaatctg gatagcaaag  6000
tgggcggcaa ctacaattat ctgtaccggc tgtttagaaa gtcaatctg aagccattcg  6060
agagggacat ctccacagaa atctaccagg ccggctcaca ccctgcaat ccgtgaagg  6120
gctttaactg ttattttccct ctgcagagct acggcttcca gccaacatat ggcgtgggct  6180
atcagcccta ccgcgtggtg gtgctgtctt ttgagctgct gcacgcacct gcaacagtgt  6240
gcggaccaaa gaagagcacc aatctggtga gaacaagtc cgtgaacttc aacttcaacg  6300
gactgaccgg aacaggcgtg ctgaccgagt ccaacaagaa gttcctgcct tttcagcagt  6360
tcggcaggga catcgcagat accacagacg ccgtgcgcga ccctcagacc ctggagatcc  6420
tggacatcac accatgctcc ttcggcggcg tgtctgtgat cacaccaggc accaatacaa  6480
gcaaccaggt ggccgtgctg tatcaggcg tgaattgtac cgaggtgcca gtggcaatcc  6540
acgcagatca gctgaccct acatgcgggg tgtactctac cggcagcaac gtgttccaga  6600
caagagccgg atgcctgatc ggagcagagc acgtgaacaa tagctatgag tgcgacatcc  6660
ctatcggcgc cggcatctgt gcctcctacc agacccagac aaaactcccca aggggatccg  6720
gctacatccc cgaggccccc agagacggcc aggcctacgt gcggaaggac ggcgagtggg  6780
tactgctcag cacctcctg ggcagcagtt ggaaaagctc catcgcctcc tttttcttta  6840
tcatcggcct gatcatcgga ctgttcctgg tgctccgcgt gggtatccac ctgtgcatca  6900
agctgaagca caccaagaaa agacagattt atacagacat cgagatgaac cgacttggaa  6960
agtaagctag ccagattctt catgtttgga ccaaatcaac ttgtgatacc atgctcaaag  7020
aggcctcaat tatattgag ttttaatttt ttatgaaaaa aactaacagc aatcatggaa  7080
gtccacgatt ttgagaccga cgagttcaat gatttcaatg aagatgacta tgccacaaga  7140
gaattcctga atcccgatga gcgcatgacg tacttgaatc atgctgatta caatttgaat  7200
tctcctctaa ttagtgatga tattgacaat ttgatcagga aattcaattc tcttccgatt  7260
ccctcgatgt gggatagtaa gaactgggat ggagttcttg agatgttaac atcatgtcaa  7320
gccaatccca tctcaacatc tcagatgcat aaatgatgg aagttggtt aatgtctgat  7380
aatcatgatg ccagtcaagg gtatagtttt tacatgaag tggacaaaga ggcagaaata  7440
acatttgacg tggtggagac cttcatccgc ggctggggca caaaccaat tgaatacatc  7500
aaaaaggaaa gatggactga ctcattcaaa attctcgctt atttgtgtca aaagtttttg  7560
gacttacaca agttgacatt aatcttaaat gctgtctctg gaggaatt gctcaacttg  7620
gcgaggactt tcaaaggcaa agtcagaaga agttctcatg gaacgaacat atgcaggatt  7680
agggttccca gcttgggtcc tacttttatt tcagaaggat gggcttactt caagaaactt  7740
gatattctaa tggaccgaaa cttctctgtta atggtcaaag atgtgattat agggaggatg  7800
caaacggtgc tatccatggt atgtagaata gacaacctgt tctcagagca agacatcttc  7860
tcccttctaa atatctacag aattgtggat aaaattgtgg agaggcaggg aaatttttct  7920
tatgacttga ttaaaatggt ggaaccgata tgcaactga agctgatgaa attagcaaga  7980
gaatcaaggc ctttagtccc acaattccct cattttgaaa atcatatcaa gacttctgtt  8040
gatgaagggg caaaaattga ccgaggtata agattcctcc atgatcagat aatgagtgtg  8100
aaaacagtgg atctcacact ggtgatttat ggatcgttca gacattgggg tcatcctttt  8160
atagattatt acactgcaga agaaaaatta cattcccaag taaccatgaa gaaagatatt  8220
gatgtgtcat atgcaaaagc acttgcaagt gatttagctc ggattgttct atttcaacag  8280
ttcaatgatc ataaaaagtg gttcgtgaat ggagacttgc tccctcatga tcatccctttc  8340
aaaagtcatg ttaaagaaaa tacatggccc acagctgctc aagttcaaga ttttggagat  8400
aaatggcatg aacttccgct gattaaatgt tttgaaatac ccgacttact agacccatcg  8460
ataatatact ctgacaaaag tcattcaatg aataggtcag aggtgttgaa acatgtccga  8520
```

```
atgaatccga acactcctat ccctagtaaa aaggtgttgc agactatgtt ggacacaaag   8580
gctaccaatt ggaaagaatt tcttaaagag attgatgaga agggcttaga tgatgatgat   8640
ctaattattg gtcttaaagg aaaggagagg gaactgaagt tggcaggtag attttttctcc  8700
ctaatgtctt ggaaattgcg agaatacttt gtaattaccg aatatttgat aaagactcat   8760
ttcgtcccta tgtttaaagg cctgacaatg gcggacgatc taactgcagt cattaaaaag   8820
atgttagatt cctcatccgg ccaaggattg aagtcatatg aggcaatttg catagccaat   8880
cacattgatt acgaaaaatg gaataaccac caaaggaagt tatcaaacgg cccagtgttc   8940
cgagttatgg gccagttctt aggttatcca tccttaatcg agagaactca tgaattttt    9000
gagaaaagtc ttatatacta caatggaaga ccagacttga tgcgtgttca caacaacaca   9060
ctgatcaatt caacctccca acgagtttgt tggcaaggac aagagggtgg actggaaggt   9120
ctacggcaaa aaggatggac tatcctcaat ctactggtta ttcaaagaga ggctaaaatc   9180
agaaacactg ctgtcaaagt cttggcacaa ggtgataatc aagttatttg cacacagtat   9240
aaaacgaaga aatcgagaaa cgttgtagaa ttacaggggtg ctctcaatca aatggtttct  9300
aataatgaca aaattatgac tgcaatcaaa atagggacag ggaagttagg acttttgata   9360
aatgacgatg agactatgca atctgcagat tacttgaatt atggaaaaat accgattttc   9420
cgtggagtga ttagagggtt agagaccaag agatggtcac gagtgacttg tgtcaccaat   9480
gaccaaaatac ccacttgtgc taatataatg agctcagttt ccacaaatgc tctcaccgta  9540
gctcattttg ctgagaaccc aatcaatgcc atgatacagt acaattattt tgggacattt   9600
gctagactct tgttgatgat gcatgatcct gctcttcgtc aatcattgta tgaagttcaa   9660
gataagatac cgggcttgca cagttctact ttcaaatacg ccatgttgta tttggaccct   9720
tccattggag gagtgtcggg catgtctttg tccaggtttt tgattagagc cttcccagat   9780
cccgtaacag aaagtctctc attctggaga ttcatccatg tacatgctcg aagtgagcat   9840
ctgaaggaga tgagtgcagt atttggaaac cccgagatag ccaagtttcg aataactcac   9900
atagacaagc tagtagaaga tccaacctct ctgaacatcg ctatgggaat gagtccagcg   9960
aacttgttaa agactgaggt taaaaatgc ttaatcgaat caagacaaac catcaggaac    10020
caggtgatta aggatgcaac catatatttg tatcatgaag aggatcggct cagaagtttc   10080
ttatggtcaa taaatcctct gttccctaga tttttaagtg aattcaaatc aggcactttt   10140
ttgggagtcg cagacgggct catcagtcta tttcaaaatt ctcgtactat tcggaactcc   10200
tttaagaaaa agtatcatag ggaattggat gatttgattg tgaggagtga ggtatcctct   10260
ttgacacatt tagggaaact tcatttgaga aggggatcat gtaaaatgtg gacatgttca   10320
gctactcatg ctgacacatt aagatacaaa tcctgggggcc gtacagttat tgggacaact   10380
gtaccccatc cattagaaat gttgggtcca caacatcgaa aagagactcc ttgtgcacca   10440
tgtaacacat cagggttcaa ttatgtttct gtgcattgtc cagacgggat ccatgacgtc   10500
tttagttcac ggggaccatt gcctgcttat ctagggtcta aaacatctga atctacatct   10560
attttgcagc cttgggaaag ggaaagcaaa gtcccactga ttaaaagagc tacacgtctt   10620
agagatgcta tctcttggtt tgttgaaccc gactctaaac tagcaatgac tatactttct   10680
aacatccact ctttaacagg cgaagaatgg accaaaaggc agcatgggtt caaaagaaca   10740
gggtctgccc ttcataggtt ttcgacatct cggatgagcc atggtgggtt cgcatctcag   10800
agcactgcag cattgaccag gttgatggca actacagaca ccatgagggga tctgggagat   10860
cagaatttcg acttttttat tccaagcaacg ttgctctatg ctcaaattac caccactgtt  10920
gcaagagacg gatggatcac cagttgtaca gatcattatc atattgcctg taagtcctgt   10980
ttgagaccca tagaagagat caccctggac tcaagtatgg actacacgcc cccagatgta   11040
tcccatgtgc tgaagacatg gaggaatggg gaaggttcgt ggggacaaga gataaaacag   11100
atctatcctt tagaagggaa ttggaagaat ttagcacctg ctgagcaatc ctatcaagtc   11160
ggcagatgta taggtttctct atatggagac ttggcgtata gaaaatctac tcatgccgag  11220
gacagttctc tatttcctct atctatacaa ggtcgtatta gaggtcgagg tttcttaaaa   11280
gggtgctag acggattaat gagagcaagt tgctgccaag taatacaccg gagaagtctg   11340
gctcatttga agaggccggc caacgcagtg tacggaggtt tgatttactt gattgataaa   11400
ttgagtgtat cacctccatt cctttctctt actagatcag gacctattag agacgaatta   11460
gaaacgattc cccacaagat cccaacctcc tatccgacaa gcaaccgtga tatggggggtg  11520
attgtcagaa attacttcaa ataccaatgc cgtcattagta aaaagggaaa atacagatca  11580
cattattcac aattatggtt attctcagat gtcttatcca tagacttcat tggaccattg   11640
tctatttcca ccaccctctt gcaaatccta tacaagccat tttatctgg aaagataag    11700
aatgagttga gagagctggc aaatctttct tcattgctaa gatcaggaga ggggtgggaa   11760
gacatacatg tgaaattctt caccaaggac atattattgt gtccagagga aatcagacat   11820
gcttgcaagt tcgggattgc taaggataat aataaagaca tgagctatcc cccttgggga   11880
agggaatcca gagggacaat tacaacaatc cctgtttatt atacgaccac cccttaccca   11940
aagatgctag agatgcctcc aagaatccaa aatcccctgc tgtccggaat caggttgggc   12000
caattaccaa ctggcgctca ttataaaatt cggagtatat tacatggaat gggaatccat   12060
tacagggact tcttgagttg tgggacggc tccggaggga tgactgctgc attactacga   12120
gaaaatgtgc atagcagagg aatattcaat agtctgttag aattatcagg gtcagtcatg   12180
cgaggcgcct ctcctgagcc ccccagtgcc ctagaaactt taggaggaga taatcgaga    12240
tgtgtaaatg gtgaaacatg ttgggaatat ccatctgact tatgtgaccc aaggacttgg   12300
gactatttcc tccgactcaa agcaggcttg gggcttcaaa ttgatttaat tgtaatgat    12360
atggaagttc gggattcttc tactagcctg aaaattgaga cgaatgttag aaattatgtg   12420
caccggattt tggatgagca aggagtttta atctacaaga cttatggaac atatatttgt   12480
gagagcgaaa agaatgcagt aacaatcctt ggtcccatgt tcaagacggt cgacttagtt   12540
caaacagaat ttagtagttc tcaaacgtct gaagtatata tggtatgaa aggtttgaag   12600
aaattaatcg atgaaccaa tcccgattgg tcttccatca atgatcctg gaaaaacctg    12660
tacgcattcc agtcatcaga acaggaattt gccagagcaa agaaggttag tacatacttt   12720
accttgacag gtattccctc caattcatt cctgatcctt ttgtaaacat tgagactatg   12780
ctacaaatat tcggagtacc cacggggtgtg tctcatgcgg ctgccttaaa atcatctgat   12840
agacctgcag atttattgac cattagcctt tttatatgg cgattatatc gtattataac   12900
atcaatcata tcagagtagg accgatacct ccgaacccc catcagatgg aattgcacaa   12960
aatgtgggga tcgctataac tggtataagc ttttggctga gtttgatgga aaagacatt    13020
ccactatatc aacagtgttt agcagttatc cagcaatcat tcccgattag gtgggaggct   13080
gtttcagtaa aaggaggata caagcagaag tggagtacta gaggtgatgg gctcccaaaa   13140
gatacccgaa cttcagactc cttggcccca atcgggaact ggatcagatc tctgaattg    13200
gtccgaaacc aagttcgtct aaatccattc aatgagatct tgttcaatca gctatgtcgt   13260
```

```
acagtggata atcatttgaa atggtcaaat ttgcgaagaa acacaggaat gattgaatgg  13320
atcaatagac gaatttcaaa agaagaccgg tctatactga tgttgaagag tgacctacac  13380
gaggaaaact cttggagaga ttaaaaaatc atgaggagac tccaaacttt aagtatgaaa  13440
aaaactttga tccttaagac cctcttgtgg tttttatttt ttatctggtt ttgtggtctt  13500
cgt                                                                13503

SEQ ID NO: 24          moltype = DNA  length = 13484
FEATURE                Location/Qualifiers
misc_feature           1..13484
                       note = VSV vector: Convac V4 China
source                 1..13484
                       mol_type = other DNA
                       organism = synthetic construct
SEQUENCE: 24
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc acccccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtgccacca tgttcgtgtt tctggtgctg ctgcctctgg tgagctccca  3120
gtgcgtgaac ctgaccacaa ggacccagct gccccctgcc tataccaatt ccttcacacg  3180
gggcgtgtac tatcccgaca aggtgttccg gagcagcgtg ctgcactcca cacaggatct  3240
gtttctgcct ttcttttcta acgtgacctg gttccacgcc atccacgtga gcggcaccaa  3300
tggcacaaag cggttcgaca atccagtgct gccctttaac gatggcgtgt acttcgcctc  3360
caccgagaag tctaacatca tcagaggctg gatctttggc accacactgg acagcaagac  3420
acagtccctg ctgatcgtga acaatgccac caacgtggtc atcaaggtgt gcgagttcca  3480
gttttgtaat gatccattcc tgggcgtgta ctatcacaag aacaataagt cttggatgga  3540
gagcgagttt cgcgtgtatt cctctgccaa caattgcaca tttgagtacg tgtcccagcc  3600
cttcctgatg gacctggagg gcaagcaggg caatttcaag aacctgaggg agttcgtgtt  3660
taagaatatc gatggctact tcaaaatcta ctccaagcac accccaatca acctggtgcg  3720
cgacctgcca cagggcttct ctgccctgga gccactggtg gatctgccca tcggcatcaa  3780
catcacccgg tttcagacac tgctggccct gcacagaagc tacctgacac caggcgacag  3840
ctcctctgga tggaccgcag gagcagcagc ctactatgtg ggctatctgc agcccaggac  3900
```

```
cttcctgctg aagtacaacg agaatggcac catcacagac gccgtggatt gcgccctgga  3960
tcccctgtct gagaccaagt gtacactgaa gagctttacc gtggagaagg gcatctatca  4020
gacaagcaat tcagggtgc agcctaccga gtccatcgtg cgctttccca atatcacaaa   4080
cctgtgccct tttggcgagg tgttcaacgc aacccgcttc gccagcgtgt acgcctgaa   4140
taggaagcgc atctccaact gcgtggccga ctattctgtg ctgtacaaca gcgcctcctt  4200
ctctacctttt aagtgctatg gcgtgagccc cacaaagctg aatgacctgt gctttaccaa  4260
cgtgtacgcc gattccttcg tgatcagggg cgacgaggtg cgccagatcg caccaggaca  4320
gacaggcaag atcgcagact acaattataa gctgcctgac gatttcaccg gctgcgtgat  4380
cgcctggaac tctaacaatc tggatagcaa agtgggcggc aactacaatt atctgtaccg  4440
gctgtttaga aagtctaatc tgaagccatt cgagagggac atctccacag aaatctacca  4500
ggccggctct acccctgca atggcgtgga gggctttaac tgttattcc ctctgcagag     4560
ctacggcttc cagccaacaa acggcgtggg ctatcagccc taccgcgtgg tggtgctgtc   4620
tttgagctg ctgcacgcac ctgcaacagt gtgcggacca aagaagagca ccaatctggt   4680
gaagaacaag tgcgtgaact tcaacttcaa cggactgacc ggaacaggcg tgctgaccga   4740
gtccaacaag aagttcctgc cttttcagca gttcggcagg gacatcgcag ataccacaga   4800
cgccgtgcgc gaccctcaga ccctggagat cctggacatc acaccatgct ccttcggcgg   4860
cgtgtctgtg atcacaccag gcaccaatac aagcaaccag gtggccgtgc tgtatcagga   4920
cgtgaattgt accgaggtgc cagtggcaat ccacgcagat cagctgaccc ctacatgcg    4980
ggtgtactct accggcagca acgtgttcca gacaagagcc ggatgcctga tcggagcaga   5040
gcacgtgaac aatagctatg agtgcgacat ccctatcggc gccggcatct gtgcctccta   5100
ccagacccag acaaactccc caaggtctgt gggcgataca ggcctgtcca agaatccaat    5160
cgagctggta gagggctggt tcagcagttg gaaaagctcc atcgcctcct tttctcttta    5220
catcggcctg atcatcggac tgttcctggt gctccgcgtg ggtatccacc tgtgcatcaa   5280
gctgaagcac accaagaaaa gacagattta tacagacatc gagatgaacc gcctgggaaa   5340
gggatccggc tccggcgagg gcaggggaag tctactaaca tgcggggacg tggaggaaaa   5400
tcccggcccc atgaagtgcc ttttgtactt agcctttttta ttcattgggg tgaattgcaa   5460
gttcaccata gttttccac acaaccaaaa aggaaactgg aaaatgttc cttctaatta     5520
ccattattgc ccgtcaagct cagatttaaa ttggcataat gacttaatag gcacagccat    5580
acaagtcaaa atgcccaaga gtcacaaggc tattcaagca gacggttgga tgtgtcatgc    5640
ttccaaatgg gtcactactt gtgatttccg ctggtatgga ccgaagtata taacacagtc     5700
catccgatcc ttcactccat ctgtagaaca atgcaaggaa agcattgaac aaacgaaaca    5760
aggaacttgg ctgaatccag gcttccctcc tcaaagttgt ggatatgcaa ctgtgacgga    5820
tgccgaagca gtgattgtcc aggtgactcc tcaccatgtg ctggttgatg aatacacagg    5880
agaatgggtt gattcacagt tcatcaacgg aaaatgcagc aattacatat gccccactgt    5940
ccataactct acaacctggc attctgacta taaggtcaaa gggctatgtg attctaacct    6000
catttccatg gacatcacct tcttctcaga ggacggagag ctatcatccc tgggaaagga    6060
gggcacaggg ttcagaagta actactttgc ttatgaaact ggaggcaagg cctgcaaaat    6120
gcaatactgc aagcattggg gagtcagact cccatcaggt gtctggttcg agatggctga    6180
taaggatctc tttgctgcag ccagattccc tgaatgccca gaagggtcaa gtatctctgc    6240
tccatctcag acctcagtgg atgtaagtct aattcaggac gttgagagga tcttggatta    6300
ttccctctgc caagaaacct ggagcaaaat cagagcgggt cttccaatct ctccagtgga    6360
tctcagctat cttgctccta aaaacccagg aaccggtcct gctttcacca taatcaatgg    6420
tacccctaaaa tactttgaga ccagatacat cagtgtgact gttgctgctc caatcctctc    6480
aagaatggtc ggaatgatca gtggaactac cacagaaagg gaactgtggg atgactgggc    6540
accatatgaa gacgtggaaa ttggacccaa tggagttctg aggaccagtt caggatataa    6600
gtttcctttta tacatgattg gacatggtat gttggactcc gatcttcatc ttagctcaaa    6660
ggctcaggtg ttcgaacatc ctcacattca agacgctgtc tcgcaacttc ctgatgatga    6720
gagtttattt tttggtgata ctgggctatc caaaaatcca atcgagcttg tagaaggttg    6780
gttcagtagt tggaaaagct ctattgcctc tttttttcttt atcataggt taatcattgg    6840
actattcttg gttctccgag ttggtatcca tctttgcatt aaattaaagc acaccaagaa    6900
aagacagatt tatacagaca tagagatgaa ccgacttgga aagtaagcta gccagattct    6960
tcatgtttgg accaaatcaa cttgtgatac catgctcaaa gaggcctcaa ttatatttga    7020
gttttaatt tttatgaaaa aaactaacag caatcatgga agtccacgat tttgagaccg     7080
acgagttcaa tgatttcaat gaagatgact atgccacaag agaattcctg aatcccgatg    7140
agcgcatgac gtacttgaat catgctgatt acaaatttgaa ttctcctcta attagtgatg    7200
atattgacaa tttgatcagg aaattcaatt ctcttccgat tccctcgatg tgggatagta    7260
agaactggga tggagttctt gagatgttaa catcatgtca agccaatccc atctcaacat    7320
ctcagatgca taaatggatg ggaagttggt taatgtctga taatcatgat gccagtcaag    7380
ggtatagttt tttacatgaa gtggacaaag aggcagaaat aacatttgac gtggtggaga    7440
ccttcatccg cggctggggc aacaaaccaa ttgaatacat caaaaaggaa agatggactg    7500
actcattcaa aattctcgct tatttgtgtc aaaagttttt ggacttacac aagttgacat    7560
taatcttaaa tgctgtctct gaggtggaat tgctcaactt ggcgaggact ttcaaaggca    7620
aagtcagaag aagttctcat ggaacgaaca tatgcaggat tagggttccc agcttgggtc    7680
ctacttttat ttcagaagga tgggcttact tcaagaaact tgatattcta atggaccgaa    7740
actttctgtt aatggtcaaa gatgtgatta tagggaggat gcaaacggtg ctatccatgg    7800
tatgtagaat agcaacctg ttctcagagc aagcatctt ctcccttcta aatatctaca       7860
gaattggaga taaaattgtg gagaggcagg gaaatttttc ttatgacttg attaaaatgg    7920
tggaaccgat atgccaactg aagctgatga aattagcaag agaatcaagg ccttagtcc     7980
cacaattccc tcatttgaa aatcatatca agacttctgt tgatgaaggg gcaaaaattg      8040
accgaggtat aagattcctc catgatcaga taatgagtgt gaaaacagtg gatctcacac    8100
tggtgattta tggatcgttc agacattggg gtcatccttt tatagattat tacactggac    8160
tagaaaaatt acattcccaa gtaaccatga gaaagatat gatgtgtca tatgcaaaag      8220
cacttgcaag tgatttagct cggattgttc tattcaaca gttcaatgat cataaaaagt    8280
ggttcgtgaa tggagacttt ctccctcatg atcatcccct gaagtcat gttaagaaa        8340
atacatggcc cacagctgct caagttcaag attttggaga taaatggcat gaacttccgc     8400
tgattaaatg ttttgaaata cccgacttac tagcccatc gataatatac tctgacaaaa     8460
gtcattcaat gaataggtca gaggtgttga acatgtccg aatgaatccg aacactccta     8520
tccctagtaa aaaggtgttg cagactatgt tggacacaaa ggctaccaat tggaaagaat    8580
ttcttaaaga gattgatgag aagggcttag atgatgatga tctaattatt ggtcttaaag    8640
```

```
gaaaggagag ggaactgaag ttggcaggta gattttttctc cctaatgtct tggaaattgc   8700
gagaatactt tgtaattacc gaatatttga taaagactca tttcgtccct atgtttaaag   8760
gcctgacaat ggcggacgat ctaactgcag tcattaaaaa gatgttagat tcctcatccg   8820
gccaaggatt gaagtcatat gaggcaattt gcatagccaa tcacattgat tacgaaaaat   8880
ggaataacca ccaaaggaag ttatcaaacg gcccagtgtt ccgagttatg ggccagttct   8940
taggttatcc atccttaatc gagagaactc atgaattttt tgagaaaagt cttatatact   9000
acaatggaag accagacttg atgcgtgttc acaacaacac actgatcaat tcaacctccc   9060
aacgagtttg ttggcaagga caagagggtg gactggaagg tctacggcaa aaaggatgga   9120
ctatcctcaa tctactggtt attcaaagag aggctaaaat cagaaacact gctgtcaaag   9180
tcttggcaca aggtgataat caagttattt gcacacagta taaaacgaag aaatcgagaa   9240
acgttgtaga attacagggt gctctcaatc aaatggtttc taataatgag aaaattatga   9300
ctgcaatcaa aatagggaca gggaagttag gactttgat aaatgacgat gagactatgc    9360
aatctgcaga ttacttgaat tatggaaaaa taccgatttt ccgtggagtg attagagggt   9420
tagagaccaa gagatggtca cgagtgactt gtgtcaccaa tgaccaaata cccacttgtg   9480
ctaatataat gagctcagtt tccacaaatg ctctccaccgt agctcatttt gctgagaacc   9540
caatcaatgc catgatacag tacaattatt tgggacatt tgctagactc ttgttgatga    9600
tgcatgatcc tgctcttcgt caatcattgt atgaagttca agataagata ccgggcttgc   9660
acagttctac tttcaaatac gccatgttgt atttggaccc ttccattgga ggagtgtcgg   9720
gcatgtcttt gtccaggttt ttgattagag ccttcccaga tcccgtaaca gaaagtctct   9780
cattctggag attcatccat gtacatgctc gaagtgagca tctgaaggag atgagtgcag   9840
tatttggaaa ccccgagata gccaagtttc gaataactca catagacaag ctagtagaag   9900
atccaacctc tctgaaccatc gctatgggaa tgagtccaga gaacttgtta aagactgagg   9960
ttaaaaaatg cttaatcgaa tcaagacaaa ccatcaggaa ccaggtgatt aaggatgcaa  10020
ccatatattt gtatcatgaa gaggatcggc tcagaagttt cttatggtca ataaatcctc  10080
tgttccctag atttttaagt gaattcaaat caggcacttt tttgggagtc gcagacgggc  10140
tcatcagtct atttcaaaat tctcgtacta ttcggaactc cttaagaaa aagtatcata   10200
gggaattgga tgatttgatt gtgaggagtg aggtatcctc tttgacacat ttagggaaac  10260
ttcatttgag aaggggatca tgtaaaatgt ggacatgttc agctactcat gctgacacat  10320
taagatacaa atcctgggc cgtacagtta ttgggacaac tgtacccat ccattagaaa    10380
tgttgggtcc acaacatcga aaagagactc ctttgtgcacc atgtaacaca tcagggttca  10440
attatgtttc tgtgcattgt ccagacggga tccatgacgt ctttagttca cggggaccat  10500
tgcctgctta tctagggtct aaaacatctg aatctacatc tattttgcag ccttgggaaa  10560
gggaaagcaa agtcccactg attaaaagag ctacacgtct tagagatgct atctcttggt  10620
ttgttgaacc cgactctaaa ctagcaatga ctatactttc taacatccac tctttaacag  10680
gcgaagaatg gaccaaaagg cagcatgggt tcaaagaac agggtctgcc cttcataggt   10740
tttcgacatc tcggatgagc catggtgggt tcgcatctca gagcactgca gcattgacca  10800
ggttgatggc aactacagac accatgaggg atctgggaga tcagaatttc gactttttat  10860
tccaagcaac gttgctctat gctcaaatta ccaccactgt tgcaagagac ggatggatca  10920
ccagttgtac agatcattat catattgcct gtaagtcctc tttgagaccc atagaagaga  10980
tcaccctgga ctcaagtatg gactacacgc ccccagatgt atcccatgtg ctgaagacat  11040
ggaggaatgg ggaaggttcg tggggacaag agataaaaca gatctatcct ttagaaggga  11100
attggaagaa tttagcacct gctgagcaat cctatcaagt cggcagatgt ataggttttc  11160
tatatggaga cttggcgtat agaaaatcta ctcatgccga ggacagttct ctattcctc    11220
tatctataca aggtcgtatt agaggtcgag gtttcttaaa agggttgcta gacgattaa    11280
tgagagcaag ttgctgccaa gtaatacacc ggagaagtct ggctcatttg aagaggccgg  11340
ccaacgcagt gtacggaggt ttgatttact tgattgataa attgagtgta tcacctccat  11400
tcctttctct tactagatca ggacctatta gagcgaatt agaaacgatt ccccacaaga  11460
tcccaacctc ctatccgaca agcaaccgtg atatgggggt gattgtcaga aattacttca  11520
aataccaatg ccgtcaatt gaaaaggaa aatacagatc acattattca caattatggt    11580
tattctcaga tgtcttatcc atagacttca ttggaccatt ctctatttcc accaccctct  11640
tgcaaatcct atacaagcca tttttatctg ggaaagataa gaatgagttg agagagcttg  11700
caaatctttc ttcattgcta agatcaggag aggggtggga agacatacat gtgaaattct  11760
tcaccaagga catattattg tgtccagagg aaatcagaca tgcttgcaag ttcgggattg  11820
ctaaggataa taataaagac atgagctatc cccttgggg aagggaatcc agaggacaa    11880
ttacaacaat ccctgtttat tatacgacca ccccttaccn aaagatgcta gagatgcctc  11940
caagaatcca aaatcccctg ctgtccgaa tcaggttggg ccaattacca actggcgctc    12000
attataaaat tcggagtata ttacatgaa tgggaatcca ttacagggac ttcttgagtt    12060
gtggagacgg ctccggaggg atgactgctg cattactacg agaaaatgtg catagcagag  12120
gaatattcaa tagtctgtta gaattatcag ggtcagtcat gcgagcgcc tctcctgagc    12180
ccccagtgc cctagaaact ttaggaggag ataaatcgag atgtgtaaat ggtgaaacat     12240
gttgggaata tccatctgac ttatgtgacc caaggacttg ggactatttc ctccgactca  12300
aagcaggctt gggggcttcaa attgatttaa ttgtaatgga tatggaagtt cgggattctt  12360
ctactagcct gaaaattgag acgaatgtta gaaattatgt gcaccggatt ttggatgagc  12420
aaggagtttt aatctacaag acttatgaa catatatttg tgagagcaaa agaatgcag    12480
taacaatcct tggtcccatg ttcaagacgg tcgacttagt tcaaacagaa tttagtagtt  12540
ctcaaacgtc tgaagtatat atggtatgta aaggtttgaa gaaattaatc gatgaaccca  12600
atcccgattg tcttccatc aatgaatcct ggaaaaacct gtacgcattc cagtcatcag    12660
aacaggaatt tgcagagca aagaaggtta gtacatactt taccttgaca ggtattccct  12720
cccaattcat tcctgatcct tttgtaaaca ttgagactat gctacaaata ttcggagtac  12780
ccacgggtgt gtctcatgcg gctgccttaa aatcatctga tagacctgca gatttattga  12840
ccattagcct tttttatatg gcgattatat cgtattataa catcaatcat atcagagtag  12900
gaccgatacc tccgaacccc catcagatg gaattgcaca aaatgtgggg atcgctataa   12960
ctggtataag cttttggctg agtttgatgg agaaagacat tccactatat caacagtgtt  13020
tagcagttat ccagcaatca ttcccagatta gtgggaagc tgtttcagta aaaggaggat  13080
acaagcagaa gtggagtact agaggtgatg ggtccccaaa agatacccga acttcagact  13140
ccttggcccc aatcgggaac tggatcagat ctctggaatt ggtccgaaac caagttcgtc  13200
taaatccatt caatgagatc ttgttcaatc agctatgtcg tacagtggat aatcatttga  13260
aatggtcaaa tttgcgaaga aacacaggaa tgattgaatg gatcaataga cgaatttcaa  13320
aagaagaccg gtcctatactg atgttgaaga gtgacctaca cgaggaaaac tcttggagag  13380
```

-continued

```
attaaaaaat catgaggaga ctccaaactt taagtatgaa aaaaactttg atccttaaga  13440
ccctcttgtg gtttttattt tttatctggt tttgtggtct tcgt                    13484

SEQ ID NO: 25          moltype = DNA  length = 13484
FEATURE                Location/Qualifiers
misc_feature           1..13484
                       note = VSV vector: Convac V4 South Africa
source                 1..13484
                       mol_type = other DNA
                       organism = synthetic construct
SEQUENCE: 25
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc accccctat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtgccacca tgttcgtgtt tctggtgctg ctgcctctgg tgagctccca  3120
gtgcgtgaac ttcaccacaa ggacccagct gccccctgcc tataccaatt ccttcacacg  3180
gggcgtgtac tatcccgaca aggtgttccg gagcagcgtg ctgcactcca cacaggatct  3240
gtttctgcct ttcttttcta acgtgacctg gttccacgcc atccacgtga gcggcaccaa  3300
tggcacaaag cggttcgcca atccagtgct gccctttaac gatggcgtgt acttcgcctc  3360
caccgagaag tctaacatca tcagaggctg gatctttggc accacactgg acagcaagac  3420
acagtccctg ctgatcgtga acaatgccac caacgtggtc atcaaggtgt gcgagttcca  3480
gttttgtaat gatccattcc tgggcgtgta ctatcacaag aacaataagt cttggatgga  3540
gagcgagttt cgcgtgtatt cctctgccaa caattgcaca tttgagtacg tgtcccagcc  3600
cttcctgatg gacctggagg gcaagcaggg caatttcaag aacctgaggg agttcgtgtt  3660
taagaatatc gatggctact tcaaaatcta ctccaagcac accccaatca acctggtgcg  3720
cggcctgcca cagggcttct ctgccctgga gccactggtg gatctgccca tcggcatcaa  3780
catcacccgg tttcagacac tgctggccct gcacagaagc tacctgacac caggcgacag  3840
ctcctctgga tggaccgcag gagcagcagc ctactatgtg ggctatctgc agcccaggac  3900
cttcctgctg aagtacaacg agaatggcac catcacagac gccgtggatt gcgccctgga  3960
tcccctgtct gagaccaagt gtacactgaa gagctttacc gtggagaagg gcatctatca  4020
gacaagcaat ttcagggtgc agcctaccga gtccatcgtg cgctttccca atatcacaaa  4080
```

```
cctgtgccct tttggcgagg tgttcaacgc aacccgcttc gccagcgtgt acgcctggaa  4140
taggaagcgc atctccaact gcgtggccga ctattctgtg ctgtacaaca gcgcctcctt  4200
ctctaccttt aagtgctatg gcgtgagccc cacaaagctg aatgacctgt gctttaccaa  4260
cgtgtacgcc gattccttcg tgatcagggg cgacagggtg cgccagatcg caccaggaca  4320
gacaggcaat atcgcagact acaattataa gctgcctgac gattcaccg gctgcgtgat   4380
cgcctggaac tctaacaatc tggatagcaa agtgggcggc aactacaatt atctgtaccg  4440
gctgtttaga aagtctaatc tgaagccatt cgagagggac atctccacag aaatctacca  4500
ggccggctct acccccctgca atggcgtgaa gggctttaac tgttatttcc ctctgcagag  4560
ctacggcttc cagccaacat atggcgtggg ctatccgcgt gg tggtgctgtc            4620
tttttgagctg ctgcacgcac ctgcaacagt gtgcggacca aagaagagca ccaatctggt 4680
gaagaacaag tgcgtgaact tcaacttcaa cggactgacc ggaacaggcg tgctgaccga  4740
gtccaacaag aagttcctgc cttttcagca gttcggcagg gacatcgcag ataccacaga  4800
cgccgtgcgc gaccctcaga ccctggagat cctggacatc acaccatgct ccttcggcgg  4860
cgtgtctgtg atcacaccag gcaccaatac aagcaaccag gtggccgtgc tgtatcaggg  4920
cgtgaattgt accgaggtgc cagtggcaat ccacgcagat cagctgaccc ctacatggcg  4980
ggtgtactct accggcagca acgtgttcca gacaagagcc ggatgcctga tcggagcaga  5040
gcacgtgaac aatagctatg agtgcgacat ccctatcggc gccggcatct gtgcctccta  5100
ccagacccag acaaactccc caaggtctgt gggcgataca ggcctgtcca agaatccaat  5160
cgagctggta gagggctggt tcagcagttg gaaaagctcc atcgcctcct ttttctttat  5220
catcggcctg atcatcggac tgttcctggt gctccgcgtg ggtatccacc tgtgcatcaa  5280
gctgaagcac accaagaaaa gacagattta tacagacatc gagatgaacc gcctgggaaa  5340
gggatccggc tccggcgaga gcaggggaag tctactaaca tgcggggacg tggaggaaaa  5400
tccccggcccc atgaagtgcc ttttgtactt agccttttta ttcattgggg tgaattgcaa  5460
gttcaccata gtttttccac acaaccaaaa aggaaactgg aaaaatgttc cttctaatta  5520
ccattattgc ccgtcaagct cagatttaaa ttggcataat gacttaatag gcacagccat  5580
acaagtcaaa atgcccaaga gtcacaaggc tattcaagca gacggttgga tgtgtcatgc  5640
ttccaaatgg gtcactactt gtgatttccg ctggtatgga ccgaagtata taacacagtg  5700
catccgatcc ttcactccat ctgtagaaca atgcaaggaa agcattgaac aaacgaaaca  5760
aggaacttgg ctgaatccag gcttccctcc tcaaagttgt ggatatgcaa ctgtgacgga  5820
tgccgaagca gtgattgtcc aggtgactcc tcaccatgtg ctggttgata aatacacagg  5880
agaatgggtt gattcacagt tcatcaacgg aaaatgcagc aattacatat gccccactgt  5940
ccataactct acaacctggc attctgacta taaggtcaaa gggctatgtg attctaacct  6000
catttccatg gacatcacct tcttctcaga ggacggagag ctatcatccc tgggaaagga  6060
gggcacaggg ttcagaagta actactttgc ttatgaaact ggaggcaagg cctgcaaaat  6120
gcaatactgc aagcattggg gagtcagact cccatcaggt gtctggttcg agatggctga  6180
taaggatctc tttgctgcag ccagattccc tgaatgccca gaagggtcaa gtatctctgc  6240
tccatctcag acctcagtgg atgtaagtct aattcaggac gttgagagga tcttggatta  6300
ttccctctgc caagaaacct ggagcaaaat cagagcgggt cttccaatct ctccagtgga  6360
tctcagctat cttgctccta aaaacccagg aaccggtcct gctttcacca taatcaatgg  6420
taccctaaaa tactttgaga ccagatacat cagagtcgat attgctgctc aatcctctc   6480
aagaatggtc ggaatgatca gtggaactac cacagaaagg gaactgtggg atgactgggc  6540
accatatgaa gacgtggaaa ttggacccaa tggagttctg aggaccagtt caggatataa  6600
gtttcctta tacatgattg gacatggtat gtttggactcc gatcttcatc ttagctcaaa  6660
ggctcaggtg ttcgaacatc ctcacattca agacgctgct tcgcaacttc ctgatgatga  6720
gagtttattt tttggtgata ctgggctatc caaaaatcca atcgagcttg tagaaggttg  6780
gttcagtagt tggaaaagct ctattgcctc ttttttttctt atcatagggt taatcattgg  6840
actattcttg gttctccgag ttggtatcca tctttgcatt aaattaaagc acaccaagaa  6900
aagacagatt tatacagaca tagagatgaa ccgacttgga aagtaagcta gccagattct  6960
tcatgtttgg accaaatcaa cttgtgatac catgctcaaa gaggcctcaa ttatatttga  7020
gttttttaatt tttatgaaaa aaactaacag caatcatgga agtccacgat tttgagaccg  7080
acgagttcaa tgatttcaat gaagatgact atgccacaag agaattcctg aatcccagcg  7140
agcgcatgac gtacttgaat catgctgatt acaatttgaa ttctcctcta attagtgatg  7200
atattgacaa tttgatcagg aaattcaatt ctcttccgat tccctcgatg tgggatagta  7260
agaactggga tggagttctt gagatgttaa catcatgtca agccaatccc atctcaacat  7320
ctcagatgca taaatggatg ggaagttgt taatgtctga taatcatgat gccagtcaag  7380
ggtatagttt tttacatgaa gtggacaaag aggcagaaat aacatttgac gtggtggaga  7440
ccttcatccg cggctgggc aacaaaccaa ttgaatacat caaaaaggaa agatggaactg  7500
actcattcaa aattctcgct tatttgtgtc aaaagtttt ggacttacac aagttgcat    7560
taatcttaaa tgctgtctct gaggtggaat tgctcaactt ggcgaggact ttcaaaggca  7620
aagtcagaag aagttctcat ggaacgaaca tgccaggat tagggttccc agcttgggtc   7680
ctacttttat ttcagaagga tgggcttact tcaagaaact tgatattcta atggaccgaa  7740
actttctgtt aatggtcaaa gatgtgatta tagggaggat gcaaacggtg ctatccatgg  7800
tatgtagaat agacaacctg ttctcagagc aagacatctt ctcccttcta aatatctaca  7860
gaattggaga taaattgtg gagaggcagg gaaattttc ttatgacttg attaaaatgg    7920
tggaaccgat atgcaacttg aagctgatga aattagcaag agaatcaagg cctttagtcc  7980
cacaattccc tcattttgaa aatcatatca agacttctgt tgatgaaggg caaaaattg   8040
accgaggtat aagattcctc catgatcaga taatgagtgt gaaaacagtg gatctcacac  8100
tggtgattta tggatcgttc agacattggg gtcatcctt tatagattat tacactggac  8160
tagaaaaatt acattcccaa gtaaccatga agaaagatat tgatgtgtca tatgcaaaag  8220
cacttgcaag tgatttagct cggattgttc tatttcaaca gttcaatgat cataaaaagt  8280
ggttcgtgaa tggagacttg ctccctcatg atcatccctt taaagtcat gttaaagaaa    8340
atacatggcc cacagctgct caagttcaag atttggaga taaatggcat gaacttccgc   8400
tgattaaatg ttttgaaata cccgacttac tagacccatc gataatatac tctgacaaaa  8460
gtcattcaat gaataggtca gaggtgttga aacactgccg aatgaatccg aacactccta  8520
tccctagtaa aaaggtgttg cagactatgt tggacacaaa ggctaccaat tggaaagaat  8580
ttcttaaaga gattgatgag aagggcttag atgatgatga tctaattatt ggtcttaaag  8640
gaaaggagag ggaactgaag ttggcaggta gattttctc cctaatgtct tggaaattgc   8700
gagaatactt tgtaattacc gaatatttga taaagactca tttcgtccct atgtttaaag  8760
gcctgacaat ggcggacgat ctaactgcag tcattaaaaa gatgttagat tcctcatccg  8820
```

```
gccaaggatt gaagtcatat gaggcaattt gcatagccaa tcacattgat tacgaaaaat   8880
ggaataacca ccaaaggaag ttatcaaacg gcccagtgtt ccgagttatg ggccagttct   8940
taggttatcc atccttaatc gagagaactc atgaatttt tgagaaaagt cttatatact    9000
acaatggaag accagacttg atgcgtgttc acaacaacac actgatcaat tcaacctccc   9060
aacgagtttg ttggcaagga caagagggtg gactggaagg tctacggcaa aaaggatgga   9120
ctatcctcaa tctactggtt attcaaagag aggctaaaat cagaaacact gctgtcaaag   9180
tcttggcaca aggtgataat caagttattt gcacacagta taaaacgaag aaatcgagaa   9240
acgttgtaga attacagggt gctctcaatc aaatggtttc taataatgag aaaattatga   9300
ctgcaatcaa aataggga ca gggaagttag gacttttgat aaatgacgat gagactatgc   9360
aatctgcaga ttacttgaat tatggaaaaa taccgatttt ccgtggagtg attagagggt   9420
tagagaccaa gagatggtca cgagtgactt gtgtcaccaa tgaccaaata cccacttgtg   9480
ctaatataat gagctcagtt tccacaaatg ctctcaccgt agctcatttt gctgagaacc   9540
caatcaatgc catgatacag tacaattatt ttgggacatt tgctagactc ttgttgatga   9600
tgcatgatcc tgctcttcgt caatcattgt atgaagttca agataagata ccgggcttgc   9660
acagttctac tttcaaatac gccatgttgt atttggaccc ttccattgga ggagtgtcgg   9720
gcatgtcttt gtccaggttt ttgattagag ccttcccaga tcccgtaaca gaaagtctct   9780
cattctggag attcatccat gtacatgctc gaagtgagca tctgaaggag atgagtcag    9840
tatttggaaa ccccgagata gccaagtttc gaataactca catagacaag ctagtagaag   9900
atccaacctc tctgaacatc gctatggaa tgagtccagc gaacttgtta aagactgagg    9960
ttaaaaaatg cttaatcgaa tcaagacaaa ccatcaggaa ccaggtgatt aaggatgcaa  10020
ccatatattt gtatcatgaa gaggatcggc tcagaagttt cttatggtca ataaatcctc  10080
tgttccctag atttttaagt gaattcaaat caggcacttt ttgggagtc gcagacgggc   10140
tcatcagtct atttcaaaat tctcgtacta ttcggaactc cttttaagaaa aagtatcata  10200
gggaattgga tgatttgatt gtgaggagtg aggtatcctc tttgacacat ttagggaaac  10260
ttcatttgag aaggggatca tgtaaaatgt ggacatgttc agctactcat gctgacacat  10320
taagatacaa atcctgggc cgtacagtta ttgggacaac tgtaccccat ccattagaaa   10380
tgttgggtcc acaacatcga aaagagactc cttgtgcacc atgtaacaca tcagggttca  10440
attatgtttc tgtgcattgt ccagacggga tccatgacgt ctttagttca cggggaccat  10500
tgcctgctta tctagggtct aaaacatctg aatctacatc tattttgcag ccttgggaaa  10560
gggaaagcaa agtcccactg attaaaagag ctacacgtct tagagatgct atctcttggt  10620
ttgttgaacc cgactctaaa ctagcaatga ctatactttc taacatccac tctttaacag  10680
gcgaagaatg gaccaaaagg cagcatgggt tcaaaagaac agggtctgcc cttcataggt  10740
tttcgacatc tcggatgagc catggtgggt tcgcatctca gagcactgca gcattgacca  10800
ggtgatggc aactacagac accatgaggg atctgggaga tcagaatttc gactttttat   10860
tccaagcaac gttgctctat gctcaaatta ccaccacgt tgcaagagac ggatggatca   10920
ccagttgtac agatcattat catattgcct gtaagtcctg tttgagaccc atagaagaga  10980
tcaccctgga ctcaagtatg gactacacgc cccagatgt atccatgtg ctgaagacat    11040
ggaggaatgg ggaaggttcg tggggacaag agataaaaca gatctatcct ttagaaggga  11100
attggagaa tttagcacct gctgagcaat cctatcaagt cggcagatgt ataggttttc   11160
tatatggaga cttggcgtat agaaaatcta ctcatgccga ggacagttct ctatttcctc   11220
tatctataca aggtcgtatt agaggtcgag gtttcttaaa agggttgcta gacggattaa  11280
tgagagcaag ttgctgccaa gtaatacacc ggagaagtct ggctcatttg aagaggccgg  11340
ccaacgcagt gtacggaggt ttgatttact tgattgatga attgagtgta tcacctccat  11400
tcctttctct tactagatca ggacctatta gagacgaatt agaaacgatt ccccacaaga  11460
tcccaacctc ctatccgaca agcaaccgtg atatgggggt gattgtcaga aattacttca  11520
aataccaatg ccgtctaatt gaaaagggaa aatacagatc acattattca caattatggt  11580
tattctcaga tgtcttatcc atagacttca ttggaccatt ctctatttcc accaccctct  11640
tgcaaatcct atacaagcca ttttttatctg ggaaagataa gaatgagttg agagagctgg  11700
caaatctttc ttcattgcta agatcaggag aggggtggga agacatacat gtgaaattct  11760
tcaccaagga catattattg tgtccagagg aaatcagaca tgcttgcaag ttcgggattg  11820
ctaaggataa taataaagac atgagctatc ccccttgggg aagggaatcc agagggacaa  11880
ttacaacaat ccctgtttat tatacgacca cccttaccc aaagatgcta gagatgcctc    11940
caagaatcca aaatcccctg ctgtccgaaa tcaggttggg ccaattacca actgcgctc   12000
attataaaat tcgagtata ttacatgaa tgggaatcca ttacagggac ttcttgagtt    12060
gtggagacgg ctccggaggg atgactgctg cattactacg agaaaatgtg catgcagag    12120
gaatattcaa tagtctgtta gaattatcag ggtcagtcat gcgaggcgcc tctcctgagc   12180
ccccccagtgc cctagaaact ttaggaggag ataaatcgag atgtgtaaat ggtgaaacat  12240
gttgggaata tccatctgac ttatgtgacc caaggacttg ggactatttc ctccgactca  12300
aagcaggctt ggggcttcaa attgatttaa ttgtaatgga tatggaagtt cgggattctt  12360
ctactagcct gaaaattgag acgaatgtta gaaattatgt gcaccggatt ttggatgagc  12420
aaggagtttt aatctacaag acttatgaa catatatttg tgagagcgaa aagaatgcag   12480
taacaatcct tggtcccatg ttcaagacgg tcgacttagt tcaaacagaa tttagtagtt  12540
ctcaaacgtc tgaagtatat atggtatgta aaggtttgaa gaaattaatc gatgaaccca  12600
atcccgattg gtcttccatc aatgaatcct tgaaaaacct gtacgcattc cagtcatcag   12660
aacaggaatt tgccagagca aagaaggtta gtacatactt taccttgaca ggtattccct  12720
cccaattcat tcctgatcct tttgtaaaca ttgagactat gctacaaata ttcggagtac  12780
ccacgggtgt gtctcatgcg gctgccttaa aatcatctga tagcctgca gatttattga   12840
ccattagcct ttttttatatg gcgattatat cgtattataa catcaatcat atcagagtag  12900
gaccgatacc tccgaacccc ccatcagatg gaattgcaca aaatgtgggg atcgctataa  12960
ctggtataag ctttttggctg agtttgatgg agaaagacat tccactatat caacagtgtt  13020
tagcagttat ccagcaatca ttcccgatta ggtgggaggc tgtttcagta aaaggaggat  13080
acaagcagaa gtggagtact agaggtgatg ggctcccaaa agatacccga acttcagact  13140
ccttggcccc aatcgggaac tggatcagat ctctggaatt ggtccgaaac caagttcgtc  13200
taaatccatt caatgagatc taccggaatc tcagagcttc agtcgtgaat aatcatttga  13260
aatggtcaaa tttgcgaaga aacacagaa tgattgaatg gatcaataga cgaatttcaa   13320
aagaagaccg gtctatactg atgttgaaga gtgacctaca cgaggaaaac tcttggagag  13380
attaaaaaat catgaggaga ctccaaactt taagtatgaa aaaaactttg atccttaaga  13440
ccctcttgtg gtttttattt tttatctggt tttgtggtct tcgt                   13484
```

```
SEQ ID NO: 26           moltype = DNA  length = 12156
FEATURE                 Location/Qualifiers
misc_feature            1..12156
                        note = VSV vector: Convac V5 China
source                  1..12156
                        mol_type = other DNA
                        organism = synthetic construct
SEQUENCE: 26
acgaagacaa acaaaccatt attatcatta aaaggctcag gagaaacttt aacagtaatc  60
aaaatgtctg ttacagtcaa gagaatcatt gacaacacag tcatagttcc aaaacttcct  120
gcaaatgagg atccagtgga atacccggca gattacttca gaaaatcaaa ggagattcct  180
ctttacatca atactacaaa aagtttgtca gatctaagag gatatgtcta ccaaggcctc  240
aaatccggaa atgtatcaat catacatgtc aacagctact tgtatggagc attaaaggac  300
atccggggta agttggataa agattggtca agtttcggaa taaacatcgg gaaagcaggg  360
gatacaatcg gaatatttga ccttgtatcc ttgaaagccc tggacggcgt acttccagat  420
ggagtatcgg atgcttccag aaccagcgca gatgacaaat ggttgccttt gtatctactt  480
ggcttataca gagtgggcag aacacaaatg cctgaataca gaaaaaagct catggatggg  540
ctgacaaatc aatgcaaaat gatcaatgaa cagtttgaac ctcttgtgcc agaaggtcgt  600
gacatttttg atgtgtgggg aaatgacagt aattacacaa aaattgtcgc tgcagtggac  660
atgttcttcc acatgttcaa aaaacatgaa tgtgcctcgt tcagatacgg aactattgtt  720
tccagattca aagattgtgc tgcattggca acatttggac acctctgcaa aataaccgga  780
atgtctacag aagatgtaac gacctggatc ttgaaccgag aagttgcaga tgaaatggtc  840
caaatgatgc ttccaggcca agaaattgac aaggccgatt catacatgcc ttatttgatc  900
gactttggat tgtcttctaa gtctccatat tcttccgtca aaaaccctgc cttccacttc  960
tgggggcaat tgacagctct tctgctcaga tccaccagag caaggaatgc ccgacagcct  1020
gatgacattg agtatacatc tcttactaca gcaggtttgt tgtacgctta tgcagtagga  1080
tcctctgccg acttggcaca acagttttgt gttggagata acaaatacac tccagatgat  1140
agtaccggag gattgacgac taatgcaccg ccacaaggca gagatgtggt cgaatggctc  1200
ggatggtttg aagatcaaaa cagaaaaccg actcctgata tgatgcagta tgcgaaaaga  1260
gcagtcatgt cactgcaagg cctaagagag aagacaattg gcaagtatgc taagtcagaa  1320
tttgacaaat gaccctataa ttctcagatc acctattata tattatgcta catatgaaaa  1380
aaactaacag atatcatgga taatctcaca aaagttcgtg agtatctcaa gtcctattct  1440
cgtctggatc aggcggtagg agagatagat gagatcgaag cacaacgagc tgaaaagtcc  1500
aattatgagt tgttccaaga ggatggagtg gaagagcata ctaagccctc ttattttcag  1560
gcagcagatg attctgacac agaatctgaa ccagaaattg aagacaatca aggtttgtat  1620
gcaccagatc cagaagctga gcaagttgaa ggctttatac aggggccttt agatgactat  1680
gcagatgagg aagtggatgt tgtatttact tcggactgga aacagcctga gcttgaatct  1740
gacgagcatg gaaagacctt acggttgaca tcgccagagg gtttaagtgg agagcagaaa  1800
tcccagtggc tttcgacgat taaagcagtc gtgcaaagtg ccaaatactg gaatctggca  1860
gagtgcacat ttgaagcatc gggagaaggg gtcattatga aggagcgcca gataactccg  1920
gatgtatata aggtcactcc agtgatgaac acacatccgt cccaatcaga agcagtatca  1980
gatgtttggt ctctctcaaa gacatccatg actttccaac ccaagaaagc aagtcttcag  2040
cctctcacca tatccttgga tgaattgttc tcatctagag gagagttcat ctctgtcgga  2100
ggtgacggac gaatgtctca taaagaggcc atcctgctcg gcctgagata caaaaagttg  2160
tacaatcagg cgagagtcaa atattctctg tagactatga aaaaaagtaa cagatatcac  2220
gatctaagtg ttatcccaat ccattcatca tgagttcctt aaagaagatt ctcggtctga  2280
aggggaaagg taagaaatct aagaaattag ggatcgcacc acccccttat gaagaggaca  2340
ctagcatgga gtatgctccg agcgctccaa ttgacaaatc ctattttgga gttgacgaga  2400
tggacaccta tgatccgaat caattaagat atgagaaatt cttctttaca gtgaaaatga  2460
cggttagatc taatcgtccg ttcagaacat actcagatgt ggcagccgct gtatcccatt  2520
gggatcacat gtacatcgga atggcaggga aacgtccctt ctacaaaatc ttggcttttt  2580
tgggttcttc taatctaaag gccactccag cggtattggc agatcaaggt caaccagagt  2640
atcacactca ctgcgaaggc agggcttatt tgccacatag gatggggaag acccctccca  2700
tgctcaatgt accagagcac ttcagaagac cattcaatat aggtctttac aagggaacga  2760
ttgagctcac aatgaccatc tacgatgatg agtcactgga agcagctcct atgatctggg  2820
atcatttcaa ttcttccaaa ttttctgatt tcagagagaa ggccttaatg tttggcctga  2880
ttgtcgagaa aaaggcatct ggagcgtggg tcctggattc tatcagccac ttcaaatgag  2940
ctagtctaac ttctagcttc tgaacaatcc ccggtttact cagtctctcc taattccagc  3000
ctctcgaaca actaatatcc tgtcttttct atccctatga aaaaaactaa cagagatcga  3060
tctgtttacg cgtcactatg aagtgccttt tgtacttagc ctttttattc attggggtga  3120
attgcaagtt caccatagtt tttccacaca accaaaaagg aaactggaaa aatgttcctt  3180
ctaattacca ttattgcccg tcaagctcag atttaaattg gcataatgac ttaataggca  3240
cagccataca agtcaaaatg cccaagagtc acaaggctat tcaagcagac ggttggatgt  3300
gtcatgcttc caaatgggtc actacttgtg atttccgctg gtatggaccg aagtatataa  3360
cacagtccat ccgatccttc actccatctg tagaacaatg caaggaaagc attgaacaaa  3420
cgaaacaagg aacttggctg aatccaggct tccctcctca aagttgtgga tatgcaactg  3480
tgacggatgc cgaagcagtg attgtccagg tgactcctca ccatgtgctg gttgatgaat  3540
acacaggaga atgggttgat tcacagttca tcaacggaaa atgcagcaat tacatatgcc  3600
ccactgtcca taactctaca acctggcatt ctgactataa ggtcaaaggg ctatgtgatt  3660
ctaacctcat ttccatggac atcaccttct tctcagagga cggagagcta tcatccctgg  3720
gaaaggaggg cacagggttc agaagtaact actttgctta tgaaactgga ggcaaggcct  3780
gcaaaatgca atactgcaag cattggggag tcagactccc atcaggtgtc tggttcgaga  3840
tggctgataa ggatctcttt gctgcagcca gattccctga atgcccagaa gggtcaagta  3900
tctctgctcc atctcagacc tcagtggatg taagtctaat tcaggacgtt gagaggatct  3960
tggattattc cctctgccaa gaaacctgga gcaaaatcag agcgggtctt ccaatctctc  4020
cagtggatct cagctatctt gctcctaaaa acccaggaac cggtcctgct ttcaccataa  4080
tcaatggtac cctaaaatac tttgagacca gatacatcag agtcgatatt gctgctccaa  4140
tcctctcaag aatggtcgga atgatcagtg gaactaccac agaaagggaa ctgtgggatg  4200
actgggcacc atatgaagac gtggaaattg gacccaatgg agttctgagg accagttcag  4260
```

```
gatataagtt tcctttatac atgattggac atggtatgtt ggactccgat cttcatctta   4320
gctcaaaggc tcaggtgttc gaacatcctc acattcaaga cgctgcttcg caacttcctg   4380
atgatgagag tttattttt ggtgatactg ggctatccaa aaatccaatc gagcttgtag    4440
aaggttggtt cagtagttgg aaaagctcta ttgcctcttt tttctttatc ataggggtaa   4500
tcattggact attcttggtt ctccgagttg gtatccatct ttgcattaaa ttaaagcaca   4560
ccaagaaaag acagatttat acagacatag atgatgaaccg acttggaaag taactcaaat  4620
cctgctaggt atgaaaaaaa ctaacagata tcacgctcga ggccaccatg aagtgcctgt   4680
tgtacttagc cttcctgttc atcggggtga attgccgctt tcccaatatc acaaacctgt   4740
gcccttttgg cgaggtgttc aacgcaaccc gcttcgcag cgtgtacgcc tggaatagga   4800
agcgcatctc caactgcgtg gccgactatt ctgtgctgta caacagcgcc tccttctcta   4860
cctttaagtg ctatgcgtg agccccacaa agctgaatga cctgtgcttt accaacgtgt    4920
acgccgattc cttcgtgatc aggggcgacg aggtgcgcca gatcgcacca ggacagacag   4980
gcaagatcgc agactacaat tataagctgc ctgacgattt caccggctgc gtgatcgcct   5040
ggaactctaa caatctggat agcaaagtgg gcggcaacta caattatctg taccggctgt   5100
ttagaaagtc taatctgaag ccattcgaga gggacatctc cacagaaatc taccaggccg   5160
gctctacccc ctgcaatggc gtggagggct taactgtta tttccctctg cagagctacg     5220
gcttccagcc aacaaacggc gtgggctatc agccctaccg cgtggtggtg ctgtcttttg   5280
agctgctgca cgcacctgca acagtgtgcg gaccaaagaa gagcaccaat ctggtgaaga   5340
acaagtgcgt gaacttcaac ggctctggat ccggctacat ccccgaggcc cccagagacg   5400
gccaggccta cgtgcggaag gacggcgagt gggtactgct cagcaccttc ctgggcagca   5460
gttggaaaag ctccatcgcc tcctttttct ttatcatcgg cctgatcatc ggactgttcc   5520
tggtgctccg cgtgggtatc cacctgtgca tcaagctgaa gcaccaag aaaagacaga     5580
tttatacaga catcgagatg aaccgacttg gaaagtaagc tagccagatt cttcatgttt   5640
ggaccaaatc aacttgtgat accatgctca aagaggcctc aattatattt gagtttttaa   5700
tttttatgaa aaaactaac agcaatcatg gaagtccacg attttgagac cgacgagttc    5760
aatgatttca atgaagatga ctatgccaca agagaattcc tgaatcccga tgagcgcatg   5820
acgtacttga atcatgctga ttacaatttg aattctcctc taattagtga tgatattgac   5880
aatttgatca ggaaattcaa ttctcttccg attccctcga tgtgggatag taagaactgg   5940
gatggagttc ttgagatgtt aacatcatgt caagccaatc ccatctcaac atctcagatg   6000
cataaatgga tgggaagttg gttaatgtct gataatcata atgccagtca agggtatagt   6060
tttttacatg aagtggacaa agaggcagaa ataacatttg acgtggtgga gaccttcatc   6120
cgcggctggg gcaacaaacc aattgaatac atcaaaaagg aaagatggac tgactcattc   6180
aaaattctcg cttatttgtg tcaaaagttt ttggacttac acaagttgac attaatctta   6240
aatgctgtct ctgaggtgga attgctcaac ttggcgagga ctttcaaagg caaagtcaga   6300
agaagttctc atggaacgaa catatgcagg attagggttc ccagcttggg tcctacttt    6360
atttcagaag gatgggctta cttcaagaaa cttgatattc taatggaccg aaactttctg   6420
ttaatggtca aagatgtgat tatagggagg atgcaaacgg tgctatccat ggtatgtaga   6480
atagacaacc tgttctcaga gcaagacatc ttctcccttc taaatatcta cagaattgga   6540
gataaaattg tggagaggca gggaaatttt tcttatgact tgattaaaat ggtggaaccg   6600
atatgcaact tgaagctgat gaaattagca agagaatcaa ggcctttagt cccacaattc   6660
cctcattttg aaaatcatat caagacttct gttgatgaag gggcaaaaat tgaccgaggt   6720
ataagattcc tccatgatca gataatgagt gtgaaaacag tggatctcac actggtgatt   6780
tatggatcgt tcagacattg gggtcatcct tttatagatt attacactgg actagaaaaa   6840
ttacattccc aagtaaccat gaagaaagat attgatgtgt catatgcaaa agcacttgca   6900
agtgatttag ctcggattgt tctatttcaa cagttcaatg atcataaaaa gtggttcgtg   6960
aatggagact tgctccctca tgatcatccc tttaaaagtc atgttaaaga aaatacatgg   7020
cccacagctg ctcaagttca agattttgga gataaatggt atgaacttcc gctgattaaa   7080
tgttttgaaa tacccgactt actagaccca tcgataatat actctgacaa aagtcattca   7140
atgaataggt cagaggtgtt gaaacatgtc cgaatgaatc cgaacactcc tatccctagt   7200
aaaaaggtgt tgcagactat gttggacaca aaggctacca attggaaaga atttcttaaa   7260
gagattgatg agaagggctt agatgatgat gatctaatta ttggtcttaa aggaaaggag   7320
agggaactga agttggcagg tagattttc tccctaatgt cttggaaatt gcgagaatac    7380
tttgtaatta ccgaatattt gataaagact catttcgtcc ctatgtttaa aggcctgaca   7440
atggcggacg atctaactgc agtcattaaa agatgttag attcctcatc cggccaagga   7500
ttgaagtcat atgaggcaat ttgcatagcc aatcacattg attacgaaaa atggaataac   7560
caccaaagga agttatcaaa cggcccagtg ttccgagtta tgggccagtt cttaggttat   7620
ccatccttaa tcgagagaac tcatgaattt tttgagaaaa gtcttatata ctacaatgga   7680
agaccagact tgatgcgtgt tcacaacaac acactgatca attcaacctc caacgagttt   7740
tgttggcaag gacaagaggg tggactggaa ggtctacggc aaaaaggatg gactatcctg   7800
aatctactgg ttattcaaag agaggctaaa atcagaacaa ctgtgtcaa agtcttggca    7860
caaggtgata tcaagttat ttgcacacag tataaaacga agaaatcgag aaacgttgta    7920
gaattacagg gtgctctcaa tcaaatggtt tctaataatg agaaaattat gactgcaatc   7980
aaaataggga caggaagtt aggactttg ataaatgacg atgagactat gcaatgtgca    8040
gattacttga attatggaaa aataccgatt ttccgtgagt gattagagg gttagagacc   8100
aagagatggt cacgagtgac ttgtgtcacc aatgaccaaa tacccacttg tgctaatata   8160
atgagctcag tttccacaaa tgctctcacc gtagctcatt tgctgagaa cccaatcaat   8220
gccatgatac agtacaatta ttttgggaca tttgctagac tcttgttgat gatgcatgat   8280
cctgctcttc gtcaatcatt gtatgaagtt caagataaga tacccggctt gcacagttct   8340
actttcaaat acgcatgtt gtatttggac ccttccattg gagggtgtc gggcatgtct    8400
ttgtccaggt ttttgattag agccttccca gatcccgtaa cagaaagtct ctcattctgg   8460
agattcatcc atgtacatgc tcgaagtgag catctgaagg agatgagtgc agtatttgga   8520
aacccccgaga tagccaagtt tcgaataact cacatagaca agctagtaga agatccaacc   8580
tctctgaaca tcgctatggg aatgagtcca gcgaacttgt taaagactga ggttaaaaaa   8640
tgcttaatcg aatcaagaca aaccatcagg aaccaggtga ttaaggatgc aaccatatat   8700
ttgtatcatg aagaggatcg gctcagaagt ttcttatggt caataaatcc tctgttccct   8760
agatttttaa gtgaattcaa atcaggcact ttttgggag tcgcagacgg gctcatcagt    8820
ctatttcaaa attctcgtac tattcggaac tcctttaaga aaaagtatca tagggaattg   8880
gatgatttga ttgtgaggag tgaggtatcc tctttgacac atttagggaa acttcatttg   8940
agaaggggat catgtaaaat gtggacatgt tcagctactc atgctgacac attaagatac   9000
```

```
aaatcctggg gccgtacagt tattgggaca actgtacccc atccattaga aatgttgggt   9060
ccacaacatc gaaaagagac tccttgtgca ccatgtaaca catcagggtt caattatgtt   9120
tctgtgcatt gtccagacgg gatccatgac gtctttagtt cacggggacc attgcctgct   9180
tatctagggt ctaaaacatc tgaatctaca tctattttgc agccttggga aagggaaagc   9240
aaagtcccac tgattaaaag agctacacgt cttagagatg ctatctcttg gtttgttgaa   9300
cccgactcta aactagcaat gactatactt tctaacatcc actctttaac aggcgaagaa   9360
tggaccaaaa ggcagcatgg gttcaaaaga cagggtctg cccttcatag gttttcgaca    9420
tctcggatga gccatggtgg gttcgcatct cagagcactg cagcattgac caggttgatg   9480
gcaactacag acaccagatt ggatctggga gatcagaatt cgacttttt attccaagca    9540
acgttgctct atgctcaaat taccaccact gttgcaagag acggatggat caccagttgt   9600
acagatcatt atcatattgc ctgtaagtcc tgtttgagac ccatagaaga gatcaccctg   9660
gactcaagta tggactacac gccccagat gtatcccatg tgctgaagac atggaggaat    9720
ggggaaggtt cgtggggaca agagataaaa cagatctatc ctttagaagg gaattggaag   9780
aatttagcac ctgctgagca atcctatcaa gtcggcagat gtataggttt tctatatgga   9840
gacttggcgt atagaaaatc tactcatgcc gaggacagtt ctctatttcc tctatctata   9900
caaggtcgta ttagaggtcg aggtttctta aaagggttgc tagacggatt aatgagagca   9960
agttgctgcc aagtaataca ccggagaagt ctggctcatt gaagaggcc ggccaacgca   10020
gtgtacggag gtttgattta cttgattgat aaattgagtg tatcacctcc attccttct   10080
cttactagat caggacctat tagagacgaa ttagaaacga ttccccacaa gatcccaacc   10140
tcctatccga caagcaaccg tgatatgggg gtgattgtca gaaattactt caaataccaa   10200
tgccgtctaa ttgaaaaggg aaaatacaga tcacattatt cacaattatg gttattctca   10260
gatgtcttat ccatagactt cattggacca ttctctattt ccaccacccc cttgcaaatc   10320
ctatacaagc cattttatc tgggaaagat aagaatgagt tgagagagct ggcaaatctt   10380
tcttcattgc taagatcagg agaggggtgg aagacatac atgtgaaatt cttcaccaag   10440
gacatattat tgtgtccaga ggaaatcaga catgcttgca agtcgggat tgctaaggat   10500
aataataaag acatgagcta tccccctggg ggaagggaat ccagagggac aaattacaaca   10560
atccctgttt attatacgac cacccccttac ccaaagatgc tagagatgcc tccaagaatc   10620
caaaatcccc tgctgtccgg aatcaggttg ggcaattac caactggcgc tcattataaa   10680
attcggagta tattacatgg aatgggaatc cattacaggg acttcttgag ttgtggagac   10740
ggctccggag ggatgactgc tgcattacta cgagaaatgt tcatagcag aggaatattc   10800
aatagtctgt tagaattatc agggtcagtc atgcgaggcg cctctcctga gcccccagt    10860
gccctagaaa ctttaggagg agataaatcg agatgtgtaa atggtgaaac atgttgggaa   10920
tatccatctg acttatgtga cccaaggact tgggactatt tcctccgact caaagcaggc   10980
ttggggcttc aaattgattt aattgtaatg gatatggaag ttcggggatct ttctactagt   11040
ctgaaaattg agacgaatgt tagaaattat gtgcaccgga ttttggatga gcaaggagtt   11100
ttaatctaca agacttatgg aacatatat tgtgagagcg aaaagaatgc agtaacaatc    11160
cttggtccca tgttcaagac ggtcgactta gttcaaacag aatttagtag ttctcaaacg   11220
tctgaagtat atatggtatg taaaggtttg aagaattaa tcgatgaacc caatcccgat    11280
tggtcttcca tcaatgaatc ctggaaaaac ctgtacgcat tccagtcatc agaacaggaa   11340
tttgccagag caaagaaggt tagtacatac tttaccttga caggtattcc ctcccaattc   11400
attcctgatc ctttttgtaaa cattgagact atgctacaaa tattcggagt acccacgggt   11460
gtgtctcatg cggctgcctt aaaaatcatct gatagacctg cagatttatt gaccattagc   11520
ctttttata tggcgattat atcgtattat aacatcatat atcagagt aggaccgata    11580
cctccgaacc ccccatcaga tggaattgca caaatgtgg ggatcgctat aactggtata   11640
agcttttggc tgagtttgat ggagaaagac attccactat atcaacagtg tttagcagtt   11700
atccagcaat cattcccgat taggtgggag gctgtttcag taaaaggagg atacaagcag   11760
aagtgagta ctagaggtga tgggctccca aagataccc gaacttcaga ctccttggcc   11820
ccaatcggga actggatcag atctctggaa ttggtccgaa accaagttcg tctaaatcca   11880
ttcaatgaga tcttgttcaa tcagctatgt cgtacagtgg ataatcattt gaaatggtca   11940
aatttgcgaa gaaacacagg aatgattgaa tggatcaata gacgaatttc aaaagaagac   12000
cggtctatac tgatgttgaa gagtgaccta cacgaggaaa actcttggag agattaaaaa   12060
atcatgagga gactccaaac tttaagtatg aaaaaaactt tgatccttaa gaccctcttg   12120
tggtttttat tttttatctg gttttgtggg cttcgt                            12156

SEQ ID NO: 27        moltype = DNA   length = 12156
FEATURE              Location/Qualifiers
misc_feature         1..12156
                     note = VSV vector: Convac V5 South Africa
source               1..12156
                     mol_type = other DNA
                     organism = synthetic construct
SEQUENCE: 27
acgaagacaa acaaaccatt attatcatta aaaggctcag gagaaacttt aacagtaatc    60
aaaatgtctg ttacagtcaa gagaatcatt gacaacacag tcatagtttc aaaacttcct   120
gcaaatgagg atcagtgga ataccccgca gattacttca gaaaatcaaa ggagattcct   180
ctttacatca atactacaaa aagtttgtca gatctaagag gatatgtcta ccaaggcctc   240
aaatccggaa atgtatcaat catacatgtc aacagctact gtatggagc attaaaggac    300
atccggggta agttggataa agattggtca agtttcggaa taaacatcgg gaaagcaggg   360
gatacaatcg gaatatttga ccttgtatcc ttgaaagcc tggacggcgt acttccagat   420
ggagtatcgg atgcttccag aaccagcgca gatgacaaat ggttgccttt gtatctactt   480
ggcttataca gagtgggcag aacacaaatg cctgaataca gaaaaagct catggatggg   540
ctgacaaatc aatgcaaaat gatcaatgaa cagtttgaac ctcttgtgcc agaaggtcgt   600
gacattttt atgtgtgggg aaatgacagt aattacacaa aaattgtcgc tgcagtggac   660
atgttcttcc acatgttcaa aaacatgag tgtcctcata cagacggtaca aactattgtt   720
tccagattca agattgtgc tgcattggca acatttggaa acctctgcaa ataaccgga    780
atgtctacag aagatgtaac gacctggatc ttgaaccgag aagttgcaga tgaaatggtc   840
caaatgatgt tccaggcca agaaattgac aaggccgatt catacatgcc ttatttgatc   900
gactttggat tgtcttctaa gtctccatat tcttccgtca aaaaccctgc cttccacttc   960
tgggggcaat tgacagctct tctgctcaga tccaccagag caaggaatgc cgacagcct    1020
```

-continued

```
gatgacattg agtatacatc tcttactaca gcaggtttgt tgtacgctta tgcagtagga   1080
tcctctgccg acttggcaca acagtttgt gttggagata acaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaagaa   1260
gcagtcatgt cactgcaagg cctaagagag aagacaattg gcaagtatgc taagtcagaa   1320
tttgacaaat gacccctataa ttctcagatc acctattata tattatgcta catatgaaaa   1380
aaactaacag atatcatgga taatctcaca aaagttcgtg agtatctcaa gtcctattct   1440
cgtctggatc aggcggtagg agagatagat gagatcgaag cacaacgagc tgaaaagtcc   1500
aattatgagt tgttccaaga ggatggagtg gaagagcata ctaagccctc ttatttttcag  1560
gcagcagatg attctgacac agaatctgaa ccagaaattg aagacaatca aggtttgtat   1620
gcaccagatc cagaagctga gcaagttgaa ggctttatac aggggccttt agatgactat   1680
gcagatgagg aagtggatgt tgtatttact tcggactgga aacagcctga gcttgaatct   1740
gacgagcatg gaaagacctt acggttgaca tcgccagagg gtttaagtgg agagcagaaa   1800
tcccagtggc tttcgacgat taaagcagtc gtgcaaagtg ccaaatactg gaatctggca   1860
gagtgcacat ttgaagcatc gggagaaggg gtcattatga aggagcgcca gataactccg   1920
gatgtatata aggtcactcc agtgatgaac acacatccgt cccaatcaga agcagtatca   1980
gatgtttggt ctctctcaaa gacatccatg actttccaac ccaagaaagc aagtcttcag   2040
cctctcacca tatccttgga tgaattgttc tcatctagag gagagttcat ctctgtcgga   2100
ggtgacggac gaatgtctca taaagaggcc atcctgctcg gcctgagata caaaaagttg   2160
tacaatcagg cgagagtcaa atattctctg tagactatga aaaaagtaa cagatatcac   2220
gatctaagtg ttatcccaat ccattcatca tgagttcctt aaagaagatt ctcggtctga   2280
aggggaaaag taagaaatct aagaaattag ggatcgcacc accccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgg ggcagccgct gtatcccatt   2520
gggatcacat gtacatcgga atggcaggga aacgtccctc ctacaaaatc ttggcttttt   2580
tgggttcttc taatctaaag gccactccag cggtattggc agatcaaggt caaccagagt   2640
atcacactca ctgcgaaggc agggcttatt tgccacatag gatggggaag accctctccca  2700
tgctcaatgt accagagcac ttcagaagac cattcaatat aggtctttac aagggaacga   2760
ttgagctcac aatgaccatc tacgatgatg agtcactgga agcagctcct atgatctgga   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctaac ttctagcttc tgaacaatcc ccggtttact cagtctctcc taattccagc   3000
ctctcagaca actaatatcc tgtcttttct atccctatga aaaaaactaa cagagatcga   3060
tctgtttacg cgtcactatg aagtgccttt tgtacttagc ctttttattc attggggtga   3120
attgcaagtt caccatagtt tttccacaca accaaaaagg aaactggaaa aatgttcctt   3180
ctaattacca ttattgcccg tcaagctcag atttaaattg gcataatgac ttaataggca   3240
cagccataca agtcaaaatg cccaagagtc acaaggctat tcaagcagac ggttggatgt   3300
gtcatgcttc caaatgggtc actacttgtg atttccgctg gtatgaccg aagtatataa   3360
cacagtccat ccgatccttc actccatctg tagaacaatg caaggaaagc attgaacaaa   3420
cgaaacaagg aacttggctg aatccaggct tccctcctca aagttgtgga tatgcaactg   3480
tgacggatgc cgaagcagtg attgtccagg tgactcctca ccatgctgtt gatgaat     3540
acacaggaga atgggttgat tcacagttca tcaacggaaa atgcagcaat tacatatgcc   3600
ccactgtcca taactctaca acctggcatt ctgactataa ggtcaaaggg ctatgtgatt   3660
ctaacctcat ttccatggac atcaccttct tctcagagga cggagagcta tcatccctgg   3720
gaaaggaggg cacagggttc agaagtaact actttgctta tgaaactgga ggcaaggcct   3780
gcaaaatgca atactgcaag cattggggag tcagactccc atcaggtgtc tggttcgaga   3840
tggctgataa ggatctcttt gctgcagcca gattccctga atgcccagaa gggtcaagta   3900
tctctgctcc atctcagacc tcagtggatg taagtctaat tcaggacgtt gagaggatct   3960
tggattattc cctctgccaa gaaacctgga gcaaaatcag agcgggtctt ccaatctctc   4020
cagtgatctc cagctatctt gctcctaaaa acccaggaac cggtcctgct ttcaccataa   4080
tcaatggtac cctaaaatac tttgagacca gatacatcag agtcgatatt gctgctccaa   4140
tcctctcaag aatggtcgga atgatcagtg gaactaccac agaaaggaa ctgtgggatg   4200
actgggcacc atatgaagac gtggaaattg acccaatgg agttcgagg accagttcag   4260
gatataagtt tccttatac atgattggac atggtatgt ggactccgat cttcatctta   4320
gctcaaaggc tcaggtgttc gaacatcctc acattcaaga cgctgcttcg caacttcctg   4380
atgatgagag tttattttt ggtgatactg gctatccaa aaatccaatc gagcttgtag   4440
aaggttggtt cagtagttgg aaaagctcta ttgcctcttt tttctttatc ataggttaa    4500
tcattggact attcttggtt ctccgagttg tatccatct ttgcattaaa ttaaagcaca   4560
ccaagaaaag acagatttat acagacatag atgaaccg acttggaaag taactcaaat   4620
cctgctaggt atgaaaaaa ctaacagata tcacgctcga ggccaccatg aagtgcctgt   4680
tgtacttagc cttcctgttc atcggggtga attgccgctt cccaatatc acaaacctgt   4740
gcccttttgg cgaggtgttc aacgcaaccc gcttcgccag cgtgtacgcc tggaatagga   4800
agcgcatctc caactgcgtg gccgactatt ctgtgctgta caacgcgtc tcctctctta   4860
cctttaagtg ctatggcgtg agccccacaa agctgaatga cctgtgcttt accaacgtgt   4920
acgccgattc cttcgtgatc aggggcgacg aggtgcgcca gatcgcacca ggacagacag   4980
gcaatatcgc agactacaat tataagctgc ctgacgattt caccggctgc gtgatcgcct   5040
ggaactctaa caatcctggat agcaaagtgg gcggcaacta caattatctg taccggctgt   5100
ttagaaagtc taatctgaag ccattcgaga gggacatctc cacagaaatc taccaggccg   5160
gctctacccc ctgcaatggc gtgaagggct ttaactgtta ttttccctct gagagctacg   5220
gcttccagcc aacatatggc gtgggctatc agccctaccg cgtggtggtg ctgtcttttg   5280
agctgctgca cgcacctgca acagtgtgcg gaccaaagaa gagcaccaat ctggtgaaga   5340
acaagtgcgt gaacttcaac ggctctggat ccggctacat ccccgaggcc ccagagacg   5400
gccaggccta cgtgcggaag gacggcgagt cagcacctc ctgggcagca                5460
gttggaaaag ctccatcgcc tccttttct ttatcatcgg cctgatcatc ggactgttcc   5520
tggtgctccg cgtgggtatc cacctgtgca tcaagctgaa gcacaccaag aaaagacaga   5580
tttatacaga catcgagatg aaccgacttg gaaagtaagc tagccagatt cttcatgttt   5640
ggaccaaatc aacttgtgat accatgctca aagaggcctc aattatattt gagttttaa    5700
tttttatgaa aaaaactaac agcaatcatg gaagtccacg attttgagac cgacgagttc   5760
```

```
aatgatttca atgaagatga ctatgccaca agagaattcc tgaatcccga tgagcgcatg    5820
acgtacttga atcatgctga ttacaatttg aattctcctc taattagtga tgatattgac    5880
aatttgatca ggaaattcaa ttctcttccg attccctcga tgtgggatag taagaactgg    5940
gatggagttc ttgagatgtt aacatcatgt caagccaatc ccatctcaac atctcagatg    6000
cataaatgga tgggaagttg gttaatgtct gataatcatg atgccagtca gggtatagt     6060
tttttacatg aagtggacaa agaggcagaa ataacatttg acgtggtgga gaccttcatc    6120
cgcggctggg gcaacaaacc aattgaatac atcaaaaagg aaagatggac tgactcattc    6180
aaaattctcg cttatttgtg tcaaaagttt ttggacttac acaagttgac attaatctta    6240
aatgctgtct ctgaggtgga attgctcaac ttggcgagga cttttcaaagg caaagtcaga   6300
agaagttctc atggaacgaa catatgcagg attagggttc ccagcttggg tcctactttt    6360
atttcagaag gatgggctta cttcaagaaa cttgatattc taatggaccg aaactttctg    6420
ttaatggtca aagatgtgat tatagggagg atgcaaacgg tgctatccat ggtatgtaga    6480
atagacaacc tgttctcaga gcaagacatc ttctcccttc taaatatcta cagaattgga    6540
gataaaattg tggagaggca gggaaatttt tcttatgact tgattaaaat ggtggaaccg    6600
atatgcaact tgaagctgat gaaattagca agagaatcaa ggcctttagt cccacaattc    6660
cctcattttg aaaatcatat caagacttct gttgatgaag gggcaaaaat tgaccgaggt    6720
ataagattcc tccatgatca gataatgagt gtgaaaacga tggatctcac actggtgatt    6780
tatggatcgt tcagacattg gggtcatcct tttatagatt attacactgg actagaaaaa    6840
ttacattccc aagtaaccat gaagaaagat attgatgtgt catatgcaaa agcacttgca    6900
agtgatttag ctcggattgt tctatttcaa cagttcaatg atcataaaaa gtggttcgtg    6960
aatggagact tgctccctca tgatcatccc tttaaaagtc atgttaaaga aaatacatgg    7020
cccacagctg ctcaagttca agatttttgga gataaatggc atgaacttcc gctgattaaa    7080
tgttttgaaa tacccgactt actagaccca tcgataatat actctgacaa agtgcattca    7140
atgaataggt cagaggtgtt gaaacatgtc cgaatgaatc cgaacactcc tatccctagt    7200
aaaaaggtgt tgcagactat gttggacaca aaggctacca attggaaaga atttcttaaa    7260
gagattgatg agaagggctt agatgatgat gatctaatta ttggtcttaa aggaaaggag    7320
agggaactga agttggcagg tagatttttc tccctaatgt cttggaaatt gcgagaatac    7380
tttgtaatta ccgaatattt gataaagact catttcgtcc ctatgtttaa aggcctgaca    7440
atggcggacg atctaactgc agtcattaaa aagatgttag attcctcatc cggccaagga    7500
ttgaagtcat atgaggcaat ttgcatagcc aatcacattg attacgaaaa atggaataac    7560
caccaaagga agttatcaaa cggcccagtg ttccgagtta tgggccagtt cttaggttat    7620
ccatccttaa tcgagagaac tcatgaattt tttgagaaaa gtcttatata ctacaatgga    7680
agaccagact tgatgcgtgt tcacaacaac acactgatca attcaacctc ccaacgagtt    7740
tgttggcaag gacaagaggg tggactggaa ggtctacggc aaaaaggatg gactatcctc    7800
aatctactgg ttattcaaag agaggctaaa atcagaaaca ctgctgtcaa agtcttgtga    7860
caaggtgata atcaagttat ttgcacacag tataaaacga agaaatcgag aaacgttgta    7920
gaattacagg gtgctctcaa tcaaatggtt tctaataatg agaaaattat gactgcaatc    7980
aaaataggga cagggaagtt aggactttttg ataaatgacg atgagactat gcaatctgca    8040
gattacttga attatgggaa aataccgatt ttccgtggag tgattagagg gttagagacc    8100
aagagatggt cacgagtgac ttgtgtcacc aatgaccaaa tacccacttg tgctaatata    8160
atgagctcag tttccacaaa tgctctcacc gtagctcatt ttgctgagaa cccaatcaat    8220
gccatgatac agtacaatta ttttgggaca tttgctagac tcttgttgat gatgcatgat    8280
cctgctcttc gtcaatcatt gtatgaagtt caagataaga taccgggctt gcacagttct    8340
actttcaaat acgccatgtt gtatttggac ccttccattg gaggagtgtc gggcatgtct    8400
ttgtccaggt ttttgattag agccttccca gatcccgtaa cagaaagtct ctcattctgg    8460
agattcatcc atgtacatgc tcgaagtgag catctgaagg agatgagtgc agtatttgga    8520
aaccccgaca tagccaagtt tcgaataact cacatagaca gctagtaga agatccaacc    8580
tctctgaaca tcgctatggg aatgagtcca gcgaacttgt taaagactga ggttaaaaaa    8640
tgcttaatcg aatcaagaca aaccatcagg aaccaggtga ttaaggatgc aaccatatat    8700
ttgtatcatg aagaggatcg gctcagaagt ttcttatggt caataaatcc tctgttccct    8760
agattttttaa gtgaattcaa atcaggcact tttttgggag tcgcagacgg gctcatcagt    8820
ctatttcaaa attctcgtac tattcggaac tccttaagaa aaaagtatca tagggaattga   8880
gatgatttga ttgtgaggag tgaggtatcc tctttgacac atttagggaa acttcatttg    8940
agaagggat catgtaaaat gtggacatgt tcagctactc atgctgacac attaagatac    9000
aaatcctggg gccgtacagt tattgggaca actgtacccc atccattaga aatgttgggt    9060
ccacaacatc gaaaagagac tccttgtgca ccatgtaaca catcagggtt caattatgtt    9120
tctgtgcatt gtccagacgg gatccatgac gtctttagtt cacggggacc attgcctgct    9180
tatctagggt ctaaaacatc tgaatctaca tctatttttgc agccttggga aagggaaagc    9240
aaagtcccac tgattaaaag agctacacgt cttagagtag ctatctcttg gtttgttgaa    9300
cccgactcta aactagcaat gactatactt tctaacatcc actctttaac aggcgaagaa    9360
tggaccaaaa ggcagcatgg gttcaaaaga cagggtctg cccttcatag gttttcgaca    9420
tctcggatga gccatggtgg gttcgcatct cagagcactg cagcattgac caggttgatg    9480
gcaactcag acaccatgag ggatctggga gatcagaatt tcgacttttt attccaagca    9540
acgttgctct atgctcaaat taccaccact gttgcaagag acggatggat caccagttgt    9600
acagatcatt atcatattgc ctgtaagtcc tgtttgagac ccatagaaga gatcacccctg    9660
gactcaagta tggactacac gcccccagat gtatcccatg tgctgaagac atggaggaat    9720
ggggaaggtt cgtgggaca agagataaaa cagatctatc ctttagaagg gaattggaag    9780
aatttagcac ctgctgagca atcctatcaa gtcggacagat gtataggttt tctatatgga    9840
gacttggcgt ataagaaatc tactcatgcc gaggacagtt ctctattttcc tctatctata    9900
caaggtcgta ttagaggtcg aggttttctta aaagggttgc tagacggatt aatgagagca    9960
agttgctgcc aagtaataca ccggagaagt ctggctcatt tgaagaggcc ggccaacgca   10020
gtgtacggag gtttgattta cttgattgat aaattgagtg tatcacctcc attcctttct   10080
cttactagat caggacctat tagagacgaa ttagaaacga ttccccacaa gatcccaacc   10140
tcctatccga caagcaaccg tgatatgggg gtgattgtca gaaattactt caaatacccaa   10200
tgccgtctaa ttgaaaaggg aaaatacaga tcacattatt cacaattatg gttattctca   10260
gatgtcttat ccatagactt cattggacca ttctctattt ccaccaccct cttgcaaatc   10320
ctatacaagc cattttttatc tgggaaagat aagaatgagt tgagagagct ggcaaatctt   10380
tcttcattgc taagatcagg agaggggtgg aagacatac atgtgaaatt cttcaccaag   10440
gacatattat tgtgtccaga ggaaatcaga catgcttgca agttcgggat tgctaaggat   10500
```

```
aataataaag  acatgagcta  tcccccttgg  ggaagggaat  ccagagggac  aattacaaca  10560
atccctgttt  attatacgac  cacccttca   ccaaagatgc  tagagatgcc  tccaagaatc  10620
caaaatcccc  tgctgtccgg  aatcaggttg  ggccaattac  caactggcgc  tcattataaa  10680
attcggagta  tattacatgg  aatgggaatc  cattacaggg  acttcttgag  ttgtggagac  10740
ggctccggag  ggatgaatgc  tgcattacta  cgagaaaatg  tgcatagcag  aggaatattc  10800
aatagtctgt  tagaattatc  agggtcagtc  atgcgaggcg  cctctcctga  gccccccagt  10860
gccctagaaa  ctttaggagg  agataaaatcg agatgtgtaa  atggtgaaac  atgttgggaa  10920
tatccatctg  acttatgtga  cccaaggact  tgggactatt  tcctccgact  caaagcaggc  10980
ttggggcttc  aaattgattt  aattgtaatg  gatatggaag  ttcgggattc  ttctactagt  11040
ctgaaaattg  agacgaatgt  tagaaattat  gtgcaccgga  ttttggatga  gcaaggagtt  11100
ttaatctaca  agacttatgg  aacatatatt  tgtgagagcg  aaaagaatgc  agtaacaatc  11160
cttggtccca  tgttcaagac  ggtcgactta  gttcaaacag  aatttagtag  ttctcaaacg  11220
tctgaagtat  atatggtatg  taaaggtttg  aagaaattaa  tcgatgaacc  caatcccgat  11280
tggtcttcca  tcaatgaatc  ctggaaaaac  ctgtacgcat  tccagtcatc  agaacaggaa  11340
tttgccagag  caaagaaggt  tagtacatac  tttaccttga  caggtattcc  ctcccaattc  11400
attcctgatc  ctttttgtaaa cattgagact  atgctacaaa  tattcggagt  acccacgggt  11460
gtgtctcatg  cggctgcctt  aaaatcatct  gatagacctg  cagatttatt  gaccattagc  11520
ctttttata   tggcgattat  atcgtattat  aacatcaatc  atatcagagt  aggaccgata  11580
cctccgaacc  ccccatcaga  tggaattgca  caaaatgtgg  ggatcgctat  aactggtata  11640
agcttttggc  tgagtttgat  ggagaaagac  attccactat  atcaacagtg  tttagcagtt  11700
atccagcaat  cattcccgat  taggtgggag  gctgtttcag  taaaaggagg  atacaagcag  11760
aagtgagata  ctagaggtga  tgggctccca  aaagatacc   gaacttcaga  ctccttggcc  11820
ccaatcggga  actggatcag  atctctggaa  ttggtccgaa  accaagttcg  tctaaatcca  11880
ttcaatgaga  tcttgttcaa  tcagctatgt  cgtacagtgg  ataatcattt  gaatggtca   11940
aatttgcgaa  gaaacacagg  aatgattgaa  tggatcaata  gacgaatttc  aaaagaagac  12000
cggtctatac  tgatgttgaa  gagtgaccta  cacgaggaaa  actcttggag  agattaaaaa  12060
atcatgagga  gactccaaac  tttaagtatg  aaaaaaactt  tgatccttaa  gaccctcttg  12120
tggttttat   tttttatctg  gttttgtggt  cttcgt                              12156
```

```
SEQ ID NO: 28          moltype = AA  length = 682
FEATURE                Location/Qualifiers
REGION                 1..682
                       note = SARS-CoV-2 spike protein (S) (682 aa)
source                 1..682
                       mol_type = protein
                       organism = synthetic construct
SEQUENCE: 28
MFVFLVLLPL VSSQCVNLTT RTQLPPAYTN SFTRGVYYPD KVFRSSVLHS TQDLFLPFFS       60
NVTWFHAIHV SGTNGTKRFD NPVLPFNDGV YFASTEKSNI IRGWIFGTTL DSKTQSLLIV      120
NNATNVVIKV CEFQFCNDPF LGVYYHKNNK SWMESEFRVY SSANNCTFEY VSQPFLMDLE      180
GKQGNFKNLR EFVFKNIDGY FKIYSKHTPI NLVRDLPQGF SALEPLVDLP IGINITRFQT      240
LLALHRSYLT PGDSSSGWTA GAAAYYVGYL QPRTFLLKYN ENGTITDAVD CALDPLSETK      300
CTLKSFTVEK GIYQTSNFRV QPTESIVRFP NITNLCPFGE VFNATRFASV YAWNRKRISN      360
CVADYSVLYN SASFSTFKCY GVSPTKLNDL CFTNVYADSF VIRGDEVRQI APGQTGKIAD      420
YNYKLPDDFT GCVIAWNSNN LDSKVGGNYN YLYRLFRKSN LKPFERDIST EIYQAGSTPC      480
NGVEGFNCYF PLQSYGFQPT NGVGYQPYRV VVLSFELLHA PATVCGPKKS TNLVKNKCVN      540
FNFNGLTGTG VLTESNKKFL PFQQFGRDIA DTTDAVRDPQ TLEILDITPC SFGGVSVITP      600
GTNTSNQVAV LYQDVNCTEV PVAIHADQLT PTWRVYSTGS NVFQTRAGCL IGAEHVNNSY      660
ECDIPIGAGI CASYQTQTNS PR                                              682

SEQ ID NO: 29          moltype = AA  length = 1273
FEATURE                Location/Qualifiers
REGION                 1..1273
                       note = SARS-CoV-2 spike protein (S) (1273 aa)
source                 1..1273
                       mol_type = protein
                       organism = synthetic construct
SEQUENCE: 29
MFVFLVLLPL VSSQCVNLTT RTQLPPAYTN SFTRGVYYPD KVFRSSVLHS TQDLFLPFFS       60
NVTWFHAIHV SGTNGTKRFD NPVLPFNDGV YFASTEKSNI IRGWIFGTTL DSKTQSLLIV      120
NNATNVVIKV CEFQFCNDPF LGVYYHKNNK SWMESEFRVY SSANNCTFEY VSQPFLMDLE      180
GKQGNFKNLR EFVFKNIDGY FKIYSKHTPI NLVRDLPQGF SALEPLVDLP IGINITRFQT      240
LLALHRSYLT PGDSSSGWTA GAAAYYVGYL QPRTFLLKYN ENGTITDAVD CALDPLSETK      300
CTLKSFTVEK GIYQTSNFRV QPTESIVRFP NITNLCPFGE VFNATRFASV YAWNRKRISN      360
CVADYSVLYN SASFSTFKCY GVSPTKLNDL CFTNVYADSF VIRGDEVRQI APGQTGKIAD      420
YNYKLPDDFT GCVIAWNSNN LDSKVGGNYN YLYRLFRKSN LKPFERDIST EIYQAGSTPC      480
NGVEGFNCYF PLQSYGFQPT NGVGYQPYRV VVLSFELLHA PATVCGPKKS TNLVKNKCVN      540
FNFNGLTGTG VLTESNKKFL PFQQFGRDIA DTTDAVRDPQ TLEILDITPC SFGGVSVITP      600
GTNTSNQVAV LYQDVNCTEV PVAIHADQLT PTWRVYSTGS NVFQTRAGCL IGAEHVNNSY      660
ECDIPIGAGI CASYQTQTNS PRRARSVASQ SIIAYTMSLG AENSVAYSNN SIAIPTNFTI      720
SVTTEILPVS MTKTSVDCTM YICGDSTECS NLLLQYGSFC TQLNRALTGI AVEQDKNTQE      780
VFAQVKQIYK TPPIKDFGGF NFSQILPDPS KPSKRSFIED LLFNKVTLAD AGFIKQYGDC      840
LGDIAARDLI CAQKFNGLTV LPPLLTDEMI AQYTSALLAG TITSGWTFGA GAALQIPFAM      900
QMAYRFNGIG VTQNVLYENQ KLIANQFNSA IGKIQDSLSS TASALGKLQD VVNQNAQALN      960
TLVKQLSSNF GAISSVLNDI LSRLDKVEAE VQIDRLITGR LQSLQTYVTQ QLIRAAEIRA     1020
SANLAATKMS ECVLGQSKRV DFCGKGYHLM SFPQSAPHGV VFLHVTYVPA QEKNFTTAPA     1080
ICHDGKAHFP REGVFVSNGT HWFVTQRNFY EPQIITTDNT FVSGNCDVVI GIVNNTVYDP     1140
LQPELDSFKE ELDKYFKNHT SPDVDLGDIS GINASVVNIQ KEIDRLNEVA KNLNESLIDL     1200
QELGKYEQYI KWPWYIWLGF IAGLIAIVMV TIMLCCMTSC CSCLKGCCSC GSCCKFDEDD     1260
```

```
SEPVLKGVKL HYT                                                  1273

SEQ ID NO: 30          moltype = AA  length = 781
FEATURE                Location/Qualifiers
REGION                 1..781
                       note = WuS1-RABVG (781 aa)
source                 1..781
                       mol_type = protein
                       organism = synthetic construct
SEQUENCE: 30
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRSVGDEAED FVEVHLPDVH NQVSGVDLGL PNWGKYVLLS  720
AGALTALMLI IFLMTCCRRV NRSEPTQHNL RGTGREVSVT PQSGKIISSW ESHKSGGETR  780
L                                                               781

SEQ ID NO: 31          moltype = AA  length = 682
FEATURE                Location/Qualifiers
REGION                 1..682
                       note = WuS1-RABVG (682 aa)
source                 1..682
                       mol_type = protein
                       organism = synthetic construct
SEQUENCE: 31
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PR                                        682

SEQ ID NO: 32          moltype = AA  length = 525
FEATURE                Location/Qualifiers
REGION                 1..525
                       note = SARS-CoV-2 nucleocapsid protein (N)
source                 1..525
                       mol_type = protein
                       organism = synthetic construct
SEQUENCE: 32
MATLLRSLAL FKRNKDKPPI TSGSGGAIRG IKHIIIVPIP GDSSITTRSR LLDRLVRLIG  60
NPDVSGPKLT GALIGILSLF VESPGQLIQR ITDDPDVSIR LLEVVQSDQS QSGLTFASRG  120
TNMEDEADQY FSHDDPISSD QSRFGWFGNK EISDIEVQDP EGFNMILGTI LAQIWVLLAK  180
AVTAPDTAAD SELRRWIKYT QQRRVVGEFR LERKWLDVVR NRIAEDLSLR RFMVALILDI  240
KRTPGNKPRI AEMICDIDTY IVEAGLASFI LTIKFGIETM YPALGLHEFA GELSTLESLM  300
NLYQQMGETA PYMVILENSI QNKFSAGSYP LLWSYAMGVG VELENSMGGL NFGRSYFDPA  360
YFRLGQEMVR RSAGKVSSTL ASELGITAED ARLVSEIAMH TTEDKISRAV GPRQAQVSFL  420
HGDQSENELP RLGGKEDRRV KQSRGEARES YRETGPSRAS DARAAHLPTG TPLDIDTATE  480
SSQDPQDSRR SADALLRLQA MAGISEEQGS DTDTPIVYND RNLLD                525

SEQ ID NO: 33          moltype = DNA  length = 19
FEATURE                Location/Qualifiers
misc_feature           1..19
                       note = Artificial Sequence
source                 1..19
                       mol_type = other DNA
                       organism = synthetic construct
SEQUENCE: 33
cttaatgcgc cgctacagg                                            19

SEQ ID NO: 34          moltype = DNA  length = 18
FEATURE                Location/Qualifiers
misc_feature           1..18
                       note = Artificial Sequence
source                 1..18
```

-continued

```
                        mol_type = other DNA
                        organism = synthetic construct
SEQUENCE: 34
atgtgctgcg attaatta                                                  18

SEQ ID NO: 35           moltype = DNA  length = 19
FEATURE                 Location/Qualifiers
misc_feature            1..19
                        note = Artificial Sequence
source                  1..19
                        mol_type = other DNA
                        organism = synthetic construct
SEQUENCE: 35
tgtgctgatt aagtgtaag                                                 19

SEQ ID NO: 36           moltype = DNA  length = 17
FEATURE                 Location/Qualifiers
misc_feature            1..17
                        note = Artificial Sequence
source                  1..17
                        mol_type = other DNA
                        organism = synthetic construct
SEQUENCE: 36
gttttcccag tcacgac                                                   17

SEQ ID NO: 37           moltype = DNA  length = 48
FEATURE                 Location/Qualifiers
misc_feature            1..48
                        note = Artificial Sequence
source                  1..48
                        mol_type = other DNA
                        organism = synthetic construct
SEQUENCE: 37
aaacgacggc cagtggaatt ccgttaatac gactcactat aggaaagg                 48

SEQ ID NO: 38           moltype = DNA  length = 34
FEATURE                 Location/Qualifiers
misc_feature            1..34
                        note = Artificial Sequence
source                  1..34
                        mol_type = other DNA
                        organism = synthetic construct
SEQUENCE: 38
ggttgcgcgc cgttgactca ctatagggt tagg                                 34

SEQ ID NO: 39           moltype = DNA  length = 39
FEATURE                 Location/Qualifiers
misc_feature            1..39
                        note = Artificial Sequence
source                  1..39
                        mol_type = other DNA
                        organism = synthetic construct
SEQUENCE: 39
gagagcgcgc atcgaaatta atacgactca ctatagata                           39

SEQ ID NO: 40           moltype = DNA  length = 39
FEATURE                 Location/Qualifiers
misc_feature            1..39
                        note = Artificial Sequence
source                  1..39
                        mol_type = other DNA
                        organism = synthetic construct
SEQUENCE: 40
gagacgtacg cgtaatacga ctcactatag gggagaggg                           39

SEQ ID NO: 41           moltype = DNA  length = 19
FEATURE                 Location/Qualifiers
misc_feature            1..19
                        note = Artificial Sequence
source                  1..19
                        mol_type = other DNA
                        organism = synthetic construct
SEQUENCE: 41
taatacatag ggtaatggg                                                 19

SEQ ID NO: 42           moltype = DNA  length = 46
FEATURE                 Location/Qualifiers
misc_feature            1..46
                        note = Artificial Sequence
```

```
source                      1..46
                            mol_type = other DNA
                            organism = synthetic construct
SEQUENCE: 42
gtgtcgtctc gcgcgtgcgg ccgcgctagc cagcttgggt ctccct                    46

SEQ ID NO: 43               moltype = DNA   length = 45
FEATURE                     Location/Qualifiers
misc_feature                1..45
                            note = Artificial Sequence
source                      1..45
                            mol_type = other DNA
                            organism = synthetic construct
SEQUENCE: 43
gtgtcgtctc tgggtaagga tagtgtcgtc tctggggtaa ggata                     45

SEQ ID NO: 44               moltype = DNA   length = 53
FEATURE                     Location/Qualifiers
misc_feature                1..53
                            note = Artificial Sequence
source                      1..53
                            mol_type = other DNA
                            organism = synthetic construct
SEQUENCE: 44
gtgtggtctc tgaggatagt tcagtgtggt ctctggtcgg taaggatagt tca            53

SEQ ID NO: 45               moltype = DNA   length = 37
FEATURE                     Location/Qualifiers
misc_feature                1..37
                            note = Artificial Sequence
source                      1..37
                            mol_type = other DNA
                            organism = synthetic construct
SEQUENCE: 45
gagaaggttt gagaacgcgt ctcggtacgc cgggttt                              37

SEQ ID NO: 46               moltype = DNA   length = 34
FEATURE                     Location/Qualifiers
misc_feature                1..34
                            note = Artificial Sequence
source                      1..34
                            mol_type = other DNA
                            organism = synthetic construct
SEQUENCE: 46
tgtcacggat atccatcctg ctcttgtcct gtcc                                 34

SEQ ID NO: 47               moltype = DNA   length = 36
FEATURE                     Location/Qualifiers
misc_feature                1..36
                            note = Artificial Sequence
source                      1..36
                            mol_type = other DNA
                            organism = synthetic construct
SEQUENCE: 47
cagtccaccg gtgtcacgga tatccctaat cctgct                               36

SEQ ID NO: 48               moltype = DNA   length = 30
FEATURE                     Location/Qualifiers
misc_feature                1..30
                            note = Artificial Sequence
source                      1..30
                            mol_type = other DNA
                            organism = synthetic construct
SEQUENCE: 48
ggattaggga tatccgagat ggccacactt                                      30

SEQ ID NO: 49               moltype = DNA   length = 36
FEATURE                     Location/Qualifiers
misc_feature                1..36
                            note = Artificial Sequence
source                      1..36
                            mol_type = other DNA
                            organism = synthetic construct
SEQUENCE: 49
aagtgtggcc atctcggata tccctaatcc tgctct                               36

SEQ ID NO: 50               moltype = DNA   length = 21
FEATURE                     Location/Qualifiers
misc_feature                1..21
```

```
                        note = Artificial Sequence
source                  1..21
                        mol_type = other DNA
                        organism = synthetic construct
SEQUENCE: 50
tggccacact tttaaggagc t                                             21

SEQ ID NO: 51           moltype = DNA  length = 20
FEATURE                 Location/Qualifiers
misc_feature            1..20
                        note = Artificial Sequence
source                  1..20
                        mol_type = other DNA
                        organism = synthetic construct
SEQUENCE: 51
ccaccggatc ctgatgtaat                                               20

SEQ ID NO: 52           moltype = DNA  length = 20
FEATURE                 Location/Qualifiers
misc_feature            1..20
                        note = Artificial Sequence
source                  1..20
                        mol_type = other DNA
                        organism = synthetic construct
SEQUENCE: 52
ctggccttac cttcgcatca                                               20

SEQ ID NO: 53           moltype = DNA  length = 25
FEATURE                 Location/Qualifiers
misc_feature            1..25
                        note = Artificial Sequence
source                  1..25
                        mol_type = other DNA
                        organism = synthetic construct
SEQUENCE: 53
aggattagcc agttttatcc tgact                                         25

SEQ ID NO: 54           moltype = DNA  length = 17
FEATURE                 Location/Qualifiers
misc_feature            1..17
                        note = Artificial Sequence
source                  1..17
                        mol_type = other DNA
                        organism = synthetic construct
SEQUENCE: 54
agaagccagg agctaca                                                  17

SEQ ID NO: 55           moltype = DNA  length = 36
FEATURE                 Location/Qualifiers
misc_feature            1..36
                        note = Artificial Sequence
source                  1..36
                        mol_type = other DNA
                        organism = synthetic construct
SEQUENCE: 55
gtagtgtgcg atcgcgtgcg agaggccaga acaaca                             36

SEQ ID NO: 56           moltype = DNA  length = 60
FEATURE                 Location/Qualifiers
misc_feature            1..60
                        note = Artificial Sequence
source                  1..60
                        mol_type = other DNA
                        organism = synthetic construct
SEQUENCE: 56
gtgtacgcgt tccgccagaa caacagtgta cgcgttcctg acggagaggc cagaacaaca   60

SEQ ID NO: 57           moltype = DNA  length = 82
FEATURE                 Location/Qualifiers
misc_feature            1..82
                        note = Artificial Sequence
source                  1..82
                        mol_type = other DNA
                        organism = synthetic construct
SEQUENCE: 57
gtgtgcggcc gctatagcgt aagttttttta taacaatggt gtgcggccgc tatagcgatc  60
tcctaagttt tttataacaa tg                                            82

SEQ ID NO: 58           moltype = DNA  length = 67
```

```
FEATURE              Location/Qualifiers
misc_feature         1..67
                     note = Artificial Sequence
source               1..67
                     mol_type = other DNA
                     organism = synthetic construct
SEQUENCE: 58
gtgtgcggcc gttataacaa tggtgtgcgg ccgctataac gcgtttccta agttttttat    60
aacaatg                                                              67

SEQ ID NO: 59        moltype = DNA  length = 83
FEATURE              Location/Qualifiers
misc_feature         1..83
                     note = Artificial Sequence
source               1..83
                     mol_type = other DNA
                     organism = synthetic construct
SEQUENCE: 59
gtgtgcggcc gctataacgt aagttttttta taacaatggt gtgcggccgc tataacgcgt    60
ttcctaagtt ttttataaca atg                                             83

SEQ ID NO: 60        moltype = DNA  length = 19
FEATURE              Location/Qualifiers
misc_feature         1..19
                     note = Artificial Sequence
source               1..19
                     mol_type = other DNA
                     organism = synthetic construct
SEQUENCE: 60
gacaacccag gacaggagc                                                  19

SEQ ID NO: 61        moltype = DNA  length = 20
FEATURE              Location/Qualifiers
misc_feature         1..20
                     note = Artificial Sequence
source               1..20
                     mol_type = other DNA
                     organism = synthetic construct
SEQUENCE: 61
actctcaatg ttcctccgcc                                                 20

SEQ ID NO: 62        moltype = DNA  length = 20
FEATURE              Location/Qualifiers
misc_feature         1..20
                     note = Artificial Sequence
source               1..20
                     mol_type = other DNA
                     organism = synthetic construct
SEQUENCE: 62
gccattcctg gacttgggaa                                                 20

SEQ ID NO: 63        moltype = DNA  length = 31
FEATURE              Location/Qualifiers
misc_feature         1..31
                     note = Artificial Sequence
source               1..31
                     mol_type = other DNA
                     organism = synthetic construct
SEQUENCE: 63
gtgtgcggcc gcaggttgta ctaggtgggt c                                    31

SEQ ID NO: 64        moltype = DNA  length = 20
FEATURE              Location/Qualifiers
misc_feature         1..20
                     note = Artificial Sequence
source               1..20
                     mol_type = other DNA
                     organism = synthetic construct
SEQUENCE: 64
agtgattgcc tcccaaggtc                                                 20

SEQ ID NO: 65        moltype = DNA  length = 18
FEATURE              Location/Qualifiers
misc_feature         1..18
                     note = Artificial Sequence
source               1..18
                     mol_type = other DNA
                     organism = synthetic construct
SEQUENCE: 65
```

```
tgagttcgtg agctttcg                                                  18

SEQ ID NO: 66           moltype = DNA   length = 22
FEATURE                 Location/Qualifiers
misc_feature            1..22
                        note = Artificial Sequence
source                  1..22
                        mol_type = other DNA
                        organism = synthetic construct
SEQUENCE: 66
tctctgtaga ccgtagtgcc ca                                             22

SEQ ID NO: 67           moltype = DNA   length = 19
FEATURE                 Location/Qualifiers
misc_feature            1..19
                        note = Artificial Sequence
source                  1..19
                        mol_type = other DNA
                        organism = synthetic construct
SEQUENCE: 67
caaccccga caaccagag                                                  19

SEQ ID NO: 68           moltype = DNA   length = 20
FEATURE                 Location/Qualifiers
misc_feature            1..20
                        note = Artificial Sequence
source                  1..20
                        mol_type = other DNA
                        organism = synthetic construct
SEQUENCE: 68
cacccctaaa ggagacaccg                                                20

SEQ ID NO: 69           moltype = DNA   length = 44
FEATURE                 Location/Qualifiers
misc_feature            1..44
                        note = Artificial Sequence
source                  1..44
                        mol_type = other DNA
                        organism = synthetic construct
SEQUENCE: 69
gtgtgaatct caagtgtgaa gacttcatgc atcatgggtc tcaa                     44

SEQ ID NO: 70           moltype = DNA   length = 16
FEATURE                 Location/Qualifiers
misc_feature            1..16
                        note = Artificial Sequence
source                  1..16
                        mol_type = other DNA
                        organism = synthetic construct
SEQUENCE: 70
gagcgagcaa actact                                                    16

SEQ ID NO: 71           moltype = DNA   length = 20
FEATURE                 Location/Qualifiers
misc_feature            1..20
                        note = Artificial Sequence
source                  1..20
                        mol_type = other DNA
                        organism = synthetic construct
SEQUENCE: 71
cccaagtatg ttgcaaccca                                                20

SEQ ID NO: 72           moltype = DNA   length = 22
FEATURE                 Location/Qualifiers
misc_feature            1..22
                        note = Artificial Sequence
source                  1..22
                        mol_type = other DNA
                        organism = synthetic construct
SEQUENCE: 72
tcgagcacta gcatagtcta ca                                             22

SEQ ID NO: 73           moltype = DNA   length = 31
FEATURE                 Location/Qualifiers
misc_feature            1..31
                        note = Artificial Sequence
source                  1..31
                        mol_type = other DNA
                        organism = synthetic construct
```

```
                                          -continued

SEQUENCE: 73
gtgttctaga tcagagcgac cttacatagg a                                    31

SEQ ID NO: 74          moltype = DNA  length = 36
FEATURE                Location/Qualifiers
misc_feature           1..36
                       note = Artificial Sequence
source                 1..36
                       mol_type = other DNA
                       organism = synthetic construct
SEQUENCE: 74
gtgtcgtctc tatgtcacca caacgagacc ggtgcg                               36

SEQ ID NO: 75          moltype = DNA  length = 20
FEATURE                Location/Qualifiers
misc_feature           1..20
                       note = Artificial Sequence
source                 1..20
                       mol_type = other DNA
                       organism = synthetic construct
SEQUENCE: 75
cttgatcggg ttgctagcca                                                 20

SEQ ID NO: 76          moltype = DNA  length = 20
FEATURE                Location/Qualifiers
misc_feature           1..20
                       note = Artificial Sequence
source                 1..20
                       mol_type = other DNA
                       organism = synthetic construct
SEQUENCE: 76
ccagggaatg tatgggggaa                                                 20

SEQ ID NO: 77          moltype = DNA  length = 20
FEATURE                Location/Qualifiers
misc_feature           1..20
                       note = Artificial Sequence
source                 1..20
                       mol_type = other DNA
                       organism = synthetic construct
SEQUENCE: 77
atgcttccaa caggcgtgta                                                 20

SEQ ID NO: 78          moltype = DNA  length = 21
FEATURE                Location/Qualifiers
misc_feature           1..21
                       note = Artificial Sequence
source                 1..21
                       mol_type = other DNA
                       organism = synthetic construct
SEQUENCE: 78
gttgcctata aaggggggtcc c                                              21

SEQ ID NO: 79          moltype = DNA  length = 18
FEATURE                Location/Qualifiers
misc_feature           1..18
                       note = Artificial Sequence
source                 1..18
                       mol_type = other DNA
                       organism = synthetic construct
SEQUENCE: 79
ggggtccaat tacaggca                                                   18

SEQ ID NO: 80          moltype = DNA  length = 40
FEATURE                Location/Qualifiers
misc_feature           1..40
                       note = Artificial Sequence
source                 1..40
                       mol_type = other DNA
                       organism = synthetic construct
SEQUENCE: 80
gtgttccatc ttgtgttcta gactatattg gttccatctt                           40

SEQ ID NO: 81          moltype = DNA  length = 55
FEATURE                Location/Qualifiers
misc_feature           1..55
                       note = Artificial Sequence
source                 1..55
                       mol_type = other DNA
```

```
                         organism = synthetic construct
SEQUENCE: 81
gcagagacgc gtcttttttt ataacaatgg cagagacgcg tcttttataa caatg          55

SEQ ID NO: 82            moltype = DNA  length = 56
FEATURE                  Location/Qualifiers
misc_feature             1..56
                         note = Artificial Sequence
source                   1..56
                         mol_type = other DNA
                         organism = synthetic construct
SEQUENCE: 82
gctataacgc gtatctttt tataacaatg gctataacgc gtattttata acaatg          56

SEQ ID NO: 83            moltype = DNA  length = 49
FEATURE                  Location/Qualifiers
misc_feature             1..49
                         note = Artificial Sequence
source                   1..49
                         mol_type = other DNA
                         organism = synthetic construct
SEQUENCE: 83
tatcactctg tgttttata acaatgtatc actctgtttt ataacaatg                  49

SEQ ID NO: 84            moltype = DNA  length = 20
FEATURE                  Location/Qualifiers
misc_feature             1..20
                         note = Artificial Sequence
source                   1..20
                         mol_type = other DNA
                         organism = synthetic construct
SEQUENCE: 84
gtatgctcga gtccctcacg                                                 20

SEQ ID NO: 85            moltype = DNA  length = 20
FEATURE                  Location/Qualifiers
misc_feature             1..20
                         note = Artificial Sequence
source                   1..20
                         mol_type = other DNA
                         organism = synthetic construct
SEQUENCE: 85
tctctcgtga ccttgttgct                                                 20

SEQ ID NO: 86            moltype = DNA  length = 21
FEATURE                  Location/Qualifiers
misc_feature             1..21
                         note = Artificial Sequence
source                   1..21
                         mol_type = other DNA
                         organism = synthetic construct
SEQUENCE: 86
acggctgctg aaaatgttag g                                               21

SEQ ID NO: 87            moltype = DNA  length = 20
FEATURE                  Location/Qualifiers
misc_feature             1..20
                         note = Artificial Sequence
source                   1..20
                         mol_type = other DNA
                         organism = synthetic construct
SEQUENCE: 87
agttcaagcc tagttcgcct                                                 20

SEQ ID NO: 88            moltype = DNA  length = 20
FEATURE                  Location/Qualifiers
misc_feature             1..20
                         note = Artificial Sequence
source                   1..20
                         mol_type = other DNA
                         organism = synthetic construct
SEQUENCE: 88
aggcttgaga cctctgtcct                                                 20

SEQ ID NO: 89            moltype = DNA  length = 20
FEATURE                  Location/Qualifiers
misc_feature             1..20
                         note = Artificial Sequence
source                   1..20
```

```
                            mol_type = other DNA
                            organism = synthetic construct
SEQUENCE: 89
atgaaacaag ggcagcatgc                                               20

SEQ ID NO: 90               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 90
agaagaggac gagggactgg                                               20

SEQ ID NO: 91               moltype = DNA  length = 19
FEATURE                     Location/Qualifiers
misc_feature                1..19
                            note = Artificial Sequence
source                      1..19
                            mol_type = other DNA
                            organism = synthetic construct
SEQUENCE: 91
cgggttatga tcgggtgat                                                19

SEQ ID NO: 92               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 92
ttgttgcgtg atcccgatga                                               20

SEQ ID NO: 93               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 93
tcaatgctct aagccaccca                                               20

SEQ ID NO: 94               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 94
tcggcagcaa caacatctca                                               20

SEQ ID NO: 95               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 95
ccctacctct agtgtggggt                                               20

SEQ ID NO: 96               moltype = DNA  length = 20
FEATURE                     Location/Qualifiers
misc_feature                1..20
                            note = Artificial Sequence
source                      1..20
                            mol_type = other DNA
                            organism = synthetic construct
SEQUENCE: 96
acggacctaa gctgtgcaaa                                               20

SEQ ID NO: 97               moltype = DNA  length = 52
FEATURE                     Location/Qualifiers
misc_feature                1..52
                            note = Artificial Sequence
```

```
source                    1..52
                          mol_type = other DNA
                          organism = synthetic construct
SEQUENCE: 97
ctcgcgatat cctgccctcg cgatcgccta attgcggaac cctaatcctg cc        52

SEQ ID NO: 98             moltype = DNA  length = 21
FEATURE                   Location/Qualifiers
misc_feature              1..21
                          note = Artificial Sequence
source                    1..21
                          mol_type = other DNA
                          organism = synthetic construct
SEQUENCE: 98
gccctaggtg gttaggcatt a                                          21

SEQ ID NO: 99             moltype = DNA  length = 41
FEATURE                   Location/Qualifiers
misc_feature              1..41
                          note = Artificial Sequence
source                    1..41
                          mol_type = other DNA
                          organism = synthetic construct
SEQUENCE: 99
ccttacccaa ctttgtttgg tggccggcat agtcccagcc t                    41

SEQ ID NO: 100            moltype = DNA  length = 18
FEATURE                   Location/Qualifiers
misc_feature              1..18
                          note = Artificial Sequence
source                    1..18
                          mol_type = other DNA
                          organism = synthetic construct
SEQUENCE: 100
tcagcaaaaa acccctca                                              18

SEQ ID NO: 101            moltype = DNA  length = 36
FEATURE                   Location/Qualifiers
misc_feature              1..36
                          note = Artificial Sequence
source                    1..36
                          mol_type = other DNA
                          organism = synthetic construct
SEQUENCE: 101
ggttgcgcgc atccggatat agttcctcct ttggtt                          36

SEQ ID NO: 102            moltype = DNA  length = 34
FEATURE                   Location/Qualifiers
misc_feature              1..34
                          note = Artificial Sequence
source                    1..34
                          mol_type = other DNA
                          organism = synthetic construct
SEQUENCE: 102
gaccatgatt acgccagcgg ccgcatccgg atat                            34

SEQ ID NO: 103            moltype = DNA  length = 24
FEATURE                   Location/Qualifiers
misc_feature              1..24
                          note = Artificial Sequence
source                    1..24
                          mol_type = other DNA
                          organism = synthetic construct
SEQUENCE: 103
agcggataac aatttcacac agga                                       24

SEQ ID NO: 104            moltype = DNA  length = 24
FEATURE                   Location/Qualifiers
misc_feature              1..24
                          note = Artificial Sequence
source                    1..24
                          mol_type = other DNA
                          organism = synthetic construct
SEQUENCE: 104
tattaccgcc tttgagtgag ctga                                       24

SEQ ID NO: 105            moltype = DNA  length = 20
FEATURE                   Location/Qualifiers
misc_feature              1..20
```

```
                    note = Artificial Sequence
source              1..20
                    mol_type = other DNA
                    organism = synthetic construct
SEQUENCE: 105
cttttacgg ttcctggcct                                            20

SEQ ID NO: 106      moltype = DNA  length = 19
FEATURE             Location/Qualifiers
misc_feature        1..19
                    note = Artificial Sequence
source              1..19
                    mol_type = other DNA
                    organism = synthetic construct
SEQUENCE: 106
acatttcccc gaaaagtgc                                            19
```